(12) United States Patent
Velaparthi et al.

(10) Patent No.: US 9,273,058 B2
(45) Date of Patent: Mar. 1, 2016

(54) SUBSTITUTED PYRAZOLO-PIPERAZINES AS CASEIN KINASE 1 δ/ε INHIBITORS

(71) Applicant: BRISTOL-MYERS SQUIBB COMPANY, Princeton, NJ (US)

(72) Inventors: Upender Velaparthi, Cheshire, CT (US); Chetan Padmakar Darne, Orange, CT (US); Peiying Liu, Madison, CT (US); Mark D. Wittman, Wallingford, CT (US); Bradley C. Pearce, East Hampton, CT (US); Erika M. V. Araujo, Woodbridge, CT (US); Bireshwar Dasgupta, East Hampton, CT (US); Jalathi Surendran Nair, Bangalore (IN); Sakthi Kumaran Janakiraman, Bangalore (IN); Chandrasekhar Reddy Rachamreddy, Bangalore (IN); Mettu Mallikarjuna Rao, Bangalore (IN); Arul Mozhi Selvan Subbiah Karuppiah, Bangalore (IN); Bandreddy Subba Reddy, Bangalore (IN); Pulicharla Nagalakshmi, Bangalore (IN); Rajesh Onkardas Bora, Bangalore (IN); Shilpa Holehatti Maheshwarappa, Davanagere District (IN); Selvakumar Kumaravel, Bangalore (IN); Dibakar Mullick, Howrah District (IN); Ramesh Sistla, Bangalore (IN)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/541,343

(22) Filed: Nov. 14, 2014

(65) Prior Publication Data

US 2015/0133428 A1   May 14, 2015

Related U.S. Application Data

(60) Provisional application No. 61/904,116, filed on Nov. 14, 2013.

(51) Int. Cl.
| | |
|---|---|
| C07D 487/04 | (2006.01) |
| C07D 487/10 | (2006.01) |
| C07D 487/20 | (2006.01) |
| C07D 491/147 | (2006.01) |
| C07D 491/20 | (2006.01) |
| A61K 31/4985 | (2006.01) |
| A61K 31/499 | (2006.01) |
| A61K 31/501 | (2006.01) |
| A61K 31/506 | (2006.01) |
| A61K 31/5377 | (2006.01) |
| A61P 19/02 | (2006.01) |

(52) U.S. Cl.
CPC ............ *C07D 487/04* (2013.01); *C07D 487/10* (2013.01); *C07D 491/147* (2013.01); *C07D 491/20* (2013.01)

(58) Field of Classification Search
CPC .. C07D 487/04; C07D 487/14; C07D 487/20; A61K 31/4985; A61K 31/499
USPC .......................... 544/350, 346; 514/249, 250
See application file for complete search history.

(56) References Cited

U.S. PATENT DOCUMENTS

2005/0222171 A1   10/2005   Bold et al.
2007/0155738 A1    7/2007   Steeneck et al.

FOREIGN PATENT DOCUMENTS

| FR | 2 960 876 | 12/2011 |
| WO | WO2009/065298 A1 | 5/2009 |
| WO | WO2009/095254 A1 | 8/2009 |
| WO | WO2010/034738 A2 | 4/2010 |
| WO | WO2010/036380 A1 | 4/2010 |
| WO | WO2010/059836 A1 | 5/2010 |
| WO | WO2010/099938 A1 | 9/2010 |
| WO | WO2012/019427 A1 | 2/2012 |
| WO | WO2012/117048 A1 | 9/2012 |

OTHER PUBLICATIONS

Knippschild et al. Front. Oncol. 4:96, 1-32, 2014.*
Pyne et al. Cancer Res 2011 ;71:6576-6582.*
Gautschi et al., Clin. Cancer Res., 14(6), 1639-1648, 2008.*
Mountzios et al., Cancer Treatments Reviews, 34, 175-182, 2008.*
Freshney et al.,Culture of Animal Cells, A Manual of Basic Technique, Alan R. Liss, Inc., 1983, New York, p. 4.*
Dermer et al., Bio/Technology, 1994, 12:320.*
Golub et al., Science, 286, 531-537, 1999.*
Cecil Textbook of Medicine, edited by Bennet, J.C., and Plum F., 20th edition,vol. 1, 1004-101 O, 1996.*
Cohen et al., Current Opinion in Chemical Biology, 3,459-465, 1999.*
Brockschmidt, C. et al., "Anti-apoptotic and growth-stimulatory functions of CK1 delta and epsilon in ductal adenocarcinoma of the pancreas are inhibited by IC261 in vitro and in vivo", Gut, vol. 57, pp. 799-806 (2008).
Bundgaard, H., ed., Design of Prodrugs, Elsevier (1985).
Bundgaard, H./Krogsgaard-Larsen et al., "Design and Application of Prodrugs", A Textbook of Drug Design and Development, Chapter 5, pp. 113-191 Hardwood Academic Publishers (1991).

(Continued)

*Primary Examiner* — Venkataraman Balasubramanian
(74) *Attorney, Agent, or Firm* — Hong Liu

(57) ABSTRACT

The invention provides compounds of Formula (I):

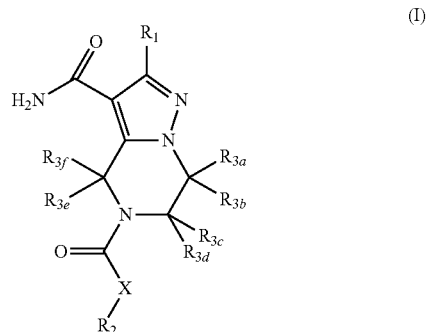

and pharmaceutically acceptable salts thereof. The compounds of Formula (I) inhibit protein kinase activity thereby making them useful as anticancer agents.

14 Claims, No Drawings

(56) References Cited

OTHER PUBLICATIONS

Bundgaard, H., "(C) Means to Enhance Penetration, (1) Prodrugs as a means to improve the delivery of peptide drugs", Advanced Drug Delivery Reviews, vol. 8, pp. 1-38 (1991).

Della, Ernest et al., "Synthesis of Bridgehead Fluorides by Fluorodeiodination", Journal of Organic Chemistry, vol. 57, pp. 2850-2855 (1992).

Hussainy, Rana Al et al., "Design, synthesis and in vitro evaluation of bridgehead fluoromethyl analogs on N-{2-[4-(2-methoxyphenyl) piperazin-1-yl}-N-(pyridine-2-yl) cyclohexanecarboxamide (WAY-100635) for the 5-HT$_{1A}$ receptor", European J. of Medicinal Chemistry, vol. 46, pp. 5728-5735 (2011).

Katritzky, A.R. et al., eds., Comprehensive Heterocyclic Chemistry, The Structure, Reactions, Synthesis and uses of Heterocyclic Compounds, First Edition, Pergamon Press, NY (1984).

Katritzky, A.R. et al., eds., Comprehensive Heterocyclic Chemistry II, A Review of the Literature 1982-1995: The Structure, Reactions, Synthesis and Uses of Heterocyclic Compounds, Pergamon Press, NY (1996).

Liu, Ning et al., "Microwave-assisted synthesis, crystal structure of pyrazolo[1,5-α]pyrazin-4(5H)-ones and their selective effects on lung cancer cells", European J. of Medicinal Chemistry, vol. 46, pp. 2359-2367 (2011).

Widder, K. et al., eds., "Drug and Enzyme Targeting", Methods in Enzymology, vol. 112, pp. 309-396 Academic Press (1985).

Zhang, Jin-Hua et al., "Synthesis and preliminary biological evaluation of novel pyrazolo[1,5-α]pyrazin-4(5H)-one derivatives as potential agents against A549 lung cancer cells", Bioorganic & Medicinal Chemistry, vol. 16, pp. 10165-10171 (2008).

* cited by examiner

SUBSTITUTED PYRAZOLO-PIPERAZINES AS CASEIN KINASE 1 δ/ε INHIBITORS

CROSS REFERENCE TO RELATED APPLICATIONS

This application is entitled to priority pursuant to 35 U.S.C. §119(e) to U.S. provisional patent application No. 61/904,116, filed on Nov. 14, 2013, which is incorporated herein in its entirety.

FIELD OF THE INVENTION

The invention relates to novel substituted pyrazoles useful as protein kinase inhibitors. This invention also relates to methods of using the compounds in the treatment of proliferative and other types of diseases and to pharmaceutical compositions containing the compounds.

BACKGROUND OF THE INVENTION

The invention relates to substituted pyrazole compounds which inhibit protein kinase enzymes, compositions which contain protein kinase inhibiting compounds and methods of using inhibitors of protein kinase enzymes to treat diseases which are characterized by an overexpression or upregulation of protein kinases. Protein kinases mediate intracellular signal transduction by affecting a phosphoryl transfer from a nucleoside triphosphate to a protein acceptor that is involved in a signaling pathway. There are a number of kinases and pathways through which extracellular and other stimuli cause a variety of cellular responses to occur inside the cell. An extracellular stimulus may affect one or more cellular responses related to cell growth, migration, differentiation, secretion of hormones, activation of transcription factors, muscle contraction, glucose metabolism, control of protein synthesis and regulation of cell cycle.

Many diseases are associated with abnormal cellular responses triggered by protein kinase-mediated events. These diseases include autoimmune diseases, inflammatory diseases, neurological and neurodegenerative diseases, cancer, cardiovascular diseases, allergies and asthma, Alzheimer's disease or hormone-related diseases. Accordingly, there has been a substantial effort in medicinal chemistry to find protein kinase inhibitors that are effective as therapeutic agents.

Serine/threonine kinases are a class of protein kinases that are among the most promising drug targets for future small molecule inhibitors. Inhibition of serine/threonine kinases is likely to have relevance to the treatment of cancer, diabetes and a variety of inflammatory disorders. The successful development of GLEEVEC® as a Bcr/Abl protein kinase inhibitor has provided further evidence that protein kinases are valid drug targets for potential cancer therapies.

Casein kinase 1 (CK1) belongs to the serine/threonine kinase family. In mammals, the enzyme exists in seven isozymic forms: α, β, γ1, γ2, γ3, δ, and ε. By phosphorylating different substrate proteins, these isoforms are able to activate, inactivate, stabilize, or destabilize the functions of the proteins, regulating the functions of various types of different organisms. For example, a tumor suppressor factor p53 and an oncogene mdm2, which are both important proteins for controlling abnormal cell growth, are substrates of casein kinase 1.

Mammalian casein kinase 1δ and casein kinase 1ε are key regulators of diverse cellular growth and survival processes including Wnt signaling, DNA repair and circadian rhythms. They have a kinase domain that is similar to those of other isoforms. However, the N-terminal and C-terminal domains thereof are different from those of other isoforms. The C-terminal domain has a plurality of autophosphorylation sites, and it is considered to be involved in regulation of autoenzyme activity. Phosphorylation of p53 by casein kinase 1δ or casein kinase 1ε leads to a consequent change in the interaction between p53 and mdm2. It has also been known that casein kinase 1ε or casein kinase 1δ is involved in a regulatory protein associated with the formation of a spindle as a central body during cell division, and that the casein kinase 1δ or casein kinase 1ε is involved in apoptosis mediated by TRAIL (tumor necrosis factor-related apoptosis inducing factor) and Fas. It has been further reported that inhibition of casein kinase 1ε or casein kinase 1δ by a nonselective casein kinase 1 inhibitory compound IC261 reduces pancreatic tumor cell growth in vitro and in vivo (Brockschmidt et al., *Gut*, 57(6): 799-806 (2008)). Hence, a medicament inhibiting the function of casein kinase 1δ or casein kinase 1ε would be expected to exert important phenotypic and therapeutic effects broadly in development and disease, especially cancer.

The present invention relates to a new class substituted pyrazoles found to be effective in inhibiting casein kinase 1δ or casein kinase 1ε. These novel compounds are provided to be useful as pharmaceuticals with desirable stability, bioavailability, therapeutic index and toxicity values that are important to their drugability.

SUMMARY OF THE INVENTION

The invention is directed to substituted pyrazole compounds of Formulae (I)-(VI) or stereoisomers, tautomers, pharmaceutically acceptable salts, solvates or prodrugs thereof, which inhibit protein kinase enzymes, especially protein kinase CK1 for the treatment of cancer.

The present invention also provides processes and intermediates for making the compounds of the present invention or stereoisomers, tautomers, pharmaceutically acceptable salts, solvates, or prodrugs thereof.

The present invention also provides pharmaceutical compositions comprising a pharmaceutically acceptable carrier and at least one of the compounds of the present invention or stereoisomers, tautomers, pharmaceutically acceptable salts, solvates, or prodrugs thereof.

The present invention also provides methods for inhibiting the activity of protein kinase CK1 comprising administering to a host in need of such treatment a therapeutically effective amount of at least one of the compounds of the present invention or stereoisomers, tautomers, pharmaceutically acceptable salts, solvates, or prodrugs thereof.

The present invention also provides methods for treating cancers comprising administering to a host in need of such treatment a therapeutically effective amount of at least one of the compounds of the present invention or stereoisomers, tautomers, pharmaceutically acceptable salts, solvates, or prodrugs thereof.

The present invention also provides the compounds of the present invention or stereoisomers, tautomers, pharmaceutically acceptable salts, solvates, or prodrugs thereof, for use in therapy.

The present invention also provides the use of the compounds of the present invention or stereoisomers, tautomers, pharmaceutically acceptable salts, solvates, or prodrugs thereof, in preparing a medicament for the treatment of cancer in a human patient, particularly a cancer receptive to treatment via inhibition of the CK1 enzyme.

These and other features of the invention will be set forth in the expanded form as the disclosure continues.

DETAILED DESCRIPTION OF THE INVENTION

The invention provides for novel substituted pyrazole compounds useful as therapeutic agents, pharmaceutical compositions employing such novel compounds and for methods of using such compounds.

In accordance with the invention, there are disclosed compounds of Formula (I) including enantiomers, diastereomers, tautomers, pharmaceutically-acceptable salts, prodrugs, hydrates, or solvates thereof,

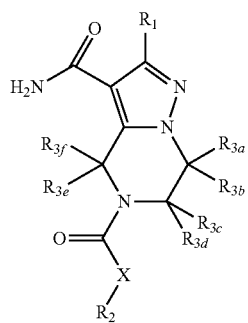

(I)

wherein:
X is independently selected from O and NH;
$R_1$ is independently selected from carbocyclyl substituted with 1-5 $R_5$, and heterocyclyl comprising carbon atoms and 1 to 3 heteroatoms selected from N, $NR_4$, O, S, and substituted with 1-5 $R_5$;
$R_2$ is independently selected from (i) alkyl optionally substituted with F, Cl, Br, $OR_b$, CN, $NR_aR_a$, —C(=O)$NR_aR_a$, $C_{2-6}$ alkenyl substituted with 0-5 $R_e$, $C_{2-6}$ alkynyl substituted with 0-5 $R_e$, carbocyclyl substituted with 1-8 $R_7$, and heterocyclyl comprising carbon atoms and 1 to 4 heteroatoms selected from N, $NR_6$, O, S, and substituted with 1-8 $R_7$, (ii) cycloalkyl substituted with 1-8 $R_7$, and (iii) cycloheteroalkyl substituted with 1-8 $R_7$;
$R_{3a}$, $R_{3b}$, $R_{3c}$, $R_{3d}$, $R_{3e}$ and $R_{3f}$ are independently selected from H, CN, $C_{1-4}$alkyl substituted with 1-3 $R_8$, —C(=O)$OR_b$, —C(=O)$NR_aR_a$, —C(=O)$R_b$, —$NR_aC(=O)R_b$, —$NR_aC(=O)OR_b$, —(CH$_2$)$_r$-carbocyclyl substituted with 1-3 $R_8$, and —(CH$_2$)$_r$-heterocyclyl substituted with 1-3 $R_8$;
alternatively, $R_{3a}$ and $R_{3b}$, or $R_{3c}$ and $R_{3d}$, or $R_{3e}$ and $R_{3f}$ together with the carbon atom to which they are both attached form a spiral carbocyclic or heterocyclic ring comprising carbon atoms and 1 to 4 heteroatoms selected from N, O, S, each substituted with 1-5 $R_8$;
alternatively, $R_{3a}$ and $R_{3c}$ or $R_{3b}$ and $R_{3d}$ together form a heterocyclic ring comprising carbon atoms and 1 to 4 heteroatoms selected from N, O, S, and substituted with 1-5 $R_8$;
$R_4$ is independently selected from H, $C_{1-4}$ alkyl substituted with 0-3 $R_e$, —(CH$_2$)$_r$CN, —(CH$_2$)$_r$OR$_b$, (CH$_2$)$_r$S(O)$_p$R$_c$, —(CH$_2$)$_r$C(=O)R$_b$, —(CH$_2$)$_r$NR$_a$R$_a$, —(CH$_2$)$_r$C(=O)NR$_a$R$_a$, —(CH$_2$)$_r$NR$_a$C(=O)R$_b$, —(CH$_2$)$_r$NR$_a$C(=O)OR$_b$, —(CH$_2$)$_r$OC(=O)NR$_a$R$_a$, —(CH$_2$)$_r$NR$_a$C(=O)NR$_a$R$_a$, —(CH$_2$)$_r$C(=O)OR$_b$, —(CH$_2$)$_r$S(O)$_2$NR$_a$R$_a$, —(CH$_2$)$_r$NR$_a$S(O)$_2$NR$_a$R$_a$, (CH$_2$)$_r$NR$_a$S(O)$_2$R$_c$, (CH$_2$)$_r$-carbocyclyl substituted with 0-3 $R_e$, and —(CH$_2$)$_r$-heterocyclyl substituted with 0-3 $R_e$;

$R_5$, at each occurrence, is independently selected from H, $C_{1-4}$ alkyl substituted with 0-3 $R_e$, F, Cl, Br, =O, CN, NO$_2$, —OR$_b$, —(CH$_2$)$_r$CN, —(CH$_2$)$_r$OR$_b$, (CH$_2$)$_r$S(O)$_p$R$_c$, —(CH$_2$)$_r$C(=O)R$_b$, —(CH$_2$)$_r$NR$_a$R$_a$, —(CH$_2$)$_r$C(=O)NR$_a$R$_a$, —(CH$_2$)$_r$NR$_a$C(=O)R$_b$, —(CH$_2$)$_r$NR$_a$C(=O)OR$_b$, —(CH$_2$)$_r$OC(=O)NR$_a$R$_a$, —(CH$_2$)$_r$NR$_a$C(=O)NR$_a$R$_a$, —(CH$_2$)$_r$C(=O)OR$_b$, —(CH$_2$)$_r$S(O)$_2$NR$_a$R$_a$, —(CH$_2$)$_r$NR$_a$S(O)$_2$NR$_a$R$_a$, —(CH$_2$)$_r$NR$_a$S(O)$_2$R$_c$, (CH$_2$)$_r$-carbocyclyl substituted with 0-3 $R_e$, and —(CH$_2$)$_r$-heterocyclyl substituted with 0-3 $R_e$;
$R_6$ is independently selected from H, —C(=O)R$_b$, —CO(=O)R$_b$, —S(O)$_p$R$_c$, $C_{1-6}$ alkyl substituted with 0-5 $R_e$, —(CH$_2$)$_r$—$C_{3-6}$carbocyclyl substituted with 0-5 $R_e$, and —(CH$_2$)$_r$-heterocyclyl substituted with 0-5 $R_e$;
$R_7$, at each occurrence, is independently selected from H, F, Cl, Br, =O, —(CR$_d$R$_d$)$_r$CN, NO$_2$, —(CR$_d$R$_d$)$_r$OR$_b$, —S(O)$_p$R$_c$, —C(=O)R$_b$, —(CR$_d$R$_d$)$_r$NR$_a$R$_a$, —(CR$_d$R$_d$)$_r$C(=O)NR$_a$R$_a$, —NR$_a$C(=O)R$_b$, —NR$_a$C(=O)OR$_b$, —OC(=O)NR$_a$R$_a$, —NR$_a$C(=O)NR$_a$R$_a$, —(CR$_d$R$_d$)$_r$C(=O)OR$_b$, —S(O)$_2$NR$_a$R$_a$, —NR$_a$S(O)$_2$NR$_a$R$_a$, —NR$_a$S(O)$_2$R$_c$, $C_{1-6}$ alkyl substituted with 0-5 $R_e$, —(CR$_d$R$_d$)$_r$—$C_{3-6}$carbocyclyl substituted with 0-5 $R_e$, and —(CR$_d$R$_d$)$_r$-heterocyclyl substituted with 0-5 $R_e$;
$R_8$, at each occurrence, is independently selected from H, F, Cl, Br, CN, $C_{1-6}$ alkyl substituted with 0-5 $R_e$, $C_{2-6}$ alkenyl, $C_{2-6}$ alkynyl, —(CH$_2$)$_r$—$C_{3-6}$ cycloalkyl substituted with 0-5 $R_e$, —(CH$_2$)$_r$-aryl substituted with 0-5 $R_e$, —(CH$_2$)$_r$-heterocyclyl substituted with 0-5 $R_e$, CO$_2$H, —(CH$_2$)$_r$OR$_b$, and —(CH$_2$)$_r$NR$_a$R$_a$;
$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —(CH$_2$)$_r$—$C_{3-10}$carbocyclyl substituted with 0-5 $R_e$, and —(CH$_2$)$_r$-heterocyclyl substituted with 0-5 $R_e$; or $R_a$ and $R_a$ together with the nitrogen atom to which they are both attached form a heterocyclic ring substituted with 0-5 $R_e$;
$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —(CH$_2$)$_r$—$C_{3-10}$carbocyclyl substituted with 0-5 $R_e$, and —(CH$_2$)$_r$-heterocyclyl substituted with 0-5 $R_e$;
$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;
$R_d$, at each occurrence, is independently selected from H and $C_{1-4}$alkyl substituted with 0-5 $R_e$;
$R_e$, at each occurrence, is independently selected from F, Cl, Br, CN, NO$_2$, =O, $C_{1-6}$ alkyl substituted with 0-5 $R_f$, $C_{2-6}$ alkenyl, $C_{2-6}$ alkynyl, —(CH$_2$)$_r$—$C_{3-6}$ cycloalkyl, —(CH$_2$)$_r$-aryl, —(CH$_2$)$_r$-heterocyclyl, CO$_2$H, —(CH$_2$)$_r$OR$_f$, SR$_f$, and —(CH$_2$)$_r$NR$_f$R$_f$;
$R_f$, at each occurrence, is independently selected from H, $C_{1-5}$ alkyl optionally substituted with F, Cl, Br, $C_{3-6}$ cycloalkyl, and phenyl, or $R_f$ and $R_f$ together with the nitrogen atom to which they are both attached form a heterocyclic ring optionally substituted with $C_{1-4}$alkyl;
p, at each occurrence, is independently selected from zero, 1, and 2; and
r, at each occurrence, is independently selected from zero, 1, 2, 3, and 4.

In another aspect, there are disclosed compounds of Formula (II) including enantiomers, diastereomers, tautomers, pharmaceutically acceptable salts, prodrugs, hydrates, or solvates thereof,

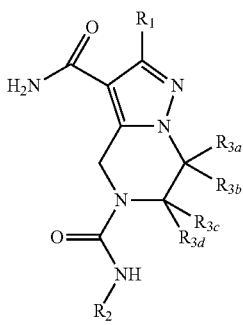

(II)

wherein:
R₁ is independently selected from aryl substituted with 1-4 $R_5$, and 5- to 12-membered heteroaryl comprising carbon atoms and 1 to 3 heteroatoms selected from N, $NR_4$, O, S, and substituted with 1-4 $R_5$;
R₂ is independently selected from (i) alkyl optionally substituted with F, Cl, Br, $OR_b$, CN, $NR_aR_a$, —C(=O)$NR_aR_a$, $C_{2-6}$ alkenyl substituted with 0-5 $R_e$, $C_{2-6}$ alkynyl substituted with 0-5 $R_e$, carbocyclyl substituted with 1-8 $R_7$, and heterocyclyl comprising carbon atoms and 1 to 4 heteroatoms selected from N, $NR_6$, O, S, and substituted with 1-8 $R_7$, (ii) cycloalkyl substituted with 1-8 $R_7$, and (iii) cycloheteroalkyl substituted with 1-8 $R_7$;
$R_{3a}$, $R_{3b}$, $R_{3c}$, and $R_{3d}$ are independently selected from H, CN, $C_{1-4}$alkyl substituted with 1-3 $R_8$, —C(=O)$OR_b$, —C(=O)$NR_aR_a$, —C(=O)$R_b$, —$NR_aC$(=O)$R_b$, —$NR_aC$(=O)$OR_b$, —(CH₂)$_r$-carbocyclyl substituted with 1-3 $R_8$, and —(CH₂)$_r$-heterocyclyl substituted with 1-3 $R_8$;
alternatively, $R_{3a}$ and $R_{3b}$, or $R_{3c}$ and $R_{3d}$, or $R_{3e}$ and $R_{3f}$ together with the carbon atom to which they are both attached form a spiral carbocyclic or heterocyclic ring comprising carbon atoms and 1 to 4 heteroatoms selected from N, O, S, each substituted with 0-5 $R_e$;
alternatively, $R_{3a}$ and $R_{3c}$ or $R_{3b}$ and $R_{3d}$ together form a heterocyclic ring comprising carbon atoms and 1 to 4 heteroatoms selected from N, O, S, and substituted with 0-5 $R_e$;
R₄ is independently selected from H and $C_{1-4}$ alkyl substituted with 0-3 $R_e$;
R₅, at each occurrence, is independently selected from H, $C_{1-4}$alkyl substituted with 0-3 $R_e$, F, Cl, Br, =O, CN, NO₂, —$OR_b$, —(CH₂)$_r$CN, —(CH₂)$_r$$OR_b$, (CH₂)$_r$S(O)$_p$$R_c$, —(CH₂)$_r$C(=O)$R_b$, —(CH₂)$_r$$NR_aR_a$, —(CH₂)$_r$C(=O)$NR_aR_a$, —(CH₂)$_r$$NR_aC$(=O)$R_b$, —(CH₂)$_r$$NR_aC$(=O)$OR_b$, —(CH₂)$_r$OC(=O)$NR_aR_a$, —(CH₂)$_r$$NR_aC$(=O)$NR_aR_a$, —(CH₂)$_r$C(=O)$OR_b$, —(CH₂)$_r$S(O)₂$NR_aR_a$, —(CH₂)$_r$$NR_aS$(O)₂$NR_aR_a$, —(CH₂)$_r$$NR_aS$(O)₂$R_c$, (CH₂)$_r$-carbocyclyl substituted with 0-3 $R_e$, and —(CH₂)$_r$-heterocyclyl substituted with 0-3 $R_e$;
R₆ is independently selected from H, —C(=O)$R_b$, —CO(=O)$R_b$, —S(O)$_p$$R_c$, $C_{1-6}$ alkyl substituted with 0-5 $R_e$, —(CH₂)$_r$—$C_{3-6}$carbocyclyl substituted with 0-5 $R_e$, and —(CH₂)$_r$-heterocyclyl substituted with 0-5 $R_e$;
R₇, at each occurrence, is independently selected from H, F, Cl, Br, =O, —(CR$_d$R$_d$)$_r$CN, NO₂, —(CR$_d$R$_d$)$_r$$OR_b$, —S(O)$_p$$R_c$, —C(=O)$R_b$, —(CR$_d$R$_d$)$_r$$NR_aR_a$, —(CR$_d$R$_d$)$_r$C(=O)$OR_b$, —$NR_aC$(=O)$R_b$, —$NR_aC$(=O)$OR_b$, —OC(=O)$NR_aR_a$, —$NR_aC$(=O)$NR_aR_a$, —(CR$_d$R$_d$)$_r$C(=O)$OR_b$, —S(O)₂$NR_aR_a$, —$NR_aS$(O)₂$NR_aR_a$, —$NR_aS$(O)₂$R_c$, $C_{1-6}$ alkyl substituted with 0-5 $R_e$, —(CR$_d$R$_d$)$_r$—$C_{3-6}$carbocyclyl substituted with 0-5 $R_c$, and —(CR$_d$R$_d$)$_r$-heterocyclyl substituted with 0-5 $R_c$;
R₈, at each occurrence, is independently selected from H, F, Cl, Br, CN, $C_{1-6}$ alkyl substituted with 0-5 $R_e$, $C_{2-6}$ alkenyl, $C_{2-6}$ alkynyl, —(CH₂)$_r$—$C_{3-6}$ cycloalkyl substituted with 0-5 $R_e$, —(CH₂)$_r$-aryl substituted with 0-5 $R_e$, —(CH₂)$_r$-heterocyclyl substituted with 0-5 $R_e$, CO₂H, —(CH₂)$_r$$OR_b$, and —(CH₂)$_r$$NR_aR_a$;
$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —(CH₂)$_r$—$C_{3-10}$carbocyclyl substituted with 0-5 $R_e$, and —(CH₂)$_r$-heterocyclyl substituted with 0-5 $R_e$; or $R_a$ and $R_a$ together with the nitrogen atom to which they are both attached form a heterocyclic ring substituted with 0-5 $R_e$;
$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —(CH₂)$_r$—$C_{3-10}$carbocyclyl substituted with 0-5 $R_e$, and —(CH₂)$_r$-heterocyclyl substituted with 0-5 $R_e$;
$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;
$R_d$, at each occurrence, is independently selected from H and $C_{1-4}$alkyl substituted with 0-5 $R_e$;
$R_e$, at each occurrence, is independently selected from F, Cl, Br, CN, NO₂, =O, $C_{1-5}$ alkyl substituted with 0-5 $R_f$, $C_{2-6}$ alkenyl, $C_{2-6}$ alkynyl, —(CH₂)$_r$—$C_{3-6}$ cycloalkyl, CO₂H, —(CH₂)$_r$$OR_f$, $SR_f$, and —(CH₂)$_r$$NR_fR_f$;
$R_f$ at each occurrence, is independently selected from H, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;
p, at each occurrence, is independently selected from zero, 1, and 2; and
r, at each occurrence, is independently selected from zero, 1, 2, 3, and 4.

In another embodiment, there are disclosed compounds of Formula (II) including enantiomers, diastereomers, tautomers, pharmaceutically-acceptable salts, prodrugs, hydrates, or solvates thereof, wherein:
R₁ is independently selected from aryl, pyridyl, pyrimidinyl, pyrazinyl, pyridazinyl, triazinyl, furyl, thienyl, imidazolyl, thiazolyl, indolyl, oxazolyl, isoxazolyl, pyrazolyl, triazolyl, tetrazolyl, indazolyl, 1,2,4-thiadiazolyl, isothiazolyl, quinolinyl, isoquinolinyl, each substituted with 1-4 $R_4$ and $R_5$;
R₄, at each occurrence, is independently selected from H and $C_{1-4}$ alkyl substituted with 0-3 $R_e$;
R₅, at each occurrence, is independently selected from H, $C_{1-4}$alkyl substituted with 0-3 $R_e$, F, Cl, Br, =O, CN, NO₂, —$OR_b$, —S(O)$_p$$R_c$, —CN, —$OR_b$, —(CH₂)$_r$C(=O)$R_b$, —(CH₂)$_r$$NR_aR_a$, —(CH₂)$_r$C(=O)$NR_aR_a$, —(CH₂)$_r$NHC(=O)$R_b$, —(CH₂)$_r$NHC(=O)$OR_b$, —(CH₂)$_r$OC(=O)$NR_aR_a$, —(CH₂)$_r$NHC(=O)$NR_aR_a$, —(CH₂)$_r$C(=O)$OR_b$, —(CH₂)$_r$S(O)₂$NR_aR_a$, —(CH₂)$_r$NHS(O)₂$NR_aR_a$, —(CH₂)$_r$NHS(O)₂$R_c$, (CH₂)$_r$-carbocyclyl substituted with 0-3 $R_e$, and —(CH₂)$_r$-heterocyclyl substituted with 0-3 $R_e$;
$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —(CH₂)$_r$—$C_{3-10}$carbocyclyl substituted with 0-5 $R_e$, and —(CH₂)$_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5$R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_e$, at each occurrence, is independently selected from F, Cl, Br, CN, $NO_2$, =O, $C_{1-6}$ alkyl substituted with 0-5 $R_f$, $C_{2-6}$ alkenyl, $C_{2-6}$ alkynyl, cycloalkyl, $CO_2H$, —$(CH_2)_rOR_f$, $SR_f$, and —$(CH_2)_rNR_fR_f$;

$R_f$, at each occurrence, is independently selected from H, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

p, at each occurrence, is independently selected from zero, 1, and 2;

r, at each occurrence, is independently selected from zero, 1, 2, 3, and 4;

and other variables are as defined in Formula (II) above.

In another embodiment, there are disclosed compounds of Formula (II) including enantiomers, diastereomers, tautomers, pharmaceutically-acceptable salts, prodrugs, hydrates, or solvates thereof, wherein:

$R_1$ is independently selected from

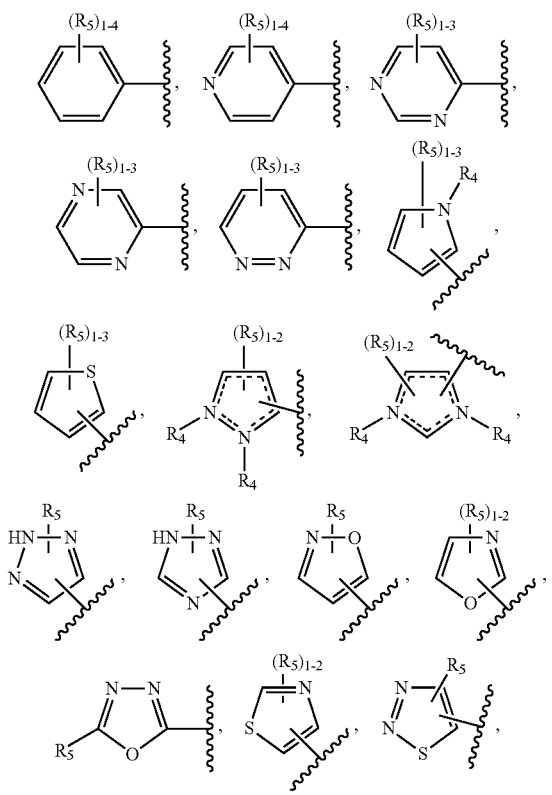

$R_4$, at each occurrence, is independently selected from H, $C_{1-4}$ alkyl substituted with 0-3 $R_e$;

$R_5$, at each occurrence, is independently selected from H, $C_{1-4}$ alkyl substituted with 0-3 $R_e$, F, Cl, Br, =O, CN, $NO_2$, —$OR_b$, —$S(O)_pR_c$, —CN, —$OR_b$, —$(CH_2)_rC(=O)R_b$, —$(CH_2)_rNR_aR_a$, —$(CH_2)_rC(=O)NR_aR_a$, —$(CH_2)_rNHC(=O)R_b$, —$(CH_2)_rNHC(=O)OR_b$, —$(CH_2)_rOC(=O)NR_aR_a$, —$(CH_2)_rNHC(=O)NR_aR_a$, —$(CH_2)_rC(=O)OR_b$, —$(CH_2)_rS(O)_2NR_aR_a$, —$(CH_2)_rNHS(O)_2NR_aR_a$, —$(CH_2)_rNHS(O)_2R_c$, $(CH_2)_r$—$C_{3-6}$cycloalkyl, —$(CH_2)_r$-aryl substituted with 0-3 $R_e$, and —$(CH_2)_r$-heterocyclyl substituted with 0-3 $R_e$;

$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_e$, at each occurrence, is independently selected from F, Cl, Br, CN, $NO_2$, =O, $C_{1-6}$ alkyl, $C_{2-6}$ alkenyl, $C_{2-6}$ alkynyl, —$(CH_2)_r$—$C_{3-6}$ cycloalkyl, and $CO_2H$;

p, at each occurrence, is independently selected from zero, 1, and 2;

r, at each occurrence, is independently selected from zero, 1, 2, 3, and 4;

and other variables are as defined in Formula (II) above.

In another aspect, there are disclosed compounds of Formula (III) including enantiomers, diastereomers, tautomers, pharmaceutically-acceptable salts, prodrugs, hydrates, or solvates thereof,

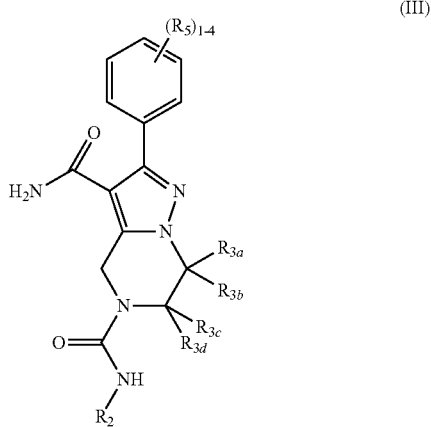

(III)

wherein:

$R_2$ is independently selected from (i) alkyl optionally substituted with F, Cl, Br, $OR_b$, CN, $NR_aR_a$, —C(=O)$NR_aR_a$, $C_{2-6}$ alkenyl substituted with 0-5 $R_e$, $C_{2-6}$ alkynyl substituted with 0-5 $R_e$, carbocyclyl substituted with 1-8 $R_7$, and heterocyclyl comprising carbon atoms and 1 to 4 heteroatoms selected from N, $NR_6$, O, S, and substituted with 1-8 $R_7$, (ii) cycloalkyl substituted with 1-8 $R_7$, and (iii) cycloheteroalkyl substituted with 1-8 $R_7$;

$R_{3a}$, $R_{3b}$, $R_{3c}$, and $R_{3d}$ are independently selected from H, CN, $C_{1-4}$alkyl substituted with 1-3 $R_8$, —C(=O)$OR_b$, —C(=O)$NR_aR_a$, —C(=O)$R_b$, —$NR_aC$(=O)$R_b$, —$NR_aC$(=O)$OR_b$, —$(CH_2)_r$-carbocyclyl substituted with 1-3 $R_8$, and —$(CH_2)_r$-heterocyclyl substituted with 1-3 $R_8$;

alternatively, $R_{3a}$, and $R_{3b}$, or $R_{3c}$ and $R_{3d}$, together with the carbon atom to which they are both attached form a spiral carbocyclic or heterocyclic ring comprising carbon atoms and 1 to 4 heteroatoms selected from N, O, S, each substituted with 1-5 $R_8$;

alternatively, $R_{3a}$ and $R_{3c}$ or $R_{3b}$ and $R_{3d}$ together form a heterocyclic ring comprising carbon atoms and 1 to 4 heteroatoms selected from N, O, S, and substituted with 1-5 $R_8$;

$R_5$, at each occurrence, is independently selected from H, $C_{1-4}$ alkyl substituted with 0-3 $R_e$, F, Cl, Br, —S(O)$_pR_c$, —CN, —$OR_b$, $NR_aR_a$, $C_{3-6}$cycloalkyl, aryl substituted with 0-3 $R_e$, and heterocyclyl substituted with 0-3 $R_e$;

$R_6$ is independently selected from H, —C(=O)$R_b$, —CO(=O)$R_b$, —S(O)$_pR_c$, $C_{1-6}$ alkyl substituted with 0-5 $R_e$, —$(CH_2)_r$—$C_{3-6}$carbocyclyl substituted with 0-5 $R_e$, and $(CH_2)_r$-heterocyclyl substituted with 0-5 $R_e$;

$R_7$, at each occurrence, is independently selected from H, F, Cl, Br, =O, —$(CR_dR_d)_rCN$, $NO_2$, —$(CR_dR_d)_rOR_b$, —S(O)$_pR_c$, —C(=O)$R_b$, —$(CR_dR_d)_rNR_aR_a$, —$(CR_dR_d)_rC$(=O)$NR_aR_a$, —$NR_aC$(=O)$R_b$, —$NR_aC$(=O)$OR_b$, —OC(=O)$NR_aR_a$, —$NR_aC$(=O)$NR_aR_a$, —$(CR_dR_d)_rC$(=O)$OR_b$, —S(O)$_2NR_aR_a$, —$NR_aS$(O)$_2NR_aR_a$, —$NR_aS$(O)$_2R_c$, $C_{1-6}$ alkyl substituted with 0-5 $R_e$, —$(CR_dR_d)_r$—$C_{3-6}$carbocyclyl substituted with 0-5 $R_e$, and —$(CR_dR_d)_r$-heterocyclyl substituted with 0-5 $R_e$;

$R_8$, at each occurrence, is independently selected from H, F, Cl, Br, CN, $C_{1-6}$ alkyl substituted with 0-5 $R_e$, $C_{2-6}$ alkenyl, $C_{2-6}$ alkynyl, —$(CH_2)_r$—$C_{3-6}$ cycloalkyl substituted with 0-5 $R_e$, —$(CH_2)_r$-aryl substituted with 0-5 $R_e$, —$(CH_2)_r$-heterocyclyl substituted with 0-5 $R_e$, $CO_2H$, —$(CH_2)_rOR_b$, and —$(CH_2)_rNR_aR_a$;

$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_d$, at each occurrence, is independently selected from H and $C_{1-4}$alkyl substituted with 0-5 $R_e$;

$R_e$, at each occurrence, is independently selected from F, Cl, Br, CN, $NO_2$, =O, $CO_2H$, $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, —$(CH_2)_rOR_f$, $SR_f$, and —$(CH_2)_rNR_fR_f$;

$R_f$, at each occurrence, is independently selected from H, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

p, at each occurrence, is independently selected from zero, 1, and 2; and r, at each occurrence, is independently selected from zero, 1, 2, 3, and 4.

In another embodiment, there are disclosed compounds of formula (III) including enantiomers, diastereomers, tautomers, pharmaceutically-acceptable salts, prodrugs, hydrates, or solvates thereof, wherein:

$R_2$ is independently selected from

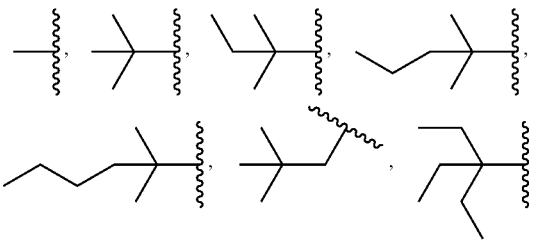

-continued

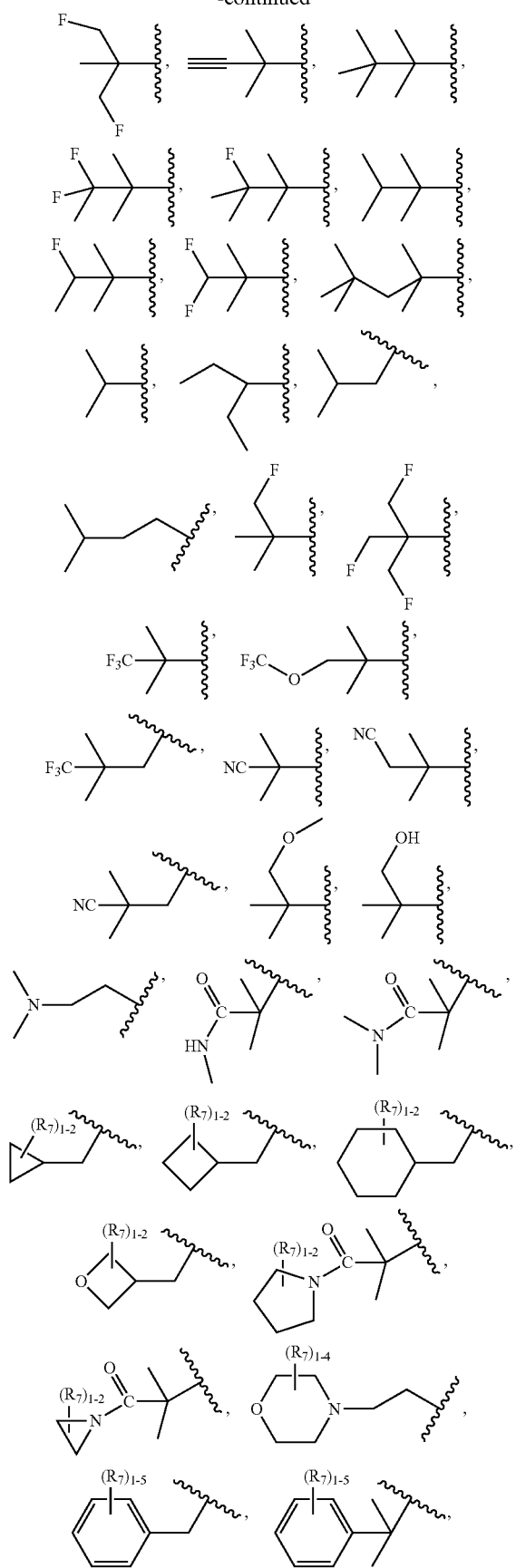

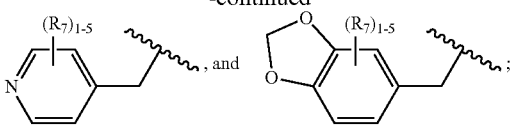

$R_{3a}$ and $R_{3b}$ are independently selected from H, $CH_2CH_3$, $CH_3$, $CH_2OH$, $CH_2CH_2OH$, $CH_2CH_2OC_{1-4}$alkyl, $CH_2F$, $CHF_2$, $CH_2CH_2F$, $CF_3$, $CH_2OCHF_2$, $CH_2CN$, $CH_2CH_2CN$, $CH_2OC_{1-4}$alkyl, $C(CH_3)_3$, $CH(CH_3)_2$, $C(CH_3)_2OH$, $C(CH_3)_2F$, $C(=O)NH-C_{3-6}$cycloalkyl, $C(=O)NH$-heterocyclyl, and $-CH_2$-heterocyclyl, wherein the heterocyclyl is independently selected from

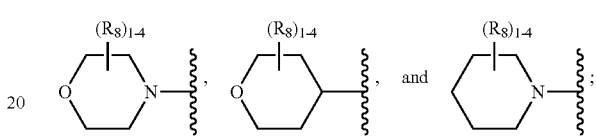

$R_{3c}$ and $R_{3d}$ are independently selected from H, $CH_3$, $CH(CH_3)_2$, $CF_3$, and $C_{3-6}$ cycloalkyl;

$R_5$, at each occurrence, is independently selected from H, $C_{1-4}$ alkyl substituted with 0-3 $R_e$, F, Cl, Br, $-S(O)_pR_c$, $-CN$, $-OR_b$, $NR_aR_a$, $C_{3-6}$cycloalkyl, and aryl substituted with 0-3 $R_e$;

$R_7$, at each occurrence, is independently selected from H, F, Cl, Br, $=O$, $-(CH_2)_rCN$, $NO_2$, $-(CH_2)_rOR_b$, $-S(O)_p R_c$, $-C(=O)R_b$, $-NR_aR_a$, $-C(=O)NR_aR_a$, $-NHC(=O)R_b$, $-NHC(=O)OR_b$, $-OC(=O)NR_aR_a$, $-NHC(=O)NR_aR_a$, $-C(=O)OR_b$, $-S(O)_2NR_aR_a$, $-NHS(O)_2 NR_aR_a$, $-NHS(O)_2R_c$, $C_{1-6}$ alkyl substituted with 0-5 $R_e$, aryl substituted with 0-5 $R_e$, and heterocyclyl substituted with 0-5 $R_e$;

$R_8$, at each occurrence, is independently selected from H, F, Cl, Br, CN, $C_{1-6}$ alkyl substituted with 0-5 $R_e$, $-(CH_2)_r-C_{3-6}$ cycloalkyl substituted with 0-5 $R_e$, $-(CH_2)_r$-aryl substituted with 0-5 $R_e$, $-(CH_2)_r$-heterocyclyl substituted with 0-5 $R_e$, $CO_2H$, $-(CH_2)_rOR_b$, and $-(CH_2)_rNR_aR_a$;

$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $-(CH_2)_r-C_{3-10}$carbocyclyl substituted with 0-5 $R_e$, and $-(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, aryl substituted with 0-5 $R_e$, and heterocyclyl substituted with 0-5 $R_e$;

$R_c$, at each occurrence, is independently selected from $C_{1-6}$ alkyl substituted with 0-5 $R_e$, $C_{3-6}$carbocyclyl, and heterocyclyl;

$R_e$, at each occurrence, is independently selected from F, Cl, Br, CN, $NO_2$, $=O$, $CO_2H$, $C_{1-6}$ alkyl, $C_{2-6}$ alkenyl, $C_{2-6}$ alkynyl, and $-(CH_2)_r-C_{3-6}$ cycloalkyl;

p, at each occurrence, is independently selected from zero, 1, and 2;

r, at each occurrence, is independently selected from zero, 1, 2, 3, and 4;

and other variables are as defined in Formula (III) above.

In another embodiment, there are disclosed compounds of formula (III) including enantiomers, diastereomers, tautomers, pharmaceutically-acceptable salts, prodrugs, hydrates, or solvates thereof, wherein:

$R_2$ is independently selected from

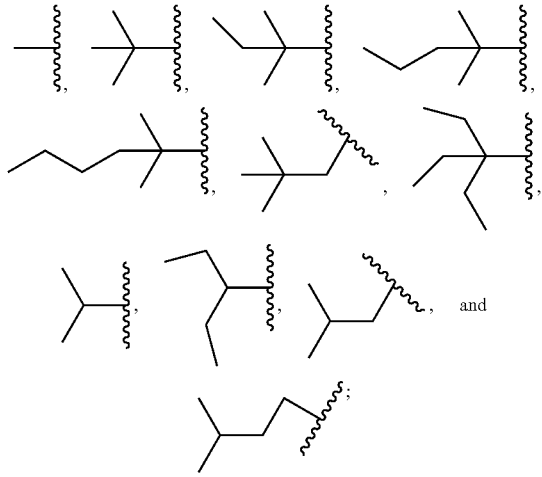

$R_{3a}$ and $R_{3b}$ are independently H;

$R_{3c}$ and $R_{3d}$ are independently H; and $R_5$, at each occurrence, is independently selected from H, F, Cl, and Br;

and other variables are as defined in Formula (III) above.

In another embodiment, there are disclosed compounds of Formula (III) including enantiomers, diastereomers, tautomers, pharmaceutically-acceptable salts, prodrugs, hydrates, or solvates thereof, wherein:

$R_2$ is independently selected from

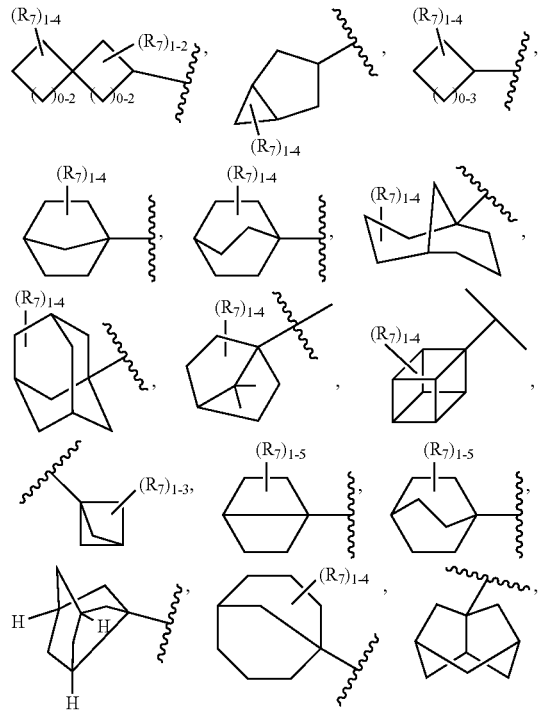

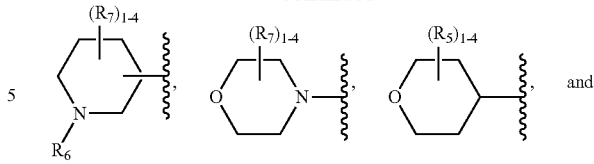

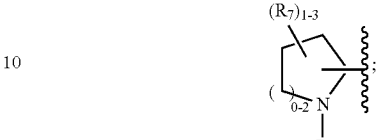

$R_{3a}$ and $R_{3b}$ are independently selected from H, $CH_2CH_3$, $CH_3$, $CH_2OH$, $CH_2CH_2OH$, $CH_2CH_2OC_{1-4}$alkyl, $CH_2F$, $CHF_2$, $CH_2CH_2F$, $CF_3$, $CH_2OCHF_2$, $CH_2CN$, $CH_2CH_2CN$, $CH_2OC_{1-4}$alkyl, $C(CH_3)_3$, $CH(CH_3)_2$, $C(CH_3)_2OH$, $C(CH_3)_2F$, $C(=O)NH-C_{3-6}$cycloalkyl, $C(=O)NH$-heterocyclyl, and $-CH_2$-heterocyclyl, wherein the heterocyclyl is independently selected from

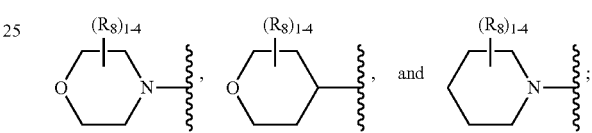

$R_{3c}$ and $R_{3d}$ are independently selected from H, $CH_3$, $CH(CH_3)_2$, $CF_3$, and $C_{3-6}$ cycloalkyl;

$R_5$, at each occurrence, is independently selected from H, $C_{1-4}$ alkyl substituted with 0-3 $R_e$, F, Cl, Br, $-S(O)_pR_c$, $-CN$, $-OR_b$, $NR_aR_a$, $C_{3-6}$cycloalkyl, and aryl substituted with 0-3 $R_e$;

$R_7$, at each occurrence, is independently selected from H, F, Cl, Br, $=O$, $-(CH_2)_rCN$, $NO_2$, $-(CH_2)_rOR_b$, $-S(O)_pR_c$, $-C(=O)R_b$, $-NR_aR_a$, $-C(=O)NR_aR_a$, $-NHC(=O)R_b$, $-NHC(=O)OR_b$, $-OC(=O)NR_aR_a$, $-NHC(=O)NR_aR_a$, $-C(=O)OR_b$, $-S(O)_2NR_aR_a$, $-NHS(O)_2 NR_aR_a$, $-NHS(O)_2R_c$, $C_{1-6}$ alkyl substituted with 0-5 $R_e$, aryl substituted with 0-5 $R_e$, and heterocyclyl substituted with 0-5 $R_e$;

$R_8$, at each occurrence, is independently selected from H, F, Cl, Br, CN, $C_{1-6}$ alkyl substituted with 0-5 $R_e$, $-(CH_2)_r-C_{3-6}$ cycloalkyl substituted with 0-5 $R_e$, $-(CH_2)_r$-aryl substituted with 0-5 $R_e$, $-(CH_2)_r$-heterocyclyl substituted with 0-5 $R_e$, $CO_2H$, $-(CH_2)_rOR_b$, and $-(CH_2)_rNR_aR_a$;

$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $-(CH_2)_r-C_{3-10}$carbocyclyl substituted with 0-5 $R_e$, and $-(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, aryl substituted with 0-5 $R_e$, and heterocyclyl substituted with 0-5 $R_e$;

$R_c$, at each occurrence, is independently selected from $C_{1-6}$ alkyl substituted with 0-5 $R_e$, $C_{3-6}$carbocyclyl, and heterocyclyl;

$R_e$, at each occurrence, is independently selected from F, Cl, Br, CN, $NO_2$, $=O$, $CO_2H$, $C_{1-6}$ alkyl, $C_{2-6}$ alkenyl, $C_{2-6}$ alkynyl, and $-(CH_2)_r-C_{3-6}$ cycloalkyl;

p, at each occurrence, is independently selected from zero, 1, and 2;

r, at each occurrence, is independently selected from zero, 1, 2, 3, and 4;

and other variables are as defined in Formula (III) above.

In another embodiment, there are disclosed compounds of Formula (III) including enantiomers, diastereomers, tautomers, pharmaceutically-acceptable salts, prodrugs, hydrates, or solvates thereof, wherein $R_{3a}$ and $R_{3b}$, or $R_{3c}$ and $R_{3d}$, together with the carbon atom to which they are both attached form a spiral carbocyclic or heterocyclic ring comprising carbon atoms and 1 to 4 heteroatoms selected from N, O, S, each substituted with 1-5 $R_8$; and other variables are as defined in Formula (III) above.

In another aspect, there are disclosed compounds of Formula (IV) including enantiomers, diastereomers, tautomers, pharmaceutically-acceptable salts, prodrugs, hydrates, or solvates thereof,

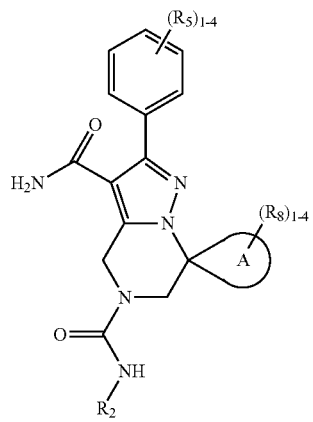

(IV)

wherein:

Ring A is $C_{3-6}$cycloalkyl or heterocyclyl;

$R_2$ is independently selected from

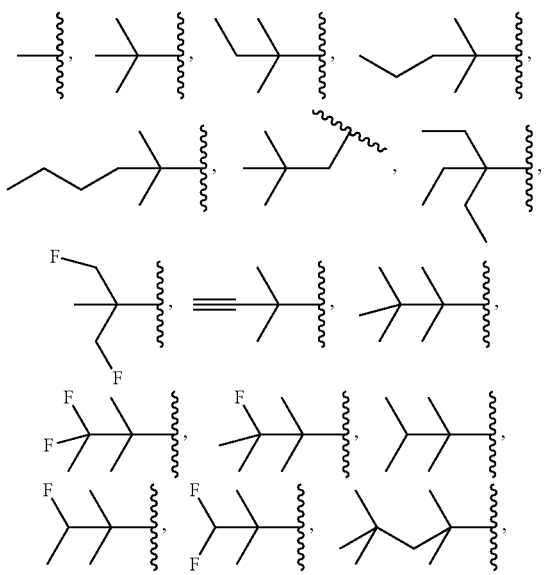

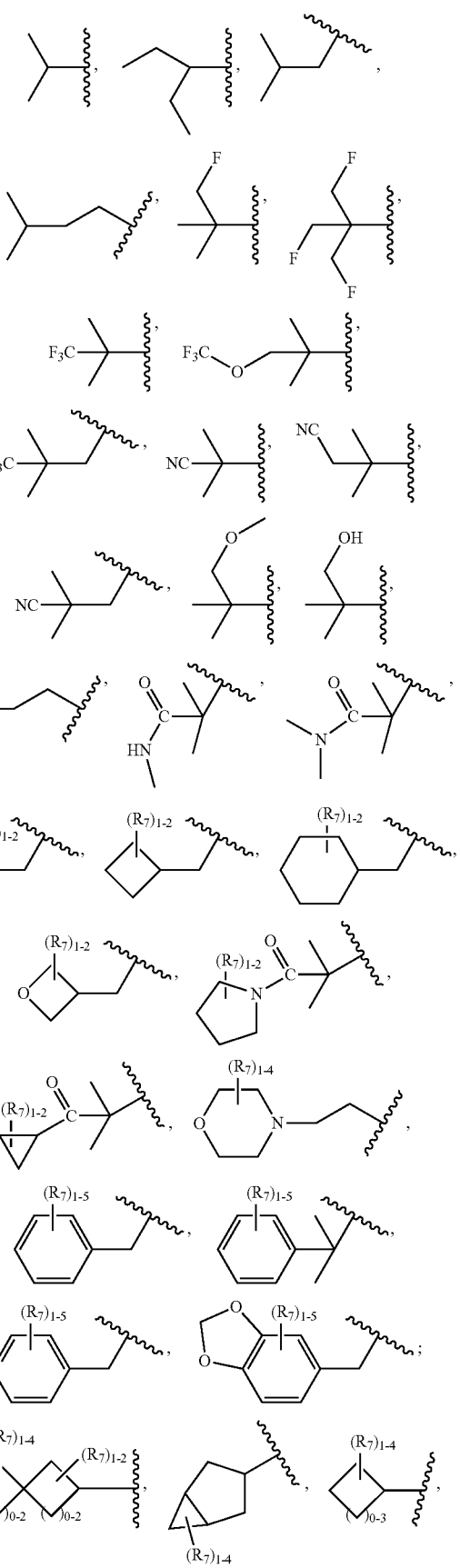

-continued

R$_5$, at each occurrence, is independently selected from H, C$_{1-4}$ alkyl substituted with 0-3 R$_e$, F, Cl, Br, —S(O)$_p$R$_c$, —CN, —OR$_b$, NR$_a$R$_a$, C$_{3-6}$cycloalkyl, aryl substituted with 0-3 R$_e$, and heterocyclyl substituted with 0-3 R$_e$;

R$_6$ is independently selected from H, —C(=O)R$_b$, —CO(=O)R$_b$, —S(O)$_p$R$_c$, C$_{1-6}$ alkyl substituted with 0-5 R$_e$, —(CH$_2$)$_r$—C$_{3-6}$carbocyclyl substituted with 0-5 R$_e$, and —(CH$_2$)$_r$-heterocyclyl substituted with 0-5 R$_e$;

R$_7$, at each occurrence, is independently selected from H, F, Cl, Br, CN, NO$_2$, —OR$_b$, —S(O)$_p$R$_c$, —C(=O)R$_b$, —NR$_a$R$_a$, —C(=O)NR$_a$R$_a$, —NHC(=O)R$_b$, —NHC(=O)OR$_b$, —OC(=O)NR$_a$R$_a$, —NHC(=O)NR$_a$R$_a$, —C(=O)OR$_b$, —S(O)$_2$NR$_a$R$_a$, C$_{1-6}$ alkyl substituted with 0-5 R$_e$, aryl substituted with 0-5 R$_e$, and heterocyclyl substituted with 0-5 R$_e$;

R$_8$, at each occurrence, is independently selected from H, F, Cl, Br, CN, C$_{1-6}$ alkyl substituted with 0-5 R$_e$, C$_{2-6}$ alkenyl, C$_{2-6}$ alkynyl, —(CH$_2$)$_r$—C$_{3-6}$ cycloalkyl substituted with 0-5 R$_e$, —(CH$_2$)$_r$-aryl substituted with 0-5 R$_e$, —(CH$_2$)$_r$-heterocyclyl substituted with 0-5 R$_e$, CO$_2$H, —(CH$_2$)$_r$OR$_b$, and —(CH$_2$)$_r$NR$_a$R$_a$;

R$_a$, at each occurrence, is independently selected from H, CN, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;

R$_b$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, aryl substituted with 0-5 R$_e$, and heterocyclyl substituted with 0-5 R$_e$;

R$_c$, at each occurrence, is independently selected from C$_{1-6}$ alkyl substituted with 0-5 R$_e$, C$_{3-6}$carbocyclyl, and heterocyclyl;

R$_e$, at each occurrence, is independently selected from F, Cl, Br, CN, NO$_2$, =O, and CO$_2$H, C$_{1-6}$ alkyl, C$_{2-6}$ alkenyl, C$_{2-6}$ alkynyl, and —(CH$_2$)$_r$—C$_{3-6}$ cycloalkyl;

p, at each occurrence, is independently selected from zero, 1, and 2; and r, at each occurrence, is independently selected from zero, 1, 2, 3, and 4.

In another embodiment, there are disclosed compounds of Formula (III) including enantiomers, diastereomers, tautomers, pharmaceutically-acceptable salts, prodrugs, hydrates, or solvates thereof, wherein:

R$_{3a}$ and R$_{3c}$ together form a carbocyclic or heterocyclic ring comprising carbon atoms and 1 to 4 heteroatoms selected from N, O, S, wherein the carbocyclic or heterocyclic ring is substituted with 1-5 R$_8$; and R$_{3b}$ and R$_{3d}$ are independently selected from H and C$_{1-4}$ alkyl;

and other variables are as defined in Formula (III) above.

In another aspect, there are disclosed compounds of Formula (V) including enantiomers, diastereomers, tautomers, pharmaceutically-acceptable salts, prodrugs, hydrates, or solvates thereof,

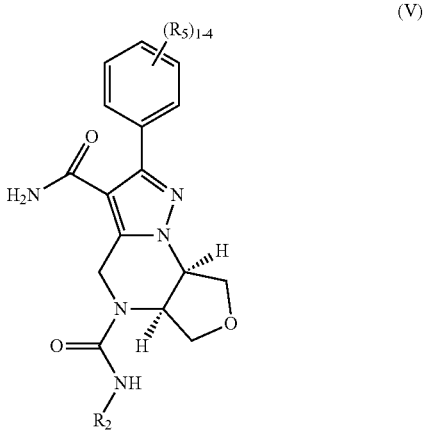

(V)

wherein:

R$_2$ is independently selected from

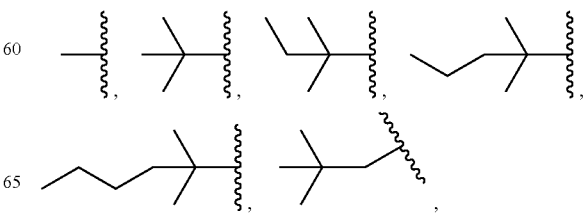

-continued

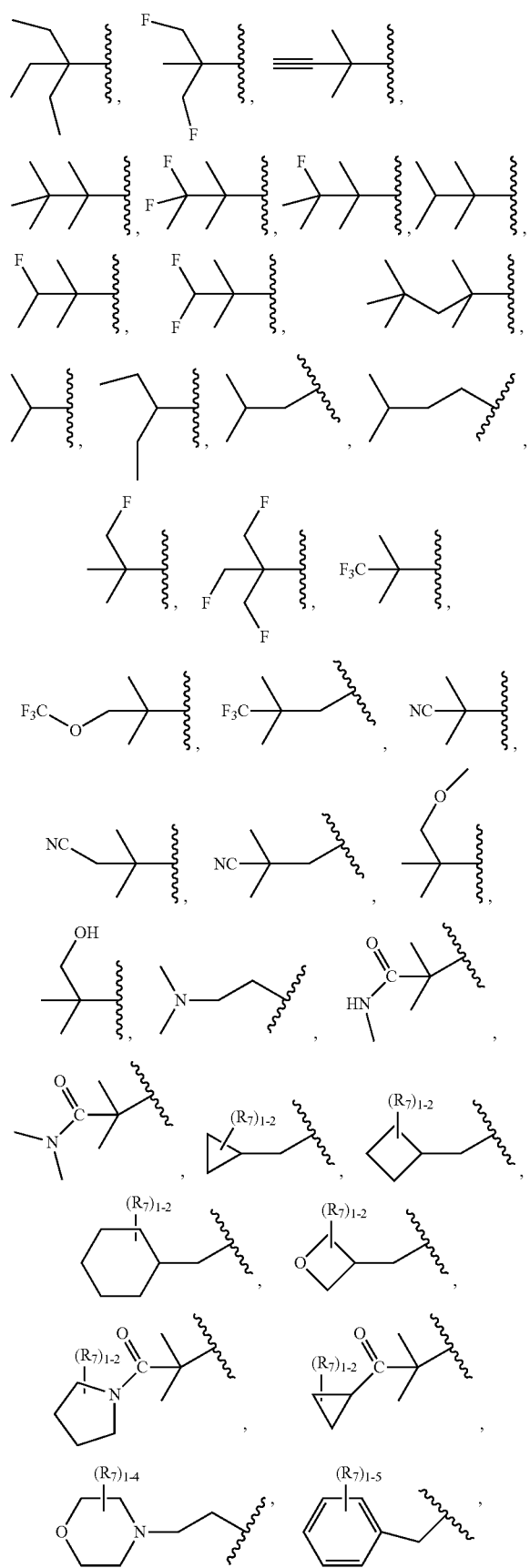
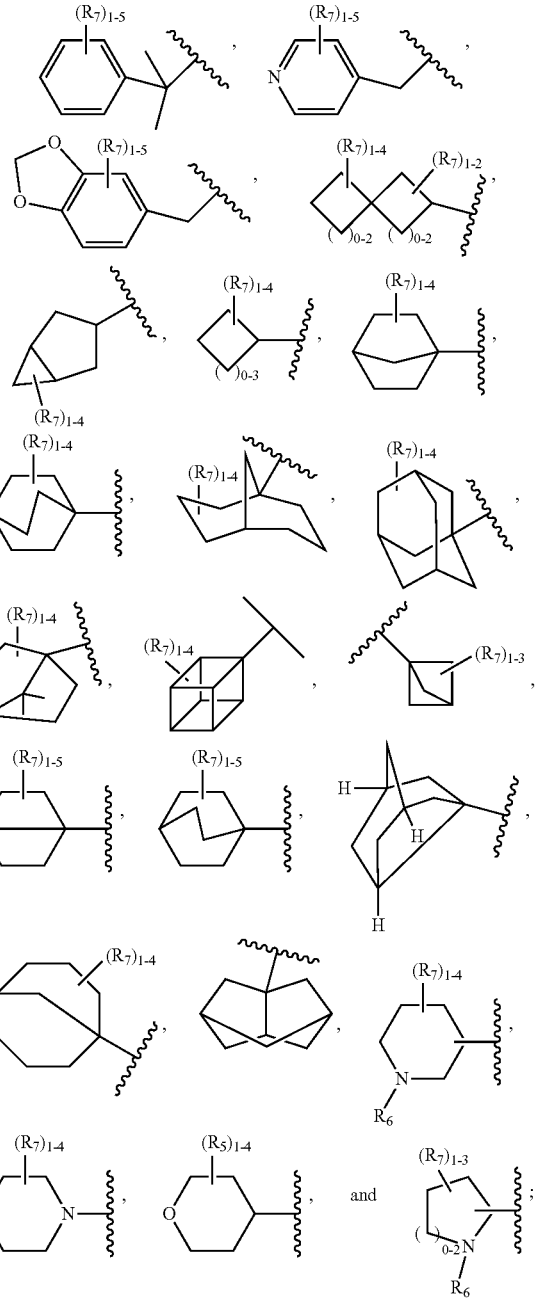

$R_5$, at each occurrence, is independently selected from H, $C_{1-4}$ alkyl substituted with 0-3 $R_e$, F, Cl, Br, —S(O)$_p R_c$, —CN, —OR$_b$, NR$_a$R$_a$, $C_{3-6}$cycloalkyl, aryl substituted with 0-3 $R_e$, and heterocyclyl substituted with 0-3 $R_e$;

$R_6$ is independently selected from H, —C(=O)R$_b$, —CO(=O)R$_b$, —S(O)$_p$R$_c$, $C_{1-6}$ alkyl substituted with 0-5 $R_e$, —(CH$_2$)$_r$—$C_{3-6}$carbocyclyl substituted with 0-5 $R_e$, and —(CH$_2$)$_r$-heterocyclyl substituted with 0-5 $R_e$;

$R_7$, at each occurrence, is independently selected from H, F, Cl, Br, CN, NO$_2$, —OR$_b$, —S(O)$_p$R$_c$, —C(=O)R$_b$, —NR$_a$R$_a$, —C(=O)NR$_a$R$_a$, —NHC(=O)R$_b$, —NHC(=O)OR$_b$, —OC(=O)NR$_a$R$_a$, —NHC(=O)NR$_a$R$_a$, —C(=O)OR$_b$, —S(O)$_2$NR$_a$R$_a$, $C_{1-6}$ alkyl substituted with 0-5 $R_e$, aryl substituted with 0-5 $R_e$, and heterocyclyl substituted with 0-5 $R_e$;

R$_a$, at each occurrence, is independently selected from H, CN, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;

R$_b$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, aryl substituted with 0-5 R$_e$, and heterocyclyl substituted with 0-5 R$_e$;

R$_c$, at each occurrence, is independently selected from C$_{1-6}$ alkyl substituted with 0-5 R$_e$, C$_{3-6}$carbocyclyl, and heterocyclyl;

R$_e$, at each occurrence, is independently selected from F, Cl, Br, CN, NO$_2$, =O, CO$_2$H, C$_{1-6}$ alkyl, C$_{2-6}$ alkenyl, C$_{2-6}$ alkynyl, and —(CH$_2$)$_r$—C$_{3-6}$ cycloalkyl;

p, at each occurrence, is independently selected from zero, 1, and 2; and r, at each occurrence, is independently selected from zero, 1, 2, 3, and 4.

All aspects of the compounds, including individual variable definitions, may be combined with other aspects to form additional compounds. For example, in one embodiment of Formula (I), R$_1$ is phenyl and R$_2$ is substituted alkyl. In another embodiment, R$_1$ is heteroaryl and R$_2$ is C$_{3-12}$cycloalkyl. In still another embodiment, R$_1$ is phenyl and R$_2$ is C$_{3-12}$cycloalkyl.

In certain embodiments, the present invention includes compounds of Formula (II), or stereoisomers, tautomers, pharmaceutically acceptable salts, solvates, or prodrugs thereof, wherein:

R$_1$ is phenyl substituted with 1-4 R$_5$;

R$_2$ is C$_{1-6}$alkyl optionally substituted with F, Cl, Br, OH, CN, and NR$_a$R$_a$;

R$_{3a}$ and R$_{3b}$ are independently selected from H, CH$_2$CH$_3$, CH$_3$, CH$_2$OH, CH$_2$CH$_2$OH, CH$_2$CH$_2$OC$_{1-4}$alkyl, CH$_2$F, CHF$_2$, CH$_2$CH$_2$F, CF$_3$, CH$_2$OCHF$_2$, CH$_2$CN, CH$_2$CH$_2$CN, CH$_2$OC$_{1-4}$alkyl, C(CH$_3$)$_3$, CH(CH$_3$)$_2$, C(CH$_3$)$_2$OH, and C(CH$_3$)$_2$F;

R$_{3c}$ and R$_{3d}$ are independently selected from H, CH$_3$, CH(CH$_3$)$_2$, CF$_3$, and C$_{3-6}$ cycloalkyl;

R$_5$, at each occurrence, is independently selected from H, C$_{1-4}$ alkyl substituted with 0-3 R$_e$, F, Cl, Br, =O, CN, NO$_2$, —OR$_b$, —(CH$_2$)$_r$CN, —(CH$_2$)$_r$OR$_b$, (CH$_2$)$_r$S(O)$_p$R$_c$, —(CH$_2$)$_r$C(=O)R$_b$, —(CH$_2$)$_r$NR$_a$R$_a$, —(CH$_2$)$_r$C(=O)NR$_a$R$_a$, —(CH$_2$)$_r$NR$_a$C(=O)R$_b$, —(CH$_2$)$_r$NR$_a$C(=O)OR$_b$, —(CH$_2$)$_r$OC(=O)NR$_a$R$_a$, —(CH$_2$)$_r$NR$_a$C(=O)NR$_a$R$_a$, —(CH$_2$)$_r$C(=O)OR$_b$, —(CH$_2$)$_r$S(O)$_2$NR$_a$R$_a$, —(CH$_2$)$_r$NR$_a$S(O)$_2$NR$_a$R$_a$, —(CH$_2$)$_r$NR$_a$S(O)$_2$R$_c$, (CH$_2$)$_r$-carbocyclyl substituted with 0-3 R$_e$, and —(CH$_2$)$_r$-heterocyclyl substituted with 0-3 R$_e$;

R$_7$, at each occurrence, is independently selected from H, F, Cl, Br, =O, CN, NO$_2$, —OR$_b$, —S(O)$_p$R$_c$, —C(=O)R$_b$, —(CR$_d$R$_d$)$_r$NR$_a$R$_a$, —(CR$_d$R$_d$)$_r$C(=O)NR$_a$R$_a$, —NR$_a$C(=O)R$_b$, —NR$_a$C(=O)OR$_b$, —OC(=O)NR$_a$R$_a$, —NR$_a$C(=O)NR$_a$R$_a$, —(CR$_d$R$_d$)$_r$C(=O)OR$_b$, —S(O)$_2$NR$_a$R$_a$, —NR$_a$S(O)$_2$NR$_a$R$_a$, —NR$_a$S(O)$_2$R$_c$, C$_{1-6}$ alkyl substituted with 0-5 R$_e$, —(CR$_d$R$_d$)$_r$—C$_{3-6}$carbocyclyl substituted with 0-5 R$_e$, and —(CR$_d$R$_d$)$_r$-heterocyclyl substituted with 0-5 R$_e$;

R$_a$, at each occurrence, is independently selected from H, CN, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;

R$_b$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$;

R$_c$, at each occurrence, is independently selected from C$_{1-6}$ alkyl substituted with 0-5 R$_e$, C$_{2-6}$alkenyl substituted with 0-5 R$_e$, C$_{2-6}$alkynyl substituted with 0-5 R$_e$, C$_{3-6}$carbocyclyl, and heterocyclyl;

R$_e$, at each occurrence, is independently selected from F, Cl, Br, CN, NO$_2$, =O, CO$_2$H, C$_{1-6}$ alkyl substituted with 0-5 R$_f$, C$_{2-6}$ alkenyl, C$_{2-6}$ alkynyl, —(CH$_2$)$_r$—C$_{3-6}$ cycloalkyl, —(CH$_2$)$_r$OR$_f$, SR$_f$, and —(CH$_2$)$_r$NR$_f$R$_f$;

R$_f$, at each occurrence, is independently selected from H, C$_{1-5}$ alkyl, C$_{3-6}$ cycloalkyl, and phenyl, or R$_f$ and R$_f$ together with the nitrogen atom to which they are both attached form a heterocyclic ring optionally substituted with C$_{1-4}$ alkyl;

p, at each occurrence, is independently selected from zero, 1, and 2; and r, at each occurrence, is independently selected from zero, 1, 2, 3, and 4.

In certain embodiments, the present invention includes compounds of Formula (II), or stereoisomers, tautomers, pharmaceutically acceptable salts, solvates, or prodrugs thereof, wherein:

R$_1$ is phenyl substituted with 1-4 R$_5$;

R$_2$ is independently selected from

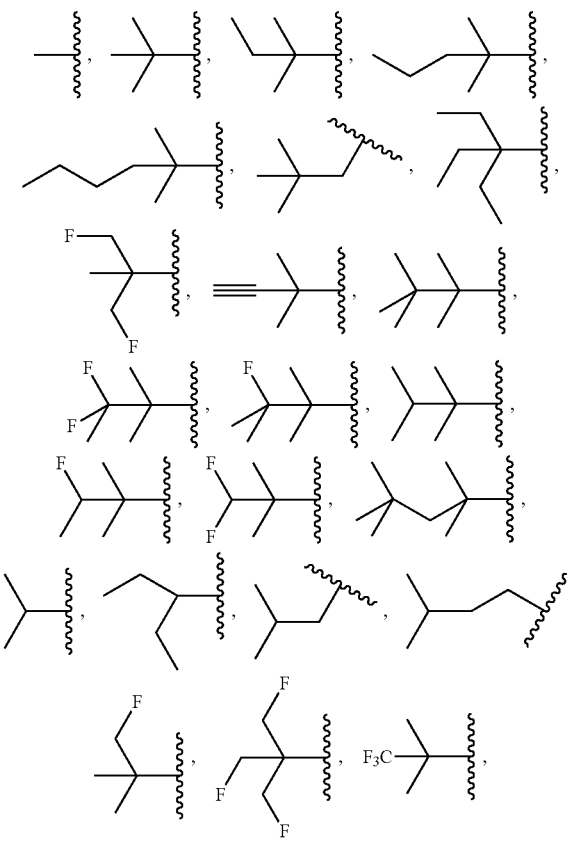

-continued

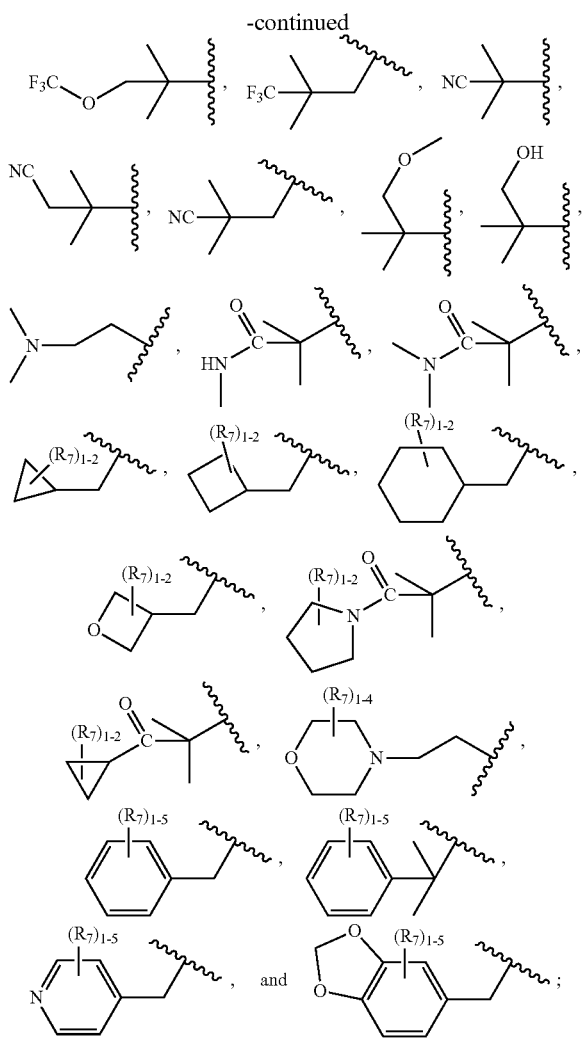

$R_{3a}$ and $R_{3b}$ are independently selected from H, CH$_2$CH$_3$, CH$_3$, CH$_2$OH, CH$_2$CH$_2$OH, CH$_2$CH$_2$OC$_{1-4}$alkyl, CH$_2$F, CHF$_2$, CH$_2$CH$_2$F, CF$_3$, CH$_2$OCHF$_2$, CH$_2$CN, CH$_2$CH$_2$CN, CH$_2$OC$_{1-4}$alkyl, C(CH$_3$)$_3$, CH(CH$_3$)$_2$, C(CH$_3$)$_2$OH, and C(CH$_3$)$_2$F;

$R_{3c}$ and $R_{3d}$ are independently selected from H, CH$_3$, CH(CH$_3$)$_2$, CF$_3$, and C$_{3-6}$ cycloalkyl;

$R_5$, at each occurrence, is independently selected from H, C$_{1-4}$ alkyl substituted with 0-3 F, Cl, Br, =O, CN, NO$_2$, —OR$_b$, —(CH$_2$)$_r$CN, —(CH$_2$)$_r$OR$_b$, (CH$_2$)$_r$S(O)$_p$R$_c$, —(CH$_2$)$_r$C(=O)R$_b$, —(CH$_2$)$_r$NR$_a$R$_a$, —(CH$_2$)$_r$C(=O)NR$_a$R$_a$, —(CH$_2$)$_r$NR$_a$C(=O)R$_b$, (CH$_2$)$_r$-carbocyclyl substituted with 0-3 R$_e$, and —(CH$_2$)$_r$-heterocyclyl substituted with 0-3 R$_e$;

$R_7$, at each occurrence, is independently selected from H, F, Cl, Br, =O, CN, NO$_2$, —OR$_b$, —S(O)$_p$R$_c$, —C(=O)R$_b$, —(CR$_d$R$_d$)$_r$NR$_a$R$_a$, —(CR$_d$R$_d$)$_r$C(=O)NR$_a$R$_a$, —NR$_a$C(=O)R$_b$, —NR$_a$C(=O)OR$_b$, —OC(=O)NR$_a$R$_a$, —NR$_a$C(=O)NR$_a$R$_a$, —(CR$_d$R$_d$)$_r$C(=O)OR$_b$, C$_{1-6}$ alkyl substituted with 0-5 R$_e$, —(CR$_d$R$_d$)$_r$—C$_{3-6}$carbocyclyl substituted with 0-5 R$_e$, and —(CR$_d$R$_d$)$_r$-heterocyclyl substituted with 0-5 R$_e$;

$R_a$, at each occurrence, is independently selected from H, CN, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;

$R_b$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$;

$R_c$, at each occurrence, is independently selected from C$_{1-6}$ alkyl substituted with 0-5 R$_e$, C$_{2-6}$alkenyl substituted with 0-5 R$_e$, C$_{2-6}$alkynyl substituted with 0-5 R$_e$, C$_{3-6}$carbocyclyl, and heterocyclyl;

$R_e$, at each occurrence, is independently selected from F, Cl, Br, CN, NO$_2$, =O, CO$_2$H, C$_{1-6}$ alkyl substituted with 0-5 R$_f$, C$_{2-6}$ alkenyl, C$_{2-6}$ alkynyl, —(CH$_2$)$_r$—C$_{3-6}$ cycloalkyl, —(CH$_2$)$_r$OR$_f$, SR$_f$, and —(CH$_2$)$_r$NR$_f$R$_f$;

$R_f$, at each occurrence, is independently selected from H, C$_{1-5}$ alkyl, C$_{3-6}$ cycloalkyl, and phenyl, or R$_f$ and R$_f$ together with the nitrogen atom to which they are both attached form a heterocyclic ring optionally substituted with C$_{1-4}$alkyl;

p, at each occurrence, is independently selected from zero, 1, and 2; and r, at each occurrence, is independently selected from zero, 1, 2, 3, and 4.

In certain embodiments, the present invention includes compounds of Formula (II), or stereoisomers, tautomers, pharmaceutically acceptable salts, solvates, or prodrugs thereof, wherein:

$R_1$ is phenyl substituted with 1-4 $R_5$;

$R_2$ is cycloalkyl substituted with 1-5 $R_7$;

$R_{3a}$ and $R_{3b}$ are independently selected from H, CH$_2$CH$_3$, CH$_3$, CH$_2$OH, CH$_2$CH$_2$OH, CH$_2$CH$_2$OC$_{1-4}$alkyl, CH$_2$F, CHF$_2$, CH$_2$CH$_2$F, CF$_3$, CH$_2$OCHF$_2$, CH$_2$CN, CH$_2$CH$_2$CN, CH$_2$OC$_{1-4}$alkyl, C(CH$_3$)$_3$, CH(CH$_3$)$_2$, C(CH$_3$)$_2$OH, and C(CH$_3$)$_2$F;

$R_{3a}$ and $R_{3d}$ are independently selected from H, CH$_3$, CH(CH$_3$)$_2$, CF$_3$, and C$_{3-6}$ cycloalkyl;

$R_5$, at each occurrence, is independently selected from H, C$_{1-4}$ alkyl substituted with 0-3 R$_e$, F, Cl, Br, =O, CN, NO$_2$, —OR$_b$, —(CH$_2$)$_r$CN, —(CH$_2$)$_r$OR$_b$, (CH$_2$)$_r$S(O)$_p$R$_c$, —(CH$_2$)$_r$C(=O)R$_b$, —(CH$_2$)$_r$NR$_a$R$_a$, —(CH$_2$)$_r$C(=O)NR$_a$R$_a$, —(CH$_2$)$_r$—NR$_a$C(=O)R$_b$, —(CH$_2$)$_r$NR$_a$C(=O)OR$_b$, —(CH$_2$)$_r$OC(=O)NR$_a$R$_a$, —(CH$_2$)$_r$NR$_a$C(=O)NR$_a$R$_a$, —(CH$_2$)$_r$C(=O)OR$_b$, —(CH$_2$)$_r$S(O)$_2$NR$_a$R$_a$, —(CH$_2$)$_r$NR$_a$S(O)$_2$NR$_a$R$_a$, —(CH$_2$)$_r$NR$_a$S(O)$_2$R$_c$, (CH$_2$)$_r$-carbocyclyl substituted with 0-3 R$_e$, and —(CH$_2$)$_r$-heterocyclyl substituted with 0-3 R$_e$;

$R_7$, at each occurrence, is independently selected from H, F, Cl, Br, =O, CN, NO$_2$, —OR$_b$, —S(O)$_p$R$_c$, —C(=O)R$_b$, —(CR$_d$R$_d$)$_r$—NR$_a$R$_a$, —(CR$_d$R$_d$)$_r$C(=O)NR$_a$R$_a$, —NR$_a$C(=O)R$_b$, —NR$_a$C(=O)OR$_b$, —OC(=O)NR$_a$R$_a$, —NR$_a$C(=O)NR$_a$R$_a$, —(CR$_d$R$_d$)$_r$C(=O)OR$_b$, —S(O)$_2$NR$_a$R$_a$, —NR$_a$S(O)$_2$NR$_a$R$_a$, —NR$_a$S(O)$_2$R$_c$, C$_{1-6}$ alkyl substituted with 0-5 R$_e$, —(CR$_d$R$_d$)$_r$—C$_{3-6}$carbocyclyl substituted with 0-5 R$_e$, and —(CR$_d$R$_d$)$_r$-heterocyclyl substituted with 0-5 R$_e$;

$R_a$, at each occurrence, is independently selected from H, CN, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;

$R_b$, at each occurrence, is independently selected from H,

C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$;

R$_c$, at each occurrence, is independently selected from C$_{1-6}$ alkyl substituted with 0-5 R$_e$, C$_{2-6}$alkenyl substituted with 0-5 R$_e$, C$_{2-6}$alkynyl substituted with 0-5 R$_e$, C$_{3-6}$carbocyclyl, and heterocyclyl;

R$_d$, at each occurrence, is independently selected from H and C$_{1-4}$alkyl substituted with 0-5 R$_e$;

R$_e$, at each occurrence, is independently selected from F, Cl, Br, CN, NO$_2$, =O, CO$_2$H, C$_{1-6}$ alkyl substituted with 0-5 R$_f$, C$_{2-6}$ alkenyl, C$_{2-6}$ alkynyl, —(CH$_2$)$_r$—C$_{3-6}$ cycloalkyl, —(CH$_2$)$_r$OR$_f$, SR$_f$ and —(CH$_2$)$_r$NR$_f$R$_f$;

R$_f$, at each occurrence, is independently selected from H, C$_{1-5}$ alkyl, C$_{3-6}$ cycloalkyl, and phenyl, or R$_f$ and R$_f$ together with the nitrogen atom to which they are both attached form a heterocyclic ring optionally substituted with C$_{1-4}$alkyl;

p, at each occurrence, is independently selected from zero, 1, and 2; and r, at each occurrence, is independently selected from zero, 1, 2, 3, and 4.

In certain embodiments, the present invention includes compounds of Formula (II), or stereoisomers, tautomers, pharmaceutically acceptable salts, solvates, or prodrugs thereof, wherein:

R$_1$ is phenyl substituted with 1-4 R$_5$;

R$_2$ is independently selected from

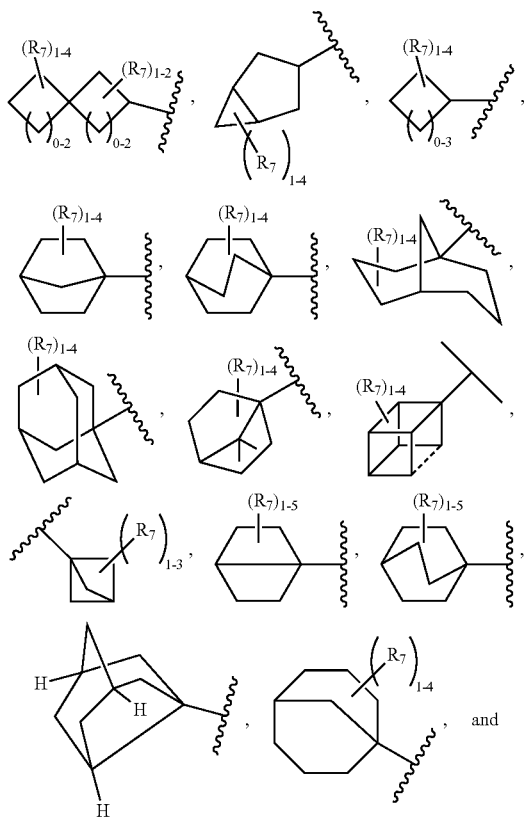

R$_{3a}$ and R$_{3b}$ are independently selected from H, CH$_2$CH$_3$, CH$_3$, CH$_2$OH, CH$_2$CH$_2$OH, CH$_2$CH$_2$OC$_{1-4}$alkyl, CH$_2$F, CHF$_2$, CH$_2$CH$_2$F, CF$_3$, CH$_2$OCHF$_2$, CH$_2$CN, CH$_2$CH$_2$CN, CH$_2$OC$_{1-4}$alkyl, C(CH$_3$)$_3$, CH(CH$_3$)$_2$, C(CH$_3$)$_2$OH, and C(CH$_3$)$_2$F;

R$_{3c}$ and R$_{3d}$ are independently selected from H, CH$_3$, CH(CH$_3$)$_2$, CF$_3$, and C$_{3-6}$ cycloalkyl;

R$_5$, at each occurrence, is independently selected from H, C$_{1-4}$ alkyl substituted with 0-3 R$_e$, F, Cl, Br, =O, CN, NO$_2$, —OR$_b$, —(CH$_2$)$_r$CN, —(CH$_2$)$_r$OR$_b$, (CH$_2$)$_r$S(O)$_p$R$_c$, —(CH$_2$)$_r$C(=O)R$_b$, —(CH$_2$)$_r$NR$_a$R$_a$, —(CH$_2$)$_r$C(=O)NR$_a$R$_a$, —(CH$_2$)$_r$NR$_a$C(=O)R$_b$, —(CH$_2$)$_r$NR$_a$C(=O)OR$_b$, —(CH$_2$)$_r$OC(=O)NR$_a$R$_a$, —(CH$_2$)$_r$NR$_a$C(=O)NR$_a$R$_a$, —(CH$_2$)$_r$C(=O)OR$_b$, —(CH$_2$)$_r$S(O)$_2$NR$_a$R$_a$, —(CH$_2$)$_r$NR$_a$S(O)$_2$NR$_a$R$_a$, —(CH$_2$)$_r$NR$_a$S(O)$_2$R$_c$, (CH$_2$)$_r$-carbocyclyl substituted with 0-3 R$_e$, and —(CH$_2$)$_r$-heterocyclyl substituted with 0-3 R$_e$;

R$_7$, at each occurrence, is independently selected from H, F, Cl, Br, =O, CN, NO$_2$, —OR$_b$, —S(O)$_p$R$_c$, —C(=O)R$_b$, —(CR$_d$R$_d$)$_r$NR$_a$R$_a$, —(CR$_d$R$_d$)$_r$C(=O)NR$_a$R$_a$, —NR$_a$C(=O)R$_b$, —NR$_a$C(=O)OR$_b$, —OC(=O)NR$_a$R$_a$, —NR$_a$C(=O)NR$_a$R$_a$, —(CR$_d$R$_d$R$_d$)$_r$C(=O)OR$_b$, —S(O)$_2$NR$_a$R$_a$, —NR$_a$S(O)$_2$NR$_a$R$_a$, —NR$_a$S(O)$_2$R$_c$, C$_{1-6}$ alkyl substituted with 0-5 R$_e$, —(CR$_d$R$_d$)$_r$—C$_{3-6}$carbocyclyl substituted with 0-5 R$_e$, and —(CR$_d$R$_d$)$_r$-heterocyclyl substituted with 0-5 R$_e$;

R$_a$, at each occurrence, is independently selected from H, CN, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;

R$_b$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$;

R$_c$, at each occurrence, is independently selected from C$_{1-6}$ alkyl substituted with 0-5 R$_e$, C$_{2-6}$alkenyl substituted with 0-5 R$_e$, C$_{2-6}$alkynyl substituted with 0-5 R$_e$, C$_{3-6}$carbocyclyl, and heterocyclyl;

R$_d$, at each occurrence, is independently selected from H and C$_{1-4}$alkyl substituted with 0-5 R$_e$;

R$_e$, at each occurrence, is independently selected from F, Cl, Br, CN, NO$_2$, =O, CO$_2$H, C$_{1-6}$ alkyl substituted with 0-5 R$_f$, C$_{2-6}$ alkenyl, C$_{2-6}$ alkynyl, —(CH$_2$)$_r$—C$_{3-6}$ cycloalkyl, —(CH$_2$)$_r$OR$_f$, SR$_f$ and —(CH$_2$)$_r$NR$_f$R$_f$;

R$_f$, at each occurrence, is independently selected from H, C$_{1-5}$ alkyl, C$_{3-6}$ cycloalkyl, and phenyl, or R$_f$ and R$_f$ together with the nitrogen atom to which they are both attached form a heterocyclic ring optionally substituted with C$_{1-4}$alkyl;

p, at each occurrence, is independently selected from zero, 1, and 2; and r, at each occurrence, is independently selected from zero, 1, 2, 3, and 4.

In certain embodiments, the present invention includes compounds of Formula (II), or stereoisomers, tautomers, pharmaceutically acceptable salts, solvates, or prodrugs thereof, wherein:

$R_1$ is phenyl substituted with 1-4 $R_5$;

$R_2$ is cycloheteroalkyl comprising carbon atoms and 1 to 4 heteroatoms selected from N, O, S, and substituted with 1-8 $R_7$;

$R_{3a}$ and $R_{3b}$ are independently selected from H, $CH_2CH_3$, $CH_3$, $CH_2OH$, $CH_2CH_2OH$, $CH_2CH_2OC_{1-4}$alkyl, $CH_2F$, $CHF_2$, $CH_2CH_2F$, $CF_3$, $CH_2OCHF_2$, $CH_2CN$, $CH_2CH_2CN$, $CH_2OC_{1-4}$alkyl, $C(CH_3)_3$, $CH(CH_3)_2$, $C(CH_3)_2OH$, and $C(CH_3)_2F$;

$R_{3c}$ and $R_{3d}$ are independently selected from H, $CH_3$, $CH(CH_3)_2$, $CF_3$, and $C_{3-6}$ cycloalkyl;

$R_5$, at each occurrence, is independently selected from H, $C_{1-4}$ alkyl substituted with 0-3 $R_e$, F, Cl, Br, =O, CN, $NO_2$, $-OR_b$, $-(CH_2)_rCN$, $-(CH_2)_rOR_b$, $(CH_2)_rS(O)_pR_c$, $-(CH_2)_rC(=O)R_b$, $-(CH_2)_rNR_aR_a$, $-(CH_2)_rC(=O)NR_aR_a$, $-(CH_2)_rNR_aC(=O)R_b$, $-(CH_2)_rNR_aC(=O)OR_b$, $-(CH_2)_rOC(=O)NR_aR_a$, $-(CH_2)_rNR_aC(=O)NR_aR_a$, $-(CH_2)_rC(=O)OR_b$, $-(CH_2)_rS(O)_2NR_aR_a$, $-(CH_2)_rNR_aS(O)_2NR_aR_a$, $-(CH_2)_rNR_aS(O)_2R_c$, $(CH_2)_r$-carbocyclyl substituted with 0-3 $R_e$, and $-(CH_2)_r$-heterocyclyl substituted with 0-3 $R_e$;

$R_6$ is independently selected from H, $-C(=O)R_b$, $-CO(=O)R_b$, $-S(O)_pR_c$, $C_{1-6}$ alkyl substituted with 0-5 $R_e$, $-(CH_2)_r$-$C_{3-6}$carbocyclyl substituted with 0-5 $R_e$, and $-(CH_2)_r$-heterocyclyl substituted with 0-5 $R_e$;

$R_7$, at each occurrence, is independently selected from H, F, Cl, Br, =O, CN, $NO_2$, $-OR_b$, $-S(O)_pR_c$, $-C(=O)R_b$, $-(CR_dR_d)_rNR_aR_a$, $-(CR_dR_d)_rC(=O)NR_aR_a$, $-NR_aC(=O)R_b$, $-NR_aC(=O)OR_b$, $-OC(=O)NR_aR_a$, $-NR_aC(=O)NR_aR_a$, $-(CR_dR_d)_rC(=O)OR_b$, $-S(O)_2NR_aR_a$, $-NR_aS(O)_2NR_aR_a$, $-NR_aS(O)_2R_c$, $C_{1-6}$ alkyl substituted with 0-5 $R_e$, $-(CR_dR_d)_r$-$C_{3-6}$carbocyclyl substituted with 0-5 $R_e$, and $-(CR_dR_d)_r$-heterocyclyl substituted with 0-5 $R_e$;

$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $-(CH_2)_r$-$C_{3-10}$carbocyclyl substituted with 0-5 $R_e$, and $-(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $-(CH_2)_r$-$C_{3-10}$carbocyclyl substituted with 0-5 $R_e$, and $-(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_d$, at each occurrence, is independently selected from H and $C_{1-4}$alkyl substituted with 0-5 $R_e$;

$R_e$, at each occurrence, is independently selected from F, Cl, Br, CN, $NO_2$, =O, $CO_2H$, $C_{1-6}$ alkyl substituted with 0-5 $R_f$, $C_{2-6}$ alkenyl, $C_{2-6}$ alkynyl, $-(CH_2)_r$-$C_{3-6}$ cycloalkyl, $-(CH_2)_rOR_f$, $SR_f$, and $-(CH_2)_rNR_fR_f$;

$R_f$, at each occurrence, is independently selected from H, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

p, at each occurrence, is independently selected from zero, 1, and 2; and r, at each occurrence, is independently selected from zero, 1, 2, 3, and 4.

In certain embodiments, the present invention includes compounds of Formula (II), or stereoisomers, tautomers, pharmaceutically acceptable salts, solvates, or prodrugs thereof, wherein:

$R_1$ is phenyl substituted with 1-4 $R_5$;

$R_2$ is independently selected from

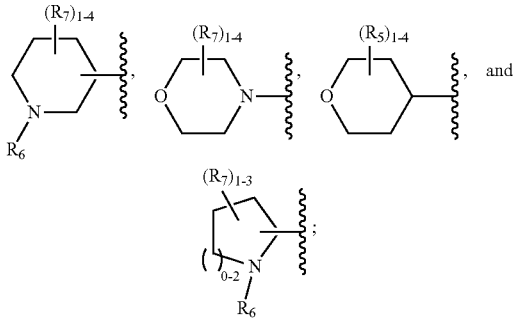

$R_{3a}$ and $R_{3b}$ are independently selected from H, $CH_2CH_3$, $CH_3$, $CH_2OH$, $CH_2CH_2OH$, $CH_2CH_2OC_{1-4}$alkyl, $CH_2F$, $CHF_2$, $CH_2CH_2F$, $CF_3$, $CH_2OCHF_2$, $CH_2CN$, $CH_2CH_2CN$, $CH_2OC_{1-4}$alkyl, $C(CH_3)_3$, $CH(CH_3)_2$, $C(CH_3)_2OH$, and $C(CH_3)_2F$;

$R_{3c}$ and $R_{3d}$ are independently selected from H, $CH_3$, $CH(CH_3)_2$, $CF_3$, and $C_{3-6}$ cycloalkyl;

$R_5$, at each occurrence, is independently selected from H, $C_{1-4}$ alkyl substituted with 0-3 $R_e$, F, Cl, Br, =O, CN, $NO_2$, $-OR_b$, $-(CH_2)_rCN$, $-(CH_2)_rOR_b$, $(CH_2)_rS(O)_pR_c$, $-(CH_2)_rC(=O)R_b$, $-(CH_2)_rNR_aR_a$, $-(CH_2)_rC(=O)NR_aR_a$, $-(CH_2)_rNR_aC(=O)R_b$, $-(CH_2)_rNR_aC(=O)OR_b$, $-(CH_2)_rOC(=O)NR_aR_a$, $-(CH_2)_rNR_aC(=O)NR_aR_a$, $-(CH_2)_rC(=O)OR_b$, $-(CH_2)_rS(O)_2NR_aR_a$, $-(CH_2)_rNR_aS(O)_2NR_aR_a$, $-(CH_2)_rNR_aS(O)_2R_e$, $(CH_2)_r$-carbocyclyl substituted with 0-3 $R_e$, and $-(CH_2)_r$-heterocyclyl substituted with 0-3 $R_e$;

$R_6$ is independently selected from H, $-C(=O)R_b$, $-CO(=O)R_b$, $-S(O)_pR_c$, $C_{1-6}$ alkyl substituted with 0-5 $R_e$, $-(CH_2)_r$-$C_{3-6}$carbocyclyl substituted with 0-5 $R_e$, and $-(CH_2)_r$-heterocyclyl substituted with 0-5 $R_e$;

$R_7$, at each occurrence, is independently selected from H, F, Cl, Br, =O, CN, $NO_2$, $-OR_b$, $-S(O)_pR_c$, $-C(=O)R_b$, $-(CR_dR_d)_rNR_aR_a$, $-(CR_dR_d)_rC(=O)NR_aR_a$, $-NR_aC(=O)R_b$, $-NR_aC(=O)OR_b$, $-OC(=O)NR_aR_a$, $-NR_aC(=O)NR_aR_a$, $-(CR_dR_d)_rC(=O)OR_b$, $C_{1-6}$ alkyl substituted with 0-5 $R_e$, $-(CR_dR_d)_r$-$C_{3-6}$carbocyclyl substituted with 0-5 $R_e$, and $-(CR_dR_d)_r$-heterocyclyl substituted with 0-5 $R_e$;

$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $-(CH_2)_r$-$C_{3-10}$carbocyclyl substituted with 0-5 $R_e$, and $-(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $-(CH_2)_r$-$C_{3-10}$carbocyclyl substituted with 0-5 $R_e$, and $-(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_d$, at each occurrence, is independently selected from H and $C_{1-4}$alkyl substituted with 0-5 $R_e$;

$R_e$, at each occurrence, is independently selected from F, Cl, Br, CN, NO$_2$, =O, CO$_2$H, $C_{1-6}$ alkyl substituted with 0-5 $R_f$, $C_{2-6}$ alkenyl, $C_{2-6}$ alkynyl, —(CH$_2$)$_r$—$C_{3-6}$ cycloalkyl, —(CH$_2$)$_r$OR$_f$, SR$_f$, and —(CH$_2$)$_r$NR$_f$R$_f$;

$R_f$, at each occurrence, is independently selected from H, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$ alkyl;

p, at each occurrence, is independently selected from zero, 1, and 2; and r, at each occurrence, is independently selected from zero, 1, 2, 3, and 4.

In certain embodiments, the present invention includes compounds of Formula (II), or stereoisomers, tautomers, pharmaceutically acceptable salts, solvates, or prodrugs thereof, wherein:

$R_1$ is phenyl substituted with 1-4 $R_5$;

$R_2$ is independently selected from (i) $C_{1-8}$alkyl, optionally substituted with F, Cl, Br, OH, CN, NR$_a$R$_a$, C(=O)NR$_a$R$_a$, $C_{2-6}$ alkenyl, $C_{2-6}$ alkynyl, carbocyclyl substituted with 1-8 $R_7$, and heterocyclyl comprising carbon atoms and 1 to 4 heteroatoms selected from N, NR$_6$, O, S, and substituted with 1-8 $R_7$, (ii) $C_{3-20}$cycloalkyl substituted with 1-8 $R_7$, and (iii) cycloheteroalkyl substituted with 1-8 $R_7$;

$R_{3a}$ and $R_{3b}$ together with the carbon atom to which they are both attached form a spiral carbocyclic or heterocyclic ring comprising carbon atoms and 1 to 4 heteroatoms selected from N, O, S, each substituted with 0-5 $R_e$;

$R_4$ is independently selected from H and $C_{1-4}$ alkyl substituted with 0-3 $R_e$;

$R_5$, at each occurrence, is independently selected from H, $C_{1-4}$ alkyl substituted with 0-3 $R_e$, F, Cl, Br, =O, CN, NO$_2$, —OR$_b$, —(CH$_2$)$_r$CN, —(CH$_2$)$_r$OR$_b$, (CH$_2$)$_r$S(O)$_p$R$_c$, —(CH$_2$)$_r$C(=O)R$_b$, —(CH$_2$)$_r$NR$_a$R$_a$, —(CH$_2$)$_r$C(=O)NR$_a$R$_a$, —(CH$_2$)$_r$NR$_a$C(=O)R$_b$, —(CH$_2$)$_r$NR$_a$C(=O)OR$_b$, —(CH$_2$)$_r$OC(=O)NR$_a$R$_a$, —(CH$_2$)$_r$NR$_a$C(=O)NR$_a$R$_a$, —(CH$_2$)$_r$C(=O)OR$_b$, —(CH$_2$)$_r$S(O)$_2$NR$_a$R$_a$, —(CH$_2$)$_r$NR$_a$S(O)$_2$NR$_a$R$_a$, —(CH$_2$)$_r$NR$_a$S(O)$_2$R$_c$, (CH$_2$)$_r$-carbocyclyl substituted with 0-3 $R_e$, and —(CH$_2$)$_r$-heterocyclyl substituted with 0-3 $R_e$;

$R_6$ is independently selected from H, —C(=O)R$_b$, —CO(=O)R$_b$, —S(O)$_p$R$_c$, $C_{1-6}$ alkyl substituted with 0-5 $R_e$, —(CH$_2$)$_r$—$C_{3-6}$carbocyclyl substituted with 0-5 $R_e$, and —(CH$_2$)$_r$-heterocyclyl substituted with 0-5 $R_e$;

$R_7$, at each occurrence, is independently selected from H, F, Cl, Br, =O, —(CR$_d$R$_d$)$_r$CN, NO$_2$, —(CR$_d$R$_d$)$_r$OR$_b$, —S(O)$_p$R$_c$, —C(=O)R$_b$, —(CR$_d$R$_d$)$_r$NR$_a$R$_a$, —(CR$_d$R$_d$)$_r$C(=O)NR$_a$R$_a$, —NR$_a$C(=O)R$_b$, —NR$_a$C(=O)OR$_b$, —OC(=O)NR$_a$R$_a$, —NR$_a$C(=O)NR$_a$R$_a$, —(CR$_d$R$_d$)$_r$C(=O)OR$_b$, —S(O)$_2$NR$_a$R$_a$, —NR$_a$S(O)$_2$NR$_a$R$_a$, —NR$_a$S(O)$_2$R$_c$, $C_{1-6}$ alkyl substituted with 0-5 $R_e$, —(CR$_d$R$_d$)$_r$—$C_{3-6}$carbocyclyl substituted with 0-5 $R_e$, and —(CR$_d$R$_d$)$_r$-heterocyclyl substituted with 0-5 $R_e$;

$R_8$, at each occurrence, is independently selected from H, F, Cl, Br, CN, $C_{1-6}$ alkyl substituted with 0-5 $R_e$, $C_{2-6}$ alkenyl, $C_{2-6}$ alkynyl, —(CH$_2$)$_r$—$C_{3-6}$ cycloalkyl substituted with 0-5 $R_e$, —(CH$_2$)$_r$-aryl substituted with 0-5 $R_e$, —(CH$_2$)$_r$-heterocyclyl substituted with 0-5 $R_e$, CO$_2$H, —(CH$_2$)$_r$OR$_b$, and —(CH$_2$)$_r$NR$_a$R$_a$;

$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —(CH$_2$)$_r$—$C_{3-10}$carbocyclyl substituted with 0-5 $R_e$, and —(CH$_2$)$_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —(CH$_2$)$_r$—$C_{3-10}$carbocyclyl substituted with 0-5 $R_e$, and —(CH$_2$)$_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_d$, at each occurrence, is independently selected from H and $C_{1-4}$ alkyl substituted with 0-5 $R_e$;

$R_e$, at each occurrence, is independently selected from F, Cl, Br, CN, NO$_2$, =O, $C_{1-6}$ alkyl substituted with 0-5 $R_f$, $C_{2-6}$ alkenyl, $C_{2-6}$ alkynyl, —(CH$_2$)$_r$—$C_{3-6}$ cycloalkyl, CO$_2$H, —(CH$_2$)$_r$OR$_f$, SR$_f$, and —(CH$_2$)$_r$NR$_f$R$_f$;

$R_f$, at each occurrence, is independently selected from H, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

p, at each occurrence, is independently selected from zero, 1, and 2; and r, at each occurrence, is independently selected from zero, 1, 2, 3, and 4.

In certain embodiments, the present invention includes compounds of Formula (II), or stereoisomers, tautomers, pharmaceutically acceptable salts, solvates, or prodrugs thereof, wherein:

$R_1$ is phenyl substituted with 1-4 $R_5$;

$R_2$ is independently selected from (i) $C_{1-8}$alkyl, optionally substituted with F, Cl, Br, OH, CN, NR$_a$R$_a$, C(=O)NR$_a$R$_a$, $C_{2-6}$ alkenyl, $C_{2-6}$ alkynyl, carbocyclyl substituted with 1-8 $R_7$, and heterocyclyl comprising carbon atoms and 1 to 4 heteroatoms selected from N, NR$_6$, O, S, and substituted with 1-8 $R_7$, (ii) $C_{3-20}$cycloalkyl substituted with 1-8 $R_7$, and (iii) cycloheteroalkyl substituted with 1-8 $R_7$;

$R_{3a}$ and $R_{3c}$ or $R_{3b}$ and $R_{3d}$ together form a heterocyclic ring comprising carbon atoms and 1 to 4 heteroatoms selected from N, O, S, and substituted with 0-5 $R_e$;

$R_4$ is independently selected from H and $C_{1-4}$ alkyl substituted with 0-3 $R_e$;

$R_5$, at each occurrence, is independently selected from H, $C_{1-4}$ alkyl substituted with 0-3 $R_e$, F, Cl, Br, =O, CN, NO$_2$, —OR$_b$, —(CH$_2$)$_r$CN, —(CH$_2$)$_r$OR$_b$, (CH$_2$)$_r$S(O)$_p$R$_c$, —(CH$_2$)$_r$C(=O)R$_b$, —(CH$_2$)$_r$NR$_a$R$_a$, —(CH$_2$)$_r$C(=O)NR$_a$R$_a$, —(CH$_2$)$_r$NR$_a$C(=O)R$_b$, —(CH$_2$)$_r$NR$_a$C(=O)OR$_b$, —(CH$_2$)$_r$OC(=O)NR$_a$R$_a$, —(CH$_2$)$_r$NR$_a$C(=O)NR$_a$R$_a$, —(CH$_2$)$_r$C(=O)OR$_b$, —(CH$_2$)$_r$S(O)$_2$NR$_a$R$_a$, —(CH$_2$)$_r$NR$_a$S(O)$_2$NR$_a$R$_a$, —(CH$_2$)$_r$NR$_a$S(O)$_2$R$_c$, (CH$_2$)$_r$-carbocyclyl substituted with 0-3 $R_e$, and —(CH$_2$)$_r$-heterocyclyl substituted with 0-3 $R_e$;

$R_6$ is independently selected from H, —C(=O)R$_b$, —CO(=O)R$_b$, —S(O)$_p$R$_c$, $C_{1-6}$ alkyl substituted with 0-5 $R_e$, —(CH$_2$)$_r$—$C_{3-6}$carbocyclyl substituted with 0-5 $R_e$, and —(CH$_2$)$_r$-heterocyclyl substituted with 0-5 $R_e$;

$R_7$, at each occurrence, is independently selected from H, F, Cl, Br, =O, —(CR$_d$R$_d$)$_r$CN, NO$_2$, —(CR$_d$R$_d$)$_r$OR$_b$, —S(O)$_p$R$_c$, —C(=O)R$_b$, —(CR$_d$R$_d$)$_r$NR$_a$R$_a$, —(CR$_d$R$_d$)$_r$C(=O)NR$_a$R$_a$, —NR$_a$C(=O)R$_b$, —NR$_a$C(=O)OR$_b$, —OC(=O)NR$_a$R$_a$, —NR$_a$C(=O)NR$_a$R$_a$, —(CR$_d$R$_d$)$_r$C(=O)OR$_b$, —S(O)$_2$NR$_a$R$_a$, —NR$_a$S(O)$_2$NR$_a$R$_a$, —NR$_a$S(O)$_2$R$_c$, $C_{1-6}$ alkyl substituted with 0-5 $R_e$, —(CR$_d$R$_d$)$_r$—$C_{3-6}$carbocyclyl substituted with 0-5 $R_e$, and —(CR$_d$R$_d$)$_r$-heterocyclyl substituted with 0-5 $R_e$;

$R_8$, at each occurrence, is independently selected from H, F, Cl, Br, CN, $C_{1-6}$ alkyl substituted with 0-5 $R_e$, $C_{2-6}$ alkenyl, $C_{2-6}$ alkynyl, —$(CH_2)_r$—$C_{3-6}$ cycloalkyl substituted with 0-5 $R_e$, —$(CH_2)_r$-aryl substituted with 0-5 $R_e$, —$(CH_2)_r$-heterocyclyl substituted with 0-5 $R_e$, $CO_2H$, —$(CH_2)_r$OR$_b$, and —$(CH_2)_rNR_aR_a$;

$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_d$, at each occurrence, is independently selected from H and $C_{1-4}$alkyl substituted with 0-5 $R_e$;

$R_e$, at each occurrence, is independently selected from F, Cl, Br, CN, $NO_2$, =O, $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, $CO_2H$, —$(CH_2)_r$OR$_f$, SR$_f$ and —$(CH_2)_rNR_fR_f$;

$R_f$, at each occurrence, is independently selected from H, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

p, at each occurrence, is independently selected from zero, 1, and 2; and r, at each occurrence, is independently selected from zero, 1, 2, 3, and 4.

In another embodiment, there are disclosed compounds of formula (VI):

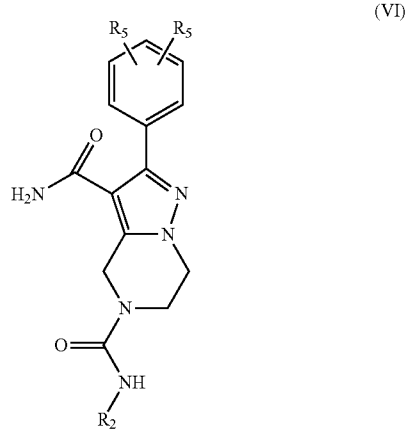

(VI)

including enantiomers, diastereomers, tautomers, pharmaceutically-acceptable salts, prodrugs, hydrates, or solvates thereof, wherein:

$R_2$ is independently selected from

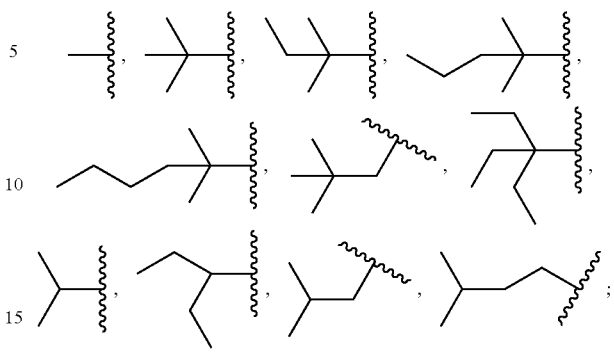

$R_{3a}$ and $R_{3b}$ are independently H;
$R_{3c}$ and $R_{3d}$ are independently H;
$R_5$, at each occurrence, is independently selected from H, F, Cl, and Br.

In certain embodiments, the present invention includes compounds of Formula (II), or stereoisomers, tautomers, pharmaceutically acceptable salts, solvates, or prodrugs thereof, wherein:

$R_1$ is heteroaryl comprising carbon atoms and 1 to 3 heteroatoms selected from N, $NR_4$, O, S, wherein the heteroaryl is substituted with 1-5 $R_5$ and selected from thiazolyl, oxazolyl, pyrazolyl, triazolyl, tetrazolyl, thiadiazolyl, isoxazolyl, imidazolyl, pyridyl, pyrimidinyl, pyrazinyl, pyridazinyl, indolyl, indazolyl, isoindolyl, indolinyl, isoindolinyl, benzimidazolyl, benzothiazolyl, benzotriazolyl, quinolinyl, and isoquinolinyl;

$R_2$ is $C_{1-6}$alkyl optionally substituted with F, Cl, Br, OH, CN, and $NR_aR_a$;

$R_{3a}$, $R_{3b}$, $R_{3c}$, $R_{3d}$, $R_{3e}$ and $R_{3f}$ are independently selected from H, CN, $C_{1-4}$alkyl substituted with 1-3 $R_8$, —C(=O)OR$_b$, —C(=O)NR$_aR_a$, —C(=O)R$_b$, —NR$_a$C(=O)R$_b$, —NR$_a$C(=O)OR$_b$, —$(CH_2)_r$-carbocyclyl substituted with 1-3 $R_8$, and —$(CH_2)_r$-heterocyclyl substituted with 1-3 $R_8$;

alternatively, $R_{3a}$ and $R_{3b}$, or $R_{3c}$ and $R_{3d}$, or $R_{3e}$ and $R_{3f}$ together with the carbon atom to which they are both attached form a spiral carbocyclic or heterocyclic ring comprising carbon atoms and 1 to 4 heteroatoms selected from N, O, S, each substituted with 1-5 $R_8$;

alternatively, $R_{3a}$ and $R_{3c}$ or $R_{3b}$ and $R_{3d}$ together form a heterocyclic ring comprising carbon atoms and 1 to 4 heteroatoms selected from N, O, S, and substituted with 1-5 $R_8$;

$R_4$ is independently selected from H and $C_{1-4}$ alkyl substituted with 0-3 $R_e$;

$R_5$, at each occurrence, is independently selected from H, $C_{1-4}$ alkyl substituted with 0-3 F, Cl, Br, =O, CN, $NO_2$, —OR$_b$, —$(CH_2)_r$CN, —$(CH_2)_r$OR$_b$, $(CH_2)_r$S(O)$_p$R$_c$, —$(CH_2)_r$C(=O)R$_b$, —$(CH_2)_r$NR$_aR_a$, —$(CH_2)_r$C(=O)NR$_aR_a$, —$(CH_2)_r$NR$_a$C(=O)R$_b$, —$(CH_2)_r$NR$_a$C(=O)OR$_b$, —$(CH_2)_r$OC(=O)NR$_aR_a$, —$(CH_2)_r$NR$_a$C(=O)NR$_aR_a$, —$(CH_2)_r$C(=O)OR$_b$, —$(CH_2)_r$S(O)$_2$NR$_aR_a$, —$(CH_2)_r$NR$_a$S(O)$_2$NR$_aR_a$, —$(CH_2)_r$NR$_a$S(O)$_2$R$_c$, $(CH_2)_r$-carbocyclyl substituted with 0-3 $R_e$, and —$(CH_2)_r$-heterocyclyl substituted with 0-3 $R_e$;

$R_7$, at each occurrence, is independently selected from H, F, Cl, Br, =O, CN, $NO_2$, —OR$_b$, —S(O)$_p$R$_c$, —C(=O)R$_b$, —$(CR_dR_d)_rNR_aR_a$, —$(CR_dR_d)_rC(=O)NR_aR_a$, —NR$_a$C(=O)R$_b$, —NR$_a$C(=O)OR$_b$, —OC(=O)NR$_aR_a$, —NR$_a$C(=O)NR$_a$R$_a$, —(CR$_d$R$_d$)$_r$C(=O)OR$_b$, —S(O)$_2$NR$_a$R$_a$, —NR$_a$S(O)$_2$NR$_a$R$_a$, —NR$_a$S(O)$_2$R$_c$, C$_{1-6}$ alkyl substituted with 0-5 R$_e$, —(CR$_d$R$_d$)$_r$—C$_{3-6}$carbocyclyl substituted with 0-5 R$_e$, and —(CR$_d$R$_d$)$_r$-heterocyclyl substituted with 0-5 R$_e$;

R$_a$, at each occurrence, is independently selected from H, CN, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;

R$_b$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$;

R$_c$, at each occurrence, is independently selected from C$_{1-6}$ alkyl substituted with 0-5 R$_e$, C$_{2-6}$alkenyl substituted with 0-5 R$_e$, C$_{2-6}$alkynyl substituted with 0-5 R$_e$, C$_{3-6}$carbocyclyl, and heterocyclyl;

R$_e$, at each occurrence, is independently selected from F, Cl, Br, CN, NO$_2$, =O, CO$_2$H, C$_{1-6}$ alkyl substituted with 0-5 R$_f$, C$_{2-6}$ alkenyl, C$_{2-6}$ alkynyl, —(CH$_2$)$_r$—C$_{3-6}$ cycloalkyl, —(CH$_2$)$_r$OR$_f$, SR$_f$, and —(CH$_2$)$_r$NR$_f$R$_f$;

R$_f$, at each occurrence, is independently selected from H, C$_{1-5}$ alkyl, C$_{3-6}$ cycloalkyl, and phenyl, or R$_f$ and R$_f$ together with the nitrogen atom to which they are both attached form a heterocyclic ring optionally substituted with C$_{1-4}$alkyl;

p, at each occurrence, is independently selected from zero, 1, and 2; and r, at each occurrence, is independently selected from zero, 1, 2, 3, and 4.

In certain embodiments, the present invention includes compounds of Formula (II), or stereoisomers, tautomers, pharmaceutically acceptable salts, solvates, or prodrugs thereof, wherein:

R$_1$ is heteroaryl comprising carbon atoms and 1 to 3 heteroatoms selected from N, NR$_4$, O, S, wherein the heteroaryl is substituted with 1-5 R$_5$ and selected from thiazolyl, oxazolyl, pyrazolyl, triazolyl, tetrazolyl, thiadiazolyl, isoxazolyl, imidazolyl, pyridyl, pyrimidinyl, pyrazinyl, pyridazinyl, indolyl, indazolyl, isoindolyl, indolinyl, isoindolinyl, benzimidazolyl, benzothiazolyl, benzotriazolyl, quinolinyl, and isoquinolinyl;

R$_2$ is cycloalkyl substituted with 1-5 R$_7$;

R$_{3a}$, R$_{3b}$, R$_{3c}$, R$_{3d}$, R$_{3e}$ and R$_{3f}$ are independently selected from H, CN, C$_{1-4}$alkyl substituted with 1-3 R$_8$, —C(=O)OR$_b$, —C(=O)NR$_a$R$_a$, —C(=O)R$_b$, —NR$_a$C(=O)R$_b$, —NR$_a$C(=O)OR$_b$, —(CH$_2$)$_r$-carbocyclyl substituted with 1-3 R$_8$, and —(CH$_2$)$_r$-heterocyclyl substituted with 1-3 R$_8$;

alternatively, R$_{3a}$ and R$_{3b}$, or R$_{3c}$ and R$_{3d}$, or R$_{3e}$ and R$_{3f}$ together with the carbon atom to which they are both attached form a spiral carbocyclic or heterocyclic ring comprising carbon atoms and 1 to 4 heteroatoms selected from N, O, S, each substituted with 1-5 R$_8$;

alternatively, R$_{3a}$ and R$_{3c}$ or R$_{3b}$ and R$_{3d}$ together form a heterocyclic ring comprising carbon atoms and 1 to 4 heteroatoms selected from N, O, S, and substituted with 1-5 R$_8$;

R$_4$ is independently selected from H and C$_{1-4}$ alkyl substituted with 0-3 R$_e$;

R$_5$, at each occurrence, is independently selected from H, C$_{1-4}$alkyl substituted with 0-3 R$_e$, F, Cl, Br, =O, CN, NO$_2$, —OR$_b$, —(CH$_2$)$_r$CN, —(CH$_2$)$_r$OR$_b$, (CH$_2$)$_r$S(O)$_p$R$_c$, —(CH$_2$)$_r$C(=O)R$_b$, —(CH$_2$)$_r$NR$_a$R$_a$, —(CH$_2$)$_r$C(=O)NR$_a$R$_a$, —(CH$_2$)$_r$NR$_a$C(=O)R$_b$, —(CH$_2$)$_r$NR$_a$C(=O)OR$_b$, —(CH$_2$)$_r$OC(=O)NR$_a$R$_a$, —(CH$_2$)$_r$NR$_a$C(=O)NR$_a$R$_a$, —(CH$_2$)$_r$C(=O)OR$_b$, —(CH$_2$)$_r$S(O)$_2$NR$_a$R$_a$, —(CH$_2$)$_r$NR$_a$S(O)$_2$NR$_a$R$_a$, —(CH$_2$)$_r$NR$_a$S(O)$_2$R$_c$, (CH$_2$)$_r$-carbocyclyl substituted with 0-3 R$_e$, and —(CH$_2$)$_r$-heterocyclyl substituted with 0-3 R$_e$;

R$_7$, at each occurrence, is independently selected from H, F, Cl, Br, =O, CN, NO$_2$, —OR$_b$, —S(O)$_p$R$_c$, —C(=O)R$_b$, —(CR$_d$R$_d$)$_r$NR$_a$R$_a$, —(CR$_d$R$_d$)$_r$C(=O)NR$_a$R$_a$, —NR$_a$C(=O)R$_b$, —NR$_a$C(=O)OR$_b$, —OC(=O)NR$_a$R$_a$, —NR$_a$C(=O)NR$_a$R$_a$, —(CR$_d$R$_d$)$_r$C(=O)OR$_b$, —S(O)$_2$NR$_a$R$_a$, —NR$_a$S(O)$_2$NR$_a$R$_a$, —NR$_a$S(O)$_2$R$_c$, C$_{1-6}$ alkyl substituted with 0-5 R$_e$, —(CR$_d$R$_d$)$_r$—C$_{3-6}$carbocyclyl substituted with 0-5 R$_e$, and —(CR$_d$R$_d$)$_r$-heterocyclyl substituted with 0-5 R$_e$;

R$_a$, at each occurrence, is independently selected from H, CN, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;

R$_b$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$;

R$_c$, at each occurrence, is independently selected from C$_{1-6}$ alkyl substituted with 0-5 R$_e$, C$_{2-6}$alkenyl substituted with 0-5 R$_e$, C$_{2-6}$alkynyl substituted with 0-5 R$_e$, C$_{3-6}$carbocyclyl, and heterocyclyl;

R$_d$, at each occurrence, is independently selected from H and C$_{1-4}$alkyl substituted with 0-5 R$_e$;

R$_e$, at each occurrence, is independently selected from F, Cl, Br, CN, NO$_2$, =O, CO$_2$H, C$_{1-6}$ alkyl substituted with 0-5 R$_f$, C$_{2-6}$ alkenyl, C$_{2-6}$ alkynyl, —(CH$_2$)$_r$—C$_{3-6}$ cycloalkyl, —(CH$_2$)$_r$OR$_f$, SR$_f$, and —(CH$_2$)$_r$NR$_f$R$_f$;

R$_f$, at each occurrence, is independently selected from H, C$_{1-5}$ alkyl, C$_{3-6}$ cycloalkyl, and phenyl, or R$_f$ and R$_f$ together with the nitrogen atom to which they are both attached form a heterocyclic ring optionally substituted with C$_{1-4}$alkyl;

p, at each occurrence, is independently selected from zero, 1, and 2; and r, at each occurrence, is independently selected from zero, 1, 2, 3, and 4.

In certain embodiments, the present invention includes compounds of Formula (II), or stereoisomers, tautomers, pharmaceutically acceptable salts, solvates, or prodrugs thereof, wherein:

R$_1$ is heteroaryl comprising carbon atoms and 1 to 3 heteroatoms selected from N, NR$_4$, O, S, wherein the heteroaryl is substituted with 1-5 R$_5$ and selected from thiazolyl, oxazolyl, pyrazolyl, triazolyl, tetrazolyl, thiadiazolyl, isoxazolyl, imidazolyl, pyridyl, pyrimidinyl, pyrazinyl, pyridazinyl, indolyl, indazolyl, isoindolyl, indolinyl, isoindolinyl, benzimidazolyl, benzothiazolyl, benzotriazolyl, quinolinyl, and isoquinolinyl;

R$_2$ is cycloheteroalkyl comprising carbon atoms and 1 to 4 heteroatoms selected from N, O, S, and substituted with 1-8 R$_7$;

R$_{3a}$, R$_{3b}$, R$_{3c}$, R$_{3d}$, R$_{3e}$ and R$_{3f}$ are independently selected from H, CN, C$_{1-4}$alkyl substituted with 1-3 R$_8$, —C(=O)OR$_b$, —C(=O)NR$_a$R$_a$, —C(=O)R$_b$, —NR$_a$C(=O)R$_b$, —$NR_aC(=O)OR_b$, —$(CH_2)_r$-carbocyclyl substituted with 1-3 $R_8$, and —$(CH_2)_r$-heterocyclyl substituted with 1-3 $R_8$;

alternatively, $R_{3a}$ and $R_{3b}$, or $R_{3c}$ and $R_{3d}$, or $R_{3e}$ and $R_{3f}$, together with the carbon atom to which they are both attached form a spiral carbocyclic or heterocyclic ring comprising carbon atoms and 1 to 4 heteroatoms selected from N, O, S, each substituted with 1-5 $R_8$;

alternatively, $R_{3a}$ and $R_{3c}$ or $R_{3b}$ and $R_{3d}$ together form a heterocyclic ring comprising carbon atoms and 1 to 4 heteroatoms selected from N, O, S, and substituted with 1-5 $R_8$;

$R_4$ is independently selected from H and $C_{1-4}$ alkyl substituted with 0-3 $R_e$;

$R_5$, at each occurrence, is independently selected from H, $C_{1-4}$ alkyl substituted with 0-3 $R_e$, F, Cl, Br, =O, CN, $NO_2$, —$OR_b$, —$(CH_2)_rCN$, —$(CH_2)_rOR_b$, $(CH_2)_rS(O)_pR_c$, —$(CH_2)_rC(=O)R_b$, —$(CH_2)_rNR_aR_a$, —$(CH_2)_rC(=O)NR_aR_a$, —$(CH_2)_rNR_aC(=O)R_b$, —$(CH_2)_rNR_aC(=O)OR_b$, —$(CH_2)_rOC(=O)NR_aR_a$, —$(CH_2)_rNR_aC(=O)NR_aR_a$, —$(CH_2)_rC(=O)OR_b$, —$(CH_2)_rS(O)_2NR_aR_a$, —$(CH_2)_rNR_aS(O)_2NR_aR_a$, —$(CH_2)_rNR_aS(O)_2R_c$, $(CH_2)_r$-carbocyclyl substituted with 0-3 $R_e$, and —$(CH_2)_r$-heterocyclyl substituted with 0-3 $R_e$;

$R_6$ is independently selected from H, —$C(=O)R_b$, —$CO(=O)R_b$, —$S(O)_pR_c$, $C_{1-6}$ alkyl substituted with 0-5 $R_e$, —$(CH_2)_r$—$C_{3-6}$carbocyclyl substituted with 0-5 $R_e$, and —$(CH_2)_r$-heterocyclyl substituted with 0-5 $R_e$;

$R_7$, at each occurrence, is independently selected from H, F, Cl, Br, =O, CN, $NO_2$, —$OR_b$, —$S(O)_pR_c$, —$C(=O)R_b$, —$(CR_dR_d)_rNR_aR_a$, —$(CR_dR_d)_rC(=O)NR_aR_a$, —$NR_aC(=O)R_b$, —$NR_aC(=O)OR_b$, —$OC(=O)NR_aR_a$, —$NR_aC(=O)NR_aR_a$, —$(CR_dR_d)_rC(=O)OR_b$, —$S(O)_2NR_aR_a$, —$NR_aS(O)_2NR_aR_a$, —$NR_aS(O)_2R_c$, $C_{1-6}$ alkyl substituted with 0-5 $R_e$, —$(CR_dR_d)_r$—$C_{3-6}$carbocyclyl substituted with 0-5 $R_e$, and —$(CR_dR_d)_r$-heterocyclyl substituted with 0-5 $R_e$;

$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_d$, at each occurrence, is independently selected from H and $C_{1-4}$alkyl substituted with 0-5 $R_e$;

$R_e$, at each occurrence, is independently selected from F, Cl, Br, CN, $NO_2$, =O, $CO_2H$, $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, —$(CH_2)_rOR_f$, $SR_f$, and —$(CH_2)_rNR_fR_f$;

$R_f$, at each occurrence, is independently selected from H, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

p, at each occurrence, is independently selected from zero, 1, and 2; and r, at each occurrence, is independently selected from zero, 1, 2, 3, and 4.

In another embodiment, the present invention provides a compound selected from any compounds or any subset list of compounds exemplified in the present application.

The compounds of Formulae (I)-(VI) may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts can be formed as known to those skilled in the art.

The compounds for Formulae (I)-(VI) may form salts with a variety of organic and inorganic acids. Such salts include those formed with hydrogen chloride, hydrogen bromide, methanesulfonic acid, sulfuric acid, acetic acid, trifluoroacetic acid, oxalic acid, maleic acid, benzenesulfonic acid, toluenesulfonic acid and various others (e.g., nitrates, phosphates, borates, tartrates, citrates, succinates, benzoates, ascorbates, salicylates and the like). Such salts can be formed as known to those skilled in the art.

In addition, zwitterions ("inner salts") may be formed.

The present invention is also intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Compounds of the Formulae (I)-(VI) may also have prodrug forms. Since prodrugs are known to enhance numerous desirable qualities of pharmaceuticals (e.g., solubility, bioavailability, manufacturing, etc.) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a mammalian subject. Prodrugs of the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate, and benzoate derivatives of alcohol and amine functional groups in the compounds of the present invention.

Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112: 309-396, Academic Press (1985);

b) Bundgaard, H., Chapter 5, "Design and Application of Prodrugs", *A Textbook of Drug Design and Development*, pp. 113-191, Krogsgaard-Larsen, P. et al., eds., Harwood Academic Publishers (1991); and c) Bundgaard, H., *Adv. Drug Deliv. Rev.*, 8:1-38 (1992);

It should further be understood that solvates (e.g., hydrates) of the compounds of Formulae (I)-(VI) are also within the scope of the invention. Methods of solvation are generally known in the art. The inventive compounds may either be in the free or hydrate form.

Compounds of this invention may have one or more asymmetric centers. Unless otherwise indicated, all chiral (enantiomeric and diastereomeric) and racemic forms of compounds of the present invention are included in the present invention. Many geometric isomers of olefins, C=N double bonds, and the like can also be present in the compounds, and all such stable isomers are contemplated in the present invention. Cis- and trans-geometric isomers of the compounds of the present invention are described and may be isolated as a mixture of isomers or as separated isomeric forms. The present compounds can be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated. When no specific mention is made of the configuration (cis, trans or R or S) of a compound (or of an asymmetric carbon), then any one of the isomers or a mixture of more than one isomer is intended. The processes for preparation can use racemates, enantiomers, or diastereomers as starting materials. All processes used to prepare compounds of the present invention and intermediates made therein are considered to be part of the present invention. When enantiomeric or diastereomeric products are prepared, they can be separated by conventional methods, for example, by chromatography or fractional crystallization. Compounds of the present invention, and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

DEFINITIONS

The following are definitions of terms used in this specification and appended claims. The initial definition provided for a group or term herein applies to that group or term throughout the specification and claims, individually or as part of another group, unless otherwise indicated.

In accordance with a convention used in the art, ⌇—— is used in structural formulas herein to depict the bond that is the point of attachment of the moiety or substituent to the core or backbone structure.

A dash "-" that is not between two letters or symbols is used to indicate a point of attachment for a substituent. For example, —CONH$_2$ is attached through the carbon atom.

As used herein, the term "alkyl" or "alkylene" is intended to include both branched and straight-chain saturated aliphatic hydrocarbon groups having the specified number of carbon atoms. For example, "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$-$C_6$ alkyl" denotes alkyl having 1 to 6 carbon atoms. Alkyl groups can be unsubstituted or substituted so that one or more of its hydrogens are replaced by another chemical group. Example alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like.

"Haloalkyl" is intended to include both branched and straight-chain saturated aliphatic hydrocarbon groups having the specified number of carbon atoms, substituted with 1 or more halogen. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" which is intended to include both branched and straight-chain saturated aliphatic hydrocarbon groups having the specified number of carbon atoms, substituted with 1 or more fluorine atoms.

The term "halogen" or "halo" refers to fluorine (F), chlorine (Cl), bromine (Br) and iodine.

"Haloalkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, pentafluorothoxy, and the like. Similarly, "haloalkylthio" or "thiohaloalkoxy" represents a haloalkyl group as defined above with the indicated number of carbon atoms attached through a sulphur bridge; for example trifluoromethyl-S—, pentafluoroethyl-S—, and the like.

As used herein, "carbocycle", "carbocyclic residue", or "carbocyclyl" is intended to mean any stable 3-, 4-, 5-, 6-, or 7-membered monocyclic or bicyclic or 7-, 8-, 9-, 10-, 11-, 12-, or 13-membered bicyclic or tricyclic hydrocarbon ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, and indanyl. When the term "carbocycle", "carbocyclic residue", or "carbocyclyl" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

The term "aryl" refers to monocyclic, bicyclic, tricyclic aromatic hydrocarbon groups having 6 to 15 carbon atoms in the ring portion, such as phenyl, naphthyl, biphenyl and diphenyl groups, each of which may be substituted. Aryl groups which are bicyclic or tricyclic must include at least one fully aromatic ring but the other fused ring or rings may be aromatic or non-aromatic. When an aryl is substituted with a further heterocyclic ring, said ring may be attached to the aryl through a carbon atom or a heteroatom and said ring in turn is optionally substituted with one to two substituents as valence allows.

The terms "aryloxy", "arylamino", "arylalkylamino", "arylthio", "arylalkanoylamino", "arylsulfonyl", "aryalkoxy", "arylsulfinyl", "arylheteroaryl", "arylalkylthio", "arylcarbonyl", "arylalkenyl", or "arylalkylsulfonyl" refer to an aryl or substituted aryl bonded to an oxygen; an amino; an alkylamino; a thio; an alkanoylamino; a sulfonyl; an alkoxy;

a sulfinyl; a heteroaryl or substituted heteroaryl; an alkylthio; a carbonyl; an alkenyl; or an alkylsulfonyl, respectively.

The term "alkenyl" refers to straight or branched chain hydrocarbon groups of 2 to 20 carbon atoms, preferably 2 to 15 carbon atoms, and most preferably 2 to 8 carbon atoms, having one to four double bonds.

The term "alkynyl" refers to straight or branched chain hydrocarbon groups of 2 to 20 carbon atoms, preferably 2 to 15 carbon atoms, and most preferably 2 to 8 carbon atoms, having one to four triple bonds.

The term "cycloalkyl" refers to an optionally substituted, saturated cyclic hydrocarbon ring systems, preferably containing 1 to 3 rings and 3 to 7 carbons per ring. Exemplary groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, or one or more groups described above as alkyl substituents. Accordingly, in compounds of Formula (I), the term "cycloalkyl" includes cyclopropyl, cyclobutyl, cyclopentyl, cyclohexyl, cycloheptyl, bicyclooctyl, etc., as well as the following ring systems,

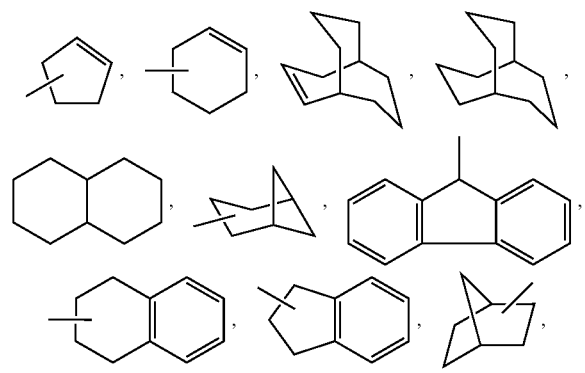

and the like, which optionally may be substituted at any available atoms of the ring(s). Preferred cycloalkyl groups include cyclopropyl, cyclopentyl, cyclohexyl,

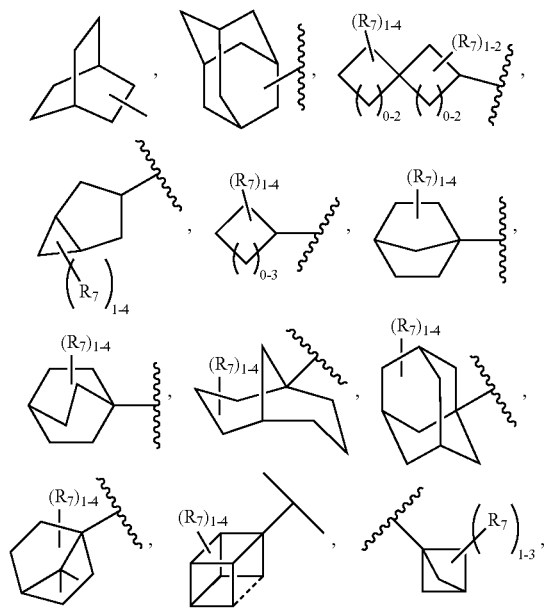

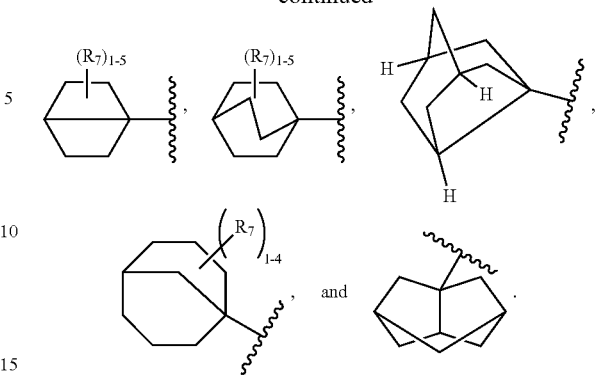

The term "cycloheteroalkyl" or "heterocycloalkyl" means a saturated or partially saturated 4-12 membered ring radical having specified number of ring carbon atoms. The cycloheteroalkyl or heterocycloalkyl contains 1 to 4 ring heteroatoms, which may be the same or different, selected from N, O or S. The cycloheteroalkyl or heterocycloalkyl ring optionally contains one or more double bonds. It can be monocyclic, bicyclic, tricyclic, fused, bridged, or spiro. For example, ($C_{3-9}$) heterocycloalkyl means a ring radical containing 3-9 ring carbon atoms. The term "cycloheteroalkyl" or "heterocycloalkyl" is intended to include all the possible isomeric forms. When the heteroatom is a ring nitrogen atom connected to other ring atoms only by single bonds, it can be substituted. Exemplary substituents, unless otherwise indicated, include H, alkyl, cycloalkyl, cycloalkylalkyl, aryl, arylalkyl, heteroaryl, heteroarylalkyl (preferably, H, $C_{1-6}$ alkyl, halo$C_{1-6}$alkyl or $C_{1-3}$alkylcarbonyl), each of which can be optionally substituted with halogen, hydroxy, alkoxy, haloalkyl, alkyl, etc. When the heteroatom is S, it can be optionally mono- or di-oxygenated (i.e., —S(O)— or —S(O)$_2$—).

As used herein, the term "heterocycle", "heterocyclyl", "heterocyclic ring" or "heterocyclic group" is intended to mean a stable 4-, 5-, 6-, or 7-membered monocyclic or bicyclic or 7-, 8-, 9-, 10-, 11-, 12-, 13-, or 14-membered bicyclic heterocyclic ring which is saturated, partially unsaturated or fully unsaturated or aromatic, and which consists of carbon atoms and 1, 2, 3 or 4 heteroatoms independently selected from N, O and S; and including any bicyclic group in which any of the above-defined heterocyclic rings is fused to a benzene ring. The nitrogen and sulfur heteroatoms may optionally be oxidized (i.e., N→O and S(O)$_p$). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on a carbon atom or on a nitrogen atom if the resulting compound is stable. A nitrogen atom in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle", "heterocyclyl", "heterocyclic ring" or "heterocyclic group" is used, it is intended to include heteroaryl.

Examples of heterocycles include, but are not limited to, acridinyl, azocinyl, benzimidazolyl, benzofuranyl, benzothiofuranyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Preferred 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Preferred 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and Spiro compounds containing, for example, the above heterocycles.

Bridged rings are also included in the definition of heterocycle. A bridged ring occurs when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "heteroaryl" refers to substituted and unsubstituted aromatic 5- or 6-membered monocyclic groups, 9- or 10-membered bicyclic groups, and 11- to 14-membered tricyclic groups which have at least one heteroatom (O, S or N) in at least one of the rings, said heteroatom-containing ring preferably having 1, 2, or 3 heteroatoms selected from O, S, and N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. Heteroaryl groups can be substituted or unsubstituted. The nitrogen atom may be substituted or unsubstituted (i.e., N or NR wherein R is H or another substituent, if defined). The nitrogen and sulfur heteroatoms may optionally be oxidized (i.e., N→O and $S(O)_p$) and the nitrogen atoms may optionally be quaternized.

Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero, one, two or three substituents.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxazolyl, benzothienyl, quinolinyl, dihydroisoquinolinyl, tetrahydroquinolinyl, isoquinolinyl, benzimidazolyl, benzopyranyl, benzoxazinyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, and the like.

Exemplary tricyclic heteroaryl groups include carbazolyl, benzidolyl, phenanthrollinyl, acridinyl, phenanthridinyl, xanthenyl and the like.

The term "heteroatoms" shall include oxygen, sulfur and nitrogen.

As referred to herein, the term "substituted" means that one or more hydrogen atoms is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

When any variable occurs more than one time in any constituent or formula for a compound, its definition at each occurrence is independent of its definition at every other occurrence. Thus, for example, if a group is shown to be substituted with 0-3 $R_e$, then said group may optionally be substituted with up to three $R_e$ groups and $R_e$ at each occurrence is selected independently from the definition of $R_e$. Also, combinations of substituents and/or variables are permissible only if such combinations result in stable compounds.

UTILITY

The compounds of the invention may be used to modulate kinase activities.

Applicants have discovered that compounds of Formulae (I)-(VI) have particular utility in treating proliferative conditions associated with the modulation of kinase activity, and particularly the inhibition of serine/threonine kinase activities. The compounds of the present invention can be used to treat proliferative disorders associated with abnormal kinase activity. As used herein, the terms "treating" and "treatment" encompass either or both responsive and prophylaxis measures, e.g., measures designed to inhibit or delay the onset of the disease or disorder, achieve a full or partial reduction of the symptoms or disease state, and/or to alleviate, ameliorate, lessen, or cure the disease or disorder and/or its symptoms.

Accordingly, one aspect of the invention is the use of a compound of the Formulae (I)-(VI), or a pharmaceutically acceptable salt thereof in the manufacture of a medicament for use in the production of an antiproliferative effect in a warm-blooded animal such as a human being.

According to a further feature of the invention there is provided a method for producing an antiproliferative effect in a warm-blooded animal, such as a human being, in need of such treatment which comprises administering to said animal an effective amount of a compound of Formulae (I)-(VI) or a pharmaceutically acceptable salt thereof as defined herein before.

The anti-proliferative treatment defined herein before may be applied as a sole therapy or may involve, in addition to a compound of the invention, one or more other substances and/or treatments. Such treatment may be achieved by way of the simultaneous, sequential or separate administration of the individual components of the treatment. The compounds of this invention may also be useful in combination with known anti-cancer and cytotoxic agents and treatments, including radiation. Compounds of Formulae (I)-(VI) may be used sequentially with known anticancer or cytotoxic agents and treatment, including radiation when a combination formulation is inappropriate.

The term "anti-cancer" agent includes any known agent that is useful for the treatment of cancer including the following: 17α-ethinylestradiol, diethylstilbestrol, testosterone, prednisone, fluoxymesterone, dromostanolone propionate, testolactone, megestrolacetate, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, ZOLADEX®; matrix metalloproteinase inhibitors; VEGF inhibitors, such as anti-VEGF antibodies (AVASTIN®) and small molecules such as ZD6474 and SU6668; Vatalanib, BAY-43-9006, SU11248, CP-547632, and CEP-7055; HER 1 and HER 2 inhibitors including anti-HER2 antibodies (HERCEPTIN®); EGFR inhibitors including gefitinib, erlotinib, ABX-EGF, EMD72000, 11F8, and cetuximab; Eg5 inhibitors, such as SB-715992, SB-743921, and MKT-833; pan Her inhibitors, such as canertinib, EKB-569, CI-1033, AEE-788, XL-647, mAb 2C4, and GW-572016; Src inhibitors, e.g., GLEEVEC® and dasatinib; CASODEX® (bicalutamide, Astra Zeneca), Tamoxifen; MEK-1 kinase inhibitors, MAPK kinase inhibitors, PI3 kinase inhibitors; PDGF inhibitors, such as imatinib; anti-angiogenic and anti-vascular agents which, by interrupting blood flow to solid tumors, render cancer cells quiescent by depriving them of nutrition; castration, which renders androgen dependent carcinomas non-proliferative; inhibitors of non-receptor and receptor tyrosine kinases; inhibitors of integrin signaling; tubulin acting agents such as vinblastine, vincristine, vinorelbine, vinflunine, paclitaxel, docetaxel, 7-O-methylthiomethylpaclitaxel, 4-desacetyl-4-methylcarbonatepaclitaxel, 3'-tert-butyl-3'-N-tert-butyloxycarbonyl-4-deacetyl-3'-dephenyl-3'-N-debenzoyl-4-O-methoxycarbonyl-paclitaxel, C-4 methyl carbonate paclitaxel, epothilone A, epothilone B, epothilone C, epothilone D, [1S-[1R*,3R*(E),7R*,10S*, 11R*,12R*,16S*]]-7-11-dihydroxy-8,8,10,12,16-pentamethyl-3-[1-methyl-2-(2-methyl-4-thiazolyl)ethenyl]-4-aza-17 oxabicyclo[14.1.0]heptadecane-5,9-dione (ixabepilone), [1S-[1R*,3R*(E),7R*,10S*,11R*,12R*,16S*]]-3-[2-[2-(aminomethyl)-4-thiazolyl]-1-methylethenyl]-7,11-dihydroxy-8,8,10,12,16-pentamethyl-4-17-dioxabicyclo [14.1.0]-heptadecane-5,9-dione, and derivatives thereof; other CDK inhibitors, antiproliferative cell cycle inhibitors, epidophyllotoxin, etoposide, VM-26; antineoplastic enzymes, e.g., topoisomerase I inhibitors, camptothecin, topotecan, SN-38; procarbazine; mitoxantrone; platinum coordination complexes such as cisplatin, carboplatin and oxaliplatin; biological response modifiers; growth inhibitors; antihormonal therapeutic agents; leucovorin; tegafur; antimetabolites such as purine antagonists (e.g., 6-thioguanine and 6-mercaptopurine; glutamine antagonists, e.g., DON (AT-125; d-oxo-norleucine); ribonucleotide reductase inhibitors; mTOR inhibitors; and haematopoietic growth factors.

Additional cytotoxic agents include, cyclophosphamide, doxorubicin, daunorubicin, mitoxanthrone, melphalan, hexamethyl melamine, thiotepa, cytarabin, idatrexate, trimetrexate, dacarbazine, L-asparaginase, bicalutamide, leuprolide, pyridobenzoindole derivatives, interferons, and interleukins.

In the field of medical oncology it is normal practice to use a combination of different forms of treatment to treat each patient with cancer. In medical oncology the other component(s) of such treatment in addition to the antiproliferative treatment defined herein may be surgery, radiotherapy or chemotherapy. Such chemotherapy may cover three main categories of therapeutic agent:

(i) antiangiogenic agents that work by different mechanisms from those defined herein before (for example, linomide, inhibitors of integrin αvβ3 function, angiostatin, razoxane);

(ii) cytostatic agents such as antiestrogens (for example, tamoxifen, toremifene, raloxifene, droloxifene, iodoxifene), progestogens (for example, megestrol acetate), aromatase inhibitors (for example, anastrozole, letrozole, borazole, exemestane), antihormones, antiprogestogens, antiandrogens (for example, flutamide, nilutamide, bicalutamide, cyproterone acetate), LHRH agonists and antagonists (for example, gosereline acetate, leuprolide), inhibitors of testosterone 5α-dihydroreductase (for example, finasteride), farnesyltransferase inhibitors, anti-invasion agents (for example, metalloproteinase inhibitors such as marimastat and inhibitors of urokinase plasminogen activator receptor function) and inhibitors of growth factor function, (such growth factors include for example, EGF, FGF, platelet derived growth factor and hepatocyte growth factor, such inhibitors include growth factor antibodies, growth factor receptor antibodies such as AVASTIN® (bevacizumab) and ERBITUX® (cetuximab); tyrosine kinase inhibitors and serine/threonine kinase inhibitors); and (iii) antiproliferative/antineoplastic drugs and combinations thereof, as used in medical oncology, such as antimetabolites (for example, antifolates such as methotrexate, fluoropyrimidines such as 5-fluorouracil, purine and adenosine analogues, cytosine arabinoside); intercalating antitumor antibiotics (for example, anthracyclines such as doxorubicin, daunomycin, epirubicin and idarubicin, mitomycin-C, dactinomycin, mithramycin); platinum derivatives (for example, cisplatin, carboplatin); alkylating agents (for example, nitrogen mustard, melphalan, chlorambucil, busulphan, cyclophosphamide, ifosfamide, nitrosoureas, thiotepa; antimitotic agents (for example, vinca alkaloids like vincristine, vinorelbine, vinblastine and vinflunine) and taxoids such as TAXOL® (paclitaxel), Taxotere (docetaxel) and newer microbtubule agents such as epothilone analogs (ixabepilone), discodermolide analogs, and eleutherobin analogs; topoisomerase inhibitors (for example, epipodophyllotoxins such as etoposide and teniposide, amsacrine, topotecan, irinotecan); cell cycle inhibitors (for example, flavopyridols);

biological response modifiers and proteasome inhibitors such as VELCADE® (bortezomib).

As stated above, the Formulae (I)-(VI) compounds of the invention are of interest for their antiproliferative effects. Such compounds of the invention are expected to be useful in a wide range of disease states including cancer, psoriasis, and rheumatoid arthritis.

More specifically, the compounds of Formulae (I)-(VI) are useful in the treatment of a variety of cancers, including (but not limited to) the following:

carcinoma, including that of the prostate, pancreatic ductal adenocarcinoma, breast, colon, lung, ovary, pancreas, and thyroid;

tumors of the central and peripheral nervous system, including neuroblastoma, glioblastoma, and medulloblastoma; and other tumors, including melanoma and multiple myeloma.

Due to the key role of kinases in the regulation of cellular proliferation in general, inhibitors could act as reversible cytostatic agents which may be useful in the treatment of any disease process which features abnormal cellular proliferation, e.g., benign prostate hyperplasia, familial adenomatosis polyposis, neurofibromatosis, pulmonary fibrosis, arthritis, psoriasis, glomerulonephritis, restenosis following angioplasty or vascular surgery, hypertrophic scar formation and inflammatory bowel disease.

The compounds of Formulae (I)-(VI) are especially useful in treatment of tumors having a high incidence of serine/threonine kinase activity, such as prostate, colon, lung, brain, thyroid and pancreatic tumors. Additionally, the compounds of the invention may be useful in treatment of sarcomas and pediatric sarcomas. By the administration of a composition (or a combination) of the compounds of this invention, development of tumors in a mammalian host is reduced.

Compounds of Formulae (I)-(VI) may also be useful in the treatment of other cancerous diseases (such as acute myelogenous leukemia) that may be associated with signal transduction pathways operating through kinases such as DYRK1a, CDK, and GSK3β. The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

Accordingly, the present invention further includes compositions comprising one or more compounds of Formulae (I)-(VI) and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences*, 17th Edition (1985), which is incorporated herein by reference in its entirety.

The pharmaceutical compositions of the invention containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

The pharmaceutical compositions may be in the form of sterile injectable aqueous solutions. Among the acceptable vehicles and solvents that may be employed are water, Ringer's solution and isotonic sodium chloride solution. The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS® Model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above.

The compounds of Formulae (I)-(VI) may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; buccally; parenterally, such as by subcutaneous, intravenous, intramuscular or intrasternal injection or infusion techniques (e.g., as sterile injectable aq. or non-aq. solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as Plastibase (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., Gantrez); and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

When a compound according to this invention is administered into a human subject, the daily dosage will normally be determined by the prescribing physician with the dosage generally varying according to the age, weight, sex and response of the individual patient, as well as the severity of the patient's symptoms. Exemplary dosage amounts for a mammal may include from about 0.05 to 1000 mg/kg; 1-1000 mg/kg; 1-50 mg/kg; 5-250 mg/kg; 250-1000 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species, that are affected by mediation of protein kinase enzyme levels.

If formulated as a fixed dose, a combination product can, for example, utilize a dosage of the compound of Formulae (I)-(VI) within the dosage range described above and the dosage of another anti-cancer agent/treatment within the approved dosage range for such known anti-cancer agent/treatment. If a combination product is inappropriate, the compounds of Formulae (I)-(VI) and the other anti-cancer agent/treatment can, for example, be administered simultaneously or sequentially. If administered sequentially, the present invention is not limited to any particular sequence of administration. For example, compounds of Formulae (I)-(VI) can be administered either prior to, or after, administration of the known anti-cancer agent or treatment.

BIOLOGICAL ASSAYS

CK1ε and CK1δ Kinase Assays

The kinase assay was performed in V-bottom 384-well plates. The final assay volume was 30 µl prepared from 15 µl additions of enzyme, substrates (fluoresceinated peptide FL-AHA-KRRRAL-PSER-VASLPGL-OH and ATP) and test compounds in assay buffer (20 mM HEPES pH 7.4, 30 mM $MgCl_2$, 0.015% Brij35 and 4 mM DTT). The reaction was incubated at room temperature for 22 hours and terminated by adding 45 µl of 35 mM EDTA to each sample. The reaction mixture was analyzed on the Caliper LABCHIP®3000 (Caliper, Hopkinton, Mass.) by electrophoretic separation of the unphosphorylated substrate and phosphorylated product. Inhibition data were calculated by comparison of the no enzyme control reactions for 100% inhibition and vehicle-only reactions for 0% inhibition. The final concentration of reagents in the assay were 200 pM CK1ε or CK1δ, 50 µM ATP, 1.5 µM FL-AHA-KRRRAL-PSER-VASLPGL-OH, and 1.6% DMSO. Dose response curves were generated to determine the concentration required to inhibit 50% of the kinase activity ($IC_{50}$). Compounds were dissolved at 10 mM in dimethylsulfoxide (DMSO) and evaluated at eleven concentrations. $IC_{50}$ values were derived by non-linear regression analysis.

The $IC_{50}$ values of some representative compounds obtained from the assays described above are shown in Table A.

TABLE A

| Example No. | CK1ε (µM) | CK1δ (µM) |
|---|---|---|
| 1 | 0.0903 | 0.0278 |
| 4 | 0.0381 | 0.0109 |
| 6 | 0.0072 | 0.0024 |
| 61 | 0.0050 | 0.0026 |
| 92 | 2.0000 | 0.4455 |
| 103 | 0.5406 | 0.0706 |
| 104 | 0.0013 | 0.0007 |
| 106 | 0.0293 | 0.0087 |
| 107 | 0.4001 | 0.1049 |
| 108 | 0.0024 | 0.0009 |

TABLE A-continued

| Example No. | CK1ε (μM) | CK1δ (μM) |
|---|---|---|
| 110 | 0.1556 | 0.0839 |
| 114 | 0.0430 | 0.0125 |
| 116 | 0.0798 | 0.0182 |
| 124 | 0.1177 | 0.1719 |
| 126 | 0.8441 | 0.4421 |
| 127 | 0.4439 | 0.3568 |
| 130 | 0.0895 | 0.0964 |
| 142 | 2.0000 | 0.8938 |
| 143 | 0.0333 | 0.0042 |
| 145 | 1.8160 | 1.0530 |
| 151 | 0.1791 | 0.1220 |
| 154 | 0.0277 | 0.0243 |
| 166 | 0.0003 | 0.0003 |
| 248 | 0.0004 | 0.0015 |
| 258 | 0.0007 | 0.0005 |
| 291 | 0.0014 | 0.0009 |
| 297 | 0.0003 | 0.0005 |
| 349 | 0.0201 | 0.0342 |
| 352 | 0.0198 | 0.0181 |
| A30 | 0.0001 | 0.0003 |

The biological activity of the exemplified compounds of this invention determined by the assays described above is shown in Table B. $IC_{50}$ ranges against CK1ε and CK1δ are as follows: A=0.01-10 nM; B=10.01-100 nM; C=100.01-2000 nM.

TABLE B

| Example No. | CK1ε | CK1δ |
|---|---|---|
| 1 | B | B |
| 2 | B | B |
| 3 | B | A |
| 4 | B | B |
| 5 | B | B |
| 6 | A | A |
| 7 | B | B |
| 8 | B | B |
| 9 | A | A |
| 10 | A | A |
| 11 | B | B |
| 12 | C | B |
| 13 | B | A |
| 14 | B | B |
| 15 | C | B |
| 16 | A | A |
| 17 | B | A |
| 18 | C | B |
| 19 | A | A |
| 20 | B | B |
| 21 | A | A |
| 22 | A | A |
| 23 | A | — |
| 24 | B | B |
| 25 | B | A |
| 26 | B | B |
| 27 | B | B |
| 28 | B | B |
| 29 | B | A |
| 30 | B | B |
| 31 | A | A |
| 32 | B | B |
| 33 | B | A |
| 34 | B | A |
| 35 | A | A |
| 36 | B | A |
| 37 | A | A |
| 38 | A | A |
| 39 | B | A |
| 40 | C | B |
| 41 | A | A |
| 42 | C | B |
| 43 | B | B |
| 44 | B | A |
| 45 | A | A |
| 46 | B | A |
| 47 | C | B |
| 48 | C | B |
| 49 | A | A |
| 50 | A | A |
| 51 | A | A |
| 52 | B | B |
| 53 | A | A |
| 54 | A | A |
| 55 | A | A |
| 56 | A | A |
| 57 | C | B |
| 58 | A | A |
| 59 | A | A |
| 60 | A | A |
| 61 | A | A |
| 62 | A | A |
| 63 | A | A |
| 64 | B | B |
| 65 | C | C |
| 66 | B | A |
| 67 | A | A |
| 68 | B | A |
| 69 | A | A |
| 70 | A | A |
| 71 | A | A |
| 72 | A | A |
| 73 | A | A |
| 74 | A | A |
| 75 | B | B |
| 76 | A | A |
| 77 | A | A |
| 78 | A | A |
| 79 | A | A |
| 80 | A | A |
| 81 | A | A |
| 82 | A | A |
| 83 | B | C |
| 84 | B | A |
| 85 | A | A |
| 86 | B | A |
| 87 | B | A |
| 88 | B | B |
| 89 | B | A |
| 90 | B | A |
| 91 | C | B |
| 92 | C | C |
| 93 | A | A |
| 94 | A | A |
| 95 | A | A |
| 96 | B | B |
| 97 | B | A |
| 98 | A | A |
| 99 | A | A |
| 100 | A | A |
| 101 | A | A |
| 102 | B | A |
| 103 | C | B |
| 104 | A | A |
| 105 | B | A |
| 106 | B | A |
| 107 | C | B |
| 108 | A | A |
| 109 | A | A |
| 110 | C | B |
| 111 | C | C |
| 112 | C | B |
| 113 | C | B |
| 114 | B | B |
| 115 | C | B |
| 116 | B | B |
| 117 | A | A |
| 118 | C | C |
| 119 | A | A |
| 120 | C | B |
| 121 | C | B |
| 122 | C | C |

TABLE B-continued

| Example No. | CK1ε | CK1δ |
|---|---|---|
| 123 | C | B |
| 124 | C | C |
| 125 | C | C |
| 126 | C | C |
| 127 | C | C |
| 128 | A | B |
| 129 | A | A |
| 130 | B | B |
| 131 | C | C |
| 132 | C | C |
| 133 | C | C |
| 134 | C | C |
| 135 | C | C |
| 136 | C | C |
| 137 | B | A |
| 138 | C | C |
| 139 | C | B |
| 140 | C | C |
| 141 | C | C |
| 142 | C | C |
| 143 | B | A |
| 144 | C | C |
| 145 | C | C |
| 146 | C | C |
| 147 | C | C |
| 148 | A | A |
| 149 | C | B |
| 150 | B | A |
| 151 | C | C |
| 152 | A | A |
| 153 | C | C |
| 154 | B | B |
| 155 | C | C |
| 156 | A | A |
| 157 | A | A |
| 158 | A | A |
| 159 | A | A |
| 160 | A | A |
| 161 | A | A |
| 162 | A | A |
| 163 | A | A |
| 164 | A | A |
| 165 | A | A |
| 166 | A | A |
| 167 | A | A |
| 168 | A | A |
| 169 | A | A |
| 170 | A | A |
| 171 | A | A |
| 172 | A | A |
| 173 | A | A |
| 174 | A | A |
| 175 | A | A |
| 176 | A | A |
| 177 | A | A |
| 178 | A | A |
| 179 | A | A |
| 180 | A | A |
| 181 | A | A |
| 182 | A | A |
| 183 | A | A |
| 184 | A | A |
| 185 | A | A |
| 186 | A | A |
| 187 | A | A |
| 188 | A | A |
| 189 | A | A |
| 190 | A | A |
| 191 | A | A |
| 192 | A | A |
| 193 | A | A |
| 194 | A | A |
| 195 | A | A |
| 196 | A | A |
| 197 | A | A |
| 198 | A | A |
| 199 | A | A |
| 200 | A | A |
| 201 | A | A |
| 202 | A | A |
| 203 | A | A |
| 204 | A | A |
| 205 | A | A |
| 206 | A | A |
| 207 | A | A |
| 208 | A | A |
| 209 | A | A |
| 210 | A | A |
| 211 | A | A |
| 212 | A | A |
| 213 | B | B |
| 214 | B | B |
| 215 | B | A |
| 216 | C | B |
| 217 | C | B |
| 218 | B | A |
| 219 | B | B |
| 220 | A | A |
| 221 | A | A |
| 222 | A | A |
| 223 | A | A |
| 224 | A | A |
| 225 | A | A |
| 226 | A | A |
| 227 | A | A |
| 228 | A | A |
| 229 | A | A |
| 230 | A | A |
| 231 | A | A |
| 232 | A | A |
| 233 | A | A |
| 234 | A | A |
| 235 | A | A |
| 236 | A | A |
| 237 | A | A |
| 238 | A | A |
| 239 | A | A |
| 240 | A | A |
| 241 | A | A |
| 242 | A | A |
| 243 | A | A |
| 244 | A | A |
| 245 | A | A |
| 246 | A | A |
| 247 | A | A |
| 248 | A | A |
| 249 | A | A |
| 250 | A | A |
| 251 | A | A |
| 252 | A | A |
| 253 | A | A |
| 254 | A | A |
| 255 | A | A |
| 256 | A | A |
| 257 | A | A |
| 258 | A | A |
| 259 | A | A |
| 260 | A | A |
| 261 | A | A |
| 262 | A | A |
| 263 | A | A |
| 264 | A | A |
| 265 | A | A |
| 266 | A | A |
| 267 | A | A |
| 268 | — | A |
| 269 | A | A |
| 270 | A | A |
| 271 | A | A |
| 272 | A | A |
| 273 | A | A |
| 274 | A | A |
| 275 | A | A |
| 276 | A | A |
| 277 | A | A |
| 278 | A | A |

TABLE B-continued

| Example No. | CK1ε | CK1δ |
|---|---|---|
| 279 | A | A |
| 280 | A | A |
| 281 | A | A |
| 282 | — | A |
| 283 | A | A |
| 284 | A | A |
| 285 | A | A |
| 286 | A | A |
| 287 | A | A |
| 288 | A | A |
| 289 | — | — |
| 290 | — | — |
| 291 | A | A |
| 292 | B | B |
| 293 | A | A |
| 294 | A | A |
| 295 | A | A |
| 296 | A | A |
| 297 | A | A |
| 298 | A | A |
| 299 | A | A |
| 300 | A | A |
| 301 | A | A |
| 302 | — | — |
| 303 | A | A |
| 304 | A | A |
| 305 | A | A |
| 306 | A | A |
| 307 | A | A |
| 308 | A | A |
| 309 | A | A |
| 310 | A | A |
| 311 | A | A |
| 312 | A | A |
| 313 | A | A |
| 314 | A | A |
| 315 | A | A |
| 316 | A | A |
| 317 | A | A |
| 318 | A | A |
| 319 | A | A |
| 320 | A | A |
| 321 | A | A |
| 322 | A | A |
| 323 | A | A |
| 324 | A | A |
| 325 | A | A |
| 326 | A | A |
| 327 | A | A |
| 328 | A | A |
| 329 | A | A |
| 330 | A | A |
| 331 | A | A |
| 332 | A | A |
| 333 | A | A |
| 334 | A | A |
| 335 | A | A |
| 336 | — | — |
| 337 | — | A |
| 338 | A | A |
| 339 | A | A |
| 340 | B | A |
| 341 | A | B |
| 342 | B | B |
| 343 | A | A |
| 344 | A | A |
| 345 | A | A |
| 346 | C | C |
| 347 | A | B |
| 348 | B | C |
| 349 | B | B |
| 350 | C | — |
| 351 | A | A |
| 352 | B | B |
| 353 | A | A |
| 354 | A | A |
| A1 | A | A |
| A2 | A | A |
| A3 | A | A |
| A4 | A | A |
| A5 | A | A |
| A6 | A | A |
| A7 | A | A |
| A8 | A | A |
| A9 | A | A |
| A10 | A | A |
| A11 | A | A |
| A12 | A | B |
| A13 | A | A |
| A14 | A | A |
| A15 | A | A |
| A16 | A | B |
| A17 | B | B |
| A18 | A | A |
| A19 | B | B |
| A20 | A | A |
| A21 | A | B |
| A22 | A | A |
| A23 | B | C |
| A24 | B | C |
| A25 | A | A |
| A26 | A | A |
| A27 | A | A |
| A28 | A | A |
| A29 | A | A |
| A30 | A | A |
| A31 | B | B |
| A32 | A | A |
| A33 | A | A |
| A34 | A | A |
| A35 | A | A |
| A36 | A | A |
| A37 | A | B |
| A38 | A | A |
| A39 | A | A |
| A40 | A | A |
| A41 | A | A |
| A42 | A | A |
| A43 | A | A |
| A44 | A | A |
| A45 | A | A |
| A46 | A | A |
| A47 | A | A |
| A48 | A | A |
| A49 | A | A |
| A50 | A | A |
| A51 | A | A |
| A52 | A | A |
| A53 | A | A |
| A54 | A | A |
| A55 | A | A |
| A56 | A | A |
| A57 | A | A |
| A58 | A | A |
| A59 | A | A |
| A60 | A | A |
| A61 | A | A |
| A62 | A | A |
| A63 | A | A |
| A64 | A | A |
| A65 | A | A |
| A66 | A | A |
| A67 | A | A |
| A68 | A | A |
| A69 | A | A |
| A70 | A | A |
| A71 | A | A |
| A72 | A | A |
| A73 | A | A |
| A74 | A | A |
| A75 | A | A |
| A76 | A | A |
| A77 | A | A |
| A78 | A | A |
| A79 | A | A |
| A80 | A | A |

TABLE B-continued

| Example No. | CK1ε | CK1δ |
|---|---|---|
| A81 | A | A |
| A82 | A | A |
| A83 | A | A |
| A84 | A | A |
| A85 | A | A |
| A86 | A | A |
| A87 | A | A |
| A88 | A | A |
| A89 | A | A |
| A90 | A | A |
| A91 | A | A |
| A92 | A | A |
| A93 | A | A |
| A94 | A | A |
| A95 | B | A |
| A96 | A | A |
| A97 | — | A |
| A98 | A | A |
| A99 | — | A |
| A100 | A | B |
| A101 | A | A |
| A102 | A | A |
| A103 | A | A |
| A104 | A | A |
| A105 | — | A |
| A106 | C | C |
| A107 | A | A |
| A108 | B | B |
| A109 | A | A |
| A110 | A | A |
| A111 | A | A |
| A112 | A | A |
| A113 | A | A |
| A114 | A | A |
| A115 | A | A |
| A116 | A | A |
| A117 | B | C |
| A118 | A | A |
| A119 | B | B |
| A120 | A | A |
| A121 | B | C |
| A122 | A | A |
| A123 | — | B |
| A124 | — | A |
| A125 | B | B |
| A126 | A | A |
| A127 | B | C |
| A128 | — | A |
| A129 | A | A |
| A130 | A | A |
| A131 | B | B |
| A132 | A | A |
| A133 | A | A |
| A134 | A | A |
| A135 | A | A |
| A136 | A | A |
| A137 | A | A |
| A138 | A | A |
| A139 | A | A |
| A140 | A | A |

METHODS OF PREPARATION

The compounds of the present invention may be prepared by methods such as those illustrated in the following schemes. Solvents, temperatures, pressures, and other reaction conditions may readily be selected by one of ordinary skill in the art. Starting materials are commercially available or readily prepared by one of ordinary skill in the art. These schemes are illustrative and are not meant to limit the possible techniques one skilled in the art may use to manufacture compounds disclosed herein. Different methods may be evident to those skilled in the art. Additionally, the various steps in the synthesis may be performed in an alternate sequence or order to give the desired compound(s). All documents cited herein are incorporated herein by reference in their entirety.

In general, the time taken to complete a reaction procedure will be judged by the person performing the procedure, preferably with the aid of information obtained by monitoring the reaction by methods such as HPLC or TLC. A reaction does not have to go to completion to be useful to this invention. The methods for the preparation of various heterocycles used to this invention can be found in standard organic reference books, for example, Katritzky, A. R. et al., eds., *Comprehensive Heterocyclic Chemistry, The Structure, Reactions, Synthesis and Uses, of Heterocyclic Compounds*, First Edition, Pergamon Press, New York (1984), and Katritzky, A. R. et al., eds., *Comprehensive Heterocyclic Chemistry II, A Review of the Literature 1982-1995: The Structure, Reactions, Synthesis and Uses, of Heterocyclic Compounds*, Pergamon Press, New York (1996).

Unless otherwise specified, the various substituents of the compounds are defined in the same manner as the Formula (I) compound of the invention.

HPLC Methods: Analytical HPLC/LC-MS retention time reported for each Example and Intermediate uses one of the following general analytical HPLC/LC-MS methods:

Method A: SunFire C18 (4.6×150) mm, 3.5μ column; flow rate 1 mL/min; gradient time 15 min; 10% Solvent B to 100% Solvent B; monitoring at 254 nm and 220 nm (Solvent A: 5% Acetonitrile, 95% water, 0.05% TFA; Solvent B: 95% Acetonitrile, 5% water, 0.05% TFA).

Method B: XBridge Phenyl (4.6×150) mm, 3.5μ, column; flow rate 1 mL/min; gradient time 15 min; 10% Solvent B to 100% Solvent B; monitoring at 254 nm and 220 nm (Solvent A: 5% Acetonitrile, 95% water, 0.05% TFA; Solvent B: 95% Acetonitrile, 5% water, 0.05% TFA).

Method C: SunFire C18 (4.6×150) mm, 3.5μ column; flow rate 1 mL/min; gradient time 23 min; 100% Solvent A to 100% Solvent B and holding 100% Solvent B for 5 min. Monitoring at 254 nm and 220 nm (Solvent A: 5% Acetonitrile, 95% water, 0.05% TFA; Solvent B: 95% Acetonitrile, 5% water, 0.05% TFA).

Method D: XBridge Phenyl (4.6×150) mm, 3.5μ column; flow rate 1 mL/min; gradient time 23 mM; 100% Mobile Phase A to 100% Mobile Phase B and holding 100% Solvent B for 5 min. Monitoring at 254 nm and 220 nm (Solvent A: 5% Acetonitrile, 95% water, 0.05% TFA; Solvent B: 95% Acetonitrile, 5% water, 0.05% TFA).

Method E: Column: Ascentis Express C18 (50×2.1) mm, 2.7 μm; flow rate 1.1 mL/min; gradient time 3 min; Temperature: 50° C., 0% Solvent B to 100% Solvent B; monitoring at 220 nm (Solvent A: 95% water: 5% Acetonitrile; 10 mM $NH_4OAc$; Solvent B: 5% water: 95% Acetonitrile; 10 mM $NH_4OAc$).

Method F: SunFire C 18 (4.6×150) mm, 3.5μ column, flow rate 1 mL/min; gradient time 23 mM; 10% Solvent B to 100% Solvent B; monitoring at 254 nm to 220 nm (Solvent A: 5% Acetonitrile, 95% water, 0.05% TFA; Solvent B: 95% Acetonitrile, 5% water, 0.05% TFA).

Method G: XBridge Phenyl (4.6×150) mm, 3.5μ column, flow rate 1 mL/min; gradient time 23 min; 10% Solvent B to 100% Solvent B; monitoring at 254 nm to 220 nm (Solvent A: 5% Acetonitrile, 95% water, 0.05% TFA; Solvent B: 95% Acetonitrile, 5% water, 0.05% TFA).

Method H: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min.

Method I: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow rate: 0.5 mL/min.

Method J: Column: Ascentis Express C18 (50×4.6) mm, 2.7 μm, flow rate 4 mL/min; gradient: 0 to 100% Solvent B over 4 min; Temperature: 50° C. Monitoring at 220 nm (Solvent A: 95:05 water: $CH_3CN$ with 10 mM $NH_4OAc$ and Solvent B: 05:95 water: $CH_3CN$ with 10 mM $NH_4OAc$).

Method K: Column: Ascentis Express C18 (50×4.6) mm, 2.7 μm, flow rate 4 mL/min; gradient: 0 to 100% Solvent B over 4 min; Temperature: 50° C.; monitoring at 220 nm (Solvent A: 95:05 water: $CH_3CN$ with 0.1% TFA and Solvent B: 05:95 water: $CH_3CN$ with 0.1% TFA).

Method L: Column: Ascentis Express C18 (50×2.1) mm, 2.7 μm, flow rate 1.1 mL/min; gradient: 0 to 100% Solvent B over 3 min; Temperature: 50° C.; monitoring at 220 nm (Solvent A: 95:05 water: $CH_3CN$ with 0.1% TFA and Solvent B: 05:95 water: $CH_3CN$ with 0.1% TFA).

Method M: SunFire C18 (4.6×150) mm, 5μ column; flow rate 1 mL/min; gradient time 15 min; 10% Solvent B to 100% Solvent B; monitoring at 254 nm and 220 nm (Solvent A: 5% Acetonitrile, 95% water, 0.05% TFA; Solvent B: 95% Acetonitrile, 5% water, 0.05% TFA).

Method N: Column: Lux Cellulose-4 (250×4.6) mm, 5μ column; flow rate 4 mL/min; Isocratic: 40% Mobile Phase B. Temperature: Ambient at 287 nm (Mobile Phase A: $CO_2$, Mobile Phase B: 0.2% diethylamine in Methanol), Back pressure: 107 bar, Diluents: Methanol.

Method O: Column: WHELK-O® 1 (R,R) (250×4.6) mm, 5μ column; Flow rate 3 mL/min; Isocratic: 25% Mobile Phase B. Temperature: Ambient at 267 nm (Mobile Phase A: $CO_2$, Mobile Phase B: 0.2% diethylamine in Methanol), Back pressure: 100 bar, Diluents: Methanol.

Method P: Column: CHIRALCEL®-OJH (250×4.6) mm, 5μ column; Mobile Phase B: Mobile Phase A (9:1); Mobile Phase B: 0.2% diethylamine in n-Hexane; Mobile Phase A: isopropanol:methanol (1:1); flow rate: 1.0 mL/min Method Q: Column: CHIRALPAK® AD-H (4.6×250) mm, 5μ column, Flow rate: 3 mL/min Isocratic: 30%; Temperature: Ambient at 267 nm (Mobile Phase A: $CO_2$, Mobile Phase B: 0.3% diethylamine in Methanol), Back pressure: 100 bar, Diluents: Methanol.

ABBREVIATIONS

The following abbreviations are used in the example section below and elsewhere herein:
Ac Acetyl
Aq. Aqueous
BAIB bis(acetoxy)iodobenzene
BMS Borane dimethylsulfide
$BH_3$.THF Borane in tetrahydrofuran
Bn Benzyl
$Boc_2O$ Di-tert-butyl dicarbonate
n-BuLi n-Butyllithium
t-BuNCO 2-Isocyanato-2-methylpropane
CAN Ceric ammonium nitrate
CDI 1,1'-Carbonyldiimidazole
DAST Diethylaminosulfur trifluoride
dba Dibenzylideneacetone
DBU 1,8-Diazabicyclo[5.4.0]undec-7-ene
DCM Dichloromethane
DCE 1,2-Dichloroethene
DEAD Diethyl azodicarboxylate
DEOXO-FLUOR® bis(2-methoxyethyl)aminosulfur trifluoride
DIAD Diisopropyl azodicarboxylate
DTBAD Di-tert-butylazodicarboxylate
diglyme 1-Methoxy-2-(2-methoxyethoxyl)ethane
DIPEA or Diisopropylethylamine Hunig's base
DMAP 4-Dimethylaminopyridine
DMF Dimethyl formamide
DMSO Dimethylsulfoxide
DPPA Diphenylphosphoryl azide
dppf 1,1'-Bis(diphenylphosphino)ferrocene
EtOAc Ethyl acetate
EtOH Ethanol
EtI Iodoethane
HATU (O-(7-azabenzotriazol-1-yl)-N,N,N',$N^1$-tetramethyluronium hexafluorophosphate)
HPLC High-performance liquid chromatography
KHDMS Potassium bis(trimethylsilyl)amide
LAH lithium diisopropylamide
LDA Lithium aluminiumhydride
LHMDS Lithium bis(trimethylsilyl)amide
MeOH Methanol
MeI Iodomethane
Ms Methanesulfonyl
NBS N-Bromosuccinimide
NHDMS Sodium hexamethyldisilizide
NIS N-Iodosuccinimide
NMP N-Methyl-2-pyrrolidone
$PPh_3$ or TPP Triphenylphosphine
$Pd(PPh_3)_4$ Tetrakis(triphenylphosphine)palladium(o)
$Pd_2(dba)_3$ Tris(dibenzylideneacetone)dipalladium(0)
$PdCl_2(dppf)$ [1,1'-Bis(diphenylphosphino)ferrocene]dichloropalladium(II)
PTSA p-Toluenesulfonic acid
Py Pyridine
Ret. Time or $r_t$ Retention Time
RT Room Temperature
SFC Supercritical fluid chromatography
SUPER-HYDRIDE® Lithium triethylborohydride
TBAF Tetrabutylammonium fluoride
TLC Thin layer chromatography
TEMPO 2,2,6,6-Tetramethylpiperidinyloxy
TEA or $Et_3N$ Triethylamine
TFA Trifluoroacetic acid
$Tf_2O$ Trifluoromethanesulfonic anhydride
THF Tetrahydrofuran
TBSCl or TBDMS-Cl tert-Butyldimethylsilyl chloride
$TMSCF_3$ Trifluoromethyltrimethylsilane
TMSCN Trimethylsilyl cyanide
TBAI Tetrabutylammonium iodide
Ts-Cl p-Toluenesulfonyl chloride Scheme 1

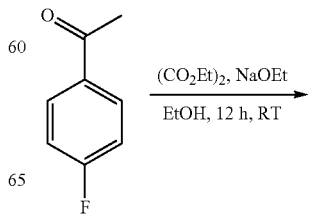

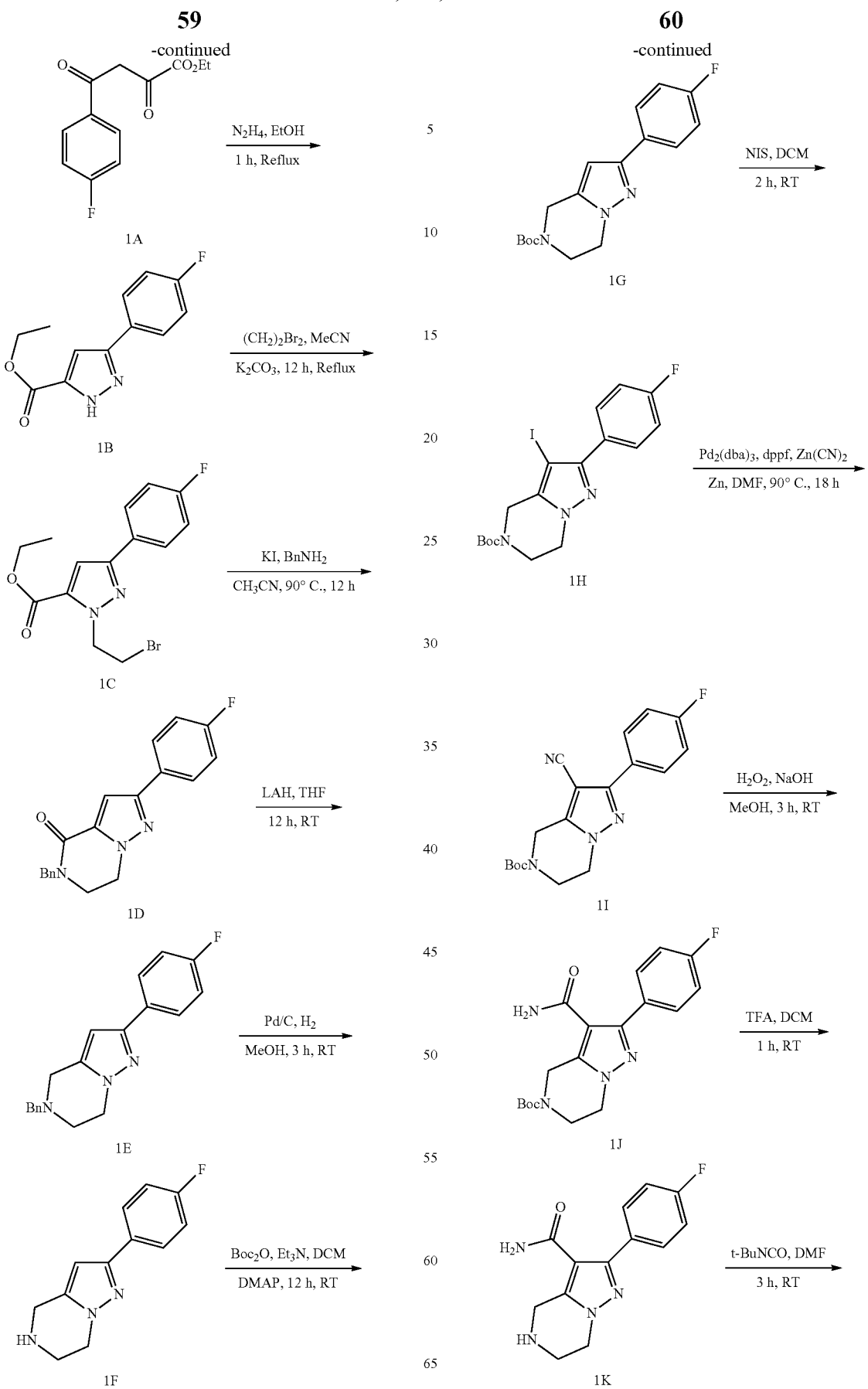

-continued

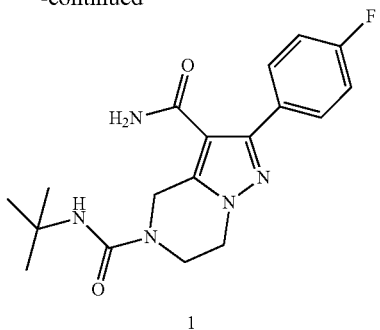

1

Intermediate 1A: Ethyl 4-(4-fluorophenyl)-2,4-dioxobutanoate

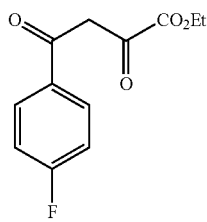 [SMILES: CCOC(=O)C(=O)CC(=O)c1ccc(F)cc1]

To a solution of sodium ethoxide (351 mL, 21% in ethanol, 1629 mmol) was added 1-(4-fluorophenyl) ethanone (150 g, 1086 mmol) in ethanol (100 mL) at 0° C. under a nitrogen atmosphere and the resulting reaction mixture was stirred at RT for 10 min Diethyl oxalate (156 mL, 1140 mmol) in ethanol (100 mL) was added and reaction was allowed to stir at RT for 12 h. Reaction mixture was cooled to 0° C. and acidified with 1.5 N HCl and the solid was filtered and the filtrate was diluted with water and extracted with DCM (3×750 mL). The combined organic layer was washed with brine, dried over Na$_2$SO$_4$, filtered and concentrated to afford Intermediate 1A (180 g, 70%) which was taken to next step without further purification. MS(ES): m/z=237 [M–H]$^+$; $^1$H NMR (300 MHz, CDCl$_3$) δ ppm 15.2 (bs, 1H), 8.00-8.09 (m, 2H), 7.15-7.25 (m, 2H), 7.05 (s, 1H), 4.42 (q, J=7.15 Hz, 2H), 1.43 (t, J=7.15 Hz, 3H).

Intermediate 1B: Ethyl 3-(4-fluorophenyl)-1H-pyrazole-5-carboxylate

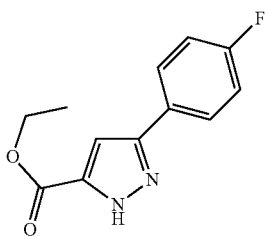 [SMILES: CCOC(=O)c1cc(-c2ccc(F)cc2)n[nH]1]

To a solution of Intermediate 1A (120 g, 504 mmol) in ethanol (1200 mL) was added hydrazine monohydrate (25.7 mL, 529 mmol) slowly and the resulting reaction mixture was refluxed for 1 h. Reaction mixture was cooled to RT, poured into ice cold water, and the resultant solid dried under vacuum to afford Intermediate 1B (80 g, 67%). MS(ES): m/z=235 [M+H]$^+$; $^1$H NMR (300 MHz, CDCl$_3$) δ ppm 7.75 (m, 2H), 7.12 (m, 2H), 7.07 (s, 1H), 4.42 (q, J=7.2 Hz, 2H), 1.42 (t, J=7.2 Hz, 3H).

Intermediate 1C: Ethyl 1-(2-bromoethyl)-3-(4-fluorophenyl)-1H-pyrazole-5-carboxylate

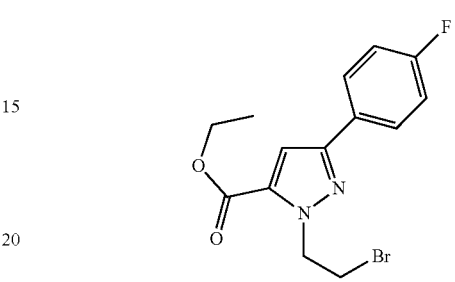

To a solution of Intermediate 1B (135 g, 576 mmol) and potassium carbonate (159 g, 1153 mmol) in acetonitrile (1400 mL) was added 1,2-dibromoethane (59.6 mL, 692 mmol) and the resulting reaction mixture was refluxed for 4 h. Acetonitrile was removed under reduced pressure and the residue was diluted with water. The aqueous layer was extracted with DCM (2×500 mL) The combined organic layer was washed with brine, dried over Na$_2$SO$_4$, filtered and concentrated. The residue was purified by ISCO using 880 g REDISEP® column and 1% methanol in chloroform as eluent. Combined fractions were concentrated to afford Intermediate 1C (90 g, 45%). MS(ES): m/z=343 [M+H]$^+$; $^1$H NMR (400 MHz, DMSO-d$_6$) δ ppm 7.91-7.97 (m, 2H), 7.41 (s, 1H), 7.24-7.30 (m, 2H), 4.96 (t, J=6.34 Hz, 2H), 4.36 (q, J=7.11 Hz, 2H), 3.90 (t, J=6.34 Hz, 2H), 1.35 (t, J=7.12 Hz, 3H).

Intermediate 1D: 5-Benzyl-2-(4-fluorophenyl)-6,7-dihydropyrazolo[1,5-a]pyrazin-4(5H)-one

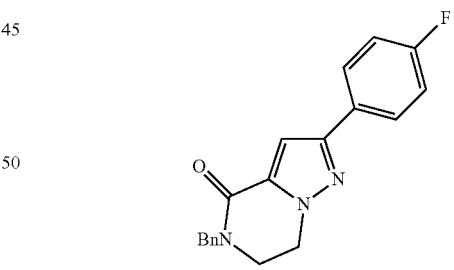

To a solution of Intermediate 1C (80 g, 234 mmol) and potassium iodide (78 g, 469 mmol) in acetonitrile (800 mL) was added benzyl amine (28.2 mL, 258 mmol) and the reaction mixture was stirred at 90° C. for 12 h. Acetonitrile was removed under reduced pressure, crude was diluted with water and the aqueous layer was extracted with DCM (3×500 mL). The combined organic layer washed with brine, dried over Na$_2$SO$_4$, filtered and concentrated. The residue was purified by silica gel chromatography (120 g REDISEP® column, eluting with 1-2% methanol in chloroform). Collected fractions were concentrated together to afford Intermediate 1D (35 g, 46%). MS(ES): m/z=322 [M+H]$^+$; $^1$H NMR (400

MHz, CDCl₃) δ ppm 7.71-7.83 (m, 2H), 7.29-7.42 (m, 5H), 7.14 (s, 1H), 7.06-7.12 (m, 2H), 4.78 (s, 2H), 4.32-4.40 (m, 2H), 3.63-3.75 (m, 2H).

Intermediate 1E: 5-Benzyl-2-(4-fluorophenyl)-4,5,6,7-tetrahydropyrazolo[1,5-a]pyrazine

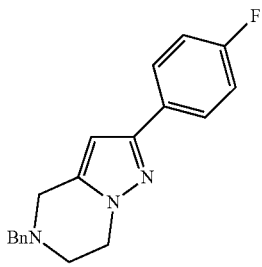 [SMILES: Fc1ccc(-c2cc3n(n2)CCN(Cc2ccccc2)C3)cc1]

To a solution of Intermediate 1D (23.00 g, 71.6 mmol) in THF (230 mL) under N₂ at −10° C. was added LAH (59.6 mL, 2.4 M solution in THF, 143 mmol). Reaction mixture was allowed to stir at room temperature for 12 h. Reaction mixture was quenched with ice-cold water and filtered through CELITE® pad and the filtrate was extracted with chloroform (3×150 mL) The combined organic layer was washed with brine, dried over Na₂SO₄, filtered and concentrated. The residue was triturated with diethyl ether (2×150 mL) and the resulting solid was filtered, rinsed with diethyl ether and dried to afford Intermediate 1E (17 g, 77%). MS(ES): m/z=308 [M+H]⁺; ¹H NMR (300 MHz, CDCl₃) δ ppm 7.67-7.82 (m, 2H), 7.31-7.47 (m, 514), 7.01-7.14 (m, 2H), 6.19 (s, 1H), 4.22 (t, J=4.2 Hz, 2H), 3.73 (s, 2H), 3.70 (s, 2H), 2.97 (t, J=5.6 Hz, 2H).

Intermediate 1F: 2-(4-Fluorophenyl)-4,5,6,7-tetrahydropyrazolo[1,5-a]pyrazine

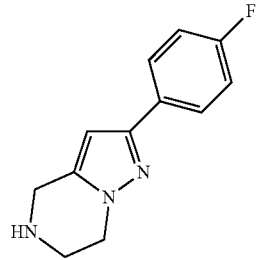 [SMILES: Fc1ccc(-c2cc3n(n2)CCNC3)cc1]

To a degassed solution of Intermediate 1E (17 g, 55.3 mmol) in methanol (170 mL) was added 10% palladium on carbon (2.94 g, 2.77 mmol) and stirred under H₂ atmospheric pressure for 3 h. The reaction mixture was filtered through CELITE® pad, washed with methanol (500 mL) and concentrated. The residue was triturated with diethyl ether (2×100 mL) and the resulting solid was filtered, rinsed with diethyl ether (200 mL) and dried under vacuum to afford Intermediate 1F (9 g, 75%). MS(ES): m/z=218 [M+H]⁺; ¹H NMR (300 MHz, DMSO-d₆) δ ppm 7.73-7.87 (m, 2H), 7.13-7.28 (m, 2H), 6.43 (s, 1H), 4.02 (t, J=5.57 Hz, 2H), 3.94 (s, 2H), 3.16 (t, J=5.57 Hz, 2H).

Intermediate 1G: tert-Butyl 2-(4-fluorophenyl)-6,7-dihydropyrazolo[1,5-a]pyrazine-5(4H)-carboxylate

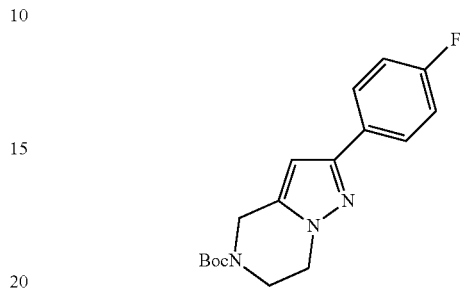

To a stirred solution of Intermediate 1F (9.50 g, 43.7 mmol) and triethylamine (18.29 mL, 131 mmol) in DCM (80 mL) was added Boc₂O (19.09 g, 87 mmol) and DMAP (0.534 g, 4.37 mmol) and the reaction mixture was stirred at RT for 12 h. DCM was removed under reduced pressure and the residue was purified by ISCO using 120 g REDISEP® column and 1-2% methanol in chloroform as eluent. Collected fractions were concentrated together to afford Intermediate 1G (11 g, 79%). MS(ES): m/z=318[M+H]⁺; ¹H NMR (400 MHz, CDCl₃) δ ppm 7.70-7.75 (m, 2H), 7.02-7.12 (m, 2H), 6.31 (s, 1H), 4.68 (s, 2H), 4.21 (t, J=5.4 Hz, 2H), 3.92 (t, J=5.7 Hz, 2H), 1.50 (s, 9H).

Intermediate 1H: tert-Butyl 2-(3-fluorophenyl)-3-iodo-6,7-dihydropyrazolo[1,5-a]pyrazine-5(4H)-carboxylate

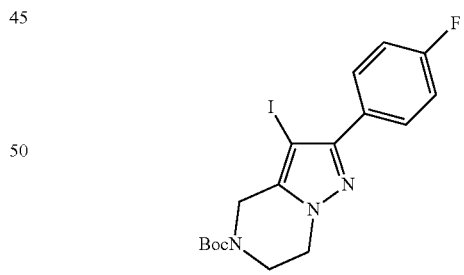

To a solution of Intermediate 1G (5.0 g, 15.76 mmol) in dichloromethane (25 mL) was added NIS (5.32 g, 23.63 mmol) and stirred at room temperature for 1 h. The reaction mixture was diluted with DCM and washed with water. The organic layer was dried over Na₂SO₄ and concentrated. The crude product was purified by ISCO using 40 g silica column using 1-2% methanol in chloroform as solvent. Collected fractions were concentrated together to afford Intermediate 1H (6 g, 86%) as white solid. MS(ES): m/z=444 [M+H]⁺; ¹H NMR (400 MHz, CDCl₃) δ ppm 7.79 (m, 2H), 7.11 (m, 2H), 4.55 (s, 2H), 4.20 (t, J=5.36 Hz, 2H), 3.92 (t, J=5.30 Hz, 2H), 1.52 (s, 9H).

Intermediate 1I: tert-Butyl 3-cyano-2-(3-fluorophenyl)-6,7-dihydropyrazolo[1,5-a]pyrazine-5(4H)-carboxylate

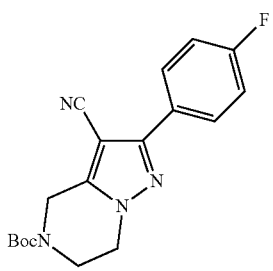 [SMILES: CC(C)(C)OC(=O)N1CCn2nc(-c3ccc(F)cc3)c(C#N)c2C1]

To a solution of Intermediate 1H (6.0 g, 13.54 mmol) in DMF (10 mL) was added zinc cyanide (2.066 g, 17.60 mmol) and zinc (0.265 g, 4.06 mmol) to give a brown suspension. The reaction mixture was degassed under nitrogen for 15 min, added Pd₂(dba)₃ (0.620 g, 0.677 mmol), dppf (0.750 g, 1.354 mmol), and stirred at 90° C. for 18 h. The reaction mixture was quenched with water and the aqueous layer was extracted with ethyl acetate (3×50 mL). Combined organic layer was washed with aqueous ammonia (2×50 mL), water, dried over Na₂SO₄, filtered and concentrated to afford crude Intermediate 1I as a brown gummy solid. The residue was purified by ISCO using 40 g REDISEP® silica gel column eluting with 3% MeOH in chloroform. The collected fractions were concentrated together to afford Intermediate 1I (3 g, 64%) as white solid. MS(ES): m/z=343 [M+H]⁺; ¹H NMR (300 MHz, DMSO-d₆) δ ppm 7.84-7.94 (m, 2H), 7.34-7.44 (m, 2H), 4.78 (s, 2H), 4.23 (t, J=5.36 Hz, 2H), 3.87 (t, J=5.45 Hz, 2H), 1.46 (s, 9H).

Intermediate 1J: tert-Butyl 3-carbamoyl-2-(3-fluorophenyl)-6,7-dihydropyrazolo[1,5-a]pyrazine-5(4H)-carboxylate

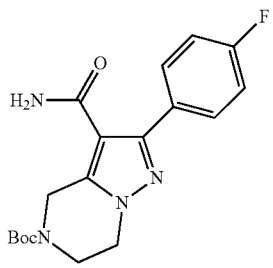 [SMILES: NC(=O)c1c(-c2ccc(F)cc2)nn2c1CNCC2]

To a solution of Intermediate 1I (3.0 g, 8.76 mmol) in MeOH (10 mL) was added NaOH (10 mL, 10% NaOH solution, 25 mmol) and H₂O₂ (2.5 mL, 30% w/v in H₂O, 22 mmol). The reaction mixture was stirred at room temperature for 3 h. Methanol was removed from the reaction mixture and the residue was diluted with 10 mL of water and extracted with ethyl acetate (3×15 mL). The combined organic layer was washed with water (15 mL), brine, dried over Na₂SO₄, filtered and concentrated to afford crude Intermediate 1J (3 g, 95%) as off-white solid, which was taken to the next step without further purification. MS(ES): m/z=361 [M+H]⁺; ¹H NMR (400 MHz, DMSO-d₆) δ ppm 7.66-7.71 (m, 2H), 7.22-7.30 (m, 2H), 6.94 (bs, 1H), 4.75 (s, 2H), 4.16 (t, J=5.40 Hz, 2H), 3.85 (t, J=5.36 Hz, 2H), 1.46 (s, 9H).

Intermediate 1K: 2-(3-Fluorophenyl)-4,5,6,7-tetrahydropyrazolo[1,5-a]pyrazine-3-carboxamide

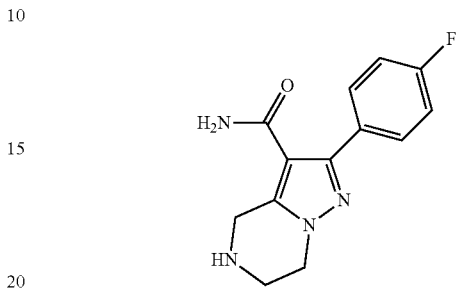

To a solution of Intermediate 1J (3.0 g, 8.32 mmol) in dichloromethane (20 mL) was added TFA (10.26 mL, 133 mmol) dropwise at 0° C. and stirred at room temperature for 3 h. Volatiles were removed, and the residue was quenched with 10% NaHCO₃ solution. The off-white solid product 1K (2 g, 92%) was filtered and dried under vacuum and was used in the next step without further purification. MS(ES): m/z=261 [M+H]⁺; ¹H NMR (400 MHz, DMSO-d₆) δ ppm 7.66-7.73 (m, 2H), 7.22-7.25 (m, 2H), 7.21 (bs, 1H), 7.20 (bs, 1H), 3.98-4.05 (m, 4H), 3.13 (bs, 2H), 2.63 (s, 1H).

Compound 1: N⁵-(tert-Butyl)-2-(3-fluorophenyl)-6,7-dihydropyrazolo[1,5-a]pyrazine-3,5(4H)-dicarboxamide

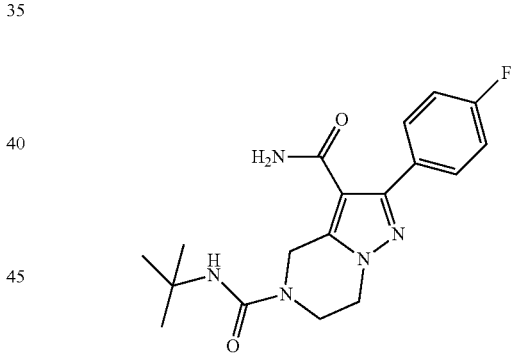

To a solution of Intermediate 1K (30 mg, 0.115 mmol) in DMF (1 mL) was added tert-butylisocyanate (28.6 mg, 0.288 mmol) at 0° C. The reaction mixture was stirred at room temperature for 3 h. The reaction mixture was quenched with water and extracted with ethyl acetate (3×5 mL). The combined organic layer was washed with water (2×5 mL), brine, dried over Na₂SO₄ and concentrated to afford the crude product as brown semi-solid. The residue was dissolved in a mixture of acetonitrile and methanol and was purified via preparative HPLC. Fractions containing the desired product (0.01 g, 24%) were combined and dried under vacuum. MS(ES): m/z=360 [M+H]⁺; HPLC Ret. Time 6.66 min. and 6.14 min. (HPLC Methods A and B); ¹H NMR (400 MHz, DMSO-d₆) δ ppm 7.69 (m, 2H), 7.25 (m, 2H), 7.25 (bs, 1H), 6.98 (bs, 1H), 6.26 (s, 1H), 4.69 (s, 2H), 4.11 (t, J=5.7 Hz, 2H), 3.80 (t, J=5.7 Hz, 2H), 1.29 (s, 9H).

The Compounds shown in Table 1 have been prepared similar to Compound 1 using Intermediate 1K and various isocyanate.

TABLE 1

| Ex. No. | Structure | Name | [M + H]+ | Ret Time (min.) | HPLC Method |
|---|---|---|---|---|---|
| 2 | 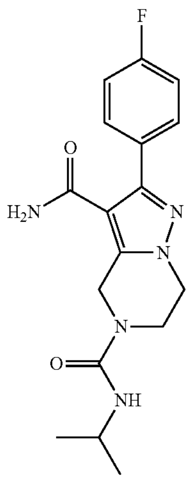 [SMILES: CC(C)NC(=O)N1CCn2nc(-c3ccc(F)cc3)c(C(N)=O)c2C1] | 2-(4-Fluorophenyl)-N$^5$-isopropyl-6,7-dihydropyrazolo[1,5-a]pyrazine-3,5(4H)-dicarboxamide | 345 | 6.606<br>6.184 | A<br>B |
| 3 | 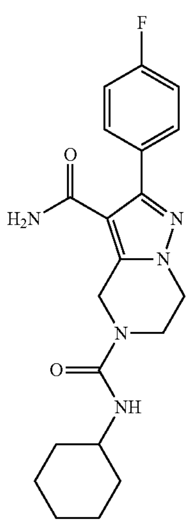 [SMILES: NC(=O)c1c(-c2ccc(F)cc2)nn2c1CN(C(=O)NC1CCCCC1)CC2] | N$^5$-Cyclohexyl-2-(4-fluorophenyl)-6,7-dihydropyrazolo[1,5-a]pyrazine-3,5(4H)-dicarboxamide | 386 | 7.948<br>7.838 | A<br>B |

Scheme 2
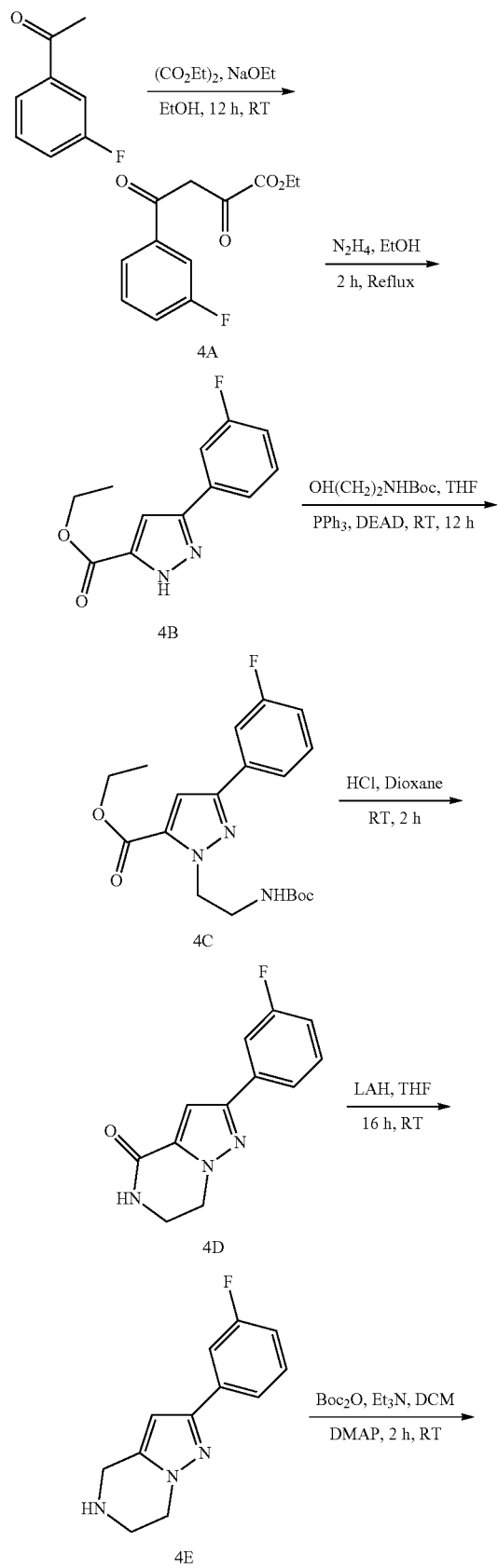
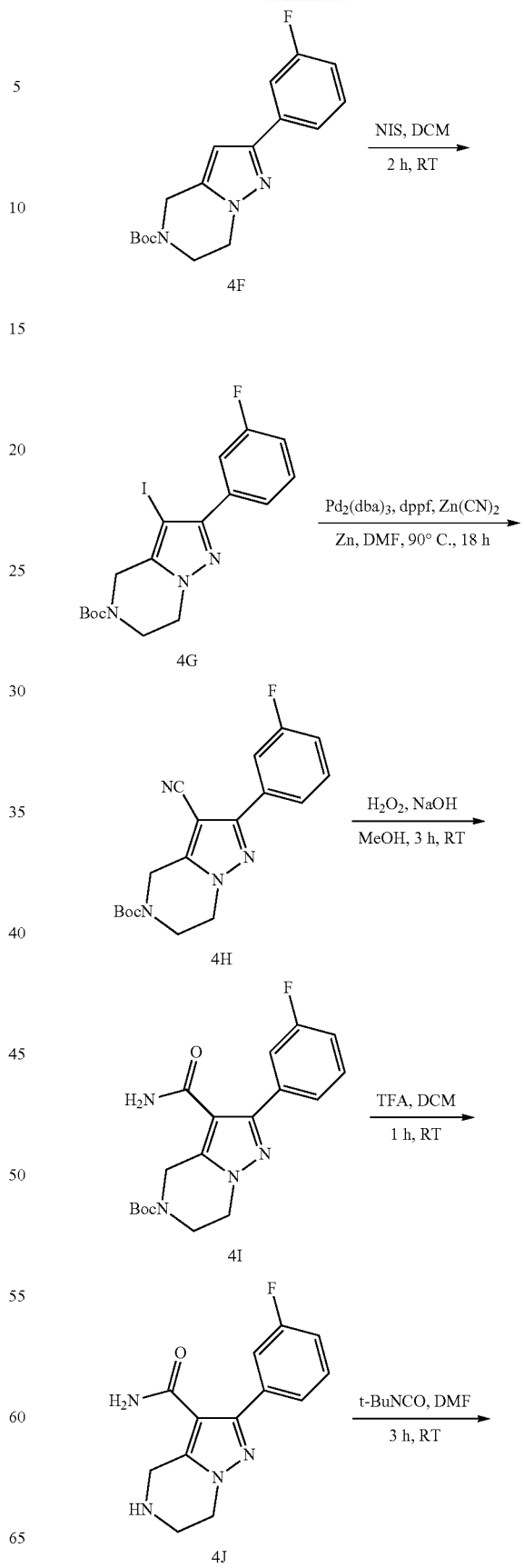

-continued

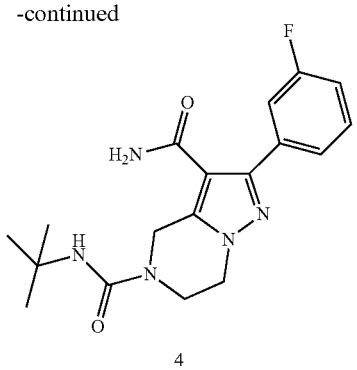

4

Intermediate 4A: Ethyl 4-(3-fluorophenyl)-2,4-dioxobutanoate

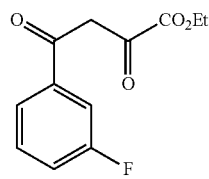 [SMILES: CCOC(=O)C(=O)CC(=O)c1cccc(F)c1]

To a solution of sodium ethoxide (123 g, 362 mmol) in ethanol (300 mL) at 0° C. was added a solution of diethyl oxalate (49.4 mL, 362 mmol) in ethanol (25 mL) and the resulting solution was stirred for 10 min. 1-(3-Fluorophenyl) ethanone (50 g, 362 mmol) in ethanol (25 mL) was added and the reaction mixture was stirred at room temperature for 16 h. Ethanol was distilled off under reduced pressure and the residue obtained was quenched with ice cold water and the brown product was filtered. This crude product was purified by ISCO using 220 g silica gel column and 20% ethyl acetate in hexane as eluent. The combined fractions were concentrated to afford Intermediate 4A (62.5 g, 73%). MS(ES): m/z=239 [M+H]$^+$; $^1$H NMR (400 MHz, CDCl$_3$) δ ppm 15.13 (bs, 1H), 7.77-7.83 (m, 1H), 7.67-7.73 (m, 1H), 7.51 (td, J=8.03, 5.48 Hz, 1H), 7.29-7.37 (m, 1H), 7.28 (s, 1H), 4.43 (q, J=7.18 Hz, 2H), 1.40-1.47 (m, 3H).

Intermediate 4B: Ethyl 3-(3-fluorophenyl)-1H-pyrazole-5-carboxylate

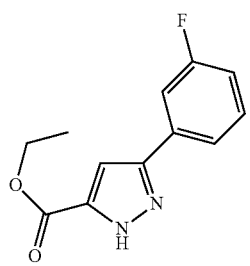 [SMILES: CCOC(=O)c1cc(-c2cccc(F)c2)n[nH]1]

To a solution of Intermediate 4A (100 g, 420 mmol) in ethanol (250 mL) was added hydrazine (13.83 mL, 441 mmol) in ethanol (250 mL) to give a brown solution. The reaction mixture was stirred at 80° C. for 2 h. Ethanol was removed under reduced pressure and the residue was diluted with water and extracted with ethyl acetate (3×100 mL). The combined organic layer was washed with water (2×100 mL), brine, dried over Na$_2$SO$_4$, filtered and concentrated under reduced pressure. The brown solid thus obtained was purified by ISCO using 20% ethyl acetate in hexane as eluent. The combined fractions were concentrated to afford Intermediate 4B (85 g, 86%) MS(ES): m/z=233 [M+H]$^+$; $^1$H NMR (400 MHz, DMSO-d$_6$) δ ppm 14.06 (bs, 1H), 7.68-7.75 (m, 2H), 7.45-7.55 (m, 1H), 7.36 (s, 1H), 7.20 (t, J=7.53 Hz, 1H), 4.34 (q, J=7.03 Hz, 2H), 1.34 (t, J=7.03 Hz, 3H).

Intermediate 4C: Ethyl 1-(2-((tert-butoxycarbonyl) amino)ethyl)-3-(3-fluorophenyl)-1H-pyrazole-5-carboxylate

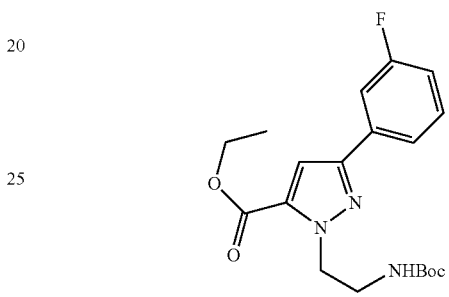

A solution of 4B (12 g, 51.2 mmol) and PPh$_3$ (20.16 g, 77 mmol) in THF (10 mL) at 0° C. was added DIAD (14.94 mL, 77 mmol) in THF (10 mL) and the resulting reaction mixture was stirred at the same temperature for 30 min. tert-Butyl(2-hydroxyethyl) carbamate (9.91 g, 61.5 mmol) was then added and the reaction mixture was stirred at room temperature for 2 h. The volatiles were evaporated from the reaction mixture under reduced pressure and the resultant residue was quenched with ice. The aqueous layer was extracted with ethyl acetate (3×1000 mL) The combined organic layer was washed with 1.5 N HCl (2×100 mL), brine, dried over Na$_2$SO$_4$, filtered and concentrated to afford crude product, which was purified by ISCO (5:1Hex/EtOAc; 120 g column). Collected fractions were concentrated together to afford pale yellow solid 4C (16 g, 83%). MS(ES): m/z=378 [M+H]$^+$; $^1$H NMR (400 MHz, CDCl$_3$) δ ppm 7.54-7.59 (m, 1H), 7.48-7.54 (m, 1H), 7.36 (td, J=8.03, 6.02 Hz, 1H), 7.13 (s, 1H), 6.98-7.05 (m, 1H), 6.32 (bs, 1H), 4.98 (quin, J=6.27 Hz, 2H), 4.37 (q, J=7.19 Hz, 2H), 3.64 (d, J=5.02 Hz, 2H), 1.39-1.41 (m, 3H), 1.27 (s, 9H).

Intermediate 4D: 2-(3-Fluorophenyl)-6,7-dihydropyrazolo[1,5-a]pyrazin-4(5H)-one

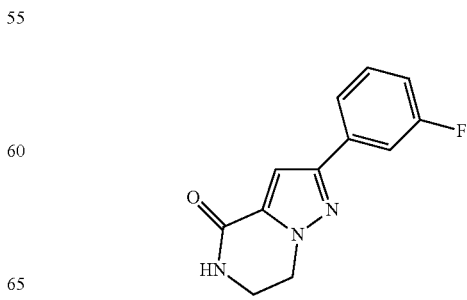

A 250 mL round-bottomed flask was charged with 4C (14 g, 37.1 mmol) and HCl in 1,4-dioxane (185 mL, 185 mmol) to give a yellow solution. The reaction mixture was stirred at room temperature for 2 h. The reaction mixture was concentrated under reduced pressure and to this residue was added 10% NaHCO₃ slowly until pH became 8.0. The aqueous layer was extracted with ethyl acetate (3×100 mL) and the combined the organic layer was washed with water (2×100 mL), brine, dried over Na₂SO₄, filtered and concentrated to give the desired product 4D as off-white solid, which was used in the next step without purification. MS(ES): m/z=231 [M+H]⁺; $^1$H NMR (400 MHz, DMSO-d₆) δ ppm 8.26 (bs, 1H), 7.70-7.75 (m, 1H), 7.63-7.69 (m, 1H), 7.47 (td, J=8.03, 6.53 Hz, 1H), 7.11-7.20 (m, 1H), 4.32-4.40 (m, 2H), 3.65 (tt, J=4.64, 3.14 Hz, 2H).

Intermediate 4E: 2-(3-Fluorophenyl)-4,5,6,7-tetrahydropyrazolo[1,5-a]pyrazine

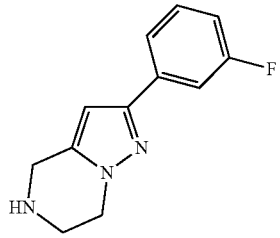 [SMILES: Fc1cccc(-c2cc3n(n2)CCNC3)c1]

To a solution of Intermediate 4D (4.5 g, 19.46 mmol) in THF (100 mL) at −10° C. was added LAH (16.22 mL, 2.4 M in THF, 38.9 mmol) dropwise. The reaction mixture was stirred at room temperature for 16 h, was quenched with saturated NH₄Cl at 0° C. and the aqueous layer was extracted with ethyl acetate (3×50 mL). Combined organic layer was washed with water (2×50 mL), brine, filtered through CELITE®, dried over Na₂SO₄ and concentrated to afford crude Compound 4E as off-white solid (4 g, 90%), which was used in the next step without purification. MS(ES): m/z=218 [M+H]⁺; $^1$H NMR (400 MHz, CDCl₃) δ ppm 7.53-7.59 (m, 1H), 7.50 (ddd, J=10.29, 2.55, 1.51 Hz, 1H), 7.35 (td, J=7.93, 6.04 Hz, 1H), 6.99 (tdd, J=8.40, 8.40, 2.64, 0.94 Hz, 1H), 6.29 (s, 1H), 4.19 (t, J=5.67 Hz, 2H), 4.12 (s, 2H), 3.33-3.40 (m, 2H).

Intermediate 4F: tert-Butyl 2-(3-fluorophenyl)-6,7-dihydropyrazolo[1,5-a]pyrazine-5(4H)-carboxylate

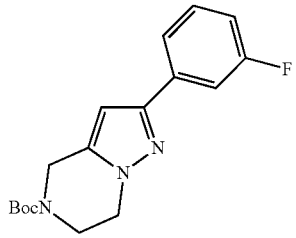 [SMILES: CC(C)(C)OC(=O)N1CCn2nc(-c3cccc(F)c3)cc2C1]

To a solution of Intermediate 4E (4.0 g, 20.71 mmol) in dichloromethane (150 mL) was added triethylamine (7.70 mL, 55.2 mmol), and DMAP (0.225 g, 1.841 mmol) to give a colorless solution. The reaction was cooled to 0° C. and Boc₂O (4.82 g, 22.10 mmol) was then added and the reaction mixture was stirred at room temperature for 2 h. The reaction mixture was diluted with dichloromethane (100 mL), washed with water (2×100 mL), dried over Na₂SO₄, filtered and concentrated to afford crude compound as off-white solid. The crude product was purified by silica gel chromatography (24 g REDISEP® column, eluting with 30% ethyl acetate in hexane). Collected fractions were concentrated together to afford Intermediate 4F (5 g, 86%) as white solid. MS(ES): m/z=318 [M+H]⁺; $^1$H NMR (400 MHz, CDCl₃) δ ppm 7.53 (dt, J=7.53, 1.25 Hz, 1H), 7.47 (ddd, J=10.54, 2.51, 1.51 Hz, 1H), 7.31-7.38 (m, 1H), 6.95-7.03 (m, 1H), 6.35 (s, 1H), 4.69 (s, 2H), 4.22 (t, J=5.27 Hz, 2H), 3.92 (t, J=5.52 Hz, 2H), 1.51 (s, 9H).

Intermediate 4G: tert-Butyl 2-(3-fluorophenyl)-3-iodo-6,7-dihydropyrazolo[1,5-a]pyrazine-5(4H)-carboxylate

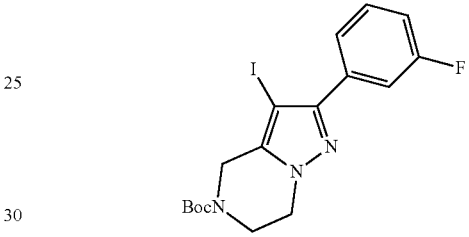

To a solution of Intermediate 4F (5.0 g, 15.76 mmol) in dichloromethane (25 mL) was added NIS (5.32 g, 23.63 mmol) and stirred at room temperature for 2 h. The reaction mixture was diluted with DCM and washed with water. The organic layer was dried over Na₂SO₄ and concentrated to afford Intermediate 4G (6 g, 86%) as colorless semi-solid which was used in the next step without any purification. MS(ES): m/z=444 [M+H]⁺; $^1$H NMR (400 MHz, CDCl₃) δ ppm 7.61-7.66 (m, 1H), 7.56 (ddd, J=10.04, 2.51, 1.51 Hz, 1H), 7.39 (td, J=8.03, 6.02 Hz, 1H), 7.04-7.10 (m, 1H), 4.56 (bs, 2H), 4.22 (t, J=5.52 Hz, 2H), 3.92 (t, J=5.52 Hz, 2H), 1.52 (s, 9H).

Intermediate 4H: tert-Butyl 3-cyano-2-(3-fluorophenyl)-6,7-dihydropyrazolo[1,5-a]pyrazine-5(4H)-carboxylate

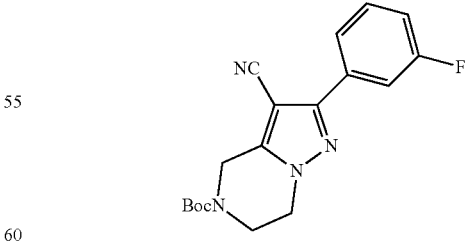

To a solution of Intermediate 4G (5.0 g, 11.28 mmol) in DMF (50 mL) was added zinc cyanide (1.722 g, 14.66 mmol) and zinc (0.221 g, 3.38 mmol) to give a brown suspension. The reaction mixture was degassed under nitrogen for 15 min and added Pd₂(dba)₃ (0.516 g, 0.564 mmol) and dppf (0.625 g, 1.128 mmol). The reaction mixture was stirred at 90° C. for 18 h. The reaction mixture was quenched with water and the aqueous layer was extracted with ethyl acetate (3×50 mL) The combined organic layer was and washed with aqueous ammonia (2×50 mL), water, dried over Na₂SO₄, filtered and concentrated to afford crude product as brown semi-solid. The crude was purified by silica gel chromatography (40 g REDISEP® column, eluting with 50% EtOAc in hexane). Collected fractions concentrated together to afford Intermediate 4H (3 g, 78%) as white solid. MS(ES): m/z=343 [M+H]⁺; ¹H NMR (400 MHz, CDCl₃) δ ppm 7.73-7.78 (m, 1H), 7.62-7.68 (m, 1H), 7.43 (td, J=8.03, 5.52 Hz, 1H), 7.08-7.15 (m, 1H), 4.82 (s, 2H), 4.24 (t, J=5.52 Hz, 2H), 3.96 (t, J=5.27 Hz, 2H), 1.52 (s, 9H).

Intermediate 4I: tert-Butyl 3-carbamoyl-2-(3-fluorophenyl)-6,7-dihydropyrazolo[1,5-a]pyrazine-5(4H)-carboxylate

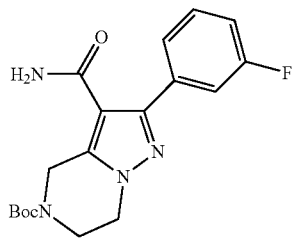 [SMILES: CC(C)(C)OC(=O)N1CCn2nc(-c3cccc(F)c3)c(C(N)=O)c2C1]

To a solution of Intermediate 4H (3.0 g, 8.76 mmol) in MeOH (10 mL) was added NaOH (10 ml, 10% NaOH solution, 25 mmol) and H₂O₂ (2.5 mL, 30% w/v in H₂O, 22 mmol). The reaction mixture was stirred at room temperature for 3 h. Methanol was removed from the reaction mixture and the residue was diluted with 10 mL of water and extracted with ethyl acetate (3×15 mL). Combined organic layer was washed with water (15 mL), brine, dried over Na₂SO₄, filtered and concentrated to afford crude Intermediate 4I (3 g, 95%) as off-white solid, which was used in the next step without further purification. MS(ES): m/z=361 [M+H]⁺; ¹H NMR (300 MHz, DMSO-d₆) δ ppm 7.53 (d, J=1.51 Hz, 1H), 7.43-7.50 (m, 2H), 7.32 (bs, 1H), 7.18-7.24 (m, 1H), 7.14 (bs, 1H), 4.75 (s, 2H), 4.17 (t, J=5.27 Hz, 2H), 3.85 (t, J=5.52 Hz, 2H), 1.41-1.49 (m, 8H).

Intermediate 4J: 2-(3-Fluorophenyl)-4,5,6,7-tetrahydropyrazolo[1,5-a]pyrazine-3-carboxamide

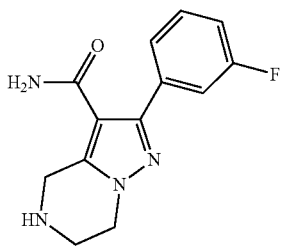 [SMILES: NC(=O)c1c(-c2cccc(F)c2)nn2c1CNCC2]

To a solution of Intermediate 4I (3.0 g, 8.32 mmol) in dichloromethane (20 mL) at 0° C. was added TFA (10.26 mL, 133 mmol) dropwise and stirred at room temperature for 1 h. TFA was removed from the reaction mixture and the residue was quenched with 10% NaHCO₃ solution. The solid was filtered to obtain Intermediate 4J (2 g, 92%) as off-white solid, which was used in the next step without purification. MS(ES): m/z=261 [M+H]⁺; ¹H NMR (400 MHz, DMSO-d₆) δ ppm 7.52-7.57 (m, 1H), 7.46-7.52 (m, 1H), 7.40-7.46 (m, 1H), 7.14-7.27 (m, 2H), 7.08 (bs, 1H), 4.03 (d, J=5.02 Hz, 4H), 3.13 (d, J=5.02 Hz, 2H), 2.64 (d, J=6.02 Hz, 1H).

Compound 4: N⁵-(tert-Butyl)-2-(3-fluorophenyl)-6,7-dihydropyrazolo[1,5-a]pyrazine-3,5(4H)-dicarboxamide

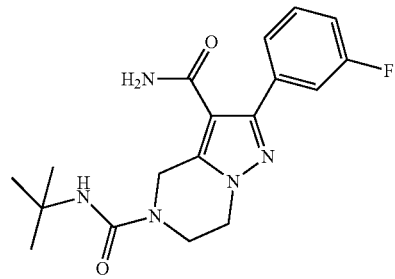 [SMILES: CC(C)(C)NC(=O)N1CCn2nc(-c3cccc(F)c3)c(C(N)=O)c2C1]

To a solution of Intermediate 4J (50 mg, 0.192 mmol) in DMF (2 mL) at 0° C. was added tert-butylisocyanate (38 mg, 0.384 mmol). The reaction mixture was stirred at room temperature for 12 h, quenched with water and extracted with ethyl acetate (3×5 mL) The combined organic layer was washed with water (2×5 mL), brine, dried over Na₂SO₄, filtered and concentrated to afford crude product as brown semi-solid. The residue was further purified by preparative HPLC to afford pure product 4 as white powder (40 mg, 57%). MS(ES): m/z=360 [M+H]⁺; HPLC Ret. Time 7.35 min. and 7.33 min. (HPLC Methods A and B); ¹H NMR (400 MHz, DMSO-d₆) δ ppm 7.51-7.54 (m, 1H), 7.47-7.50 (m, 1H), 7.44-7.46 (m, 1H), 7.18-7.24 (m, 1H), 4.74 (s, 2H), 4.17 (t, J=5.52 Hz, 2H), 3.85 (t, J=5.52 Hz, 2H), 1.45-1.48 (s, 9H).

General Methods to Synthesize Ureas:

Method A:

To a solution of Intermediate 4J (30 mg, 0.115 mmol) in DMF (1 mL) was added the corresponding isocyanate (0.288 mmol) at 0° C. and the reaction mixture was stirred at room temperature for 3 h. The reaction mixture was quenched with water and extracted with ethyl acetate (3×5 mL) The combined organic layer was washed with water (2×5 mL), brine, dried over Na₂SO₄, filtered and concentrated to afford crude product. The crude product was further purified by preparative HPLC.

Method B:

To a solution of primary amine (0.192 mmol) and triethylamine (0.480 mmol) in tetrahydrofuran (3 mL) at 0° C. was added triphosgene (0.096 mmol) and the reaction mixture stirred for 30 min. at the same temperature. Intermediate 4J (25 mg, 0.096 mmol) in THF was added and the solution was stirred at room temperature for 2 h. Reaction progress was monitored by TLC. The reaction mixture was quenched with water and extracted with ethyl acetate (3×5 mL) The combined organic layer was washed with 10% NaHCO₃ (2×5 mL), water, dried over Na₂SO₄ and concentrated to afford crude product as off-white solid. The crude product was further purified by preparative HPLC.

Method C:

To a solution of acid (0.192 mmol) and TEA (0.288 mmol) in toluene (3 mL) was added diphenylphosphoryl azide (0.192 mmol) to give a colorless solution. The reaction mixture was stirred at 90° C. for 1.5 h and cooled to RT. Intermediate 4J (25 mg, 0.096 mmol) in THF was added and the reaction mixture was stirred at 60° C. for 4 h. Reaction progress was monitored by TLC. The reaction mixture was quenched with water and extracted with ethyl acetate (3×5 mL). The combined organic layer was washed with 10% NaHCO$_3$ (2×5 mL), water, dried over Na$_2$SO$_4$ and concentrated to afford crude product as off-white solid. The crude product was further purified by preparative HPLC.

Method D:

To a solution of primary amine (0.192 mmol) and triethylamine (0.480 mmol) in tetrahydrofuran (3 mL) at 0° C. were added phenyl chloroformate (0.096 mmol) and the reaction mixture stirred for 60 min. at RT. The reaction mixture was quenched with water and the phenyl carbamate formed was extracted and the Intermediate 4J (25 mg, 0.096 mmol) in THF was added to the extract and the resulting solution was stirred at room temperature for 2 h. Reaction progress was monitored by TLC. The reaction mixture was quenched with water and extracted with ethyl acetate (3×5 mL) The combined organic layer was washed with 10% NaHCO$_3$ (2×5 mL), water, dried over Na$_2$SO$_4$ and concentrated to afford crude product as off-white solid. The crude product was further purified by preparative HPLC.

The Compounds described in Table 2 were synthesized analogous to Compound 4 by reacting Intermediate 4J with corresponding reagents.

TABLE 2

| Ex. No. | Structure | Name | Synthetic Method | [M + H]$^+$ | Ret Time (min.) | HPLC Method |
|---|---|---|---|---|---|---|
| 5 | 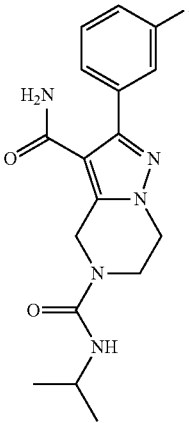 | 2-(3-Fluorophenyl)-N$^5$-isopropyl-6,7-dihydropyrazolo[1,5-a]pyrazine-3,5(4H)-dicarboxamide | A | 346 | 6.41<br>5.79 | A<br>B |
| 6 | 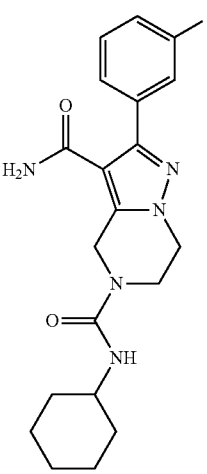 | N$^5$-Cyclohexyl-2-(3-fluorophenyl)-6,7-dihydropyrazolo[1,5-a]pyrazine-3,5(4H)-dicarboxamide | A | 386 | 14.34<br>13.57 | C<br>D |

TABLE 2-continued

| Ex. No. | Structure | Name | Synthetic Method | [M + H]+ | Ret Time (min.) | HPLC Method |
|---|---|---|---|---|---|---|
| 7 | 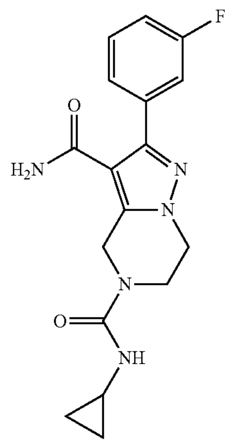 [SMILES: NC(=O)c1c(-c2cccc(F)c2)nn2c1CN(C(=O)NC1CC1)CC2] | N5-Cyclopropyl-2-(3-fluorophenyl)-6,7-dihydropyrazolo[1,5-a]pyrazine-3,5(4H)-dicarboxamide | B | 344 | 6.06<br>5.39 | A<br>B |
| 8 | 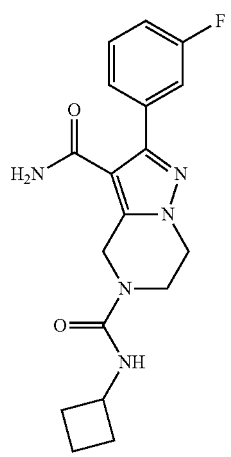 [SMILES: NC(=O)c1c(-c2cccc(F)c2)nn2c1CN(C(=O)NC1CCC1)CC2] | N5-Cyclobutyl-2-(3-fluorophenyl)-6,7-dihydropyrazolo[1,5-a]pyrazine-3,5(4H)-dicarboxamide | B | 358 | 6.89<br>6.48 | A<br>B |
| 9 | 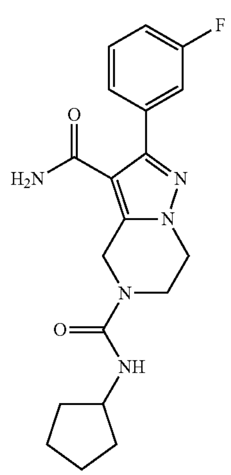 [SMILES: NC(=O)c1c(-c2cccc(F)c2)nn2c1CN(C(=O)NC1CCCC1)CC2] | N5-Cyclopentyl-2-(3-fluorophenyl)-6,7-dihydropyrazolo[1,5-a]pyrazine-3,5(4H)-dicarboxamide | B | 372 | 7.43<br>6.95 | A<br>B |

TABLE 2-continued

| Ex. No. | Structure | Name | Synthetic Method | [M + H]+ | Ret Time (min.) | HPLC Method |
|---|---|---|---|---|---|---|
| 10 | 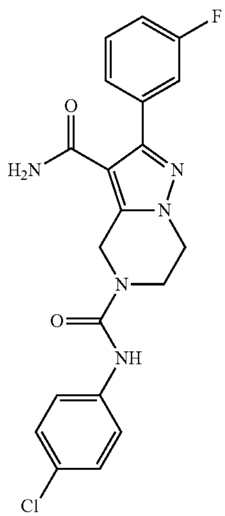 [SMILES: NC(=O)c1c(-c2cccc(F)c2)nn2c1CN(C(=O)Nc1ccc(Cl)cc1)CC2] | N5-(4-Chlorophenyl)-2-(3-fluorophenyl)-6,7-dihydropyrazolo[1,5-a]pyrazine-3,5(4H)-dicarboxamide | A | 414 | 8.87<br>8.36 | A<br>B |
| 11 | 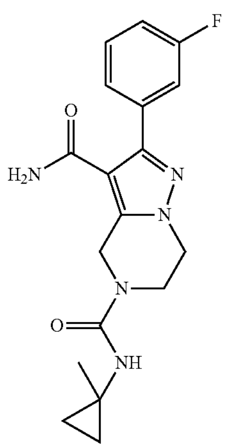 [SMILES: CC1(NC(=O)N2CCn3nc(-c4cccc(F)c4)c(C(N)=O)c3C2)CC1] | 2-(3-Fluorophenyl)-N5-(1-methylcyclopropyl)-6,7-dihydropyrazolo[1,5-a]pyrazine-3,5(4H)-dicarboxamide | C | 358 | 6.46<br>6.06 | A<br>B |
| 12 | 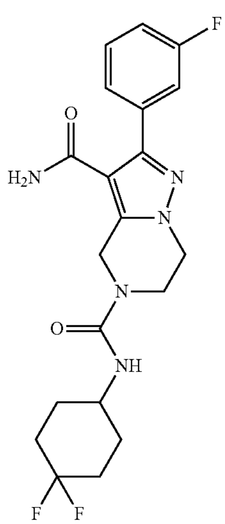 [SMILES: NC(=O)c1c(-c2cccc(F)c2)nn2c1CN(C(=O)NC1CCC(F)(F)CC1)CC2] | N5-(4,4-Difluorocyclohexyl)-2-(3-fluorophenyl)-6,7-dihydropyrazolo[1,5-a]pyrazine-3,5(4H)-dicarboxamide | B | 422 | 7.42<br>6.63 | A<br>B |

TABLE 2-continued

| Ex. No. | Structure | Name | Synthetic Method | [M + H]⁺ | Ret Time (min.) | HPLC Method |
|---|---|---|---|---|---|---|
| 13 | 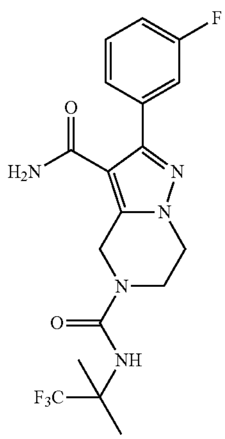 [SMILES: CC(C)(NC(=O)N1CCn2nc(-c3cccc(F)c3)c(C(N)=O)c2C1)C(F)(F)F] | 2-(3-Fluorophenyl)-N⁵-(1,1,1-trifluoro-2-methylpropan-2-yl)-6,7-dihydropyrazolo[1,5-a]pyrazine-3,5(4H)-dicarboxamide | B | 414 | 7.96<br>7.52 | A<br>B |
| 14 | 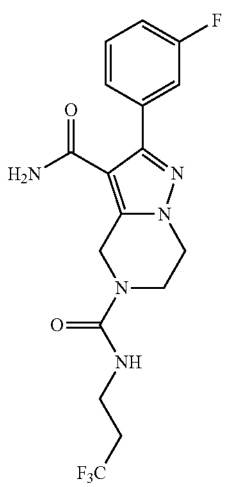 [SMILES: NC(=O)c1c(-c2cccc(F)c2)nn2c1CN(C(=O)NCCC(F)(F)F)CC2] | 2-(3-Fluorophenyl)-N⁵-(3,3,3-trifluoropropyl)-6,7-dihydropyrazolo[1,5-a]pyrazine-3,5(4H)-dicarboxamide | C | 400 | 7.19<br>6.79 | A<br>B |
| 15 | 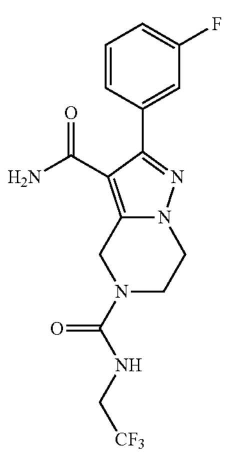 [SMILES: NC(=O)c1c(-c2cccc(F)c2)nn2c1CN(C(=O)NCC(F)(F)F)CC2] | 2-(3-Fluorophenyl)-N⁵-(2,2,2-trifluoroethyl)-6,7-dihydropyrazolo[1,5-a]pyrazine-3,5(4H)-dicarboxamide | C | 386 | 7.00<br>6.58 | A<br>B |

TABLE 2-continued

| Ex. No. | Structure | Name | Synthetic Method | [M + H]+ | Ret Time (min.) | HPLC Method |
|---|---|---|---|---|---|---|
| 16 | 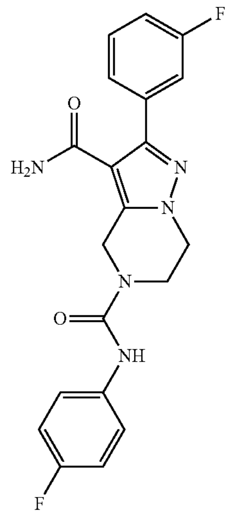 [SMILES: NC(=O)c1c(-c2cccc(F)c2)nn2c1CN(C(=O)Nc1ccc(F)cc1)CC2] | 2-(3-Fluorophenyl)-N5-(4-fluorophenyl)-6,7-dihydropyrazolo[1,5-a]pyrazine-3,5(4H)-dicarboxamide | B | 398 | 7.99 7.62 | A B |
| 17 | 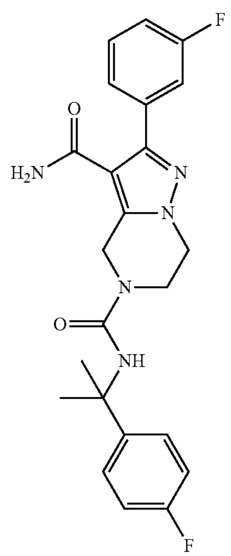 [SMILES: CC(C)(NC(=O)N1CCn2nc(-c3cccc(F)c3)c(C(N)=O)c2C1)c1ccc(F)cc1] | 2-(3-Fluorophenyl)-N5-(2-(4-fluorophenyl)propan-2-yl)-6,7-dihydropyrazolo[1,5-a]pyrazine-3,5(4H)-dicarboxamide | B | 440 | 8.82 8.34 | A B |
| 18 | 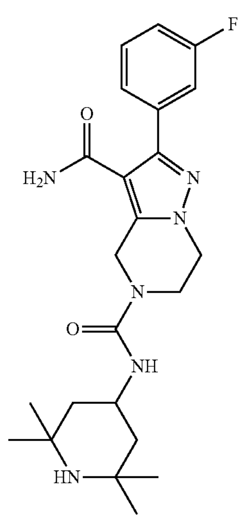 [SMILES: CC1(C)CC(NC(=O)N2CCn3nc(-c4cccc(F)c4)c(C(N)=O)c3C2)CC(C)(C)N1] | 2-(3-Fluorophenyl)-N5-(2,2,6,6-tetramethylpiperidin-4-yl)-6,7-dihydropyrazolo[1,5-a]pyrazine-3,5(4H)-dicarboxamide | B | 443 | 9.09 10.11 | C D |

TABLE 2-continued

| Ex. No. | Structure | Name | Synthetic Method | [M + H]⁺ | Ret Time (min.) | HPLC Method |
|---|---|---|---|---|---|---|
| 19 | 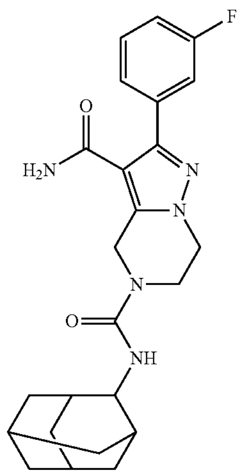 [SMILES: NC(=O)c1c(-c2cccc(F)c2)nn2c1CN(C(=O)NC1C3CC4CC(C3)CC1C4)CC2] | N⁵-(Adamantan-2-yl)-2-(3-fluorophenyl)-6,7-dihydropyrazolo[1,5-a]pyrazine-3,5(4H)-dicarboxamide | B | 348 | 9.70 8.89 | A B |
| 20 | 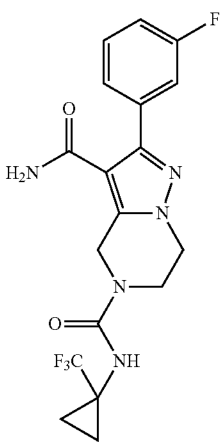 [SMILES: NC(=O)c1c(-c2cccc(F)c2)nn2c1CN(C(=O)NC1(C(F)(F)F)CC1)CC2] | 2-(3-Fluorophenyl)-N⁵-(1-(trifluoromethyl)cyclopropyl)-6,7-dihydropyrazolo[1,5-a]pyrazine-3,5(4H)-dicarboxamide | B | 412 | 7.25 6.77 | A B |
| 21 | 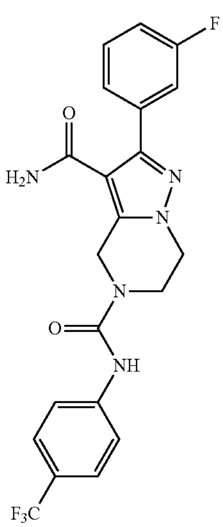 [SMILES: NC(=O)c1c(-c2cccc(F)c2)nn2c1CN(C(=O)Nc1ccc(C(F)(F)F)cc1)CC2] | 2-(3-Fluorophenyl)-N⁵-(4-(trifluoromethyl)phenyl)-6,7-dihydropyrazolo[1,5-a]pyrazine-3,5(4H)-dicarboxamide | B | 448 | 9.55 8.88 | A B |

TABLE 2-continued

| Ex. No. | Structure | Name | Synthetic Method | [M + H]+ | Ret Time (min.) | HPLC Method |
|---|---|---|---|---|---|---|
| 22 | 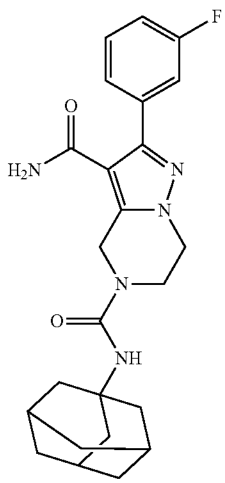 [SMILES: NC(=O)c1c(-c2cccc(F)c2)nn2c1CN(C(=O)NC13CC4CC(CC(C4)C1)C3)CC2] | N5-(Adamantan-1-yl)-2-(3-fluorophenyl)-6,7-dihydropyrazolo[1,5-a]pyrazine-3,5(4H)-dicarboxamide | A | 438 | 9.93 9.17 | A B |
| 23 | 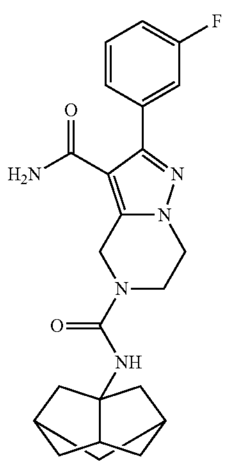 [SMILES: NC(=O)c1c(-c2cccc(F)c2)nn2c1CN(C(=O)NC13CC4CC(CC1C4)C3)CC2] | 2-(3-Fluorophenyl)-N5-((2R,5S)-octahydro-2,5-methanopentalen-6a-yl)-6,7-dihydropyrazolo[1,5-a]pyrazine-3,5(4H)-dicarboxamide | C | 424 | 9.30 8.62 | A B |
| 24 | 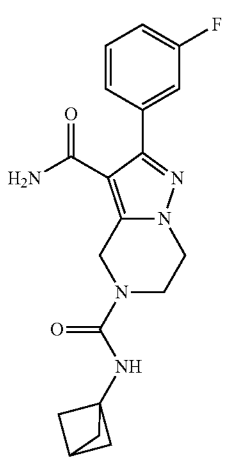 [SMILES: NC(=O)c1c(-c2cccc(F)c2)nn2c1CN(C(=O)NC13CC(C1)C3)CC2] | N5-(Bicyclo[1.1.1]pentan-1-yl)-2-(3-fluorophenyl)-6,7-dihydropyrazolo[1,5-a]pyrazine-3,5(4H)-dicarboxamide | B | 370 | 7.16 6.91 | A B |

TABLE 2-continued

| Ex. No. | Structure | Name | Synthetic Method | [M + H]+ | Ret Time (min.) | HPLC Method |
| --- | --- | --- | --- | --- | --- | --- |
| 25 | 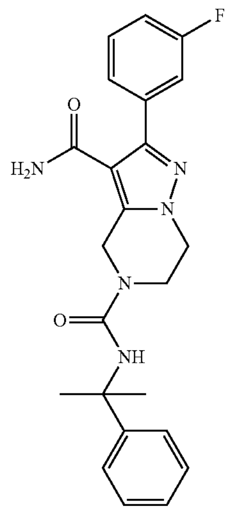 [SMILES: CC(C)(NC(=O)N1CCn2nc(-c3cccc(F)c3)c(C(N)=O)c2C1)c1ccccc1] | 2-(3-Fluorophenyl)-N5-(2-phenylpropan-2-yl)-6,7-dihydropyrazolo[1,5-a]pyrazine-3,5(4H)-dicarboxamide | B | 422 | 8.53<br>8.10 | A<br>B |
| 26 | 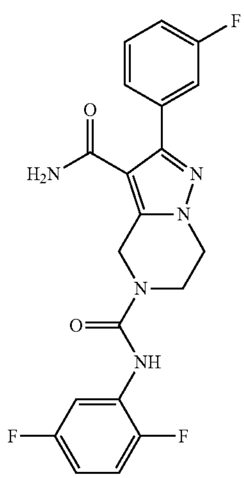 [SMILES: NC(=O)c1c(-c2cccc(F)c2)nn2c1CN(C(=O)Nc1cc(F)ccc1F)CC2] | N5-(2,5-Difluorophenyl)-2-(3-fluorophenyl)-6,7-dihydropyrazolo[1,5-a]pyrazine-3,5(4H)-dicarboxamide | B | 416 | 8.21<br>7.87 | A<br>B |
| 27 | 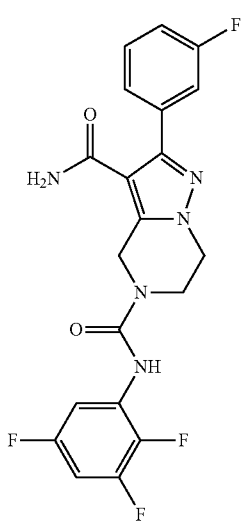 [SMILES: NC(=O)c1c(-c2cccc(F)c2)nn2c1CN(C(=O)Nc1cc(F)cc(F)c1F)CC2] | 2-(3-Fluorophenyl)-N5-(2,3,5-trifluorophenyl)-6,7-dihydropyrazolo[1,5-a]pyrazine-3,5(4H)-dicarboxamide | B | 434 | 9.69<br>9.03 | A<br>B |

TABLE 2-continued

| Ex. No. | Structure | Name | Synthetic Method | [M + H]+ | Ret Time (min.) | HPLC Method |
|---|---|---|---|---|---|---|
| 28 | 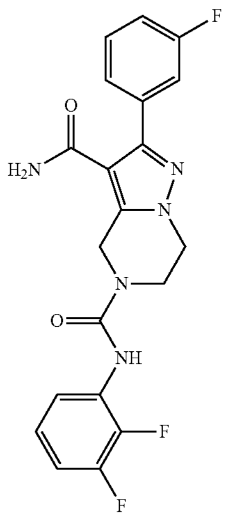 [SMILES: NC(=O)c1c(-c2cccc(F)c2)nn2c1CN(C(=O)Nc1cccc(F)c1F)CC2] | N5-(2,3-Difluorophenyl)-2-(3-fluorophenyl)-6,7-dihydropyrazolo[1,5-a]pyrazine-3,5(4H)-dicarboxamide | B | 416 | 8.05<br>7.76 | A<br>B |
| 29 | 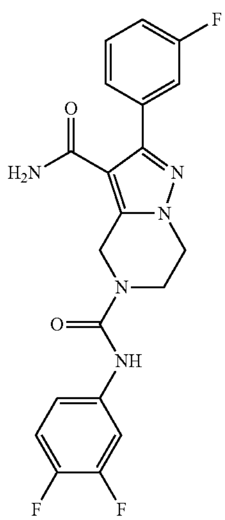 [SMILES: NC(=O)c1c(-c2cccc(F)c2)nn2c1CN(C(=O)Nc1ccc(F)c(F)c1)CC2] | N5-(3,4-Difluorophenyl)-2-(3-fluorophenyl)-6,7-dihydropyrazolo[1,5-a]pyrazine-3,5(4H)-dicarboxamide | B | 416 | 8.72<br>8.25 | A<br>B |
| 30 | 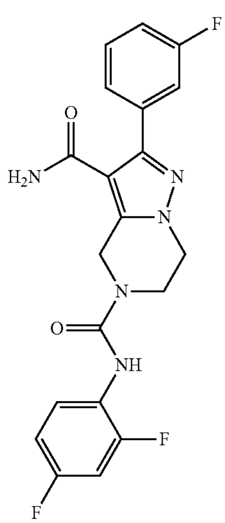 [SMILES: NC(=O)c1c(-c2cccc(F)c2)nn2c1CN(C(=O)Nc1ccc(F)cc1F)CC2] | N5-(2,4-Difluorophenyl)-2-(3-fluorophenyl)-6,7-dihydropyrazolo[1,5-a]pyrazine-3,5(4H)-dicarboxamide | B | 416 | 7.88<br>7.55 | A<br>B |

TABLE 2-continued

| Ex. No. | Structure | Name | Synthetic Method | [M + H]+ | Ret Time (min.) | HPLC Method |
|---|---|---|---|---|---|---|
| 31 | 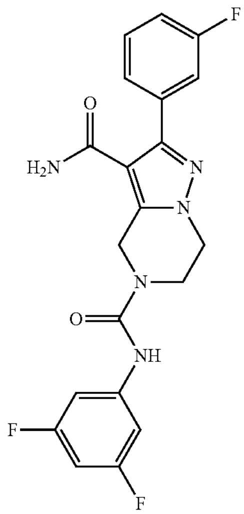 [SMILES: NC(=O)c1c(-c2cccc(F)c2)nn2c1CN(C(=O)Nc1cc(F)cc(F)c1)CC2] | N5-(3,5-Difluorophenyl)-2-(3-fluorophenyl)-6,7-dihydropyrazolo[1,5-a]pyrazine-3,5(4H)-dicarboxamide | B | 416 | 9.04<br>8.54 | A<br>B |
| 32 | 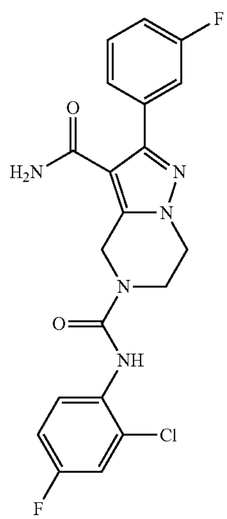 [SMILES: NC(=O)c1c(-c2cccc(F)c2)nn2c1CN(C(=O)Nc1ccc(F)cc1Cl)CC2] | N5-(2-Chloro-4-fluorophenyl)-2-(3-fluorophenyl)-6,7-dihydropyrazolo[1,5-a]pyrazine-3,5(4H)-dicarboxamide | B | 432 | 8.29<br>7.96 | A<br>B |
| 33 | 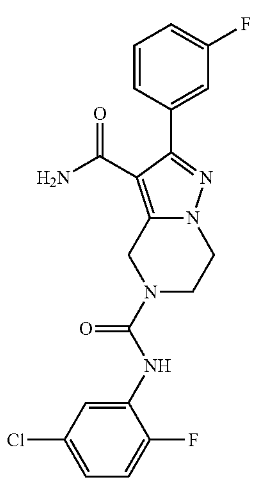 [SMILES: NC(=O)c1c(-c2cccc(F)c2)nn2c1CN(C(=O)Nc1cc(Cl)ccc1F)CC2] | N5-(5-Chloro-2-fluorophenyl)-2-(3-fluorophenyl)-6,7-dihydropyrazolo[1,5-a]pyrazine-3,5(4H)-dicarboxamide | B | 432 | 8.79<br>8.41 | A<br>B |

TABLE 2-continued

| Ex. No. | Structure | Name | Synthetic Method | [M + H]⁺ | Ret Time (min.) | HPLC Method |
|---|---|---|---|---|---|---|
| 34 | 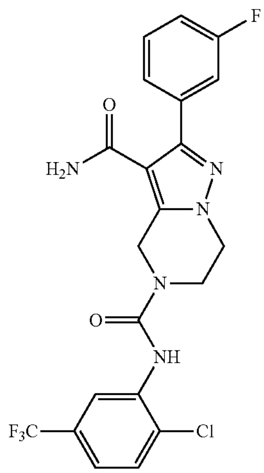 | N⁵-(2-Chloro-5-(trifluoromethyl)phenyl)-2-(3-fluorophenyl)-6,7-dihydropyrazolo[1,5-a]pyrazine-3,5(4H)-dicarboxamide | B | 482 | 9.25 9.83 | B A |
| 35 | 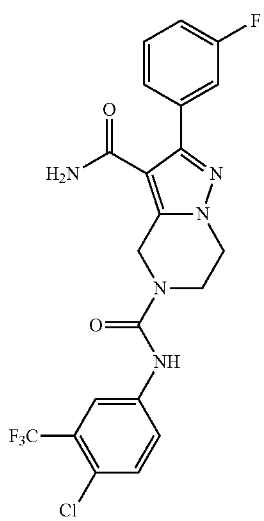 [SMILES: NC(=O)c1c(-c2cccc(F)c2)nn2c1CN(C(=O)Nc1ccc(Cl)c(C(F)(F)F)c1)CC2] | N⁵-(4-Chloro-3-(trifluoromethyl)phenyl)-2-(3-fluorophenyl)-6,7-dihydropyrazolo[1,5-a]pyrazine-3,5(4H)-dicarboxamide | B | 482 | 9.64 10.37 | B A |
| 36 | 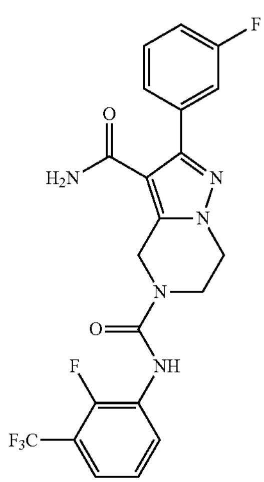 | N⁵-(2-Fluoro-3-(trifluoromethyl)phenyl)-2-(3-fluorophenyl)-6,7-dihydropyrazolo[1,5-a]pyrazine-3,5(4H)-dicarboxamide | B | 466 | 8.79 9.26 | B A |

TABLE 2-continued

| Ex. No. | Structure | Name | Synthetic Method | [M + H]+ | Ret Time (min.) | HPLC Method |
|---|---|---|---|---|---|---|
| 37 | 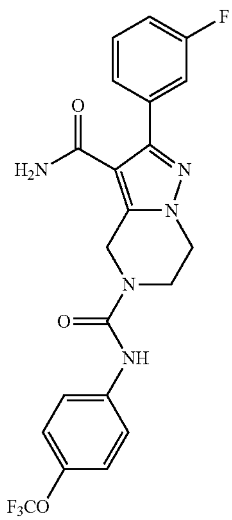 [SMILES: NC(=O)c1c(-c2cccc(F)c2)nn2c1CN(C(=O)Nc1ccc(OC(F)(F)F)cc1)CC2] | 2-(3-Fluorophenyl)-N5-(4-(trifluoromethoxy)phenyl)-6,7-dihydropyrazolo[1,5-a]pyrazine-3,5(4H)-dicarboxamide | B | 464 | 9.93<br>9.67 | B<br>A |
| 38 | 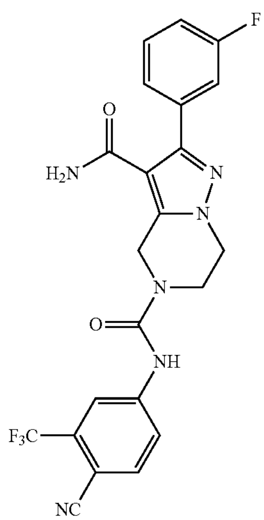 [SMILES: N#Cc1ccc(NC(=O)N2CCn3nc(-c4cccc(F)c4)c(C(N)=O)c3C2)cc1C(F)(F)F] | N5-(4-Cyano-3-(trifluoromethyl)phenyl)-2-(3-fluorophenyl)-6,7-dihydropyrazolo[1,5-a]pyrazine-3,5(4H)-dicarboxamide | B | 473 | 9.03<br>9.49 | B<br>A |
| 39 | 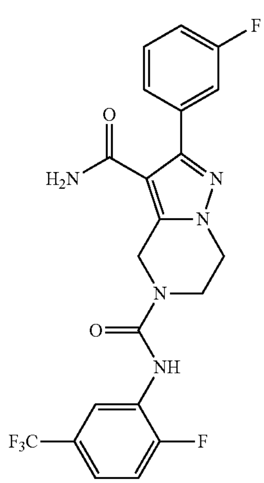 | N5-(2-Fluoro-5-(trifluoromethyl)phenyl)-2-(3-fluorophenyl)-6,7-dihydropyrazolo[1,5-a]pyrazine-3,5(4H)-dicarboxamide | B | 466 | 9.71<br>9.32 | B<br>A |

TABLE 2-continued

| Ex. No. | Structure | Name | Synthetic Method | [M + H]+ | Ret Time (min.) | HPLC Method |
|---|---|---|---|---|---|---|
| 40 | 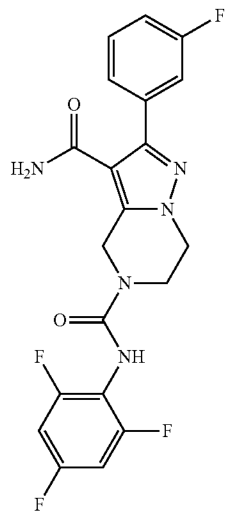 [SMILES: NC(=O)c1c(-c2cccc(F)c2)nn2c1CN(C(=O)Nc1c(F)cc(F)cc1F)CC2] | 2-(3-Fluorophenyl)-N5-(2,4,6-trifluorophenyl)-6,7-dihydropyrazolo[1,5-a]pyrazine-3,5(4H)dicarboxamide | B | 434 | 8.39<br>7.76 | B<br>A |
| 41 | 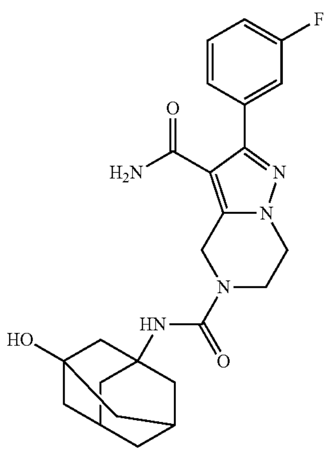 [SMILES: NC(=O)c1c(-c2cccc(F)c2)nn2c1CN(C(=O)NC13CC4CC(CC(O)(C4)C1)C3)CC2] | 2-(3-Fluorophenyl)-N5-(3-hydroxyadamantan-1-yl)-6,7-dihydropyrazolo[1,5-a]pyrazine-3,5(4H)-dicarboxamide | B | 454 | 7.22<br>6.70 | B<br>A |
| 42 | 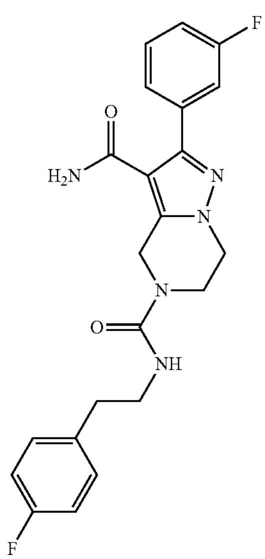 [SMILES: NC(=O)c1c(-c2cccc(F)c2)nn2c1CN(C(=O)NCCc1ccc(F)cc1)CC2] | N5-(4-Fluorophenethyl)-2-(3-fluorophenyl)-6,7-dihydropyrazolo[1,5-a]pyrazine-3,5(4H)-dicarboxamide | A | 426 | 1.276 | E |

TABLE 2-continued

| Ex. No. | Structure | Name | Synthetic Method | [M + H]+ | Ret Time (min.) | HPLC Method |
|---|---|---|---|---|---|---|
| 43 | 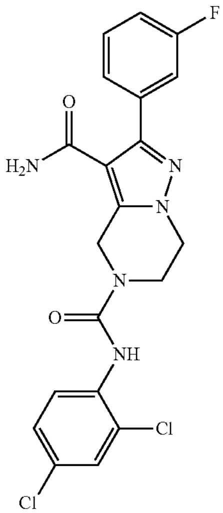 [SMILES: NC(=O)c1c(-c2cccc(F)c2)nn2c1CN(C(=O)Nc1ccc(Cl)cc1Cl)CC2] | N5-(2,4-Dichlorophenyl)-2-(3-fluorophenyl)-6,7-dihydropyrazolo[1,5-a]pyrazine-3,5(4H)-dicarboxamide | A | 449 | 1.441 | E |
| 44 | 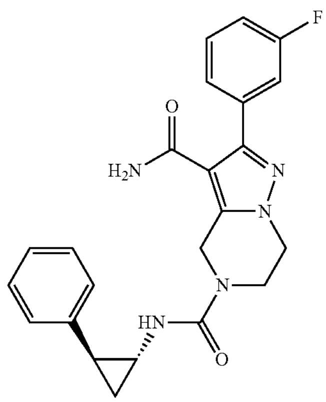 [SMILES: NC(=O)c1c(-c2cccc(F)c2)nn2c1CN(C(=O)N[C@@H]1C[C@H]1c1ccccc1)CC2] | 2-(3-Fluorophenyl)-N5-((1R,2S)-2-phenylcyclopropyl)-6,7-dihydropyrazolo[1,5-a]pyrazine-3,5(4H)-dicarboxamide | A | 420 | 1.325 | E |
| 45 | 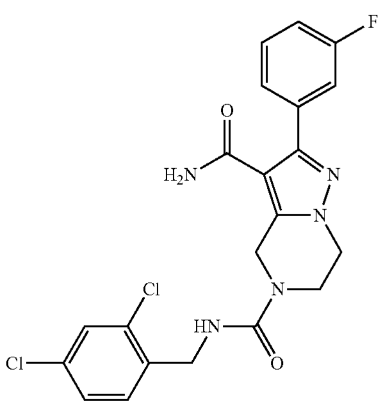 [SMILES: NC(=O)c1c(-c2cccc(F)c2)nn2c1CN(C(=O)NCc1ccc(Cl)cc1Cl)CC2] | N5-(2,4-Dichlorobenzyl)-2-(3-fluorophenyl)-6,7-dihydropyrazolo[1,5-a]pyrazine-3,5(4H)-dicarboxamide | A | 464 | 1.483 | E |

TABLE 2-continued

| Ex. No. | Structure | Name | Synthetic Method | [M + H]⁺ | Ret Time (min.) | HPLC Method |
|---|---|---|---|---|---|---|
| 46 | 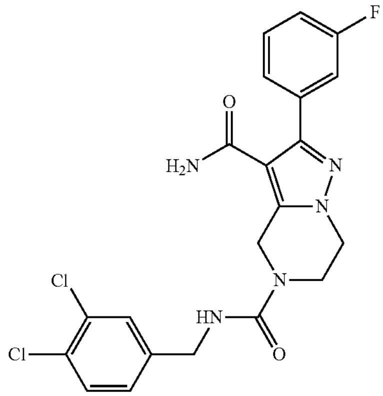 [SMILES: NC(=O)c1c(-c2cccc(F)c2)nn2c1CN(C(=O)NCc1ccc(Cl)c(Cl)c1)CC2] | N⁵-(3,4-Dichlorobenzyl)-2-(3-fluorophenyl)-6,7-dihydropyrazolo[1,5-a]pyrazine-3,5(4H)-dicarboxamide | A | 463 | 1.484 | E |
| 47 | 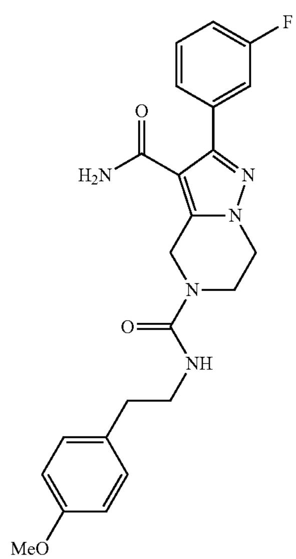 [SMILES: COc1ccc(CCNC(=O)N2CCn3nc(-c4cccc(F)c4)c(C(N)=O)c3C2)cc1] | 2-(3-Fluorophenyl)-N⁵-(4-methoxyphenethyl)-6,7-dihydropyrazolo[1,5-a]pyrazine-3,5(4H)-dicarboxamide | A | 438 | 1.230 | E |
| 48 | 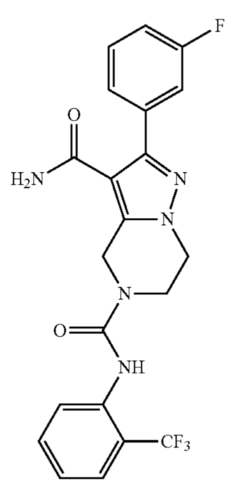 [SMILES: NC(=O)c1c(-c2cccc(F)c2)nn2c1CN(C(=O)Nc1ccccc1C(F)(F)F)CC2] | 2-(3-Fluorophenyl)-N⁵-(2-(trifluoromethyl)phenyl)-6,7-dihydropyrazolo[1,5-a]pyrazine-3,5(4H)-dicarboxamide | A | 448 | 1.269 | E |

TABLE 2-continued

| Ex. No. | Structure | Name | Synthetic Method | [M + H]+ | Ret Time (min.) | HPLC Method |
|---|---|---|---|---|---|---|
| 49 | 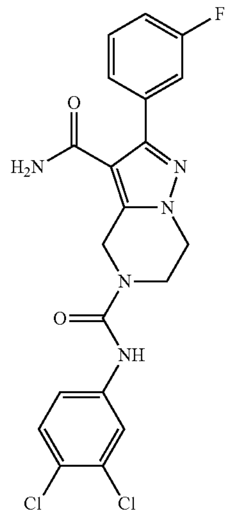 [SMILES: NC(=O)c1c(-c2cccc(F)c2)nn2c1CN(C(=O)Nc1ccc(Cl)c(Cl)c1)CC2] | N5-(3,4-Dichlorophenyl)-2-(3-fluorophenyl)-6,7-dihydropyrazolo[1,5-a]pyrazine-3,5(4H)-dicarboxamide | A | 448 | 1.572 | E |
| 50 | 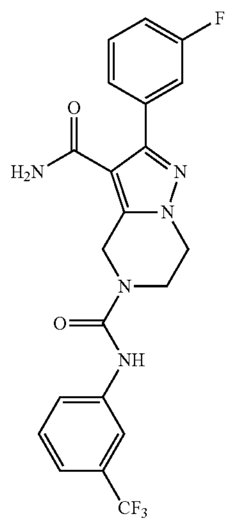 [SMILES: NC(=O)c1c(-c2cccc(F)c2)nn2c1CN(C(=O)Nc1cccc(C(F)(F)F)c1)CC2] | 2-(3-Fluorophenyl)-N5-(3-(trifluoromethyl)phenyl)-6,7-dihydropyrazolo[1,5-a]pyrazine-3,5(4H)-dicarboxamide | A | 448 | 1.516 | E |
| 51 | 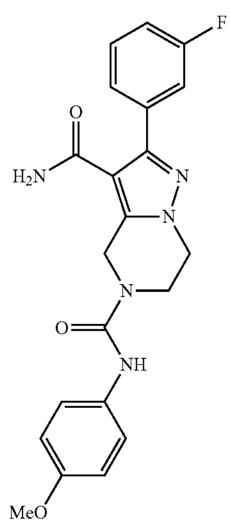 [SMILES: COc1ccc(NC(=O)N2CCn3nc(-c4cccc(F)c4)c(C(N)=O)c3C2)cc1] | 2-(3-Fluorophenyl)-N5-(4-methoxyphenyl)-6,7-dihydropyrazolo[1,5-a]pyrazine-3,5(4H)-dicarboxamide | A | 410 | 1.134 | E |

TABLE 2-continued

| Ex. No. | Structure | Name | Synthetic Method | [M + H]+ | Ret Time (min.) | HPLC Method |
|---|---|---|---|---|---|---|
| 52 | 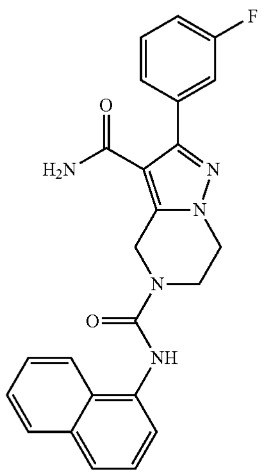 [SMILES: NC(=O)c1c(-c2cccc(F)c2)nn2c1CN(C(=O)Nc1cccc3ccccc13)CC2] | 2-(3-Fluorophenyl)-N5-(naphthalen-1-yl)-6,7-dihydropyrazolo[1,5-a]pyrazine-3,5(4H)-dicarboxamide | A | 430 | 1.303 | E |
| 53 | 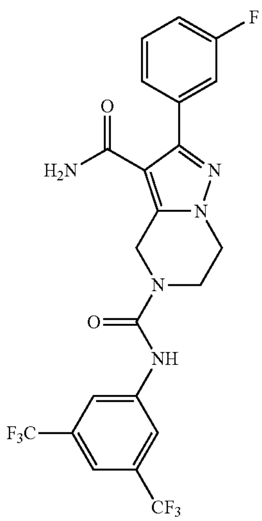 [SMILES: NC(=O)c1c(-c2cccc(F)c2)nn2c1CN(C(=O)Nc1cc(C(F)(F)F)cc(C(F)(F)F)c1)CC2] | N5-(3,5-Bis(trifluoromethyl)phenyl)-2-(3-fluorophenyl)-6,7-dihydropyrazolo[1,5-a]pyrazine-3,5(4H)-dicarboxamide | A | 516 | 1.837 | E |
| 54 | 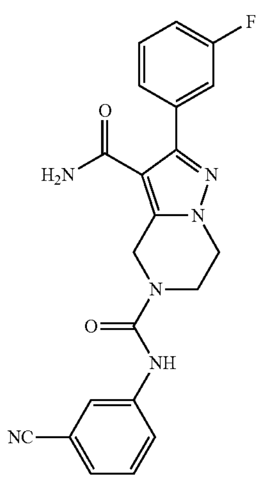 [SMILES: N#Cc1cccc(NC(=O)N2CCn3nc(-c4cccc(F)c4)c(C(N)=O)c3C2)c1] | N5-(3-Cyanophenyl)-2-(3-fluorophenyl)-6,7-dihydropyrazolo[1,5-a]pyrazine-3,5(4H)-dicarboxamide | A | 405 | 1.190 | E |

TABLE 2-continued

| Ex. No. | Structure | Name | Synthetic Method | [M + H]⁺ | Ret Time (min.) | HPLC Method |
|---|---|---|---|---|---|---|
| 55 | 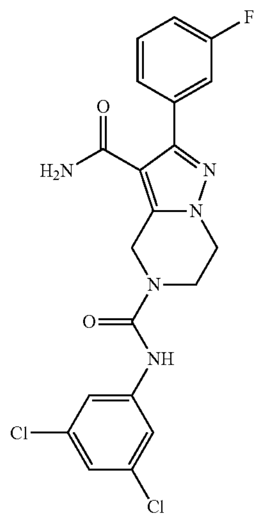 [SMILES: NC(=O)c1c(-c2cccc(F)c2)nn2c1CN(C(=O)Nc1cc(Cl)cc(Cl)c1)CC2] | N⁵-(3,5-Dichlorophenyl)-2-(3-fluorophenyl)-6,7-dihydropyrazolo[1,5-a]pyrazine-3,5(4H)-dicarboxamide | A | 449 | 1.64 | E |
| 56 | 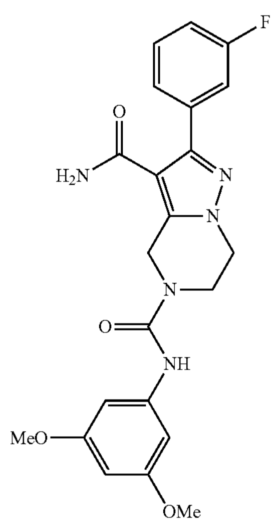 [SMILES: COc1cc(NC(=O)N2CCn3nc(-c4cccc(F)c4)c(C(N)=O)c3C2)cc(OC)c1] | N⁵-(3,5-Dimethoxyphenyl)-2-(3-fluorophenyl)-6,7-dihydropyrazolo[1,5-a]pyrazine-3,5(4H)-dicarboxamide | A | 440 | 1.248 | E |
| 57 | 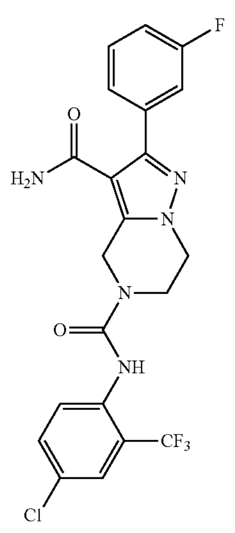 | N⁵-(4-Chloro-2-(trifluoromethyl)phenyl)-2-(3-fluorophenyl)-6,7-dihydropyrazolo[1,5-a]pyrazine-3,5(4H)-dicarboxamide | A | 482 | 1.466 | E |

TABLE 2-continued

| Ex. No. | Structure | Name | Synthetic Method | [M + H]+ | Ret Time (min.) | HPLC Method |
|---|---|---|---|---|---|---|
| 58 | 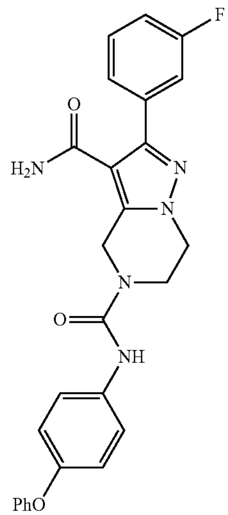 [SMILES: NC(=O)c1c(-c2cccc(F)c2)nn2c1CN(C(=O)Nc1ccc(Oc3ccccc3)cc1)CC2] | 2-(3-Fluorophenyl)-N5-(4-phenoxyphenyl)-6,7-dihydropyrazolo[1,5-a]pyrazine-3,5(4H)-dicarboxamide | A | 472 | 1.613 | E |
| 59 | 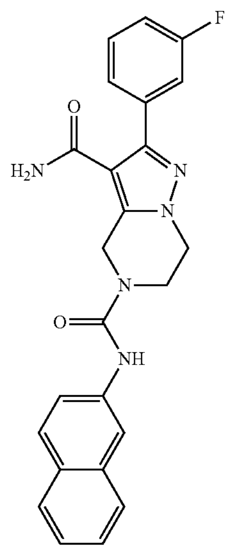 [SMILES: NC(=O)c1c(-c2cccc(F)c2)nn2c1CN(C(=O)Nc1ccc3ccccc3c1)CC2] | 2-(3-Fluorophenyl)-N5-(naphthalen-2-yl)-6,7-dihydropyrazolo[1,5-a]pyrazine-3,5(4H)-dicarboxamide | A | 430 | 1.459 | E |
| 60 | 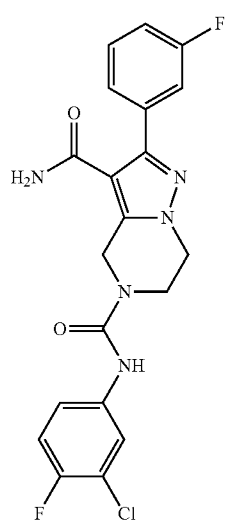 | N5-(3-Chloro-4-fluorophenyl)-2-(3-fluorophenyl)-6,7-dihydropyrazolo[1,5-a]pyrazine-3,5(4H)-dicarboxamide | A | 432 | 1.424 | E |

TABLE 2-continued

| Ex. No. | Structure | Name | Synthetic Method | [M + H]+ | Ret Time (min.) | HPLC Method |
|---|---|---|---|---|---|---|
| 61 | 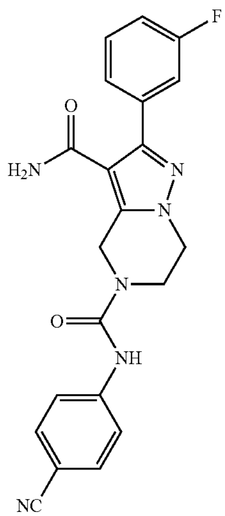 [SMILES: N#Cc1ccc(NC(=O)N2CCn3nc(-c4cccc(F)c4)c(C(N)=O)c3C2)cc1] | N5-(4-Cyanophenyl)-2-(3-fluorophenyl)-6,7-dihydropyrazolo[1,5-a]pyrazine-3,5(4H)-dicarboxamide | A | 405 | 1.186 | E |
| 62 | 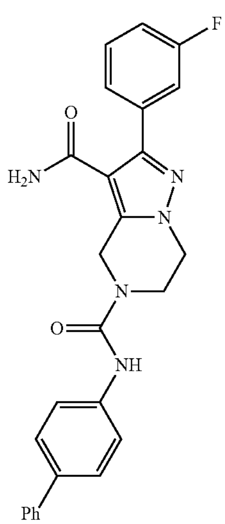 [SMILES: NC(=O)c1c(-c2cccc(F)c2)nn2c1CN(C(=O)Nc1ccc(-c3ccccc3)cc1)CC2] | N5-([1,1'-Biphenyl]-4-yl)-2-(3-fluorophenyl)-6,7-dihydropyrazolo[1,5-a]pyrazine-3,5(4H)-dicarboxamide | A | 456 | 1.621 | E |

TABLE 2-continued

| Ex. No. | Structure | Name | Synthetic Method | [M + H]+ | Ret Time (min.) | HPLC Method |
|---|---|---|---|---|---|---|
| 63 | 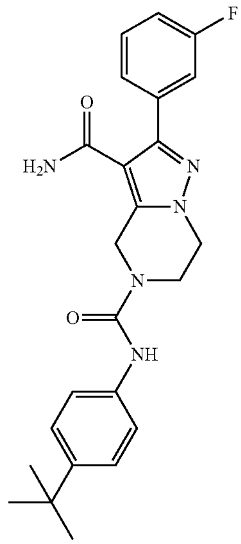 [SMILES: CC(C)(C)c1ccc(NC(=O)N2CCn3nc(-c4cccc(F)c4)c(C(N)=O)c3C2)cc1] | N5-(4-(tert-Butyl)phenyl)-2-(3-fluorophenyl)-6,7-dihydropyrazolo[1,5-a]pyrazine-3,5(4H)-dicarboxamide | A | 436 | 1.657 | E |
| 64 | 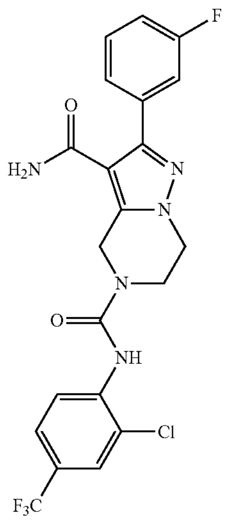 [SMILES: NC(=O)c1c(-c2cccc(F)c2)nn2c1CN(C(=O)Nc1ccc(C(F)(F)F)cc1Cl)CC2] | N5-(2-Chloro-4-(trifluoromethyl)phenyl)-2-(3-fluorophenyl)-6,7-dihydropyrazolo[1,5-a]pyrazine-3,5(4H)-dicarboxamide | A | 482 | 1.610 | E |
| 65 | 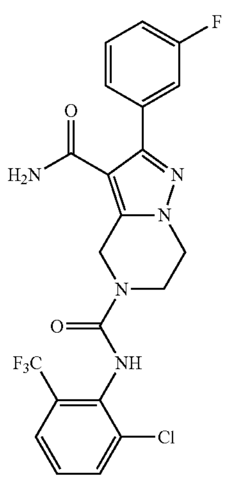 [SMILES: NC(=O)c1c(-c2cccc(F)c2)nn2c1CN(C(=O)Nc1c(Cl)cccc1C(F)(F)F)CC2] | N5-(2-Chloro-6-(trifluoromethyl)phenyl)-2-(3-fluorophenyl)-6,7-dihydropyrazolo[1,5-a]pyrazine-3,5(4H)-dicarboxamide | A | 482 | 1.259 | E |

TABLE 2-continued

| Ex. No. | Structure | Name | Synthetic Method | [M + H]⁺ | Ret Time (min.) | HPLC Method |
|---|---|---|---|---|---|---|
| 66 | 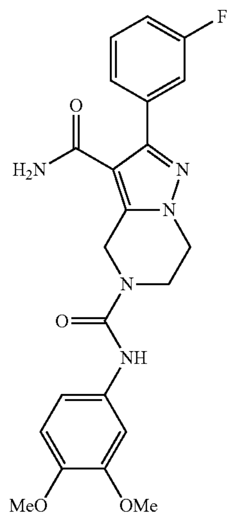 [SMILES: COc1ccc(NC(=O)N2CCn3nc(-c4cccc(F)c4)c(C(N)=O)c3C2)cc1OC] | N⁵-(3,4-Dimethoxyphenyl)-2-(3-fluorophenyl)-6,7-dihydropyrazolo[1,5-a]pyrazine-3,5(4H)-dicarboxamide | A | 440 | 1.066 | E |
| 67 | 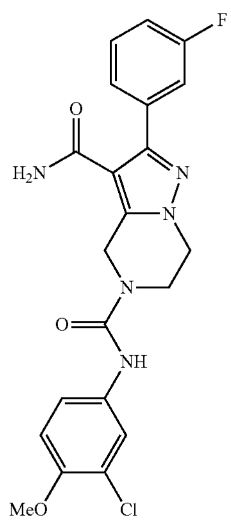 [SMILES: COc1ccc(NC(=O)N2CCn3nc(-c4cccc(F)c4)c(C(N)=O)c3C2)cc1Cl] | N⁵-(3-Chloro-4-methoxyphenyl)-2-(3-fluorophenyl)-6,7-dihydropyrazolo[1,5-a]pyrazine-3,5(4H)-dicarboxamide | A | 444 | 1.310 | E |
| 68 | 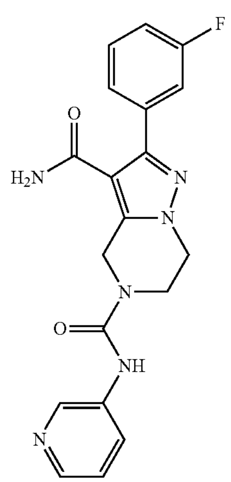 [SMILES: NC(=O)c1c(-c2cccc(F)c2)nn2c1CN(C(=O)Nc1cccnc1)CC2] | 2-(3-Fluorophenyl)-N⁵-(pyridin-3-yl)-6,7-dihydropyrazolo[1,5-a]pyrazine-3,5(4H)-dicarboxamide | A | 381 | 0.886 | E |

TABLE 2-continued

| Ex. No. | Structure | Name | Synthetic Method | [M + H]⁺ | Ret Time (min.) | HPLC Method |
|---|---|---|---|---|---|---|
| 69 | 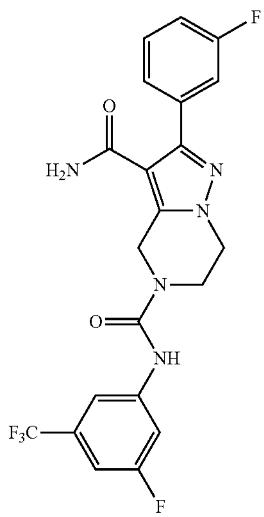 [SMILES: NC(=O)c1c(-c2cccc(F)c2)nn2c1CN(C(=O)Nc1cc(F)cc(C(F)(F)F)c1)CC2] | N⁵-(3-Fluoro-5-(trifluoromethyl)phenyl)-2-(3-fluorophenyl)-6,7-dihydropyrazolo[1,5-a]pyrazine-3,5(4H)-dicarboxamide | A | 466 | 1.631 | E |
| 70 | 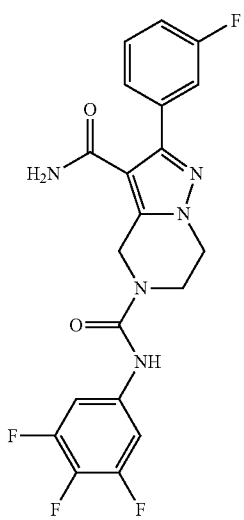 [SMILES: NC(=O)c1c(-c2cccc(F)c2)nn2c1CN(C(=O)Nc1cc(F)c(F)c(F)c1)CC2] | 2-(3-Fluorophenyl)-N⁵-(3,4,5-trifluorophenyl)-6,7-dihydropyrazolo[1,5-a]pyrazine-3,5(4H)-dicarboxamide | B | 434 | 14.7<br>13.49 | F<br>G |
| 71 | 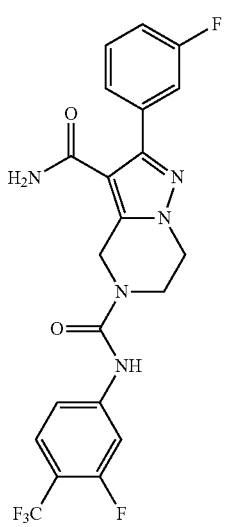 | N⁵-(3-Fluoro-4-(trifluoromethyl)phenyl)-2-(3-fluorophenyl)-6,7-dihydropyrazolo[1,5-a]pyrazine-3,5(4H)-dicarboxamide | B | 466 | 16.11<br>14.743 | F<br>G |

TABLE 2-continued

| Ex. No. | Structure | Name | Synthetic Method | [M + H]+ | Ret Time (min.) | HPLC Method |
|---|---|---|---|---|---|---|
| 72 | 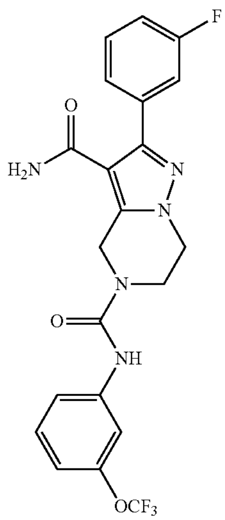 | 2-(3-Fluorophenyl)-N5-(3-(trifluoromethoxy)phenyl)-6,7-dihydropyrazolo[1,5-a]pyrazine-3,5(4H)-dicarboxamide | B | 464 | 15.59<br>14.07 | F<br>G |
| 73 | 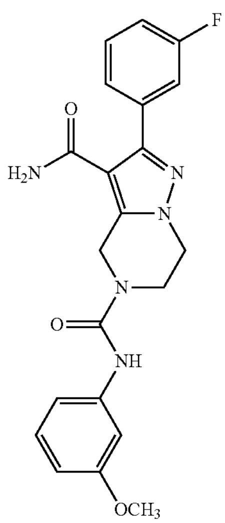 [SMILES: COc1cccc(NC(=O)N2CCn3nc(-c4cccc(F)c4)c(C(N)=O)c3C2)c1] | 2-(3-Fluorophenyl)-N5-(3-methoxyphenyl)-6,7-dihydropyrazolo[1,5-a]pyrazine-3,5(4H)-dicarboxamide | B | 410 | 11.76<br>11.05 | F<br>G |
| 74 | 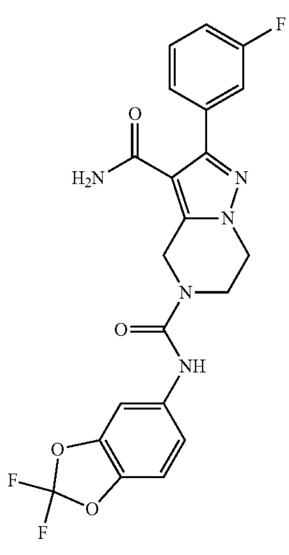 [SMILES: NC(=O)c1c(-c2cccc(F)c2)nn2c1CN(C(=O)Nc1ccc3c(c1)OC(F)(F)O3)CC2] | N5-(2,2-Difluorobenzo[d][1,3]dioxol-5-yl)-2-(3-fluorophenyl)-6,7-dihydropyrazolo[1,5-a]pyrazine-3,5(4H)-dicarboxamide | B | 460 | 14.82<br>13.56 | F<br>G |

TABLE 2-continued

| Ex. No. | Structure | Name | Synthetic Method | [M + H]+ | Ret Time (min.) | HPLC Method |
|---|---|---|---|---|---|---|
| 75 | 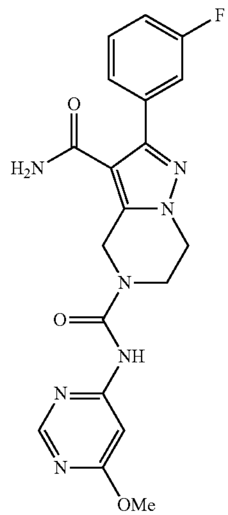 [SMILES: COc1cc(NC(=O)N2CCn3nc(-c4cccc(F)c4)c(C(N)=O)c3C2)ncn1] | 2-(3-Fluorophenyl)-N5-(6-methoxypyrimidin-4-yl)-6,7-dihydropyrazolo[1,5-a]pyrazine-3,5(4H)-dicarboxamide | B | 412 | 12.78<br>12.18 | C<br>D |
| 76 | 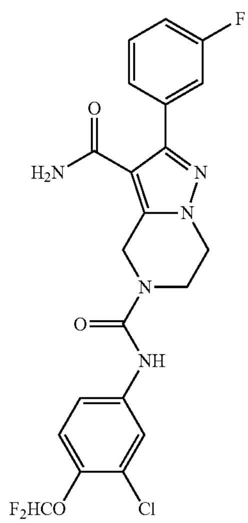 [SMILES: NC(=O)c1c(-c2cccc(F)c2)nn2c1CN(C(=O)Nc1ccc(OC(F)F)c(Cl)c1)CC2] | N5-(3-Chloro-4-(difluoromethoxy)phenyl)-2-(3-fluorophenyl)-6,7-dihydropyrazolo[1,5-a]pyrazine-3,5(4H)-dicarboxamide | B | 480 | 9.16<br>9.59 | B<br>A |
| 77 | 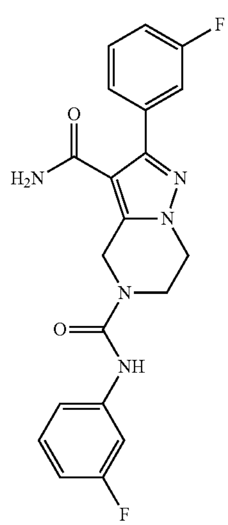 [SMILES: NC(=O)c1c(-c2cccc(F)c2)nn2c1CN(C(=O)Nc1cccc(F)c1)CC2] | N5,2-Bis(3-fluorophenyl)-6,7-dihydropyrazolo[1,5-a]pyrazine-3,5(4H)-dicarboxamide | B | 398 | 16.34<br>15.21 | C<br>D |

TABLE 2-continued

| Ex. No. | Structure | Name | Synthetic Method | [M + H]+ | Ret Time (min.) | HPLC Method |
|---|---|---|---|---|---|---|
| 78 | 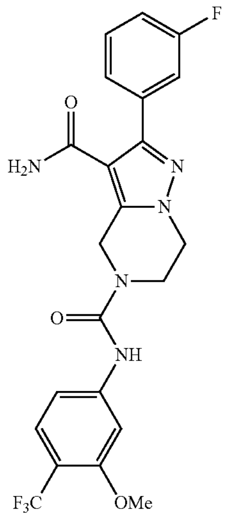 [SMILES: COc1cc(NC(=O)N2CCn3nc(-c4cccc(F)c4)c(C(N)=O)c3C2)ccc1C(F)(F)F] | 2-(3-Fluorophenyl)-N5-(3-methoxy-4-(trifluoromethyl)phenyl)-6,7-dihydropyrazolo[1,5-a]pyrazine-3,5(4H)-dicarboxamide | B | 478 | 14.53 13.53 | F G |
| 79 | 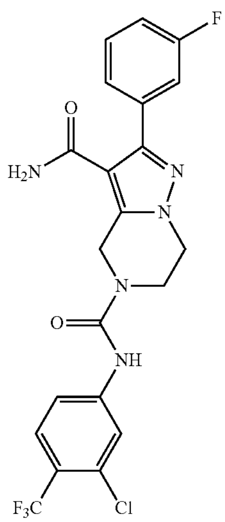 [SMILES: NC(=O)c1c(-c2cccc(F)c2)nn2c1CN(C(=O)Nc1ccc(C(F)(F)F)c(Cl)c1)CC2] | N5-(3-Chloro-4-(trifluoromethyl)phenyl)-2-(3-fluorophenyl)-6,7-dihydropyrazolo[1,5-a]pyrazine-3,5(4H)-dicarboxamide | B | 482 | 15.22 16.90 | G F |
| 80 | 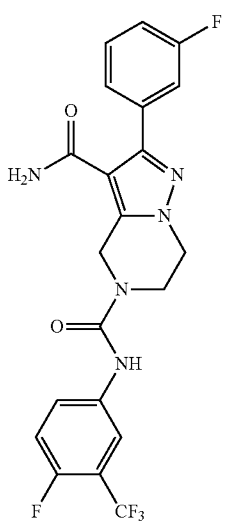 [SMILES: NC(=O)c1c(-c2cccc(F)c2)nn2c1CN(C(=O)Nc1ccc(F)c(C(F)(F)F)c1)CC2] | N5-(4-Fluoro-3-(trifluoromethyl)phenyl)-2-(3-fluorophenyl)-6,7-dihydropyrazolo[1,5-a]pyrazine-3,5(4H)-dicarboxamide | B | 466 | 15.43 13.97 | F G |

TABLE 2-continued

| Ex. No. | Structure | Name | Synthetic Method | [M + H]+ | Ret Time (min.) | HPLC Method |
|---|---|---|---|---|---|---|
| 81 | 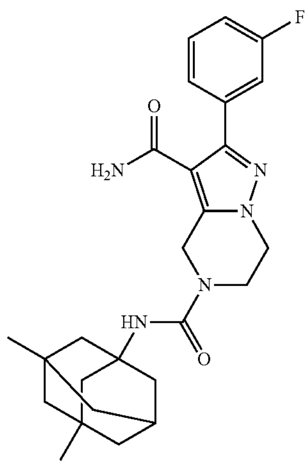 [SMILES: CC12CC3CC(C)(C1)CC(NC(=O)N1CCn4nc(-c5cccc(F)c5)c(C(N)=O)c4C1)(C3)C2] | N5-(3,5-Dimethyladamantan-1-yl)-2-(3-fluorophenyl)-6,7-dihydropyrazolo[1,5-a]pyrazine-3,5(4H)-dicarboxamide | C | 466 | 18.48 16.03 | C D |
| 82 | 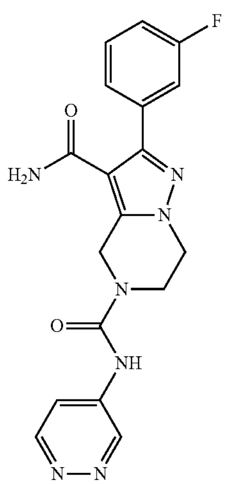 | 2-(3-Fluorophenyl)-N5-(pyridazin-4-yl)-6,7-dihydropyrazolo[1,5-a]pyrazine-3,5(4H)-dicarboxamide | D | 382 | 9.58 8.68 | D C |
| 83 | 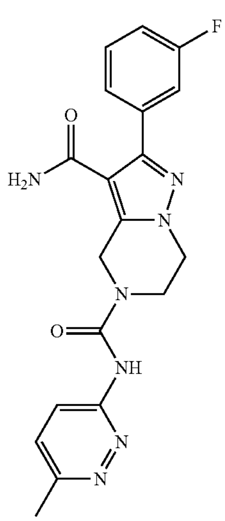 [SMILES: Cc1ccc(NC(=O)N2CCn3nc(-c4cccc(F)c4)c(C(N)=O)c3C2)nn1] | 2-(3-Fluorophenyl)-N5-(6-methylpyridazin-3-yl)-6,7-dihydropyrazolo[1,5-a]pyrazine-3,5(4H)-dicarboxamide | D | 396 | 9.79 9.27 | D C |

TABLE 2-continued

| Ex. No. | Structure | Name | Synthetic Method | [M + H]+ | Ret Time (min.) | HPLC Method |
|---|---|---|---|---|---|---|
| 84 | 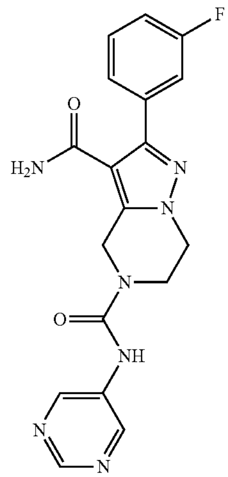 [SMILES: NC(=O)c1c(-c2cccc(F)c2)nn2c1CN(C(=O)Nc1cncnc1)CC2] | 2-(3-Fluorophenyl)-N5-(pyrimidin-5-yl)-6,7-dihydropyrazolo[1,5-a]pyrazine-3,5(4H)-dicarboxamide | B | 382 | 10.43<br>10.80 | D<br>C |
| 85 | 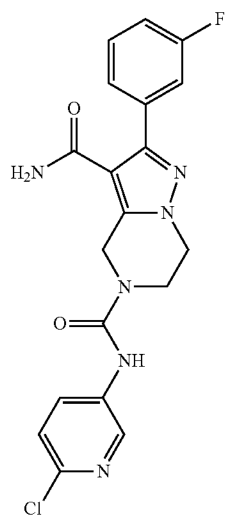 [SMILES: NC(=O)c1c(-c2cccc(F)c2)nn2c1CN(C(=O)Nc1ccc(Cl)nc1)CC2] | N5-(6-Chloropyridin-3-yl)-2-(3-fluorophenyl)-6,7-dihydropyrazolo[1,5-a]pyrazine-3,5(4H)-dicarboxamide | D | 415 | 7.21<br>7.31 | B<br>A |
| 86 | 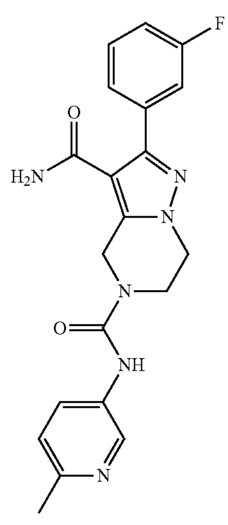 [SMILES: Cc1ccc(NC(=O)N2CCn3nc(-c4cccc(F)c4)c(C(N)=O)c3C2)cn1] | 2-(3-Fluorophenyl)-N5-(6-methylpyridin-3-yl)-6,7-dihydropyrazolo[1,5-a]pyrazine-3,5(4H)-dicarboxamide | D | 395 | 8.46<br>9.74 | C<br>D |

TABLE 2-continued

| Ex. No. | Structure | Name | Synthetic Method | [M + H]⁺ | Ret Time (min.) | HPLC Method |
|---|---|---|---|---|---|---|
| 87 | 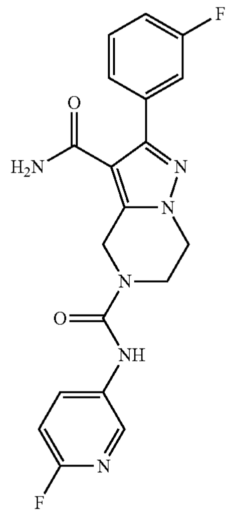 [SMILES: NC(=O)c1c(-c2cccc(F)c2)nn2c1CN(C(=O)Nc1ccc(F)nc1)CC2] | 2-(3-Fluorophenyl)-N⁵-(6-fluoropyridin-3-yl)-6,7-dihydropyrazolo[1,5-a]pyrazine-3,5(4H)-dicarboxamide | D | 399 | 6.79<br>6.71 | A<br>B |
| 88 | 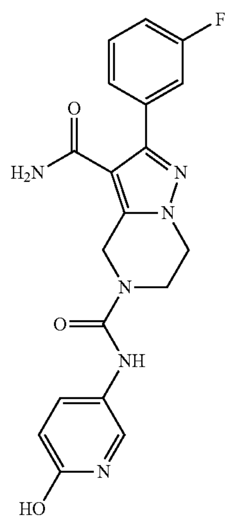 [SMILES: NC(=O)c1c(-c2cccc(F)c2)nn2c1CN(C(=O)Nc1ccc(O)nc1)CC2] | 2-(3-Fluorophenyl)-N⁵-(6-hydroxypyridin-3-yl)-6,7-dihydropyrazolo[1,5-a]pyrazine-3,5(4H)-dicarboxamide | D | 397 | 9.57<br>9.86 | D<br>C |
| 89 | 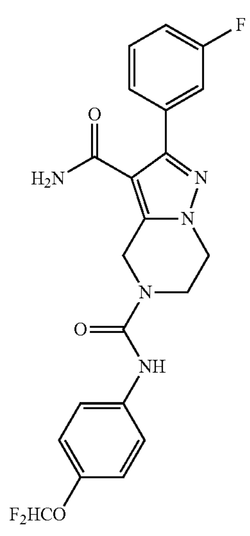 [SMILES: NC(=O)c1c(-c2cccc(F)c2)nn2c1CN(C(=O)Nc1ccc(OC(F)F)cc1)CC2] | N⁵-(4-(Difluoromethoxy)phenyl)-2-(3-fluorophenyl)-6,7-dihydropyrazolo[1,5-a]pyrazine-3,5(4H)-dicarboxamide | B | 446 | 8.53<br>8.82 | B<br>A |

TABLE 2-continued

| Ex. No. | Structure | Name | Synthetic Method | [M + H]+ | Ret Time (min.) | HPLC Method |
|---|---|---|---|---|---|---|
| 90 | 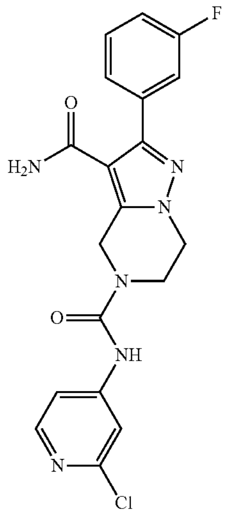 [SMILES: NC(=O)c1c(-c2cccc(F)c2)nn2c1CN(C(=O)Nc1ccnc(Cl)c1)CC2] | N5-(2-Chloropyridin-4-yl)-2-(3-fluorophenyl)-6,7-dihydropyrazolo[1,5-a]pyrazine-3,5(4H)-dicarboxamide | D | 415 | 7.22<br>7.10 | A<br>B |
| 91 | 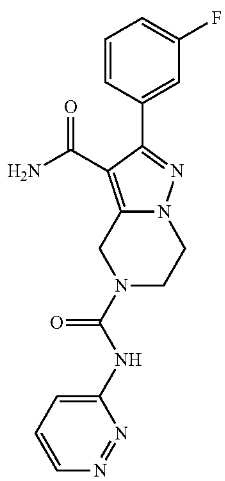 [SMILES: NC(=O)c1c(-c2cccc(F)c2)nn2c1CN(C(=O)Nc1cccnn1)CC2] | 2-(3-Fluorophenyl)-N5-(pyridazin-3-yl)-6,7-dihydropyrazolo[1,5-a]pyrazine-3,5(4H)-dicarboxamide | B | 382 | 10.07<br>9.86 | D<br>C |
| 92 | 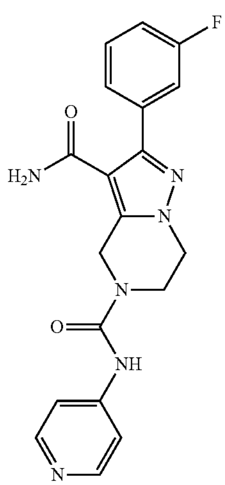 [SMILES: NC(=O)c1c(-c2cccc(F)c2)nn2c1CN(C(=O)Nc1ccncc1)CC2] | 2-(3-Fluorophenyl)-N5-(pyridin-4-yl)-6,7-dihydropyrazolo[1,5-a]pyrazine-3,5(4H)-dicarboxamide | D | 381 | 8.81<br>8.49 | A<br>B |

TABLE 2-continued

| Ex. No. | Structure | Name | Synthetic Method | [M + H]+ | Ret Time (min.) | HPLC Method |
|---|---|---|---|---|---|---|
| 93 | 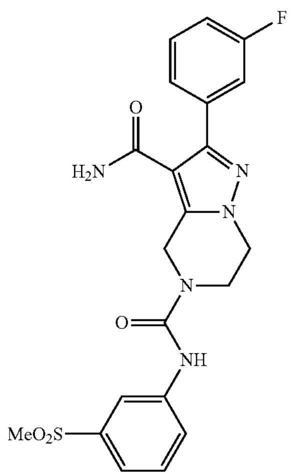 [SMILES: CS(=O)(=O)c1cccc(NC(=O)N2CCn3nc(-c4cccc(F)c4)c(C(N)=O)c3C2)c1] | 2-(3-Fluorophenyl)-N5-(3-(methylsulfonyl)phenyl)-6,7-dihydropyrazolo[1,5-a]pyrazine-3,5(4H)-dicarboxamide | A | 458 | 13.71<br>13.43 | C<br>D |
| 94 | 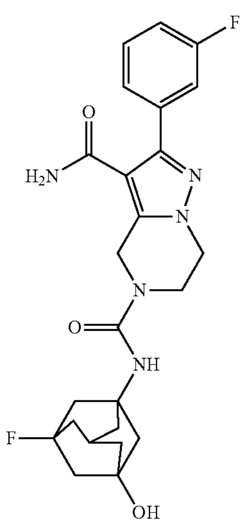 [SMILES: NC(=O)c1c(-c2cccc(F)c2)nn2c1CN(C(=O)NC13CC4CC(O)(CC(F)(C4)C1)C3)CC2] | N5-(3-Fluoro-5-hydroxyadamantan-1-yl)-2-(3-fluorophenyl)-6,7-dihydropyrazolo[1,5-a]pyrazine-3,5(4H)-dicarboxamide | C | 472 | 13.06<br>12.08 | C<br>D |
| 95 | 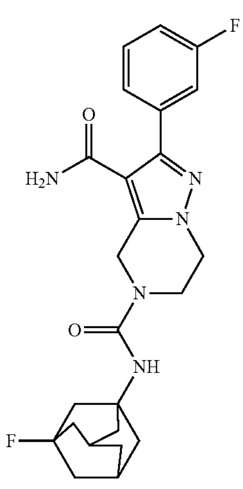 [SMILES: NC(=O)c1c(-c2cccc(F)c2)nn2c1CN(C(=O)NC13CC4CC(CC(F)(C4)C1)C3)CC2] | N5-(3-Fluoroadamantan-1-yl)-2-(3-fluorophenyl)-yl)-6,7-dihydropyrazolo[1,5-a]pyrazine-3,5(4H)-dicarboxamide | C | 456 | 8.32<br>9.03 | B<br>A |

TABLE 2-continued

| Ex. No. | Structure | Name | Synthetic Method | [M + H]+ | Ret Time (min.) | HPLC Method |
|---|---|---|---|---|---|---|
| 96 | 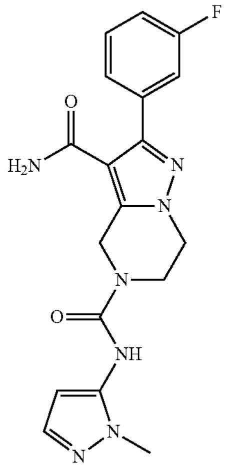 [SMILES: Cn1nccc1NC(=O)N1CCn2nc(-c3cccc(F)c3)c(C(N)=O)c2C1] | 2-(3-Fluorophenyl)-N5-(1-methyl-1H-pyrazol-5-yl)-6,7-dihydropyrazolo[1,5-a]pyrazine-3,5(4H)-dicarboxamide | B | 384 | 10.41<br>10.56 | D<br>C |

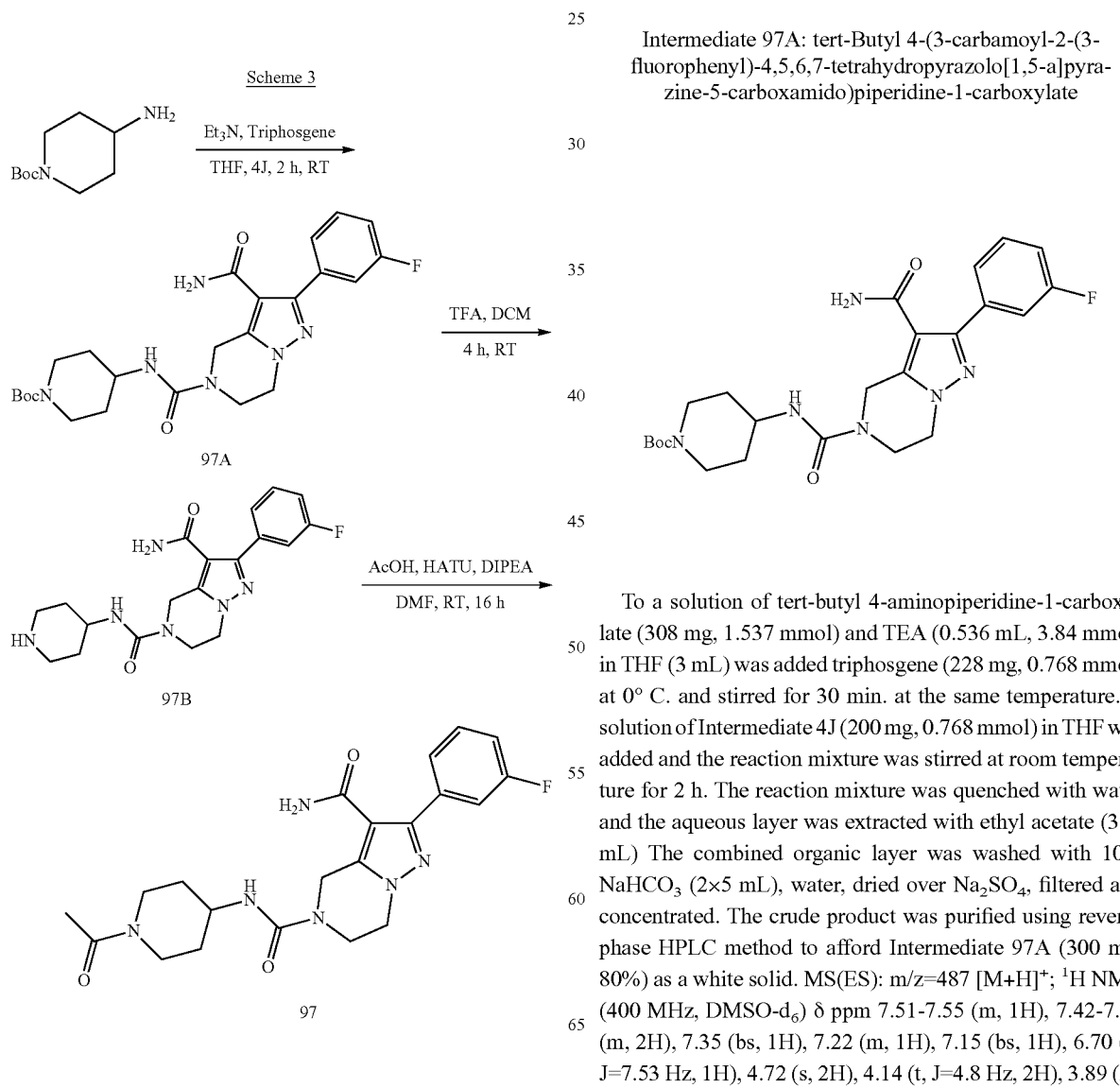

Intermediate 97A: tert-Butyl 4-(3-carbamoyl-2-(3-fluorophenyl)-4,5,6,7-tetrahydropyrazolo[1,5-a]pyrazine-5-carboxamido)piperidine-1-carboxylate To a solution of tert-butyl 4-aminopiperidine-1-carboxylate (308 mg, 1.537 mmol) and TEA (0.536 mL, 3.84 mmol) in THF (3 mL) was added triphosgene (228 mg, 0.768 mmol) at 0° C. and stirred for 30 min. at the same temperature. A solution of Intermediate 4J (200 mg, 0.768 mmol) in THF was added and the reaction mixture was stirred at room temperature for 2 h. The reaction mixture was quenched with water and the aqueous layer was extracted with ethyl acetate (3×5 mL) The combined organic layer was washed with 10% NaHCO$_3$ (2×5 mL), water, dried over Na$_2$SO$_4$, filtered and concentrated. The crude product was purified using reverse phase HPLC method to afford Intermediate 97A (300 mg, 80%) as a white solid. MS(ES): m/z=487 [M+H]+; $^1$H NMR (400 MHz, DMSO-d$_6$) δ ppm 7.51-7.55 (m, 1H), 7.42-7.51 (m, 2H), 7.35 (bs, 1H), 7.22 (m, 1H), 7.15 (bs, 1H), 6.70 (d, J=7.53 Hz, 1H), 4.72 (s, 2H), 4.14 (t, J=4.8 Hz, 2H), 3.89 (m, 2H), 3.84 (t, J=4.4 Hz, 2H), 3.65 (m, 1H), 2.85-2.78 (m, 2H), 1.75 (m, 2H), 1.41 (s, 9H), 1.32 (m, 2H).

Intermediate 97B: 2-(3-Fluorophenyl)-N⁵-(piperidin-4-yl)-6,7-dihydropyrazolo[1,5-a]pyrazine-3,5(4H)-dicarboxamide

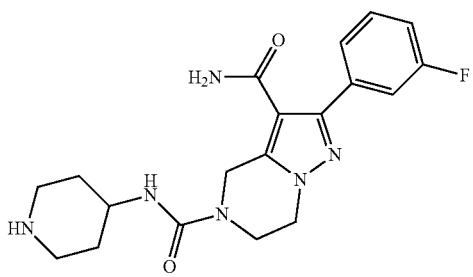 [SMILES: NC(=O)c1c(-c2cccc(F)c2)nn2c1CN(C(=O)NC1CCNCC1)CC2]

To a solution of Intermediate 97A (300 mg, 0.617 mmol) in DCM (3 mL) was added TFA (0.238 mL, 3.08 mmol) at 0° C. and the reaction mixture was stirred at room temperature for 4 h. The reaction mixture was concentrated and the resultant residue was basified to pH=8.0 with 10% NaHCO₃ solution. The aqueous layer was extracted with DCM (3×5 mL) and the combined organic layer was washed with water (2×5 mL), brine, dried over Na₂SO₄, filtered and concentrated to afford Intermediate 97B (200 mg, 80%) as white solid. MS(ES): m/z=387 [M+H]⁺; ¹H NMR (400 MHz, DMSO-d₆) δ ppm 8.50 (bs, 1H), 7.46 (m, 3H), 7.32 (bs, 1H), 7.21 (m, 1H), 7.11 (bs, 1H), 6.86 (d, J=7.03 Hz, 1H), 4.74 (s, 2H), 4.15 (t, J=5.27 Hz, 2H), 3.86 (t, J=5.27 Hz, 2H), 3.72 (m, 1H), 3.27 (s, 2H), 2.96 (m, 2H), 1.93 (m, 2H), 1.54 (m, 2H).

Compound 97:
Method AA (Amides):

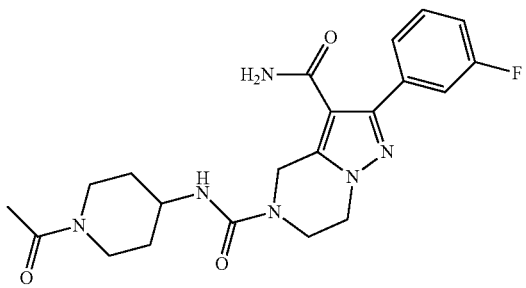 [SMILES: CC(=O)N1CCC(NC(=O)N2CCn3nc(-c4cccc(F)c4)c(C(N)=O)c3C2)CC1]

To a solution of Intermediate 97B (0.025 g, 0.065 mmol) in dry DMF (0.8 mL) was added HATU (0.049 g, 0.129 mmol) and DIPEA (0.034 mL, 0.194 mmol). To this was added acetic acid (7 μL, 0.129 mmol) and the reaction was stirred at RT for 16 h. The reaction was monitored by TLC, which showed the completion of the reaction. The DMF was removed under high vacuum. The reaction mixture was quenched with 10% sodium bicarbonate solution and extracted with DCM (3×30 mL) The combined organic layer was washed with sodium bicarbonate solution, water, and brine, dried over Na₂SO₄, filtered and concentrated to give the crude product. The crude product was further purified by preparative HPLC purification to afford the pure product 97 as a white solid (9 mg, 32%). MS(ES): m/z=429 [M+H]⁺; HPLC Ret. Time 10.76 min. and 10.46 min. (HPLC Methods C and D); ¹H NMR (400 MHz, DMSO-d₆) δ ppm 7.51-7.56 (m, 1H), 7.42-7.51 (m, 2H), 7.34 (br. s., 1H), 7.17-7.23 (m, 1H), 7.14 (br. s., 1H), 6.67-6.75 (m, 1H), 4.73 (s, 2H), 4.30 (d, J=13.05 Hz, 1H), 4.14 (t, J=5.27 Hz, 2H), 3.84 (t, J=5.27 Hz, 2H), 3.79 (d, J=14.56 Hz, 1H), 3.66-3.75 (m, 1H), 3.08 (t, J=11.29 Hz, 1H), 2.57-2.67 (m, 1H), 2.00 (s, 3H), 1.72-1.86 (m, 2H), 1.35-1.44 (m, 1H), 1.27-1.34 (m, 1H).

Method AB (Sulfonamides):

To a solution of Intermediate 97B (0.025 g, 0.065 mmol) and DIPEA (0.034 mL, 0.194 mmol) in dry DCM (0.8 mL) was added cyclopropanesulfonyl chloride (0.018 g, 0.129 mmol) and the reaction was stirred at RT for 16 hours. The reaction mixture was quenched with 10% sodium bicarbonate solution and extracted with DCM (3×30 ml). The combined organic layer was washed with sodium bicarbonate solution, water, and brine, dried over Na₂SO₄, filtered and concentrated to furnish the crude product. The crude product was further purified by preparative HPLC purification.

Method AC (Reductive Amination):

To a solution of Intermediate 97B (0.025 g, 0.065 mmol) in dry DCM (0.5 mL) and methanol (0.5 mL) was added 3,3,3-trifluoropropanal (0.014 g, 0.129 mmol) and stirred at RT for 30 minutes. To this mixture, sodium cyanoborohydride (8.13 mg, 0.129 mmol) was added, the reaction mixture was stirred at RT for 3 h and the solvent was removed under reduced pressure. The residue was partitioned between ethyl acetate and water, layers separated, and the aqueous layer was extracted with EtOAc (3×10 mL) The combined organic layer was washed with water, brine, dried over Na₂SO₄ and concentrated under reduced pressure to afford crude product, which was further purified by preparative HPLC purification.

Method AD (Carbamates):

Step 1: Pyridin-2-yl(1,1,1-trifluoro-2-methylpropan-2-yl) carbonate: To a solution of di(pyridin-2-yl) carbonate (250 mg, 1.156 mmol) in DCM (5 mL) was added DMAP (706 mg, 5.78 mmol) followed by DIPEA (0.202 mL, 1.156 mmol) and 1,1,1-trifluoro-2-methylpropan-2-ol (148 mg, 1.156 mmol). The reaction mixture was stirred at RT overnight, concentrated and the crude was taken to the next step without further purification.

Step 2: To a stirred solution of 97B (0.015 g, 0.039 mmol) in DCM (1.500 mL) was added DIPEA (0.020 mL, 0.116 mmol) and pyridin-2-yl(1,1,1-trifluoro-2-methylpropan-2-yl)carbonate (9.67 mg, 0.039 mmol) and resulting mixture was stirred at 25° C. overnight. The reaction mixture was concentrated and the crude obtained was purified by preparative HPLC purification.

The Compounds described in Table 3 were synthesized analogous to Compound 97 by reacting Intermediate 97B with corresponding acids, sulfonyl chlorides and aldehydes.

TABLE 3
| Ex. No. | Structure | Name | Synthetic method | [M + H]+ | Ret. Time (min.) | HPLC Method |
|---|---|---|---|---|---|---|
| 98 | 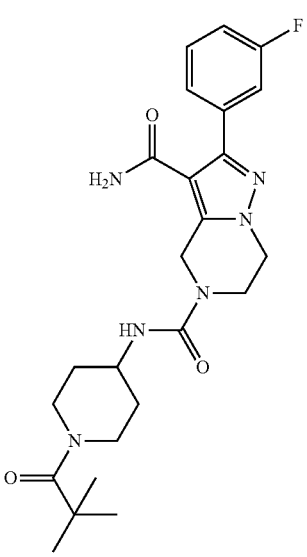 [SMILES: CC(C)(C)C(=O)N1CCC(NC(=O)N2CCn3nc(-c4cccc(F)c4)c(C(N)=O)c3C2)CC1] | 2-(3-Fluorophenyl)-N⁵-(1-pivaloylpiperidin-4-yl)-6,7-dihydropyrazolo[1,5-a]pyrazine-3,5(4H)-dicarboxamide | AA | 471 | 13.96<br>13.29 | A<br>B |
| 99 | 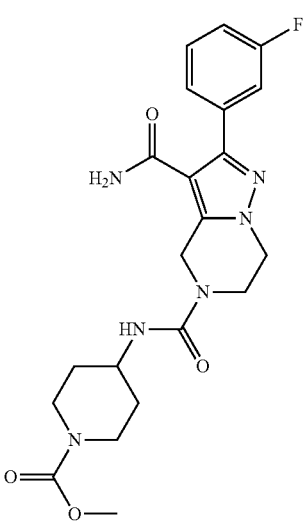 [SMILES: COC(=O)N1CCC(NC(=O)N2CCn3nc(-c4cccc(F)c4)c(C(N)=O)c3C2)CC1] | Methyl 4-(3-carbamoyl-2-(3-fluorophenyl)-4,5,6,7-tetrahydropyrazolo[1,5-a]pyrazine-5-carboxamido)piperidine-1-carboxylate | AB | 445 | 6.88<br>6.39 | A<br>B |

TABLE 3-continued
| Ex. No. | Structure | Name | Synthetic method | [M + H]+ | Ret. Time (min.) | HPLC Method |
|---|---|---|---|---|---|---|
| 100 | 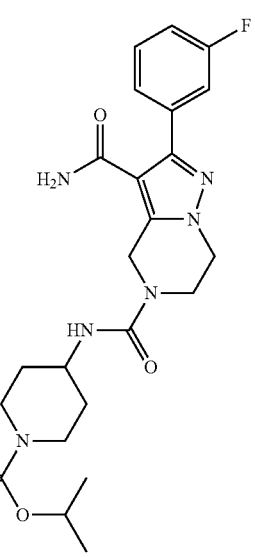 | Isopropyl 4-(3-carbamoyl-2-(3-fluorophenyl)-4,5,6,7-tetrahydropyrazolo[1,5-a]pyrazine-5-carboxamido)piperidine-1-carboxylate | AB | 473 | 8.01<br>7.40 | A<br>B |
| 101 | 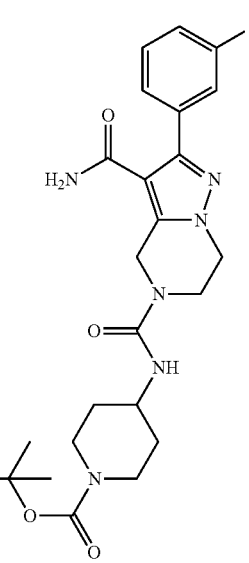 | 1,1,1-Trifluoro-2-methylpropan-2-yl 4-(3-carbamoyl-2-(3-fluorophenyl)-4,5,6,7-tetrahydropyrazolo[1,5-a]pyrazine-5-carboxamido)piperidine-1-carboxylate | AD | 541 | 9.026<br>8.726 | A<br>B |

TABLE 3-continued
| Ex. No. | Structure | Name | Synthetic method | [M + H]+ | Ret. Time (min.) | HPLC Method |
|---|---|---|---|---|---|---|
| 102 | 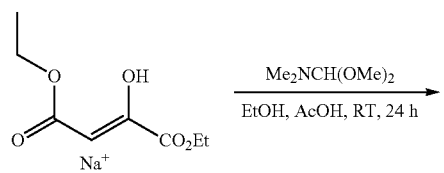 | N5-(1-(Cyclopropylsulfonyl)piperidin-4-yl)-2-(3-fluorophenyl)-6,7-dihydropyrazolo[1,5-a]pyrazine-3,5(4H)-dicarboxamide | AB | 491 | 7.38<br>6.96 | A<br>B |
| 103 | 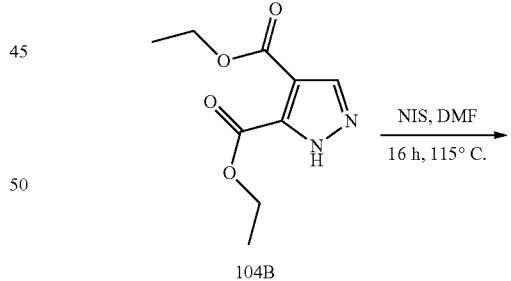 | 2-(3-Fluorophenyl)-N5-(1-(3,3,3-trifluoropropyl)piperidin-4-yl)-6,7-dihydropyrazolo[1,5-a]pyrazine-3,5(4H)-dicarboxamide | AC | 483 | 9.28<br>10.56 | C<br>D |
Scheme 4
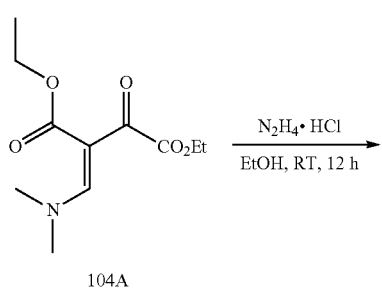
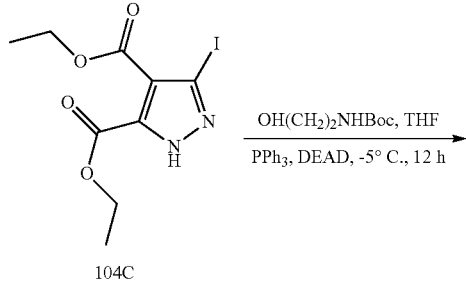
104A
104B
104C

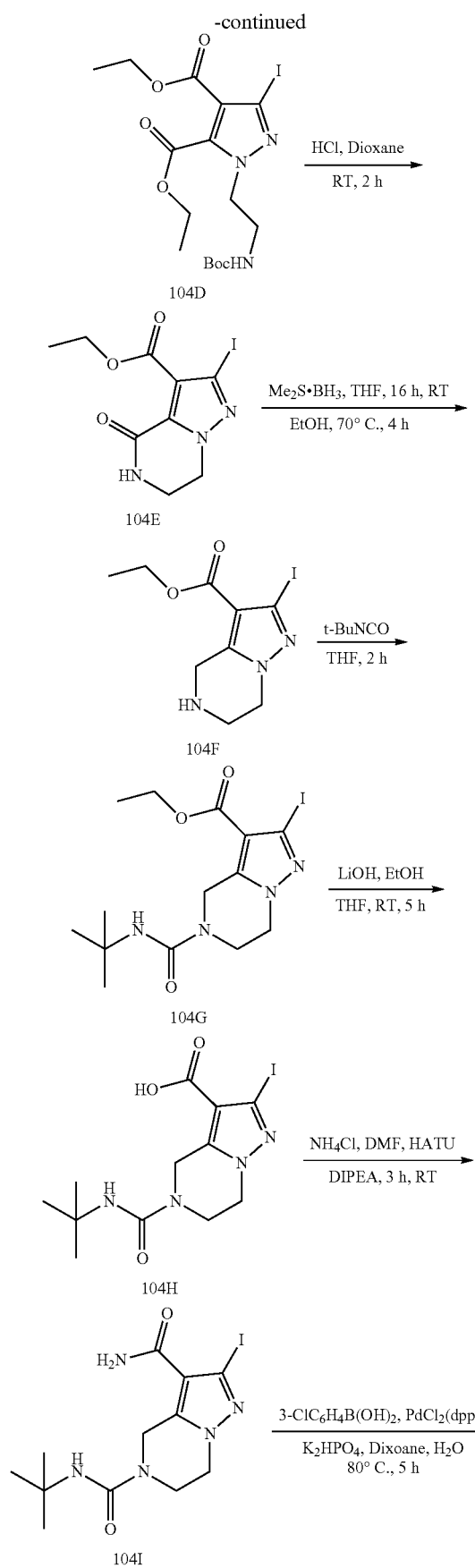

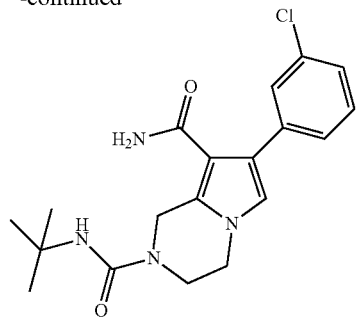

104

Intermediate 104A: Diethyl 2-((dimethylamino)methylene)-3-oxosuccinate

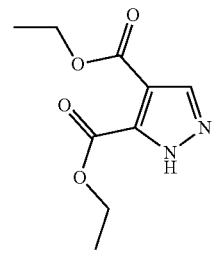

To a solution of diethyl oxalacetate sodium salt (100 g, 476 mmol) in ethanol (250.00 mL) was added 1,1-dimethoxy-N,N-dimethylmethanamine (113 g, 952 mmol) and the reaction was stirred at room temperature for 30 min. Acetic acid (54.5 mL, 952 mmol) was added slowly over a period of 3 h and stirred at room temperature for 24 h. The volatile components were evaporated under reduced pressure and the oily residue was purified by silica gel chromatography (750 g REDISEP® column, eluting with 30% EtOAc in hexane). Fractions containing the product were combined and evaporated to afford Intermediate 104A (43 g, 30.8%). MS(ES): m/z=244 [M+H]$^+$; $^1$H NMR (400 MHz, CDCl$_3$) δ ppm 7.84 (s, 1H), 4.31 (q, J=7.2 Hz, 2H), 4.18 (q, J=5.4 Hz, 2H), 3.35 (s, 3H), 3.04 (s, 3H), 1.36 (t, J=7.2 Hz, 3H), 1.26 (t, J=7.2 Hz, 3H).

Intermediate 104B: Diethyl 1H-pyrazole-4,5-dicarboxylate

To a stirred solution of 104A (45 g, 185 mmol) in ethanol (150 mL) was added N$_2$H$_4$.HCl (12.67 g, 185 mmol) and the reaction mixture was stirred at RT overnight. The volatiles were evaporated under vacuum and the crude residue was dissolved in water and was extracted with EtOAc (3×50 mL). The combined organic layer was dried over Na₂SO₄, filtered and evaporated under vacuum. The resulting crude product obtained was purified by ISCO using EtOAc and hexane to afford 104B (21.00 g, 97 mmol, 52.4%). MS(ES): m/z=211 [M−H]⁺; ¹H NMR (300 MHz, CDCl₃) δ ppm 8.22 (s, 1H) 4.48 (q, J=7.11 Hz, 2H) 4.36 (q, J=7.18 Hz, 2H) 1.33-1.49 (m, 6H).

Intermediate 104C: Diethyl 3-iodo-1H-pyrazole-4,5-dicarboxylate

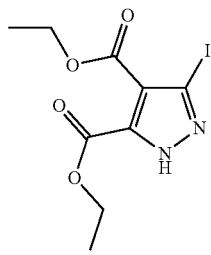 [SMILES: CCOC(=O)c1[nH]nc(I)c1C(=O)OCC]

To a stirred solution of 104B (19 g, 90 mmol) in DMF (50 mL) was added NIS (30.2 g, 134 mmol) and the reaction mixture was stirred for 16 h at 115° C. LCMS indicated the completion of the reaction. DMF was evaporated, the crude was dissolved in EtOAc, washed with water, sodium thiosulfate solution, dried, filtered and evaporated under vacuum to furnish crude product, which was purified by ISCO using EtOAc and hexane system. Fractions collected at 18-20% EtOAc in hexane were evaporated to get 104C (12.5 g, 37.0 mmol, 41.3% yield). MS(ES): m/z=338 [M+H]⁺; ¹H NMR (400 MHz, DMSO-d₆) δ ppm 14.25 (bs, 1H), 4.27 (m, 4H), 1.26 (m, 6H).

Intermediate 104D: Diethyl 1-(2-((tert-butoxycarbonyl)amino)ethyl)-3-iodo-1H-pyrazole-4,5-dicarboxylate

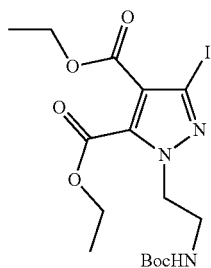 [SMILES: CCOC(=O)c1c(I)nn(CCNC(=O)OC(C)(C)C)c1C(=O)OCC]

To a stirred solution of Intermediate 104C (10.000 g, 29.6 mmol) in THF (100 mL) cooled at −5° C. was added triphenylphosphine (11.64 g, 44.4 mmol) and DIAD (8.63 mL, 44.4 mmol) dropwise and stirred for 30 min. at the same temperature. Solution of tert-butyl(2-hydroxyethyl) carbamate (7.15 g, 44.4 mmol) in THF (10 mL) was added at −5° C. and the stirring was continued for additional 1.5 h. The volatiles were evaporated under vacuum and crude was purified by silica gel chromatography (120 g REDISEP® column, eluting with 18% EtOAc in hexane). Fractions containing the product were combined and evaporated to afford the Intermediate 104D (8.2 g, 57%). MS(ES): m/z=482 [M+H]⁺; ¹H NMR (400 MHz, CDCl₃) δ ppm 4.79 (bs, 1H), 4.28-4.48 (m, 6H), 3.58 (d, J=5.02 Hz, 2H), 1.43 (s, 9H), 1.33-1.40 (m, 6H).

Intermediate 104E: Ethyl 2-iodo-4-oxo-4,5,6,7-tetrahydropyrazolo[1,5-a]pyrazine-3-carboxylate

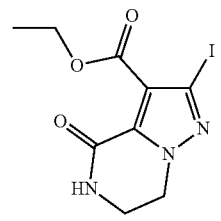 [SMILES: CCOC(=O)c1c(I)nn2c1C(=O)NCC2]

The Intermediate 104D (7 g, 14.54 mmol) was dissolved in HCl in dioxane (2.210 mL, 4M solution, 72.7 mmol) and the reaction mixture was stirred at RT for 3 h. Volatiles were evaporated from the reaction mixture and the residue was dissolved in cold water and basified by adding solid NaHCO₃ (pH=8-9). The aqueous layer was extracted with DCM (4×25 mL) and the combined organic layer was dried, filtered and evaporated under vacuum at 60° C. for 2 h to give 104E (4.750 g, 14.17 mmol, 97%). MS(ES): m/z=336 [M+H]⁺; ¹H NMR (400 MHz, DMSO-d₆) δ ppm 8.43 (bs, 1H), 4.31-4.37 (m, 2H), 4.24 (q, J=7.11 Hz, 2H), 3.56-3.62 (m, 2H), 1.27 (t, J=7.09 Hz, 3H).

Intermediate 104F: Ethyl 2-iodo-4,5,6,7-tetrahydropyrazolo[1,5-a]pyrazine-3-carboxylate

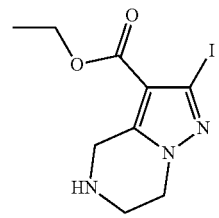

To a stirred solution of Intermediate 104E (5 g, 14.92 mmol) in THF (200 mL) was added dropwise borane dimethyl sulfide complex (15 mL, 158 mmol) at RT. The resulting mixture was stirred at RT for 18 h. The reaction mixture was quenched with ethanol (100 mL) slowly and stirred at 70° C. for 4 h. Volatiles were evaporated under vacuum and the crude was purified by ISCO using methanol (2%) in chloroform as eluent to furnish 104F (2.9 g, 60%). MS(ES): m/z=321 [M+H]⁺; ¹H NMR (400 MHz, CD₃OD) δ ppm 4.25-4.34 (m, 2H), 4.22 (s, 2H), 4.12 (t, J=5.46 Hz, 2H), 3.20-3.28 (m, 2H), 1.38 (td, J=7.12, 1.69 Hz, 3H).

Intermediate 104G: Ethyl 5-(tert-butylcarbamoyl)-2-iodo-4,5,6,7-tetrahydropyrazolo[1,5-a]pyrazine-3-carboxylate

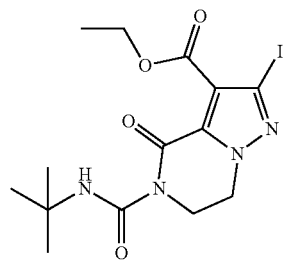 [SMILES: CCOC(=O)c1c(I)nn2c1C(=O)N(C(=O)NC(C)(C)C)CC2]

To a stirred solution of Intermediate 104F (2.4 g, 7.47 mmol) in THF (20 mL) was added 2-isocyanato-2-methylpropane (0.741 g, 7.47 mmol) and the reaction mixture was stirred for 1.5 h. The volatiles were evaporated under reduced pressure. The crude was purified by silica gel chromatography (120 g REDISEP® column, eluting with 28% EtOAc in hexane). Fractions containing the product were combined and evaporated to afford Intermediate 104G (2.2 g, 70%). MS(ES): m/z=421 [M+H]$^+$; $^1$H NMR (400 MHz, DMSO-d$_6$) δ ppm 6.25 (s, 1H), 4.72 (s, 2H), 4.25 (q, J=6.8 Hz, 2H), 4.10 (t, J=5.24 Hz, 2H), 3.75 (m, 2H), 1.30 (t, J=7.2 Hz, 3H) 1.28 (s, 9H).

Intermediate 104H: 5-(tert-Butylcarbamoyl)-2-iodo-4,5,6,7-tetrahydropyrazolo[1,5-a]pyrazine-3-carboxylic acid

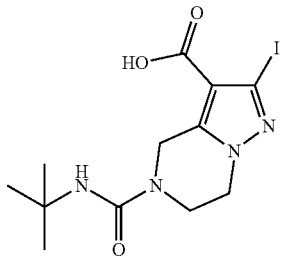 [SMILES: CC(C)(C)NC(=O)N1CCn2nc(I)c(C(=O)O)c2C1]

To a stirred solution of Intermediate 104G (2.1 g, 5.00 mmol) in EtOH (10 mL) and THF (5 mL) was added a solution of lithium hydroxide (0.718 g, 30.0 mmol) in water (1 mL) and stirred at RT for 5 h. Solvent was evaporated under reduced pressure and the crude was dissolved in water and acidified with 1.5 N HCl at 0° C. The resultant precipitate was filtered and dried under vacuum to afford Intermediate 104H (1.8 g, 81%). MS(ES): m/z=393 [M+H]$^+$; $^1$H NMR (300 MHz, DMSO-d$_6$) δ ppm 12.61 (s, 1H), 6.27 (s, 1H), 4.69 (s, 2H), 4.09 (t, J=5.26 Hz, 2H), 3.74 (t, J=5.26, 2H), 1.28 (s, 9H).

Intermediate 104I: N$^5$-(tert-Butyl)-2-iodo-6,7-dihydropyrazolo[1,5-a]pyrazine-3,5(4H)-dicarboxamide

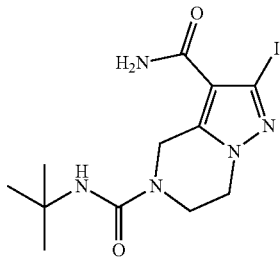 [SMILES: CC(C)(C)NC(=O)N1CCn2nc(I)c(C(N)=O)c2C1]

To a stirred solution of Intermediate 104H (1.800 g, 4.59 mmol) in DMF (20 mL) was added ammonium chloride (1.473 g, 27.5 mmol), HATU (3.49 g, 9.18 mmol) and DIPEA (3.21 mL, 18.36 mmol) and the resulting reaction mixture was stirred for 3 h at RT. DMF was evaporated from the reaction mixture, water was added and extracted with EtOAc. The combined organic layer was washed with cold water, dried over Na$_2$SO$_4$ and concentrated under vacuum to give the crude product, which was purified by ISCO using 70% ethyl acetate in hexane as eluent. The fractions containing the desired product were combined and evaporated to afford Intermediate 104I (1.5 g, 85%). MS(ES): m/z=392 [M+H]$^+$; $^1$H NMR (300 MHz, DMSO-d$_6$) δ ppm 7.37 (bs, 1H), 6.86 (bs, 1H), 6.24 (s, 1H), 4.67 (s, 2H), 4.07 (t, J=5.31 Hz, 2H), 3.73 (t, J=5.31 Hz, 2H), 1.20 (s, 9H).

Compound 104: N$^5$-(tert-Butyl)-2-(3-chlorophenyl)-6,7-dihydropyrazolo[1,5-a]pyrazine-3,5(4H)-dicarboxamide

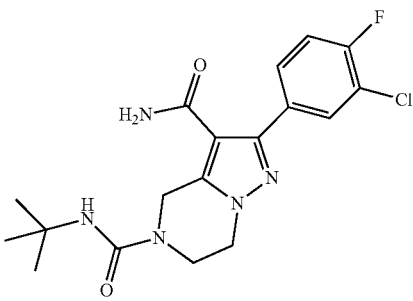 [SMILES: CC(C)(C)NC(=O)N1CCn2nc(-c3ccc(F)c(Cl)c3)c(C(N)=O)c2C1]

To a stirred solution of 104I (120 mg, 0.307 mmol) and (3-chloro-4-fluorophenyl)boronic acid (107 mg, 0.613 mmol) in 1,4-dioxane (2 mL) and water (0.20 mL) was added potassium phosphate dibasic (160 mg, 0.920 mmol). The reaction mixture was degassed for 5 min. with nitrogen, PdCl$_2$(dppf)-CH$_2$Cl$_2$ (12.52 mg, 0.015 mmol) was added and stirred at 80° C. for 5 h. Reaction progress was monitored by LCMS. The reaction mixture was diluted with water (15 mL) and the aqueous layer was back extracted with ethyl acetate (3×15 mL) The combined organic layer washed with brine (2×25 mL), dried over Na$_2$SO$_4$, filtered and concentrated. The crude product was purified by silica gel chromatography (12 g REDISEP® column, eluting with 2% MeOH in CHCl$_3$). Fractions containing the product were combined and evaporated to afford Compound 104 (35 mg, 29%) as an off-white solid. HPLC retention time 8.42 min and 7.94 min (Methods A and B respectively). MS(ES): m/z=394.2 [M+H]$^+$; $^1$H NMR (400 MHz, DMSO-d$_6$) δ ppm 7.87 (dd, J=7.31, 2.16 Hz, 1H), 7.70 (ddd, J=8.64, 4.78, 2.20 Hz, 1H), 7.45 (t, J=9 Hz, 1H), 7.32 (br. s, 1H), 7.18 (br. s, 1H), 6.25 (s, 1H), 4.69 (s, 2H), 4.11 (t, J=5.40 Hz, 2H), 3.79 (t, J=5.40 Hz, 2H), 1.29 (s, 9H).

The Compounds described in Table 4 were synthesized analogous to Compound 104 by reacting Intermediate 104I with corresponding boronic acids.

TABLE 4

| Ex. No. | Structure | Name | [M + H]+ | Ret Time (min.) | HPLC Method |
|---|---|---|---|---|---|
| 105 | 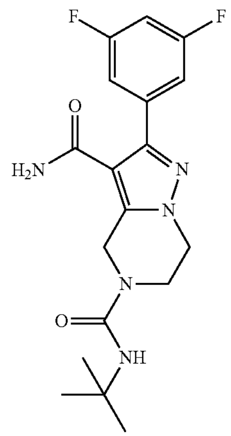 [SMILES: CC(C)(C)NC(=O)N1CCn2nc(-c3cc(F)cc(F)c3)c(C(N)=O)c2C1] | $N^5$-(tert-Butyl)-2-(3,5-difluorophenyl)-6,7-dihydropyrazolo[1,5-a]pyrazine-3,5(4H)-dicarboxamide | 378 | 7.929<br>8.332 | A<br>B |
| 106 | 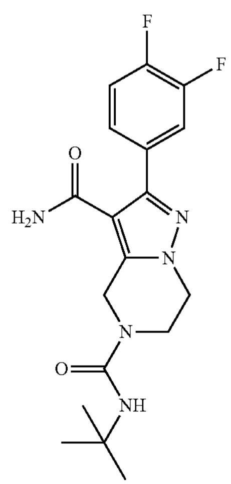 [SMILES: CC(C)(C)NC(=O)N1CCn2nc(-c3ccc(F)c(F)c3)c(C(N)=O)c2C1] | $N^5$-(tert-Butyl)-2-(3,4-difluorophenyl)-6,7-dihydropyrazolo[1,5-a]pyrazine-3,5(4H)-dicarboxamide | 378 | 7.811<br>8.249 | A<br>B |
| 107 | 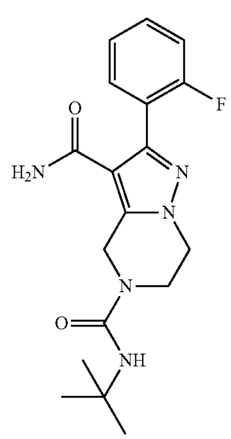 [SMILES: CC(C)(C)NC(=O)N1CCn2nc(-c3ccccc3F)c(C(N)=O)c2C1] | $N^5$-(tert-Butyl)-2-(2-fluorophenyl)-6,7-dihydropyrazolo[1,5-a]pyrazine-3,5(4H)-dicarboxamide | 360 | 7.23<br>7.50 | A<br>B |

TABLE 4-continued

| Ex. No. | Structure | Name | [M + H]+ | Ret Time (min.) | HPLC Method |
|---|---|---|---|---|---|
| 108 | 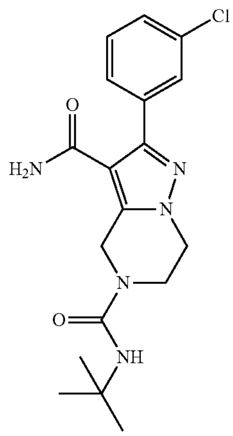 [SMILES: CC(C)(C)NC(=O)N1CCn2nc(-c3cccc(Cl)c3)c(C(N)=O)c2C1] | $N^5$-(tert-Butyl)-2-(3-chlorophenyl)-6,7-dihydropyrazolo[1,5-a]pyrazine-3,5(4H)-dicarboxamide | 375 | 8.11<br>8.47 | A<br>B |
| 109 | 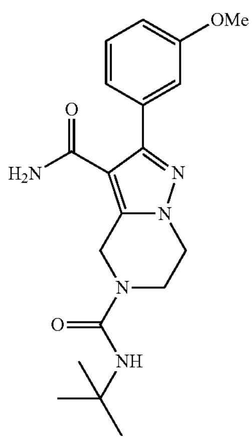 [SMILES: COc1cccc(-c2nn3c(c2C(N)=O)CN(C(=O)NC(C)(C)C)CC3)c1] | $N^5$-(tert-Butyl)-2-(3-methoxyphenyl)-6,7-dihydropyrazolo[1,5-a]pyrazine-3,5(4H)-dicarboxamide | 372 | 13.92<br>13.02 | C<br>D |
| 110 | 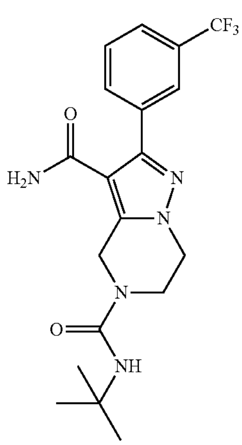 [SMILES: CC(C)(C)NC(=O)N1CCn2nc(-c3cccc(C(F)(F)F)c3)c(C(N)=O)c2C1] | $N^5$-(tert-Butyl)-2-(3-(trifluoromethyl)phenyl)-6,7-dihydropyrazolo[1,5-a]pyrazine-3,5(4H)-dicarboxamide | 410 | 8.778<br>8.210 | A<br>B |

TABLE 4-continued

| Ex. No. | Structure | Name | [M + H]+ | Ret Time (min.) | HPLC Method |
|---|---|---|---|---|---|
| 111 | 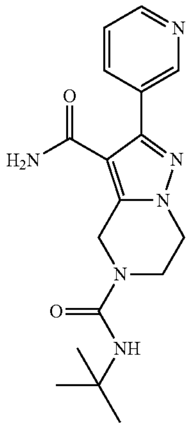 [SMILES: CC(C)(C)NC(=O)N1CCn2nc(-c3cccnc3)c(C(N)=O)c2C1] | N5-(tert-Butyl)-2-(pyridin-3-yl)-6,7-dihydropyrazolo[1,5-a]pyrazine-3,5(4H)-dicarboxamide | 343 | 7.373<br>7.996 | C<br>D |
| 112 | 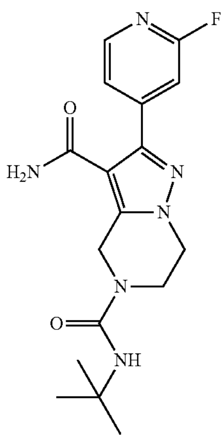 [SMILES: CC(C)(C)NC(=O)N1CCn2nc(-c3ccnc(F)c3)c(C(N)=O)c2C1] | N5-(tert-Butyl)-2-(2-fluoropyridin-4-yl)-6,7-dihydropyrazolo[1,5-a]pyrazine-3,5(4H)-dicarboxamide | 361 | 10.988 | D |
| 113 | 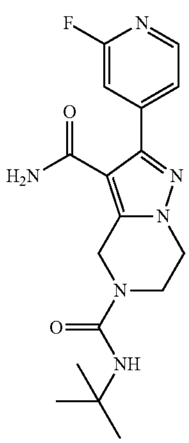 [SMILES: CC(C)(C)NC(=O)N1CCn2nc(-c3ccnc(F)c3)c(C(N)=O)c2C1] | N5-(tert-Butyl)-2-(5-fluoropyridin-3-yl)-6,7-dihydropyrazolo[1,5-a]pyrazine-3,5(4H)-dicarboxamide | 361 | 10.918<br>10.306 | C<br>D |

TABLE 4-continued

| Ex. No. | Structure | Name | [M + H]+ | Ret Time (min.) | HPLC Method |
|---|---|---|---|---|---|
| 114 | 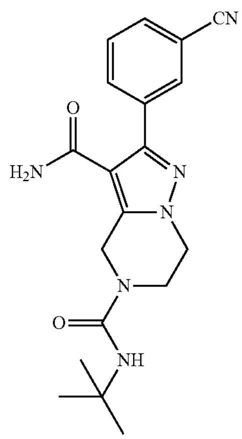 | N5-(tert-Butyl)-2-(3-cyanophenyl)-6,7-dihydropyrazolo[1,5-a]pyrazine-3,5(4H)-dicarboxamide | 367 | 13.465<br>12.598 | C<br>D |
| 115 | 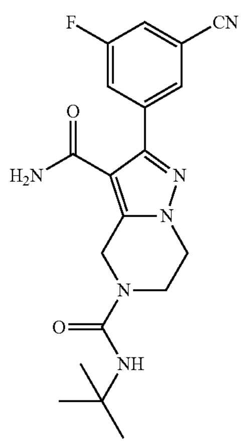 [SMILES: CC(C)(C)NC(=O)N1CCn2nc(-c3cc(F)cc(C#N)c3)c(C(N)=O)c2C1] | N5-(tert-Butyl)-2-(3-cyano-5-fluorophenyl)-6,7-dihydropyrazolo[1,5-a]pyrazine-3,5(4H)-dicarboxamide | | 7.747<br>7.337 | A<br>B |
| 116 | 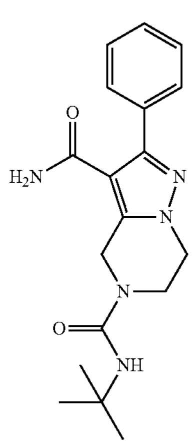 | N5-(tert-Butyl)-2-phenyl-6,7-dihydropyrazolo[1,5-a]pyrazine-3,5(4H)-dicarboxamide | 342 | 1.027 | E |

TABLE 4-continued

| Ex. No. | Structure | Name | [M + H]+ | Ret Time (min.) | HPLC Method |
|---|---|---|---|---|---|
| 117 | 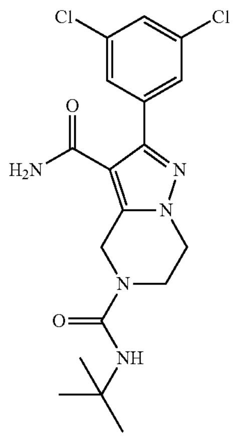 [SMILES: CC(C)(C)NC(=O)N1CCn2nc(-c3cc(Cl)cc(Cl)c3)c(C(N)=O)c2C1] | N5-(tert-Butyl)-2-(3,5-dichlorophenyl)-6,7-dihydropyrazolo[1,5-a]pyrazine-3,5(4H)-dicarboxamide | 410 | 1.47 | E |
| 118 | 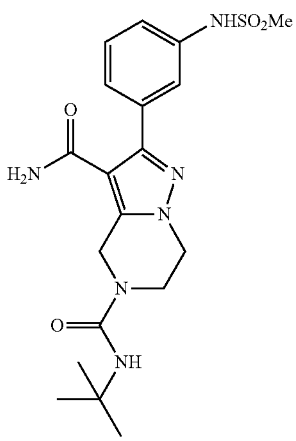 | N5-(tert-Butyl)-2-(3-(methylsulfonamido)phenyl)-6,7-dihydropyrazolol[1,5-a]pyrazine-3,5(4H)-dicarboxamide | 435 | 0.929 | E |
| 119 | 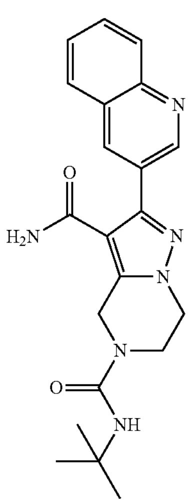 [SMILES: CC(C)(C)NC(=O)N1CCn2nc(-c3cnc4ccccc4c3)c(C(N)=O)c2C1] | N5-(tert-Butyl)-2-(quinolin-3-yl)-6,7-dihydropyrazolo[1,5-a]pyrazine-3,5(4H)-dicarboxamide | 393 | 1.051 | E |

TABLE 4-continued

| Ex. No. | Structure | Name | [M + H]+ | Ret Time (min.) | HPLC Method |
|---|---|---|---|---|---|
| 120 | 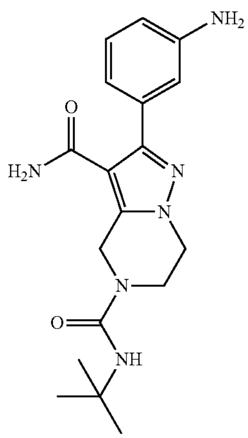 [SMILES: CC(C)(C)NC(=O)N1CCn2nc(-c3cccc(N)c3)c(C(N)=O)c2C1] | 2-(3-Aminophenyl)-N5-(tert-butyl)-6,7-dihydropyrazolo[1,5-a]pyrazine-3,5(4H)-dicarboxamide | 357 | 0.856 | E |
| 121 | 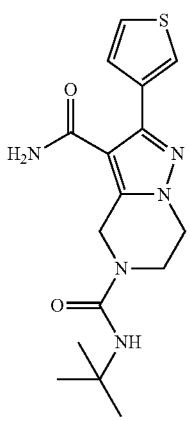 [SMILES: CC(C)(C)NC(=O)N1CCn2nc(-c3ccsc3)c(C(N)=O)c2C1] | N5-(tert-Butyl)-2-(thiophen-3-yl)-6,7-dihydropyrazolo[1,5-a]pyrazine-3,5(4H)-dicarboxamide | 348 | 0.972 | E |
| 122 | 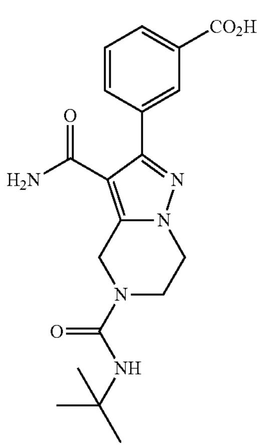 [SMILES: CC(C)(C)NC(=O)N1CCn2nc(-c3cccc(C(=O)O)c3)c(C(N)=O)c2C1] | 3-(5-(tert-Butylcarbamoyl)-3-carbamoyl-4,5,6,7-tetrahydropyrazolo[1,5-a]pyrazin-2-yl)benzoic acid | 386 | 0.614 | E |

TABLE 4-continued

| Ex. No. | Structure | Name | [M + H]+ | Ret Time (min.) | HPLC Method |
|---|---|---|---|---|---|
| 123 | 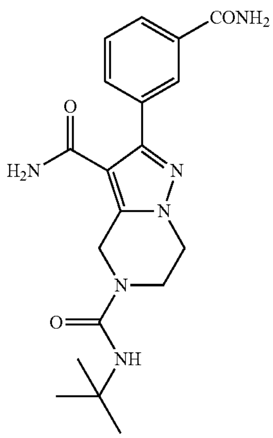 [SMILES: CC(C)(C)NC(=O)N1CCn2nc(-c3cccc(C(N)=O)c3)c(C(N)=O)c2C1] | $N^5$-(tert-Butyl)-2-(3-carbamoylphenyl)-6,7-dihydropyrazolo[1,5-a]pyrazine-3,5(4H)-dicarboxamide | 385 | 0.776 | E |
| 124 | 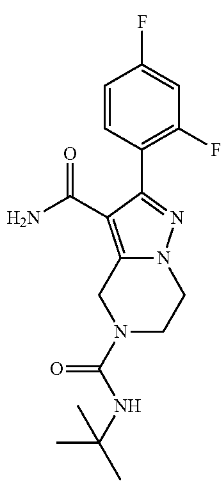 [SMILES: CC(C)(C)NC(=O)N1CCn2nc(-c3ccc(F)cc3F)c(C(N)=O)c2C1] | $N^5$-(tert-Butyl)-2-(2,4-difluorophenyl)-6,7-dihydropyrazolo[1,5-a]pyrazine-3,5(4H)-dicarboxamide | 378 | 1.091 | E |
| 125 | 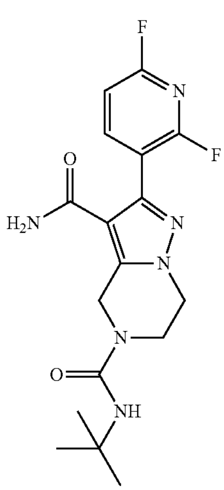 [SMILES: CC(C)(C)NC(=O)N1CCn2nc(-c3ccc(F)nc3F)c(C(N)=O)c2C1] | $N^5$-(tert-Butyl)-2-(2,6-difluoropyridin-3-yl)-6,7-dihydropyrazolo[1,5-a]pyrazine-3,5(4H)-dicarboxamide | 379 | 0.986 | E |

TABLE 4-continued

| Ex. No. | Structure | Name | [M + H]+ | Ret Time (min.) | HPLC Method |
|---|---|---|---|---|---|
| 126 | 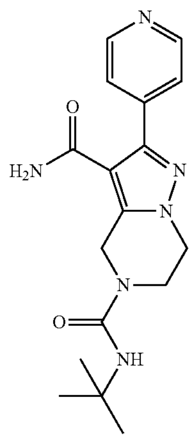 [SMILES: CC(C)(C)NC(=O)N1CCn2nc(-c3ccncc3)c(C(N)=O)c2C1] | N5-(tert-Butyl)-2-(pyridin-4-yl)-6,7-dihydropyrazolo[1,5-a]pyrazine-3,5(4H)-dicarboxamide | 343 | 7.548<br>7.983 | C<br>D |
| 127 | 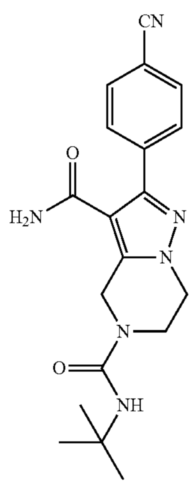 [SMILES: CC(C)(C)NC(=O)N1CCn2nc(-c3ccc(C#N)cc3)c(C(N)=O)c2C1] | N5-(tert-Butyl)-2-(4-cyanophenyl)-6,7-dihydropyrazolo[1,5-a]pyrazine-3,5(4H)-dicarboxamide | 376 | 13.058<br>12.571 | C<br>D |
| 128 | 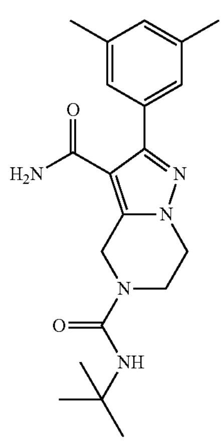 [SMILES: Cc1cc(C)cc(-c2nn3c(c2C(N)=O)CN(C(=O)NC(C)(C)C)CC3)c1] | N5-(tert-Butyl)-2-(3,5-dimethylphenyl)-6,7-dihydropyrazolo[1,5-a]pyrazine-3,5(4H)-dicarboxamide | 370 | 1.307 | E |

TABLE 4-continued

| Ex. No. | Structure | Name | [M + H]+ | Ret Time (min.) | HPLC Method |
|---|---|---|---|---|---|
| 129 | 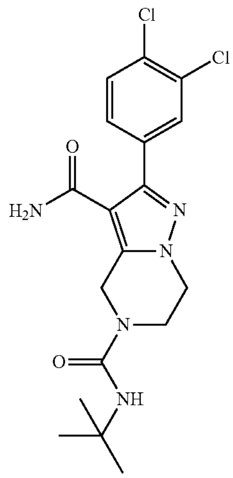 [SMILES: CC(C)(C)NC(=O)N1CCn2nc(-c3ccc(Cl)c(Cl)c3)c(C(N)=O)c2C1] | N5-(tert-Butyl)-2-(3,4-dichlorophenyl)-6,7-dihydropyrazolo[1,5-a]pyrazine-3,5(4H)-dicarboxamide | 410 | 1.423 | E |
| 130 | 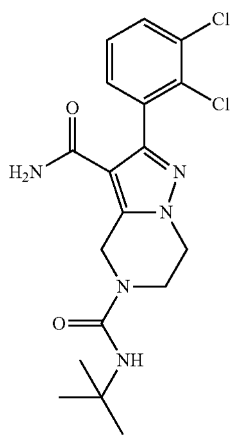 [SMILES: CC(C)(C)NC(=O)N1CCn2nc(-c3cccc(Cl)c3Cl)c(C(N)=O)c2C1] | N5-(tert-Butyl)-2-(2,3-dichlorophenyl)-6,7-dihydropyrazolo[1,5-a]pyrazine-3,5(4H)-dicarboxamide | 410 | 1.266 | E |
| 131 | 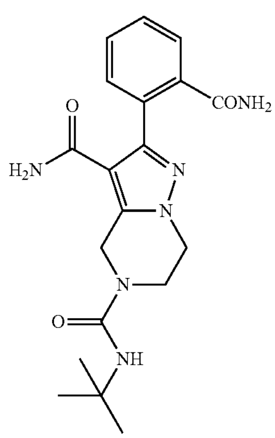 [SMILES: CC(C)(C)NC(=O)N1CCn2nc(-c3ccccc3C(N)=O)c(C(N)=O)c2C1] | N5-(tert-Butyl)-2-(2-carbamoylphenyl)-6,7-dihydropyrazolo[1,5-a]pyrazine-3,5(4H)-dicarboxamide | 385 | 0.733 | E |

TABLE 4-continued

| Ex. No. | Structure | Name | [M + H]+ | Ret Time (min.) | HPLC Method |
|---|---|---|---|---|---|
| 132 | 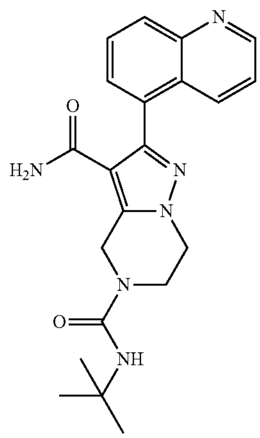 [SMILES: CC(C)(C)NC(=O)N1CCn2nc(-c3cccc4ncccc34)c(C(N)=O)c2C1] | N5-(tert-Butyl)-2-(quinolin-5-yl)-6,7-dihydropyrazolo[1,5-a]pyrazine-3,5(4H)-dicarboxamide | 393 | 0.918 | E |
| 133 | 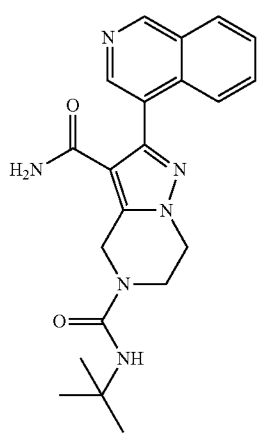 [SMILES: CC(C)(C)NC(=O)N1CCn2nc(-c3cncc4ccccc34)c(C(N)=O)c2C1] | N5-(tert-Butyl)-2-(isoquinolin-4-yl)-6,7-dihydropyrazolo[1,5-a]pyrazine-3,5(4H)-dicarboxamide | 393 | 0.979 | E |
| 134 | 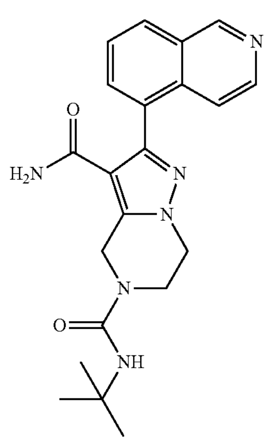 [SMILES: CC(C)(C)NC(=O)N1CCn2nc(-c3cccc4cnccc34)c(C(N)=O)c2C1] | N5-(tert-Butyl)-2-(isoquinolin-5-yl)-6,7-dihydropyrazolo[1,5-a]pyrazine-3,5(4H)-dicarboxamide | 393 | 0.916 | E |

TABLE 4-continued

| Ex. No. | Structure | Name | [M + H]+ | Ret Time (min.) | HPLC Method |
|---|---|---|---|---|---|
| 135 | 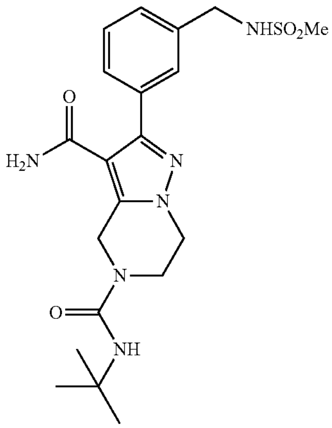 | N5-(tert-Butyl)-2-(3-(methylsulfonamidomethyl)phenyl)-6,7-dihydropyrazolo[1,5-a]pyrazine-3,5(4H)-dicarboxamide | 449 | 0.922 | E |
| 136 | 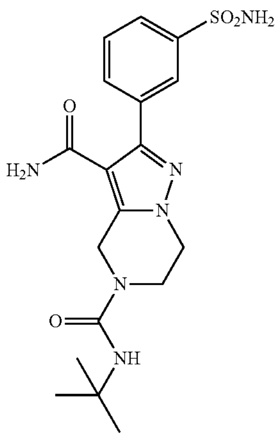 [SMILES: CC(C)(C)NC(=O)N1CCn2nc(-c3cccc(S(N)(=O)=O)c3)c(C(N)=O)c2C1] | N5-(tert-Butyl)-2-(3-sulfamoylphenyl)-6,7-dihydropyrazolo[1,5-a]pyrazine-3,5(4H)-dicarboxamide | 421 | 0.822 | E |
| 137 | 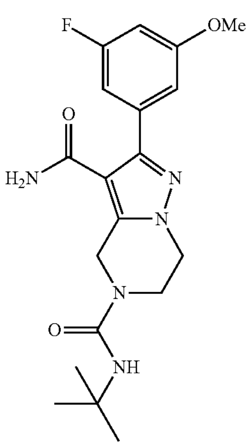 [SMILES: COc1cc(F)cc(-c2nn3c(c2C(N)=O)CN(C(=O)NC(C)(C)C)CC3)c1] | N5-(tert-Butyl)-2-(3-fluoro-5-methoxyphenyl)-6,7-dihydropyrazolo[1,5-a]pyrazine-3,5(4H)-dicarboxamide | 390 | 1.18 | E |

TABLE 4-continued

| Ex. No. | Structure | Name | [M + H]+ | Ret Time (min.) | HPLC Method |
|---|---|---|---|---|---|
| 138 | 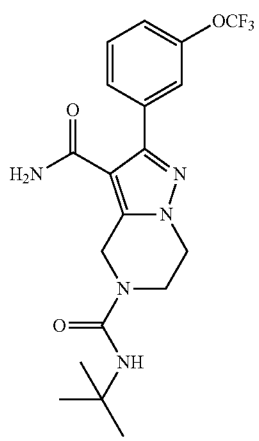 [SMILES: CC(C)(C)NC(=O)N1CCn2nc(-c3cccc(OC(F)(F)F)c3)c(C(N)=O)c2C1] | $N^5$-(tert-Butyl)-2-(3-(trifluoromethoxy)phenyl)-6,7-dihydropyrazolo[1,5-a]pyrazine-3,5(4H)-dicarboxamide | 426 | 1.416 | E |
| 139 | 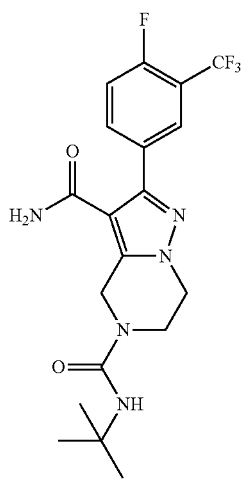 [SMILES: CC(C)(C)NC(=O)N1CCn2nc(-c3ccc(F)c(C(F)(F)F)c3)c(C(N)=O)c2C1] | $N^5$-(tert-Butyl)-2-(4-fluoro-3-(trifluoromethyl)phenyl)-6,7-dihydropyrazolo[1,5-a]pyrazine-3,5(4H)-dicarboxamide | 428 | 1.424 | E |
| 140 | 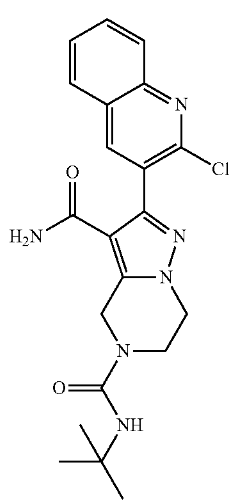 [SMILES: CC(C)(C)NC(=O)N1CCn2nc(-c3cc4ccccc4nc3Cl)c(C(N)=O)c2C1] | $N^5$-(tert-Butyl)-2-(2-chloroquinolin-3-yl)-6,7-dihydropyrazolo[1,5-a]pyrazine-3,5(4H)-dicarboxamide | 427 | 1.150 | E |

TABLE 4-continued

| Ex. No. | Structure | Name | [M + H]+ | Ret Time (min.) | HPLC Method |
|---|---|---|---|---|---|
| 141 | 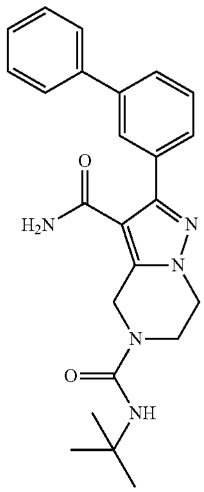 [SMILES: CC(C)(C)NC(=O)N1CCn2nc(-c3cccc(-c4ccccc4)c3)c(C(N)=O)c2C1] | 2-([1,1'-Biphenyl]-3-yl)-N5-(tert-butyl)-6,7-dihydropyrazolo[1,5-a]pyrazine-3,5(4H)-dicarboxamide | 418 | 9.383<br>8.932 | A<br>B |
| 142 | 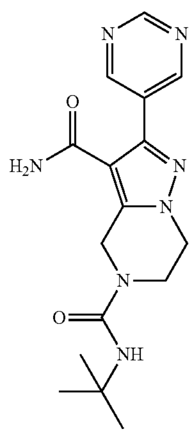 [SMILES: CC(C)(C)NC(=O)N1CCn2nc(-c3cncnc3)c(C(N)=O)c2C1] | N5-(tert-Butyl)-2-(pyrimidin-5-yl)-6,7-dihydropyrazolo[1,5-a]pyrazine-3,5(4H)-dicarboxamide | 344 | 9.416<br>8.804 | C<br>D |
| 143 | 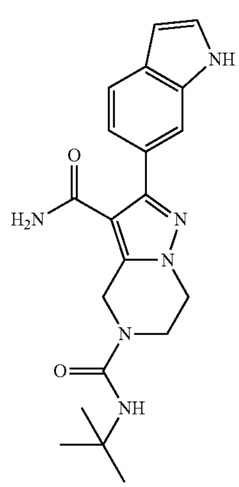 [SMILES: CC(C)(C)NC(=O)N1CCn2nc(-c3ccc4cc[nH]c4c3)c(C(N)=O)c2C1] | N5-(tert-Butyl)-2-(1H-indol-6-yl)-6,7-dihydropyrazolo[1,5-a]pyrazine-3,5(4H-dicarboxamide | 381 | 7.368<br>7.150 | A<br>B |

TABLE 4-continued

| Ex. No. | Structure | Name | [M + H]⁺ | Ret Time (min.) | HPLC Method |
| --- | --- | --- | --- | --- | --- |
| 144 | 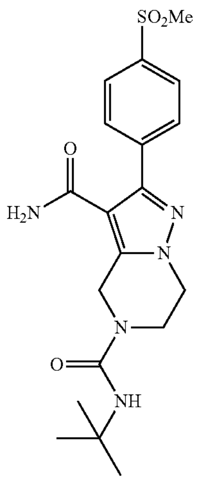 [SMILES: CC(C)(C)NC(=O)N1CCn2nc(-c3ccc(S(C)(=O)=O)cc3)c(C(N)=O)c2C1] | $N^5$-(tert-Butyl)-2-(4-(methylsulfonyl)phenyl)-6,7-dihydropyrazolo[1,5-a]pyrazine-3,5(4H)-dicarboxamide | 420 | 6.356<br>6.183 | A<br>B |
| 145 | 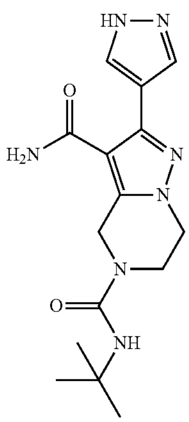 [SMILES: CC(C)(C)NC(=O)N1CCn2nc(-c3cn[nH]c3)c(C(N)=O)c2C1] | $N^5$-(tert-Butyl)-2-(1H-pyrazol-4-yl)-6,7-dihydropyrazolo[1,5-a]pyrazine-3,5(4H)-dicarboxamide | 332 | 9.380<br>8.760 | C<br>D |
| 146 | 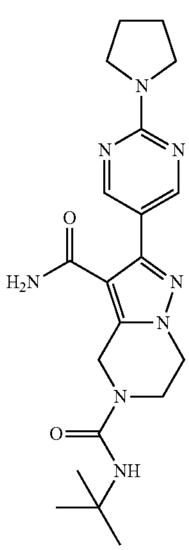 [SMILES: CC(C)(C)NC(=O)N1CCn2nc(-c3cnc(N4CCCC4)nc3)c(C(N)=O)c2C1] | $N^5$-(tert-Butyl)-2-(2-(pyrrolidin-1-yl)pyrimidin-5-yl)-6,7-dihydropyrazolo[1,5-a]pyrazine-3,5(4H)-dicarboxamide | 413 | 10.486<br>10.870 | C<br>D |

TABLE 4-continued

| Ex. No. | Structure | Name | [M + H]+ | Ret Time (min.) | HPLC Method |
|---|---|---|---|---|---|
| 147 | 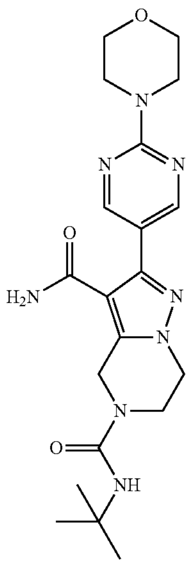 [SMILES: CC(C)(C)NC(=O)N1CCn2nc(-c3cnc(N4CCOCC4)nc3)c(C(N)=O)c2C1] | N5-(tert-Butyl)-2-(2-morpholinopyrimidin-5-yl)-6,7-dihydropyrazolo[1,5-a]pyrazine-3,5(4H)-dicarboxamide | 429 | 11.715<br>11.137 | C<br>D |
| 148 | 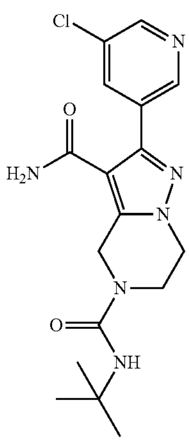 [SMILES: CC(C)(C)NC(=O)N1CCn2nc(-c3cncc(Cl)c3)c(C(N)=O)c2C1] | N5-(tert-Butyl)-2-(5-chloropyridin-3-yl)-6,7-dihydropyrazolo[1,5-a]pyrazine-3,5(4H)-dicarboxamide | 377 | 11.980<br>11.969 | C<br>D |
| 149 | 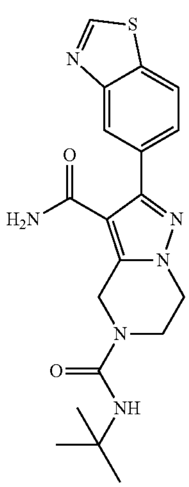 [SMILES: CC(C)(C)NC(=O)N1CCn2nc(-c3ccc4scnc4c3)c(C(N)=O)c2C1] | 2-(Benzo[d]thiazol-5-yl)-N5-(tert-butyl)-6,7-dihydropyrazolo[1,5-a]pyrazine-3,5(4H)-dicarboxamide | 399 | 6.621<br>6.505 | A<br>B |

TABLE 4-continued

| Ex. No. | Structure | Name | [M + H]+ | Ret Time (min.) | HPLC Method |
|---|---|---|---|---|---|
| 150 | 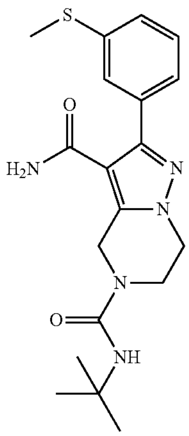 [SMILES: CSc1cccc(-c2nn3c(c2C(N)=O)CN(C(=O)NC(C)(C)C)CC3)c1] | N5-(tert-Butyl)-2-(3-(methylthio)phenyl)-6,7-dihydropyrazolo[1,5-a]pyrazine-3,5(4H)-dicarboxamide | 388 | 8.062<br>7.836 | A<br>B |
| 151 | 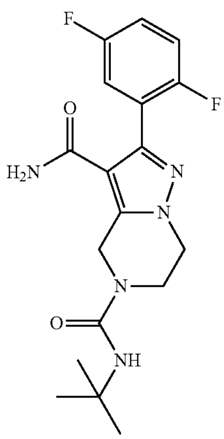 [SMILES: CC(C)(C)NC(=O)N1CCn2nc(-c3cc(F)ccc3F)c(C(N)=O)c2C1] | N5-(tert-Butyl)-2-(2,5-difluorophenyl)-6,7-dihydropyrazolo[1,5-a]pyrazine-3,5(4H)-dicarboxamide | 376 | 7.431<br>7.184 | A<br>B |
| 152 | 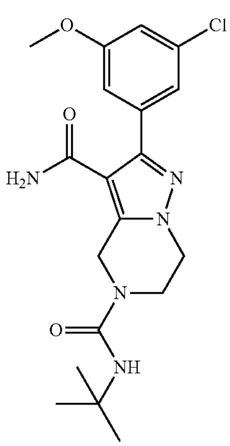 [SMILES: COc1cc(Cl)cc(-c2nn3c(c2C(N)=O)CN(C(=O)NC(C)(C)C)CC3)c1] | N5-(tert-Butyl)-2-(3-chloro-5-methoxyphenyl)-6,7-dihydropyrazolo[1,5-a]pyrazine-3,5(4H)-dicarboxamide | 406 | 8.476<br>8.041 | A<br>B |

TABLE 4-continued

| Ex. No. | Structure | Name | [M + H]⁺ | Ret Time (min.) | HPLC Method |
|---|---|---|---|---|---|
| 153 | 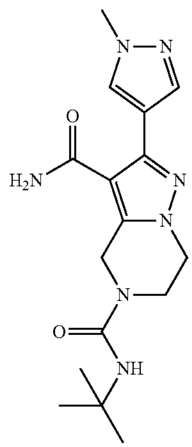 [SMILES: Cn1cc(-c2nn3c(c2C(N)=O)CN(C(=O)NC(C)(C)C)CC3)cn1] | N⁵-(tert-Butyl)-2-(1-methyl-1H-pyrazol-4-yl)-6,7-dihydropyrazolo[1,5-a]pyrazine-3,5(4H)-dicarboxamide | 346 | 9.716<br>9.562 | C<br>D |
| 154 | 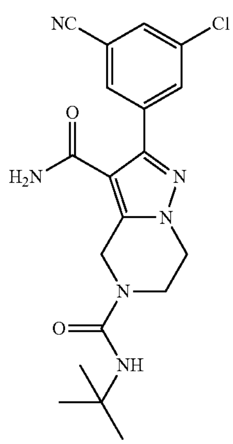 [SMILES: CC(C)(C)NC(=O)N1CCn2nc(-c3cc(Cl)cc(C#N)c3)c(C(N)=O)c2C1] | N⁵-(tert-Butyl)-2-(3-chloro-5-cyanophenyl)-6,7-dihydropyrazolo[1,5-a]pyrazine-3,5(4H)-dicarboxamide | 401 | 8.297<br>7.933 | A<br>B |
| 155 | 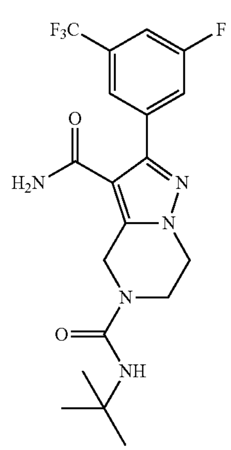 [SMILES: CC(C)(C)NC(=O)N1CCn2nc(-c3cc(F)cc(C(F)(F)F)c3)c(C(N)=O)c2C1] | N⁵-(tert-Butyl)-2-(3-fluoro-5-(trifluoromethyl)phenyl)-6,7-dihydropyrazolo[1,5-a]pyrazine-3,5(4H)-dicarboxamide | 428 | 9.239<br>8.535 | A<br>B |

Scheme 5

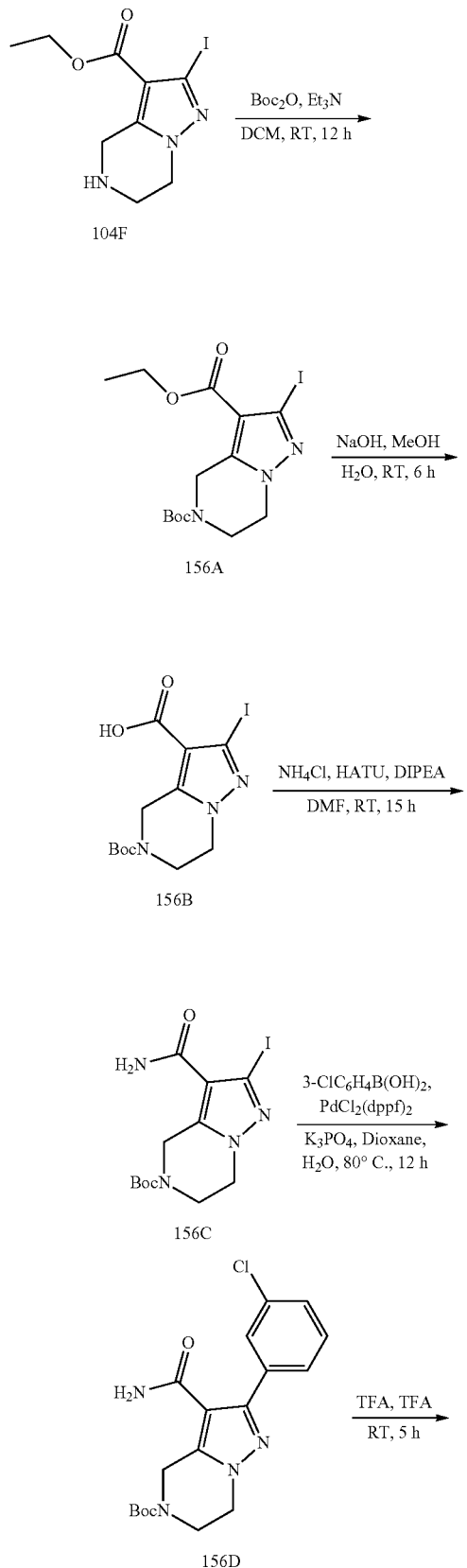

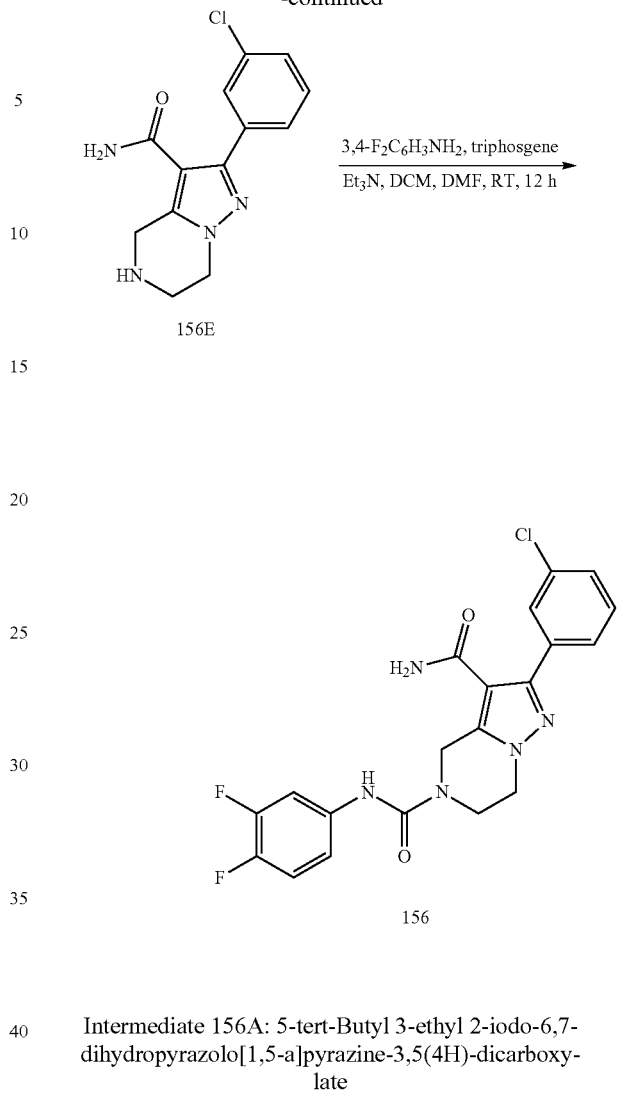

Intermediate 156A: 5-tert-Butyl 3-ethyl 2-iodo-6,7-dihydropyrazolo[1,5-a]pyrazine-3,5(4H)-dicarboxylate To a stirred solution of 104F (0.7 g, 2.180 mmol) in dichloromethane (10 mL) was added triethylamine (0.912 mL, 6.54 mmol) and Boc$_2$O (0.952 g, 4.36 mmol). The resulting reaction mixture was stirred at RT overnight and the reaction progress was monitored by LCMS. Reaction mixture was diluted with dichloromethane (20 mL), washed with water, brine, dried over Na$_2$SO$_4$, filtered and concentrated. The crude product obtained was purified by ISCO (24 g silica gel column) using petroleum ether and ethyl acetate (9:1) mixture as eluent. Fractions were collected and concentrated to afford Intermediate 156A (800 mg, 87%). MS(ES): m/z=422 [M+H]$^+$; $^1$H NMR (400 MHz, CDCl$_3$) δ ppm 4.86 (s, 2H), 4.32 (q, J=6.8 Hz, 2H), 4.20 (m, 2H), 3.87 (t, J=5.6 Hz, 2H), 1.50 (s, 9H), 1.38 (t, J=7.2 Hz, 3H).

Intermediate 156B: 5-(tert-Butoxycarbonyl)-2-iodo-4,5,6,7-tetrahydropyrazolo[1,5-a]pyrazine-3-carboxylic acid

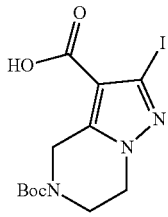

To a stirred solution of 156A (0.80 g, 1.899 mmol) in methanol (7 mL) was added sodium hydroxide (0.760 g, 1.899 mmol) in water (3 mL) The resulting reaction mixture was stirred at RT for 6 h. Methanol was removed under reduced pressure and the aqueous layer was acidified with 1.5 N HCl solution. The aqueous layer was back extracted with dichloromethane (3×25 mL) The combined organic layer was dried over $Na_2SO_4$, filtered and concentrated to give the desired Intermediate 156B (700 mg, 94%). MS(ES): m/z=394 [M+H]$^+$; $^1$H NMR (400 MHz, CDCl$_3$) δ ppm 4.89 (s, 2H), 4.22 (t, J=5.2 Hz, 2H), 3.88 (t, J=5.6 Hz, 2H), 1.51 (s, 9H).

Intermediate 156C: tert-Butyl 3-carbamoyl-2-iodo-6,7-dihydropyrazolo[1,5-a]pyrazine-5(4H)-carboxylate

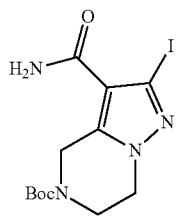 [SMILES: CC(C)(C)OC(=O)N1CCn2nc(I)c(C(N)=O)c2C1]

To a stirred solution of 156B (0.700 g, 1.780 mmol) and ammonium chloride (0.190 g, 3.56 mmol) in DMF (7 mL) were added HATU (1.354 g, 3.56 mmol) and DIPEA (0.933 mL, 5.34 mmol). Resulting reaction mixture was stirred at RT overnight. The reaction mixture was diluted with water (20 mL) and the aqueous layer was back extracted with ethyl acetate (2×30 mL). The combined organic layer was washed with brine, dried over $Na_2SO_4$, filtered and concentrated. The crude product was purified by ISCO (24 g silica gel column) using 2% methanol in chloroform as eluent to afford pure Intermediate 156C (670 mg, 96%). MS(ES): m/z=[M+H]$^+$; $^1$H NMR (400 MHz, DMSO-d$_6$) δ ppm 7.38 (bs, 1H), 6.86 (bs, 1H), 4.72 (s, 2H), 4.12 (t, J=5.2 Hz, 2H), 3.77 (t, J=5.7 Hz, 2H), 1.43 (s, 9H).

Intermediate 156D: tert-Butyl 3-carbamoyl-2-(3-chlorophenyl)-6,7-dihydropyrazolo[1,5-a]pyrazine-5(4H)-carboxylate

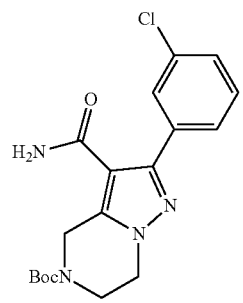 [SMILES: CC(C)(C)OC(=O)N1CCn2nc(-c3cccc(Cl)c3)c(C(N)=O)c2C1]

To a stirred solution of Intermediate 156C (500 mg, 1.275 mmol) and (3-chlorophenyl)boronic acid (399 mg, 2.55 mmol) in 1,4-dioxane (5 mL) and water (1 mL) was added and potassium phosphate tribasic (666 mg, 3.82 mmol). The reaction mixture was purged with nitrogen for 5 min. PdCl$_2$ (dppf)-CH$_2$Cl$_2$ (52.1 mg, 0.064 mmol) was added and the reaction mixture was stirred at 80° C. for 12 h. The reaction mixture was diluted with water (20 mL) and extracted with ethyl acetate (3×25 mL). The combined organic layer was washed with brine, dried over $Na_2SO_4$ and concentrated. The crude was purified by ISCO (24 g silica column) using 2% methanol in chloroform. Fractions were collected and concentrated to afford Intermediate 156D (380 mg, 79%). MS(ES): m/z 377 [M+H]$^+$; $^1$H NMR (300 MHz, CDCl$_3$) δ ppm 7.60 (s, 1H), 7.46 (m, 3H), 5.32 (bs, 2H), 4.97 (s, 2H), 4.21 (t, J=5.1 Hz, 2H), 3.94 (t, J=5.7 Hz, 2H), 1.29 (s, 9H).

Intermediate 156E: 2-(3-Chlorophenyl)-4,5,6,7-tetrahydropyrazolo[1,5-a]pyrazine-3-carboxamide

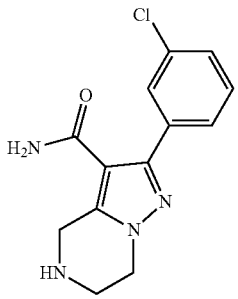 [SMILES: NC(=O)c1c(-c2cccc(Cl)c2)nn2c1CNCC2]

To a stirred solution of 156D (350 mg, 0.929 mmol) in DCM (10 mL) was added dropwise TFA (2 mL) at 0° C. and the reaction mixture was stirred at RT overnight. TFA and DCM were removed under reduced pressure, crude was basified with saturated sodium hydroxide solution, the resultant solid was filtered, washed with water, dried under vacuum to afford 156E (250 mg, 97%). MS(ES): m/z=277 [M+H]$^+$; $^1$H NMR (400 MHz, DMSO-d$_6$) δ ppm 7.71-7.73 (m, 1H), 7.65

(dt, J=7.04, 1.72 Hz, 1H), 7.37-7.45 (m, 2H), 7.20 (bs, 1H), 7.10 (bs, 1H), 4.00-4.05 (m, 4H), 3.12 (d, J=4.83 Hz, 2H), 2.63 (s, 1H).

Compound 156: 2-(3-Chlorophenyl)-N5-(3,4-difluorophenyl)-6,7-dihydropyrazolo[1,5-a]pyrazine-3,5(4H)-dicarboxamide

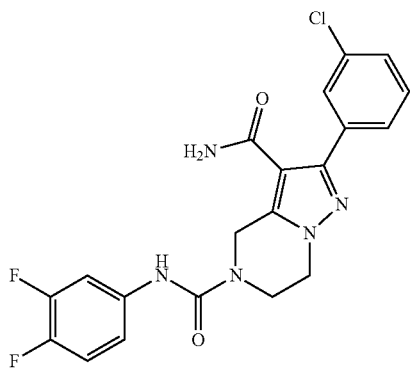 [SMILES: NC(=O)c1c(-c2cccc(Cl)c2)nn2c1CN(C(=O)Nc1ccc(F)c(F)c1)CC2]

To a stirred solution of 3,4-difluoroaniline (23.33 mg, 0.181 mmol) in DCM (2 mL) under nitrogen was added triethylamine (0.025 mL, 0.181 mmol) and the reaction mixture was cooled to 0° C. and triphosgene (26.8 mg, 0.090 mmol) in DCM (1 mL) was added and stirred at the same temperature for 10 min. A solution of 156E (25 mg, 0.090 mmol) in DMF (1 mL) was added dropwise and the resulting reaction mixture was stirred at RT overnight. It was diluted with water and the aqueous layer was back extracted with ethyl acetate (3×10 mL) The combined organic layer was washed with brine, dried over $Na_2SO_4$ and concentrated. The crude product obtained was purified by reverse phase preparative HPLC to afford pure product 156 as off-white solid (10 mg, 25%). MS(ES): m/z=432 [M+H]$^+$; HPLC Ret. Time 9.92 min. and 8.82 min. (HPLC Methods A and B); $^1$H NMR (400 MHz, $CD_3OD$) δ ppm 7.68-7.71 (m, 1H), 7.60 (ddd, J=5.32, 3.47, 1.63 Hz, 1H), 7.48-7.53 (m, 1H), 7.44-7.48 (m, 2H), 7.16-7.20 (m, 2H), 5.01 (s, 2H), 4.31 (t, J=5.40 Hz, 2H), 4.08 (t, J=5.40 Hz, 2H).

General Methods for the Syntheses of Ureas:
Method A:
To a solution of Intermediate 156E (30 mg, 0.115 mmol) in DMF (1 mL) was added the corresponding isocyanate (0.288 mmol) at 0° C. The reaction mixture was stirred at room temperature for 3 h. The reaction mixture was quenched with water and extracted with ethyl acetate (3×5 mL). The combined organic layer was washed with water (2×5 mL), brine solution, dried over $Na_2SO_4$, filtered and concentrated to afford crude product which was purified by preparative HPLC.

Method B:
To a solution of primary amine (0.192 mmol) and triethylamine (0.480 mmol) in tetrahydrofuran (3 mL) at 0° C. was added triphosgene (0.096 mmol) and the reaction mixture stirred for 30 min at the same temperature. Intermediate 156E (25 mg, 0.096 mmol) in DMF was added and the solution was stirred at RT for 2 h. The reaction mixture was quenched with water and extracted with ethyl acetate (3×5 mL). The combined organic layer was washed with 10% $NaHCO_3$ (2×5 mL), water, dried over $Na_2SO_4$ and concentrated to afford crude product, which was further purified by preparative HPLC.

Method C:
To a solution of carboxylic acid (0.153 mmol) in toluene (1 mL) was added TEA (0.071 mL, 0.509 mmol), followed by DPPA (0.044 mL, 0.204 mmol) to give a clear solution and the reaction mixture was heated to 85° C. and stirred for 1 h. The reaction mixture was cooled to RT and to it was added a solution of Intermediate 156E (27 mg, 0.102 mmol) in THF (0.5 mL) and stirred at RT for 12 h. The reaction mixture was diluted with EtOAc (10 mL), washed with water, solution of 10% aq. $NaHCO_3$, brine, dried over $Na_2SO_4$, filtered and the filtrate concentrated and concentrated to afford crude product which was further purified by preparative HPLC.

Method D:
To a solution of primary amine (0.192 mmol) and triethylamine (0.480 mmol) in tetrahydrofuran (3 mL) at 0° C. were added phenyl chloroformate (0.096 mmol) and the reaction mixture stirred for 60 min at RT. The reaction mixture was quenched with water and the phenyl carbamate formed was extracted and the Intermediate 156E (25 mg, 0.096 mmol) in THF was added to the extract and the resulting solution was stirred at room temperature for 2 h. The reaction mixture was quenched with water and extracted with ethyl acetate (3×5 mL). The combined organic layer was washed with 10% $NaHCO_3$ (2×5 mL), water, dried over $Na_2SO_4$ and concentrated to afford crude product which was further purified by preparative HPLC.

The Compounds described in Table 5 were synthesized analogous to Compound 156 by reacting Intermediate 156E with corresponding reagents.

TABLE 5

| Ex. No. | Structure | Name | Method | [M + H]$^+$ | Ret Time (min.) | HPLC Method |
|---|---|---|---|---|---|---|
| 157 | 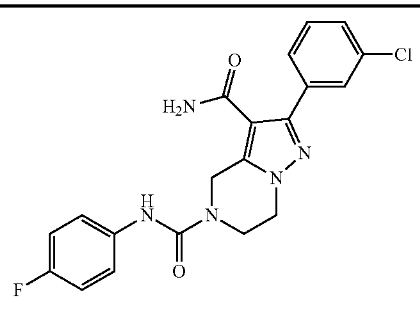 | 2-(3-Chlorophenyl)-N$^5$-(4-fluorophenyl)-6,7-dihydropyrazolo[1,5-a]pyrazine-3,5(4H)-dicarboxamide | B | 414 | 8.789<br>8.522 | A<br>B |

TABLE 5-continued

| Ex. No. | Structure | Name | Method | [M + H]+ | Ret Time (min.) | HPLC Method |
|---|---|---|---|---|---|---|
| 158 | 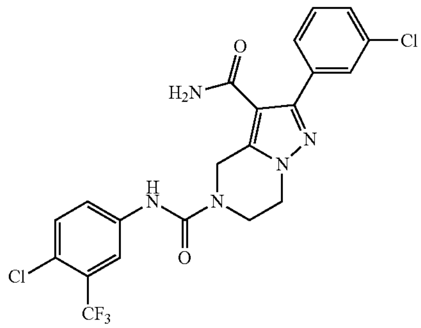 [SMILES: NC(=O)c1c(-c2cccc(Cl)c2)nn2c1CN(C(=O)Nc1ccc(Cl)c(C(F)(F)F)c1)CC2] | N5-(4-Chloro-3-(trifluoromethyl)phenyl)-2-(3-chlorophenyl)-6,7-dihydropyrazolo[1,5-a]pyrazine-3,5(4H)-dicarboxamide | B | 498 | 10.821<br>10.044 | A<br>B |
| 159 | 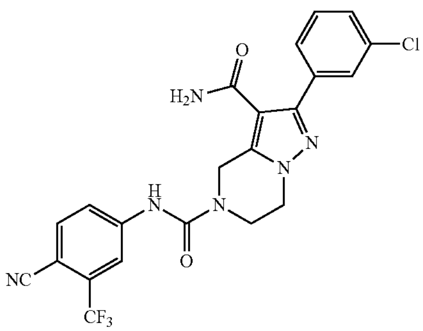 [SMILES: N#Cc1ccc(NC(=O)N2CCn3nc(-c4cccc(Cl)c4)c(C(N)=O)c3C2)cc1C(F)(F)F] | 2-(3-Chlorophenyl)-N5-(4-cyano-3-(trifluoromethyl)phenyl)-6,7-dihydropyrazolo[1,5-a]pyrazine-3,5(4H)-dicarboxamide | B | 487 | 10.126<br>9.668 | A<br>B |
| 160 | 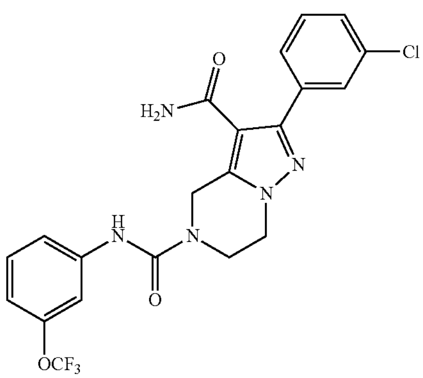 [SMILES: NC(=O)c1c(-c2cccc(Cl)c2)nn2c1CN(C(=O)Nc1cccc(OC(F)(F)F)c1)CC2] | 2-(3-Chlorophenyl)-N5-(3-(trifluoromethoxy)phenyl)-6,7-dihydropyrazolo[1,5-a]pyrazine-3,5(4H)-dicarboxamide | B | 480 | 10.292<br>9.665 | A<br>B |
| 161 | 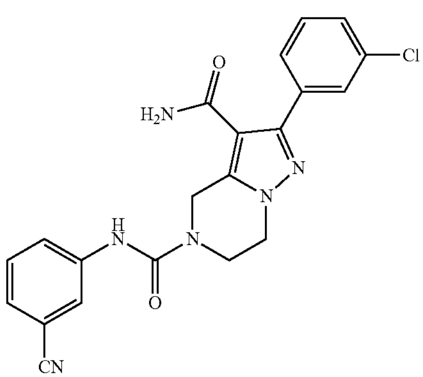 [SMILES: N#Cc1cccc(NC(=O)N2CCn3nc(-c4cccc(Cl)c4)c(C(N)=O)c3C2)c1] | 2-(3-Chlorophenyl)-N5-(3-cyanophenyl)-6,7-dihydropyrazolo[1,5-a]pyrazine-3,5(4H)-dicarboxamide | B | 421 | 8.541<br>8.323 | A<br>B |

TABLE 5-continued

| Ex. No. | Structure | Name | Method | [M + H]+ | Ret Time (min.) | HPLC Method |
|---|---|---|---|---|---|---|
| 162 | 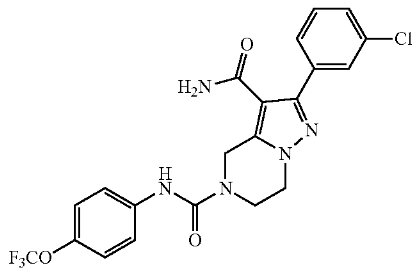 [SMILES: NC(=O)c1c(-c2cccc(Cl)c2)nn2c1CN(C(=O)Nc1ccc(OC(F)(F)F)cc1)CC2] | 2-(3-Chlorophenyl)-N5-(4-(trifluoromethoxy)phenyl)-6,7-dihydropyrazolo[1,5-a]pyrazine-3,5(4H)-dicarboxamide | B | 480 | 10.148 9.559 | A B |
| 163 | 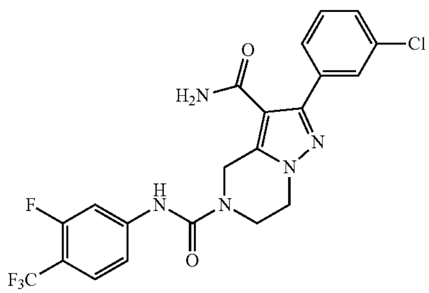 [SMILES: NC(=O)c1c(-c2cccc(Cl)c2)nn2c1CN(C(=O)Nc1ccc(C(F)(F)F)c(F)c1)CC2] | 2-(3-Chlorophenyl)-N5-(3-fluoro-4-(trifluoromethyl)phenyl)-6,7-dihydropyrazolo[1,5-a]pyrazine-3,5(4H)-dicarboxamide | B | 482 | 10.510 9.833 | A B |
| 164 | 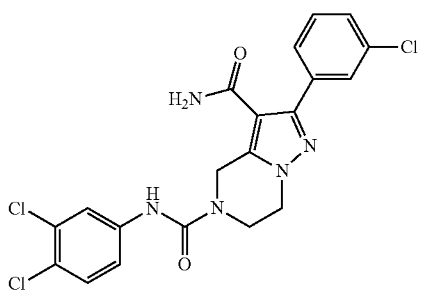 [SMILES: NC(=O)c1c(-c2cccc(Cl)c2)nn2c1CN(C(=O)Nc1ccc(Cl)c(Cl)c1)CC2] | 2-(3-Chlorophenyl)-N5-(3,4-dichlorophenyl)-6,7-dihydropyrazolo[1,5-a]pyrazine-3,5(4H)-dicarboxamide | A | 464 | 10.453 9.768 | A B |
| 165 | 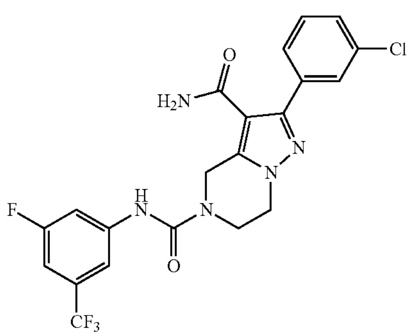 [SMILES: NC(=O)c1c(-c2cccc(Cl)c2)nn2c1CN(C(=O)Nc1cc(F)cc(C(F)(F)F)c1)CC2] | 2-(3-Chlorophenyl)-N5-(3-fluoro-5-(trifluoromethyl)phenyl)-6,7-dihydropyrazolo[1,5-a]pyrazine-3,5(4H)-dicarboxamide | A | 482 | 10.696 9.888 | A B |
| 166 | 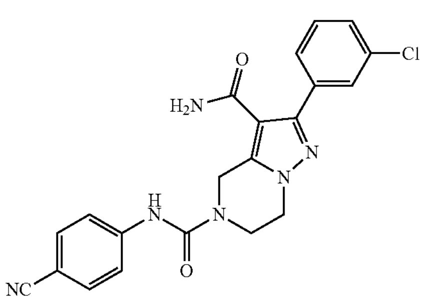 [SMILES: N#Cc1ccc(NC(=O)N2CCn3nc(-c4cccc(Cl)c4)c(C(N)=O)c3C2)cc1] | 2-(3-Chlorophenyl)-N5-(4-cyanophenyl)-6,7-dihydropyrazolo[1,5-a]pyrazine-3,5(4H)-dicarboxamide | A | 421 | 8.576 8.300 | A B |

TABLE 5-continued

| Ex. No. | Structure | Name | Method | [M + H]+ | Ret Time (min.) | HPLC Method |
|---|---|---|---|---|---|---|
| 167 | 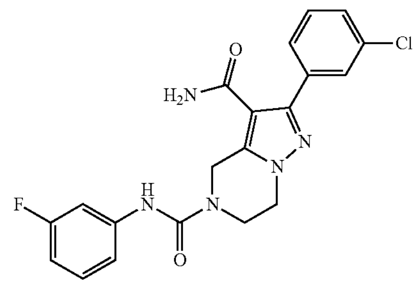 [SMILES: NC(=O)c1c(-c2cccc(Cl)c2)nn2c1CN(C(=O)Nc1cccc(F)c1)CC2] | 2-(3-Chlorophenyl)-N5-(3-fluorophenyl)-6,7-dihydropyrazolo[1,5-a]pyrazine-3,5(4H)-dicarboxamide | B | 414 | 8.971 8.618 | A B |
| 168 | 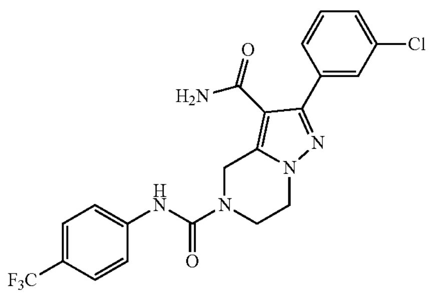 [SMILES: NC(=O)c1c(-c2cccc(Cl)c2)nn2c1CN(C(=O)Nc1ccc(C(F)(F)F)cc1)CC2] | 2-(3-Chlorophenyl)-N5-(4-(trifluoromethyl)phenyl)-6,7-dihydropyrazolo[1,5-a]pyrazine-3,5(4H)-dicarboxamide | B | 464 | 10.253 9.605 | A B |
| 169 | 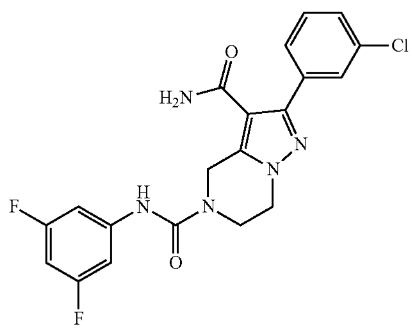 [SMILES: NC(=O)c1c(-c2cccc(Cl)c2)nn2c1CN(C(=O)Nc1cc(F)cc(F)c1)CC2] | 2-(3-Chlorophenyl)-N5-(3,5-difluorophenyl)-6,7-dihydropyrazolo[1,5-a]pyrazine-3,5(4H)-dicarboxamide | B | 432 | 9.478 9.190 | A B |
| 170 | 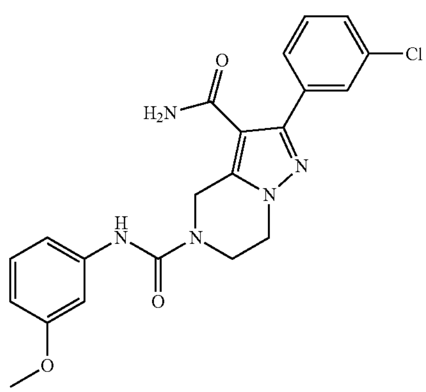 [SMILES: COc1cccc(NC(=O)N2CCn3nc(-c4cccc(Cl)c4)c(C(N)=O)c3C2)c1] | 2-(3-Chlorophenyl)-N5-(3-methoxyphenyl)-6,7-dihydropyrazolo[1,5-a]pyrazine-3,5(4H)-dicarboxamide | B | 426 | 8.657 8.368 | A B |
| 171 | 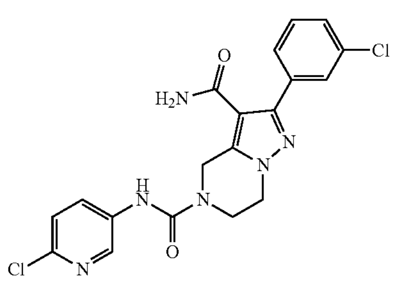 [SMILES: NC(=O)c1c(-c2cccc(Cl)c2)nn2c1CN(C(=O)Nc1ccc(Cl)nc1)CC2] | 2-(3-Chlorophenyl)-N5-(6-chloropyridin-3-yl)-6,7-dihydropyrazolo[1,5-a]pyrazine-3,5(4H)-dicarboxamide | D | 431 | 8.037 7.886 | A B |

TABLE 5-continued

| Ex. No. | Structure | Name | Method | [M + H]+ | Ret Time (min.) | HPLC Method |
|---|---|---|---|---|---|---|
| 172 | 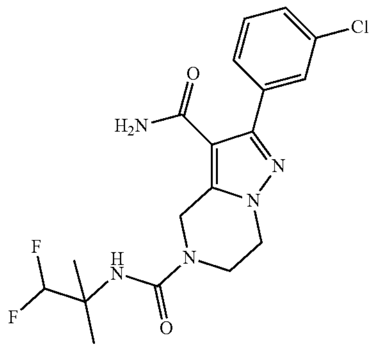 [SMILES: CC(C)(NC(=O)N1CCn2nc(-c3cccc(Cl)c3)c(C(N)=O)c2C1)C(F)F] | 2-(3-Chlorophenyl)-N5-(1,1-difluoro-2-methylpropan-2-yl)-6,7-dihydropyrazolo[1,5-a]pyrazine-3,5(4H)-dicarboxamide | C | 412.0 | 1.952 | K |
| 173 | 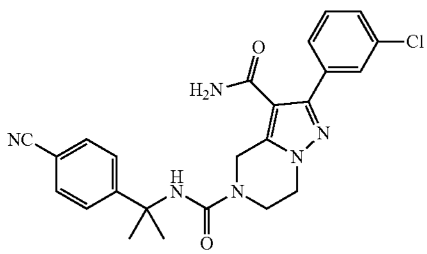 [SMILES: CC(C)(NC(=O)N1CCn2nc(-c3cccc(Cl)c3)c(C(N)=O)c2C1)c1ccc(C#N)cc1] | 2-(3-Chlorophenyl)-N5-(2-(4-cyanophenyl)propan-2-yl)-6,7-dihydropyrazolo[1,5-a]pyrazine-3,5(4H)-dicarboxamide | C | 463 | 1.37<br>1.34 | E<br>L |
| 174 | 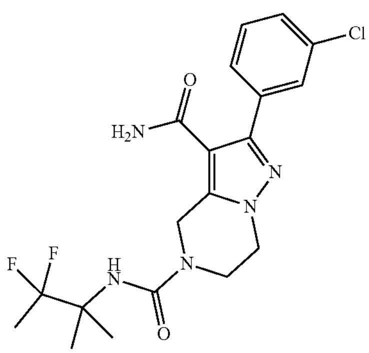 [SMILES: CC(F)(F)C(C)(C)NC(=O)N1CCn2nc(-c3cccc(Cl)c3)c(C(N)=O)c2C1] | 2-(3-Chlorophenyl)-N5-(3,3-difluoro-2-methylbutan-2-yl)-6,7-dihydropyrazolo[1,5-a]pyrazine-3,5(4H)-dicarboxamide | C | 426 | 1.289<br>1.314 | L<br>E |
| 175 | 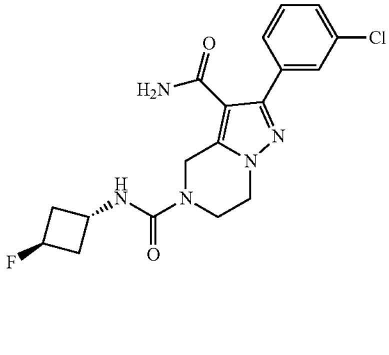 [SMILES: NC(=O)c1c(-c2cccc(Cl)c2)nn2c1CN(C(=O)N[C@H]1C[C@H](F)C1)CC2] | 2-(3-Chlorophenyl)-N5-((1r,3r)-3-fluorocyclobutyl)-6,7-dihydropyrazolo[1,5-a]pyrazine-3,5(4H)-dicarboxamide | C | 392 | 1.06<br>1.07 | L<br>E |

TABLE 5-continued

| Ex. No. | Structure | Name | Method | [M + H]+ | Ret Time (min.) | HPLC Method |
|---|---|---|---|---|---|---|
| 176 | 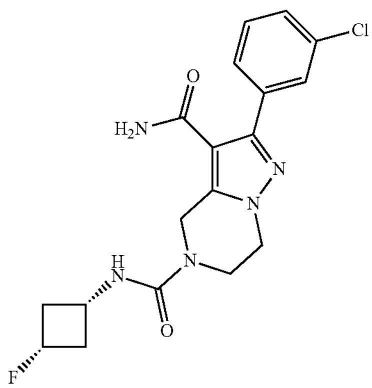 [SMILES: NC(=O)c1c(-c2cccc(Cl)c2)nn2c1CN(C(=O)N[C@H]1C[C@@H](F)C1)CC2] | 2-(3-Chlorophenyl)-N5-((1s,3s)-3-fluorocyclobutyl)-6,7-dihydropyrazolo[1,5-a]pyrazine-3,5(4H)-dicarboxamide | C | 392 | 7.484<br>7.133 | A<br>B |
| 177 | 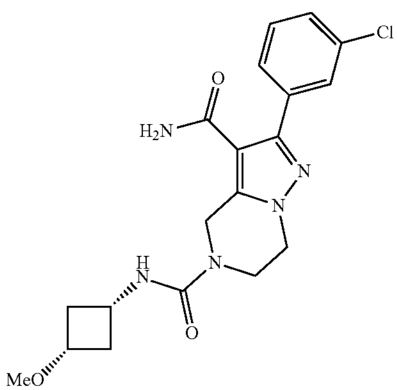 [SMILES: CO[C@H]1C[C@@H](NC(=O)N2CCn3nc(-c4cccc(Cl)c4)c(C(N)=O)c3C2)C1] | 2-(3-Chlorophenyl)-N5-((1s,3s)-3-methoxycyclobutyl)-6,7-dihydropyrazolo[1,5-a]pyrazine-3,5(4H)-dicarboxamide | C | 404 | 1.590<br>1.585 | K<br>J |
| 178 | 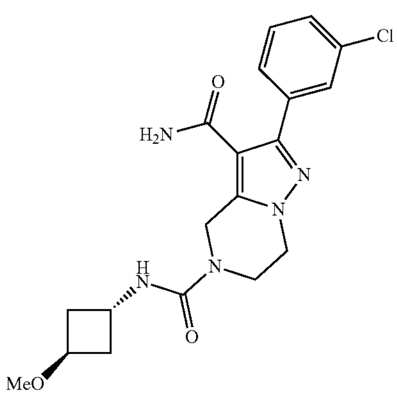 [SMILES: CO[C@H]1C[C@H](NC(=O)N2CCn3nc(-c4cccc(Cl)c4)c(C(N)=O)c3C2)C1] | 2-(3-Chlorophenyl)-N5-((1r,3r)-3-methoxycyclobutyl)-6,7-dihydropyrazolo[1,5-a]pyrazine-3,5(4H)-dicarboxamide | C | 404 | 1.009 | E |
| 179 | 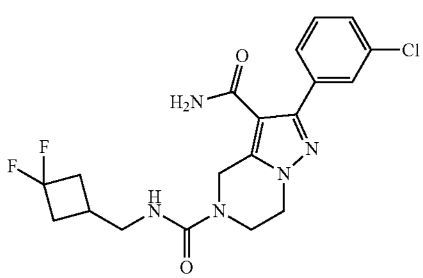 [SMILES: NC(=O)c1c(-c2cccc(Cl)c2)nn2c1CN(C(=O)NCC1CC(F)(F)C1)CC2] | 2-(3-Chlorophenyl)-N5-((3,3-difluorocyclobutyl)methyl)-6,7-dihydropyrazolo[1,5-a]pyrazine-3,5(4H)-dicarboxamide | C | 424.2 | 1.261<br>1.278 | E<br>L |

TABLE 5-continued

| Ex. No. | Structure | Name | Method | [M + H]+ | Ret Time (min.) | HPLC Method |
|---|---|---|---|---|---|---|
| 180 | 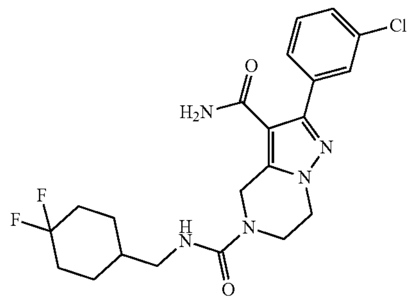 [SMILES: NC(=O)c1c(-c2cccc(Cl)c2)nn2c1CN(C(=O)NCC1CCC(F)(F)CC1)CC2] | 2-(3-Chlorophenyl)-N5-((4,4-difluorocyclohexyl)methyl)-6,7-dihydropyrazolo[1,5-a]pyrazine-3,5(4H)-dicarboxamide | C | 452 | 9.479 9.176 | M B |
| 181 | 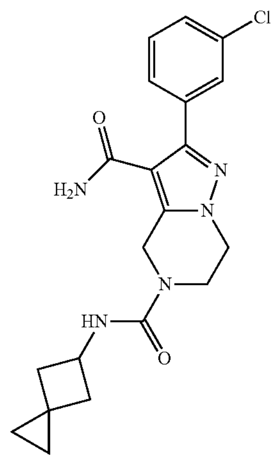 [SMILES: NC(=O)c1c(-c2cccc(Cl)c2)nn2c1CN(C(=O)NC1CC3(CC3)C1)CC2] | 2-(3-Chlorophenyl)-N5-(spiro[2.3]hexan-5-yl)-6,7-dihydropyrazolo[1,5-a]pyrazine-3,5(4H)-dicarboxamide | C | 400.0 | 1.300 1.306 | E L |
| 182 | 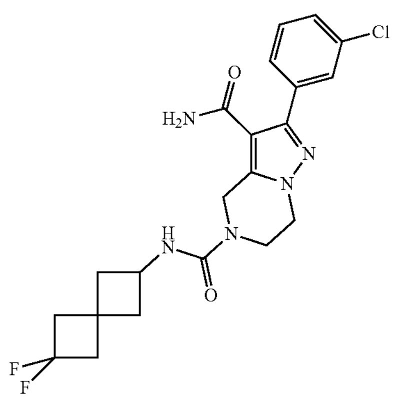 [SMILES: NC(=O)c1c(-c2cccc(Cl)c2)nn2c1CN(C(=O)NC1CC3(C1)CC(F)(F)C3)CC2] | 2-(3-Chlorophenyl)-N5-(6,6-difluorospiro[3.3]heptan-2-yl)-6,7-dihydropyrazolo[1,5-a]pyrazine-3,5(4H)-dicarboxamide | C | 450.2 | 8.357 8.916 | B A |
| 183 | 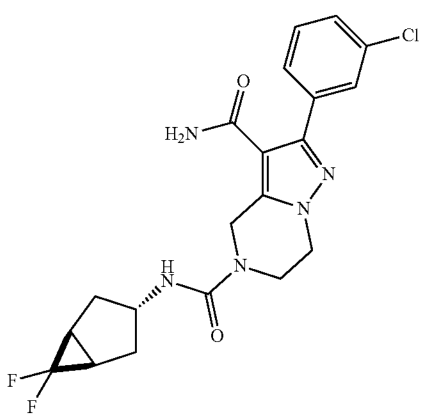 | 2-(3-Chlorophenyl)-N5-((1R,3s,5S)-6,6-difluorobicyclo[3.1.0]hexan-3-yl)-6,7-dihydropyrazolo[1,5-a]pyrazine-3,5(4H)-dicarboxamide | C | 436.0 | 1.961 1.967 | E L |

TABLE 5-continued

| Ex. No. | Structure | Name | Method | [M + H]⁺ | Ret Time (min.) | HPLC Method |
|---|---|---|---|---|---|---|
| 184 | 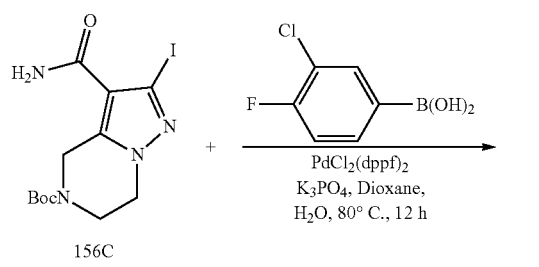 | 2-(3-Chlorophenyl)-N⁵-((1R,3r,5S)-6,6-difluorobicyclo[3.1.0]hexan-3-yl)-6,7-dihydropyrazolo[1,5-a]pyrazine-3,5(4H)-dicarboxamide | C | 436.0 | 2.048<br>2.030 | E<br>L |

Scheme 6

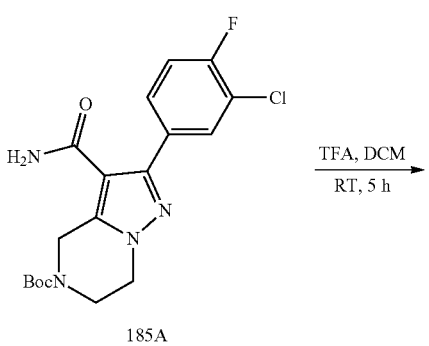

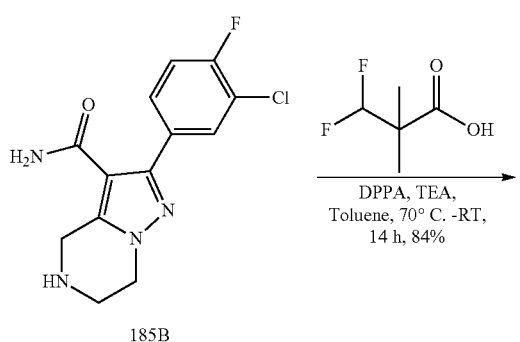

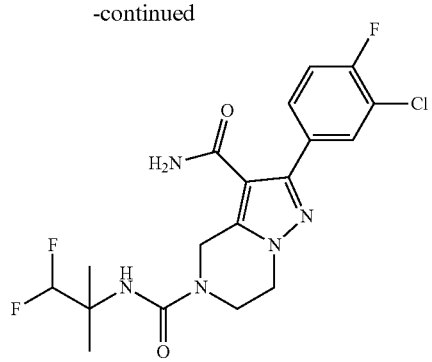

Intermediate 185A: tert-Butyl 3-carbamoyl-2-(3-chloro-4-fluorophenyl)-6,7-dihydropyrazolo[1,5-a]pyrazine-5(4H)-carboxylate

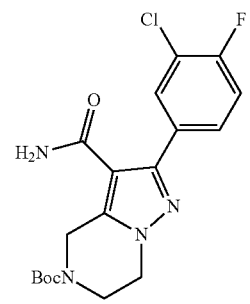 [SMILES: CC(C)(C)OC(=O)N1CCn2nc(-c3ccc(F)c(Cl)c3)c(C(N)=O)c2C1]

To a stirred solution of Intermediate 156C (5 g, 12.7 mmol), (3-chloro-4-fluorophenyl)boronic acid (3.33 g, 19.12 mmol) in 1,4-dioxane (75 mL) and water (7.5 mL) was added and K₃PO₄ (8.12 g, 38.2 mmol) and the reaction mixture was purged with nitrogen for 5 min PdCl₂(dppf)-CH₂Cl₂ (0.521 g, 0.637 mmol) was added and the reaction mixture was stirred at 80° C. for 12 h. The reaction mixture was diluted with water (75 mL) and extracted with EtOAc (3×75 mL). The combined organic layer was washed with brine, dried over Na₂SO₄, filtered and the filtrate concentrated. The crude reaction mixture was purified by silica gel chromatography (24 g REDISEP® column, eluting with 2% MeOH in CHCl₃). Fractions were collected and concentrated to afford Intermediate 185A (4.2 g, 78%) as white solid. MS(ES): m/z=395 [M+H]$^+$; $^1$H NMR $^1$H NMR (300 MHz, DMSO-d₆) δ ppm 7.81-7.87 (m, 1H), 7.63-7.72 (m, 1H), 7.47 (s, 1H), 7.15-7.37 (m, 2H), 4.74 (s, 2H), 4.16 (s, 2H), 3.80-3.88 (m, 2H), 1.45 (s, 9H).

Intermediate 185B: 2-(3-Chloro-4-fluorophenyl)-4,5,6,7-tetrahydropyrazolo[1,5-a]pyrazine-3-carboxamide

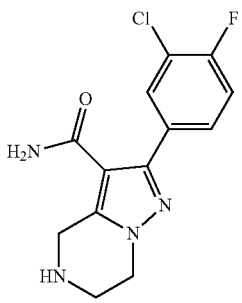 [SMILES: NC(=O)c1c(-c2ccc(F)c(Cl)c2)nn2c1CNCC2]

To a stirred solution of Intermediate 185A (4.2 g, 10.64 mmol) in DCM (15 mL) was added TFA (12.29 mL, 160 mmol) dropwise at 0° C. and the reaction mixture was stirred at RT for 12 h. The reaction mixture was concentrated under reduced pressure and the crude was basified with saturated aq. NaOH solution and stirred for 10 min. The solid product separated was filtered, washed with water, and dried under vacuum to afford 185B as a white solid (2.8 g, 87%). MS(ES): m/z=295 [M+H]$^+$; $^1$H NMR $^1$H NMR (400 MHz, DMSO-d₆) δ ppm 7.86 (dd, J=7.53, 2.01 Hz, 1H), 7.69 (ddd, J=8.66, 4.89, 2.01 Hz, 1H), 7.44 (t, J=8.78 Hz, 1H), 7.11-7.20 (m, 2H), 3.99-4.04 (m, 4H), 3.12 (d, J=6.02 Hz, 2H), 2.62 (s, 1H).

Compound 185: 2-(3-Chloro-4-fluorophenyl)-N⁵-(1,1-difluoro-2-methylpropan-2-yl)-6,7-dihydropyrazolo[1,5-a]pyrazine-3,5(4H)-dicarboxamide

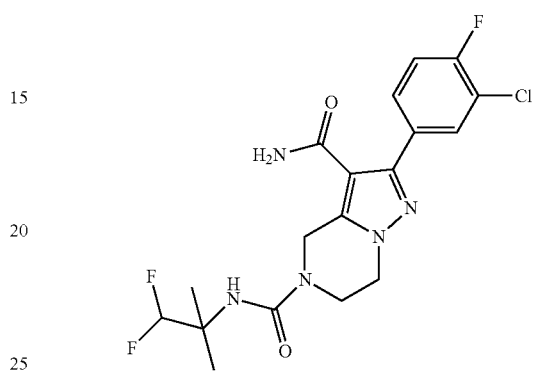

A stirred solution of 3,3-difluoro-2,2-dimethylpropanoic acid (28.1 mg, 0.204 mmol) in toluene (2 mL) at RT was added TEA (0.043 mL, 0.305 mmol) and DPPA (0.047 mL, 0.204 mmol) and the solution was stirred at 70° C. for 2 h. The reaction mixture was cooled to RT, to which was added Intermediate 185B (30 mg, 0.102 mmol) in THF (1 mL) and stirred for 12 h. The reaction mass was diluted with ethyl acetate (5 mL), the organic layer was separated, washed with 10% aqueous NaHCO₃, water, brine, dried over Na₂SO₄, filtered and the filtrate concentrated. The crude compound was purified by preparative HPLC to afford Compound 185 as pale yellow solid (37 mg, 84% yield). The HPLC retention times are 2.020 min and 2.030 min (Methods J and K respectively); MS(ES): m/z=430.2[M+H]$^+$; $^1$H NMR (400 MHz, DMSO-d₆) δ ppm 7.79-7.90 (m, 1H), 7.63-7.76 (m, 1H), 7.41-7.52 (m, 1H), 7.2-7.4 (m, 2H) 6.66-6.74 (m, 1H), 6.24-6.62 (m, 1H), 4.64-4.79 (m, 2H), 4.06-4.17 (m, 2H), 3.78-3.91 (m, 2H), 1.25 (s, 6H).

The Compounds shown in Table 6 have been prepared similar to Compound 185 by coupling of Intermediate 185B with various in-situ generated isocyanates from different carboxylic acids.

TABLE 6

| Ex. No. | Structure | Name | [M + H]+ | Ret Time (min.) | HPLC Methods |
|---|---|---|---|---|---|
| 186 | 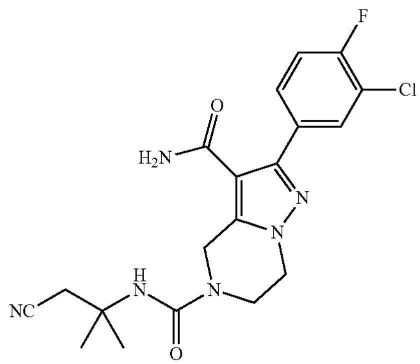 [SMILES: CC(C)(CC#N)NC(=O)N1CCn2nc(-c3ccc(F)c(Cl)c3)c(C(N)=O)c2C1] | 2-(3-Chloro-4-fluorophenyl)-N5-(1-cyano-2-methylpropan-2-yl)-6,7-dihydropyrazolo[1,5-a]pyrazine-3,5(4H)-dicarboxamide | 419 | 1.133<br>1.139 | E<br>L |
| 187 | 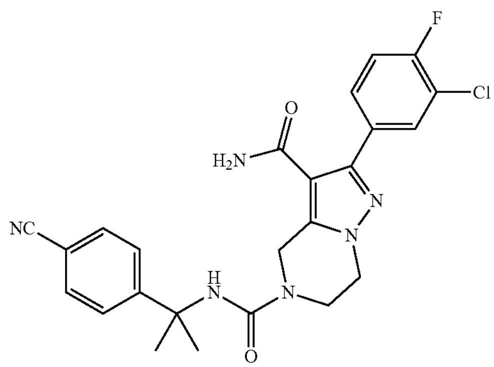 [SMILES: CC(C)(NC(=O)N1CCn2nc(-c3ccc(F)c(Cl)c3)c(C(N)=O)c2C1)c1ccc(C#N)cc1] | 2-(3-Chloro-4-fluorophenyl)-N5-(2-(4-cyanophenyl)propan-2-yl)-6,7-dihydropyrazolo[1,5-a]pyrazine-3,5(4H)-dicarboxamide | 481 | 1.419<br>1.391 | E<br>L |
| 188 | 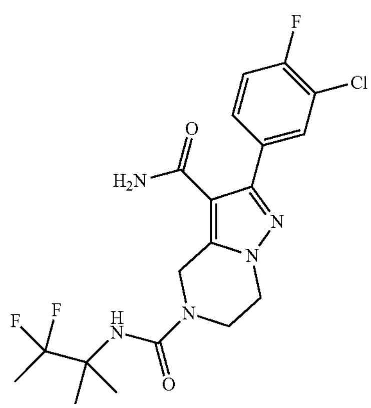 [SMILES: CC(F)(F)C(C)(C)NC(=O)N1CCn2nc(-c3ccc(F)c(Cl)c3)c(C(N)=O)c2C1] | 2-(3-Chloro-4-fluorophenyl)-N5-(3,3-difluoro-2-methylbutan-2-yl)-6,7-dihydropyrazolo[1,5-a]pyrazine-3,5(4H)-dicarboxamide | 444 | 9.037<br>8.358 | A<br>B |
| 189 | 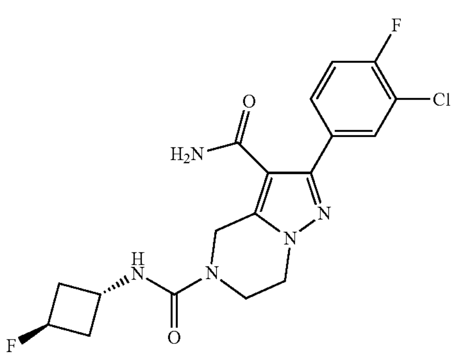 [SMILES: NC(=O)c1c(-c2ccc(F)c(Cl)c2)nn2c1CN(C(=O)N[C@H]1C[C@H](F)C1)CC2] | 2-(3-Chloro-4-fluorophenyl)-N5-((1r,3r)-3-fluorocyclobutyl)-6,7-dihydropyrazolo[1,5-a]pyrazine-3,5(4H)-dicarboxamide | 410 | 1.22<br>1.23 | L<br>E |

TABLE 6-continued

| Ex. No. | Structure | Name | [M + H]+ | Ret Time (min.) | HPLC Methods |
|---|---|---|---|---|---|
| 190 | 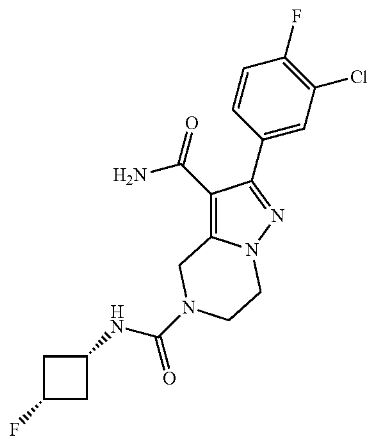 [SMILES: NC(=O)c1c(-c2ccc(F)c(Cl)c2)nn2c1CN(C(=O)N[C@H]1C[C@@H](F)C1)CC2] | 2-(3-Chloro-4-fluorophenyl)-N⁵-((1s,3s)-3-fluorocyclobutyl)-6,7-dihydropyrazolo[1,5-a]pyrazine-3,5(4H)-dicarboxamide | 410 | 7.795<br>7.504 | A<br>B |
| 191 | 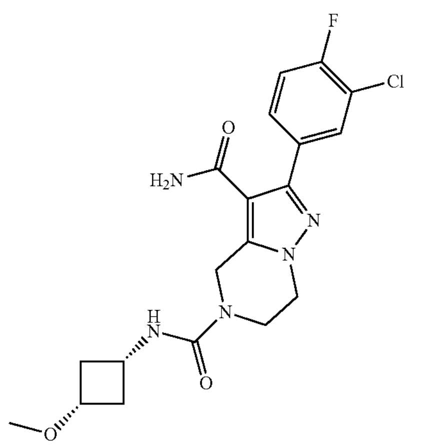 [SMILES: CO[C@H]1C[C@@H](NC(=O)N2CCn3nc(-c4ccc(F)c(Cl)c4)c(C(N)=O)c3C2)C1] | 2-(3-Chloro-4-fluorophenyl)-N⁵-((1s,3s)-3-methoxycyclobutyl)-6,7-dihydropyrazolo[1,5-a]pyrazine-3,5(4H)-dicarboxamide | 422 | 1.651<br>1.655 | J<br>K |
| 192 | 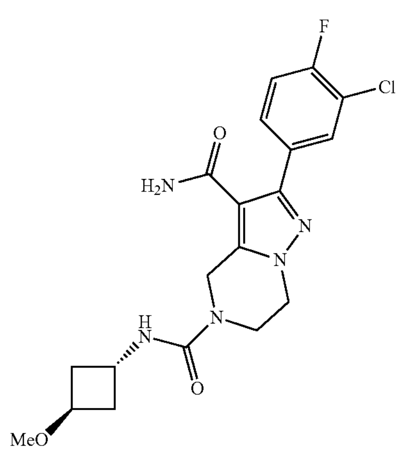 [SMILES: CO[C@H]1C[C@H](NC(=O)N2CCn3nc(-c4ccc(F)c(Cl)c4)c(C(N)=O)c3C2)C1] | 2-(3-Chloro-4-fluorophenyl)-N⁵-((1r,3r)-3-methoxycyclobutyl)-6,7-dihydropyrazolo[1,5-a]pyrazine-3,5(4H)-dicarboxamide | 422 | 1.065 | E |

TABLE 6-continued

| Ex. No. | Structure | Name | [M + H]⁺ | Ret Time (min.) | HPLC Methods |
|---|---|---|---|---|---|
| 193 | 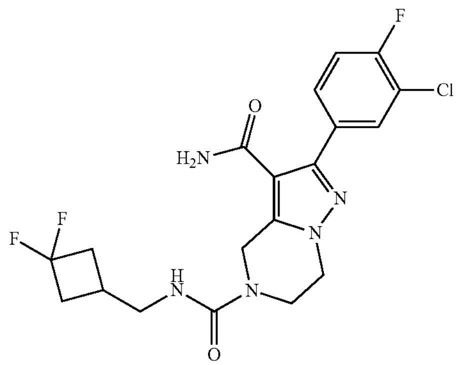 [SMILES: NC(=O)c1c(-c2ccc(F)c(Cl)c2)nn2c1CN(C(=O)NCC1CC(F)(F)C1)CC2] | 2-(3-Chloro-4-fluorophenyl)-N$^5$-((3,3-difluorocyclobutyl)methyl)-6,7-dihydropyrazolo[1,5-a]pyrazine-3,5(4H)-dicarboxamide | 442.2 | 1.317 1.334 | E L |
| 194 | 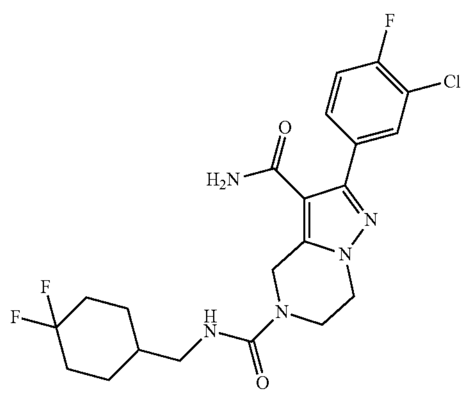 [SMILES: NC(=O)c1c(-c2ccc(F)c(Cl)c2)nn2c1CN(C(=O)NCC1CCC(F)(F)CC1)CC2] | 2-(3-Chloro-4-fluorophenyl)-N$^5$-((4,4-difluorocyclohexyl)methyl)-6,7-dihydropyrazolo[1,5-a]pyrazine-3,5(4H)-dicarboxamide | 470 | 8.87 8.68 | M B |
| 195 | 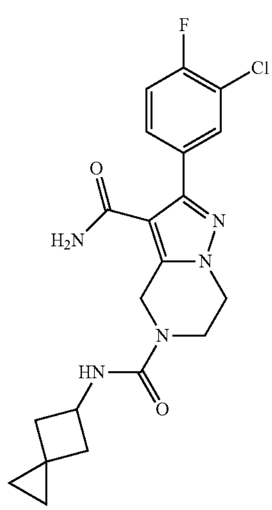 [SMILES: NC(=O)c1c(-c2ccc(F)c(Cl)c2)nn2c1CN(C(=O)NC1CC3(CC3)C1)CC2] | 2-(3-Chloro-4-fluorophenyl)-N$^5$-(spiro[2.3]hexan-5-yl)-6,7-dihydropyrazolo[1,5-a]pyrazine-3,5(4H)-dicarboxamide | 418.0 | 1.362 1.374 | E L |

TABLE 6-continued

| Ex. No. | Structure | Name | [M + H]+ | Ret Time (min.) | HPLC Methods |
|---|---|---|---|---|---|
| 196 | 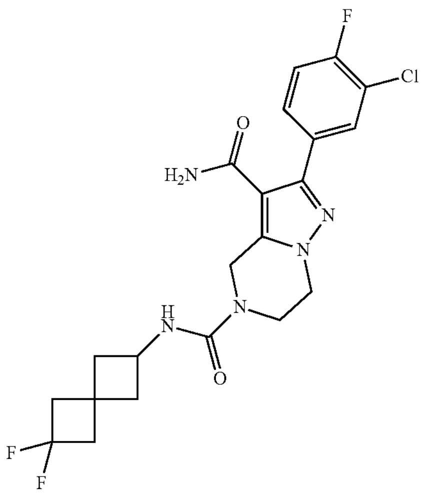 [SMILES: NC(=O)c1c(-c2ccc(F)c(Cl)c2)nn2c1CN(C(=O)NC1CC3(C1)CC(F)(F)C3)CC2] | 2-(3-Chloro-4-fluorophenyl)-N5-(6,6-difluorospiro[3.3]heptan-2-yl)-6,7-dihydropyrazolo[1,5-a]pyrazine-3,5(4H)-dicarboxamide | 468.2 | 8.629 9.143 | B A |
| 197 | 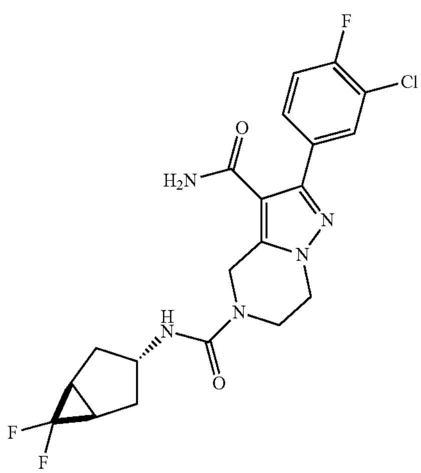 | 2-(3-Chloro-4-fluorophenyl)-N5-((1R,3s,5S)-6,6-difluorobicyclo[3.1.0]hexan-3-yl)-6,7-dihydropyrazolo[1,5-a]pyrazine-3,5(4H)-dicarboxamide | 454 | 2.025 2.026 | E L |
| 198 | 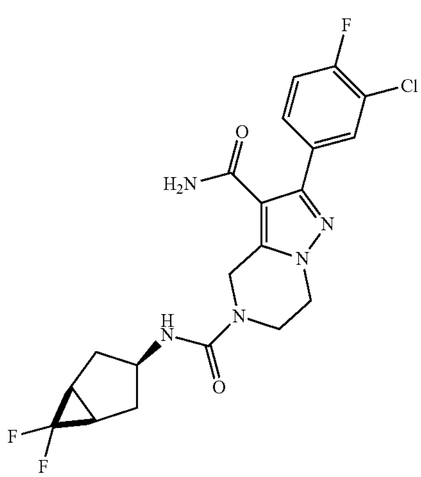 | 2-(3-Chloro-4-fluorophenyl)-N5-(1R,3r,5S)-6,6-difluorobicyclo[3.1.0]hexan-3-yl)-6,7-dihydropyrazolo[1,5-a]pyrazine-3,5(4H)-dicarboxamide | 454 | 2.110 2.091 | J K |

Scheme 7

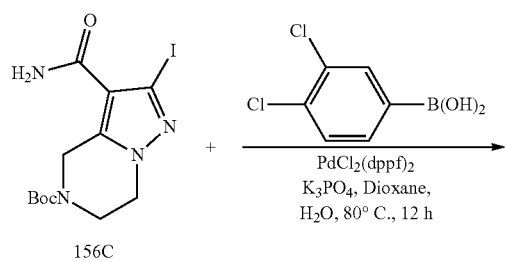

156C

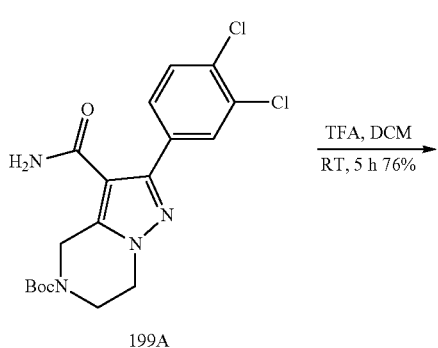

199A

TFA, DCM
RT, 5 h 76%

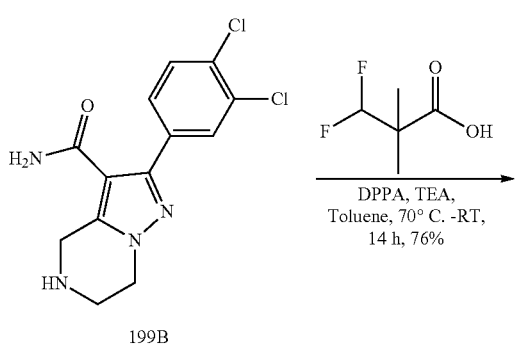

199B

DPPA, TEA,
Toluene, 70° C. -RT,
14 h, 76%

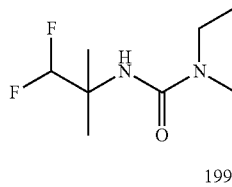

199

Intermediate 199A: tert-Butyl 3-carbamoyl-2-(3,4-dichlorophenyl)-6,7-dihydropyrazolo[1,5-a]pyrazine-5(4H)-carboxylate

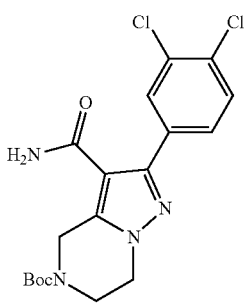 [SMILES: CC(C)(C)OC(=O)N1CCn2nc(-c3ccc(Cl)c(Cl)c3)c(C(N)=O)c2C1]

To a stirred solution of Intermediate 156C (9 g, 23 mmol), (3,4-dichlorophenyl) boronic acid (6.57 g, 34.4 mmol) in 1,4-dioxane (150 mL) and water (10 mL) was added $K_3PO_4$ (14.61 g, 68.8 mmol) and the reaction mixture was purged with nitrogen for 15 min. $PdCl_2(dppf)\text{-}CH_2Cl_2$ (1.124 g, 1.377 mmol) was added and the reaction mixture was stirred at 80° C. for 12 h. The reaction mixture was diluted with water (300 mL) and extracted with EtOAc (3×80 mL) The combined organic layer was washed with brine, dried over $Na_2SO_4$, filtered and the filtrate concentrated. The crude reaction mixture was purified by silica gel chromatography (40 g REDISEP® column, eluting with 65% EtOAc in hexanes). Fractions were collected and concentrated to afford Intermediate 199A as pale yellow solid (8 g, 85%). MS(ES): m/z=411.0 [M+H]$^+$; $^1$H NMR: (400 MHz, DMSO-$d_6$) δ ppm 7.92-7.87 (m, 1H), 7.69-7.64 (m, 2H), 7.44-7.18 (m, 2H), 4.74 (s, 2H), 4.17 (t, 2H), 3.84 (t, 2H), 1.45 (s, 9H).

Intermediate 199B: 2-(3,4-Dichlorophenyl)-4,5,6,7-tetrahydropyrazolo[1,5-a]pyrazine-3-carboxamide

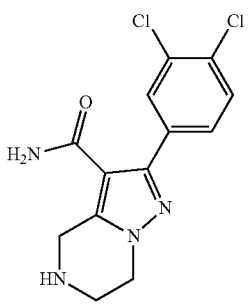 [SMILES: NC(=O)c1c(-c2ccc(Cl)c(Cl)c2)nn2c1CNCC2]

To a stirred solution of 199A (9 g, 21.88 mmol) in DCM (20 mL) was added dropwise TFA (15 mL, 21.88 mmol) at 0° C. and the reaction mixture was stirred at RT for 12 h. The volatiles were removed under reduced pressure and crude product was basified with a 10% aq. NaOH solution and stirred for 10 min. The solid product separated was filtered, washed with water, and dried under vacuum to afford 199B as an off-white solid (5.2 g, 76%). MS(ES): m/z=311.0 [M+H]$^+$;

¹H NMR: (400 MHz, DMSO-d₆) δ ppm 7.92 (s, 1H), 7.67 (m, 2H), 7.32-7.09 (m, 2H), 4.02 (s, 4H), 3.12 (br. s., 2H), 2.70-2.58 (m, 1H).

Compound 199: 2-(3,4-Dichlorophenyl)-N⁵-(1,1-difluoro-2-methylpropan-2-yl)-6,7-dihydropyrazolo[1,5-a]pyrazine-3,5(4H)-dicarboxamide

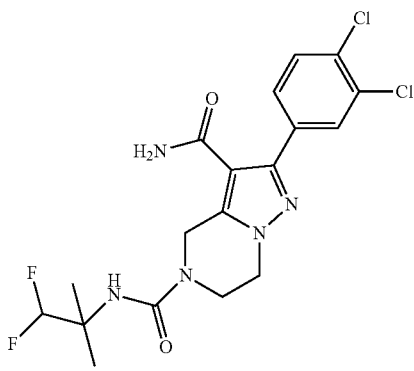 [SMILES: CC(C)(NC(=O)N1CCn2nc(-c3ccc(Cl)c(Cl)c3)c(C(N)=O)c2C1)C(F)F]

A stirred solution of 3,3-difluoro-2,2-dimethylpropanoic acid (26.6 mg, 0.193 mmol) in toluene (2 mL) at RT was added TEA (0.040 mL, 0.289 mmol) and DPPA (0.044 mL, 0.193 mmol) and the solution was stirred at 70° C. for 2 h. The reaction mass was cooled to RT and to it was added Intermediate 199B (30 mg, 0.096 mmol) dissolved in THF (1 mL) and the reaction mixture was stirred at RT for 12 h. The reaction mass was diluted with ethyl acetate (5 mL), the organic layer was separated, washed with 10% aqueous solution of NaHCO₃, water, brine, dried over Na₂SO₄, filtered and the filtrate concentrated. The crude compound was purified by preparative HPLC to afford Compound 199 as pale yellow solid (33 mg, 76% yield). The HPLC retention times are 2.173 min and 2.179 min (Methods J and K respectively); MS(ES): m/z=446.0 [M+H]⁺; ¹H NMR (400 MHz, DMSO-d₆) δ ppm 7.92 (s, 1H), 7.68 (s, 2H), 7.2-7.4 (m, 2H), 6.70 (s, 1H) 6.24-6.61 (m, 1H) 4.74 (s, 2H) 4.08-4.20 (m, 2H) 3.81-3.89 (m, 2H) 1.31 (s, 6H).

The Compounds shown in Table 7 have been prepared similar to Compound 199 by coupling of Intermediate 199B with various in-situ generated isocyanates from different carboxylic acids.

TABLE 7

| Ex. No. | Structure | Name | [M + H]⁺ | Ret Time (min.) | HPLC Methods |
|---|---|---|---|---|---|
| 200 | 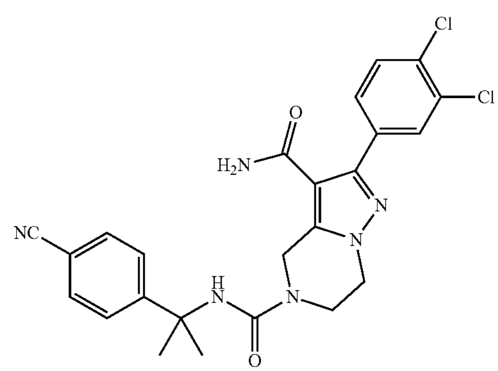 | N⁵-(2-(4-Cyanophenyl)propan-2-yl)-2-(3,4-dichlorophenyl)-6,7-dihydropyrazolo[1,5-a]pyrazine-3,5(4H)-dicarboxamide | 497 | 1.54<br>1.53 | E<br>L |
| 201 | 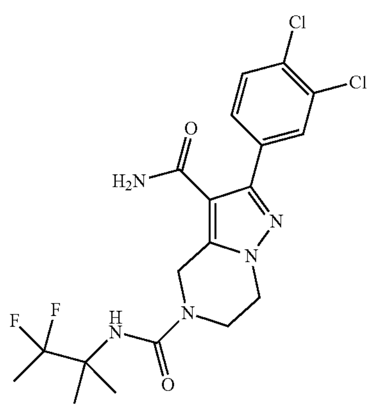 [SMILES: CC(F)(F)C(C)(C)NC(=O)N1CCn2nc(-c3ccc(Cl)c(Cl)c3)c(C(N)=O)c2C1] | 2-(3,4-Dichlorophenyl)-N⁵-(3,3-difluoro-2-methylbutan-2-yl)-6,7-dihydropyrazolo[1,5-a]pyrazine-3,5(4H)-dicarboxamide | 460 | 1.536<br>1.528 | L<br>E |

TABLE 7-continued

| Ex. No. | Structure | Name | [M + H]+ | Ret Time (min.) | HPLC Methods |
|---|---|---|---|---|---|
| 202 | 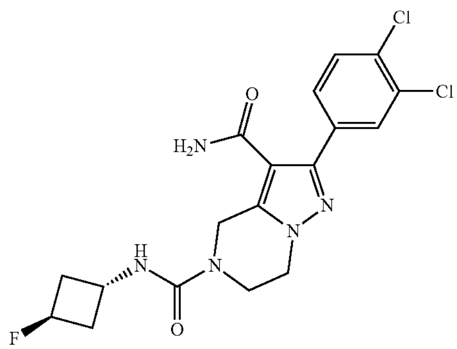 | 2-(3,4-Dichlorophenyl)-N5-((1r,3r)-3-fluorocyclobutyl)-6,7-dihydropyrazolo[1,5-a]pyrazine-3,5(4H)-dicarboxamide | 426 | 2.14<br>2.24 | L<br>E |
| 203 | 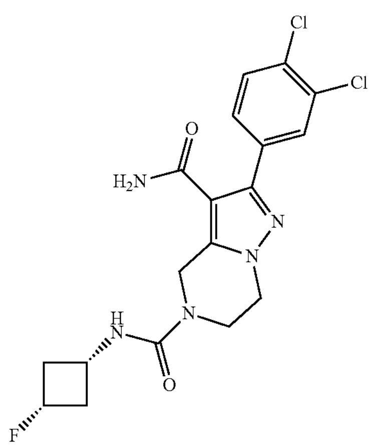 [SMILES: NC(=O)c1c(-c2ccc(Cl)c(Cl)c2)nn2c1CN(C(=O)N[C@H]1C[C@@H](F)C1)CC2] | 2-(3,4-Dichlorophenyl)-N5-((1s,3s)-3-fluorocyclobutyl)-6,7-dihydropyrazolo[1,5-a]pyrazine-3,5(4H)-dicarboxamide | 426 | 8.470<br>8.080 | A<br>B |
| 204 | 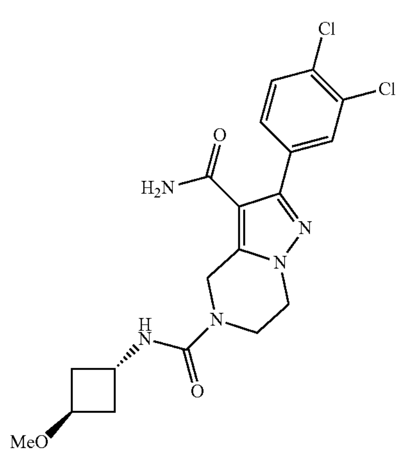 [SMILES: CO[C@H]1C[C@H](NC(=O)N2CCn3nc(-c4ccc(Cl)c(Cl)c4)c(C(N)=O)c3C2)C1] | 2-(3,4-Dichlorophenyl)-N5-((1r,3r)-3-methoxycyclobutyl)-6,7-dihydropyrazolo[1,5-a]pyrazine-3,5(4H)-dicarboxamide | 438 | 1.200 | E |

TABLE 7-continued

| Ex. No. | Structure | Name | [M + H]+ | Ret Time (min.) | HPLC Methods |
|---|---|---|---|---|---|
| 205 | 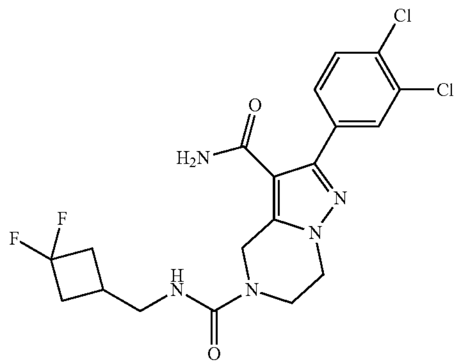 [SMILES: NC(=O)c1c(-c2ccc(Cl)c(Cl)c2)nn2c1CN(C(=O)NCC1CC(F)(F)C1)CC2] | 2-(3,4-Dichlorophenyl)-N5-((3,3-difluorocyclobutyl)methyl)-6,7-dihydropyrazolo[1,5-a]pyrazine-3,5(4H)-dicarboxamide | 458.2 | 1.446<br>1.462 | E<br>L |
| 206 | 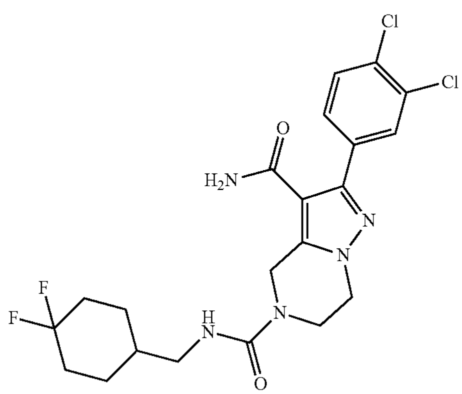 | 2-(3,4-Dichlorophenyl)-N5-((4,4-difluorocyclohexyl)methyl)-6,7-dihydropyrazolo[1,5-a]pyrazine-3,5(4H)-dicarboxamide | 486 | 8.628<br>8.480 | M<br>B |
| 207 | 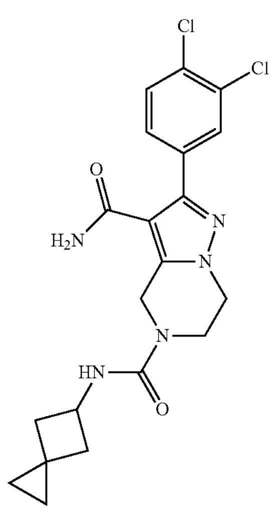 [SMILES: NC(=O)c1c(-c2ccc(Cl)c(Cl)c2)nn2c1CN(C(=O)NC1CC3(CC3)C1)CC2] | 2-(3,4-Dichlorophenyl)-N5-(spiro[2.3]hexan-5-yl)-6,7-dihydropyrazolo[1,5-a]pyrazine-3,5(4H)-dicarboxamide | 434.0 | 1.487<br>1.484 | E<br>L |

TABLE 7-continued

| Ex. No. | Structure | Name | [M + H]+ | Ret Time (min.) | HPLC Methods |
|---|---|---|---|---|---|
| 208 | 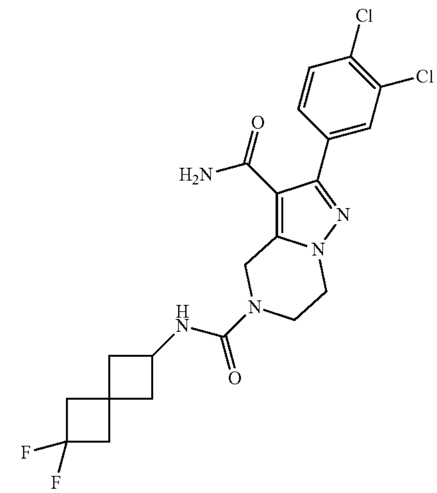 | 2-(3,4-Dichlorophenyl)-N5-(6,6-difluorospiro[3.3]heptan-2-yl)-6,7-dihydropyrazolo[1,5-a]pyrazine-3,5(4H)-dicarboxamide | 484.0 | 9.095<br>9.676 | B<br>A |

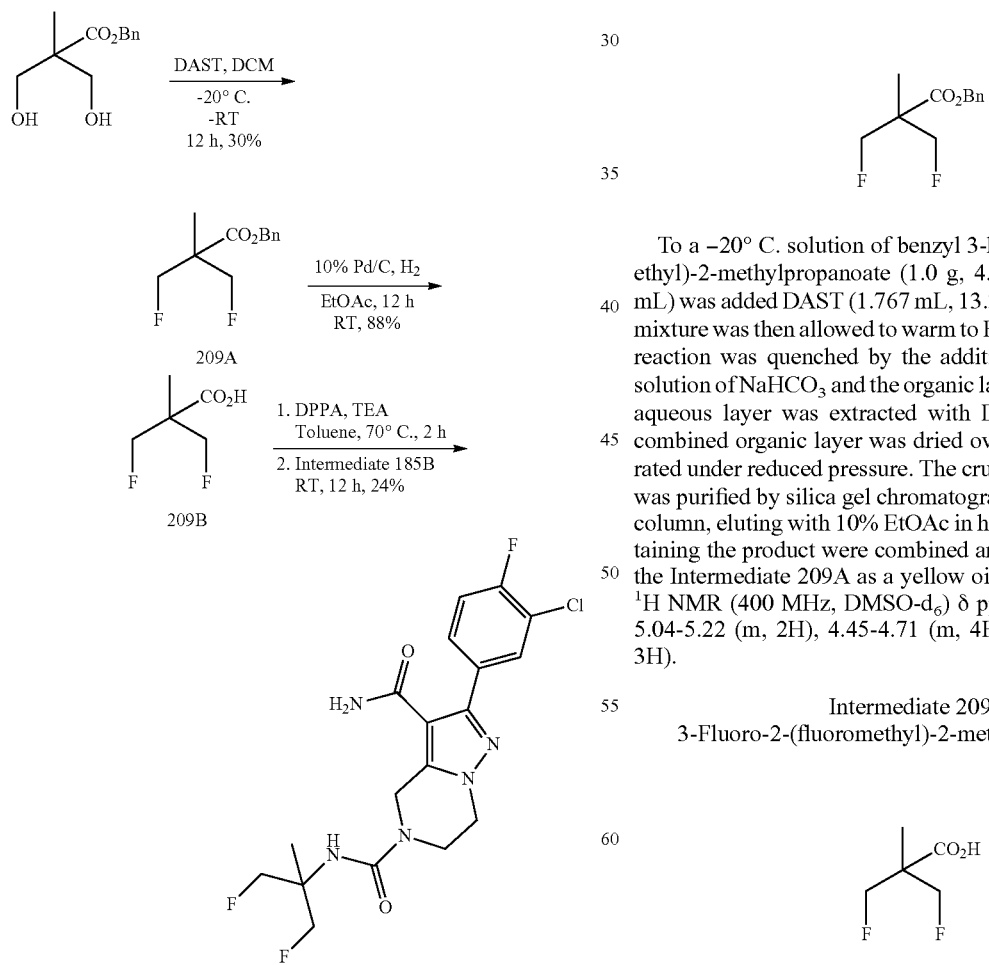

Scheme 8

Intermediate 209A: Benzyl 3-fluoro-2-(fluoromethyl)-2-methylpropanoate

To a −20° C. solution of benzyl 3-hydroxy-2-(hydroxymethyl)-2-methylpropanoate (1.0 g, 4.5 mmol) in DCM (15 mL) was added DAST (1.767 mL, 13.38 mmol). The reaction mixture was then allowed to warm to RT and stir for 12 h. The reaction was quenched by the addition of a 10% aqueous solution of NaHCO$_3$ and the organic layer was separated. The aqueous layer was extracted with DCM (2×25 mL). The combined organic layer was dried over Na$_2$SO$_4$ and evaporated under reduced pressure. The crude compound obtained was purified by silica gel chromatography (12 g REDISEP® column, eluting with 10% EtOAc in hexanes). Fractions containing the product were combined and evaporated to afford the Intermediate 209A as a yellow oil (300 mg, 30% yield). $^1$H NMR (400 MHz, DMSO-d$_6$) δ ppm 7.30-7.43 (m, 5H), 5.04-5.22 (m, 2H), 4.45-4.71 (m, 4H), 1.19 (t, J=1.76 Hz, 3H).

Intermediate 209B: 3-Fluoro-2-(fluoromethyl)-2-methylpropanoic acid

To a stirred solution of Intermediate 209A (0.300 g, 1.314 mmol) in EtOAc (5 mL) was added 10% Pd/C (0.140 g, 0.131 mmol). The reaction mixture was stirred for 12 h under an atmosphere of hydrogen (15 psi). The reaction mixture was then filtered through a pad of CELITE® and the cake was washed with EtOAc. The filtrate was concentrated under reduced pressure to afford Intermediate 209B as a yellow liquid (160 mg, 88%). The crude product was used without further purification. $^1$H NMR (400 MHz, DMSO-$d_6$) δ ppm 13.02 (bs, 1H), 4.40-4.66 (m, 4H), 1.06-1.20 (m, 3H).

Compound 209: 2-(3-Chloro-4-fluorophenyl)-$N^5$-(1,3-difluoro-2-methylpropan-2-yl)-6,7-dihydropyrazolo[1,5-a]pyrazine-3,5(4H)-dicarboxamide

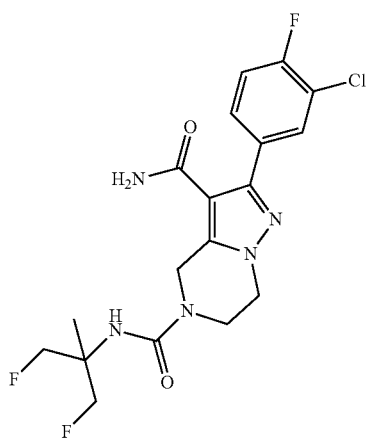 [SMILES: CC(CF)(CF)NC(=O)N1CCn2nc(-c3ccc(F)c(Cl)c3)c(C(N)=O)c2C1]

A stirred solution of Intermediate 209B (28.1 mg, 0.204 mmol) in toluene (2 mL) at RT under nitrogen was added TEA (0.043 mL, 0.305 mmol), DPPA (0.047 mL, 0.204 mmol) and the solution was heated at 70° C. and stirred for 2 h. The reaction mass was cooled to RT and to it was added Intermediate 185B (30 mg, 0.102 mmol) in THF (1 mL) was added and the reaction mixture was stirred at RT for 12 h. The reaction mass was diluted with ethyl acetate (25 mL), the organic layer was separated, washed with a 10% aqueous solution of NaHCO$_3$, water, brine dried over Na$_2$SO$_4$, filtered, and the filtrate evaporated. The crude compound was purified by preparative HPLC to afford Compound 209 as pale yellow solid (11 mg, 24% yield). The HPLC Retention times 1.963 min. and 1.968 min. (Methods J and K respectively); MS(ES): m/z=430.2 [M+H]$^+$; $^1$H NMR (400 MHz, DMSO-$d_6$) δ ppm 7.85 (dd, J=7.31, 2.16 Hz, 1H), 7.64-7.73 (m, 1H), 7.42-7.52 (m, 1H), 7.15-7.30 (m, 2H), 6.62 (s, 1H), 4.73 (s, 2H), 4.64 (s, 2H), 4.52 (s, 2H), 4.14 (s, 2H), 3.84 (s, 2H), 1.31 (t, J=2.07 Hz, 3H).

The Compounds shown in Table 8 have been prepared similar to Compound 209 by coupling of in-situ generated isocyanate of 209B with 185B analogs.

TABLE 8

| Ex. No. | Structure | Name | [M + H]$^+$ | Ret Time (min.) | HPLC Methods |
|---|---|---|---|---|---|
| 210 | 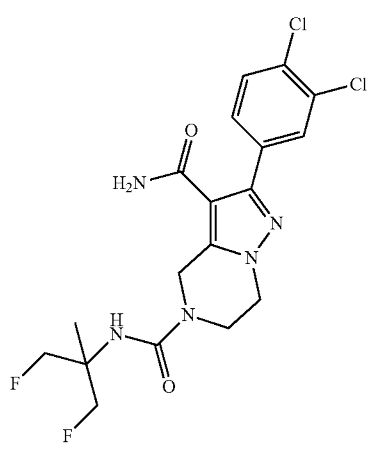 [SMILES: CC(CF)(CF)NC(=O)N1CCn2nc(-c3ccc(Cl)c(Cl)c3)c(C(N)=O)c2C1] | 2-(3,4-Dichlorophenyl)-$N^5$-(1,3-difluoro-2-methylpropan-2-yl)-6,7-dihydropyrazolo[1,5-a]pyrazine-3,5(4H)-dicarboxamide | 446.0 | 2.132 | E |

TABLE 8-continued

| Ex. No. | Structure | Name | [M + H]+ | Ret Time (min.) | HPLC Methods |
|---|---|---|---|---|---|
| 211 | 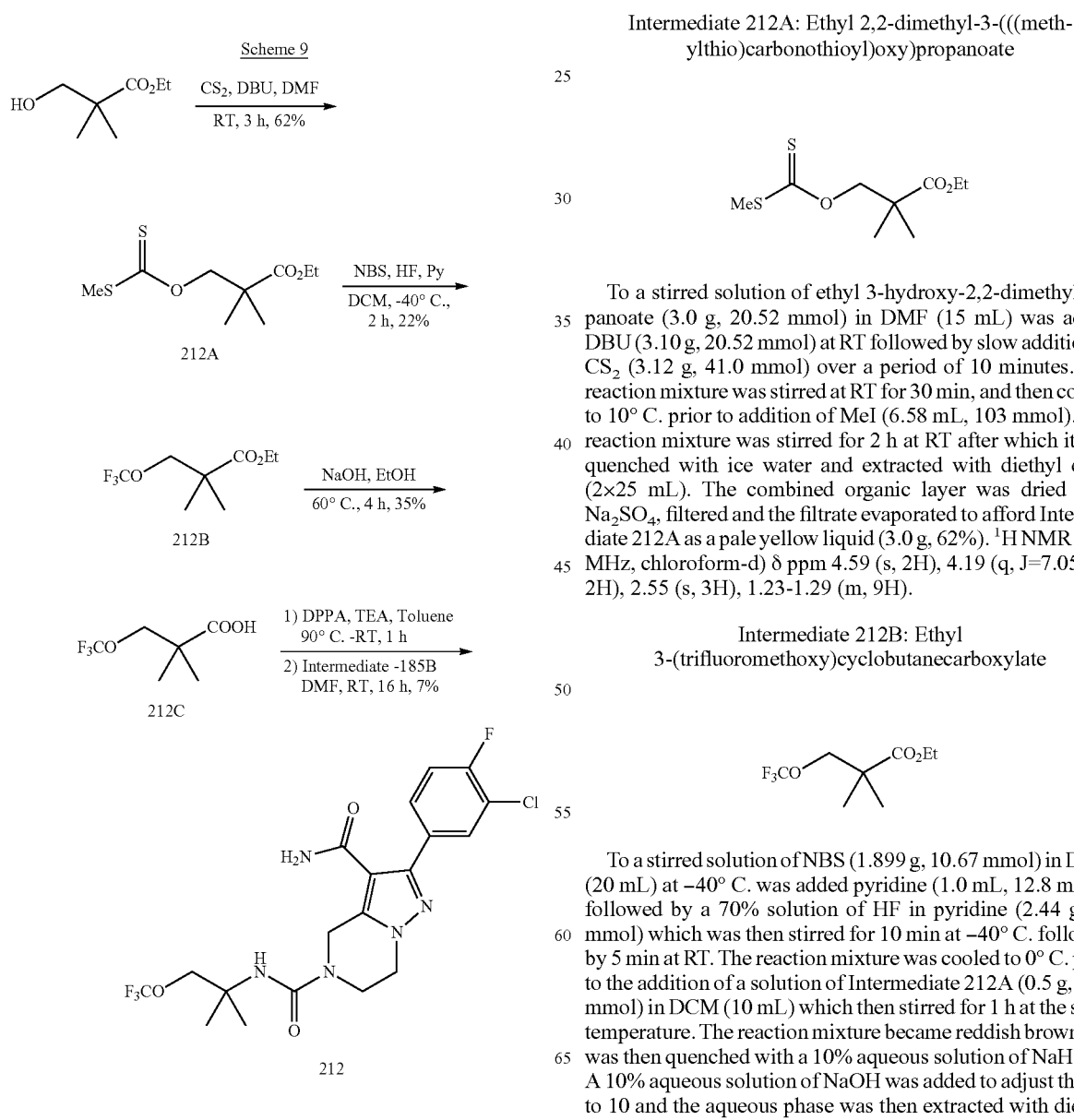 | 2-(3-Chlorophenyl)-N[5]-(1,3-difluoro-2-methylpropan-2-yl)-6,7-dihydropyrazolo[1,5-a]pyrazine-3,5(4H)-dicarboxamide | 412.0 | 1.171<br>1.294 | E<br>L |

Intermediate 212A: Ethyl 2,2-dimethyl-3-(((methylthio)carbonothioyl)oxy)propanoate To a stirred solution of ethyl 3-hydroxy-2,2-dimethylpropanoate (3.0 g, 20.52 mmol) in DMF (15 mL) was added DBU (3.10 g, 20.52 mmol) at RT followed by slow addition of $CS_2$ (3.12 g, 41.0 mmol) over a period of 10 minutes. The reaction mixture was stirred at RT for 30 min, and then cooled to 10° C. prior to addition of MeI (6.58 mL, 103 mmol). The reaction mixture was stirred for 2 h at RT after which it was quenched with ice water and extracted with diethyl ether (2×25 mL). The combined organic layer was dried over $Na_2SO_4$, filtered and the filtrate evaporated to afford Intermediate 212A as a pale yellow liquid (3.0 g, 62%). $^1$H NMR (300 MHz, chloroform-d) δ ppm 4.59 (s, 2H), 4.19 (q, J=7.05 Hz, 2H), 2.55 (s, 3H), 1.23-1.29 (m, 9H).

Intermediate 212B: Ethyl 3-(trifluoromethoxy)cyclobutanecarboxylate

To a stirred solution of NBS (1.899 g, 10.67 mmol) in DCM (20 mL) at −40° C. was added pyridine (1.0 mL, 12.8 mmol) followed by a 70% solution of HF in pyridine (2.44 g, 85 mmol) which was then stirred for 10 min at −40° C. followed by 5 min at RT. The reaction mixture was cooled to 0° C. prior to the addition of a solution of Intermediate 212A (0.5 g, 2.13 mmol) in DCM (10 mL) which then stirred for 1 h at the same temperature. The reaction mixture became reddish brown and was then quenched with a 10% aqueous solution of $NaHSO_3$. A 10% aqueous solution of NaOH was added to adjust the pH to 10 and the aqueous phase was then extracted with diethyl ether (2×25 mL). The combined organic layers were washed with a 1.5 N aqueous solution of HCl, dried over Na$_2$SO$_4$, and evaporated to afford Intermediate 212B as a light brown liquid. It was reacted in the saponification without further purification (100 mg, 22% yield).

Intermediate 212C:
3-(Trifluoromethoxy)cyclobutanecarboxylic acid

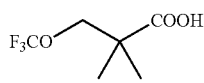

To a stirred solution of Intermediate 212B (0.10 g, 0.47 mmol) in THF (5 mL) was added NaOH (0.038 g, 0.943 mmol) in water (1 mL) and the mixture was allowed to stir at 60° C. for 4 h. The reaction mixture was quenched with a 1.5 N aqueous solution of HCl and extracted with EtOAc (2×20 mL) The combined organic layers were dried over Na$_2$SO$_4$, filtered and the filtrate evaporated to afford Intermediate 212C as a light brown liquid (30 mg, 35% yield). $^1$H NMR (300 MHz, DMSO-d$_6$) δ ppm 12.01-12.03 (bs, 1H), 3.34 (m, 2H), 1.04 (s, 6H).

Compound 212: 2-(3-Chloro-4-fluorophenyl)-N$^5$-(2-methyl-1-(trifluoromethoxy)propan-2-yl)-6,7-dihydropyrazolo[1,5-a]pyrazine-3,5(4H)-dicarboxamide

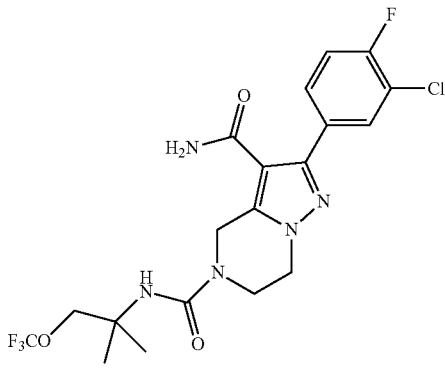 [SMILES: CC(C)(COC(F)(F)F)NC(=O)N1CCn2nc(-c3ccc(F)c(Cl)c3)c(C(N)=O)c2C1]

To a stirred solution of Intermediate 212C (95 mg, 0.509 mmol) in toluene (5 ml) was added TEA (0.118 mL, 0.848 mmol), DPPA (0.047 mL, 0.204 mmol) and the reaction mixture was stirred at 90° C. for 1 h. The reaction mixture was cooled RT and to it was added a solution of Intermediate 185B (50 mg, 0.170 mmol) in DMF (2 ml) and stirred at RT for 16 h. The reaction was quenched with a 10% aqueous solution of NaHCO$_3$ and extracted with EtOAc (2×20 mL). The combined organic layer dried over Na$_2$SO$_4$, filtered and the filtrate evaporated. The crude compound was purified by preparative HPLC to afford Compound 212 as an off-white solid (6 mg, 7% yield). HPLC retention times 9.95 min. and 9.08 min. (Methods A and B respectively). MS(ES): m/z 478 [M+H]$^+$; $^1$H NMR (400 MHz, MeOH-d$_1$) δ ppm 7.75-7.77 (m, 1H), 7.58-7.62 (m, 1H), 7.29-7.33 (t, J=8.84 Hz, 1H), 4.85 (s, 2H), 4.23 (s, 2H), 4.18-4.21 (t, J=5.24 Hz, 2H), 3.90-3.92 (t, J=5.24 Hz, 2H), 1.37 (s, 6H).

Scheme 10

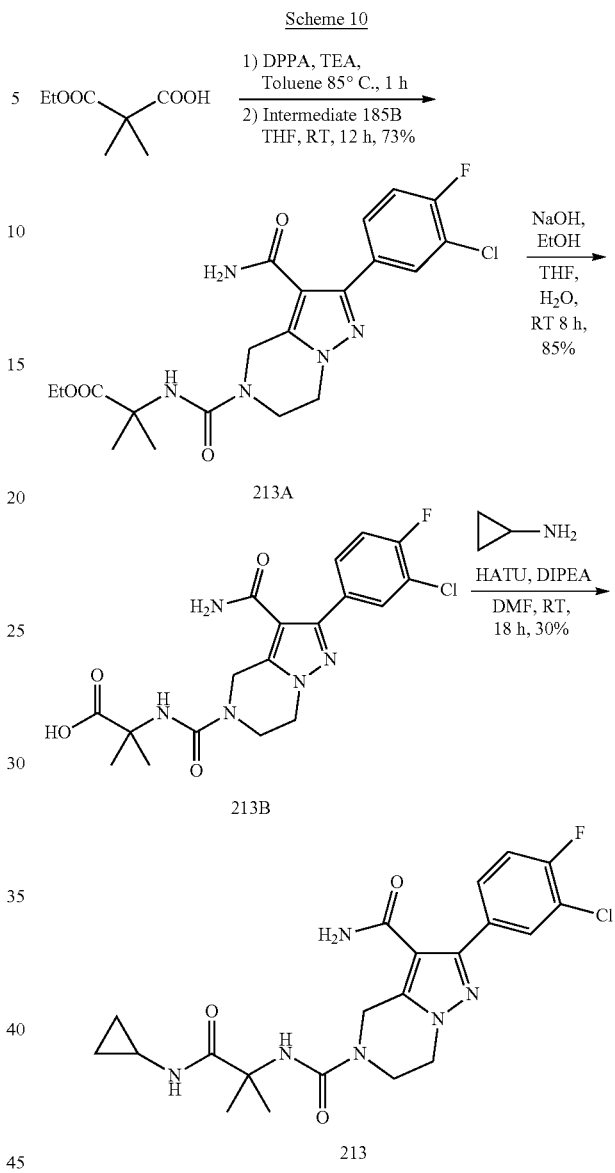

Intermediate 213A: Ethyl 2-(3-carbamoyl-2-(3-chloro-4-fluorophenyl)-4,5,6,7-tetrahydropyrazolo[1,5-a]pyrazine-5-carboxamido)-2-methylpropanoate

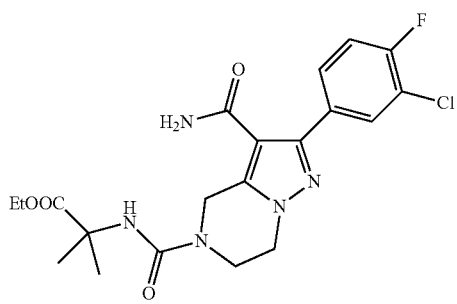 [SMILES: CCOC(=O)C(C)(C)NC(=O)N1CCn2nc(-c3ccc(F)c(Cl)c3)c(C(N)=O)c2C1]

To a stirred solution of 3-ethoxy-2,2-dimethyl-3-oxopropanoic acid (543 mg, 3.39 mmol) in toluene (25 mL) at RT under nitrogen was added TEA (1.182 mL, 8.48 mmol), DPPA (0.731 mL, 3.39 mmol) and the reaction mixture was heated to 85° C. and stirred for 1 h. The reaction mass was cooled to RT and in to it was added a solution of Intermediate 185B (500 mg, 1.697 mmol) in THF (4 mL) and stirred at RT for 12 h. The reaction mass was concentrated and the residue was extracted with ethyl acetate (3×10 mL) The combined organic layer was washed with water, brine, dried over $Na_2SO_4$, filtered and the filtrate concentrated. The crude product was triturated with diethyl ether to afford Intermediate 213A as an off-white solid (550 mg, 70% yield). MS(ES): m/z=452 [M+H]$^+$; $^1$H NMR (300 MHz, DMSO-d$_6$) δ ppm 7.85 (dd, J=7.2, 2.3 Hz, 1H), 7.68 (s, 1H), 7.51-7.42 (m, 1H), 7.40-7.32 (m, 1H), 7.25-7.14 (m, 1H), 7.06 (s, 1H), 4.73 (s, 2H), 4.17-4.09 (m, 2H), 4.01 (q, J=7.2 Hz, 2H), 3.89-3.79 (m, 2H), 1.37 (s, 6H), 1.09 (t, J=7.0 Hz, 3H).

Intermediate 213B: 2-(3-Carbamoyl-2-(3-chloro-4-fluorophenyl)-4,5,6,7-tetrahydropyrazolo[1,5-a]pyrazine-5-carboxamido)-2-methylpropanoic acid

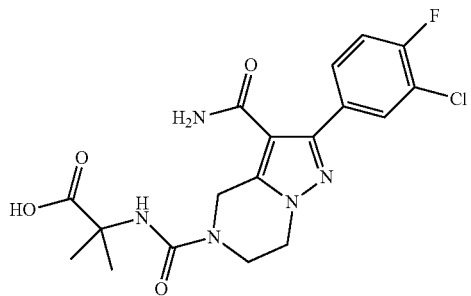 [SMILES: CC(C)(NC(=O)N1CCn2nc(-c3ccc(F)c(Cl)c3)c(C(N)=O)c2C1)C(=O)O]

To a solution of Intermediate 213A (500 mg, 1.106 mmol) in ethanol (20 mL) and THF (20 mL) was added a solution of NaOH (89 mg, 2.213 mmol) in water (10 mL) and the reaction mixture was stirred at RT for 8 h. The reaction mixture was concentrated to dryness under reduced pressure. The crude product was dissolved in water and the pH of solution was adjusted to 4 using a 1.5N aqueous solution of HCl which was then stirred for 10 min. The precipitate was filtered, dried and triturated with diethyl ether to afford Intermediate 213B as pale brown solid (400 mg, 85%). MS(ES): m/z=424 [M+H]$^+$; $^1$H NMR (400 MHz, DMSO-d$_6$) δ ppm 11.99 (s, 1H), 7.89-7.84 (m, 1H), 7.73-7.67 (m, 1H), 7.50-7.44 (m, 1H), 7.35 (s, 1H), 7.20 (br. s., 1H), 6.93 (s, 1H), 4.74 (s, 2H), 4.16-4.10 (m, 2H), 3.85 (d, J=5.5 Hz, 2H), 1.38 (s, 6H).

Intermediate 213: 2-(3-Chloro-4-fluorophenyl)-N$^5$-(1-(cyclopropylamino)-2-methyl-1-oxopropan-2-yl)-6,7-dihydropyrazolo[1,5-a]pyrazine-3,5(4H)-dicarboxamide

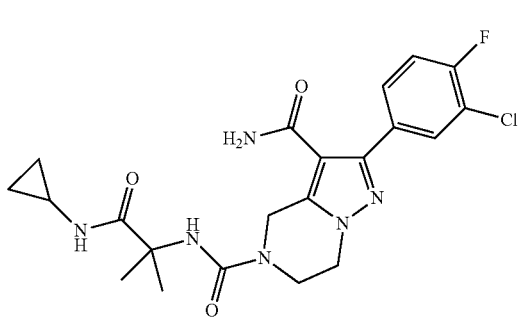 [SMILES: CC(C)(NC(=O)N1CCn2nc(-c3ccc(F)c(Cl)c3)c(C(N)=O)c2C1)C(=O)NC1CC1]

To a suspension of Intermediate 213B (40 mg, 0.094 mmol), HATU (71.8 mg, 0.189 mmol) and DIPEA (0.082 ml, 0.472 mmol) in DMF (6 mL) was added cyclopropylamine (6.65 µL, 0.094 mmol) and the mixture was stirred at RT for 18 h. The reaction mixture was quenched with ice cold water and extracted with EtOAc (3×25 mL). The organic layer was washed with brine, dried over $Na_2SO_4$, filtered and the filtrate concentrated. The crude product was purified by preparative HPLC to afford Compound 213 as an off-white solid (13.5 mg, 30%). HPLC retention time 6.9 and 6.75 min (Methods B and C respectively). MS(ES): m/z=463 [M+H]$^+$; $^1$H NMR (400 MHz, DMSO-d$_6$) δ ppm 7.86 (dd, J=7.28, 2.26 Hz, 1H), 7.64-7.74 (m, 1H), 7.38-7.50 (m, 2H), 7.14-7.37 (m, 2H), 6.65 (s, 1H), 4.74 (s, 2H), 4.14 (t, J=5.27 Hz, 2H), 3.83 (t, J=5.27 Hz, 2H), 2.53-2.58 (m, 1H), 1.33 (s, 6H), 0.52-0.60 (m, 2H), 0.31-0.40 (m, 2H).

The Compounds shown in Table 9 have been prepared similar to Compound 213 by coupling of Intermediate 213B with various amines.

TABLE 9

| Ex. No. | Structure | Name | [M + H]$^+$ | Ret Time (min.) | HPLC Methods |
|---|---|---|---|---|---|
| 214 | 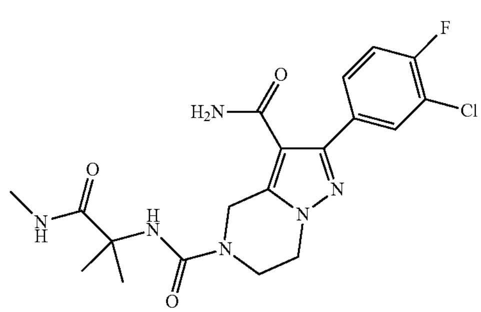 [SMILES: CNC(=O)C(C)(C)NC(=O)N1CCn2nc(-c3ccc(F)c(Cl)c3)c(C(N)=O)c2C1] | 2-(3-Chloro-4-fluorophenyl)-N$^5$-(2-methyl-1-(methylamino)-1-oxopropan-2-yl)-6,7-dihydropyrazolo[1,5-a]pyrazine-3,5(4H)-dicarboxamide | 437 | 6.25<br>6.38 | B<br>C |

TABLE 9-continued

| Ex. No. | Structure | Name | [M + H]+ | Ret Time (min.) | HPLC Methods |
|---|---|---|---|---|---|
| 215 | 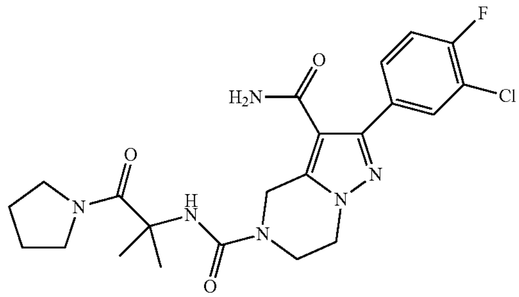 [SMILES: CC(C)(NC(=O)N1CCn2nc(-c3ccc(F)c(Cl)c3)c(C(N)=O)c2C1)C(=O)N1CCCC1] | 2-(3-Chloro-4-fluorophenyl)-N5-(2-methyl-1-oxo-1-(pyrrolidin-1-yl)propan-2-yl)-6,7-dihydropyrazolo[1,5-a]pyrazine-3,5(4H)-dicarboxamide | 477 | 6.92<br>6.80 | C<br>B |
| 216 | 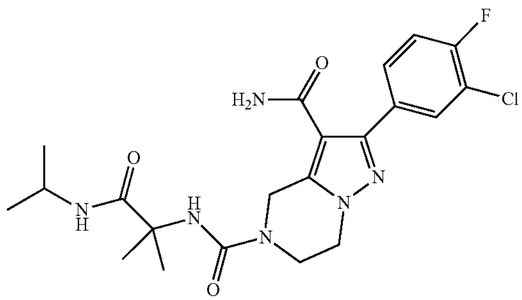 [SMILES: CC(C)NC(=O)C(C)(C)NC(=O)N1CCn2nc(-c3ccc(F)c(Cl)c3)c(C(N)=O)c2C1] | 2-(3-Chloro-4-fluorophenyl)-N5-(1-(isopropylamino)-2-methyl-1-oxopropan-2-yl)-6,7-dihydropyrazolo[1,5-a]pyrazine-3,5(4H)-dicarboxamide | 465 | 7.22<br>6.89 | B<br>C |
| 217 | 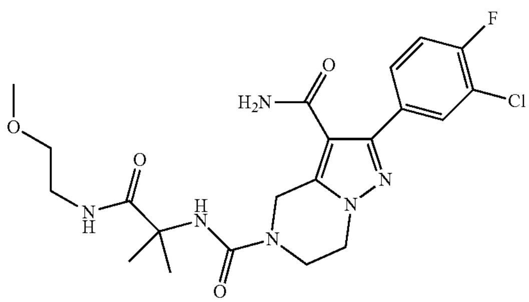 [SMILES: COCCNC(=O)C(C)(C)NC(=O)N1CCn2nc(-c3ccc(F)c(Cl)c3)c(C(N)=O)c2C1] | 2-(3-Chloro-4-fluorophenyl)-N5-(1-((2-methoxyethyl)amino)-2-methyl-1-oxopropan-2-yl)-6,7-dihydropyrazolo[1,5-a]pyrazine-3,5(4H)-dicarboxamide | 481 | 6.65<br>6.51 | C<br>B |
| 218 | 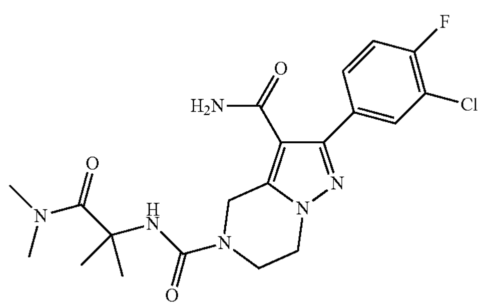 [SMILES: CN(C)C(=O)C(C)(C)NC(=O)N1CCn2nc(-c3ccc(F)c(Cl)c3)c(C(N)=O)c2C1] | 2-(3-Chloro-4-fluorophenyl)-N5-(1-(dimethylamino)-2-methyl-1-oxopropan-2-yl)-6,7-dihydropyrazolo[1,5-a]pyrazine-3,5(4H)-dicarboxamide | 451 | 6.62<br>6.50 | C<br>B |
| 219 | 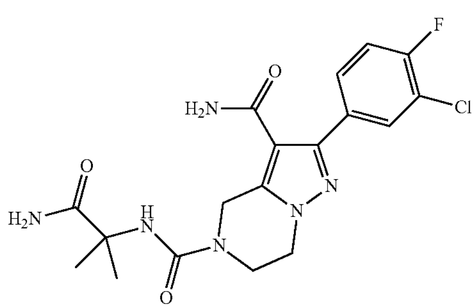 [SMILES: CC(C)(NC(=O)N1CCn2nc(-c3ccc(F)c(Cl)c3)c(C(N)=O)c2C1)C(N)=O] | N5-(1-Amino-2-methyl-1-oxopropan-2-yl)-2-(3-chloro-4-fluorophenyl)-6,7-dihydropyrazolo[1,5-a]pyrazine-3,5(4H)-dicarboxamide | 423 | 6.12<br>6.27 | B<br>C |

Scheme 11

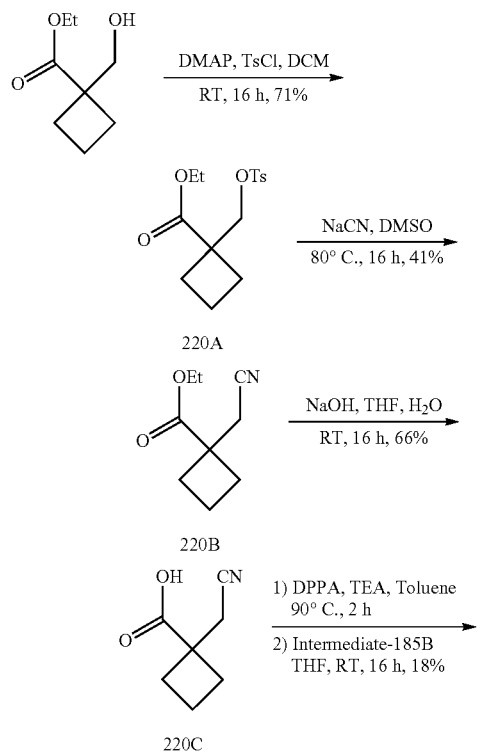

Intermediate 220A: Ethyl
1-((tosyloxy)methyl)cyclobutanecarboxylate

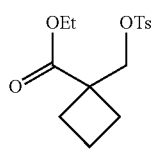 [SMILES: CCOC(=O)C1(COS(=O)(=O)c2ccc(C)cc2)CCC1]

To a stirred ice-cooled solution of ethyl 1-(hydroxymethyl) cyclobutanecarboxylate (0.5 g, 3.16 mmol) in DCM (5 mL) was added DMAP (0.386 g, 3.16 mmol) and p-TSCl (0.603 g, 3.16 mmol) and the reaction mixture was allowed to warm to RT and stir for 16 h. The reaction mixture was diluted with water and extracted with DCM (2×30 mL). The combined organic layer was washed with a 1 N aqueous solution of HCl, brine, and then dried over $Na_2SO_4$, filtered and the filtrate concentrated to afford Intermediate 220A as a pale yellow oil (0.7 g, 71% yield). $^1$H NMR (300 MHz, DMSO-$d_6$) δ ppm 7.81-7.76 (m, 2H), 7.54-7.45 (m, 2H), 4.25 (s, 2H), 4.12-3.95 (m, 5H), 2.31-2.17 (m, 2H), 2.00-1.73 (m, 4H), 1.08 (d, J=14.4 Hz, 3H).

Intermediate 220B: Ethyl
1-(cyanomethyl)cyclobutanecarboxylate

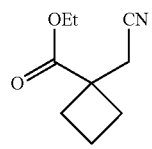 [SMILES: CCOC(=O)C1(CC#N)CCC1]

To a stirred solution of Intermediate 220A (0.5 g, 1.601 mmol) in DMSO (2.5 mL) was added NaCN (0.196 g, 4.00 mmol) and the reaction mixture was stirred at 80° C. for 16 h. The reaction mixture was diluted with water and extracted with diethyl ether (3×30 mL) The combined organic layer was washed with water, dried over $Na_2SO_4$, filtered and the filtrate concentrated to afford Intermediate 220B as a brown oil (0.110 g, 41% yield). $^1$H NMR (400 MHz, DMSO-$d_6$) δ ppm 4.19-4.01 (m, 2H), 3.01-2.97 (m, 2H), 2.45-2.32 (m, 2H), 2.08-1.83 (m, 4H), 1.25-1.18 (m, 3H).

Intermediate 220C:
1-(Cyanomethyl)cyclobutanecarboxylic acid

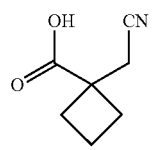

To a stirred solution of Intermediate 220B (0.110 g, 0.658 mmol) in ethanol (3.5 mL), THF (3.5 mL) and water (3 mL) was added NaOH (0.079 g, 1.974 mmol) and the reaction mixture was stirred at RT for 16 h. The reaction mixture was concentrated and the residue was diluted with water (3 mL) and extracted with EtOAc (3×20 mL) The pH of the aqueous layer was adjusted to 3 using a 1.5N aqueous solution of HCl and extracted with EtOAc (3×10 mL). The combined organic layer was washed with water, dried over $Na_2SO_4$, filtered and the filtrate concentrated. The residual mass was then azeotroped with toluene to obtain the Intermediate 220C as a brown oil (0.06 g, 66% yield). ¹H NMR (400 MHz, DMSO-d₆) δ ppm 12.65 (br. s., 1H), 3.04-2.79 (m, 2H), 2.42-2.17 (m, 2H), 2.09-1.67 (m, 4H).

Compound 220: 2-(3-Chloro-4-fluorophenyl)-$N^5$-(1-(cyanomethyl)cyclobutyl)-6,7-dihydro pyrazolo[1,5-a]pyrazine-3,5(4H)-dicarboxamide

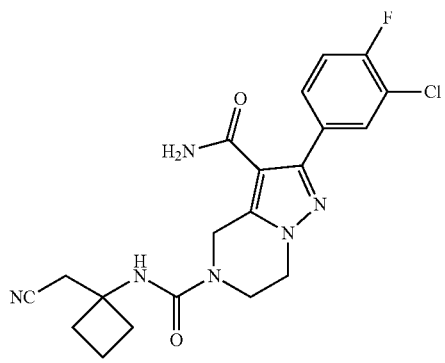 [SMILES: N#CCC1(NC(=O)N2CCn3nc(-c4ccc(F)c(Cl)c4)c(C(N)=O)c3C2)CCC1]

To a stirred solution of Intermediate 220C (0.020 g, 0.145 mmol) in toluene (0.5 mL) was added TEA (0.081 mL, 0.578 mmol), DPPA (0.078 mL, 0.361 mmol) and the reaction mixture was warmed to 90° C. and stirred for 2 h. The reaction mixture was cooled to RT and to it was added a solution of Intermediate 185B (0.040 g, 0.145 mmol) in THF (0.5 mL) and stirred at RT for 16 h. The reaction mixture was quenched with a 10% aqueous solution of NaHCO₃ and extracted with EtOAc (3×10 mL) The combined organic layer was washed with water, dried over Na₂SO₄, filtered and the filtrate concentrated. The crude product was purified by preparative HPLC to afford Compound 220 as a pale yellow solid (20 mg, 32%). HPLC retention times 1.21 min. and 1.21 min. (Method E and L respectively). MS(ES): m/z=431 [M+H]⁺; ¹H NMR (400 MHz, DMSO-d₆) δ ppm 7.85 (dd, J=7.28, 2.26 Hz, 1H), 7.66-7.71 (m, 1H), 7.46 (t, J=9.04 Hz, 1H), 7.34 (br. s., 1H), 7.29 (s, 1H), 7.18 (br. s., 1H), 4.74 (s, 2H), 4.14 (t, J=5.27 Hz, 2H), 3.86 (t, J=5.27 Hz, 2H), 3.11 (s, 2H), 2.17-2.27 (m, 2H), 2.02-2.11 (m, 2H), 1.78-1.91 (m, 2H).

The Compounds shown in Table 10 have been prepared similar to Compound 220 by coupling of coupling of in-situ generated isocyanate of 220C with 185B analogs.

TABLE 10

| Ex. No. | Structure | Name | [M + H]⁺ | Ret Time (min.) | HPLC Methods |
|---|---|---|---|---|---|
| 221 | 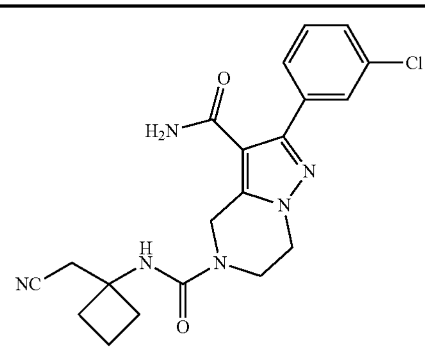 | 2-(3-Chlorophenyl)-$N^5$-(1-(cyanomethyl)cyclobutyl)-6,7-dihydropyrazolo[1,5-a]pyrazine-3,5(4H)-dicarboxamide | 413 | 1.15<br>1.15 | E<br>L |
| 222 | 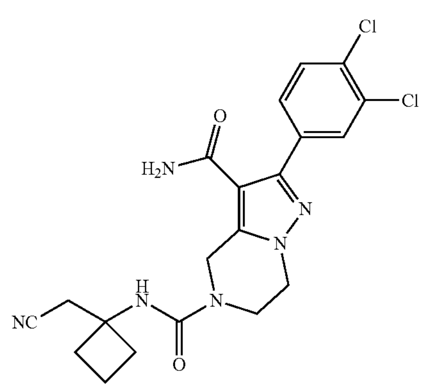 [SMILES: N#CCC1(NC(=O)N2CCn3nc(-c4ccc(Cl)c(Cl)c4)c(C(N)=O)c3C2)CCC1] | $N^5$-(1-(Cyanomethyl)cyclobutyl)-2-(3,4-dichlorophenyl)-6,7-dihydropyrazolo[1,5-a]pyrazine-3,5(4H)-dicarboxamide | 447 | 1.34<br>1.34 | E<br>L |

Scheme 12

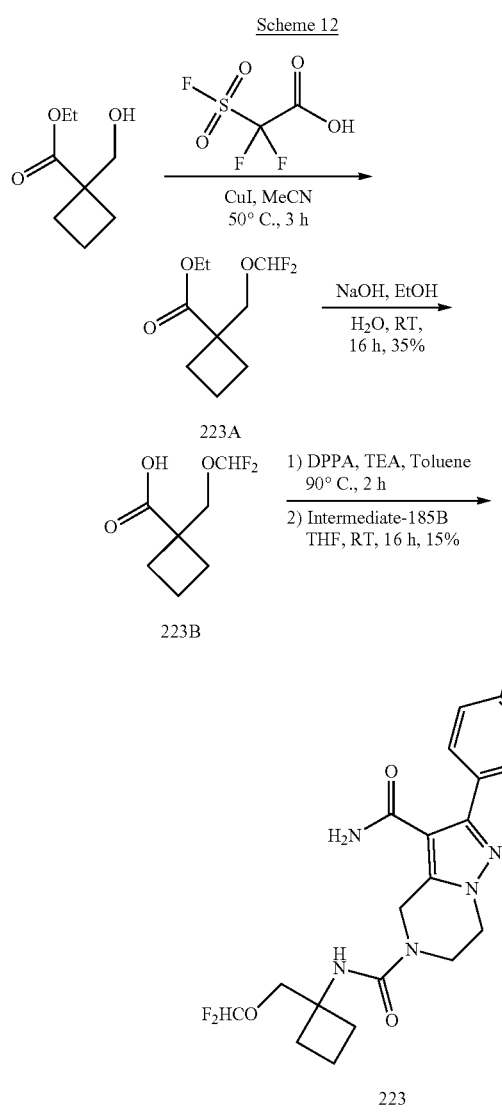

Intermediate 223A: Ethyl 1-((difluoromethoxy)methyl)cyclobutanecarboxylate

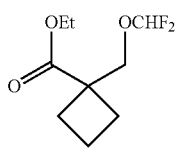 [SMILES: CCOC(=O)C1(COC(F)F)CCC1]

To a stirred solution of ethyl 1-(hydroxymethyl)cyclobutanecarboxylate (0.2 g, 1.264 mmol) in acetonitrile (2 mL) was added CuI (0.120 g, 0.632 mmol) and the reaction mass was heated to 50° C. 2,2-Difluoro-2-(fluorosulfonyl)acetic acid (0.196 mL, 1.896 mmol) added dropwise to the solution and the reaction mixture was stirred at 50° C. for 4 h. The reaction mixture was cooled to RT and extracted with EtOAc (3×15 mL). The combined organic layer was washed with a 10% aqueous solution of NaHCO₃, dried over Na₂SO₄, filtered and the filtrate concentrated to afford Intermediate 223A as a brown oil (0.2 g, 76%). ¹H NMR (300 MHz, DMSO-d₆) δ ppm 6.94-6.39 (m, 1H), 4.16-3.99 (m, 4H), 2.41-2.17 (m, 2H), 2.08-1.73 (m, 4H), 1.26-1.09 (m, 3H).

Intermediate 223B: 1-((Difluoromethoxy)methyl)cyclobutanecarboxylic acid

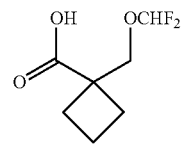

To a stirred solution of Intermediate 223A (0.263 g, 1.263 mmol) in ethanol (3.5 mL), THF (3.5 mL), and water (3 mL) was added NaOH (0.152 g, 3.79 mmol) and the reaction mixture was stirred at RT for 16 h. The reaction mixture was concentrated and the residue dissolved in water and extracted with ethyl acetate (3×15 mL) The aqueous layer was then acidified to pH 2-3 using a 1.5 N aqueous solution of HCl and extracted with EtOAc (3×15 mL). The combined organic layer was washed with water, dried over Na₂SO₄ and concentrated to afford Intermediate 223B as a brown oil (0.08 g, 35% yield). ¹H NMR (400 MHz, DMSO-d₆) δ ppm 12.41 (s, 1H), 6.97-6.40 (m, 1H), 4.15-3.90 (m, 2H), 2.38-2.09 (m, 2H), 2.01-1.51 (m, 4H).

Compound 223: 2-(3-Chloro-4-fluorophenyl)-N⁵-(1-((difluoromethoxy)methyl)cyclobutyl)-6,7-dihydropyrazolo[1,5-a]pyrazine-3,5(4H)-dicarboxamide

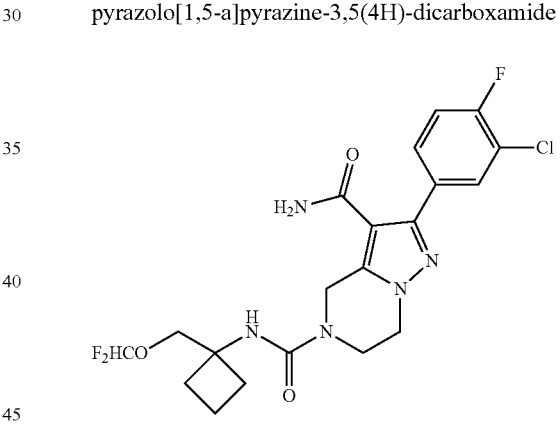

To a stirred solution of Intermediate 223B (0.024 g, 0.136 mmol) in toluene (1 mL) was added TEA (0.076 mL, 0.543 mmol), DPPA (0.074 mL, 0.339 mmol) and the reaction mixture was heated to 90° C. for 2 h. The reaction mixture was cooled to RT and to it was added a solution of Intermediate 185B (0.040 g, 0.136 mmol) in THF (0.5 mL) and stirred for 12 h. The reaction mixture was quenched with a 10% aqueous solution of NaHCO₃ and extracted with EtOAc (3×10 mL) The combined organic layer was washed with water, dried over Na₂SO₄, filtered and the filtrate concentrated. The crude product was purified by preparative HPLC to afford Compound 223 as an off-white solid (10 mg, 15%). HPLC retention times 2.35 min. and 2.35 min (Method E and L respectively). MS(ES): m/z=472 [M+H]⁺; ¹H NMR (400 MHz, DMSO-d₆) δ ppm 7.85 (dd, J=7.28, 2.26 Hz, 1H), 7.66-7.71 (m, 1H), 7.42-7.48 (m, 1H), 7.30-7.37 (m, 7.11-7.22 (m, 1H), 6.99 (s, 1H), 6.47-6.87 (m, 1H), 4.72 (s, 2H), 4.09-4.14 (t, J=5.52 Hz, 2H), 4.04 (s, 2H), 3.84 (t, J=5.52 Hz, 2H), 2.04-2.15 (m, 4H), 1.80 (d, J=9.04 Hz, 2H).

The Compounds shown in Table 11 have been prepared similar to Compound 223 by coupling of in-situ generated isocyanate of 223B with 185B analogs.

TABLE 11

| Ex. No. | Structure | Name | [M + H]+ | Ret Time (min.) | HPLC Methods |
|---|---|---|---|---|---|
| 224 | 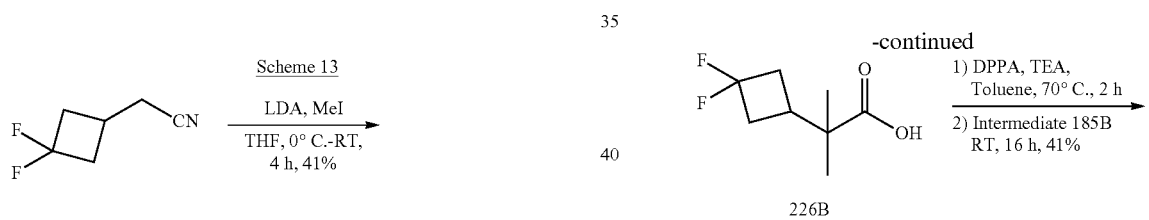 | 2-(3,4-Dichlorophenyl)-N5-(1-((difluoromethoxy)methyl)cyclobutyl)-6,7-dihydropyrazolo[1,5-a]pyrazine-3,5(4H)-dicarboxamide | 488 | 2.48<br>2.50 | L<br>E |
| 225 | 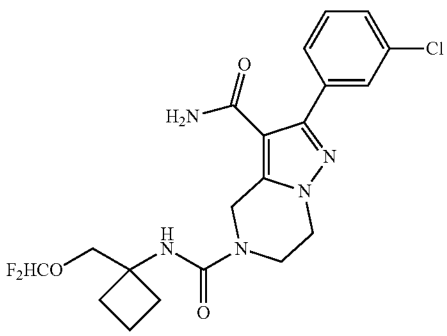 [SMILES: NC(=O)c1c(-c2cccc(Cl)c2)nn2c1CN(C(=O)NC1(COC(F)F)CCC1)CC2] | 2-(3-Chlorophenyl)-N5-(1-((difluoromethoxy)methyl)cyclobutyl)-6,7-dihydropyrazolo[1,5-a]pyrazine-3,5(4H)-dicarboxamide | 454 | 2.30<br>2.30 | L<br>E |

Scheme 13

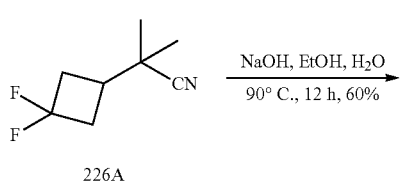

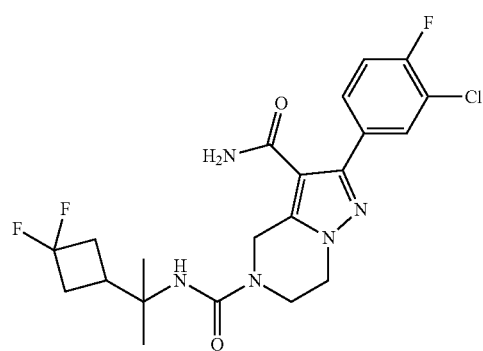

226A

226B

226

1) DPPA, TEA, Toluene, 70° C., 2 h
2) Intermediate 185B RT, 16 h, 41%

LDA, MeI
THF, 0° C.-RT, 4 h, 41%

NaOH, EtOH, H₂O
90° C., 12 h, 60%

Intermediate 226A: 2-(3,3-Difluorocyclobutyl)-2-methylpropanenitrile

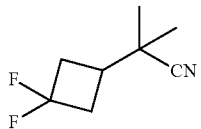

To a solution of 2-(3,3-difluorocyclobutyl)acetonitrile (300 mg, 2.288 mmol) in anhydrous THF (5 mL) was added a solution of LDA (6.86 mL, 6.86 mmol, 1 M in THF) dropwise at 0° C. and stirred at the same temperature for 1 h. MeI (0.715 mL, 11.44 mmol) was added dropwise at 0° C. and the reaction mixture was allowed to warm to RT and stir for 3 h. An aqueous saturated solution of NH$_4$Cl was added and the compound was extracted with EtOAc (3×10 mL) The organic layer was washed with brine, dried over Na$_2$SO$_4$, filtered and the filtrate evaporated in vacuo. The residue was purified by silica gel chromatography (12 g REDISEP® column, eluting with 30% EtOAc in petroleum ether). Fractions containing the product were combined and evaporated to afford the Intermediate 226A as a yellow oil (150 mg, 41%). $^1$H NMR (400 MHz, chloroform-d) δ ppm 2.42-2.76 (m, 4H), 2.14 (td, J=8.66, 3.26 Hz, 1H), 1.317 (s, 6H).

Intermediate 226B: 2-(3,3-Difluorocyclobutyl)-2-methylpropanoic acid

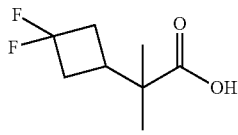

To a solution of Intermediate 226A (150 mg, 0.942 mmol) in ethanol (10 mL) and H$_2$O (10 mL) was added a 10% aqueous solution of NaOH (10 mL, 0.942 mmol) and the reaction mixture was stirred at 90° C. for 12 h. The reaction was then concentrated and the pH of the resultant residue was adjusted to 4 with a 1.5 N aq. solution of HCl and then extracted with EtOAc (3×10 mL). The combined organic layer was dried over Na$_2$SO$_4$, filtered and the filtrate evaporated under reduced pressure to afford Intermediate 226B as a yellow sticky liquid (100 mg, 60%). $^1$H NMR (400 MHz, chloroform-d) δ ppm 12.30 (bs, 1H), 2.40-2.57 (m, 5H), 1.23 (s, 6H).

Compound 226: 2-(3-Chloro-4-fluorophenyl)-N$^5$-(2-(3,3-difluorocyclobutyl)propan-2-yl)-6,7-dihydropyrazolo[1,5-a]pyrazine-3,5(4H)-dicarboxamide

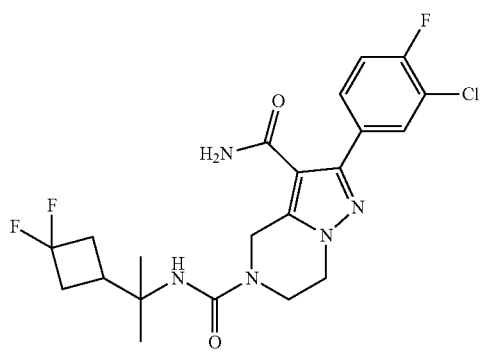 [SMILES: CC(C)(NC(=O)N1CCn2nc(-c3ccc(F)c(Cl)c3)c(C(N)=O)c2C1)C1CC(F)(F)C1]

To a stirred solution of Intermediate 226B (18.14 mg, 0.102 mmol) in toluene (1 mL) at RT under nitrogen was added TEA (0.043 mL, 0.305 mmol), DPPA (0.047 mL, 0.204 mmol) and the mixture was heated at 70° C. for 2 h. The reaction mass was cooled to RT and to it was added a solution of Intermediate 185B (30 mg, 0.102 mmol) in THF (1 mL) and stirred for 16 h. The reaction mass was diluted with EtOAc (5 mL), the organic layer was separated, washed successively with a 10% aqueous solution of NaHCO$_3$, water and brine, then dried over Na$_2$SO$_4$, filtered and the filtrate concentrated under reduced pressure. The crude product was purified by preparative HPLC to afford Compound 226 as a pale yellow solid (20 mg, 41% yield). HPLC retention times are 1.528 min. and 1.525 min. (Methods E and L respectively). MS(ES): m/z=470.2 [M+H]$^+$; $^1$H NMR (400 MHz, DMSO-d$_6$) δ ppm 7.85 (d, J=7.28 Hz, 1H), 7.63-7.71 (m, 1H), 7.47 (d, J=9.29 Hz, 1H), 7.12-7.4 (bs, 2H), 6.21 (s, 1H), 4.68 (s, 2H), 4.12 (s, 2H), 3.79 (s, 2H) 2.65-2.83 (m, 1H), 2.27-2.47 (m, 4H), 1.23 (s, 6H).

The Compounds shown in Table 12 have been prepared similar to Compound 226 by coupling of in-situ generated isocyanate of 226B with 185B analogs.

TABLE 12

| Ex. No. | Structure | Name | [M + H]$^+$ | Ret Time (min.) | HPLC Methods |
|---|---|---|---|---|---|
| 227 | 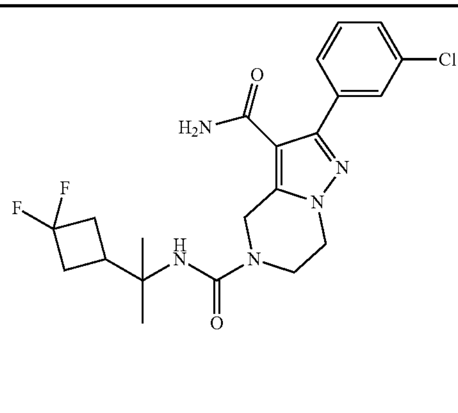 | 2-(3-Chlorophenyl)-N$^5$-(2-(3,3-difluorocyclobutyl)propan-2-yl)-6,7-dihydropyrazolo[1,5-a]pyrazine-3,5(4H)-dicarboxamide | 452.2 | 1.477 | L |

TABLE 12-continued

| Ex. No. | Structure | Name | [M + H]+ | Ret Time (min.) | HPLC Methods |
|---|---|---|---|---|---|
| 228 | 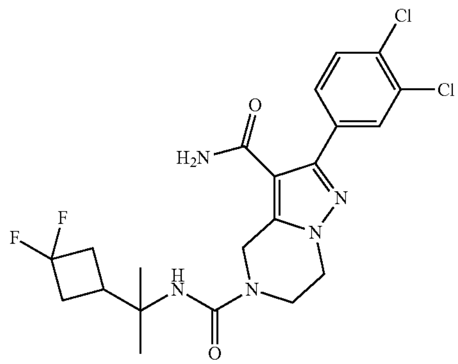 [SMILES: CC(C)(NC(=O)N1CCn2nc(-c3ccc(Cl)c(Cl)c3)c(C(N)=O)c2C1)C1CC(F)(F)C1] | 2-(3,4-Dichlorophenyl)-N5-(2-(3,3-difluorocyclobutyl)propan-2-yl)-6,7-dihydropyrazolo[1,5-a]pyrazine-3,5(4H)-dicarboxamide | 486.2 | 1.652<br>1.597 | E<br>L |

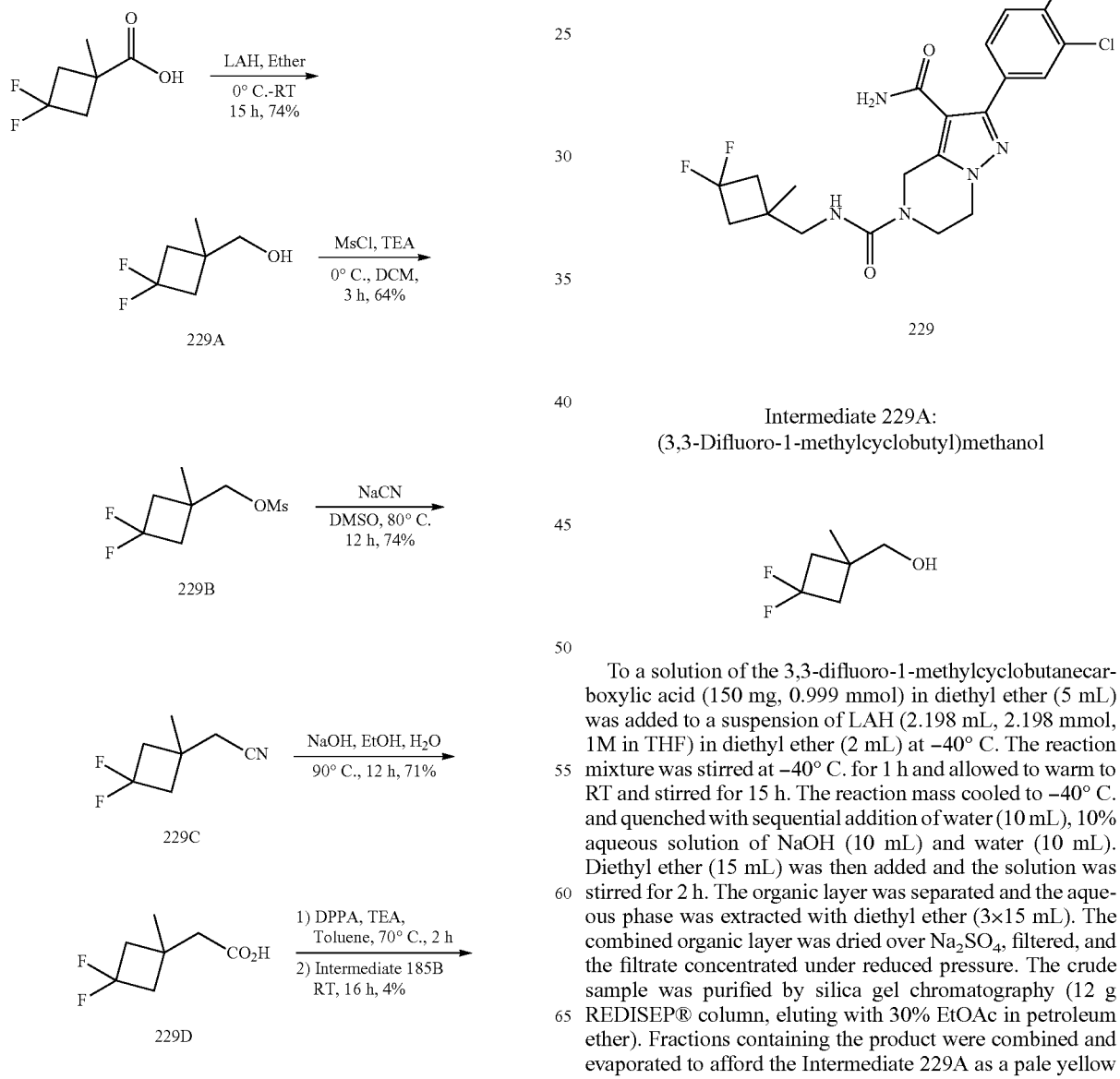

Intermediate 229A: (3,3-Difluoro-1-methylcyclobutyl)methanol

To a solution of the 3,3-difluoro-1-methylcyclobutanecarboxylic acid (150 mg, 0.999 mmol) in diethyl ether (5 mL) was added to a suspension of LAH (2.198 mL, 2.198 mmol, 1M in THF) in diethyl ether (2 mL) at −40° C. The reaction mixture was stirred at −40° C. for 1 h and allowed to warm to RT and stirred for 15 h. The reaction mass cooled to −40° C. and quenched with sequential addition of water (10 mL), 10% aqueous solution of NaOH (10 mL) and water (10 mL). Diethyl ether (15 mL) was then added and the solution was stirred for 2 h. The organic layer was separated and the aqueous phase was extracted with diethyl ether (3×15 mL). The combined organic layer was dried over $Na_2SO_4$, filtered, and the filtrate concentrated under reduced pressure. The crude sample was purified by silica gel chromatography (12 g REDISEP® column, eluting with 30% EtOAc in petroleum ether). Fractions containing the product were combined and evaporated to afford the Intermediate 229A as a pale yellow oil (100 mg, 74%). ¹H NMR (400 MHz, DMSO-d₆) δ ppm 4.92 (t, J=5.52 Hz, 1H) 3.27 (d, J=4.02 Hz, 2H), 2.55-2.45 (m, 2H), 2.07-2.21 (m, 2H), 1.07-1.17 (m, 3H).

Intermediate 229B: (3,3-Difluoro-1-methylcyclobutyl)methyl methanesulfonate

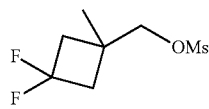

To a solution of Intermediate 229A (100 mg, 0.735 mmol) and TEA (0.102 mL, 0.735 mmol) in DCM was added methanesulfonyl chloride (0.059 mL, 0.735 mmol) dropwise at 5° C. and the reaction mixture was stirred for 3 h. The reaction mass was diluted with DCM, washed with water and brine, dried over Na₂SO₄, filtered and the filtrate evaporated under reduced pressure. The crude product was purified by silica gel chromatography (12 g REDISEP® column, eluting with 30% EtOAc in petroleum ether). Fractions containing the product were combined and evaporated to afford the Intermediate 229B as a yellow oil (100 mg, 63.5%). ¹H NMR (400 MHz, DMSO-d₆) δ ppm 4.27 (s, 2H), 3.01 (s, 3H), 2.55-2.69 (m, 2H), 2.06-2.37 (m, 2H), 1.15 (s, 3H).

Intermediate 229C: 2-(3,3-Difluoro-1-methylcyclobutyl)acetonitrile

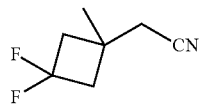

To a solution of Intermediate 229B (200 mg, 0.934 mmol) in DMSO (3 mL) was added NaCN (114 mg, 2.334 mmol) at RT and the reaction mixture was heated to 80° C. and stirred for 12 h. The reaction mixture was cooled to RT, was diluted with water and was extracted with EtOAc (3×10 mL) To the combined organic layer was washed with water and brine, dried over Na₂SO₄, filtered and the filtrate concentrated under reduced pressure. The residue was purified by silica gel chromatography (12 g REDISEP® column, eluting with 30% EtOAc in petroleum ether). Fractions containing the product were combined and evaporated to afford Intermediate 229C as a brown oil (100 mg, 74%). ¹H NMR (400 MHz, DMSO-d₆) δ ppm 2.56-2.42 (m, 6H), 1.17 (s, 3H).

Intermediate 229D: 2-(3,3-Difluoro-1-methylcyclobutyl)acetic acid

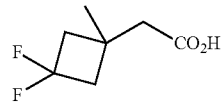

To a solution of Intermediate 229C (100 mg, 0.689 mmol) in ethanol (1 mL) and H₂O (1 mL) was added a 10% aq. solution of NaOH (2 mL, 0.689 mmol) and the reaction mixture was stirred at 90° C. for 12 h. The reaction mixture was concentrated and the pH of the residue was adjusted to 4 with an aqueous solution of 1.5 N HCl, and the compound was extracted with EtOAc (3×10 mL). The combined organic layer was dried on Na₂SO₄, filtered and the filtrate evaporated under reduced pressure to afford Intermediate 229D as a yellow sticky liquid (80 mg, 71%). The crude intermediate was taken as such for further reaction without purification. ¹H NMR (400 MHz, DMSO-d₆) δ ppm 12.14 (brs, 1H), 2.11-2.39 (m, 6H), 1.15 (s, 3H).

Compound 229: 2-(3-Chloro-4-fluorophenyl)-N⁵-((3,3-difluoro-1-methylcyclobutyl)methyl)-6,7-dihydropyrazolo[1,5-a]pyrazine-3,5(4H)-dicarboxamide

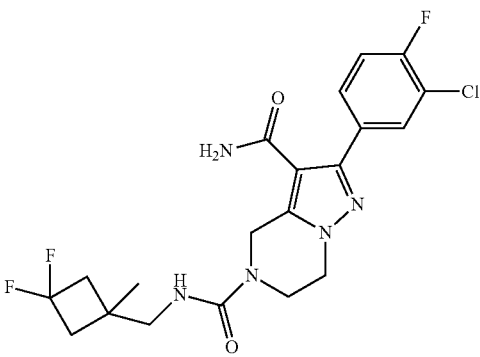 [SMILES: CC1(CNC(=O)N2CCn3nc(-c4ccc(F)c(Cl)c4)c(C(N)=O)c3C2)CC(F)(F)C1]

To a stirred solution of Intermediate 229D (16.71 mg, 0.102 mmol) in toluene (1 mL) at RT under nitrogen was added TEA (0.043 mL, 0.305 mmol), DPPA (0.047 mL, 0.204 mmol) and the reaction mixture was heated at 70° C. for 2 h. The reaction mass was cooled to RT and to it was added a solution of Intermediate 185B (30 mg, 0.102 mmol) in THF (1 mL) and stirred at RT for 16 h. The reaction mass was diluted with ethyl acetate (5 mL), the organic layer was separated, washed successively with an aqueous solution of NaHCO₃, water, brine, then dried over Na₂SO₄, filtered and the filtrate concentrated under reduced pressure. The crude product was purified by preparative HPLC to afford Compound 229 as a pale yellow solid (2 mg, 4%). The HPLC retention times are 1.484 min. and 1.500 min. (Methods E and L respectively); MS(ES): m/z=456.2 [M+H]⁺; ¹H NMR (400 MHz, DMSO-d₆) δ ppm 7.85 (dd, J=7.31, 2.16 Hz, 1H), 7.68 (ddd, J=8.67, 4.78, 2.16 Hz, 1H), 7.42 (m, 1H), 7.36 (bs, 1H), 7.18 (bs, 1H), 7.11 (s, 1H), 4.76 (s, 2H), 4.14 (t, J=5.30 Hz, 2H), 3.86 (t, J=5.33 Hz, 2H), 3.17 (d, J=5.90 Hz, 2H), 2.55-2.70 (m, 2H), 2.17 (d, J=9.79 Hz, 2H), 1.15 (s, 3H).

The Compounds shown in Table 13 have been prepared similar to Compound 229 coupling of in-situ generated isocyanate of 229D with 185B analogs.

TABLE 13

| Ex. No. | Structure | Name | [M + H]+ | Ret Time (min.) | HPLC Methods |
|---|---|---|---|---|---|
| 230 | 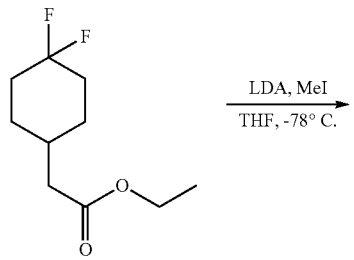 | 2-(3-Chlorophenyl)-N5-((3,3-difluoro-1-methylcyclobutyl)methyl)-6,7-dihydropyrazolo[1,5-a]pyrazine-3,5(4H)-dicarboxamide | 438.2 | 1.432<br>1.458 | E<br>L |
| 231 | 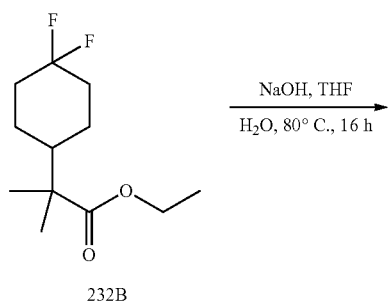 | 2-(3,4-Dichlorophenyl)-N5-((3,3-difluoro-1-methylcyclobutyl)methyl)-6,7-dihydropyrazolo[1,5-a]pyrazine-3,5(4H)-dicarboxamide | 472.2 | 1.600<br>1.621 | E<br>L |

Scheme 15

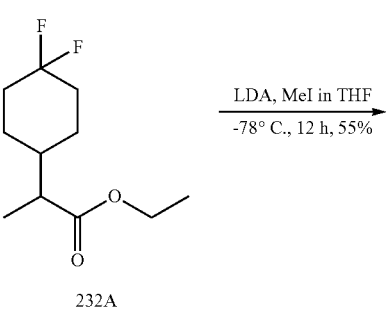

LDA, MeI in THF
-78° C., 12 h, 55%

232A

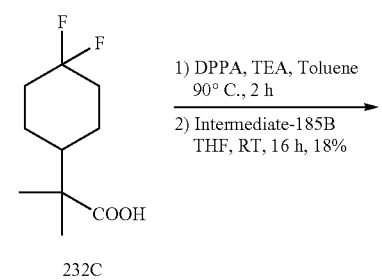

232B

NaOH, THF
H₂O, 80° C., 16 h

-continued

232C

1) DPPA, TEA, Toluene
   90° C., 2 h
2) Intermediate-185B
   THF, RT, 16 h, 18%

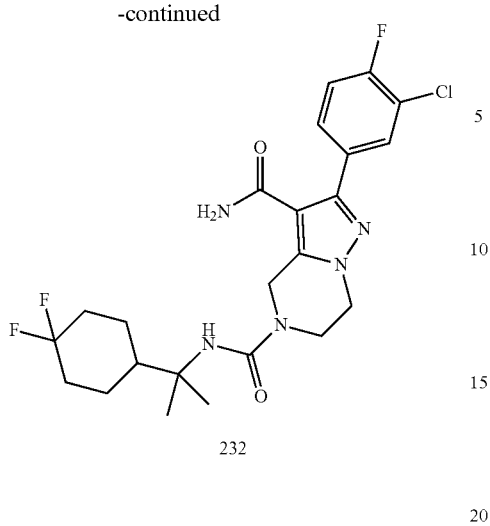

232

Intermediate 232A: Ethyl 2-(4,4-difluorocyclohexyl)propanoate

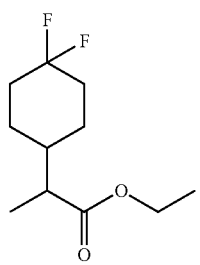

To a solution of ethyl 2-(4,4-difluorocyclohexyl)acetate (0.500 g, 2.424 mmol) in THF (10 mL) was added LDA (2.424 mL, 4.85 mmol, 2M in THF) dropwise at −78° C. and the reaction mixture was stirred at the same temperature for 45 min. MeI (0.606 mL, 9.70 mmol) was then added at −78° C. and the reaction mixture was slowly warmed to RT and stirred for 12 h. The reaction mixture was quenched with a saturated aqueous solution of NH$_4$Cl and extracted with EtOAc (2×25 mL). The combined organic layer was dried over Na$_2$SO$_4$, filtered and the filtrate concentrated. The crude product was purified by silica gel chromatography (12 g REDISEP® column, eluting with 5% EtOAc in hexane). Fractions containing the product were combined and evaporated to afford Intermediate 232A as a pale yellow liquid (0.27 g, 50%). $^1$H NMR (300 MHz, chloroform-d) δ ppm 4.22-4.08 (m, 1H), 2.32 (quin, J=7.1 Hz, 1H), 2.20-2.02 (m, 2H), 1.88-1.76 (m, 2H), 1.75-1.62 (m, 3H), 1.51-1.35 (m, 2H), 1.33-1.23 (m, 4H), 1.20-1.11 (m, 3H).

Intermediate 232B: Ethyl 2-(4,4-difluorocyclohexyl)-2-methylpropanoate

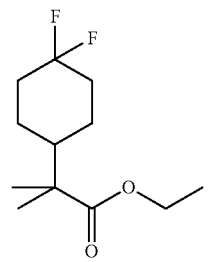 [SMILES: CCOC(=O)C(C)(C)C1CCC(F)(F)CC1]

To a solution of Intermediate 232A (0.27 g, 1.226 mmol) in THF (5 mL) was added LDA (1.226 mL, 2.452 mmol, 2M in THF) dropwise at −78° C. and the resulting solution was stirred at the same temperature for 45 min. MeI (0.307 mL, 4.90 mmol) was then added at −78° C. and the reaction mixture was allowed to warmed to RT and stir for 12 h. The reaction mixture was quenched with a saturated aqueous solution of NH$_4$Cl and extracted with EtOAc (2×25 mL). The combined organic layer was dried over Na$_2$SO$_4$, filtered and the filtrate concentrated. The crude product was purified by silica gel chromatography (12 g REDISEP® column, eluting with 2% EtOAc in hexane.) Fractions containing the product were combined and evaporated to afford Intermediate 232B as a pale yellow liquid. (0.15 g, 55%). $^1$H NMR (300 MHz, DMSO-d$_6$) δ ppm 4.07 (q, J=7.2 Hz, 2H), 2.01 (d, J=12.1 Hz, 2H), 1.92-1.74 (m, 2H), 1.73-1.53 (m, 4H), 1.31-1.20 (m, 2H), 1.11 (br. s., 4H), 1.03 (d, J=2.6 Hz, 6H).

Intermediate 232C: 2-(4,4-Difluorocyclohexyl)-2-methylpropanoic acid

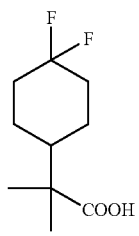

To a solution of Intermediate 232B (0.15 g, 0.640 mmol) in ethanol (2 mL) and water (1 mL) was added NaOH (0.256 g, 6.40 mmol) and the reaction mixture was stirred at 80° C. for 12 h. The reaction mixture was concentrated under reduced pressure and the residue was acidified with an aqueous solution of 1.5N HCl and extracted with EtOAc (2×20 mL) The combined organic layer was dried over Na$_2$SO$_4$, filtered and the filtrate concentrated to afford Intermediate 232C as a yellow solid (90 mg, 68%). $^1$H NMR (300 MHz, DMSO-d$_6$)

δ ppm 12.20 (br. s., 1H), 2.11-1.94 (m, 2H), 1.91-1.55 (m, 5H), 1.34-1.14 (m, 2H), 1.09-0.96 (m, 6H).

Compound 232: 2-(3-Chloro-4-fluorophenyl)-N⁵-(2-(4,4-difluorocyclohexyl)propan-2-yl)-6,7-dihydropyrazolo[1,5-a]pyrazine-3,5(4H)-dicarboxamide

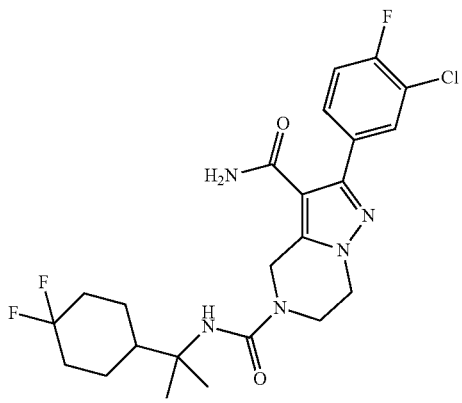 [SMILES: CC(C)(NC(=O)N1CCn2nc(-c3ccc(F)c(Cl)c3)c(C(N)=O)c2C1)C1CCC(F)(F)CC1]

To a solution of Intermediate 232C (56.0 mg, 0.271 mmol) in toluene (2 mL) was added TEA (0.057 mL, 0.407 mmol), DPPA (0.078 mL, 0.339 mmol) and the reaction mixture heated to 80° C. and stirred for 2 h. The reaction mixture was cooled to RT and to it was added a solution of Intermediate 185B (40 mg, 0.136 mmol) in THF (1 mL) and stirred for 12 h. The reaction mixture was diluted with water (15 mL) and extracted with ethyl acetate (2×20 mL) The combined organic layer was washed with brine, dried over $Na_2SO_4$, filtered and the filtrate concentrated. The crude compound was purified by reverse phase preparative HPLC to afford Compound 232 (37 mg, 52%). HPLC retention time 1.70 min. and 1.70 min. (Methods J and K respectively). MS(ES): m/z=498 [M+H]⁺; ¹H NMR (400 MHz, DMSO-d₆) ppm 7.85 (dd, J=7.3, 2.3 Hz, 1H), 7.73-7.65 (m, 1H), 7.50-7.43 (m, 1H), 7.35 (br. s., 1H), 7.20 (br. s., 1H), 6.21 (s, 1H), 4.69 (s, 2H), 4.12 (t, J=5.0 Hz, 2H), 3.80 (t, J=5.3 Hz, 2H), 2.20 (t, J=12.0 Hz, 1H), 2.08-1.95 (m, 2H), 1.81-1.58 (m, 4H), 1.30-1.13 (m, 8H).

The Compounds shown in Table 14 have been prepared similar to Compound 232 coupling of in-situ generated isocyanate of 232C with 185B analogs.

TABLE 14

| Ex. No. | Structure | Name | [M + H]⁺ | Ret Time (min.) | HPLC Methods |
|---|---|---|---|---|---|
| 233 | 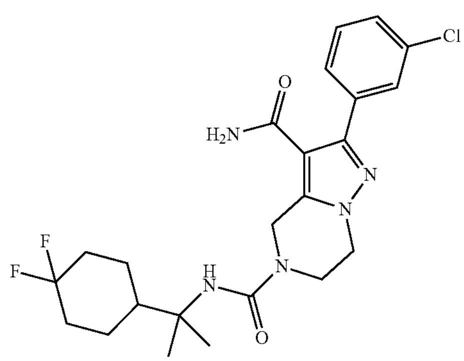 [SMILES: CC(C)(NC(=O)N1CCn2nc(-c3cccc(Cl)c3)c(C(N)=O)c2C1)C1CCC(F)(F)CC1] | 2-(3-Chlorophenyl)-N⁵-(2-(4,4-difluorocyclohexyl)propan-2-yl)-6,7-dihydropyrazolo[1,5-a]pyrazine-3,5(4H)-dicarboxamide | 480.2 | 9.125<br>10.088 | B<br>M |
| 234 | 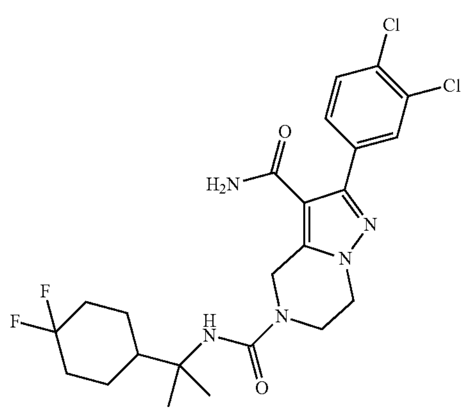 [SMILES: CC(C)(NC(=O)N1CCn2nc(-c3ccc(Cl)c(Cl)c3)c(C(N)=O)c2C1)C1CCC(F)(F)CC1] | 2-(3,4-Dichlorophenyl)-N⁵-(2-(4,4-difluorocyclohexyl)propan-2-yl)-6,7-dihydropyrazolo[1,5-a]pyrazine-3,5(4H)-dicarboxamide | 514.3 | 1.817<br>1.817 | E<br>L |

Scheme 16

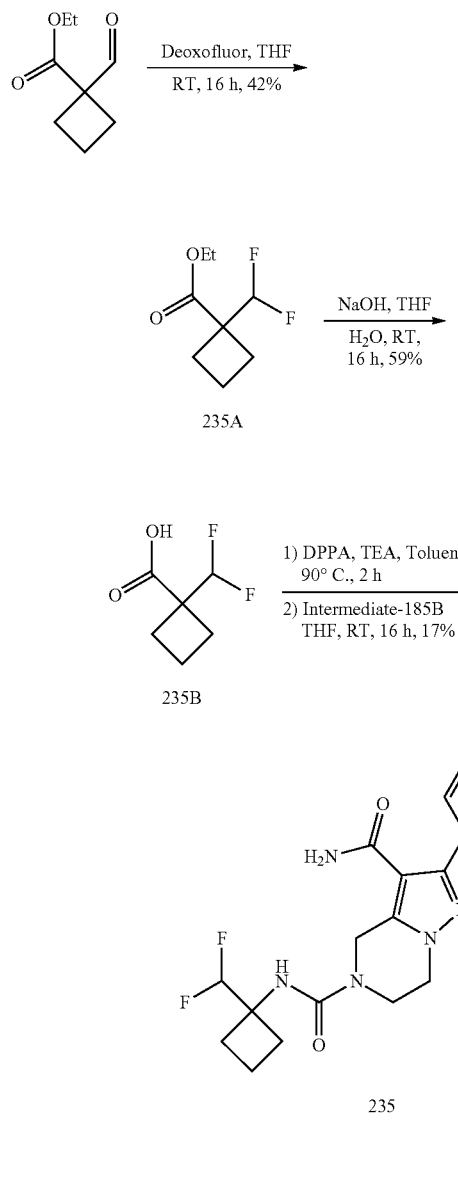

Intermediate 235A: Ethyl 1-(difluoromethyl)cyclobutanecarboxylate

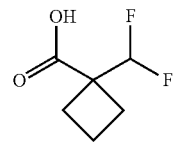

To a solution of ethyl 1-formylcyclobutanecarboxylate (0.5 g, 3.20 mmol) was added DEOXO-FLUOR® (50% in THF) (2.36 mL, 6.40 mmol) and the solution was allowed to stir at RT for 16 h. The reaction mixture was cooled to 0° C. and quenched with a 10% aqueous solution of NaHCO$_3$ and extracted with ethyl acetate (3×25 mL) The combined organic layer was washed with water, dried over Na$_2$SO$_4$, filtered and the filtrate concentrated to afford crude Intermediate 235A as brown oil (0.24 g, 42% yield). The crude product was subjected to saponification conditions without further purification.

Intermediate 235B: 1-(Difluoromethyl)cyclobutanecarboxylic acid

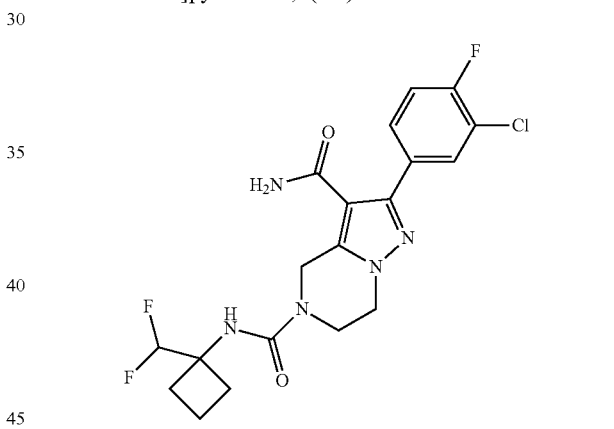

To a stirred solution of Intermediate 235A (0.24 g, 1.347 mmol) in ethanol (3.5 mL), THF (3.5 mL) was added NaOH (0.162 g, 4.04 mmol) in water (3 mL) and the reaction mixture was stirred at RT for 16 h. The reaction mixture was concentrated and the residue was diluted with water (3 mL) and extracted with ethyl acetate. The aqueous layer was then acidified to pH 3-4 using an aqueous solution of 1.5 N HCl and extracted with ethyl acetate (3×25 mL) The combined organic layer was washed with water, dried over Na$_2$SO$_4$, filtered and the filtrate concentrated. The residual mass was then azeotroped with toluene to afford Intermediate 235B as a brown solid (0.12 g, 59% yield). $^1$H NMR (400 MHz, DMSO-d$_6$) δ ppm 13.33 (s, 1H), 6.55-5.94 (m, 1H), 3.28-3.03 (m, 2H), 2.41-2.10 (m, 2H), 2.00-1.68 (m, 2H).

Compound 235: 2-(3-Chloro-4-fluorophenyl)-N$^5$-(1-(difluoromethyl)cyclobutyl)-6,7-dihydro pyrazolo[1,5-a]pyrazine-3,5(4H)-dicarboxamide To a stirred solution of Intermediate 235B (0.082 g, 0.543 mmol) in toluene (0.5 mL) was added TEA (0.076 mL, 0.543 mmol) and DPPA (0.074 mL, 0.339 mmol) and the reaction mass was warmed to 90° C. for 2 h. The reaction mixture was cooled to RT and to it was added a solution of Intermediate 185B (0.04 g, 0.136 mmol) in THF (0.5 mL) and stirred for 12 h. The reaction mixture was quenched with an aqueous solution of 10% NaHCO$_3$ and extracted with ethyl acetate (3×10 mL) The combined organic layer was washed with water, dried over Na$_2$SO$_4$, filtered and the filtrate concentrated. The crude product was purified by preparative HPLC to afford Compound 235 as pale yellow solid (10 mg, 17% yield). HPLC retention times 1.40 and 1.41 min (Method E and L respectively). MS(ES): m/z=442 [M+H]$^+$; $^1$H NMR (400 MHz, DMSO-d$_6$) δ ppm 7.85 (dd, J=7.28, 2.26 Hz, 1H), 7.68 (ddd, J=8.53, 4.77, 2.26 Hz, 1H), 7.43-7.49 (m, 1H), 7.35 (br. s., 1H), 7.30 (s, 1H), 7.20 (br. s., 1H), 6.04-6.34 (m, 1H), 4.75 (s, 2H), 4.14 (t, J=5.27 Hz, 2H), 3.86 (t, J=5.52 Hz, 2H), 2.28-2.35 (m, 3H), 2.09-2.19 (m, 2H), 1.71-1.97 (m, 2H).

The Compounds shown in Table 15 have been prepared similar to Compound 235 coupling of in-situ generated isocyanate of 235B with 185B analogs.

TABLE 15
| Ex. No. | Structure | Name | [M + H]+ | Ret Time (min.) | HPLC Methods |
|---|---|---|---|---|---|
| 236 | 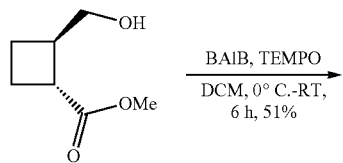 | 2-(3-Chlorophenyl)-N5-(1-(difluoromethyl)cyclobutyl)-6,7-dihydropyrazolo[1,5-a]pyrazine-3,5(4H)-dicarboxamide | 424 | 1.43<br>1.41 | E<br>L |
| 237 | 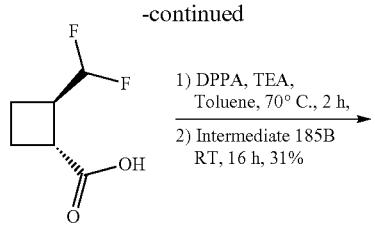 | 2-(3,4-Dichlorophenyl)-N5-(1-(difluoromethyl)cyclobutyl)-6,7-dihydropyrazolo[1,5-a]pyrazine-3,5(4H)-dicarboxamide | 458 | 1.54<br>1.54 | E<br>L |
Scheme 17
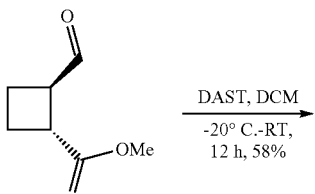
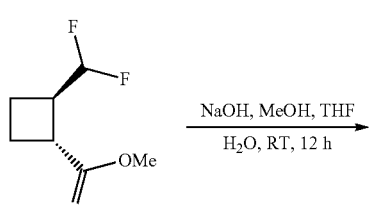
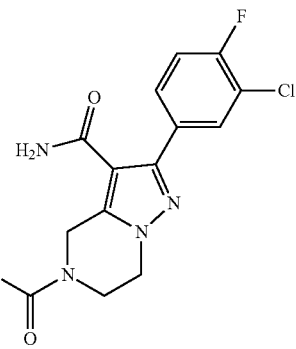
238

Intermediate 238A: (1R,2R)-Methyl 2-formylcyclobutanecarboxylate

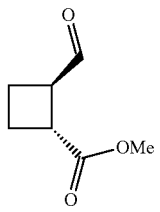

To a stirred solution of (1S,2R)-methyl 2-(hydroxymethyl)cyclobutanecarboxylate (100 mg, 0.694 mmol) in DCM (5 mL) was added bis(acetoxy)iodobenzene (335 mg, 1.040 mmol) and TEMPO (10.84 mg, 0.069 mmol) at 0° C. The temperature of the reaction was allowed to slowly warm to RT and stirred for 6 h. Water was added to reaction mass and the compound was extracted with DCM (3×10 mL). The combined organic layer was dried over $Na_2SO_4$, filtered and the filtrate evaporated. The crude product was purified by silica gel chromatography (12 g REDISEP® column, eluting with 40% EtOAc in petroleum ether). Fractions containing the product were combined and evaporated to afford Intermediate 238A as yellow oil (50 mg, 51% yield). $^1$H NMR (400 MHz, DMSO-$d_6$) δ ppm 9.62 (s, 1H) 3.71 (s, 3H), 3.69-3.36 (m, 2H), 2.31-2.16 (m, 4H).

Intermediate 238B: (1R,2R)-Methyl 2-(difluoromethyl)cyclobutanecarboxylate

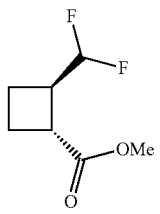 [SMILES: COC(=O)[C@@H]1CC[C@H]1C(F)F]

To a solution of Intermediate 238A (300 mg, 2.110 mmol) in DCM (3 mL) was added DAST (0.697 mL, 5.28 mmol) at −20° C. The reaction mixture was slowly warmed to RT and stirred for 12 h. The reaction mixture was quenched with a 10% aqueous solution of $NaHCO_3$ and extracted with DCM (3×10 mL). The combined organic layer was dried over $Na_2SO_4$, filtered and the filtrate evaporated under reduced pressure. The crude product was purified by silica gel chromatography (12 g REDISEP® column, eluting with 10% EtOAc in petroleum ether). Fractions containing the product were combined and evaporated to afford Intermediate 238B as a yellow oil (200 mg, 58% yield). $^1$H NMR (400 MHz, chloroform-d) δ ppm 5.87-6.21 (m, 1H), 3.70 (s, 3H), 2.86-3.27 (m, 2H), 1.82-2.32 (m, 4H).

Intermediate 238C: (1R,2R)-2-(Difluoromethyl)cyclobutanecarboxylic acid

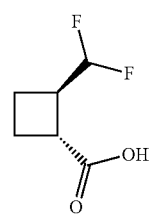

To a solution of Intermediate 238B (200 mg, 1.218 mmol) in THF (1 mL), MeOH (0.3 mL) and water (1 mL) was added NaOH (97 mg, 2.437 mmol) and the resulting solution was stirred at RT for 12 h. The volatiles were removed under reduced pressure and the residue was added water and extracted with ethyl acetate. The pH of the aqueous layer was adjusted to 4 using an aqueous solution of 1.5 N HCl and the compounds were extracted with EtOAc (3×10 mL). The combined organic layer was dried on $Na_2SO_4$, filtered and filtrate evaporated under reduced pressure to afford Intermediate 238C as a viscous liquid (120 mg, 65.6% yield). The crude product was taken further without any purification. $^1$H NMR (400 MHz, DMSO-$d_6$) δ ppm 12.24 (bs, 1H), 5.87-6.21 (m, 1H), 3.03 (q, J=8.85 Hz, 1H), 2.89 (dd, J=8.82, 4.05 Hz, 1H) 1.94-2.14 (m, 2H) 1.79-1.94 (m, 2H).

Compound 238: 2-(3-Chloro-4-fluorophenyl)-$N^5$-((1R,2S)-2-(difluoromethyl)cyclobutyl)-6,7-dihydropyrazolo[1,5-a]pyrazine-3,5(4H)-dicarboxamide

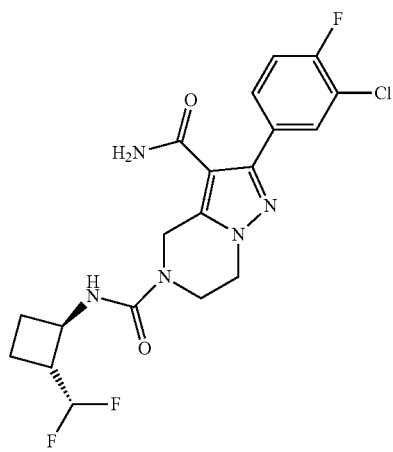

A stirred solution of Intermediate 238C (15.28 mg, 0.102 mmol) in toluene (1 mL) was added TEA (0.043 mL, 0.305 mmol), DPPA (0.047 mL, 0.204 mmol) and the reaction mixture was heated to 70° C. for 2 h. The reaction mixture was cooled to RT and to it was added a solution of Intermediate 185B (30 mg, 0.102 mmol) in THF (1 mL) and stirred at RT for 16 h. The reaction mixture was diluted with EtOAc (5 mL), the organic layer was separated, washed with a 10% aqueous solution of $NaHCO_3$, water, dried over $Na_2SO_4$, filtered and the filtrate concentrated under reduced pressure. The crude sample was purified by preparative HPLC to afford Intermediate 238 as a pale yellow solid (14 mg, 31% yield). The HPLC retention times are 1.314 min. and 1.302 min. (Methods E and L respectively); MS(ES): m/z=442.2 $[M+H]^+$; $^1$H NMR (400 MHz, DMSO-$d_6$) δ 7.85 (dd, J=2.2, 7.3 Hz, 1H), 7.69 (ddd, J=2.2, 4.8, 8.7 Hz, 1H), 7.47 (dd, J=8.8, 9.3 Hz, 1H), 7.40-7.32 (m, 1H), 7.22 (d, J=7.4 Hz, 2H), 6.29-5.89 (m, 1H), 4.73 (s, 2H), 4.19-4.05 (m, 3H), 3.89-3.69 (m, 2H), 2.75 (dd, J=8.7, 12.1 Hz, 1H), 2.15-2.01 (m, 1H), 1.94 (t, J=9.9 Hz, 1H), 1.80-1.55 (m, 2H).

The Compounds shown in Table 16 have been prepared similar to Compound 238 coupling of in-situ generated isocyanate of 238C with 185B analogs.

TABLE 16
| Ex. No. | Structure | Name | [M + H]+ | Ret Time (min.) | HPLC Methods |
|---|---|---|---|---|---|
| 239 | 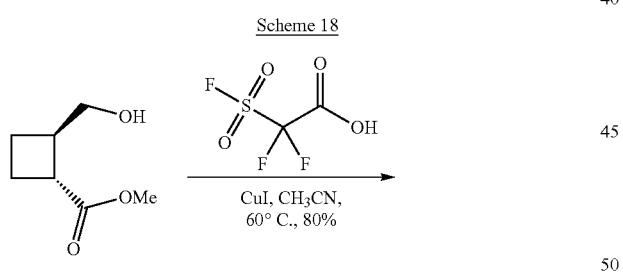 | 2-(3-Chlorophenyl)-N5-((1R,2S)-2-(difluoromethyl)cyclobutyl)-6,7-dihydropyrazolo[1,5-a]pyrazine-3,5(4H)-dicarboxamide | 424.2 | 1.257<br>1.245 | E<br>L |
| 240 | 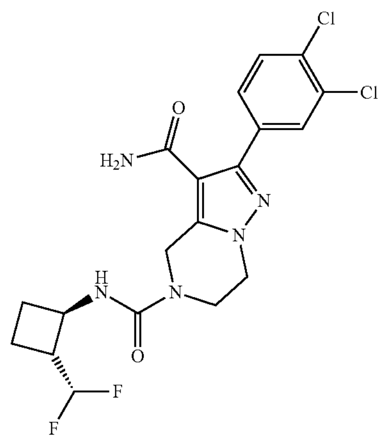 | 2-(3,4-Dichlorophenyl)-N5-((1R,2S)-2-(difluoromethyl)cyclobutyl)-6,7-dihydropyrazolo[1,5-a]pyrazine-3,5(4H)-dicarboxamide | 458.2 | 1.442<br>1.433 | E<br>L |
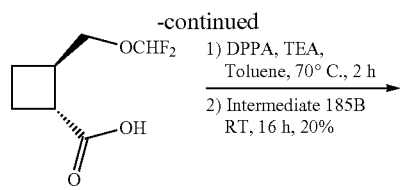
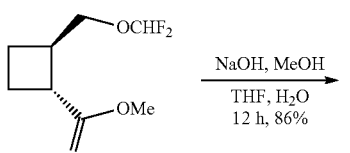
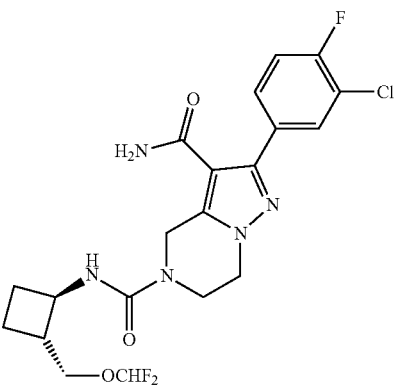

Intermediate 241A: (1R,2R)-Methyl 2-((difluoromethoxy)methyl)cyclobutanecarboxylate

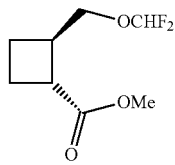

To a solution of (1R,2R)-methyl 2-(hydroxymethyl)cyclobutanecarboxylate (100 mg, 0.694 mmol) in acetonitrile (5 mL) was added CuI(I) (66.1 mg, 0.347 mmol) and the reaction mixture was heated to 60° C. To the stirred solution was added 2,2-difluoro-2-(fluorosulphonyl)acetic acid (124 mg, 0.694 mmol) and the reaction mixture was stirred for an additional 12 h at 60° C. The reaction mixture was cooled to 0° C., a saturated aqueous solution of NaHCO$_3$ was added and extracted with ethyl acetate (3×10 mL) The combined organic layer was dried over Na$_2$SO$_4$, filtered and the filtrate evaporated under reduced pressure to afford Intermediate 241A as a yellow oil (100 mg, 80%). The crude product was used in the next step without further purification. $^1$H NMR (300 MHz, chloroform-d) δ ppm 5.92-6.56 (m, 1H), 3.86 (d, J=5.29 Hz, 2H), 3.70 (s, 3H), 3.01 (d, J=8.88 Hz, 2H), 2.18 (d, J=10.15 Hz, 2H), 1.68-2.02 (m, 2H).

Intermediate 241B: (1R,2R)-2-((Difluoromethoxy)methyl)cyclobutanecarboxylic acid

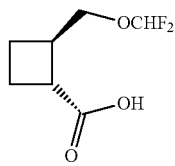

To a solution of Intermediate 241A (100 mg, 0.515 mmol) in a 1:0.3:1THF:MeOH:water was added NaOH (41.2 mg, 1.030 mmol) and the resulting solution was stirred at RT for 12 h. The volatiles were removed under reduced pressure and the aqueous layer was washed with ethyl acetate. The pH of the aqueous layer was adjusted to 4 by adding an aqueous solution of 1.5 N HCl and extracted with ethyl acetate (3×10 mL) The combined organic layer was dried over Na$_2$SO$_4$ and evaporated under vacuum to afford Intermediate 241B as yellow sticky liquid (80 mg, 86%). $^1$H NMR (300 MHz, DMSO-d$_6$) δ ppm 12.10 (s, 1H), 6.35-6.95 (m, 1H), 3.74-3.89 (m, 2H), 2.85 (q, J=8.70 Hz, 1H) 2.63-2.77 (m, 1H) 1.95-2.10 (m, 4H).

Compound 241: 2-(3-Chloro-4-fluorophenyl)-N$^5$-((1R,2R)-2-((difluoromethoxy)methyl)cyclobutyl)-6,7-dihydropyrazolo[1,5-a]pyrazine-3,5(4H)-dicarboxamide

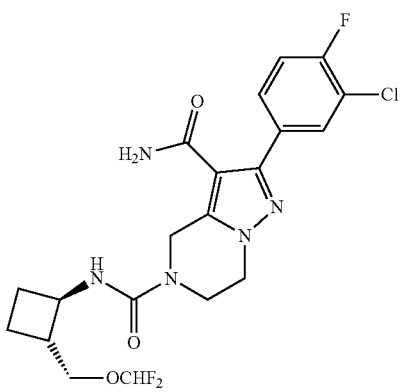

A stirred solution of Intermediate 241B (18.34 mg, 0.102 mmol) in toluene (1 mL) at RT under nitrogen was added TEA (0.043 mL, 0.305 mmol), DPPA (0.047 mL, 0.204 mmol) and the reaction mixture was heated at 70° C. for 2 h. The reaction mass was cooled to RT and to it was added a solution of Intermediate 185B (30 mg, 0.102 mmol) in THF (1 mL) and stirred for 16 h. The reaction mass was diluted with ethyl acetate (5 mL) and the organic layer was separated. The organic layer was washed sequentially with an aqueous solution of 10% NaHCO$_3$, water, and brine, then dried over Na$_2$SO$_4$, filtered and the filtrate concentrated under reduced pressure. The crude product was purified by preparative HPLC to afford Compound 241 as pale yellow solid (10 mg, 20% yield). The HPLC Retention times are 1.453 min. and 1.467 min. (Methods J and K respectively); MS(ES): m/z=472.2[M+H]$^+$; $^1$H NMR (400 MHz, DMSO-d$_6$) δ ppm 7.85 (dd, J=7.28, 2.13 Hz, 1H), 7.69 (ddd, J=8.63, 4.80, 2.13 Hz, 1H), 7.39-7.52 (m, 1H), 7.11-7.33 (2bs, 2H), 7.10 (d, J=7.34 Hz, 1H), 6.36-6.88 (m, 1H), 4.73 (s, 2H), 4.13 (t, J=5.27 Hz, 2H), 3.72-3.99 (m, 5H), 2.00-2.16 (m, 1H), 1.68-1.94 (m, 2H), 1.33-1.53 (m, 1H).

The Compounds shown in Table 17 have been prepared similar to Compound 241 coupling of in-situ generated isocyanate of 241B with 185B analogs.

TABLE 17
| Ex. No. | Structure | Name | [M + H]+ | Ret Time (min.) | HPLC Methods |
|---|---|---|---|---|---|
| 242 | 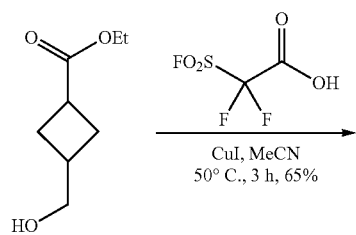 | 2-(3-Chlorophenyl)-N5-((1R,2R)-2-((difluoromethoxy)methyl)cyclobutyl)-6,7-dihydropyrazolo[1,5-a]pyrazine-3,5(4H)-dicarboxamide | 454.2 | 1.405 1.420 | E L |
| 243 | 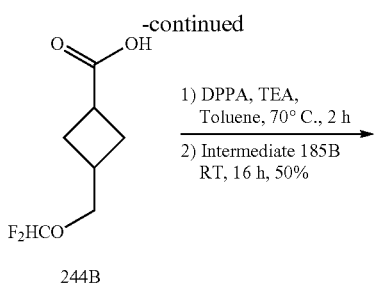 | 2-(3,4-Dichlorophenyl)-N5-((1R,2R)-2-((difluoromethoxy)methyl)cyclobutyl)-6,7-dihydropyrazolo[1,5-a]pyrazine-3,5(4H)-dicarboxamide | 488.2 | 1.565 1.576 | E L |
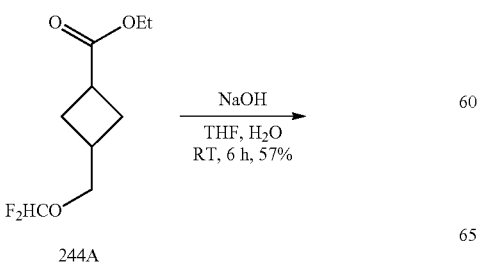
Scheme 19
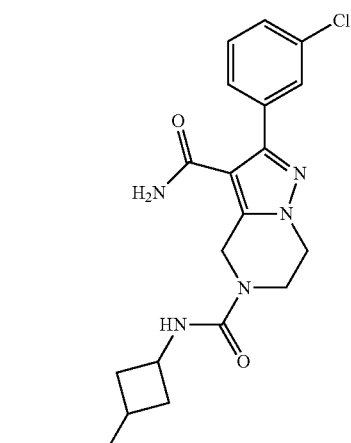
244 and 245

Intermediate 244A: Ethyl 3-((difluoromethoxy)methyl)cyclobutanecarboxylate

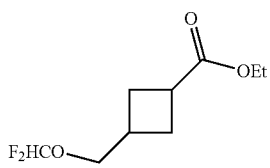 [SMILES: CCOC(=O)C1CC(COC(F)F)C1]

To a solution of CuI (0.120 g, 0.632 mmol) and ethyl 3-(hydroxymethyl)cyclobutanecarboxylate (0.2 g, 1.264 mmol) in MeCN (5 mL) was added 2,2-difluoro-2-(fluorosulfonyl)acetic acid (0.195 mL, 1.896 mmol) dropwise warmed at 50° C. and the reaction mixture was stirred for 3 h. The reaction mixture was filtered through a Buchner funnel and the filtrate was concentrated. The crude product was purified by silica gel chromatography (40 g REDISEP® column, eluting with 2% EtOAc in hexane). Fractions containing the product were combined and evaporated to afford cis and trans mixture of Intermediate 244A as a colorless oil (0.3 g, 55%). $^1$H NMR (300 MHz, chloroform-d) δ ppm 5.93-6.50 (m, 1H), 4.07-4.24 (m, 2H), 3.59-3.76 (m, 2H), 2.95-3.19 (m, 1H), 2.47-2.58 (m, 1H), 2.21-2.43 (m, 2H), 1.98-2.16 (m, 2H), 1.19-1.35 (m, 3H).

Intermediate 244B: 34-(Difluoromethoxy)methyl)cyclobutanecarboxylic acid

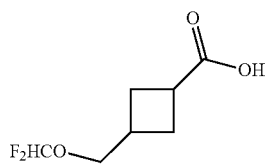 [SMILES: O=C(O)C1CC(COC(F)F)C1]

The a solution of Intermediate 244A (0.3 g, 1.441 mmol) in THF (5 mL) was added NaOH (0.144 g, 3.60 mmol) in water (2 mL) and the resulting solution was stirred at RT for 16 h. The volatiles were removed under a reduced pressure and pH was adjusted to 3 with an aqueous solution of 1.0 N HCl and extracted with ethyl acetate (3×10 mL) The combined organic layer was washed with water, brine, dried over Na$_2$SO$_4$, filtered and the filtrate concentrated to afford Intermediate 244B as a yellow liquid (0.15 g, 57%, cis and trans mixture). The crude product was reacted to the next step without further purification. $^1$H NMR (400 MHz, DMSO-d$_6$) δ ppm 12.01 (br. s., 1H), 6.41-6.90 (m, 1H), 3.35-3.46 (m, 2H), 2.88-3.11 (m, 1H), 2.06-2.34 (m, 3H), 1.83-2.04 (m, 2H).

Compounds 244 and 245: 2-(3-Chlorophenyl)-N$^5$-(3-((difluoromethoxy)methyl)cyclobutyl)-6,7-dihydropyrazolo[1,5-a]pyrazine-3,5(4H)-dicarboxamide

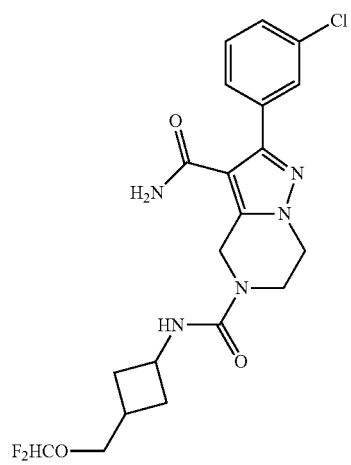 [SMILES: NC(=O)c1c(-c2cccc(Cl)c2)nn2c1CN(C(=O)NC1CC(COC(F)F)C1)CC2]

A solution of Intermediate 244B (52.1 mg, 0.289 mmol), TEA (0.081 mL, 0.578 mmol), DPPA (0.062 mL, 0.289 mmol) in toluene (5 mL) was heated to 90° C. and stirred for 2 h. The reaction mixture was cooled to RT and in to it was added a solution of Intermediate 156E (60 mg, 0.193 mmol) in THF (1 mL) and stirred at RT for 4 h. The reaction mixture was quenched with water and the aq. layer was extracted with EtOAc (3×5 mL) The combined organic layer was washed with an aqueous solution of 10% NaHCO$_3$, water, then dried over Na$_2$SO$_4$, filtered and the filtrate concentrated to afford crude product. The crude reaction mixture was purified by preparative TLC. The crude material was loaded on a 0.5 mm silica gel plate which was developed using 6% MeOH in CHCl$_3$. Band containing the desired product was separated and extracted into 10% MeOH in DCM, and was then filtered and concentrated to afford mixture of Compounds 244 and 245 as an off-white solid. Individual isomers were separated using preparative SFC.

Compound 244: Retention time 4.22 min (HPLC Method Q); MS(ES): m/z=454 [M+H]$^+$; Yield=8 mg, 25%; $^1$H NMR (400 MHz, DMSO-d$_6$) δ ppm 7.69-7.71 (m, 1H), 7.63 (dt, J=6.65, 1.95 Hz, 1H), 7.39-7.46 (m, 2H), 7.34 (br. s., 1H), 7.16 (br. s., 1H), 7.02 (d, J=7.53 Hz, 1H), 6.44-6.85 (m, 1H), 4.71 (s, 2H), 4.13 (s, 2H), 4.05 (d, J=7.53 Hz, 1H), 3.82 (s, 2H), 3.78 (d, J=6.02 Hz, 2H), 2.13-2.31 (m, 3H), 1.68-1.78 (m, 2H).

Compound 245: Retention time 4.88 min (HPLC Method Q); MS(ES): m/z=454 [M+H]$^+$; Yield=8 mg, 25%; $^1$H NMR (400 MHz, DMSO-d$_6$) δ ppm 7.70 (t, J=1.51 Hz, 1H), 7.61-7.66 (m, 1H), 7.39-7.47 (m, 2H), 7.34 (br. s., 1H), 7.17 (br. s., 1H), 7.11 (s, 1H), 6.48-6.88 (m, 1H), 4.72 (s, 2H), 4.18-4.27 (m, 1H), 4.13 (t, J=5.27 Hz, 2H), 3.88 (d, J=7.53 Hz, 2H), 3.83 (t, J=5.27 Hz, 2H), 2.36-2.46 (m, 1H), 1.99-2.17 (m, 4H).

Scheme 20

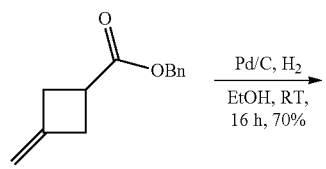

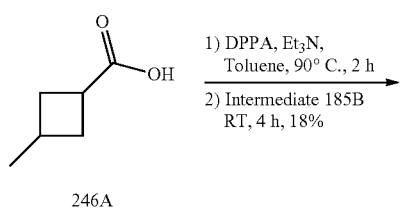

246A

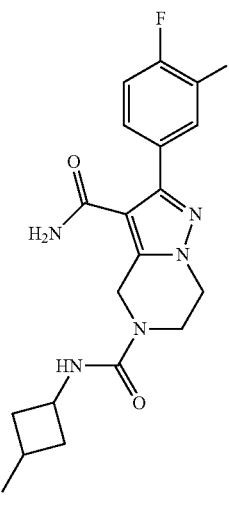

246 and 247

Intermediate 246A: 3-Methylcyclobutanecarboxylic acid

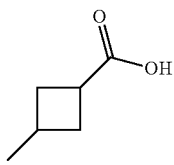

A solution of benzyl 3-methylenecyclobutanecarboxylate (1.0 g, 4.94 mmol) and 10% Pd/C (0.526 g, 0.494 mmol) in ethanol (5 mL) was stirred under a atmosphere of hydrogen (1 bar) for 3 h. The reaction mixture was filtered through a Buchner funnel and the filtrate was evaporated under reduced pressure to afford Intermediate 246A as a mixture of cis and trans isomers (0.4 g, 70%, colorless liquid). This was used to the next step without further purification. $^1$H NMR (300 MHz, DMSO-$d_6$) δ ppm 2.70-3.05 (m, 1H), 2.13-2.45 (m, 3H), 1.61-1.84 (m, 2H), 1.08 (dd, J=6.99, 3.59 Hz, 1.6H) 0.93-1.02 (m, 1.4 H).

Compounds 246 and 247: 2-(3-Chloro-4-fluorophenyl)-$N^5$-(3-methylcyclobutyl)-6,7-dihydropyrazolo[1,5-a]pyrazine-3,5(4H)-dicarboxamide

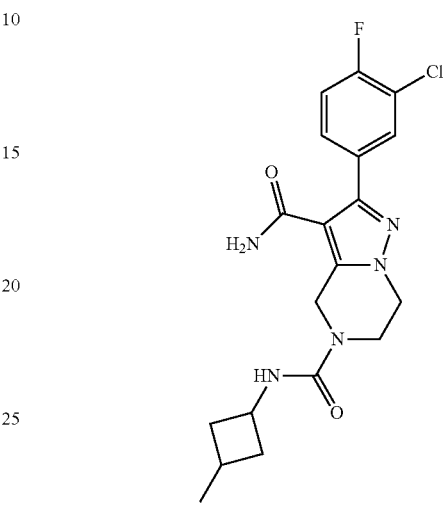

A solution of Intermediate 246A (77 mg, 0.679 mmol), TEA (0.142 mL, 1.018 mmol) and DPPA (0.146 mL, 0.679 mmol) in toluene (5 mL) was stirred at 90° C. for 2 h. The reaction mixture was cooled to RT and to it was added a solution of Intermediate 185B (100 mg, 0.339 mmol) in THF (1 mL) and stirred at RT for 4 h. The reaction mixture was quenched with water and the aqueous layer was extracted with ethyl acetate (3×5 mL) The combined organic layer was washed with an aqueous solution of 10% aq. NaHCO$_3$, water, dried over Na$_2$SO$_4$, filtered and the filtrate concentrated to afford the crude product as an off-white solid. The crude material was purified by preparative TLC. The crude material was loaded on a 0.5 mm silica gel plate and developed using 6% MeOH in CHCl$_3$. The band containing the desired product was separated and extracted into 10% MeOH in DCM, filtered and the filtrate concentrated to afford a mixture cis and trans isomers as an off-white solid. The individual isomers were separated using preparative chiral SFC purification.

Compound 246: Retention time=21.82 min. (HPLC Method P); MS(ES): m/z=406 [M+H]$^+$; Yield=13 mg, 9%; $^1$H NMR (400 MHz, DMSO-$d_6$) δ ppm 7.85 (dd, J=7.28, 2.26 Hz, 1H), 7.64-7.71 (m, 1H), 7.47 (d, J=9.54 Hz, 1H), 7.34 (br. s., 1H), 7.17 (br. s., 1H), 6.96 (d, J=7.53 Hz, 1H), 4.70 (s, 2H), 4.11 (t, J=5.27 Hz, 2H), 3.87-4.00 (m, 1H), 3.81 (t, J=5.52 Hz, 2H), 2.25-2.36 (m, 2H), 1.84-2.00 (m, 1H), 1.47-1.59 (m, 2H), 1.03 (d, J=6.53 Hz, 3H).

Compound 247: Retention time=26.26 min. (HPLC Method P); MS(ES): m/z=406 [M+H]$^+$; Yield=13 mg, 9%; $^1$H NMR (400 MHz, DMSO-$d_6$) δ ppm 7.85 (dd, J=7.28, 2.26 Hz, 1H), 7.64-7.71 (m, 1H), 7.47 (d, J=9.54 Hz, 1H), 7.34 (br. s., 1H), 7.17 (br. s., 1H), 6.96 (d, J=7.53 Hz, 1H), 4.70 (s, 2H), 4.20-4.30 (m, 1H), 4.11 (t, J=5.27 Hz, 2H), 3.81 (t, J=5.52 Hz, 2H), 2.18-2.23 (m, 1H), 2.068-2.14 (m, 2H), 1.80-1.85 (m, 2H), 1.09-1.12 (d, J=6.53 Hz, 3H).

The Compounds shown in Table 18 have been prepared similar to Compounds 246 and 247 by coupling of in-situ generated isocyanate of 246A with 185B analogs.

TABLE 18
| Ex. No. | Structure | Name | [M + H]+ | Ret Time (min.) | HPLC Methods |
|---|---|---|---|---|---|
| 248 | 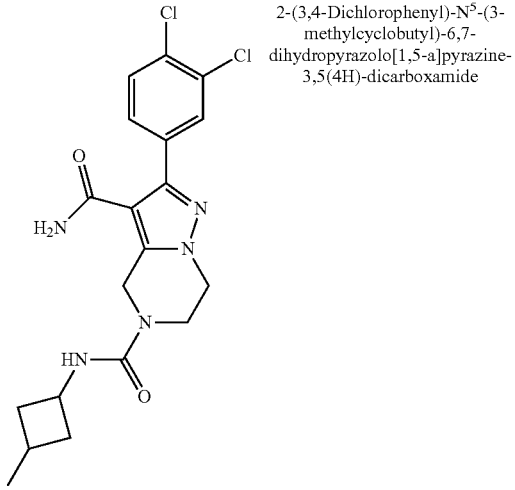 | 2-(3,4-Dichlorophenyl)-N$^5$-(3-methylcyclobutyl)-6,7-dihydropyrazolo[1,5-a]pyrazine-3,5(4H)-dicarboxamide | 422 | 14.52 | P |
| 249 | 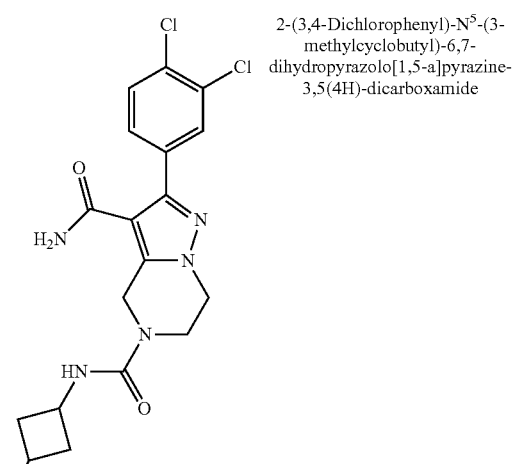 | 2-(3,4-Dichlorophenyl)-N$^5$-(3-methylcyclobutyl)-6,7-dihydropyrazolo[1,5-a]pyrazine-3,5(4H)-dicarboxamide | 422 | 17.37 | P |
| 250 | 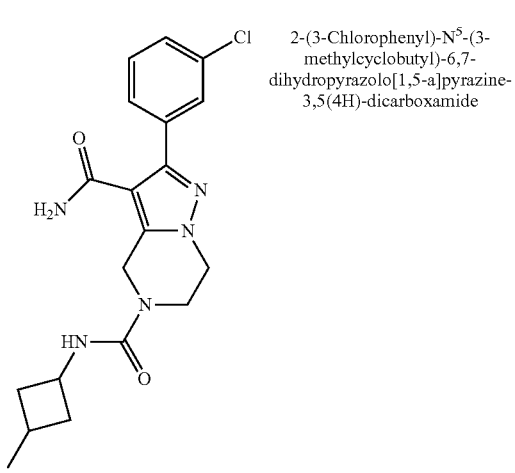 | 2-(3-Chlorophenyl)-N$^5$-(3-methylcyclobutyl)-6,7-dihydropyrazolo[1,5-a]pyrazine-3,5(4H)-dicarboxamide | 388 | 4.54 | P |

TABLE 18-continued

| Ex. No. | Structure | Name | [M + H]+ | Ret Time (min.) | HPLC Methods |
|---|---|---|---|---|---|
| 251 | 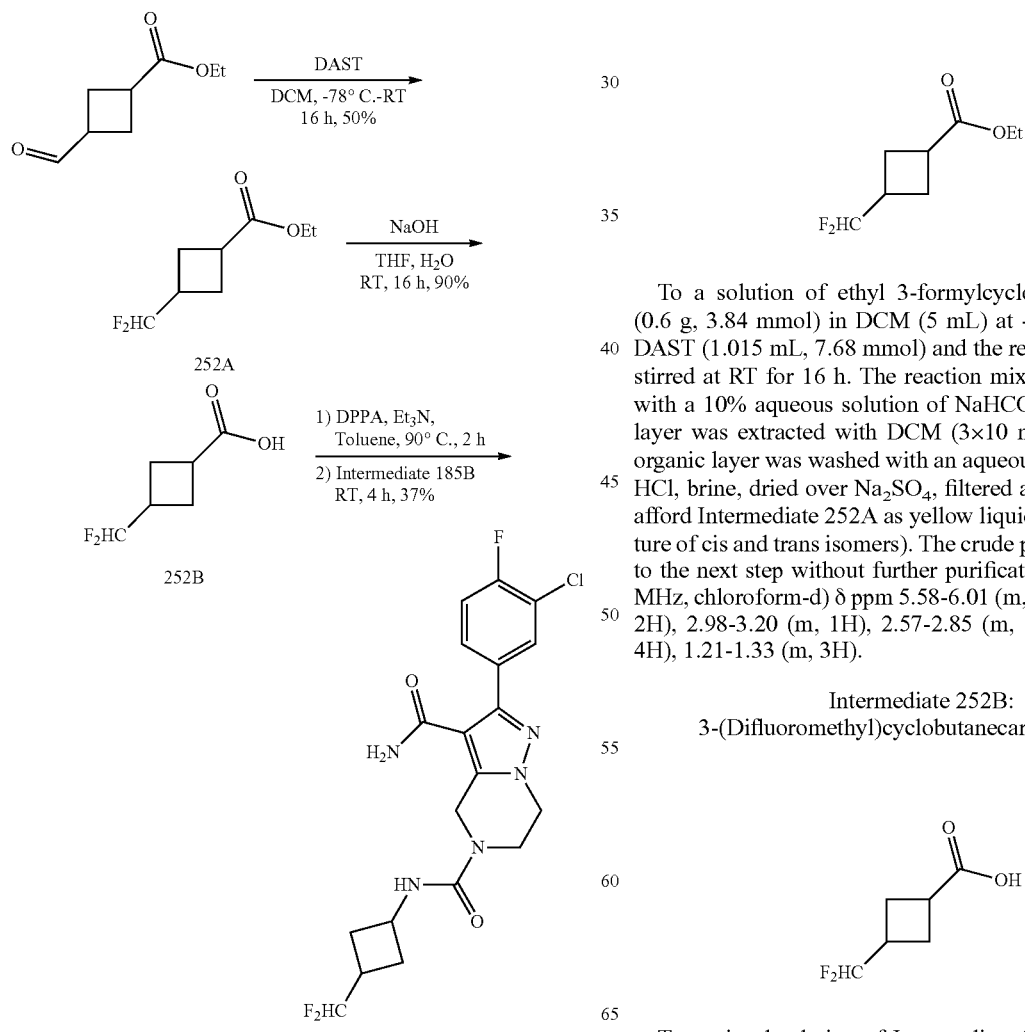 | 2-(3-Chlorophenyl)-N5-(3-methylcyclobutyl)-6,7-dihydropyrazolo[1,5-a]pyrazine-3,5(4H)-dicarboxamide | 388 | 5.34 | P |

Intermediate 252A: Ethyl 3-(difluoromethyl)cyclobutanecarboxylate

To a solution of ethyl 3-formylcyclobutanecarboxylate (0.6 g, 3.84 mmol) in DCM (5 mL) at −78° C. was added DAST (1.015 mL, 7.68 mmol) and the reaction mixture was stirred at RT for 16 h. The reaction mixture was quenched with a 10% aqueous solution of NaHCO$_3$ and the aqueous layer was extracted with DCM (3×10 mL) The combined organic layer was washed with an aqueous solution of 1.5 N HCl, brine, dried over Na$_2$SO$_4$, filtered and concentrated to afford Intermediate 252A as yellow liquid (0.5 g, 73%, mixture of cis and trans isomers). The crude product was reacted to the next step without further purification. $^1$H NMR (400 MHz, chloroform-d) δ ppm 5.58-6.01 (m, 1H), 4.07-4.22 (m, 2H), 2.98-3.20 (m, 1H), 2.57-2.85 (m, 1H), 2.20-2.48 (m, 4H), 1.21-1.33 (m, 3H).

Intermediate 252B: 3-(Difluoromethyl)cyclobutanecarboxylic acid

To a stirred solution of Intermediate 252A (0.2 g, 1.122 mmol) in THF (5 mL) was added NaOH (0.112 g, 2.81 mmol)

in water (2 mL) at RT. After 16 h, THF was removed under a reduced pressure and the pH of aqueous solution was adjusted to 3 using a 1.0 N aq. solution of HCl and extracted with ethyl acetate (3×10 mL). The combined organic layer was washed with water, brine, dried over Na$_2$SO$_4$, filtered and the filtrate concentrated to afford Intermediate 252B as yellow liquid (0.12 g, 71%, mixture of cis and trans isomers). The crude product was used in a subsequent reaction without further purification. $^1$H NMR (400 MHz, DMSO-d$_6$) δ ppm 12.01-12.22 (m, 1H), 5.84-6.32 (m, 1H), 2.97-3.13 (m, 1H), 2.59-2.77 (m, 1H), 2.06-2.32 (m, 4H).

Compounds 252 and 253: 2-(3-Chloro-4-fluorophenyl)-N$^5$-(3-(difluoromethyl)cyclobutyl)-6,7-dihydropyrazolo[1,5-a]pyrazine-3,5(4H)-dicarboxamide

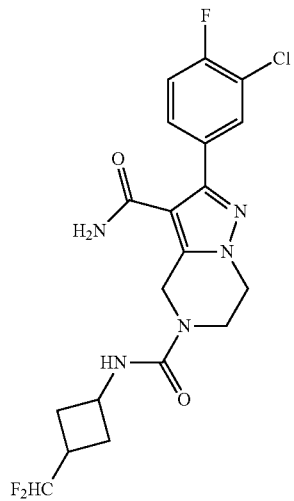 [SMILES: NC(=O)c1c(-c2ccc(F)c(Cl)c2)nn2c1CN(C(=O)NC1CC(C(F)F)C1)CC2]

A solution of Intermediate 252B (54.3 mg, 0.361 mmol), TEA (0.076 mL, 0.542 mmol) and DPPA (0.078 mL, 0.361 mmol) in toluene (5 mL) was stirred at 90° C. for 1.5 h. The reaction mixture was cooled to RT and in to it was added a solution of Intermediate 185B (50 mg, 0.181 mmol) in THF and stirred at RT for 4 h. The reaction mixture was quenched with water and extracted with ethyl acetate (3×5 mL). The combined organic layer was washed with a 10% aqueous solution of NaHCO$_3$, water, and then dried over Na$_2$SO$_4$, filtered and the filtrate concentrated. The crude product was purified by preparative TLC. The crude material was loaded on a 0.5 mm silica gel plate and developed using 6% MeOH in CHCl$_3$. Band containing desired product was removed and extracted into 10% MeOH in DCM, filtered and concentrated to offered Compounds 252 and 253 as off-white solid (mixture of cis and trans isomers). Both isomers were separated by chiral SFC.

Compound 252: (13 mg, 21%); Retention time: 5.48 min (HPLC Method N); MS(ES): m/z=442 [M+H]$^+$; $^1$H NMR (400 MHz, DMSO-d$_6$) δ ppm 7.71 (t, J=1.51 Hz, 1H), 7.62-7.67 (m, 1H), 7.40-7.49 (m, 2H), 7.35 (br. s., 1H), 7.17 (br. s., 1H), 7.11 (d, J=7.53 Hz, 1H), 5.82-6.17 (m, 1H), 4.72 (s, 2H), 4.06-4.20 (m, 3H), 3.84 (t, J=5.52 Hz, 2H), 2.43 (d, J=18.07 Hz, 1H), 2.17-2.30 (m, 2H), 1.88-1.99 (m, 2H).

Compound 253: (10 mg, 16%); Retention time: 6.40 min (HPLC Method N); MS(ES): m/z=442 [M+H]; $^1$H NMR (400 MHz, DMSO-d$_6$) δ ppm 7.71 (s, 1H), 7.65 (s, 1H), 7.41-7.48 (m, 2H), 7.36 (br. s., 1H), 7.16-7.17 (m, J=7.03 Hz, 1H), 5.82-6.37 (m, 1H), 4.73 (s, 2H), 4.20-4.30 (m, 1H), 4.14 (br. s., 2H), 3.80-3.88 (m, 2H), 2.55-2.65 (m, 1H), 2.15-2.25 (m, 4H).

The Compounds shown in Table 19 have been prepared similar to Compounds 252 and 253 by coupling of in-situ generated isocyanate of 252B with 185B analogs.

TABLE 19

| Ex. No. | Structure | Name | [M + H]$^+$ | Ret Time (min.) | HPLC Methods |
|---|---|---|---|---|---|
| 254 | 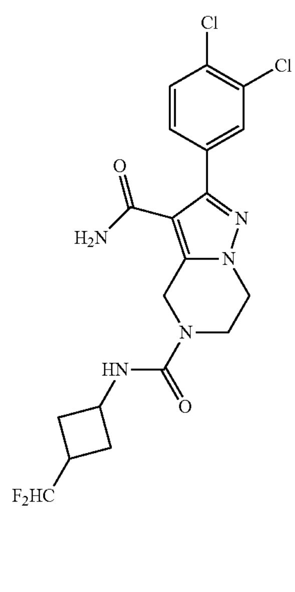 [SMILES: NC(=O)c1c(-c2ccc(Cl)c(Cl)c2)nn2c1CN(C(=O)NC1CC(C(F)F)C1)CC2] | 2-(3,4-Dichlorophenyl)-N$^5$-(3-(difluoromethyl)cyclobutyl)-6,7-dihydropyrazolo[1,5-a]pyrazine-3,5(4H)-dicarboxamide | 459 | 4.1 | Q |

TABLE 19-continued
| Ex. No. | Structure | Name | [M + H]+ | Ret Time (min.) | HPLC Methods |
|---|---|---|---|---|---|
| 255 | 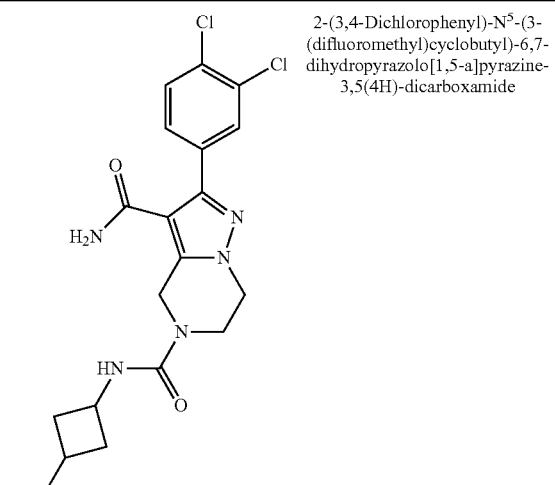 | 2-(3,4-Dichlorophenyl)-$N^5$-(3-(difluoromethyl)cyclobutyl)-6,7-dihydropyrazolo[1,5-a]pyrazine-3,5(4H)-dicarboxamide | 459 | 5.79 | Q |
| 256 | 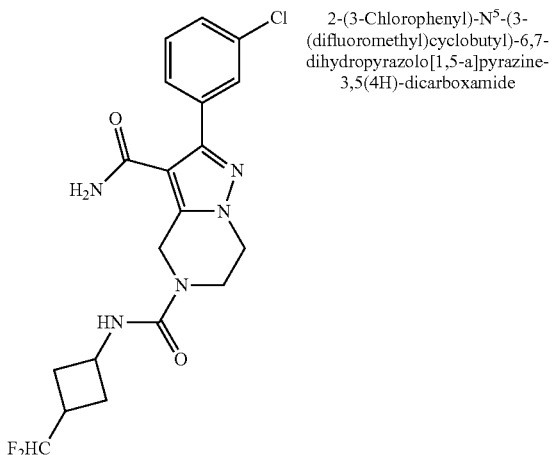 | 2-(3-Chlorophenyl)-$N^5$-(3-(difluoromethyl)cyclobutyl)-6,7-dihydropyrazolo[1,5-a]pyrazine-3,5(4H)-dicarboxamide | 424 | 6.44 | N |
| 257 | 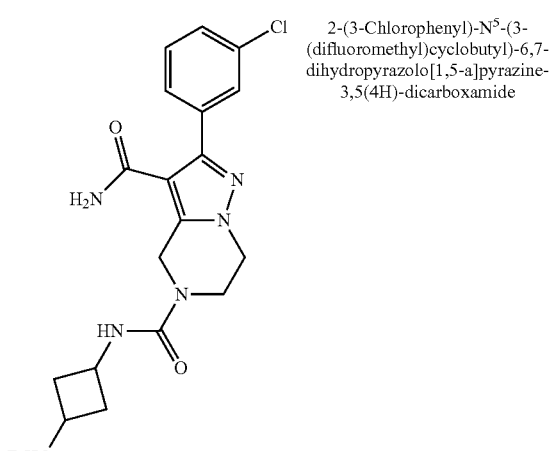 | 2-(3-Chlorophenyl)-$N^5$-(3-(difluoromethyl)cyclobutyl)-6,7-dihydropyrazolo[1,5-a]pyrazine-3,5(4H)-dicarboxamide | 424 | 7.18 | N |

Scheme 22

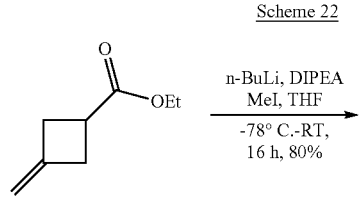

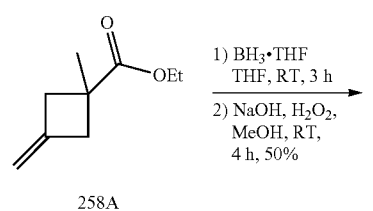

258A

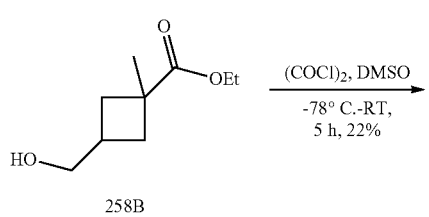

258B

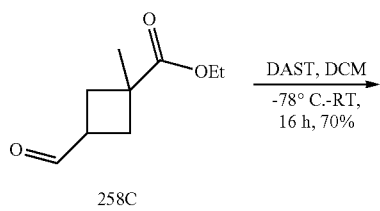

258C

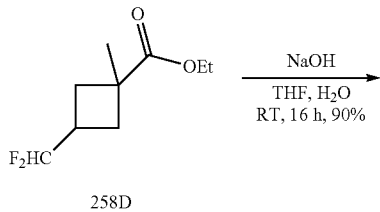

258D

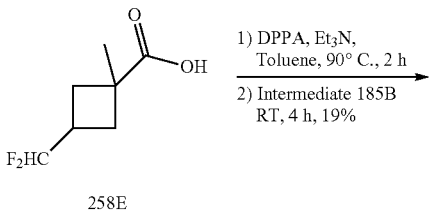

258E

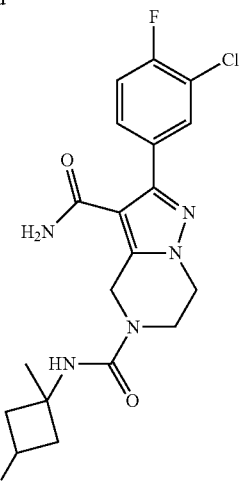

258 and 259

Intermediate 258A: Ethyl 1-methyl-3-methylenecyclobutanecarboxylate

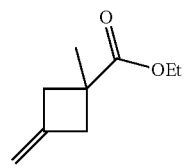

To a stirred solution of LDA (60 mL, 54 mmol, 1.0 M in THF (150 mL) at −78° C., was added ethyl 3-methylenecyclobutanecarboxylate (5.0 g, 35.7 mmol) and the reaction mixture was slowly allowed to warm to 0° C. and stir for 20 min. The reaction mixture was again cooled to −78° C. and MeI (8.92 mL, 143 mmol) was added and the reaction mixture was warmed to RT and stirred for 16 h. The reaction mixture was quenched with a saturated aq. solution of NH$_4$Cl and the aqueous layer was extracted with diethyl ether (3×5 mL). The combined organic layer was washed with an aqueous solution of 1.5N HCl, brine, then dried over Na$_2$SO$_4$, filtered and the filtrate concentrated. The crude product was purified by silica gel chromatography (24 g REDISEP® column, eluting with 1% EtOAc in hexanes). Fractions containing the product were combined and evaporated to afford Intermediate 258A as a pale yellow liquid (3.5 g, 63%). $^1$H NMR (400 MHz, DMSO-d$_6$) δ ppm 4.83-4.93 (m, 2H), 4.18 (q, J=7.18 Hz, 3.12-3.24 (m, 2H), 2.41-2.55 (m, 2H), 1.45 (s, 3H), 1.23-1.36 (m, 3H).

Intermediate 258B: Ethyl 3-(hydroxymethyl)-1-methylcyclobutanecarboxylate

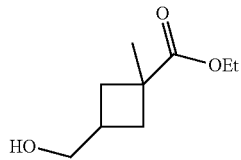

To a solution of Intermediate 258A (1.0 g, 6.48 mmol) in anhydrous THF (50 mL) at −10° C. was added BH₃.THF (3.24 mL, 6.48 mmol, 2 M in THF) dropwise. The resulting reaction mixture was allowed to warm to RT and stir for 4 h. The reaction mixture was cooled to −20° C., methanol (5 mL) was added and stirred for 15 min. followed by the addition of a 10% aq. NaOH solution (1 mL, 3.24 mmol) and H₂O₂ (0.596 mL, 9.73 mmol, 30% v/v) sequentially and the resultant reaction mixture was stirred at RT for 2 h. It was then neutralized with an aqueous 1.5N HCl and the aqueous layer was extracted with ethyl acetate (3×15 mL) The combined organic layer was washed with water, brine, and then dried over Na₂SO₄, filtered and the filtrate concentrated to afford the crude product. The crude was purified by silica gel chromatography (24 g REDISEP® column, eluting with 30% EtOAc in hexanes). Fractions containing the product were combined and evaporated to afford Intermediate 258B pale yellow liquid (0.5 g, 45%, mixture of cis and trans isomers). ¹H NMR (400 MHz, DMSO-d₆) δ ppm 4.43-4.52 (m, 1H), 3.99-4.13 (m, 2H), 3.27-3.28 (m, 2H), 2.26-2.40 (m, 3H), 1.61-1.82 (m, 2H), 1.34 (s, 1H), 1.26 (s, 2H), 1.13-1.22 (m, 3H).

Intermediate 258C: Ethyl 3-formyl-1-methylcyclobutanecarboxylate

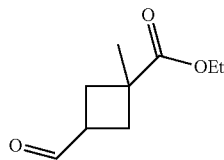

To a solution of oxalyl chloride (0.549 mL, 6.27 mmol) in DCM (15 mL) was added DMSO (0.890 mL, 12.54 mmol) as a solution in DCM (5 mL) slowly at −78° C. The resultant solution was stirred for 30 min prior to dropwise addition of Intermediate 258B (0.5 g, 3.14 mmol) as solution in DCM (5 mL). The resultant mixture was stirred for an additional 2 h at −78° C. TEA (4.37 mL, 31.4 mmol) was added to the reaction and the reaction mixture was allowed to stir at −78° C. for 30 min. The mixture was then warmed to RT and a saturated aqueous NH₄Cl solution was added and extracted with dichloromethane (3×10 mL). The combined organic layer was washed with brine, dried over Na₂SO₄, filtered and the filtrate concentrated under reduced pressure. The crude product was purified by silica gel chromatography (12 g REDISEP® column, eluting with 30% EtOAc in hexane). Fractions containing the product were combined and evaporated to afford Intermediate 258C as a pale yellow liquid (0.12 g, 22%, mixture of cis and trans isomers). ¹H NMR (400 MHz, DMSO-d₆) δ ppm 9.63 (d, J=1.51 Hz, 1H), 3.95-4.15 (m, 2H), 3.08-3.28 (m, 1H), 2.53-2.61 (m, 2H), 2.16-2.28 (m, 1H), 1.93-2.14 (m, 2H), 1.37-1.43 (s, 1H), 1.21-1.30 (s, 2H), 1.13-1.21 (m, 3H).

Intermediate 258D: Ethyl 3-(difluoromethyl)-1-methylcyclobutanecarboxylate

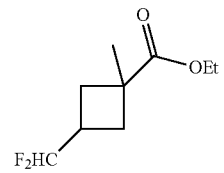

To a solution of Intermediate 258C (0.1 g, 0.588 mmol) in DCM (5 mL) at −78° C. was added DAST (0.155 mL, 1.175 mmol) and the reaction mixture was stirred at RT for 16 h. The reaction mixture was quenched with a 10% aq. solution of NaHCO₃ and the aqueous layer was extracted with DCM (3×10 mL). The combined organic layers were washed with a 1.5N aq. solution of HCl, followed by brine, and was then dried over Na₂SO₄, filtered and concentrated to afford Intermediate 258D (0.08 g, 70%, as a mixture of cis and trans isomers) as a yellow liquid. The crude product was used in the next step without purification. ¹H NMR (400 MHz, chloroform-d) δ ppm 5.58-6.01 (m, 1H), 4.07-4.22 (m, 2H), 2.61-2.85 (m, 1H), 2.47-2.56 (m, 2H), 1.85-2.05 (m, 2H), 1.36 (s, 1H), 1.28 (s, 2H), 1.21-1.26 (m, 3H).

Intermediate 258E: 3-(Difluoromethyl)-1-methylcyclobutanecarboxylic acid

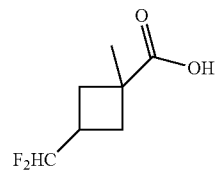

A solution of Intermediate 258D (0.07 g, 0.364 mmol) and NaOH (0.036 g, 0.910 mmol) in THF (2 mL) and water (1 mL) was stirred at RT for 16 h. The volatiles were evaporated under reduced pressure, the pH was adjusted to =3 with a 1.0N aq. solution of HCl, and the aqueous layer was extracted with EtOAc (3×10 mL). The combined organic layers were washed with water, brine, dried over Na₂SO₄, filtered and concentrated to afford Intermediate 258E (0.05 g, 84%, a mixture of cis and trans isomers) as a yellow liquid. The crude product was used in the next step without purification. ¹H NMR (400 MHz, DMSO-d₆) δ ppm 12.20-12.36 (m, 1H), 5.86-6.24 (m, 1H), 2.57-2.86 (m, 1H), 2.27-2.46 (m, 2H), 1.77-1.93 (m, 2H), 1.36 (s, 1H), 1.27 (s, 2H).

Compounds 258 and 259: 2-(3-Chloro-4-fluorophenyl)-N⁵-(3-(difluoromethyl)-1-methylcyclobutyl)-6,7-dihydropyrazolo[1,5-a]pyrazine-3,5(4H)-dicarboxamide

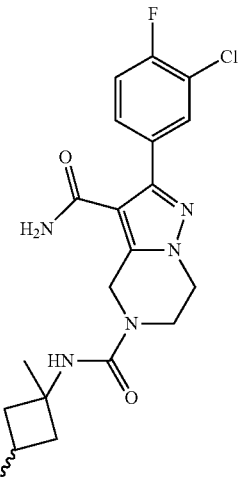

A solution of Intermediate 258E (84 mg, 0.509 mmol), TEA (0.142 mL, 1.018 mmol), DPPA (0.146 mL, 0.679 mmol) in toluene (5 mL) was stirred at 90° C. for 2 h. The reaction mixture was cooled to RT and to it was added a solution of Intermediate 185B (100 mg, 0.339 mmol) in THF (3 mL) and stirred at RT for 4 h. The reaction mixture was quenched with water and the aqueous layer was extracted with ethyl acetate (3×5 mL). The combined organic layer was washed with an aqueous solution of 10% NaHCO$_3$, water, dried over Na$_2$SO$_4$, filtered and the filtrate concentrated. The crude product was purified by preparative TLC. The crude product was loaded on a 0.5 mm silica gel plate and was developed using 6% MeOH in CHCl$_3$. The band containing the desired product was removed and extracted with 10% MeOH in DCM, filtered and concentrated to afford Compounds 258 and 259, a mixture of cis and trans isomers, as an off-white solid. The compound was subjected to chiral separation using preparative SFC to afford the cis and trans isomers.

Compound 258: Retention times 8.64 min. (Method O); Yield=10 mg, 6%; MS(ES): m/z=456 [M+H]$^+$; $^1$H NMR (300 MHz, DMSO-d$_6$) δ ppm 7.86 (dd, J=7.37, 2.08 Hz, 1H), 7.69 (ddd, J=8.69, 4.91, 2.27 Hz, 1H), 7.48 (d, J=9.44 Hz, 1H), 7.36 (br. s., 1H), 7.21 (br. s., 1H), 6.85 (s, 1H), 5.87-6.29 (m, 1H), 4.73 (s, 2H), 4.14 (t, J=5.29 Hz, 2H), 3.84 (t, J=5.10 Hz, 2H), 2.66-2.80 (m, 1H), 2.31-2.42 (m, 1H), 1.92 (dd, J=13.22, 7.93 Hz, 2H), 1.34 (s, 3H).

Compound 259: Retention time 11.9 min. (Method O); Yield=21 mg, 13%; MS(ES): m/z=456 [M+H]$^+$; $^1$H NMR (400 MHz, DMSO-d$_6$) δ ppm 7.86 (dd, J=7.28, 2.26 Hz, 1H), 7.69 (ddd, J=8.66, 4.64, 2.26 Hz, 1H) 7.44-7.53 (m, 1H), 7.36 (br. s., 1H), 7.19 (br. s., 1H), 6.85 (s, 1H), 5.90-6.22 (m, 1H), 4.71 (s, 2H), 4.13 (t, J=5.27 Hz, 2H), 3.81 (t, J=5.27 Hz, 2H), 2.60 (d, J=9.04 Hz, 1H), 2.16-2.26 (m, 2H), 1.96-2.06 (m, 2H), 1.24 (s, 3H).

Scheme 23

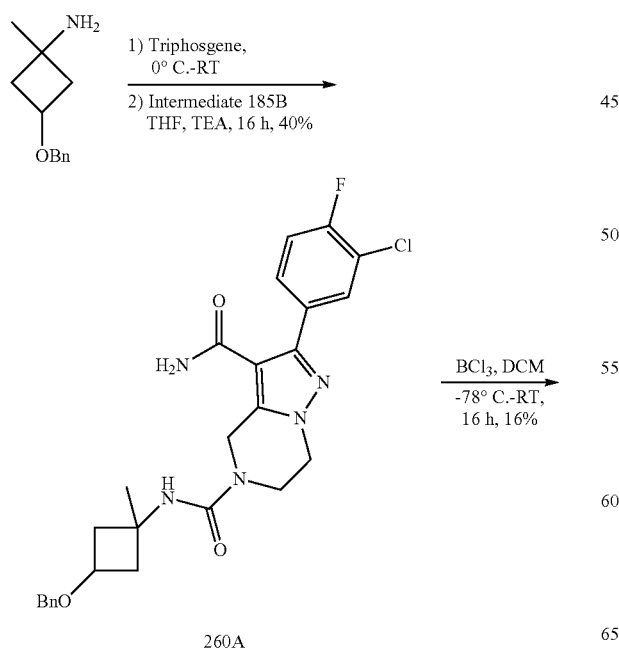

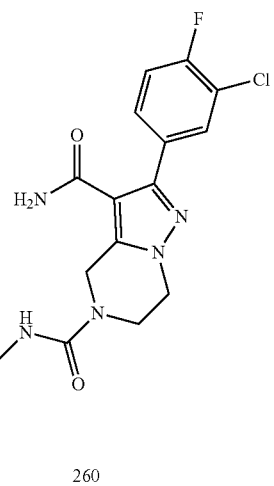

260

Intermediate 260A: N$^5$-(3-(Benzyloxy)-1-methylcyclobutyl)-2-(3-chloro-4-fluorophenyl)-6,7-dihydropyrazolo[1,5-a]pyrazine-3,5(4H)-dicarboxamide

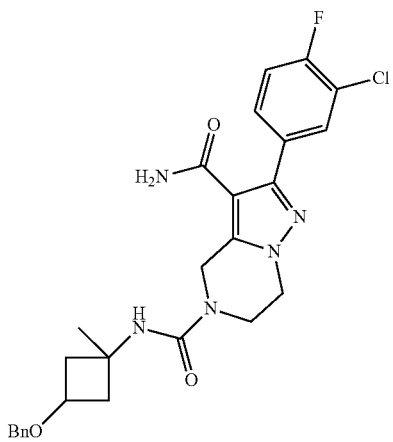 [SMILES: CC1(NC(=O)N2CCn3nc(-c4ccc(F)c(Cl)c4)c(C(N)=O)c3C2)CC(OCc2ccccc2)C1]

To a stirred solution of 3-(benzyloxy)-1-methylcyclobutanamine (64.9 mg, 0.339 mmol) in THF (10 mL) was added TEA (0.14 mL, 1.357 mmol) followed by triphosgene (100 mg, 0.339 mmol) at 0° C. After stirring for 10 min, a solution of Intermediate 185B (100 mg, 0.34 mmol) in THF (2 mL) was added at 0° C. and the resulting solution was allowed to warm to RT and stir for 16 h. The reaction mixture was quenched with a saturated aqueous solution of NH$_4$Cl and extracted with DCM (3×20 mL). The combined organic layers were dried over Na$_2$SO$_4$ and evaporated to afford the crude reaction mixture which was purified by silica gel chromatography (12 g REDISEP® column, eluting with 2% MeOH in CHCl$_3$). Fractions containing the product were combined and evaporated to afford Intermediate 260A (70 mg, 40% yield) as a pale yellow solid. MS(ES): m/z=512 [M+H]+.

Compound 260: 2-(3-Chloro-4-fluorophenyl)-N5-(3-hydroxy-1-methylcyclobutyl)-6,7-dihydropyrazolo[1,5-a]pyrazine-3,5(4H)-dicarboxamide

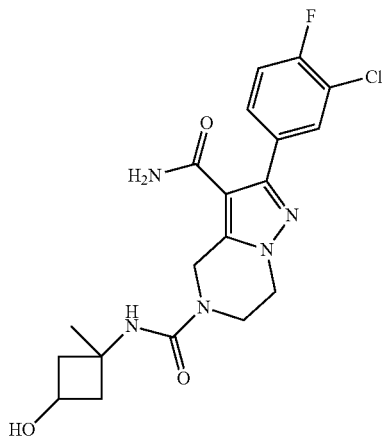 [SMILES: CC1(NC(=O)N2CCn3nc(-c4ccc(F)c(Cl)c4)c(C(N)=O)c3C2)CC(O)C1]

To a stirred solution of Intermediate 260A (70 mg, 0.137 mmol) in DCM (10 mL), cooled to −78° C., was added BCl3 (0.547 ml, 0.547 mmol, 1.0 M in DCM) and the resulting mixture was allowed to warm to RT and stir for 16 h. The reaction mixture was quenched with a saturated aqueous solution of NH4Cl and extracted with DCM (3×25 mL). The combined organic layers were dried over Na2SO4 and evaporated. The crude compound was purified by preparative HPLC to afford Compound 260 as an off-white solid (9.0 mg, 16% yield). HPLC Ret. Times 6.51 min. and 6.54 min. (HPLC Methods A and B). MS(ES): m/z=422 [M+H]+; 1H NMR (400 MHz, DMSO-d6) δ ppm 7.86 (dd, J=7.31, 2.16 Hz, 1H), 7.69 (dt, J=6.24, 2.49 Hz, 1H), 7.43-7.48 (t, 1H), 7.11-7.41 (m, 2H), 6.96 (s, 1H), 6.68 (s, 1H), 4.90 (dd, J=10.42, 6.15 Hz, 1H), 4.70 (s, 2H), 4.08-4.18 (m, 2H), 3.97 (m, 1H), 3.82 (s, 2H), 2.45-2.56 (m, 1H), 2.26-2.38 (m, 1H), 1.95-1.98 (m, 1H), 1.70-1.75 (m, 1H), 1.74 (s, 1.5H), 1.24-1.40 (s, 1.5H).

Scheme 24

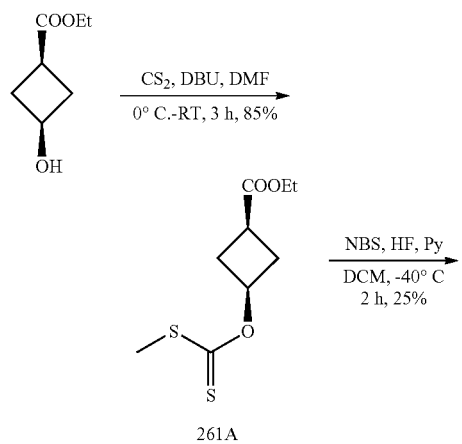

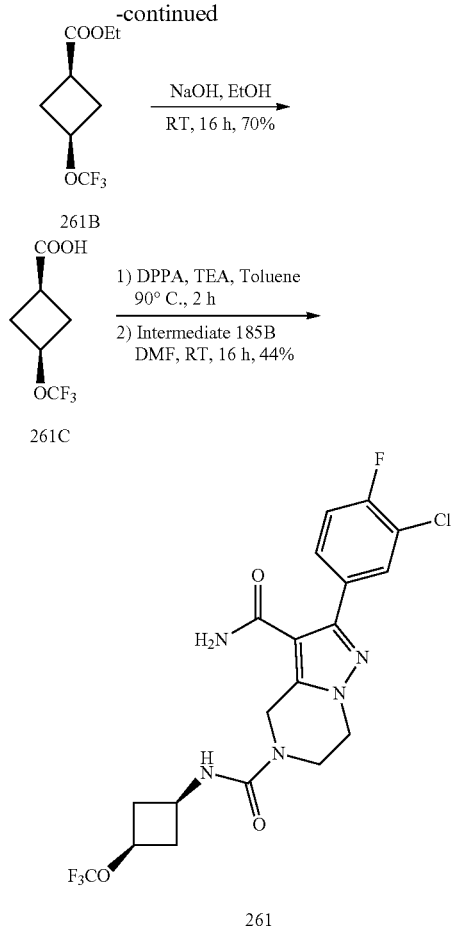

Intermediate 261A: (1s,3s)-Ethyl 3-(((methylthio)carbonothioyl)oxy)cyclobutanecarboxylate To a stirred solution of (1s,3s)-ethyl 3-hydroxycyclobutanecarboxylate (1.6 g, 11.10 mmol) in DMF (20 mL) at 0° C. was added DBU (3.34 g, 13.32 mmol). The resulting mixture stirred for 10 min. prior to the addition of carbon disulfide (2.68 mL, 44.4 mmol), followed by MeI (3.47 ml, 55.5 mmol), at 0° C. The reaction mixture stirred at RT for 2 h. The reaction was quenched with ice cold water and extracted with diethyl ether (2×25 mL) The combined organic layers were dried over Na2SO4 and concentrated under reduced pressure. The crude product was purified by silica gel chromatography (24 g REDISEP® column, eluting with 10% EtOAc in hexanes). Fractions containing the product were combined and evaporated to afford the Intermediate 261A as colorless liquid (2.2 g, 85%). 1H NMR (300 MHz, chloroform-d) δ ppm;

5.43-5.54 (m, 1H), 4.13-4.24 (m, 2H), 2.73-2.86 (m, 3H), 2.45-2.56 (m, 5H), 1.24-1.33 (m, 3H).

Intermediate 261B: (1s,3s)-Ethyl 3-(trifluoromethoxy)cyclobutanecarboxylate

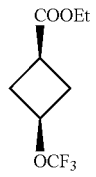 [SMILES: CCOC(=O)[C@H]1C[C@@H](OC(F)(F)F)C1]

To a stirred solution of NBS (8.35 g, 46.9 mmol) in DCM (20 ml) at −40° C. was added pyridine (3.00 mL, 37.6 mmol) followed by 70% HF in pyridine (10.73 g, 376 mmol) and stirred at the same temperature for 10 min and warmed 0° C. Thereafter a solution of Intermediate 261A (2.2 g, 9.39 mmol) in DCM (10 mL) was added at 0° C. to the above stirred solution and stirred for 1 h at the same temperature. Reaction mixture turned reddish brown. It was quenched with 10% NaHSO$_3$ followed by 10% NaOH solution and the pH was made alkaline up to 10 and extracted with DCM (2×50 ml). The combined organic layer was dried over Na$_2$SO$_4$ and evaporated. The crude product was purified by silica gel chromatography (24 g REDISEP® column, eluting with 10% EtOAc in hexane). Fractions containing the product were combined and evaporated to afford the Intermediate 261B as colorless liquid (0.5 g 25% yield), $^1$H NMR (400 MHz, chloroform-d) δ ppm; 4.52-4.62 (m, 1H), 4.11-4.19 (m, 2H), 2.56-2.79 (m, 5H), 1.24-1.30 (m, 3H).

Intermediate 261C: (1s,3s)-3-(Trifluoromethoxy)cyclobutanecarboxylic acid

To a stirred solution of Intermediate 261B (0.5 g, 2.357 mmol) in THF (10 mL) and ethanol (10 mL) was added a solution of NaOH (0.189 g, 4.71 mmol) in water (5 mL) and the resulting reaction mixture was stirred at RT for 16 h. After completion of the reaction, the volatiles were evaporated and the crude reaction mixture was quenched with a 1.5 N aqueous solution of HCl which was then extracted with EtOAc (2×25 mL). The combined organic layers were dried over Na$_2$SO$_4$ and evaporated to afford Intermediate 261C as a light brown liquid which was reacted in the Curtius rearrangement without any purification (0.3 g, 70%). $^1$H NMR (400 MHz, DMSO-d$_6$) δ ppm 12.34 (br. s., 1H), 4.75 (quin, J=7.53 Hz, 1H), 2.53-2.75 (m, 3H), 2.24-2.32 (m, 2H).

Compound 261: 2-(3-Chloro-4-fluorophenyl)-N$^5$-((1r,3r)-3-(trifluoromethoxy)cyclobutyl)-6,7-dihydropyrazolo[1,5-a]pyrazine-3,5(4H)-dicarboxamide

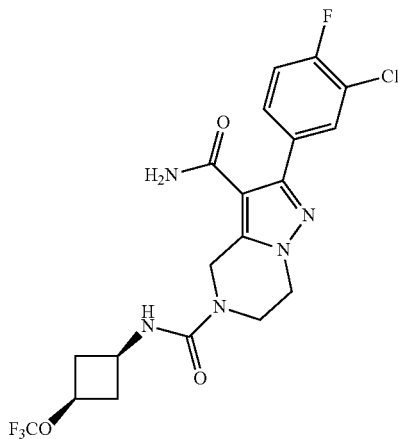 [SMILES: NC(=O)c1c(-c2ccc(F)c(Cl)c2)nn2c1CN(C(=O)N[C@H]1C[C@@H](OC(F)(F)F)C1)CC2]

To a stirred solution of Intermediate 261C (50 mg, 0.272 mmol) in toluene (3 mL) was added TEA (0.118 mL, 0.848 mmol) and DPPA (0.047 mL, 0.204 mmol) and stirred at 90° C. for 1 h. The reaction mixture was cooled RT and to it was added a solution of Intermediate 185B (50 mg, 0.170 mmol) in DMF (2 ml) and stirred at RT for 15 h. The reaction was quenched with a 10% aqueous solution of NaHCO$_3$ and extracted with ethyl acetate (2×20 mL). The combined organic layer was dried over Na$_2$SO$_4$ and concentrated under a reduced pressure. The crude product was purified by preparative HPLC to afford Compound 261 as an off-white solid (17 mg, 25% yield). HPLC Method A and B: 9.40 and 8.70 min respectively. MS(ES): m/z=476 [M+H]$^+$; $^1$H NMR (400 MHz, DMSO-d$_6$) δ ppm: 7.85 (dd, J=7.28, 2.20 Hz, 1H), 7.65-7.71 (m, 1H), 7.47 (t, J=9.04 Hz, 1H), 7.17 (d, J=7.78 Hz, 2H), 4.73 (s, 2H), 4.52-4.61 (m, 1H), 4.14 (t, J=5.24 Hz, 2H), 3.80-3.91 (m, 3H), 2.63-2.71 (m, 2H), 2.18-2.27 (m, 2H).

The Compounds shown in Table 20 have been prepared similar to Compound 261 by coupling of in-situ generated isocyanate of 261C with 185B analogs.

TABLE 20
| Ex. No. | Structure | Name | [M + H]+ | Ret Time (min.) | HPLC Methods |
|---|---|---|---|---|---|
| 262 | 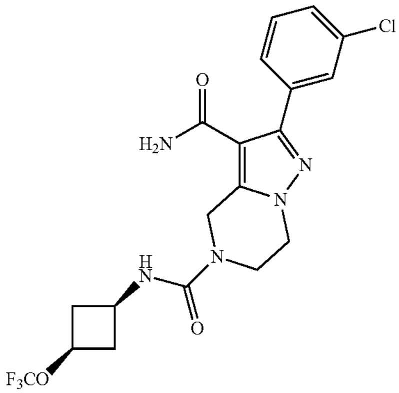 [SMILES: NC(=O)c1c(-c2cccc(Cl)c2)nn2c1CN(C(=O)N[C@H]1C[C@@H](OC(F)(F)F)C1)CC2] | 2-(3-Chlorophenyl)-N5-((1r,3r)-3-(trifluoromethoxy)cyclobutyl)-6,7-dihydropyrazolo[1,5-a]pyrazine-3,5(4H)-dicarboxamide | 458 | 9.20<br>8.50 | A<br>B |
| 263 | 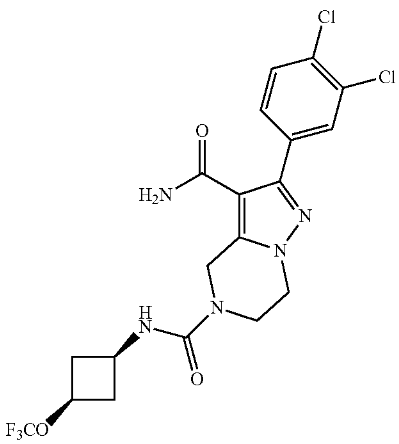 [SMILES: NC(=O)c1c(-c2ccc(Cl)c(Cl)c2)nn2c1CN(C(=O)N[C@H]1C[C@@H](OC(F)(F)F)C1)CC2] | 2-(3,4-Dichlorophenyl)-N5-((1r,3r)-3-(trifluoromethoxy)cyclobutyl)-6,7-dihydropyrazolo[1,5-a]pyrazine-3,5(4H)-dicarboxamide | 492 | 10.00<br>9.30 | A<br>B |
Scheme 25
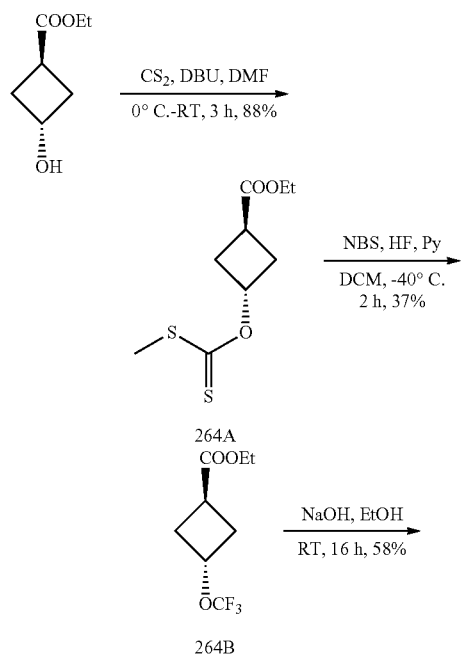
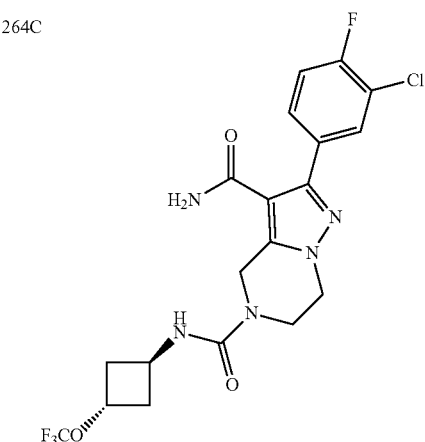

Intermediate 264A: (1r,3r)-Ethyl 3-(((methylthio)carbonothioyl)oxy)cyclobutanecarboxylate

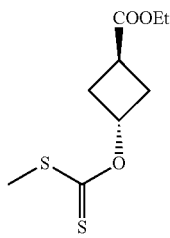

To a stirred solution of (1r,3r)-ethyl 3-hydroxycyclobutanecarboxylate (2.8 g, 19.42 mmol) in DMF (20 mL) at 0° C. was added DBU (5.85 g, 23.31 mmol) and the solution was stirred for 10 min. prior to the addition of carbon disulfide (4.68 mL, 78 mmol), followed by MeI (6.07 mL, 97 mmol) at 0° C. The resulting red solution was stirred at RT for 15 h. The reaction mixture was quenched with water and extracted with diethyl ether (2×100 mL). The combined organic layers were dried over $Na_2SO_4$ and evaporated to afford Intermediate 264A as a light brown liquid (4.0 g, 88%). $^1$H NMR (300 MHz, DMSO-$d_6$) δ ppm 5.43-5.68 (m, 1H), 4.00-4.16 (t, 2H), 3.05-3.17 (m, 1H), 2.55-2.78 (m, 3H), 1.93-2.43 (m, 2H), 0.98-1.38 (m, 3H).

Intermediate 264B: (1r,3r)-Ethyl 3-(trifluoromethoxy)cyclobutanecarboxylate

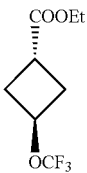

To a stirred solution of 1,3-dibromo-5,5-dimethylhydantoin (5.49 g, 19.20 mmol) in DCM (30 ml) at −78° C. was added 70% HF in pyridine (6.65 ml, 26 mmol) and stirred at the same temperature for 10 and then added Intermediate 264A (1.5 g, 6.4 mmol) in DCM (15 mL) and stirred at 0° C. for 2 h. Reaction mixture turned reddish brown. Reaction mixture was diluted with diethyl ether, quenched with aqueous 10% NaOH to adjust the pH 10 and extracted with diethyl ether (2×100 mL). The combined organic layer was dried over $Na_2SO_4$ and evaporated to afford Intermediate 264B as a light brown colored liquid was taken for the next step without any purification. (0.5 g, 37% yield).

Intermediate 264C: (1r,3r)-3-(Trifluoromethoxy)cyclobutanecarboxylic acid

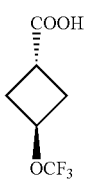

To a stirred solution of Intermediate 264B (0.5 g, 2.36 mmol) in THF (10 mL) was added a solution of NaOH (0.189 g, 4.71 mmol) in water (2 mL) which was stirred at RT for 16 h. The reaction mixture was concentrated and the residue was dissolved in water and extracted with EtOAc. The pH of the aqueous layer was adjusted to 3 with an aqueous solution of HCl and then extracted with EtOAc (2×25 mL). The combined organic layers were dried over $Na_2SO_4$ and evaporated to afford Intermediate 264C (0.25 g, 58% yield) as a pale yellow liquid. The crude compound was used directly in the Curtius rearrangement without purification. $^1$H NMR (400 MHz, DMSO-$d_6$) δ ppm 12.42 (br. s., 1H), 4.91 (quin, J=7.53 Hz, 1H), 3.05 (m, 1H), 2.47-2.56 (m, 4H).

Compound 264: 2-(3-Chloro-4-fluorophenyl)-$N^5$-((1r,3r)-3-(trifluoromethoxy)cyclobutyl)-6,7-dihydropyrazolo[1,5-a]pyrazine-3,5(4H)-dicarboxamide

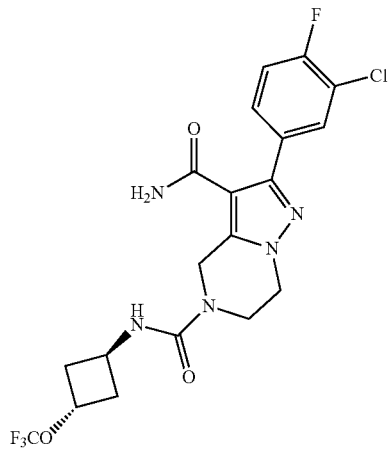 [SMILES: NC(=O)c1c(-c2ccc(F)c(Cl)c2)nn2c1CN(C(=O)N[C@H]1C[C@H](OC(F)(F)F)C1)CC2]

To a stirred solution of Intermediate 264C (30 mg, 0.1 mmol) in toluene (2 ml) was added TEA (0.071 ml, 0.51 mmol), DPPA (0.028 ml, 0.12 mmol) and heated at 90° C. for 1 h. The reaction mixture was cooled RT and to it was added a solution of Intermediate 185B (30 mg, 0.1 mmol) in DMF (1 ml) and stirred at RT for 15 h. The reaction mixture was quenched with 10% aqueous solution of $NaHCO_3$ and extracted with ethyl acetate (2×20 mL). The combined organic layer was dried over $Na_2SO_4$ and evaporated under reduced pressure. The crude product was purified by preparative HPLC to afford Compound 264 as an off-white solid (17 mg, 33% yield). HPLC retention times 9.4 min. and 8.8 min. (Methods A and B respectively). MS(ES): m/z=476 [M+H]$^+$; $^1$H NMR (400 MHz, DMSO-$d_6$) δ ppm 7.87-7.81 (m, 1H), 7.71-7.64 (m, 1H), 7.48 (d, J=9.5 Hz, 1H), 7.36 (br. s., 1H), 7.22-7.08 (m, 2H), 5.03-4.94 (m, 1H), 4.73 (s, 2H), 4.28-4.17 (m, 1H), 4.13 (d, J=5.5 Hz, 2H), 3.83 (t, J=5.5 Hz, 2H), 2.48-2.35 (m, 4H).

The Compounds shown in Table 21 have been prepared similar to Compound 264 by coupling of in-situ generated isocyanate of 264C with 199B.

TABLE 21
| Ex. No. | Structure | Name | [M + H]+ | Ret Time (min.) | HPLC Methods |
|---|---|---|---|---|---|
| 265 | 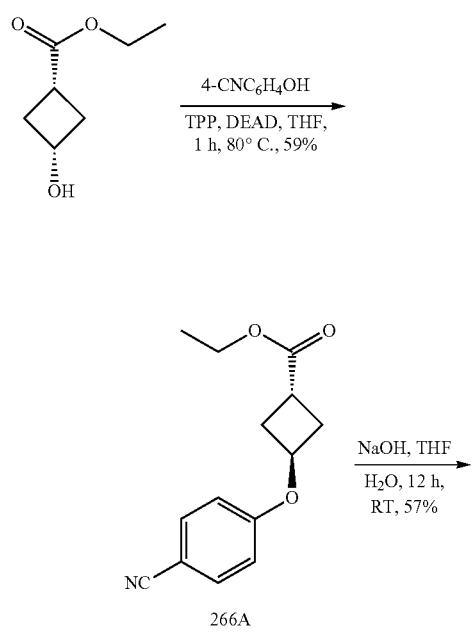 | 2-(3,4-Dichlorophenyl)-N5-((1r,3r)-3-(trifluoromethoxy)cyclobutyl)-6,7-dihydropyrazolo[1,5-a]pyrazine-3,5(4H)-dicarboxamide | 492 | 9.82<br>9.25 | A<br>B |
Scheme 26
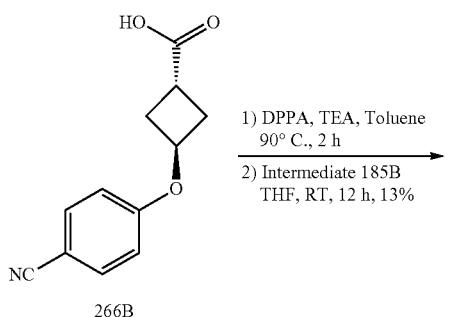
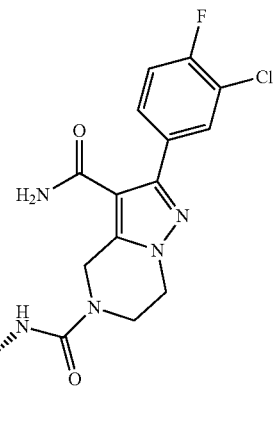
Intermediate 266A: (1r,3r)-Ethyl 3-(4-cyanophenoxyl)cyclobutanecarboxylate
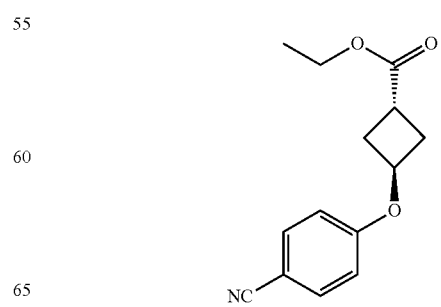

To a solution of (1s,3s)-ethyl 3-hydroxycyclobutanecarboxylate (0.9 g, 6.24 mmol), 4-hydroxybenzonitrile (1.487 g, 12.49 mmol) and triphenylphosphine (3.27 g, 12.49 mmol) in anhydrous THF (10 mL) was added a solution of DEAD (2.451 mL, 12.49 mmol) in THF at RT. The reaction mixture was then allowed to stir at 70° C. for 3 h after which time the volatiles were removed. The crude product was purified by silica gel chromatography (12 g REDISEP® column, eluting with 10% EtOAc in hexanes). Fractions containing the product were combined and evaporated to afford Intermediate 266A as a colorless gummy solid (0.1 g, 14%). $^1$H NMR (300 MHz, DMSO-$d_6$) δ ppm 7.87-7.59 (d, 2H), 7.14-6.84 (d, 2H), 5.04-4.78 (m, 1H), 4.12 (q, J=7.1 Hz, 2H), 3.27-3.05 (m, 1H), 2.69 (m, 2H), 2.45-2.25 (m, 2H), 1.21 (t, J=7.0 Hz, 3H).

Intermediate 266B:
(1r,3r)-3-(4-Cyanophenoxyl)cyclobutanecarboxylic acid

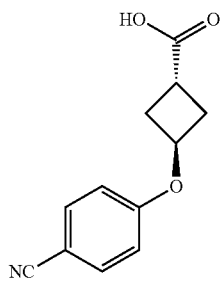

To a solution of Intermediate 266A (300 mg, 1.223 mmol) in THF (2 mL) and water (1 mL) was added NaOH (147 mg, 3.67 mmol) at RT. The reaction mixture was allowed to stir at RT for 12 h. The reaction mixture was concentrated and the residue was acidified to pH=2 with a 1.5N aqueous solution of HCl and extracted with EtOAc (3×15 mL). The combined organic layers were dried over Na$_2$SO$_4$, filtered and concentrated. The resulting solid was triturated with Et$_2$O (2×10 mL) to afford Intermediate 266B as an off-white solid (0.15 g, 57%). $^1$H NMR (400 MHz, DMSO-$d_6$) δ ppm 12.50-11.92 (br. s., 1H), 7.86-7.59 (d, 2H), 7.12-6.84 (d, 2H), 5.01-4.74 (m, 1H), 3.17-2.97 (m, 1H), 2.78-2.58 (m, 2H), 2.42-2.22 (m, 2H).

Compound 266: 2-(3-Chloro-4-fluorophenyl)-N$^5$-((1r,3r)-3-(4-cyanophenoxyl)cyclobutyl)-6,7-dihydropyrazolo[1,5-a]pyrazine-3,5(4H)-dicarboxamide

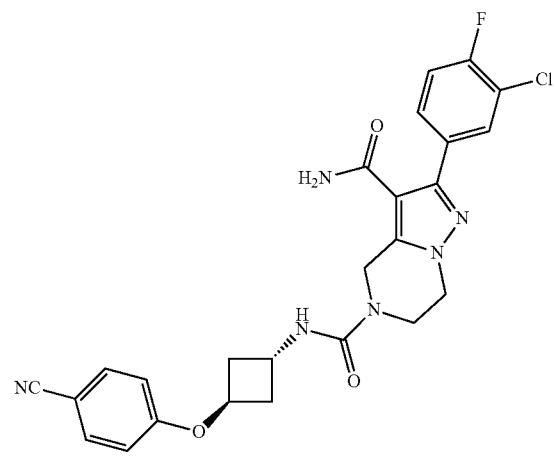 [SMILES: N#Cc1ccc(O[C@H]2C[C@H](NC(=O)N3CCn4nc(-c5ccc(F)c(Cl)c5)c(C(N)=O)c4C3)C2)cc1]

To a stirred solution of Intermediate 266B (44.2 mg, 0.204 mmol) in toluene (1 mL) was added TEA (0.095 mL, 0.679 mmol), DPPA (0.058 mL, 0.271 mmol) and the reaction mixture was heated to 90° C. for 1 h. The reaction mixture was cooled to RT and to it was added a solution of Intermediate 185B (40 mg, 0.136 mmol) in THF (1 mL) and stirred for 12 h. The reaction mixture was diluted with EtOAc (10 mL), washed with water and 10% aqueous solution of NaHCO$_3$, brine, dried over Na$_2$SO$_4$, filtered and the filtrate concentrated. The crude product was further purified by preparative HPLC to afford Compound 266 as an off-white solid (9 mg, 13%). HPLC retention times 1.555 and 1.547 min (Methods E and L respectively). MS(ES): m/z=472 [M+H]$^+$; $^1$H NMR (400 MHz, DMSO-$d_6$) δ ppm 7.85 (dd, J=2.0, 7.5 Hz, 1H), 7.78 (s, 2H), 7.71-7.64 (m, 1H), 7.47 (t, J=9.0 Hz, 1H), 7.36 (br. s., 1H), 7.19 (d, J=6.5 Hz, 2H), 7.00 (d, J=8.5 Hz, 2H), 4.93 (br. s., 1H), 4.74 (s, 2H), 4.29 (d, J=6.5 Hz, 1H), 4.19-4.11 (m, 2H), 3.85 (br. s., 2H), 2.48-2.44 (m, 2H), 2.42-2.29 (m, 2H).

The Compounds shown in Table 22 have been prepared similar to Compound 266 by coupling of in-situ generated isocyanate of 266B with 185B analogs.

TABLE 22
| Ex. No. | Structure | Name | [M + H]+ | Ret Time (min.) | HPLC Methods |
|---|---|---|---|---|---|
| 267 | 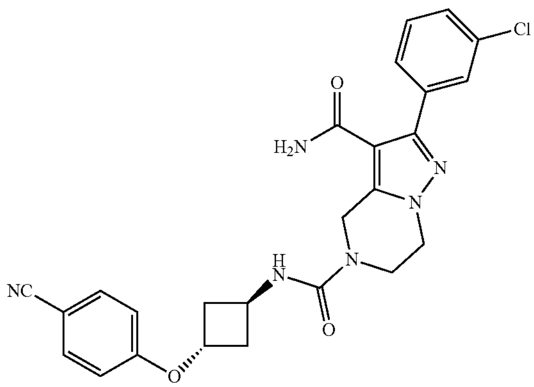 [SMILES: N#Cc1ccc(O[C@H]2C[C@H](NC(=O)N3CCn4nc(-c5cccc(Cl)c5)c(C(N)=O)c4C3)C2)cc1] | 2-(3-Chlorophenyl)-N5-((1r,3r)-3-(4-cyanophenoxy)cyclobutyl)-6,7-dihydropyrazolo[1,5-a]pyrazine-3,5(4H)-dicarboxamide | 491.2 | 1.511<br>1.504 | E<br>L |
| 268 | 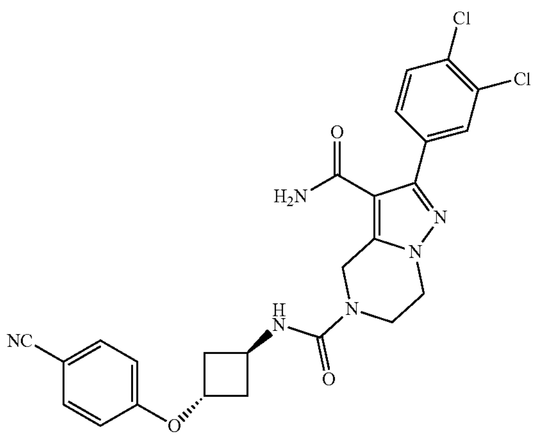 [SMILES: N#Cc1ccc(O[C@H]2C[C@H](NC(=O)N3CCn4nc(-c5ccc(Cl)c(Cl)c5)c(C(N)=O)c4C3)C2)cc1] | N5-((1r,3r)-3-(4-Cyanophenoxy)cyclobutyl)-2-(3,4-dichlorophenyl)-6,7-dihydropyrazolo[1,5-a]pyrazine-3,5(4H)-dicarboxamide | 525.2 | 1.660<br>1.654 | E<br>L |
Scheme 27
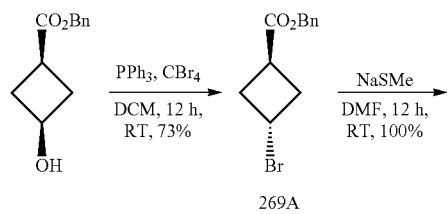
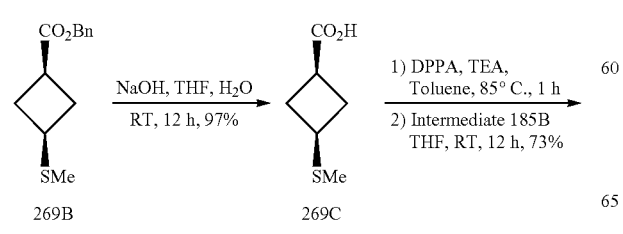
-continued
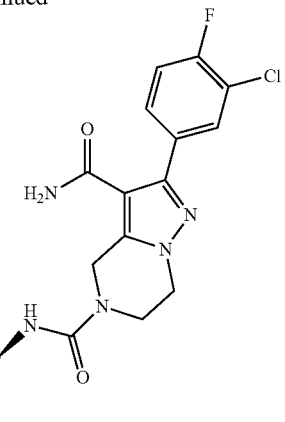
269
Intermediate 269A: (1r,3r)-Benzyl 3-bromocyclobutanecarboxylate
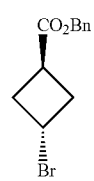

To a stirred solution of (1s,3s)-benzyl 3-hydroxycyclobutanecarboxylate (2.0 g, 9.7 mmol) in DCM (80 mL) was added PPh₃ (11.45 g, 43.6 mmol) followed by the addition of CBr₄ (12.86 g, 38.8 mmol) portionwise at 0° C. The reaction mixture was allowed to warm to RT and stir for 12 h. The reaction mixture was quenched with water (10 mL) and extracted with DCM (3×10 mL). The combined organic layers were dried over Na₂SO₄, filtered and the filtrate concentrated. The crude product was purified by silica gel chromatography (40 g REDISEP® column, eluting with 5% EtOAc in hexanes). Fractions containing the product were combined and evaporated to afford Intermediate 269A as a colorless liquid (1.9 g, 73% yield). ¹H NMR (400 MHz, DMSO-d₆) δ ppm 7.36 (s, 5H), 5.11 (s, 2H), 4.78-4.65 (m, 1H), 3.55-3.42 (m, 1H), 2.94-2.80 (m, 2H), 2.73-2.59 (m, 2H).

Intermediate 269B: (1s,3s)-Benzyl 3-(methylthio)cyclobutanecarboxylate

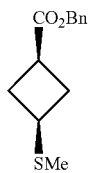 [SMILES: CS[C@H]1C[C@@H](C(=O)OCc2ccccc2)C1]

To a solution of Intermediate 269A (400 mg, 1.486 mmol) in DMF (4 mL) was added NaSMe (208 mg, 2.97 mmol) and the reaction mixture was stirred at RT for 12 h. The reaction mixture was poured into water (50 mL) and extracted with Et₂O (3×30 mL) The combined organic layer was washed with water, brine, dried over Na₂SO₄, filtered and concentrated to afford Intermediate 269B as a colorless liquid (0.35 g, 100%). ¹H NMR (300 MHz, chloroform-d) δ ppm 7.43-7.30 (m, 5H), 5.14 (s, 2H), 3.43-3.27 (m, 1H), 3.15-2.97 (m, 1H), 2.66-2.49 (m, 2H), 2.46-2.29 (m, 2H), 2.09 (s, 3H).

Intermediate 269C: (1s,3s)-3-(Methylthio)cyclobutanecarboxylic acid

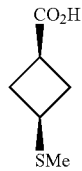

To a solution of Intermediate 269B (200 mg, 0.846 mmol) in THF (2 mL) and water (1 mL) was added NaOH (102 mg, 2.538 mmol) and the reaction mixture was stirred at RT for 12 h. The reaction mixture was concentrated, acidified to pH 2 with an aqueous solution of 1.5 N HCl and extracted with EtOAc (3×15 mL) The combined organic layer was dried over Na₂SO₄, filtered and concentrated to afford Intermediate 269C as a colorless gum (0.12 g, 97%). ¹H NMR (400 MHz, DMSO-d₆) δ ppm 12.10 (br. s., 1H), 3.06-2.77 (m, 1H), 2.46-2.36 (m, 3H), 2.19-2.09 (m, 2H), 2.06-1.94 (s, 3H).

Compound 269: 2-(3-Chloro-4-fluorophenyl)-N⁵-((1s,3s)-3-(methylthio)cyclobutyl)-6,7-dihydropyrazolo[1,5-a]pyrazine-3,5(4H)-dicarboxamide

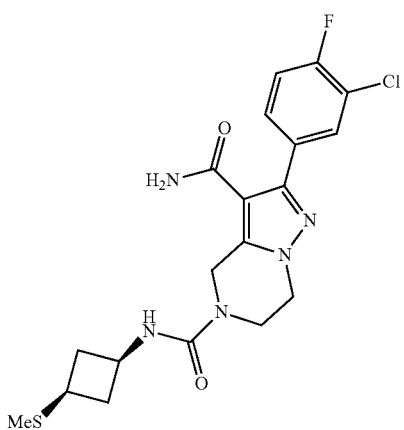 [SMILES: CS[C@H]1C[C@@H](NC(=O)N2CCn3nc(-c4ccc(F)c(Cl)c4)c(C(N)=O)c3C2)C1]

To a solution of Intermediate 269C (74.4 mg, 0.509 mmol) in toluene (2 mL) was added TEA (0.236 mL, 1.697 mmol), DPPA (0.146 mL, 0.679 mmol) and the clear solution was heated at 85° C. and stirred for 1 h. The reaction mixture was cooled to RT and to it was added a solution of Intermediate 185B (100 mg, 0.339 mmol) in THF (1 mL) and stirred at RT for 12 h. The reaction mixture was diluted with EtOAc (10 mL) and washed successively with water, 10% aqueous solution of NaHCO₃, brine, then dried over Na₂SO₄, filtered and concentrated. The crude product was purified by preparative HPLC to afford Compound 269 as an off-white solid (0.015 g, 10%). HPLC retention times 1.303 min. and 1.307 min. (Methods E and L respectively). MS(ES): m/z=438.2 [M+H]⁺; ¹H NMR: (400 MHz, DMSO-d₆) δ ppm 7.85 (dd, J=7.53, 2.01 Hz, 1H), 7.63-7.73 (m, 1H), 7.47 (t, J=9.04 Hz, 1H), 7.35 (br. s., 1H), 7.17 (d, J=10.04 Hz, 1H), 7.12 (d, J=8.03 Hz, 1H), 4.72 (s, 2H), 4.09-4.16 (m, 2H), 3.96-4.07 (m, 1H), 3.79-3.88 (m, 2H), 3.03 (tt, J=9.66, 7.40 Hz, 1H), 2.53-2.62 (m, 2H), 2.01-2.05 (s, 3H), 1.89-2.00 (m, 2H).

The Compounds shown in Table 23 have been prepared similar to Compound 269 by coupling of in-situ generated isocyanate of 269C with 185B analogs.

TABLE 23
| Ex. No. | Structure | Name | [M + H]+ | Ret Time (min.) | HPLC Methods |
|---|---|---|---|---|---|
| 270 | 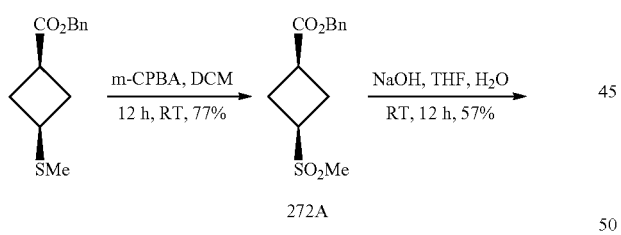 | 2-(3-Chlorophenyl)-N5-((1s,3s)-3-(methylthio)cyclobutyl)-6,7-dihydropyrazolo[1,5-a]pyrazine-3,5(4H)-dicarboxamide | 420.2 | 1.246<br>1.252 | E<br>L |
| 271 | 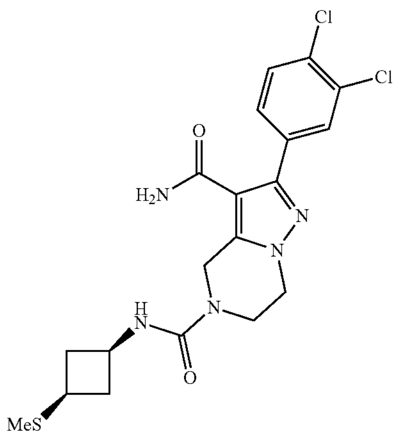 [SMILES: CS[C@H]1C[C@@H](NC(=O)N2CCn3nc(-c4ccc(Cl)c(Cl)c4)c(C(N)=O)c3C2)C1] | 2-(3,4-Dichlorophenyl)-N5-((1s,3s)-3-(methylthio)cyclobutyl)-6,7-dihydropyrazolo[1,5-a]pyrazine-3,5(4H)-dicarboxamide | 454.2 | 1.425<br>1.432 | E<br>L |
Scheme 28
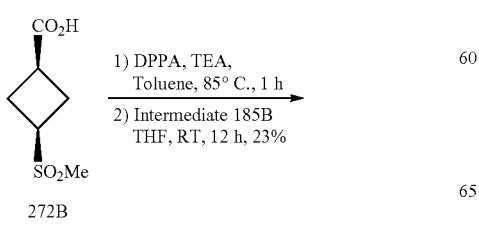
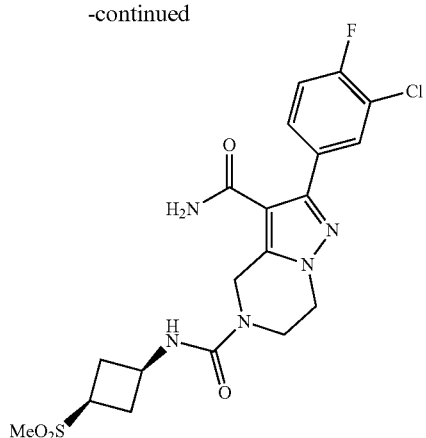
272
Intermediate 272A: (1s,3s)-Benzyl 3-(methylsulfonyl)cyclobutanecarboxylate
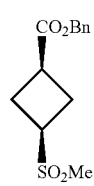

307

To a stirred solution of (1s,3s)-benzyl 3-(methylthio)cyclobutanecarboxylate (0.4 g, 1.693 mmol) in DCM (10 mL) was added mCPBA (2.337 g, 6.77 mmol) and the reaction mixture was stirred at RT for 12 h. The reaction mixture was diluted with DCM (40 mL) and washed successively with a saturated aqueous solution of NaHSO$_3$, 10% aq. solution of NaHCO$_3$, and brine, then dried over Na$_2$SO$_4$, filtered and concentrated to afford Intermediate 272A as colorless semi-solid (0.35 g, 77). $^1$H NMR (400 MHz, chloroform-d) δ ppm 7.41-7.30 (m, 5H), 5.15 (s, 2H), 3.70 (m, 1H), 3.18 (m, 1H), 2.83 (m, 2H), 2.80 (s, 3H), 2.65-2.51 (m, 2H).

Intermediate 272B:
(1s,3s)-3-(Methylsulfonyl)cyclobutanecarboxylic acid

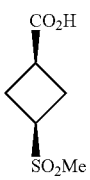

To a stirred solution of Intermediate 272A (400 mg, 1.491 mmol) in THF (4 mL) and water (2 mL) was added NaOH (179 mg, 4.47 mmol) and the reaction mixture was stirred at RT for 12 h. The reaction mixture was concentrated under reduced pressure and the pH of the aqueous solution was adjusted to 2 with a 1.5N aq. solution of HCl which was extracted with EtOAc (3×15 mL). The combined organic layers were dried over Na$_2$SO$_4$, filtered and concentrated. The crude product was purified by silica gel chromatography (12 g REDISEP® column, eluting with 10% EtOAc in hexanes). Fractions containing the product were combined and evaporated to afford Intermediate 272B as an off-white solid (150 mg, 57%). $^1$H NMR (400 MHz, DMSO-d$_6$) δ ppm 12.60-12.22 (br. s., 1H), 3.90 (m, 1H), 3.09 (m, 1H), 2.85 (s, 3H), 2.46-2.33 (m, 4H).

308

Compound 272: 2-(3-Chloro-4-fluorophenyl)-N$^5$-((1s,3s)-3-(methylsulfonyl)cyclobutyl)-6,7-dihydropyrazolo[1,5-a]pyrazine-3,5(4H)-dicarboxamide

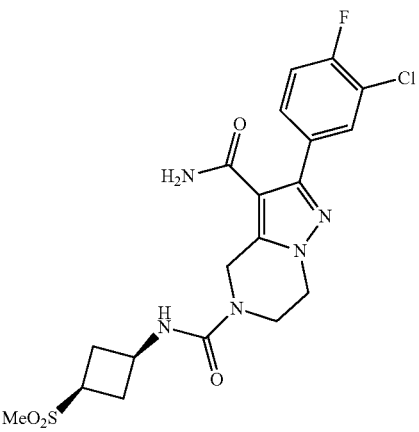 [SMILES: CS(=O)(=O)[C@H]1C[C@@H](NC(=O)N2CCn3nc(-c4ccc(F)c(Cl)c4)c(C(N)=O)c3C2)C1]

To a solution of Intermediate 272B (24.19 mg, 0.136 mmol) in toluene (1 mL) was added TEA (0.095 mL, 0.679 mmol), DPPA (0.058 mL, 0.271 mmol) and the solution and stirred at 85° C. for 1 h. The reaction mixture was cooled to RT and to it was added a solution of Intermediate 185B (40 mg, 0.136 mmol) in THF (0.5 mL) and stirred at RT for 12 h. The reaction mixture was diluted with EtOAc (10 mL), washed with water, brine, dried over Na$_2$SO$_4$, filtered and concentrated. The crude product obtained was purified by preparative HPLC to afford Compound 272 as an off-white solid (0.015 g, 23% yield). HPLC retention time 0.999 min. and 0.999 min. (Methods E and L respectively). MS(ES): m/z=470.2 [M+H]$^+$; $^1$H NMR: (400 MHz, DMSO-d$_6$) δ ppm 7.84 (dd, J=7.0, 2.0 Hz, 1H), 7.68 (ddd, J=8.5, 4.8, 2.3 Hz, 1H), 7.47 (d, J=9.5 Hz, 1H), 7.36 (br. s., 1H), 7.29 (d, J=7.5 Hz, 1H), 7.24-7.13 (m, 1H), 4.73 (s, 2H), 4.22-4.08 (m, 3H), 3.83 (t, J=5.3 Hz, 2H), 3.72-3.60 (m, 1H), 2.86 (s, 3H), 2.48-2.40 (m, 2H), 2.32-2.20 (m, 2H).

The Compounds shown in Table 24 have been prepared similar to Compound 272 by coupling of in-situ generated isocyanate of 272B with 185B analogs.

TABLE 24
| Ex. No. | Structure | Name | [M + H]+ | Ret Time (min.) | HPLC Methods |
|---|---|---|---|---|---|
| 273 | 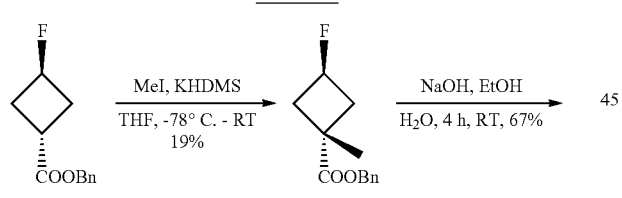 | 2-(3-Chlorophenyl)-$N^5$-((1s,3s)-3-(methylsulfonyl)cyclobutyl)-6,7-dihydropyrazolo[1,5-a]pyrazine-3,5(4H)-dicarboxamide | 452.2 | 0.941 0.938 | E L |
| 274 | 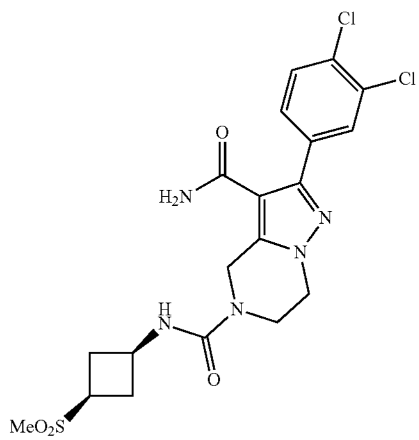 [SMILES: CS(=O)(=O)[C@H]1C[C@@H](NC(=O)N2CCn3nc(-c4ccc(Cl)c(Cl)c4)c(C(N)=O)c3C2)C1] | 2-(3,4-Dichlorophenyl)-$N^5$-((1s,3s)-3-(methylsulfonyl)cyclobutyl)-6,7-dihydropyrazolo[1,5-a]pyrazine-3,5(4H)-dicarboxamide | 486.2 | 1.128 1.129 | E L |
Scheme 29
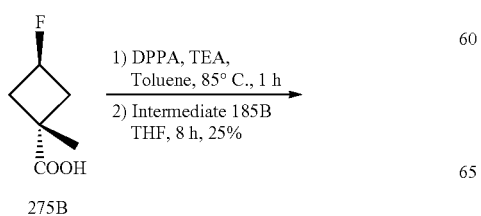
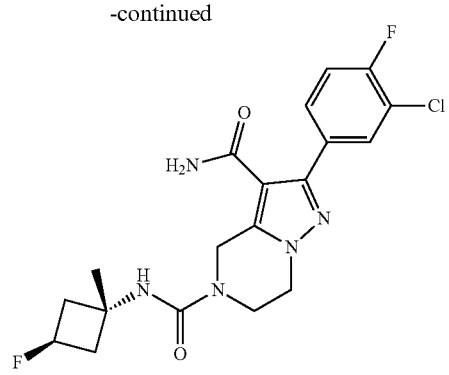
275
Intermediate 275A: (1r,3r)-Benzyl 3-fluoro-1-methylcyclobutanecarboxylate

To a solution of benzyl 3-fluorocyclobutanecarboxylate (0.5 g, 2.4 mmol) and MeI (0.6 mL, 9.60 mmol) in THF (12 mL) at −78° C. under nitrogen was added a solution of KHMDS (19.21 mL, 0.5 M in toluene, 9.6 mmol) and allowed to stir at −78° C. for 6 h. The reaction was then warmed to RT and stirred further for 16 h. The reaction mass was quenched with a saturated aq. NH₄Cl solution and extracted with diethyl ether (2×25 mL). The organic layer was washed with water, dried over Na₂SO₄, filtered and the filtrate concentrated under vacuum. The crude product was purified by silica gel chromatography (4 g REDISEP® column, eluting with 25% EtOAc in hexane). Fractions containing the product were combined and evaporated to afford Intermediate 275A as colorless liquid (0.1 g, 19% yield). $^1$H NMR (400 MHz, chloroform-d) δ ppm 7.42-7.30 (m, 5H), 5.14 (s, 3H), 2.93-2.75 (m, 2H), 2.24-2.08 (m, 2H), 1.48 (s, 3H).

Intermediate 275B:
(1r,3r)-3-Fluoro-1-methylcyclobutanecarboxylic acid

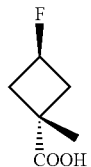

To a solution of Intermediate 275A (0.100 g, 0.450 mmol) in ethanol (5 mL) and water (1 mL) was added a 5N aq. solution of NaOH (0.45 mL, 2.250 mmol) and the reaction mixture was stirred at RT for 4 h. The reaction mixture was concentrated under vacuum; the residue was dissolved in water and extracted with diethyl ether (2×10 mL) The organic layer was discarded; the pH of the aq. layer was adjusted to 5 using a 2N aq. solution of HCl and was extracted with DCM (2×10 mL). The combined organic layer was dried over Na₂SO₄, filtered and the filtrate concentrated to afford Intermediate 275B as pale yellow liquid (40 mg, 67% yield). $^1$H NMR (400 MHz, DMSO-d₆) δ ppm 12.52 (br. s., 1H), 5.17-4.94 (m, 1H), 2.73 (dt, J=10.3, 3.4 Hz, 2H), 2.06 (d, J=6.0 Hz, 2H), 1.35 (s, 3H).

Compound 275: 2-(3-Chloro-4-fluorophenyl)-N⁵-((1r,3r)-3-fluoro-1-methylcyclobutyl)-6,7-dihydropyrazolo[1,5-a]pyrazine-3,5(4H)-dicarboxamide

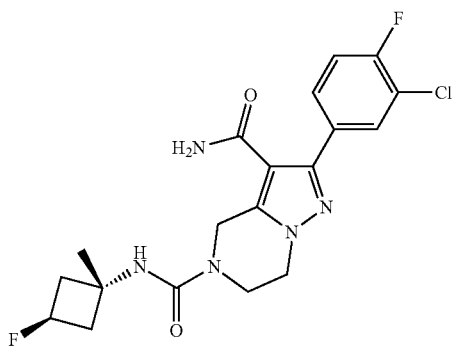 [SMILES: C[C@]1(NC(=O)N2CCn3nc(-c4ccc(F)c(Cl)c4)c(C(N)=O)c3C2)C[C@H](F)C1]

A stirred solution of Intermediate 275B (39.5 mg, 0.299 mmol) in toluene (5 mL) at RT under nitrogen was added TEA (0.189 mL, 1.357 mmol), DPPA (0.125 mL, 0.543 mmol) and heated at 85° C. for 1 h. The reaction mass was cooled to RT and to it was added a solution of Intermediate 185B (80 mg, 0.271 mmol) in DMF and stirred at RT for 8 h. The reaction mass was concentrated and the residue was partitioned between EtOAc and water. The organic layer was separated, dried over sodium sulfate, filtered and concentrated. The crude product was purified by silica gel chromatography (4 g REDISEP® column, eluting with 10% MeOH in CHCl₃). Fractions containing the product were combined and evaporated to afford Compound 275 as off-white solid (29.66 mg, 25% yield). HPLC retention time 7.96 and 8.35 min (Methods B and C respectively). MS(ES): m/z=425 [M+H]⁺; $^1$H NMR: (300 MHz, DMSO-d₆) δ ppm 7.84 (dd, J=7.37, 2.08 Hz, 1H), 7.63-7.73 (m, 1H), 7.46 (t, J=9.07 Hz, 1H), 7.16-7.39 (m, 2H), 6.83 (s, 1H), 4.94-5.26 (m, 1H).

Scheme 30

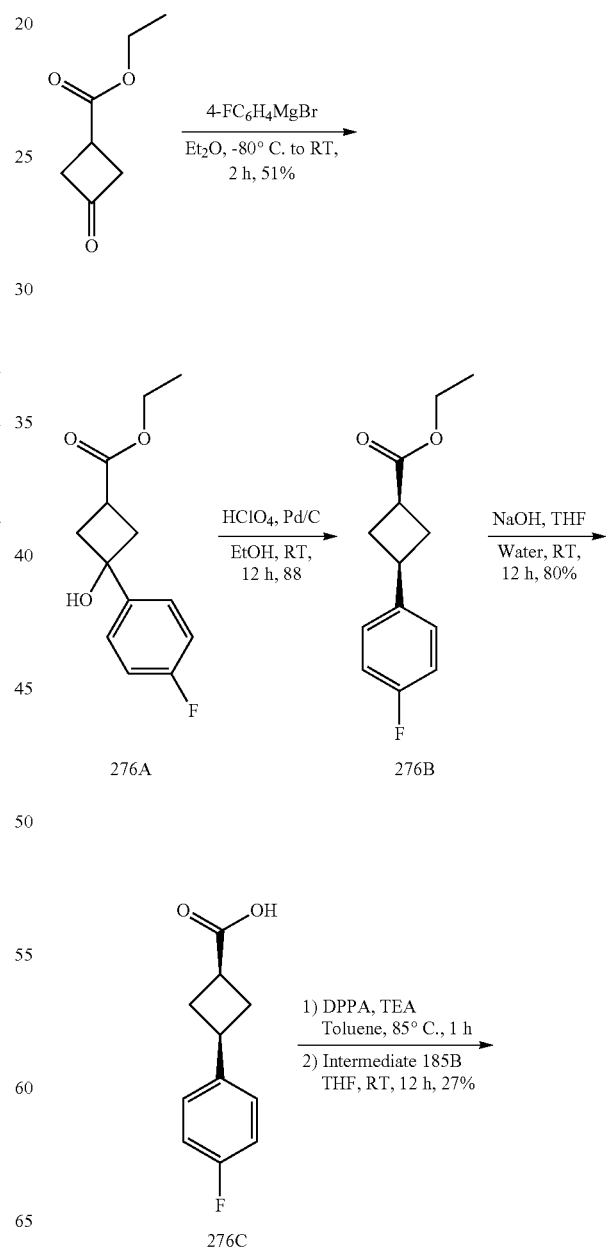

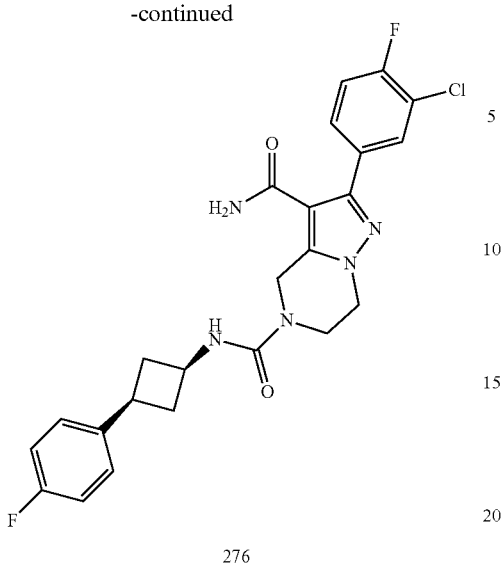

276

Intermediate 276A: Ethyl 3-(4-fluorophenyl)-3-hydroxycyclobutanecarboxylate

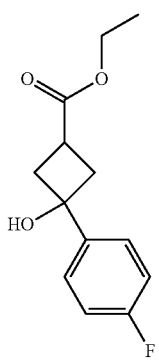 [SMILES: CCOC(=O)C1CC(O)(c2ccc(F)cc2)C1]

To a stirred solution of ethyl 3-oxocyclobutanecarboxylate (2 g, 14.07 mmol) in dry Et$_2$O (30 mL), cooled to −80° C., was added 4-fluorophenyl magnesium bromide (16.88 mL, 16.88 mmol, 1 M in THF) dropwise. The reaction mixture was then allowed to warm to RT and stir for an additional 2 h. The reaction mixture was quenched with a saturated aq. solution of NH$_4$Cl (50 mL) and extracted with EtOAc (3×30 mL). The combined organic layer was washed with brine, dried over Na$_2$SO$_4$, filtered and concentrated. The crude reaction mixture was purified by silica gel chromatography (24 g REDISEP® column, eluting with 15% EtOAc in hexanes). Fractions containing the product were combined and evaporated to afford Intermediate 276A as a colorless liquid (1.7 g, 51%). $^1$H NMR (400 MHz, DMSO-d$_6$) δ ppm 7.54 (dd, J=5.5, 9.0 Hz, 2H), 7.15 (t, J=8.8 Hz, 2H), 4.09 (q, J=7.4 Hz, 2H), 2.83-2.71 (m, 1H), 2.61 (s, 2H), 2.55-2.51 (m, 2H), 1.24-1.12 (t, 3H).

Intermediate 276B: ((1s,3s)-Ethyl 3-(4-fluorophenyl)cyclobutanecarboxylate

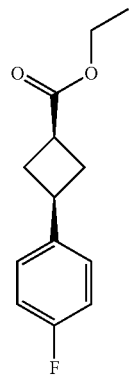 [SMILES: CCOC(=O)[C@H]1C[C@@H](c2ccc(F)cc2)C1]

To a solution of Intermediate 276A (1.7 g, 7.14 mmol) in ethanol (50 mL) was added perchloric acid (0.429 mL, 7.14 mmol). The reaction mixture was purged with an atmosphere of N$_2$ prior to the addition of Pd/C (600 mg). The reaction vessel is placed under an atmosphere of H$_2$ (balloon pressure) and the reaction mixture is allowed to stir at RT for 12 h. The reaction mixture was filtered and the filtrate was concentrated under reduced pressure. The residue was partitioned between water and Et$_2$O. The organic layer was separated and the aqueous phase was extracted with Et$_2$O (3×30 mL) The combined organic layers were washed with brine, dried over Na$_2$SO$_4$, filtered and concentrated to afford Intermediate 276B as a colorless liquid (1.4 g, 88% yield). $^1$H NMR (300 MHz, DMSO-d$_6$) δ ppm 7.24 (d, J=5.7 Hz, 2H), 7.19-7.05 (m, 2H), 4.07 (d, J=7.2 Hz, 2H), 3.51-3.36 (m, 1H), 3.20-3.03 (m, 1H), 2.53 (s, 2H), 2.27-2.08 (m, 2H), 1.19 (t, J=7.2 Hz, 3H).

Intermediate 276C: (1s,3s)-3-(4-Fluorophenyl)cyclobutanecarboxylic acid

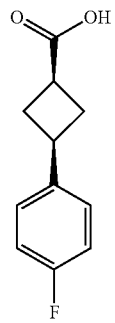 [SMILES: O=C(O)[C@H]1C[C@@H](c2ccc(F)cc2)C1]

To a solution of Intermediate 276B (100 mg, 0.450 mmol) in THF (2 mL) and water (1 mL) was added NaOH (54.0 mg, 1.350 mmol) and the reaction mixture was stirred at RT for 12 h. The reaction mixture was concentrated and the residue was acidified to pH=2 with a 1.5N aq. solution of HCl and the aq. solution was extracted with EtOAc (3×15 mL). The combined organic layers were dried over Na$_2$SO$_4$, filtered and concentrated to afford Intermediate 276C as a colorless gummy solid (70 mg, 80%). $^1$H NMR (300 MHz, DMSO-d$_6$) δ ppm 12.99 (br. s., 1H), 7.26 (dd, J=5.5, 8.5 Hz, 2H), 7.17-7.03 (m, 2H), 3.50-3.30 (m, 1H), 3.01 (s, 1H), 2.50-2.43 (m, 2H), 2.24-2.09 (m, 2H).

Compound 276: 2-(3-Chloro-4-fluorophenyl)-N$^5$-((1s,3s)-3-(4-fluorophenyl)cyclobutyl)-6,7-dihydro-pyrazolo[1,5-a]pyrazine-3,5(4H)-dicarboxamide

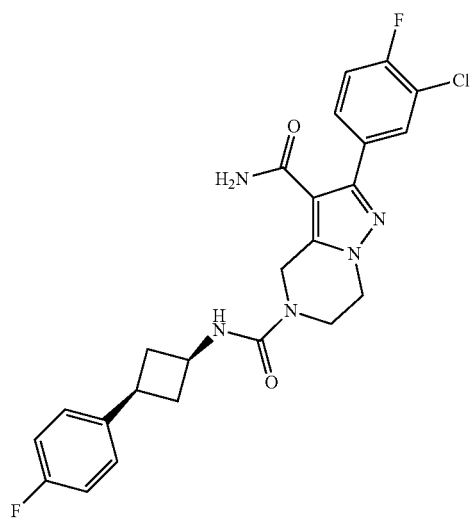 [SMILES: NC(=O)c1c(-c2ccc(F)c(Cl)c2)nn2c1CN(C(=O)N[C@H]1C[C@@H](c3ccc(F)cc3)C1)CC2]

To a solution of Intermediate 276C (26.4 mg, 0.136 mmol) in toluene (1 mL) was added TEA (0.095 mL, 0.679 mmol), DPPA (0.058 mL, 0.271 mmol) and the reaction mixture was stirred at 85° C. for 1 h. The reaction mixture was cooled to RT and to it was added a solution of Intermediate 185B (40 mg, 0.136 mmol) in THF (0.500 mL) and stirred at RT for 12 h. The reaction mixture was diluted with EtOAc (10 mL) and washed with water, 10% NaHCO$_3$, brine, dried over Na$_2$SO$_4$, filtered and the filtrate concentrated. The crude product was purified by preparative HPLC to afford Compound 276 as an off-white solid (0.018 g, 27%). HPLC retention times 1.649 min. and 1.651 min (Methods E and L respectively). MS(ES): m/z=486.2 [M+H]$^+$; $^1$H NMR (400 MHz, DMSO-d$_6$) δ ppm 7.89-7.81 (m, 1H), 7.72-7.62 (m, 1H), 7.51-7.43 (m, 1H), 7.42-7.23 (m, 3H), 7.19 (br. s., 1H), 7.16-7.05 (m, 3H), 4.73 (s, 2H), 4.19-4.09 (m, 3H), 3.84 (t, J=5.3 Hz, 2H), 3.19-3.01 (m, 1H), 2.63-2.54 (m, 2H), 2.11-1.99 (m, 2H).

The Compounds shown in Table 25 have been prepared similar to Compound 276 by coupling of in-situ generated isocyanate of 276C with 185B analogs.

TABLE 25

| Ex. No. | Structure | Name | [M + H]$^+$ | Ret Time (min.) | HPLC Methods |
|---|---|---|---|---|---|
| 277 | 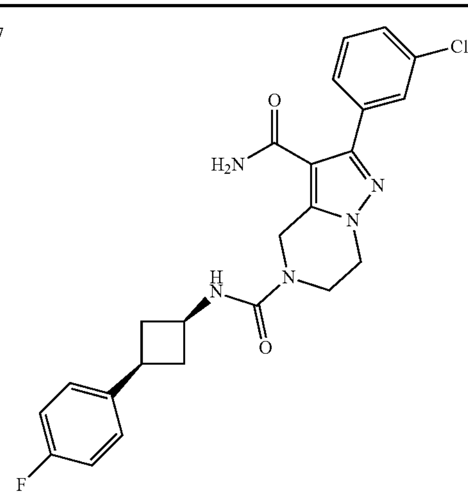 | 2-(3-Chlorophenyl)-N$^5$-((1s,3s)-3-(4-fluorophenyl)cyclobutyl)-6,7-dihydropyrazolo[1,5-a]pyrazine-3,5(4H)-dicarboxamide | 468.3 | 1.606<br>1.608 | E<br>L |

TABLE 25-continued
| Ex. No. | Structure | Name | [M + H]+ | Ret Time (min.) | HPLC Methods |
|---|---|---|---|---|---|
| 278 | 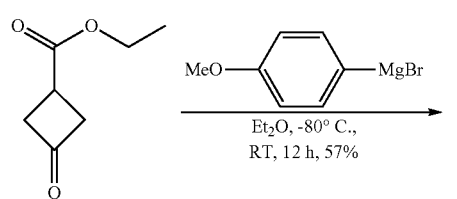 | 2-(3,4-Dichlorophenyl)-N[5]-((1s,3s)-3-(4-fluorophenyl)cyclobutyl)-6,7-dihydropyrazolo[1,5-a]pyrazine-3,5(4H)-dicarboxamide | 502.2 | 1.758 1.761 | E L |
Scheme 31
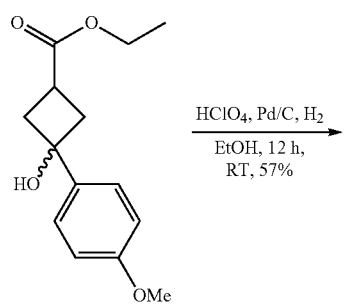 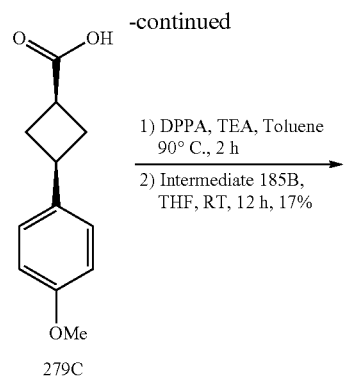
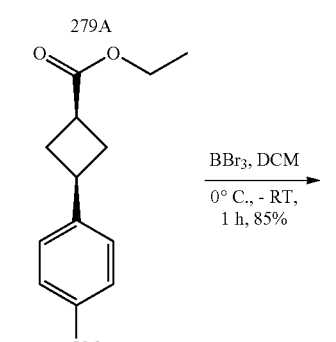 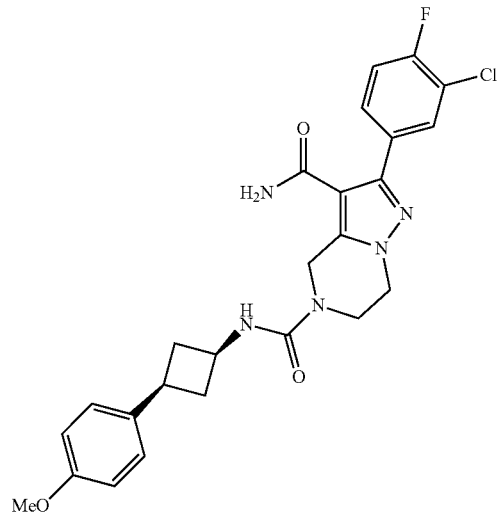

Intermediate 279A: Ethyl 3-hydroxy-3-(4-methoxyphenyl)cyclobutanecarboxylate

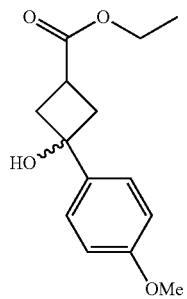 [SMILES: CCOC(=O)C1CC(O)(c2ccc(OC)cc2)C1]

To a solution of ethyl 3-oxocyclobutanecarboxylate (3.0 g, 21.1 mmol) in anhydrous Et$_2$O (60 mL), cooled to −80° C., was added dropwise a solution of (4-methoxyphenyl)magnesium bromide (50.6 mL, 25.3 mmol, 2M in THF). The reaction mixture was allowed to warm to RT and stir for 2 h. The reaction mixture was quenched with a saturated aq. solution of NH$_4$Cl (20 mL) and then extracted with EtOAc (3×30 mL) The combined organic layers were washed with brine, dried over Na$_2$SO$_4$, filtered and concentrated. The crude product was purified by silica gel chromatography (40 g REDISEP® column, eluting with 15% EtOAc in hexanes). Fractions containing the product were combined and evaporated to afford Intermediate 279A as a colorless liquid (3 g, 57%). $^1$H NMR (300 MHz, DMSO-d$_6$) δ ppm 7.42 (d, J=8.7 Hz, 2H), 6.89 (d, J=8.7 Hz, 2H), 5.58 (s, 1H), 4.08 (d, J=7.2 Hz, 2H), 3.75 (s, 3H), 2.76-2.67 (m, 1H), 2.60 (s, 2H), 2.47 (s, 2H), 1.22-1.16 (m, 3H).

Intermediate 279B: (1s,3s)-Ethyl 3-(4-methoxyphenyl)cyclobutanecarboxylate

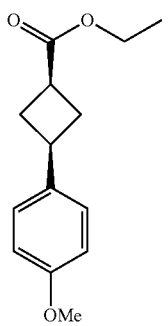 [SMILES: CCOC(=O)[C@H]1C[C@@H](c2ccc(OC)cc2)C1]

To a solution of Intermediate 279A (3.0 g, 12 mmol) in ethanol (100 mL) was added perchloric acid (0.721 mL, 11.99 mmol). The reaction mixture was purged with an atmosphere of N$_2$ prior to the addition of palladium on carbon (1.020 g, 0.959 mmol). The reaction vessels is placed under an atmosphere of H$_2$ (balloon pressure) and the reaction mixture is allowed to stir at RT for 12 h. The reaction mixture was filtered through a bed of CELITE® and the filtrate was concentrated under reduced pressure. The crude reaction mixture was purified by silica gel chromatography (24 g REDISEP® column, eluting with 5% EtOAc in hexanes). Fractions containing the product were combined and evaporated to afford Intermediate 279B as a colorless gum (1.6 g, 57%). $^1$H NMR (300 MHz, DMSO-d$_6$) δ ppm 7.14 (d, J=8.3 Hz, 2H), 6.92-6.81 (d, 2H), 4.14-4.01 (m, 2H), 3.72 (s, 3H), 3.45-3.34 (m, 1H), 3.09 (s, 1H), 2.48-2.39 (m, 2H), 2.24-2.05 (m, 2H), 1.23-1.14 (t, 3H).

Intermediate 279C: (1s,3s)-3-(4-Methoxyphenyl)cyclobutanecarboxylic acid

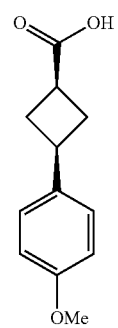

To a solution of Intermediate 279B (200 mg, 0.854 mmol) in THF (2 mL) and water (1 mL) was added NaOH (102 mg, 2.56 mmol) at RT and the reaction mixture was stirred at RT for 12 h. The reaction mixture was concentrated and the residue was acidified to a pH of 2 with a 1.5N aq. solution of HC and extracted with EtOAc (3×15 mL) The combined organic layer was dried over Na$_2$SO$_4$, filtered and the filtrate concentrated to afford Intermediate 279C as a colorless gum (0.15 g, 85%). $^1$H NMR (400 MHz, DMSO-d$_6$) δ ppm 12.39-11.78 (br. s., 1H), 7.27-7.05 (d, 2H), 6.95-6.70 (d, 2H), 3.72 (s, 3H), 3.31-3.22 (m, 1H), 3.15-2.98 (m, 1H), 2.47 (m, 2H), 2.27-2.01 (m, 2H).

Compound 279: 2-(3-Chloro-4-fluorophenyl)-N$^5$-((1s,3s)-3-(4-methoxyphenyl)cyclobutyl)-6,7-dihydropyrazolo[1,5-a]pyrazine-3,5(4H)-dicarboxamide

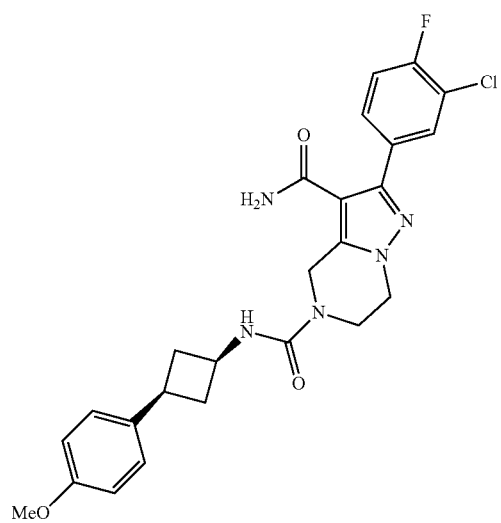 [SMILES: COc1ccc([C@H]2C[C@@H](NC(=O)N3CCn4nc(-c5ccc(F)c(Cl)c5)c(C(N)=O)c4C3)C2)cc1]

To a solution of Intermediate 279C (52.5 mg, 0.254 mmol) in toluene (1 mL) was added TEA (0.118 mL, 0.848 mmol), DPPA (0.073 mL, 0.339 mmol) and the reaction mixture was heated to 90° C. for 1 h. The reaction mixture was cooled to RT and to it was added a solution of Intermediate 185B (40 mg, 0.136 mmol) in THF (1 mL) and stirred for 12 h. The reaction mixture was diluted with EtOAc (10 mL), washed with a 10% aqueous solution of $NaHCO_3$, brine, dried over $Na_2SO_4$, filtered and the filtrate concentrated. The crude product was purified by preparative HPLC to afford Compound 279 as an off-white solid (15 mg, 17%). HPLC retention times 1.655 min. and 1.663 min. (Methods E and L respectively). MS(ES): m/z=498.3 [M+H]$^+$; $^1$H NMR (400 MHz, DMSO-$d_6$) δ ppm 7.85 (dd, J=2.3, 7.3 Hz, 1H), 7.68 (ddd, J=2.3, 4.8, 8.5 Hz, 1H), 7.51-7.41 (m, 1H), 7.36 (br. s., 1H), 7.30-7.14 (m, 3H), 7.09 (d, J=7.5 Hz, 1H), 6.91-6.83 (m, 2H), 4.74 (s, 2H), 4.19-4.06 (m, 3H), 3.84 (t, J=5.3 Hz, 2H), 3.75-3.67 (m, 3H), 3.07-2.95 (m, 1H), 2.61-2.53 (m, 2H), 2.08-1.95 (m, 2H).

The Compounds shown in Table 26 have been prepared similar to Compound 279 by coupling of in-situ generated isocyanate of 279C with 185B analogs.

TABLE 26

| Ex. No. | Structure | Name | [M + H]$^+$ | Ret Time (min.) | HPLC Methods |
|---|---|---|---|---|---|
| 280 | 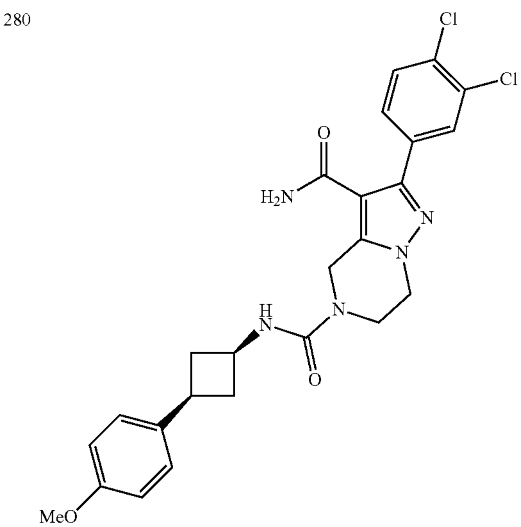 | 2-(3,4-dichlorophenyl)-N$^5$-((1s,3s)-3-(4-methoxyphenyl)cyclobutyl)-6,7-dihydropyrazolo[1,5-a]pyrazine-3,5(4H)-dicarboxamide | 514.2 | 1.751 | L |
| 281 | 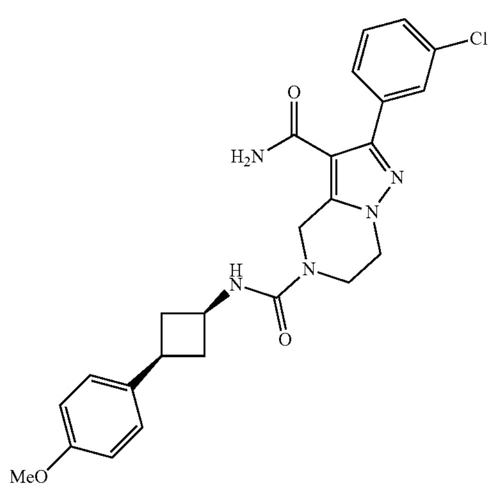 [SMILES: COc1ccc([C@H]2C[C@@H](NC(=O)N3CCn4nc(-c5cccc(Cl)c5)c(C(N)=O)c4C3)C2)cc1] | 2-(3-Chlorophenyl)-N$^5$-((1s,3s)-3-(4-methoxyphenyl)cyclobutyl)-6,7-dihydropyrazolo[1,5-a]pyrazine-3,5(4H)-dicarboxamide | 480.3 | 1.611 1.620 | E L |

Scheme 32

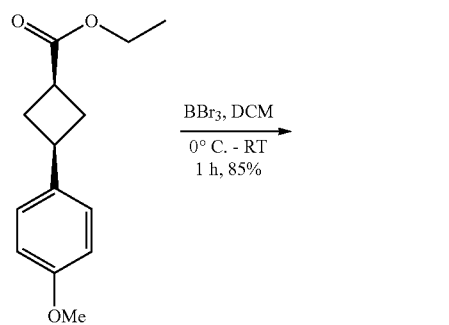

BBr₃, DCM
0° C. - RT
1 h, 85%

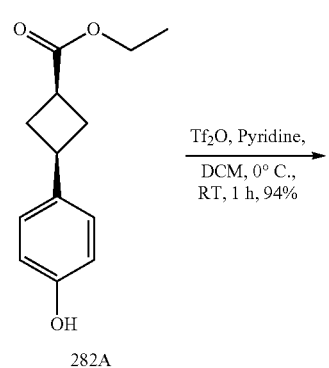

282A

Tf₂O, Pyridine,
DCM, 0° C.,
RT, 1 h, 94%

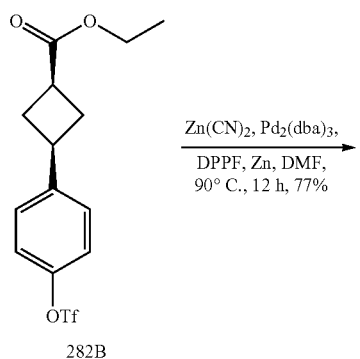

282B

Zn(CN)₂, Pd₂(dba)₃,
DPPF, Zn, DMF,
90° C., 12 h, 77%

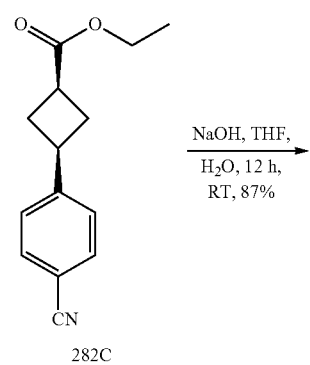

282C

NaOH, THF,
H₂O, 12 h,
RT, 87%

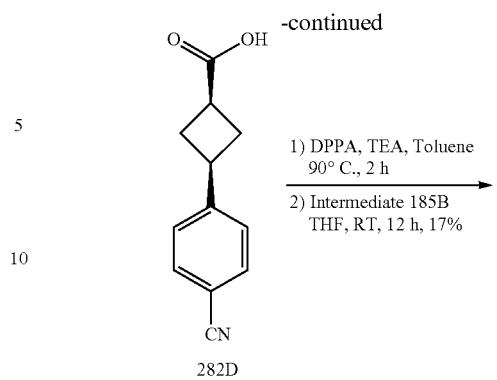

282D

1) DPPA, TEA, Toluene
90° C., 2 h
2) Intermediate 185B
THF, RT, 12 h, 17%

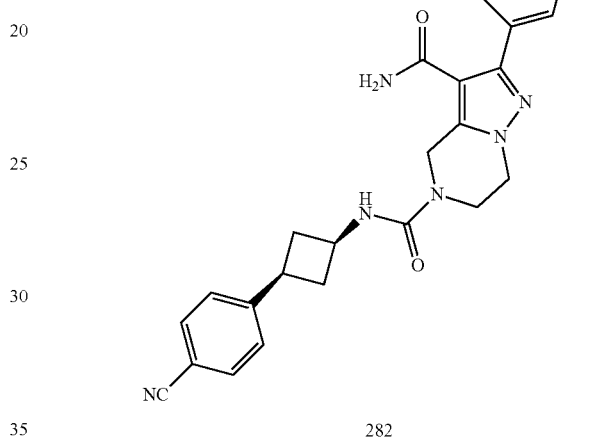

282

Intermediate 282A: (1s,3s)-Ethyl 3-(4-hydroxyphenyl)cyclobutanecarboxylate

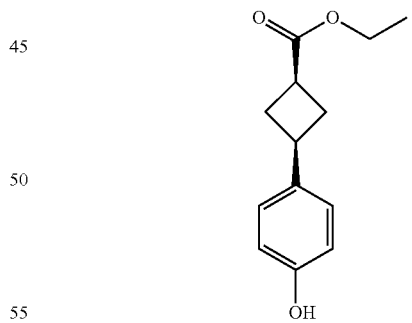

To a solution of (1s,3s)-ethyl 3-(4-methoxyphenyl)cyclobutanecarboxylate (1.6 g, 6.83 mmol) in DCM (40 mL) was added BBr3 (20.49 mL, 20.49 mmol) dropwise at 0° C. and the reaction mass was allowed to warm to RT and stir for 1 h. The reaction mixture was then diluted with DCM (30 mL), washed with water (20 mL) and a 10% aqueous solution of NaHCO₃ (20 mL), dried over Na₂SO₄, filtered and concentrated to afford Intermediate 282A as colorless gum (0.9 g, 60%). ¹H NMR (300 MHz, DMSO-d₆) δ ppm 9.20 (s, 1H), 7.02 (d, J=8.3 Hz, 2H), 6.69 (d, J=8.3 Hz, 2H), 4.07 (d, J=7.2 Hz, 2H), 3.31-3.22 (m, 1H), 3.15-2.98 (m, 1H), 2.48-2.39 (m, 2H), 2.21-2.03 (m, 2H), 1.19 (t, J=7.0 Hz, 3H).

Intermediate 282B: (1s,3s)-Ethyl 3-(4-(((trifluoromethyl)sulfonyl)oxy)phenyl)cyclobutanecarboxylate

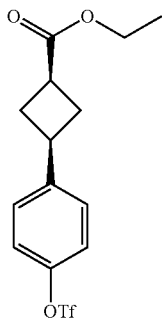 [SMILES: CCOC(=O)[C@H]1C[C@@H](c2ccc(OS(=O)(=O)C(F)(F)F)cc2)C1]

To a solution of Intermediate 282A (0.2 g, 0.908 mmol) in DCM (5 mL) was added pyridine (0.147 mL, 1.816 mmol) and followed by dropwise introduction of trifluoromethanesulfonic anhydride (0.229 mL, 1.362 mmol) at 0° C. The reaction mixture was allowed to warm to RT and stir for 1 h, after which it was diluted with DCM (30 mL) and washed sequentially with a 10% aqueous solution of NaHCO$_3$ (15 mL), a 1.5N aq. solution of HCl (10 mL), and brine, then was dried over Na$_2$SO$_4$, filtered and concentrated to afford Intermediate 282B as a brown liquid (0.3 g, 94%). $^1$H NMR (400 MHz, DMSO-d$_6$) δ ppm 7.43 (d, J=2.0 Hz, 4H), 4.08 (d, J=7.0 Hz, 2H), 3.59-3.46 (m, 1H), 3.22-3.10 (m, 1H), 2.63-2.54 (m, 2H), 2.30-2.16 (m, 2H), 1.20 (t, J=7.3 Hz, 3H).

Intermediate 282C: (1s,3s)-Ethyl 3-(4-cyanophenyl)cyclobutanecarboxylate

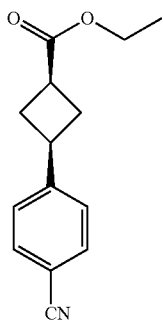 [SMILES: CCOC(=O)[C@H]1C[C@@H](c2ccc(C#N)cc2)C1]

To a solution of Intermediate 282B (0.3 g, 0.851 mmol) in DMF (3 mL) was added zinc (0.017 g, 0.255 mmol) and zinc cyanide (0.250 g, 2.129 mmol) at RT. The reaction mixture was degassed with N$_2$ for 15 min. prior to the addition of DPPF (0.047 g, 0.085 mmol) and Pd$_2$(dba)$_3$ (0.039 g, 0.043 mmol). The resulting solution was again degassed with N$_2$ for 15 min. The reaction mixture was heated to 90° C. and stirred for 12 h. The reaction mixture was quenched with water (40 mL) and extracted with EtOAc (3×20 mL). The combined organic layer was dried over Na$_2$SO$_4$, filtered and the filtrate concentrated. The crude product was purified by silica gel chromatography (24 g REDISEP® column, eluting with 10% EtOAc in hexane). Fractions containing the product were combined and evaporated to afford Intermediate 282C as a colorless liquid (0.15 g, 77%). $^1$H NMR (400 MHz, DMSO-d$_6$) δ ppm 7.85-7.68 (d, 2H), 7.44 (d, J=8.0 Hz, 2H), 4.08 (q, J=7.0 Hz, 2H), 3.70-3.46 (m, 1H), 3.18 (s, 1H), 2.65-2.54 (m, 2H), 2.24 (m, J=12.0 Hz, 2H), 1.23-1.16 (m, 3H).

Intermediate 282D: (1s,3s)-3-(4-Cyanophenyl)cyclobutanecarboxylic acid

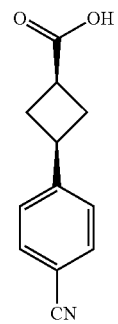

To a solution of Intermediate 282C (0.17 g, 0.741 mmol) in THF (2 mL) and water (2 mL) was added LiOH (0.036 g, 1.483 mmol) at RT and the reaction mixture was stirred for 12 h. The reaction mixture was concentrated and the residue was acidified to a pH of 2 with an aqueous solution of 1.5N HCl and extracted with EtOAc (3×15 mL). The combined organic layer was dried over Na$_2$SO$_4$, filtered and concentrated to afford Intermediate 282D as a colorless liquid (0.13 g, 87%). $^1$H NMR (400 MHz, DMSO-d$_6$) δ ppm 12.34-12.02 (s, 1H), 7.79 (d, J=8.5 Hz, 2H), 7.44 (d, J=8.0 Hz, 2H), 3.66-3.41 (m, 1H), 3.18-2.98 (m, 1H), 2.66-2.53 (m, 2H), 2.31-2.10 (m, 2H).

Compound 282: 2-(3-Chloro-4-fluorophenyl)-N$^5$-((1s,3s)-3-(4-cyanophenyl)cyclobutyl)-6,7-dihydropyrazolo[1,5-a]pyrazine-3,5(4H)-dicarboxamide

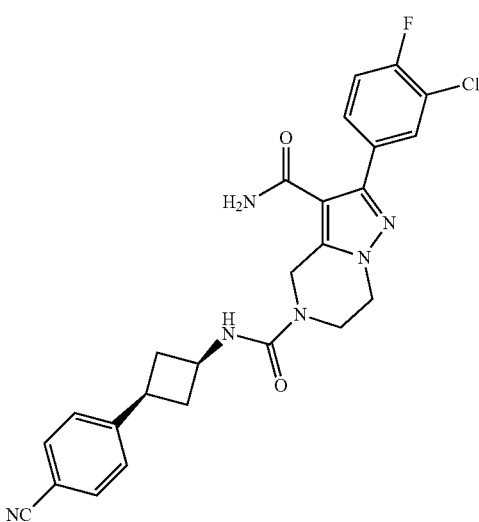 [SMILES: N#Cc1ccc([C@H]2C[C@@H](NC(=O)N3CCn4nc(-c5ccc(F)c(Cl)c5)c(C(N)=O)c4C3)C2)cc1]

To a solution of Intermediate 282D (41.0 mg, 0.204 mmol) in toluene (1 mL) was added TEA (0.095 mL, 0.679 mmol), DPPA (0.058 mL, 0.271 mmol) and the reaction mixture was heated to 90° C. and stirred for 1 h. The reaction mixture was cooled to RT and to it was added a solution of Intermediate 185B (40 mg, 0.136 mmol) in THF (1 mL) and stirred for 12 h. The reaction mixture was diluted with EtOAc (10 mL), washed successively with 10% aqueous solution of NaHCO$_3$, brine, dried over Na$_2$SO$_4$, filtered and the filtrate concentrated. The crude product was purified by preparative HPLC to afford Compound 282 as an off-white solid (28 mg, 40%). HPLC retention times 1.569 and 1.603 min (Methods E and L respectively). MS(ES): m/z=493.2 [M+H]$^+$; $^1$H NMR (400 MHz, DMSO-d$_6$) δ ppm 7.86-7.83 (m, 1H), 7.81-7.78 (m, 2H), 7.68 (ddd, J=2.3, 4.8, 8.5 Hz, 1H), 7.51-7.44 (m, 3H), 7.36 (br. s., 1H), 7.19 (br. s., 1H), 7.11 (d, J=7.5 Hz, 1H), 4.73 (s, 2H), 4.22-4.08 (m, 3H), 3.84 (t, J=5.3 Hz, 2H), 3.24-3.16 (m, 1H), 2.69-2.58 (m, 2H), 2.15-2.06 (m, 2H).

The Compounds shown in Table 27 have been prepared similar to Compound 282 by coupling of in-situ generated isocyanate of 282D with 185B analogs.

Scheme 33

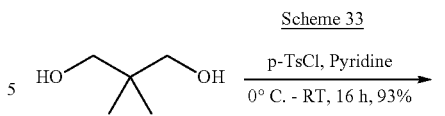

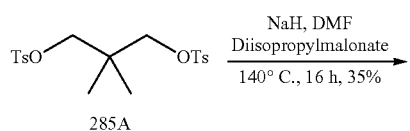

285A

TABLE 27

| Ex. No. | Structure | Name | [M + H]$^+$ | Ret Time (min.) | HPLC Methods |
|---|---|---|---|---|---|
| 283 | 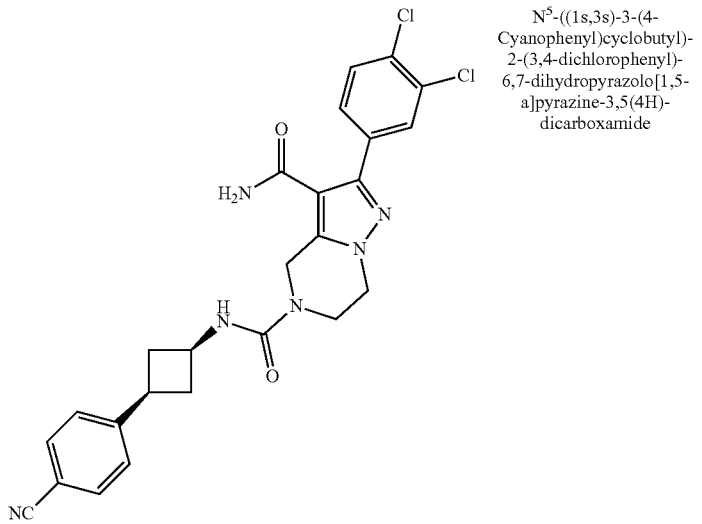 | N$^5$-((1s,3s)-3-(4-Cyanophenyl)cyclobutyl)-2-(3,4-dichlorophenyl)-6,7-dihydropyrazolo[1,5-a]pyrazine-3,5(4H)-dicarboxamide | 509.2 | 1.671 1.704 | E L |
| 284 | 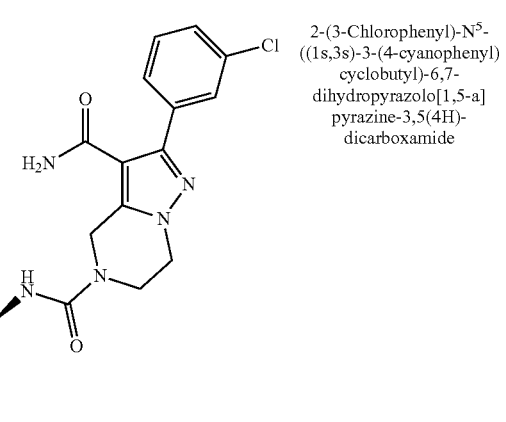 | 2-(3-Chlorophenyl)-N$^5$-((1s,3s)-3-(4-cyanophenyl)cyclobutyl)-6,7-dihydropyrazolo[1,5-a]pyrazine-3,5(4H)-dicarboxamide | 475.3 | 1.546 1.553 | E L |

DMSO-$d_6$) δ ppm 7.70-7.77 (m, 4H), 7.47 (d, J=8.03 Hz, 4H), 3.72 (s, 4H), 2.42 (s, 6H), 0.77 (s, 6H).

Intermediate 285B: Diisopropyl 3,3-dimethylcyclobutane-1,1-dicarboxylate

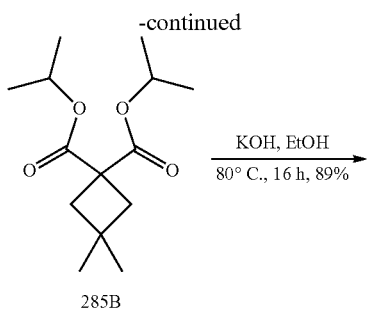

285B

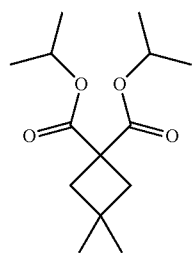 [SMILES: CC(C)OC(=O)C1(C(=O)OC(C)C)CC(C)(C)C1]

To a stirred suspension of NaH (2.036 g, 50.9 mmol, 60 wt % oil suspension) in DMF (50 mL) was added diisopropyl malonate (3.19 g, 16.97 mmol) dropwise at RT and the reaction mixture was stirred for 30 min. A solution of Intermediate 285A (7.0 g, 16.97 mmol) in DMF (20 mL) was added and the resulting reaction mixture was stirred at 140° C. for 16 h. The reaction mixture was cooled to RT, quenched with crushed ice and extracted with diethyl ether (2×250 mL). The combined organic layers were washed with water, dried over $Na_2SO_4$ and concentrated. The crude product was purified by silica gel chromatography (40 g REDISEP® column, eluting with 10% EtOAc in hexanes). Fractions containing the product were combined and evaporated to afford Intermediate 285B (1.5 g, 35%). $^1$H NMR (300 MHz, chloroform-d) δ ppm 5.00-5.14 (m, 2H), 2.34-2.38 (m, 4H), 1.21-1.34 (m, 12H), 1.11-1.15 (m, 6H).

Intermediate 285C: 3,3-Dimethylcyclobutane-1,1-dicarboxylic acid

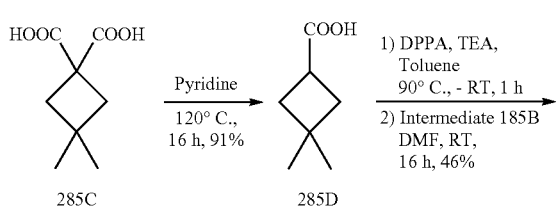

285C          285D

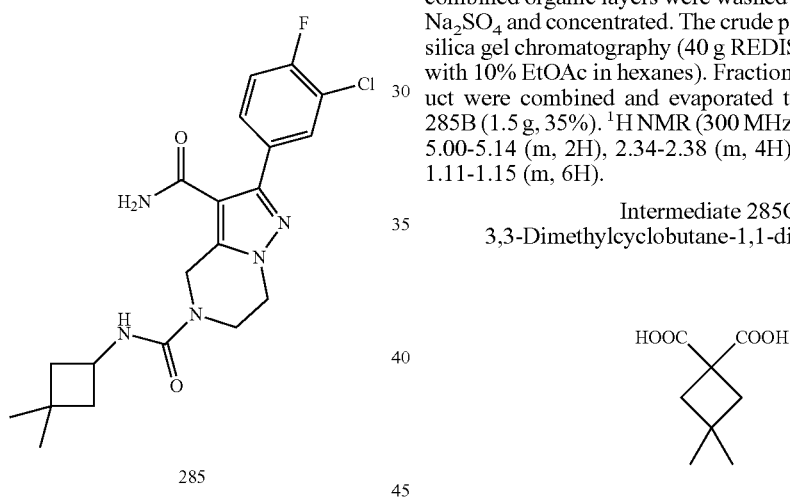

285

Intermediate 285A: 2,2-Dimethylpropane-1,3-diyl bis(4-methylbenzenesulfonate)

To a stirred solution of p-toluenesulfonyl chloride (16.47 g, 86 mmol) in pyridine (20 mL) was added a solution of 2,2-dimethylpropane-1,3-diol (3.0 g, 28.8 mmol) in pyridine (20 mL) at 0° C. and the reaction mixture was allowed to stir at RT for 16 h. After the completion of the reaction, the reaction mixture was quenched with crushed ice and extracted with EtOAc (2×100 mL). The combined organic layer was washed with a 1.5 N aq. solution of HCl, followed by water, then dried over $Na_2SO_4$ and concentrated to afford Intermediate 285A as a pale yellow solid (11 g, 93% yield). $^1$H NMR (400 MHz, To a stirred solution of Intermediate 285B (1.5 g, 5.85 mmol) in ethanol (20 ml) was added a solution of KOH (1.313 g, 23.41 mmol) in water (10 mL). The resulting solution was stirred at 80° C. for 16 h. The reaction mixture was cooled to RT, quenched with crushed ice and extracted with diethyl ether (2×50 mL). The combined organic layers were dried over $Na_2SO_4$ and evaporated to afford Intermediate 285C as a viscous liquid (0.9 g, 89% yield). $^1$H NMR (400 MHz, DMSO-$d_6$) δ ppm 12.64 (br. s., 2H), 2.17-2.29 (m, 4H), 1.01-1.12 (m, 6H).

Intermediate 285D: 3,3-Dimethylcyclobutanecarboxylic acid

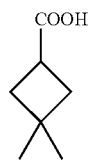

A solution of Intermediate 285C (250 mg, 1.452 mmol) in pyridine (5 mL) was stirred at 120° C. for 16 h. The reaction mixture was then cooled to RT, quenched with a 1.5 N aq. solution of HCl at 0° C., and extracted with diethyl ether (2×50 mL). The combined organic layers were washed with brine, dried over $Na_2SO_4$ and evaporated to afford Intermediate 285D as a viscous liquid (170 mg, 91% yield). $^1$H NMR (400 MHz, DMSO-$d_6$) δ ppm 2.90-3.02 (m, 1H), 1.84-1.95 (m, 4H), 1.07-1.14 (m, 3H), 0.99-1.07 (m, 3H).

Compound 285: 2-(3-Chloro-4-fluorophenyl)-$N^5$-(3,3-dimethylcyclobutyl)-6,7-dihydropyrazolo[1,5-a]pyrazine-3,5(4H)-dicarboxamide

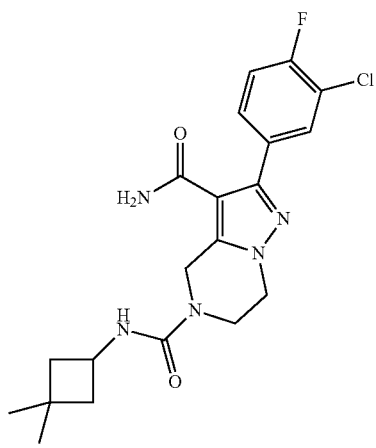 [SMILES: CC1(C)CC(NC(=O)N2CCn3nc(-c4ccc(F)c(Cl)c4)c(C(N)=O)c3C2)C1]

To a stirred solution of Intermediate 285D (13 mg, 0.1 mmol) in toluene (2 ml) was added TEA (0.071 ml, 0.509 mmol), DPPA (0.028 ml, 0.122 mmol) and the reaction mixture was heated to 90° C. for 1 h. The reaction mixture was cooled to RT and to it was added a solution of Intermediate 185B (30 mg, 0.102 mmol) in DMF (1 mL) and stirred at RT for 16 h. The reaction mixture was quenched with 10% $NaHCO_3$ and extracted with ethyl acetate (2×20 mL). The combined organic layer was dried over $Na_2SO_4$, filtered and the filtrate evaporated under reduced pressure. The crude product was purified by preparative HPLC to afford Compound 285 (20 mg, 46%). HPLC retention times 9.40 min. and 8.50 min (Methods A and B respectively). MS(ES): m/z=420 $[M+H]^+$; $^1$H NMR (400 MHz, DMSO-$d_6$) δ ppm 7.81-7.90 (m, 1H), 7.64-7.74 (m, 1H), 7.42-7.46 (m, 1H), 7.14-7.40 (d, 2H), 6.98 (s, 1H), 4.72 (s, 2H), 4.06-4.20 (m, 3H), 3.82 (t, J=5.27 Hz, 2H), 1.95-2.05 (m, 2H), 1.72-1.83 (m, 2H), 1.11 (d, J=7.53 Hz, 6H).

The Compounds shown in Table 28 have been prepared similar to Compound 285 by coupling of in-situ generated isocyanate of 285D with 185B analogs.

TABLE 28

| Ex. No. | Structure | Name | $[M + H]^+$ | Ret Time (min.) | HPLC Methods |
|---|---|---|---|---|---|
| 286 | 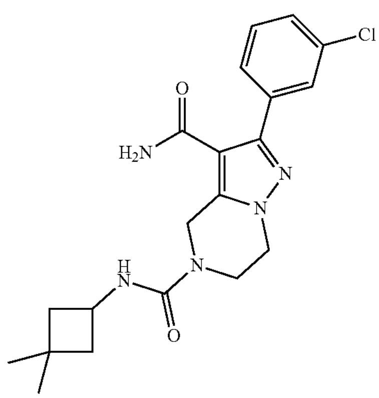 [SMILES: CC1(C)CC(NC(=O)N2CCn3nc(-c4cccc(Cl)c4)c(C(N)=O)c3C2)C1] | 2-(3-Chloro-4-fluorophenyl)-$N^5$-(3,3-dimethylcyclobutyl)-6,7-dihydropyrazolo[1,5-a]pyrazine-3,5(4H)-dicarboxamide | 402 | 9.14<br>8.24 | A<br>B |

TABLE 28-continued

| Ex. No. | Structure | Name | [M + H]⁺ | Ret Time (min.) | HPLC Methods |
|---|---|---|---|---|---|
| 287 | 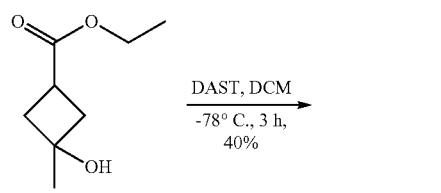 | 2-(3,4-Dichlorophenyl)-$N^5$-(3,3-dimethylcyclobutyl)-6,7-dihydropyrazolo[1,5-a]pyrazine-3,5(4H)-dicarboxamide | 436 | 9.8<br>8.8 | A<br>B |

Scheme 34

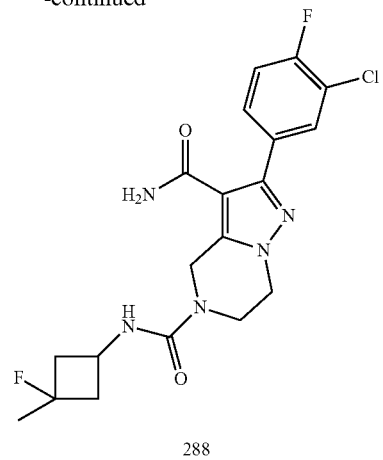

288

Intermediate 288A: Ethyl 3-fluoro-3-methylcyclobutanecarboxylate

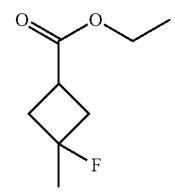

To a solution of ethyl 3-hydroxy-3-methylcyclobutanecarboxylate (500 mg, 3.16 mmol) in DCM (5 mL) was added DAST (0.626 mL, 4.74 mmol) at −78° C. and the reaction mixture was slowly allowed to warm to RT and stir for 3 h. The reaction mixture was diluted with DCM (25 mL), washed with H₂O and a saturated aq. solution of NaHCO₃, then dried

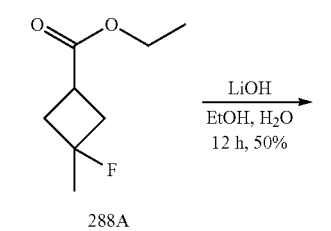

288A

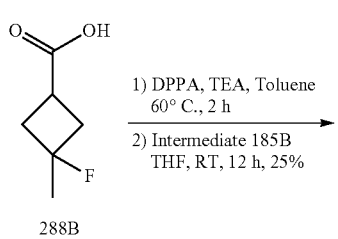

288B over Na$_2$SO$_4$, filtered and concentrated. The crude product was purified by silica gel chromatography (12 g REDISEP® column, eluting with 25% EtOAc in hexanes). Fractions containing the product were combined and evaporated to afford Intermediate 288A as a pale yellow liquid (0.2 g, 40% yield). $^1$H NMR (400 MHz, DMSO-d$_6$) δ ppm 4.08 (q, J=7.0 Hz, 2H), 3.22-3.09 (m, 1H), 2.60-2.53 (m, 1H), 2.37-2.22 (m, 3H), 1.44 (d, J=18 Hz, 3H), 1.22-1.11 (m, 3H).

Intermediate 288B:
3-Fluoro-3-methylcyclobutanecarboxylic acid

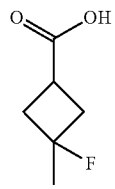

To a solution of Intermediate 288A (0.2 g, 1.249 mmol) in ethanol (2 mL) and H$_2$O (1 mL) was added LiOH (0.060 g, 2.497 mmol) and the reaction mixture was stirred at RT for 12 h. Ethanol was concentrated under reduced pressure and the residue was acidified with a 1.5N aq. solution of HCl and extracted with DCM (3×20 mL) The combined organic layers were dried over Na$_2$SO$_4$, filtered and the filtrate concentrated to afford 288B as a yellow liquid (80 mg, 50% yield). $^1$H NMR (400 MHz, DMSO-d$_6$) δ ppm 12.29 (br. s., 1H), 3.13-2.99 (m, 1H), 2.56-2.52 (m, 1H), 2.48-2.42 (m, 1H), 2.35-2.22 (m, 2H), 1.44 (d, J=18 Hz, 3H).

Compound 288: 2-(3,4-Dichlorophenyl)-N$^5$-(3-fluoro-3-methylcyclobutyl)-6,7-dihydropyrazolo[1,5-a]pyrazine-3,5(4H)-dicarboxamide

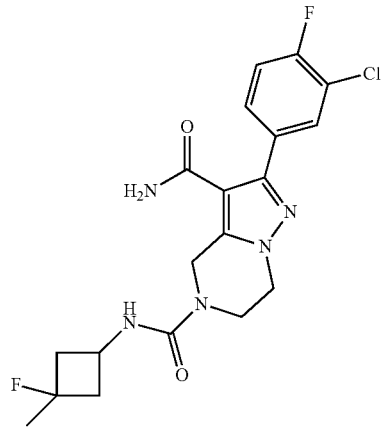 [SMILES: CC1(F)CC(NC(=O)N2CCn3nc(-c4ccc(F)c(Cl)c4)c(C(N)=O)c3C2)C1]

To a solution of Intermediate 288B (76 mg, 0.578 mmol) in toluene (2 mL) was added TEA (0.121 mL, 0.868 mmol), DPPA (0.166 mL, 0.723 mmol) and the reaction mixture was stirred at 60° C. for 2 h. The reaction mixture was cooled to RT and to it was added a solution of Intermediate 185B (90 mg, 0.289 mmol) in THF (1 mL) and stirred for 12 h. The reaction mixture was diluted with water (25 mL) and extracted with ethyl acetate (3×20 mL). The combined organic layer was washed with brine, dried over Na$_2$SO$_4$, filtered and the filtrate concentrated. The crude product was purified by preparative HPLC to afford Compound 288 as an off-white solid (15 mg, 25% yield). MS(ES): m/z=423 [M+H]$^+$; HPLC retention time 1.25 min and 1.29 min (Methods E and L respectively). $^1$H NMR (400 MHz, DMSO-d$_6$) δ ppm 7.84 (dd, J=7.28, 2.13 Hz, 1H), 7.67 (ddd, J=8.64, 4.82, 2.16 Hz, 1H), 7.46 (t, J=9.04 Hz, 1H), 7.34 (br. s., 1H), 7.17 (br. s., 1H), 7.07 (d, J=6.53 Hz, 1H), 4.72 (s, 2H), 4.18-4.28 (m, 1H), 4.13 (t, J=5.27 Hz, 2H), 3.82 (t, J=5.33 Hz, 2H), 2.43-2.48 (m, 1H), 2.07-2.22 (m, 2H), 1.37-1.48 (m, 3H).

The Compounds shown in Table 29 have been prepared similar to Compound 288 by coupling of in-situ generated isocyanate of 288B with 185B analogs

TABLE 29

| Ex. No. | Structure | Name | [M + H]$^+$ | Ret Time (min.) | HPLC Methods |
|---|---|---|---|---|---|
| 289 | 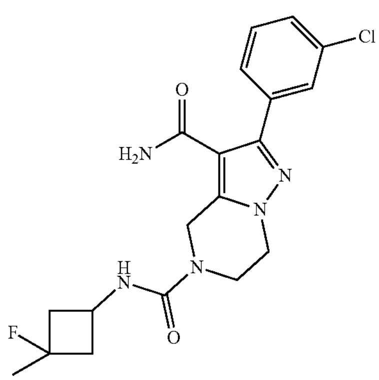 [SMILES: CC1(F)CC(NC(=O)N2CCn3nc(-c4cccc(Cl)c4)c(C(N)=O)c3C2)C1] | 2-(3-Chlorophenyl)-N$^5$-(3-fluoro-3-methylcyclobutyl)-6,7-dihydropyrazolo[1,5-a]pyrazine-3,5(4H)-dicarboxamide | 406.2 | 7.609<br>7.955 | B<br>M |

TABLE 29-continued

| Ex. No. | Structure | Name | [M + H]+ | Ret Time (min.) | HPLC Methods |
|---|---|---|---|---|---|
| 290 | 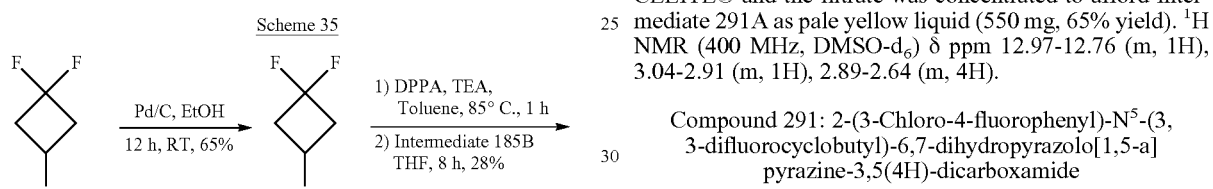 | 2-(3,4-Dichlorophenyl)-N5-(3-fluoro-3-methylcyclobutyl)-6,7-dihydropyrazolo[1,5-a]pyrazine-3,5(4H)-dicarboxamide | 440.2 | 8.447<br>8.893 | B<br>M |

Scheme 35

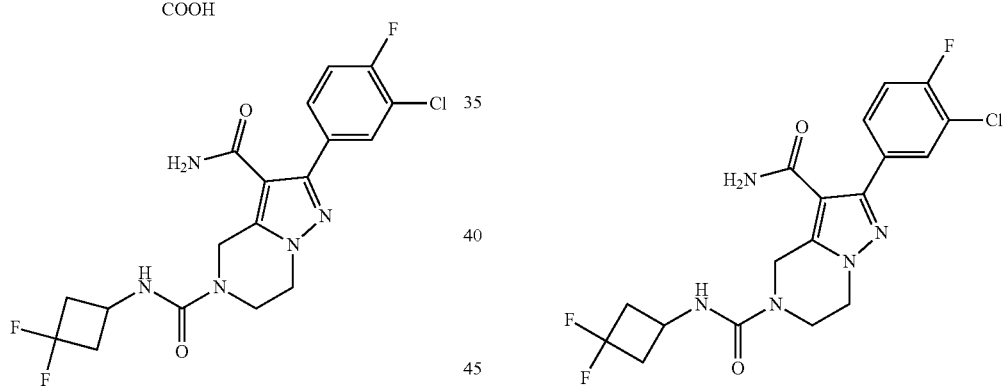

291

Intermediate 291A:
3,3-Difluorocyclobutanecarboxylic acid

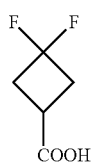

To a solution of benzyl 3,3-difluorocyclobutanecarboxylate (1.4 g, 6.2 mmol) in ethanol (50 mL) was added palladium on activated carbon (500 mg) and the reaction mixture was stirred at RT under an atmosphere of hydrogen (1 atm) for 12 h. The reaction mixture was filtered through a pad of CELITE® and the filtrate was concentrated to afford Intermediate 291A as pale yellow liquid (550 mg, 65% yield). $^1$H NMR (400 MHz, DMSO-d$_6$) δ ppm 12.97-12.76 (m, 1H), 3.04-2.91 (m, 1H), 2.89-2.64 (m, 4H).

Compound 291: 2-(3-Chloro-4-fluorophenyl)-N5-(3,3-difluorocyclobutyl)-6,7-dihydropyrazolo[1,5-a]pyrazine-3,5(4H)-dicarboxamide A stirred solution of Intermediate 291A (236 mg, 1.731 mmol) in toluene (12 mL) was added TEA (0.709 mL, 5.09 mmol), DPPA (0.467 mL, 2.036 mmol) and the reaction mixture was heated at 85° C. for 1 h. The reaction mass was cooled to RT and to it was added a solution of Intermediate 185B (300 mg, 1.018 mmol) in TIE (1 mL) and stirred at RT for 8 h. The reaction mixture was diluted with water and the aqueous layer was extracted with ethyl acetate (2×15 mL) The combined organic layer was washed with brine, dried over Na$_2$SO$_4$, filtered and the filtrate concentrated. The crude product was purified by preparative HPLC to afford Compound 291 as an off-white solid (121 mg, 27.5%). HPLC retention times 7.98 min. and 5.58 min (Methods B and A respectively). MS(ES): m/z=428 [M+H]+; $^1$H NMR (400 MHz, DMSO-d$_6$) δ ppm 7.81-7.86 (m, 1H), 7.63-7.71 (m, 1H), 7.42-7.50 (m, 1H), 7.30-7.38 (m, 1H), 7.23-7.27 (m, 1H), 7.12-7.20 (m, 1H), 4.71-4.76 (m, 2H), 4.11-4.17 (m, 2H), 3.95-4.07 (m, 1H), 3.80-3.86 (m, 2H), 2.78-2.90 (m, 2H), 2.54-2.70 (m, 2H).

The Compounds shown in Table 30 have been prepared similar to Compound 291 by coupling of in-situ generated isocyanate of 291A with 185B analogs.

TABLE 30

| Ex. No. | Structure | Name | [M + H]⁺ | Ret Time (min.) | HPLC Methods |
|---|---|---|---|---|---|
| 292 | 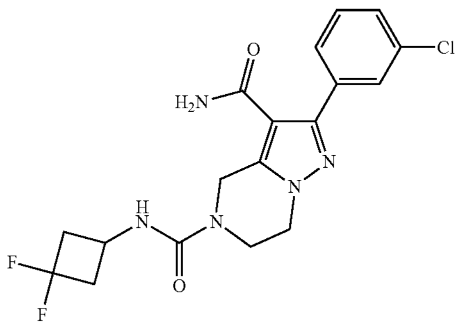 [SMILES: NC(=O)c1c(-c2cccc(Cl)c2)nn2c1CN(C(=O)NC1CC(F)(F)C1)CC2] | 2-(3-Chlorophenyl)-N⁵-(3,3-difluorocyclobutyl)-6,7-dihydropyrazolo[1,5-a]pyrazine-3,5(4H)-dicarboxamide | 410 | 1.18 1.16 | L E |
| 293 | 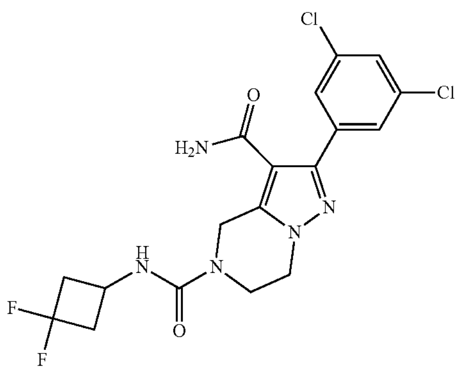 [SMILES: NC(=O)c1c(-c2cc(Cl)cc(Cl)c2)nn2c1CN(C(=O)NC1CC(F)(F)C1)CC2] | 2-(3,5-Dichlorophenyl)-N⁵-(3,3-difluorocyclobutyl)-6,7-dihydropyrazolo[1,5-a]pyrazine-3,5(4H)-dicarboxamide | 444 | 1.39 1.39 | L E |
| 294 | 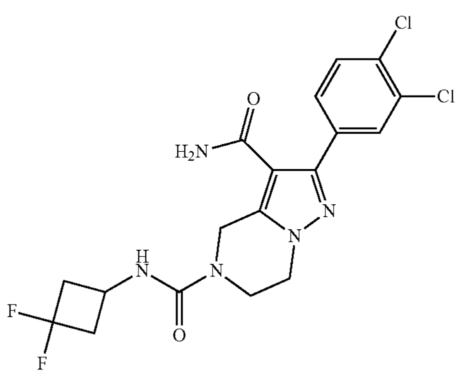 [SMILES: NC(=O)c1c(-c2ccc(Cl)c(Cl)c2)nn2c1CN(C(=O)NC1CC(F)(F)C1)CC2] | 2-(3,4-Dichlorophenyl)-N⁵-(3,3-difluorocyclobutyl)-6,7-dihydropyrazolo[1,5-a]pyrazine-3,5(4H)-dicarboxamide | 444 | 1.35 1.35 | L E |
| 295 | 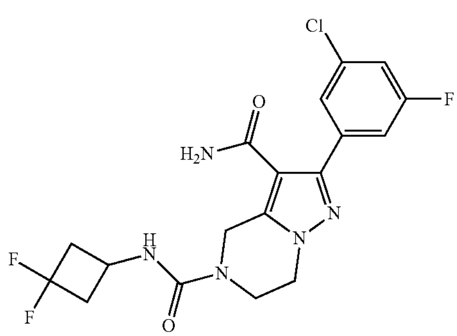 [SMILES: NC(=O)c1c(-c2cc(F)cc(Cl)c2)nn2c1CN(C(=O)NC1CC(F)(F)C1)CC2] | 2-(3-Chloro-5-fluorophenyl)-N⁵-(3,3-difluorocyclobutyl)-6,7-dihydropyrazolo[1,5-a]pyrazine-3,5(4H)-dicarboxamide | 428 | 1.26 1.27 | L E |

Scheme 36

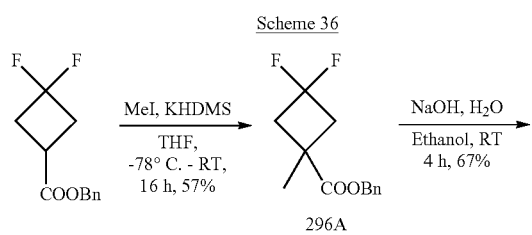

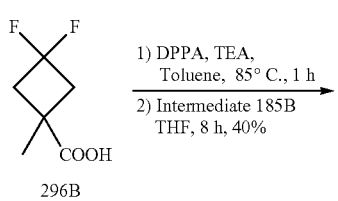

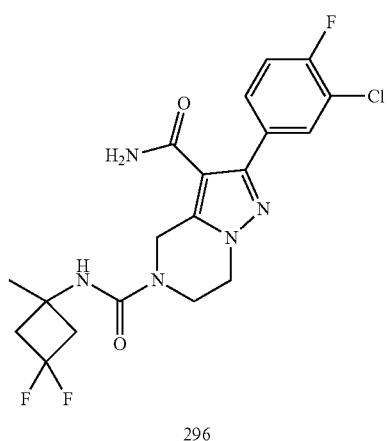

296

Intermediate 296A: Benzyl 3,3-difluoro-1-methylcyclobutanecarboxylate

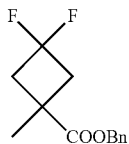

To a solution of benzyl 3,3-difluorocyclobutanecarboxylate (2 g, 8.84 mmol) and MeI (2.202 mL, 35.4 mmol), in THF (15 mL) at −78° C. under a N₂ atmosphere was added a solution of KHMDS (35.4 mL, 17.68 mmol, 0.5 M in toluene). The reaction mixture was then stirred at −78° C. for 6 h after which it was allowed to warm to RT and stir overnight. The reaction mass was then quenched with a saturated aq. solution of NH₄Cl and extracted with diethyl ether (3×25 mL). The combined organic fractions were washed with water, dried over Na₂SO₄, filtered and concentrated under vacuum. The crude product was purified by silica gel chromatography (40 g REDISEP® column, eluting with 20% EtOAc in hexanes). Fractions containing the product were combined and evaporated to afford the Intermediate 296A as a pale yellow liquid (1.2 g, 56.5%). ¹H NMR (400 MHz, chloroform-d) δ ppm 7.50-7.23 (m, 5H), 5.17 (s, 2H), 3.22-2.97 (m, 2H), 2.60-2.28 (m, 2H), 1.51 (s, 3H).

Intermediate 296B: 3,3-Difluoro-1-methylcyclobutanecarboxylic acid

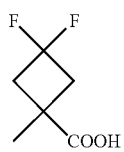

To a solution of Intermediate 296A (1.2 g, 4.99 mmol) in ethanol (5 mL) was added a 5N aq. solution of NaOH (4.99 mL, 24.97 mmol) and the reaction mixture was stirred at RT for 4 h. The reaction mixture was concentrated under reduced pressure; the residue was dissolved in water and extracted with diethyl ether (3×5 mL) The pH of the aqueous solution was adjusted to 7.0 using a 2N aq. solution of HCl and extracted with DCM (3×10 mL). The combined organic layers were dried over Na₂SO₄, filtered and concentrated to afford Intermediate 296B as a pale yellow liquid (500 mg, 67%). ¹H NMR (400 MHz, DMSO-d₆) δ ppm 12.73-12.70 (m, 1H), 3.03-2.89 (m, 2H), 2.49-2.41 (m, 2H), 1.40 (s, 3H).

Compound 296: 2-(3-Chloro-4-fluorophenyl)-N⁵-(3,3-difluoro-1-methylcyclobutyl)-6,7-dihydropyrazolo[1,5-a]pyrazine-3,5(4H)-dicarboxamide

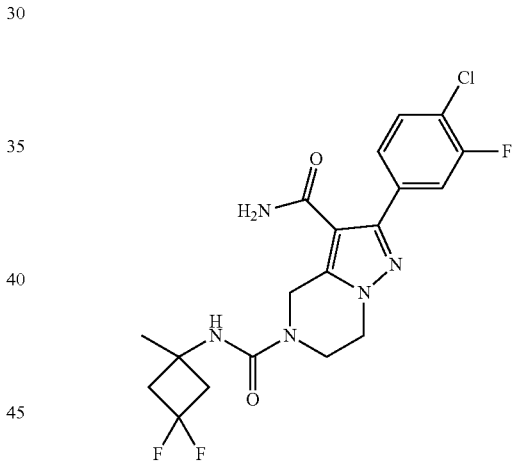

To a solution of Intermediate 296B (30.6 mg, 0.204 mmol) in toluene (6 mL) was added TEA (0.071 mL, 0.509 mmol), DPPA (0.047 mL, 0.204 mmol) and the reaction mixture was heated to 85° C. and stirred for 1 h. The reaction mass was cooled to RT and to it was added a solution of Intermediate 185B (30 mg, 0.102 mmol) in THF (1 mL) and stirred for 12 h. The reaction mixture was concentrated and the residue was extracted with ethyl acetate (3×10 mL). The combined organic layer was washed with water, dried over sodium sulfate, filtered and the filtrate concentrated. The crude product was purified by preparative HPLC to afford Compound 296 as an off-white solid (16 mg, 34.8%). HPLC retention time 1.33 min. and 1.35 min. (Methods J and K respectively). MS(ES): m/z=442 [M+H]⁺; ¹H NMR (400 MHz, DMSO-d₆) δ ppm 7.82-7.89 (m, 1H), 7.66-7.73 (m, 1H), 7.43-7.51 (m, 1H), 7.09-7.33 (m, 1H), 4.73 (s, 2H), 4.12-4.18 (m, 2H), 3.78-3.88 (m, 2H), 2.80-2.94 (m, 2H), 2.55-2.65 (m, 2H), 1.45 (s, 3H).

The Compounds shown in Table 31 have been prepared similar to Compound 296 by coupling of in-situ generated isocyanate of 296B with 185B analogs.

TABLE 31

| Ex. No. | Structure | Name | [M + H]+ | Ret Time (min.) | HPLC Methods |
|---|---|---|---|---|---|
| 297 | 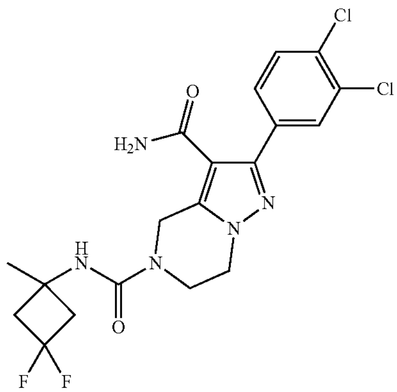 [SMILES: CC1(NC(=O)N2CCn3nc(-c4ccc(Cl)c(Cl)c4)c(C(N)=O)c3C2)CC(F)(F)C1] | 2-(3,4-Dichlorophenyl)-N5-(3,3-difluoro-1-methylcyclobutyl)-6,7-dihydropyrazolo[1,5-a]pyrazine-3,5(4H)-dicarboxamide | 458 | 1.48<br>1.47 | L<br>E |
| 298 | 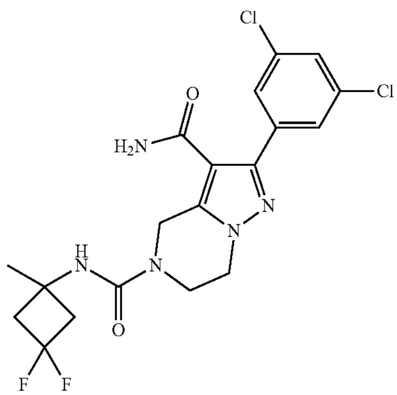 | 2-(3,5-Dichlorophenyl)-N5-(3,3-difluoro-1-methylcyclobutyl)-6,7-dihydropyrazolo[1,5-a]pyrazine-3,5(4H)-dicarboxamide | 458 | 1.52<br>1.50 | L<br>E |
| 299 | 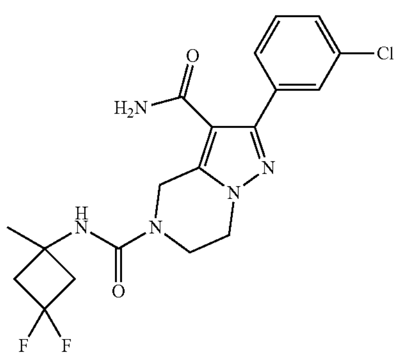 [SMILES: CC1(NC(=O)N2CCn3nc(-c4cccc(Cl)c4)c(C(N)=O)c3C2)CC(F)(F)C1] | 2-(3-Chlorophenyl)-N5-(3,3-difluoro-1-methylcyclobutyl)-6,7-dihydropyrazolo[1,5-a]pyrazine-3,5(4H)-dicarboxamide | 424 | 7.95<br>8.51 | B<br>C |
| 300 | 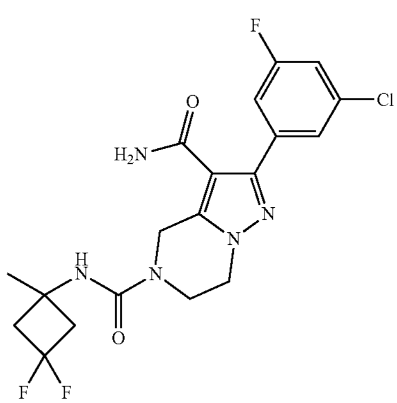 [SMILES: CC1(NC(=O)N2CCn3nc(-c4cc(F)cc(Cl)c4)c(C(N)=O)c3C2)CC(F)(F)C1] | 2-(3-Chloro-5-fluorophenyl)-N5-(3,3-difluoro-1-methylcyclobutyl)-6,7-dihydropyrazolo[1,5-a]pyrazine-3,5(4H)-dicarboxamide | 442 | 1.35<br>1.44 | E<br>L |

Scheme 37

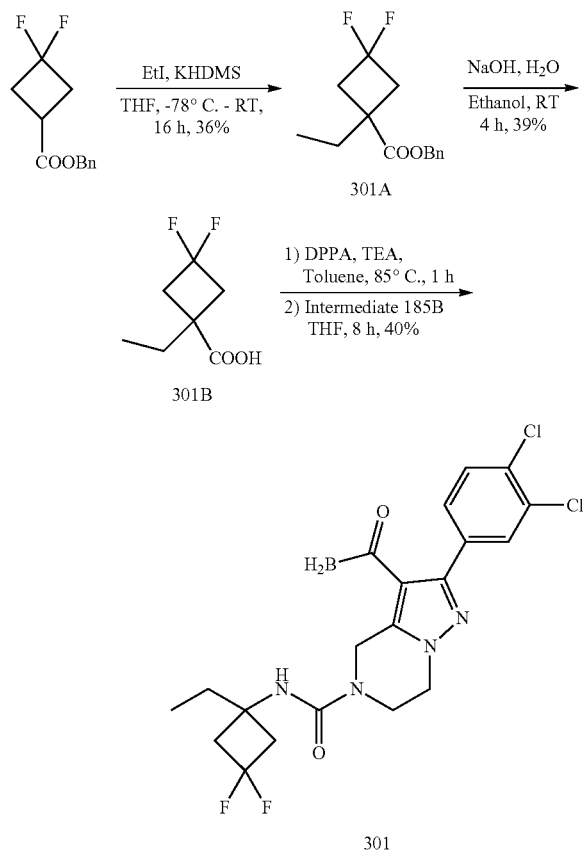

Intermediate 301A: Benzyl 1-ethyl-3,3-difluorocyclobutanecarboxylate

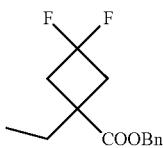

To a solution of benzyl 3,3-difluorocyclobutanecarboxylate (500 mg, 2.210 mmol) and EtI (0.714 mL, 8.84 mmol) in THF (15 mL) at −78° C. under a $N_2$ atmosphere was added a solution of KHMDS (8.84 mL, 4.42 mmol, 0.5 M in toluene). The resulting solution was stirred at −78° C. for 6 h. The reaction was then allowed to warm to RT and stirred overnight. The reaction mass was then quenched with a saturated aq. solution of $NH_4Cl$ and the aqueous layer was extracted with diethyl ether (3×25 mL) The combined organic fractions were washed with water, dried over $Na_2SO_4$, filtered and concentrated under vacuum. The crude product was purified by silica gel chromatography (4 g REDISEP® column, eluting with 15% EtOAc in hexanes). Fractions containing the product were combined and evaporated to afford Intermediate 301A as a pale yellow liquid (200 mg, 35.6%). $^1$H NMR (300 MHz, chloroform-d) δ ppm 7.32-7.44 (m, 5H), 5.19 (s, 2H), 2.90-3.11 (m, 2H), 2.38-2.57 (m, 2H), 1.28 (dt, J=8.97, 7.03 Hz, 2H), 0.79-0.93 (m, 3H).

Intermediate 301B: 1-Ethyl-3,3-difluorocyclobutanecarboxylic acid

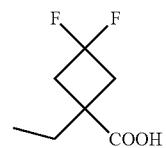

To a solution of Intermediate 301A (0.2 g, 0.787 mmol) in ethanol (5 mL) and water (1 mL) was added a 5N aq. solution of NaOH (0.787 mL, 3.93 mmol) and the reaction mixture was stirred at RT for 4 h. The reaction mixture was concentrated under reduced pressure and the residue was diluted with water and extracted with diethyl ether (3×5 mL). The pH of the aqueous solution was adjusted to 7.0 using a 2N aq. solution of HCl and the aqueous phase was extracted with DCM (3×10 mL). The combined organic layers were dried over $Na_2SO_4$, filtered and concentrated to afford Intermediate 301B as a pale yellow liquid (50 mg, 38.7%). $^1$H NMR (300 MHz, DMSO-$d_6$) δ ppm 12.63-12.75 (m, 1H), 2.80-2.97 (m, 2H), 2.57-245 (m, 2H), 1.77 (q, J=7.55 Hz, 2H), 0.81 (t, J=7.37 Hz, 3H).

Compound 301: 2-(3,4-Dichlorophenyl)-$N^5$-(1-ethyl-3,3-difluorocyclobutyl)-6,7-dihydropyrazolo[1,5-a]pyrazine-3,5(4H)-dicarboxamide

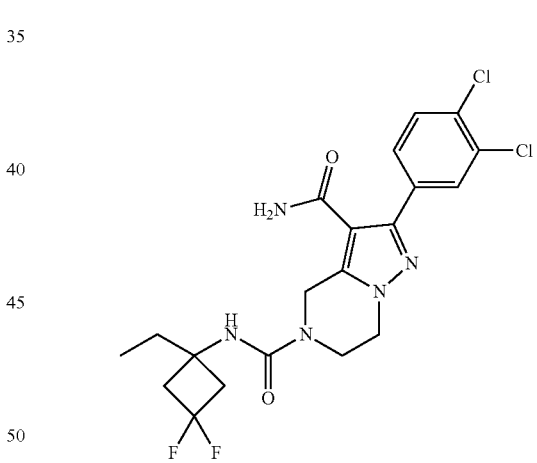

A stirred solution of Intermediate 301B (26.9 mg, 0.164 mmol) in toluene (4 mL) at RT under nitrogen was added TEA (0.067 mL, 0.482 mmol), DPPA (0.044 mL, 0.193 mmol) and heated at 85° C. for 1 h. The reaction mass was cooled to RT and to it was added a solution of Intermediate 185B (30 mg, 0.096 mmol) in THF and stirred for 8 h. The reaction mixture was diluted with water and the aqueous layer was extracted with ethyl acetate (2×15 mL). The combined organic layer was washed with brine, dried over $Na_2SO_4$, filtered and the filtrate concentrated. The crude product obtained was purified by preparative HPLC to afford Compound 301 as an off-white solid (18.1 mg, 40%). HPLC retention times 1.60 min. and 1.59 min. (Methods L and E respectively). MS(ES): m/z=472 [M+H]$^+$; $^1$H NMR (400 MHz, DMSO-$d_6$) δ ppm 7.89-7.92 (m, 1H), 7.65-7.70 (m, 2H), 7.22-7.43 (m, 2H), 7.09 (s, 1H), 4.72 (s, 2H), 4.14 (t, J=5.27 Hz, 2H), 3.84 (t, J=5.52 Hz, 2H), 2.70-2.83 (m, 2H), 2.53-2.65 (m, 2H), 1.79 (q, J=7.36 Hz, 2H), 0.77 (t, J=7.28 Hz, 3H).

Scheme 38

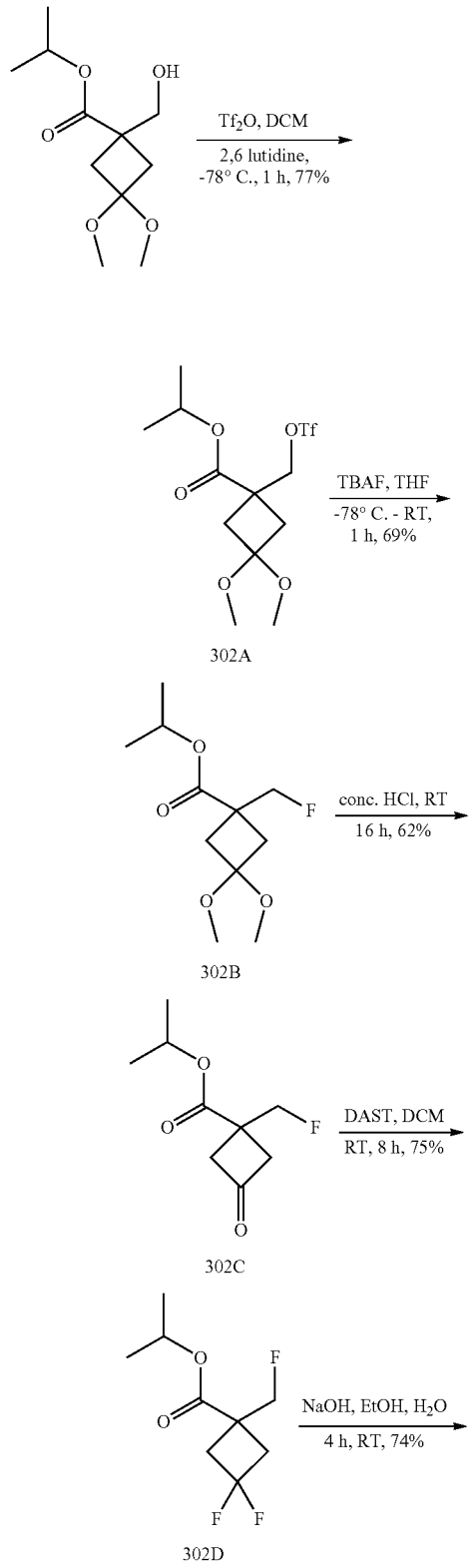

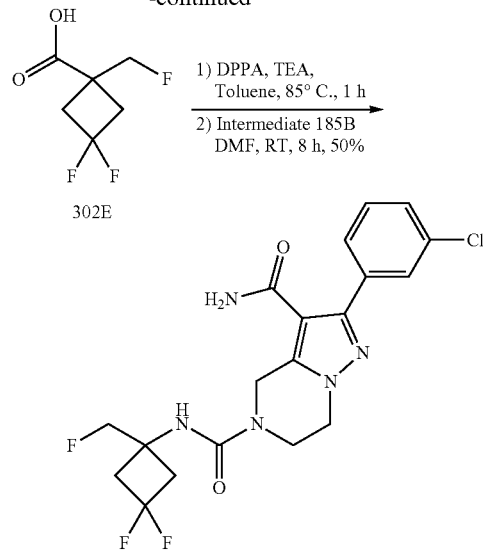

Intermediate 302A: Isopropyl 3,3-dimethoxy-1-(((((trifluoromethyl)sulfonyl)oxy)methyl)cyclobutanecarboxylate

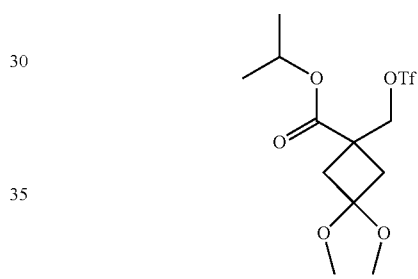

To a solution of isopropyl 1-(hydroxymethyl)-3,3-dimethoxycyclobutanecarboxylate (1.5 g, 6.46 mmol) and 2,6-lutidine (1.122 mL, 9.69 mmol) in DCM (30 mL) cooled to −78° C., was added trifluoromethanesulfonic anhydride (1.309 mL, 7.75 mmol) dropwise and the resulting solution was stirred for 1 h. The reaction mixture was quenched with water and extracted with DCM (3×25 mL). The combined organic layers were washed sequentially with a saturated aq. solution of NaHCO$_3$, a 1N aq. solution of HCl and brine, then dried over Na$_2$SO$_4$, filtered and concentrated to afford Intermediate 302A as a pale brown liquid (1.8 g, 77%). The crude product was taken to the next step without further purification. $^1$H NMR (400 MHz, chloroform-d) δ ppm 4.99-5.13 (m, 1H), 4.79 (s, 2H), 3.16 (d, J=1.51 Hz, 6H), 2.62 (d, J=13.55 Hz, 2H), 2.22 (d, J=14.05 Hz, 2H), 1.27 (d, J=6.53 Hz, 6H).

Intermediate 302B: Isopropyl 1-(fluoromethyl)-3,3-dimethoxycyclobutanecarboxylate

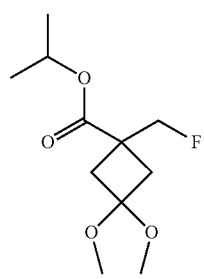 [SMILES: COC1(OC)CC(CF)(C(=O)OC(C)C)C1]

To a solution of Intermediate 302A (1.8 g, 4.94 mmol) in THF (30 mL) was added TBAF (5.93 mL, 5.93 mmol, 1M in THF) at −78° C. and the reaction mixture was stirred at RT for 1 h. It was then quenched with ice-cold water and extracted with ethyl acetate (3×25 mL). The combined organic layer was dried over sodium sulfate, filtered and the filtrate concentrated. The crude product was purified by silica gel chromatography (4 g REDISEP® column, eluting with 25% ethyl acetate in hexanes). Fractions containing the product were combined and evaporated to afford the Intermediate 302B as a pale yellow liquid (0.8 g, 69%). $^1$H NMR (400 MHz, chloroform-d) δ ppm 5.06 (s, 1H), 4.51-4.72 (m, 2H), 3.15 (s, 6H), 2.56 (dd, J=13.55, 2.01 Hz, 2H), 2.21 (d, J=14.06 Hz, 2H), 1.26 (d, J=6.02 Hz, 6H).

Intermediate 302C: Isopropyl 1-(fluoromethyl)-3-oxocyclobutanecarboxylate

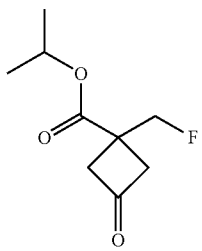

To a stirred solution of Intermediate 302B (0.6 g, 2.56 mmol) was added a conc. aq. solution of HCl (1.576 mL, 20.49 mmol) and the reaction mass was stirred at RT for 16 h. The reaction was extracted with DCM (3×10 mL) and the organic layer was washed with water and a 10% aq. solution of NaHCO$_3$, and then dried over Na$_2$SO$_4$, filtered and concentrated to afford Intermediate 302C as a pale yellow liquid (0.3 g, 62%). $^1$H NMR (400 MHz, chloroform-d) δ ppm 5.12 (s, 1H), 4.67-4.87 (m, 2H), 3.44-3.64 (m, 2H), 3.12-3.31 (m, 2H), 1.29 (d, J=6.53 Hz, 6H).

Intermediate 302D: Isopropyl 3,3-difluoro-1-(fluoromethyl)cyclobutanecarboxylate

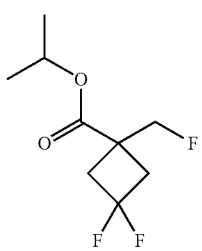

To a solution of Intermediate 302C (0.3 g, 1.594 mmol) in DCM (6 mL) was added DAST (0.211 mL, 1.594 mmol) dropwise under nitrogen and the reaction mixture was stirred at RT for 8 h. The reaction mass was diluted with DCM (25 mL), washed sequentially with a 10% aq. solution of NaHCO$_3$, water and brine, then dried over Na$_2$SO$_4$, filtered and the filtrate concentrated to afford Intermediate 302D as a pale yellow liquid (0.25 g, 75%). The crude compound was taken to the next step without further purification. $^1$H NMR (400 MHz, chloroform-d) δ ppm 5.08 (s, 1H), 4.46-4.84 (m, 2H), 3.03 (t, J=13.55 Hz, 2H), 2.58-2.79 (m, 2H), 1.15-1.32 (m, 6H).

Intermediate 302E: 3,3-Difluoro-1-(fluoromethyl)cyclobutanecarboxylic acid

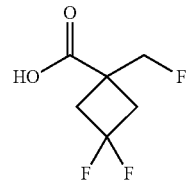 [SMILES: O=C(O)C1(CF)CC(F)(F)C1]

To a solution of Intermediate 302D (0.25 g, 1.189 mmol) in ethanol (5 mL) was added NaOH (1.189 mL, 5.95 mmol, 5 M in water) and the reaction mixture was stirred at RT for 8 h. The reaction mixture was concentrated in vacuo, dissolved in water and extracted with diethyl ether. The pH of the aq. solution was adjusted to 7 using a 2N aq. solution of HCl and extracted with DCM (3×10 mL) The combined organic layer was dried over Na$_2$SO$_4$, filtered, and the filtrate concentrated to afford Intermediate 302E as a pale yellow liquid (0.12 g, 60%). $^1$H NMR (400 MHz, DMSO-d$_6$) δ ppm 13.02-13.40 (br. s., 1H), 4.53-4.76 (m, 2H), 2.95 (q, J=13.22 Hz, 2H), 2.59-2.78 (m, 2H).

Compound 302: 2-(3-Chlorophenyl)-N$^5$-(3,3-difluoro-1-(fluoromethyl)cyclobutyl)-6,7-dihydropyrazolo[1,5-a]pyrazine-3,5(4H)-dicarboxamide

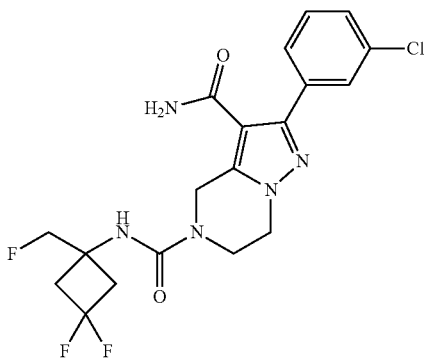 [SMILES: NC(=O)c1c(-c2cccc(Cl)c2)nn2c1CN(C(=O)NC1(CF)CC(F)(F)C1)CC2]

To a stirred solution of Intermediate 302E (26.7 mg, 0.159 mmol) in toluene (3 mL) was added TEA (0.101 mL, 0.723 mmol), DPPA (0.066 mL, 0.289 mmol) and the solution was heated to 85° C. for 1 hr. The reaction mass was cooled to RT and to it was added a solution of Intermediate 156E (40 mg, 0.145 mmol) in DMF (1 mL) and the reaction mixture was stirred at RT for 8 h. It was then concentrated and extracted with ethyl acetate (3×10 mL) The combined organic layer was dried over Na$_2$SO$_4$, filtered and the filtrate concentrated. The crude product was further purified by preparative HPLC to afford Compound 302 as an off-white solid (32 mg, 50%). HPLC retention times 1.41 min. and 1.41 min. (Methods E and L respectively). MS(ES): m/z=441 [M+H]$^+$; $^1$H NMR (400 MHz, DMSO-d$_6$) δ ppm 7.71 (t, J=1.76 Hz, 1H), 7.64 (dt, J=6.65, 1.95 Hz, 1H), 7.41-7.47 (m, 2H), 7.37 (s, 2H), 7.19 (br. s., 1H), 4.75 (s, 2H), 4.44-4.61 (m, 2H), 4.15 (t, J=5.52 Hz, 2H), 3.86 (t, J=5.52 Hz, 2H), 2.81 (t, J=12.30 Hz, 4H).

The Compounds shown in Table 32 have been prepared similar to Compound 302 by coupling of in-situ generated isocyanate of 302E with 199B.

TABLE 32

| Ex. No. | Structure | Name | [M + H]+ | Ret Time (min.) | HPLC Methods |
|---|---|---|---|---|---|
| 303 | 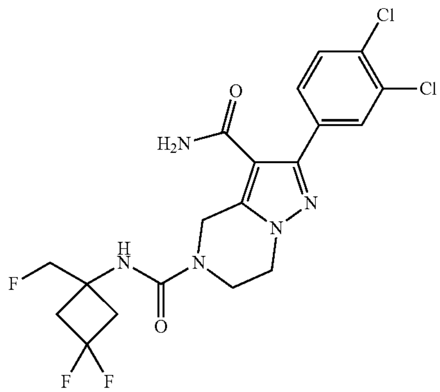 [SMILES: NC(=O)c1c(-c2ccc(Cl)c(Cl)c2)nn2c1CN(C(=O)NC1(CF)CC(F)(F)C1)CC2] | 2-(3,4-Dichlorophenyl)-N5-(3,3-difluoro-1-(fluoromethyl)cyclobutyl)-6,7-dihydropyrazolo[1,5-a]pyrazine-3,5(4H)-dicarboxamide | 476 | 1.58<br>1.59 | E<br>L |

Scheme 39

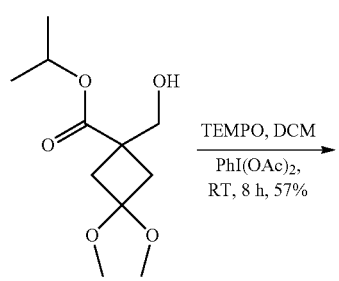

TEMPO, DCM
─────────────
PhI(OAc)₂,
RT, 8 h, 57%

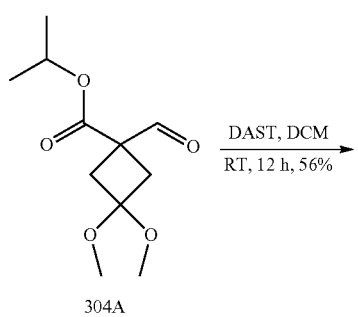

304A

DAST, DCM
─────────────
RT, 12 h, 56%

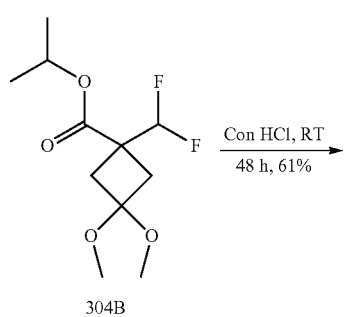

304B

Con HCl, RT
─────────────
48 h, 61%

-continued

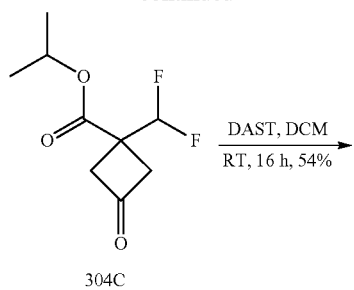

304C

DAST, DCM
─────────────
RT, 16 h, 54%

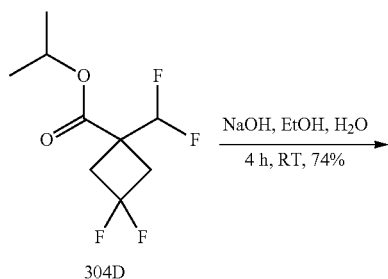

304D

NaOH, EtOH, H₂O
─────────────
4 h, RT, 74%

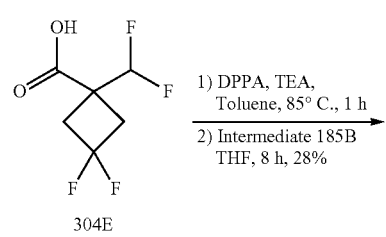

304E

1) DPPA, TEA,
Toluene, 85° C., 1 h
─────────────
2) Intermediate 185B
THF, 8 h, 28%

-continued

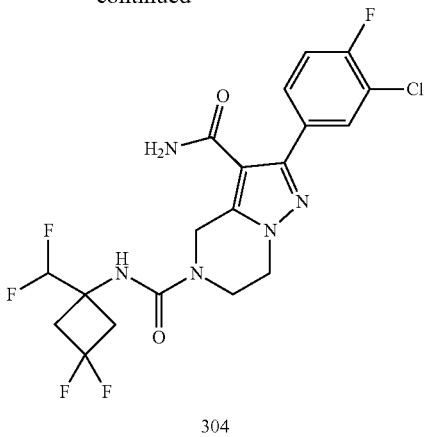

304

Intermediate 304A: Isopropyl
1-formyl-3,3-dimethoxycyclobutanecarboxylate

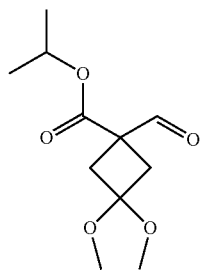 [SMILES: COC1(OC)CC(C=O)(C(=O)OC(C)C)C1]

To a solution of isopropyl 1-(hydroxymethyl)-3,3-dimethoxycyclobutanecarboxylate (2.3 g, 9.90 mmol) in DCM (45 mL) was added iodosobenzene diacetate (4.78 g, 14.85 mmol) and TEMPO (0.155 g, 0.990 mmol) and the mixture was stirred at RT for 8 h. The reaction mass was diluted with DCM (25 mL), washed with and a 10% aq. solution of NaHCO$_3$, dried over Na$_2$SO$_4$, filtered and the filtrate concentrated. The crude product was purified by silica gel chromatography (40 g REDISEP® column, eluting with 5% MeOH in CHCl$_3$). Fractions containing the product were combined and evaporated to afford Intermediate 304A as a pale yellow liquid (1.3 g, 57%). $^1$H NMR (300 MHz, DMSO-d$_6$) δ ppm 9.62 (s, 1H), 4.96 (s, 1H), 3.04 (d, J=7.18 Hz, 6H), 2.59-2.66 (m, 2H), 2.47 (m, 2H), 1.20 (d, J=6.42 Hz, 6H).

Intermediate 304B: Isopropyl 1-(difluoromethyl)-3,3-dimethoxycyclobutanecarboxylate

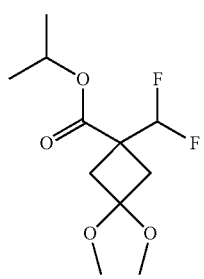 [SMILES: COC1(OC)CC(C(=O)OC(C)C)(C(F)F)C1]

To a solution of Intermediate 304A (1.3 g, 5.65 mmol) in DCM (20 mL) was added DAST (1.492 mL, 11.29 mmol) dropwise under nitrogen and the resulting solution was stirred at RT for 16 h. The reaction mass was diluted with DCM (25 mL), quenched with a 10% aq. solution of NaHCO$_3$, washed with water, brine, Na$_2$SO$_4$, filtered and the filtrate concentrated to afford Intermediate 304B (0.8 g, 56%). $^1$H NMR (400 MHz, chloroform-d) δ ppm 5.86-6.19 (m, 1H), 5.05-5.15 (m, 1H), 3.15 (d, J=3.51 Hz, 6H), 2.55-2.64 (m, 2H), 2.45 (d, J=13.55 Hz, 2H), 1.22-1.29 (m, 6H).

Intermediate 304C: Isopropyl 1-(difluoromethyl)-3-oxocyclobutanecarboxylate

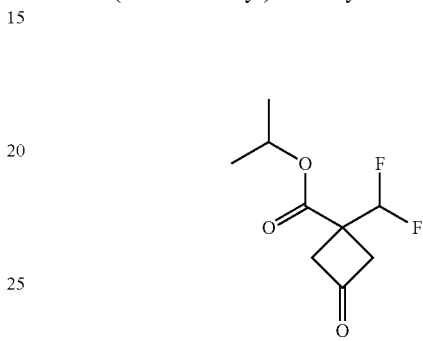

To a stirred solution of Intermediate 304B (300 mg, 1.189 mmol) was added a conc. aq. solution of HCl (0.457 mL, 5.94 mmol) and the reaction mass was stirred at RT for 48 h. The reaction was quenched with water and extracted with DCM (2×25 mL). The organic layer was washed with water, a 10% aq. solution of NaHCO$_3$, dried over Na$_2$SO$_4$, filtered and the filtrate concentrated. The crude product was purified by silica gel chromatography (4 g REDISEP® column, eluting with 25% ethyl acetate in hexanes). Fractions containing the product were combined and evaporated to afford Intermediate 304C as a pale yellow liquid (150 mg, 61%). $^1$H NMR (400 MHz, chloroform-d) δ ppm 6.40 (s, 1H), 5.15 (s, 1H), 3.33-3.51 (m, 4H), 1.23-1.33 (m, 6H).

Intermediate 304D: Isopropyl 1-(difluoromethyl)-3,3-difluorocyclobutanecarboxylate

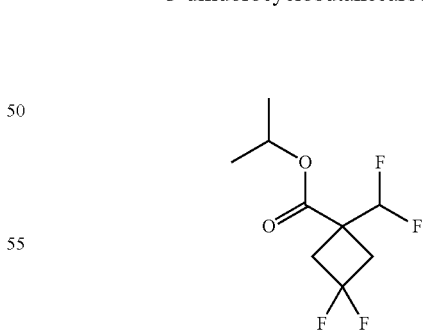

To a solution of Intermediate 304C (150 mg, 0.727 mmol) in DCM (10 mL) was added DAST (0.192 mL, 1.455 mmol) dropwise under nitrogen. The reaction mixture was stirred at RT for 16 h, then diluted with DCM (15 mL) and quenched with a 10% aq. solution of NaHCO$_3$. The organic layer was separated, washed with water, brine, dried over Na$_2$SO$_4$, filtered and the filtrate concentrated. The crude product was purified by silica gel chromatography (4 g REDISEP® column, eluting with 10% ethyl acetate in hexanes). Fractions containing the product were combined and evaporated to afford Intermediate 304D as a pale yellow liquid (90 mg, 54%). $^1$H NMR (400 MHz, chloroform-d) δ ppm 6.16 (s, 1H), 5.03-5.18 (m, 1H), 2.89-3.06 (m, 4H), 1.22-1.35 (m, 6H).

Intermediate 304E: 1-(Difluoromethyl)-3,3-difluoro-cyclobutanecarboxylic acid

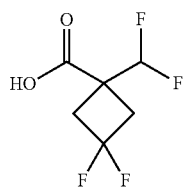 [SMILES: O=C(O)C1(C(F)F)CC(F)(F)C1]

To a solution of Intermediate 304D (500 mg, 2.191 mmol) in ethanol (10 mL) and water (2 mL) was added NaOH (2.191 mL, 10.96 mmol, 5 M in water) and the resulting solution was stirred at RT for 4 h. EtOH was removed under reduced pressure, and the aqueous solution was acidified with a 1.5 N aq. solution of HCl which was then extracted with DCM (3×30 mL). The combined organic layer was washed with brine, dried over Na$_2$SO$_4$, filtered and the filtrate was concentrated to afford Intermediate 304E as a pale yellow liquid (300 mg, 74% yield). $^1$H NMR (400 MHz, DMSO-d$_6$) δ ppm 13.87 (br. s., 1H), 6.21-6.63 (m, 1H), 2.77-3.11 (m, 4H).

Compound 304: 2-(3-Chloro-4-fluorophenyl)-N$^5$-(1-(difluoromethyl)-3,3-difluorocyclobutyl)-6,7-dihydropyrazolo[1,5-a]pyrazine-3,5(4H)-dicarboxamide

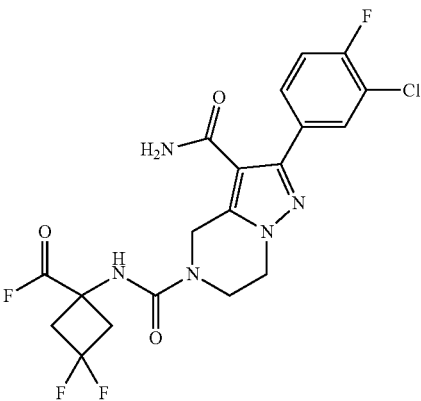 [SMILES: NC(=O)c1c(-c2ccc(F)c(Cl)c2)nn2c1CN(C(=O)NC1(C(=O)F)CC(F)(F)C1)CC2]

To a solution of Intermediate 304E (26.3 mg, 0.141 mmol) in toluene (3 mL) was added TEA (0.090 mL, 0.643 mmol) and DPPA (0.059 mL, 0.257 mmol) and the resulting solution was heated at 85° C. for 1 h. The reaction mixture was cooled to RT and to it was added a solution of Intermediate 185B (40 mg, 0.129 mmol) in DMF (1 mL) and stirred at RT for 8 h. It was concentrated and the residue was extracted with ethyl acetate (3×10 mL). The combined organic layer was dried over sodium sulfate, filtered and the filtrate concentrated. The crude product was further purified by preparative HPLC to afford Compound 304 as an off-white solid (18 mg, 28%). HPLC retention times 1.57 min. and 1.59 min. (Methods E and L respectively). ES(MS): m/z=478 [M+H]$^+$; $^1$H NMR (400 MHz, DMSO-d$_6$) δ ppm 7.90 (d, J=1.5 Hz, 1H), 7.72-7.63 (m, 3H), 7.45-7.21 (m, 2H), 6.47-6.11 (m, 1H), 4.77 (s, 2H), 4.17 (t, J=5.3 Hz, 2H), 3.88 (t, J=5.3 Hz, 2H), 3.06-2.91 (m, 2H), 2.90-2.76 (m, 2H).

The Compounds shown in Table 33 have been prepared similar to Compound 304 by coupling of in-situ generated isocyanate of 282E with 185B analogs.

TABLE 33

| Ex. No. | Structure | Name | [M + H]$^+$ | Ret Time (min.) | HPLC Methods |
|---|---|---|---|---|---|
| 305 | 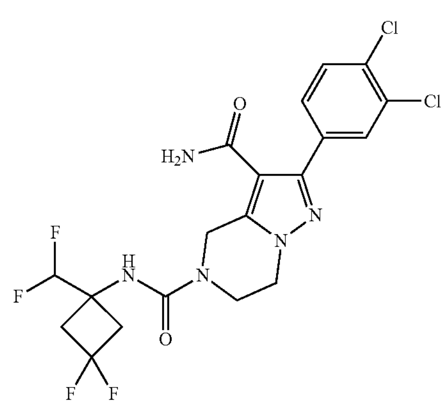 [SMILES: NC(=O)c1c(-c2ccc(Cl)c(Cl)c2)nn2c1CN(C(=O)NC1(C(F)F)CC(F)(F)C1)CC2] | 2-(3,4-Dichlorophenyl)-N$^5$-(1-(difluoromethyl)-3,3-difluorocyclobutyl)-6,7-dihydropyrazolo[1,5-a]pyrazine-3,5(4H)-dicarboxamide | 494 | 1.66<br>1.71 | E<br>L |

TABLE 33-continued

| Ex. No. | Structure | Name | [M + H]+ | Ret Time (min.) | HPLC Methods |
|---|---|---|---|---|---|
| 306 | 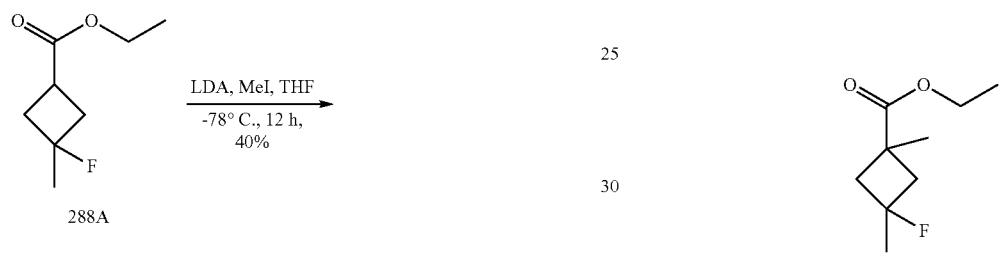 | 2-(3-Chlorophenyl)-N<sup>5</sup>-(1-(difluoromethyl)-3,3-difluorocyclobutyl)-6,7-dihydropyrazolo[1,5-a]pyrazine-3,5(4H)-dicarboxamide | 460 | 1.52<br>1.55 | E<br>L |

Scheme 40

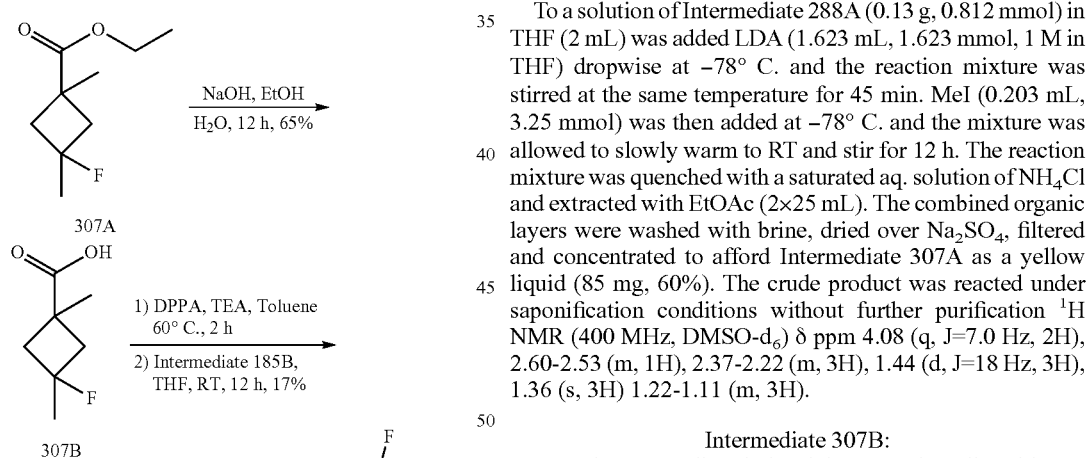

Intermediate 307A: Ethyl 3-fluoro-1,3-dimethylcyclobutanecarboxylate

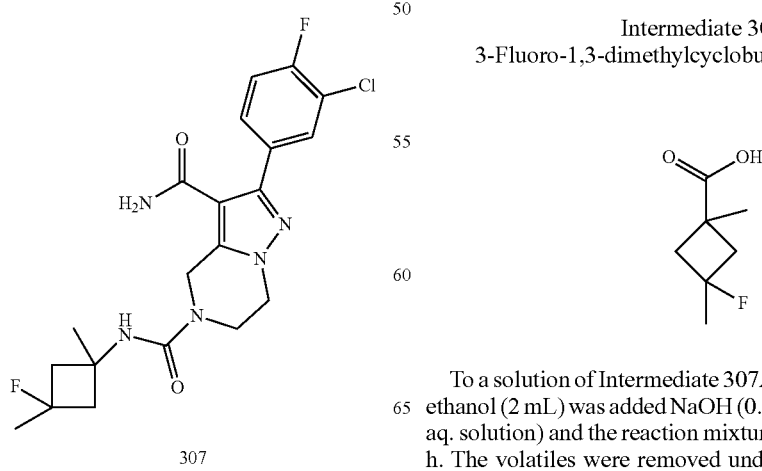

To a solution of Intermediate 288A (0.13 g, 0.812 mmol) in THF (2 mL) was added LDA (1.623 mL, 1.623 mmol, 1 M in THF) dropwise at −78° C. and the reaction mixture was stirred at the same temperature for 45 min. MeI (0.203 mL, 3.25 mmol) was then added at −78° C. and the mixture was allowed to slowly warm to RT and stir for 12 h. The reaction mixture was quenched with a saturated aq. solution of NH₄Cl and extracted with EtOAc (2×25 mL). The combined organic layers were washed with brine, dried over Na₂SO₄, filtered and concentrated to afford Intermediate 307A as a yellow liquid (85 mg, 60%). The crude product was reacted under saponification conditions without further purification $^1$H NMR (400 MHz, DMSO-d₆) δ ppm 4.08 (q, J=7.0 Hz, 2H), 2.60-2.53 (m, 1H), 2.37-2.22 (m, 3H), 1.44 (d, J=18 Hz, 3H), 1.36 (s, 3H) 1.22-1.11 (m, 3H).

Intermediate 307B: 3-Fluoro-1,3-dimethylcyclobutanecarboxylic acid

To a solution of Intermediate 307A (85 mg, 0.360 mmol) in ethanol (2 mL) was added NaOH (0.144 mL, 0.719 mmol, 5M aq. solution) and the reaction mixture was stirred at RT for 12 h. The volatiles were removed under reduced pressure, and the residue was diluted with water (15 mL) and extracted with diethyl ether (1×25 mL). The aqueous layer was then acidified with a 1.5N aq. solution of HCl and extracted with EtOAc (2×25 mL). The combined organic layer was dried over Na$_2$SO$_4$, filtered and the filtrate concentrated to afford Intermediate 307B as a pale yellow liquid (30 mg, 43%). $^1$H NMR (300 MHz, DMSO-d$_6$) δ ppm 12.29 (br. s., 1H), 2.60-2.53 (m, 1H), 2.37-2.22 (m, 3H), 1.44 (d, J=18 Hz, 3H), 1.36 (s, 3H).

Compound 307: 2-(3-Chloro-4-fluorophenyl)-N$^5$-(3-fluoro-1,3-dimethylcyclobutyl)-6,7-dihydropyrazolo[1,5-a]pyrazine-3,5(4H)-dicarboxamide

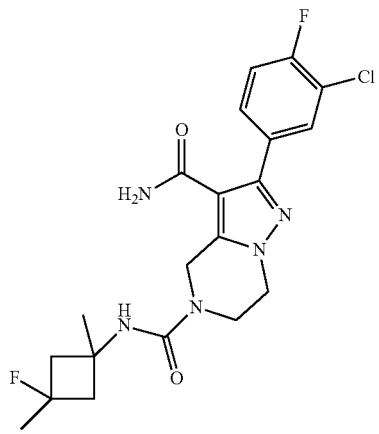 [SMILES: CC1(F)CC(C)(NC(=O)N2CCn3nc(-c4ccc(F)c(Cl)c4)c(C(N)=O)c3C2)C1]

To a solution of Intermediate 307B (29.8 mg, 0.204 mmol) in toluene (2 mL) were added TEA (0.043 mL, 0.305 mmol), DPPA (0.058 mL, 0.254 mmol) and the reaction mixture was heated at 60° C. and stirred for 2 h. The reaction mixture was cooled to RT and to it was added a solution of Intermediate 185B (30 mg, 0.102 mmol) in THF (1 mL) and stirred for 12 h. The reaction mixture was diluted with water (20 mL) and extracted with ethyl acetate (2×25 mL). The combined organic layer was washed with brine, dried over Na$_2$SO$_4$, filtered and the filtrate concentrated. The crude product was purified by preparative HPLC to afford Compound 307 as an off-white solid (7.55 mg, 17%). HPLC retention time 5.901 min. and 8.366 min. (Methods A and B respectively). MS(ES): m/z=438 [M+H]$^+$; $^1$H NMR (400 MHz, DMSO-d$_6$) δ ppm 7.85 (dd, J=7.0, 2.0 Hz, 1H), 7.68 (ddd, J=8.5, 4.8, 2.3 Hz, 1H), 7.46 (t, J=9.0 Hz, 1H), 7.36 (br. s., 1H), 7.20 (br. s., 1H), 6.88 (s, 1H), 4.71 (s, 2H), 4.12 (t, J=5.3 Hz, 2H), 3.82 (t, J=5.3 Hz, 2H), 2.44 (m, 2H), 2.29-2.17 (m, 2H), 1.46 (d, J=10.8 Hz, 3H), 1.43 (s, 3H).

Scheme 41

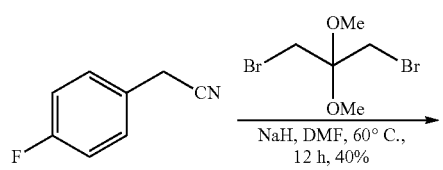

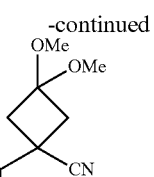
308A

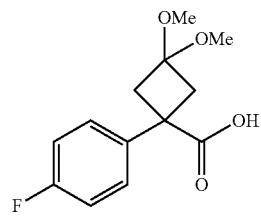
308B

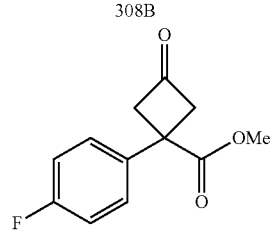
308C

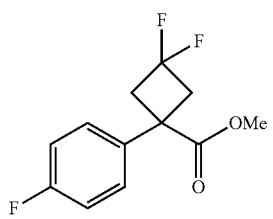
308D

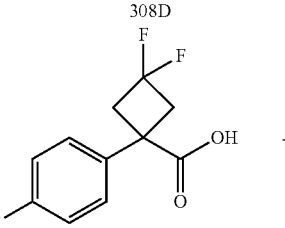
308E

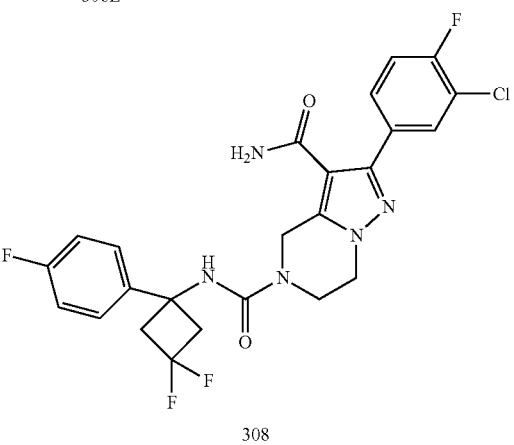
308

Intermediate 308A: 1-(4-Fluorophenyl)-3,3-dimethoxycyclobutanecarbonitrile

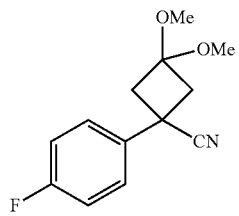

To a solution of NaH (1.302 g, 32.6 mmol, 60 wt % in mineral oil) in dry DMF (10 mL) cooled to 0° C., was added dropwise a solution 2-(4-fluorophenyl)acetonitrile (2.0 g, 14.8 mmol) in DMF (10 mL) To the stirred suspension at 0° C. was then added 1,3-dibromo-2,2-dimethoxypropane (3.88 g, 14.80 mmol). The reaction mixture was then heated to 60° C. and stirred for 12 h. The reaction mixture was cooled to RT, quenched with water and extracted with EtOAc (3×20 mL). The combined organic layers were washed with water and brine, dried over $Na_2SO_4$ and evaporated. The crude compound was purified by silica gel chromatography (24 g REDISEP® column, eluting with 20% EtOAc in hexanes). Fractions containing the product were combined and evaporated to afford Intermediate 308A as a yellow liquid (1.4 g, 40%). $^1$H NMR (400 MHz, chloroform-d) δ ppm 7.45 (dd, J=8.94, 5.05 Hz, 2H), 7.09 (t, J=8.66 Hz, 2H), 3.28 (s, 3H), 3.05-3.19 (m, 5H), 2.64-2.72 (m, 2H).

Intermediate 308B: 1-(4-Fluorophenyl)-3,3-dimethoxycyclobutanecarboxylic acid

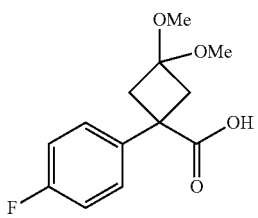 [SMILES: COC1(OC)CC(C(=O)O)(c2ccc(F)cc2)C1]

A solution of Intermediate 308A (1.4 g, 5.95 mmol) in ethanol (20 mL) and $H_2O$ (20 mL) was added a10% aq. solution of NaOH (10 mL, 5.95 mmol) and the reaction mixture was heated at reflux for 12 h. The reaction mixture was concentrated under reduced pressure to afford Intermediate 308B (1.0 g, 66% yield) as a gummy solid. The crude product was used in the subsequent reaction without purification. $^1$H NMR (400 MHz, chloroform-d) δ ppm 7.45 (dd, J=8.94, 5.05 Hz, 2H), 7.09 (t, J=8.66 Hz, 2H), 2.82-3.0 (m, 8H), 2.64-2.72 (m, 2H).

Intermediate 308C: Methyl 1-(4-fluorophenyl)-3-oxocyclobutanecarboxylate

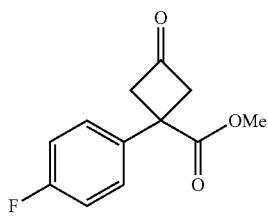 [SMILES: COC(=O)C1(c2ccc(F)cc2)CC(=O)C1]

To a stirred solution of Intermediate 308B (1.0 g, 3.93 mmol) in MeOH (15 mL) was added a concentrated aq. solution of HCl (5 mL) and the solution was stirred at RT for 12 h. The volatiles were removed under reduced pressure and the resulting residue was purified by silica gel chromatography (24 g REDISEP® column, eluting with 20% EtOAc in hexanes). Fractions containing the product were combined and evaporated to afford Intermediate 308C as a colorless oil (700 mg, 80%). $^1$H NMR (400 MHz, chloroform-d) δ ppm 7.45 (dd, J=8.94, 5.05 Hz, 2H), 7.09 (t, J=8.66 Hz, 2H), 3.89 (m, 2H), 3.71 (s, 3H), 3.57-3.72 (m, 2H).

Intermediate 308D: Methyl 3,3-difluoro-1-(4-fluorophenyl)cyclobutanecarboxylate

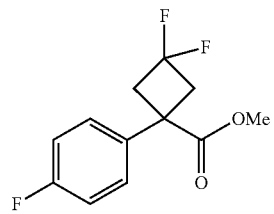 [SMILES: COC(=O)C1(c2ccc(F)cc2)CC(F)(F)C1]

To a solution of Intermediate 308C (600 mg, 2.70 mmol) in DCM (15 mL) at −20° C. was added DAST (0.535 mL, 4.05 mmol) and the reaction mixture was stirred at RT for 12 h. The reaction mixture was quenched by the addition of a 10% aq. solution of $NaHCO_3$ and extracted with DCM (3×15 mL). The combined organic layer was dried over $Na_2SO_4$ and evaporated under vacuum. The crude sample was purified by silica gel chromatography (24 g REDISEP® column, eluting with 10% EtOAc in hexanes). Fractions containing the product were combined and evaporated to afford Intermediate 308D as a yellow oil (400 mg, 61%). $^1$H NMR (400 MHz, chloroform-d) δ ppm 7.20-7.32 (m, 2H), 7.05 (t, J=8.69 Hz, 2H), 3.69 (s, 3H), 3.40-3.53 (m, 2H), 2.96-3.09 (m, 2H).

Intermediate 308E: 3,3-Difluoro-1-(4-fluorophenyl)cyclobutanecarboxylic acid

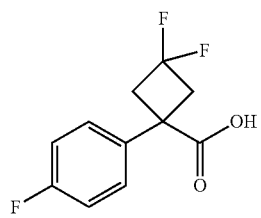

To a stirred solution of Intermediate 308D (400 mg, 1.638 mmol) in MeOH (5 mL), water (2 mL) and THF (2 mL) was added NaOH (197 mg, 4.91 mmol) and stirred for 12 h at RT. The reaction mixture was concentrated under vacuo and the pH of the residue was adjusted to 2.0 using 1.5 N HCl and the compound was extracted with ethyl acetate (3×10 mL) The combined organic layer was dried over $Na_2SO_4$, filtered and the filtrate concentrated under reduced pressure to afford Intermediate 308E as a pale yellow solid (250 mg, 66%). $^1$H NMR (400 MHz, DMSO-$d_6$) δ ppm 13.03 (bs, 1H), 7.33-7.43 (m, 2H), 7.21 (m, 2H), 3.32-3.37 (m, 2H), 2.99-3.15 (m, 2H).

Compound 308: 2-(3-Chloro-4-fluorophenyl)-N⁵-(3,3-difluoro-1-(4-fluorophenyl)cyclobutyl)-6,7-dihydropyrazolo[1,5-a]pyrazine-3,5(4H)-dicarboxamide

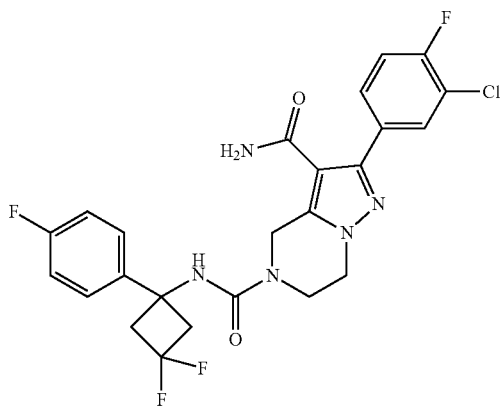 [SMILES: NC(=O)c1c(-c2ccc(F)c(Cl)c2)nn2c1CN(C(=O)NC1(c3ccc(F)cc3)CC(F)(F)C1)CC2]

A stirred solution of Intermediate 308E (62.5 mg, 0.271 mmol) in toluene (2 mL) was added TEA (0.057 mL, 0.407 mmol), DPPA (0.062 mL, 0.271 mmol) and the reaction mixture was heated to 70° C. for 2 h. The reaction mass was cooled to RT and to it was added a solution of Intermediate 185B (40 mg, 0.136 mmol) in THF (1 mL) and the reaction mixture was stirred at RT for 12 h. The reaction mass was diluted with ethyl acetate (5 mL), the organic layer was separated, washed with a 10% aq. NaHCO₃ solution, water, brine, dried over Na₂SO₄, filtered and the filtrate concentrated under vacuum. The crude compound was purified by preparative HPLC to afford Compound 308 as a pale yellow solid (54 mg, 75%). The HPLC Retention times are 2.339 min. and 2.344 min. (Methods J and K respectively); MS(ES): -m/z=522 [M+H]⁺; ¹H NMR (400 MHz, DMSO-$d_6$) δ ppm 7.82-7.88 (m, 1H), 7.77-7.82 (m, 1H), 7.61-7.72 (m, 1H), 7.47 (s, 3H), 7.30-7.41 (m, 1H), 7.14 (s, 3H), 4.72 (s, 2H), 4.08-4.18 (m, 2H), 3.78-3.88 (m, 2H), 3.10-3.22 (m, 4H).

The Compounds shown in Table 34 have been prepared similar to Compound 308 by coupling of in-situ generated isocyanate of 308E with 185B analogs.

TABLE 34

| Ex. No. | Structure | Name | [M + H]⁺ | Ret Time (min.) | HPLC Methods |
|---|---|---|---|---|---|
| 309 | 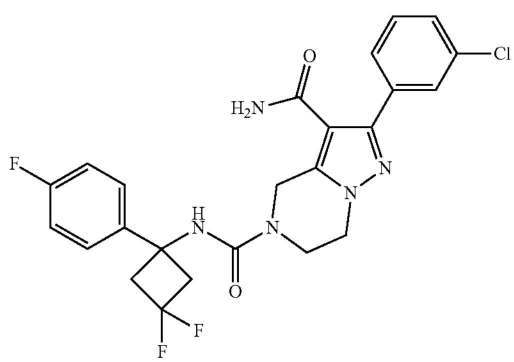 [SMILES: NC(=O)c1c(-c2cccc(Cl)c2)nn2c1CN(C(=O)NC1(c3ccc(F)cc3)CC(F)(F)C1)CC2] | 2-(3-Chlorophenyl)-N⁵-(3,3-difluoro-1-(4-fluorophenyl)cyclobutyl)-6,7-dihydropyrazolo[1,5-a]pyrazine-3,5(4H)-dicarboxamide | 504.0 | 2.511<br>2.444 | E<br>L |
| 310 | 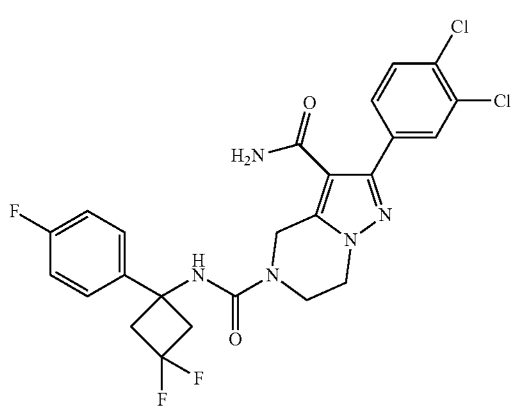 [SMILES: NC(=O)c1c(-c2ccc(Cl)c(Cl)c2)nn2c1CN(C(=O)NC1(c3ccc(F)cc3)CC(F)(F)C1)CC2] | 2-(3,4-Dichlorophenyl)-N⁵-(3,3-difluoro-1-(4-fluorophenyl)cyclobutyl)-6,7-dihydropyrazolo[1,5-a]pyrazine-3,5(4H)-dicarboxamide | 538.0 | 2.664<br>2.572 | E<br>L |

Scheme 42

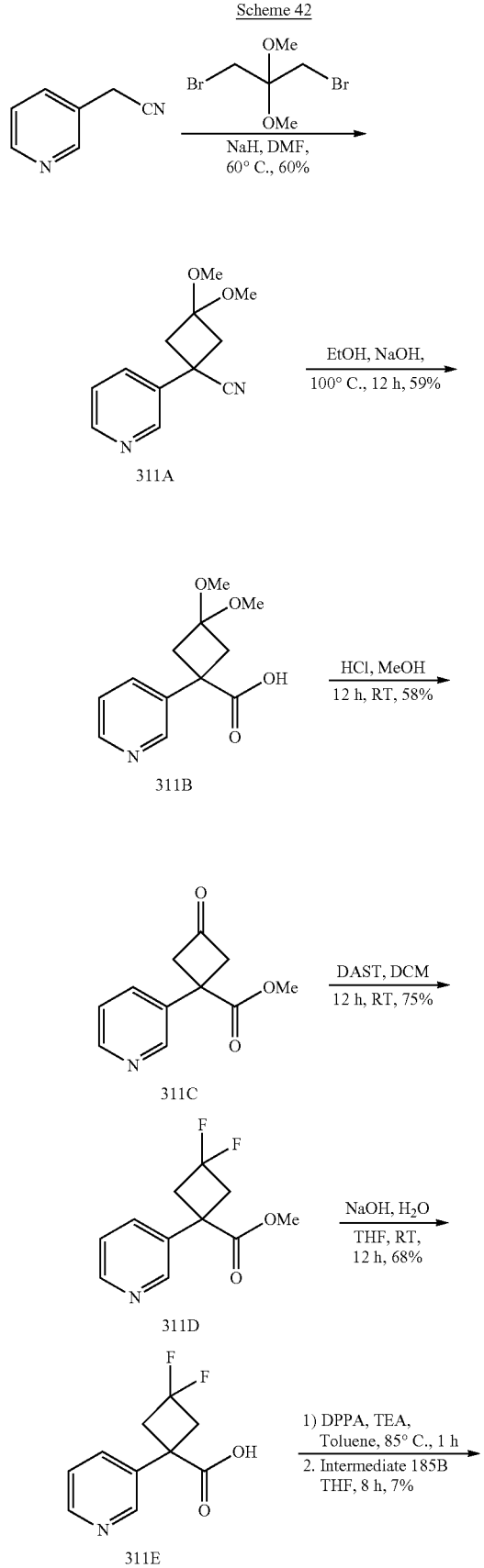

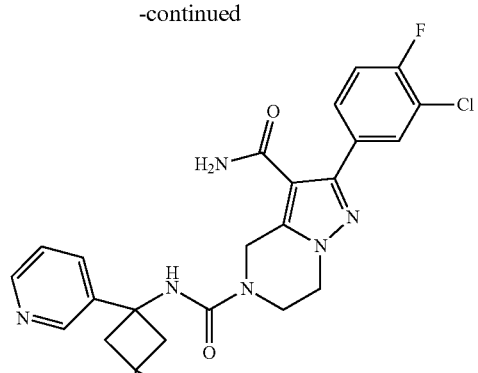

311

Intermediate 311A: 3,3-Dimethoxy-1-(pyridin-3-yl)cyclobutanecarbonitrile

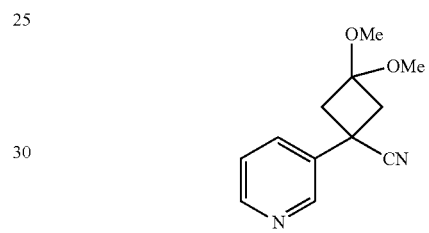

To a stirred suspension of NaH (1.466 g, 36.6 mmol, 60% in mineral oil) in DMF (25 mL) was added 2-(pyridin-3-yl)acetonitrile (1.954 mL, 18.32 mmol) followed by 1,3-dibromo-2,2-dimethoxypropane (4 g, 15.27 mmol) and the reaction mixture was warmed to 60° C. and stirred for 12 h. The reaction mixture was cooled to RT, poured into water (250 mL) and extracted with EtOAc (3×50 mL). The organic layer was separated, washed with water, brine, dried over $Na_2SO_4$, filtered and the filtrate concentrated. The crude product was purified by silica gel chromatography (40 g REDISEP® column, eluting with 50% EtOAc in hexanes). Fractions containing the product were combined and evaporated to afford Intermediate 311A as a white solid (2 g, 60%). MS(ES): m/z=219.2 [M+H]$^+$; $^1$H NMR (300 MHz, DMSO-$d_6$) δ ppm 8.71 (dd, J=0.8, 2.6 Hz, 1H), 8.58 (dd, J=1.7, 4.7 Hz, 1H), 7.89 (s, 1H), 7.51-7.45 (m, 1H), 3.19 (s, 3H), 3.08 (s, 3H), 2.89 (s, 1H), 2.83 (s, 1H), 2.78 (s, 1H), 2.73 (d, J=0.8 Hz, 1H).

Intermediate 311B: 3,3-Dimethoxy-1-(pyridin-3-yl)cyclobutanecarboxylic acid

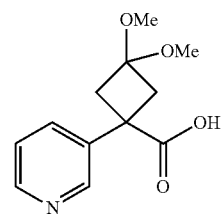 [SMILES: COC1(OC)CC(C(=O)O)(c2cccnc2)C1]

To a stirred solution of Intermediate 311A (2.2 g, 10.08 mmol) in EtOH (10 mL) was added a 10% aq. solution of NaOH (10 mL, 10 mmol) and the reaction mixture was stirred at 100° C. for 12 h. EtOH was removed under reduced pressure and the pH of the aq. solution was adjusted to 4 with a 1.5N aq. solution of HCl and extracted with EtOAc (5×20 mL). The combined organic layer was dried over Na$_2$SO$_4$, filtered and the filtrate concentrated to afford Intermediate 311B as a pale yellow semi-solid (1.4 g, 59%). MS(ES): m/z=238.0 [M+H]$^+$; $^1$H NMR (300 MHz, DMSO-d$_6$) δ ppm 12.35 (br. s., 1H), 8.56-8.42 (m, 2H), 7.75-7.64 (m, 1H), 7.44-7.30 (m, 1H), 3.08 (s, 3H), 3.03-2.90 (m, 4H), 2.56 (d, J=13.2 Hz, 1H), 1.91 (s, 2H).

Intermediate 311C: Methyl 3-oxo-1-(pyridin-3-yl)cyclobutanecarboxylate

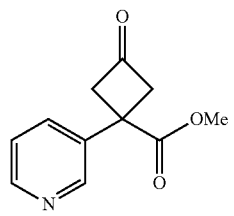 [SMILES: COC(=O)C1(c2cccnc2)CC(=O)C1]

To a solution of Intermediate 311B (1.4 g, 5.9 mmol) was added methanolic HCl (10 mL, 5.90 mmol, 4M) and stirred at RT for 12 h. The volatiles were removed under reduced pressure, the reaction mixture was then partitioned between a 10% aq. solution of NaHCO$_3$ and EtOAc. The organic layer was separated and the aqueous phase was extracted with EtOAc (5×20 mL) The combined organic layer was dried over Na$_2$SO$_4$, filtered and the filtrate concentrated. The crude product was purified by silica gel chromatography (24 g REDISEP® column, eluting with 50% EtOAc in hexanes). Fractions containing the product were combined and evaporated to afford Intermediate 311C as a colorless semi-solid (0.7 g, 58%). MS(ES): m/z=206.2 [M+H]$^+$; $^1$H NMR (300 MHz, DMSO-d$_6$) δ ppm 8.62 (d, J=1.8 Hz, 1H), 8.53 (dd, J=1.6, 4.8 Hz, 1H), 7.89-7.70 (m, 1H), 7.51-7.19 (m, 1H), 3.92-3.72 (m, 4H), 3.64 (s, 3H).

Intermediate 311D: Methyl 3,3-difluoro-1-(pyridin-3-yl)cyclobutanecarboxylate

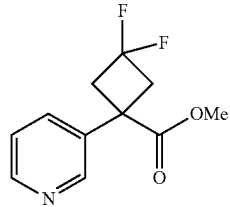 [SMILES: COC(=O)C1(c2cccnc2)CC(F)(F)C1]

To a stirred solution of Intermediate 311C (300 mg, 1.462 mmol) in DCM (10 mL) was added DAST (0.483 mL, 3.65 mmol) dropwise at 0° C. The resulting solution was then allowed to warm to RT and stir for 12 h. The reaction mixture was quenched with a saturated aq. solution of NaHCO$_3$ at 0° C. and the organic layer was separated and the aq. layer was extracted with DCM (2×10 mL). The combined organic layer was dried over Na$_2$SO$_4$, filtered and the filtrate concentrated. The crude product was purified by silica gel chromatography (24 g REDISEP® column, eluting with 50% EtOAc in hexanes). Fractions containing the product were combined and evaporated to afford Intermediate 311D as a colorless liquid (250 mg, 75%). MS(ES): m/z=228.2 [M+H]$^+$; $^1$H NMR (400 MHz, DMSO-d$_6$) δ ppm 8.62 (dd, J=1.0, 2.5 Hz, 1H), 8.54 (dd, J=1.5, 4.5 Hz, 1H), 7.87-7.77 (m, 1H), 7.45 (s, 1H), 3.64 (s, 3H), 3.44 (s, 2H), 3.28 (s, 2I).

Intermediate 311E: 2 3,3-Difluoro-1-(pyridin-3-yl)cyclobutanecarboxylic acid

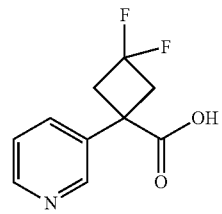 [SMILES: O=C(O)C1(c2cccnc2)CC(F)(F)C1]

To a solution of Intermediate 311D (250 mg, 1.100 mmol) in THF (2 mL) and water (1 mL) was added NaOH (132 mg, 3.30 mmol) and the reaction mixture was stirred at RT for 12 h. The reaction mixture was concentrated; the pH of the residue was adjusted to 2 with a 1.5N aq. solution of HCl and extracted with EtOAc (3×15 mL). The combined organic layer was dried over Na$_2$SO$_4$, filtered and concentrated to afford Intermediate 311E as a colorless semi-solid (160 mg, 68% yield). $^1$H NMR (400 MHz, DMSO-d$_6$) δ ppm 12.35 (br. s., 1H), 8.65-8.54 (m, 1H), 8.53-8.46 (m, 1H), 7.83-7.74 (m, 1H), 7.46-7.35 (m, 1H), 3.47-3.35 (m, 2H), 3.23-3.08 (m, 2H).

Intermediate 311: 2-(3-Chloro-4-fluorophenyl)-N$^5$-(3,3-difluoro-1-(pyridin-3-yl)cyclobutyl)-6,7-dihydropyrazolo[1,5-a]pyrazine-3,5(4H)-dicarboxamide

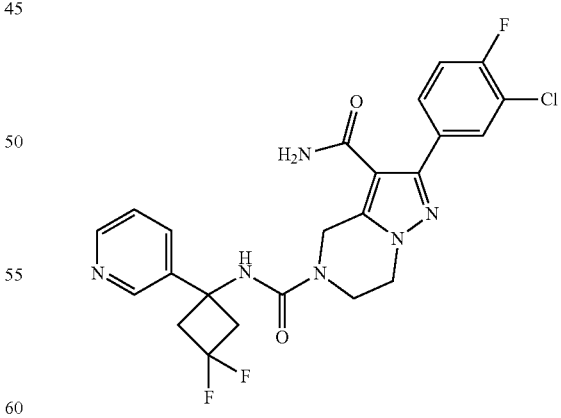

To a solution of Intermediate 311E (43.4 mg, 0.204 mmol) in toluene (2 mL) was added TEA (0.095 mL, 0.679 mmol), DPPA (75 mg, 271 mmol) and the solution was heated to 85° C. and stirred for 1 h. The reaction mixture was cooled to RT and to it was added a solution of Intermediate 185B (40 mg, 0.136 mmol) in THF (1 mL) and stirred for 12 h. The reaction mixture was diluted with EtOAc (10 mL), washed with water, solution of 10% aq. NaHCO$_3$, brine, dried over Na$_2$SO$_4$, filtered and the filtrate concentrated. The crude product obtained was purified by preparative HPLC to afford Compound 311 as an off-white solid (0.005 g, 7%). HPLC retention time 1.242 min. and 1.014 min. (Methods E and L respectively). MS(ES): m/z=505.2 [M+H]$^+$; $^1$H NMR: (400 MHz, DMSO-d$_6$) δ ppm 8.67 (dd, J=2.51, 1.00 Hz, 1H), 8.38-8.50 (m, 1H), 7.89 (s, 1H), 7.80-7.86 (m, 2H), 7.68 (ddd, J=8.66, 4.89, 2.01 Hz, 1H), 7.44-7.52 (m, 1H), 7.31-7.40 (m, 2H), 7.21 (br. s., 1H), 4.74 (s, 2H), 4.15 (t, J=5.27 Hz, 2H), 3.84 (t, J=5.27 Hz, 2H), 3.09-3.29 (m, 4H).

The Compounds shown in Table 35 have been prepared similar to Compound 311 by coupling of in-situ generated isocyanate of 311E with 185B analogs.

TABLE 35

| Ex. No. | Structure | Name | [M + H]$^+$ | Ret Time (min.) | HPLC Methods |
|---|---|---|---|---|---|
| 312 | 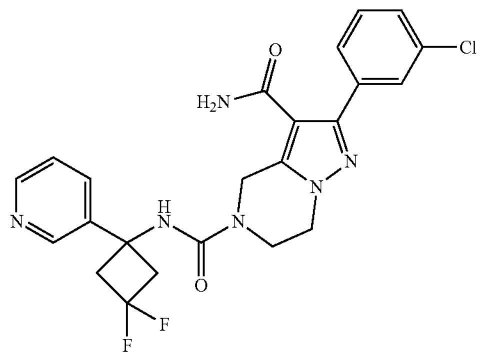 | 2-(3-Chlorophenyl)-N$^5$-(3,3-difluoro-1-(pyridin-3-yl)cyclobutyl)-6,7-dihydropyrazolo[1,5-a]pyrazine-3,5(4H)-dicarboxamide | 487.2 | 1.188<br>0.963 | E<br>L |
| 313 | 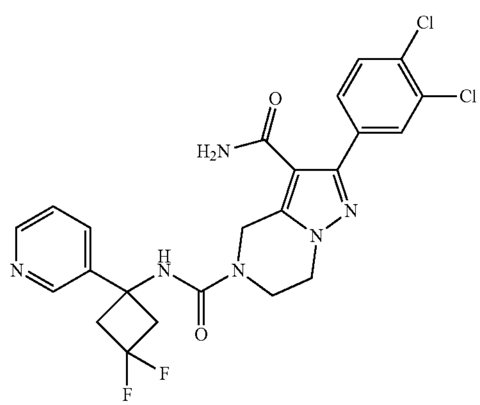 [SMILES: NC(=O)c1c(-c2ccc(F)c(Cl)c2)nn2c1CN(C(=O)NC1(c3cccnc3)CC(F)(F)C1)CC2] | 2-(3,4-Dichlorophenyl)-N$^5$-(3,3-difluoro-1-(pyridin-3-yl)cyclobutyl)-6,7-dihydropyrazolo[1,5-a]pyrazine-3,5(4H)-dicarboxamide | 521.2 | 1.365<br>1.118 | E<br>L |

Scheme 43

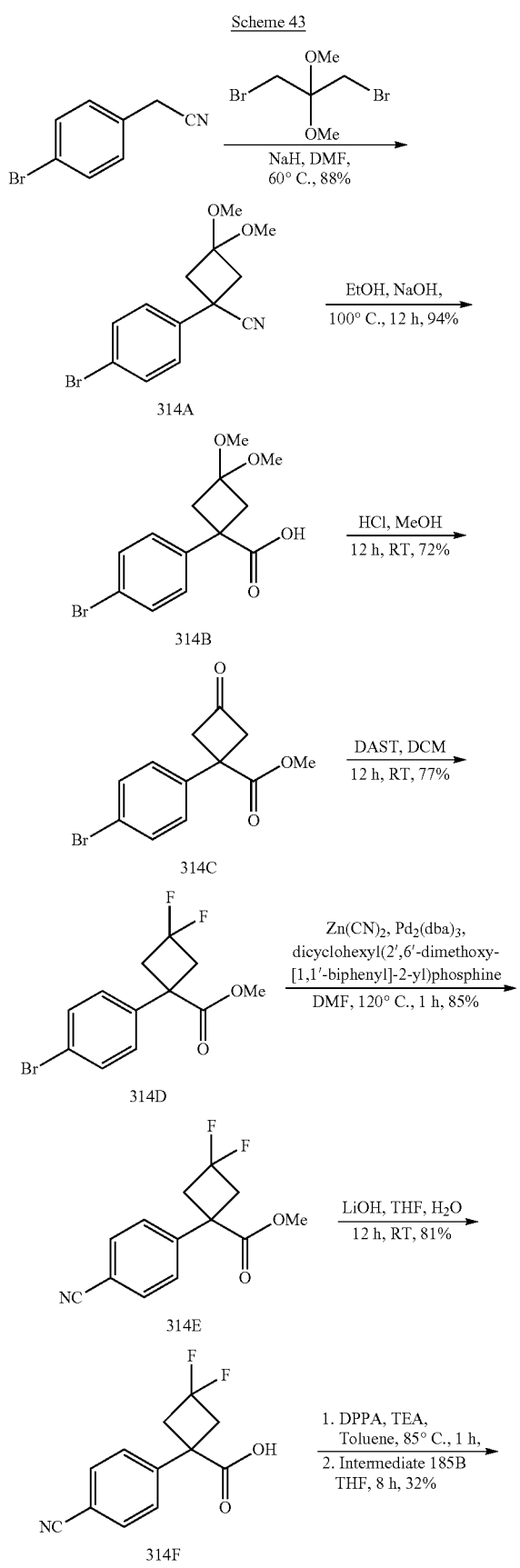

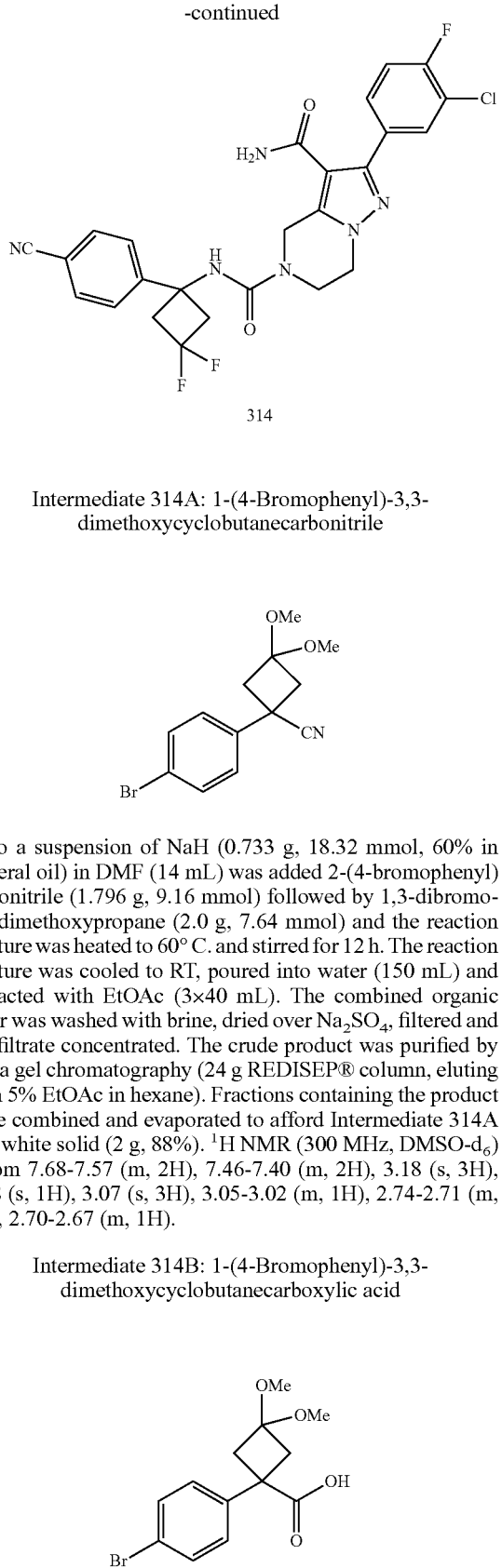

Intermediate 314A: 1-(4-Bromophenyl)-3,3-dimethoxycyclobutanecarbonitrile

To a suspension of NaH (0.733 g, 18.32 mmol, 60% in mineral oil) in DMF (14 mL) was added 2-(4-bromophenyl)acetonitrile (1.796 g, 9.16 mmol) followed by 1,3-dibromo-2,2-dimethoxypropane (2.0 g, 7.64 mmol) and the reaction mixture was heated to 60° C. and stirred for 12 h. The reaction mixture was cooled to RT, poured into water (150 mL) and extracted with EtOAc (3×40 mL). The combined organic layer was washed with brine, dried over Na$_2$SO$_4$, filtered and the filtrate concentrated. The crude product was purified by silica gel chromatography (24 g REDISEP® column, eluting with 5% EtOAc in hexane). Fractions containing the product were combined and evaporated to afford Intermediate 314A as a white solid (2 g, 88%). $^1$H NMR (300 MHz, DMSO-d$_6$) δ ppm 7.68-7.57 (m, 2H), 7.46-7.40 (m, 2H), 3.18 (s, 3H), 3.08 (s, 1H), 3.07 (s, 3H), 3.05-3.02 (m, 1H), 2.74-2.71 (m, 1H), 2.70-2.67 (m, 1H).

Intermediate 314B: 1-(4-Bromophenyl)-3,3-dimethoxycyclobutanecarboxylic acid

To a stirred solution of Intermediate 314A (2 g, 6.75 mmol) in EtOH (10 mL) was added 10% aq. solution of NaOH (10 mL, 6.75 mmol) at RT and the reaction mixture was heated to 85° C. for 12 h. EtOH was removed under reduced pressure and the pH of the resulting aq. solution was adjusted to 2 with a 1.5 N aq. solution of HCl and extracted with EtOAc (5×20 mL). The combined organic layer was washed with brine, dried over Na₂SO₄, filtered and the filtrate concentrated to afford Intermediate 314B as a pale yellow semi-solid (2 g, 94%). MS(ES): m/z=313.0 [M−H]⁺; ¹H NMR (300 MHz, DMSO-d₆) δ ppm 12.39 (br. s., 1H), 7.66-7.39 (m, 2H), 7.34-7.11 (m, 2H), 3.07 (s, 3H), 3.00 (s, 3H), 2.95 (d, J=13.6 Hz, 1H), 2.43 (s, 1H), 1.91 (s, 2H).

Intermediate 314C: Methyl 1-(4-bromophenyl)-3-oxocyclobutanecarboxylate

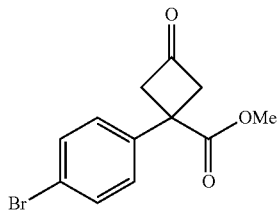 [SMILES: COC(=O)C1(c2ccc(Br)cc2)CC(=O)C1]

To a flask charged with Intermediate 314B (2.0 g, 6.35 mmol) was added methanolic HCl (10 mL, 6.35 mmol, 4 M) and the reaction mixture was stirred at RT for 12 h. The reaction mixture was concentrated and the crude product was purified by silica gel chromatography (24 g REDISEP® column, eluting with 7% EtOAc in hexanes). Fractions containing the product were combined and evaporated to afford Intermediate 314C as a colorless liquid (1.3 g, 72%). MS(ES): ¹H NMR (400 MHz, DMSO-d₆) δ ppm 7.65-7.51 (m, 2H), 7.39-7.23 (m, 2H), 3.85-3.74 (m, 2H), 3.68-3.52 (m, 5H).

Intermediate 314D: Methyl 1-(4-bromophenyl)-3,3-difluorocyclobutanecarboxylate

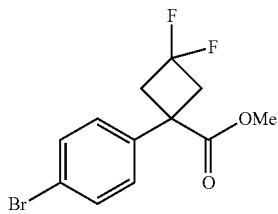 [SMILES: COC(=O)C1(c2ccc(Br)cc2)CC(F)(F)C1]

To a stirred solution of Intermediate 314C (1.2 g, 4.24 mmol) in DCM (50 mL) was added DAST (1.232 mL, 9.32 mmol) dropwise at 0° C. The reaction mixture was allowed to warm to RT and stir for 12 h. The reaction mixture was quenched with an aq. solution of NaHCO₃ (20 mL) at 0° C. and extracted with DCM (3×10 mL). The combined organic layer was washed with brine, dried over Na₂SO₄, and the filtrate concentrated. The crude product was purified by silica gel chromatography (24 g REDISEP® column, eluting with 8% EtOAc in hexanes). Fractions containing the product were combined and evaporated to afford Intermediate 314D as a colorless liquid (1 g, 77%). ¹H NMR (400 MHz, DMSO-d₆) δ ppm 7.68-7.51 (m, 2H), 7.41-7.26 (m, 2H), 3.62 (s, 3H), 3.49-3.34 (m, 2H), 3.17 (s, 2H).

Intermediate 314E: Methyl 1-(4-cyanophenyl)-3,3-difluorocyclobutanecarboxylate

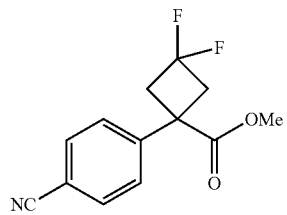

To a solution of Intermediate 314D (500 mg, 1.639 mmol) in DMF (10 mL) was added Zn(CN)₂ (289 mg, 2.458 mmol) and the reaction mixture was degassed with N₂ gas for 15 min Pd₂(dba)₃ (75 mg, 0.082 mmol) and dicyclohexyl(2',6'-dimethoxy-[1,1'-biphenyl]-2-yl)phosphine (67.3 mg, 0.164 mmol) were then added and the reaction mixture was heated at 120° C. for 1 h. The reaction mixture was cooled to RT, diluted with water (50 mL) and extracted with EtOAc (3×40 mL) The combined organic layer was washed with water, brine, dried over Na₂SO₄, filtered and the filtrate concentrated. The crude product was purified by silica gel chromatography (24 g REDISEP® column, eluting with 10% EtOAc in hexane). Fractions containing the product were combined and evaporated to afford Intermediate 314E as a colorless liquid (350 mg, 85%). ¹H NMR (400 MHz, DMSO-d₆) δ ppm 7.87 (d, J=8.5 Hz, 2H), 7.58 (d, J=8.5 Hz, 2H), 3.62 (s, 3H), 3.51-3.37 (m, 2H), 3.28-3.13 (m, 2H).

Intermediate 314F: 1-(4-Cyanophenyl)-3,3-difluorocyclobutanecarboxylic acid

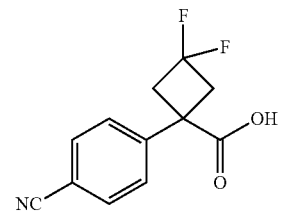 [SMILES: N#Cc1ccc(C2(C(=O)O)CC(F)(F)C2)cc1]

To a stirred solution of Intermediate 314E (300 mg, 1.194 mmol) in THF (2 mL) and water (2 mL) was added LiOH (57.2 mg, 2.388 mmol) and the reaction mixture was stirred at RT for 12 h. The reaction mixture was concentrated to remove THF and the aq. layer was acidified to a pH of 2 with a 1.5N aq. solution of HCl and extracted with EtOAc (3×15 mL) The combined organic layer was washed with brine, dried over Na₂SO₄, filtered and the filtrate concentrated to afford Intermediate 314F (230 mg, 81%) as a colorless semi-solid. ¹H NMR (300 MHz, DMSO-$d_6$) δ ppm 12.39 (br. s., 1H), 7.91-7.79 (m, 2H), 7.62-7.49 (m, 2H), 3.50-3.25 (m, 2H), 3.11 (d, J=14.0 Hz, 2H).

Compound 314: 2-(3-Chloro-4-fluorophenyl)-$N^5$-(1-(4-cyanophenyl)-3,3-difluorocyclobutyl)-6,7-dihydropyrazolo[1,5-a]pyrazine-3,5(4H)-dicarboxamide

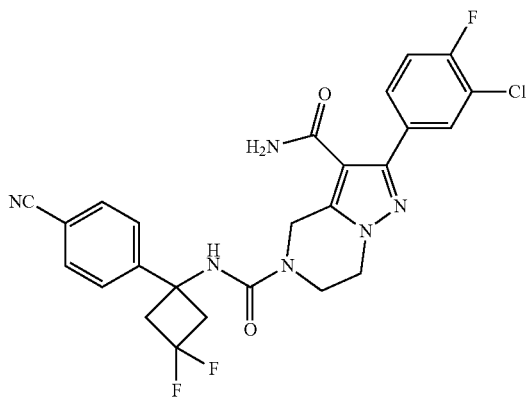 [SMILES: N#Cc1ccc(C2(NC(=O)N3CCn4nc(-c5ccc(F)c(Cl)c5)c(C(N)=O)c4C3)CC(F)(F)C2)cc1]

To a solution of Intermediate 314F (36.2 mg, 0.153 mmol) in toluene (1 mL) was added TEA (0.071 mL, 0.509 mmol), DPPA (0.044 mL, 0.204 mmol) and the reaction mixture was heated to 85° C. and stirred for 1 h. The reaction mixture was cooled to RT and to it was added a solution of Intermediate 185B (30 mg, 0.102 mmol) in THF (0.5 mL) and stirred at RT for 12 h. The reaction mixture was diluted with EtOAc (10 mL), washed successively with water, a 10% aq. solution of NaHCO$_3$ and brine, then dried over Na$_2$SO$_4$, filtered and concentrated. The crude product was purified by preparative HPLC to afford Compound 314 as an off-white solid (0.017 g, 32%). HPLC retention times 1.604 min. and 1.605 min. (Methods E and L respectively). MS(ES): m/z=529.2 [M+H]$^+$; $^1$H NMR: (400 MHz, DMSO-$d_6$) δ ppm 7.92 (s, 1H), 7.86-7.77 (m, 3H), 7.67 (ddd, J=8.7, 4.9, 2.0 Hz, 1H), 7.64-7.58 (m, 2H), 7.50-7.41 (m, 1H), 7.36 (br. s., 1H), 7.18 (br. s., 1H), 4.73 (s, 2H), 4.14 (t, J=5.3 Hz, 2H), 3.84 (t, J=5.3 Hz, 2H), 3.17 (t, J=12.3 Hz, 4H).

The Compounds shown in Table 36 have been prepared similar to Compound 314 by coupling of in-situ generated isocyanate of 314F with 185B analogs.

TABLE 36

| Ex. No. | Structure | Name | [M + H]$^+$ | Ret Time (min.) | HPLC Methods |
|---|---|---|---|---|---|
| 315 | 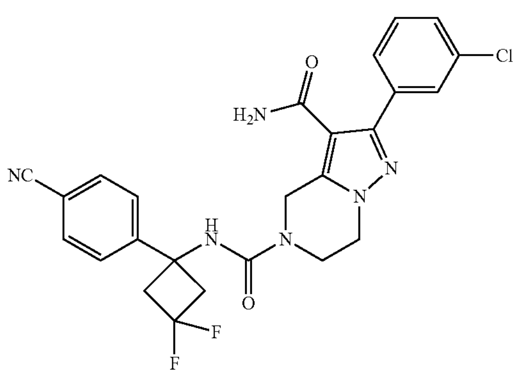 [SMILES: N#Cc1ccc(C2(NC(=O)N3CCn4nc(-c5cccc(Cl)c5)c(C(N)=O)c4C3)CC(F)(F)C2)cc1] | 2-(3-Chlorophenyl)-$N^5$-(1-(4-cyanophenyl)-3,3-difluorocyclobutyl)-6,7-dihydropyrazolo[1,5-a]pyrazine-3,5(4H)-dicarboxamide | 511.3 | 1.570<br>1.567 | E<br>L |
| 316 | 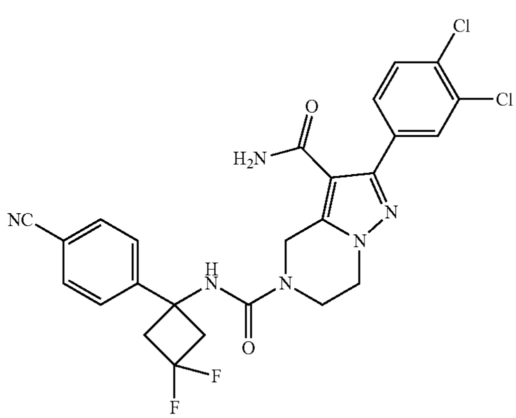 [SMILES: N#Cc1ccc(C2(NC(=O)N3CCn4nc(-c5ccc(Cl)c(Cl)c5)c(C(N)=O)c4C3)CC(F)(F)C2)cc1] | $N^5$-(1-(4-Cyanophenyl)-3,3-difluorocyclobutyl)-2-(3,4-dichlorophenyl)-6,7-dihydropyrazolo[1,5-a]pyrazine-3,5(4H)-dicarboxamide | 545.2 | 1.644<br>1.648 | E<br>L |

Scheme 44

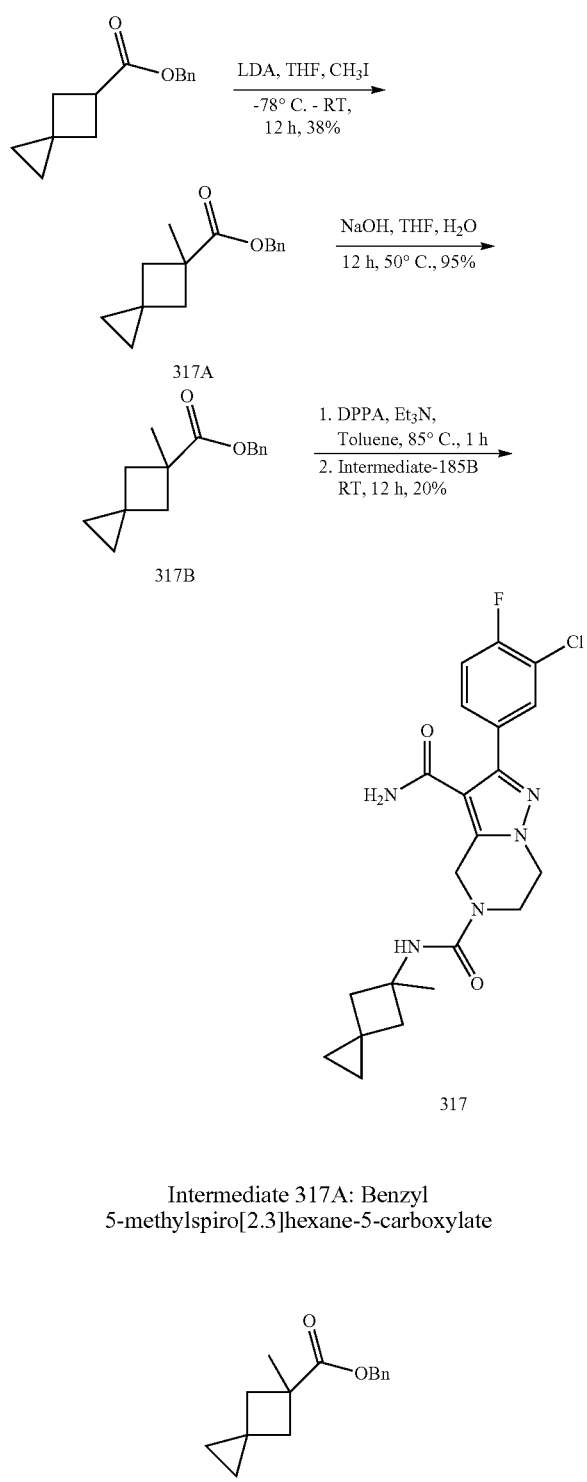

and extracted with EtOAc (3×10 mL) The combined organic layer was washed with brine, dried over Na₂SO₄, filtered and concentrated. The crude product was purified by silica gel chromatography (24 g REDISEP® column, eluting with 5% EtOAc in hexanes). Fractions containing the product were combined and evaporated to afford the Intermediate 317A as a colorless liquid (200 mg, 38% yield). MS(ES): m/z=231.2 [M+H]⁺; ¹H NMR (400 MHz, chloroform-d) δ ppm 7.50-7.28 (m, 5H), 5.36-4.94 (s, 2H), 2.87-2.47 (m, 2H), 2.01-1.77 (m, 2H), 1.62-1.39 (s, 3H), 0.60-0.22 (m, 4H).

Intermediate 317B:
5-Methylspiro[2.3]hexane-5-carboxylic acid

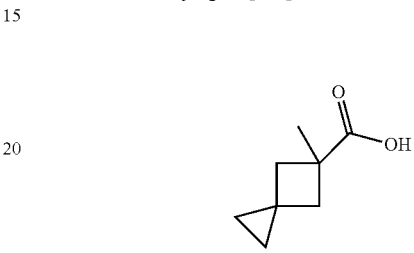

To a stirred solution of Intermediate 317A (200 mg, 0.868 mmol) in THF (2 mL) and water (1 mL) was added NaOH (104 mg, 2.61 mmol) at RT and the reaction mixture was warmed to 50° C. and stirred for 12 h. The reaction mixture was concentrated under a reduced pressure, the residue was to pH 2 with a 1.5 N aq. solution of HCl and extracted with Et₂O (3×15 mL) The combined organic layer was dried over Na₂SO₄, filtered and the filtrate concentrated to afford Intermediate 317B as a colorless liquid (0.12 g, 99%). ¹H NMR (300 MHz, DMSO-d₆) δ ppm 12.38-11.71 (m, 1H), 2.68-2.50 (m, 2H), 1.86-1.66 (m, 2H), 1.43 (s, 3H), 0.62-0.19 (m, 4H).

Compound 317: 2-(3-Chloro-4-fluorophenyl)-N⁵-(5-methylspiro[2.3]hexan-5-yl)-6,7-dihydropyrazolo[1,5-a]pyrazine-3,5(4H)-dicarboxamide Intermediate 317A: Benzyl 5-methylspiro[2.3]hexane-5-carboxylate

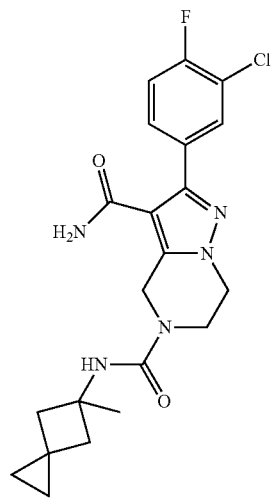

To a solution of LDA (3.47 mL, 6.94 mmol 2M in THF) in THF (5 mL) cooled to −78° C., was added dropwise a solution of benzyl spiro[2.3]hexane-5-carboxylate (0.5 g, 2.312 mmol) in THF (2 mL). The resulting solution was stirred for 30 min. prior to the dropwise addition of MeI (0.723 mL, 11.56 mmol) at −78° C. The resulting reaction mixture was allowed to warm to RT and stir for 12 h. The reaction mixture was quenched with a saturated aq. solution of NH₄Cl (20 mL)

To a solution of Intermediate 317B (28.5 mg, 0.204 mmol) in toluene (3 mL) was added TEA (0.071 mL, 0.509 mmol), DPPA (0.044 mL, 0.204 mmol) and the solution was warmed to 85° C. and stirred for 1 h. The reaction mixture was cooled to RT and to it was added a solution of Intermediate 185B (30 mg, 0.102 mmol) in THF (1 mL) and stirred at RT for 12 h. The reaction mixture was diluted with EtOAc (10 mL), washed with water, brine, dried over $Na_2SO_4$, filtered and the filtrate concentrated. The crude product obtained was purified by preparative HPLC to afford the title Compound 317 as an off-white solid (0.009 g, 20% yield). HPLC retention times 1.448 min. and 1.553 min. (Methods E and L respectively). MS(ES): m/z=432.0 [M+H]+; $^1$H NMR: (400 MHz, DMSO-$d_6$) δ ppm 7.86 (dd, J=7.28, 2.26 Hz, 1H), 7.69 (ddd, J=8.66, 4.64, 2.26 Hz, 1H), 7.42-7.52 (m, 1H), 7.07-7.39 (m, 2H), 6.94 (s, 1H), 4.71 (s, 2H), 4.13 (t, J=5.52 Hz, 2H), 3.82 (t, J=5.27 Hz, 2H), 2.44 (d, J=12.55 Hz, 2H), 1.85-1.93 (m, 2H), 1.51 (s, 3H), 0.32-0.49 (m, 4H).

The Compounds shown in Table 37 have been prepared similar to Compound 317 by coupling of in-situ generated isocyanate of 317B with 185B analogs.

TABLE 37

| Ex. No. | Structure | Name | [M + H]+ | Ret Time (min.) | HPLC Methods |
|---|---|---|---|---|---|
| 318 | 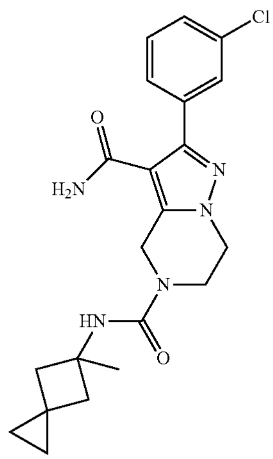 [SMILES: CC1(NC(=O)N2CCn3nc(-c4cccc(Cl)c4)c(C(N)=O)c3C2)CC2(CC2)C1] | 2-(3-Chlorophenyl)-N$^5$-(5-methylspiro[2.3]hexan-5-yl)-6,7-dihydropyrazolo[1,5-a]pyrazine-3,5(4H)-dicarboxamide | 414.0 | 1.459<br>1.449 | E<br>L |
| 319 | 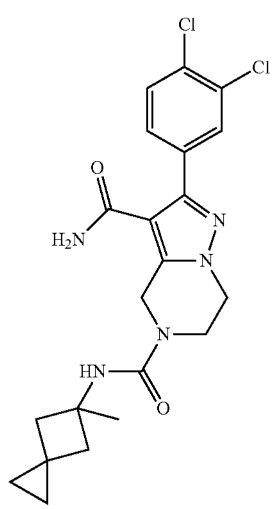 [SMILES: CC1(NC(=O)N2CCn3nc(-c4ccc(Cl)c(Cl)c4)c(C(N)=O)c3C2)CC2(CC2)C1] | 2-(3,4-Dichlorophenyl)-N$^5$-(5-methylspiro[2.3]hexan-5-yl)-6,7-dihydropyrazolo[1,5-a]pyrazine-3,5(4H)-dicarboxamide | 448.0 | 1.615<br>1.617 | E<br>L |

Scheme 45

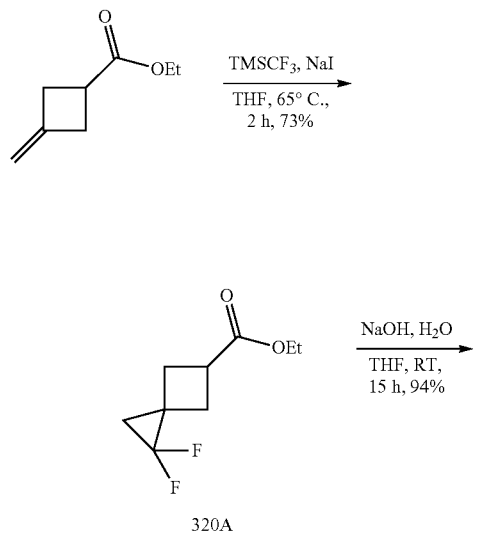

320A

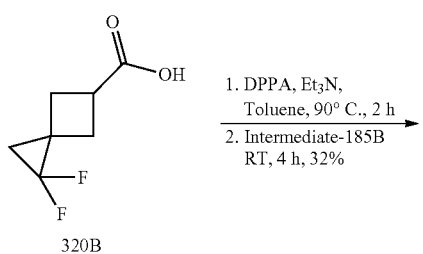

320B

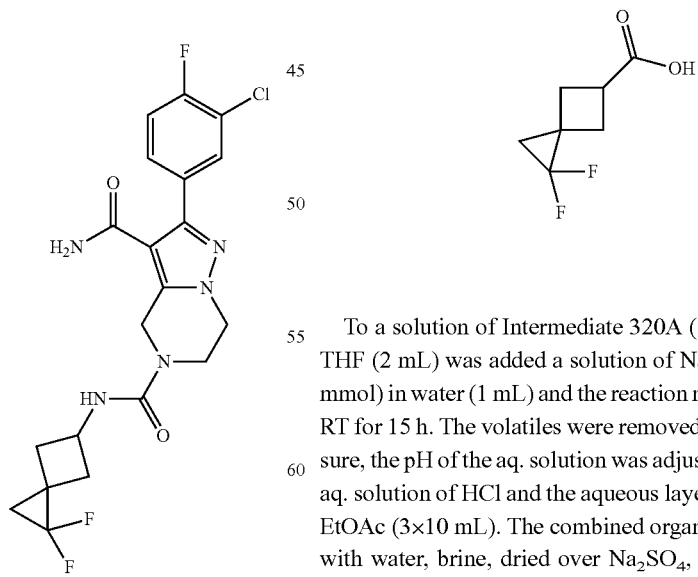

320 and 321

Intermediate 320A: Ethyl 1,1-difluorospiro[2.3]hexane-5-carboxylate

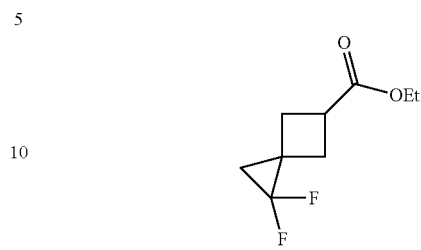

The solution of ethyl 3-methylenecyclobutanecarboxylate (1 g, 7.13 mmol), NaI (0.214 g, 1.427 mmol) and TMSCF$_3$ (2.54 g, 17.83 mmol) in THF (10 mL) was stirred at 65° C. for 2 h. The reaction mixture was quenched with a 10% aq. solution of NaHCO$_3$ and the aqueous layer was extracted with diethyl ether (3×10 mL). The combined organic layer was washed with a 10% aq. solution of NaHCO$_3$, followed by brine, then dried over Na$_2$SO$_4$, filtered and the filtrate concentrated. The crude was purified by silica gel chromatography (12 g REDISEP® column, eluting with 20% EtOAc in hexane). Fractions containing the product were combined and evaporated to afford Intermediate 320A as a pale yellow liquid (1 g, 73%, mixture of cis and trans isomers). $^1$H NMR (400 MHz, chloroform-d) δ ppm 4.13-4.24 (m, 2H) 2.56-2.65 (m, 1H), 2.01-2.06 (m, 2H), 1.91-1.98 (m, 2H) 1.16-1.45 (m, 5H).

Intermediate 320B: 1,1-Difluorospiro[2.3]hexane-5-carboxylic acid

To a solution of Intermediate 320A (1.0 g, 5.26 mmol) in THF (2 mL) was added a solution of NaOH (0.526 g, 13.14 mmol) in water (1 mL) and the reaction mixture was stirred at RT for 15 h. The volatiles were removed under reduced pressure, the pH of the aq. solution was adjusted to ~3 using a 1 N aq. solution of HCl and the aqueous layer was extracted with EtOAc (3×10 mL). The combined organic layer was washed with water, brine, dried over Na$_2$SO$_4$, filtered and concentrated to afford Intermediate 323 (0.8 g, 94%, cis and trans mixture) as a yellow liquid. The crude product was used in the next step without further purification. $^1$H NMR (400 MHz, DMSO-d$_6$) δ ppm 12.39 (br. s., 1H), 3.01-3.22 (m, 1H) 2.55-2.63 (m, 2H), 1.89-2.02 (m, 2H) 1.14-1.23 (m, 2H).

Compounds 320 and 321: 2-(3-Chloro-4-fluorophenyl)-N$^5$-(1,1-difluorospiro[2.3]hexan-5-yl)-6,7-dihydropyrazolo[1,5-a]pyrazine-3,5(4H)-dicarboxamide

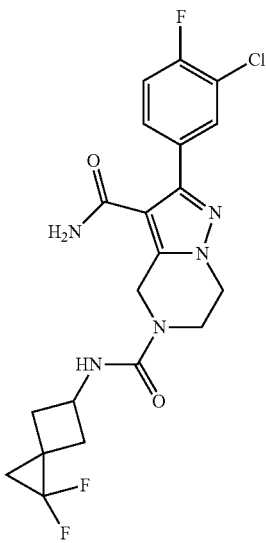

A solution of Intermediate 320B (83 mg, 0.509 mmol), TEA (0.142 mL, 1.018 mmol) and DPPA (0.11 mL, 0.509 mmol) in toluene (10 mL) was heated to 90° C. and stirred for 2 h. The reaction mixture was cooled to RT and to it was added a solution of Intermediate 185B (100 mg, 0.339 mmol) in THF (3 mL) and stirred for 4 h. The reaction mixture was quenched with water and the aq layer was extracted with ethyl acetate (3×5 mL). The combined organic layer was washed with a 10% aq. solution of NaHCO$_3$ and then water, dried over Na$_2$SO$_4$, filtered and concentrated. The crude material was purified by preparative TLC and was loaded on a 0.5 mm silica gel plate and developed using 6% MeOH in CHCl$_3$. The band containing the desired product was separated and extracted into 10% MeOH in DCM, then was filtered and concentrated to afford mixture of 320 and 321 as an off-white solid. The individual isomers were separated by preparative chiral SFC.

Compound 320: Retention time 3.22 min (HPLC Method O); MS(ES): m/z=454 [M+H]$^+$; Yield=25 mg, 16%; $^1$H NMR (400 MHz, DMSO-d$_6$) δ ppm 7.86 (dd, J=7.28, 2.26 Hz, 1H), 7.66-7.73 (m, 1H), 7.44-7.51 (m, 1H), 7.35 (br. s., 1H), 7.29 (d, J=7.03 Hz, 1H), 7.19 (br. s., 1H), 4.75 (s, 2H), 4.12-4.25 (m, 3H), 3.85 (t, J=5.27 Hz, 2H), 2.37-2.44 (m, 2H), 2.24-2.32 (m, 2H), 1.38 (t, J=8.53 Hz, 2H).

Compound 321: Retention time 3.79 min (HPLC Method O); MS(ES): m/z=454 [M+H]$^+$; Yield=25 mg, 16%; $^1$H NMR (400 MHz, DMSO-d$_6$) δ ppm 7.80-7.93 (m, 1H), 7.63-7.74 (m, 1H), 7.48 (d, J=9.54 Hz, 1H), 7.35 (br s, 1H), 7.17 (m, 2H), 4.74 (s, 2H), 4.20-4.31 (m, 1H), 4.14 (d, J=10.54 Hz, 2H), 3.77-3.93 (m, 2H), 2.39-2.49 (m, 1H), 2.22 (t, J=8.53 Hz, 4H), 1.42-1.46 (t, J=8.53 Hz, 2H).

The Compounds shown in Table 38 have been prepared similar to Compounds 320 and 321 by coupling of in-situ generated isocyanate of 320B with 185B analogs.

TABLE 38

| Ex. No. | Structure | Name | [M + H]$^+$ | Ret Time (min.) | HPLC Methods |
|---|---|---|---|---|---|
| 322 | 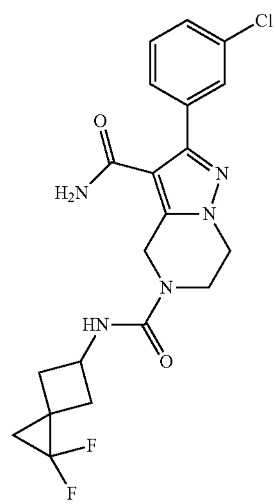 [SMILES: NC(=O)c1c(-c2cccc(Cl)c2)nn2c1CN(C(=O)NC1CC3(C1)CC3(F)F)CC2] | 2-(3-Chlorophenyl)-N$^5$-(1,1-difluorospiro[2.3]hexan-5-yl)-6,7-dihydropyrazolo[1,5-a]pyrazine-3,5(4H)-dicarboxamide | 436 | 4.92 | N |

TABLE 38-continued

| Ex. No. | Structure | Name | [M + H]+ | Ret Time (min.) | HPLC Methods |
|---|---|---|---|---|---|
| 323 | 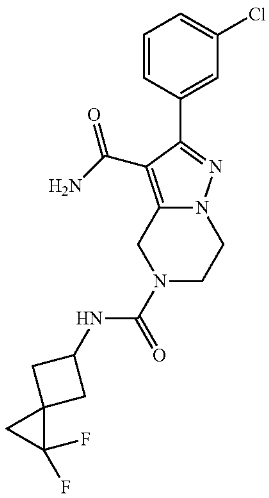 [SMILES: NC(=O)c1c(-c2cccc(Cl)c2)nn2c1CN(C(=O)NC1CC3(C1)CC3(F)F)CC2] | 2-(3-Chlorophenyl)-N5-(1,1-difluorospiro[2.3]hexan-5-yl)-6,7-dihydropyrazolo[1,5-a]pyrazine-3,5(4H)-dicarboxamide | 436 | 6.83 | N |
| 324 | 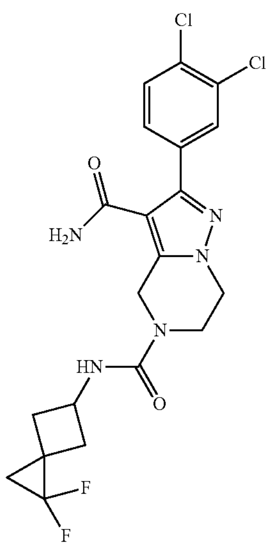 [SMILES: NC(=O)c1c(-c2ccc(Cl)c(Cl)c2)nn2c1CN(C(=O)NC1CC3(C1)CC3(F)F)CC2] | 2-(3,4-Dichlorophenyl)-N5-(1,1-difluorospiro[2.3]hexan-5-yl)-6,7-dihydropyrazolo[1,5-a]pyrazine-3,5(4H)-dicarboxamide | 471 | 8.54 | N |
| 325 | 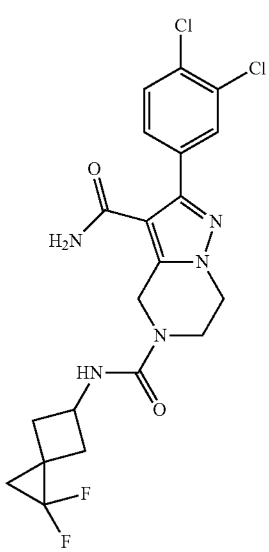 [SMILES: NC(=O)c1c(-c2ccc(Cl)c(Cl)c2)nn2c1CN(C(=O)NC1CC3(C1)CC3(F)F)CC2] | 2-(3,4-Dichlorophenyl)-N5-(1,1-difluorospiro[2.3]hexan-5-yl)-6,7-dihydropyrazolo[1,5-a]pyrazine-3,5(4H)-dicarboxamide | 471 | 9.88 | N |

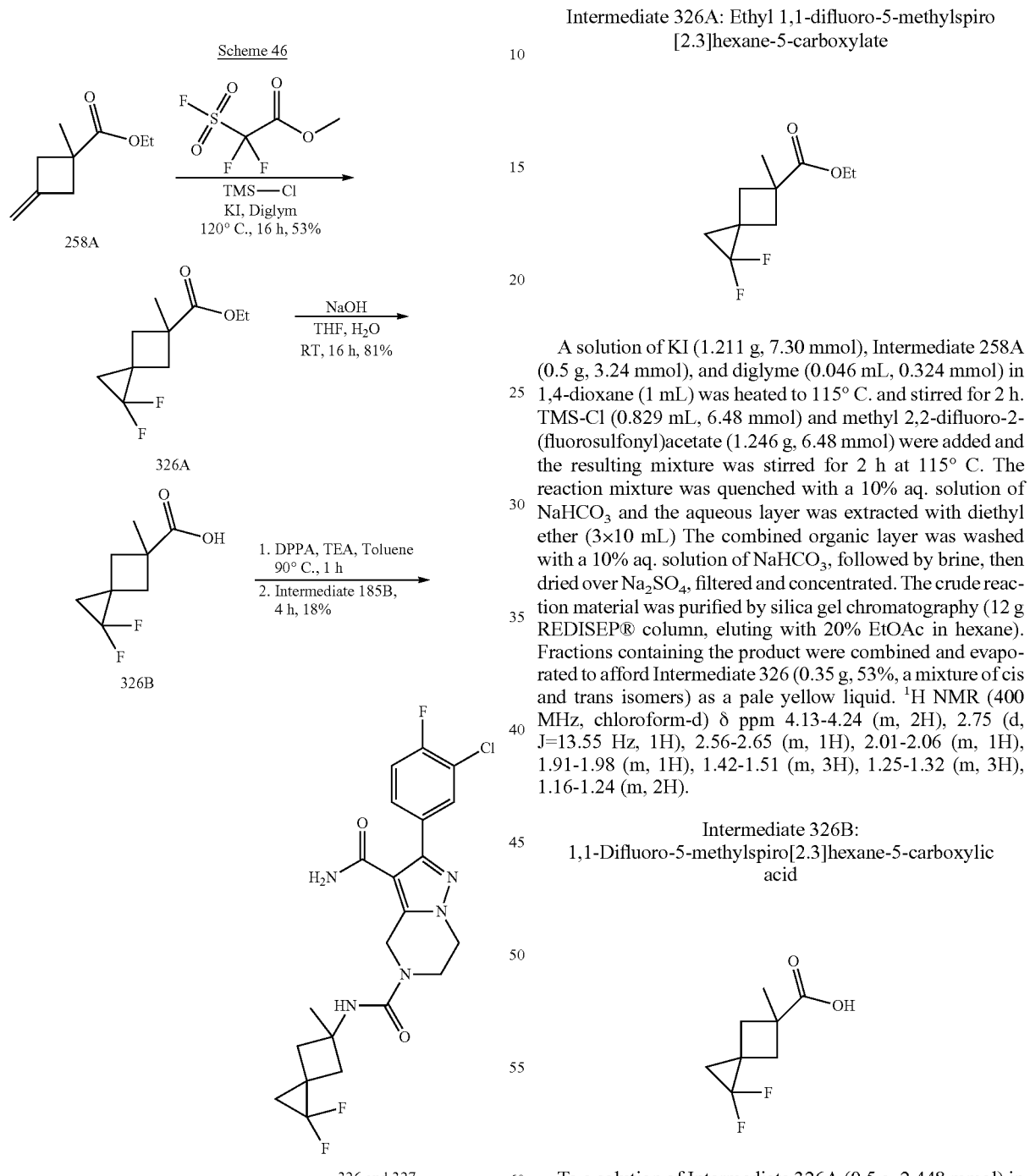

Intermediate 326A: Ethyl 1,1-difluoro-5-methylspiro[2.3]hexane-5-carboxylate

A solution of KI (1.211 g, 7.30 mmol), Intermediate 258A (0.5 g, 3.24 mmol), and diglyme (0.046 mL, 0.324 mmol) in 1,4-dioxane (1 mL) was heated to 115° C. and stirred for 2 h. TMS-Cl (0.829 mL, 6.48 mmol) and methyl 2,2-difluoro-2-(fluorosulfonyl)acetate (1.246 g, 6.48 mmol) were added and the resulting mixture was stirred for 2 h at 115° C. The reaction mixture was quenched with a 10% aq. solution of NaHCO$_3$ and the aqueous layer was extracted with diethyl ether (3×10 mL) The combined organic layer was washed with a 10% aq. solution of NaHCO$_3$, followed by brine, then dried over Na$_2$SO$_4$, filtered and concentrated. The crude reaction material was purified by silica gel chromatography (12 g REDISEP® column, eluting with 20% EtOAc in hexane). Fractions containing the product were combined and evaporated to afford Intermediate 326 (0.35 g, 53%, a mixture of cis and trans isomers) as a pale yellow liquid. $^1$H NMR (400 MHz, chloroform-d) δ ppm 4.13-4.24 (m, 2H), 2.75 (d, J=13.55 Hz, 1H), 2.56-2.65 (m, 1H), 2.01-2.06 (m, 1H), 1.91-1.98 (m, 1H), 1.42-1.51 (m, 3H), 1.25-1.32 (m, 3H), 1.16-1.24 (m, 2H).

Intermediate 326B: 1,1-Difluoro-5-methylspiro[2.3]hexane-5-carboxylic acid

To a solution of Intermediate 326A (0.5 g, 2.448 mmol) in THF (10 mL) and water (5 mL) was added NaOH (0.245 g, 6.12 mmol) and the reaction mixture was stirred at RT for 16 h. The volatiles were removed from the reaction mixture and the pH of the resulting residue was adjusted to ~3 using a 1.0 N aq. solution of HCl. The aqueous layer was extracted with EtOAc (3×10 mL) The combined organic layer was washed with water, brine, dried over Na$_2$SO$_4$, filtered and concentrated to afford Intermediate 326B (0.35 g, 81%, a mixture of cis and trans isomers) as a yellow liquid used directly in the next step without purification. $^1$H NMR (400 MHz, DMSO-d$_6$) δ ppm 12.39 (br. s., 1H), 2.55-2.63 (m, 2H), 1.89-2.02 (m, 2H), 1.34-1.45 (m, 3H), 1.14-1.23 (m, 2H).

Compounds 326 and 327: 2-(3-Chloro-4-fluorophenyl)-N5-(1,1-difluoro-5-methylspiro[2.3]hexan-5-yl)-6,7-dihydropyrazolo[1,5-a]pyrazine-3,5(4H)-dicarboxamide

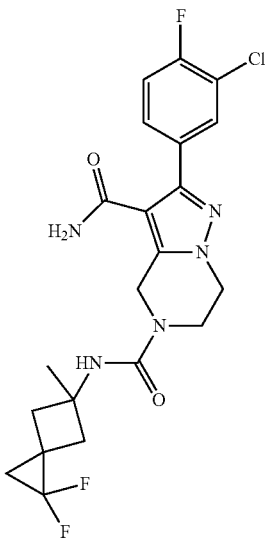 [SMILES: CC1(NC(=O)N2CCn3nc(-c4ccc(F)c(Cl)c4)c(C(N)=O)c3C2)CC2(C1)CC2(F)F]

To a solution of Intermediate 326B (90 mg, 0.509 mmol), TEA (0.142 mL, 1.018 mmol) in toluene (10 mL) was added DPPA (0.110 mL, 0.509 mmol) and the reaction mixture was stirred at 90° C. for 2 h. The reaction mixture was cooled to RT and to it was added a solution of Intermediate 185B (100 mg, 0.339 mmol) in THF (3 mL) and stirred at RT for 4 h. The reaction mixture was quenched with water and the aq. layer was extracted with ethyl acetate (3×5 mL). The combined organic layers were washed with a 10% aq. solution of NaHCO$_3$ and water, then dried over Na$_2$SO$_4$, filtered and concentrated. The crude reaction material was purified by preparative TLC and was loaded on a 0.5 mm silica gel plate. The plate was developed using 6% MeOH in CHCl$_3$. The band containing the desired product was separated and extracted into 10% MeOH in DCM, and was then filtered and concentrated to afford cis and trans mixture of Compounds 326 and 327 as an off-white solid. The individual isomers were separated by preparative chiral SFC.

Compound 326: Retention time=6.52 min (Method Q); MS(ES): m/z=468 [M+H]$^+$; Yield=0.03 g, 18%; $^1$H NMR (300 MHz, DMSO-d$_6$) δ ppm 7.85 (dd, J=7.18, 2.27 Hz, 1H), 7.64-7.73 (m, 1H), 7.48 (d, J=9.07 Hz, 1H), 7.36 (br. s., 1H), 7.20 (br. s., 1H), 7.08 (s, 1H), 4.72 (s, 2H), 4.09-4.17 (m, 2H), 3.82 (t, J=4.91 Hz, 2H), 2.53-2.61 (m, 2H), 2.04 (d, J=13.22 Hz, 2H), 1.32-1.44 (m, 5H).

Compound 327: Retention time=7.49 min (Method Q); MS(ES): m/z=468 [M+H]$^+$; Yield=0.03 g, 18%; $^1$H NMR (400 MHz, DMSO-d$_6$) δ ppm 7.85-7.89 (m, 1H), 7.66-7.73 (m, 1H), 7.48 (d, J=9.54 Hz, 1H), 7.35 (br. s., 1H), 7.20 (br. s., 1H), 6.97 (s, 1H), 4.73 (s, 2H), 4.15 (t, J=5.27 Hz, 2H), 3.84 (t, J=5.27 Hz, 2H), 2.57 (d, J=12.55 Hz, 2H), 2.00 (d, J=13.05 Hz, 2H), 1.51 (s, 3H), 1.42 (t, J=8.53 Hz, 2H).

The Compounds shown in Table 39 have been prepared similar to Compounds 326 and 327 by coupling of in-situ generated isocyanate of 326B with 185B analogs.

TABLE 39

| Ex. No. | Structure | Name | [M + H]$^+$ | Ret Time (min.) | HPLC Methods |
|---|---|---|---|---|---|
| 328 | 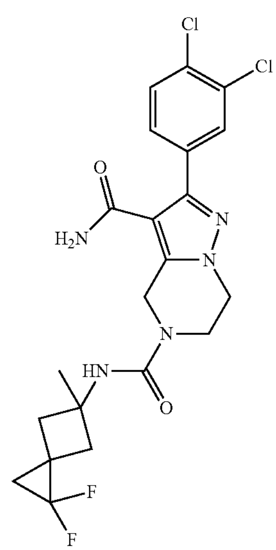 [SMILES: CC1(NC(=O)N2CCn3nc(-c4ccc(Cl)c(Cl)c4)c(C(N)=O)c3C2)CC2(C1)CC2(F)F] | 2-(3,4-Dichlorophenyl)-N$^5$-(1,1-difluoro-5-methylspiro[2.3]hexan-5-yl)-6,7-dihydropyrazolo[1,5-a]pyrazine-3,5(4H)-dicarboxamide | 484 | 9.08 | N |

TABLE 39-continued

| Ex. No. | Structure | Name | [M + H]+ | Ret Time (min.) | HPLC Methods |
|---|---|---|---|---|---|
| 329 | 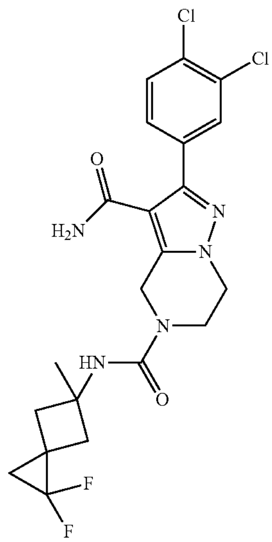 [SMILES: CC1(NC(=O)N2CCn3nc(-c4ccc(Cl)c(Cl)c4)c(C(N)=O)c3C2)CC2(C1)CC2(F)F] | 2-(3,4-Dichlorophenyl)-N5-(1,1-difluoro-5-methylspiro[2.3]hexan-5-yl)-6,7-dihydropyrazolo[1,5-a]pyrazine-3,5(4H)-dicarboxamide | 484 | 10.33 | N |
| 330 | 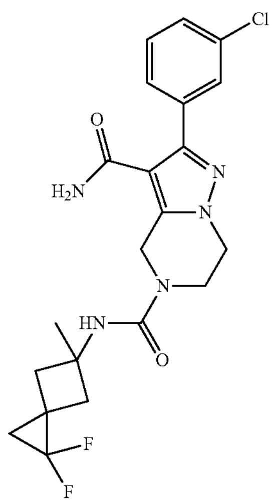 | 2-(3-Chlorophenyl)-N5-(1,1-difluoro-5-methylspiro[2.3]hexan-5-yl)-6,7-dihydropyrazolo[1,5-a]pyrazine-3,5(4H)-dicarboxamide | 450 | 6.59 | N |
| 331 | 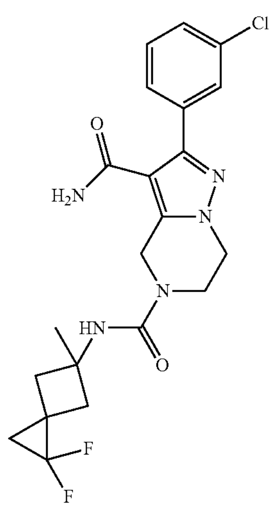 [SMILES: CC1(NC(=O)N2CCn3nc(-c4cccc(Cl)c4)c(C(N)=O)c3C2)CC2(C1)CC2(F)F] | 2-(3-Chlorophenyl)-N5-(1,1-difluoro-5-methylspiro[2.3]hexan-5-yl)-6,7-dihydropyrazolo[1,5-a]pyrazine-3,5(4H)-dicarboxamide | 450 | 7.62 | N |

Scheme 47

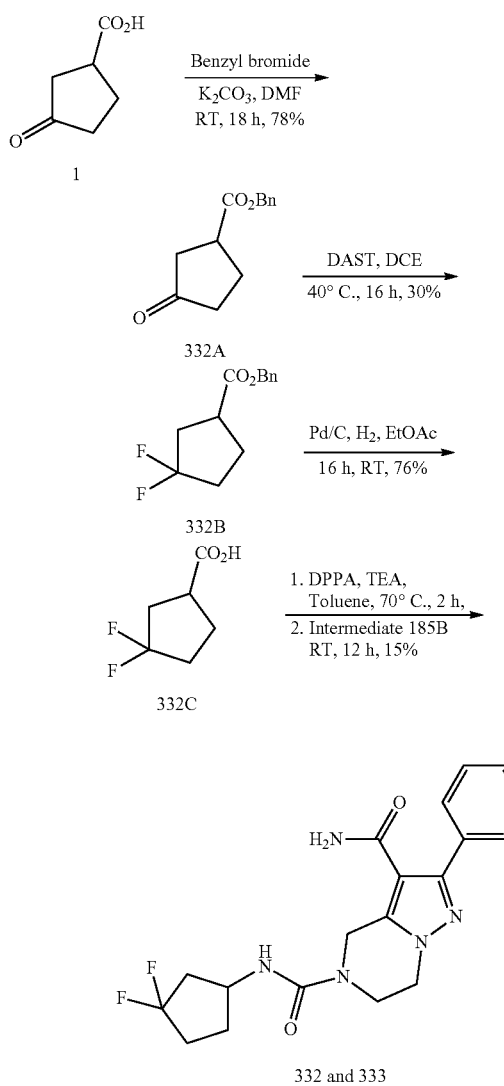

Intermediate 332A: Benzyl 3-oxocyclopentanecarboxylate

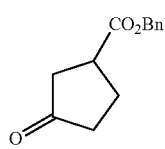 [SMILES: O=C1CCC(C(=O)OCc2ccccc2)C1]

To a stirred solution of 3-oxocyclopentanecarboxylic acid (1.5 g, 11.71 mmol) in DMF (20 mL) was added $K_2CO_3$ (1.780 g, 12.88 mmol) followed by benzyl bromide (1.360 mL, 11.71 mmol) under nitrogen. The reaction mixture was then stirred for 18 h at RT. The reaction mixture was poured into water (100 mL) and extracted with ethyl acetate (2×100 mL). The combined organic layer was washed with brine, dried over anhydrous $Na_2SO_4$ and concentrated under reduced pressure. The crude compound was purified by silica gel chromatography (12 g REDISEP® column, eluting with 20% EtOAc in hexane). Fractions containing the product were combined and evaporated to afford Intermediate 332A (2.1 g, 78% yield) as an oil. $^1$H NMR (400 MHz, chloroform-d) δ ppm 7.42-7.31 (m, 5H), 5.16 (s, 2H), 3.22-3.12 (m, 1H), 2.58-2.45 (m, 2H), 2.44-2.29 (m, 2H), 2.23 (s, 2H).

Intermediate 332B: Benzyl 3,3-difluorocyclopentanecarboxylate

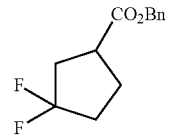 [SMILES: O=C(OCc1ccccc1)C1CCC(F)(F)C1]

To a stirred ice-cooled solution of Intermediate 332A (0.2 g, 0.916 mmol) in anhydrous DCE (4 mL) was added DAST (0.303 mL, 2.291 mmol) under nitrogen. The reaction mixture was then allowed to heat to 40° C. and stir for 16 h. The reaction mixture was quenched with an aq. solution of $NaHCO_3$ at 0° C. and extracted with DCM (2×50 mL). The combined organic layer was dried over anhydrous $Na_2SO_4$ and concentrated under reduced pressure. The crude compound was purified by silica gel chromatography (12 g REDISEP® column, eluting with 10% EtOAc in hexanes). Fractions containing the product were combined and evaporated to afford Intermediate 332B as a colorless oil (0.07 g, 30% yield). $^1$H NMR (400 MHz, chloroform-d) δ ppm 7.41-7.31 (m, 5H), 5.15 (s, 2H), 3.05 (m, 1H), 2.49-2.33 (m, 2H), 2.26-2.00 (m, 4H).

Intermediate 332C: 3,3-Difluorocyclopentanecarboxylic acid

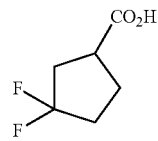

To a stirred solution of Intermediate 332B (0.07 g, 0.291 mmol) in EtOAc (2 mL) was added 10% Pd/C (0.016 g, 0.015 mmol) and the resulting mixture was stirred for 16 h under an atmosphere of hydrogen (15 psi, balloon pressure). The reaction mixture was filtered through a pad of CELITE® and the filter cake was washed with EtOAc. The combined filtrate was concentrated under reduced pressure to afford Intermediate 332C as a colorless oil (0.035 g, 76% yield). $^1$H NMR (400 MHz, DMSO-$d_6$) δ ppm 12.41 (br. s., 1H), 3.04-2.94 (m, 1H), 2.39-2.23 (m, 2H), 2.20-2.01 (m, 3H), 1.95-1.84 (m, 1H).

Compounds 332 and 333: 2-(3-Chloro-4-fluorophenyl)-$N^5$-(3,3-difluorocyclopentyl)-6,7-dihydropyrazolo[1,5-a]pyrazine-3,5(4H)-dicarboxamide

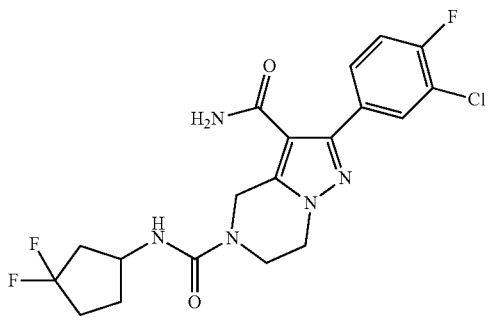 [SMILES: NC(=O)c1c(-c2ccc(F)c(Cl)c2)nn2c1CN(C(=O)NC1CCC(F)(F)C1)CC2]

A stirred solution of Intermediate 332C (32.6 mg, 0.217 mmol) in toluene (1 mL) at RT under nitrogen was added with TEA (0.045 mL, 0.325 mmol) and DPPA (0.050 mL, 0.217 mmol) and heated to 70° C. for 2 h. The reaction mass was cooled to RT and to it was added a solution of Intermediate 185B (30 mg, 0.108 mmol) in THF (1 mL) and stirred at RT for 16 h. The reaction mass was diluted with ethyl acetate (25 mL), washed with water and brine, dried over anhydrous $Na_2SO_4$, filtered, and the filtrate concentrated under reduced pressure. The individual isomers were separated by preparative chiral SFC (Column: WHELK-O® 1 (R,R) (250×4.6 mm), 5μ column, 5 Co-Solvent: 0.2% DEA, Column Temperature: 24.4, Total Flow: 3 mL, $CO_2$ Flow Rate: 2.1, Co-Solvent Flow Rate: 0.9, Co-Solvent %: 30%, Back Pressure: 101 bar.

Compound 332: (retention time 4.6 min), (7 mg, 16%); MS(ES): m/z=424.1 $[M+H]^+$; $^1H$ NMR (400 MHz, DMSO-$d_6$) δ ppm 7.69-7.72 (m, 1H), 7.64 (dt, J=6.65, 1.95 Hz, 1H), 7.40-7.48 (m, 2H), 7.36 (br. s., 1H), 7.18 (br. s., 1H), 6.98 (d, J=7.03 Hz, 1H), 4.73 (s, 2H), 4.10-4.20 (m, 3H), 3.84 (t, J=5.52 Hz, 2H), 2.34-2.46 (m, 1H), 2.15-2.27 (m, 1H), 1.96-2.12 (m, 3H), 1.67-1.78 (m, 1H).

Compound 333: (retention time 4.92 min), (6 mg, 15%); MS(ES): m/z=424.1 $[M+H]^+$; $^1H$ NMR (400 MHz, DMSO-$d_6$) δ ppm 7.71 (t, J=1.76 Hz, 1H), 7.62-7.66 (m, 1H), 7.42-7.47 (m, 2H), 7.37 (br. s., 1H), 7.18 (br. s., 1H), 6.99 (d, J=15.56 Hz, 1H), 4.73 (s, 2H), 4.11-4.18 (m, 3H), 3.84 (t, J=5.52 Hz, 2H), 2.38-2.46 (m, 1H), 2.17-2.30 (m, 1H), 1.98-2.11 (m, 3H), 1.67-1.77 (m, 1H).

Scheme 48

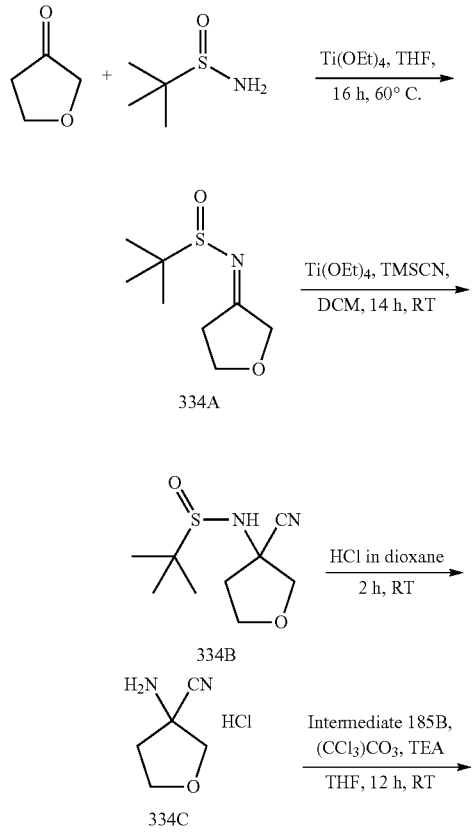

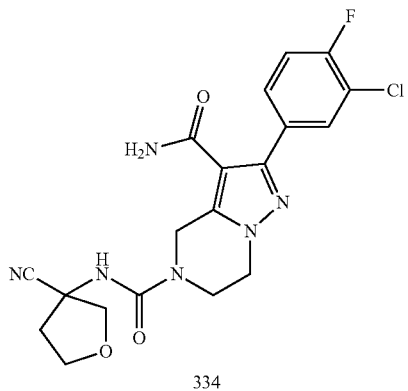

334

Intermediate 334A: N-(Dihydrofuran-3(2H)-ylidene)-2-methylpropane-2-sulfinamide

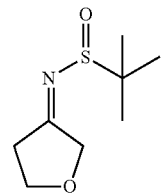

To a stirred solution of dihydrofuran-3(2H)-one (0.901 mL, 11.62 mmol) in THF (20 mL) at RT under nitrogen was added $Ti(OEt)_4$ (4.87 mL, 23.23 mmol), 2-methylpropane-2-sulfinamide (1.549 g, 12.78 mmol) and the reaction mixture was stirred at 60° C. for 8 h. The reaction mixture was quenched with a saturated aq. solution of $NaHCO_3$ with vigorous stirring. The precipitate was filtered and washed with EtOAc and the aq. layer was extracted with EtOAc. The combined organic layer was dried over sodium sulfate, filtered and concentrated. The crude product was purified by silica gel chromatography (40 g REDISEP® column, eluting with 25% ethyl acetate in hexanes). Fractions containing the product were combined and evaporated to afford Compound 334A as a pale yellow liquid (700 mg, 32%). The crude compound was taken to next step without purification.

Intermediate 334B: N-(3-Cyanotetrahydrofuran-3-yl)-2-methylpropane-2-sulfinamide

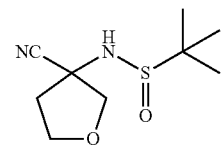

To a solution of Intermediate 334A (300 mg, 1.585 mmol) in DCM (10 mL) at RT was added TMSCN (198 μL, 1.477 mmol) dropwise, followed by Ti(OEt)₄ (318 μL, 1.426 mmol). The resulting solution was stirred for 12 h. The reaction was quenched by pouring it into a vigorously stirred saturated aq. solution of NaHCO₃ (20 mL). The precipitate was filtered off and the aqueous layer was extracted with EtOAc. The combined organic layers were dried over sodium sulfate, filtered and concentrated. The crude compound was triturated with diethyl ether to afford Intermediate 334B (150 mg, 44% yield) as a pale brown solid. ¹H NMR (400 MHz, DMSO-d₆) δ ppm 6.48-6.36 (m, 1H), 4.05 (d, J=9.0 Hz, 1H), 3.87 (d, J=8.5 Hz, 3H), 2.49-2.33 (m, 2H), 1.21-1.10 (m, 9H).

Intermediate 334C:
3-Aminotetrahydrofuran-3-carbonitrile, HCl

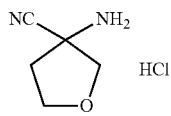

To a flask charged with Intermediate 334B (80 mg, 0.370 mmol) was added a 4 M solution of HCl in dioxane (925 μl, 3.70 mmol) and the reaction mixture was stirred at RT for 2 h. The reaction mixture was concentrated under vacuum and the crude product triturated with diethyl ether to afford Intermediate 334C as a pale yellow solid (40 mg, 72.8%). ¹H NMR (400 MHz, DMSO-d₆) δ ppm 9.18-9.06 (br. s., 2H), 4.18-4.06 (m, 1H), 4.04-3.86 (m, 3H), 2.72-2.57 (m, 1H), 2.47-2.32 (m, 1H).

Compound 334: 2-(3-Chloro-4-fluorophenyl)-$N^5$-(3-cyanotetrahydrofuran-3-yl)-6,7-dihydropyrazolo[1,5-a]pyrazine-3,5(4H)-dicarboxamide

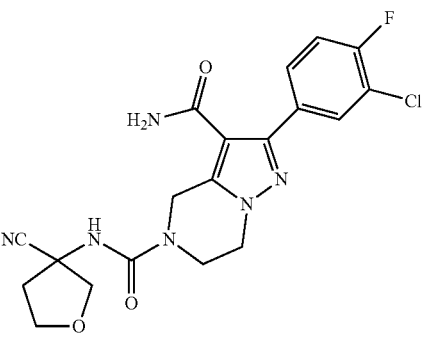 [SMILES: N#CC1(NC(=O)N2CCn3nc(-c4ccc(F)c(Cl)c4)c(C(N)=O)c3C2)CCOC1]

To a solution of Intermediate 334B (30.3 mg, 0.204 mmol) and TEA (0.142 mL, 1.018 mmol) in THF (8 mL) was added triphosgene (54.4 mg, 0.183 mmol) at 0° C. and the reaction mixture was stirred for 30 min at the same temperature. A solution of Intermediate 185B (60 mg, 0.204 mmol) in THF (1 mL) was added and the reaction mixture was stirred at RT for 12 h. The reaction mixture was diluted with water and extracted with ethyl acetate (3×15 mL). The combined organic layer was dried over sodium sulfate, filtered and the filtrate concentrated. The crude product was purified by preparative HPLC to afford Compound 334 as an off-white solid (20.6 mg, 23%). HPLC retention time 7.12 and 7.33 min (Methods B and C respectively). MS(ES): m/z=433 [M+H]⁺; ¹H NMR (400 MHz, DMSO-d₆) δ ppm 7.86 (dd, J=7.28, 2.26 Hz, 1H), 7.65-7.72 (m, 2H), 7.44-7.51 (m, 1H), 7.17-7.41 (m, 2H), 4.79 (s, 2H), 4.16-4.23 (m, 3H), 3.81-3.96 (m, 5H), 2.40-2.49 (m, 2H).

The Compounds shown in Table 40 have been prepared similar to Compound 334 by coupling of in-situ generated isocyanate of 334B with 199B.

TABLE 40

| Ex. No. | Structure | Name | [M + H]⁺ | Ret Time (min.) | HPLC Methods |
|---|---|---|---|---|---|
| 335 | 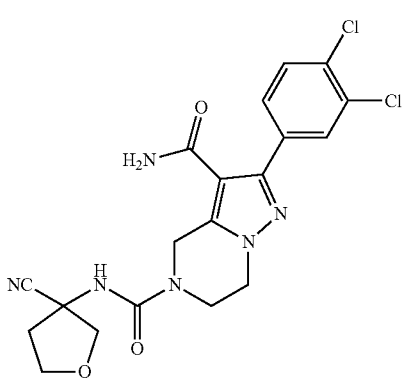 [SMILES: N#CC1(NC(=O)N2CCn3nc(-c4ccc(Cl)c(Cl)c4)c(C(N)=O)c3C2)CCOC1] | $N^5$-(3-Cyanotetrahydrofuran-3-yl)-2-(3,4-dichlorophenyl)-6,7-dihydropyrazolo[1,5-a]pyrazine-3,5(4H)-dicarboxamide | 451 | 1.24 1.24 | E L |

Scheme 49

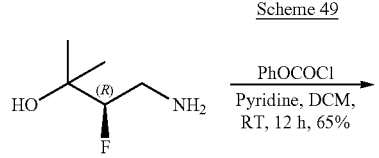

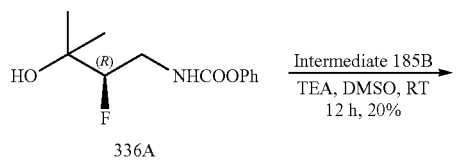

336A

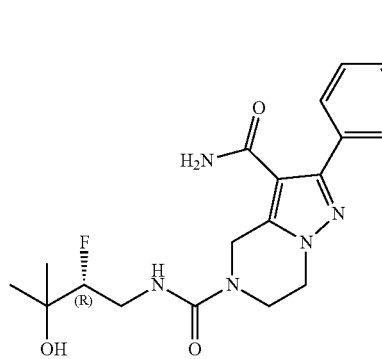

336

Intermediate 336A: (R)-Phenyl(2-fluoro-3-hydroxy-3-methylbutyl)carbamate

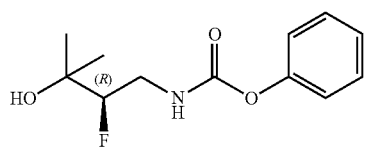

To a solution of (R)-4-amino-3-fluoro-2-methylbutan-2-ol (100 mg, 0.825 mmol) in DCM (3 mL) was added phenyl chloroformate (0.124 mL, 0.990 mmol) at 0° C. followed by pyridine (0.100 mL, 1.238 mmol); the reaction mixture was stirred at RT for 12 h. The reaction mixture was quenched with water and extracted with ethyl acetate (3×10 mL). The combined organic layer was washed with a 1.5 N aq. solution of HCl, dried over Na$_2$SO$_4$, filtered and the filtrate evaporated under vacuum to afford Intermediate 336A as a colorless liquid (130 mg, 65%). The crude product was used in the subsequent transformation without further purification. $^1$H NMR (300 MHz, chloroform-d) δ ppm 7.33-7.44 (m, 2H), 7.06-7.31 (m, 3H), 5.48 (bs, 1H), 4.30-4.56 (m, 1H), 3.73 (m, 1H), 3.33-3.51 (m, 1H), 1.91 (m, 1H), 1.32 (dd, J=11.95, 1.23 Hz, 6H).

Compound 336: (R)-2-(3-Chloro-4-fluorophenyl)-N$^5$-(2-fluoro-3-hydroxy-3-methylbutyl)-6,7-dihydropyrazolo[1,5-a]pyrazine-3,5(4H)-dicarboxamide

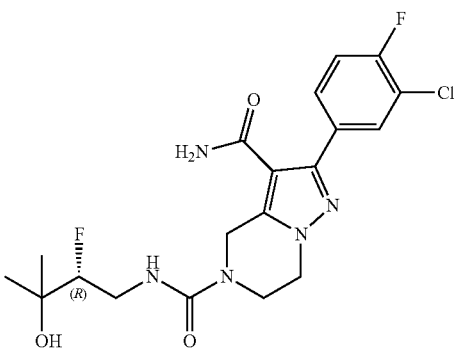

To a stirred solution of 185B (0.03 g, 0.102 mmol) in DMSO (1 mL) was added Intermediate 336A (0.025 g, 0.102 mmol) and TEA (0.043 mL, 0.305 mmol) under nitrogen and the reaction mixture was stirred at RT for 12 h. The reaction mixture was diluted with ethyl acetate (50 mL), washed with water, brine, dried over anhydrous Na$_2$SO$_4$, filtered and the filtrate was concentrated. The crude product was purified by preparative HPLC to afford Compound 336 as a pale yellow solid (9 mg, 20%). The HPLC Retention times are 1.168 min and 1.209 min (Methods E and L respectively). MS(ES): –m/z=442.2 [M+H]$^+$; $^1$H NMR (400 MHz, DMSO-d$_6$) δ ppm 7.85 (dd, J=7.28, 2.13 Hz, 1H), 7.68 (ddd, J=8.64, 4.82, 2.16 Hz, 1H), 7.46 (t, J=9.00 Hz, 1H), 7.40-7.20 (2bs, 2H), 7.11 (t, J=5.40 Hz, 1H), 4.69-4.79 (m, 3H), 4.29-4.10 (dd, J=9.19, 1.85 Hz, 1H), 4.09-4.22 (m, 2H), 3.80-3.89 (m, 2H), 3.45-3.63 (m, 1H), 3.09-3.22 (m, 1H), 1.12 (dd, J=5.08, 1.13 Hz, 6H).

The Compounds shown in Table 41 have been prepared similar to Compound 336 by coupling of 336A with 185B analogs.

TABLE 41
| Ex. No. | Structure | Name | [M + H]+ | Ret Time (min.) | HPLC Methods |
|---|---|---|---|---|---|
| 337 | 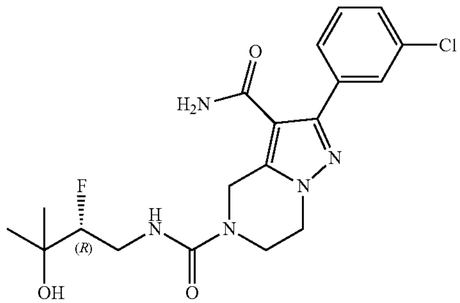 | (R)-2-(3-Chlorophenyl)-N⁵-(2-fluoro-3-hydroxy-3-methylbutyl)-6,7-dihydropyrazolo[1,5-a]pyrazine-3,5(4H)-dicarboxamide | 424.2 | 1.111<br>1.152 | E<br>L |
| 338 | 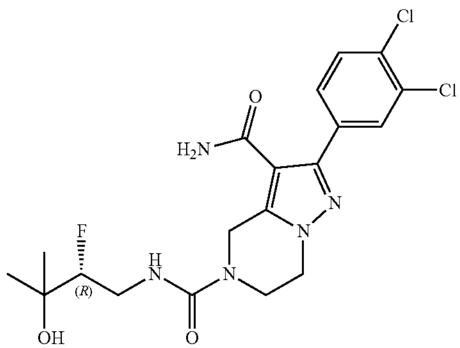 | (R)-2-(3,4-Dichlorophenyl)-N⁵-(2-fluoro-3-hydroxy-3-methylbutyl)-6,7-dihydropyrazolo[1,5-a]pyrazine-3,5(4H)-dicarboxamide | 458.2 | 1.247<br>1.230 | E<br>L |
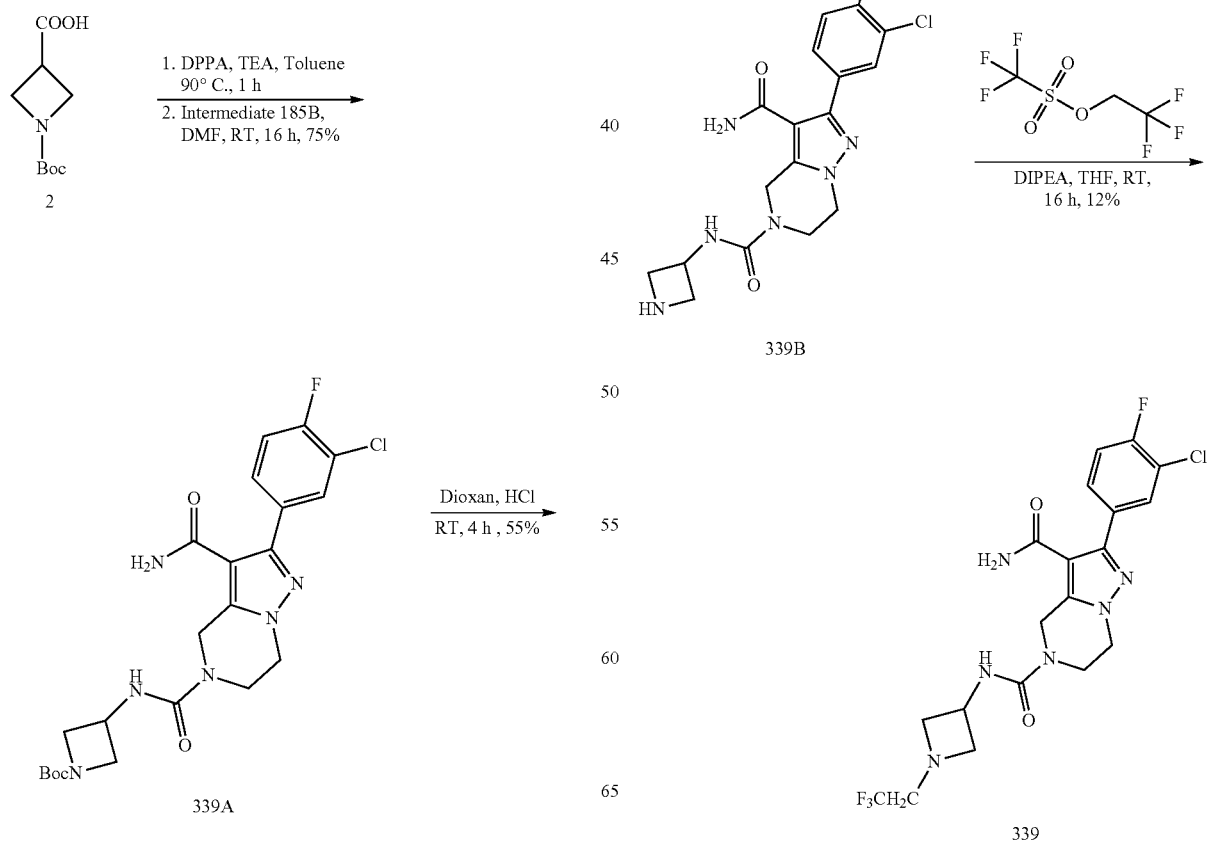

Intermediate 339A: tert-Butyl 3-(3-carbamoyl-2-(3-chloro-4-fluorophenyl)-4,5,6,7-tetrahydropyrazolo[1,5-a]pyrazine-5-carboxamido)azetidine-1-carboxylate

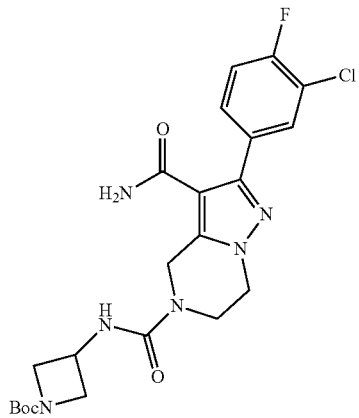 [SMILES: CC(C)(C)OC(=O)N1CC(NC(=O)N2CCn3nc(-c4ccc(F)c(Cl)c4)c(C(N)=O)c3C2)C1]

To a stirred solution of Intermediate 1-(tert-butoxycarbonyl)azetidine-3-carboxylic acid (273 mg, 1.47 mmol) in toluene (6 mL) was added TEA (0.472 ml, 3.39 mmol) followed by DPPA (0.22 ml, 1.0 mmol) and the mixture was stirred at 90° C. for 1 h. The reaction mixture was cooled to RT and a solution of Intermediate 185B (200 mg, 0.679 mmol) in DMF (2 mL) was added and stirring continued at RT for 16 h. The reaction was quenched with a 10% aq. solution of NaHCO$_3$, the organic layer was separated, dried over sodium sulfate, and concentrated. The crude product was purified by silica gel chromatography (4 g REDISEP® column, eluting with 5% MeOH in CHCl$_3$). Fractions containing the product were combined and evaporated to afford Intermediate 339A as a buff colored solid (250 mg, 75% yield) MS(ES): m/z=493.

Intermediate 339B: N$^5$-(Azetidin-3-yl)-2-(3-chloro-4-fluorophenyl)-6,7-dihydropyrazolo[1,5-a]pyrazine-3,5(4H)-dicarboxamide

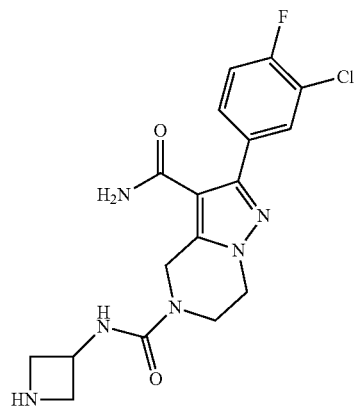 [SMILES: NC(=O)c1c(-c2ccc(F)c(Cl)c2)nn2c1CN(C(=O)NC1CNC1)CC2]

To a stirred solution of Intermediate 339A (0.25 g, 0.50 mmol) in MeOH (5 mL) was added a 4M solution of HCl in dioxane (5 mL, 20 mmol). The resulting solution was allowed to stir at RT for 4 h. The reaction mixture was then concentrated and triturated with diethyl ether to afford Intermediate 339B (0.2 g, 55%). MS(ES): m/z=393 [M+H]$^+$; $^1$H NMR (400 MHz, DMSO-d$_6$) δ ppm 7.84 (dd, J=7.03, 2.01 Hz, 1H) 7.64-7.70 (m, 1H), 7.45 (q, J=8.70 Hz, 1H), 7.18-7.39 (m, 2H), 6.61 (d, J=7.53 Hz, 1H), 5.53 (s, 1H), 4.73 (s, 2H), 4.13 (m, 1H), 3.97-4.04 (m, 2H), 3.83 (br. s., 2H) 3.05-3.16 (m, 4H).

Compound 339: 2-(3-Chloro-4-fluorophenyl)-N$^5$-(1-(2,2,2-trifluoroethyl)azetidin-3-yl)-6,7-dihydropyrazolo[1,5-a]pyrazine-3,5(4H)-dicarboxamide

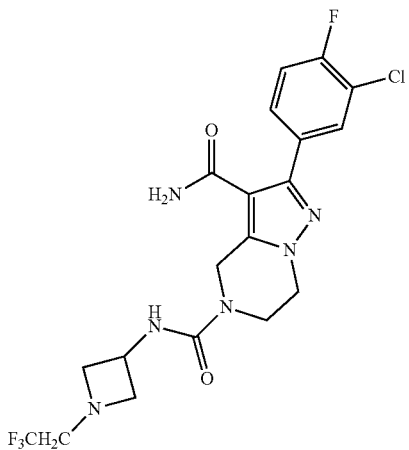

To a stirred solution of Intermediate 339B (100 mg, 0.255 mmol) in THF (10 mL) was added DIPEA (0.222 mL, 1.273 mmol) followed by 2,2,2-trifluoroethyl trifluoromethanesulfonate (118 mg, 0.509 mmol) and stirred at RT for 16 h. The reaction mixture was quenched with a 10% aqueous solution of NaHCO$_3$ and extracted with EtOAc (2×20 mL) The combined organic layer was dried over Na$_2$SO$_4$, filtered and the filtrate evaporated. The crude compound was purified by preparative HPLC to afford Compound 339 as an off-white solid (15 mg, 12%). HPLC retention times 10.73 min. and 11.90 min (Methods C and D). MS(ES): m/z=475 [M+H]$^+$; $^1$H NMR (300 MHz, DMSO-d$_6$) δ ppm 7.84 (dd, J=7.37, 2.08 Hz, 1H), 7.62-7.72 (m, 1H), 7.41-7.50 (m, 1H), 7.36 (br. s., 1H), 7.27 (d, J=6.80 Hz, 1H), 7.18 (br. s., 1H), 4.73 (s, 2H) 4.19-4.31 (m, 1H), 4.06-4.17 (m, 2H), 3.84 (d, J=5.67 Hz, 2H), 3.57-3.69 (m, 2H), 3.09-3.23 (m, 4H).

Scheme 51

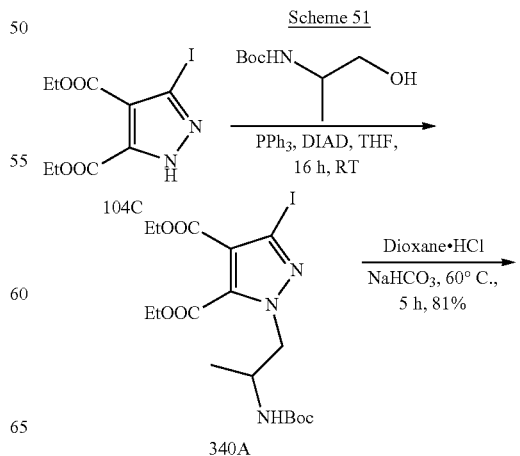

-continued
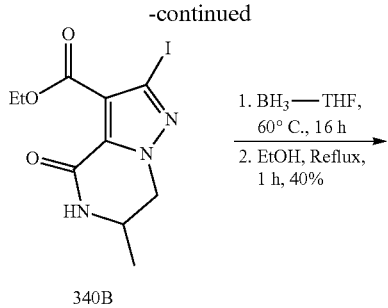
340B
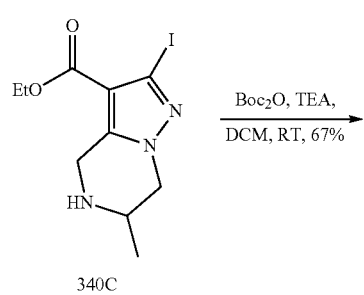
340C
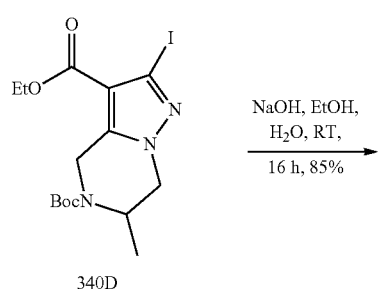
340D
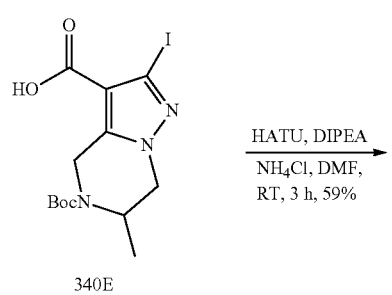
340E
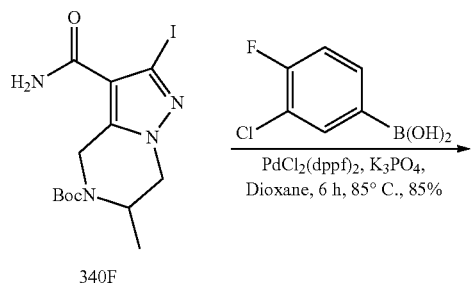
340F
-continued
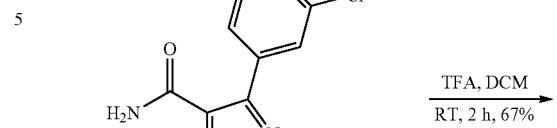
340G
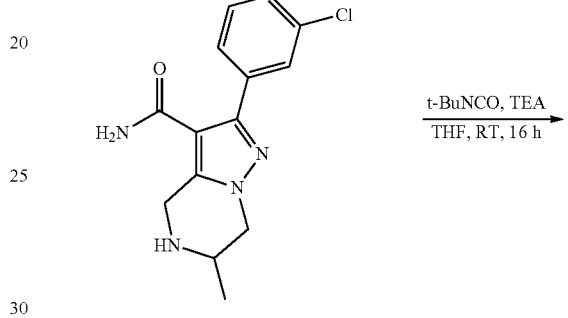
340H
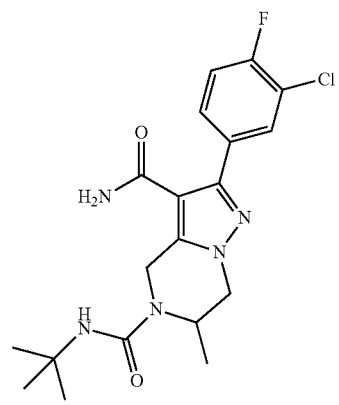
340 and 341
Intermediate 340A: Diethyl 1-(2-((tert-butoxycarbonyl)amino)propyl)-3-iodo-1H-pyrazole-4,5-dicarboxylate
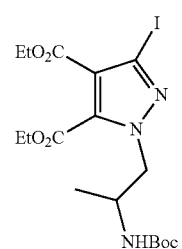

To a stirred suspension of PPh₃ (12.41 g, 47.3 mmol) in THF (100 mL) was added DIAD (9.20 mL, 47.3 mmol) at 10° C. and allowed to stir at 0° C. for 0.5 h. Intermediate 104C (8.0 g, 23.66 mmol) was added as a solution in THF (10 mL) at 0° C. and stirred at RT for 45 min. The reaction mixture was cooled again to 0° C. and tert-butyl (1-hydroxypropan-2-yl) carbamate (5.39 g, 30.8 mmol) was added as a solution in THF (10 mL) and the mixture was stirred at RT for 16 h. The reaction mixture was diluted with ethyl acetate (100 mL), washed with water and brine. The organic layer was dried over Na₂SO₄, filtered and the filtrate concentrated under reduced pressure. The crude compound was purified by silica gel chromatography (40 g REDISEP® column, eluting with 15% EtOAc in hexane). Fractions containing the product were combined and evaporated to afford the Intermediate 340A as a brown liquid (7.0 g) contaminated with impurities arising from the coupling reagents. MS(ES): m/z=496 [M+H]⁺. The crude intermediate was taken to the next step without further purification.

Intermediate 340B: Ethyl 2-iodo-6-methyl-4-oxo-4,5,6,7-tetrahydropyrazolo[1,5-a]pyrazine-3-carboxylate

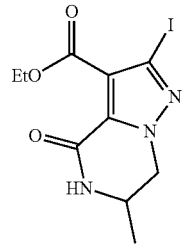

To a stirred solution of Intermediate 340A (7.0 g, 14.13 mmol) in 1,4-dioxane (10 mL) was added 4 M HCl in dioxane (25 mL, 100 mmol) and the solution was stirred at RT for 2 h. The reaction mixture was concentrated and the residue was diluted with EtOAc (20 mL). The EtOAc solution was washed successively with water, a saturated aq. solution of NaHCO₃, and brine. The organic layer was dried over Na₂SO₄, filtered and concentrated under reduced pressure. The residue obtained was heated in a ROTAVAPOR® at 60° C. for 5 h. The solid product was washed with ether to afford Intermediate 340B (4.0 g, 87%). MS(ES): m/z=350 [M+H]⁺; ¹H NMR (300 MHz, DMSO-d₆) δ ppm 8.49 (s, 1H), 4.27-4.49 (m, 1H), 4.11-4.26 (m, 2H), 4.03 (d, J=11.71 Hz, 2H), 1.06-1.39 (m, 6H).

Intermediate 340C: Ethyl 2-iodo-6-methyl-4,5,6,7-tetrahydropyrazolo[1,5-a]pyrazine-3-carboxylate

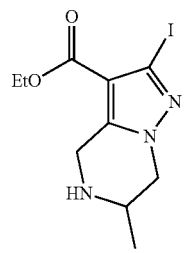 [SMILES: CCOC(=O)c1c(I)nn2c1CNC(C)C2]

To a solution of Intermediate 340B (4.0 g, 11.46 mmol) in THF (40 mL) was added BH₃·THF (40.1 mL, 80 mmol, 1M in THF) and the reaction mixture was stirred at 70° C. for 16 h. Ethanol (10 mL) was added and the reaction mixture was heated to reflux for 1 h. The reaction mixture was concentrated to afford Intermediate 340C (1.9 g, 40% yield) as a pale brown liquid. MS(ES): m/z=336 [M+H]⁺. The crude compound was taken to the next step without further purification.

Intermediate 340D: 5-tert-Butyl 3-ethyl 2-iodo-6-methyl-6,7-dihydropyrazolo[1,5-a]pyrazine-3,5(4H)-dicarboxylate

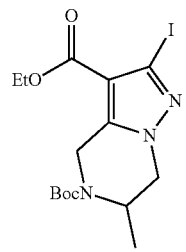 [SMILES: CCOC(=O)c1c(I)nn2c1CN(C(=O)OC(C)(C)C)C(C)C2]

To a stirred solution of Intermediate 340C (0.81 g, 2.417 mmol) in DCM (10 mL) was added TEA (0.404 mL, 2.90 mmol) followed by Boc₂O (0.617 mL, 2.66 mmol) and the resulting solution was stirred at RT for 16 h. It was then diluted with DCM (10 mL) washed with water and brine. The crude compound was purified by silica gel chromatography (12 g REDISEP® column, eluting with 1% MeOH in CHCl₃). Fractions containing the product were combined and evaporated to afford Intermediate 340D as a colorless semisolid (0.7 g, 67%). MS(ES): m/z=435 [M+H]⁺; ¹H NMR (400 MHz, DMSO-d₆) δ ppm 5.07 (d, J=18.57 Hz, 1H), 4.69 (br. s., 1H), 4.39 (d, J=18.57 Hz, 1H), 4.06-4.28 (m, 4H), 1.45 (s, 9H), 1.23-1.34 (m, 3H), 1.08 (d, J=7.03 Hz, 3H).

Intermediate 340E: 5-(tert-Butoxycarbonyl)-2-iodo-6-methyl-4,5,6,7-tetrahydropyrazolo[1,5-a]pyrazine-3-carboxylic acid

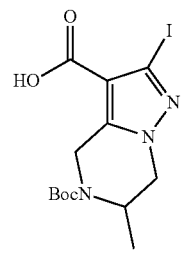 [SMILES: CC1Cn2nc(I)c(C(=O)O)c2CN1C(=O)OC(C)(C)C]

To a stirred solution of Intermediate 340D (0.85 g, 1.953 mmol) in EtOH (2.0 mL) was added a solution of NaOH (0.391 g, 9.76 mmol) in water (1.0 mL) and the resulting solution was stirred at RT for 16 h. The reaction mixture was concentrated and the residue was acidified by the addition of a 1N aq. solution of HCl (5 mL) which was allowed to stir for 10 min. The generated precipitate was filtered and dried to afford Intermediate 340E as a white solid (0.65 g, 82%). MS(ES): m/z=408 [M+H]⁺; ¹H NMR (300 MHz, DMSO-d₆) δ ppm 5.05 (d, J=18.89 Hz, 1H), 4.67 (br. s., 1H), 4.36 (d, J=18.13 Hz, 1H), 4.13-4.25 (m, 1H), 3.93-4.13 (m, 2H), 1.44 (s, 9H), 1.08 (t, J=6.99 Hz, 3H).

Intermediate 340F: tert-Butyl 3-carbamoyl-2-iodo-6-methyl-6,7-dihydropyrazolo[1,5-a]pyrazine-5 (4H)-carboxylate

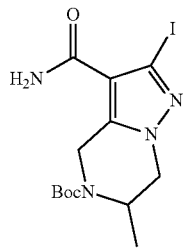 [SMILES: CC1Cn2nc(I)c(C(N)=O)c2CN1C(=O)OC(C)(C)C]

To a stirred solution of Intermediate 340E (0.65 g, 1.596 mmol) in DMF (3.0 mL) was added NH$_4$Cl (0.427 g, 7.98 mmol), HATU (1.214 g, 3.19 mmol) and DIPEA (0.836 mL, 4.79 mmol) and the resulting solution was allowed to stir at RT for 3 h. It was diluted with ethyl acetate (10 mL), washed with water, brine, dried over Na$_2$SO$_4$, filtered and the filtrate concentrated. The crude compound was purified by silica gel chromatography (12 g REDISEP® column, eluting with 2% MeOH in CHCl$_3$). Fractions containing the product were combined and evaporated to afford Intermediate 340F as a colorless liquid (0.38 g, 59%). MS(ES): m/z=407 [M+H]$^+$; $^1$H NMR (300 MHz, DMSO-d$_6$) δ ppm 6.79-7.56 (m, 2H), 5.01 (d, J=18.51 Hz, 1H), 4.66 (br. s., 1H), 4.39 (d, J=18.13 Hz, 1H), 3.96-4.20 (m, 2H), 1.44 (s, 9H), 1.07 (d, J=6.80 Hz, 3H).

Intermediate 340G: text-Butyl 3-carbamoyl-2-iodo-6-methyl-6,7-dihydropyrazolo[1,5-a]pyrazine-5(4H)-carboxylate

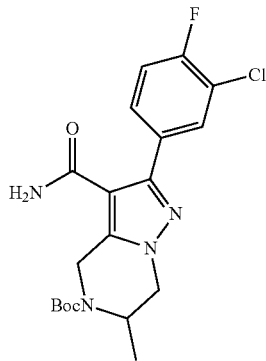 [SMILES: CC1Cn2nc(-c3ccc(F)c(Cl)c3)c(C(N)=O)c2CN1C(=O)OC(C)(C)C]

To a stirred suspension of Intermediate 340F (0.32 g, 0.788 mmol) in 1,4-dioxane (8.0 mL) was added (3-chloro-4-fluorophenyl)boronic acid (0.179 g, 1.024 mmol), K$_3$PO$_4$ (1.292 g, 2.58 mmol) and the contents of the flask were purged with N$_2$ for 10 min. PdCl$_2$(dppf)-CH$_2$Cl$_2$ (0.042 g, 0.052 mmol) was then added and the reaction mixture was stirred at 80° C. for 6 h. The reaction mixture was cooled to RT; diluted with ethyl acetate (10 mL), washed with water, dried over Na$_2$SO$_4$, filtered and the filtrate concentrated under reduced pressure. The crude compound was purified by silica gel chromatography (12 g REDISEP® column, eluting with 2% MeOH in CHCl$_3$). Fractions containing the product were combined and evaporated to afford Intermediate 340G as a pale yellow solid (0.27 g, 84%). MS(ES): m/z=408 [M+H]$^+$; $^1$H NMR (300 MHz, DMSO-d$_6$) δ ppm 7.85-7.92 (m, 1H), 7.71 (ddd, J=8.69, 4.91, 2.27 Hz, 1H), 7.46 (d, J=17.75 Hz, 1H), 7.24-7.38 (m, 2H), 4.99 (d, J=17.75 Hz, 1H), 4.72 (br. s., 1H), 4.44 (d, J=17.75 Hz, 1H), 4.08-4.28 (m, 2H), 1.46 (s, 9H), 1.15 (s, 3H).

Intermediate 340H: 2-(3-Chloro-4-fluorophenyl)-6-methyl-4,5,6,7-tetrahydropyrazolo[1,5-a]pyrazine-3-carboxamide, TFA

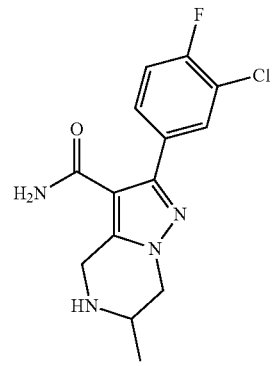 [SMILES: CC1Cn2nc(-c3ccc(F)c(Cl)c3)c(C(N)=O)c2CN1]

To a stirred solution of Intermediate 340G (0.09 g, 0.220 mmol) in DCM (3.0 mL) was added TFA (0.017 mL, 0.220 mmol) and the resulting solution was stirred at RT for 2 h. It was then concentrated and the residue was triturated with hexane to afford Intermediate 340H as a white solid (0.1 g). MS(ES): m/z=308 (M+H)$^+$; $^1$H NMR (400 MHz, DMSO-d$_6$) δ ppm 7.80-7.85 (m, 1H), 7.64-7.71 (m, 1H), 7.40-7.55 (m, 2H), 7.13-7.27 (m, 1H), 4.71 (d, J=16.06 Hz, 1H) 4.53 (dd, J=13.55, 4.02 Hz, 2H), 3.90-4.11 (m, 2H), 1.40 (d, J=6.53 Hz, 3H).

Compounds 340 and 341: N$^5$-(tert-Butyl)-2-(3-chloro-4-fluorophenyl)-6-methyl-6,7-dihydropyrazolo[1,5-a]pyrazine-3,5(4H)-dicarboxamide

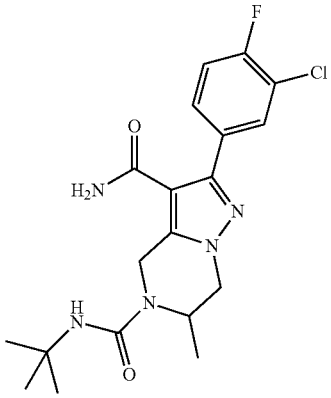 [SMILES: CC1Cn2nc(-c3ccc(F)c(Cl)c3)c(C(N)=O)c2CN1C(=O)NC(C)(C)C]

To a stirred suspension of Intermediate 340H (0.12 g, 0.284 mmol) in THF (3.0 mL) was added TEA (0.198 mL, 1.419 mmol) followed by 2-isocyanato-2-methylpropane (0.028 g, 0.284 mmol) and the resulting solution was stirred at RT for 2 h. The reaction mixture was diluted with EtOAc (10 mL) washed successively with water, a saturated aq. solution of NaHCO₃ solution and brine. The organic layer was dried over Na₂SO₄, filtered and the filtrate concentrated under reduced pressure. The crude compound was purified by silica gel chromatography (12 g REDISEP® column, eluting with 2% MeOH in CHCl₃) to afford the racemic compound. The individual isomers were separated by preparative Chiral SFC (Column: Lux cellulose-4 (250×4.6) mm, flow rate 4 mL/min, Mobile Phase A: CO₂, Mobile Phase B: 0.3% DEA in methanol, back pressure: 97 bar. Retention time: 1.95 min. and 3.03 min. respectively for Compounds 340 and 341.

Compound 340: (24.5 mg, 20%, off-white solid); MS(ES): m/z=408 [M+H]⁺; ¹H NMR (400 MHz, DMSO-d₆) δ ppm 7.87-7.92 (m, 1H), 7.68-7.77 (m, 1H), 7.46 (d, J=18.07 Hz, 1H), 7.21-7.39 (m, 2H), 6.18 (s, 1H), 5.04 (d, J=17.57 Hz, 1H), 4.70-4.80 (m, 1H), 4.31 (d, J=17.57 Hz, 1H), 3.99-4.19 (m, 2H), 1.21-1.39 (m, 9H), 1.06-1.16 (m, 3H).

Compound 341: (28 mg, 24%, off-white solid); MS(ES): m/z=408 [M+H]⁺; ¹H NMR (400 MHz, DMSO-d₆) δ ppm 7.87-7.92 (m, 1H), 7.68-7.77 (m, 1H), 7.46 (d, J=18.07 Hz, 1H), 7.21-7.39 (m, 2H), 6.18 (s, 1H), 5.04 (d, J=17.57 Hz, 1H), 4.70-4.80 (m, 1H), 4.31 (d, J=17.57 Hz, 1H), 3.99-4.19 (m, 2H), 1.21-1.39 (m, 9H), 1.06-1.16 (m, 3H).

The Compounds shown in Table 42 have been prepared similar to Compounds 340 and 341 by coupling of 340H with different isocyanates.

TABLE 42

| Ex. No. | Structure | Name | [M + H]⁺ | Ret Time (min.) | HPLC Methods |
|---|---|---|---|---|---|
| 342 | 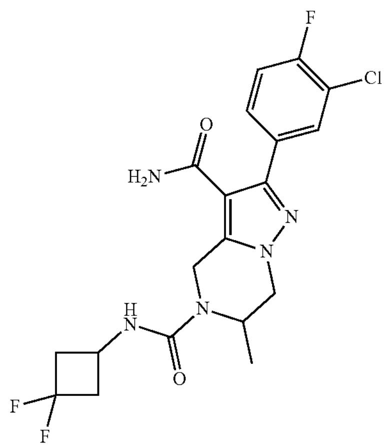 [SMILES: CC1Cn2nc(-c3ccc(F)c(Cl)c3)c(C(N)=O)c2CN1C(=O)NC1CC(F)(F)C1] | 2-(3-Chloro-4-fluorophenyl)-N⁵-(3,3-difluorocyclobutyl)-6-methyl-6,7-dihydropyrazolo[1,5-a]pyrazine-3,5(4H)-dicarboxamide | 442 | 1.61 | N |
| 343 | 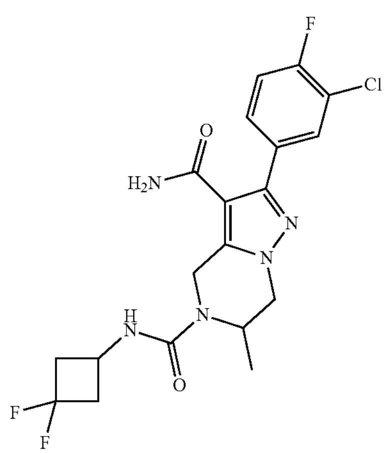 [SMILES: CC1Cn2nc(-c3ccc(F)c(Cl)c3)c(C(N)=O)c2CN1C(=O)NC1CC(F)(F)C1] | 2-(3-Chloro-4-fluorophenyl)-N⁵-(3,3-difluorocyclobutyl)-6-methyl-6,7-dihydropyrazolo[1,5-a]pyrazine-3,5(4H)-dicarboxamide | 442 | 2.48 | N |

TABLE 42-continued
| Ex. No. | Structure | Name | [M + H]+ | Ret Time (min.) | HPLC Methods |
|---|---|---|---|---|---|
| 344 | 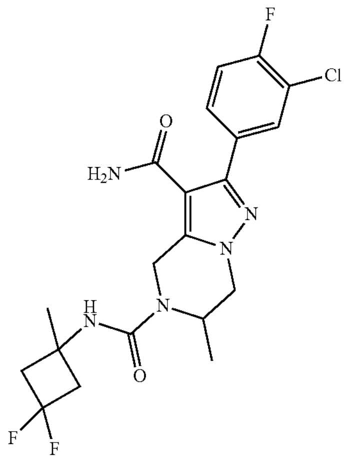 [SMILES: CC1Cn2nc(-c3ccc(F)c(Cl)c3)c(C(N)=O)c2CN1C(=O)NC1(C)CC(F)(F)C1] | 2-(3-Chloro-4-fluorophenyl)-N5-(3,3-difluoro-1-methylcyclobutyl)-6-methyl-6,7-dihydropyrazolo[1,5-a]pyrazine-3,5(4H)-dicarboxamide | 456 | 2.65 | N |
| 345 | 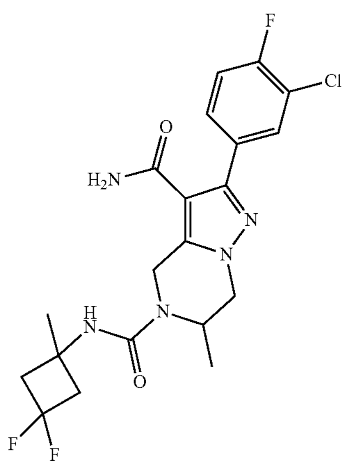 [SMILES: CC1Cn2nc(-c3ccc(F)c(Cl)c3)c(C(N)=O)c2CN1C(=O)NC1(C)CC(F)(F)C1] | 2-(3-Chloro-4-fluorophenyl)-N5-(3,3-difluoro-1-methylcyclobutyl)-6-methyl-6,7-dihydropyrazolo[1,5-a]pyrazine-3,5(4H)-dicarboxamide | 456 | 4.38 | Q |
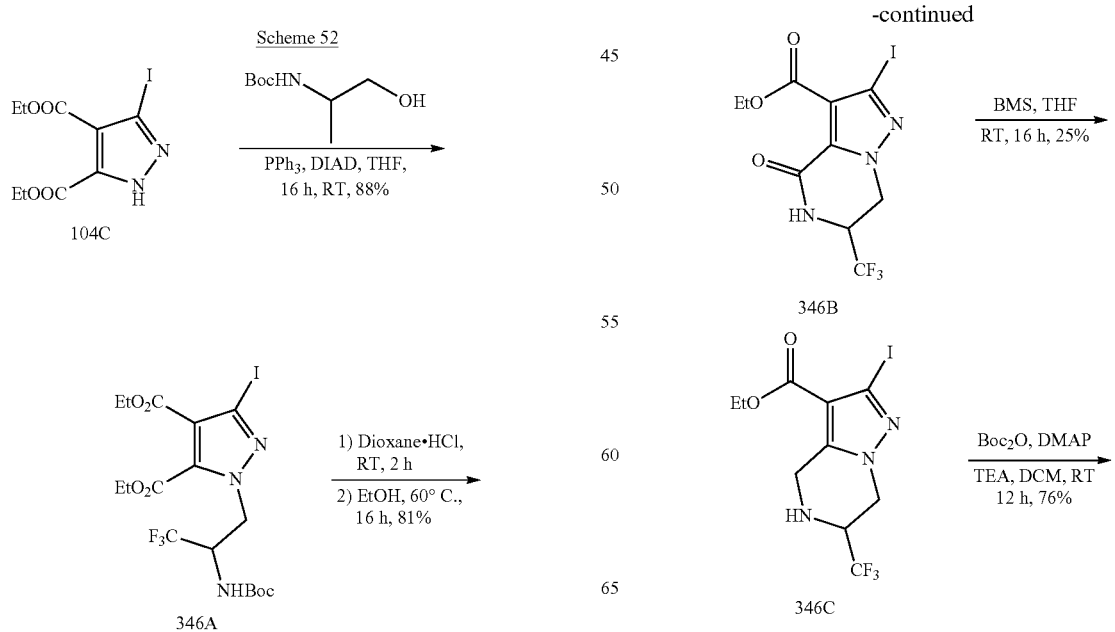

415
-continued

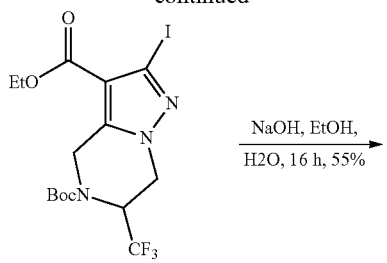
346D

NaOH, EtOH,
H2O, 16 h, 55%

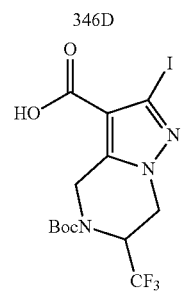
346E

HATU, DIPEA
NH4Cl, DMF,
16 h, RT, 50%

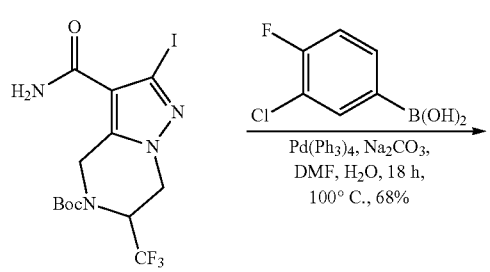
346F

Pd(Ph3)4, Na2CO3,
DMF, H2O, 18 h,
100° C., 68%

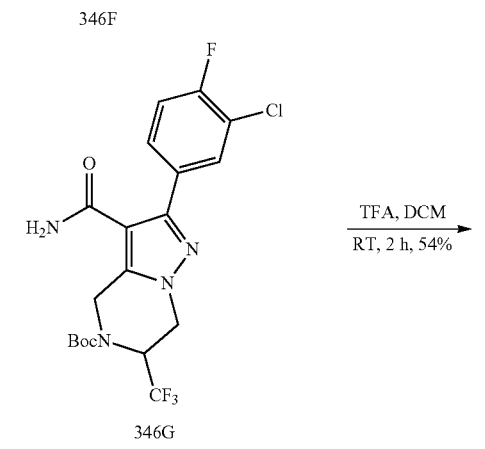
346G

TFA, DCM
RT, 2 h, 54%

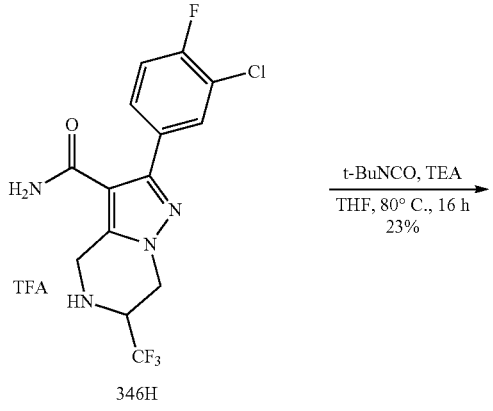
346H t-BuNCO, TEA
THF, 80° C., 16 h
23%

416
-continued

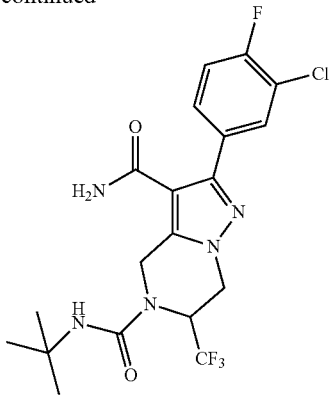
346 and 347

Intermediate 346A: Diethyl 1-(2-((tert-butoxycarbonyl)amino)-3,3,3-trifluoropropyl)-3-iodo-1H-pyrazole-4,5-dicarboxylate

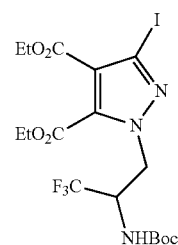

To a stirred solution of PPh3 (3.10 g, 11.83 mmol) in THF (50 mL) was added DIAD (2.300 mL, 11.83 mmol) at 0° C. and the mixture stirred for 15 min prior to the addition of Intermediate 104C (2 g, 5.92 mmol) in THF (10 mL) which was allowed to stir for 15 min. A solution of text-butyl (1,1,1-trifluoro-3-hydroxypropan-2-yl)carbamate (1.763 g, 7.69 mmol) in THF (10 mL) was then added and the solution was stirred at RT for 16 h. The reaction mixture was poured into water and extracted with EtOAc (2×100 mL) The combined organic layer was washed with brine, dried over anhydrous Na2SO4, filtered and the filtrate concentrated under reduced pressure. The crude compound was purified by silica gel chromatography (24 g REDISEP® column, eluting with 10% EtOAc in hexanes). Fractions containing the product were combined and evaporated to afford Intermediate 346A (3 g, 88%) as an oil. $^1$H NMR (400 MHz, DMSO-$d_6$) δ ppm 7.94-7.84 (m, 1H), 4.87-4.80 (m, 1H), 4.79-4.67 (m, 1H), 4.40-4.31 (m, 3H), 4.30-4.21 (m, 2H), 1.33 (s, 9H), 1.30-1.25 (m, 6H).

Intermediate 346B: Ethyl 2-iodo-4-oxo-6-(trifluoromethyl)-4,5,6,7-tetrahydropyrazolo[1,5-a]pyrazine-3-carboxylate

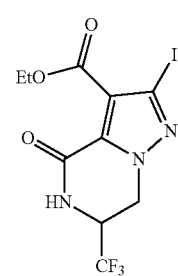 [SMILES: CCOC(=O)c1c(I)nn2c1C(=O)NC(C(F)(F)F)C2]

Intermediate 346A (3 g, 5.46 mmol) was dissolved in 4 M HCl in 1,4-dioxane (50 mL) and stirred at RT for 2 h. The volatiles were removed under reduced pressure, and the crude residue was dissolved in EtOAc (250 mL) and washed with an aq. solution of NaHCO$_3$, then dried over Na$_2$SO$_4$ and concentrated under reduced pressure. The crude was dissolved in EtOH (25 mL) and stirred at 60° C. for 16 h. Ethanol was removed under reduced pressure and the resulting residue was stirred with hexanes for 15 min. The triturated solid was filtered and dried to afford Intermediate 346B (0.96 g, 41.4%) as an off-white solid. MS(ES): –m/z=404.0 [M+H]$^+$; $^1$H NMR (400 MHz, DMSO-d$_6$) δ ppm 9.34 (d, J=4.5 Hz, 1H), 4.84-4.73 (m, 2H), 4.71-4.60 (m, 1H), 4.34-4.20 (m, 2H), 1.32-1.23 (m, 3H).

Intermediate 346C: Ethyl 2-iodo-6-(trifluoromethyl)-4,5,6,7-tetrahydropyrazolo[1,5-a]pyrazine-3-carboxylate

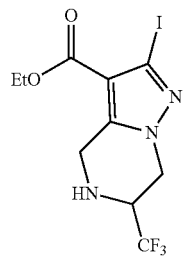 [SMILES: CCOC(=O)c1c(I)nn2c1CNC(C(F)(F)F)C2]

To a stirred solution of Intermediate 346B (0.1 g, 0.248 mmol) in THF (1 mL) was added BH$_3$.DMS complex (0.236 mL, 2.481 mmol) under nitrogen and the reaction mixture was stirred at RT for 16 h. The reaction mixture was then cooled to 0° C., quenched with methanol (1 mL) and stirred for 15 min at RT. The volatiles were removed under reduced pressure and the crude compound was purified by silica gel chromatography (12 g REDISEP® column, eluting with 25% EtOAc in hexanes). Fractions containing the product were combined and evaporated to afford Intermediate 346C as a white solid (0.025 g, 25%). MS(ES): –m/z=390.4 [M+H]$^+$; $^1$H NMR (400 MHz, DMSO-d$_6$) δ ppm 4.37-4.27 (m, 2H), 4.22 (q, J=7.4 Hz, 3H), 4.12-4.00 (m, 3H), 1.33-1.26 (m, 3H).

Intermediate 346D: 5-tert-Butyl 3-ethyl 2-iodo-6-(trifluoromethyl)-6,7-dihydropyrazolo[1,5-a]pyrazine-3,5(4H)-dicarboxylate

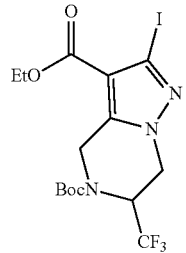 [SMILES: CCOC(=O)c1c(I)nn2c1CN(C(=O)OC(C)(C)C)C(C(F)(F)F)C2]

To a stirred solution of Intermediate 346C (0.025 g, 0.064 mmol) in DCM (5 mL) was added TEA (0.027 mL, 0.193 mmol) and DMAP (0.785 mg, 6.42 mop, followed by Boc$_2$O (0.018 mL, 0.077 mmol) and the resulting solution was allowed to stir at RT for 12 h. The reaction mixture was then diluted with DCM (20 mL), washed with water, dried over anhydrous Na$_2$SO$_4$, filtered and the filtrate concentrated under reduced pressure. The crude compound was purified by silica gel chromatography (12 g REDISEP® column, eluting with 20% EtOAc in hexanes). Fractions containing the product were combined and evaporated to afford Intermediate 346D as a white solid (0.025 g, 76%). MS(ES): m/z=490.4 [M+H]$^+$; $^1$H NMR (400 MHz, DMSO-d$_6$) δ ppm 5.55-5.38 (m, 1H), 5.18-5.08 (m, 1H), 4.54 (br. s., 3H), 4.24 (d, J=7.0 Hz, 2H), 1.48 (s, 9H), 1.31 (t, J=7.3 Hz, 3H).

Intermediate 346E: 5-(tert-Butoxycarbonyl)-2-iodo-6-(trifluoromethyl)-4,5,6,7-tetrahydropyrazolo[1,5-a]pyrazine-3-carboxylic acid

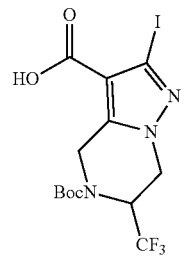

To a solution of Intermediate 346D (0.22 g, 0.450 mmol) in ethanol (2 mL) and water (2 mL) was added NaOH (0.036 g, 0.899 mmol) and the solution was stirred at RT for 16 h. The reaction mixture was concentrated under reduced pressure and the pH of the crude product was adjusted to 2 with an aqueous solution of 1.5N HCl and extracted with EtOAc (2×20 mL). The combined organic layer was dried over anhydrous Na$_2$SO$_4$, filtered and the filtrate concentrated under reduced pressure to afford Intermediate 346E as a white solid (0.12 g, 55%). MS(ES): m/z=462.4 [M+H]$^+$; $^1$H NMR (400 MHz, DMSO-d$_6$) δ ppm 12.4 (br, s., 1H), 5.55-5.38 (m, 1H), 5.18-5.08 (m, 1H), 4.54 (m, 3H), 1.48 (s, 9H).

Intermediate 346F: tert-Butyl 3-carbamoyl-2-iodo-6-(trifluoromethyl)-6,7-dihydropyrazolo[1,5-a]pyrazine-5(4H)-carboxylate

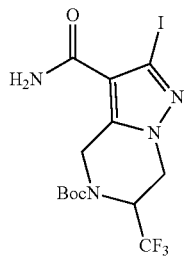 [SMILES: CC(C)(C)OC(=O)N1Cc2c(C(N)=O)c(I)nn2CC1C(F)(F)F]

To a solution of Intermediate 346E (0.12 g, 0.260 mmol) in DMF (1 mL) was added NH$_4$Cl (0.028 g, 0.520 mmol), HATU (0.099 g, 0.260 mmol) and DIPEA (0.136 mL, 0.781 mmol) under nitrogen and the resulting solution was stirred at RT for 16 h. The reaction mixture was poured into water and the aqueous layer was extracted with EtOAc (2×25 mL). The combined organic layers were dried over anhydrous Na$_2$SO$_4$ and concentrated under reduced pressure. The crude compound was purified by silica gel chromatography (12 g REDISEP® column, eluting with 3% MeOH in CHCl₃). Fractions containing the product were combined and evaporated to afford Intermediate 346F as a white solid (0.07 g, 50%). MS(ES): m/z=460.9 [M+H]⁺.

Intermediate 346G: text-Butyl 3-carbamoyl-2-(3-chloro-4-fluorophenyl)-6-(trifluoromethyl)-6,7-dihydropyrazolo[1,5-a]pyrazine-5(4H)-carboxylate

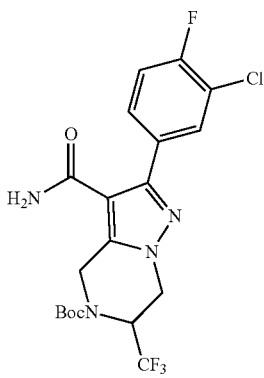 [SMILES: CC(C)(C)OC(=O)N1Cc2c(C(N)=O)c(-c3ccc(F)c(Cl)c3)nn2CC1C(F)(F)F]

To a solution of Intermediate 346F (0.35 g, 0.761 mmol) and (3-chloro-4-fluorophenyl)boronic acid (0.215 g, 0.837 mmol) in DMF (2 mL) was added a solution of Na₂CO₃ (0.242 g, 2.282 mmol) in water (1 mL) and the reaction mixture was purged with nitrogen for 5 min. Pd(PPh₃)₄ (0.044 g, 0.038 mmol) was then added and the reaction mixture was stirred at 100° C. for 18 h. The reaction mixture was cooled to RT and extracted with EtOAc (2×50 mL). The combined organic layer was dried over anhydrous Na₂SO₄, filtered and the filtrate concentrated under reduced pressure. The crude compound was purified by silica gel chromatography (12 g REDISEP® column, eluting with 5% MeOH in CHCl₃). Fractions containing the product were combined and evaporated to afford Intermediate 346G as a white solid (0.25 g, 68%). MS(ES): m/z=464.5 [M+H]⁺; ¹H NMR (400 MHz, DMSO-d₆) δ ppm 7.92-7.82 (m, 1H), 7.73-7.67 (m, 1H), 7.65-7.52 (m, 1H), 7.51-7.44 (m, 1H), 7.41-7.21 (m, 2H), 5.17-5.05 (m, 1H), 4.65-4.48 (m, 3H), 1.50 (s, 9H).

Intermediate 346H: 2-(3-Chloro-4-fluorophenyl)-6-(trifluoromethyl)-4,5,6,7-tetrahydropyrazolo[1,5-a]pyrazine-3-carboxamide.TFA

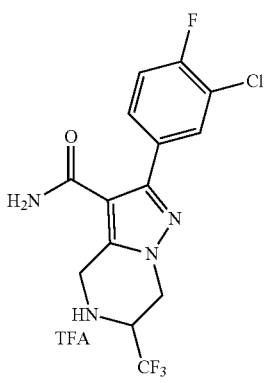 [SMILES: NC(=O)c1c(-c2ccc(F)c(Cl)c2)nn2c1CNC(C(F)(F)F)C2]

To a solution of Intermediate 346G (0.3 g, 0.648 mmol) in DCM (5 mL) was added TFA (0.499 mL, 6.48 mmol) under nitrogen and the resulting solution was stirred at RT for 2 h. The volatiles were removed under reduced pressure and the crude product was triturated with diethyl ether to afford Intermediate 346H as a white solid (0.21 g, 54%). MS(ES): m/z=363.4 [M+H]⁺;

Compounds 346 and 347: N⁵-(tert-Butyl)-2-(3-chloro-4-fluorophenyl)-6-(trifluoromethyl)-6,7-dihydropyrazolo[1,5-a]pyrazine-3,5(4H)-dicarboxamide

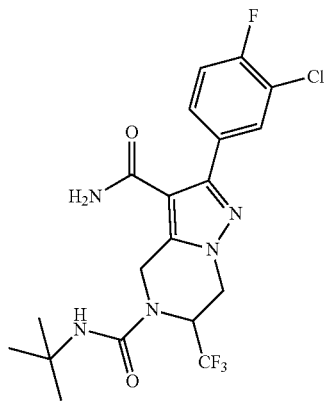 [SMILES: CC(C)(C)NC(=O)N1Cc2c(C(N)=O)c(-c3ccc(F)c(Cl)c3)nn2CC1C(F)(F)F]

To a solution of Intermediate 346H (50 mg 0.10 mmol), 2-isocyanato-2-methylpropane (10.40 mg, 0.105 mmol) in THF (1 mL) was added TEA (0.044 mL, 0.315 mmol) under nitrogen and the resulting solution was stirred at 80° C. for 16 h. The reaction mixture was cooled to RT and concentrated under reduced pressure. The crude material was dissolved in EtOAc (50 mL), washed with water, brine, dried over anhydrous Na₂SO₄, filtered and the filtrate concentrated under reduced pressure. The compound was subjected to chiral separation using preparative SFC to afford R and S enantiomers (Column: Lux cellulose-4 (250×4.6) mm, 5 µm, flow rate 3 mL/min, Mobile Phase A: CO₂, Mobile Phase B: 0.3% DEA in methanol, back pressure: 100 bar. Retention times 2.61 min. and 5.05 min. respectively for Compounds 346 and 347.

Compound 346: (11.34 mg, 23%); MS(ES): m/z=462 [M+H]⁺; ¹H NMR (400 MHz, DMSO-d₆) δ ppm 7.86 (dd, J=7.53, 2.01 Hz, 1H), 7.69 (ddd, J=8.66, 4.89, 2.01 Hz, 1H), 7.46 (t, J=8.78 Hz, 1H), 7.40 (br. s., 1H), 7.29 (br. s., 1H), 6.47 (s, 1H), 5.63 (br. s., 1H), 5.10 (d, J=17.07 Hz, 1H), 4.46-4.55 (m, 3H), 1.31 (s, 9H).

Compound 347: (10.41 mg, 21%) MS(ES): m/z=462 [M+H]⁺; ¹H NMR (400 MHz, DMSO-d₆) δ ppm 7.86 (dd, J=7.28, 2.26 Hz, 1H), 7.66-7.72 (m, 1H), 7.47 (d, J=9.04 Hz, 1H), 7.25-7.42 (m, 2H), 6.47 (s, 1H), 5.63 (d, J=4.52 Hz, 1H), 5.12 (s, 1H), 4.47-4.55 (m, 3H), 1.31 (s, 9H).

Scheme 53
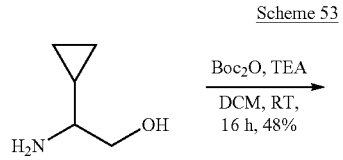
Boc₂O, TEA
DCM, RT,
16 h, 48%
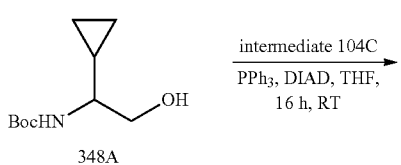
348A
intermediate 104C
PPh₃, DIAD, THF,
16 h, RT
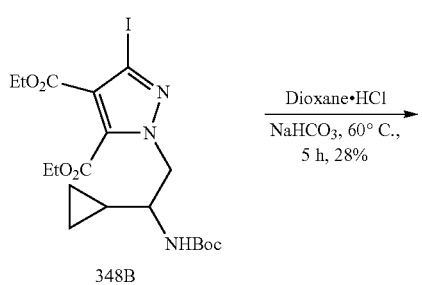
348B
Dioxane·HCl
NaHCO₃, 60° C.,
5 h, 28%
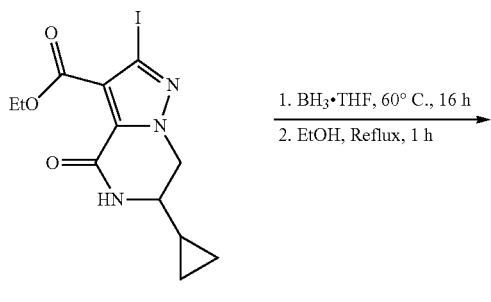
348C
1. BH₃·THF, 60° C., 16 h
2. EtOH, Reflux, 1 h
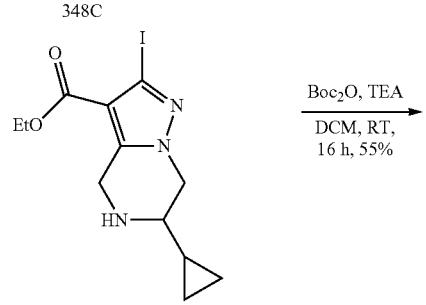
348D
Boc₂O, TEA
DCM, RT,
16 h, 55%
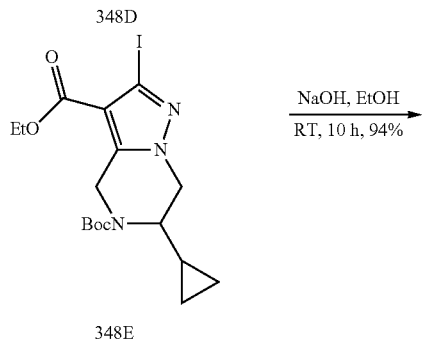
348E
NaOH, EtOH
RT, 10 h, 94%
-continued
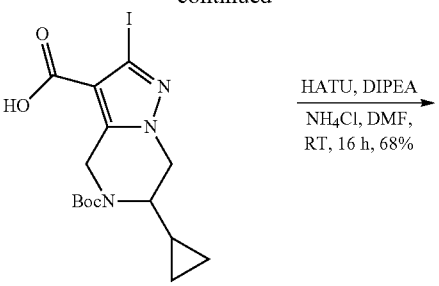
348F
HATU, DIPEA
NH₄Cl, DMF,
RT, 16 h, 68%
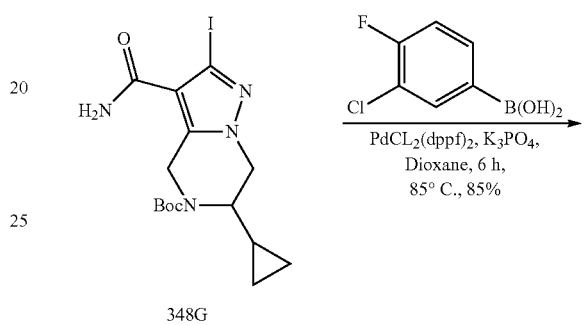
348G
PdCl₂(dppf)₂, K₃PO₄,
Dioxane, 6 h,
85° C., 85%
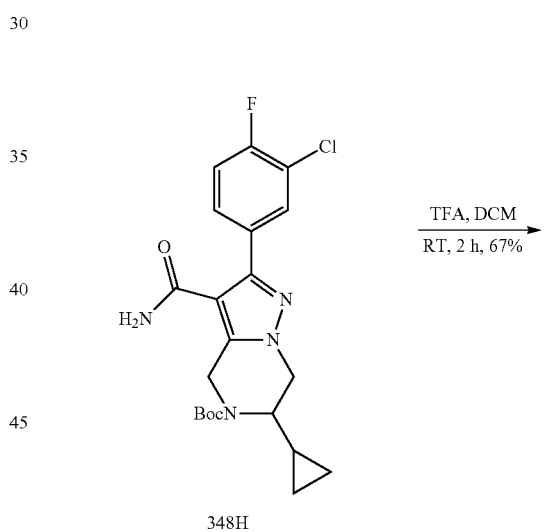
348H
TFA, DCM
RT, 2 h, 67%
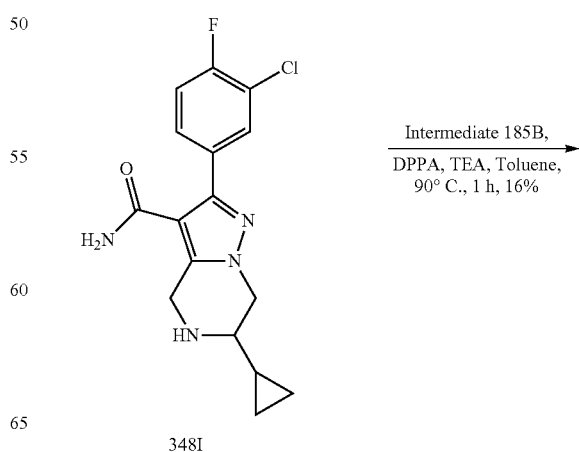
348I
Intermediate 185B,
DPPA, TEA, Toluene,
90° C., 1 h, 16%

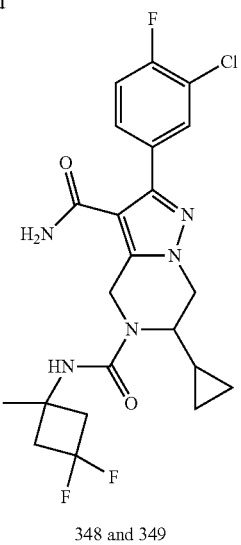

348 and 349

Intermediate 348A: tert-Butyl (1-cyclopropyl-2-hydroxyethyl)carbamate

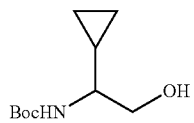

To a stirred solution of tert-butyl (1-cyclopropyl-2-hydroxyethyl)carbamate (6.5 g, 64.3 mmol) in DCM (10.0 mL) was added TEA (10.75 mL, 77 mmol), followed by Boc$_2$O (16.41 mL, 70.7 mmol) and the resulting solution was stirred at RT for 16 h. The reaction mixture was concentrated and the residue was extracted with DCM (50 mL). The organic layer was washed with water, brine, dried over Na$_2$SO$_4$, filtered and the filtrate concentrated under reduced pressure. The crude compound was purified by silica gel chromatography (120 g REDISEP® column, eluting with 20% EtOAc in hexanes). Fractions containing the product were combined and evaporated to afford Intermediate 348A as a colorless liquid (6.2 g, 48%). $^1$H NMR (400 MHz, DMSO-d$_6$) δ ppm 6.47 (d, J=7.03 Hz, 1H), 4.45-4.58 (m, 1H), 3.38-3.45 (m, 2H), 2.98 (br. s., 1H), 1.31-1.47 (m, 9H), 0.76-0.89 (m, 1H), 0.34-0.45 (m, 1H), 0.18-0.32 (m, 2H), 0.07-0.15 (m, 1H).

Intermediate 348B: Diethyl1-(2-((tert-butoxycarbonyl)amino)-2-cyclopropylethyl)-3-iodo-1H-pyrazole-4,5-dicarboxylate

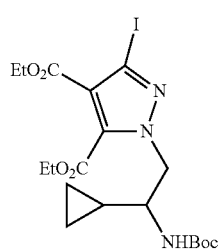 [SMILES: CCOC(=O)c1c(I)nn(CC(NC(=O)OC(C)(C)C)C2CC2)c1C(=O)OCC]

To a stirred solution of PPh$_3$ (15.52 g, 59.2 mmol) in THF (40.0 mL) cooled to −10° C. was added DIAD (11.50 mL, 59.2 mmol) and the resulting solution stirred at 0° C. for 0.5 h. Intermediate 104C (10 g, 29.6 mmol) was added as a solution in THF (10 mL) at 0° C. and stirred at RT for 45 min. A solution of Intermediate 348A (7.74 g, 38.5 mmol) in THF (10 mL) at was added at 0° C. and the reaction mixture was allowed to stir at RT for 16 h. The reaction mixture was diluted with EtOAc (50 mL) washed with water and brine. The organic layer was dried over Na$_2$SO$_4$ and concentrated under reduced pressure. The crude compound was purified by silica gel chromatography (120 g REDISEP® column, eluting with 15% EtOAc in hexanes). Fractions containing the product were combined and evaporated to afford Intermediate 348B along with impurities arising from the coupling reagents (8.01 g, 84%); the crude material was taken to the next step without further purification. MS(ES): m/z=522 [M+H]$^+$.

Intermediate 348C: Ethyl 6-cyclopropyl-2-iodo-4-oxo-4,5,6,7-tetrahydropyrazolo[1,5-a]pyrazine-3-carboxylate

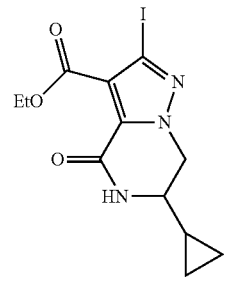 [SMILES: CCOC(=O)c1c(I)nn2c1C(=O)NC(C1CC1)C2]

To a stirred solution of Intermediate 348B (8.0 g, 15.34 mmol) in 1,4-dioxane (10.0 mL) was added 4 M HCl in dioxane (40.0 mL, 160 mmol) and the resulting solution stirred at RT for 2 h. The reaction mixture was concentrated and diluted with EtOAc (50 mL). The organic layer was washed successively with water, a saturated aq. solution of NaHCO$_3$, and brine, then dried over Na$_2$SO$_4$, filtered and the filtrate concentrated under reduced pressure. The residue obtained was heated in a ROTAVAPOR® at 60° C. for 5 h. The solid product was triturated with diethyl ether to afford Intermediate 348C as an off-white solid (1.6 g, 28%). MS(ES): m/z=376 [M+H]$^+$; $^1$H NMR (300 MHz, DMSO-d$_6$) δ ppm 8.67 (d, J=2.27 Hz, 1H), 4.47 (dd, J=13.22, 4.53 Hz, 1H), 4.17-4.33 (m, 3H), 3.15 (d, J=9.07 Hz, 1H), 1.28 (s, 3H), 0.90 (d, J=8.69 Hz, 1H), 0.40-0.54 (m, 2H), 0.20-0.37 (m, 2H).

Intermediate 348D: Ethyl 6-cyclopropyl-2-iodo-4,5,6,7-tetrahydropyrazolo[1,5-a]pyrazine-3-carboxylate

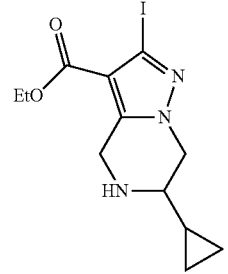 [SMILES: CCOC(=O)c1c(I)nn2c1CNC(C1CC1)C2]

To a solution of Intermediate 348C (1.3 g, 3.47 mmol) in THF (10 mL) was added BH$_3$.THF (6.06 mL, 12.13 mmol, 1 M in THF) and the resulting solution was stirred at 60° C. for 16 h. The reaction mixture was quenched with ethanol (10 mL) and heated to reflux for 1 h. The reaction mixture was concentrated under reduced pressure to afford crude Intermediate 348D (1.2 g), which was taken to the next step without further purification. MS(ES): m/z=362 [M+H]$^+$.

Intermediate 348E: 5-tert-Butyl 3-ethyl 6-cyclopropyl-2-iodo-6,7-dihydropyrazolo[1,5-a]pyrazine-3,5(4H)-dicarboxylate

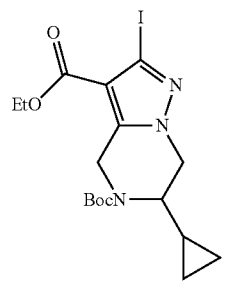 [SMILES: CCOC(=O)c1c(I)nn2c1CN(C(=O)OC(C)(C)C)C(C1CC1)C2]

To a solution of Intermediate 348D (1.2 g, 3.32 mmol) in DCM (10.0 mL) was added TEA (0.556 mL, 3.99 mmol), followed by Boc$_2$O (0.849 mL, 3.65 mmol) and the solution was stirred at RT for 16 h. The reaction mixture was diluted with DCM (15 mL) and the organic layer was washed with water, brine, dried over Na$_2$SO$_4$, filtered and the filtrate concentrated. The crude compound was purified by silica gel chromatography (24 g REDISEP® column, eluting with 25% EtOAc in hexane). Fractions containing the product were combined and evaporated to afford the Intermediate 348E as a colorless semi-solid (0.85 g, 55%). MS(ES): m/z=462 [M+H]$^+$; $^1$H NMR (300 MHz, DMSO-d$_6$) δ ppm 5.13 (d, J=18.89 Hz, 1H), 4.48 (d, J=18.89 Hz, 1H), 4.13-4.31 (m, 4H), 3.84 (br. s., 1H), 1.38-1.47 (m, 9H), 1.31 (s, 3H), 0.84-0.96 (m, 1H), 0.46 (d, J=8.31 Hz, 2H), 0.38 (d, J=4.91 Hz, 2H).

Intermediate 348F: 5-(tert-Butoxycarbonyl)-6-cyclopropyl-2-iodo-4,5,6,7-tetrahydropyrazolo[1,5-a]pyrazine-3-carboxylic acid

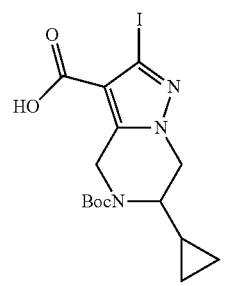 [SMILES: CC(C)(C)OC(=O)N1Cc2c(C(=O)O)c(I)nn2CC1C1CC1]

To a stirred solution of Intermediate 348E (0.85 g, 1.843 mmol) in ethanol (2 mL) and water (1 mL) was added NaOH (0.369 g, 9.21 mmol) and the resulting solution was stirred at RT for 10 h. The reaction mixture was diluted with DCM (10 mL) and washed successively with an aqueous solution of 1N HCl, water and brine. The organic layer was then dried over Na$_2$SO$_4$, filtered and the filtrate concentrated under reduced pressure to afford the Intermediate 348F as an off-white solid (0.75 g, 94%). MS(ES): m/z=434 [M+H]$^+$; $^1$H NMR (300 MHz, DMSO-d$_6$) δ ppm 12.6 (br. s., 1H), 5.11 (d, J=18.89 Hz, 1H), 4.45 (d, J=18.51 Hz, 1H), 4.16-4.25 (m, 2H), 3.82 (br. s., 1H), 1.43 (s, 9H), 0.82-0.96 (m, 1H), 0.47 (d, J=7.93 Hz, 2H), 0.35 (dd, J=6.80, 4.91 Hz, 2H).

Intermediate 348G: tert-Butyl 3-carbamoyl-6-cyclopropyl-2-iodo-6,7-dihydropyrazolo[1,5-a]pyrazine-5(4H)-carboxylate

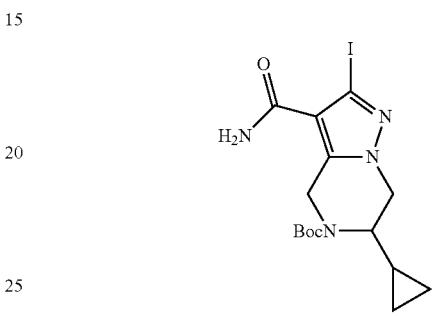

To a stirred solution of Intermediate 348F (0.75 g, 1.731 mmol) in DMF (4.0 mL) was added NH$_4$Cl (0.463 g, 8.66 mmol), HATU (1.316 g, 3.46 mmol) and DIPEA (1.512 mL, 8.66 mmol) and the resulting solution was stirred at RT for 16 h. The reaction mixture was diluted with ethyl acetate (10 mL), washed with water and brine. The organic layer was dried over Na$_2$SO$_4$, filtered and the filtrate concentrated under reduced pressure. The crude compound was purified by silica gel chromatography (24 g REDISEP® column, eluting with 65% EtOAc in hexanes). Fractions containing the product were combined and evaporated to afford Intermediate 348G as a colorless liquid (0.51 g, 68%). MS(ES): m/z=433 [M+H]$^+$; $^1$H NMR (300 MHz, DMSO-d$_6$) δ ppm 6.83-7.50 (m, 2H), 5.07 (d, J=18.13 Hz, 1H), 4.50 (d, J=18.51 Hz, 1H), 4.20 (d, J=2.27 Hz, 2H), 3.84 (br. s., 1H), 1.43 (s, 9H), 0.89 (d, J=9.82 Hz, 1H), 0.47 (d, J=7.93 Hz, 2H), 0.27-0.40 (m, 2H).

Intermediate 348H: tert-Butyl 3-carbamoyl-2-(3-chloro-4-fluorophenyl)-6-cyclopropyl-6,7-dihydropyrazolo[1,5-a]pyrazine-5(4H)-carboxylate

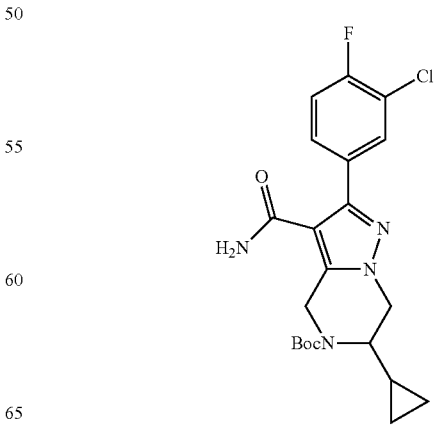

To a stirred suspension of Intermediate 348G (0.47 g, 1.087 mmol) in 1,4-dioxane (5 mL) was added K₃PO₄ (1.631 mL, 3.26 mmol), (3-chloro-4-fluorophenyl)boronic acid (0.246 g, 1.414 mmol) and the reaction mixture was purged with nitrogen for 10 min. PdCl$_2$(dppf)-CH$_2$Cl$_2$ (0.053 g, 0.065 mmol) was then added and the reaction mixture was heated to 80° C. and stirred for 6 h. The reaction mixture was filtered through CELITE® and the filtrate was diluted with ethyl acetate (10 mL), and washed with water and brine. The organic layer was dried over Na$_2$SO$_4$, filtered and the filtrate concentrated under reduced pressure. The crude compound was purified by silica gel chromatography (12 g REDISEP® column, eluting with 2% MeOH in CHCl$_3$). Fractions containing the product were combined and evaporated to afford Intermediate 348H as an off-white solid (0.4 g, 85%). MS(ES): m/z=435 [M+H]⁺; ¹H NMR (300 MHz, DMSO-d$_6$) δ ppm 7.85-7.95 (m, 1H), 7.66-7.77 (m, 1H), 7.47 (t, J=9.07 Hz, 1H), 7.20-7.39 (m, 2H), 5.05 (d, J=17.37 Hz, 1H), 4.55 (d, J=17.37 Hz, 1H), 4.24 (br. s., 2H), 3.89 (br. s., 1H), 1.45 (s, 9H), 0.87-1.05 (m, 1H), 0.31-0.55 (m, 4H).

Intermediate 348I: 2-(3-Chloro-4-fluorophenyl)-6-cyclopropyl-4,5,6,7-tetrahydropyrazolo[1,5-a]pyrazine-3-carboxamide

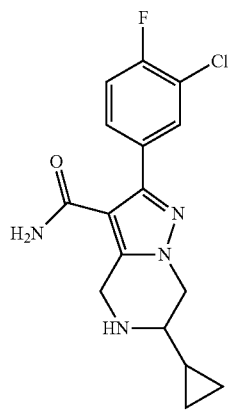 [SMILES: NC(=O)c1c(-c2ccc(F)c(Cl)c2)nn2c1CNC(C1CC1)C2]

To a stirred solution of Intermediate 348H (0.43 g, 0.989 mmol) in DCM (8.0 mL) was added TFA (4.0 mL, 51.9 mmol) and the resulting solution was stirred at RT for 2 h. The reaction mixture was concentrated and the residue was extracted with DCM (10 mL), and washed successively with water, a saturated aq. NaHCO$_3$ solution and brine. The organic layer was dried over Na$_2$SO$_4$, filtered and the filtrate concentrated under reduced pressure to afford Intermediate 348I as an off-white solid (0.3 g, 67%). MS(ES): m/z=335 [M+H]⁺; ¹H NMR (400 MHz, DMSO-d$_6$) δ ppm 7.80-7.91 (m, 1H), 7.64-7.70 (m, 1H), 7.35-7.50 (m, 1H), 7.02-7.29 (m, 2H), 4.12-4.25 (m, 2H), 3.93 (d, J=16.56 Hz, 1H), 3.68-3.81 (m, 2H), 2.40 (br. s., 1H), 0.82-0.98 (m, 1H), 0.48 (d, J=8.03 Hz, 2H), 0.37 (d, J=5.02 Hz, 2H).

Compounds 348 and 349: 2-(3-Chloro-4-fluorophenyl)-6-cyclopropyl-N⁵-(3,3-difluoro-1-methylcyclobutyl)-6,7-dihydropyrazolo[1,5-a]pyrazine-3,5(4H)-dicarboxamide

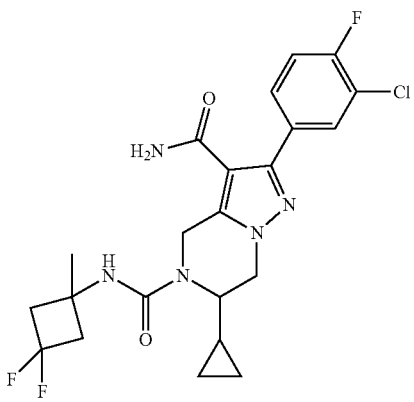 [SMILES: CC1(NC(=O)N2Cc3c(C(N)=O)c(-c4ccc(F)c(Cl)c4)nn3CC2C2CC2)CC(F)(F)C1]

To a stirred solution of 3,3-difluoro-1-methylcyclobutanecarboxylic acid (0.047 g, 0.311 mmol) in toluene (2.0 mL) was added TEA (0.167 mL, 1.195 mmol), followed by DPPA (0.104 mL, 0.478 mmol) and the reaction mixture was stirred at 80° C. for 1 h. The reaction mixture was cooled to RT and to it was added a solution of Intermediate 348I (0.08 g, 0.239 mmol) in THF (1.0 mL) and stirred at RT for 14 h. The reaction mixture was diluted with EtOAc (10 mL), washed with water and brine. The organic layer was dried over Na$_2$SO$_4$, filtered and the filtrate concentrated under reduced pressure. The crude compound was purified by silica gel chromatography (12 g REDISEP® column, eluting with 1% MeOH in CHCl$_3$) to afford the racemic compound. The individual isomers were separated by preparative Chiral SFC (Column: Lux cellulose-4 (250×4.6) mm, 5 μm, flow rate 4 mL/min, Mobile Phase A: CO$_2$, Mobile Phase B: 0.2% DEA in methanol, back pressure: 100 bar. Retention time: 3.84 min. and 8.08 min. respectively for Compounds 348 and 349.

Compound 348: (20 mg, 16%, off-white solid); MS(ES): m/z=482 [M+H]⁺; ¹H NMR (400 MHz, DMSO-d$_6$) δ ppm 7.86-7.93 (m, 1H), 7.66-7.75 (m, 1H), 7.42-7.49 (m, 1H), 7.28-7.41 (m, 2H), 7.07 (s, 1H), 5.06 (d, J=17.07 Hz, 1H), 4.51 (d, J=17.57 Hz, 1H), 4.15-4.26 (m, 2H), 3.97 (dd, J=9.29, 3.76 Hz, 1H), 2.75-2.91 (m, 2H), 2.54-2.64 (m, 2H), 1.43 (s, 3H), 0.92-1.26 (m, 1H), 0.30-0.55 (m, 4H).

Compound 349: (21 mg, 17%, off-white solid); MS(ES): m/z=482 [M+H]⁺; ¹H NMR (400 MHz, DMSO-d$_6$) δ ppm 7.86-7.93 (m, 1H), 7.66-7.75 (m, 1H), 7.42-7.49 (m, 1H), 7.28-7.41 (m, 2H), 7.07 (s, 1H), 5.06 (d, J=17.07 Hz, 1H), 4.51 (d, J=17.57 Hz, 1H), 4.15-4.26 (m, 2H), 3.97 (dd, J=9.29, 3.76 Hz, 1H), 2.75-2.91 (m, 2H), 2.54-2.64 (m, 2H), 1.43 (s, 3H), 0.92-1.26 (m, 1H), 0.30-0.55 (m, 4H).

Scheme 54
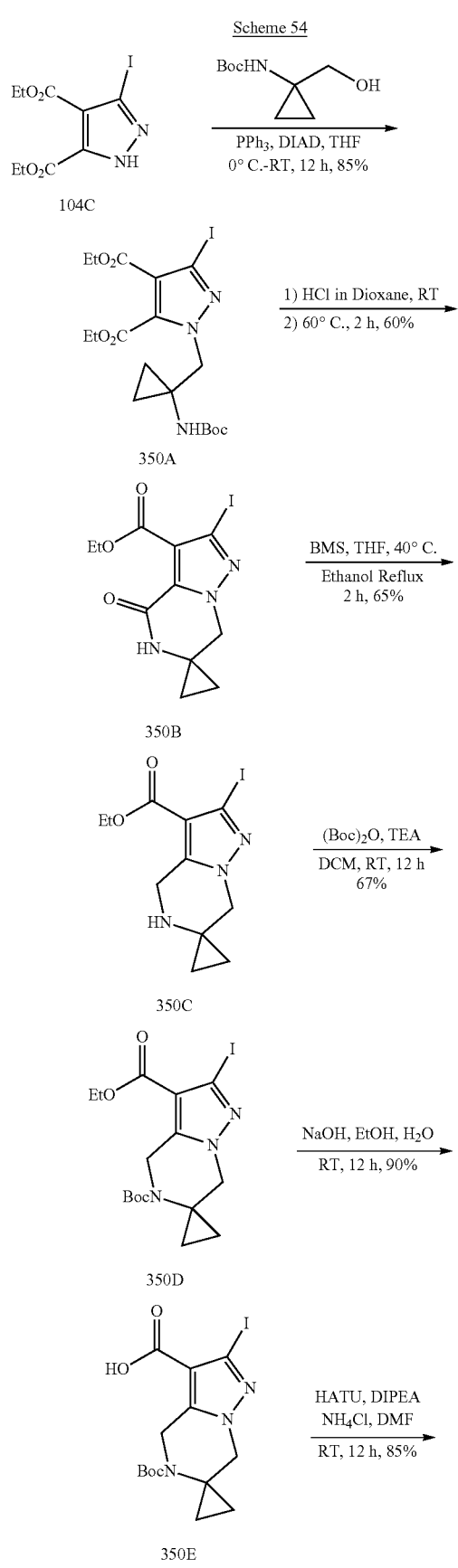
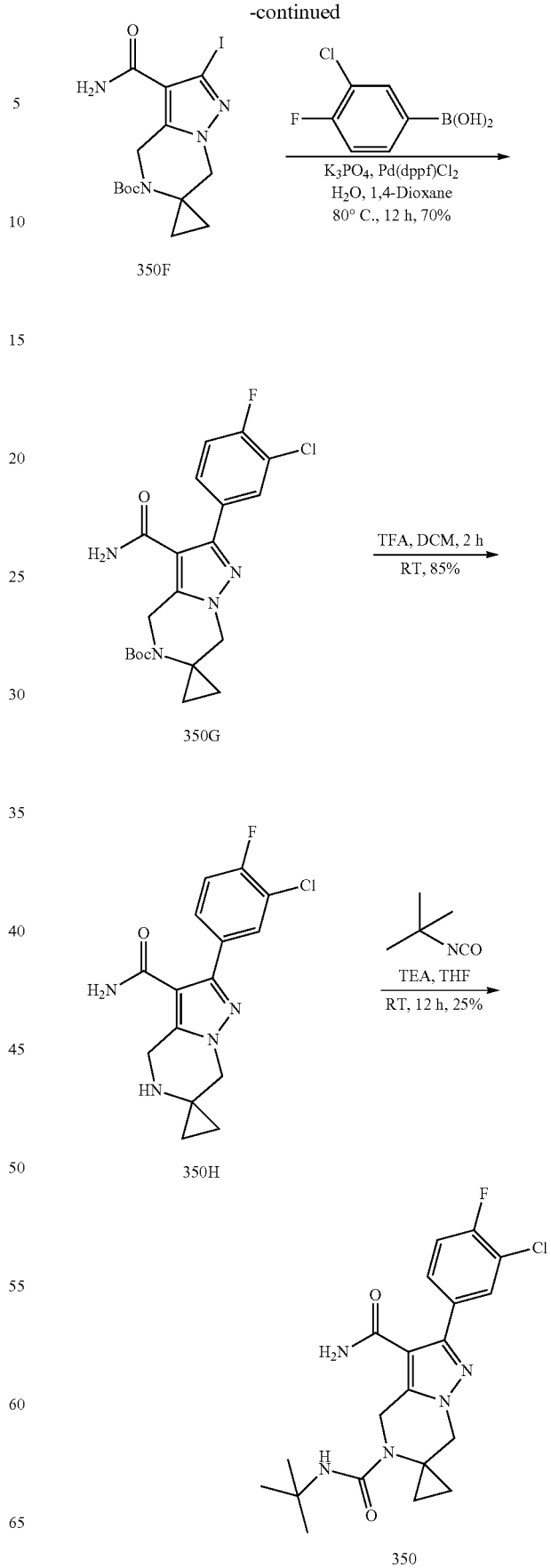

Intermediate 350A: Diethyl 1-((1-((tert-butoxycarbonyl)amino)cyclopropyl)methyl)-3-iodo-1H-pyrazole-4,5-dicarboxylate

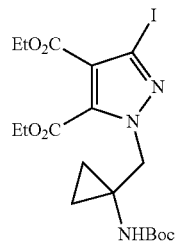 [SMILES: CCOC(=O)c1c(I)nn(CC2(NC(=O)OC(C)(C)C)CC2)c1C(=O)OCC]

To a stirred solution of PPh$_3$ (15.52 g, 59.2 mmol) in THF (80.0 mL) cooled to 0° C. was added DIAD (11.50 mL, 59.2 mmol) and the resulting solution stirred at 0° C. for 0.5 h. Intermediate 104C (8.00 g, 23.66 mmol) was added as a solution in THF (20 mL) at 0° C. and stirred at RT for 45 min. A solution of tert-butyl (1-(hydroxymethyl)cyclopropyl)carbamate (5.32 g, 28.4 mmol) in THF (10 mL) at was added at 0° C. and the reaction mixture was allowed to stir at RT for 16 h. The reaction mixture was diluted with water (250 mL) and extracted with EtOAc (2×200 mL). The combined organic layer was washed with brine dried over Na$_2$SO$_4$, filtered and concentrated. The crude product was purified by silica gel chromatography (220 g REDISEP® column, eluting with 20% EtOAc in hexane). Fractions containing the product were combined and evaporated to afford Intermediate 350A as a pale yellow liquid (10 g, 85%). MS(ES): m/z=508 [M+H]$^+$; $^1$H NMR (400 MHz, chloroform-d) δ ppm 4.45 (s, 2H), 4.41-4.25 (m, 4H), 1.46 (s, 9H), 1.40-1.30 (m, 4H), 1.24 (s, 3H), 1.03-0.94 (m, 2H), 0.90-0.78 (m, 2H).

Intermediate 350B: Ethyl 2'-iodo-4'-oxo-5',7'-dihydro-4'H-spiro[cyclopropane-1,6'-pyrazolo[1,5-a]pyrazine]-3'-carboxylate

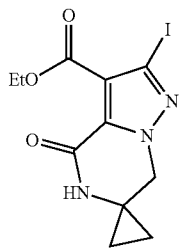 [SMILES: CCOC(=O)c1c(I)nn2c1C(=O)NC1(CC1)C2]

To a stirred solution of Intermediate 350A (2.1 g, 4.14 mmol) in 1,4-dioxane (10.0 mL) was added 4 M HCl in dioxane (10 mL, 41 mmol) and the resulting solution stirred at RT for 1 h. The reaction mixture was concentrated and diluted with EtOAc (50 mL) The organic layer was washed successively with water, a saturated aq. solution of NaHCO$_3$, and brine, then dried over Na$_2$SO$_4$, filtered and the filtrate concentrated under reduced pressure. The residue obtained was heated in a ROTAVAPOR® at 60° C. for 5 h. The solid product was triturated with diethyl ether to afford Intermediate 350B as a pale yellow solid (1.1 g, 60%). MS(ES): m/z=362 [M+H]$^+$; $^1$H NMR (400 MHz, chloroform-d) δ ppm 6.93 (s, 1H), 4.41 (q, J=7.0 Hz, 2H), 4.26 (s, 2H), 1.41 (t, J=7.0 Hz, 3H), 1.11-0.85 (m, 4H).

Intermediate 350C: Ethyl 2'-iodo-5',7'-dihydro-4'H-spiro[cyclopropane-1,6'-pyrazolo[1,5-a]pyrazine]-3'-carboxylate

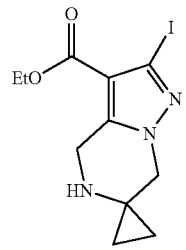 [SMILES: CCOC(=O)c1c(I)nn2c1CNC1(CC1)C2]

To a solution of Intermediate 350B (1.1 g, 3.05 mmol) in THF (10 mL) was added BH$_3$.DMS (0.578 mL, 6.09 mmol, 2M) and the resulting solution was stirred at 40° C. for 18 h. The reaction mixture was cooled to RT, quenched with ethanol (10 mL) and heated to reflux for 1 h. Reaction mixture was concentrated under reduced pressure. The crude product was purified by silica gel chromatography (24 g REDISEP® column, eluting with 2% MeOH in CHCl$_3$). Fractions containing the product were combined and evaporated to afford Intermediate 350C (0.7 g, 66%) as a gummy solid. MS(ES): m/z=348 [M+H]+.

$^1$H NMR (400 MHz, chloroform-d) δ ppm 4.41 (q, J=7.0 Hz, 2H), 3.92 (s, 1H), 1.38 (m, 4H), 1.36 (t, J=7.0 Hz, 3H), 0.90 (m, 2H), 0.68 (m, 2H).

Intermediate 350D: 5'-tert-Butyl 3'-ethyl 2'-iodo-4'H-spiro[cyclopropane-1,6'-pyrazolo[1,5-a]pyrazine]-3',5'(7'H)-dicarboxylate

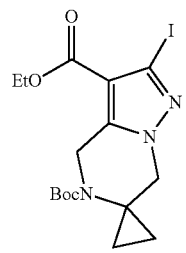 [SMILES: CCOC(=O)c1c(I)nn2c1CN(C(=O)OC(C)(C)C)C1(CC1)C2]

To a solution of Intermediate 350C (0.70 g, 2.016 mmol) in DCM (10.0 mL) was added TEA (0.281 mL, 2.016 mmol), followed by Boc$_2$O (0.702 mL, 3.02 mmol) and the solution was stirred at RT for 16 h. The reaction mixture was diluted with DCM (25 mL) and the organic layer was washed with water, brine, dried over Na$_2$SO$_4$, filtered and the filtrate concentrated. The crude product was purified by silica gel chromatography (24 g REDISEP® column, eluting with 30% EtOAc in petroleum ether). Fractions containing the product were combined and evaporated to afford Intermediate 350D as an off-white solid (0.6 g, 67%). MS(ES): m/z=448 [M+H]$^+$; $^1$H NMR (400 MHz, chloroform-d) ppm 4.88 (br. s., 2H), 4.33 (q, J=7.0 Hz, 2H), 4.03 (br. s., 2H), 1.48 (m, 9H), 1.41 (t, J=7.0 Hz, 3H), 1.17 (m, 2H), 0.97-0.85 (m, 2H).

Intermediate 350E: 5'-(tert-Butoxycarbonyl)-2'-iodo-5',7'-dihydro-4'H-spiro[cyclopropane-1,6'-pyrazolo[1,5-a]pyrazine]-3'-carboxylic acid

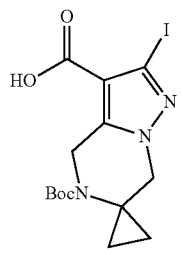 [SMILES: CC(C)(C)OC(=O)N1Cc2c(C(=O)O)c(I)nn2CC12CC2]

To a stirred solution of Intermediate 350D (0.500 g, 1.118 mmol) in ethanol (10 mL) and water (1 mL) was added NaOH (0.369 g, 9.21 mmol) and the resulting solution was stirred at RT for 12 h. The volatiles were removed under reduced pressure and the residue was acidified with an aqueous solution of 1.5 N HCl. The solid product separated was filtered through a Buchner funnel and dried under vacuum to afford Intermediate 350E as a white solid (0.43 g, 90%). MS(ES): m/z=420 [M+H]$^+$; $^1$H NMR (400 MHz, chloroform-d) δ ppm 6.19 (br. s., 1H), 4.92 (br. s., 2H), 4.06 (br. s., 2H), 1.48 (s, 9H), 1.19 (br. s., 2H), 1.01-0.83 (m, 2H).

Intermediate 350F: tert-Butyl 3'-carbamoyl-2'-iodo-4'H-spiro[cyclopropane-1,6'-pyrazolo[1,5-a]pyrazine]-5'(7'H)-carboxylate

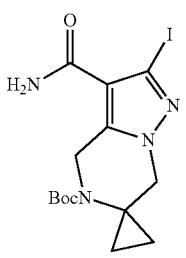 [SMILES: CC(C)(C)OC(=O)N1Cc2c(C(N)=O)c(I)nn2CC12CC2]

To a stirred solution of Intermediate 350E (0.43 g, 1.026 mmol) in DMF (4 mL) was added NH$_4$Cl (0.274 g, 5.13 mmol), HATU (0.780 g, 2.051 mmol) and DIPEA (0.537 mL, 3.08 mmol) and the resulting solution was stirred at RT for 16 h. The reaction mixture was diluted with water (50 mL) and extracted with EtOAc (3×25 mL) The combined organic layer was washed with brine, dried over Na$_2$SO$_4$, filtered and the filtrate concentrated. The residue was triturated with diethyl ether, filtered and dried to afford Intermediate 350F as an off-white solid (0.4 g, 89%). MS(ES): m/z=419 [M+H]$^+$; $^1$H NMR (400 MHz, chloroform-d) δ ppm 6.56 (br. s., 1H), 5.54 (br. s., 1H), 4.96 (br. s., 2H), 4.04 (br. s., 2H), 1.44 (s, 9H), 1.18 (m, 2H), 0.97-0.84 (m, 2H).

Intermediate 350G: tert-Butyl 3'-carbamoyl-2'-(3-chloro-4-fluorophenyl)-4'H-spiro[cyclopropane-1,6'-pyrazolo[1,5-a]pyrazine]-5'(7'H)-carboxylate

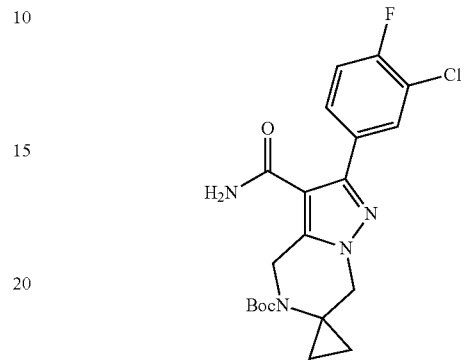

To a stirred suspension of Intermediate 350F (0.400 g, 0.956 mmol) in 1,4-dioxane (5 mL) was added K$_3$PO$_4$ (0.500 g, 2.80 mmol), (3-chloro-4-fluorophenyl)boronic acid (0.250 g, 1.435 mmol) and the reaction mixture was purged with nitrogen for 10 min. PdCl$_2$(dppf)-CH$_2$Cl$_2$ (0.047 g, 0.057 mmol) was then added and the reaction mixture was heated to 80° C. and stirred for 12 h. The reaction mixture was diluted with water (25 mL) and extracted with EtOAc (3×25 mL) The combined organic layers were washed with brine, dried over Na$_2$SO$_4$, filtered and the filtrate concentrated. The crude product was purified by silica gel chromatography (24 g REDISEP® column, eluting with 3% MeOH in CHCl$_3$). Fractions containing the product were combined and evaporated to afford Intermediate 350G as a pale yellow solid (0.29 g, 70%). MS(ES): m/z=421 [M+H]$^+$; $^1$H NMR (400 MHz, chloroform-d) δ ppm 7.69 (dd, J=7.0, 2.3 Hz, 1H), 7.50 (ddd, J=8.5, 4.6, 2.1 Hz, 1H), 7.33-7.15 (m, 1H), 5.34 (br. s., 2H), 4.97 (br. s., 2H), 4.05 (br. s., 2H), 1.44 (s, 9H), 1.22-1.24 (m, 2H), 1.02-0.79 (m, 2H).

Intermediate 350H: 2'-(3-Chloro-4-fluorophenyl)-5',7'-dihydro-4'H-spiro[cyclopropane-1,6'-pyrazolo[1,5-a]pyrazine]-3'-carboxamide

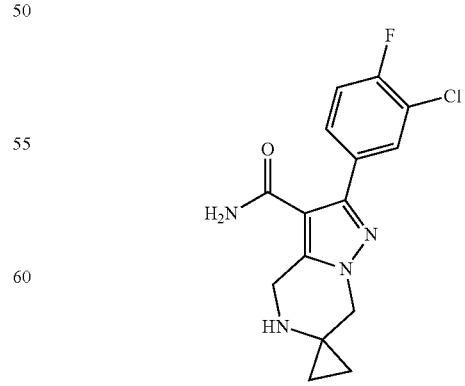

To a solution of Intermediate 350G (0.29 g, 0.689 mmol) in DCM (5 mL) was added TFA (3 mL) and the resulting solution was stirred at RT for 2 h. The volatiles were removed under reduced pressure. The residue was basified with a 10% aqueous solution of NaHCO$_3$ and extracted with EtOAc (3×20 mL). The combined organic layer was washed with brine, dried over Na$_2$SO$_4$, filtered and the filtrate concentrated to afford Intermediate 350H as a yellow solid (0.2 g, 85%). MS(ES): m/z=321 [M+H]$^+$; $^1$H NMR (300 MHz, chloroform-d) δ ppm 7.71 (dd, J=7.2, 2.3 Hz, 1H), 7.51 (ddd, J=8.3, 4.5, 2.3 Hz, 1H), 7.33-7.11 (m, 1H), 5.33 (br. s., 2H), 4.40 (s, 2H), 4.03 (s, 2H), 1.02-0.88 (m, 2H), 0.80-0.59 (m, 2H).

Compound 350: N$^{5'}$-(tert-Butyl)-2'-(3-chloro-4-fluorophenyl)-4'H-spiro[cyclopropane-1,6'-pyrazolo[1,5-a]pyrazine]-3',5'(7'H)-dicarboxamide

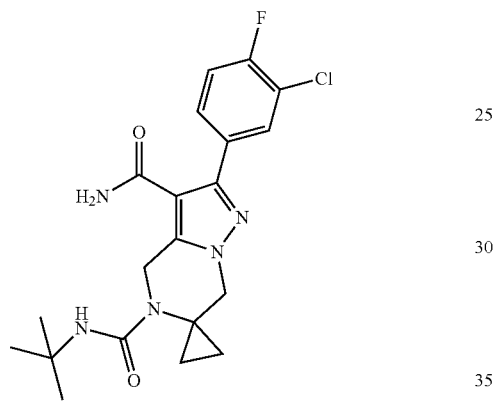

To a solution of Intermediate 350H (30 mg, 0.094 mmol) in THF (2 mL) was added TEA (0.026 mL, 0.187 mmol) and tert-butyl isocyanate (0.022 mL, 0.187 mmol) and the resulting solution was stirred at RT for 12 h. The reaction mixture was diluted with water and extracted with EtOAc (3×20 mL). The combined organic layer was washed with brine, dried over Na$_2$SO$_4$, filtered and the filtrate concentrated. The crude product was purified by preparative HPLC to afford Compound 350 as an off-white solid (10 mg, 25%). HPLC retention times 9.363 min. and 13.023 min. (Methods A and F respectively). MS(ES): m/z=420 [M+H]$^+$; $^1$H NMR (400 MHz, DMSO-d$_6$) δ ppm 7.85 (dd, J=7.31, 2.16 Hz, 1H), 7.68 (ddd, J=8.63, 4.80, 2.20 Hz, 1H), 7.45 (t, J=9 Hz, 1H), 7.30 (br. s, 1H), 7.16 (br. s, 1H), 4.78 (br. s, 2H), 4.10 (br. s, 2H), 1.26 (s, 9H), 1.09 (s, 4H).

Scheme 55

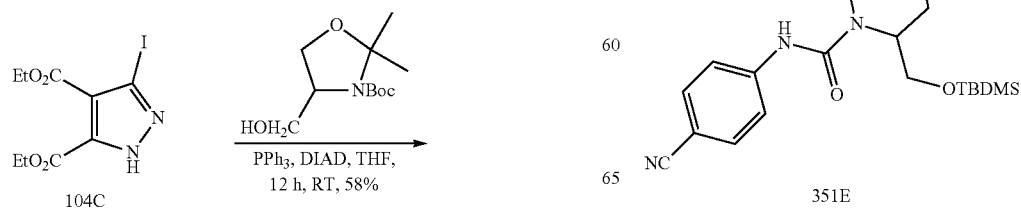

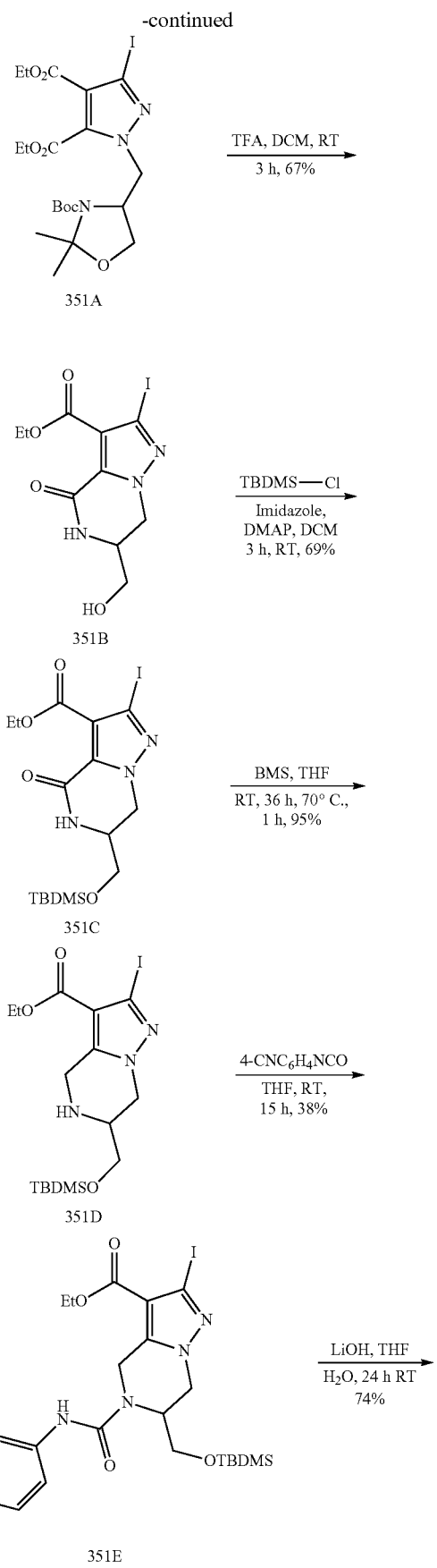

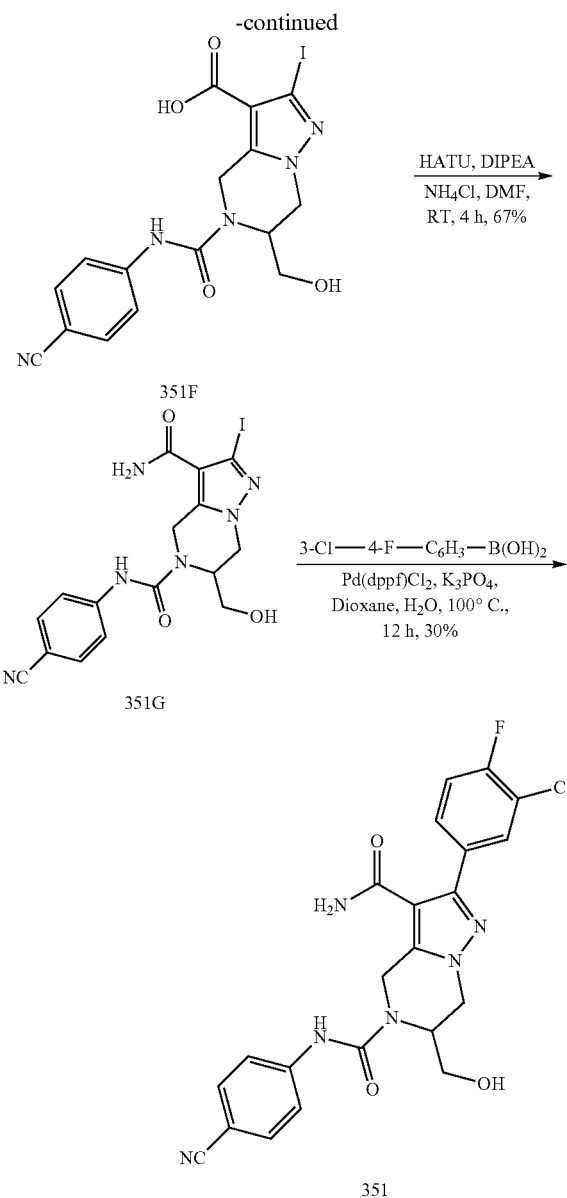

351F

351G

351

Intermediate 351A: Diethyl 1-((3-(tert-butoxycarbonyl)-2,2-dimethyloxazolidin-4-yl)methyl)-3-iodo-1H-pyrazole-4,5-dicarboxylate

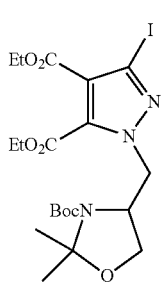 [SMILES: CCOC(=O)c1c(I)nn(CC2COC(C)(C)N2C(=O)OC(C)(C)C)c1C(=O)OCC]

To a stirred solution of triphenylphosphine (5.84 g, 22.25 mmol) in THF (20 mL) was added DIAD (4.50 g 22.25 mmol) dropwise at 0° C. and the resulting solution was stirred for 15 min. Intermediate 104C (3.0 g, 8.90 mmol) in THF (20 mL) was added slowly at 0° C. and stirred at room temperature for 45 min. Intermediate tert-butyl 4-(hydroxymethyl)-2,2-dimethyloxazolidine-3-carboxylate (2.470 g, 10.68 mmol) in THF (20 mL) was added at 0° C. and resulting solution was stirred at room temperature overnight. The volatiles were removed under reduced pressure and the crude compound was purified by silica gel chromatography (40 g REDISEP® column, eluting with 10-13% ethyl acetate in hexanes). Fractions containing the product were combined and evaporated to afford Intermediate 351A (3.5 g, 58.5%) as a pale yellow oil. MS(ES): m/z=552 [M+H]$^+$; $^1$H NMR (300 MHz, DMSO-d$_6$) δ ppm 4.53-4.18 (m, 6H), 3.96-3.82 (m, 2H), 1.50-1.21 (m, 2H).

Intermediate 351B: Ethyl 6-(hydroxymethyl)-2-iodo-4-oxo-4,5,6,7-tetrahydropyrazolo[1,5-a]pyrazine-3-carboxylate

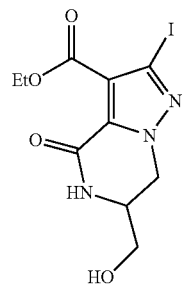 [SMILES: CCOC(=O)c1c(I)nn2c1C(=O)NC(CO)C2]

To a solution of Intermediate 351A (3.3 g, 5.99 mmol) in dioxane (10 mL) was added 4 M HCl in dioxane (5 mL, 5.99 mmol) and the resulting reaction mixture was stirred at RT for 3 h. The reaction mixture was concentrated and the crude product was basified with a 10% aqueous solution of sodium bicarbonate and extracted with EtOAc (3×100 mL). The combined organic layer was dried over sodium sulfate, filtered and concentrated slowly (2 to 3 h) using a rotary evaporator at 60° C. to obtain Intermediate 351B (1.6 g, 67.4%) as a white solid. MS(ES): m/z=366 [M+H]$^+$; $^1$H NMR (400 MHz, DMSO-d$_6$) δ ppm 8.43 (d, J=3.0 Hz, 1H), 5.14 (t, J=5.5 Hz, 1H), 4.46-4.41 (m, 1H), 4.37-4.30 (m, 1H), 4.25 (q, J=7.0 Hz, 2H), 3.84-3.75 (m, 1H), 3.54-3.47 (m, 1H), 3.36 (s, 1H), 1.28 (t, J=7.0 Hz, 3H).

Intermediate 351C: Ethyl 6-(((tert-butyldimethylsilyl)oxy)methyl)-2-iodo-4-oxo-4,5,6,7-tetrahydropyrazolo[1,5-a]pyrazine-3-carboxylate

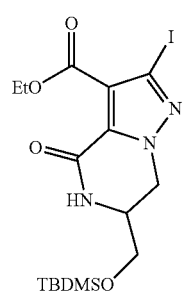 [SMILES: CCOC(=O)c1c(I)nn2c1C(=O)NC(CO[Si](C)(C)C(C)(C)C)C2]

To a solution of Intermediate 351B (1.2 g, 3.29 mmol) in DCM (12 mL) was added imidazole (0.336 g, 4.93 mmol), TBDMS-Cl (0.644 g, 4.27 mmol), DMAP (0.028 g, 0.23 mmol) and the reaction mixture was stirred at RT for 3 h. The reaction mixture was diluted with water and extracted with DCM (3×40 mL). The combined organic layer was washed with water, dried over sodium sulfate and concentrated. The crude product obtained was purified by silica gel chromatography (40 g REDISEP® column, eluting with 50% ethyl acetate in hexanes). Fractions containing the product were combined and evaporated to afford Intermediate 351C (1.1 g, 69%), MS(ES): m/z=480.2 [M+H]$^+$; $^1$H NMR (400 MHz, DMSO-d$_6$) δ ppm 8.43 (d, J=4.0 Hz, 1H), 4.52-4.45 (m, 1H), 4.35 (dd, J=4.0, 13.6 Hz, 1H), 4.27-4.18 (m, 2H), 3.86-3.79 (m, 1H), 3.71 (dd, J=4.0, 10.5 Hz, 1H), 3.55 (dd, J=6.0, 10.5 Hz, 1H), 1.27 (t, J=7.0 Hz, 3H), 0.81-0.75 (m, 9H), −0.02 (d, J=1.0 Hz, 6H).

Intermediate 351D: Ethyl 6-(((tert-butyldimethylsilyl)oxy)methyl)-2-iodo-4,5,6,7-tetrahydropyrazolo[1,5-a]pyrazine-3-carboxylate

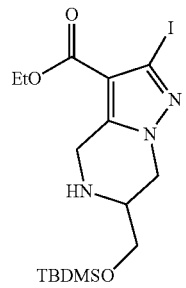 [SMILES: CCOC(=O)c1c(I)nn2c1CNC(CO[Si](C)(C)C(C)(C)C)C2]

To a solution of Intermediate 351C (1.2 g, 2.503 mmol) in THF (120 ml) was added neat borane dimethylsulfide complex (0.713 mL, 7.51 mmol) dropwise and the resulting solution was heated at 40° C. for 36 h. The reaction mixture was cooled to room temperature and ethanol (10 mL) was added dropwise. The reaction mixture was stirred at 70° C. for 1 h and concentrated to afford Intermediate 351D as a white semi-solid (1.23 g, 95%), which was taken to the next step without further purification. MS(ES): m/z=466 [M+H]$^+$.

Intermediate 351E: Ethyl 6-(((tert-butyldimethylsilyl)oxy)methyl)-5-((4-cyanophenyl) carbamoyl)-2-iodo-4,5,6,7-tetrahydropyrazolo[1,5-a]pyrazine-3-carboxylate

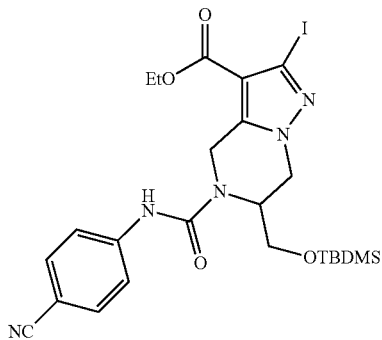 [SMILES: CCOC(=O)c1c(I)nn2c1CN(C(=O)Nc1ccc(C#N)cc1)C(CO[Si](C)(C)C(C)(C)C)C2]

To a solution of Intermediate 351D (1.2 g, 2.58 mmol) in THF (12 ml) was added 4-isocyanatobenzonitrile (0.446 g, 3.09 mmol) and the solution was stirred at room temperature overnight. The reaction mixture was concentrated and the crude product was purified by silica gel chromatography (40 g REDISEP® column, eluting with 16% EtOAc in hexanes). Fractions containing the product were combined and evaporated to afford Intermediate 351E (0.6 g, 38%) as a white solid. MS(ES): m/z=610 [M+H]$^+$; $^1$H NMR (400 MHz, DMSO-d$_6$) δ ppm 9.32 (s, 1H), 7.75-7.63 (m, 4H), 5.24 (d, J=18.6 Hz, 1H), 4.85-4.77 (m, 1H), 4.47 (d, J=18.6 Hz, 1H), 4.35 (d, J=2.5 Hz, 2H), 4.30-4.22 (m, 2H), 3.73-3.64 (m, 2H), 1.31 (t, J=7.0 Hz, 3H), 0.76-0.71 (m, 9H), −0.04 (m, 6H).

Intermediate 351F: 5-((4-Cyanophenyl)carbamoyl)-6-(hydroxymethyl)-2-iodo-4,5,6,7-tetrahydropyrazolo[1,5-a]pyrazine-3-carboxylic acid

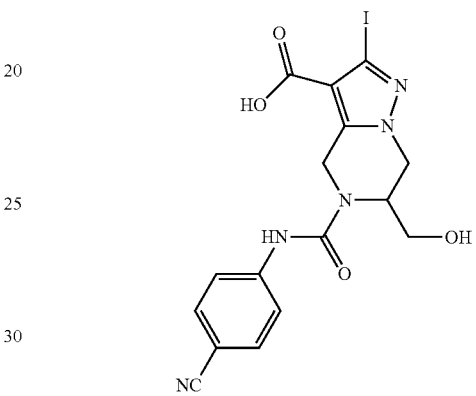

To a solution of Intermediate 351E (0.7 g, 1.148 mmol) in THF (10 mL) and water (5 ml) was added LiOH (0.083 g, 3.45 mmol) and the reaction mass was stirred at RT for 24 h. The volatiles were evaporated; the residue was diluted with water (10 mL) and neutralized with an aqueous solution of 1.0 N HCl. The solid product separated was filtered and dried to afford Intermediate 351F (0.4 g, 74%) as an off-white solid which was taken to the next step without further purification. MS(ES): m/z=468 [M+H]$^+$; $^1$H NMR (300 MHz, DMSO-d$_6$) δ ppm 12.35-12.80 (br, 1H), 9.33 (s, 1H), 7.69-7.74 (m, 2H), 7.62-7.68 (m, 2H), 5.20-5.30 (m, 1H), 5.10-5.19 (m, 1H), 4.72 (d, J=4.53 Hz, 1H), 4.46 (d, J=18.51 Hz, 1H), 4.27-4.38 (m, 2H), 3.40-3.48 (m, 2H).

Intermediate 351G: N$^5$-(4-Cyanophenyl)-6-(hydroxymethyl)-2-iodo-6,7-dihydropyrazolo[1,5-a]pyrazine-3,5(4H)-dicarboxamide

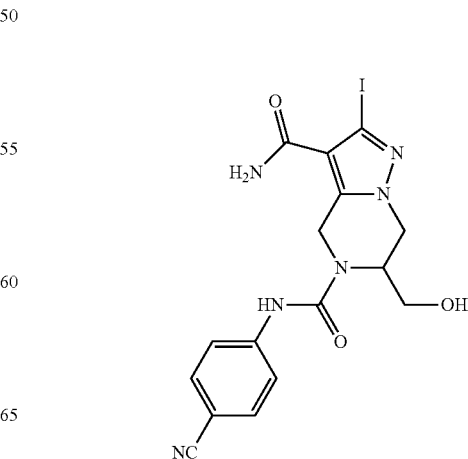

To a solution of Intermediate 351F (0.12 g, 0.257 mmol) in dry DMF (3 mL) was added HATU (0.195 g, 0.512 mmol), diisopropylethylamine (224 µL, 1.128 mmol) and ammonium chloride (0.0687 g, 1.128 mmol) and the reaction mixture was stirred at room temperature for 4 h. The reaction mixture was concentrated completely to dryness and the crude was partitioned between ethyl acetate and water. The organic layer was separated, washed with brine, dried over Na$_2$SO$_4$, filtered and the filtrate concentrated. The crude product was purified by silica gel chromatography (12 g REDISEP® column, eluting with 3-5% methanol in chloroform). Fractions containing the product were combined to afford Intermediate 351G (0.08 g, 67%) as an off-white solid. MS(ES): m/z=467 [M+H]$^+$; $^1$H NMR (400 MHz, DMSO-d$_6$) δ ppm 9.29 (s, 1H), 7.69-7.74 (m, 2H), 7.63-7.69 (m, 2H), 7.37-7.48 (m, 1H), 6.93 (br. s., 1H), 5.22 (d, J=18.07 Hz, 1H), 5.13 (t, J=5.27 Hz, 1H), 4.72 (d, J=4.52 Hz, 1H), 4.51 (d, J=18.57 Hz, 1H), 4.31-4.38 (m, 1H), 4.20-4.28 (m, 1H), 3.43 (t, J=6.02 Hz, 2H).

Compound 351: 2-(3-Chloro-4-fluorophenyl)-N$^5$-(4-cyanophenyl)-6-(hydroxymethyl)-6,7-dihydropyrazolo[1,5-a]pyrazine-3,5(4H)-dicarboxamide

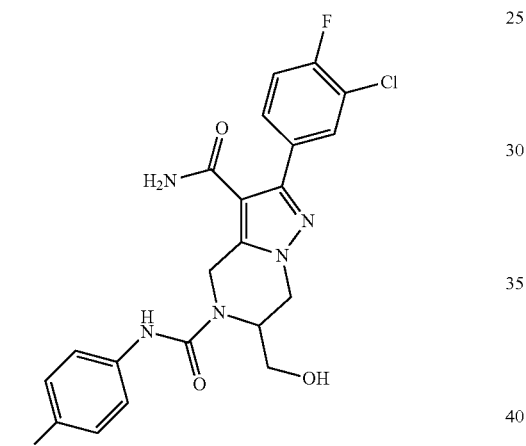

A solution of Intermediate 351G (0.07 g, 0.15 mmol), (3-chloro-4-fluorophenyl) boronic acid (0.0393 g, 0.225 mmol) and K$_3$PO$_4$ (0.096, 0.45 mmol) in 1,4-dioxane (3 mL) and water (0.5 mL) was degassed with nitrogen for 10 min. PdCl$_2$(dppf)-CH$_2$Cl$_2$ adduct (7.36 mg, 9.01 µmol) was added and the reaction mixture was stirred at 80° C. for 12 h. The reaction mixture was concentrated and crude was partitioned between ethyl acetate and water. The organic layer was separated, washed with brine, dried over Na$_2$SO$_4$, filtered and the filtrate concentrated. The crude was purified via preparative HPLC to afford 351 as an off-white solid (20 mg, 30%). HPLC retention times 8.10 min. and 7.95 min. (Methods A and B); MS(ES): m/z=469 [M+H]$^+$; $^1$H NMR (400 MHz, DMSO-d$_6$) δ ppm 9.35 (br. s., 1H), 7.90 (dd, J=7.28, 2.26 Hz, 1H), 7.66-7.76 (m, 5H), 7.45-7.51 (m, 1H), 7.30-7.43 (m, 2H), 5.20 (d, J=17.57 Hz, 2H), 4.80 (d, J=5.02 Hz, 1H), 4.54 (d, J=17.57 Hz, 1H), 4.36-4.42 (m, 1H), 4.24-4.31 (m, 1H), 3.50 (d, J=6.02 Hz, 2H).

Scheme 56

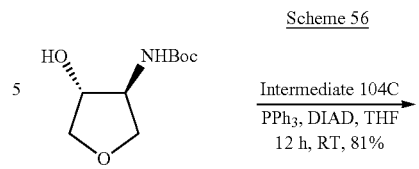

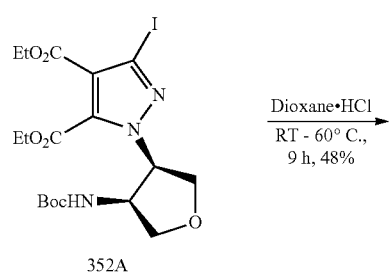

352A

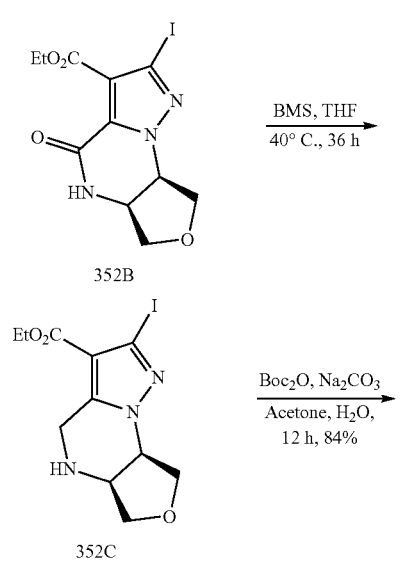

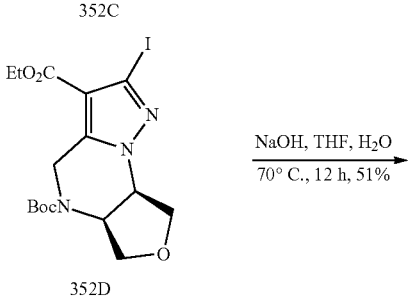

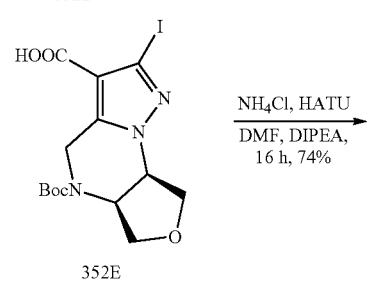

-continued

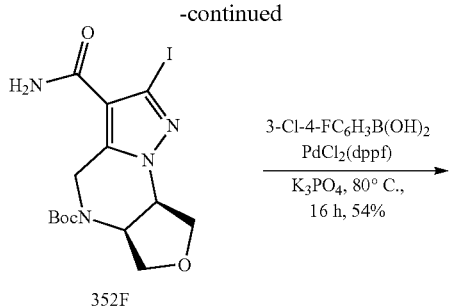

352F

3-Cl-4-FC$_6$H$_3$B(OH)$_2$
PdCl$_2$(dppf)
K$_3$PO$_4$, 80° C.,
16 h, 54%

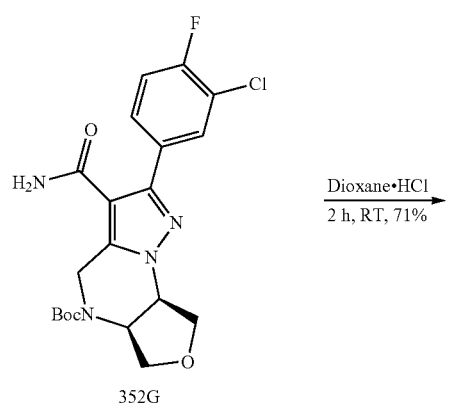

352G

Dioxane•HCl
2 h, RT, 71%

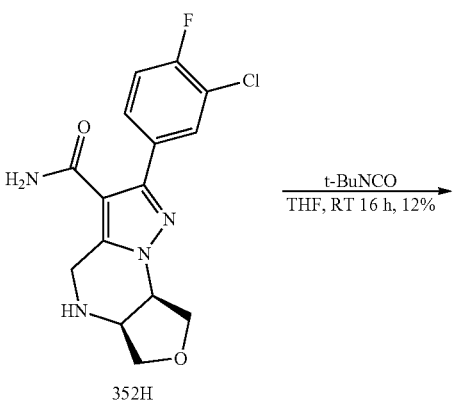

352H t-BuNCO
THF, RT 16 h, 12%

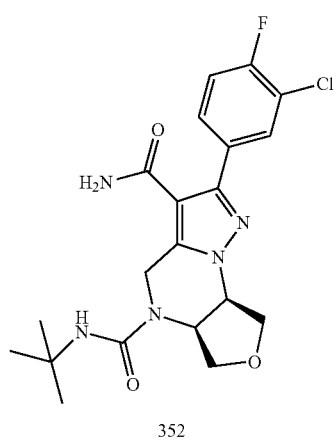

352

Intermediate 352A: Diethyl 1-((3R,4S)-4-((tert-butoxycarbonyl)amino)tetrahydrofuran-3-yl)-3-iodo-1H-pyrazole-4,5-dicarboxylate

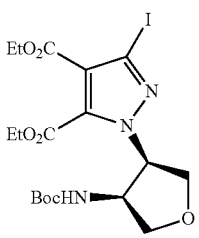 [SMILES: CCOC(=O)c1c(I)nn([C@H]2COC[C@H]2NC(=O)OC(C)(C)C)c1C(=O)OCC]

To a solution of PPh$_3$ (2.72 g, 10.35 mmol) in THF (10 mL) at 0° C. was added DIAD (2.013 mL, 10.35 mmol) dropwise and stirred for 15 min. A solution of Intermediate 104C (1.4 g, 4.14 mmol) in THF (10 mL) was added to the above reaction mixture and was stirred at 0° C. for 45 min. A solution of tert-butyl ((3S,4R)-4-hydroxytetrahydrofuran-3-yl)carbamate (1.683 g, 8.28 mmol) in THF (10 mL) was added dropwise at 0° C. and the reaction mixture was stirred at RT for 12 h. The reaction mixture was then concentrated and the crude compound was purified by silica gel chromatography (24 g REDISEP® column, eluting with 30% EtOAc in hexanes). Fractions containing the product were combined and evaporated to afford Intermediate 352A (1.7 g, 81%) as a white solid. MS(ES): m/z=522 [M−H]$^+$; The crude product was taken to the next step without further purification.

Intermediate 352B: (5aS,8aR)-Ethyl 2-iodo-4-oxo-4,5,5a,6,8,8a-hexahydrofuro[3,4-e]pyrazolo[1,5-a]pyrazine-3-carboxylate

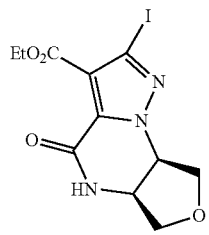 [SMILES: CCOC(=O)c1c(I)nn2c1C(=O)N[C@@H]1COC[C@@H]12]

To an ice cold solution of Intermediate 352A (6.0 g, 11.5 mmol) in dioxane (20 mL) was added a 4 M solution of HCl in dioxane (100 mL, 11.47 mmol) and the reaction mixture was stirred at RT for 4 h. The reaction mixture was concentrated; the pH of the residue was adjusted to 8 with a 10% aqueous solution of NaHCO$_3$ and the mixture was stirred at RT for 30 min. then was extracted with EtOAc (3×100 mL). The combined organic layers were washed with water, dried over Na$_2$SO$_4$, concentrated and kept under vacuum at 60° C. for 6 h to obtain Intermediate 352B as an off-white solid (2.1 g, 48%). MS(ES): −m/z=378 [M+H]$^+$; $^1$H NMR (400 MHz, DMSO-d$_6$) δ ppm 8.67 (d, J=3.5 Hz, 1H), 5.11-5.04 (m, 1H), 4.45 (dq, J=4.0, 6.5 Hz, 1H), 4.31-4.12 (m, 4H), 4.04-3.94 (m, 1H), 3.57 (dd, J=6.0, 9.0 Hz, 1H), 1.32-1.22 (m, 3H).

Intermediate 352C: (5aS,8aR)-Ethyl 2-iodo-4,5,5a,6,8,8a-hexahydrofuro[3,4-e]pyrazolo[1,5-a]pyrazine-3-carboxylate

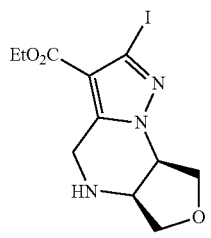 [SMILES: CCOC(=O)c1c(I)nn2c1CN[C@@H]1COC[C@@H]12]

To a stirred solution of Intermediate 352B (0.5 g, 1.33 mmol) in THF (1 mL) was added borane dimethyl sulfide complex (0.378 mL, 3.98 mmol) and the reaction mixture was stirred at 40° C. for 16 h. Additional quantity of borane dimethyl sulfide complex (0.126 mL, 1.326 mmol) was added and the reaction was stirred further for 16 h. The reaction was quenched by adding ethanol (3 mL) and allowing the solution to heat to reflux for 2 h. The reaction mixture was concentrated to afford crude Intermediate 352C as an off-white semi-solid which was taken as such for next step without further purification.

Intermediate 352D: (5aS,8aR)-5-tert-Butyl 3-ethyl 2-iodo-5a,6,8,8a-tetrahydrofuro[3,4-e]pyrazolo[1,5-a]pyrazine-3,5(4H)-dicarboxylate

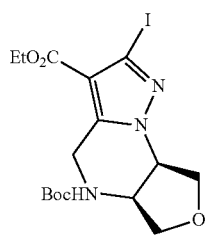

To a stirred solution of Intermediate 352C (1.0 g, 2.75 mmol) in DCM (10 mL) was added TEA (1.151 mL, 8.26 mmol) and stirred for 10 min., followed by the addition of Boc$_2$O (0.767 mL, 3.30 mmol). The reaction mixture was allowed to stir at RT for 16 h., at which point it was diluted with water (50 mL) and extracted with DCM (3×50 mL). The combined organic layers were washed with water, dried over Na$_2$SO$_4$ and concentrated. The crude compound was purified by silica gel chromatography (12 g REDISEP® column, eluting with 50% EtOAc in hexanes). Fractions containing the product were combined and evaporated to afford Intermediate 352D (0.56, 44% yield) as an off-white solid. MS(ES): −m/z=464 [M+H]$^+$; $^1$H NMR (300 MHz, DMSO-d$_6$) δ ppm 5.30 (d, J=18.5 Hz, 1H), 4.88 (dd, J=3.0, 7.2 Hz, 1H), 4.51- 4.36 (m, 1H), 4.33-4.14 (m, 2H), 4.13-4.00 (m, 1H), 3.98-3.86 (m, 1H), 3.82-3.71 (m, 1H), 1.49-1.39 (m, 9H), 1.35-1.25 (m, 3H).

Intermediate 352E: (5aS,8aR)-5-(tert-Butoxycarbonyl)-2-iodo-4,5,5a,6,8,8a-hexahydrofuro[3,4-e]pyrazolo[1,5-a]pyrazine-3-carboxylic acid

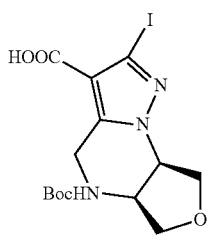

To a stirred solution of Intermediate 352D (0.85 g, 1.835 mmol) in THF (5 mL) was added a solution of NaOH (0.220 g, 5.50 mmol) in water (4 mL) and the reaction mixture was heated to 70° C. for 16 h. The reaction mixture was concentrated and the pH of the residue was adjusted to 4-5 using an aqueous solution of citric acid. The formed precipitate was filtered, washed with n-hexanes and dried to afford Intermediate 352E (0.48 g, 51%) as an off-white solid. MS(ES): −m/z=434 [M−H]$^+$; $^1$H NMR (300 MHz, DMSO-d$_6$) δ ppm 12.80-12.67 (m, 1H), 5.30 (d, J=18.5 Hz, 2H), 4.87 (dd, J=3.4, 6.8 Hz, 1H), 4.46-4.32 (m, 1H), 4.12-4.04 (m, 1H), 3.98-3.90 (m, 1H), 3.89-3.82 (m, 1H), 3.80-3.69 (m, 1H), 1.43 (s, 9H).

Intermediate 352F: (5aS,8aR)-tert-Butyl 3-carbamoyl-2-iodo-5a,6,8,8a-tetrahydrofuro[3,4-e]pyrazolo[1,5-a]pyrazine-5(4H)-carboxylate

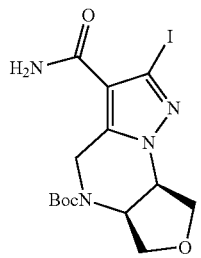 [SMILES: CC(C)(C)OC(=O)N1Cc2c(C(N)=O)c(I)nn2[C@H]2COC[C@H]21]

To a stirred solution of Intermediate 352E (0.480 g, 1.103 mmol) in DMF (10 mL) at RT was added DIPEA (0.963 mL, 5.51 mmol), HATU (0.839 g, 2.206 mmol), and NH$_4$Cl (0.295 g, 5.51 mmol). After stirring for 12 h, the reaction mixture was diluted with water and extracted with EtOAc (3×50 mL). The combined organic layers were washed with water, dried over Na$_2$SO$_4$ and concentrated to afford Intermediate 352F (0.39 g, 74%) as a pale yellow oil. MS(ES): m/z=435 [M+H]$^+$; $^1$H NMR (300 MHz, DMSO-d$_6$) δ ppm 7.95 (s, 2H), 5.30-5.13 (m, 2H), 4.86 (dd, J=3.4, 7.6 Hz, 1H), 4.38 (d, J=15.9 Hz, 1H), 4.14-4.03 (m, 1H), 3.98-3.82 (m, 2H), 3.75 (dd, J=6.6, 9.3 Hz, 1H), 1.43 (s, 9H).

Intermediate 352G: (5aS,8aR)-tert-Butyl 3-carbamoyl-2-(3-chloro-4-fluorophenyl)-5a,6,8,8a-tetrahydrofuro[3,4-e]pyrazolo[1,5-a]pyrazine-5(4H)-carboxylate

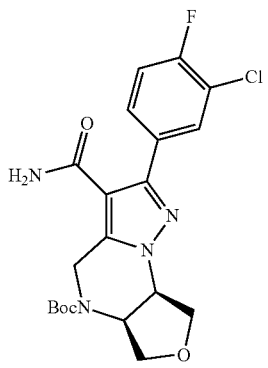 [SMILES: CC(C)(C)OC(=O)N1Cc2c(C(N)=O)c(-c3ccc(F)c(Cl)c3)nn2[C@H]2COC[C@H]21]

To a stirred solution of Intermediate 352F (0.370 g, 0.852 mmol) and (3-chloro-4-fluorophenyl)boronic acid (0.297 g, 1.704 mmol) in dioxane (2 mL) was added a solution of K₃PO₄ (0.543 g, 2.56 mmol) in water (0.5 mL) and the reaction mixture was purged with nitrogen for 10 min. PdCl₂(dppf)CH₂Cl₂ (0.052 g, 0.064 mmol) was then added and the reaction mixture was heated to 80° C. and stirred for 16 h. The reaction mixture was diluted with water and extracted with EtOAc (3×30 mL). The combined organic layers were washed with water, dried over Na₂SO₄ and concentrated. The crude compound was purified by silica gel chromatography (12 g REDISEP® column, eluting with 4% MeOH in CHCl₃). Fractions containing the product were combined and evaporated to afford Intermediate 352G (0.270 g, 54%) as an off-white solid. MS(ES): m/z=437 [M+H]⁺.

Intermediate 352H: (5aS,8aR)-2-(3-Chloro-4-fluorophenyl)-4,5,5a,6,8,8a-hexahydrofuro[3,4-e]pyrazolo[1,5-a]pyrazine-3-carboxamide HCl

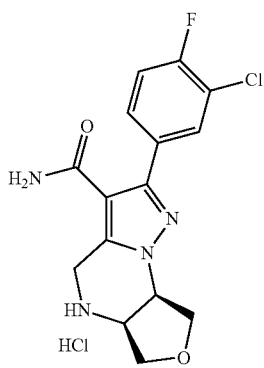 [SMILES: NC(=O)c1c(-c2ccc(F)c(Cl)c2)nn2c1CN[C@@H]1COC[C@@H]12 ; Cl]

To a stirred solution of Intermediate 352G (0.2 g, 0.458 mmol) in dioxane (1 mL) was added a solution of HCl in dioxane (2 mL, 8.0 mmol, 4 M). After stirring at RT for 2 h, the reaction mixture was concentrated and the crude product was triturated with hexanes to afford Intermediate 352H (0.17 g, 71%) as an off-white solid. MS(ES): –m/z=337 [M+H]⁺. ¹H NMR (400 MHz, DMSO-d₆) δ ppm 7.90 (ddd, J=1.8, 7.5, 14.3 Hz, 1H), 7.80-7.68 (m, 2H), 7.54-7.47 (m, 1H), 7.38 (dd, J=8.3, 9.8 Hz, 1H), 5.10 (br. s., 1H), 4.63 (br. s., 1H), 4.56 (s, 2H), 4.20-3.98 (m, 4H), 3.57 (s, 1H).

Compound 352: (5aS,8aR)—N⁵-(tert-Butyl)-2-(3-chloro-4-fluorophenyl)-5a,6,8,8a-tetrahydrofuro[3,4-e]pyrazolo[1,5-a]pyrazine-3,5(4H)-dicarboxamide

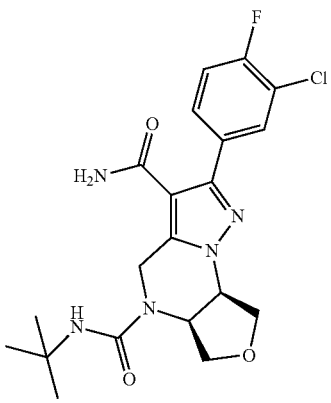 [SMILES: CC(C)(C)NC(=O)N1Cc2c(C(N)=O)c(-c3ccc(F)c(Cl)c3)nn2[C@H]2COC[C@H]21]

To a stirred solution of 352H (0.05 g, 0.148 mmol) in THF was added 2-isocyanato-2-methylpropane (0.022 g, 0.223 mmol), TEA (0.062 mL, 0.445 mmol) and the resulting solution was stirred at RT for 16 h. Water (0.2 mL) was added and the reaction mixture was concentrated. The crude product was further purified by preparative HPLC to afford Compound 352 (8 mg, 12%) as an off-white solid. HPLC retention times 1.37 min. and 1.46 min. (Methods E and L respectively). MS(ES): m/z=436 [M+H]⁺; ¹H NMR (400 MHz, DMSO-d₆) δ ppm 7.89 (dd, J=7.3, 2.3 Hz, 1H), 7.72 (ddd, J=8.7, 4.9, 2.0 Hz, 1H), 7.49-7.44 (m, 1H), 7.42-7.31 (m, 2H), 6.41 (s, 1H), 5.36-5.29 (m, 1H), 5.16 (d, J=17.6 Hz, 1H), 4.79 (dd, J=7.0, 3.5 Hz, 1H), 4.30 (d, J=17.1 Hz, 1H), 4.18 (d, J=10.0 Hz, 1H), 3.97-3.87 (m, 2H), 3.76-3.70 (m, 1H), 1.27 (s, 9H).

The Compounds shown in Table 43 have been prepared similar to Compound 352 by coupling of 352H with different isocyanates.

TABLE 43
| Ex. No. | Structure | Name | [M + H]+ | Ret Time (min.) | HPLC Methods |
|---|---|---|---|---|---|
| 353 | 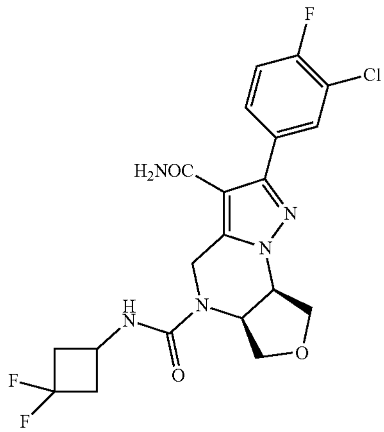 [SMILES: NC(=O)c1c(-c2ccc(F)c(Cl)c2)nn2c1CN(C(=O)NC1CC(F)(F)C1)[C@@H]1COC[C@@H]12] | (5aS,8aR)-2-(3-Chloro-4-fluorophenyl)-N5-(3,3-difluorocyclobutyl)-5a,6,8,8a-tetrahydrofuro[3,4-e]pyrazolo[1,5-c]pyrazine-3,5(4H)-dicarboxamide | 470 | 1.39<br>1.46 | E<br>L |
| 354 | 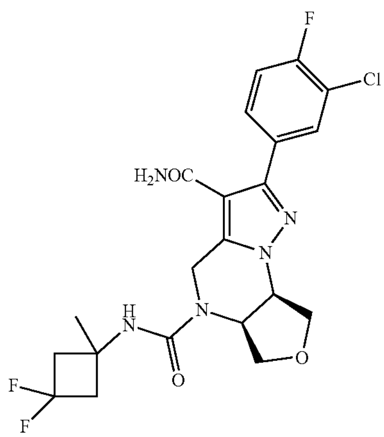 [SMILES: CC1(NC(=O)N2Cc3c(C(N)=O)c(-c4ccc(F)c(Cl)c4)nn3[C@H]3COC[C@H]32)CC(F)(F)C1] | (5aS,8aR)-2-(3-Chloro-4-fluorophenyl)-N5-(3,3-difluoro-1-methylcyclobutyl)-5a,6,8,8a-tetrahydrofuro[3,4-e]pyrazolo[1,5-a]pyrazine-3,5(4H)-dicarboxamide | 484 | 1.49<br>1.55 | E<br>L |
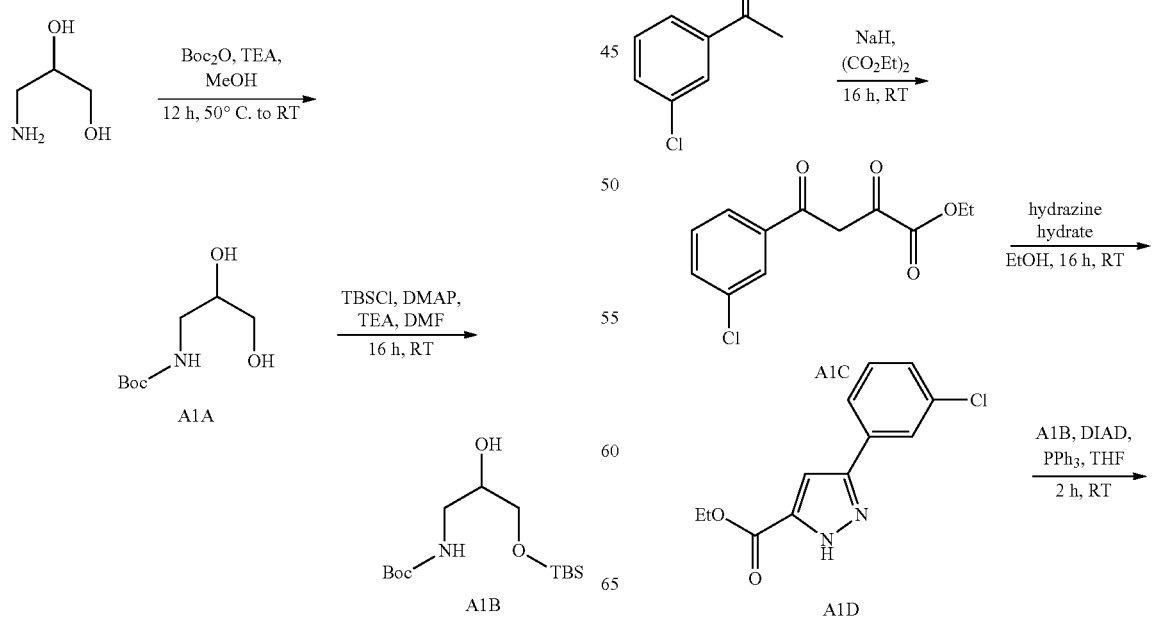

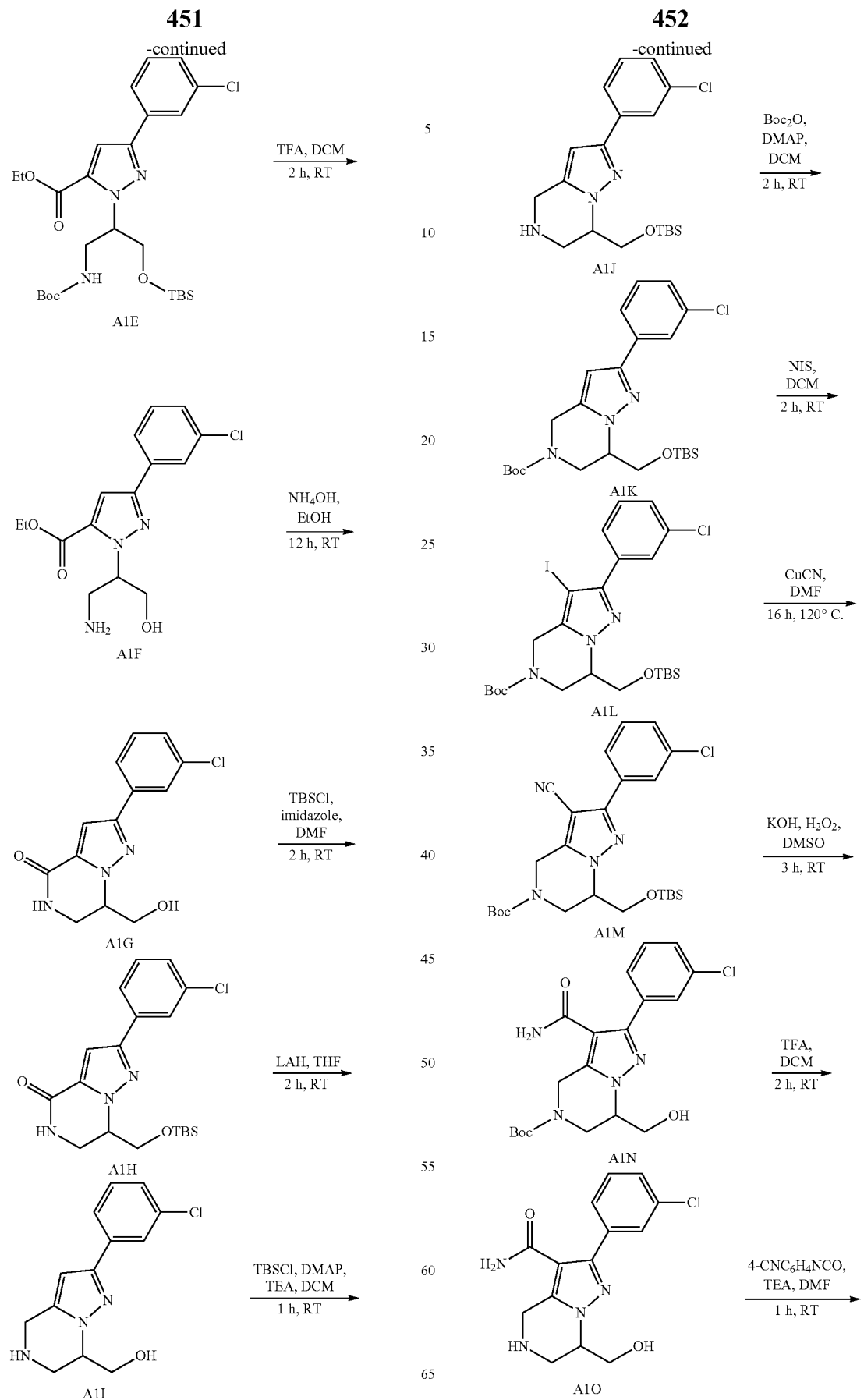

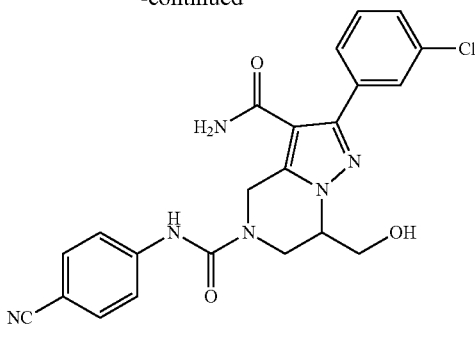

A1

Intermediate A1A:
tert-Butyl(2,3-dihydroxypropyl)carbamate

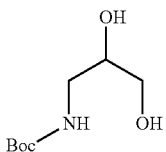

The above Intermediate was synthesized according to a patent literature procedure reported in U.S. Publication No. 2006/69156 A1 (2006).

To a solution of 3-aminopropane-1,2-diol (10.0 g, 110 mmol) in MeOH (407 mL) was added Boc$_2$O (35.9 g, 165 mmol) and TEA (55 mL, 395 mmol) and the reaction mixture was heated at 50° C. for 20 min., followed by stirring at room temperature for 12 h. The reaction was then concentrated under reduced pressure to provide a residue. It was purified by silica gel chromatography (330 g REDISEP® column, eluting with 5% MeOH in DCM). Fractions containing the product were combined and evaporated to afford Intermediate A1A (20.14 g, 96%) as a colorless oil. $^1$H NMR (400 MHz, DMSO-d$_6$) δ ppm 6.61 (br. s., 1H), 4.63 (d, J=4.9 Hz, 1H), 4.47 (t, J=5.6 Hz, 1H), 3.45 (d, J=5.6 Hz, 1H), 3.31-3.23 (m, 2H), 3.09-2.98 (m, 1H), 2.85 (d, J=6.6 Hz, 1H), 1.38 (s, 9H).

Intermediate A1B: tert-Butyl (3-((tert-butyldimethylsilyl)oxy)-2-hydroxypropyl) carbamate

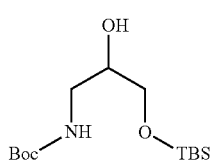

The above Intermediate was synthesized according to a patent literature procedure reported in U.S. Publication No. 2003/187026 A1 (2003).

To a solution of Intermediate A1A (20.14 g, 105 mmol) in DCM (168 mL) were added TEA (17.62 mL, 126 mmol), TBSCl (18.00 g, 116 mmol) and DMAP (0.515 g, 4.21 mmol) and the reaction mixture was stirred at room temperature for 16 h. The mixture was then diluted with DCM (100 mL) and the organic layer was washed with water (3×100 mL), brine, dried over anhydrous MgSO$_4$, filtered and the filtrate was concentrated under reduced pressure to provide a crude residue. It was purified by silica gel chromatography (330 g REDISEP® column, eluting with a gradient of 0 to 30% EtOAc in hexanes). Fractions containing the product were combined and evaporated to afford Intermediate A1B (24.46 g, 76%) as a pale yellow oil. $^1$H NMR (400 MHz, DMSO-d$_6$) δ ppm 6.58 (br. s., 1H), 4.69 (d, J=4.4 Hz, 1H), 3.55-3.42 (m, 3H), 1.37 (s, 9H), 0.92-0.82 (m, 9H).

Intermediate A1C: Ethyl 4-(3-chlorophenyl)-2,4-dioxobutanoate

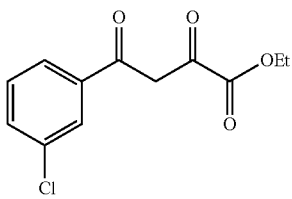 [SMILES: CCOC(=O)C(=O)CC(=O)c1cccc(Cl)c1]

To an ice-cold solution of 1-(3-chlorophenyl)ethanone (16.79 mL, 129 mmol) and diethyl oxalate (18.05 mL, 136 mmol) in DMF (78.0 mL) was added, portionwise over 30 min., NaH (6.09 g, 155 mmol, 60% dispersion in mineral oil) and the resultant mixture was stirred at that temperature for 20 min. and then at room temperature for 16 h. The reaction mixture was diluted with water and acidified to pH=4-5 with 1N aq. HCl. The mixture was further diluted with copious amounts of water. The aq. layer was extracted with EtOAc (4×100 mL) and the combined organic layer was washed with water, brine, dried over anhydrous MgSO$_4$, filtered and the filtrate was concentrated under reduced pressure to provide a crude residue. It was purified by silica gel chromatography (220 g REDISEP® column, eluting with a 0 to 15% EtOAc in hexanes). Fractions containing the product were combined and evaporated to afford Intermediate A1C (27.1 g, 84%) as a solid. MS(ES): m/z=277.10 [M+Na]$^+$; $^1$H NMR (400 MHz, chloroform-d) δ ppm 7.99 (t, J=1.8 Hz, 1H), 7.95-7.86 (m, 1H), 7.60 (ddd, J=8.0, 2.1, 1.0 Hz, 1H), 7.48 (t, J=7.9 Hz, 1H), 7.06 (s, 1H), 4.43 (q, J=7.3 Hz, 2H), 1.44 (t, J=7.2 Hz, 3H).

Intermediate A1D: Ethyl 3-(3-chlorophenyl)-1H-pyrazole-5-carboxylate

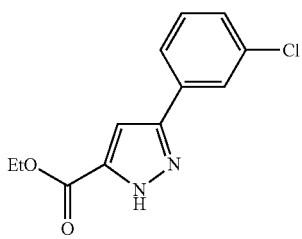 [SMILES: CCOC(=O)c1cc(-c2cccc(Cl)c2)n[nH]1]

To a suspension of Intermediate A1C (14.57 g, 57.2 mmol) in EtOH (191 mL) was added hydrazine hydrate (5.57 mL, 57.2 mmol, 64% solution) and the reaction mixture was stirred at room temperature for 16 h. The reaction turned homogenous over time and then a solid precipitated out. The thick precipitate was filtered off. The filter cake was washed with a little EtOH to afford the product as a white solid. The filtrate was rotavaped to dryness to afford the crude product as a yellow solid. It was suspended in minimum amount of EtOH or MeCN and filtered off to give more of the product. The process of rotavaping the filtrate to dryness and suspending the subsequent solid in EtOH or MeCN was repeated 2-3 more times to provide more white product during each filtration cycle. The combined solid was dried under vacuum for 3 h to afford Intermediate A1D (10.9 g, 76%). MS(ES): m/z=273 [M+Na]+; 1H NMR (400 MHz, DMSO-d6) δ ppm 13.91 (br. s., 1H), 7.97 (t, J=1.8 Hz, 1H), 7.86 (dt, J=7.8, 1.4 Hz, 1H), 7.55-7.33 (m, 4H), 4.34 (q, J=7.2 Hz, 2H), 1.34 (t, J=7.2 Hz, 3H).

Intermediate A1E: Ethyl 3-(3-chlorophenyl)-1-(2,2,3,3,11,11-hexamethyl-9-oxo-4,10-dioxa-8-aza-3-siladodecan-6-yl)-1H-pyrazole-5-carboxylate

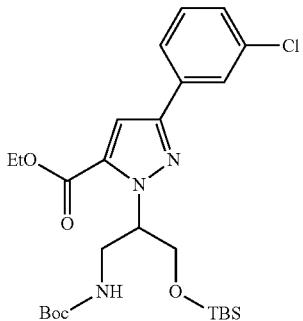

To an ice-cold suspension of Intermediate A1D (7.0 g, 27.9 mmol) and PPh3 (10.99 g, 41.9 mmol) in THF (112 mL) was added a solution of DIAD (8.57 mL, 41.9 mmol) in THF (15 mL). Soon the reaction mixture turned homogenous. It was stirred at that temperature for 30 min., followed by the addition of a solution of Intermediate A1B (10.24 g, 33.5 mmol) in THF (15 mL). The resultant reaction mixture was stirred at room temperature for 2 h and then diluted with EtOAc (150 mL) The organic layer was washed with brine, dried over anhydrous MgSO4, filtered and the filtrate was concentrated under reduced pressure to provide a crude oil. It was purified by silica gel chromatography (220 g REDISEP® column, eluting with 0 to 15% EtOAc in hexanes).

Fractions containing the product were combined and evaporated to afford Intermediate A1E (12.5 g, 83%) as a thick syrup. MS(ES): m/z=438.1 [M-Boc]+; 1H NMR (400 MHz, chloroform-d) δ ppm 7.97 (s, 1H), 7.91-7.83 (m, 1H), 7.53-7.37 (m, 3H), 7.01 (s, 1H), 5.54 (br. s., 1H), 4.32 (q, J=7.0 Hz, 2H), 3.94 (d, J=6.0 Hz, 2H), 3.48 (s, 1H), 3.39 (d, J=7.5 Hz, 1H), 1.41-1.29 (m, 1H), 0.74 (s, 9H).

Intermediate A1F: Ethyl 1-(1-amino-3-hydroxypropan-2-yl)-3-(3-chlorophenyl)-1H-pyrazole-5-carboxylate, 2 HCl

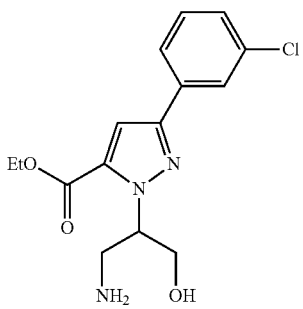 [SMILES: CCOC(=O)c1cc(-c2cccc(Cl)c2)nn1C(CN)CO]

To a solution of Intermediate A1E (21 g, 39 mmol) in 1,4-dioxane (156 mL) was added a solution of HCl (166 mL, 663 mmol, 4 M in 1,4-dioxane) and the reaction mixture was stirred at room temperature for 6 h. The white precipitate that was generated was filtered off and the filter cake was washed with a little dioxane. The solid was dried under vacuum for 16 h to afford Intermediate A1F as a bis HCl salt (11.9 g, 77%). MS(ES): m/z=324.0 [M+H]+.

Intermediate A1G: 2-(3-Chlorophenyl)-7-(hydroxymethyl)-6,7-dihydropyrazolo[1,5-a]pyrazin-4(5H)-one

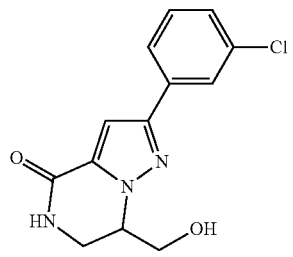 [SMILES: O=C1NCC(CO)n2nc(-c3cccc(Cl)c3)cc21]

To a suspension of Intermediate A1F (5.23 g, 13.18 mmol) in EtOH (132 mL) was added NH4OH (171 mL, 1318 mmol) and the reaction mixture was stirred at RT for 16 h. Soon the mixture became homogenous and a white precipitate formed overnight. The solid was filtered off and the filtrate was concentrated under reduced pressure to provide more product. The combined white solid was dried overnight to afford Intermediate A1G (3.5 g, 96%). MS(ES): m/z=278.0 [M+H]+. 1H NMR (400 MHz, DMSO-d6) δ ppm 8.22 (br. s., 1H), 7.94 (t, J=1.6 Hz, 1H), 7.86 (dt, J=7.7, 1.3 Hz, 1H), 7.52-7.38 (m, 2H), 7.34 (s, 1H), 7.07 (br. s., 1H), 5.29 (t, J=5.8 Hz, 1H), 4.54-4.42 (m, 1H), 3.86-3.71 (m, 3H), 3.65 (dt, J=13.4, 4.1 Hz, 1H).

Intermediate A1H: 7-(((tert-Butyldimethylsilyl)oxy)methyl)-2-(3-chlorophenyl)-6,7-dihydropyrazolo[1,5-a]pyrazin-4(5H)-one

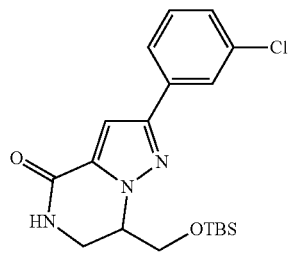 [SMILES: CC(C)(C)[Si](C)(C)OCC1CNC(=O)c2cc(-c3cccc(Cl)c3)nn21]

To a solution of Intermediate A1G (4.365 g, 15.72 mmol) in DMF (157 mL) was added imidazole (1.380 g, 20.28 mmol) and TBSCl (2.84 g, 18.86 mmol) and the reaction mixture was stirred at room temperature for 2 h. Most of the DMF was concentrated under reduced pressure and the residue was diluted with water to generate a white precipitate. This solid was filtered off and the filter cake was dried under vacuum for 4 h to afford Intermediate A1H (5.1 g, 83%). MS(ES): m/z=392.1 [M+H]+. 1H NMR (400 MHz, DMSO-d6) δ ppm 8.21 (br. s., 1H), 7.94 (t, J=1.6 Hz, 1H), 7.86 (dt, J=7.5, 1.3 Hz, 1H), 7.52-7.37 (m, 2H), 7.35 (s, 1H), 4.58 (br. s., 1H), 4.09-3.92 (m, 2H), 3.63 (s, 1H), 0.91-0.79 (m, 9H).

Intermediate A1I: (2-(3-Chlorophenyl)-4,5,6,7-tetrahydropyrazolo[1,5-a]pyrazin-7-yl)methanol

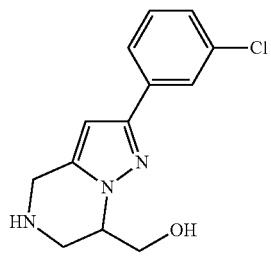 [SMILES: OCC1CNCc2cc(-c3cccc(Cl)c3)nn21]

To a solution of Intermediate A1H (4.945 g, 12.61 mmol) in THF (126 mL) was added, dropwise at −15° C., a 1M solution of LAH in THF (31.5 mL, 31.5 mmol) and the reaction mixture was stirred at that temperature for 3 h. LC-MS shows mainly unreacted starting material. Hence, more 1M LAH solution in THF (6.31 mL, 6.31 mmol, 0.5 equivalent) was added dropwise at −15° C. and the RM was allowed to gradually warm to room temperature and stirred further for 16 h. The reaction mixture was carefully quenched at −15° C. with a sequential addition of H$_2$O (31.5 mL), NaOH (15% aq. solution, 31.5 mL) and H$_2$O (92 mL). The slurry was then allowed to stir at room temperature for =30 min., followed by the addition of anhydrous MgSO$_4$. The mixture was stirred further for 15 min. and then the inorganics were filtered off. The filter cake was washed with THF (150 mL) The biphasic filtrate was concentrated under reduced pressure to remove THF. The residual aq. layer was extracted with DCM (3×50 mL). The combined organic layer was washed with brine, dried over anhydrous MgSO$_4$, filtered and concentrated under reduced pressure to afford TBS cleaved Intermediate A1I (3.1 g, 93%) as a slightly impure yellow sticky solid. MS(ES): m/z=264.0 [M+H]$^+$.

Intermediate A1J: 7-(((tert-Butyldimethylsilyl)oxy) methyl)-2-(3-chlorophenyl)-4,5,6,7-tetrahydropyrazolo[1,5-a]pyrazine

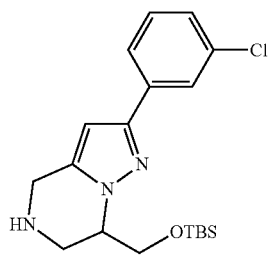 [SMILES: CC(C)(C)[Si](C)(C)OCC1CNCc2cc(-c3cccc(Cl)c3)nn21]

To a solution of Intermediate A1I (2.37 g, 8.97 mmol) in DCM (90 mL) were added TBSCl (2.57 g, 17.05 mmol), DMAP (0.164 g, 1.346 mmol) and TEA (3.75 mL, 26.9 mmol) and the reaction mixture was stirred at room temperature for 6 h. It was then diluted with a saturated solution of aq. NaHCO$_3$ and the two layers were separated. The aq. layer was back-extracted with DCM (2×50 mL) The combined organic layer was washed with water, brine, dried over anhydrous MgSO$_4$, filtered and concentrated under reduced pressure to give an oil. It was purified by silica gel chromatography (120 g REDISEP® column, eluting with a gradient of 40-65% EtOAc in hexanes). Fractions containing the product were combined and evaporated to afford Intermediate A1J (3.194 g, 94%) as a colorless oil. MS(ES): m/z=378.1 [M+H]$^+$.

Intermediate A1K: tert-Butyl 7-(((tert-butyldimethylsilyl)oxy)methyl)-2-(3-chlorophenyl)-6,7-dihydropyrazolo[1,5-a]pyrazine-5(4H)-carboxylate

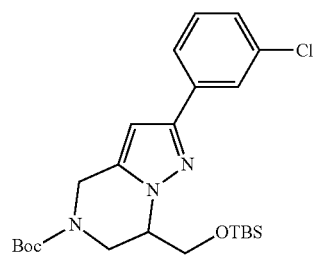 [SMILES: CC(C)(C)OC(=O)N1Cc2cc(-c3cccc(Cl)c3)nn2C(CO[Si](C)(C)C(C)(C)C)C1]

To a solution of Intermediate A1J (3.194 g, 8.45 mmol) in DCM (85 mL) were added Boc$_2$O (2.213 g, 10.14 mmol), DMAP (0.103 g, 0.845 mmol) and TEA (3.53 mL, 25.4 mmol) and the reaction mixture was stirred at room temperature for 2 h. It was then quenched with a saturated solution of aq. NaHCO$_3$ and the two layers were separated. The aq. layer was back-extracted with DCM (2×50 mL). The combined organic layer was washed with brine, dried, over anhydrous MgSO$_4$, filtered and concentrated under reduced pressure to give a solid. It was purified by silica gel chromatography (120 g REDISEP® column, eluting with 20% EtOAc in hexanes). Fractions containing the product were combined and evaporated to afford Intermediate A1K (3.392 g, 84%) as an oil. MS(ES): m/z=478.08 [M+H]$^+$.

Intermediate A1L: tert-Butyl 7-(((tert-butyldimethylsilyl)oxy)methyl)-2-(3-chlorophenyl)-3-iodo-6,7-dihydropyrazolo[1,5-a]pyrazine-5(4H)-carboxylate

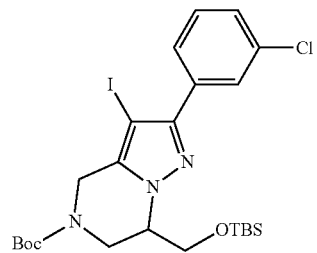 [SMILES: CC(C)(C)OC(=O)N1Cc2c(I)c(-c3cccc(Cl)c3)nn2C(CO[Si](C)(C)C(C)(C)C)C1]

To a solution of Intermediate A1K (3.392 g, 7.09 mmol) in DCM (37.8 mL) and MeOH (9.46 mL) was added NIS (7.66 g, 34.1 mmol) and the reaction mixture was stirred at rt for 2 h. The solution was then concentrated under reduced pressure to provide a solid. It was purified by silica gel chromatography (120 g REDISEP® column, eluting with a gradient of 10-15% EtOAc in hexanes). Fractions containing the product were combined and evaporated to afford Intermediate A1L (4.28 g, >99%) as a semi-solid. MS(ES): m/z=604.08 [M+H]$^+$.

Intermediate A1M: tert-Butyl 7-(((tert-butyldimethylsilyl)oxy)methyl)-2-(3-chlorophenyl)-3-cyano-6,7-dihydropyrazolo[1,5-a]pyrazine-5(4H)-carboxylate

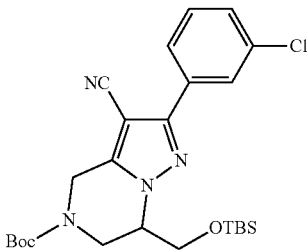 [SMILES: CC(C)(C)OC(=O)N1Cc2c(C#N)c(-c3cccc(Cl)c3)nn2C(CO[Si](C)(C)C(C)(C)C)C1]

To a solution of Intermediate A1L (1.0 g, 1.656 mmol) in DMF (16.56 mL) was added CuCN (0.371 g, 4.14 mmol) and the reaction mixture was heated in a sealed tube in an oil bath at 120° C. for 16 h. The inorganics were then filtered off and the filter cake was washed with EtOAc. The combined filtrate was concentrated under reduced pressure to give a crude residue. It was purified by silica gel chromatography (80 g REDISEP® column, eluting with a gradient of 10 to 15% EtOAc in hexanes). Fractions containing the product were combined and evaporated to afford Intermediate A1M (0.425 g, 51%) as an oil. MS(ES): m/z=504.08 [M+H]$^+$; $^1$H NMR (400 MHz, DMSO-d$_6$) δ ppm 7.90-7.78 (m, 2H), 7.69-7.50 (m, 2H), 4.88 (d, J=17.6 Hz, 1H), 4.71 (d, J=17.6 Hz, 1H), 4.48 (br. s., 1H), 4.13 (br. s., 1H), 4.00-3.91 (m, 2H), 3.81 (br. s., 1H), 1.53-1.43 (m, 9H), 0.88-0.77 (m, 9H).

Intermediate A1N: tert-Butyl 3-carbamoyl-2-(3-chlorophenyl)-7-(hydroxymethyl)-6,7-dihydropyrazolo[1,5-a]pyrazine-5(4H)-carboxylate

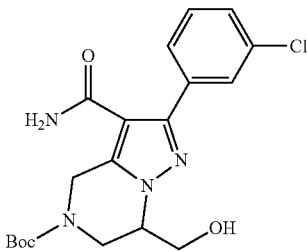 [SMILES: CC(C)(C)OC(=O)N1Cc2c(C(N)=O)c(-c3cccc(Cl)c3)nn2C(CO)C1]

To a solution of Intermediate A1M (1.4 g, 2.78 mmol) in DMSO (27 mL) was added a 5M solution of aq. KOH (2.78 mL, 13.91 mmol) and H$_2$O$_2$ (5.68 mL, 55.7 mmol, 30% w/v in H$_2$O) and the reaction mixture was stirred at room temperature for 3 h. It was then diluted with a lot of water and the aq. phase was extracted with EtOAc (3×50 mL). The combined organic layer was washed with water, brine, dried over anhydrous MgSO$_4$, filtered and concentrated under reduced pressure to give a crude solid. It was purified by silica gel chromatography (80 g REDISEP® column, eluting with 100% EtOAc). Fractions containing the product were combined and evaporated to afford TBS cleaved Intermediate A1N (0.95 g, 84%) as a white solid. MS(ES): m/z=407 [M+H]$^+$.

Intermediate A1O: 2-(3-Chlorophenyl)-7-(hydroxymethyl)-4,5,6,7-tetrahydropyrazolo[1,5-a]pyrazine-3-carboxamide

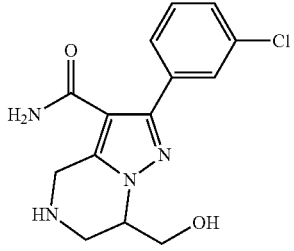 [SMILES: NC(=O)c1c(-c2cccc(Cl)c2)nn2c1CNCC2CO]

To a solution of Intermediate A1N (0.17 g, 0.418 mmol) in DCM (4.18 mL) was added TFA (0.644 mL, 8.36 mmol) and the reaction mixture was stirred at room temperature for 1 h. The volatiles were then evaporated under reduced pressure and the residue was basified with saturated solution of aq. NaHCO$_3$. The two layers were separated and the aq. layer was extracted with DCM (3×10 mL). The combined organic layer was washed with brine, dried over anhydrous MgSO$_4$, filtered and concentrated under reduced pressure to give a crude solid. It was purified by silica gel chromatography (25 g REDISEP® column, eluting with 35% MeOH in DCM). Fractions containing the product were combined and evaporated to afford Intermediate A1O (0.073 g, 57%) as a white solid. MS(ES): m/z=307 [M+H]$^+$.

Compound A1: 2-(3-Chlorophenyl)-N$^5$-(4-cyanophenyl)-7-(hydroxymethyl)-6,7-dihydropyrazolo[1,5-a]pyrazine-3,5(4H)-dicarboxamide

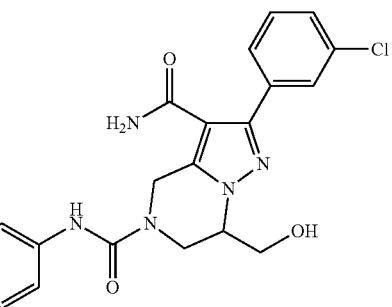

To a solution of Intermediate A1O (0.027 g, 0.088 mmol) in DMF (1.76 mL) were added 4-isocyanatobenzonitrile (0.019 g, 0.132 mmol) and TEA (0.037 mL, 0.264 mmol) and the reaction mixture was stirred at room temperature for 2 h. The mixture was then filtered off and the filtrate was purified via preparative LC/MS. Fractions containing the desired product were combined and evaporated to afford Compound A1 (0.029 g, 70%). MS(ES): m/z=451 [M+H]$^+$; HPLC Ret. Time 1.41 min. and 2.16 min. (HPLC Methods H and I); $^1$H NMR (600 MHz, DMSO-d$_6$) δ ppm 7.77-7.69 (m, 3H), 7.69-7.60 (m, 3H), 7.50-7.40 (m, 2H), 7.38 (br. s., 1H), 7.23 (br. s., 1H), 4.99-4.84 (m, 2H), 4.38-4.28 (m, 1H), 4.12-4.01 (m, 2H), 3.96-3.87 (m, 1H), 3.81 (dd, J=11.0, 7.3 Hz, 1H), 1.91 (s, 1H).

The Compounds described in Table 44 were synthesized analogous to Compound A1 by reacting Intermediate A1O with corresponding isocyanates.

TABLE 44

| Ex. No. | Structure | Name | [M + H]+ | Ret Time (min.) | HPLC Methods |
|---|---|---|---|---|---|
| A2 | 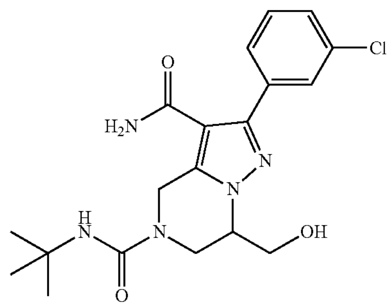 | N5-(tert-Butyl)-2-(3-chlorophenyl)-7-(hydroxymethyl)-6,7-dihydropyrazolo[1,5-a]pyrazine-3,5(4H)-dicarboxamide | 406.10 | 1.28<br>2.26 | H<br>I |
| A3 | 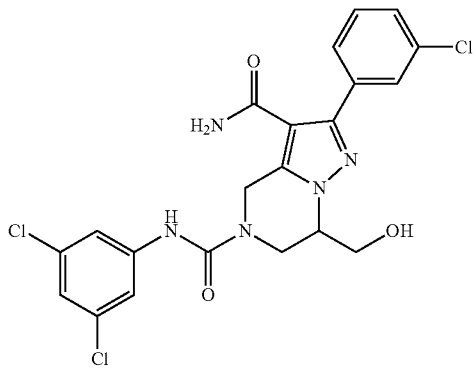 [SMILES: NC(=O)c1c(-c2cccc(Cl)c2)nn2c1CN(C(=O)Nc1cc(Cl)cc(Cl)c1)CC2CO] | 2-(3-Chlorophenyl)-N5-(3,5-dichlorophenyl)-7-(hydroxymethyl)-6,7-dihydropyrazolo[1,5-a]pyrazine-3,5(4H)-dicarboxamide | 495.90 | 2.29<br>2.70 | H<br>I |

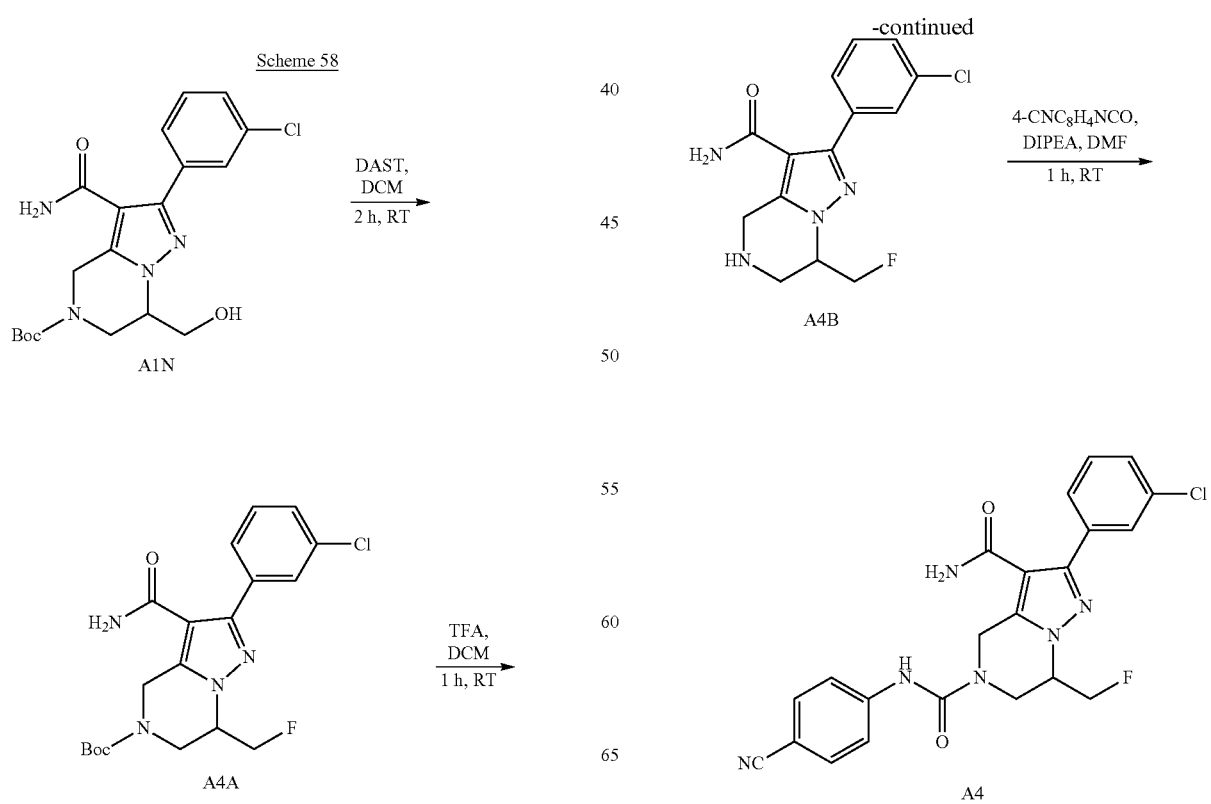

Intermediate A4A: tert-Butyl 3-carbamoyl-2-(3-chlorophenyl)-7-(fluoromethyl)-6,7-dihydropyrazolo[1,5-a]pyrazine-5(4H)-carboxylate

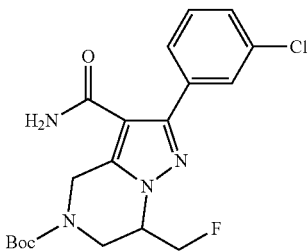 [SMILES: CC(C)(C)OC(=O)N1Cc2c(C(N)=O)c(-c3cccc(Cl)c3)nn2C(CF)C1]

To a suspension of Intermediate A1N (0.15 g, 0.369 mmol) in DCM (4.92 mL) cooled to −78° C., was added DAST (0.073 mL, 0.553 mmol). Soon the reaction mixture turned homogenous. The reaction was stirred at room temperature for 2 h. It was quenched with a saturated solution of aq. NaHCO$_3$. The organic layer was separated and the aq. layer was extracted with DCM (3×10 mL). The combined organic layer was washed with brine, dried over anhydrous MgSO$_4$, filtered and the filtrate concentrated under reduced pressure to give an oil. It was purified by silica gel chromatography (25 g REDISEP® column, eluting with 55% EtOAc in hexanes). Fractions containing the product were combined and evaporated to afford Intermediate A4A (0.054 g, 35.8%) as a white solid. MS(ES): m/z=409 [M+H]$^+$.

Intermediate A4B: 2-(3-Chlorophenyl)-7-(fluoromethyl)-4,5,6,7-tetrahydropyrazolo[1,5-a]pyrazine-3-carboxamide, 2 TFA

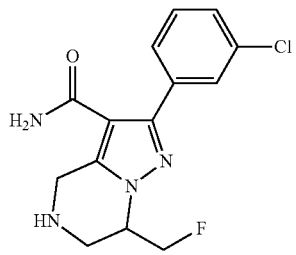

To a solution of Intermediate A4A (0.054 g, 0.132 mmol) in DCM (1.321 mL) was added TFA (0.102 mL, 1.321 mmol) and the reaction mixture was stirred at room temperature for 1 h. It was then concentrated under reduced pressure to provide a residue. The residue was dried under vacuum to afford Intermediate A4B as the his TFA salt (0.071 g, >99%). MS(ES): m/z=309.0 [M+H]$^+$.

Compound A4: 2-(3-Chlorophenyl)-N$^5$-(4-cyanophenyl)-7-(fluoromethyl)-6,7-dihydropyrazolo[1,5-a]pyrazine-3,5(4H)-dicarboxamide

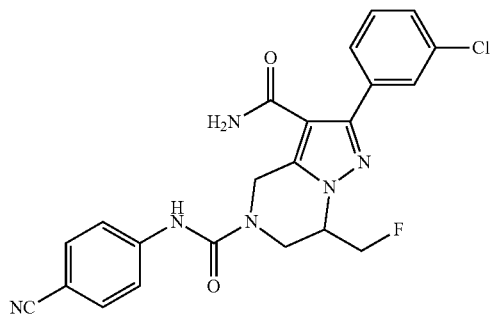 [SMILES: N#Cc1ccc(NC(=O)N2Cc3c(C(N)=O)c(-c4cccc(Cl)c4)nn3C(CF)C2)cc1]

To a solution of Intermediate A4B (0.035 g, 0.065 mmol) in DMF (0.65 mL) was added 4-isocyanatobenzonitrile (0.019 g, 0.130 mmol) and DIPEA (0.057 mL, 0.326 mmol) and the reaction mixture was stirred at room temperature for 1 h. The mixture was then filtered off and the filtrate was purified via preparative LC/MS. Fractions containing the desired product were combined and evaporated to afford Compound A4 (0.017 g, 59%). MS(ES): m/z=453.30 [M+H]$^+$; HPLC Ret. Time 1.44 min. and 2.31 min. (HPLC Methods H and I); $^1$H NMR (500 MHz, DMSO-d$_6$) δ ppm 7.73 (d, J=7.6 Hz, 3H), 7.67 (d, J=8.5 Hz, 3H), 7.51-7.38 (m, 3H), 7.31 (br. s., 1H), 5.08 (d, J=5.8 Hz, 1H), 5.04-4.86 (m, 3H), 4.81 (d, J=7.9 Hz, 1H), 4.70 (br. s., 1H), 4.65 (br. s., 1H), 4.18 (d, J=10.1 Hz, 1H), 4.04 (dd, J=14.0, 6.4 Hz, 1H).

The Compound described in Table 45 was synthesized analogous to Compound A4 by reacting Intermediate A4B with corresponding isocyanate.

TABLE 45

| Ex. No. | Structure | Name | [M + H]$^+$ | Ret Time (min.) | HPLC Methods |
|---|---|---|---|---|---|
| A5 | 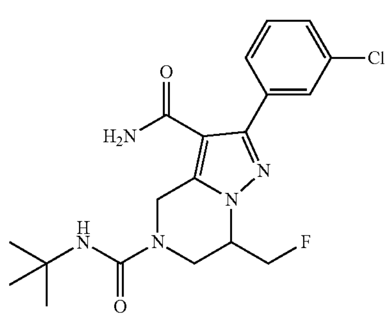 [SMILES: CC(C)(C)NC(=O)N1Cc2c(C(N)=O)c(-c3cccc(Cl)c3)nn2C(CF)C1] | N$^5$-(tert-butyl)-2-(3-chlorophenyl)-7-(fluoromethyl)-6,7-dihydropyrazolo[1,5-a]pyrazine-3,5(4H)-dicarboxamide | 408.08 | 1.41<br>2.36 | H<br>I |

Scheme 59

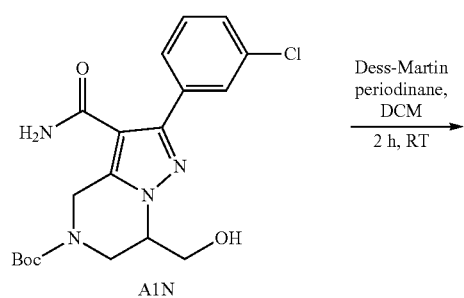

A1N

Dess-Martin periodinane, DCM
2 h, RT

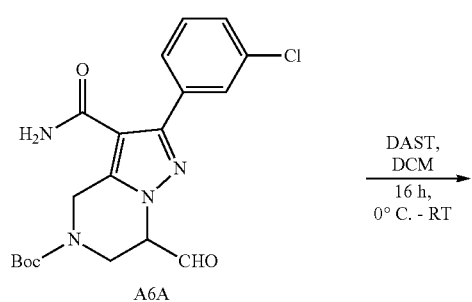

A6A

DAST, DCM
16 h,
0° C. - RT

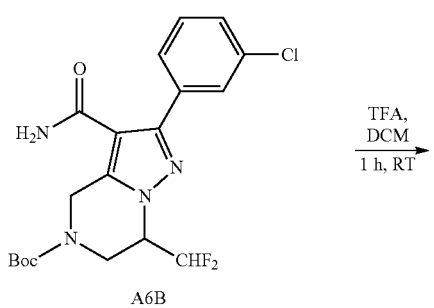

A6B

TFA, DCM
1 h, RT

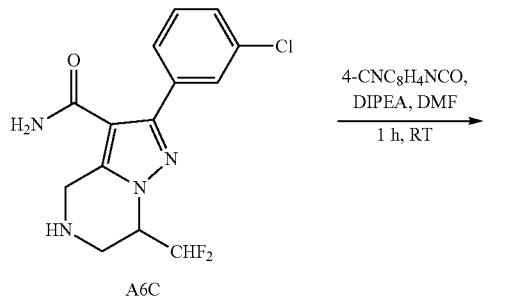

A6C

4-CNC₈H₄NCO, DIPEA, DMF
1 h, RT

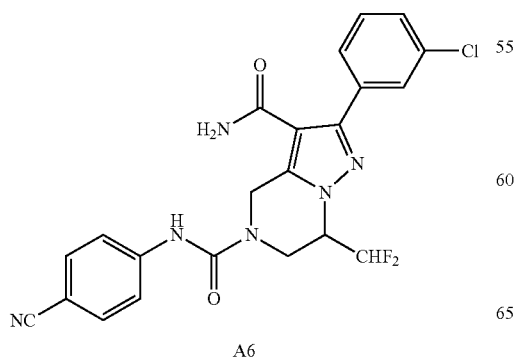

A6

Intermediate A6A: tert-Butyl 3-carbamoyl-2-(3-chlorophenyl)-7-formyl-6,7-dihydropyrazolo[1,5-a]pyrazine-5(4H)-carboxylate

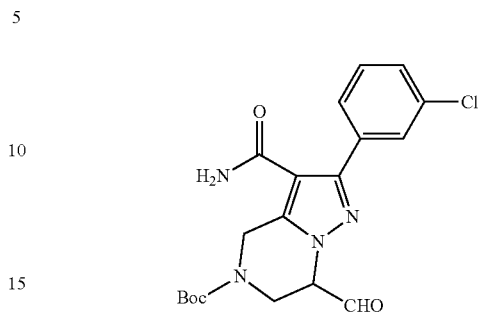

To a suspension of Intermediate A1N (0.2 g, 0.492 mmol) in DCM (4.92 mL) was added Dess-Martin periodinane (0.271 g, 0.639 mmol) and the reaction mixture was stirred at rt for 16 h. The mixture was then quenched with a saturated solution of aq. NaHCO₃. The two layers were separated and the aq. layer was extracted with DCM (2×10 mL). The combined organic layer was washed with brine, dried over anhydrous MgSO₄, filtered and the filtrate was concentrated under reduced pressure to give an oil. It was purified by silica gel chromatography (40 g REDISEP® column, eluting with a gradient of 75% EtOAc in hexanes to 100% EtOAc). Fractions containing the product were combined and evaporated to afford Intermediate A6A (0.054 g, 35.8%) as a white solid. MS(ES): m/z=409 [M+H]⁺; ¹H NMR (400 MHz, chloroform-d) δ ppm 9.75 (s, 1H), 7.65-7.54 (m, 1H), 7.54-7.33 (m, 4H), 5.50 (br. s., 1H), 4.96 (d, J=16.8 Hz, 2H), 4.77 (br. s., 1H), 4.59 (d, J=16.1 Hz, 1H), 3.65 (d, J=12.3 Hz, 1H), 1.58-1.37 (m, 9H).

Intermediate A6B: tert-Butyl 3-carbamoyl-2-(3-chlorophenyl)-7-(difluoromethyl)-6,7-dihydropyrazolo[1,5-a]pyrazine-5(4H)-carboxylate

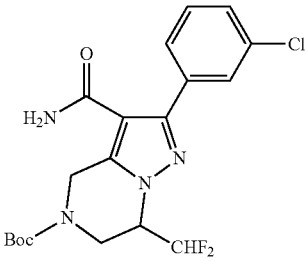 [SMILES: CC(C)(C)OC(=O)N1Cc2c(C(N)=O)c(-c3cccc(Cl)c3)nn2C(C(F)F)C1]

To a solution of Intermediate A6A (0.105 g, 0.259 mmol) in DCM (2.59 mL) at 0° C. was added, DAST (0.103 mL, 0.778 mmol) and the reaction mixture was stirred at room temperature for 16 h. The reaction was then quenched with a saturated solution of aq. NaHCO₃. The two layers were separated and the aq. layer was extracted with DCM (2×10 mL). The combined organic layer was washed with brine, dried over anhydrous MgSO₄, filtered and the filtrate concentrated under reduced pressure to give an oil. It was purified by silica gel chromatography (25 g REDISEP® column, eluting with a gradient of 55 to 65% EtOAc in hexanes). Fractions contain-

467 ing the product were combined and evaporated to afford Intermediate A6B as a yellow solid. MS(ES): m/z=427 [M+H]$^+$.

Intermediate A6C: 2-(3-Chlorophenyl)-7-(difluoromethyl)-4,5,6,7-tetrahydropyrazolo[1,5-a]pyrazine-3-carboxamide, 2 TFA

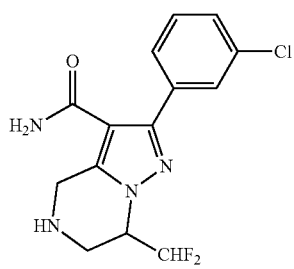 [SMILES: NC(=O)c1c(-c2cccc(Cl)c2)nn2c1CNCC2C(F)F]

Intermediate A6C was synthesized analogous to Intermediate A4B (Scheme 58) by reacting Intermediate A6B with TFA. Intermediate A6C (0.029 g, 20% from) was subjected to analoging as the bis TFA salt. MS(ES): m/z=327 [M+H]$^+$.

Compound A6: 2-(3-Chlorophenyl)-N$^5$-(4-cyanophenyl)-7-(difluoromethyl)-6,7-dihydropyrazolo[1,5-a]pyrazine-3,5(4H)-dicarboxamide

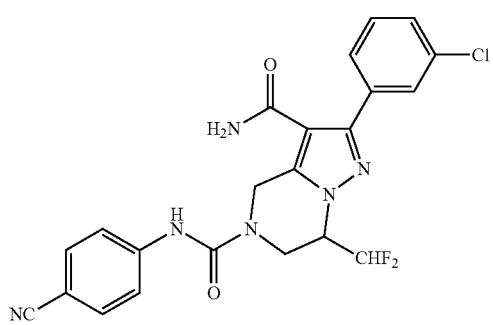 [SMILES: N#Cc1ccc(NC(=O)N2Cc3c(C(N)=O)c(-c4cccc(Cl)c4)nn3C(C(F)F)C2)cc1]

Compound A6 was synthesized analogous to Compound A4 by reacting Intermediate A6C with 4-isocyanatobenzonitrile. MS(ES): m/z=471.08 [M+H]$^+$; HPLC Ret. time 1.48 min. and 2.35 min. (HPLC Methods H and I respectively); $^1$H NMR (500 MHz, DMSO-d$_6$) δ ppm 7.96 (s, 1H), 7.78-7.70 (m, 3H), 7.67 (d, J=8.5 Hz, 3H), 7.54-7.42 (m, 3H), 7.35 (br. s., 1H), 6.55 (br. s., 1H), 5.16 (d, J=17.1 Hz, 1H), 4.93 (br. s., 1H), 4.82 (d, J=17.4 Hz, 1H), 4.50 (dd, J=14.3, 3.1 Hz, 1H), 3.93-3.79 (m, 1H).

468

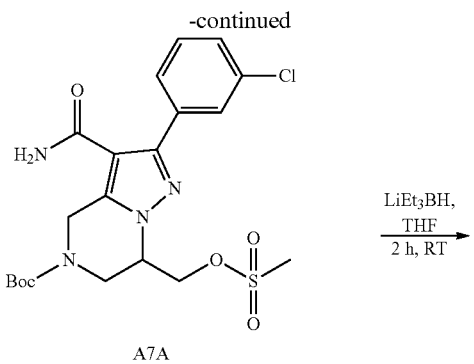

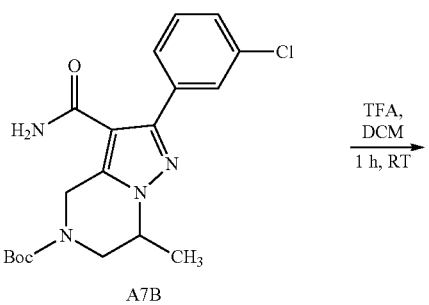

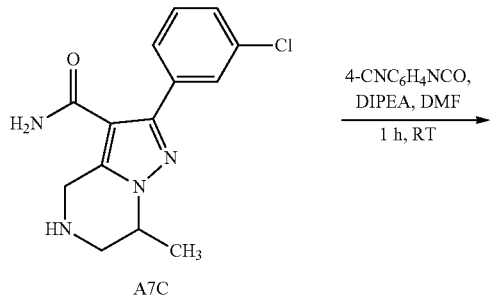

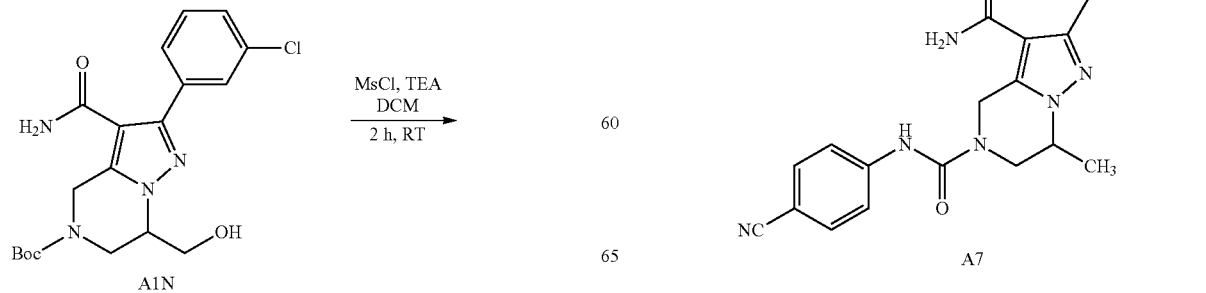

Intermediate A7A: tert-Butyl 3-carbamoyl-2-(3-chlorophenyl)-7-(((methylsulfonyl)oxy)methyl)-6,7-dihydropyrazolo[1,5-a]pyrazine-5(4H)-carboxylate

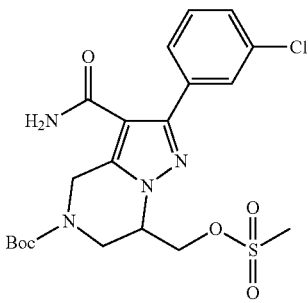 [SMILES: CC(C)(C)OC(=O)N1Cc2c(C(N)=O)c(-c3cccc(Cl)c3)nn2C(COS(C)(=O)=O)C1]

To an ice-cold suspension of Intermediate A1N (0.3 g, 0.737 mmol) in DCM (7.37 mL) was added TEA (0.123 mL, 0.885 mmol), followed by a dropwise addition of methanesulfonyl chloride (0.063 mL, 0.811 mmol). The resultant homogenous reaction mixture was stirred at room temperature for 2 h. The reaction was then quenched with a saturated solution of aq. NaHCO$_3$. The two layers were separated and the aq. layer was extracted with DCM (2×10 mL). The combined organic layer was washed with brine, dried over anhydrous MgSO$_4$, filtered and the filtrate was concentrated under reduced pressure to give an oil. It was purified by silica gel chromatography (40 g REDISEP® column, eluting with a gradient of 75% to 85% EtOAc in hexanes). Fractions containing the product were combined and evaporated to afford Intermediate A7A (0.208 g, 58.2%) as a white foam. MS(ES): m/z=485 [M+H]$^+$.

Intermediate A7B: tert-Butyl 3-carbamoyl-2-(3-chlorophenyl)-7-methyl-6,7-dihydropyrazolo[1,5-a]pyrazine-5(4H)-carboxylate

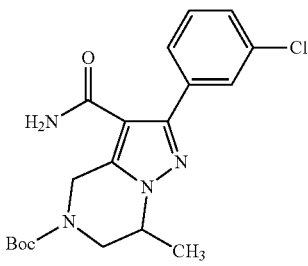 [SMILES: CC1CN(C(=O)OC(C)(C)C)Cc2c(C(N)=O)c(-c3cccc(Cl)c3)nn21]

To a solution of Intermediate A7A (0.08 g, 0.165 mmol) in THF (3.30 mL) was added dropwise at room temperature, a 1M solution of LiEt$_3$BH in THF (1.650 mL, 1.650 mmol) and the reaction mixture was stirred for 2 h. It was then carefully quenched with water and extracted with DCM (3×10 mL). The combined organic layer was washed with brine, dried over anhydrous MgSO$_4$, filtered and the filtrate concentrated under reduced pressure to give an oil. It was purified by silica gel chromatography (25 g REDISEP® column, eluting with a 50% EtOAc in hexanes). Fractions containing the product were combined and evaporated to afford Intermediate A7B (0.053 g, 81%) as a white foam. MS(ES): m/z=391.1 [M+H]$^+$.

Intermediate A7C: 2-(3-Chlorophenyl)-7-methyl-4,5,6,7-tetrahydropyrazolo[1,5-a]pyrazine-3-carboxamide, 2 TFA

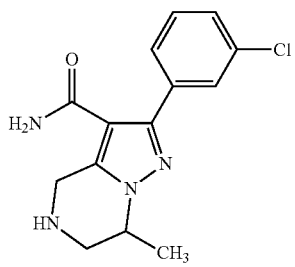 [SMILES: CC1CNCc2c(C(N)=O)c(-c3cccc(Cl)c3)nn21]

Intermediate A7C was synthesized analogous to Intermediate A4B by reacting Intermediate A7B with TFA. Intermediate A7C (0.07 g, >99%) was subjected to analoging as the bis TFA salt. MS(ES): m/z=291 [M+H]$^+$.

Compound A7: 2-(3-Chlorophenyl)-N5-(4-cyanophenyl)-7-methyl-6,7-dihydropyrazolo[1,5-a]pyrazine-3,5(4H)-dicarboxamide

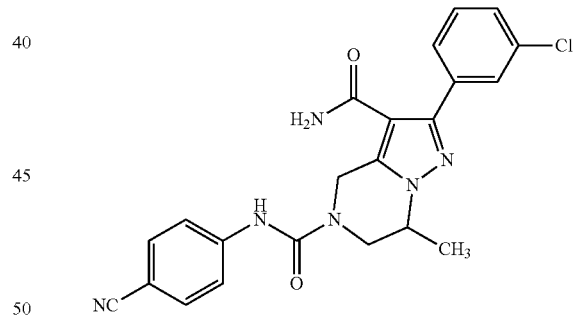

Compound A7 was synthesized analogous to Compound A4 by reacting Intermediate A7C with 4-isocyanatobenzonitrile. MS(ES): m/z=435.0 [M+H]$^+$; HPLC Ret. Time 1.48 min and 2.41 min. (Methods H and I respectively); $^1$H NMR (500 MHz, DMSO-d$_6$) δ ppm 9.38 (s, 1H), 7.77-7.59 (m, 6H), 7.49-7.41 (m, 2H), 7.38 (br. s., 1H), 7.22 (br. s., 1H), 4.97 (d, J=17.1 Hz, 1H), 4.86 (d, J=17.1 Hz, 1H), 4.53-4.38 (m, 1H), 4.11 (dd, J=13.7, 3.7 Hz, 1H), 3.72 (dd, J=14.2, 6.9 Hz, 1H), 2.89 (s, 1H), 2.73 (s, 1H), 1.49 (d, J=6.4 Hz, 3H).

The Compound described in Table 46 was synthesized analogous to Compound A7 by reacting Intermediate A7C with corresponding isocyanate.

TABLE 46

| Ex. No. | Structure | Name | [M + H]+ | Ret Time (min.) | HPLC Methods |
|---|---|---|---|---|---|
| A8 | (structure) | N⁵-(tert-butyl)-2-(3-chlorophenyl)-7-methyl-6,7-dihydropyrazolo[1,5-a]pyrazine-3,5(4H)-dicarboxamide | 390.0 | 1.41<br>2.41 | H<br>I |

Scheme 61

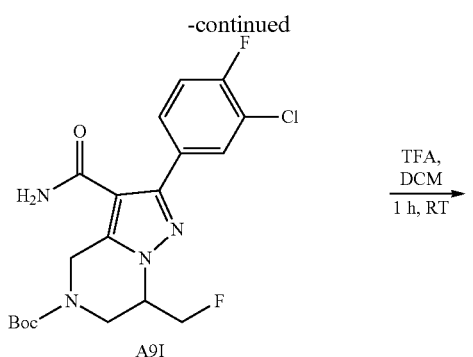

A9I

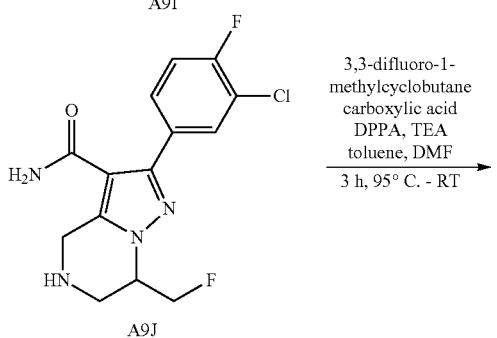

A9J

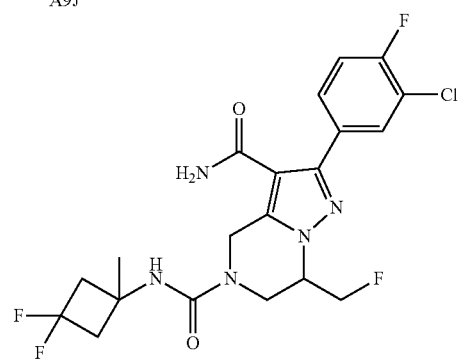

A9 and A10

Intermediate A9A: Diethyl 1-(2,2,3,3,11,11-hexamethyl-9-oxo-4,10-dioxa-8-aza-3-siladodecan-6-yl)-3-iodo-1H-pyrazole-4,5-dicarboxylate

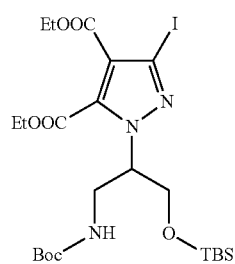

A solution of Intermediate 104C (1.0 g, 2.96 mmol), Intermediate A1B (1.13 g, 3.70 mmol), triphenylphosphine (0.78 g, 2.96 mmol) and TEA (0.41 mL, 2.96 mmol) in THF (14.79 mL) was cooled to 0° C. and to it was added DTBAD (0.7 g, 2.96 mmol). The reaction mixture was then allowed to stir at room temperature for 16 h and then diluted with water and EtOAc. The two layers were separated and the aq. layer was extracted with EtOAc (2×20 mL) The combined organic layer was washed with brine, dried over anhydrous MgSO₄, filtered and the filtrate was concentrated to give an oil. It was purified by silica gel chromatography (80 g REDISEP® column, eluting with a gradient of 0 to 15% EtOAc in hexanes). Fractions containing the product were combined and evaporated to afford Intermediate A9A (1.2 g, 65%) as a solid. MS(ES): m/z=648.1 [M+Na]⁺.

Intermediate A9B: Ethyl 7-(hydroxymethyl)-2-iodo-4-oxo-4,5,6,7-tetrahydropyrazolo[1,5-a]pyrazine-3-carboxylate

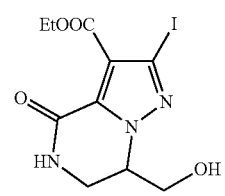 [SMILES: CCOC(=O)c1c(I)nn2c1C(=O)NCC2CO]

To a solution of Intermediate A9A (21.5 g, 34.4 mmol) in DCM (344 mL) was added TFA (47.7 mL, 619 mmol) and the reaction mixture was allowed to stir at room temperature for 48 h. The volatiles were then concentrated under reduced pressure. The residue thus obtained was directly taken up in EtOH (75 mL) and to it was added ammonium hydroxide (581 mL, 447 mmol, 30% aq.). Soon a precipitate generated. The stirring was continued for 1 h at room temperature. The generated solid was filtered off. The filter cake was rinsed with a small amount of EtOH. The combined filtrate was partially evaporated under reduced pressure to generate more precipitate. This solid was combined with the initial filter cake and air-dried to afford Intermediate A9B (18 g, 71.6%) as a white solid. MS(ES): m/z=365.8 [M+H]⁺.

Intermediate A9C: Ethyl 7-(((tert-butyldimethylsilyl)oxy)methyl)-2-iodo-4-oxo-4,5,6,7-tetrahydropyrazolo[1,5-a]pyrazine-3-carboxylate

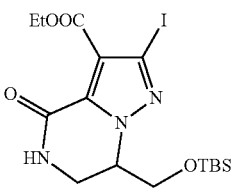 [SMILES: CCOC(=O)c1c(I)nn2c1C(=O)NCC2CO[Si](C)(C)C(C)(C)C]

To a solution of Intermediate A9B (16.79 g, 46.0 mmol) in DMF (230 mL) was added TBSCl (8.32 g, 55.2 mmol), followed by imidazole (4.70 g, 69.0 mmol) and the reaction mixture was stirred at room temperature for 1 h. The mixture was then concentrated to dryness, the residue was diluted with water and extracted with DCM (2×200 mL). The combined organic layer was washed with brine, dried over anhydrous MgSO₄, filtered and the filtrate was concentrated to give an oil. It was purified by silica gel chromatography (REDISEP® 330 g, eluting with a gradient of 10 to 55% EtOAc in hexanes). Fractions containing the product were combined and evaporated to afford Intermediate A9C (16 g, 72.6%) as a solid. MS(ES): m/z=479.9 [M+H]⁺.

Intermediate A9D: 5-tert-Butyl 3-ethyl 7-(((tert-butyldimethylsilyl)oxy)methyl)-2-iodo-4-oxo-6,7-dihydropyrazolo[1,5-a]pyrazine-3,5(4H)-dicarboxylate

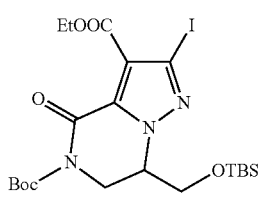 [SMILES: CCOC(=O)c1c(I)nn2c1C(=O)N(C(=O)OC(C)(C)C)CC2CO[Si](C)(C)C(C)(C)C]

To a solution of Intermediate A9C (11.74 g, 24.49 mmol) in toluene (188 mL) was added DMAP (4.49 g, 36.7 mmol), followed by Boc₂O (6.41 g, 29.4 mmol) and the reaction mixture was heated in an oil bath at 60° C. for 1 h and then at room temperature for 16 h. It was then concentrated to dryness to afford a solid residue, which was purified by silica gel chromatography (REDISEP® 220 g, eluting with a gradient of 5 to 25% EtOAc in hexanes). Fractions containing the product were combined and evaporated to afford Intermediate A9D (13.7 g, 96%) as a white solid. MS(ES): m/z=580.1 [M+H]⁺.

Intermediate A9E: 5-tert-Butyl 3-ethyl 7-(((tert-butyldimethylsilyl)oxy)methyl)-2-iodo-6,7-dihydropyrazolo[1,5-a]pyrazine-3,5(4H)-dicarboxylate

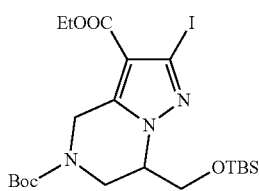 [SMILES: CCOC(=O)c1c(I)nn2c1CN(C(=O)OC(C)(C)C)CC2CO[Si](C)(C)C(C)(C)C]

To a −10° C. solution of Intermediate A9D (1.0 g, 1.726 mmol) in THF (4.31 mL), SUPER-HYDRIDE® (2.07 mL, 2.071 mmol, 1M in THF) was added dropwise over 30 min., and the reaction mixture was stirred at 0° C. for 2 h. It was then quenched with water and extracted with EtOAc (2×25 mL). The combined organic layer was washed with brine, dried over anhydrous MgSO₄, filtered and the filtrate was concentrated to afford the partially reduced intermediate as a foam. MS(ES): m/z=604.15 [M+Na]⁺. It was used in the next step without further purification.

To a −78° C. solution of the above intermediate in DCM (~8 mL) was added, triethylsilane (0.85 mL, 5.18 mmol), followed by BF₃.OEt₂ (0.65 mL, 5.18 mmol) and the reaction mixture was stirred at that temperature for 1 h. Thereafter, more triethylsilane (0.852 mL, 5.18 mmol) and BF₃.OEt₂ (0.656 mL, 5.18 mmol) were added and stirring continued at −78° C. for 3 h. The reaction was quenched with a satd. aq. solution of NaHCO₃, the two layers were separated and the aq. layer was extracted with DCM (2×15 mL). The combined organic layer was washed with brine, dried over anhydrous MgSO₄, filtered and the filtrate was concentrated to afford an oil. It was purified by silica gel chromatography (80 g REDISEP® column, eluting with a gradient of 5 to 15% EtOAc in hexanes). Fractions containing the product were combined and evaporated to afford Intermediate A9E (0.42 g, 43%) as a white solid. MS(ES): m/z=566.15 [M+H]⁺.

Intermediate A9F: 5-(tert-Butoxycarbonyl)-7-(hydroxymethyl)-2-iodo-4,5,6,7-tetrahydropyrazolo[1,5-a]pyrazine-3-carboxylic acid

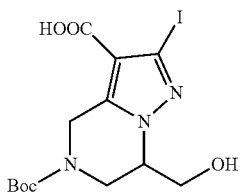

To a solution of Intermediate A9E (10.0 g, 17.68 mmol) in Ethanol (26.8 mL) and THF (53.6 mL) was added a suspension of LiOH (6.05 g, 248 mmol) in water (17.86 mL) and the reaction mixture was stirred at room temperature for 48 h. The volatiles were concentrated under reduced pressure and the aq. residue was extracted with Et₂O. The Et₂O layer was discarded and the aq. layer was acidified with a 1N aqueous solution of HCl to pH=2. It was then extracted with DCM (4×50 mL) The combined organic layer was washed with brine, dried over anhydrous MgSO₄, filtered and the filtrate was concentrated to afford Intermediate A9F (6.87 g, 92%) as a white solid, with the concomitant loss of the TBS group. MS(ES): m/z=446.1 [M+Na]⁺.

Intermediate A9G: tert-Butyl 3-carbamoyl-7-(hydroxymethyl)-2-iodo-6,7-dihydropyrazolo[1,5-a]pyrazine-5(4H)-carboxylate

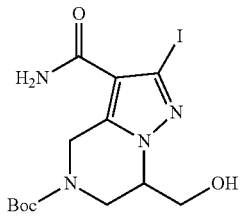

To a solution of Intermediate A9F (6.87 g, 16.23 mmol) in DMF (27.1 mL) was added DIPEA (11.34 mL, 64.9 mmol) and HATU (12.34 g, 32.5 mmol) and the mixture was stirred at room temperature for 30 min., followed by the addition of NH₄Cl (3.47 g, 64.9 mmol). The resultant mixture was then continued stirring at room temperature for 16 h. It was diluted with water (250 mL) and extracted with DCM (3×70 mL). The combined organic layer was washed with copious amounts of water, brine, dried over anhydrous MgSO₄, filtered and the filtrate was concentrated to afford an oil. It was purified by silica gel chromatography (120 g REDISEP® column, eluting with 5% EtOAc in hexanes). Fractions containing the product were combined and evaporated to afford Intermediate A9G (6.75 g, 98%) as a solid. MS(ES): m/z=423.1 [M+H]+.

Intermediate A9H: tert-Butyl 3-carbamoyl-2-(3-chloro-4-fluorophenyl)-7-(hydroxymethyl)-6,7-dihydropyrazolo[1,5-a]pyrazine-5 (4H)-carboxylate

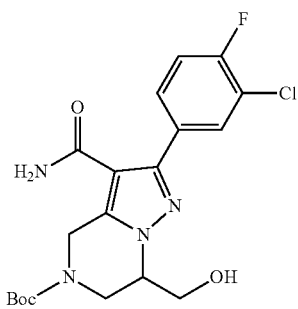 [SMILES: CC(C)(C)OC(=O)N1Cc2c(C(N)=O)c(-c3ccc(F)c(Cl)c3)nn2C(CO)C1]

To a degassed solution of Intermediate A9G (5.1 g, 12.08 mmol) and (3-chloro-4-fluorophenyl)boronic acid (3.16 g, 18.12 mmol) in a 2M aqueous solution of $K_3PO_4$ (18.12 mL, 36.2 mmol) and 1,4-Dioxane (121 mL) was added $PdCl_2$ (dppf) (0.884 g, 1.208 mmol). The reaction mixture was degassed again for 5 min. and then heated in a sealed tube in an oil bath at 85° C. for 16 h. The mixture was concentrated under reduced pressure to near dryness, the residue was partitioned between DCM and water, the two layers were separated and the aq. layer was extracted with DCM (2×40 mL) The combined organic layers were washed with brine, dried over anhydrous $MgSO_4$, filtered and the filtrate was concentrated to afford an oil. It was purified by silica gel chromatography (120 g REDISEP® column, eluting with a gradient of 65 to 90% EtOAc in hexanes). Fractions containing the product were combined and evaporated to afford Intermediate A9H (5.08 g, >99%) as a pale brown solid. MS(ES): m/z=425.2 [M+H]+.

Intermediate A9I: tert-Butyl 3-carbamoyl-2-(3-chloro-4-fluorophenyl)-7-(fluoromethyl)-6,7-dihydropyrazolo[1,5-a]pyrazine-5(4H)-carboxylate

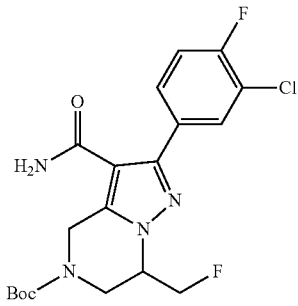 [SMILES: CC(C)(C)OC(=O)N1Cc2c(C(N)=O)c(-c3ccc(F)c(Cl)c3)nn2C(CF)C1]

To a −78° C. solution of Intermediate A9H (1.84 g, 4.33 mmol) in DCM (43.3 mL) was added DAST (0.57 mL, 4.33 mmol) dropwise and then the reaction mixture was allowed to stir at room temperature for 2 h. It was quenched with a satd. aq. solution of $NaHCO_3$, the organic layer was separated and the aq. layer was extracted with DCM (2×20 mL). The combined organic layer was washed with brine, dried over anhydrous $MgSO_4$, filtered and the filtrate was concentrated under reduced pressure to give a solid. It was purified by silica gel chromatography (120 g REDISEP® column, eluting with a gradient of 10 to 55% EtOAc in hexanes). Fractions containing the product were combined and evaporated to afford Intermediate A9I (0.56 g, 30.2%) as a white solid. MS(ES): m/z=427.2 [M+H]+.

Intermediate A9J: 2-(3-Chloro-4-fluorophenyl)-7-(fluoromethyl)-4,5,6,7-tetrahydropyrazolo[1,5-a]pyrazine-3-carboxamide

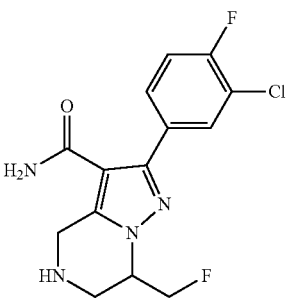

To a solution of Intermediate A9I (0.2 g, 0.466 mmol) in DCM (4.66 mL) was added TFA (0.72 mL, 9.32 mmol) and the reaction mixture was stirred at room temperature for 2 h. The volatiles were evaporated and the residue was basified with a satd. aq. solution of $NaHCO_3$ and extracted with a 5% solution of MeOH in DCM (3×10 mL). The combined organic layer was washed with brine, dried over anhydrous $MgSO_4$, filtered and the filtrate was concentrated under reduced pressure to give Intermediate A9J (0.15 g, 100%) as an off-white solid. MS(ES): m/z=327.2 [M+H]+.

Compounds A9 and A10: 2-(3-Chloro-4-fluorophenyl)-$N^5$-(3,3-difluoro-1-methylcyclobutyl)-7-(fluoromethyl)-6,7-dihydropyrazolo[1,5-a]pyrazine-3,5 (4H)-dicarboxamide

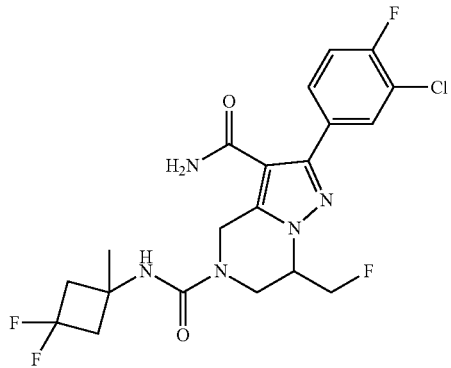 [SMILES: CC1(NC(=O)N2Cc3c(C(N)=O)c(-c4ccc(F)c(Cl)c4)nn3C(CF)C2)CC(F)(F)C1]

To a solution of 3,3-difluoro-1-methylcyclobutanecarboxylic acid (0.029 g, 0.191 mmol) in toluene (2.040 mL) was added TEA (0.085 mL, 0.612 mmol) and diphenyl phosphorazidate (0.043 mL, 0.191 mmol). This mixture was heated in an oil bath at 95° C. for 2 h. It was then cooled to room temperature and to it was added a solution of Intermediate A9J (0.05 g, 0.153 mmol) in DMF (1.02 mL). The resultant reaction mixture was stirred at room temperature for 1 h. The volatiles were concentrated under reduced pressure and the residue was purified by preparative HPLC to afford a racemic mixture of A9 and A10. The individual enantiomers A9 and A10 were separated by Chiral SFC purification using CHIRALPAK® AD preparative column (21×250) mm, 10 μM column, Solvent A: 0.1% diethylamine in heptane, Solvent B: 100% EtOH, start % B: 30, isocratic, flow rate 15.0 mL/min for 20 min. UV monitored at 254 nm. Compound A9 (S)-isomer was eluted at 7.241 min. (14.3 mg, 100% ee, Yield=19.7%) and A10 (R)-isomer was eluted at 14.182 min. (14.9 mg, 100% ee, Yield=20.5%). MS: m/z=473.9 [M+H]$^+$; HPLC Ret. Time 1.594 min. and 2.865 min. (Methods H and I respectively); $^1$H NMR (500 MHz, DMSO-d$_6$) δ ppm 7.90-7.83 (m, 1H), 7.75-7.64 (m, 1H), 7.48 (t, J=9.0 Hz, 1H), 7.41 (br. s., 1H), 7.28 (br. s., 1H), 7.20 (s, 1H), 5.01 (dd, J=9.9, 4.4 Hz, 1H), 4.96-4.89 (m, 1H), 4.86-4.67 (m, 3H), 4.58 (br. s., 1H), 4.53 (br. s., 1H), 4.01 (dd, J=13.9, 4.0 Hz, 1H), 3.87 (dd, J=14.5, 6.4 Hz, 1H), 2.89-2.78 (m, 2H), 2.65-2.53 (m, 3H), 1.44 (s, 3H).

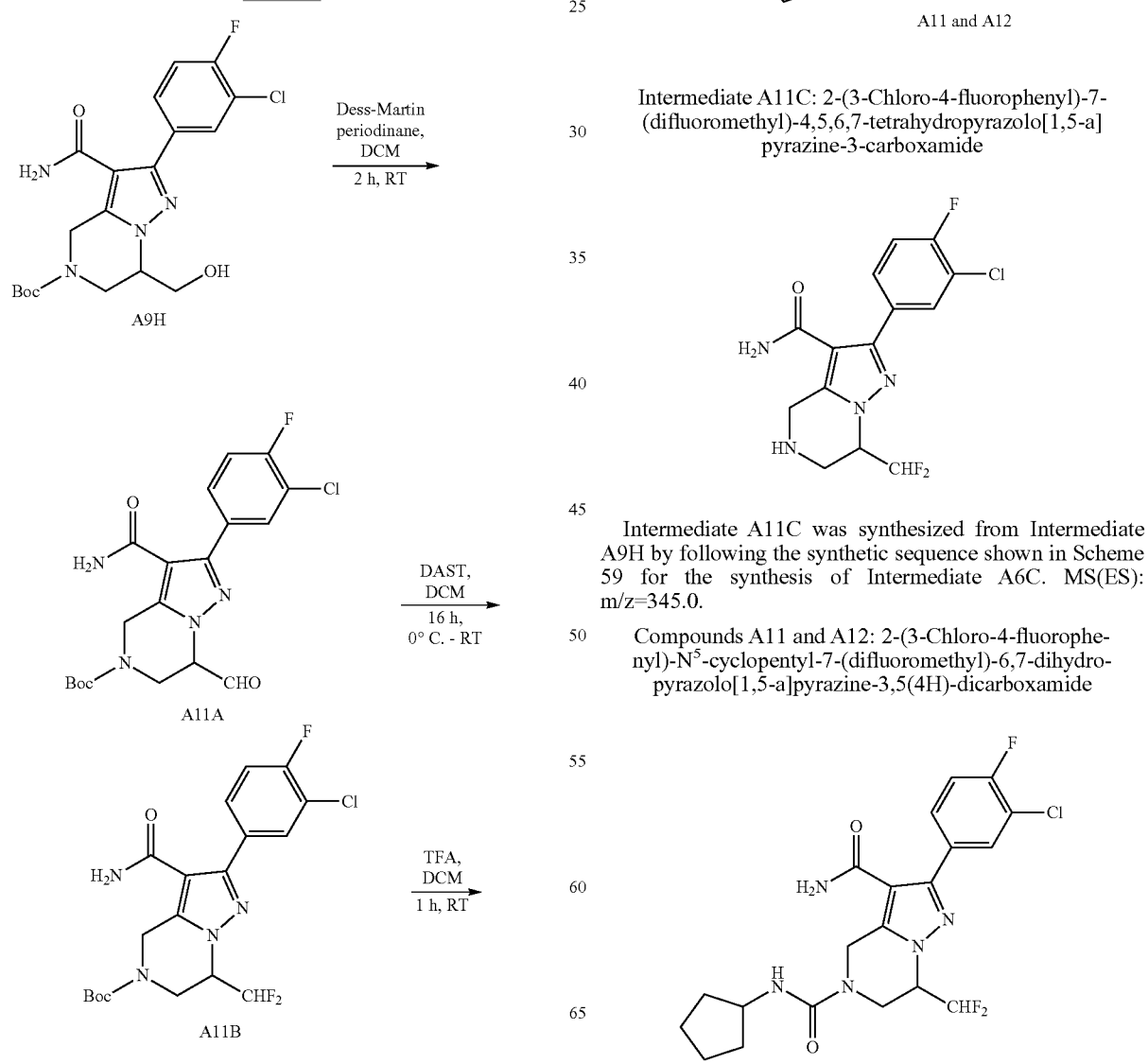

Intermediate A11C: 2-(3-Chloro-4-fluorophenyl)-7-(difluoromethyl)-4,5,6,7-tetrahydropyrazolo[1,5-a]pyrazine-3-carboxamide Intermediate A11C was synthesized from Intermediate A9H by following the synthetic sequence shown in Scheme 59 for the synthesis of Intermediate A6C. MS(ES): m/z=345.0.

Compounds A11 and A12: 2-(3-Chloro-4-fluorophenyl)-N$^5$-cyclopentyl-7-(difluoromethyl)-6,7-dihydropyrazolo[1,5-a]pyrazine-3,5(4H)-dicarboxamide The racemic mixture of A11 and A12 was synthesized analogous to Compounds A9 and A10 (Scheme 61) by reacting Intermediate A11C with 3,3-difluoro-1-methylcyclobutanecarboxylic acid. The individual enantiomers A11 and A12 were separated by chiral SFC purification using CHIRALPAK® AS preparative column (21×250) mm, 10 μm column, Solvent A: 0.1% diethylamine in heptane, Solvent B: 100% EtOH, start % B: 22, isocratic, flow rate 15.0 mL/min for 30 min. UV monitored at 254 nm. Compound A11 (S)-isomer was eluted at 8.523 min. (6.9 mg, 100% ee, Yield=10.44%) and A12 (R)-isomer was eluted at 10.878 min. (7.2 mg, 100% ee, Yield=10.89%). MS: m/z=454.5 [M−H]+; HPLC Ret. Time 1.55 min. and 2.45 min. (Methods H and I respectively); $^1$H NMR (500 MHz, DMSO-$d_6$) δ ppm 7.86 (d, J=6.6 Hz, 1H), 7.70 (br. s., 1H), 7.55-7.48 (m, 1H), 7.46 (d, J=14.3 Hz, 1H), 7.33 (br. s., 1H), 6.73 (d, J=7.0 Hz, 1H), 6.46 (br. s., 1H), 4.89 (d, J=17.6 Hz, 1H), 4.80 (br. s., 1H), 4.65 (d, J=17.2 Hz, 1H), 4.33-4.19 (m, 1H), 4.01-3.86 (m, 1H), 3.75 (d, J=12.8 Hz, 1H), 1.81 (d, J=5.9 Hz, 2H), 1.65 (br. s., 2H), 1.56-1.35 (m, 4H).

The Compounds described in Table 47 were synthesized analogous to Compounds A11 and A12 by reacting Intermediate A11C with the corresponding carboxylic acid.

TABLE 47

| Ex. No. | Structure | Name | [M + H]+ | Ret Time (min.) | HPLC Methods |
|---|---|---|---|---|---|
| A13 | 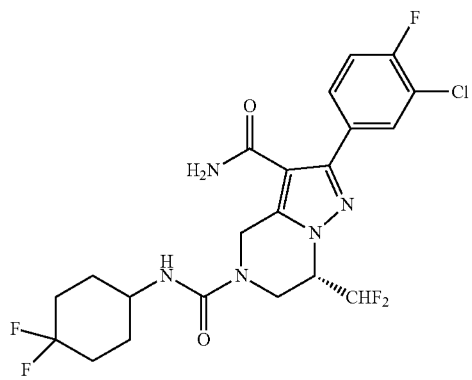 [SMILES: NC(=O)c1c(-c2ccc(F)c(Cl)c2)nn2c1CN(C(=O)NC1CCC(F)(F)CC1)C[C@H]2C(F)F] | (S)-2-(3-Chloro-4-fluorophenyl)-N$^5$-(4,4-difluorocyclohexyl)-7-(difluoromethyl)-6,7-dihydropyrazolo[1,5-a]pyrazine-3,5(4H)-dicarboxamide | 506.5 | 1.57<br>2.44 | H<br>I |
| A14 | 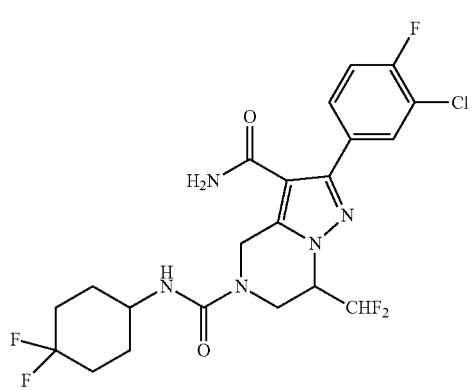 [SMILES: NC(=O)c1c(-c2ccc(F)c(Cl)c2)nn2c1CN(C(=O)NC1CCC(F)(F)CC1)CC2C(F)F] | (R)-2-(3-Chloro-4-fluorophenyl)-N$^5$-(4,4-difluorocyclohexyl)-7-(difluoromethyl)-6,7-dihydropyrazolo[1,5-a]pyrazine-3,5(4H)-dicarboxamide | 506.5 | 1.63<br>2.44 | H<br>I |

Scheme 63

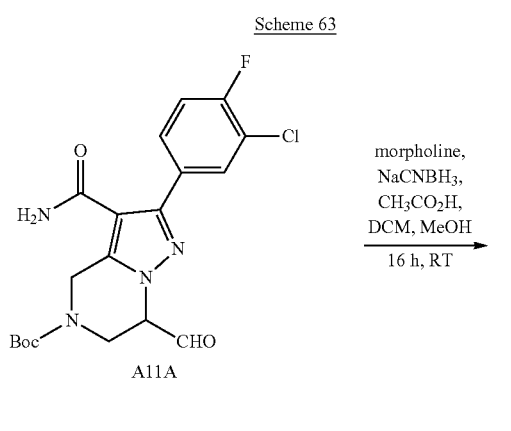

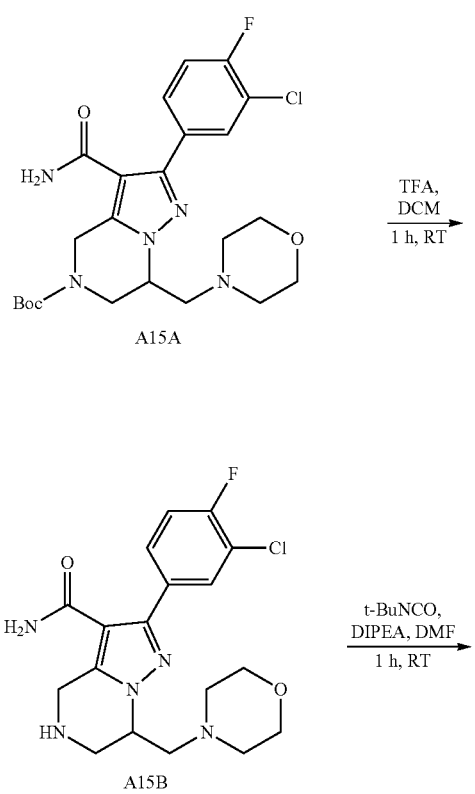

Intermediate A15A: tert-Butyl 3-carbamoyl-2-(3-chloro-4-fluorophenyl)-7-(morpholinomethyl)-6,7-dihydropyrazolo[1,5-a]pyrazine-5(4H)-carboxylate

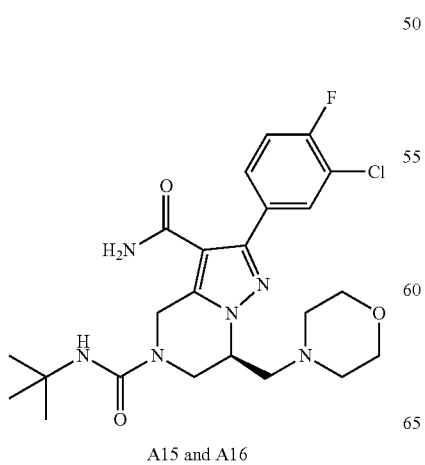

To a solution of Intermediate A11A (0.17 g, 0.402 mmol) in DCM (5.36 mL) and MeOH (2.68 mL) was added morpholine (0.088 mL, 1.005 mmol), followed by sodium cyanoborohydride (0.076 g, 1.21 mmol) and glacial acetic acid (0.023 mL, 0.402 mmol). The reaction mixture was stirred at room temperature for 8 h. It was quenched with a satd. aq. solution of NaHCO$_3$, the two layers were separated and the aq. layer was extracted with DCM (2×10 mL). The combined organic layer was washed with brine, dried over anhydrous MgSO$_4$, filtered and the filtrate was concentrated under reduced pressure to afford an oil. It was purified by silica gel chromatography (24 g REDISEP® column, eluting with a gradient of 40 to 60% EtOAc in DCM). Fractions containing the product were combined and evaporated to afford Intermediate A15A (0.086 g, 43.3%) as an off-white foam. MS(ES): m/z=494.1 [M+H]$^+$.

Intermediate A15B: 2-(3-Chloro-4-fluorophenyl)-7-(morpholinomethyl)-4,5,6,7-tetrahydropyrazolo[1,5-a]pyrazine-3-carboxamide, 2 TFA To a solution of Intermediate A15A (0.086 g, 0.174 mmol) in DCM (1.74 mL) was added TFA (0.134 mL, 1.741 mmol) and the reaction mixture was stirred at room temperature for 1 h. It was then concentrated to dryness under reduced pressure to afford crude Intermediate A15B (0.105 g, >99%) as the bis TFA salt. MS(ES): m/z=394.0.

Compounds A15 and A16: $N^5$-(tert-Butyl)-2-(3-chloro-4-fluorophenyl)-7-(morpholinomethyl)-6,7-dihydropyrazolo[1,5-a]pyrazine-3,5(4H)-dicarboxamide

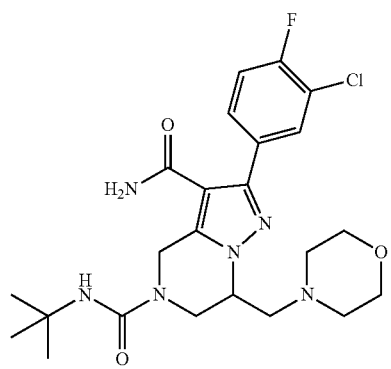 [SMILES: CC(C)(C)NC(=O)N1Cc2c(C(N)=O)c(-c3ccc(F)c(Cl)c3)nn2C(CN2CCOCC2)C1]

A solution of Intermediate A15B (0.054 g, 0.087 mmol), DIPEA (0.091 mL, 0.521 mmol) and 2-isocyanato-2-methylpropane (0.030 mL, 0.260 mmol) in DMF (0.87 mL) was stirred at room temperature for 1 h. The reaction mixture was purified by preparative HPLC to afford a racemic mixture of A15 and A16. The individual enantiomers A15 and A16 were separated by Chiral SFC purification using CHIRALCEL® OD preparative column (21×250) mm, 10 µm column, Solvent A: 0.1% diethylamine in heptane, Solvent B: 100% EtOH, start % B: 7, isocratic, flow rate 15.0 mL/min for 53 min. UV monitored at 254 nm. Compound A15 (S)-isomer was eluted at 42.08 min. (9.1 mg, 100% ee, Yield=21%) and A16 (R)-isomer was eluted at 35.463 min. (9.5 mg, 100% ee, Yield=22%). MS: m/z=493.2 [M+H]$^+$; HPLC Ret. Time 1.62 min. and 2.52 min. (Methods H and I respectively); $^1$H NMR (500 MHz, DMSO-d$_6$) ppm 7.84 (dd, J=7.2, 2.0 Hz, 1H), 7.73-7.63 (m, 1H), 7.47 (t, J=9.0 Hz, 1H), 7.36 (br. s., 1H), 7.24 (br. s., 1H), 6.05 (s, 1H), 4.98 (d, J=17.2 Hz, 1H), 4.46 (d, J=16.9 Hz, 2H), 4.14 (d, J=16.9 Hz, 1H), 3.59-3.53 (m, 1H), 3.45-3.38 (m, 2H), 2.71 (d, J=4.0 Hz, 1H), 2.58 (d, J=18.0 Hz, 2H), 2.40 (d, J=5.5 Hz, 2H), 1.29 (s, 9H).

Scheme 64

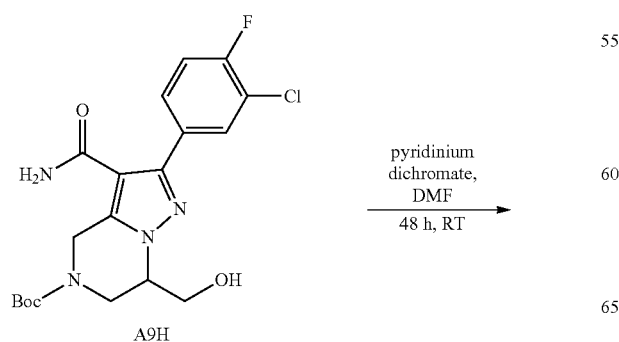

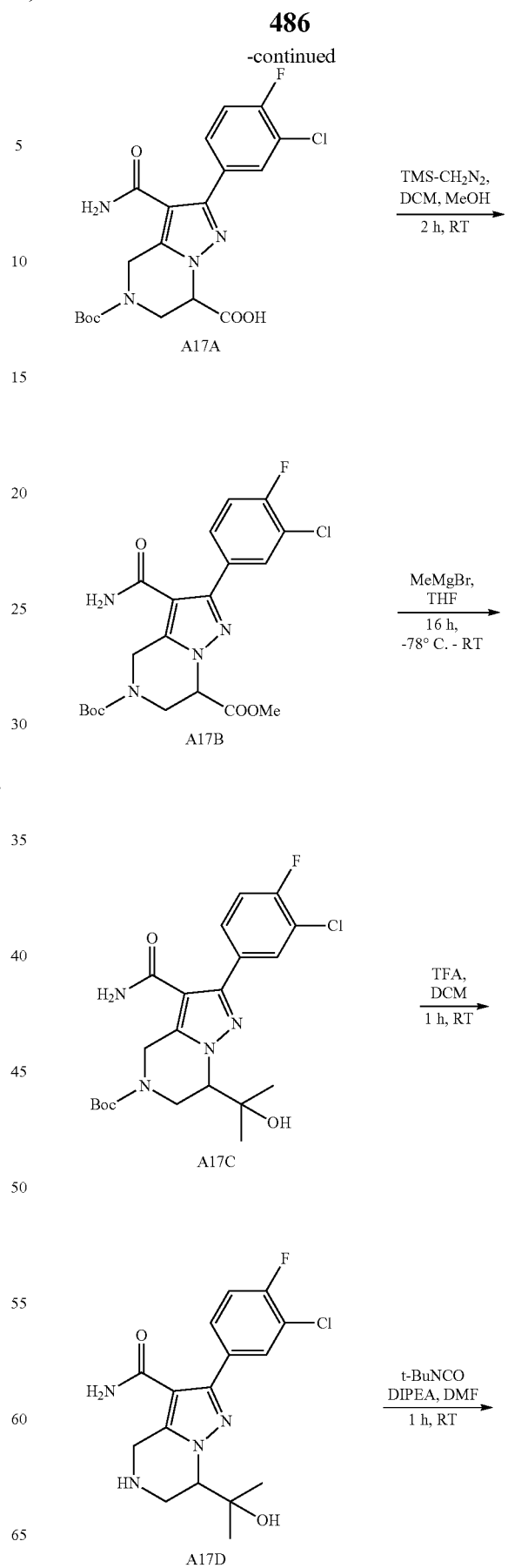

-continued

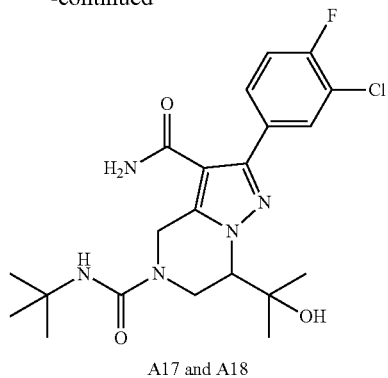

A17 and A18

Intermediate A17A: 5-(tert-Butoxycarbonyl)-3-carbamoyl-2-(3-chloro-4-fluorophenyl)-4,5,6,7-tetrahydropyrazolo[1,5-a]pyrazine-7-carboxylic acid

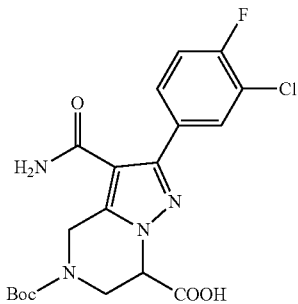 [SMILES: CC(C)(C)OC(=O)N1Cc2c(C(N)=O)c(-c3ccc(F)c(Cl)c3)nn2C(C(=O)O)C1]

To a solution of Intermediate A9H (2.0 g, 4.71 mmol) in DMF (47.1 mL) was added pyridinium dichromate (12.40 g, 33.0 mmol) and the reaction mixture was stirred at room temperature for 48 h. It was then diluted with water (250 mL) and extracted with EtOAc (3×50 mL) The combined organic layer was washed with water, brine, dried over anhydrous MgSO₄, filtered and the filtrate was concentrated under reduced pressure to afford crude Intermediate A17A (1.47 g, 71.2%) as a brown solid. MS(ES): m/z=439.3 [M+H]⁺.

Intermediate A17B: 5-tert-Butyl 7-methyl 3-carbamoyl-2-(3-chloro-4-fluorophenyl)-6,7-dihydropyrazolo[1,5-a]pyrazine-5,7(4H)-dicarboxylate

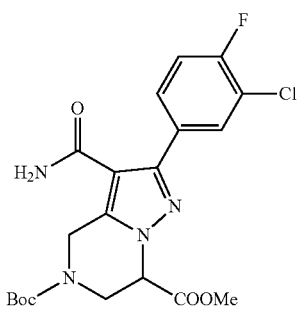 [SMILES: COC(=O)C1CN(C(=O)OC(C)(C)C)Cc2c(C(N)=O)c(-c3ccc(F)c(Cl)c3)nn21]

To a solution of crude Intermediate A17A (1.47 g, 3.35 mmol) in DCM (16.75 mL) and MeOH (16.75 mL) was added TMS-diazomethane (5.02 mL, 10.05 mmol, 2M solution in THF) and the reaction mixture was stirred at room temperature for 2 h. The mixture was then concentrated to dryness under reduced pressure. The residue was purified by silica gel chromatography (40 g REDISEP® column, eluting with a gradient of 45 to 55% EtOAc in hexanes). Fractions containing the product were combined and evaporated to afford Intermediate A17B (0.9 g, 59.4%) as a white amorphous solid. MS(ES): m/z=451.3 [M−H]⁺.

Intermediate A17C: tert-Butyl 3-carbamoyl-2-(3-chloro-4-fluorophenyl)-7-(2-hydroxypropan-2-yl)-6,7-dihydropyrazolo[1,5-a]pyrazine-5(4H)-carboxylate

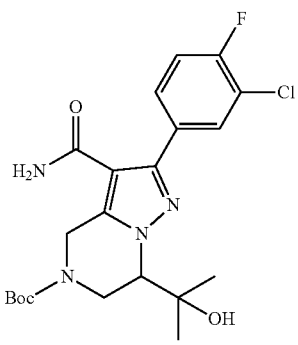 [SMILES: CC(C)(C)OC(=O)N1Cc2c(C(N)=O)c(-c3ccc(F)c(Cl)c3)nn2C(C(C)(C)O)C1]

To a −78° C. solution of Intermediate A17B (0.9 g, 1.990 mmol) in THF (19.90 mL), a solution of methylmagnesium bromide (3.32 mL, 9.95 mmol, 3M in hexanes) was added dropwise. The reaction mixture was gradually allowed to attain room temperature and stirred for 16 h. It was quenched with a satd. aq. solution of NH₄Cl, the two layers were separated and the aq. layer was extracted with EtOAc (2×60 mL). The combined organic layer was washed with brine, dried over anhydrous MgSO₄, filtered and the filtrate was concentrated under reduced pressure to give an oil. It was purified by silica gel chromatography (80 g REDISEP® column, eluting with a gradient of 60 to 70% EtOAc in DCM). Fractions containing the product were combined and evaporated to afford Intermediate A17C (0.84 g, 93%) as a yellow solid. (ES): m/z=453.08 [M−H]⁺.

Intermediate A17D: 2-(3-Chloro-4-fluorophenyl)-7-(2-hydroxypropan-2-yl)-4,5,6,7-tetrahydropyrazolo[1,5-a]pyrazine-3-carboxamide

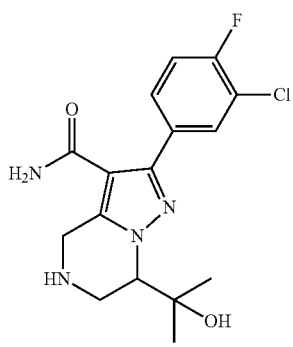 [SMILES: CC(C)(O)C1CNCc2c(C(N)=O)c(-c3ccc(F)c(Cl)c3)nn21]

To a solution of Intermediate A17C (0.45 g, 0.994 mmol) in DCM (10.0 mL) was added TFA (1.53 mL, 19.87 mmol) and the reaction mixture was stirred at room temperature for 1 h. The volatiles were concentrated under reduced pressure and the residue was neutralized with a satd. aq. solution of NaHCO₃, extracted with a 5% solution of MeOH in DCM (3×20 mL). The combined organic layer was washed with brine, dried over anhydrous MgSO₄, filtered and the filtrate was concentrated under reduced pressure to give Intermediate A17D (0.34 g, 96%) as a solid. (ES): m/z=375.02 [M+Na]⁺.

Compounds A17 and A18: N⁵-(tert-Butyl)-2-(3-chloro-4-fluorophenyl)-7-(2-hydroxypropan-2-yl)-6,7-dihydropyrazolo[1,5-a]pyrazine-3,5(4H)-dicarboxamide

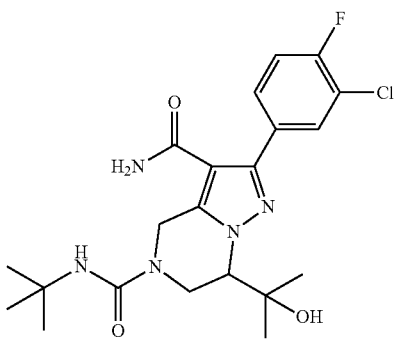 [SMILES: CC(C)(C)NC(=O)N1Cc2c(C(N)=O)c(-c3ccc(F)c(Cl)c3)nn2C(C(C)(C)O)C1]

A solution of Intermediate A17D (0.05 g, 0.142 mmol), 2-isocyanato-2-methylpropane (0.05 mL, 0.425 mmol) and DIPEA (0.09 mL, 0.5 mmol) in DMF (1.4 mL) was stirred at room temperature for 1 h. The reaction mixture was purified via preparative HPLC. Fractions containing the desired product were combined and evaporated to afford a racemic mixture of A17 and A18. Individual enantiomers A17 and A18 were separated by chiral SFC separation using CHIRALPAK® AD preparative column (21×250) mm, 10 µm column, Solvent A: 0.1% diethylamine in heptane, Solvent B: 100% EtOH, start % B: 30, isocratic, flow rate 15.0 mL/min for 25 min. UV monitored at 254 nm. Compound A17 (S)-isomer was eluted at 5.011 min. (10.0 mg, 100% ee, Yield=16%) and A18 (R)-isomer was eluted at 15.26 min. (12.5 mg, 100% ee, Yield=19.5%). MS: m/z=452.4 [M+H]⁺; HPLC Ret. Time 1.50 min. and 2.49 min. (Methods H and I respectively); ¹H NMR (500 MHz, DMSO-d₆) δ ppm 7.85 (d, J=5.5 Hz, 1H), 7.74-7.63 (m, 1H), 7.47 (t, J=9.0 Hz, 1H), 7.37 (br. s., 1H), 7.27 (br. s., 1H), 6.21 (s, 1H), 4.83 (d, J=16.9 Hz, 1H), 4.57 (d, J=17.6 Hz, 1H), 4.23-4.11 (m, 2H), 3.55 (d, J=10.3 Hz, 1H), 1.33-1.26 (m, 13H), 1.23 (br. s., 1H), 0.97 (s, 3H).

The Compounds described in Table 48 were synthesized analogous to Compounds A17 and A18 by reacting Intermediate A17D with the corresponding carboxylic acid.

TABLE 48

| Ex. No. | Structure | Name | [M + H]⁺ | Ret Time (min.) | HPLC Methods |
|---|---|---|---|---|---|
| A19 | 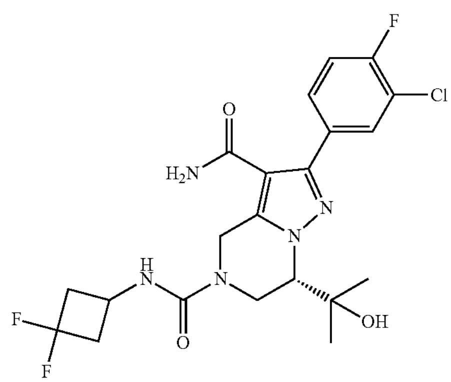 [SMILES: CC(C)(O)[C@@H]1CN(C(=O)NC2CC(F)(F)C2)Cc2c(C(N)=O)c(-c3ccc(F)c(Cl)c3)nn21] | (S)-2-(3-Chloro-4-fluorophenyl)-N⁵-(3,3-difluorocyclobutyl)-7-(2-hydroxypropan-2-yl)-6,7-dihydropyrazolo[1,5-a]pyrazine-3,5(4H)-dicarboxamide | 486.4 | 1.40 2.35 | H I |
| A20 | 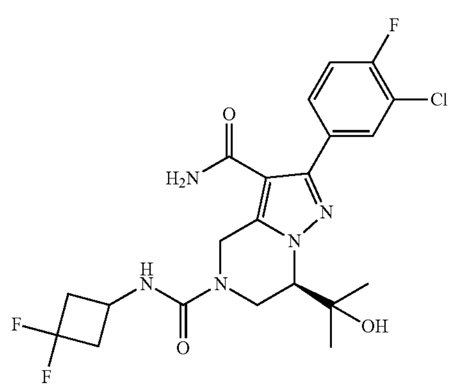 [SMILES: CC(C)(O)[C@H]1CN(C(=O)NC2CC(F)(F)C2)Cc2c(C(N)=O)c(-c3ccc(F)c(Cl)c3)nn21] | (R)-2-(3-Chloro-4-fluorophenyl)-N⁵-(3,3-difluorocyclobutyl)-7-(2-hydroxypropan-2-yl)-6,7-dihydropyrazolo[1,5-a]pyrazine-3,5(4H)-dicarboxamide | 486.4 | 1.40 2.37 | H I |

Scheme 65

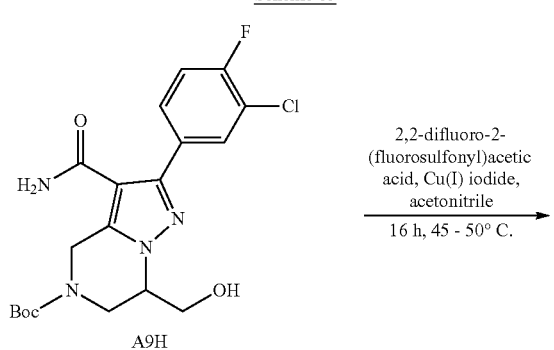

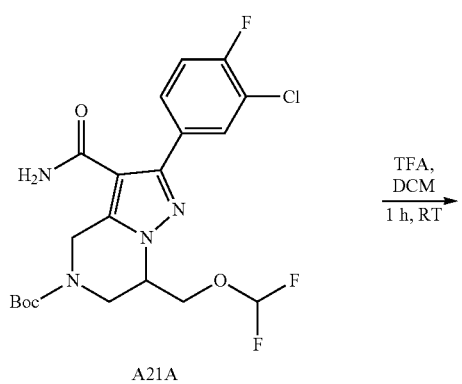

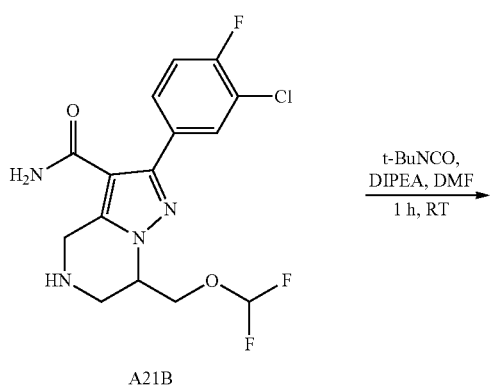

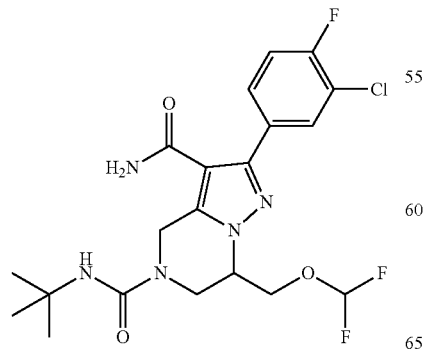

Intermediate A21A: tert-Butyl 3-carbamoyl-2-(3-chloro-4-fluorophenyl)-7-(((difluoromethoxy)methyl)-6,7-dihydropyrazolo[1,5-a]pyrazine-5(4H)-carboxylate

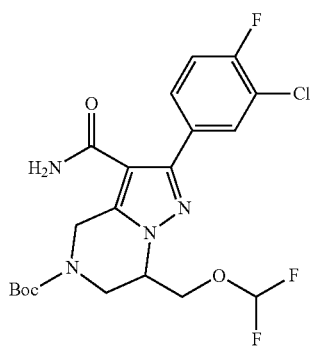 [SMILES: CC(C)(C)OC(=O)N1Cc2c(C(N)=O)c(-c3ccc(F)c(Cl)c3)nn2C(COC(F)F)C1]

To a degassed mixture of Intermediate A9H (0.4 g, 0.942 mmol) and copper(I) iodide (0.054 g, 0.282 mmol) in acetonitrile (9.42 mL) was added 2,2-difluoro-2-(fluorosulfonyl)acetic acid (0.117 mL, 1.130 mmol) and the reaction mixture was heated in an oil bath at 45-50° C. for 16 h. It was then concentrated to dryness and the residue was dissolved in EtOAc. The organic layer was washed with water, brine, dried over anhydrous MgSO$_4$, filtered and the filtrate was concentrated under reduced pressure to afford a crude solid. It was purified by silica gel chromatography (24 g, Premium column, eluting with 35% EtOAc in DCM). Fractions containing the product were combined and evaporated to afford Intermediate A21A (0.06 g, 13.%) as a white solid. MS(ES): m/z=475.04 [M+H]$^+$.

Intermediate A21B: 2-(3-Chloro-4-fluorophenyl)-7-((difluoromethoxy)methyl)-4,5,6,7-tetrahydropyrazolo[1,5-a]pyrazine-3-carboxamide, 2 TFA

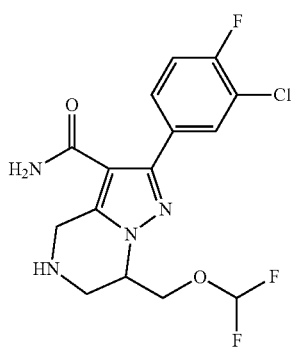 [SMILES: NC(=O)c1c(-c2ccc(F)c(Cl)c2)nn2c1CNCC2COC(F)F]

To a solution of Intermediate A21A (0.06 g, 0.126 mmol) in DCM (1.26 mL) was added TFA (0.195 mL, 2.53 mmol) and the reaction mixture was stirred at room temperature for 1 h.

It was then concentrated to dryness to obtain crude Intermediate A21B (0.075 g, >99%) as the bis TFA salt. MS(ES): m/z=375.0 [M+H]+.

Compounds A21 and A22: $N^5$-(tert-Butyl)-2-(3-chloro-4-fluorophenyl)-7-((difluoromethoxy)methyl)-6,7-dihydropyrazolo[1,5-a]pyrazine-3,5(4H)-dicarboxamide

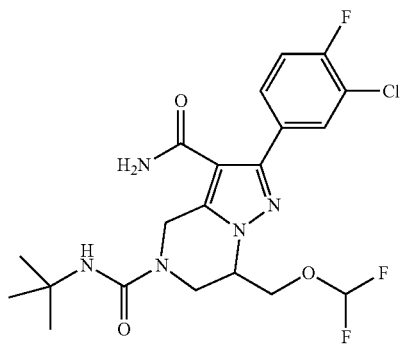 [SMILES: CC(C)(C)NC(=O)N1Cc2c(C(N)=O)c(-c3ccc(F)c(Cl)c3)nn2C(COC(F)F)C1]

A solution of Intermediate A21B (0.076 g, 0.126 mmol), 2-isocyanato-2-methylpropane (0.043 mL, 0.38 mmol) and DIPEA (0.13 mL, 0.756 mmol) in DMF (1.26 mL) was stirred at room temperature for 1 h. The reaction mixture was purified by preparative HPLC to afford a racemic mixture of A21 and A22. The individual enantiomers A21 and A22 were separated by chiral SFC purification using CHIRALPAK® AD preparative column (21×250) mm, 10 μm column, Solvent A: 0.1% diethylamine in heptane, Solvent B: 100% EtOH, start % B: 30, isocratic, flow rate 15.0 mL/min for 85 min. UV monitored at 254 nm. Compound A21 (S)-isomer was eluted at 40.51 min. (2.6 mg, 100% ee, Yield=5.1%) and A22 (R)-isomer was eluted at 54.09 min. (2.9 mg, 100% ee, Yield=5.7%). MS: m/z=474.3 [M+H]+; HPLC Ret. Time 1.71 min. and 2.54 min. (Methods H and I respectively); $^1$H NMR (500 MHz, DMSO-$d_6$) δ ppm 7.94-7.83 (m, 1H), 7.77-7.64 (m, 1H), 7.48 (t, J=9.0 Hz, 1H), 7.40 (br. s., 1H), 7.30 (br. s., 1H), 6.75 (s, 1H), 6.30 (s, 1H), 4.80 (d, J=16.9 Hz, 1H), 4.66 (d, J=16.9 Hz, 1H), 4.50 (br. s., 1H), 4.37-4.21 (m, 2H), 3.99 (dd, J=14.1, 3.9 Hz, 1H), 3.77 (dd, J=14.3, 6.6 Hz, 1H), 1.29 (s, 1H).

Scheme 66

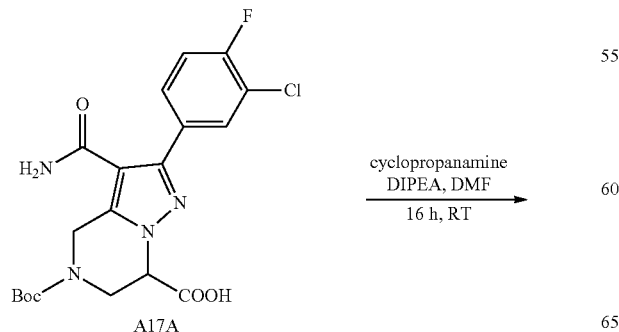

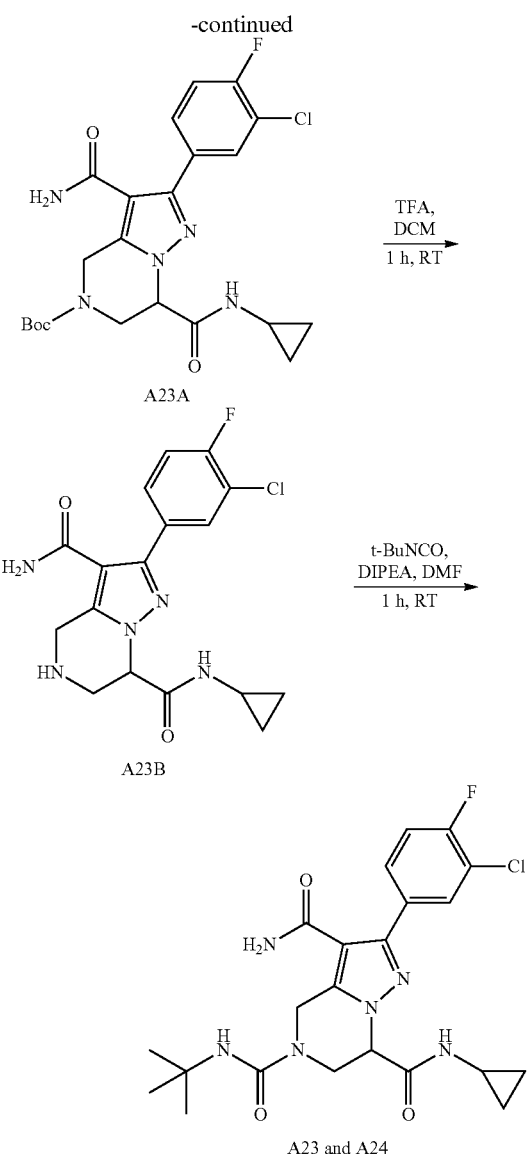

Intermediate A23B: 2-(3-Chloro-4-fluorophenyl)-$N^7$-cyclopropyl-4,5,6,7-tetrahydropyrazolo[1,5-a]pyrazine-3,7-dicarboxamide, 2 TFA

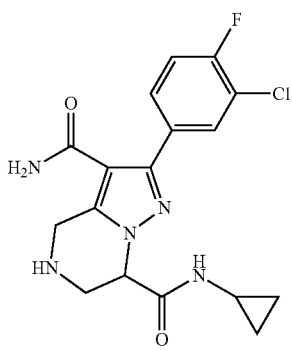 [SMILES: NC(=O)c1c(-c2ccc(F)c(Cl)c2)nn2c1CNCC2C(=O)NC1CC1]

A solution of Intermediate A17A (0.103 g, 0.235 mmol), cyclopropanamine (0.033 mL, 0.469 mmol), HATU (0.178 g, 0.469 mmol) and DIPEA (0.164 mL, 0.939 mmol) in DMF (2.0 mL) was stirred at room temperature for 16 h. The reaction mixture was diluted with water and extracted with EtOAc (2×10 mL). The combined organic layer was washed with water, brine, dried over anhydrous MgSO$_4$, filtered and concentrated to afford the intermediate amide A23A. (ES): m/z=478.1 [M+H]$^+$. It was subjected to the deprotection of the Boc group without purification.

To a solution of intermediate cyclopropylamide A23A in DCM (2 mL) was added TFA (0.362 mL, 4.69 mmol) and the reaction mixture was stirred at room temperature for 1 h. The mixture was then concentrated to dryness to afford crude Intermediate A23B (0.14 g, >99%) as the bis TFA salt. MS(ES): m/z=378.0 [M+H]$^+$.

Compounds A23 and A24: $N^5$-(tert-Butyl)-2-(3-chloro-4-fluorophenyl)-$N^7$-cyclopropyl-6,7-dihydro-pyrazolo[1,5-a]pyrazine-3,5,7(4H)-tricarboxamide

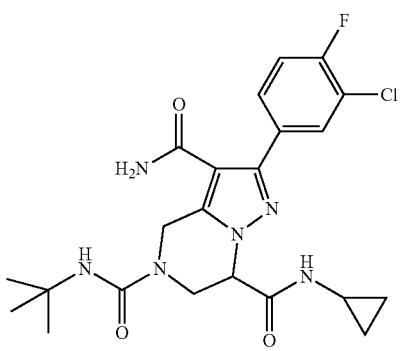 [SMILES: CC(C)(C)NC(=O)N1Cc2c(C(N)=O)c(-c3ccc(F)c(Cl)c3)nn2C(C(=O)NC2CC2)C1]

A solution of Intermediate A23B (0.06 g, 0.099 mmol), 2-isocyanato-2-methylpropane (0.034 mL, 0.297 mmol) and DIPEA (0.104 mL, 0.594 mmol) in DMF (0.990 mL) was stirred at room temperature for 1 h. The reaction mixture was purified via preparative HPLC to afford a racemic mixture of A23 and A24. Individual enantiomers A23 and A24 were separated by chiral SFC separation using CHIRALPAK® AD preparative column (21×250) mm, 10 µm column, Solvent A: 0.1% diethylamine in heptane, Solvent B: 100% EtOH, start %B: 30, isocratic, flow rate 15.0 mL/min for 25 min. UV monitored at 254 nm. Compound A23 (S)-isomer was eluted at 7.651 min. (2.0 mg, 100% ee, Yield=4.7%) and A24 (R)-isomer was eluted at 14.88 min. (1.8 mg, 100% ee, Yield=3.8%). MS(ES): m/z=477.3 [M+H]$^+$; HPLC Ret. Time 1.57 min. and 2.30 min. (Methods H and I respectively); $^1$H NMR (500 MHz, DMSO-d$_6$) δ ppm 8.45 (d, J=3.7 Hz, 1H), 7.82 (d, J=7.3 Hz, 1H), 7.72-7.61 (m, 1H), 7.47 (t, J=8.8 Hz, 1H), 7.38 (br. s., 1H), 7.28 (br. s., 1H), 6.17 (s, 1H), 4.83-4.73 (m, 2H), 4.00 (dd, J=14.1, 5.7 Hz, 1H), 3.87 (dd, J=14.1, 4.2 Hz, 1H), 3.52-3.45 (m, 1H), 3.44-3.39 (m, 2H), 2.69-2.59 (m, 1H), 1.30-1.23 (m, 1H).

Scheme 67

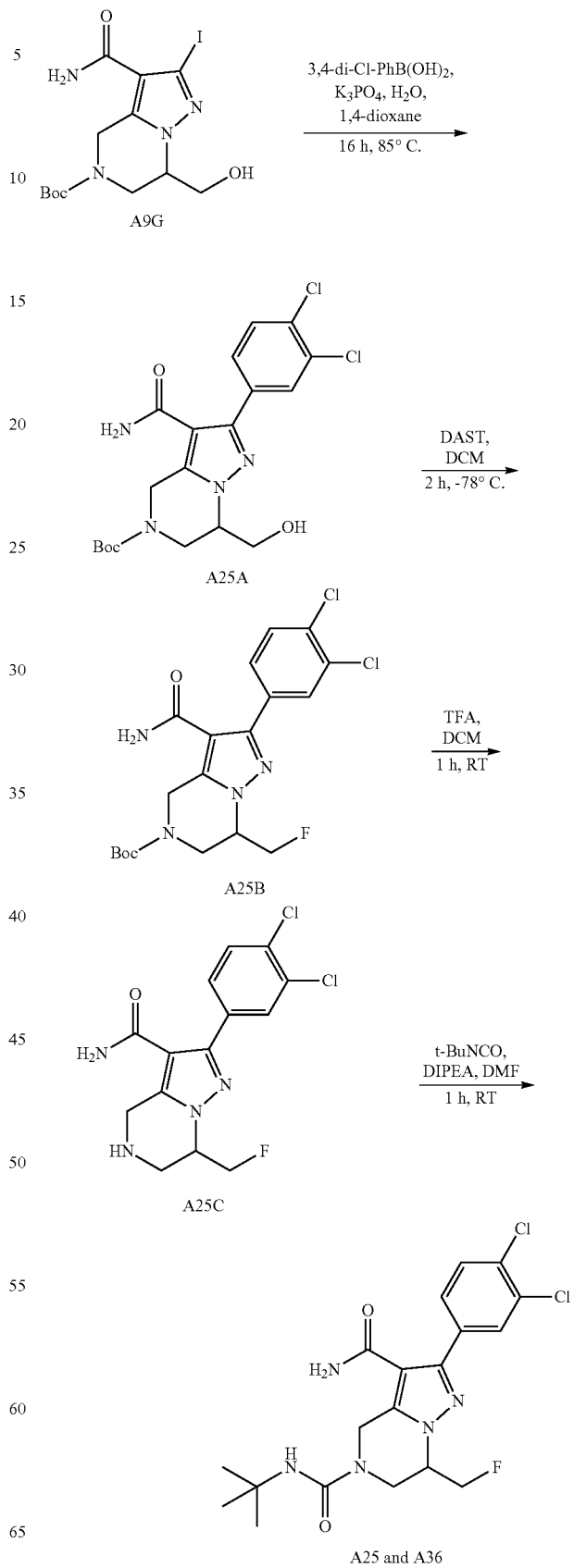

Intermediate A25C: 2-(3,4-Dichlorophenyl)-7-(fluoromethyl)-4,5,6,7-tetrahydropyrazolo[1,5-a]pyrazine-3-carboxamide

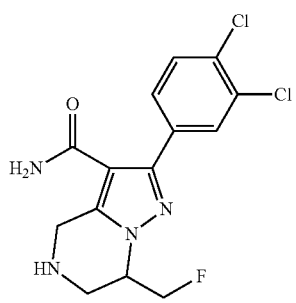 [SMILES: NC(=O)c1c(-c2ccc(Cl)c(Cl)c2)nn2c1CNCC2CF]

Intermediate A25C was synthesized analogous to Intermediate A9J by first coupling Intermediate A9G with 3,4-dichlorophenylboronic acid, followed by the synthetic sequence described in Scheme 61. MS(ES): m/z=343.1 [M+H]$^+$.

Compounds A25 and A26: N$^5$-(4-Cyanophenyl)-2-(3,4-dichlorophenyl)-7-(fluoromethyl)-6,7-dihydropyrazolo[1,5-a]pyrazine-3,5(4H)-dicarboxamide

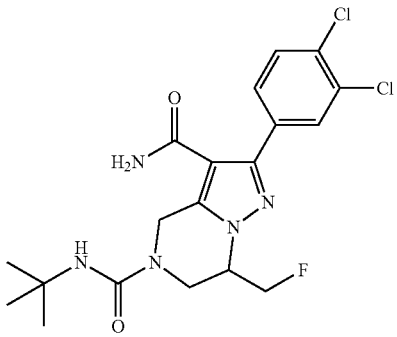 [SMILES: CC(C)(C)NC(=O)N1Cc2c(C(N)=O)c(-c3ccc(Cl)c(Cl)c3)nn2C(CF)C1]

A solution of Intermediate A25C (0.05 g, 0.146 mmol), 2-isocyanato-2-methylpropane (0.050 mL, 0.437 mmol) and DIPEA (0.089 mL, 0.510 mmol) in DMF (2.91 mL) was stirred at room temperature for 1 h. The reaction mixture was purified by preparative HPLC to afford a racemic mixture of A25 and A26. The individual enantiomers A25 and A26 were separated by Chiral SFC purification using CHIRALPAK® IA preparative column (30×250) mm, 5 µm column, flow rate 70.0 mL/min for 16 min.; mobile phase: 40% MeOH in CO$_2$. Temperature: 35° C., UV monitored at 265 nm, Back pressure: 150 bar. Compound A25 (S)-isomer was eluted at 9.23 min. (9.0 mg, 100% ee, Yield=14%) and A26 (R)-isomer was eluted at 12.89 min. (8.3 mg, 100% ee, Yield=13%). MS(ES): m/z=442.3 [M+H]$^+$; HPLC Ret. Time 1.61 min. and 2.57 min. (Methods H and I respectively); $^1$H NMR (500 MHz, DMSO-d$_6$) δ ppm 7.92 (s, 1H), 7.69 (s, 2H), 7.41 (br. s., 1H), 7.35 (br. s., 1H), 6.28 (s, 1H), 5.03 (dd, J=9.9, 4.8 Hz, 1H), 4.94 (dd, J=9.7, 4.2 Hz, 1H), 4.81 (d, J=17.2 Hz, 2H), 4.73 (d, J=7.0 Hz, 1H), 4.63 (d, J=17.2 Hz, 1H), 4.55 (br. s., 1H), 4.51 (br. s., 1H), 4.02 (dd, J=14.1, 4.2 Hz, 1H), 3.78 (dd, J=13.8, 7.2 Hz, 1H), 1.28 (s, 9H).

Compounds A27 and A28: 2-(3,4-Dichlorophenyl)-N$^5$-(3,3-difluoro-1-methylcyclobutyl)-7-(fluoromethyl)-6,7-dihydropyrazolo[1,5-a]pyrazine-3,5(4H)-dicarboxamide

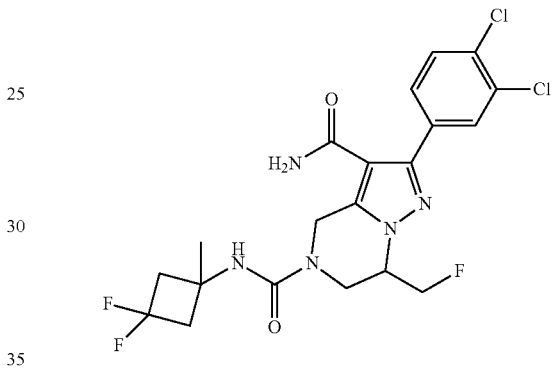

A racemic mixture of Compounds A27 and A28 was synthesized analogous to Compounds A9 and A10 (Scheme 61) by reacting Intermediate A25C with 3,3-difluoro-1-methylcyclobutanecarboxylic acid. The individual enantiomers A27 and A28 were separated by chiral SFC purification using CHIRALPAK® AD preparative column (21×250) mm, 10 µm column, Solvent A: 0.1% diethylamine in heptane, Solvent B: 100% EtOH, start % B: 20, isocratic, flow rate 15.0 mL/min for 20 min. UV monitored at 254 nm. Compound A27 (S)-isomer was eluted at 8.853 min (5.5 mg, 100% ee, Yield=11.3%) and A28 (R)-isomer was eluted at 10.996 min. (6.4 mg, 100% ee, Yield=13.2%). MS(ES): m/z=489.9 [M+H]$^+$; HPLC Ret. Time 1.717 min. and 3.017 min. (H and I respectively); $^1$H NMR (500 MHz, DMSO-d$_6$) δ ppm 7.92 (s, 1H), 7.73-7.65 (m, 2H), 7.43 (br. s., 1H), 7.36 (br. s., 1H), 7.21 (s, 1H), 5.02 (dd, J=9.7, 4.6 Hz, 1H), 4.93 (dd, J=10.3, 4.8 Hz, 1H), 4.86-4.67 (m, 3H), 4.59 (br. s., 1H), 4.54 (br. s., 1H), 4.01 (dd, J=14.1, 4.2 Hz, 1H), 3.95-3.81 (m, 1H), 2.90-2.80 (m, 2H), 2.65-2.54 (m, 2H), 1.44 (s, 3H).

The Compounds described in Table 49 were synthesized analogous to Compounds A27 and A28 by reacting Intermediate A25C with the corresponding carboxylic acid.

TABLE 49
| Ex. No. | Structure | Name | [M + H]+ | Ret Time (min.) | HPLC Methods |
|---|---|---|---|---|---|
| A29 | 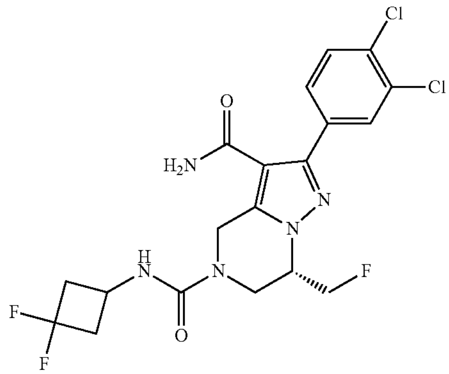 [SMILES: NC(=O)c1c(-c2ccc(Cl)c(Cl)c2)nn2c1CN(C(=O)NC1CC(F)(F)C1)C[C@H]2CF] | (S)-2-(3,4-dichlorophenyl)-N5-(3,3-difluorocyclobutyl)-7-(fluoromethyl)-6,7-dihydropyrazolo[1,5-a]pyrazine-3,5(4H)-dicarboxamide | 476.4 | 1.55<br>2.44 | H<br>I |
| A30 | 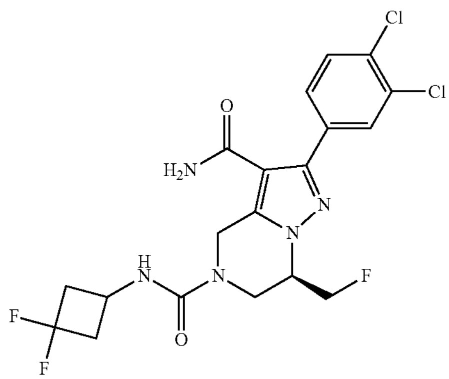 [SMILES: NC(=O)c1c(-c2ccc(Cl)c(Cl)c2)nn2c1CN(C(=O)NC1CC(F)(F)C1)C[C@@H]2CF] | (R)-2-(3,4-dichlorophenyl)-N5-(3,3-difluorocyclobutyl)-7-(fluoromethyl)-6,7-dihydropyrazolo[1,5-a]pyrazine-3,5(4H)-dicarboxamide | 476.3 | 1.57<br>2.46 | H<br>I |
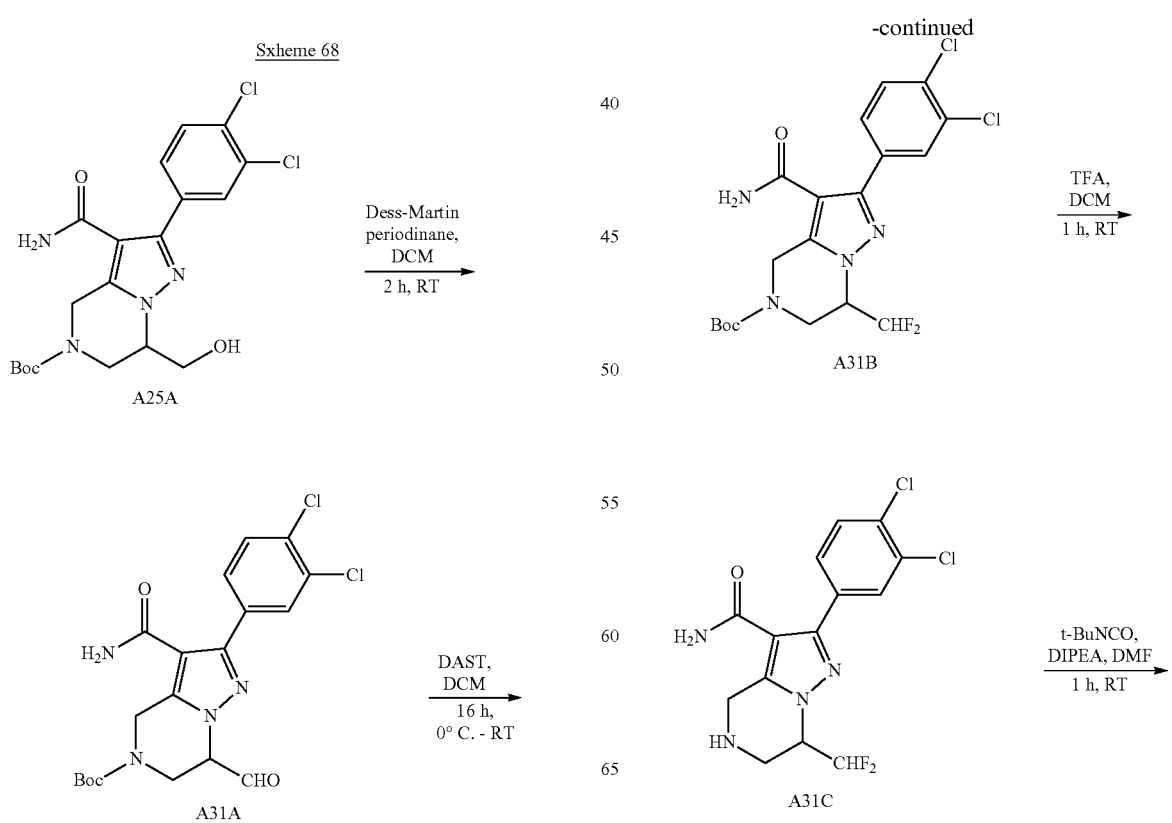
Scheme 68

-continued

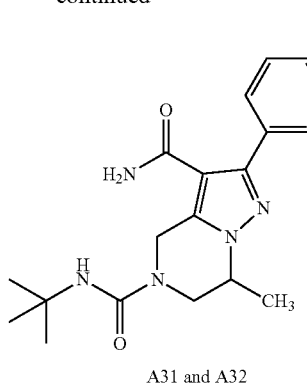

A31 and A32

Intermediate A31C: 2-(3,4-Dichlorophenyl)-7-(difluoromethyl)-4,5,6,7-tetrahydropyrazolo[1,5-a]pyrazine-3-carboxamide

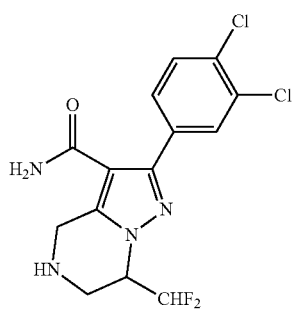 [SMILES: NC(=O)c1c(-c2ccc(Cl)c(Cl)c2)nn2c1CNCC2C(F)F]

Intermediate A31C was synthesized from Intermediate A25A using a synthetic sequence analogous to the preparation of Intermediate A6C (Scheme 59). MS(ES): m/z 361.2 [M+H]$^+$.

Compounds A31 and A32: $N^5$-(tert-Butyl)-2-(3,4-dichlorophenyl)-7-(difluoromethyl)-6,7-dihydropyrazolo[1,5-a]pyrazine-3,5(4H)-dicarboxamide

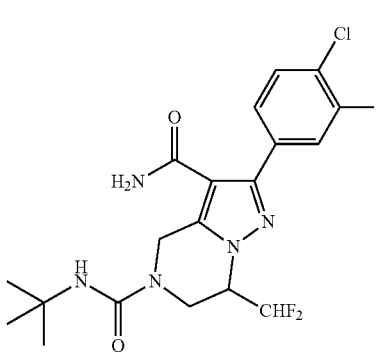

The racemic mixture of Compounds A31 and A32 was synthesized analogous to Compounds A15 and A16 by reacting Intermediate A31C with 2-isocyanato-2-methylpropane. The reaction mixture was purified via preparative HPLC to afford a racemic mixture of A31 and A32. The individual enantiomers A31 and A32 were separated by chiral SFC separation using CHIRALPAK® AD preparative column (21×250) mm, 10 μm column, Solvent A: 0.1% diethylamine in heptane, Solvent B: 100% EtOH, start % B: 15, isocratic, flow rate 15.0 mL/min for 120 min. UV monitored at 254 nm. A31 (S)-isomer was eluted at 12.428 min. (0.8 mg, 100% ee, Yield=1.1%) and A32 (R)-isomer was eluted at 21.622 min. (1.1 mg, 100% ee, Yield=1.6%). MS(ES): m/z=460.4 [M+H]$^+$. HPLC Ret. Time 1.62 min. and 2.68 min (Methods H and I respectively).

Scheme 69

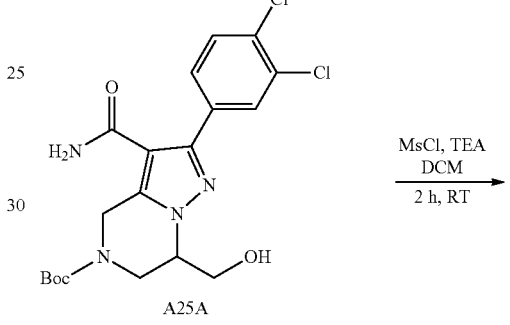

A25A

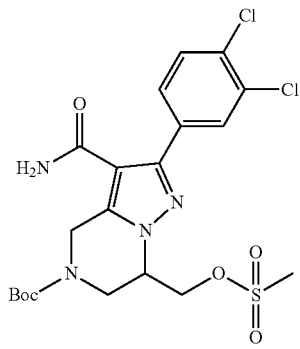

A33A

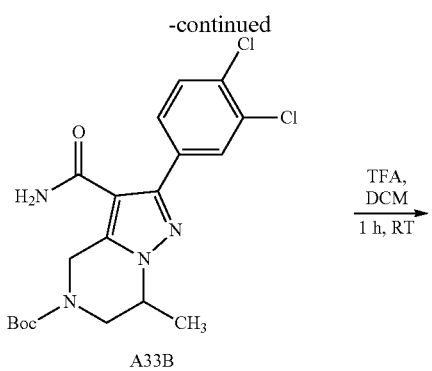

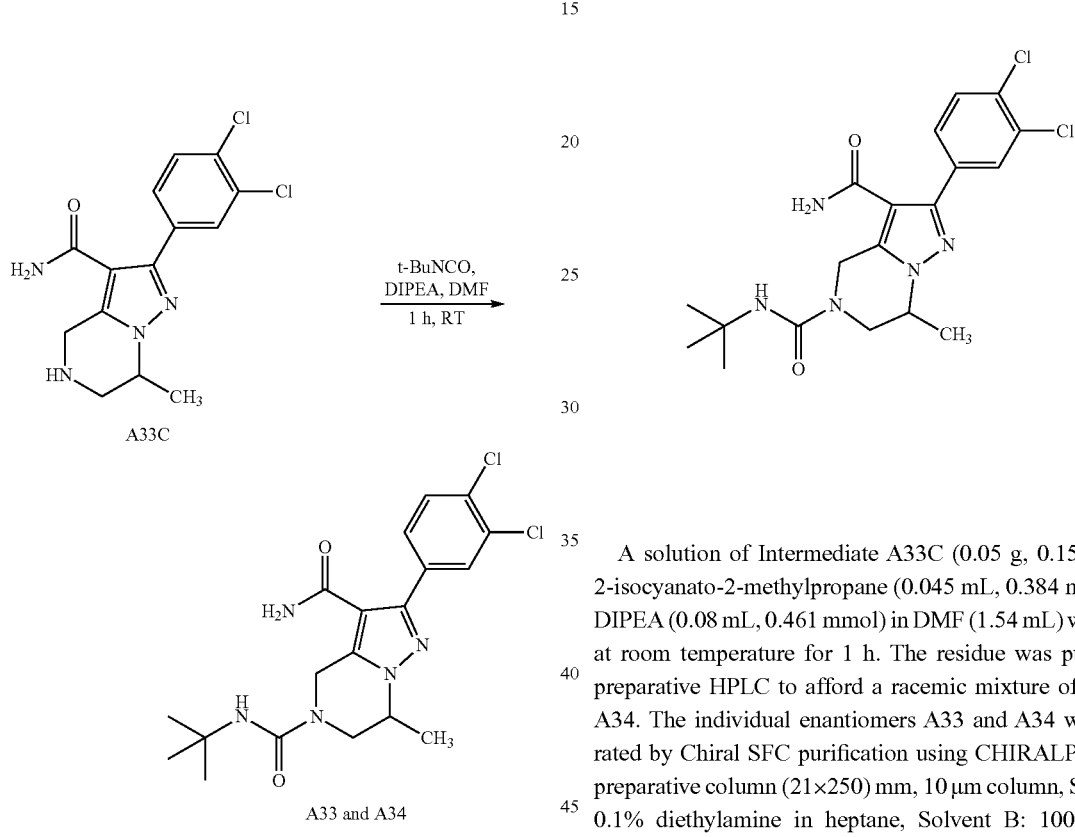

Intermediate A33C: 2-(3,4-Dichlorophenyl)-7-methyl-4,5,6,7-tetrahydropyrazolo[1,5-a]pyrazine-3-carboxamide

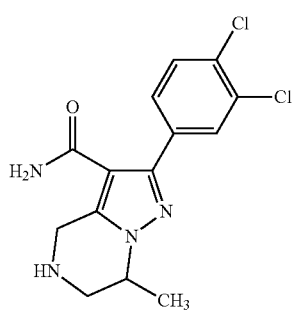 [SMILES: CC1CNCc2c(C(N)=O)c(-c3ccc(Cl)c(Cl)c3)nn21]

Intermediate A33C was synthesized from Intermediate A25A using a synthetic sequence analogous to the preparation of Intermediate A7C (Scheme 60). MS(ES): m/z=325.1 [M+H]$^+$.

Compounds A33 and A34: N$^5$-(tert-Butyl)-2-(3,4-dichlorophenyl)-7-methyl-6,7-dihydropyrazolo[1,5-a]pyrazine-3,5(4H)-dicarboxamide A solution of Intermediate A33C (0.05 g, 0.154 mmol), 2-isocyanato-2-methylpropane (0.045 mL, 0.384 mmol) and DIPEA (0.08 mL, 0.461 mmol) in DMF (1.54 mL) was stirred at room temperature for 1 h. The residue was purified by preparative HPLC to afford a racemic mixture of A33 and A34. The individual enantiomers A33 and A34 were separated by Chiral SFC purification using CHIRALPAK® AD preparative column (21×250) mm, 10 μm column, Solvent A: 0.1% diethylamine in heptane, Solvent B: 100% EtOH, start % B: 5.0, isocratic, flow rate 15.0 mL/min for 70 min. UV monitored at 254 nm. Compound A33 (S)-isomer was eluted at 44.01 min. (14.2 mg, 100% ee, Yield=21.8%) and A34 (R)-isomer was eluted at 33.14 min. (14.6 mg, 100% ee, Yield=22.4%). MS(ES): m/z=424.3 [M+H]$^+$; HPLC Ret. Time 1.64 min. and 2.61 min. (Methods H and I respectively); $^1$H NMR (500 MHz, DMSO-d$_6$) δ ppm 7.68 (s, 2H), 7.38 (br. s., 1H), 7.30 (br. s., 1H), 6.24 (s, 1H), 4.79 (d, J=16.9 Hz, 1H), 4.61 (d, J=16.9 Hz, 1H), 4.38-4.24 (m, 1H), 3.95 (dd, J=13.8, 3.5 Hz, 1H), 3.48 (dd, J=13.9, 7.3 Hz, 1H), 3.38 (d, J=4.8 Hz, 1H), 1.45 (d, J=6.2 Hz, 3H), 1.29 (s, 9H).

The Compounds described in Table 50 were synthesized analogous to A33 and A34 by reacting Intermediate A33C with the corresponding carboxylic acid.

TABLE 50

| Ex. No. | Structure | Name | Synthetic method | [M + H]⁺ | Ret. Time (min.) | HPLC Method |
|---|---|---|---|---|---|---|
| A35 | 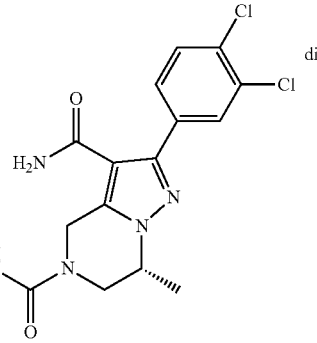 | (R)-2-(3,4-Dichlorophenyl)-N⁵-(3,3-difluorocyclobutyl)-7-methyl-6,7-dihydropyrazolo[1,5-a]pyrazine-3,5(4H)-dicarboxamide | D | 458.4 | 1.57, 2.52 | H I |
| A36 | 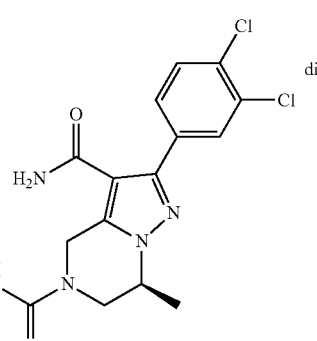 | (S)-2-(3,4-Dichlorophenyl)-N⁵-(3,3-difluorocyclobutyl)-7-methyl-6,7-dihydropyrazolo[1,5-c]pyrazine-3,5(4H)-dicarboxamide | D | 458.4 | 1.57, 2.52 | H |

Scheme 70

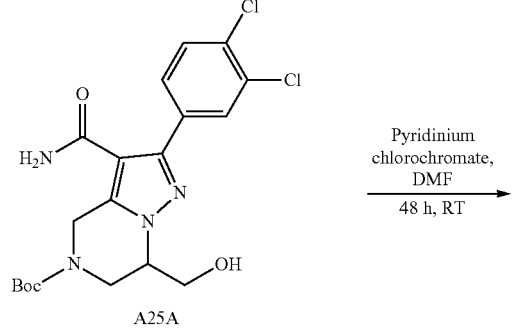

A25A

Pyridinium chlorochromate, DMF
48 h, RT

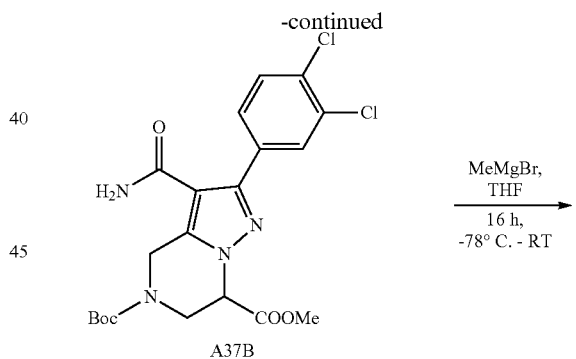

A37B

MeMgBr, THF
16 h, −78° C. - RT

-continued

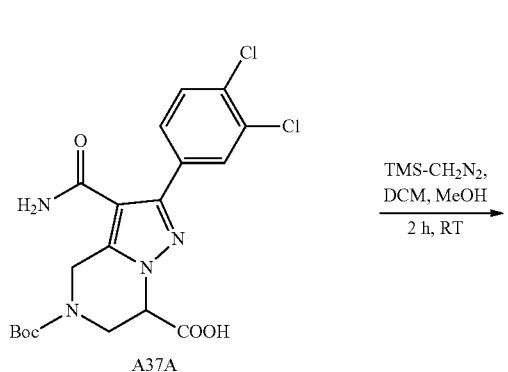

A37A

TMS-CH₂N₂, DCM, MeOH
2 h, RT

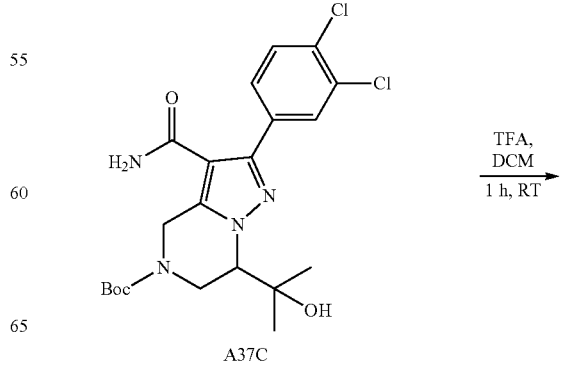

A37C

TFA, DCM
1 h, RT

507

-continued

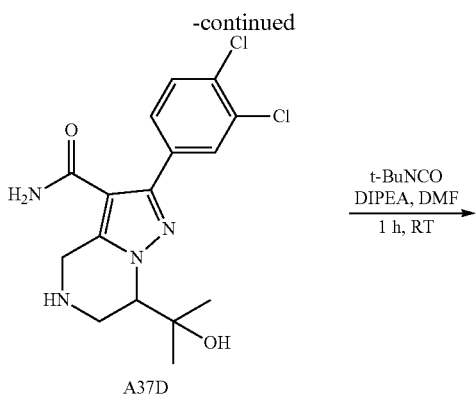

A37D t-BuNCO
DIPEA, DMF
1 h, RT →

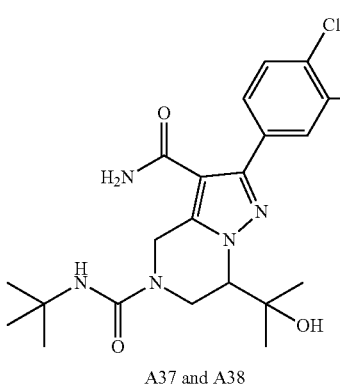

A37 and A38

Intermediate A37D: 2-(3,4-Dichlorophenyl)-7-(2-hydroxypropan-2-yl)-4,5,6,7-tetrahydropyrazolo[1,5-a]pyrazine-3-carboxamide

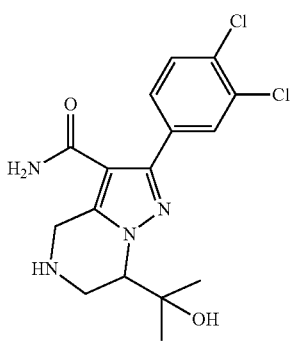 [SMILES: CC(C)(O)C1CNCc2c(C(N)=O)c(-c3ccc(Cl)c(Cl)c3)nn21]

508

Intermediate A37D was synthesized from Intermediate A25A by using a synthetic sequence analogous to the preparation of Intermediate A17D (Scheme 64). MS(ES): m/z=369.1 [M+H]$^+$.

Compounds A37 and A38: N$^5$-(tert-Butyl)-2-(3,4-dichlorophenyl)-7-(2-hydroxypropan-2-yl)-6,7-dihydropyrazolo[1,5-a]pyrazine-3,5(4H)-dicarboxamide

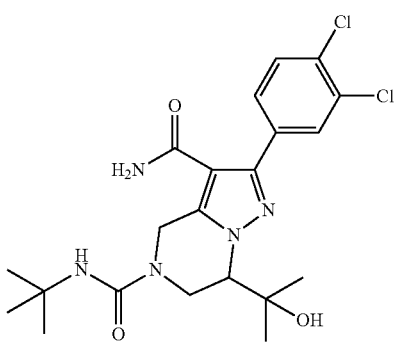 [SMILES: CC(C)(C)NC(=O)N1Cc2c(C(N)=O)c(-c3ccc(Cl)c(Cl)c3)nn2C(C(C)(C)O)C1]

The racemic mixture of Compounds A37 and A38 was synthesized analogous to Compounds A17 and A18 (Scheme 64) by reacting Intermediate A37D with 2-isocyanato-2-methylpropane. The reaction mixture was purified via preparative HPLC to afford a racemic mixture of Compounds A37 and A38. The individual enantiomers A37 and A38 were separated by chiral SFC separation using CHIRALPAK® AD preparative column (21×250) mm, 10 µm column, Solvent A: 0.1% diethylamine in heptane, Solvent B: 100% EtOH, start % B: 30, isocratic, flow rate 15.0 mL/min for 25 min. UV monitored at 254 nm Compound A37 (S)-isomer was eluted at 5.078 min. (10.5 mg, 100% ee, Yield=16.6%) and A38 (R)-isomer was eluted at 16.331 min. (13.4 mg, 100% ee, Yield=21.1%). MS(ES): m/z=468.3 [M+H]$^+$; HPLC Ret. Time 1.61 min. and 2.60 min. (Methods H and I respectively); $^1$H NMR (500 MHz, DMSO-d$_6$) δ ppm 7.89 (s, 1H), 7.71-7.62 (m, 2H), 7.38 (br. s., 1H), 7.34 (br. s., 1H), 6.20 (s, 1H), 4.82 (d, J=17.2 Hz, 1H), 4.55 (d, J=17.2 Hz, 1H), 4.15 (d, J=3.7 Hz, 2H), 2.55 (s, 2H), 1.34-1.23 (m, 1H), 0.96 (s, 3H).

Scheme 71

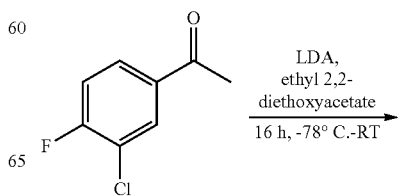

LDA,
ethyl 2,2-diethoxyacetate
16 h, -78° C.-RT →

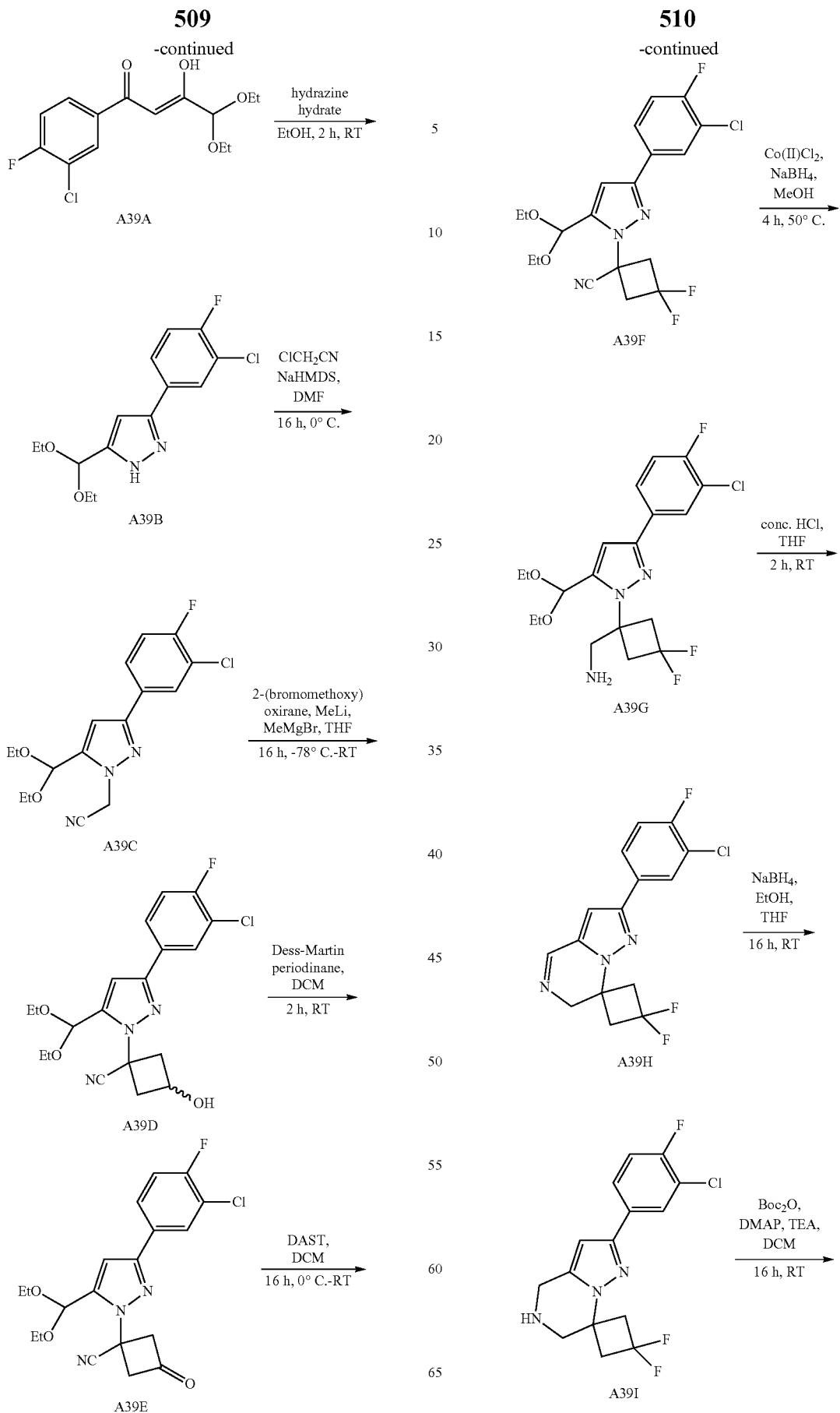

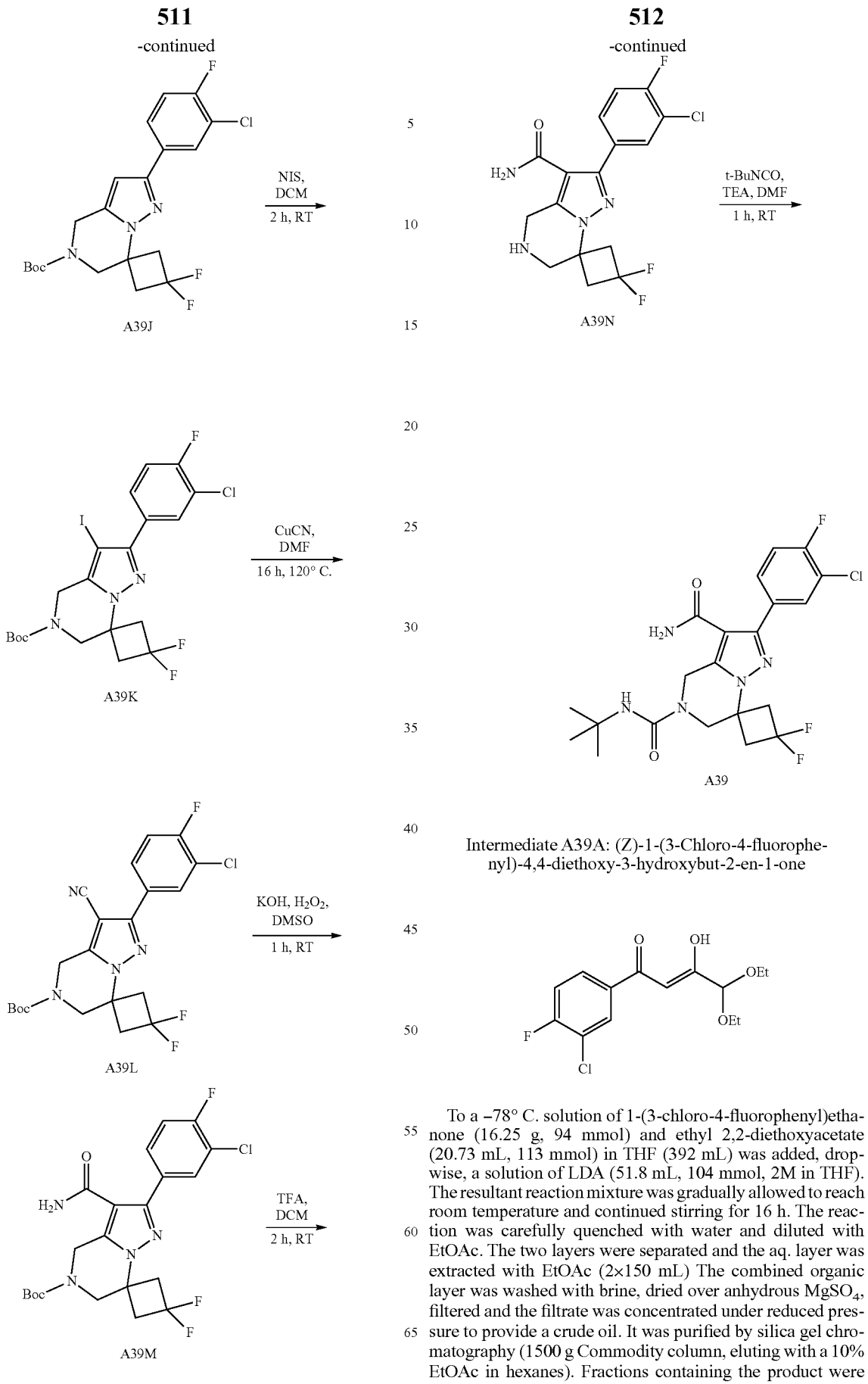

Intermediate A39A: (Z)-1-(3-Chloro-4-fluorophenyl)-4,4-diethoxy-3-hydroxybut-2-en-1-one To a −78° C. solution of 1-(3-chloro-4-fluorophenyl)ethanone (16.25 g, 94 mmol) and ethyl 2,2-diethoxyacetate (20.73 mL, 113 mmol) in THF (392 mL) was added, dropwise, a solution of LDA (51.8 mL, 104 mmol, 2M in THF). The resultant reaction mixture was gradually allowed to reach room temperature and continued stirring for 16 h. The reaction was carefully quenched with water and diluted with EtOAc. The two layers were separated and the aq. layer was extracted with EtOAc (2×150 mL) The combined organic layer was washed with brine, dried over anhydrous MgSO₄, filtered and the filtrate was concentrated under reduced pressure to provide a crude oil. It was purified by silica gel chromatography (1500 g Commodity column, eluting with a 10% EtOAc in hexanes). Fractions containing the product were combined and evaporated to afford Intermediate A39A (9.97 g, 35%) as a solid. MS(ES): m/z=257 [M-OEt]+.

Intermediate A39B: 3-(3-Chloro-4-fluorophenyl)-5-(diethoxymethyl)-1H-pyrazole

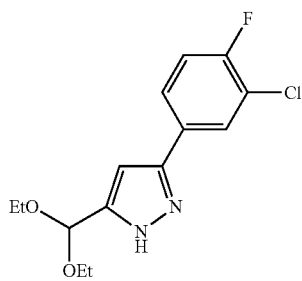 [SMILES: CCOC(OCC)c1cc(-c2ccc(F)c(Cl)c2)n[nH]1]

To a solution of Intermediate A39A (19.37 g, 64.0 mmol) in EtOH (128 mL) was added hydrazine hydrate (4.9 mL, 64.0 mmol, 64% solution) and the reaction continued stirring at room temperature for 2 h. Ethanol was concentrated under reduced pressure and the residue was partitioned between water and EtOAc. The two layers were separated and the aq. layer was extracted with EtOAc (2×200 mL). The combined organic layer was washed with water, brine, dried over anhydrous MgSO$_4$, filtered and the filtrate was concentrated under reduced pressure to provide a crude oil. It was purified by silica gel chromatography (330 g REDISEP® column, eluting with a gradient of 0 to 20% EtOAc in hexanes). Fractions containing the product were combined and evaporated to afford Intermediate A39B (17.08 g, 89%) as a bright yellow syrup that later on solidified. MS(ES): m/z=253 [M-OEt]+; $^1$H NMR (400 MHz, chloroform-d) δ ppm 7.87 (dd, J=7.0, 2.3 Hz, 1H), 7.68 (ddd, J=8.5, 4.6, 2.1 Hz, 1H), 7.19 (t, J=8.7 Hz, 1H), 6.57 (s, 1H), 5.75 (s, 1H), 3.76-3.57 (m, 4H), 1.35-1.24 (m, 7H).

Intermediate A39C: 2-(3-(3-Chloro-4-fluorophenyl)-5-(diethoxymethyl)-1H-pyrazol-1-yl)acetonitrile

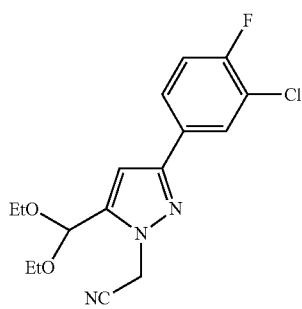 [SMILES: CCOC(OCC)c1cc(-c2ccc(F)c(Cl)c2)nn1CC#N]

To a 0° C. solution of Intermediate A39B (1.21 g, 4.04 mmol) in DMF (10.22 mL) was added a solution of NHMDS (4.24 mL, 4.24 mmol, 1M in THF) and the reaction was continued stirring at that temperature for 30 min., followed by the addition of 2-chloroacetonitrile (0.283 mL, 4.44 mmol). The resultant mixture was stirred at room temperature for 16 h. It was quenched by the addition of a satd. aq. solution of NH$_4$Cl and the aq. layer was extracted with EtOAc (3×25 mL). The combined organic layer was washed with water, brine, dried over anhydrous MgSO$_4$, filtered, and the filtrate was concentrated under reduced pressure to provide a crude oil. It was purified by silica gel chromatography (120 g REDISEP® column, 20% EtOAc in hexanes). Fractions containing the product were combined and evaporated to afford A39C (1.0 g, 73.3%) as a white solid. MS(ES): m/z=338.2 [M+H]+.

Intermediate A39D: 1-(3-(3-Chloro-4-fluorophenyl)-5-(diethoxymethyl)-1H-pyrazol-1-yl)-3-hydroxycyclobutanecarbonitrile

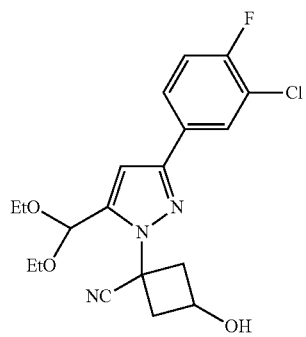 [SMILES: CCOC(OCC)c1cc(-c2ccc(F)c(Cl)c2)nn1C1(C#N)CC(O)C1]

To a −78° C. solution of Intermediate A39C (0.5 g, 1.480 mmol) in THF (7.40 mL), a 1.6M solution of methyllithium (0.925 mL, 1.480 mmol) was added dropwise and the reaction was allowed to stir at that temperature for 1 h. Subsequently, a solution of 2-(bromomethyl)oxirane (0.125 mL, 1.480 mmol) in THF (2 mL) was introduced dropwise. The reaction was allowed to stir at −78° C. for 1 h. Then, a solution of methylmagnesium bromide (0.493 mL, 1.480 mmol, 3M in hexane) was added at −78° C. and the resultant reaction mixture was allowed to warm to room temperature. After 16 h, the reaction was quenched with by adding a satd. aq. solution of NH$_4$Cl, the two layers were separated and the aq. layer was extracted with EtOAc (2×20 mL). The combined organic layer was washed with brine, dried over anhydrous MgSO$_4$, filtered and the filtrate was concentrated under reduced pressure to provide a crude oil. It was purified by silica gel chromatography (40 g REDISEP® column, eluting with a gradient of 0 to 20% EtOAc in hexanes). Fractions containing the product were combined and evaporated to afford Intermediate A39D (0.197 g, 33.8%) as a solid. MS(ES): m/z=394.1 [M+H]+.

Intermediate A39E: 1-(3-(3-Chloro-4-fluorophenyl)-5-(diethoxymethyl)-1H-pyrazol-1-yl)-3-oxocyclobutanecarbonitrile

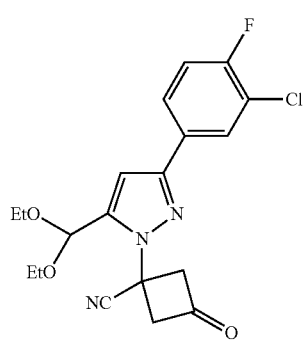 [SMILES: CCOC(OCC)c1cc(-c2ccc(F)c(Cl)c2)nn1C1(C#N)CC(=O)C1]

To a solution of Intermediate A39D (4.6 g, 11.68 mmol) in DCM (58.4 mL) was added Dess-Martin periodinane (7.43 g, 17.52 mmol) and the reaction mixture was stirred at room temperature for 2 h. It was then quenched with the addition of a satd. aq. solution of NaHCO₃ and satd. aq. solution of sodium sulfite. The two layers were separated and the aq. layer was extracted with DCM (2×70 mL), the combined organic layers was washed with brine, dried over anhydrous MgSO₄, filtered and the filtrate was concentrated under reduced pressure to provide a crude oil. It was purified by silica gel chromatography (220 g REDISEP® column, eluting with a gradient of 0 to 15% EtOAc in hexanes). Fractions containing the product were combined and evaporated to afford Intermediate A39E (3.98 g, 87%) as a colorless syrup. MS(ES): m/z=392.1 [M+H]⁺.

Intermediate A39F: 1-(3-(3-Chloro-4-fluorophenyl)-5-(diethoxymethyl)-1H-pyrazol-1-yl)-3,3-difluorocyclobutanecarbonitrile

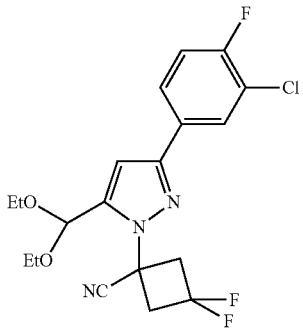 [SMILES: CCOC(OCC)c1cc(-c2ccc(F)c(Cl)c2)nn1C1(C#N)CC(F)(F)C1]

To a 0° C. solution of Intermediate A39E (3.98 g, 10.16 mmol) in DCM (67.7 mL) was added DAST (4.03 mL, 30.5 mmol) and the reaction mixture was stirred at room temperature for 18 h. It was quenched with by adding satd. aq. solution of NaHCO₃, the two layers were separated and the aq. layer was extracted with DCM (2×60 mL). The combined organic layer was washed with brine, dried over anhydrous MgSO₄, filtered and the filtrate was concentrated under reduced pressure to provide a crude oil. It was purified by silica gel chromatography (220 g REDISEP® column, eluting with a gradient of 10 to 15% EtOAc in hexanes). Fractions containing the product were combined and evaporated to afford Intermediate A39F (3.075 g, 73.2%) as a pale yellow oil. MS(ES): m/z=414.17 [M+H]⁺.

Intermediate A39G: (1-(3-(3-Chloro-4-fluorophenyl)-5-(diethoxymethyl)-1H-pyrazol-1-yl)-3,3-difluorocyclobutyl)methanamine

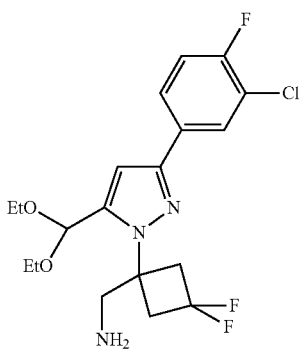 [SMILES: CCOC(OCC)c1cc(-c2ccc(F)c(Cl)c2)nn1C1(CN)CC(F)(F)C1]

To a 0° C. suspension of Intermediate A39F (3.075 g, 7.43 mmol) and cobalt(II) chloride (2.96 g, 22.29 mmol) in MeOH (74.3 mL) was slowly added NaBH₄ (2.81 g, 74.3 mmol). The reaction mixture instantly turned black and a vigorous gas evolution was observed. The reaction was heated in an oil bath at 50° C. for 4 h and then allowed to stir at room temperature for 16 h. The reaction mixture was then filtered through a CELITE® plug and the filtrate was concentrated under reduced pressure to afford a residue. This residue was suspended in DCM and filtered off. The filtrate was concentrated and purified by silica gel chromatography (120 g REDISEP® column, eluting with a gradient of 65 to 75% EtOAc in hexanes). Fractions containing the product were combined and evaporated to afford Intermediate A39G (1.1 g, 35.4%) as a colorless oil. ¹H NMR (400 MHz, chloroform-d) δ ppm 7.86 (dd, J=7.2, 2.1 Hz, 1H), 7.65 (ddd, J=8.6, 4.6, 2.1 Hz, 1H), 7.17 (t, J=8.7 Hz, 1H), 6.70 (s, 1H), 5.61 (s, 1H), 3.75-3.45 (m, 7H), 3.21 (s, 2H), 3.01 (ddd, J=15.4, 13.1, 4.9 Hz, 2H), 1.27 (t, J=7.0 Hz, 6H).

Intermediate A39H: 2'-(3-Chloro-4-fluorophenyl)-3,3-difluoro-6'H-spiro[cyclobutane-1,7'-pyrazolo[1,5-a]pyrazine]

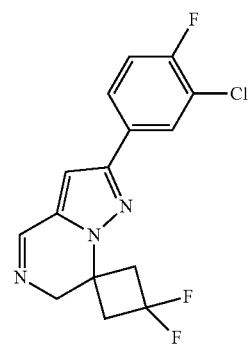 [SMILES: Fc1ccc(-c2cc3n(n2)C2(CN=C3)CC(F)(F)C2)cc1Cl]

To a solution of Intermediate A39G (1.017 g, 2.434 mmol) in THF (24.34 mL) was added a conc. aqueous solution of HCl (0.61 mL, 7.30 mmol). A precipitate formed and the reaction continued to stir at room temperature for 2 h. The solvent was evaporated and the aq. residue was basified with a satd. aq. solution of NaHCO₃ and extracted with EtOAc (3×25 mL). The combined organic layer was washed with brine, dried over anhydrous MgSO₄, filtered and the filtrate was concentrated under reduced pressure to afford crude Intermediate A39H (0.79 g, 100%) as a white solid. MS(ES): m/z=326.0 [M+H]⁺.

Intermediate A39I: 2'-(3-Chloro-4-fluorophenyl)-3,3-difluoro-5',6'-dihydro-4'H-spiro[cyclobutane-1,7'-pyrazolo[1,5-a]pyrazine]

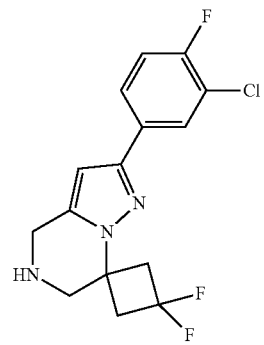 [SMILES: Fc1ccc(-c2cc3n(n2)C2(CNC3)CC(F)(F)C2)cc1Cl]

To a solution of Intermediate A39H (0.79 g, 2.425 mmol) in EtOH (24.25 mL) and THF (24.25 mL) was added NaBH₄ (0.459 g, 12.13 mmol) at room temperature and the reaction mixture was stirred for 16 h. It was diluted with water and extracted with DCM (3×25 mL). The combined organic layer was washed with brine, dried over anhydrous MgSO₄, filtered and the filtrate was concentrated under reduced pressure. It was purified by silica gel chromatography (12 g REDISEP® column, eluting with a gradient of 55 to 100% EtOAc in hexanes). Fractions containing the product were combined and evaporated to afford Intermediate A39I (0.139 g, 17.49%) as a white solid. MS(ES): m/z=328.1 [M+H]⁺.

Intermediate A39J: tert-Butyl 2'-(3-chloro-4-fluorophenyl)-3,3-difluoro-4'H-spiro[cyclobutane-1,7'-pyrazolo[1,5-a]pyrazine]-5'(6'H)-carboxylate

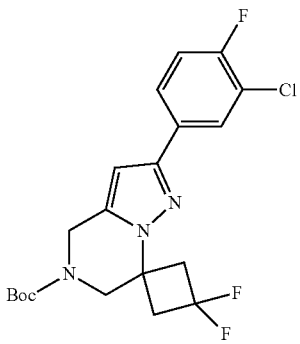 [SMILES: CC(C)(C)OC(=O)N1Cc2cc(-c3ccc(F)c(Cl)c3)nn2C2(C1)CC(F)(F)C2]

To a solution of Intermediate A39I (0.137 g, 0.418 mmol) in DCM (4.18 mL) was added TEA (0.175 mL, 1.254 mmol), DMAP (5.11 mg, 0.042 mmol) and Boc₂O (0.109 g, 0.502 mmol) and the reaction mixture was stirred for 16 h. It was quenched by adding satd. aq. solution of NaHCO₃, the two layers were separated and the aq. layer was extracted with DCM (2×10 mL). The combined organic layer was washed with brine, dried over anhydrous MgSO₄, filtered and the filtrate was concentrated under reduced pressure. It was purified by silica gel chromatography (24 g REDISEP® column, eluting with 21% EtOAc in hexanes). Fractions containing the product were combined and evaporated to afford Intermediate A39J (0.14 g, 78%) as a white solid. MS(ES): m/z=428.1 [M+H]⁺.

Intermediate A39K: tert-Butyl 2'-(3-chloro-4-fluorophenyl)-3,3-difluoro-3'-iodo-4'H-spiro[cyclobutane-1,7'-pyrazolo[1,5-a]pyrazine]-5'(6'H)-carboxylate

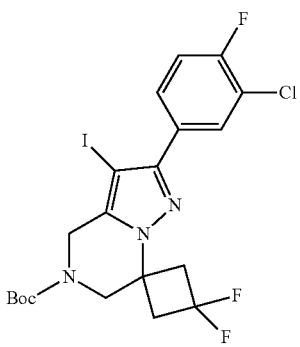 [SMILES: CC(C)(C)OC(=O)N1Cc2c(I)c(-c3ccc(F)c(Cl)c3)nn2C2(C1)CC(F)(F)C2]

To a solution of Intermediate A39J (0.14 g, 0.327 mmol) in DCM (2.62 mL) and MeOH (0.654 mL) was added NIS (0.221 g, 0.982 mmol) and the reaction mixture was continued stirring at room temperature for 3 h. It was then concentrated under reduced pressure and the residue was purified by silica gel chromatography (24 g REDISEP® column, eluting with 18% EtOAc in hexanes). Fractions containing the product were combined and evaporated to afford Intermediate A39K (0.179 g, 100%) as a white foam. MS(ES): m/z=554.0 [M+H]⁺.

Intermediate A39L: tert-Butyl 2'-(3-chloro-4-fluorophenyl)-3'-cyano-3,3-difluoro-4'H-spiro[cyclobutane-1,7'-pyrazolo[1,5-a]pyrazine]-5'(6'H)-carboxylate

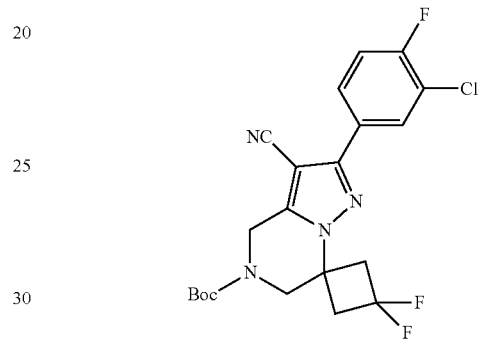

To a degassed solution of Intermediate A39K (0.148 g, 0.267 mmol) in DMF (5.35 mL) was added copper(I) cyanide (0.061 g, 0.668 mmol) and the mixture was degassed again for 5 min. with N₂ and then heated in a sealed tube in an oil bath at 120° C. for 20 h. The reaction mixture was filtered and the filtrate concentrated under reduced pressure to afford a crude residue, which was purified by silica gel chromatography (12 g REDISEP® column, eluting with 30% EtOAc in hexanes). Fractions containing the product were combined and evaporated to afford Intermediate A39L (0.095 g, 52.59%) as an off-white solid. MS(ES): m/z=478.3 [M+Na]⁺.

Intermediate A39M: tert-Butyl 3'-carbamoyl-2'-(3-chloro-4-fluorophenyl)-3,3-difluoro-4'H-spiro[cyclobutane-1,7'-pyrazolo[1,5-a]pyrazine]-5'(6'H)-carboxylate

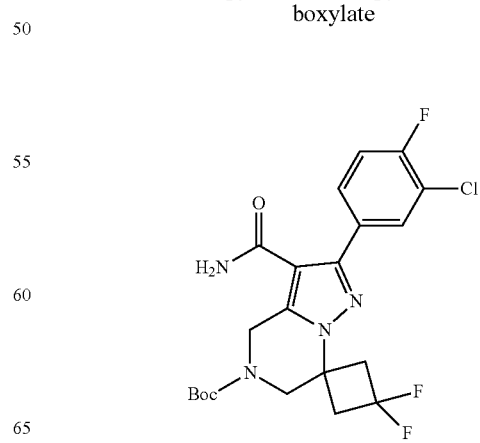

To an ice-cold solution of Intermediate A39L (0.095 g, 0.210 mmol) in DMSO (2.1 mL) was added a 5M aq. solution of KOH (0.21 mL, 1.049 mmol), followed by the dropwise addition of a 30% aq. solution of $H_2O_2$ (0.429 mL, 4.20 mmol). The reaction mixture was stirred at room temperature for 1 h. It was then diluted with water and extracted with EtOAc (2×10 mL). The combined organic layer was washed with brine, dried over anhydrous $MgSO_4$, filtered and the filtrate was concentrated under reduced pressure to give a yellow oil. It was purified by silica gel chromatography (12 g REDISEP® column, eluting with 30% EtOAc in DCM). Fractions containing the product were combined and evaporated to afford Intermediate A39M (0.073 g, 73.9%) as a white solid. MS(ES): m/z=471.1 $[M+H]^+$.

Intermediate A39N: 2'-(3-Chloro-4-fluorophenyl)-3,3-difluoro-5',6'-dihydro-4'H-spiro[cyclobutane-1,7'-pyrazolo[1,5-a]pyrazine]-3'-carboxamide, TFA

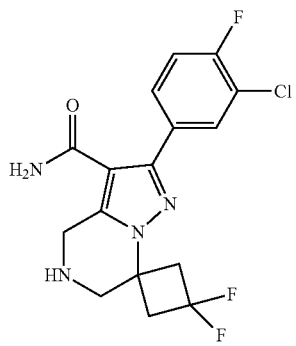 [SMILES: NC(=O)c1c(-c2ccc(F)c(Cl)c2)nn2c1CNCC21CC(F)(F)C1]

To a solution of Intermediate A39M (0.073 g, 0.155 mmol) in DCM (1.55 mL) was added TFA (0.24 mL, 3.10 mmol) and the reaction mixture was continued stirring at room temperature for 2 h. It was then concentrated to dryness and the residue was dried under vacuum for 20 min. to afford crude Intermediate A39N (0.073 g, >99%) as the mono TFA salt.

Compound A39: $N^{5'}$-(tert-Butyl)-2'-(3-chloro-4-fluorophenyl)-3,3-difluoro-4'H-spiro[cyclobutane-1,7'-pyrazolo[1,5-a]pyrazine]-3',5'(6'H)-dicarboxamide

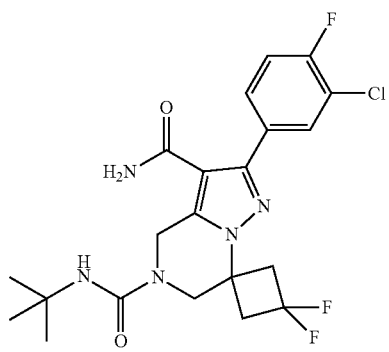 [SMILES: CC(C)(C)NC(=O)N1Cc2c(C(N)=O)c(-c3ccc(F)c(Cl)c3)nn2C2(C1)CC(F)(F)C2]

To a solution of Intermediate A39N (0.037 g, 0.076 mmol) and DIPEA (0.067 mL, 0.382 mmol) in DMF (0.763 mL) was added 2-isocyanato-2-methylpropane (0.018 mL, 0.153 mmol) and the reaction mixture was continued stirring at room temperature for 2 h. It was then purified by preparative HPLC to afford Compound A39 (16 mg, 44.2%). MS(ES): m/z=470.4 $[M+H]^+$; HPLC Ret. Time 1.87 min. and 2.81 min. (HPLC Methods H and I); $^1$H NMR (500 MHz, DMSO-$d_6$) δ ppm 7.83 (d, J=7.0 Hz, 1H), 7.66 (br. s., 1H), 7.45 (t, J=9.0 Hz, 1H), 7.36 (br. s., 1H), 7.27 (br. s., 1H), 6.33 (s, 1H), 4.73 (s, 2H), 4.45-4.30 (m, 2H), 3.32 (d, J=13.6 Hz, 2H), 2.96 (t, J=11.9 Hz, 2H), 1.26 (s, 9H).

Compound A40: 2-(3-Chlorophenyl)-$N^5$-(1-(trifluoromethyl)cyclopropyl)-6,7-dihydropyrazolo[1,5-a]pyrazine-3,5(4H)-dicarboxamide

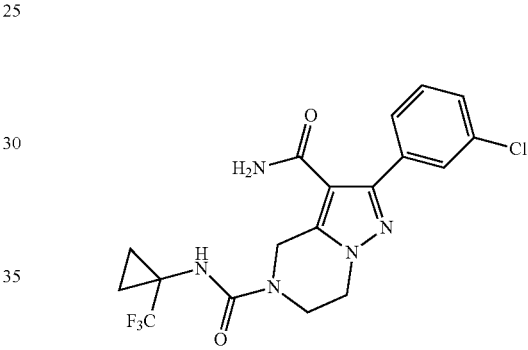

To a solution of 1-(trifluoromethyl)cyclopropanamine (22.60 mg, 0.181 mmol) in THF (2 mL) at 0° C. were added TEA (0.063 mL, 0.452 mmol) and triphosgene (20.11 mg, 0.068 mmol) in THF (2 mL) The suspension was stirred at 0° C. for 30 min. Then a solution of Intermediate 156E in DMF (1 mL) was added. The reaction mixture was stirred at RT overnight. The reaction mixture was quenched with MeOH and concentrated. The residue was dissolved in DMF and purified by preparative HPLC. Fractions containing the desired product were combined and dried under vacuum to afford Compound A40 (29 mg, 75%). MS(ES): m/z=547 $[M+H]^+$; HPLC Ret. Time 1.23 min. and 2.16 min. (HPLC Methods H and I); $^1$H NMR (500 MHz, DMSO-$d_6$) δ ppm 7.56 (s, 1H), 7.49 (d, J=7.0 Hz, 1H), 7.34-7.18 (m, 3H), 7.04 (br. s., 1H), 4.60 (s, 2H), 4.06-3.92 (m, 2H), 3.77-3.65 (m, 2H), 1.13-0.97 (m, 2H), 0.93-0.88 (m., 2H).

The Compounds described in Table 51 were synthesized analogous to Compound A40 using Intermediate 156E and corresponding amines.

TABLE 51

| Ex. No. | Structure | Name | [M + H]+ | Ret Time (min.) | HPLC Method |
|---|---|---|---|---|---|
| A41 | 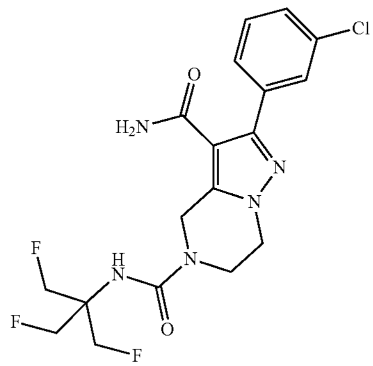 [SMILES: NC(=O)c1c(-c2cccc(Cl)c2)nn2c1CN(C(=O)NC(CF)(CF)CF)CC2] | 2-(3-Chlorophenyl)-N5-(1,3-difluoro-2-(fluoromethyl)propan-2-yl)-6,7-dihydropyrazolo[1,5-a]pyrazine-3,5(4H)-dicarboxamide | 430.1 | 1.44<br>2.12 | H<br>I |
| A42 | 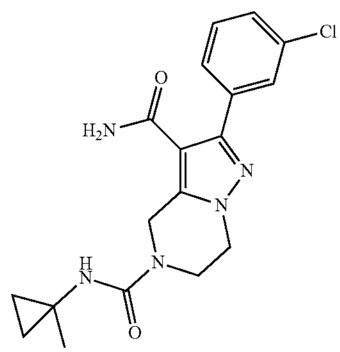 [SMILES: CC1(NC(=O)N2CCn3nc(-c4cccc(Cl)c4)c(C(N)=O)c3C2)CC1] | 2-(3-Chlorophenyl)-N5-(1-methylcyclopropyl)-6,7-dihydropyrazolo[1,5-a]pyrazine-3,5(4H)-dicarboxamide | 374.2 | 1.50<br>2.23 | H<br>I |
| A43 | 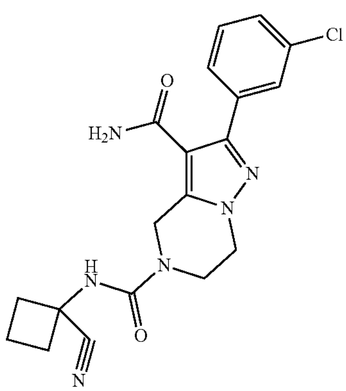 [SMILES: N#CC1(NC(=O)N2CCn3nc(-c4cccc(Cl)c4)c(C(N)=O)c3C2)CCC1] | 2-(3-Chlorophenyl)-N5-(1-cyanocyclobutyl)-6,7-dihydropyrazolo[1,5-a]pyrazine-3,5(4H)-dicarboxamide | 399.2 | 1.43<br>2.15 | H<br>I |
| A44 | 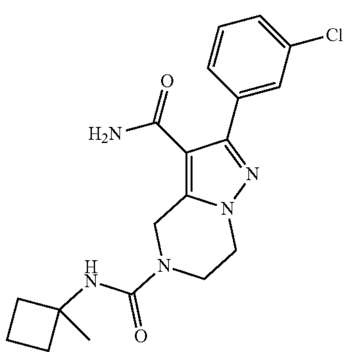 [SMILES: CC1(NC(=O)N2CCn3nc(-c4cccc(Cl)c4)c(C(N)=O)c3C2)CCC1] | 2-(3-Chlorophenyl)-N5-(1-methylcyclobutyl)-6,7-dihydropyrazolo[1,5-a]pyrazine-3,5(4H)-dicarboxamide | 387.1 | 1.54<br>2.42 | H<br>I |

TABLE 51-continued

| Ex. No. | Structure | Name | [M + H]+ | Ret Time (min.) | HPLC Method |
|---|---|---|---|---|---|
| A45 | 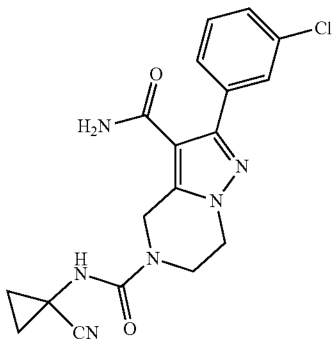 [SMILES: N#CC1(NC(=O)N2CCn3nc(-c4cccc(Cl)c4)c(C(N)=O)c3C2)CC1] | 2-(3-Chlorophenyl)-N⁵-(1-cyanocyclopropyl)-6,7-dihydropyrazolo[1,5-a]pyrazine-3,5(4H)-dicarboxamide | 385.2 | 1.03<br>1.87 | H<br>I |
| A46 | 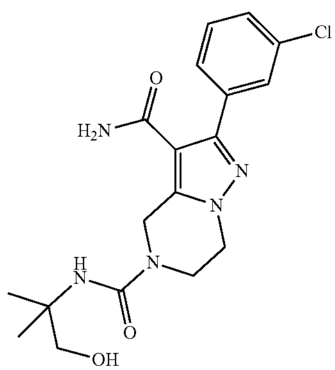 [SMILES: CC(C)(CO)NC(=O)N1CCn2nc(-c3cccc(Cl)c3)c(C(N)=O)c2C1] | 2-(3-Chlorophenyl)-N⁵-(1-hydroxy-2-methylpropan-2-yl)-6,7-dihydropyrazolo[1,5-a]pyrazine-3,5(4H)-dicarboxamide | 392.5 | 1.05<br>2.01 | H<br>I |
| A47 | 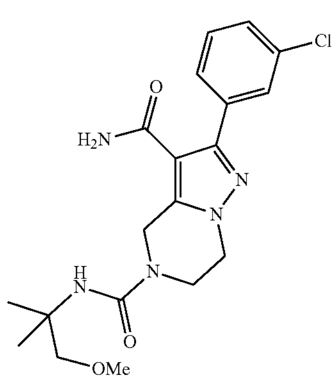 [SMILES: COCC(C)(C)NC(=O)N1CCn2nc(-c3cccc(Cl)c3)c(C(N)=O)c2C1] | 2-(3-Chlorophenyl)-N⁵-(1-methoxy-2-methylpropan-2-yl)-6,7-dihydropyrazolo[1,5-a]pyrazine-3,5(4H)-dicarboxamide | 406.3 | 1.49<br>2.28 | H<br>I |

The Compounds described in Table 52 were synthesized analogous to Compound A40 using Intermediate 185B and corresponding amines.

TABLE 52

| Ex. No. | Structure | Name | [M + H]⁺ | Ret Time (min.) | HPLC Method |
|---|---|---|---|---|---|
| A46 | 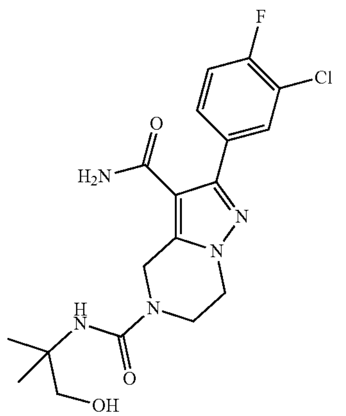 [SMILES: CC(C)(CO)NC(=O)N1CCn2nc(-c3ccc(F)c(Cl)c3)c(C(N)=O)c2C1] | 2-(3-Chloro-4-fluorophenyl)-N⁵-(1-hydroxy-2-methylpropan-2-yl)-6,7-dihydropyrazolo[1,5-a]pyrazine-3,5(4H)-dicarboxamide | 410.1 | 1.18<br>2.10 | H<br>I |
| A49 | 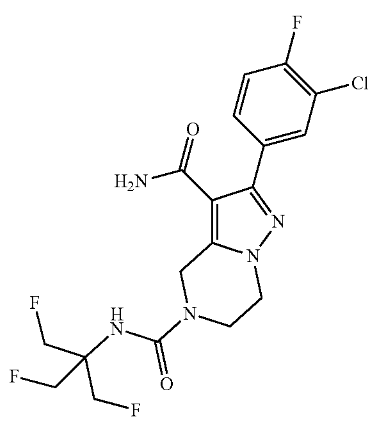 [SMILES: NC(=O)c1c(-c2ccc(F)c(Cl)c2)nn2c1CN(C(=O)NC(CF)(CF)CF)CC2] | 2-(3-Chloro-4-fluorophenyl)-N⁵-(1,3-difluoro-2-(fluoromethyl)propan-2-yl)-6,7-dihydropyrazolo[1,5-a]pyrazine-3,5(4H)-dicarboxamide | 448.1 | 1.39<br>2.17 | H<br>I |
| A50 | 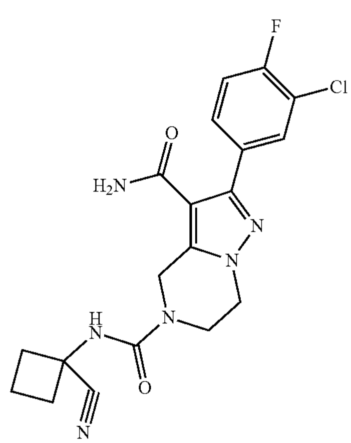 [SMILES: N#CC1(NC(=O)N2CCn3nc(-c4ccc(F)c(Cl)c4)c(C(N)=O)c3C2)CCC1] | 2-(3-Chloro-4-fluorophenyl)-N⁵-(1-cyanocyclopropyl)-6,7-dihydropyrazolo[1,5-a]pyrazine-3,5(4H)-dicarboxamide | 479.1 | 1.56<br>2.36 | H<br>I |

Scheme 72

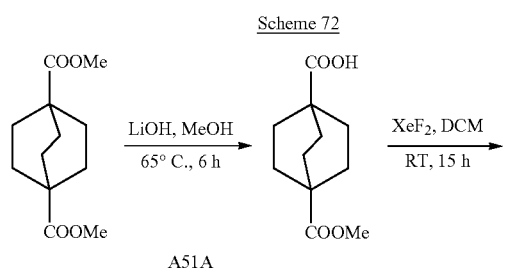

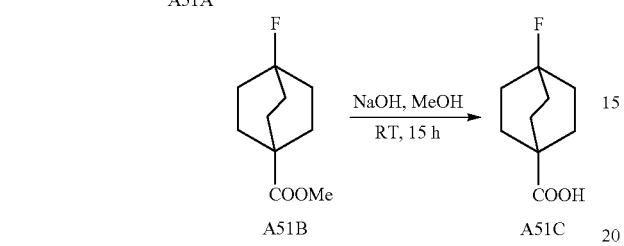

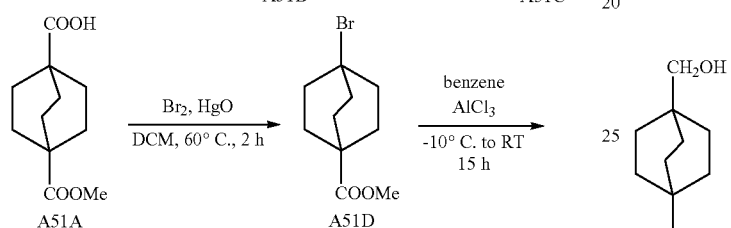

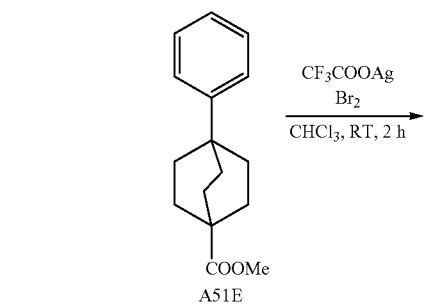

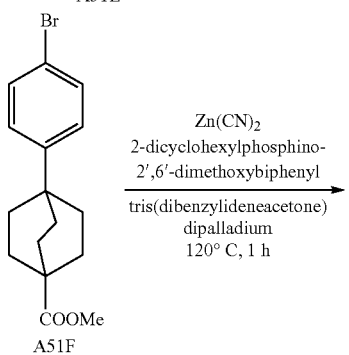

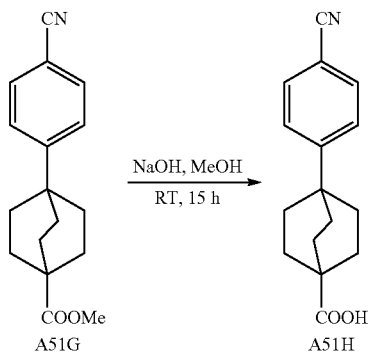

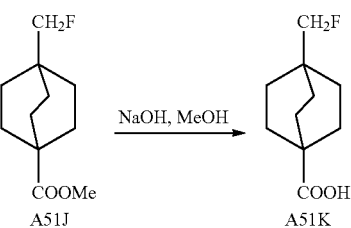

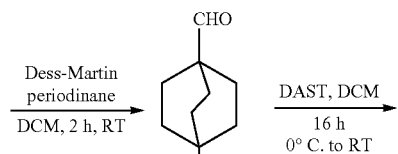

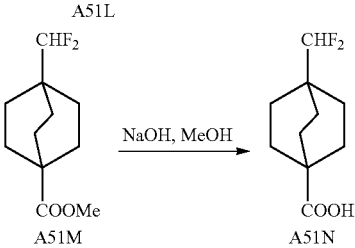

Intermediate A51A: 4-(Methoxycarbonyl)bicyclo[2.2.2]octane-1-carboxylic acid

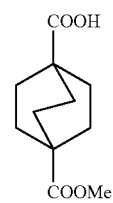 [SMILES: COC(=O)C12CCC(C(=O)O)(CC1)CC2]

To a solution of dimethyl bicyclo[2.2.2]octane-1,4-dicarboxylate (0.92 g, 4.07 mmol) in MeOH (5 mL) was added LiOH (0.102 g, 4.27 mmol) in water (4 mL) at RT. The reaction mixture was heated at 65° C. for 6 h. It was then cooled to RT and concentrated. The residue was acidified with 1N HCl to pH ~2. The solid (presumed side product diacid) was removed by filtration. The filtrate was extracted with EtOAc, and the combined organic layer was washed with brine, dried over $Na_2SO_4$, and filtered. The filtrate was concentrated to afford Intermediate A51A as a white solid, which was used for the next step without further purification.

MS(ES): m/z=213 [M+H]+; 1H NMR (400 MHz, DMSO-d6) δ ppm 12.11 (s, 1H), 3.66 (s, 3H), 1.78-1.58 (m, 1H).

Intermediate A51B: Methyl 4-fluorobicyclo[2.2.2]octane-1-carboxylate

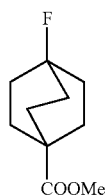 [SMILES: COC(=O)C12CCC(F)(CC1)CC2]

To a suspension of Intermediate A5IA (227 mg, 1.070 mmol) in CH2Cl2 (4 mL) was added difluoroxenon (272 mg, 1.604 mmol). The suspension was stirred at RT overnight. The reaction mixture was concentrated and the residue was purified by silica gel chromatography (40 g REDISEP® column, eluting with 0-20% EtOAc in hexane). Fractions containing the product were combined and evaporated to afford Intermediate A51B (80 mg, 40.2%). 1H NMR (400 MHz, chloroform-d) δ ppm 3.66 (s, 3H), 2.05-1.94 (m, 6H), 1.90-1.79 (m, 6H).

Intermediate A51C: 4-Fluorobicyclo[2.2.2]octane-1-carboxylic acid

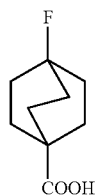

To a solution of Intermediate A51B (80 mg, 0.430 mmol) in MeOH (2 mL) was added 1M solution of NaOH (1 mL, 1.00 mmol) dropwise. The reaction mixture was stirred at RT overnight and concentrated. The residue was acidified with 1N HCl to pH ~2, extracted with EtOAc. The combined organic layer was washed with brine, dried over Na2SO4, and filtered. The filtrate was concentrated to afford Intermediate A51C (66 mg, 89%) as a white solid, which was used for the next step without further purification. 1H NMR (400 MHz, methanol-d4) δ ppm 2.10-1.95 (m, 6H), 1.90-1.78 (m, 6H).

Intermediate A51D: Methyl 4-bromobicyclo[2.2.2]octane-1-carboxylate

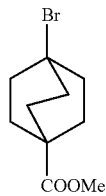 [SMILES: COC(=O)C12CCC(Br)(CC1)CC2]

To a solution of Intermediate A51A (1.5 g, 7.07 mmol) in CH2Cl2 was added mercury(II) oxide (2.60 g, 12.01 mmol). The suspension was heated at reflux condition. To the reaction mixture was added a solution of bromine (0.473 ml, 9.19 mmol) in CH2Cl2 (5 mL) dropwise under refluxing. The reaction mixture was heated at reflux for 1.5 h and cooled to RT. It was passed through a pad of CELITE®, washed with EtOAc. The filtrate was concentrated. The residue was purified by silica gel chromatography (40 g REDISEP® column, eluting with 0-30% EtOAc in hexane. Fractions containing the product were combined and evaporated to afford Intermediate A51D (1.2 g, 68.7%). 1H NMR (400 MHz, chloroform-d) δ ppm 3.65 (s, 3H), 2.35-2.19 (m, 6H), 2.04-1.90 (m, 6H).

Intermediate A51E: Methyl 4-phenylbicyclo[2.2.2]octane-1-carboxylate

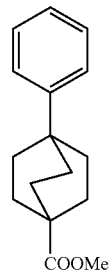

To a suspension of aluminum trichloride (809 mg, 6.07 mmol) in benzene (4 mL, 1.214 mmol) at −10° C. was added a solution of Intermediate A51D (300 mg, 1.214 mmol) in benzene (2 mL) under nitrogen. The reaction mixture was gradually warmed up to RT and stirred overnight. It was carefully poured into ice water, extracted with EtOAc. The combined organic layer was washed with brine, dried over Na2SO4, and filtered. The filtrate was concentrated to afford Intermediate A51E (250 mg, 84%) as a tan solid, which was used for the next step without further purification. MS(ES): m/z=245 [M+H]+; 1H NMR (400 MHz, chloroform-d) δ ppm 7.42-7.29 (m, 4H), 7.29-7.16 (m, 1H), 3.77-3.65 (s, 3H), 2.07-1.80 (m, 1H).

Intermediate A51F: Methyl 4-(4-bromophenyl)bicyclo[2.2.2]octane-1-carboxylate

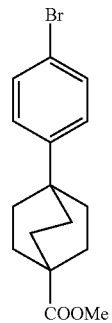

To a suspension of Intermediate A51E (330 mg, 1.351 mmol) and silver trifluoroacetate (350 mg, 1.585 mmol) in CHCl$_3$ (15 mL) was added Br$_2$ (0.073 mL, 1.418 mmol) in CHCl$_3$ (2 mL) The reaction mixture was stirred at RT for 2 h. The reaction mixture was passed through a pad of CELITE® and washed with CH$_2$Cl$_2$. The filtrate was concentrated and the residue was purified by silica gel chromatography (40 g REDISEP® column, eluting with 0-30% EtOAc in hexane). Fractions containing the product were combined and evaporated to afford Intermediate A51F (310 mg, 71%). MS(ES): m/z=323 [M+H]$^+$; $^1$H NMR (400 MHz, chloroform-d) δ ppm 7.46-7.35 (m, J=8.5 Hz, 2H), 7.25-7.15 (m, J=8.5 Hz, 2H), 2.02-1.89 (m, 6H), 1.89-1.78 (m, 6H).

Intermediate A51G: Methyl 4-(4-cyanophenyl)bicyclo[2.2.2]octane-1-carboxylate

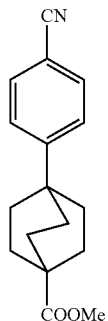 [SMILES: COC(=O)C12CCC(c3ccc(C#N)cc3)(CC1)CC2]

To a microwave vial were added Intermediate A51F (101 mg, 0.312 mmol), dicyanozinc (55.0 mg, 0.469 mmol), 2-dicyclohexylphosphino-2',6'-dimethoxybiphenyl (25.7 mg, 0.062 mmol), DMF (3 mL), and two drops of water. Nitrogen was bubbled into the reaction mixture for 2 min To this mixture was added tris(dibenzylideneacetone)dipalladium (0) (28.6 mg, 0.031 mmol) and nitrogen was bubbled for another 2 min. The reaction mixture was heated at 120° C. in microwave for 1 h. The reaction mixture was diluted with water and extracted with EtOAc. The combined organic layer was washed with brine, dried over Na$_2$SO$_4$, and filtered. The filtrate was concentrated. The crude product was purified by silica gel chromatography (40 g REDISEP® column, eluting with 0-20% EtOAc in hexane). Fractions containing the product were combined and evaporated to afford Intermediate A51G (70 mg, 83%). MS(ES): m/z=270 [M+H]$^+$; $^1$H NMR (400 MHz, chloroform-d) δ ppm 7.68-7.54 (m, J=8.5 Hz, 2H), 7.48-7.36 (m, J=8.8 Hz, 2H), 3.70 (s, 3H), 2.00-1.82 (m, 12H).

Intermediate A51H: 4-(4-Cyanophenyl)bicyclo[2.2.2]octane-1-carboxylic acid

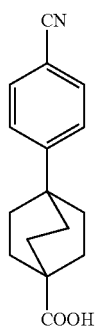 [SMILES: N#Cc1ccc(C23CCC(C(=O)O)(CC2)CC3)cc1]

Intermediate A51H was prepared analogous to Intermediate A51C by reacting Intermediate A51G with sodium hydroxide. (ES): m/z=247 [M–H]$^+$; HPLC Ret. Time 1.59 min.

Intermediate A51I: Methyl 4-(hydroxymethyl)bicyclo[2.2.2]octane-1-carboxylate

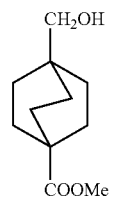 [SMILES: COC(=O)C12CCC(CO)(CC1)CC2]

To a solution of Intermediate A51A (1.0531 g, 4.96 mmol) in THF (40 mL) at 0° C. were added TEA (1.729 mL, 12.40 mmol) and ethyl carbonochloridate (1.131 g, 10.42 mmol) in THF (2 mL) dropwise. The reaction mixture became a suspension (Et$_3$N HCl salt). The reaction mixture was stirred at 0° C. for 30 min. The suspension was filtered and washed with THF. The filtrate was added to a suspension of sodium borohydride (0.751 g, 19.85 mmol) in water (2 mL) at 0° C. The reaction mixture was stirred at RT for 1 h. The reaction mixture partitioned with EtOAc and water. The organic layer was washed with brine, dried over Na$_2$SO$_4$, and filtered. The filtrate was concentrated. The residue was purified by silica gel chromatography (40 g REDISEP® column, eluting with 10-50% EtOAc in hexane). Fractions containing the product were combined and evaporated to afford Intermediate A51I (0.9 g, 91%). (ES): m/z=199 [M+H]$^+$; $^1$H NMR (400 MHz, chloroform-d) δ ppm 3.66 (s, 3H), 3.30 (s, 2H), 1.91-1.73 (m, 6H), 1.52-1.41 (m, 6H).

Intermediate A51J: Methyl 4-(fluoromethyl)bicyclo[2.2.2]octane-1-carboxylate

To a solution of Intermediate A51I (306 mg, 1.543 mmol) in CH$_2$Cl$_2$ (5 mL) at −78° C. under nitrogen was added DAST (0.245 mL, 1.852 mmol). The reaction mixture was stirred at RT for 3 h. The reaction mixture was cooled to 0° C. and carefully quenched with a saturated solution of NaHCO$_3$. The layers were separated. The aqueous layer was extracted with CH$_2$Cl$_2$. The combined organic layer was washed with brine, dried over Na$_2$SO$_4$, and filtered. The filtrate was concentrated. The residue was purified by silica gel chromatography (40 g REDISEP® column, eluting with 10-50% EtOAc in hexane). Fractions containing the product were combined and evaporated to afford Intermediate A51J (130 mg, 42%). $^1$H NMR (400 MHz, chloroform-d) δ ppm 3.66 (s, 3H), 2.15-1.95 (m, 4H), 1.94-1.22 (m, 1H).

Intermediate A51K: 4-(Fluoromethyl)bicyclo[2.2.2]octane-1-carboxylic acid

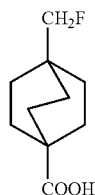

To a solution of Intermediate A51J (70 mg, 0.353 mmol) in MeOH was added 1M solution of NaOH (1 mL, 1.00 mmol). The reaction mixture was stirred at RT overnight. It was concentrated. The residue was diluted with water, acidified with 1N HCl to pH ~2, and extracted with EtOAc. The combined organic layer was washed with brine, dried over Na$_2$SO$_4$, and filtered. The filtrate was concentrated to afford Intermediate A51K as a white solid, which was used for the next step without further purification. $^1$H NMR (400 MHz, CDCl$_3$) δ ppm 2.45-1.46 (m, 14H).

Intermediate A51L: Methyl 4-formylbicyclo[2.2.2]octane-1-carboxylate

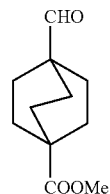 [SMILES: COC(=O)C12CCC(C=O)(CC1)CC2]

To a solution of Intermediate A51I (540 mg, 2.72 mmol) in CH$_2$Cl$_2$ (20 mL) was added Dess-Martin periodinane (1502 mg, 3.54 mmol). The reaction mixture was stirred at RT overnight. The reaction mixture was cooled to 0° C. and carefully quenched with a solution of NaHCO$_3$. The layers were separated. The aqueous layer was extracted with CH$_2$Cl$_2$. The combined organic layer was washed with brine, dried over Na$_2$SO$_4$, and filtered. The filtrate was concentrated. The residue was purified by silica gel chromatography (40 g REDISEP® column, eluting with 10-50% EtOAc in hexane). Fractions containing the product were combined and evaporated to afford Intermediate A51L (400 mg, 74.8%). (ES): m/z=199 [M+H]$^+$; $^1$H NMR (400 MHz, chloroform-d) δ ppm 9.48 (s, 1H), 3.68 (s, 3H), 1.94-1.78 (m, 6H), 1.78-1.61 (m, 6H).

Intermediate A51M: Methyl 4-(difluoromethyl)bicyclo[2.2.2]octane-1-carboxylate

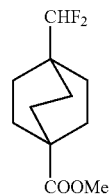 [SMILES: COC(=O)C12CCC(C(F)F)(CC1)CC2]

To a solution of Intermediate A51L (400 mg, 2.038 mmol) at 0° C. in CH$_2$Cl$_2$ (8 mL) was added DAST (0.673 mL, 5.10 mmol). The reaction mixture was stirred at RT overnight. The reaction mixture was cooled to 0° C. and carefully quenched with a solution of NaHCO$_3$. The layers were separated. The aqueous layer was extracted with CH$_2$Cl$_2$. The combined organic layer was washed with brine, dried over Na$_2$SO$_4$, and filtered. The filtrate was concentrated. The residue was purified by silica gel chromatography (40 g REDISEP® column, eluting with 0-20% EtOAc in hexane). Fractions containing the product were combined and evaporated to afford Intermediate A51M (280 mg, 62.9%). MS(ES): m/z=199 [M+H]$^+$; $^1$H NMR (400 MHz, chloroform-d) δ ppm 5.54-5.26 (m, 1H), 3.68 (s, 3H), 1.89-1.76 (m, 6H), 1.65-1.50 (m, 6H).

Intermediate A51N: 4-(Difluoromethyl)bicyclo[2.2.2]octane-1-carboxylic acid

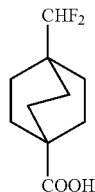

Intermediate A51N was prepared analogous to Intermediate A51C by reacting Intermediate A51M with sodium hydroxide. (ES): m/z=205 [M+H]$^+$.

Scheme 73

NMR (400 MHz, chloroform-d) δ ppm 4.30-4.13 (m, 2H), 3.22 (s, 3H), 2.32-1.20 (m, 1H).

Intermediate A51P: 2,2-Difluoro-4-methoxybicyclo[2.2.2]octane-1-carboxylic acid

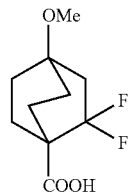

Intermediate A51P was prepared analogous to Intermediate A51C by reacting Intermediate A51O with sodium hydroxide. $^1$H NMR (400 MHz, chloroform-d) δ 3.22 (s, 3H), 2.32-1.20 (m, 1H).

Compound A51: 2-(3-Chloro-4-fluorophenyl)-N$^5$-(4-(4-cyanophenyl)bicyclo[2.2.2]octan-1-yl)-6,7-dihydropyrazolo[1,5-a]pyrazine-3,5(4H)-dicarboxamide

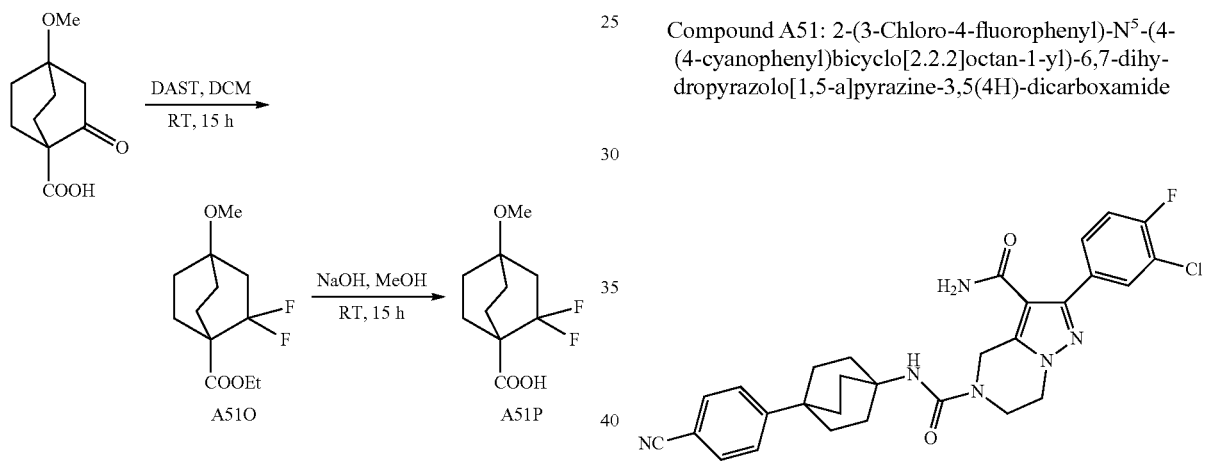

Intermediate A51O: Ethyl 2,2-difluoro-4-methoxybicyclo[2.2.2]octane-1-carboxylate

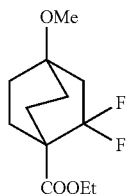

CH$_2$Cl$_2$, followed by addition of three drops of EtOH (0.077 mL, 1.326 mmol). The reaction mixture was stirred at rt for 3 h and then heat at 60° C. overnight. More DEOXO-FLUOR® (1.956 ml, 10.61 mmol) was added and the reaction mixture was heated at 60° C. for another 16 h. It was carefully quenched with a solution of NaHCO$_3$ at 0° C. The reaction mixture was extracted with CH$_2$Cl$_2$. The combined organic layer was washed with brine, dried over Na$_2$SO$_4$, and filtered. The filtrate was concentrated. The residue was purified by silica gel chromatography (40 g REDISEP® column, eluting with 10-55% EtOAc in hexane). Fractions containing the product were combined and evaporated to afford Intermediate A51T (600 mg, 55%). $^1$H To a solution of Intermediate A51K (45 mg, 0.176 mmol) in toluene (6 mL) were added TEA (0.11 mL, 0.75 mmol) and diphenyl phosphorazidate (73 mg, 0.265 mmol). The reaction mixture was heated at 90° C. for 2 h and cooled to RT. A solution of 2-(3-chloro-4-fluorophenyl)-4,5,6,7-tetrahydropyrazolo[1,5-a]pyrazine-3-carboxamide (25 mg, 0.085 mmol) in DMF (1 mL) was then added to the above reaction mixture. The reaction mixture was stirred at RT overnight and concentrated. The residue was purified by preparative HPLC. Fractions containing the desired product were combined and dried under vacuum to afford Compound A51 (24.5 mg, 54.7%). MS(ES): m/z=547 [M+H]$^+$; HPLC Ret. Time 1.83 min. and 2.76 min. (HPLC Methods H and I); $^1$H NMR (500 MHz, DMSO-d$_6$) δ ppm 7.85 (d, J=7.0 Hz, 1H), 7.77-7.62 (m, 3H), 7.55 (d, J=8.4 Hz, 2H), 7.46 (t, J=9.0 Hz, 1H), 7.35 (br. s., 1H), 7.21 (br. s., 1H), 4.69 (s, 2H), 4.12 (t, J=5.1 Hz, 2H), 3.81 (t, J=5.1 Hz, 2H), 2.02-1.91 (m, 6H), 1.91-1.79 (m, 6H).

The Compounds described in Table 53 were synthesized analogous to Compound A51 using 2-(3-chloro-4-fluorophenyl)-4,5,6,7-tetrahydropyrazolo[1,5-a]pyrazine-3-carboxamide and corresponding acids.

TABLE 53

| Ex. No. | Structure | Name | [M + H]+ | Ret Time (min.) | HPLC Method |
|---|---|---|---|---|---|
| A52 | 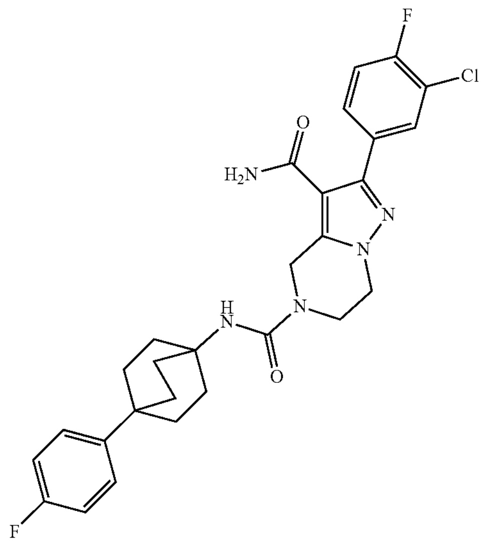 [SMILES: NC(=O)c1c(-c2ccc(F)c(Cl)c2)nn2c1CN(C(=O)NC13CCC(c4ccc(F)cc4)(CC1)CC3)CC2] | 2-(3-Chloro-4-fluorophenyl)-N$^5$-(4-(4-fluorophenyl)bicyclo[2.2.2]octan-1-yl)-6,7-dihydropyrazolo[1,5-a]pyrazine-3,5(4H)-dicarboxamide | 540.4 | 1.93 2.91 | H I |
| A53 | 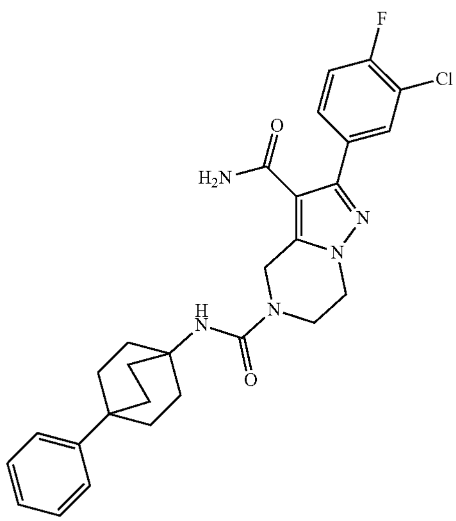 [SMILES: NC(=O)c1c(-c2ccc(F)c(Cl)c2)nn2c1CN(C(=O)NC13CCC(c4ccccc4)(CC1)CC3)CC2] | 2-(3-Chloro-4-fluorophenyl)-N$^5$-(4-phenylbicyclo[2.2.2]octan-1-yl)-6,7-dihydropyrazolo[1,5-a]pyrazine-3,5(4H)-dicarboxamide | 522.5 | 2.90 1.92 | H I |
| A54 | 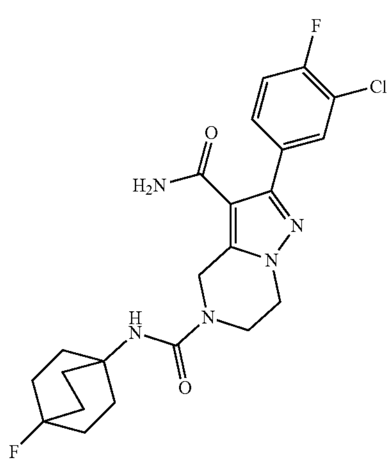 [SMILES: NC(=O)c1c(-c2ccc(F)c(Cl)c2)nn2c1CN(C(=O)NC13CCC(F)(CC1)CC3)CC2] | 2-(3-Chloro-4-fluorophenyl)-N$^5$-(4-fluorobicyclo[2.2.2]octan-1-yl)-6,7-dihydropyrazolo[1,5-a]pyrazine-3,5(4H)-dicarboxamide | 464.3 | 1.49 2.45 | H I |

TABLE 53-continued

| Ex. No. | Structure | Name | [M + H]+ | Ret Time (min.) | HPLC Method |
|---|---|---|---|---|---|
| A55 | 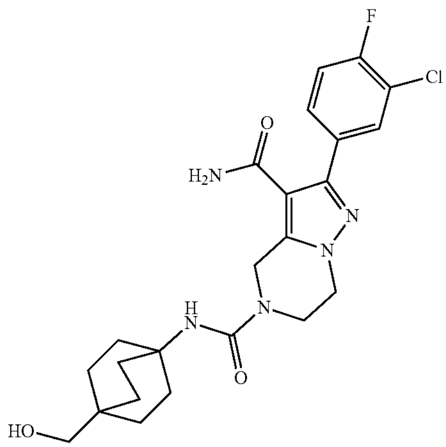 [SMILES: NC(=O)c1c(-c2ccc(F)c(Cl)c2)nn2c1CN(C(=O)NC13CCC(CO)(CC1)CC3)CC2] | 2-(3-Chloro-4-fluorophenyl)-N5-(4-(hydroxymethyl)bicyclo[2.2.2]octan-1-yl)-6,7-dihydropyrazolo[1,5-a]pyrazine-3,5(4H)-dicarboxamide | 475.9 | 1.28<br>2.46 | H<br>I |
| A56 | 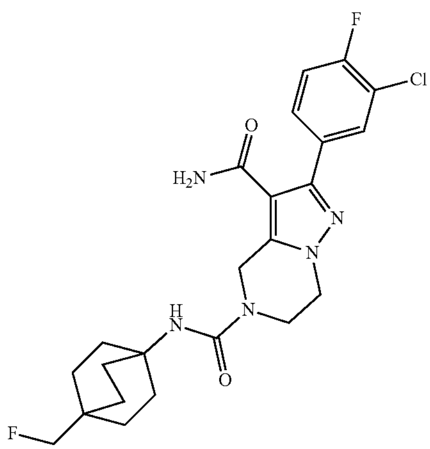 [SMILES: NC(=O)c1c(-c2ccc(F)c(Cl)c2)nn2c1CN(C(=O)NC13CCC(CF)(CC1)CC3)CC2] | 2-(3-Chloro-4-fluorophenyl)-N5-(4-(fluoromethyl)bicyclo[2.2.2]octan-1-yl)-6,7-dihydropyrazolo[1,5-a]pyrazine-3,5(4H)-dicarboxamide | 478.3 | 1.49<br>2.50 | H<br>I |
| A57 | 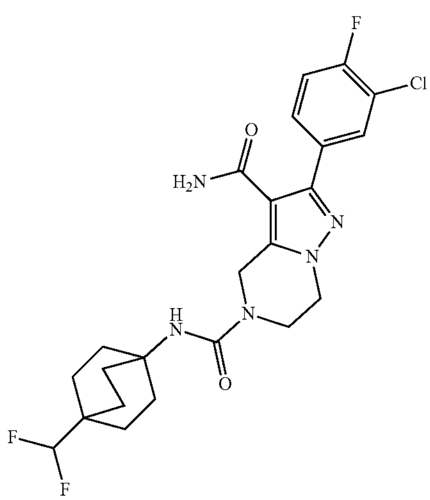 [SMILES: NC(=O)c1c(-c2ccc(F)c(Cl)c2)nn2c1CN(C(=O)NC13CCC(C(F)F)(CC1)CC3)CC2] | 2-(3-Chloro-4-fluorophenyl)-N5-(4-(difluoromethyl)bicyclo[2.2.2]octan-1-yl)-6,7-dihydropyrazolo[1,5-a]pyrazine-3,5(4H)-dicarboxamide | 496.3 | 1.58<br>2.55 | H<br>I |

TABLE 53-continued

| Ex. No. | Structure | Name | [M + H]+ | Ret Time (min.) | HPLC Method |
|---|---|---|---|---|---|
| A58 | 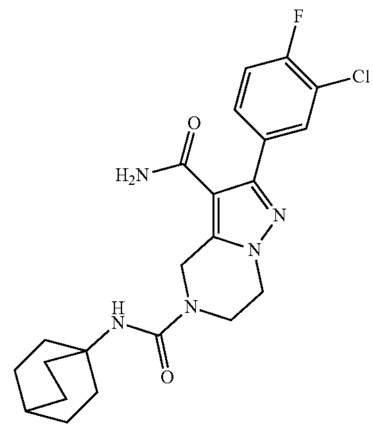 [SMILES: NC(=O)c1c(-c2ccc(F)c(Cl)c2)nn2c1CN(C(=O)NC13CCC(CC1)CC3)CC2] | N5-(Bicyclo[2.2.2]octan-1-yl)-2-(3-chloro-4-fluorophenyl)-6,7-dihydropyrazolo[1,5-a]pyrazine-3,5(4H)-dicarboxamide | 446.3 | 1.80<br>2.61 | H<br>I |
| A59 | 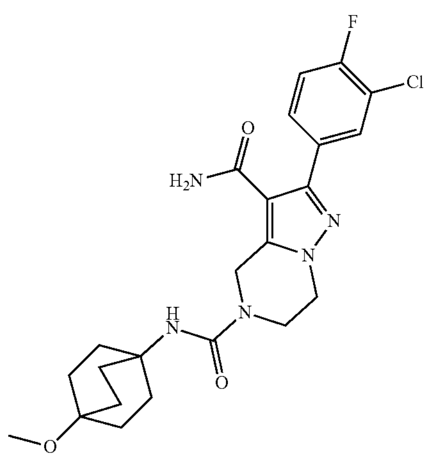 [SMILES: COC12CCC(NC(=O)N3CCn4nc(-c5ccc(F)c(Cl)c5)c(C(N)=O)c4C3)(CC1)CC2] | 2-(3-Chloro-4-fluorophenyl)-N5-(4-methoxybicyclo[2.2.2]octan-1-yl)-6,7-dihydropyrazolo[1,5-a]pyrazine-3,5(4H)-dicarboxamide | 476.3 | 1.48<br>2.12 | H<br>I |
| A60 | 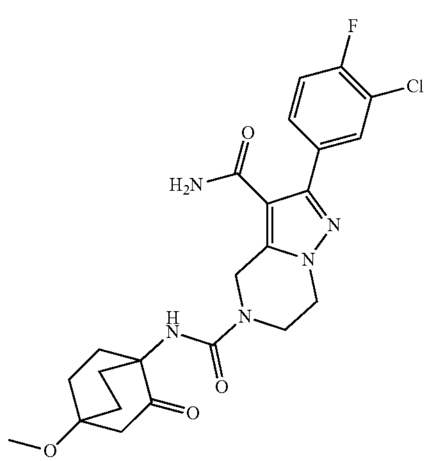 [SMILES: COC12CCC(NC(=O)N3CCn4nc(-c5ccc(F)c(Cl)c5)c(C(N)=O)c4C3)(CC1)C(=O)C2] | 2-(3-Chloro-4-fluorophenyl)-N5-(4-methoxy-2-oxobicyclo[2.2.2]octan-1-yl)-6,7-dihydropyrazolo[1,5-a]pyrazine-3,5(4H)-dicarboxamide | 490.3 | 1.20<br>2.11 | H<br>I |

TABLE 53-continued

| Ex. No. | Structure | Name | [M + H]+ | Ret Time (min.) | HPLC Method |
|---|---|---|---|---|---|
| A61 | 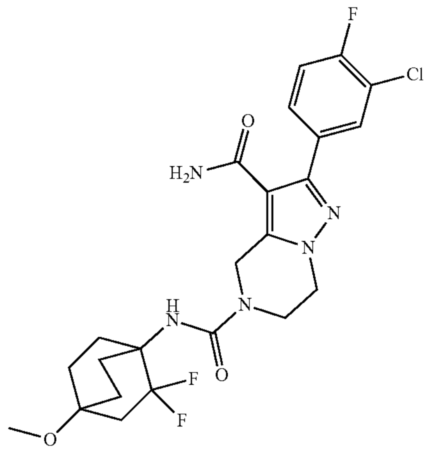 [SMILES: COC12CCC(NC(=O)N3CCn4nc(-c5ccc(F)c(Cl)c5)c(C(N)=O)c4C3)(CC1)C(F)(F)C2] | 2-(3-Chloro-4-fluorophenyl)-N5-(2,2-difluoro-4-methoxybicyclo[2.2.2]octan-1-yl)-6,7-dihydropyrazolo[1,5-a]pyrazine-3,5(4H)-dicarboxamide | 512.3 | 2.31<br>1.64 | H<br>I |
| A62 | 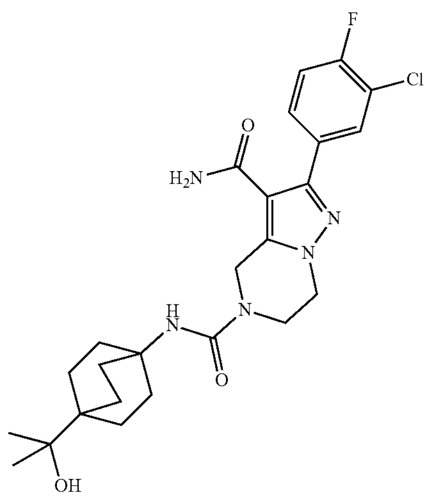 [SMILES: CC(C)(O)C12CCC(NC(=O)N3CCn4nc(-c5ccc(F)c(Cl)c5)c(C(N)=O)c4C3)(CC1)CC2] | 2-(3-Chloro-4-fluorophenyl)-N5-(4-(2-hydroxypropan-2-yl)bicyclo[2.2.2]octan-1-yl)-6,7-dihydropyrazolo[1,5-a]pyrazine-3,5(4H)-dicarboxamide | 504.4 | 2.45<br>2.93 | H<br>I |
| A63 | 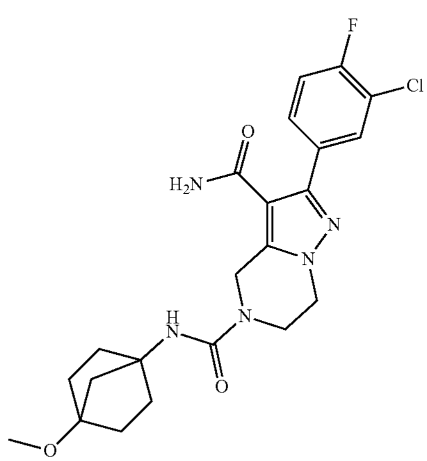 [SMILES: COC12CCC(NC(=O)N3CCn4nc(-c5ccc(F)c(Cl)c5)c(C(N)=O)c4C3)(CC1)C2] | 2-(3-Chloro-4-fluorophenyl)-N5-(4-methoxybicyclo[2.2.1]heptan-1-yl)-6,7-dihydropyrazolo[1,5-a]pyrazine-3,5(4H)-dicarboxamide | 462.4 | 1.30<br>2.29 | H<br>I |

TABLE 53-continued

| Ex. No. | Structure | Name | [M + H]+ | Ret Time (min.) | HPLC Method |
|---|---|---|---|---|---|
| A64 | 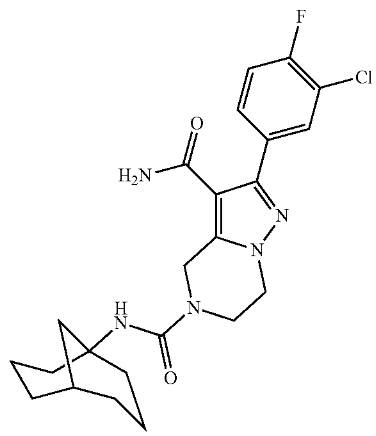 [SMILES: NC(=O)c1c(-c2ccc(F)c(Cl)c2)nn2c1CN(C(=O)NC13CCCC(CCC1)C3)CC2] | N5-((1r,5r)-Bicyclo[3.3.1]nonan-1-yl)-2-(3-chloro-4-fluorophenyl)-6,7-dihydropyrazolo[1,5-a]pyrazine-3,5(4H)-dicarboxamide | 460.4 | 1.76<br>2.77 | H<br>I |
| A65 | 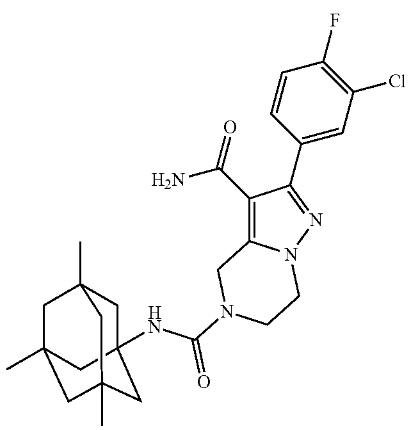 [SMILES: CC12CC3(C)CC(C)(C1)CC(NC(=O)N1CCn4nc(-c5ccc(F)c(Cl)c5)c(C(N)=O)c4C1)(C2)C3] | 2-(3-Chloro-4-fluorophenyl)-N5-((3s,5s,7s)-3,5,7-trimethyladamantan-1-yl)-6,7-dihydropyrazolo[1,5-a]pyrazine-3,5(4H)-dicarboxamide | 514.5 | 2.18<br>3.15 | H<br>I |
| A66 | 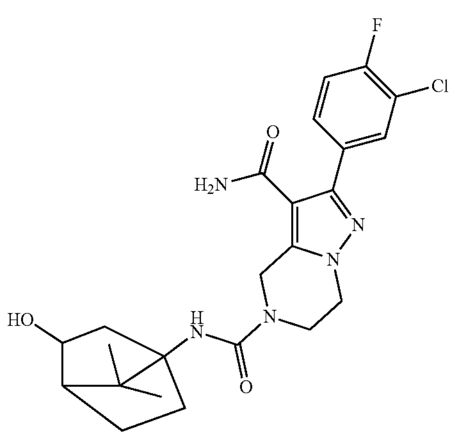 [SMILES: CC1(C)C2CCC1(NC(=O)N1CCn3nc(-c4ccc(F)c(Cl)c4)c(C(N)=O)c3C1)CC2O] | 2-(3-Chloro-4-fluorophenyl)-N5-(3-hydroxy-7,7-dimethylbicyclo[2.2.1]heptan-1-yl)-6,7-dihydropyrazolo[1,5-a]pyrazine-3,5(4H)-dicarboxamide | 490.2 | 1.50<br>2.47 | H<br>I |

TABLE 53-continued

| Ex. No. | Structure | Name | [M + H]+ | Ret Time (min.) | HPLC Method |
|---|---|---|---|---|---|
| A67 | 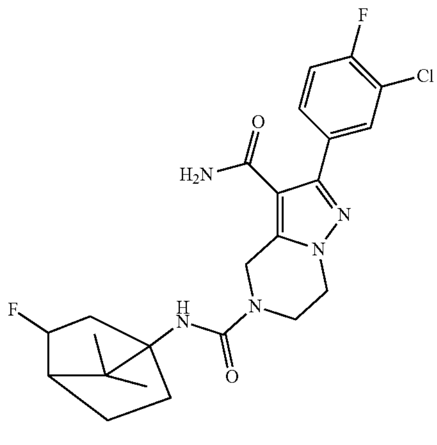 [SMILES: CC1(C)C2CCC1(NC(=O)N1CCn3nc(-c4ccc(F)c(Cl)c4)c(C(N)=O)c3C1)CC2F] | 2-(3-Chloro-4-fluorophenyl)-N5-(3-fluoro-7,7-dimethylbicyclo[2.2.1]heptan-1-yl)-6,7-dihydropyrazolo[1,5-a]pyrazine-3,5(4H)-dicarboxamide | 492.2 | 1.74 2.66 | H I |
| A68 | 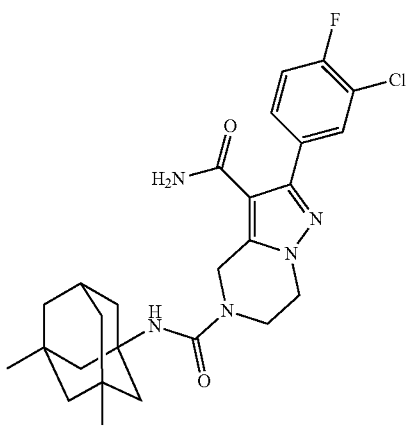 [SMILES: CC12CC3CC(C)(C1)CC(NC(=O)N1CCn4nc(-c5ccc(F)c(Cl)c5)c(C(N)=O)c4C1)(C3)C2] | 2-(3-Chloro-4-fluorophenyl)-N5-((1r,3R,5S,7r)-3,5-dimethyladamantan-1-yl)-6,7-dihydropyrazolo[1,5-a]pyrazine-3,5(4H)-dicarboxamide | 500.4 | 2.02 3.00 | H I |
| A69 | 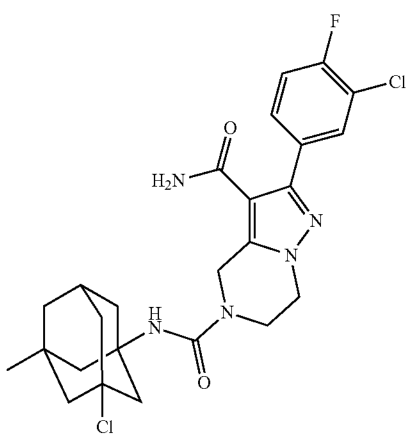 [SMILES: CC12CC3CC(Cl)(C1)CC(NC(=O)N1CCn4nc(-c5ccc(F)c(Cl)c5)c(C(N)=O)c4C1)(C3)C2] | 2-(3-Chloro-4-fluorophenyl)-N5-((1S,3R,5S,7R)-3-chloro-5-methyladamantan-1-yl)-6,7-dihydropyrazolo[1,5-a]pyrazine-3,5(4H)-dicarboxamide | 506.4 | 1.77 2.74 | H I |

TABLE 53-continued

| Ex. No. | Structure | Name | [M + H]+ | Ret Time (min.) | HPLC Method |
|---|---|---|---|---|---|
| A70 | 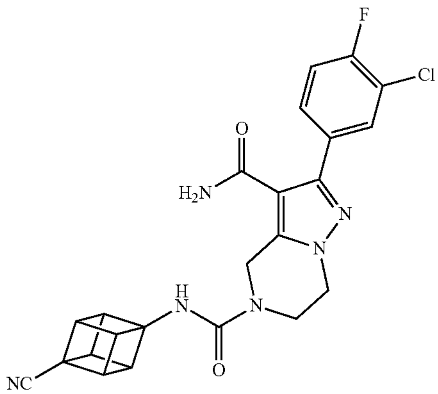 [SMILES: N#CC12C3C4C1C1C2C3C41NC(=O)N1CCn2nc(-c3ccc(F)c(Cl)c3)c(C(N)=O)c2C1] | N5-(4-Cyanocuban-1-yl)-2-(3-chloro-4-fluorophenyl)-6,7-dihydropyrazolo[1,5-a]pyrazine-3,5(4H)-dicarboxamide | 465.22 | 1.30 2.22 | H I |
| A71 | 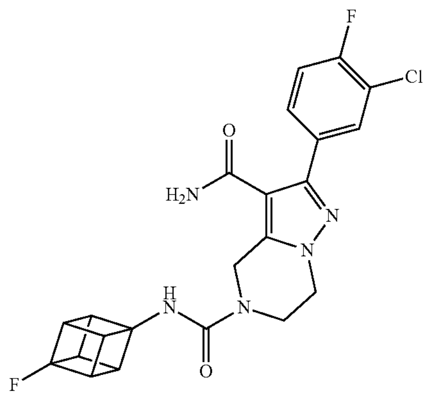 [SMILES: NC(=O)c1c(-c2ccc(F)c(Cl)c2)nn2c1CN(C(=O)NC13C4C5C1C1C3C4C51F)CC2] | N5-(4-Fluorocuban-1-yl)-2-(3-chloro-4-fluorophenyl)-6,7-dihydropyrazolo[1,5-a]pyrazine-3,5(4H)-dicarboxamide | 458.3 | 1.41 2.38 | H I |
| A72 | 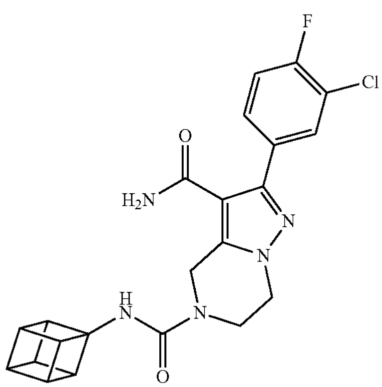 [SMILES: NC(=O)c1c(-c2ccc(F)c(Cl)c2)nn2c1CN(C(=O)NC13C4C5C6C4C1C6C53)CC2] | N5-(Cuban-1-yl)-2-(3-chloro-4-fluorophenyl)-6,7-dihydropyrazolo[1,5-a]pyrazine-3,5(4H)-dicarboxamide | 440.3 | 1.43 2.51 | H I |
| A73 | 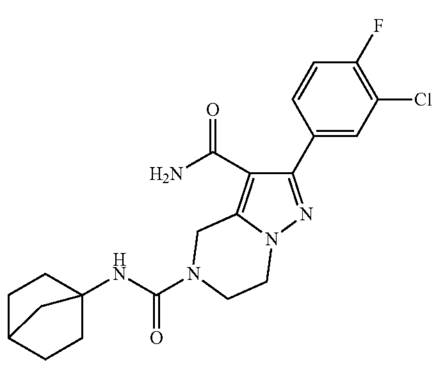 [SMILES: NC(=O)c1c(-c2ccc(F)c(Cl)c2)nn2c1CN(C(=O)NC13CCC(CC1)C3)CC2] | N5-(Bicyclo[2.2.1]heptan-1-yl)-2-(3-chloro-4-fluorophenyl)-6,7-dihydropyrazolo[1,5-a]pyrazine-3,5(4H)-dicarboxamide | 432.2 | 1.58 2.54 | H I |

Compound A74: 2-(3-Chlorophenyl)-N⁵-(4-(4-cyanophenyl)bicyclo[2.2.2]octan-1-yl)-6,7-dihydropyrazolo[1,5-a]pyrazine-3,5(4H)-dicarboxamide

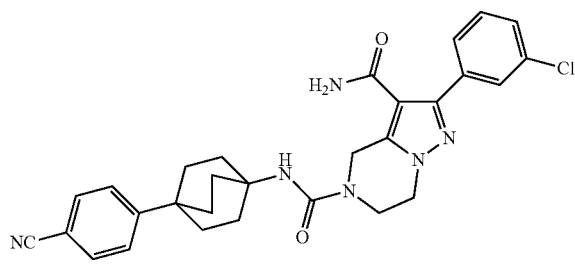 [SMILES: N#Cc1ccc(C23CCC(NC(=O)N4CCn5nc(-c6cccc(Cl)c6)c(C(N)=O)c5C4)(CC2)CC3)cc1]

To a solution of Intermediate A51K (45 mg, 0.176 mmol) in toluene (6 mL) were added TEA (0.11 mL, 0.75 mmol) and diphenyl phosphorazidate (73 mg, 0.265 mmol). The reaction mixture was heated at 90° C. for 2 h and cooled to rt. A solution of 2-(3-chlorophenyl)-4,5,6,7-tetrahydropyrazolo[1,5-a]pyrazine-3-carboxamide (30 mg, 0.108 mmol) in DMF (1 mL) was then added to the above reaction mixture. The reaction mixture was stirred at rt overnight and concentrated. The residue was purified by preparative HPLC. Fractions containing the desired product were combined and dried under vacuum to afford Compound A74 (3.8 mg, 6.6%). MS(ES): m/z=529 [M+H]⁺; HPLC Ret. Time 1.76 min. and 2.71 min. (HPLC Methods H and I); ¹H NMR (500 MHz, DMSO-$d_6$) δ ppm 7.78-7.68 (m, 2H), 7.64 (d, J=7.0 Hz, 1H), 7.55 (d, J=8.4 Hz, 2H), 7.50-7.38 (m, 2H), 7.35 (br. s., 1H), 7.21 (br. s., 1H), 4.69 (s, 2H), 4.20-4.06 (m, 2H), 3.81 (d, J=5.1 Hz, 2H), 2.03-1.91 (m, 6H), 1.91-1.79 (m, 6H).

The Compounds described in Table 54 were synthesized analogous to Compound A74 using 2-(3-chlorophenyl)-4,5,6,7-tetrahydropyrazolo[1,5-a]pyrazine-3-carboxamide and corresponding acids.

TABLE 54

| Ex. No. | Structure | Name | [M + H]⁺ | Ret Time (min.) | HPLC Method |
|---|---|---|---|---|---|
| A75 | 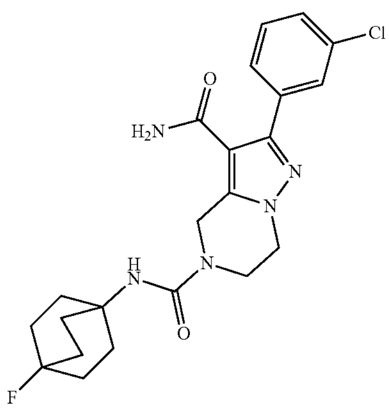 [SMILES: NC(=O)c1c(-c2cccc(Cl)c2)nn2c1CN(C(=O)NC13CCC(F)(CC1)CC3)CC2] | 2-(3-Chlorophenyl)-N⁵-(4-fluorobicyclo[2.2.2]octan-1-yl)-6,7-dihydropyrazolo[1,5-a]pyrazine-3,5(4H)-dicarboxamide | 446.4 | 1.43<br>2.42 | H<br>I |
| A76 | 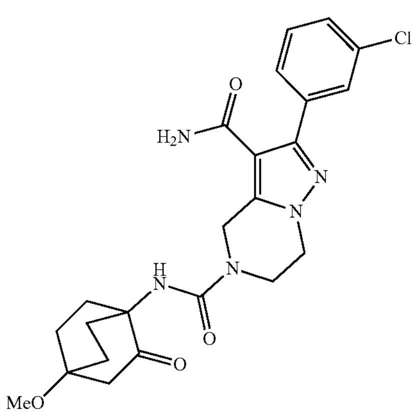 [SMILES: COC12CCC(NC(=O)N3CCn4nc(-c5cccc(Cl)c5)c(C(N)=O)c4C3)(CC1)C(=O)C2] | 2-(3-Chlorophenyl)-N⁵-(4-methoxy-2-oxobicyclo[2.2.2]octan-1-yl)-6,7-dihydropyrazolo[1,5-a]pyrazine-3,5(4H)-dicarboxamide | 472.3 | 1.13<br>2.07 | H<br>I |

TABLE 54-continued

| Ex. No. | Structure | Name | [M + H]+ | Ret Time (min.) | HPLC Method |
|---|---|---|---|---|---|
| A77 | 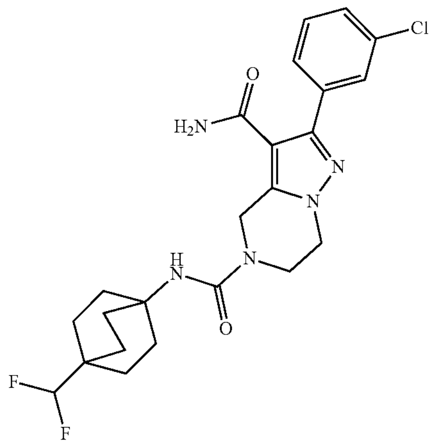 [SMILES: NC(=O)c1c(-c2cccc(Cl)c2)nn2c1CN(C(=O)NC13CCC(C(F)F)(CC1)CC3)CC2] | 2-(3-Chlorophenyl)-N$^5$-(4-(difluoromethyl)bicyclo[2.2.2]octan-1-yl)-6,7-dihydropyrazolo[1,5-a]pyrazine-3,5(4H)-dicarboxamide | 478.3 | 1.54<br>2.52 | H<br>I |
| A78 | 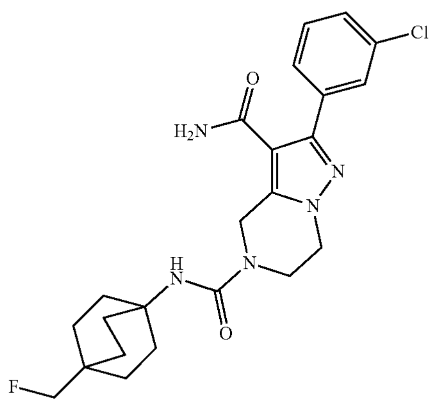 [SMILES: NC(=O)c1c(-c2cccc(Cl)c2)nn2c1CN(C(=O)NC13CCC(CF)(CC1)CC3)CC2] | 2-(3-Chlorophenyl)-N$^5$-(4-(fluoromethyl)bicyclo[2.2.2]octan-1-yl)-6,7-dihydropyrazolo[1,5-a]pyrazine-3,5(4H)-dicarboxamide | 459.9 | 1.46<br>2.61 | H<br>I |
| A79 | 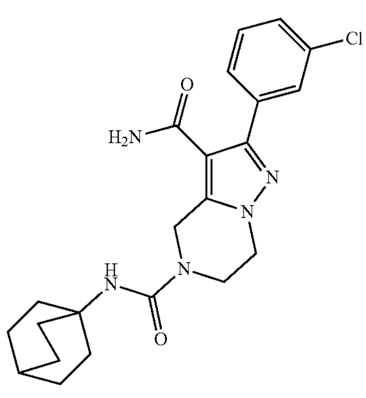 [SMILES: NC(=O)c1c(-c2cccc(Cl)c2)nn2c1CN(C(=O)NC13CCC(CC1)CC3)CC2] | N$^5$-(Bicyclo[2.2.2]octan-1-yl)-2-(3-chlorophenyl)-6,7-dihydropyrazolo[1,5-a]pyrazine-3,5(4H)-dicarboxamide | 428.3 | 1.77<br>2.59 | H<br>I |

TABLE 54-continued

| Ex. No. | Structure | Name | [M + H]+ | Ret Time (min.) | HPLC Method |
|---|---|---|---|---|---|
| A80 | 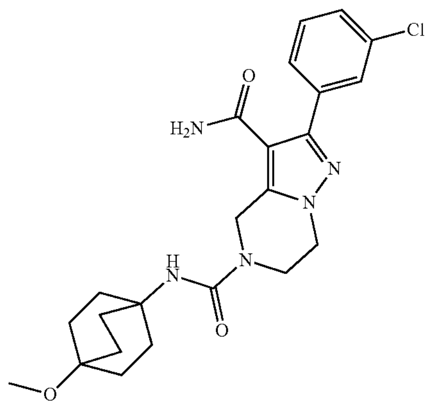 [SMILES: COC12CCC(NC(=O)N3CCn4nc(-c5cccc(Cl)c5)c(C(N)=O)c4C3)(CC1)CC2] | 2-(3-Chlorophenyl)-N5-(4-methoxybicyclo[2.2.2]octan-1-yl)-6,7-dihydropyrazolo[1,5-a]pyrazine-3,5(4H)-dicarboxamide | 458.3 | 1.44<br>2.25 | H<br>I |
| A81 | 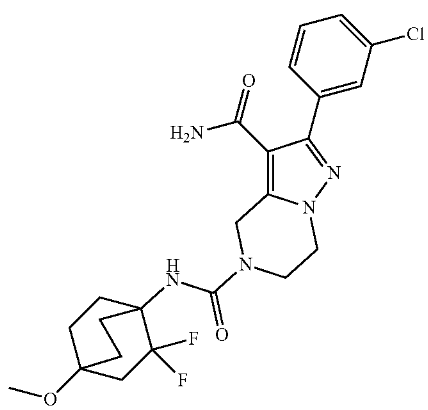 [SMILES: COC12CCC(NC(=O)N3CCn4nc(-c5cccc(Cl)c5)c(C(N)=O)c4C3)(CC1)C(F)(F)C2] | 2-(3-Chlorophenyl)-N5-(2,2-difluoro-4-methoxybicyclo[2.2.2]octan-1-yl)-6,7-dihydropyrazolo[1,5-a]pyrazine-3,5(4H)-dicarboxamide | 494.3 | 1.69<br>2.24 | H<br>I |
| A82 | 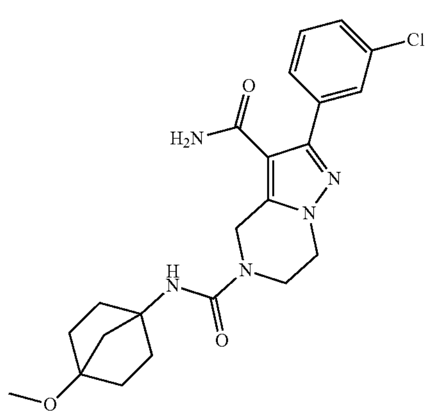 [SMILES: COC12CCC(NC(=O)N3CCn4nc(-c5cccc(Cl)c5)c(C(N)=O)c4C3)(CC1)C2] | 2-(3-Chlorophenyl)-N5-(4-methoxybicyclo[2.2.1]heptan-1-yl)-6,7-dihydropyrazolo[1,5-a]pyrazine-3,5(4H)-dicarboxamide | 444.4 | 1.24<br>2.23 | H<br>I |

TABLE 54-continued

| Ex. No. | Structure | Name | [M + H]+ | Ret Time (min.) | HPLC Method |
|---|---|---|---|---|---|
| A83 | 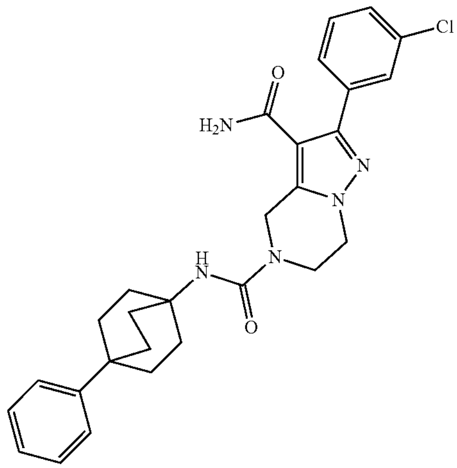 [SMILES: NC(=O)c1c(-c2cccc(Cl)c2)nn2c1CN(C(=O)NC13CCC(c4ccccc4)(CC1)CC3)CC2] | 2-(3-Chlorophenyl)-N5-(4-phenylbicyclo[2.2.2]octan-1-yl)-6,7-dihydropyrazolo[1,5-a]pyrazine-3,5(4H)-dicarboxamide | 504.4 | 1.87<br>2.89 | H<br>I |
| A84 | 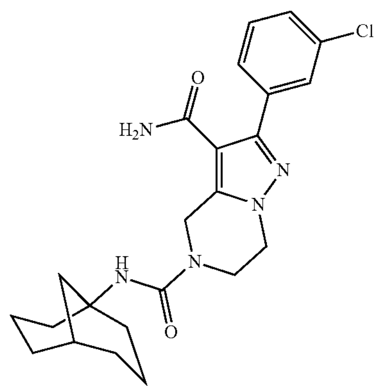 [SMILES: NC(=O)c1c(-c2cccc(Cl)c2)nn2c1CN(C(=O)NC13CCCC(CCC1)C3)CC2] | N5-((1r,5r)-Bicyclo[3.3.1]nonan-1-yl)-2-(3-chlorophenyl)-6,7-dihydropyrazolo[1,5-a]pyrazine-3,5(4H)-dicarboxamide | 442.4 | 1.70<br>2.74 | H<br>I |
| A85 | 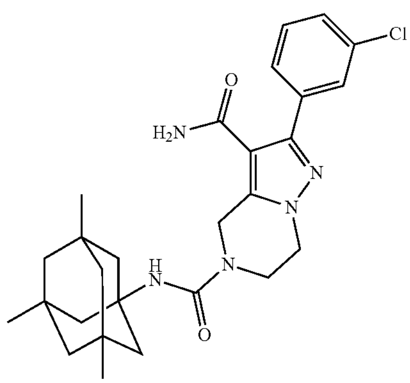 [SMILES: CC12CC3(C)CC(C)(C1)CC(NC(=O)N1CCn4nc(-c5cccc(Cl)c5)c(C(N)=O)c4C1)(C2)C3] | 2-(3-Chlorophenyl)-N5-((3s,5s,7s)-3,5,7-trimethyladamantan-1-yl)-6,7-dihydropyrazolo[1,5-a]pyrazine-3,5(4H)-dicarboxamide | 496.5 | 1.95<br>3.07 | H<br>I |
| A86 | 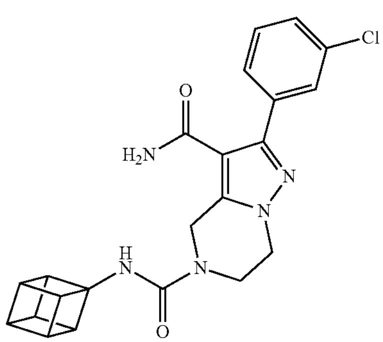 [SMILES: NC(=O)c1c(-c2cccc(Cl)c2)nn2c1CN(C(=O)NC13C4C5C6C4C1C6C53)CC2] | N5-(Cuban-1-yl)-2-(3-chlorophenyl)-6,7-dihydropyrazolo[1,5-a]pyrazine-3,5(4H)-dicarboxamide | 422.3 | 1.66<br>2.43 | H<br>I |

TABLE 54-continued

| Ex. No. | Structure | Name | [M + H]+ | Ret Time (min.) | HPLC Method |
|---|---|---|---|---|---|
| A87 | 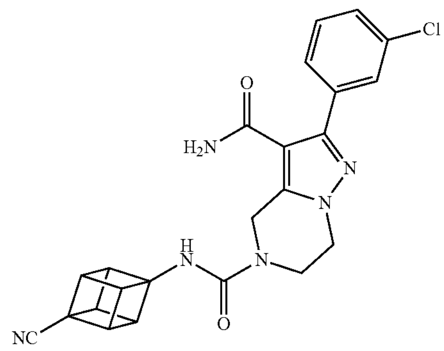 [SMILES: N#CC12C3C4C1C1C2C3C41NC(=O)N1CCn2nc(-c3cccc(Cl)c3)c(C(N)=O)c2C1] | N5-(4-Cyanocuban-1-yl)-2-(3-chlorophenyl)-6,7-dihydropyrazolo[1,5-a]pyrazine-3,5(4H)-dicarboxamide | 447.21 | 1.25<br>2.15 | H<br>I |
| A88 | 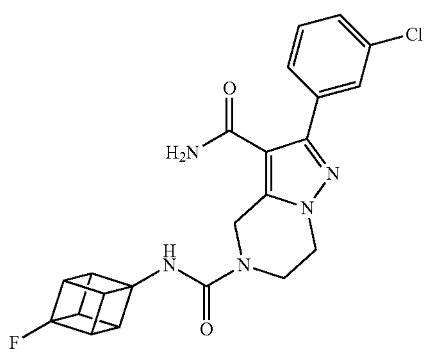 [SMILES: NC(=O)c1c(-c2cccc(Cl)c2)nn2c1CN(C(=O)NC13C4C5C1C1C3C4C51F)CC2] | N5-(4-Fluorocuban-1-yl)-2-(3-chlorophenyl)-6,7-dihydropyrazolo[1,5-a]pyrazine-3,5(4H)-dicarboxamide | 440.3 | 1.37<br>2.34 | H<br>I |

The Compounds described in Table 55 were synthesized analogous to Compound A51 using 2-(3,4-dichlorophenyl)-4,5,6,7-tetrahydropyrazolo[1,5-a]pyrazine-3-carboxamide and corresponding acids.

TABLE 55

| Ex. No. | Structure | Name | [M + H]+ | Ret Time (min.) | HPLC Method |
|---|---|---|---|---|---|
| A89 | 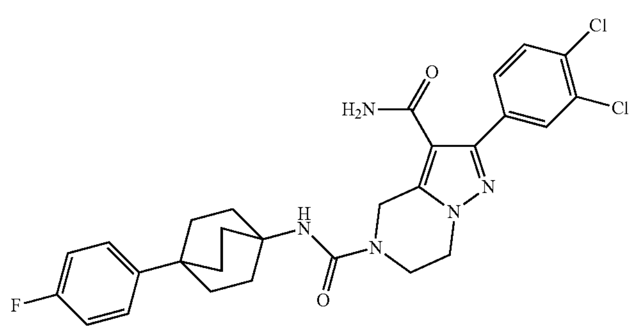 [SMILES: NC(=O)c1c(-c2ccc(Cl)c(Cl)c2)nn2c1CN(C(=O)NC13CCC(c4ccc(F)cc4)(CC1)CC3)CC2] | 2-(3,4-Dichlorophenyl)-N5-(4-(4-fluorophenyl)bicyclo[2.2.2]octan-1-yl)-6,7-dihydropyrazolo[1,5-a]pyrazine-3,5(4H)-dicarboxamide | 540.4 | 1.93<br>2.91 | H<br>I |

TABLE 55-continued

| Ex. No. | Structure | Name | [M + H]+ | Ret Time (min.) | HPLC Method |
|---|---|---|---|---|---|
| A90 | 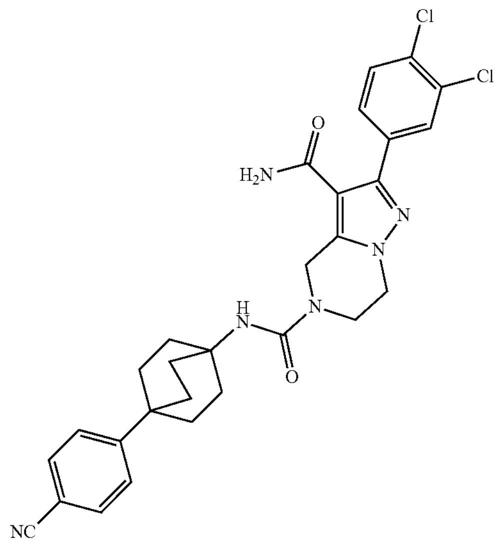 [SMILES: N#Cc1ccc(C23CCC(NC(=O)N4CCn5nc(-c6ccc(Cl)c(Cl)c6)c(C(N)=O)c5C4)(CC2)CC3)cc1] | $N^5$-(4-(4-Cyanophenyl)bicyclo[2.2.2]octan-1-yl)-2-(3,4-dichlorophenyl)-6,7-dihydropyrazolo[1,5-a]pyrazine-3,5(4H)-dicarboxamide | 556.4 | 2.02<br>3.00 | H<br>I |
| A91 | 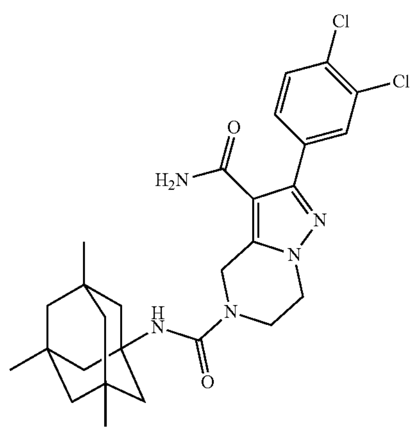 [SMILES: CC12CC3(C)CC(C)(C1)CC(NC(=O)N1CCn4nc(-c5ccc(Cl)c(Cl)c5)c(C(N)=O)c4C1)(C2)C3] | 2-(3,4-Dichlorophenyl)-$N^5$-((3s,5s,7s)-3,5,7-trimethyladamantan-1-yl)-6,7-dihydropyrazolo[1,5-a]pyrazine-3,5(4H)-dicarboxamide | 530.2 | 2.08<br>3.20 | H<br>I |
| A92 | 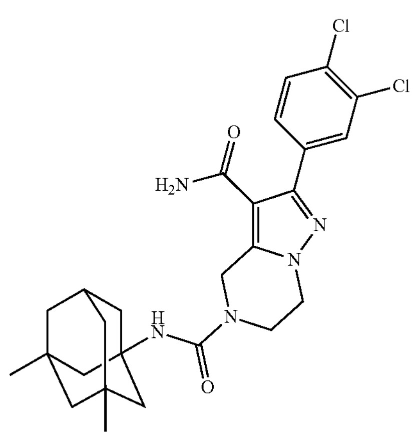 [SMILES: CC12CC3CC(C)(C1)CC(NC(=O)N1CCn4nc(-c5ccc(Cl)c(Cl)c5)c(C(N)=O)c4C1)(C3)C2] | 2-(3,4-Dichlorophenyl)-$N^5$-((1r,3R,5S,7r)-3,5-dimethyladamantan-1-yl)-6,7-dihydropyrazolo[1,5-a]pyrazine-3,5(4H)-dicarboxamide | 515.4 | 2.13<br>3.07 | H<br>I |

TABLE 55-continued

| Ex. No. | Structure | Name | [M + H]+ | Ret Time (min.) | HPLC Method |
|---|---|---|---|---|---|
| A93 | 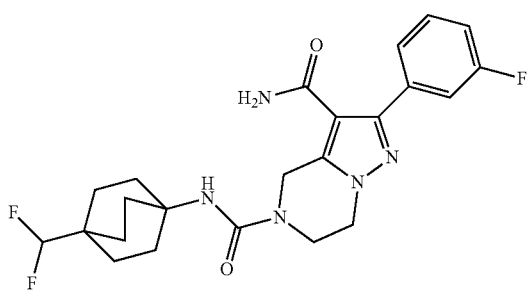 [SMILES: NC(=O)c1c(-c2cccc(F)c2)nn2c1CN(C(=O)NC13CCC(C(F)F)(CC1)CC3)CC2] | N5-((1S,3R,5S,7R)-3-Chloro-5-methyladamantan-1-yl)-2-(3,4-dichlorophenyl)-6,7-dihydropyrazolo[1,5-a]pyrazine-3,5(4H)-dicarboxamide | 522.1 | 1.94<br>2.92 | H<br>I |

Compound A94: N5-(4-(Difluoromethyl)bicyclo[2.2.2]octan-1-yl)-2-(3-fluorophenyl)-6,7-dihydropyrazolo[1,5-a]pyrazine-3,5(4H)-dicarboxamide

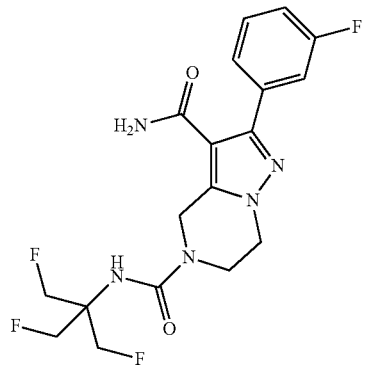 [SMILES: NC(=O)c1c(-c2cccc(F)c2)nn2c1CN(C(=O)NC(CF)(CF)CF)CC2]

Compound A94 were synthesized analogous to Compound A51 using 2-(3-fluorophenyl)-4,5,6,7-tetrahydropyrazolo[1,5-a]pyrazine-3-carboxamide and 4-(difluoromethyl)bicyclo[2.2.2]octane-1-carboxylic acid. MS(ES): m/z=462.3 [M+H]+; HPLC Ret. Time 1.41 min. and 2.37 min. (HPLC Methods H and I); $^1$H NMR (500 MHz, DMSO-d$_6$) δ ppm 7.59-7.39 (m, 3H), 7.34 (br. s., 1H), 7.25-7.08 (m, 2H), 6.24 (s, 1H), 5.68 (t, J=55 Hz t, 1H), 4.67 (s, 2H), 4.12 (t, J=5.0 Hz, 2H), 3.79 (t, J=5.1 Hz, 2H), 1.94-1.77 (m, 6H), 1.62-1.49 (m, 6H).

Compound A95: N5-(1,3-Difluoro-2-(fluoromethyl)propan-2-yl)-2-(3-fluorophenyl)-6,7-dihydropyrazolo[1,5-a]pyrazine-3,5(4H)-dicarboxamide Compound A95 were synthesized analogous to Compound A40 using 2-(3-fluorophenyl)-4,5,6,7-tetrahydropyrazolo[1,5-a]pyrazine-3-carboxamide and 1,3-difluoro-2-(fluoromethyl)propan-2-amine. MS(ES): m/z=414.3 [M+H]+; HPLC Ret. Time 1.25 min and 1.92 min. (HPLC Methods H and I); $^1$H NMR (500 MHz, DMSO-d$_6$) δ ppm 7.59-7.39 (m, 3H), 7.34 (br. s., 1H), 7.25-7.08 (m, 2H), 6.24 (s, 1H), 5.68 (t, J=55 Hz t, 1H), 4.67 (s, 2H), 4.12 (t, J=5.0 Hz, 2H), 3.79 (t, J=5.1 Hz, 2H), 1.94-1.77 (m, 6H), 1.62-1.49 (m, 6H).

Scheme 74

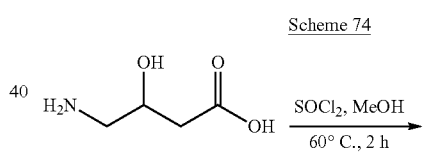

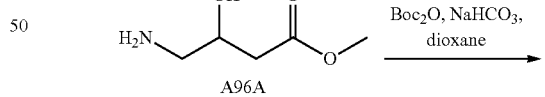

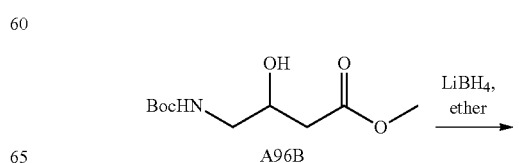

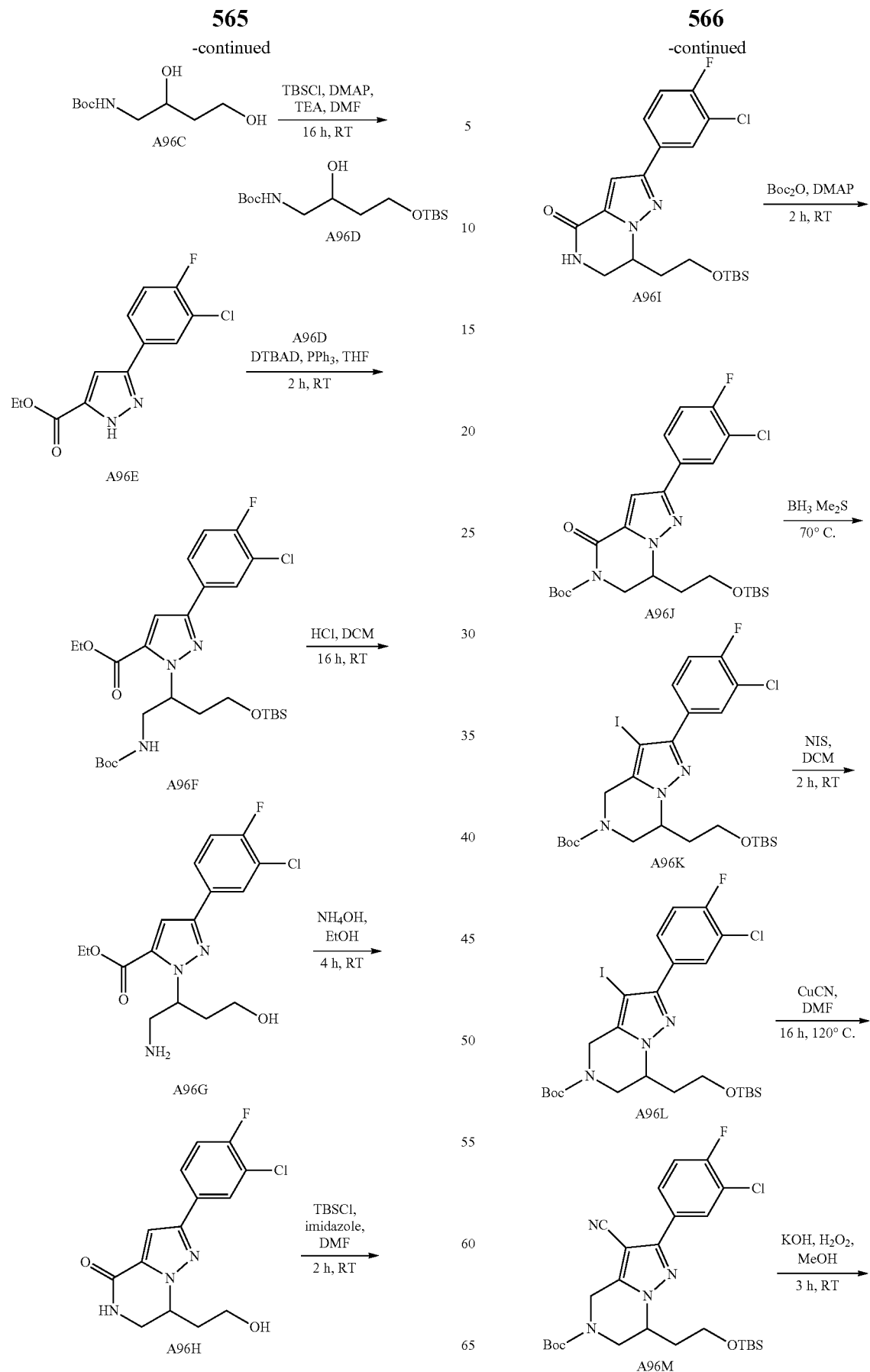

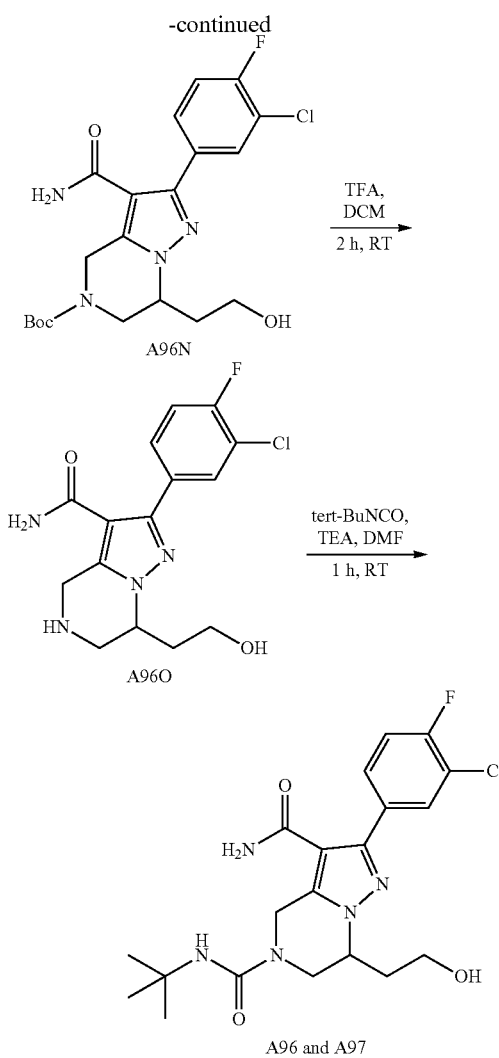

A96N

A96O

A96 and A97

Intermediate A96B: Methyl 4-((tert-butoxycarbonyl)amino)-3-hydroxybutanoate

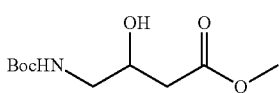

To a suspension of 4-amino-3-hydroxybutanoic acid (17.8 g, 149 mmol) in MeOH (150 mL) and DMF (2 mL) at 0° C. was added $SOCl_2$ (23.99 mL, 329 mmol) dropwise via a dropping funnel. The reaction mixture gradually became a clear solution. It was stirred at RT for 30 min. and then heated at 60° C. for 2 h. It was cooled to RT, concentrated, suspended in dioxane (150 mL), and added to a saturated sodium bicarbonate solution (74.7 mL, 149 mmol). BOC-anhydride (41.6 mL, 179 mmol) was added and the reaction mixture was stirred at RT for 16 h. The reaction mixture was extracted with EtOAc. The combined organic layer was washed with brine, dried over $Na_2SO_4$, and filtered. The filtrate was concentrated. The crude product was purified by silica gel chromatography (240 g REDISEP® column, eluting with 30-70% EtOAc in hexane). Fractions containing the product were combined and evaporated to afford Intermediate A96B (25 g, 71.7% for two steps). $^1$H NMR (400 MHz, chloroform-d) δ ppm 4.22-4.04 (m, 1H), 3.74 (s, 3H), 3.51 (d, J=7.5 Hz, 1H), 3.20-3.08 (m, 1H), 2.57-2.48 (m, 2H), 1.52-1.40 (m, 9H).

Intermediate A96C: tert-Butyl(2,4-dihydroxybutyl)carbamate

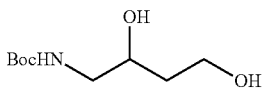 [SMILES: CC(C)(C)OC(=O)NCC(O)CCO]

To a solution of Intermediate A96B (25 g, 107 mmol) in diethyl ether (200 mL) and MeOH (7.59 mL, 188 mmol) at 0° C. was added $LiBH_4$ (3.50 g, 161 mmol) in portions carefully. The reaction was stirred at RT for 1 h and heated at 60° C. for 1 h. The reaction was carefully quenched with MeOH and concentrated. The residue was diluted with a solution of saturated $NH_4Cl$ and extracted with EtOAc. The combined organic layer was washed with brine, dried over $Na_2SO_4$, and filtered. The filtrate was concentrated to afford Intermediate A96C (19 g, 86%) as an off-white solid. It was used for the next step without further purification. $^1$H NMR (400 MHz, chloroform-d) δ ppm 4.03-3.77 (m, 3H), 3.30 (ddd, J=14.1, 6.1, 3.1 Hz, 1H), 3.22-3.03 (m, 1H), 1.78-1.65 (m, 2H), 1.46 (s, 9H).

Intermediate A96D: tert-Butyl (4-((tert-butyldimethylsilyl)oxy)-2-hydroxybutyl) carbamate

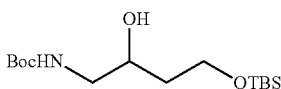 [SMILES: CC(C)(C)OC(=O)NCC(O)CCO[Si](C)(C)C(C)(C)C]

To a solution of A96C (10 g, 48.7 mmol) and TEA (2.55 mL, 18.30 mmol) in $CH_2Cl_2$ (80 mL) were added TBS-Cl (8.08 g, 53.6 mmol) and DMAP (0.060 g, 0.487 mmol). It was stirred at RT for 4 h. The reaction mixture was diluted with water and extracted with EtOAc. The organic layer was washed with brine, dried over $Na_2SO_4$, and filtered. The filtrate was concentrated. The residue was purified by silica gel chromatography (240 g REDISEP® column, eluting with 10-50% EtOAc in hexane). Fractions containing the product were combined and evaporated to afford Intermediate A96D (12 g, 77%). $^1$H NMR (400 MHz, chloroform-d) δ ppm 3.99-3.72 (m, 3H), 3.41-3.22 (m, 1H), 3.22-3.03 (m, 1H), 1.78-1.60 (m, 2H), 1.46 (s, 9H), 0.96-0.84 (m, 9H), 0.19-0.06 (m, 6H).

Intermediate A96F: Ethyl 3-(3-chloro-4-fluorophenyl)-1-(2,2,3,3,12,12-hexamethyl-10-oxo-4,11-dioxa-9-aza-3-silatridecan-7-yl)-1H-pyrazole-5-carboxylate

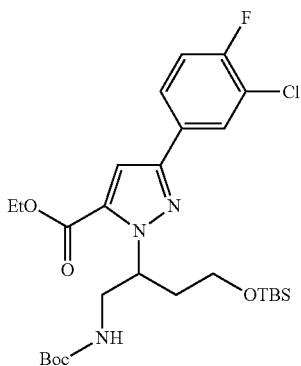 [SMILES: CCOC(=O)c1cc(-c2ccc(F)c(Cl)c2)nn1C(CCO[Si](C)(C)C(C)(C)C)CNC(=O)OC(C)(C)C]

To a solution of ethyl 3-(3-chloro-4-fluorophenyl)-1H-pyrazole-5-carboxylate (10.7 g, 40 mmol) in THF (100 mL) at 0° C. were added Intermediate A96D (15.25 g, 48 mmol), TEA (5.6 mL, 40 mmol), triphenylphosphine (10.5 g, 40 mmol), and DTBAD (9.17 g, 40 mmol). The reaction mixture was stirred at RT for 2 h and concentrated. The residue was diluted with water and EtOAc. The layers were separated. The aqueous layer was extracted with EtOAc. The combined organic layer was washed with brine, dried over $Na_2SO_4$, and filtered. The filtrate was concentrated. The crude product was purified by silica gel chromatography (330 g REDISEP® column, eluting with 10-40% EtOAc in hexane). Fractions containing the product were combined and evaporated to afford Intermediate A96F (16.5 g, 73%). MS(ES): m/z=592.3 $[M+Na]^+$.

Intermediate A96G: Ethyl 1-(1-amino-4-hydroxybutan-2-yl)-3-(3-chloro-4-fluorophenyl)-1H-pyrazole-5-carboxylate bis HCl salt

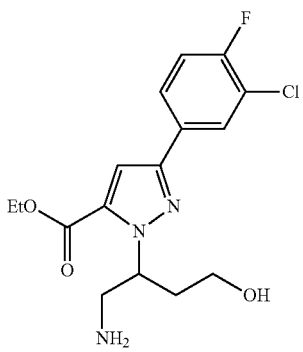 [SMILES: CCOC(=O)c1cc(-c2ccc(F)c(Cl)c2)nn1C(CN)CCO]

To a solution of Intermediate A96F in $CH_2Cl_2$ (120 mL) was added 4M HCl solution in dioxane (10.70 mL, 42.8 mmol). The reaction mixture was stirred at RT overnight. The solid Intermediate A96G was collected by filtration. It was used for the next step without further purification. MS(ES): m/z=356.1 $[M+H]^+$.

Intermediate A96H: 2-(3-Chloro-4-fluorophenyl)-7-(2-hydroxyethyl)-6,7-dihydropyrazolo[1,5-a]pyrazin-4(5H)-one

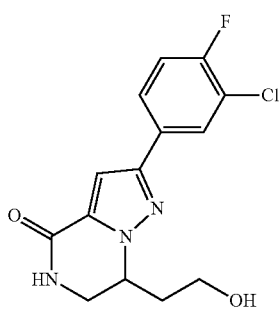 [SMILES: O=C1NCC(CCO)n2nc(-c3ccc(F)c(Cl)c3)cc21]

To a suspension of Intermediate A96G (4.20 g, 10.7 mmol) in ethanol (80 mL) was added 30% water solution of ammonia (80 mL, 3697 mmol). It was stirred at RT for 2 h and concentrated. The solid was collected by filtration, washed with water, and dried. The crude product Intermediate A96H was used for the next step without further purification.

MS(ES): m/z=310.0 $[M+H]^+$; $^1H$ NMR (400 MHz, DMSO-$d_6$) δ ppm 8.27 (br. s., 1H), 8.07 (dd, J=7.3, 2.3 Hz, 1H), 7.89 (ddd, J=8.7, 4.8, 2.1 Hz, 1H), 7.48 (t, J=9.0 Hz, 1H), 7.34 (s, 1H), 4.74 (t, J=5.0 Hz, 1H), 4.67-4.47 (m, 1H), 3.79 (ddd, J=13.3, 4.4, 2.4 Hz, 1H), 3.66-3.55 (m, 2H), 3.50 (ddd, J=13.4, 5.6, 3.4 Hz, 1H), 2.17 (dd, J=13.8, 6.0 Hz, 1H), 2.03-1.81 (m, 1H).

Intermediate A96I: 7-(2-((tert-Butyldimethylsilyl)oxy)ethyl)-2-(3-chloro-4-fluorophenyl)-6,7-dihydropyrazolo[1,5-a]pyrazin-4(5H)-one

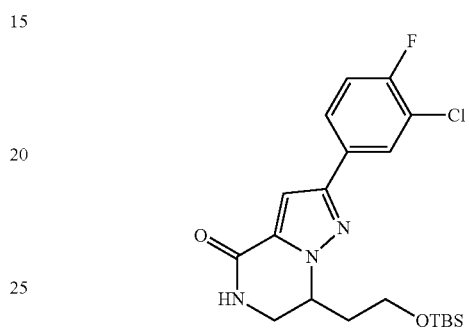

To a suspension of Intermediate A96H in $CH_2Cl_2$ (300 mL) and DMF (15 mL) were added TEA (10.80 mL, 77 mmol), TBS-Cl (9.34 g, 62.0 mmol), and DMAP (0.316 g, 2.58 mmol). The suspension was stirred at RT overnight. The reaction mixture was diluted with water, extracted with $CH_2Cl_2$. The organic layer was washed with brine, dried over $Na_2SO_4$, and filtered. The filtrate was concentrated. The crude product was purified by silica gel chromatography (330 g REDISEP® column, eluting with 0-40% EtOAc in $CH_2Cl_2$). Fractions containing the product were combined and evaporated to afford Intermediate A96I (17.8 g, 81%). MS(ES): m/z=446.2 $[M+Na]^+$. $^1H$ NMR (400 MHz, chloroform-d) δ ppm 7.91 (dd, J=7.2, 2.1 Hz, 1H), 7.66 (ddd, J=8.6, 4.6, 2.1 Hz, 1H), 7.27-7.10 (m, 2H), 6.25 (br. s., 1H), 4.78-4.51 (m, 1H), 4.02-3.79 (m, 3H), 3.72 (ddd, J=13.1, 5.5, 3.5 Hz, 1H), 2.47-2.23 (m, 1H), 2.23-1.96 (m, 1H), 1.00-0.88 (m, 9H), 0.18-0.05 (m, 6H).

Intermediate A96J: tert-Butyl 7-(2-((tert-butyldimethylsilyl)oxy)ethyl)-2-(3-chloro-4-fluorophenyl)-4-oxo-6,7-dihydropyrazolo[1,5-a]pyrazine-5(4H)-carboxylate

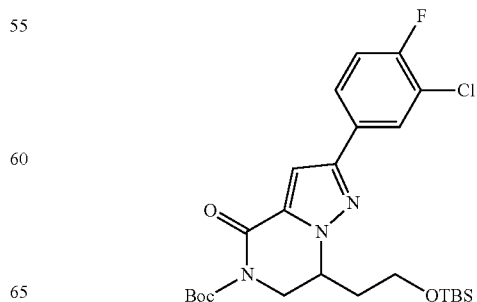

To a suspension of Intermediate A96I (13.64 g, 32.2 mmol) in toluene (120 mL) were added DMAP (5.90 g, 48.3 mmol) and BOC-anhydride (8.96 mL, 38.6 mmol). The reaction mixture was stirred at RT for 1 h and it became a clear solution about 5 min. after addition. The reaction mixture was concentrated and the residue was purified by silica gel chromatography (240 g REDISEP® column, eluting with 0-40% EtOAc in $CH_2Cl_2$). Fractions containing the product were combined and evaporated to afford Intermediate A96J (17.8 g, 81%). MS(ES): m/z=524.4 $[M+H]^+$; $^1H$ NMR (400 MHz, chloroform-d) δ 7.90 (dd, J=7.0, 2.0 Hz, 1H), 7.66 (ddd, J=8.5, 4.6, 2.1 Hz, 1H), 7.29 (s, 1H), 7.25-7.03 (m, 2H), 4.84-4.63 (m, 1H), 4.38-4.18 (m, 2H), 4.05-3.79 (m, 2H), 2.51-2.24 (m, 1H), 2.03 (dtd, J=14.4, 7.2, 2.3 Hz, 1H), 1.61 (s, 9H), 0.95 (s, 9H), 0.14 (s, 3H), 0.12 (s, 3H).

Intermediate A96K: tert-Butyl 7-(2-((tert-butyldimethylsilyl)oxy)ethyl)-2-(3-chloro-4-fluorophenyl)-6,7-dihydropyrazolo[1,5-a]pyrazine-5(4H)-carboxylate

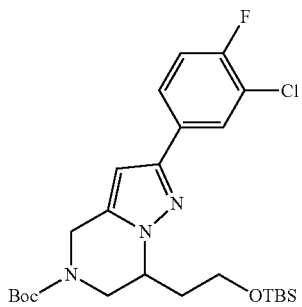 [SMILES: CC(C)(C)OC(=O)N1Cc2cc(-c3ccc(F)c(Cl)c3)nn2C(CCO[Si](C)(C)C(C)(C)C)C1]

To a solution of Intermediate A96J (1.5 g, 2.86 mmol) in THF (15 mL) was added 2M solution of $BH_3.Me_2S$ in THF (4.29 mL, 8.59 mmol) dropwise at RT. The reaction mixture was heated to reflux for 4 h and cooled to 0° C. It was carefully quenched with MeOH. The reaction mixture was concentrated. The residue was diluted with a solution of $NH_4Cl$, extracted with EtOAc. The combined organic layer was washed with brine, dried over $Na_2SO_4$, and filtered. The filtrate was concentrated to afford Intermediate A96K (1.2 g, 82%), which was used for the next step without further purification. MS(ES): m/z=510.3 $[M+H]^+$.

Intermediate A96L: tert-Butyl 7-(2-((tert-butyldimethylsilyl)oxy)ethyl)-2-(3-chloro-4-fluorophenyl)-3-iodo-6,7-dihydropyrazolo[1,5-a]pyrazine-5(4H)-carboxylate

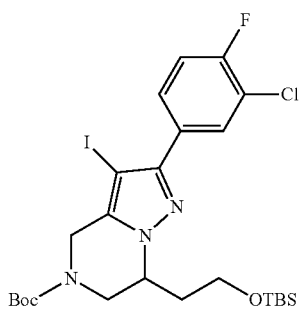 [SMILES: CC(C)(C)OC(=O)N1Cc2c(I)c(-c3ccc(F)c(Cl)c3)nn2C(CCO[Si](C)(C)C(C)(C)C)C1]

To a solution of Intermediate A96K (3.53 g, 6.92 mmol) in $CH_2Cl_2$ (25 mL) and MeOH (10 mL) was added NIS (1.868 g, 8.30 mmol). The reaction mixture was stirred at RT for 3 h and concentrated. The residue was purified by silica gel chromatography (80 g REDISEP® column, eluting with 0-25% EtOAc in hexane). Fractions containing the product were combined and evaporated to afford Intermediate A96L (3 g, 76%). MS(ES): m/z=636.2 $[M+H]^+$.

Intermediate A96M: tert-Butyl 7-(2-((tert-butyldimethylsilyl)oxy)ethyl)-2-(3-chloro-4-fluorophenyl)-3-cyano-6,7-dihydropyrazolo[1,5-a]pyrazine-5(4H)-carboxylate

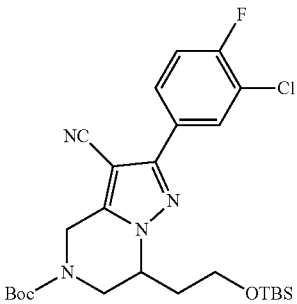 [SMILES: CC(C)(C)OC(=O)N1Cc2c(C#N)c(-c3ccc(F)c(Cl)c3)nn2C(CCO[Si](C)(C)C(C)(C)C)C1]

To a solution of Intermediate A96L (3 g, 4.72 mmol) in DMF (12 mL) was added copper (I) cyanide (1.056 g, 11.79 mmol). The reaction mixture was heated at 120° C. overnight. It was cooled to RT, diluted with EtOAc, passed through a pad of CELITE®, washed with EtOAc. The filtrate was concentrated. The residue was purified by silica gel chromatography (80 g REDISEP® column, eluting with 0-35% EtOAc in hexane). Fractions containing the product were combined and evaporated to afford Intermediate A96M (1.2 g, 48%). MS(ES): m/z=557.2 $[M+Na]^+$.

Intermediate A96N: tert-Butyl 3-carbamoyl-2-(3-chloro-4-fluorophenyl)-7-(2-hydroxyethyl)-6,7-dihydropyrazolo[1,5-a]pyrazine-5(4H)-carboxylate

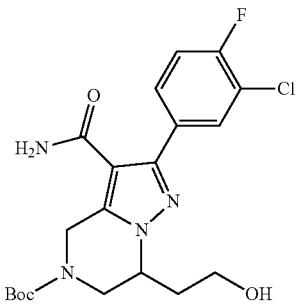 [SMILES: CC(C)(C)OC(=O)N1Cc2c(C(N)=O)c(-c3ccc(F)c(Cl)c3)nn2C(CCO)C1]

To a solution of Intermediate A96M (1.2 g, 2.242 mmol) in ethanol (10 mL) and THF (10 mL) were added potassium hydroxide (2.242 mL, 11.21 mmol) and 30% $H_2O_2$ (4.58 mL, 44.8 mmol). The reaction mixture was stirred at RT for two days. It was concentrated. The residue was extracted with EtOAc. The combined organic layer was washed with brine, dried over $Na_2SO_4$, filtered. The filtrate was concentrated.

The crude Intermediate A96N (820 mg, 83%). was used for the next step without further purification. MS(ES): m/z=439.1 [M+H]+.

Intermediate A96O: 2-(3-Chloro-4-fluorophenyl)-7-(2-hydroxyethyl)-4,5,6,7-tetrahydropyrazolo[1,5-a]pyrazine-3-carboxamide HCl salt

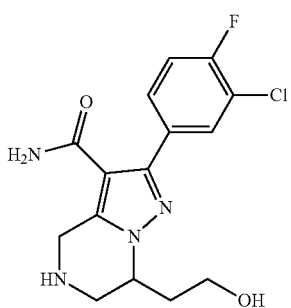 [SMILES: NC(=O)c1c(-c2ccc(F)c(Cl)c2)nn2c1CNCC2CCO]

To a solution of Intermediate A96N (95 mg, 0.216 mmol) in MeOH (10 mL) was added 4M HCl solution in dioxane (0.5 mL, 2.00 mmol). The reaction mixture was stirred at RT for 4 h and concentrated. The crude material Intermediate A96O was used for the next step without further purification. MS(ES): m/z=339.1 [M+H]+.

Compounds A96 and A97: $N^5$-(tert-Butyl)-2-(3-chloro-4-fluorophenyl)-7-(2-hydroxyethyl)-6,7-dihydropyrazolo[1,5-a]pyrazine-3,5(4H)-dicarboxamide

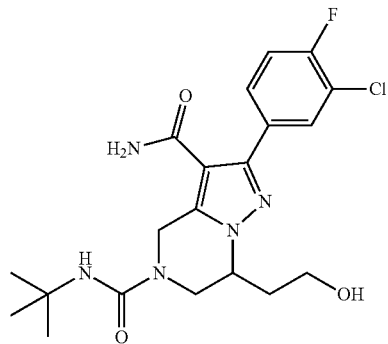 [SMILES: CC(C)(C)NC(=O)N1Cc2c(C(N)=O)c(-c3ccc(F)c(Cl)c3)nn2C(CCO)C1]

To a solution of Intermediate A96N (35 mg, 0.093 mmol) in DMF (1 mL) were added Hunig's base (0.033 mL, 0.187 mmol) and 2-isocyanato-2-methylpropane (13.87 mg, 0.140 mmol). The reaction mixture was stirred at RT for 2 h. It was purified by preparative HPLC to afford racemate Compounds A96 and A97. The racemate was further separated by chiral HPLC to give enantiomer A96 (Ret. Time 13.39 min, 8.6 mg, 21%) and enantiomer A97 (Ret. Time 16.87 min, 9.0 mg, 22%). Chiral HPLC Method: Column: CHIRALPAK® AD 21×250 mm, 10 μm; Mobile Phase A: 0.1% diethylamine/heptane; Mobile Phase B: ethanol; Gradient: hold at 12%-100% B over 31 minutes; Flow rate: 15 mL/min; MS(ES): m/z=438.5 [M+H]+; HPLC Ret. Time 1.27 and 2.28 min. (HPLC Methods H and I); $^1$H NMR (500 MHz, DMSO-$d_6$) δ ppm 7.84 (d, J=7.0 Hz, 1H), 7.68 (br. s., 1H), 7.46 (t, J=9.0 Hz, 1H), 7.34 (br. s., 1H), 7.23 (br. s., 1H), 6.30 (s, 1H), 4.95 (br. s., 1H), 4.84 (d, J=16.9 Hz, 1H), 4.53 (d, J=17.2 Hz, 1H), 4.35 (d, J=4.4 Hz, 1H), 3.98-3.82 (m, 1H), 3.78-3.60 (m, 3H), 2.12 (dd, J=13.4, 5.7 Hz, 1H), 1.79 (d, J=5.9 Hz, 1H), 1.28 (s, 9H).

Scheme 75

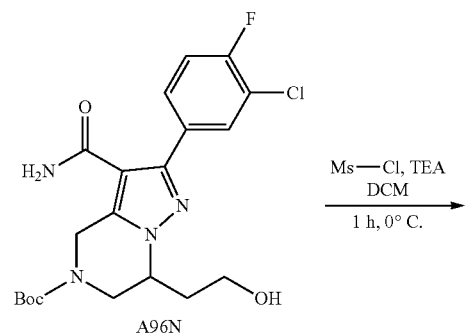

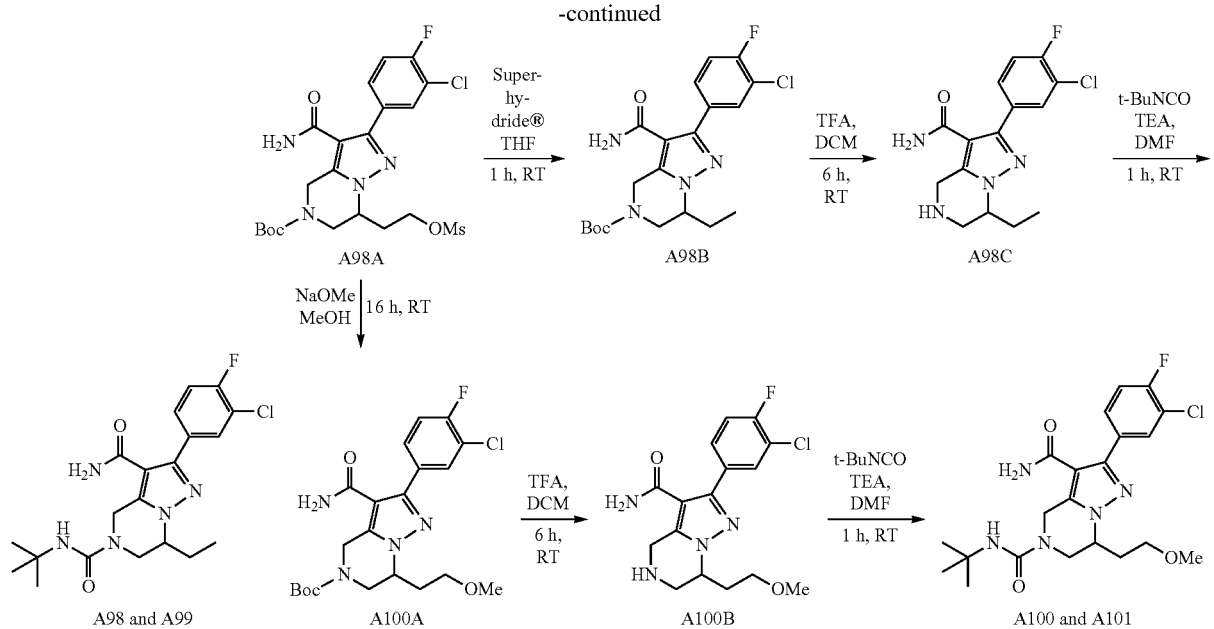

Intermediate A98A: tert-Butyl 3-carbamoyl-2-(3-chloro-4-fluorophenyl)-7-(2-((methylsulfonyl)oxy)ethyl)-6,7-dihydropyrazolo[1,5-a]pyrazine-5(4H)-carboxylate

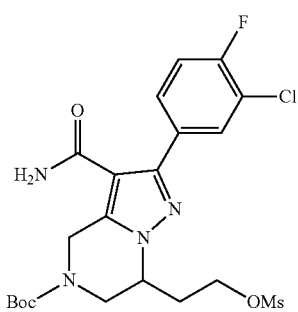 [SMILES: CC(C)(C)OC(=O)N1Cc2c(C(N)=O)c(-c3ccc(F)c(Cl)c3)nn2C(CCOS(C)(=O)=O)C1]

To a solution of Intermediate A96N (500 mg, 1.139 mmol) in CH$_2$Cl$_2$ (12 mL) at 0° C. under nitrogen were added TEA (0.206 mL, 1.481 mmol) and Ms-Cl (0.107 mL, 1.367 mmol). The reaction mixture was stirred at 0° C. for 1 h before it was quenched with a saturated solution of NaHCO$_3$ and extracted with CH$_2$Cl$_2$. The combined organic layer was washed with brine, dried over Na$_2$SO$_4$, and filtered. The filtrate was concentrated. The crude product was purified by silica gel chromatography (40 g REDISEP® column, eluting with 35-80% EtOAc in hexane). Fractions containing the product were combined and evaporated to afford Intermediate A98A (380 m g, 65%). MS(ES): m/z=517.1 [M+H]$^+$; $^1$H NMR (400 MHz, chloroform-d) δ ppm 7.68 (dd, J=7.0, 2.0 Hz, 1H), 7.49 (ddd, J=8.5, 4.5, 2.3 Hz, 1H), 7.32-7.19 (m, 1H), 5.19 (d, J=16.8 Hz, 1H), 4.73 (d, J=18.8 Hz, 1H), 4.52 (t, J=6.0 Hz, 3H), 4.31-4.16 (m, 1H), 3.76-3.59 (m, 1H), 3.09 (s, 3H), 2.50-2.32 (m, 1H), 2.32-2.14 (m, 1H), 1.56-1.47 (m, 9H).

Intermediate A98B: tert-Butyl 3-carbamoyl-2-(3-chloro-4-fluorophenyl)-7-ethyl-6,7-dihydropyrazolo[1,5-a]pyrazine-5(4H)-carboxylate

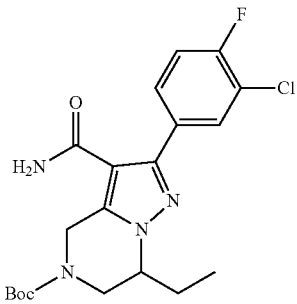 [SMILES: CCC1CN(C(=O)OC(C)(C)C)Cc2c(C(N)=O)c(-c3ccc(F)c(Cl)c3)nn21]

To a solution of tert-butyl 3-carbamoyl-2-(3-chloro-4-fluorophenyl)-7-(2-((methylsulfonyl)oxy)ethyl)-6,7-dihydropyrazolo[1,5-a]pyrazine-5(4H)-carboxylate (200 mg, 0.387 mmol) in THF (6 mL) at 0° C. under nitrogen was added 1M THF solution of SUPER-HYDRIDE® (1.934 mL, 1.934 mmol). The reaction mixture was stirred at RT for 1 h and quenched with water. It was extracted with EtOAc. The combined organic layer was washed with brine, dried over Na$_2$SO$_4$, and filtered. The filtrate was concentrated. The crude product was purified by silica gel chromatography (40 g REDISEP® column, eluting with 35-80% EtOAc in hexane). Fractions containing the product were combined and evaporated to afford Intermediate A98B (128 m g, 78%). MS(ES): m/z=423.1 [M+H]+.

Intermediate A98C: 2-(3-Chloro-4-fluorophenyl)-7-ethyl-4,5,6,7-tetrahydropyrazolo[1,5-a]pyrazine-3-carboxamide TFA salt

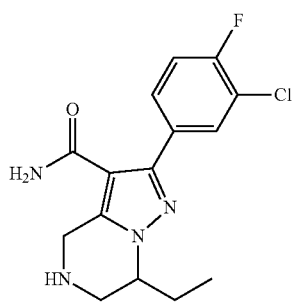 [SMILES: CCC1CNCc2c(C(N)=O)c(-c3ccc(F)c(Cl)c3)nn21]

To a solution of Intermediate A98B (160 mg, 0.378 mmol) in CH$_2$Cl$_2$ (20 mL) was added TFA (2 mL, 26.0 mmol). The reaction mixture was stirred at RT overnight and concentrated. The crude Intermediate A97C as a TFA salt was used for the next step without further purification. MS(ES): m/z=4323.1 [M+H]+.

Compounds A98 and A99: N$^5$-(tert-Butyl)-2-(3-chloro-4-fluorophenyl)-7-ethyl-6,7-dihydropyrazolo[1,5-a]pyrazine-3,5(4H)-dicarboxamide

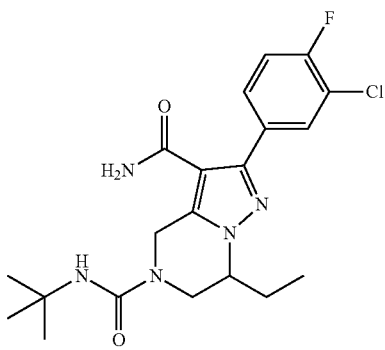 [SMILES: CCC1CN(C(=O)NC(C)(C)C)Cc2c(C(N)=O)c(-c3ccc(F)c(Cl)c3)nn21]

To a solution of Intermediate A98C (40 mg, 0.092 mmol) in DMF (1 mL) were added Hunig's base (0.064 mL, 0.366 mmol) and 2-isocyanato-2-methylpropane (13.62 mg, 0.137 mmol). The reaction mixture was stirred at RT for 2 h. It was purified by preparative. HPLC to afford racemate Compounds A98 and A99. The racemate was further separated by chiral HPLC to give enantiomer A98 (Ret. Time 28.91 min, 12.1 mg, 31.3%) and enantiomer A99 (Ret. Time 32.84 min, 13.1 mg, 33.9%). Chiral HPLC Method: Column: CHIRALPAK® AD 21×250 mm, 10 μm; Mobile Phase A: 0.1% diethylamine/heptane; Mobile Phase B: ethanol; Gradient: hold at 15%-100% B over 40 minutes; Flow rate: 15 mL/min; MS(ES): m/z=422.5 [M+H]+; HPLC Ret. Time 1.65 and 2.62 min (HPLC Methods H and I); $^1$H NMR (500 MHz, DMSO-d$_6$) δ ppm 7.85 (d, J=7.3 Hz, 1H), 7.69 (br. s., 1H), 7.46 (t, J=9.0 Hz, 1H), 7.35 (br. s., 1H), 7.21 (br. s., 1H), 6.22 (s, 1H), 4.77 (d, J=17.2 Hz, 1H), 4.65 (d, J=16.9 Hz, 1H), 4.14 (d, J=3.7 Hz, 1H), 3.86-3.77 (m, 1H), 3.77-3.63 (m, 1H), 3.39-3.30 (m, 2H), 2.07-1.94 (m, 1H), 1.77-1.63 (m, 1H), 1.29 (s, 9H), 0.99 (t, J=7.5 Hz, 3H).

Intermediate A100A: tert-Butyl 3-carbamoyl-2-(3-chloro-4-fluorophenyl)-7-(2-methoxyethyl)-6,7-dihydropyrazolo[1,5-a]pyrazine-5(4H)-carboxylate

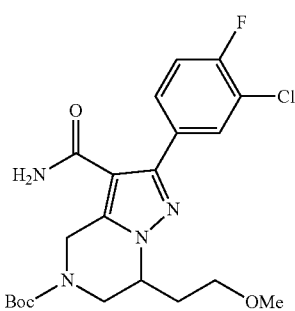

To a solution of Intermediate A98A (170 mg, 0.329 mmol) in MeOH (5 mL) was added 25% sodium methoxide solution in MeOH (426 mg, 1.973 mmol). The reaction mixture was stirred at RT overnight. It was concentrated. The residue was diluted with water, extracted with EtOAc. The combined organic layer was washed with brine, dried over Na$_2$SO$_4$, and filtered. The filtrate was concentrated. The crude product was purified by silica gel chromatography (40 g REDISEP® column, eluting with 35-80% EtOAc in hexane). Fractions containing the product were combined and evaporated to afford Intermediate A100A (120 mg, 81%). MS(ES): m/z=453.1 [M+H]+; $^1$H NMR (400 MHz, chloroform-d) δ ppm 7.77-7.64 (m, 1H), 7.55-7.44 (m, 1H), 7.34-7.16 (m, 1H), 5.44-5.27 (m, 1H), 4.79 (d, J=17.8 Hz, 1H), 4.56-4.39 (m, 1H), 4.14-4.04 (m, 1H), 3.74 (dd, J=13.8, 3.8 Hz, 1H), 3.62 (t, J=6.1 Hz, 2H), 3.39 (s, 3H), 2.45-2.25 (m, 1H), 1.98 (ddt, J=14.3, 8.5, 5.8 Hz, 1H), 1.59-1.48 (m, 9H).

Intermediate A100B: 2-(3-Chloro-4-fluorophenyl)-7-(2-methoxyethyl)-4,5,6,7-tetrahydropyrazolo[1,5-a]pyrazine-3-carboxamide TFA salt

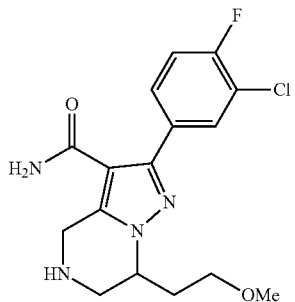 [SMILES: COCCC1CNCc2c(C(N)=O)c(-c3ccc(F)c(Cl)c3)nn21]

To a solution of Intermediate A100A (120 mg, 0.265 mmol) in CH$_2$Cl$_2$ (15 mL) was added TFA (1 mL, 12.98 mmol). The reaction mixture was stirred at RT for 6 h and concentrated. The crude Intermediate A100B as a TFA salt was used for the next step without further purification. MS(ES): m/z=353.0 [M+H]+.

Compounds A100 and A101: $N^5$-(tert-Butyl)-2-(3-chloro-4-fluorophenyl)-7-(2-methoxyethyl)-6,7-dihydropyrazolo[1,5-a]pyrazine-3,5(4H)-dicarboxamide

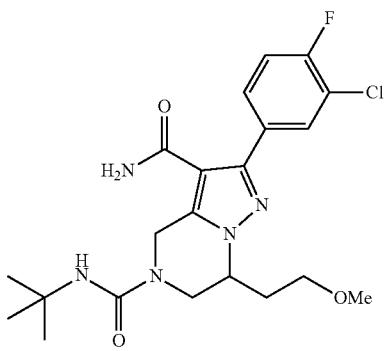 [SMILES: COCCC1CN(C(=O)NC(C)(C)C)Cc2c(C(N)=O)c(-c3ccc(F)c(Cl)c3)nn21]

To a solution of Intermediate A100B (35 mg, 0.075 mmol) in DMF (1 mL) were added Hunig's base (0.026 mL, 0.150 mmol) and 2-isocyanato-2-methylpropane (11.15 mg, 0.112 mmol). The reaction mixture was stirred at RT for 2 h. It was purified by preparative HPLC to afford racemate Compounds A100 and A101. The racemate was further separated by chiral HPLC to give enantiomer A100 (Ret. Time 24.56 min, 9.7 mg, 28.6%) and enantiomer A101 (Ret. Time 30.65 min, 9.8 mg, 28.9%). Chiral HPLC Method: Column: CHIRALPAK® AD 21×250 mm, 10 μm; Mobile Phase A: 0.1% diethylamine/heptane; Mobile Phase B: ethanol; Gradient: hold at 12%-100% B over 40 minutes; Flow rate: 15 mL/min; MS(ES): m/z=452.5 [M+H]+; HPLC Ret. Time 1.60 and 2.57 min (HPLC Methods H and I); $^1$H NMR (500 MHz, DMSO-$d_6$) δ ppm 7.85 (d, J=6.6 Hz, 1H), 7.68 (d, J=5.5 Hz, 1H), 7.46 (t, J=9.2 Hz, 1H), 7.35 (br. s., 1H), 7.23 (br. s., 1H), 6.17 (s, 1H), 4.83 (d, J=16.9 Hz, 1H), 4.57 (d, J=16.9 Hz, 1H), 4.33 (d, J=4.4 Hz, 1H), 3.94-3.83 (m, 1H), 3.76-3.67 (m, 1H), 3.56 (q, J=5.6 Hz, 3H), 3.42-3.32 (m, 3H), 2.19 (dd, J=13.6, 5.9 Hz, 1H), 1.88 (dd, J=13.8, 7.9 Hz, 1H), 1.29 (s, 9H).

Scheme 76

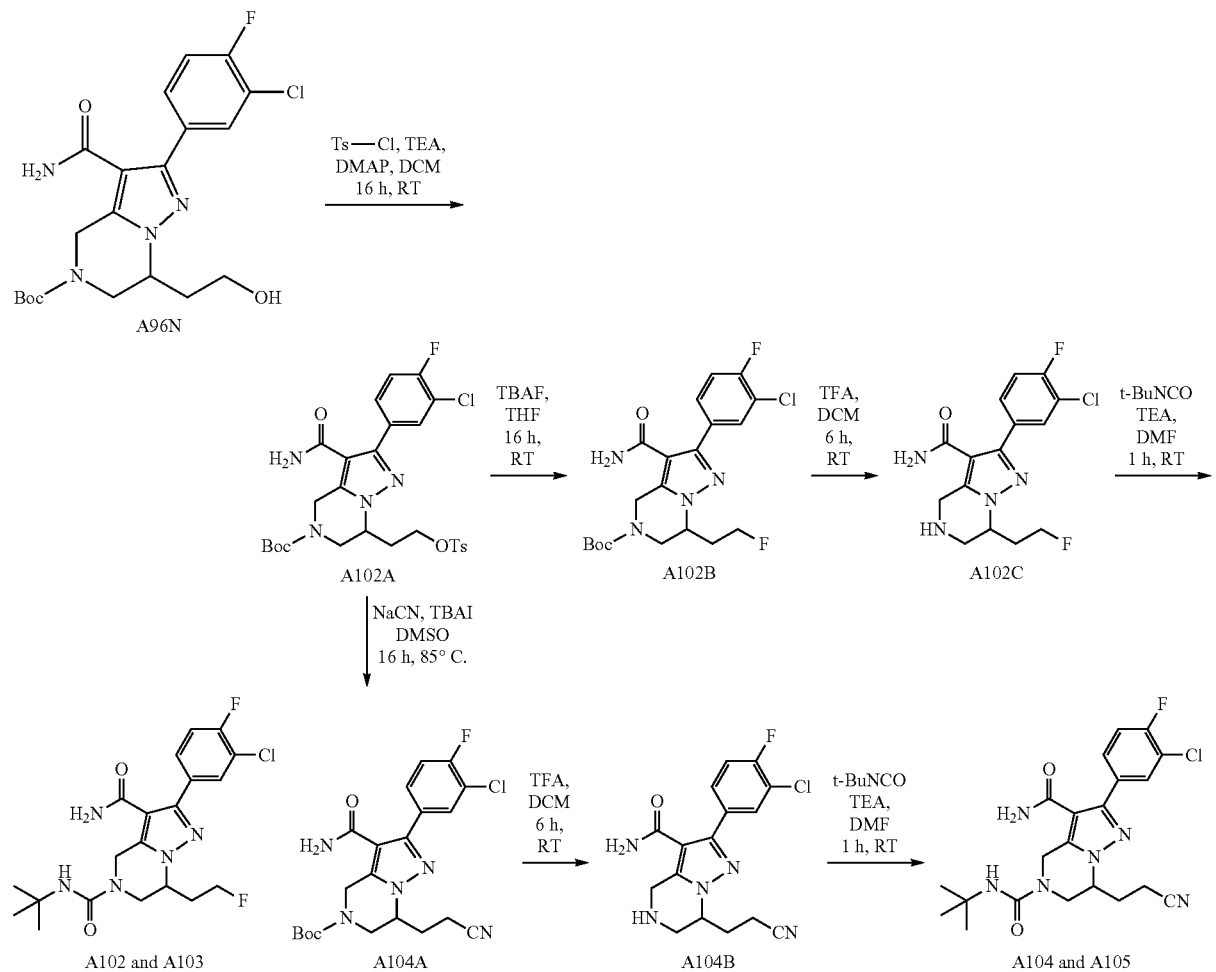

Intermediate A102A: tert-Butyl 3-carbamoyl-2-(3-chloro-4-fluorophenyl)-7-(2-(tosyloxy)ethyl)-6,7-dihydropyrazolo[1,5-a]pyrazine-5(4H)-carboxylate

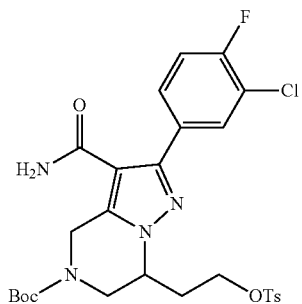 [SMILES: Cc1ccc(S(=O)(=O)OCCC2CN(C(=O)OC(C)(C)C)Cc3c(C(N)=O)c(-c4ccc(F)c(Cl)c4)nn32)cc1]

To a solution of Intermediate A96N (0.76 g, 1.732 mmol) in CH$_2$Cl$_2$ (30 mL) were added TEA (0.483 mL, 3.46 mmol), Ts-Cl (0.220 mL, 2.078 mmol), and DMAP (10.58 mg, 0.087 mmol). The reaction mixture was stirred at RT overnight and concentrated. The residue was purified by silica gel chromatography (40 g REDISEP® column, eluting with 35-80% EtOAc in hexane). Fractions containing the product were combined and evaporated to afford Intermediate A102A (0.76 g, 76%). MS(ES): m/z=593.1 [M+H]$^+$; $^1$H NMR (400 MHz, chloroform-d) δ ppm 7.85-7.78 (m, 2H), 7.64 (dd, J=7.0, 2.0 Hz, 1H), 7.46 (ddd, J=8.5, 4.5, 2.3 Hz, 1H), 7.39-7.18 (m, 3H), 5.12 (br. s., 1H), 4.73 (d, J=18.6 Hz, 1H), 4.43 (br. s., 1H), 4.32 (t, J=6.3 Hz, 2H), 4.06 (dd, J=14.1, 3.5 Hz, 1H), 3.67 (d, J=12.0 Hz, 1H), 2.45 (s, 3H), 2.41-2.29 (m, 1H), 2.19-2.08 (m, 1H), 1.59-1.44 (m, 9H).

Intermediate A102B: tert-Butyl 3-carbamoyl-2-(3-chloro-4-fluorophenyl)-7-(2-fluoroethyl)-6,7-dihydropyrazolo[1,5-a]pyrazine-5(4H)-carboxylate

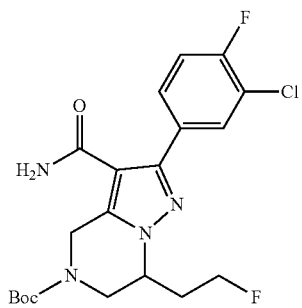 [SMILES: CC(C)(C)OC(=O)N1Cc2c(C(N)=O)c(-c3ccc(F)c(Cl)c3)nn2C(CCF)C1]

To a solution of Intermediate A102A (260 mg, 0.438 mmol) in THF (15 mL) at 0° C. under nitrogen was added 1M THF solution of tetrabutylammonium fluoride (0.526 mL, 0.526 mmol). The reaction mixture was stirred at RT overnight. It was concentrated. The residue was purified by silica gel chromatography (40 g REDISEP® column, eluting with 35-80% EtOAc in hexane). Fractions containing the product were combined and evaporated to afford Intermediate A102B (140 mg, 72%). MS(ES): m/z=441.1 [M+H]$^+$.

Intermediate A102C: 2-(3-Chloro-4-fluorophenyl)-7-(2-fluoroethyl)-4,5,6,7-tetrahydropyrazolo[1,5-a]pyrazine-3-carboxamide TFA salt

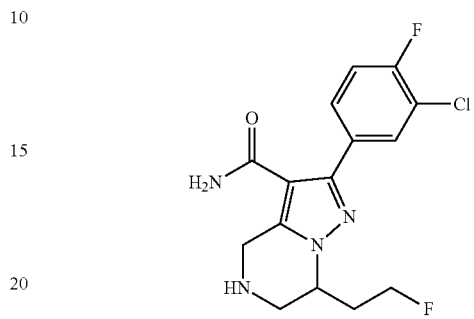

To a solution of afford Intermediate A102B (140 mg, 0.318 mmol) in CH$_2$Cl$_2$ (10 mL) was added TFA (1 mL, 12.98 mmol). The reaction mixture was stirred at RT for 4 h and concentrated. The crude Intermediate A102C was used for the next step without further purification. MS(ES): m/z=341.1 [M+H]$^+$.

Compounds A102 and A103: N$^5$-(tert-Butyl)-2-(3-chloro-4-fluorophenyl)-7-(2-fluoroethyl)-6,7-dihydropyrazolo[1,5-a]pyrazine-3,5(4H)-dicarboxamide

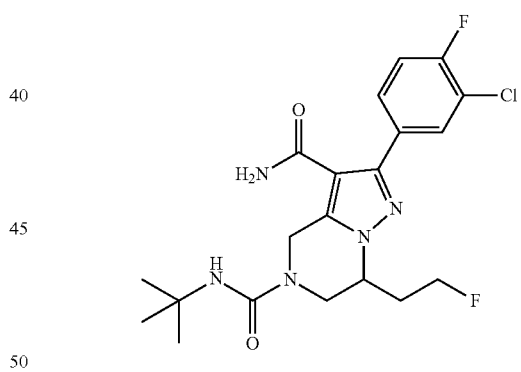

To a solution of Intermediate A102C (40 mg, 0.088 mmol) in DMF (1 mL) were Hunig's base (0.030 mL, 0.173 mmol) and 2-isocyanato-2-methylpropane (13.08 mg, 0.132 mmol). The reaction mixture was stirred at RT for 2 h. It was purified by preparative HPLC to afford racemate Compounds A102 and A103. The racemate was further separated by chiral HPLC to give enantiomer (A102 (Ret time 19.38 min, 8.5 mg, 22%) and enantiomer A103 (Ret time 25.82 min, 8.5 mg, 22%). Chiral HPLC Method: Column: CHIRALPAK® AD 21×250 mm, 10 μm; Mobile Phase A: 0.1% diethylamine/heptane; Mobile Phase B: ethanol; Gradient: hold at 13% B-100% B over 32 minutes; Flow rate: 15 mL/min; MS(ES): m/z=440.5 [M+H]$^+$; HPLC Ret. Time 1.57 and 2.51 min (HPLC Methods H and I); $^1$H NMR (500 MHz, DMSO-d$_6$) δ ppm 7.85 (d, J=6.6 Hz, 1H), 7.69 (br. s., 1H), 7.47 (t, J=9.0 Hz, 1H), 7.36 (br. s., 1H), 7.24 (br. s., 1H), 6.23 (s, 1H), 4.85-4.71 (m, 2H), 4.71-4.61 (m, 2H), 4.38 (br. s., 1H), 3.81 (d, J=4.0 Hz, 2H), 3.39 (s, 4H), 2.42-2.21 (m, 1H), 2.21-1.98 (m, 1H), 1.28 (s, 9H).

Intermediate 104A: tert-Butyl 3-carbamoyl-2-(3-chloro-4-fluorophenyl)-7-(2-cyanoethyl)-6,7-dihydropyrazolo[1,5-a]pyrazine-5(4H)-carboxylate

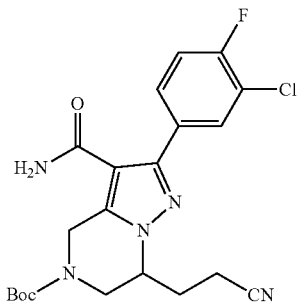 [SMILES: CC(C)(C)OC(=O)N1Cc2c(C(N)=O)c(-c3ccc(F)c(Cl)c3)nn2C(CCC#N)C1]

To a solution of Intermediate A102A (180 mg, 0.304 mmol) in DMSO (2 mL) were added tetrabutylammonium iodide (11.21 mg, 0.030 mmol) and sodium cyanide (74.4 mg, 1.518 mmol). The reaction mixture was heated at 85° C. for 16 h and cooled to RT. The reaction mixture was diluted with water, extracted with EtOAc. The combined organic layer was washed with brine, dried over Na$_2$SO$_4$, and filtered. The filtrate was concentrated. The crude product was purified by silica gel chromatography (40 g REDISEP® column, eluting with 35-80% EtOAc in hexane). Fractions containing the product were combined and evaporated to afford Intermediate A104A (80 mg, 59%). MS(ES): m/z=448.1 [M+H]$^+$.

Intermediate 104B: 2-(3-Chloro-4-fluorophenyl)-7-(2-cyanoethyl)-4,5,6,7-tetrahydropyrazolo[1,5-a]pyrazine-3-carboxamide TFA salt

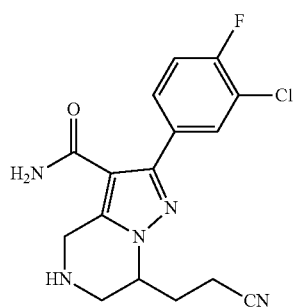

To a solution of Intermediate A104A (80 mg, 0.179 mmol) in CH$_2$Cl$_2$ (10 mL) was added TFA (1 mL, 12.98 mmol). The reaction mixture was stirred at RT for 4 h and concentrated. The crude Intermediate A104B was used for the next step without further purification. MS(ES): m/z=348.1 [M+H]$^+$.

Compounds A104 and A105: N$^5$-(tert-Butyl)-2-(3-chloro-4-fluorophenyl)-7-(2-cyanoethyl)-6,7-dihydropyrazolo[1,5-a]pyrazine-3,5(4H)-dicarboxamide

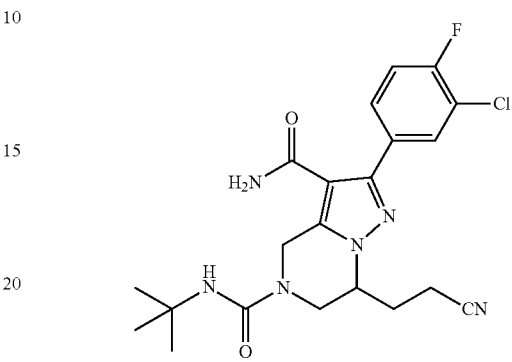

To a solution of Intermediate A104B (40 mg, 0.087 mmol) in DMF (1 mL) were added Hunig's base (0.030 mL, 0.173 mmol) and 2-isocyanato-2-methylpropane (12.88 mg, 0.130 mmol). The reaction mixture was stirred at RT for 2 h. It was purified by preparative HPLC to afford racemate Compounds A104 and A105. The racemate was further separated by chiral HPLC to give enantiomer A104 (Ret time 12.08 min, 9.2 mg, 24%) and enantiomer A105 (Ret time 15.60 min, 9.7 mg, 25%). Chiral HPLC Method: Column: CHIRALPAK® AD 21×250 mm, 10 μm; Mobile Phase A: 0.1% diethylamine/heptane; Mobile Phase B: ethanol; Gradient: hold at 15%-100% B over 20 minutes; Flow rate: 15 mL/min; MS(ES): m/z=422.5 [M+H]$^+$; HPLC Ret. Time 1.65 and 2.62 min (HPLC Methods H and I); $^1$H NMR (500 MHz, DMSO-d$_6$) δ ppm 7.85 (d, J=7.3 Hz, 1H), 7.69 (br. s., 1H), 7.46 (t, J=9.0 Hz, 1H), 7.35 (br. s., 1H), 7.21 (br. s., 1H), 6.22 (s, 1H), 4.77 (d, J=17.2 Hz, 1H), 4.65 (d, J=16.9 Hz, 1H), 4.14 (d, J=3.7 Hz, 1H), 3.86-3.77 (m, 1H), 3.77-3.63 (m, 1H), 3.39-3.30 (m, 2H), 2.07-1.94 (m, 1H), 1.77-1.63 (m, 1H), 1.29 (s, 9H), 0.99 (t, J=7.5 Hz, 3H).

Scheme 77

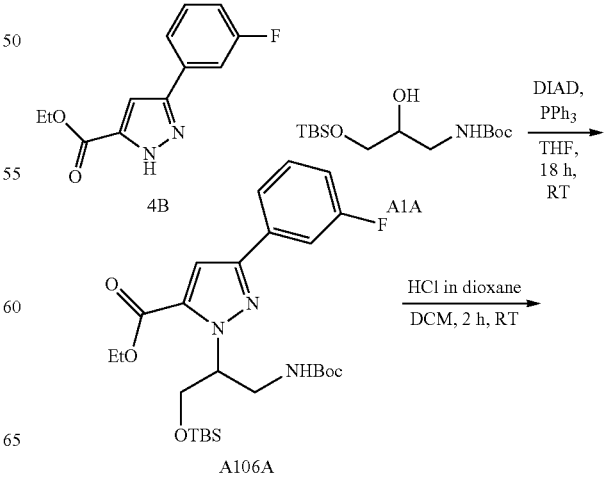

-continued
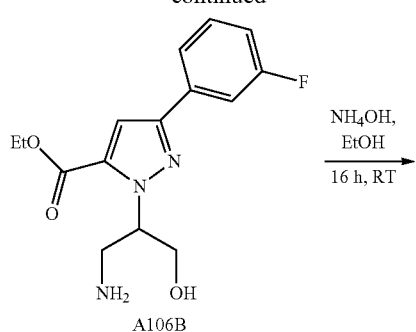
A106B
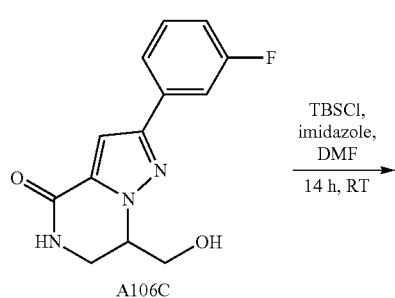
A106C
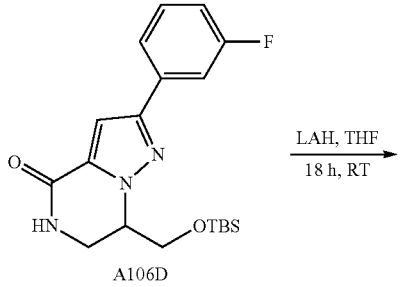
A106D
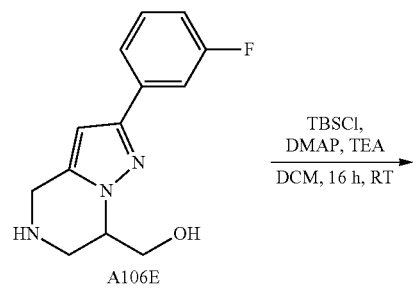
A106E
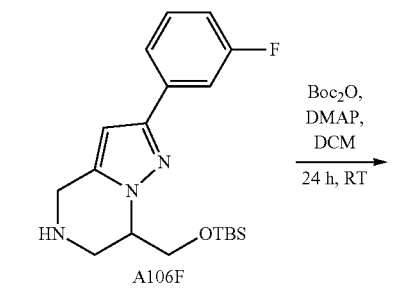
A106F
-continued
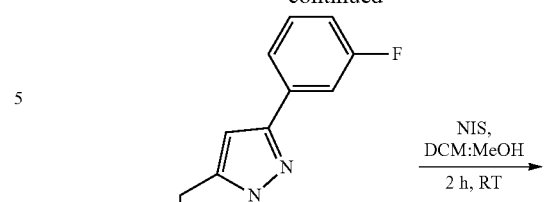
A106G
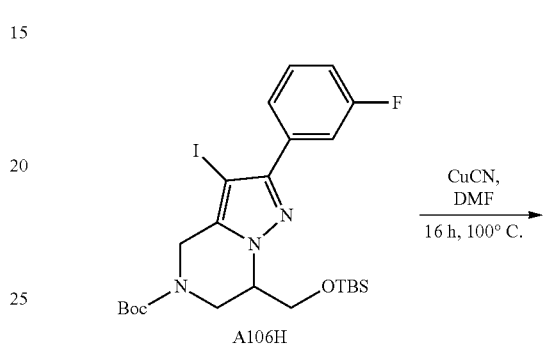
A106H
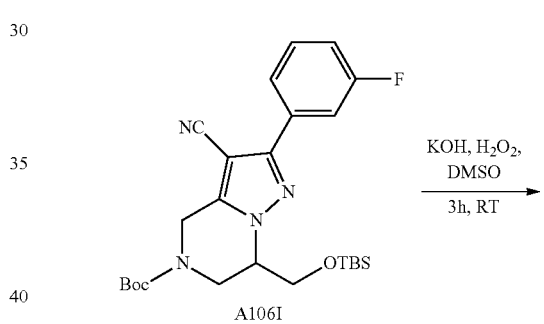
A106I
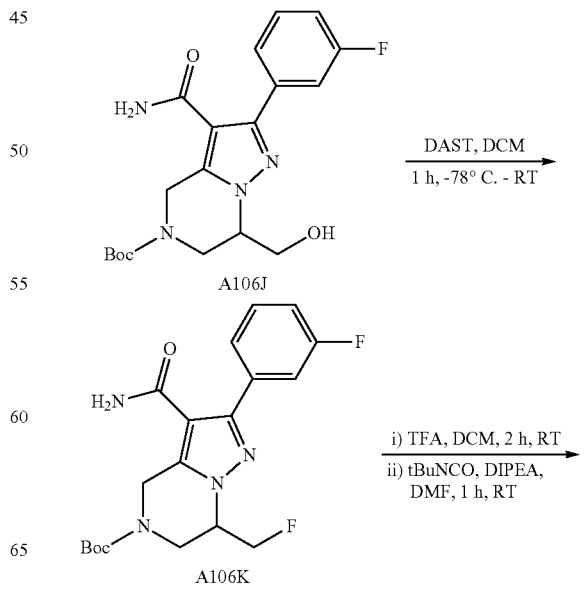
A106J
A106K -continued

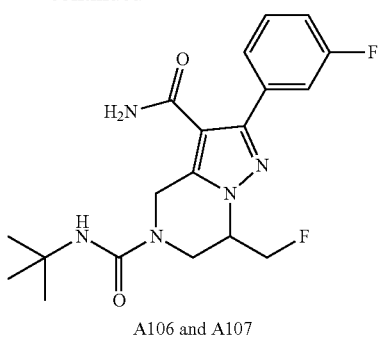

A106 and A107

Intermediate A106A: Ethyl 3-(3-fluorophenyl)-1-(2,2,3,3,11,11-hexamethyl-9-oxo-4,10-dioxa-8-aza-3-siladodecan-6-yl)-1H-pyrazole-5-carboxylate

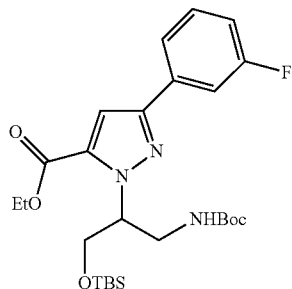 [SMILES: CCOC(=O)c1cc(-c2cccc(F)c2)nn1C(CNC(=O)OC(C)(C)C)CO[Si](C)(C)C(C)(C)C]

To a flask charged with triphenylphosphine (2.93 g, 11.16 mmol), sealed with a septum and purged with a dry atmosphere of nitrogen, was added THF (20 mL) via syringe and the reaction mixture was cooled to 0° C. Next, DIAD (2.170 mL, 11.16 mmol) was added via syringe resulting in a thick milky yellow solution. A solution of Intermediate A1A (3.28 g, 10.73 mmol) in THF (5.0 mL) was added to the ice-cold solution. After 15 minutes, pyrazole 4B (2.01 g, 8.58 mmol) was added as a solution in THF (5.0 mL). The reaction was then allowed to warm to RT. After 18 h, the reaction mixture was diluted with EtOAc (150 mL) The organic layer was washed with brine, dried over anhydrous $Na_2SO_4$, filtered and concentrated under reduced pressure to provide a crude oil. The crude reaction mixture was purified by silica gel chromatography (220 g REDISEP® column, eluting with 0 to 15% EtOAc in hexanes). Fractions containing the product were combined and evaporated to afford Intermediate A106A (4.5 g, 80%) as a thick syrup. MS(ES): m/z=522.09 [M+H]$^+$; $^1$H NMR (400 MHz, chloroform-d) δ ppm 7.49-7.60 (2H, m), 7.32-7.41 (1H, m), 7.12 (1H, s), 6.99-7.07 (1H, m), 5.52-5.64 (1H, m), 4.92-5.07 (1H, m), 4.37 (2H, q, J=7.28 Hz), 3.97 (2H, d, J=6.53 Hz), 3.67-3.83 (2H, m), 1.37-1.50 (9H, m), 0.75-0.86 (9H, m), 0.04-0.11 (2H, m), −0.12-0.00 (6H, m).

Intermediate A106B: Ethyl 1-(1-amino-3-hydroxypropan-2-yl)-3-(3-fluorophenyl)-1H-pyrazole-5-carboxylate

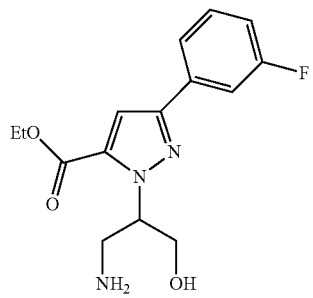 [SMILES: CCOC(=O)c1cc(-c2cccc(F)c2)nn1C(CN)CO]

To an ice-cooled solution of Intermediate A106A (4.35 g, 8.34 mmol) in DCM (50 mL) was added a 4M solution of HCl in 1,4-dioxane (12.5 mL, 50.0 mmol). The reaction mixture was allowed to stir at RT for 2 h. The white precipitate that was generated was filtered off and the filter cake was washed with diethyl ether. The solid was dried under vacuum for 16 h to afford Intermediate A106B as an HCl salt (2.56 g, >98%). MS(ES): m/z=308.0 [M+H]$^+$. $^1$H NMR (400 MHz, DMSO-$d_6$) δ ppm 8.04 (1H, br. s.), 7.72-7.80 (1H, m), 7.44-7.54 (1H, m), 7.13-7.23 (1H, m), 5.46-5.58 (1H, m), 5.24 (1H, br. s.), 4.35 (2H, q, J=7.11 Hz), 3.58-3.80 (3H, m), 3.40 (1H, d, J=11.29 Hz), 1.31-1.40 (2H, m).

Intermediate A106C: 2-(3-Fluorophenyl)-7-(hydroxymethyl)-6,7-dihydropyrazolo[1,5-a]pyrazin-4(5H)-one

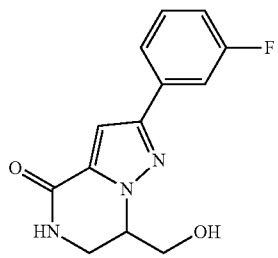 [SMILES: O=C1NCC(CO)n2nc(-c3cccc(F)c3)cc21]

To a suspension of Intermediate A106B (2.56 g, 8.34 mmol) in EtOH (50 mL) was added NH$_4$OH (32.5 mL, 334 mmol, 40% wt). After a few moments, the reaction mixture became homogeneous and the solution was allowed to stir at RT for 16 h. The crude reaction mixture was concentrated in vacuo and diluted with EtOAc. The aqueous solution was neutralized to pH=7 using a 1.0 M aqueous solution of HCl. The organic layer was separated and the aqueous layer was extracted with EtOAc. The combined organic layers were then washed with brine, dried over sodium sulfate, and concentrated to afford Intermediate A106C (2.1 g, 96%) as a white solid. MS(ES): m/z=261.97 [M+H]$^+$. NMR (400 MHz, chloroform-d) δ ppm 7.49-7.61 (2H, m), 7.36-7.45 (1H, m), 7.16-7.21 (1H, s), 7.06 (1H, tdd, J=8.41, 8.41, 2.51, 1.00 Hz), 6.28 (1H, br. s.), 4.56-4.67 (1H, m), 4.07-4.23 (2H, m), 3.72-3.85 (2H, m), 3.14-3.37 (1H, m).

Intermediate A106D: 7-(((tert-Butyldimethylsilyl)oxy)methyl)-2-(3-fluorophenyl)-6,7-dihydropyrazolo[1,5-a]pyrazin-4(5H)-one

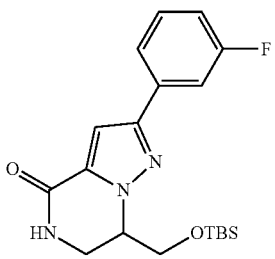 [SMILES: CC(C)(C)[Si](C)(C)OCC1CNC(=O)c2cc(-c3cccc(F)c3)nn21]

To a solution of Intermediate A106C (11.5 g, 44.1 mmol) in DMF (120 mL) was added imidazole (3.66 g, 53.8 mmol) and TBSCl (7.64 g, 50.7 mmol) and the reaction mixture was stirred at RT for 14 h. The solution was concentrated and the crude material was diluted with equal parts water and DCM (250 mL each). The organic layer was separated and washed several more times with water before being dried over sodium sulfate and concentrated to afford Intermediate A106D (13.57 g, 82%) as a white solid. MS(ES): m/z=375.95 [M+H]⁺. ¹H NMR (400 MHz, chloroform-d) δ ppm 7.52-7.63 (1H, m), 7.35-7.46 (1H, m), 7.13-7.20 (1H, m), 6.99-7.11 (1H, m), 6.01-6.25 (1H, m), 4.48-4.62 (1H, m), 4.10 (1H, dd, J=10.04, 4.27 Hz), 3.84-4.03 (3H, m), 0.90-0.93 (9H, m), 0.07-0.12 (6H, m).

Intermediate A106E: (2-(3-Fluorophenyl)-4,5,6,7-tetrahydropyrazolo[1,5-a]pyrazin-7-yl)methanol

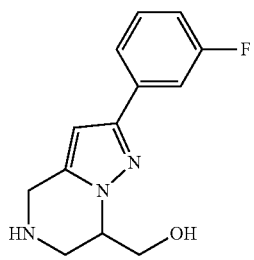 [SMILES: OCC1CNCc2cc(-c3cccc(F)c3)nn21]

To a solution of Intermediate A106D (5.162 g, 13.75 mmol) in THF (125 mL) cooled to −15° C., was introduced a 1 M solution of LAH in THF (38.5 mL, 38.5 mmol) dropwise. The reaction mixture was allowed to gradually reach room temperature and stir for an additional 18 h. The reaction mixture was carefully quenched at −15° C. with sequential addition of H₂O (38.5 mL), NaOH (15% aq. solution, 38.5 mL) and H₂O (114 mL). The slurry was then allowed to stir at RT for 30 minutes, followed by the addition of anhydrous MgSO₄. The mixture was allowed to stir for 15 minutes and then the inorganics were filtered off. The filter cake was washed with DCM (150 mL). The biphasic filtrate was concentrated under reduced pressure to remove THF. The aqueous layer was then extracted with DCM (3×50 mL). The combined organic layers were washed with brine, dried over anhydrous Na₂SO₄, filtered and concentrated under reduced pressure to afford Intermediate A106E (3.41 g, >98%) as a white sticky solid. MS(ES): m/z=247.94 [M+H]⁺. ¹H NMR (400 MHz, chloroform-d) δ ppm 7.55 (1H, dt, J=7.84, 1.10 Hz), 7.48 (1H, ddd, J=10.16, 2.51, 1.63 Hz), 7.31-7.40 (1H, m), 6.96-7.04 (1H, m), 6.32 (1H, s), 4.26-4.35 (1H, m), 4.07-4.15 (2H, m), 4.01-4.07 (1H, m), 3.91-3.98 (1H, m), 3.41 (1H, dd, J=13.30, 4.77 Hz), 3.12 (1H, dd, J=13.18, 7.15 Hz).

Intermediate A106F: 7-(((tert-Butyldimethylsilyl)oxy)methyl)-2-(3-fluorophenyl)-4,5,6,7-tetrahydropyrazolo[1,5-a]pyrazine

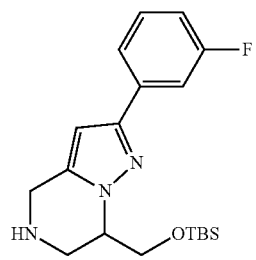 [SMILES: CC(C)(C)[Si](C)(C)OCC1CNCc2cc(-c3cccc(F)c3)nn21]

To a flask charged with Intermediate A106E (3.41 g, 13.79 mmol) was added DMAP (0.084 g, 0.690 mmol) and triethylamine (2.307 mL, 16.55 mmol). The reaction mixture was dissolved in DCM (125 mL) and finally TBSCl (2.286 g, 15.17 mmol) was added. The reaction mixture was then allowed to stir at 22° C. for 16 h after which the mixture was diluted with a saturated aq. solution of NaHCO₃ and the two layers were separated. The aqueous phase was extracted with DCM (2×50 mL). The combined organic layers were washed with water, brine, dried over anhydrous Na₂SO₄, filtered and concentrated under reduced pressure to afford a pale yellow oil. Crude Intermediate A106F (5.12 g, 92%) was found to be 90% pure and carried forward to amine protection with Boc-anhydride without further purification. MS(ES): m/z=361.94 [M+H]⁺.

Intermediate A106G: tert-Butyl 7-(((tert-butyldimethylsilyl)oxy)methyl)-2-(3-fluorophenyl)-6,7-dihydropyrazolo[1,5-a]pyrazine-5(4H)-carboxylate

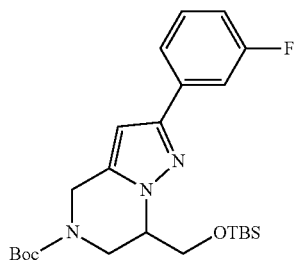 [SMILES: CC(C)(C)OC(=O)N1Cc2cc(-c3cccc(F)c3)nn2C(CO[Si](C)(C)C(C)(C)C)C1]

To a solution of Intermediate A106F (4.33 g, 11.98 mmol) in DCM (100 mL) was added triethylamine (6.68 mL, 47.9 mmol) and DMAP (0.073 g, 0.599 mmol). To the colorless solution was then added di-tert-butyl dicarbonate (3.92 g, 17.97 mmol) resulting in gas evolution. The reaction mixture was allowed to stir at 22° C. for 24 h prior to being quenched with a saturated aqueous solution of NaHCO₃. The layers were separated, and the aqueous layer was extracted twice more with DCM. The combined organic layers were washed with water, followed by brine, dried over sodium sulfate, and concentrated in vacuo. The crude product was purified by silica gel chromatography (120 g REDISEP® column, eluting with 20% EtOAc in hexanes). Fractions containing the product were combined and evaporated to afford Intermediate A106G (4.87 g, 88%) as a colorless oil. MS(ES): m/z=461.77 [M+H]$^+$. $^1$H NMR (400 MHz, chloroform-d) δ ppm 7.45-7.58 (1H, m), 7.35 (1H, td, J=8.03, 6.02 Hz), 6.95-7.05 (1H, m), 6.29-6.39 (1H, m), 4.55-4.79 (2H, m), 4.33 (1H, br. s.), 4.06-4.22 (2H, m), 3.74-4.03 (2H, m), 1.49-1.54 (9H, m), 0.83-0.95 (9H, m), −0.01-0.14 (6H, m).

Intermediate A106H: tert-Butyl 7-(((tert-butyldimethylsilyl)oxy)methyl)-2-(3-fluorophenyl)-3-iodo-6,7-dihydropyrazolo[1,5-a]pyrazine-5(4H)-carboxylate

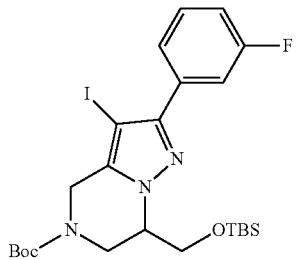 [SMILES: CC(C)(C)OC(=O)N1Cc2c(I)c(-c3cccc(F)c3)nn2C(CO[Si](C)(C)C(C)(C)C)C1]

To a solution of Intermediate A106G (4.87 g, 10.6 mmol) in DCM (56 mL) and MeOH (14 mL) was added NIS (7.12 g, 31.6 mmol) and the reaction mixture was allowed to stir at RT for 90 min. The solution was then concentrated under reduced pressure to provide a red oil. The crude reaction mixture was purified by silica gel chromatography (120 g REDISEP® column, eluting with a gradient of 0-30% EtOAc in hexanes). Fractions containing the product were combined and evaporated to afford Intermediate A106H (5.70 g, 92%) as a sticky solid. MS(ES): m/z=587.95 [M+H]$^+$. $^1$H NMR (400 MHz, chloroform-d) δ ppm 7.65 (1H, dq, J=7.78, 0.84 Hz), 7.54-7.60 (1H, m), 7.36-7.44 (1H, m), 7.08 (1H, tdd, J=8.44, 8.44, 2.57, 0.88 Hz), 4.50-4.71 (1H, m), 4.41-4.49 (1H, m), 4.02-4.40 (3H, m), 3.83-3.99 (1H, m), 3.75-3.82 (1H, m), 1.53 (8H, s), 0.84-0.93 (10H, m), −0.01-0.15 (6H, m).

Intermediate A106I: tert-Butyl 7-(((tert-butyldimethylsilyl)oxy)methyl)-2-(3-fluorophenyl)-3-cyano-6,7-dihydropyrazolo[1,5-a]pyrazine-5(4H)-carboxylate

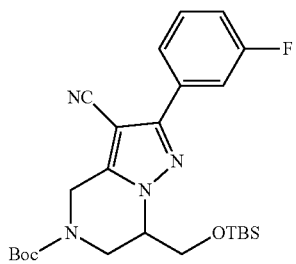 [SMILES: CC(C)(C)OC(=O)N1Cc2c(C#N)c(-c3cccc(F)c3)nn2C(CO[Si](C)(C)C(C)(C)C)C1]

To a flask charged with Intermediate A106H (3.84 g, 6.54 mmol) was added DMF (43.6 mL) and copper (I) cyanide (1.463 g, 16.34 mmol). The heterogeneous reaction mixture was equipped with a reflux condenser and was heated to 100° C. for 18 h. The reaction mixture was cooled to RT and the solution was filtered through a pad of CELITE®. The filter cake was washed with EtOAc. The combined filtrate was concentrated under reduced pressure to afford the crude reaction mixture as a dark green oil. The product was purified by silica gel chromatography (80 g REDISEP® column, eluting with a gradient of 5-30% EtOAc in hexanes). Fractions containing the product were combined and evaporated to afford Intermediate A106I (1.441 g, 45%) as a white solid. MS(ES): m/z=431.0 [M+H$_2$O-OtBu]$^+$; $^1$H NMR (400 MHz, chloroform-d) δ ppm 7.62-7.83 (2H, m), 7.39-7.51 (1H, m), 7.08-7.19 (1H, m), 4.67-4.96 (2H, m), 4.34 (1H, br. s.), 3.84-4.19 (4H, m), 1.47-1.54 (9H, m), 0.79-0.91 (9H, m), −0.02-0.10 (6H, m).

Intermediate A106J: tert-Butyl 3-carbamoyl-2-(3-fluorophenyl)-7-(hydroxymethyl)-6,7-dihydropyrazolo[1,5-a]pyrazine-5(4H)-carboxylate

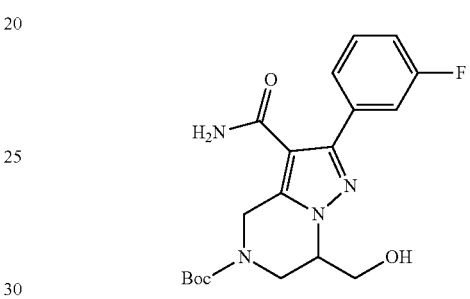

To an ice-cooled solution of Intermediate A106I (1.44 g, 2.96 mmol) in DMSO (20 mL) was added a 5 M aq. solution of KOH (2.96 mL, 14.8 mmol) and H$_2$O$_2$ (6.05 mL, 59.2 mmol, 30% w/v in H$_2$O) and the reaction mixture was stirred at 22° C. for 3 h. The reaction mixture was then partitioned between equal parts water and EtOAc and the layers were separated. The aqueous phase was extracted twice more with EtOAc. The combined organic layers were washed with water, brine, dried over anhydrous MgSO$_4$, filtered and concentrated under reduced pressure to afford a white solid. The crude reaction mixture was purified by silica gel chromatography (120 g REDISEP® column, eluting with a gradient from 75-100% EtOAc in hexanes). Fractions containing the product were combined and evaporated to afford Intermediate A106J (0.997 g, 52%) as a white solid contaminated with dimethyl sulfone. MS(ES): m/z=412.96 [M+Na]$^+$.

Intermediate A106K: tert-Butyl 3-carbamoyl-7-(fluoromethyl)-2-(3-fluorophenyl)-6,7-dihydropyrazolo[1,5-a]pyrazine-5(4H)-carboxylate

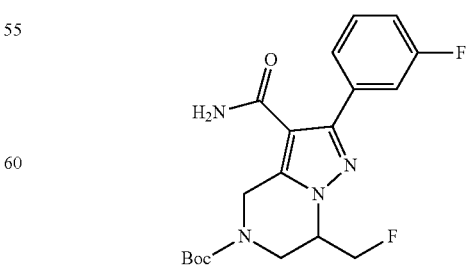

A suspension of Intermediate A106J (131.5 mg, 0.337 mmol) in DCM (5.5 mL) was allowed to cool to −78° C.

DAST (0.067 mL, 0.505 mmol) was added dropwise to the solution and was then allowed to warm to RT. After stirring at 22° C. for 1 h, the reaction was quenched by the addition of a saturated aq. solution of NaHCO$_3$ at 0° C. The two layers were separated and the aqueous layer was extracted with DCM (3×10 mL). The combined organic layers were washed with brine, dried over anhydrous MgSO$_4$, filtered and concentrated under reduced pressure to afford an orange oil. The crude reaction mixture was purified by silica gel chromatography (24 g REDISEP® column, eluting with 75% EtOAc in hexanes). Fractions containing the product were combined and evaporated to afford Intermediate A106K (52.8 mg, 40%) as a white solid. MS(ES): m/z=393.0 [M+H]$^+$.

Compounds A106 and A107: N$^5$-(tert-Butyl)-7-(fluoromethyl)-2-(3-fluorophenyl)-6,7-dihydropyrazolo[1,5-a]pyrazine-3,5(4H)-dicarboxamide Scheme 78

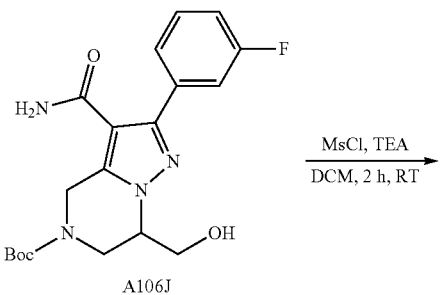

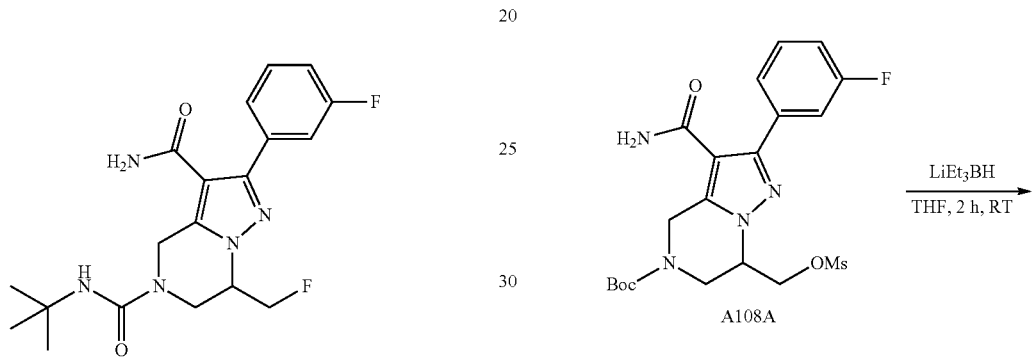

To a solution of Intermediate A106K (0.021 g, 0.054 mmol) in DCM (15 mL) was added trifluoroacetic acid (0.041 mL, 0.537 mmol). The reaction mixture was then allowed to stir at RT for 3 h prior to the removal of the volatiles to afford the crude bis TFA salt.

The TFA salt was then dissolved in DMF (1.0 mL) and treated with DIPEA (0.047 mL, 0.269 mmol). The resulting mixture was allowed to stir for 5 minutes prior to the addition of 2-isocyanato-2-methylpropane (0.012 mL, 0.105 mmol). The reaction was allowed to stir for 2 h after which it was filtered and purified via preparative HPLC. Fractions containing the desired product were combined and evaporated to afford the racemic compound. The compound was further purified through chiral separation using preparative HPLC: CHIRALPAK® AD, 21×250 mm, 10 μm column eluted with 70% heptane with 0.1% diethylamine: 30% EtOH at 15 mL/min. The first eluting enantiomer, r$_f$=6.8 min: (S)-A106 (0.0068 g, 65%) and the second eluting enantiomer, r$_f$=12.6 min: (R)-A107 (0.0051 g, 48%) were thus separated. MS(ES), m/z=392.2 [M+H]$^+$; HPLC Ret. Time 1.38 min. and 2.22 min. (HPLC Methods H and I). $^1$H NMR (500 MHz, DMSO-d$_6$) δ ppm 7.53 (d, J=7.7 Hz), 7.42-7.51 (2H, m), 7.39 (1H, br. s.), 7.17-7.23 (1H, m), 6.30 (1H, s), 4.90-5.05 (m, 1H), 4.70-4.85 (m, 2H), 4.62 (d, J=16.9 Hz, 1H), 4.03 (dd, J=13.8, 3.9 Hz, 1H), 3.76 (dd, J=14.1, 7.2 Hz, 1H), 1.28 (s, 9H).

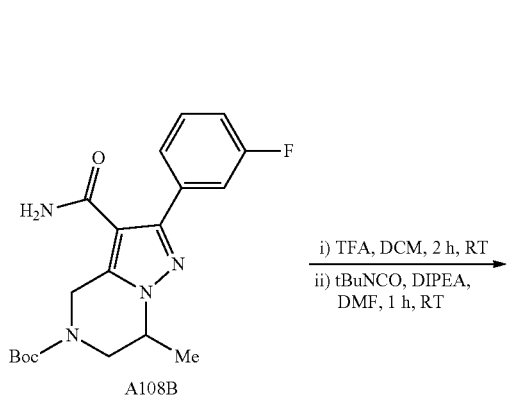

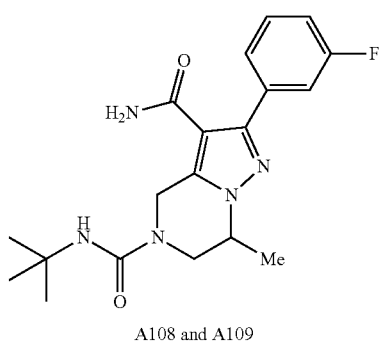

Intermediate A108A: tert-Butyl 3-carbamoyl-2-(3-fluorophenyl)-7-(((methylsulfonyl)oxy)methyl)-6,7-dihydropyrazolo[1,5-a]pyrazine-5(4H)-carboxylate

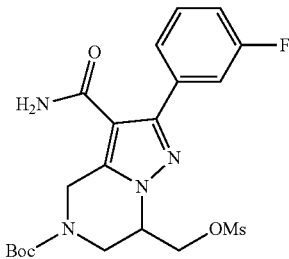 [SMILES: CC(C)(C)OC(=O)N1Cc2c(C(N)=O)c(-c3cccc(F)c3)nn2C(COS(C)(=O)=O)C1]

To an ice-cold suspension of Intermediate A106J (148.2 mg, 0.380 mmol) in DCM (3.8 mL) was added triethylamine (0.063 mL, 0.456 mmol) followed by the dropwise addition of methanesulfonyl chloride (0.032 mL, 0.418 mmol). The resultant homogeneous reaction mixture was allowed to warm to RT and continue to stir for an additional 2 h. The reaction was then quenched with a saturated aq. solution of NaHCO$_3$. The two layers were separated and the aqueous layer was extracted with DCM (2×10 mL). The combined organic layers were washed with brine, dried over anhydrous MgSO$_4$, filtered and the filtrate concentrated under reduced pressure to afford a colorless oil. The crude reaction mixture was purified by silica gel chromatography (24 g REDISEP® column, eluting with a gradient of 60-85% EtOAc in hexanes). Fractions containing the product were combined and evaporated to afford Intermediate A108A (0.0948 g, 33%) as a white solid. MS(ES): m/z=468.9 [M+H]$^+$.

Intermediate A108B: tert-Butyl 3-carbamoyl-2-(3-fluorophenyl)-7-methyl-6,7-dihydropyrazolo[1,5-a]pyrazine-5(4H)-carboxylate

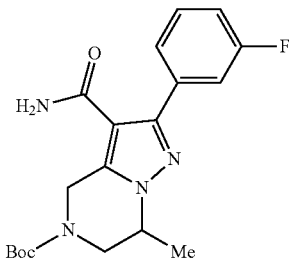 [SMILES: CC1CN(C(=O)OC(C)(C)C)Cc2c(C(N)=O)c(-c3cccc(F)c3)nn21]

To a solution of Intermediate A108A (0.0948 g, 0.202 mmol) in THF (2.0 mL) at RT was added dropwise a 1M solution of LiEt$_3$BH in THF (2.02 mL, 2.02 mmol), and the reaction mixture was stirred for 2 h. The reaction was then carefully quenched with a saturated aq. solution of NaHCO$_3$. The organic phase was separated and the aqueous layer was extracted twice more with DCM. The combined organic layers were washed with brine, dried over sodium sulfate, and concentrated to provide a pale yellow oil. The crude reaction mixture was purified by silica gel chromatography (24 g REDISEP® column, eluting with a gradient of 50-90% EtOAc in hexanes). Fractions containing the product were combined and evaporated to afford Intermediate A108B (0.029 g, 81%) as a white foam. MS(ES): m/z=375.08 [M+H]$^+$.

Compounds A108 and A109: N$^5$-(tert-Butyl)-2-(3-fluorophenyl)-7-methyl-6,7-dihydropyrazolo[1,5-a]pyrazine-3,5(4H)-dicarboxamide

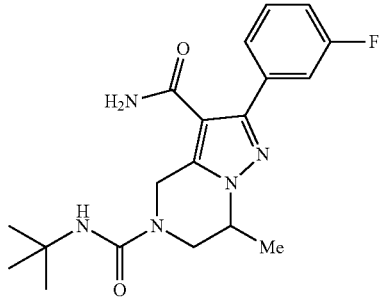 [SMILES: CC1CN(C(=O)NC(C)(C)C)Cc2c(C(N)=O)c(-c3cccc(F)c3)nn21]

Compounds A108 and A109 were synthesized analogous to Compounds A106 and A107 by reacting deprotected A108B with 2-isocyanato-2-methylpropane. The compound was purified by preparative HPLC and further purified through chiral separation using preparative HPLC: CHIRALPAK® AD, 21×250 mm, 10 µm column eluted with 85% heptane with 0.1% diethylamine: 15% EtOH at 15 mL/min. The first eluting enantiomer, r$_t$=10.0 min: (R)-A108 (0.014 g, 45%) and the second eluting enantiomer, r$_t$=18.0 min: (S)-A109 (0.0146 g, 47%) were thus separated. MS(ES): m/z=374.2 [M+H]$^+$; HPLC Ret. Time 1.46 min and 2.26 min (Methods H and I respectively); $^1$H NMR (500 MHz, DMSO-d$_6$) δ ppm 7.52 (1H, d, J=7.70 Hz), 7.39-7.49 (2H, m), 7.34 (1H, br. s.), 7.12-7.23 (2H, m), 6.17-6.28 (1H, m), 4.78 (1H, d, J=16.87 Hz), 4.53-4.64 (1H, m), 4.23-4.35 (1H, m), 3.90-3.99 (1H, m), 3.47 (1H, dd, J=13.76, 7.15 Hz), 1.44 (3H, d, J=6.24 Hz), 1.22-1.32 (9H, s).

Scheme 79

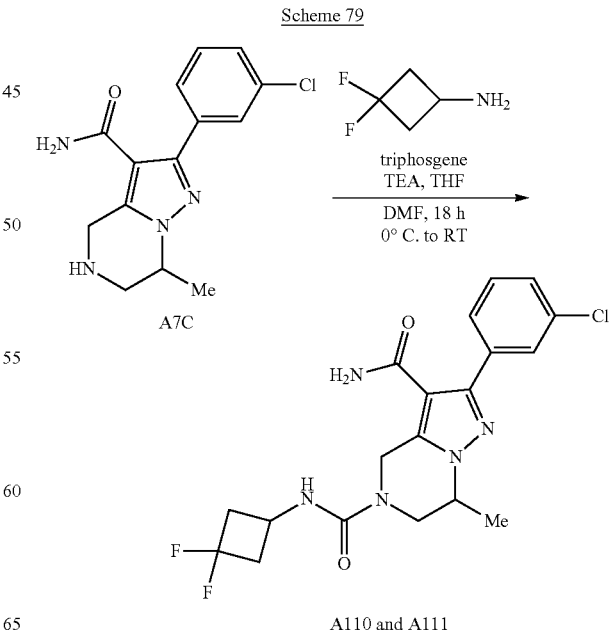

Compounds A110 and A111: 2-(3-Chlorophenyl)-N⁵-(3,3-difluorocyclobutyl)-7-methyl-6,7-dihydropyrazolo[1,5-a]pyrazine-3,5(4H)-dicarboxamide

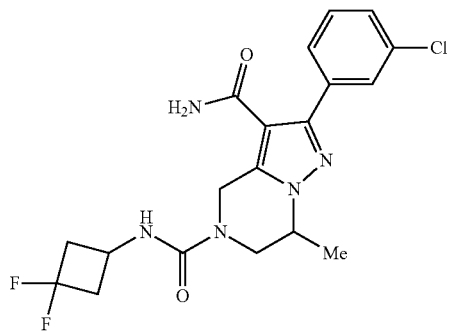 [SMILES: CC1CN(C(=O)NC2CC(F)(F)C2)Cc2c(C(N)=O)c(-c3cccc(Cl)c3)nn21]

To an ice-cold solution of triphosgene (0.069 g, 0.232 mmol) in THF (5 mL) was added a solution of 3,3-difluorocyclobutanamine (0.066 g, 0.619 mmol) and TEA (0.173 mL, 1.238 mmol) in THF (5 mL). The reaction mixture was stirred at 0° C. for 30 minutes, followed by the addition of A7C (0.090 g, 0.310 mmol) and TEA (0.173 mL, 1.238 mmol) in DMF (2.5 mL). The resulting mixture was stirred at RT for 16 h and then concentrated under reduced pressure. The crude material was purified via preparative HPLC. Fractions containing the desired product were combined and dried via centrifugal evaporation to obtain the racemic compound. The compound was further purified through chiral separation using preparative HPLC: CHIRALPAK® AD, 21×250 mm, 10 μm column eluted with 80% heptane with 0.1% diethylamine: 20% EtOH at 15 mL/min. The first eluting enantiomer, $r_t$=20.2 min: (S)-A110 and the second eluting enantiomer, $r_t$=30.6 min: (R)-A111 were thus separated. MS(ES), m/z=424 [M+H]⁺; HPLC Ret. Time 1.41 min. and 2.33 min. (Methods H and I respectively). ¹H NMR (500 MHz, DMSO-d₆) δ 7.70 (s, 1H), 7.64 (d, J=7.0 Hz, 1H), 7.50-7.40 (m, 2H), 4.85-4.63 (m, 2H), 4.40-4.30 (m, 1H), 4.08-3.88 (m, 2H), 3.56 (dd, J=13.8, 6.8 Hz, 1H), 2.85 (d, J=4.4 Hz, 2H), 2.70-2.57 (m, 2H), 1.45 (d, J=6.2 Hz, 3H).

Scheme 80

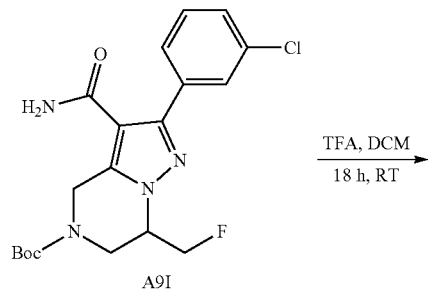

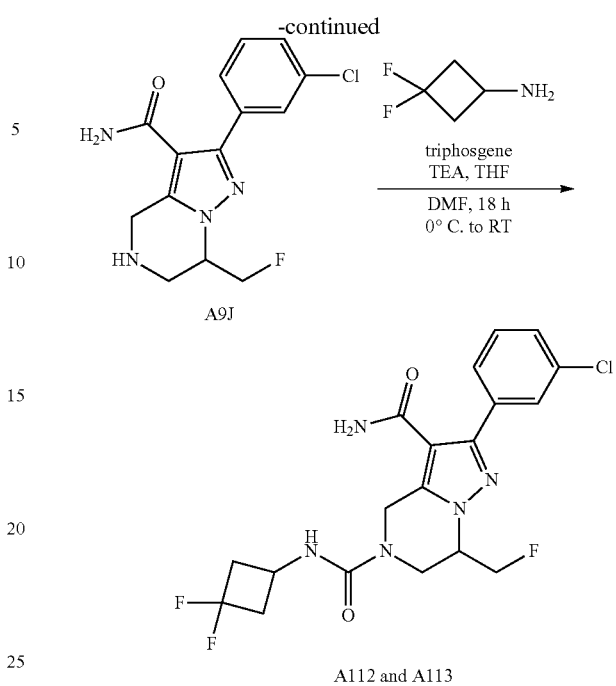

Compounds A112 and A113: 2-(3-Chlorophenyl)-N⁵-(3,3-difluorocyclobutyl)-7-(fluoromethyl)-6,7-dihydropyrazolo[1,5-a]pyrazine-3,5(4H)-dicarboxamide

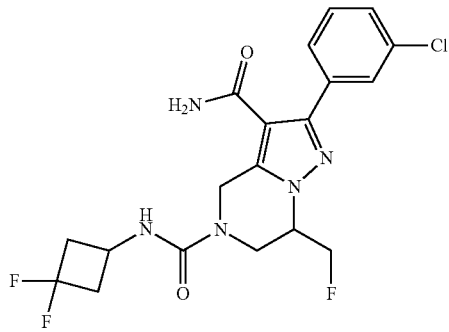 [SMILES: NC(=O)c1c(-c2cccc(Cl)c2)nn2c1CN(C(=O)NC1CC(F)(F)C1)CC2CF]

To an ice-cold solution of triphosgene (0.029 g, 0.097 mmol) in THF (3 mL) was added a solution of 3,3-difluorocyclobutanamine HCl (0.037 g, 0.259 mmol) and TEA (0.072 mL, 0.518 mmol) in THF (3 mL) The reaction mixture was stirred at 0° C. for 30 minutes, followed by the addition of A9J (0.04 g, 0.130 mmol) and TEA (0.072 mL, 0.518 mmol) as a solution in DMF (1.5 mL). The resulting reaction mixture was stirred at RT for 16 h. It was concentrated and the crude material was purified via preparative HPLC. Fractions containing the desired product were combined and dried via centrifugal evaporation to obtain the racemic compound. The compound was further purified through chiral separation using preparative HPLC: CHIRALPAK® AD, 21×250 mm, 10 μm column eluted with 80% heptane with 0.1% diethylamine: 20% EtOH at 15 mL/min. The first eluting enantiomer, $r_t$=12.2 min: (5)-A112 and the second eluting enantiomer, $r_t$=22.5 min: (R)-A113 were thus separated. MS(ES), m/z=442 [M+H]⁺; HPLC Ret. Time 1.35 min. and 2.26 min.

(Methods H and I respectively). $^1$H NMR (500 MHz, DMSO-$d_6$) δ 7.71 (s, 1H), 7.65 (d, J=6.6 Hz, 1H), 7.50-7.42 (m, 2H), 5.05-4.89 (m, 1H), 4.82-4.69 (m, 2H), 4.63-4.51 (m, 1H), 4.08-3.97 (m, 2H), 3.88 (dd, J=14.3, 6.6 Hz, 1H), 3.39 (d, J=3.7 Hz, 2H), 2.89-2.80 (m, 2H), 2.64 (br. s., 2H).

Intermediate (R)-A9H: (R)-tert-Butyl 3-carbamoyl-2-(3-chloro-4-fluorophenyl)-7-(hydroxymethyl)-6,7-dihydropyrazolo[1,5-a]pyrazine-5(4H)-carboxylate

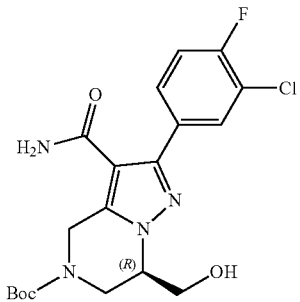

Intermediate (R)-A9H was prepared analogously to Intermediate A1N as depicted in Scheme 57 substituting enantiopure Intermediate (S)-A1A for racemic Intermediate A1A and substituting Intermediate A96E for Intermediate A1D. The chiral amino alcohol Intermediate (S)-A1A was derived from commercially available (S)-3-aminopropane-1,2-diol through the same synthetic sequence described in Scheme 57.

Compound A114: (R)-2-(3-Chloro-4-fluorophenyl)-N$^5$-(3,3-difluorocyclobutyl)-7-(fluoromethyl)-6,7-dihydropyrazolo[1,5-a]pyrazine-3,5(4H)-dicarboxamide

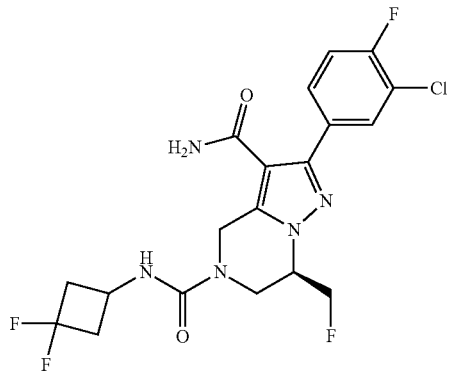 [SMILES: NC(=O)c1c(-c2ccc(F)c(Cl)c2)nn2c1CN(C(=O)NC1CC(F)(F)C1)C[C@@H]2CF]

Intermediate (R)-A9H was used in the asymmetric synthesis of Compound (R)-A114 using the synthetic sequence outlined above for related Compounds A112 and A113 in Scheme 80. MS(ES) m/z=460 [M+H]$^+$; Ret. Time=1.44 and 2.33 min. (Methods H and I respectively). $^1$H NMR (500 MHz, DMSO-$d_6$) δ 7.84 (d, J=7.3 Hz, 1H), 7.67 (br. s., 1H), 7.47 (t, J=9.2 Hz, 1H), 5.05-4.87 (m, 1H), 4.85-4.67 (m, 3H), 4.61-4.49 (m, 1H), 4.01 (d, J=11.7 Hz, 2H), 3.90 (s, 1H), 2.84 (br. s., 2H), 2.64 (br. s., 2H).

Compound A115: (S)-2-(3-Chloro-4-fluorophenyl)-N$^5$-(3,3-difluorocyclobutyl)-7-methyl-6,7-dihydropyrazolo[1,5-a]pyrazine-3,5(4H)-dicarboxamide

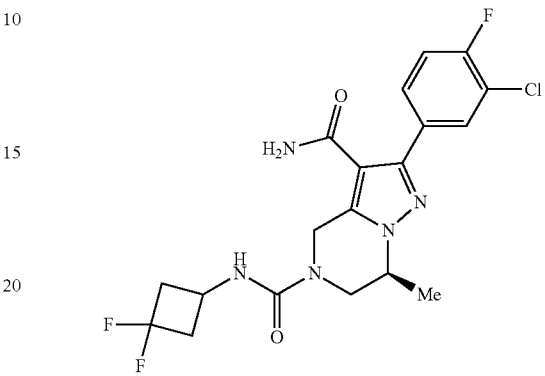

Intermediate (R)-A9H was used in the asymmetric synthesis of Compound (S)-A115 using the synthetic sequence outlined above for related Compounds A110 and A111 in Scheme 79. MS(ES) m/z=442 [M+H]$^+$; Ret. Time=1.48 and 2.48 min. (Methods H and I respectively). $^1$H NMR (500 MHz, DMSO-$d_6$) δ 7.84 (d, J=7.3 Hz, 1H), 7.67 (d, J=5.1 Hz, 1H), 7.47 (t, J=8.8 Hz, 1H), 4.85-4.64 (m, 2H), 4.40-4.29 (m, 1H), 4.09-3.89 (m, 2H), 3.56 (dd, J=13.8, 6.8 Hz, 1H), 3.37 (d, J=8.4 Hz, 1H), 2.84 (br. s., 1H), 2.63 (d, J=11.0 Hz, 2H), 1.44 (d, J=6.6 Hz, 3H).

Scheme 81

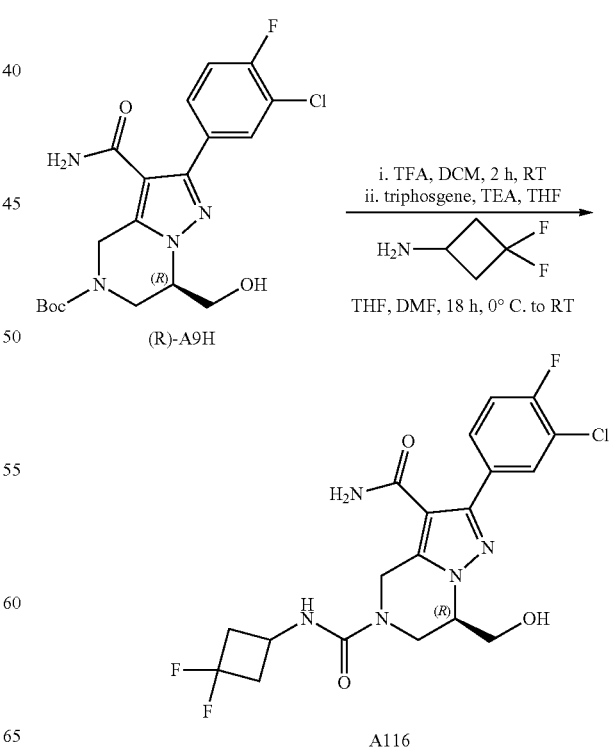

Compound A116: (R)-2-(3-Chloro-4-fluorophenyl)-N⁵-(3,3-difluorocyclobutyl)-7-(hydroxymethyl)-6,7-dihydropyrazolo[1,5-a]pyrazine-3,5(4H)-dicarboxamide

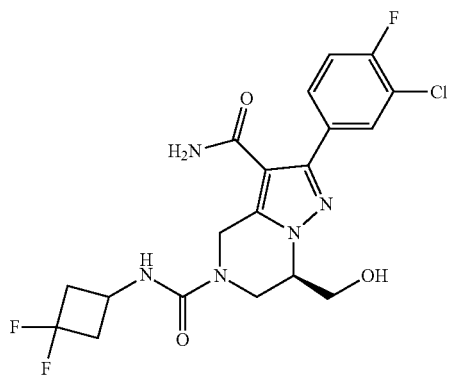 [SMILES: NC(=O)c1c(-c2ccc(F)c(Cl)c2)nn2c1CN(C(=O)NC1CC(F)(F)C1)C[C@@H]2CO]

Intermediate (R)-A9H was used in the enantiospecific preparation of Compound A116 as shown in Scheme 81 using a synthetic sequence analogous to Compound A115. MS(ES) m/z=458 [M+H]⁺; Ret. time=1.23 and 2.24 min. (Methods H and I respectively); ¹H NMR (500 MHz, DMSO-d₆) δ 7.85 (d, J=6.6 Hz, 1H), 7.68 (br. s., 1H), 7.47 (t, J=9.0 Hz, 1H), 7.30-7.12 (m, 2H), 4.85-4.60 (m, 2H), 4.22 (br. s., 1H), 4.08-3.96 (m, 1H), 3.95-3.82 (m, 3H), 3.81-3.73 (m, 1H), 3.37 (br. s., 2H), 2.84 (br. s., 2H), 2.71-2.56 (m, 2H).

Scheme 82

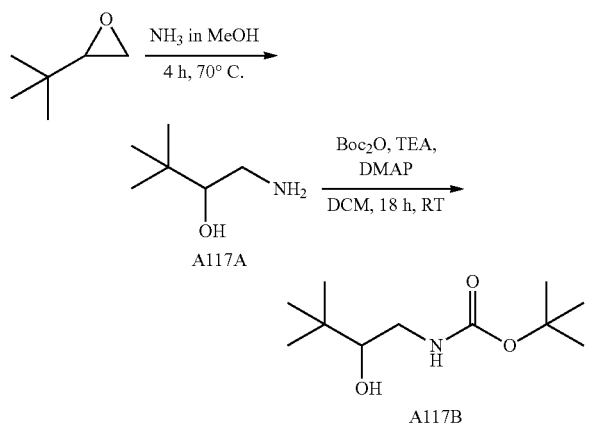

Intermediate A117A:
1-Amino-3,3-dimethylbutan-2-ol

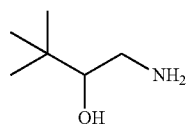

In a sealed pressure tube at RT was added 2-(tert-butyl)oxirane (1.0 g, 9.98 mmol) and ammonia in methanol (7N) (4.28 mL, 30.0 mmol). The reaction vessel was sealed and heated at 70° C. for 4 h. The reaction mixture was cooled to RT and concentrated and under reduced pressure. Crude Intermediate A117A (0.968, 83% yield) was used as such without further purification. ¹H NMR (400 MHz, DMSO-d₆) δ 3.15-2.88 (m, 1H), 2.66-2.46 (m, 1H), 2.42-2.21 (m, 1H), 0.88-0.73 (m, 9H).

Intermediate A117B: tert-Butyl (2-hydroxy-3,3-dimethylbutyl)carbamate

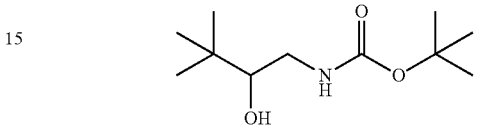

To a solution of Intermediate A117A (0.812 g, 6.93 mmol) in DCM (20 mL) was added TEA (2.414 mL, 17.32 mmol), DMAP (0.042 g, 0.346 mmol) and di-tert-butyl dicarbonate (2.268 g, 10.39 mmol). The reaction mixture was allowed to stir overnight at RT. The reaction mixture was diluted with EtOAc (500 mL) and washed with brine, dried (MgSO₄) and concentrated. The crude product was purified by silica gel chromatography (80 g REDISEP® column, eluting with a gradient from 0-30% EtOAc in hexanes). Fractions containing the product were combined and concentrated to afford Intermediate A117B (1.2 g, 80% yield). ¹H NMR (400 MHz, DMSO-d₆) δ 4.07-3.93 (m, 1H), 3.92-3.80 (m, 1H), 3.62 (dd, J=10.3, 7.8 Hz, 1H), 1.46 (s, 9H), 0.87 (s, 9H).

Scheme 83

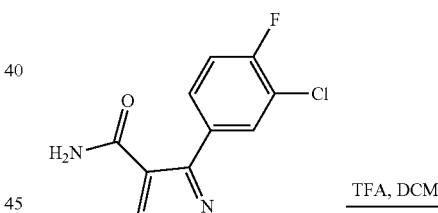

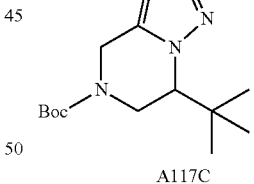

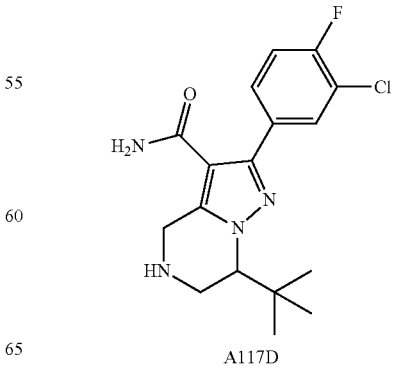

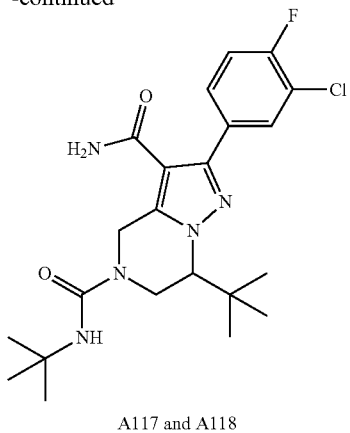

A117 and A118

Intermediate A117C: tert-Butyl 7-(tert-butyl)-3-carbamoyl-2-(3-chloro-4-fluorophenyl)-6,7-dihydropyrazolo[1,5-a]pyrazine-5(4H)-carboxylate

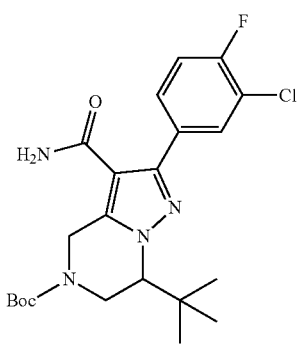 [SMILES: CC(C)(C)OC(=O)N1Cc2c(C(N)=O)c(-c3ccc(F)c(Cl)c3)nn2C(C(C)(C)C)C1]

Intermediate A117C was prepared using an analogous synthetic strategy to that employed for the preparation of Intermediate A1N (outlined in Scheme 57). Intermediate A117B was used in substitution for Intermediate A1B in the initial Mitsunobu coupling reaction. MS(ES) m/z=451 [M+H]⁺.

Compounds A117 and A118: $N^5$-7-Di-tert-butyl-2-(3-chloro-4-fluorophenyl)-6,7-dihydropyrazolo[1,5-a]pyrazine-3,5(4H)-dicarboxamide

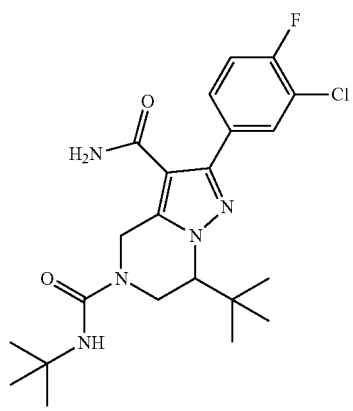 [SMILES: CC(C)(C)NC(=O)N1Cc2c(C(N)=O)c(-c3ccc(F)c(Cl)c3)nn2C(C(C)(C)C)C1]

To a solution of Intermediate A117C (0.305 g, 0.676 mmol) DCM (20 mL) was added TFA (0.313 mL, 4.06 mmol) and the resulting solution was allowed to stir at RT for 18 h. The reaction was then concentrated under reduced pressure and the afforded crude his TFA salt Intermediate A117D (0.314 g, >98% yield) used in the subsequent reaction with no purification. To a solution of Intermediate A117D (0.05 g, 0.713 mmol) in DMF (2 mL) at RT under nitrogen was added DIPEA (0.124 mL, 0.713 mmol) and 2-isocyanato-2-methylpropane (0.041 g, 0.413 mmol). The reaction mixture was stirred for 1 h. The reaction mixture was filtered and concentrated. The crude material was purified via preparative HPLC. Fractions containing the desired product were combined and dried via centrifugal evaporation to obtain the racemic product. The compound was further purified through chiral separation using preparative SFC: CHIRALPAK® AD, 30×250 mm, 5 μm column eluted with 10% EtOH in $CO_2$ at 70 mL/min and 150 bar, monitored by UV at 254 nm. The first eluting enantiomer, $r_t$=9.3 min: (R)-A117 and the second eluting enantiomer, $r_t$=11.2 min: (S)-A118 were thus separated. MS(ES) m/z=450 [M+H]⁺; Ret. time=1.98 and 2.86 min (Methods H and I respectively). ¹H NMR (500 MHz, DMSO-$d_6$) δ 7.86 (d, J=7.3 Hz, 1H), 7.77-7.63 (m, 6H), 5.19-4.72 (m, 2H), 4.60 (d, J=13.9 Hz, 1H), 4.18 (br. s., 1H), 3.42 (s, 1H), 1.02 (s, 9H).

Scheme 84

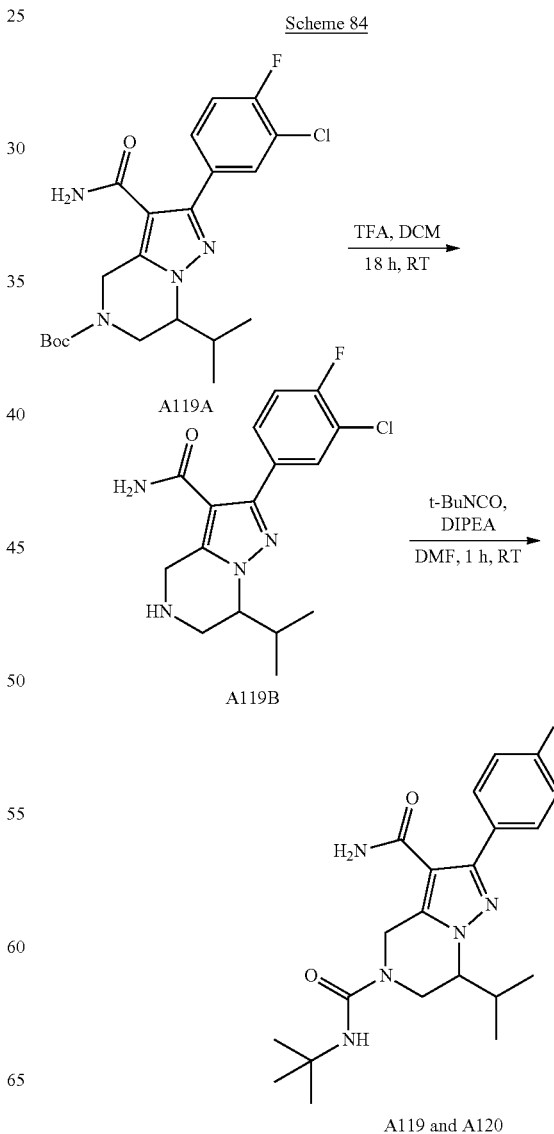

A119 and A120

Intermediate A119A: tert-Butyl 3-carbamoyl-2-(3-chloro-4-fluorophenyl)-7-isopropyl-6,7-dihydropyrazolo[1,5-a]pyrazine-5(4H)-carboxylate

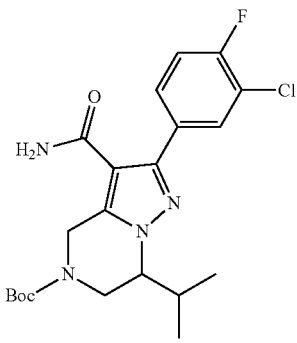 [SMILES: CC(C)C1CN(C(=O)OC(C)(C)C)Cc2c(C(N)=O)c(-c3ccc(F)c(Cl)c3)nn21]

Intermediate A119A was prepared using an analogous synthetic strategy to that employed for the preparation of Intermediate A117C. An analogous amino alcohol to Intermediate A117B was prepared commencing with 2-(iso-propyl)oxirane and used in substitution for Intermediate A1B in the initial Mitsunobu coupling reaction. MS(ES) m/z=437 [M+H]$^+$.

Compounds A119 and A120: N$^5$-(tert-Butyl)-2-(3-chloro-4-fluorophenyl)-7-isopropyl-6,7-dihydropyrazolo[1,5-a]pyrazine-3,5(4H)-dicarboxamide

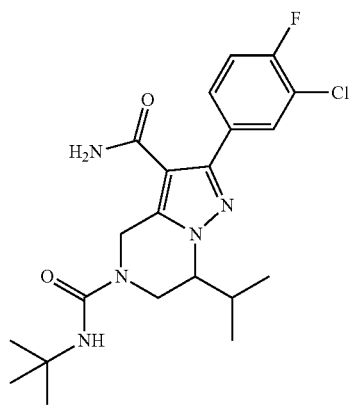 [SMILES: CC(C)C1CN(C(=O)NC(C)(C)C)Cc2c(C(N)=O)c(-c3ccc(F)c(Cl)c3)nn21]

Compounds A119 and A120 were prepared analogously to Compounds A117 and A118 using Intermediate A119A. The racemic compound obtained from preparative HPLC was further purified through chiral separation using preparative HPLC: CHIRALPAK® AD, 21×250 mm, 10 µm column eluted with 80% heptane with 0.1% diethylamine: 20% EtOH at 15 mL/min. The first eluting enantiomer, r$_t$=8.4 min: (R)-A119 and the second eluting enantiomer, r$_t$=15.5 min: (S)-A120 were thus separated. MS(ES) m/z=436 [M+H]$^+$; Ret. time=1.77 and 2.79 min. (Methods H and I respectively). $^1$H NMR (500 MHz, DMSO-d$_6$) δ ppm 7.85 (1H, d, J=6.60 Hz), 7.66-7.72 (1H, m), 7.41-7.49 (1H, m), 7.15-7.38 (2H, m), 6.08-6.21 (1H, m), 4.62-4.77 (2H, m), 4.08 (1H, d, J=4.77 Hz), 3.85-3.97 (1H, m), 3.61 (1H, dd, J=13.76, 3.85 Hz), 3.28-3.37 (1H, m), 2.29-2.43 (1H, m), 1.21-1.32 (9H, m), 0.99 (3H, d, J=6.97 Hz), 0.85 (3H, d, J=6.97 Hz).

Scheme 85

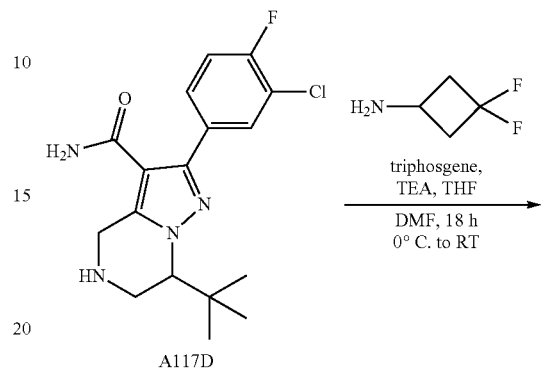

A117D

Compounds A121 and A122: 7-(tert-Butyl)-2-(3-chloro-4-fluorophenyl)-N5-(3,3-difluorocyclobutyl)-6,7-dihydropyrazolo[1,5-a]pyrazine-3,5(4H)-dicarboxamide

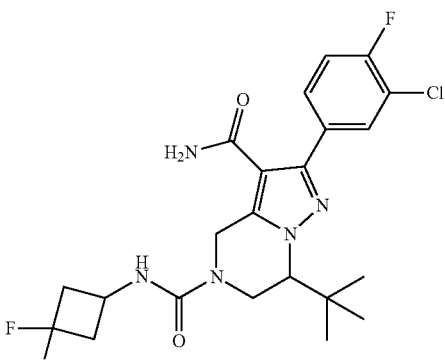

To an ice-cooled stirred solution of triphosgene (0.023 g, 0.078 mmol) in THF (3 mL) was added a solution of 3,3-difluorocyclobutanamine, HCl (0.030 g, 0.208 mmol) and TEA (0.085 mL, 0.607 mmol) in THF (3 mL) and DMF (0.5 mL). The reaction mixture was stirred for 10 min. prior to the addition of a solution of Intermediate A117D (0.035 g, 0.104 mmol) and TEA (0.085 mL, 0.607 mmol) in DMF (1.5 mL). The reaction mixture was allowed to warm to RT and stir overnight. It was concentrated and the crude material was purified via preparative HPLC. Fractions containing the desired product were combined and dried via centrifugal evaporation to obtain the racemic compound which was further purified through chiral separation using preparative HPLC: CHIRALPAK® AD, 21×250 mm, 10 μm column eluted with 80% heptane with 0.1% diethylamine: 20% EtOH at 15 mL/min The first eluting enantiomer, $r_t$=11.5 min: (R)-A121 and the second eluting enantiomer, $r_t$=21.9 min: (S)-A122 were thus separated. MS(ES) m/z=484 [M+H]$^+$; Ret. time=1.81 and 2.80 min. (Methods H and I respectively); $^1$H NMR (500 MHz, DMSO-d$_6$) δ ppm 7.84 (1H, dd, J=6.97, 1.83 Hz), 7.62-7.72 (1H, m), 7.47 (1H, t, J=9.17 Hz), 7.22-7.43 (2H, m), 7.17 (1H, d, J=6.60 Hz), 4.86 (1H, d, J=17.24 Hz), 4.59 (1H, d, J=17.24 Hz), 4.49 (1H, d, J=14.30 Hz), 3.97-4.11 (2H, m), 3.28 (1H, dd, J=14.12, 3.85 Hz), 2.76-2.90 (3H, m), 2.57-2.70 (2H, m), 0.98 (9H, s).

Scheme 86

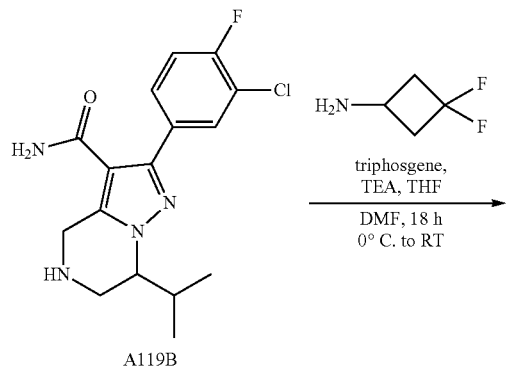

Compounds A123 and A124: 2-(3-Chloro-4-fluorophenyl)-N$^5$-(3,3-difluorocyclobutyl)-7-isopropyl-6,7-dihydropyrazolo[1,5-a]pyrazine-3,5(4H)-dicarboxamide

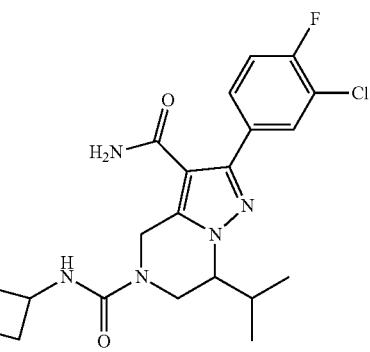

Compounds A123 and A124 were prepared analogously to Compounds A121 and A122 using Intermediate A119B. The racemic compound obtained from preparative HPLC was further purified through chiral separation using preparative HPLC: CHIRALPAK® AD, 21×250 mm, 10 μm column eluted with 80% heptane with 0.1% diethylamine: 20% EtOH at 15 mL/min The first eluting enantiomer, $r_t$=11.5 min: (R)-A123 and the second eluting enantiomer, $r_t$=21.9 min: (S)-A124 were thus separated. MS(ES) m/z=484 [M+H]$^+$; Ret. time=1.61 and 2.69 min (Methods H and I respectively). $^1$H NMR (500 MHz, DMSO-d$_6$) δ ppm 7.84 (1H, d, J=6.97 Hz), 7.64-7.71 (1H, m), 7.47 (1H, t, J=9.17 Hz), 7.23-7.41 (3H, m), 4.68-4.83 (2H, m), 4.11 (1H, d, J=4.77 Hz), 3.96-4.07 (2H, m), 3.64 (1H, dd, J=13.75, 3.48 Hz), 2.59-2.72 (2H, m), 2.35 (1H, dd, J=13.39, 6.42 Hz), 0.95-1.02 (3H, m), 0.85 (3H, d, J=6.60 Hz).

Scheme 87

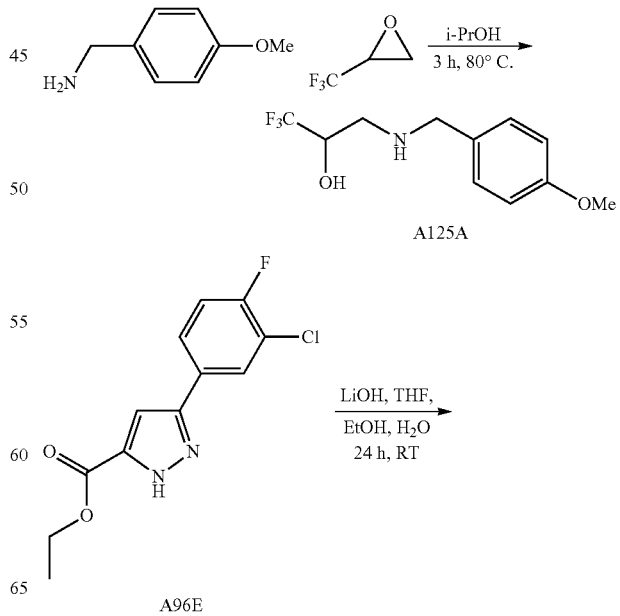

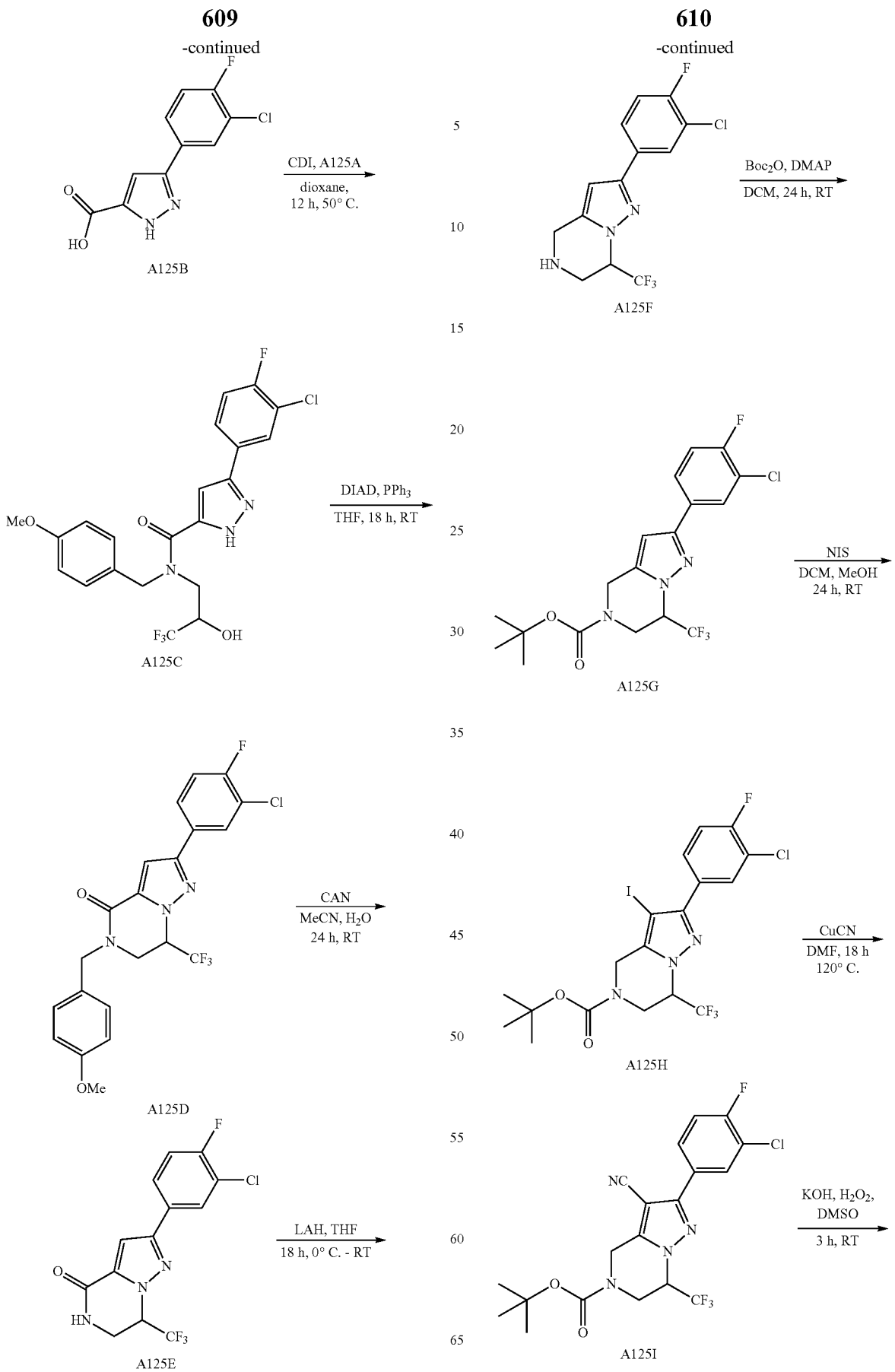

-continued

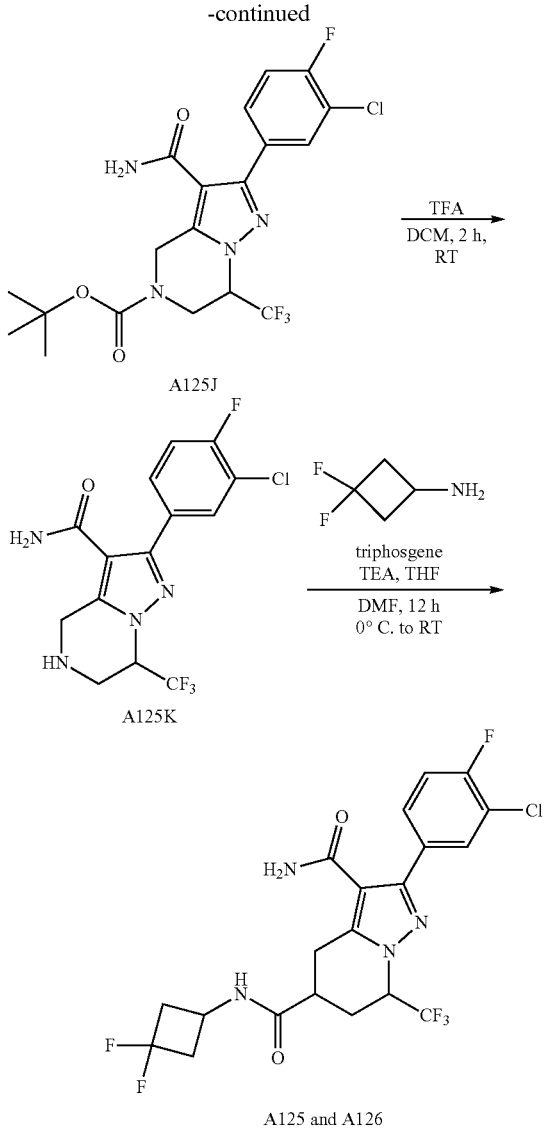

A125J

A125K

A125 and A126

Intermediate A125: 1,1,1-Trifluoro-3-((4-methoxybenzyl)amino)propan-2-ol

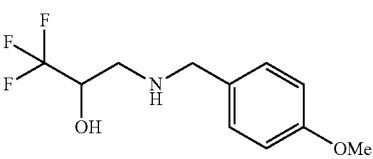 [SMILES: COc1ccc(CNCC(O)C(F)(F)F)cc1]

To a solution of 2-(trifluoromethyl)oxirane (2.00 g, 17.8 mmol) in isopropanol (20 mL) in a pressure tube was added (4-methoxyphenyl)methanamine (7.35 g, 53.5 mmol). The reaction vessel was capped and heated at 80° C. for 3 h. The reaction mixture was concentrated and purified by silica gel chromatography (80 g REDISEP® column, eluting with a gradient from 0-60% EtOAc in hexanes). The required fractions were concentrated to obtain Intermediate A125A (3.1 g, 70.6% yield) as a white solid. MS(ES) m/z=287 [M+H]$^+$. $^1$H NMR (400 MHz, DMSO-d$_6$) δ 7.29-7.17 (m, 2H), 6.87 (d, J=8.5 Hz, 2H), 6.25 (br. s., 1H), 4.04 (td, J=7.8, 3.3 Hz, 1H), 3.72 (s, 3H), 3.66 (d, J=1.8 Hz, 2H), 2.74-2.55 (m, 2H), 2.08 (br. s., 1H).

Intermediate A125B: 3-(3-Chloro-4-fluorophenyl)-1H-pyrazole-5-carboxylic acid

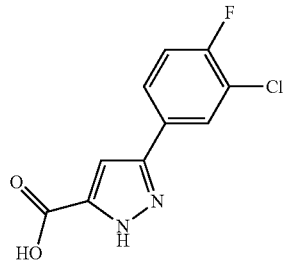 [SMILES: O=C(O)c1cc(-c2ccc(F)c(Cl)c2)n[nH]1]

To a solution of Intermediate A96E (5.0 g, 18.6 mmol) in EtOH (10 mL) and THF (20 mL) at RT was added a solution of LiOH (5.35 g, 223 mmol) in water (6.67 mL). The reaction mixture was stirred at RT overnight. The reaction mixture was concentrated and the resulting residue was dissolved in water (200 mL) and extracted with ether. The organic layer was separated and the aqueous layer was acidified to a pH of 2 using a conc.aq. solution of HCl. The aqueous layer was extracted with EtOAc (3×200 mL). The combined organic layers were washed with brine, dried (MgSO$_4$) and concentrated to obtain Intermediate A125B (3.02 g, 67.4% yield). Product was used as such without further purification. MS(ES) m/z=241 [M+H]$^+$.

Intermediate A125C: 3-(3-Chloro-4-fluorophenyl)-N-(4-methoxybenzyl)-N-(3,3,3-trifluoro-2-hydroxypropyl)-1H-pyrazole-5-carboxamide

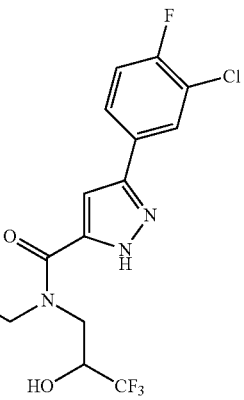

To a solution of Intermediate A125B (0.8 g, 3.32 mmol) in 1,4-dioxane heated at 50° C. was added CDI (0.593 g, 3.66 mmol). The reaction was heated for 30 min, and Intermediate A125A (0.911 g, 3.66 mmol) was added. The reaction mixture was allowed to stir for an additional 30 min. at 50° C. The reaction mixture was diluted with water once cooled to RT and was extracted with EtOAc (3×100 mL) The combined organic layers were washed with brine, dried (MgSO$_4$), and concentrated. The residue was purified by silica gel chromatography (80 g REDISEP® column, eluting with a gradient from 0-30% EtOAc in hexanes). Fractions containing the product were combined and concentrated to afford Intermediate A125C (1.015 g, 64.7% yield). MS(ES) m/z=472 [M+H]+.

Intermediate A125D: 2-(3-Chloro-4-fluorophenyl)-5-(4-methoxybenzyl)-7-(trifluoromethyl)-6,7-dihydropyrazolo[1,5-a]pyrazin-4(5H)-one

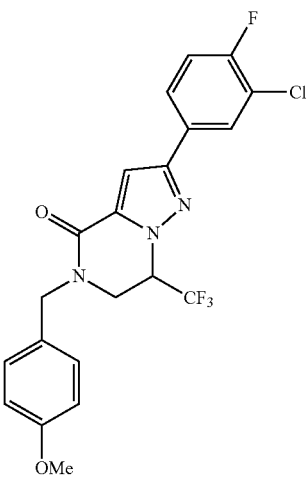 [SMILES: COc1ccc(CN2CC(C(F)(F)F)n3nc(-c4ccc(F)c(Cl)c4)cc3C2=O)cc1]

To an ice-cold stirred solution of triphenylphosphine (0.733 g, 2.80 mmol) in THF (30 mL) was added DIAD (0.544 mL, 2.80 mmol) resulting in a thick milky yellow solution. After 10 min a solution of Intermediate A125C (1.015 g, 2.151 mmol) in THF (5.0 mL) was added. The reaction was then allowed to warm to RT and stir overnight. The reaction mixture was diluted with EtOAc (200 mL) and washed with brine, dried (MgSO4) and concentrated in vacuo. The crude yellow oil was purified by silica gel chromatography (80 g REDISEP® column, eluting with a gradient from 0-40% EtOAc in hexanes). Fractions containing the product were combined and concentrated to afford Intermediate A125D (0.614 g, 62.8% yield). MS(ES) m/z=454 [M+H]+. $^1$H NMR (400 MHz, chloroform-d) δ 7.88 (dd, J=7.0, 2.0 Hz, 1H), 7.66 (ddd, J=8.6, 4.6, 2.1 Hz, 1H), 7.31-7.14 (m, 4H), 6.94-6.85 (m, 2H), 5.01-4.89 (m, 1H), 4.72 (s, 2H), 4.06-3.96 (m, 1H), 3.85-3.74 (m, 4H).

Intermediate A125E: 2-(3-Chloro-4-fluorophenyl)-7-(trifluoromethyl)-6,7-dihydropyrazolo[1,5-a]pyrazin-4(5H)-one

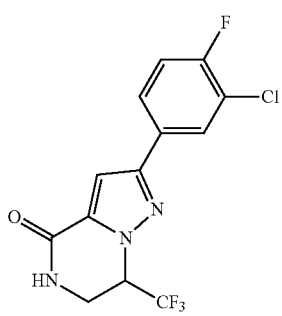 [SMILES: O=C1NCC(C(F)(F)F)n2nc(-c3ccc(F)c(Cl)c3)cc21]

To a solution of Intermediate A125D (0.405 g, 0.892 mmol) in acetonitrile (5 mL) and water (0.556 mL) at RT was added CAN (1.957 g, 3.57 mmol). The reaction mixture was allowed to stir at RT for 24 h. The reaction mixture was concentrated, the residue was dissolved in methanol and purified by reverse phase preparative HPLC using 30×100 mm XTERRA® column and 30-100% B, 18 minute gradient, 20 minute run. (Solvent A: 90% water, 10% methanol, 0.1% TFA: Solvent B: 10% water, 90% methanol, 0.1% TFA). Required fractions were concentrated to obtain Intermediate A125E (0.1 g, 34% yield). MS(ES) m/z=334 [M+H]+.

Intermediate A125F: 2-(3-Chloro-4-fluorophenyl)-7-(trifluoromethyl)-4,5,6,7-tetrahydropyrazolo[1,5-a]pyrazine

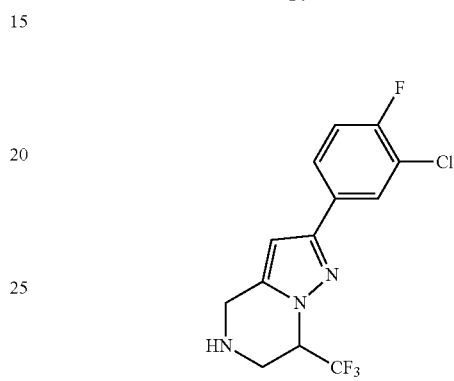

To a solution of Intermediate A125E (0.1 g, 0.300 mmol) in anhydrous THF (10 mL) at 0° C. under nitrogen was added a solution of LiAlH4 (0.180 mL, 0.360 mmol, 2M in THF). The reaction mixture was allowed to warm to RT and stir for 4 hours. The reaction mixture was cooled to 0° C. and an additional equivalent of LAH was added and the solution was warmed to RT and stirred for 5 h. The reaction mixture was again cooled to 0° C. and quenched by slow addition of a saturated aq. solution of Rochelle's salt. The solution was then extracted with EtOAc (3×) and the combined organic layers were washed with brine, dried (MgSO4) and concentrated. The crude residue was purified by silica gel chromatography (24 g REDISEP® column, eluting with a gradient from 0-80% EtOAc in hexanes). Fractions containing the product were combined and concentrated to afford Intermediate A125F (0.06 g, 63% yield, contaminated with 15% of the des-chloro byproduct). MS(ES) m/z=320 [M+H]+.

Intermediate A125G: tert-Butyl 2-(3-chloro-4-fluorophenyl)-7-(trifluoromethyl)-6,7-dihydropyrazolo[1,5-a]pyrazine-5(4H)-carboxylate

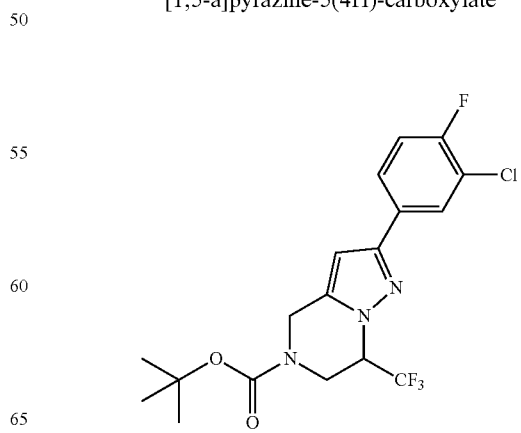

To a solution of Intermediate A125F (0.06 g, 0.188 mmol) in DCM (10 mL) was added TEA (0.065 mL, 0.469 mmol), DMAP (1.146 mg, 9.38 μmol) and Boc₂O (0.061 g, 0.282 mmol). The reaction mixture was stirred overnight at RT. The reaction mixture was diluted with EtOAc (300 mL) and washed with brine, dried (MgSO₄) and concentrated. The crude product was purified by silica gel chromatography using (24 g REDISEP® column, eluting with a gradient from 0-30% EtOAc in hexanes). Fractions containing the product were combined and concentrated to afford Intermediate A125G (0.055 g, 70% yield). MS(ES) m/z=420 [M+H]⁺.

Intermediate A12H: tert-Butyl 2-(3-chloro-4-fluorophenyl)-3-iodo-7-(trifluoromethyl)-6,7-dihydropyrazolo[1,5-a]pyrazine-5(4H)-carboxylate

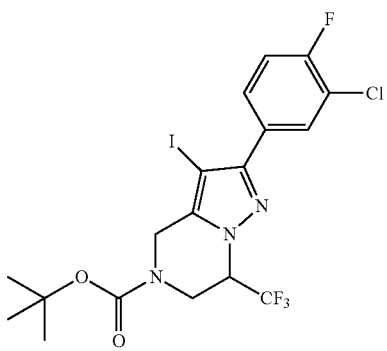 [SMILES: CC(C)(C)OC(=O)N1Cc2c(I)c(-c3ccc(F)c(Cl)c3)nn2C(C(F)(F)F)C1]

To a solution of Intermediate A125G (0.055 g, 0.131 mmol) in a 4:1 mixture of CH₂Cl₂ (10 mL) and MeOH (2.5 mL) was added NIS (0.088 g, 0.393 mmol). The reaction mixture was stirred at RT. After 90 min, another equivalent of NIS was added and the resulting solution was stirred overnight at RT. The reaction mixture was concentrated in vacuo affording the crude product as a red oil. The product was purified by silica gel chromatography using (24 g REDISEP® column, eluting with a gradient from 0-30% EtOAc in hexanes). Fractions containing the product were combined and concentrated to afford Intermediate A125H (0.059 g, 83% yield). MS(ES) m/z=546 [M+H]⁺.

Intermediate A125I: tert-Butyl 2-(3-chloro-4-fluorophenyl)-3-cyano-7-(trifluoromethyl)-6,7-dihydropyrazolo[1,5-a]pyrazine-5(4H)-carboxylate

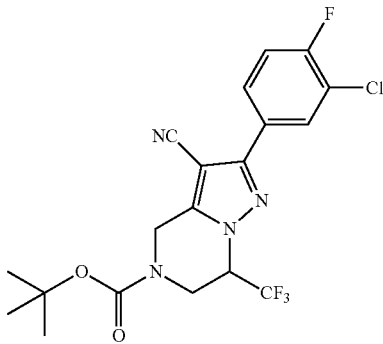 [SMILES: CC(C)(C)OC(=O)N1Cc2c(C#N)c(-c3ccc(F)c(Cl)c3)nn2C(C(F)(F)F)C1]

To a solution of Intermediate A125H (0.115 g, 0.245 mmol) in DMF (20 mL) was added CuCN (0.055 g, 0.613 mmol). The reaction mixture was heated in a sealed tube to 120° C. for 16 h. The reaction mixture was filtered through a pad of CELITE®, the filter cake washed with EtOAc and the combined filtrate was concentrated under reduced pressure. The crude product was purified by silica gel chromatography (24 g REDISEP® column, eluting with a gradient from 0-40% EtOAc in hexanes). Fractions containing the product were combined and concentrated to afford Intermediate A125I (0.075 g, 83% yield). MS(ES) m/z=369 [M+H]⁺.

Intermediate A125J: tert-Butyl 3-carbamoyl-2-(3-chloro-4-fluorophenyl)-7-(trifluoromethyl)-6,7-dihydropyrazolo[1,5-a]pyrazine-5(4H)-carboxylate

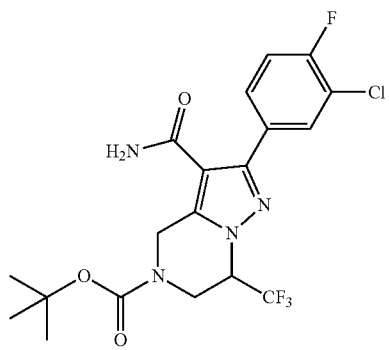 [SMILES: CC(C)(C)OC(=O)N1Cc2c(C(N)=O)c(-c3ccc(F)c(Cl)c3)nn2C(C(F)(F)F)C1]

To a solution of Intermediate A125I (0.061 g, 0.137 mmol) in EtOH (10 mL) at RT was added a 5M aq. solution of KOH (0.137 mL, 0.686 mmol). The reaction mixture was cooled to 0° C. and hydrogen peroxide (0.280 mL, 2.74 mmol, 30% w/v in H₂O) was added dropwise. The reaction mixture was allowed to warm to RT and stir overnight. The reaction mixture was concentrated and residue was diluted with EtOAc. The solution was washed with water, brine, dried (MgSO₄) and concentrated. The crude product was purified by silica gel chromatography (24 g REDISEP® column, eluting with a gradient from 0-20% MeOH in DCM). The required fractions were concentrated to obtain Intermediate A125J (0.046 g, 72% yield). MS(ES) m/z=463 [M+H]⁺.

Intermediate A125K: 2-(3-Chloro-4-fluorophenyl)-7-(trifluoromethyl)-4,5,6,7-tetrahydropyrazolo[1,5-a]pyrazine-3-carboxamide, TFA

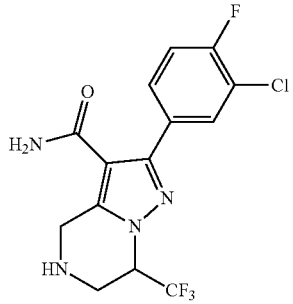

To a solution of Intermediate A125J (0.141 g, 0.305 mmol) in DCM (10 mL) was added TFA (0.141 mL, 1.828 mmol).

The reaction mixture was stirred overnight at RT. The reaction mixture was concentrated to obtain crude Intermediate A125K (0.145 g, 0.304 mmol, 100% yield) as the TFA salt. The product was used as such without further purification. Yield was assumed to be quantitative. MS(ES) m/z=363 [M+H]⁺.

Compounds A125 and A126: 2-(3-Chloro-4-fluorophenyl)-N⁵-(3,3-difluorocyclobutyl)-7-(trifluoromethyl)-6,7-dihydropyrazolo[1,5-a]pyrazine-3,5(4H)-dicarboxamide

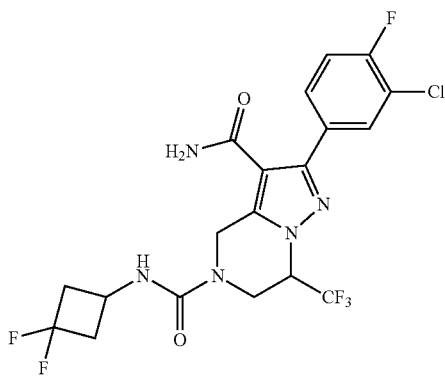 [SMILES: NC(=O)c1c(-c2ccc(F)c(Cl)c2)nn2c1CN(C(=O)NC1CC(F)(F)C1)CC2C(F)(F)F]

To a stirred ice-cooled suspension of triphosgene (0.034 g, 0.114 mmol) in THF (3 mL) was added a solution of 3,3-difluorocyclobutanamine HCl (0.044 g, 0.303 mmol) and TEA (0.085 mL, 0.607 mmol) in THF (3 mL) and DMI (0.5 mL). The reaction mixture was stirred for 10 min. prior to the introduction of a solution of A125K (0.055 g, 0.152 mmol) and TEA (0.085 mL, 0.607 mmol) in DMF (1.5 mL), The reaction mixture was warmed to RT and stirred overnight. The reaction mixture was concentrated and purified via preparative HPLC. Fractions containing the desired product were combined and concentrated to obtain the product as a racemate, purified via preparative HPLC. Fractions containing the desired product were combined and dried via centrifugal evaporation to obtain the racemic compound which was further purified through chiral separation using preparative HPLC: CHIRALPAK® AD, 21×250 mm, 10 μm column eluted with 80% heptane with 0.1% diethylamine: 20% EtOH at 15 mL/min The first eluting enantiomer, $r_t$=22.1 min: (S)-A125 and the second eluting enantiomer, $r_t$=25.2 min: (R)-A126 were thus separated. MS(ES) m/z=496 [M+H]⁺; Ret. time=1.66 and 2.35 min. (Methods H and I respectively); ¹H NMR (500 MHz, DMSO-d₅) S 7.84 (d, J=7.0 Hz, 1H), 7.69 (br. s., 1H), 7.33 (d, J=6.2 Hz, 1H), 5.44 (br. s., 1H), 5.12 (d, J=17.2 Hz, 1H), 4.78-4.47 (m, 2H), 4.12-3.96 (m, 1H), 3.60 (d, J=15.0 Hz, 1H), 2.93-2.80 (m, 2H), 2.71-2.55 (m, 2H).

Scheme 88

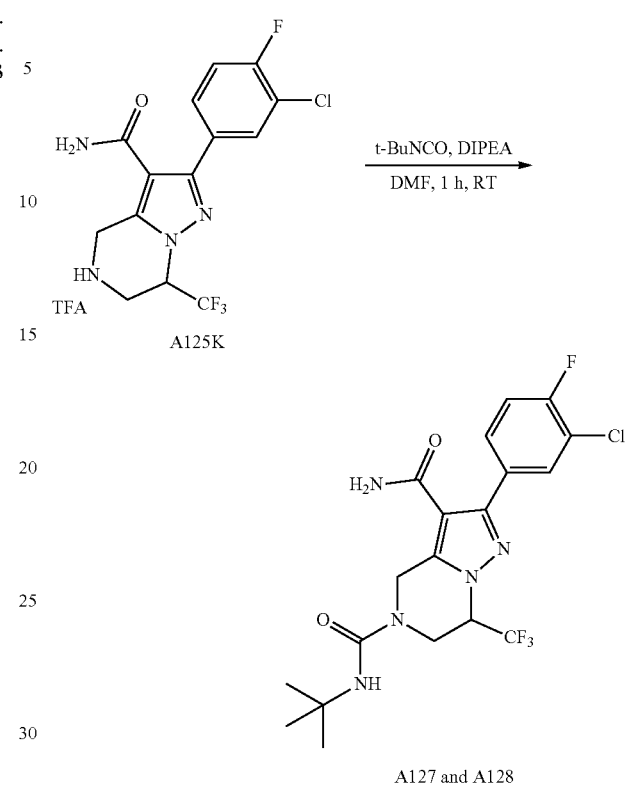

A125K

Compounds A127 and A128: N⁵-(tert-Butyl)-2-(3-chloro-4-fluorophenyl)-7-(trifluoromethyl)-6,7-dihydropyrazolo[1,5-a]pyrazine-3,5(4H)-dicarboxamide

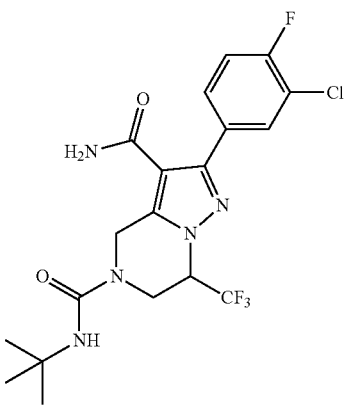 [SMILES: CC(C)(C)NC(=O)N1Cc2c(C(N)=O)c(-c3ccc(F)c(Cl)c3)nn2C(C(F)(F)F)C1]

To a solution of A125K (0.055 g, 0.152 mmol) in DMF (2 mL) at RT under nitrogen was added DIPEA (0.132 mL, 0.758 mmol) and 2-isocyanato-2-methylpropane (0.030 g, 0.303 mmol). The reaction mixture was stirred for 1 h and then filtered and concentrated. The crude material was purified via preparative HPLC. Fractions containing the desired product were combined and dried via centrifugal evaporation to obtain the racemic compound which was further purified through chiral separation using preparative HPLC: CHIRALPAK® AD, 21×250 mm, 10 μm column eluted with 80% heptane with 0.1% diethylamine: 20% EtOH at 15 mL/min The first eluting enantiomer, $r_t$=15.2 min: (S)-A127 and the second eluting enantiomer, $r_t$=18.4 min: (R)-A128 were thus separated. MS(ES) m/z=462 [M+H]$^+$; HPLC Ret. Time=1.71 and 3.02 min. (Methods H and I respectively). $^1$H NMR (500 MHz, DMSO-d$_6$) δ 7.85 (d, J=7.3 Hz, 1H), 7.69 (br. s., 1H), 7.41 (br. s., 1H), 5.37 (br. s., 1H), 5.18 (d, J=17.2 Hz, 1H), 4.72 (d, J=14.7 Hz, 1H), 4.48 (d, J=17.2 Hz, 1H), 3.54 (d, J=15.4 Hz, 1H), 1.28 (s, 9H).
Scheme 89
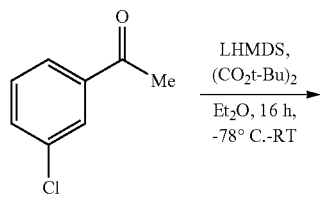
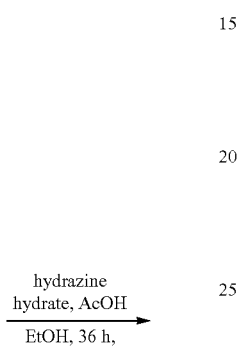
A129A
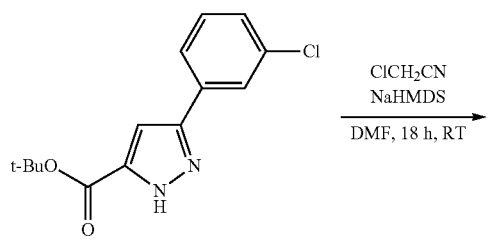
A129B
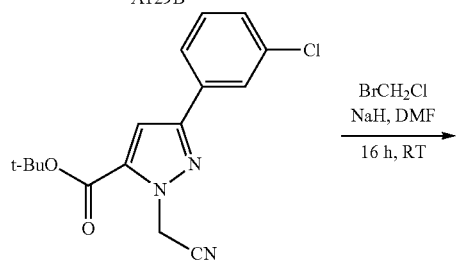
A129C
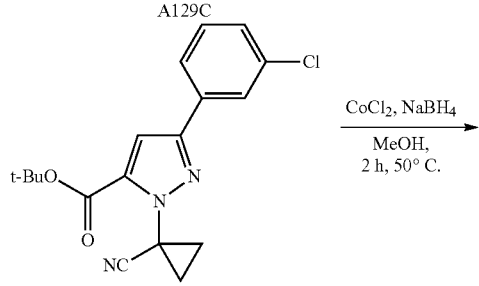
A129D
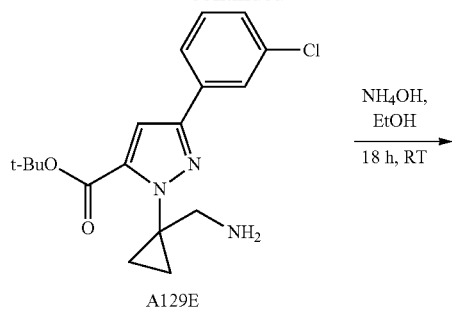
A129E
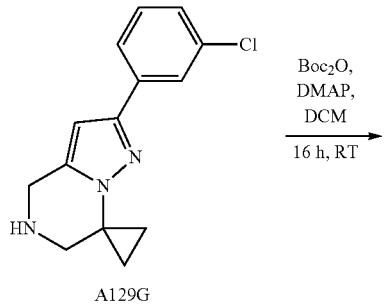
A129F
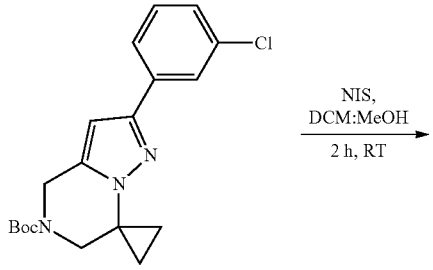
A129G
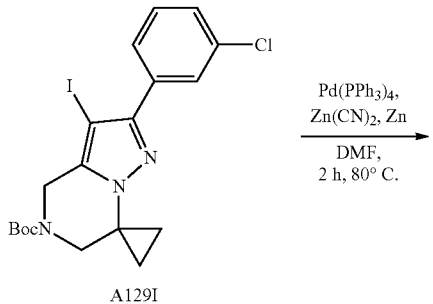
A129H
A129I -continued

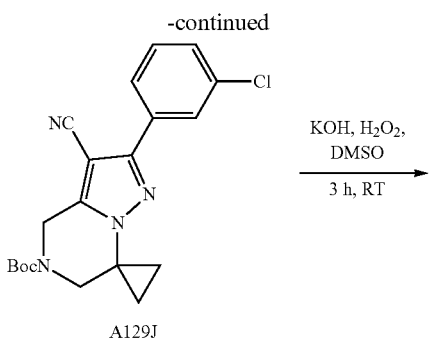

A129J 7.99 (1H, m), 7.86 (1H, dt, J=7.78, 1.38 Hz), 7.58 (1H, ddd, J=7.97, 2.20, 1.13 Hz), 7.43-7.49 (1H, m), 6.94-6.99 (1H, m), 1.58-1.63 (9H, m).

Intermediate A129B: tert-Butyl 3-(3-chlorophenyl)-1H-pyrazole-5-carboxylate

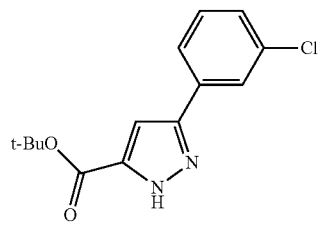 [SMILES: CC(C)(C)OC(=O)c1cc(-c2cccc(Cl)c2)n[nH]1]

To a solution of Intermediate A129A (2.17 g, 7.68 mmol) in ethanol (80 mL) was added hydrazine hydrate (0.471 mL, 7.68 mmol, 80% wt). The solution was allowed to stir for 18 h at RT. There was little conversion to the desired pyrazole so at this point acetic acid (5 mL) was added and the reaction mixture was heated to 60° C. for 24 h. The reaction mixture was diluted with EtOAc (100 mL) and quenched by the addition of a saturated aq. solution of NaHCO$_3$. The organic layer was separated and washed with brine (2×100 mL). The organic layer was dried over sodium sulfate and concentrated in vacuo. The crude reaction mixture was purified by silica gel chromatography (80 g REDISEP® column, eluting with a gradient of 0-60% EtOAc in hexanes). Fractions containing the product were combined and evaporated to afford Intermediate A129B (1.82 g, 83%) as a yellow crystalline solid. $^1$H NMR (400 MHz, DMSO-d$_6$) δ ppm 13.70-14.15 (1H, m), 7.93 (1H, t, J=1.76 Hz), 7.83 (1H, d, J=7.28 Hz), 7.22-7.53 (3H, m), 1.51-1.59 (9H, m).

Intermediate A129C: tert-Butyl 3-(3-chlorophenyl)-1-(cyanomethyl)-1H-pyrazole-5-carboxylate

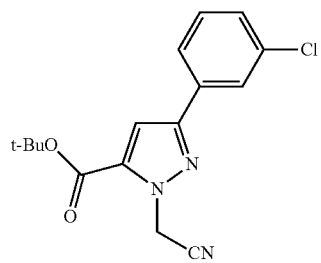 [SMILES: CC(C)(C)OC(=O)c1cc(-c2cccc(Cl)c2)nn1CC#N]

A129K

Intermediate A129A: tert-Butyl 4-(3-chlorophenyl)-2,4-dioxobutanoate

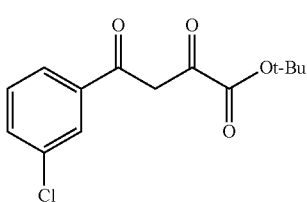

Under an atmosphere of nitrogen, a solution of 3'-chloroacetophenone (1.015 mL, 7.82 mmol) in anhydrous diethyl ether (50 mL) was allowed to cool to −78° C. for 15 minutes prior to the slow addition of a 1.0 M solution of LHMDS (8.60 mL, 8.60 mmol) in THF. The enolate formation was allowed to stir for 45 minutes at −78° C., after which di-tert-butyl oxalate (1.898 g, 9.38 mmol) was added as a single portion. The pale yellow reaction mixture was allowed to warm to RT and stir for 18 hours. The dark-green solution was then quenched with 50 mL of a 1.0 M aq. solution of HCl. The two layers were separated and the aq. layer was extracted twice more with EtOAc. The combined organic layers were washed with brine, dried over anhydrous MgSO$_4$, filtered and the filtrate concentrated under reduced pressure to afford an orange oil. The crude reaction mixture was purified by silica gel chromatography (40 g REDISEP® column, eluting with a gradient from 100% hexanes to 80:20 hexanes:EtOAc solution). Fractions containing the product were combined and evaporated to afford Intermediate A129A (2.17 g, 98%) as a yellow solid. $^1$H NMR (400 MHz, chloroform-d) δ ppm 7.94-

To a flask charged with an ice-cooled solution of Intermediate A129B (1.82 g, 6.53 mmol) in DMF (15 mL) is added a 2.0 M solution of NHMDS in THF (3.43 mL, 6.86 mmol) dropwise. The reaction mixture is allowed to stir for 5 minutes and the ice bath was subsequently removed, chloroacetonitrile (0.456 mL, 7.19 mmol), which had been freshly passed through a column of CELITE® and sodium bicarbonate, was added to the reaction mixture. The reaction was allowed to warm to 22° C. and stir for an additional 18 h. The reaction was quenched by the addition of 1.0 mL of a saturated aqueous solution of ammonium chloride. The reaction was diluted with equal parts water and EtOAc and the resulting mixture was allowed to stir vigorously for 15 min. The organic layer was separated, dried over sodium sulfate, and concentrated in vacuo to afford an orange solid. The crude reaction mixture was purified by silica gel chromatography (80 g REDISEP® column, eluting with a gradient of 0-50% EtOAc in hexanes). Fractions containing the product were combined and evaporated to afford Intermediate A129C (1.87 g, 90%) as a white solid. MS(ES): m/z=261.91 [M+H$_2$O-OtBu]$^+$. $^1$H NMR (400 MHz, chloroform-d) δ ppm 7.78-7.83 (1H, m), 7.66-7.73 (1H, m), 7.31-7.40 (2H, m), 7.08-7.15 (1H, m), 5.50-5.60 (2H, m), 1.59-1.69 (9H, m).

Intermediate A129D: tert-Butyl 3-(3-chlorophenyl)-1-(1-cyanocyclopropyl)-1H-pyrazole-5-carboxylate

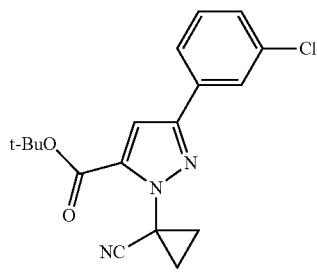 [SMILES: CC(C)(C)OC(=O)c1cc(-c2cccc(Cl)c2)nn1C1(C#N)CC1]

To an ice-cooled solution of Intermediate A129C (1.87 g, 5.88 mmol) and 1-bromo-2-chloroethane (0.844 mL, 7.36 mmol) in DMF (20 mL) was added sodium hydride (0.588 g, 14.71 mmol) (60% dispersion in mineral oil) portionwise. The orange cloudy solution was allowed to slowly warm to RT over several hours. The reaction was allowed to stir at RT for 16 h prior to quenching with the addition of 10 mL of a saturated aq. solution of NH$_4$Cl. The mixture was then partitioned in equal parts water and EtOAc (250 mL each) by vigorous stirring for 15 minutes. The organic layer was separated, washed with brine, dried over sodium sulfate, and concentrated in vacuo to afford an orange oil. The crude reaction mixture was purified by silica gel chromatography (80 g REDISEP® column eluting with a gradient of 0-50% EtOAc in hexanes). Fractions containing the product were combined and evaporated to afford Intermediate A129D (1.02 g, 50%) as a white solid. MS(ES): m/z=287.96 [M+H$_2$O-OtBu]$^+$. $^1$H NMR (400 MHz, chloroform-d) δ ppm 7.78-7.82 (1H, m), 7.64-7.68 (1H, m), 7.33-7.37 (2H, m), 7.11 (1H, s), 1.67 (9H, s), 1.64 (2H, s), 1.54-1.58 (2H, m).

Intermediate A129E: tert-Butyl 1-(1-(aminomethyl) cyclopropyl)-3-(3-chlorophenyl)-1H-pyrazole-5-carboxylate

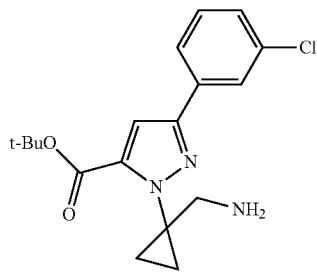 [SMILES: CC(C)(C)OC(=O)c1cc(-c2cccc(Cl)c2)nn1C1(CN)CC1]

To a solution of Intermediate A129D (0.211 g, 0.613 mmol) in MeOH (15 mL) was added cobalt(II) chloride (0.239 g, 1.838 mmol). The bright purple solution was allowed to cool to 0° C. prior to the slow and careful addition of sodium borohydride (0.232 g, 6.13 mmol). After stirring at 0° C. for 10 minutes, the reaction mixture was warmed to 50° C. After stirring for two h, the reaction was allowed to cool to RT and the heterogeneous mixture is plugged through a fritted glass funnel packed with a short pad of CELITE®. The filtrate was diluted with EtOAc and 100 mL of a 1.0 M solution of HCl. The acidic aqueous solution dissolved all of the cobalt salts (color change from dark brown to light pink). The pH of the aqueous layer was adjusted to pH=7 with a 1.0 M aq. solution of NaOH. The organic layer was then separated and the aqueous phase was extracted 3 times with EtOAc. The combined organic phases were washed with a brine solution, dried over sodium sulfate, and concentrated under vacuum to afford a colorless oil, crude Intermediate A129E (0.213 g, 100%) as a white foam. MS(ES): m/z=273.9 [M+H$_2$O-OtBu]$^+$. $^1$H NMR (400 MHz, chloroform-d) δ ppm 7.74-7.85 (1H, m), 7.59-7.69 (1H, m), 7.21-7.34 (1H, m), 6.98-7.06 (1H, m), 3.06 (2H, s), 1.54-1.63 (9H, m), 1.29-1.42 (4H, m), 1.08-1.16 (2H, m).

Intermediate A129F: 2'-(3-Chlorophenyl)-5',6'-dihydro-4'H-spiro[cyclopropane-1,7'-pyrazolo[1,5-a]pyrazin]-4'-one

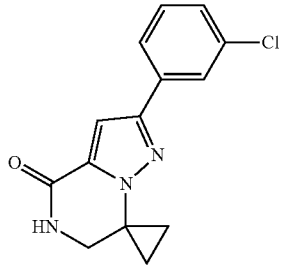 [SMILES: O=C1NCC2(CC2)n2nc(-c3cccc(Cl)c3)cc21]

To a solution of Intermediate A129E (0.213 g, 0.612 mmol) in EtOH (5.0 mL) was added ammonium hydroxide (0.954 mL, 24.5 mmol, 40 wt %). The dark solution was allowed to stir at RT for 18 h. The crude reaction mixture was concentrated under reduced pressure and diluted with EtOAc. The aqueous solution was neutralized to pH=7 using a 1.0 M aq. solution of HCl. The organic layer was separated and the aqueous layer was extracted twice more with EtOAc. The combined organic layers was then washed with brine, dried over sodium sulfate, and concentrated to afford Intermediate A129F (0.118 g, 69%) as a white solid. MS(ES): m/z=273.9 [M+H]$^+$. $^1$H NMR (400 MHz, chloroform-d) δ ppm 7.80-7.84 (1H, m), 7.65 (1H, dt, J=7.34, 1.47 Hz), 7.28-7.37 (2H, m), 7.15-7.19 (1H, m), 6.59 (1H, br. s.), 3.68-3.74 (2H, m), 1.71-1.77 (2H, m), 1.08-1.15 (2H, m).

Intermediate A129G: 2'-(3-Chlorophenyl)-5',6'-dihydro-4'H-spiro[cyclopropane-1,7'-pyrazolo[1,5-a]pyrazine]

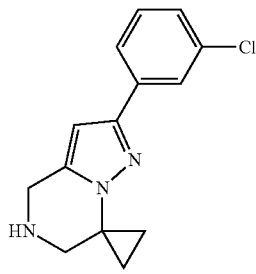 [SMILES: Clc1cccc(-c2cc3n(n2)C2(CC2)CNC3)c1]

A solution of Intermediate A129F (0.166 g, 0.606 mmol) in anhydrous THF (6.1 mL) placed under an atmosphere of N₂ was allowed to cool to −5° C. A 1.0 M solution of LAH (1.456 mL, 1.456 mmol) in THF was added dropwise. The ice bath was removed once the bubbling had subsided. The reaction was then allowed to warm to RT and stir for an additional 18 h. The reaction mixture was cooled to 0° C. and carefully quenched with the sequential addition of 1.5 mL of H₂O, 1.5 mL of a 15% aq. solution of NaOH, and 4.5 mL of H₂O. The cooling bath was removed and the biphasic mixture was allowed to stir at RT for 30 min. Anhydrous MgSO₄ was added to the mixture and was stirred for 15 min. The reaction mixture was then filtered through pad of CELITE®. The filtrate was washed twice with DCM (2×20 mL). The organic layer of the filtrate was separated, the aqueous layer was extracted with 2×50 mL of DCM. The combined organic layers were washed with brine, dried over sodium sulfate, and concentrated in vacuo to provide a pale green oil. The crude reaction mixture was purified by silica gel chromatography (40 g REDISEP® column, eluting with a gradient from 50-100% EtOAc in hexanes). Fractions containing the product were combined and evaporated to afford Intermediate A129G (0.115 g, 73%) as a white solid. MS(ES): m/z=260.0 [M+H]⁺.

Intermediate A129H: tert-Butyl 2'-(3-chlorophenyl)-4'H-spiro[cyclopropane-1,7'-pyrazolo[1,5-a]pyrazine]-5'(6'H)-carboxylate

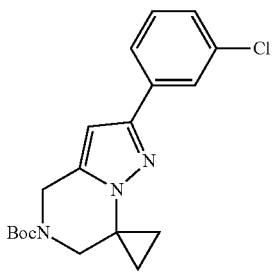 [SMILES: CC(C)(C)OC(=O)N1Cc2cc(-c3cccc(Cl)c3)nn2C2(CC2)C1]

To a 20 mL reaction vial, charged with a solution of Intermediate A129G (0.175 g, 0.674 mmol) in DCM (4 mL) was added triethylamine (0.376 mL, 2.70 mmol) and DMAP (4.12 mg, 0.034 mmol). To the resulting homogeneous solution was added di-tert-butyl dicarbonate (221 mg, 1.011 mmol). After stirring at RT for 16 h, the reaction was quenched by the addition of 20 mL of a saturated aq. solution of NaHCO₃. The layers were separated, and the aqueous layer was washed twice more with DCM. The combined organic layers were washed with water, followed by brine, dried over sodium sulfate, and concentrated in vacuo. The crude reaction mixture was purified by silica gel chromatography (40 g REDISEP® column, eluting with a gradient from 0 to 40% EtOAc in hexanes). Fractions containing the product were combined and evaporated to afford Intermediate A129H (0.240 g, 99%) as a colorless oil. MS(ES): m/z=360.08 [M+H]⁺. ¹H NMR (400 MHz, chloroform-d) δ ppm 7.75 (1H, t, J=1.76 Hz), 7.61 (1H, d, J=7.53 Hz), 7.21-7.34 (2H, m), 6.35 (1H, s), 4.80 (2H, br. s.), 3.81 (2H, s), 1.63-1.69 (2H, m), 1.50-1.54 (9H, m), 0.95-1.08 (2H, m).

Intermediate A129I: tert-Butyl 2'-(3-chlorophenyl)-3'-iodo-4'H-spiro[cyclopropane-1,7'-pyrazolo[1,5-a]pyrazine]-5'(6'H)-carboxylate

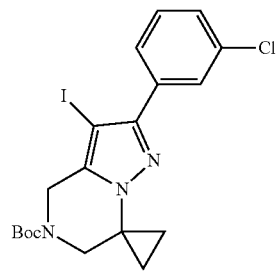 [SMILES: CC(C)(C)OC(=O)N1Cc2c(I)c(-c3cccc(Cl)c3)nn2C2(CC2)C1]

To a flask charged with a solution of Intermediate A129H (241 mg, 0.670 mmol) in a 4:1 solution of DCM (5.4 mL) and MeOH (1.4 mL), was added NIS (452 mg, 2.009 mmol) and the solution was allowed to stir at 22° C. After 1 h, the volatiles were removed under reduced pressured and the red oil was purified by silica gel chromatography (24 g REDISEP® column, eluting with a gradient from 0-25% EtOAc in hexanes). Fractions containing the product were combined and evaporated to afford Intermediate A129I (0.270 g, 83%) as a white foam. MS(ES): m/z=485.8 [M+H]⁺. ¹H NMR (400 MHz, chloroform-d) δ ppm 7.78-7.82 (1H, m), 7.73 (1H, dt, J=6.59, 1.98 Hz), 7.32-7.37 (2H, m), 4.59-4.76 (2H, m), 3.82 (2H, br. s.), 1.65 (2H, s), 1.52 (9H, s), 1.04 (2H, br. s.).

Intermediate A129J: tert-Butyl 7'-(3-chlorophenyl)-8'-cyano-1'H-spiro[cyclopropane-1,4'-pyrrolo[1,2-a]pyrazine]-2'(3'H)-carboxylate

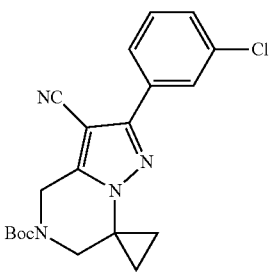 [SMILES: CC(C)(C)OC(=O)N1Cc2c(C#N)c(-c3cccc(Cl)c3)nn2C2(CC2)C1]

To a flask charged with Intermediate A129I (267.4 mg, 0.550 mmol), was added Pd(Ph₃P)₄ (63.6 mg, 0.055 mmol), dicyanozinc (71.1 mg, 0.606 mmol), and zinc (7.20 mg, 0.110 mmol). The flask was sealed with a septum and the contents were degassed with N₂ for 5 min. DMF (2.4 mL) was added and the yellow solution was degassed for an additional 5 min. The reaction mixture was then allowed to heat to 80° C. After 2 h, the reaction mixture was diluted with equal parts water and EtOAc. The organic layer was separated and the aqueous phase was extracted (3×50 mL) with EtOAc. The combined organic layers were washed with brine, dried over sodium sulfate, and concentrated in vacuo. The crude reaction mixture was purified by silica gel chromatography (40 g REDISEP® column, eluting with a gradient from 25-60% EtOAc in hexanes). Fractions containing the product were combined and evaporated to afford Intermediate A129J (0.186 g, 86%) as a white solid. MS(ES): m/z=385.0 [M+H]⁺. ¹H NMR (400 MHz, chloroform-d) δ ppm 7.89 (1H, d, J=1.00 Hz), 7.81-7.86 (1H, m), 7.29-7.40 (2H, m), 4.92 (2H, br. s.), 3.84 (2H, s), 1.66-1.71 (2H, m), 1.52 (9H, s), 1.10 (2H, d, J=2.51 Hz).

Intermediate A129K: tert-Butyl 8'-carbamoyl-7'-(3-chlorophenyl)-1'H-spiro[cyclopropane-1,4'-pyrrolo[1,2-a]pyrazine]-2'(3'H)-carboxylate

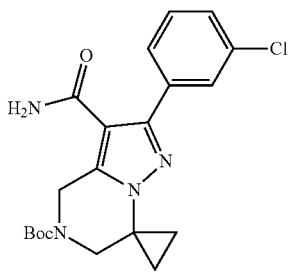 [SMILES: CC(C)(C)OC(=O)N1Cc2c(C(N)=O)c(-c3cccc(Cl)c3)nn2C2(CC2)C1]

To a solution of Intermediate A129J (0.145 g, 0.377 mmol) in DMSO (2 mL) at RT was added dropwise a 5 M aq. solution of KOH (0.38 mL, 1.884 mmol) followed by a 30 wt % solution of H₂O₂ (0.77 mL, 0.754 mmol). The reaction was allowed to stir at 22° C. for 3 h after which the mixture was partitioned between equal parts EtOAc and water. The organic phase was separated and the aqueous layer was extracted twice more with EtOAc. The combined organic layers were washed with brine, dried over anhydrous MgSO₄, filtered and the filtrate concentrated under reduced pressure to afford a white solid. The crude reaction mixture was purified by silica gel chromatography (40 g REDISEP® column, eluting with a gradient from 75-100% EtOAc in hexanes). Fractions containing the product were combined and evaporated to afford Intermediate A129K (0.117 g, 42%) as a white solid. MS(ES): m/z=403.08 [M+H]⁺. ¹H NMR (400 MHz, chloroform-d) δ ppm 8.67 (2H, br. s.), 7.35-7.58 (4H, m), 5.31-6.03 (2H, m), 4.96-5.15 (2H, m), 3.82 (2H, s), 1.59-1.69 (2H, m), 1.42-1.57 (9H, m), 0.94-1.17 (2H, m).

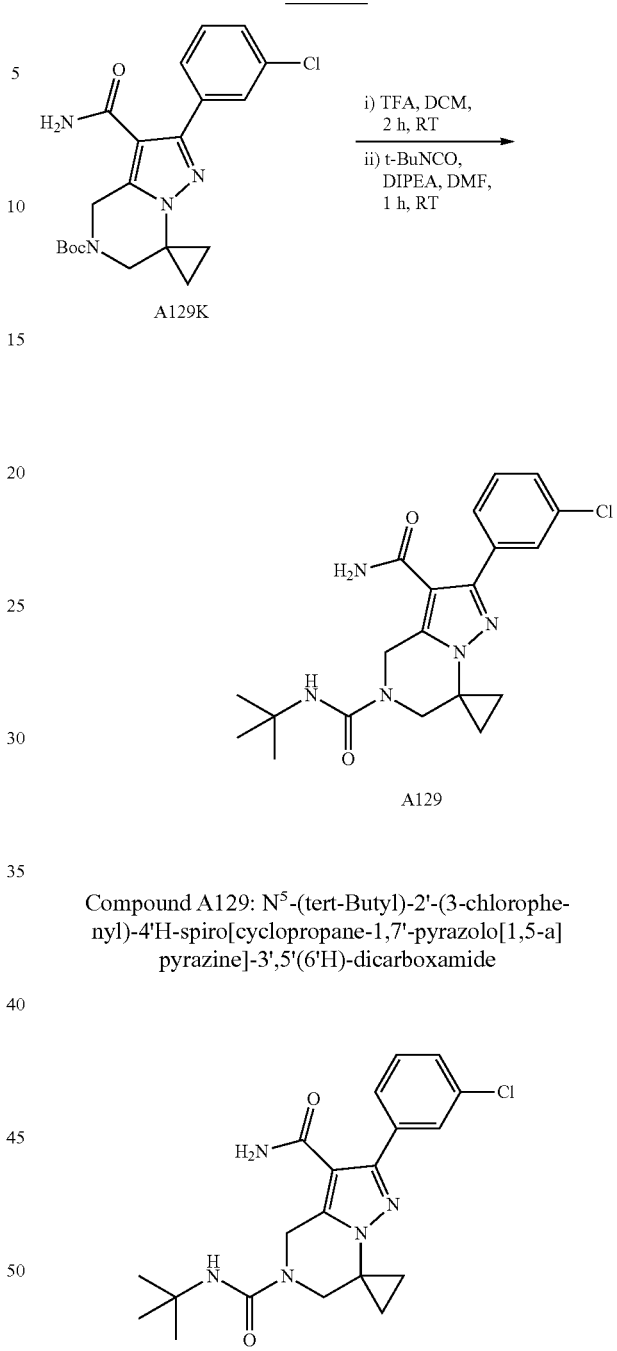

Compound A129: N⁵-(tert-Butyl)-2'-(3-chlorophenyl)-4'H-spiro[cyclopropane-1,7'-pyrazolo[1,5-a]pyrazine]-3',5'(6'H)-dicarboxamide Compound A129 was synthesized analogous to Compound A106 by reacting deprotected A129K with 2-isocyanato-2-methylpropane. The product was purified by preparative HPLC (0.0202 g, 50%): MS(ES): m/z=402.2 [M+H]⁺; HPLC Ret. Time 1.73 min and 2.62 min. (Methods H and I respectively); ¹H NMR (500 MHz, DMSO-d₆) δ ppm 7.66 (1H, s), 7.55-7.63 (1H, m), 7.12-7.46 (4H, m), 6.22 (1H, s), 4.78 (2H, s), 3.82 (2H, s), 1.38-1.46 (2H, m), 1.23-1.32 (9H, m), 1.03-1.10 (2H, in).

The Compound described in Table 56 was synthesized analogous to Compound A129 by reacting deprotected Intermediate A129K with the corresponding carboxylic acid.

TABLE 56
| Ex. No. | Structure | Name | [M + H]⁺ | Ret. Time (min.) | HPLC Method |
|---|---|---|---|---|---|
| A130 | 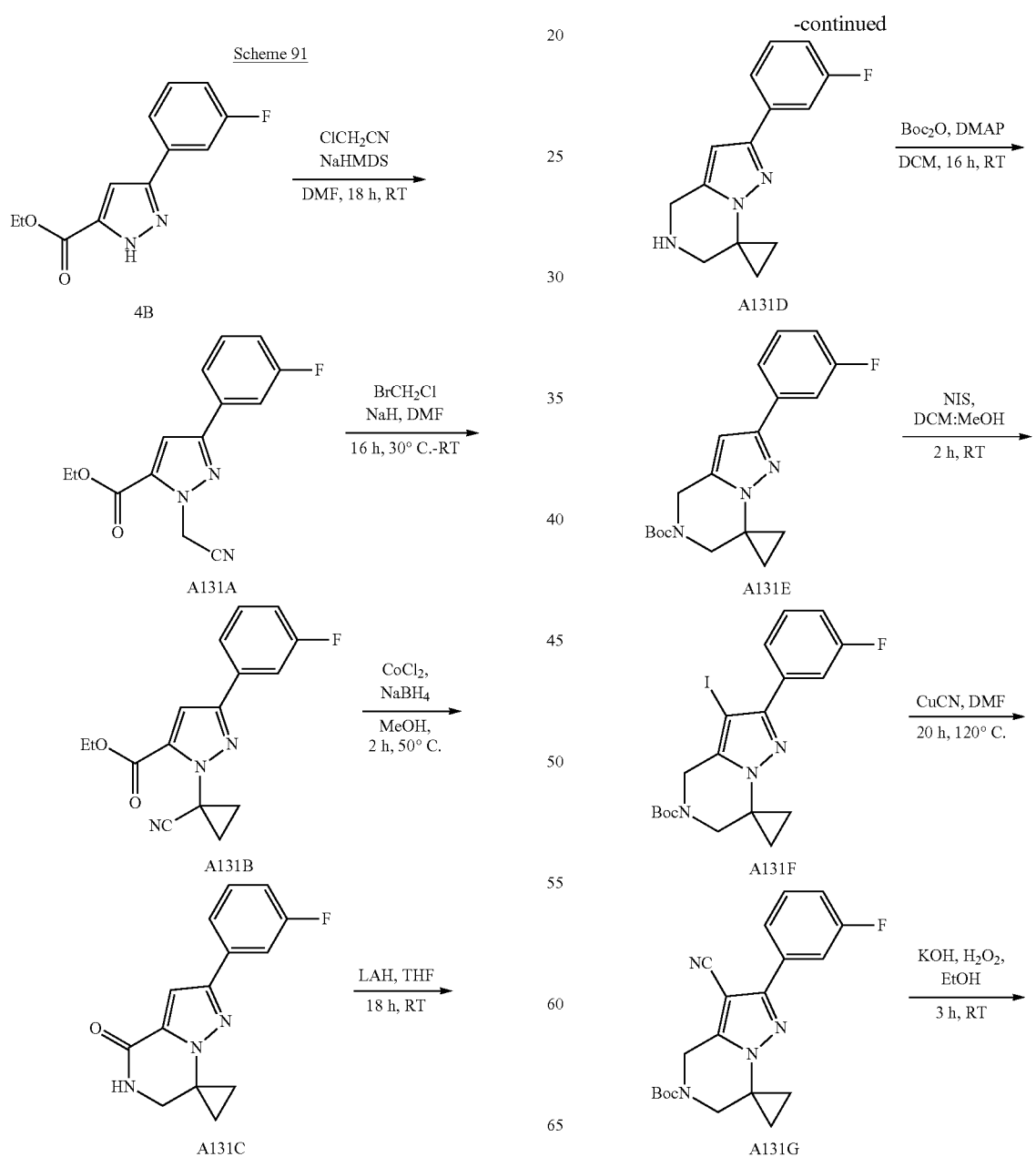 | 2'-(3-Chlorophenyl)-N⁵'-(3,3-difluorocyclobutyl)-4'H-spiro[cyclopropane-1,7'-pyrazolo[1,5-a]pyrazine]-3',5'(6'H)-dicarboxamide | 436.4 | 1.54<br>2.60 | H<br>I |

-continued

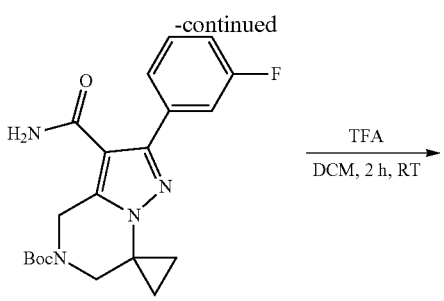

A131H

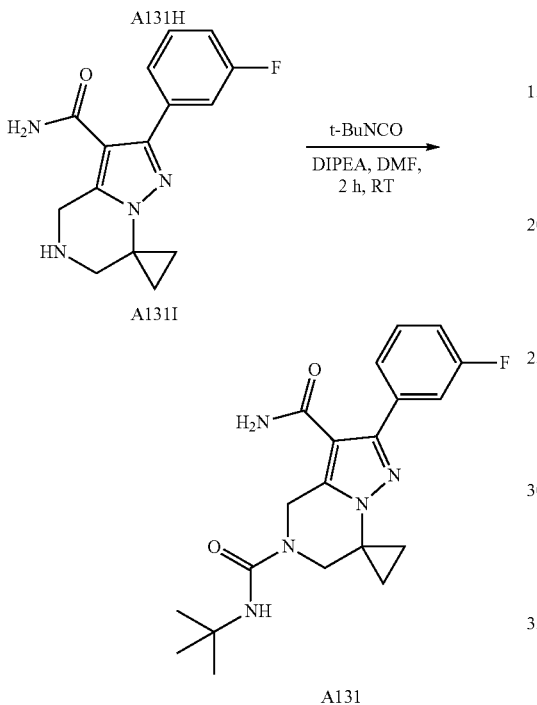

Intermediate A131A: Ethyl 1-(cyanomethyl)-3-(3-fluorophenyl)-1H-pyrazole-5-carboxylate

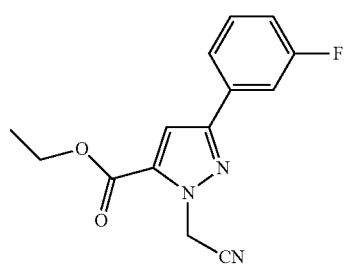 [SMILES: CCOC(=O)c1cc(-c2cccc(F)c2)nn1CC#N]

To an ice-cooled solution of Intermediate 4B (7.0 g, 29.9 mmol) in DMF (45 mL), is added dropwise a solution of LHMDS (31.4 mL, 31.4 mmol, 1M in THF). The reaction mixture is allowed to stir for 5 min. and the ice bath is subsequently removed. 2-Chloroacetonitrile (2.482 g, 32.9 mmol) was added to the reaction mixture. The reaction was allowed to warm to RT and stir for 18 h. The reaction was quenched by the addition of 1.0 mL of a satd. aq. solution of NH₄Cl. The reaction was diluted with equal parts water and EtOAc and the resulting mixture was allowed to stir vigorously for 15 min. The organic layer was separated, dried over sodium sulfate, and concentrated in vacuo. The crude reaction mixture was purified by silica gel chromatography (120 g REDISEP® column, eluting with a gradient from 0-40% EtOAc in hexanes). Fractions containing the product were combined and concentrated to afford Intermediate A131A (6.15 g, 75%) as a white solid. MS(ES) m/z=274 [M+H]⁺.

Intermediate A131B: Ethyl 1-(1-cyanocyclopropyl)-3-(3-fluorophenyl)-1H-pyrazole-5-carboxylate

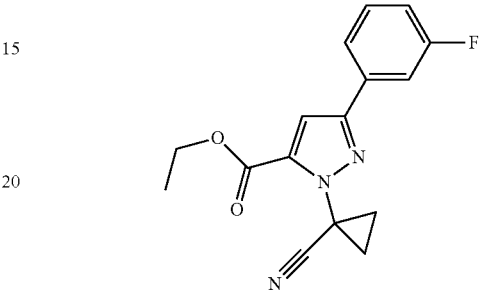

To an ice-cooled solution of Intermediate A131A (3.75 g, 13.72 mmol) and 1-bromo-2-chloroethane (2.362 g, 16.47 mmol) in DMF (40 mL) was added NaH (1.372 g, 34.3 mmol) (60% dispersion in mineral oil) portionwise. The orange cloudy solution was allowed to slowly warm to RT and stir for 16 h. The reaction mixture was quenched by the addition of 10 mL of saturated aq. solution of NH₄Cl. The mixture was partitioned in a mixture of water and EtOAc. The organic layer was separated, washed with brine, dried over sodium sulfate, and concentrated in vacuo. The crude orange oil was purified by silica gel chromatography (80 g REDISEP® column, eluting with a gradient from 0-40% EtOAc in hexanes). Fractions containing the product were combined and concentrated to afford Intermediate A131B (0.51 g, 12%) as a yellow solid. MS(ES) m/z=300 [M+H]⁺.

Intermediate A131C: 2'-(3-Fluorophenyl)-5',6'-dihydro-4'H-spiro[cyclopropane-1,7'-pyrazolo[1,5-a]pyrazin]-4'-one

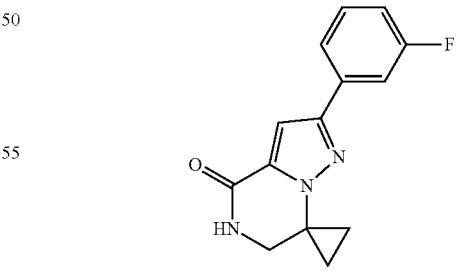

To an ice-cooled solution of Intermediate A131B (0.4 g, 1.336 mmol) and cobalt(II) chloride (0.521 g, 4.01 mmol) in MeOH (50 mL) was slowly added sodium borohydride (0.506 g, 13.36 mmol). The solution instantly turned black with vigorous gas evolution. The reaction was heated to 50° C. for 2 h. The reaction mixture was filtered through CELITE® and the filtrate was concentrated. The crude reaction mixture was purified by silica gel chromatography (24 g REDISEP® column, eluting with a gradient from 0-40% EtOAc in hexanes). Fractions containing the product were combined and evaporated to afford Intermediate A131C (0.16 g, 47%). MS(ES) m/z=258 [M+H]+.

Intermediate A131D: 2'-(3-Fluorophenyl)-5',6'-dihydro-4'H-spiro[cyclopropane-1,7'-pyrazolo[1,5-a]pyrazine]

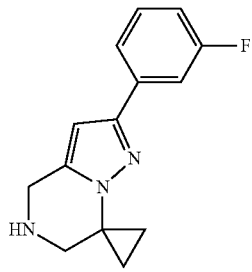 [SMILES: Fc1cccc(-c2cc3n(n2)C2(CC2)CNC3)c1]

To a stirred solution of Intermediate A131C (0.16 g, 0.622 mmol) in THF (10 mL) under an inert atmosphere of nitrogen at −10° C. was added dropwise a 1.0 M solution of LiAlH4 (1.866 mL, 1.866 mmol) in THF. The reaction was allowed to slowly reach RT. The reaction mixture was allowed to stir overnight at RT and then heated at 50° C. for 4 h. The reaction was quenched by slow addition of a saturated solution of Rochelle's salt at 0° C. The mixture was diluted with DCM, the organic layer was separated, and the aqueous layer was extracted with DCM (2×100 mL). The combined organic layers were washed with brine, dried (MgSO4) and concentrated to obtain Intermediate A131D (0.14 g, 0.575 mmol, 93% yield) as an off-white solid. The product was used as such without further purification. MS(ES) m/z=244 [M+H]+.

Intermediate A131E: tert-Butyl 2'-(3-fluorophenyl)-4'H-spiro[cyclopropane-1,7'-pyrazolo[1,5-a]pyrazine]-5'(6'H)-carboxylate

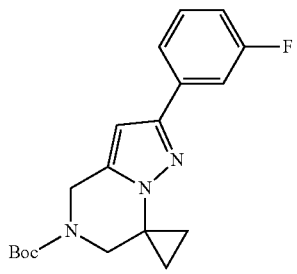 [SMILES: CC(C)(C)OC(=O)N1Cc2cc(-c3cccc(F)c3)nn2C2(CC2)C1]

To a solution of Intermediate A131D (0.14 g, 0.575 mmol) in MeOH (5 mL) was added TEA (0.289 mL, 2.072 mmol) and di-tert-butyl dicarbonate (0.188 g, 0.863 mmol). The solution was allowed to stir overnight at RT. It was concentrated and purified by silica gel chromatography (24 g REDISEP® column, eluting with a gradient from 0-30% EtOAc in hexanes). Fractions containing the product were combined and concentrated to afford Intermediate A131E (0.156 g, 79% yield). MS(ES) m/z=344 [M+H]+.

Intermediate A131F: tert-Butyl 2'-(3-fluorophenyl)-3'-iodo-4'H-spiro[cyclopropane-1,7'-pyrazolo[1,5-a]pyrazine]-5'(6'H)-carboxylate

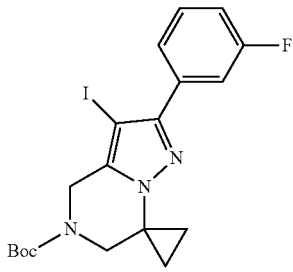 [SMILES: CC(C)(C)OC(=O)N1Cc2c(I)c(-c3cccc(F)c3)nn2C2(CC2)C1]

To a solution of Intermediate A131E (0.156 g, 0.454 mmol) in a 4:1 solution of CH2Cl2 (5 mL) and MeOH (1.25 mL) was added NIS (0.307 g, 1.363 mmol) and the reaction mixture was allowed to stir at RT. After stirring for 90 min, the solution was concentrated in vacuo affording the crude product as red oil. The product was purified by silica gel chromatography (24 g REDISEP® column, eluting with a gradient from 0-30% EtOAc in hexanes). Fractions containing the product were combined and concentrated to afford Intermediate A131F (0.14 g, 66% yield). MS(ES) m/z=470 [M+H]+.

Intermediate A131G: tert-Butyl 3'-cyano-2'-(3-fluorophenyl)-4'H-spiro[cyclopropane-1,7'-pyrazolo[1,5-a]pyrazine]-5'(6'H)-carboxylate

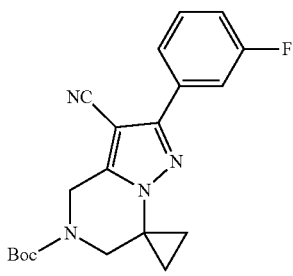 [SMILES: CC(C)(C)OC(=O)N1Cc2c(C#N)c(-c3cccc(F)c3)nn2C2(CC2)C1]

To a solution of Intermediate A131F (0.14 g, 0.298 mmol) in DMF (10 mL) was added copper cyanide (0.067 g, 0.746 mmol). The reaction mixture was heated in a sealed tube to 120° C. for 16 h. The reaction mixture was cooled to RT and filtered. The filter cake was washed with EtOAc and the combined filtrate was concentrated. The residue was purified by silica gel chromatography (24 g REDISEP® column, eluting with a gradient from 0-40% EtOAc in hexanes). Fractions containing the product were combined and concentrated to afford Intermediate A131G (0.091 g, 83% yield). MS(ES) m/z=369 [M+H]⁺.

Intermediate A131H: tert-Butyl 3'-carbamoyl-2'-(3-fluorophenyl)-4'H-Spiro[cyclopropane-1,7'-pyrazolo[1,5-a]pyrazine]-5'(6'H)-carboxylate

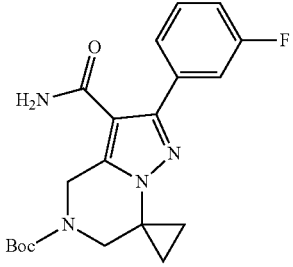 [SMILES: CC(C)(C)OC(=O)N1Cc2c(C(N)=O)c(-c3cccc(F)c3)nn2C2(CC2)C1]

To a solution of Intermediate A131G (0.091 g, 0.247 mmol) in EtOH (20 mL) at RT was added KOH (0.247 mL, 1.235 mmol). The reaction mixture was cooled to 0° C. prior to the dropwise addition of hydrogen peroxide (0.505 mL, 4.94 mmol, 30 wt %). The reaction mixture was allowed to warm to RT and stir overnight. The reaction mixture was concentrated and the residue was dissolved in EtOAc. The organic phase was washed with water, brine, dried (MgSO₄) and concentrated. The residue was purified by silica gel chromatography (12 g REDISEP® column, eluting with a gradient from 0-20% MeOH in DCM). The required fractions were concentrated to obtain Intermediate A131H (0.075 g, 79% yield). MS(ES) m/z=387 [M+H]⁺.

Intermediate A131I: 2'-(3-Fluorophenyl)-5',6'-dihydro-4'H-spiro[cyclopropane-1,7'-pyrazolo[1,5-a]pyrazine]-3'-carboxamide, TFA

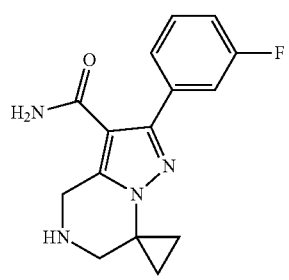 [SMILES: NC(=O)c1c(-c2cccc(F)c2)nn2c1CNCC21CC1]

To a solution of Intermediate A131H (0.085 g, 0.220 mmol) in DCM (5 mL) at RT was added TFA (0.085 mL, 1.100 mmol) and the mixture was stirred overnight. The reaction mixture was concentrated to obtain the TFA salt of Intermediate A131I (0.063 g, 0.220 mmol, 100% yield). The crude product was used as such without further purification. Yield was assumed to be quantitative. MS(ES) m/z=287 [M+H]⁺.

Compound A131: $N^{5'}$-(tert-Butyl)-2'-(3-fluorophenyl)-4'H-spiro[cyclopropane-1,7'-pyrazolo[1,5-a]pyrazine]-3',5'(6'H)-dicarboxamide

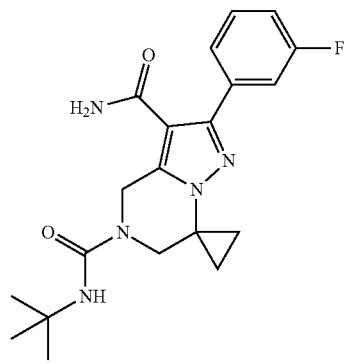 [SMILES: CC(C)(C)NC(=O)N1Cc2c(C(N)=O)c(-c3cccc(F)c3)nn2C2(CC2)C1]

To a solution of Intermediate A131I (0.085 g, 0.297 mmol) in DMF (2 mL) at RT under nitrogen was added DIPEA (0.259 mL, 1.484 mmol) and 2-isocyanato-2-methylpropane (0.059 g, 0.594 mmol). The reaction mixture was stirred for 1 h. The crude material was purified via preparative HPLC. Fractions containing the desired product were combined and evaporated to obtain Compound A131 (27.2 mg, 23.7% yield). MS(ES) m/z=386 [M+H]⁺; Ret. time=1.58 and 2.46 min (Methods H and I respectively); ¹H NMR (500 MHz, DMSO-d₆) δ 7.54-7.29 (m, 2H), 7.23-7.10 (m, 1H), 6.23 (s, 1H), 5.45 (s, 1H), 4.79 (s, 1H), 3.83 (s, 1H), 3.37 (d, J=7.3 Hz, 3H), 1.46-1.36 (m, 1H), 1.28 (s, 5H), 1.19 (s, 4H), 1.11-1.00 (m, 1H).

The Compounds described in Table 57 were prepared following the synthetic sequence outlined in Scheme 91 substituting Intermediate 4B with Intermediate A96E.

TABLE 57
| Ex. No. | Structure | Name | [M + H]+ | Ret. Time (min.) | HPLC Method |
|---|---|---|---|---|---|
| A132 | 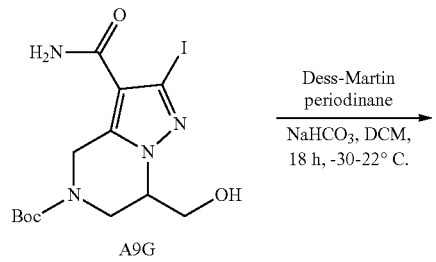 | N5-(tert-Butyl)-2'-(3-chloro-4-fluorophenyl)-4'H-spiro[cyclopropane-1,7'-pyrazolo[1,5-a]pyrazine]-3',5'(6'H)-dicarboxamide | 420.3 | 1.68<br>2.70 | H<br>I |
| A133 | 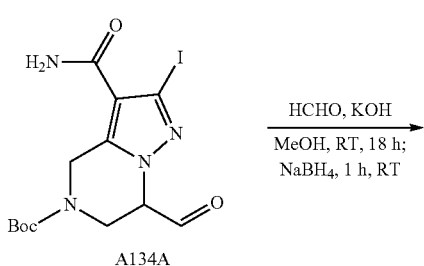 | 2'-(3-Chloro-4-fluorophenyl)-N5'-(3,3-difluorocyclobutyl)-4'H-spiro[cyclopropane-1,7'-pyrazolo[1,5-a]pyrazine]-3',5'(6'H)-dicarboxamide | 436.4 | 1.58<br>2.60 | H<br>I |
Scheme 92
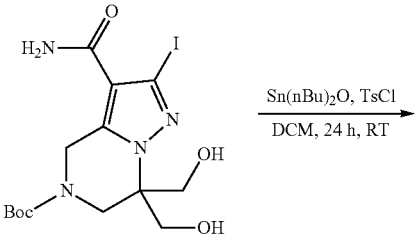
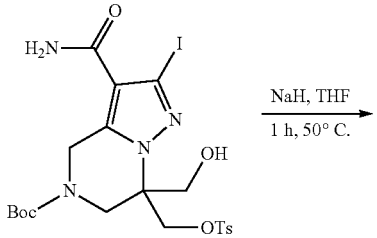
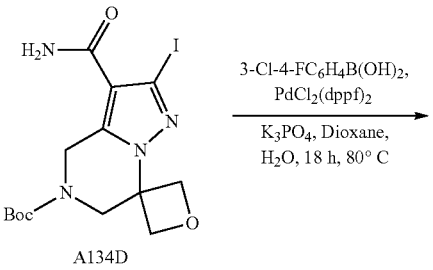

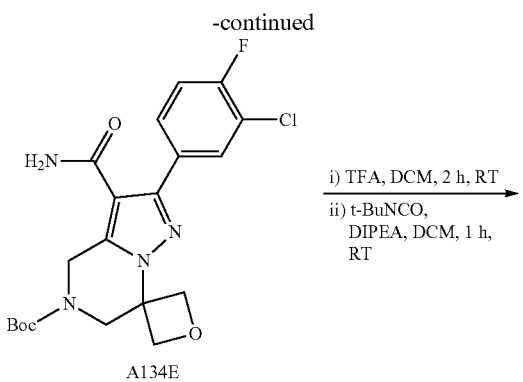

A134E i) TFA, DCM, 2 h, RT
ii) t-BuNCO, DIPEA, DCM, 1 h, RT

A134

Intermediate A134A: tert-Butyl 3-carbamoyl-7-formyl-2-iodo-6,7-dihydropyrazolo[1,5-a]pyrazine-5(4H)-carboxylate

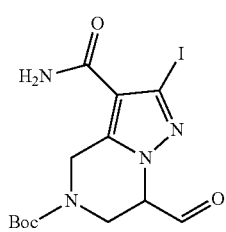 [SMILES: CC(C)(C)OC(=O)N1Cc2c(C(N)=O)c(I)nn2C(C=O)C1]

A solution of Intermediate A9G (0.421 g, 0.997 mmol) and NaHCO₃ (84 mg, 0.997 mmol) in anhydrous DCM (5.0 mL) was allowed to cool to –30° C. for several minutes prior to the addition of Dess-Martin periodinane (0.508 g, 1.197 mmol). The reaction was maintained at –30° C. for 2 h after which the temperature was allowed to gradually reach 22° C. After having stirred for 18 h, the reaction was diluted with DCM and a saturated aq. solution of NaHCO₃. The organic layer was separated and the aqueous phase is extracted with DCM (3×10 mL) The combined organic layers were washed with brine, dried over anhydrous MgSO₄, filtered and the filtrate concentrated under reduced pressure. The crude reaction mixture was purified by silica gel chromatography (40 g REDISEP® column, eluting with a gradient from 50-100% EtOAc in hexanes).

Fractions containing the product were combined and evaporated to afford Intermediate A134A (0.200 g, 47%) as a white foam. MS(ES): m/z=364.9 [M+H₂O-OtBu]⁺. ¹H NMR (400 MHz, chloroform-d) δ ppm 9.62-9.78 (1H, m), 5.81-6.83 (2H, m), 4.49-5.55 (4H, m), 3.58 (1H, d, J=11.80 Hz), 1.39-1.50 (9H, m).

Intermediate A134B: tert-Butyl 3-carbamoyl-7,7-bis(hydroxymethyl)-2-iodo-6,7-dihydropyrazolo[1,5-a]pyrazine-5(4H)-carboxylate

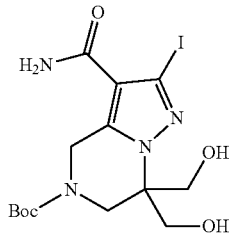 [SMILES: CC(C)(C)OC(=O)N1Cc2c(C(N)=O)c(I)nn2C(CO)(CO)C1]

To a solution of Intermediate A134A (0.200 g, 0.476 mmol) in MeOH (4.0 mL) was added dropwise at RT an 85% aq. solution of KOH (2.380 mL, 4.76 mmol) and a 37% w/w aq. solution of formaldehyde (0.886 mL, 11.90 mmol) in MeOH (1 mL). The reaction was allowed to stir at RT for 18 h after which the mixture was partitioned between equal parts EtOAc and water. The organic phase was separated and the aqueous layer was extracted twice more. The organic layers were combined, dried over sodium sulfate, and concentrated to provide the crude β-hydroxy aldehyde Intermediate. The crude material was dissolved in MeOH (2.0 mL) and treated with NaBH₄ (0.036 g, 0.952 mmol). After stirring at RT for 1 h, the reaction mixture was partitioned between equal parts water and EtOAc. The organic layer was separated and the aqueous phase was extracted twice more with EtOAc. The combined organic layers were dried over sodium sulfate, filtered, and concentrated to provide a crude colorless oil. The crude product was purified by silica gel chromatography (40 g REDISEP® column, eluting with a gradient from 50-100% EtOAc in hexanes). Fractions containing the product were combined and evaporated to afford Intermediate A134B (0.096 g, 45%) as a white solid. MS(ES): m/z=397.0 [M+H₂O-OtBu]⁺. ¹H NMR (400 MHz, chloroform-d) δ ppm 6.29-6.87 (1H, m), 5.84-6.34 (1H, m), 4.85-5.03 (2H, m), 3.72-3.97 (5H, m), 3.58 (2H, br. s.), 1.42-1.52 (9H, m).

Intermediate A134C: tert-Butyl 3-carbamoyl-7-(hydroxymethyl)-2-iodo-7-((tosyloxy)methyl)-6,7-dihydropyrazolo[1,5-a]pyrazine-5(4H)-carboxylate To a solution of Intermediate A134B (0.095 g, 0.210 mmol) and dibutyltin oxide (0.0261 g, 0.105 mmol) in DCM (1.0 mL) was added triethylamine (0.029 mL, 0.210 mmol) followed by p-toluenesulfonyl chloride (0.040 g, 0.210 mmol). The reaction was then allowed to stir at 22° C. After 24 h, the reaction mass was filtered and the filtrate was concentrated. The crude reaction mixture was purified by silica gel chromatography (24 g REDISEP® column, eluting with a gradient from 50-100% EtOAc in hexanes). Fractions containing the product were combined and evaporated to afford Intermediate A134C (0.033 g, 26%) as a white foam. MS(ES): m/z=550.9 [M+H₂O-OtBu]⁺.

Intermediate A134D: tert-Butyl 3'-carbamoyl-2'-iodo-4'H-spiro[oxetane-3,7'-pyrazolo[1,5-a]pyrazine-5'(6'H)-carboxylate

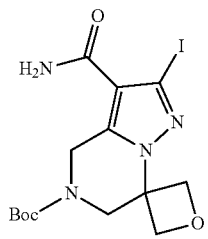

To an ice-cooled solution of Intermediate A134C (0.033 g, 0.054 mmol) in MT (1.0 mL) was added NaH (0.005 g, 0.136 mmol, 60% dispersion in mineral oil). The reaction was allowed to stir at 0° C. for 30 min. prior to heating the mixture to 50° C. for 1 h. The reaction was allowed to cool to RT, diluted with EtOAc, and quenched with the addition of a saturated aq. solution of NH₄Cl. The organic layer was separated and the aqueous phase was extracted twice with EtOAc. The combined organic phases were dried over sodium sulfate and concentrated under reduced pressure to afford an oil which was purified by silica gel chromatography (12 g REDISEP® column, eluting with a gradient from 50-100% EtOAc in hexanes). Fractions containing the product were combined and evaporated to afford Intermediate A134D (0.018 g, 76%) as a white solid. MS(ES): m/z 379.0 [M+H₂O-OtBu]⁺. ¹H NMR (400 MHz, chloroform-d) δ ppm 6.43-6.90 (1H, m), 5.38-5.70 (1H, m), 5.19-5.29 (2H, m), 4.87-4.99 (2H, m), 4.61 (2H, d, J=6.78 Hz), 4.07-4.23 (2H, m), 1.41-1.55 (9H, m).

Intermediate A134E: tert-Butyl 3'-carbamoyl-2'-(3-chloro-4-fluorophenyl)-4'H-spiro[oxetane-3,7'-pyrazolo[1,5-a]pyrazine-5'(6'H)-carboxylate

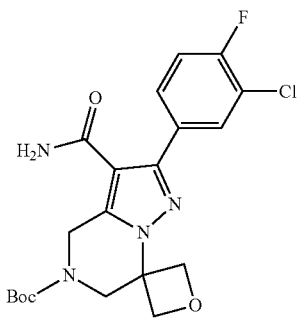 [SMILES: CC(C)(C)OC(=O)N1Cc2c(C(N)=O)c(-c3ccc(F)c(Cl)c3)nn2C2(COC2)C1]

To a pressure vial equipped with a stir bar and charged with Intermediate A134D (0.018 g, 0.041 mmol) was added (3-chloro-4-fluorophenyl)boronic acid (10.8 mg, 0.062 mmol) and PdCl₂(dppf) (3.03 mg, 4.15 µmol). The reaction vial was capped and purged with dry N₂ for 5 minutes. Anhydrous 1,4-dioxane (1.0 mL) and a 2M aq. solution of K₃PO₄ (0.062 mL, 0.124 mmol) were added. The resulting red slurry was allowed to heat to 80° C. for 18 h under a N₂ atmosphere. The reaction was allowed to cool to RT and quenched by the addition of 50 mL of water followed by dilution with DCM. The organic phase was separated and the aqueous phase was extracted twice more with additional DCM. The combined organic layers were washed with a brine solution, dried over sodium sulfate, and concentrated in vacuo to provide a colorless oil. The crude reaction mixture is purified by silica gel chromatography (12 g REDISEP® column, eluting with a 30-100% EtOAc in hexanes). Fractions containing the product were combined and evaporated to afford Intermediate A134E (0.017 g, 84%) as a white foam. MS(ES): m/z=437.0 [M+H]⁺.

Compound 134: N⁵'-(tert-Butyl)-2'-(3-chloro-4-fluorophenyl)-4'H-spiro[oxetane-3,7'-pyrazolo[1,5-a]pyrazine]-3',5'(6'H)-dicarboxamide

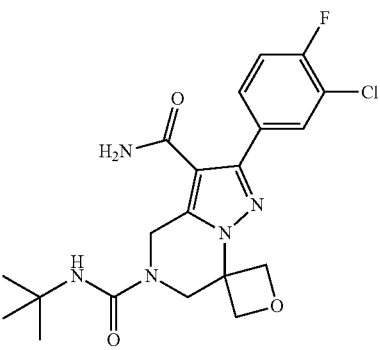 [SMILES: CC(C)(C)NC(=O)N1Cc2c(C(N)=O)c(-c3ccc(F)c(Cl)c3)nn2C2(COC2)C1]

Compound A134 was synthesized analogous to Compound A106 by reacting deprotected A134E with 2-isocyanato-2-methylpropane. The product was purified by preparative HPLC. MS(ES): m/z=436.5 [M+H]⁺; HPLC Ret. Time 1.43 min and 1.43 min. (Methods H and I); ¹H NMR (500 MHz, DMSO-d₆) δ ppm 7.88-7.93 (1H, m), 7.70-7.77 (1H, m), 7.49 (1H, t, J=8.99 Hz), 7.21-7.44 (2H, m), 6.46 (1H, d, J=15.77 Hz), 4.98-5.08 (2H, m), 4.60-4.71 (4H, m), 4.18 (2H, s), 1.23-1.31 (9H, s).

Scheme 93

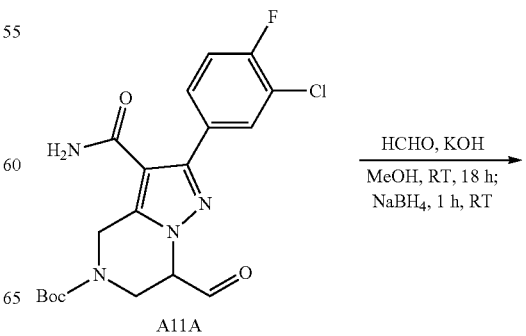

A11A

643
-continued

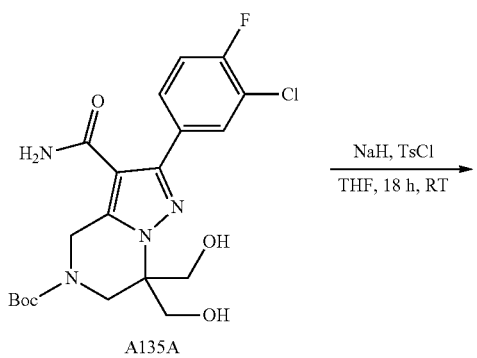
A135A

NaH, TsCl
THF, 18 h, RT
→

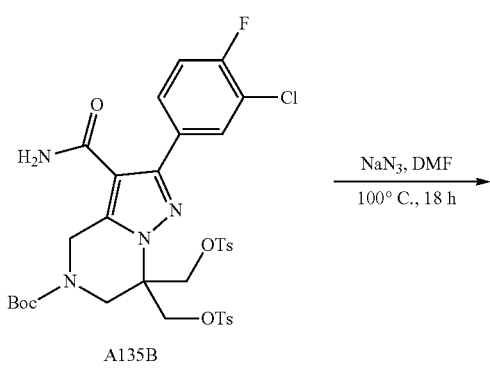
A135B

NaN₃, DMF
100° C., 18 h
→

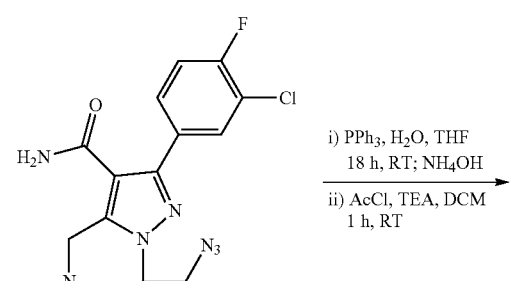
A135C i) PPh₃, H₂O, THF
18 h, RT; NH₄OH
ii) AcCl, TEA, DCM
1 h, RT

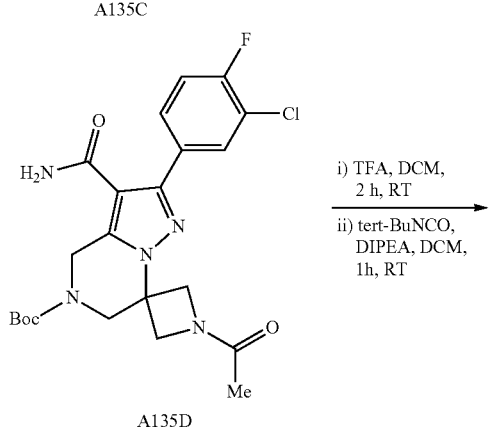
A135D i) TFA, DCM, 2 h, RT
ii) tert-BuNCO, DIPEA, DCM, 1h, RT

644
-continued

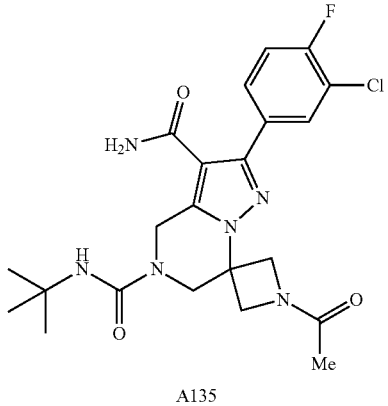 [SMILES: CC(=O)N1CC2(C1)CN(C(=O)NC(C)(C)C)Cc1c(C(N)=O)c(-c3ccc(F)c(Cl)c3)nn12 ; "A135"]
A135

Intermediate A135A: tert-Butyl 3-carbamoyl-2-(3-chloro-4-fluorophenyl)-7,7-bis(hydroxymethyl)-6,7-dihydropyrazolo[1,5-a]pyrazine-5(4H)-carboxylate To a solution of Intermediate A9H (0.425 g, 1.005 mmol) in MeOH (5.0 mL) at RT was added dropwise an 85% aq. solution of KOH (5.03 mL, 10.05 mmol) and a 37% w/w aq. solution of formaldehyde (1.871 mL, 25.1 mmol) in MeOH (1 mL). The reaction was allowed to stir at RT for 18 h after which the mixture was partitioned between equal parts EtOAc and water. The organic phase was separated and the aqueous layer was extracted twice more. The combined organic layers were dried over sodium sulfate, and concentrated to provide the crude β-hydroxy aldehyde Intermediate. The crude material was dissolved in MeOH (2.0 mL) and treated with NaBH₄ (0.076 g, 2.010 mmol). After stirring at 22° C. for 1 h, the reaction mixture was partitioned in equal parts water and EtOAc. The organic layer was separated and the aqueous phase was extracted twice more with EtOAc. The combined organic layers were dried over sodium sulfate, filtered, and concentrated to provide a crude colorless oil. The crude product was purified by silica gel chromatography (40 g REDISEP® column, eluting with a gradient from 60-100% EtOAc in hexanes). Fractions containing the product were combined and evaporated to afford Intermediate A135A (0.210 g, 46%) as a white solid. MS(ES): m/z=399.0 [M+H₂O-OtBu]⁺. ¹H NMR (400 MHz, chloroform-d) δ ppm 7.64 (1H, ddd, J=7.84, 7.09, 2.13 Hz), 7.40-7.52 (1H, m), 7.23-7.32 (2H, m), 5.33-5.61 (1H, m), 4.97 (2H, s), 4.70-4.82 (1H, m), 3.70-4.06 (6H, m), 3.26-3.52 (2H, m), 1.50-1.56 (9H, m).

Intermediate A135B: tert-Butyl 3-carbamoyl-2-(3-chloro-4-fluorophenyl)-7,7-bis((tosyloxy)methyl)-6,7-dihydropyrazolo[1,5-a]pyrazine-5(4H)-carboxylate

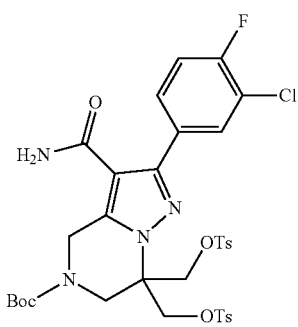 [SMILES: Cc1ccc(S(=O)(=O)OCC2(COS(=O)(=O)c3ccc(C)cc3)CN(C(=O)OC(C)(C)C)Cc3c(C(N)=O)c(-c4ccc(F)c(Cl)c4)nn32)cc1]

To an ice-cooled solution of Intermediate A135A (0.210 g, 0.462 mmol) in THF (5.0 mL) was added NaH (0.0739 g, 0.210 mmol, 60% dispersion in mineral oil) portionwise. After 10 minutes, a solution of p-toluenesulfonyl chloride (0.264 g, 1.385 mmol) in THF was added dropwise at 0° C. The reaction was then allowed to warm to 22° C. After 18 h, the reaction was quenched at 0° C. with a saturated aq. solution of NH₄Cl and diluted with EtOAc. The organic layer was separated and the aqueous phase was extracted twice more with EtOAc. The combined organic layers were dried over sodium sulfate, filtered, and concentrated to afford a colorless oil. The crude reaction mixture is purified by silica gel chromatography (40 g REDISEP® column, eluting with a gradient from 40-100% EtOAc in hexanes) to separate the bistosylate from the monotosylated product. Fractions containing the product were combined and evaporated to afford Intermediate A135B (0.183 g, 52%) as a white solid. MS(ES): m/z=707.2 [M+H₂O-OtBu]⁺.

Intermediate A135C: tert-Butyl 7-(azidomethyl)-3-carbamoyl-2-(3-chloro-4-fluorophenyl)-7-((tosyloxy)methyl)-6,7-dihydropyrazolo[1,5-a]pyrazine-5(4H)-carboxylate

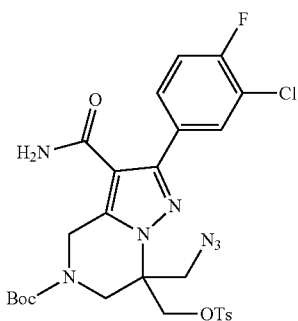 [SMILES: Cc1ccc(S(=O)(=O)OCC2(CN=[N+]=[N-])CN(C(=O)OC(C)(C)C)Cc3c(C(N)=O)c(-c4ccc(F)c(Cl)c4)nn32)cc1]

To a solution of Intermediate A135B (0.092 g, 0.121 mmol) in DMF (2.0 mL) was added sodium azide (9.40 mg, 0.145 mmol). The reaction was allowed to heat at 80° C. for 18 h followed by 20 h at 100° C. The mixture was allowed to cool to RT and partitioned between equal parts EtOAc and water. The aqueous layer was extracted twice more with EtOAc and the combined organic layers are washed with brine, dried over sodium sulfate, filtered, and concentrated to afford the crude material as a colorless oil.

The crude reaction mixture is purified by silica gel chromatography (40 g REDISEP® column, eluting with a gradient from 0-30% EtOAc in hexanes) to separate the azide from the unreacted bistosylate. Fractions containing the product were combined and evaporated to afford Intermediate A135C (0.029 g, 38%) as a white solid. MS(ES): m/z=578.1 [M+H₂O-OtBu]⁺.

Intermediate A135D: tert-Butyl 1-acetyl-3'-carbamoyl-2'-(3-chloro-4-fluorophenyl)-4'H-Spiro[azetidine-3,7'-pyrazolo[1,5-a]pyrazine-5'(6'H)-carboxylate

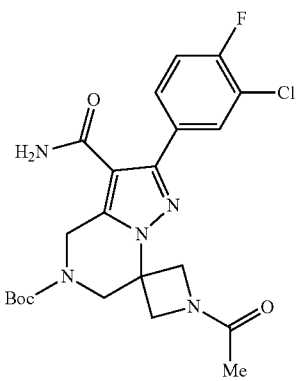 [SMILES: CC(=O)N1CC2(C1)CN(C(=O)OC(C)(C)C)Cc1c(C(N)=O)c(-c3ccc(F)c(Cl)c3)nn12]

To a flask equipped with a stir bar and charged with a solution of Intermediate A135C (29 mg, 0.046 mmol) in THF was added triphenylphosphine (13.20 mg, 0.050 mmol) and water (0.824 μL, 0.046 mmol). After stirring for 18 h at 22° C. there was complete conversion to the intermediate iminophosphorane. The hydrolysis of the iminophosphorane is accomplished by treating the crude reaction mixture with NH₄OH (0.030 mL, 0.229 mmol, 40 wt %). After stirring at 22° C. for 2 h, the reaction mixture was allowed to heat to 40° C. for 2 h after which the volatiles were removed under reduced pressure. The intermediate crude azetidine was then acylated without purification. The crude oil was dissolved in DCM (0.50 mL) and treated with TEA (0.024 mL, 0.174 mmol) and a 1.0 M solution of acetyl chloride (0.065 mL, 0.065 mmol) in DCM. The reaction was allowed to stir at room temperature for 1 h after which the reaction mixture was diluted with equal parts EtOAc and water and the aqueous phase is extracted twice more with EtOAc. The combined organic layers were dried over sodium sulfate and concentrated under reduced pressure. The crude reaction mixture is purified by silica gel chromatography (24 g REDISEP® column, eluting with a gradient from 20-90% EtOAc in hexanes). Fractions containing the product were combined and evaporated to afford Intermediate A135D (0.0125 g, 48% over 3 steps) as a white solid. MS(ES): m/z=422.1 [M+H$_2$O-OtBu]$^+$.

Compound A135: 1-Acetyl-N$^{5'}$-(tert-butyl)-2'-(3-chloro-4-fluorophenyl)-4'H-spiro[azetidine-3,7'-pyrazolo[1,5-a]pyrazine]-3',5'(6'H)-dicarboxamide

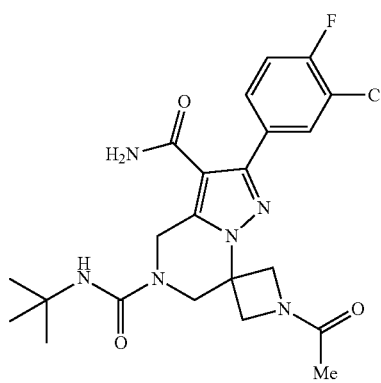

Compound A135 was synthesized analogous to Compound A106 by reacting deprotected A135D with 2-isocyanato-2-methylpropane. The product was purified by preparative HPLC. MS(ES): m/z=476.9 [M+H]$^+$; HPLC Ret. Time 1.28 min and 2.27 min (Methods H and I respectively); $^1$H NMR (500 MHz, DMSO-d$_6$) δ ppm 7.89 (1H, d, J=6.97 Hz), 7.64-7.77 (1H, m), 7.14-7.51 (3H, m), 6.33-6.43 (1H, m), 4.61-4.79 (2 H, m), 4.54 (1H, d, J=8.80 Hz), 4.19-4.35 (2H, m), 4.00-4.16 (3H, m), 1.80-1.92 (3H, m), 1.29 (9H, s).

Scheme 94

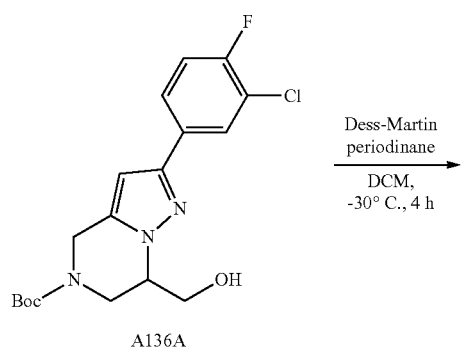

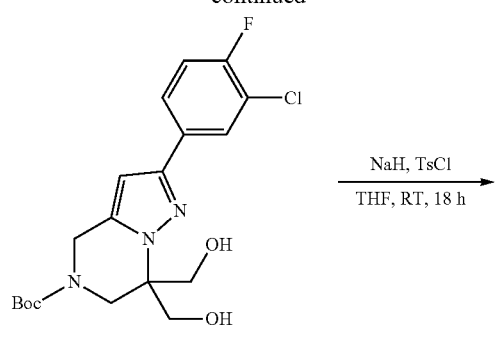

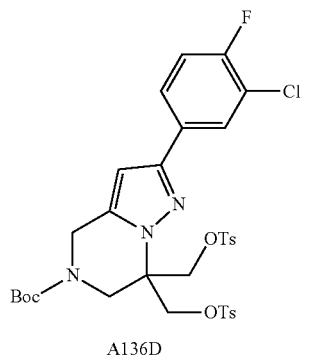

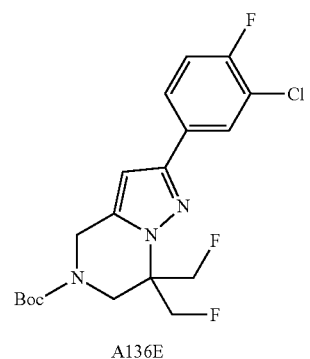

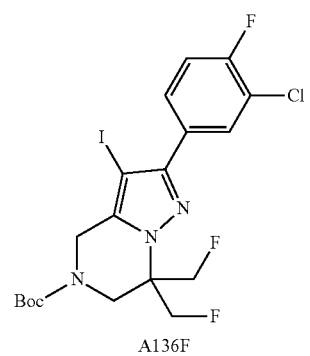

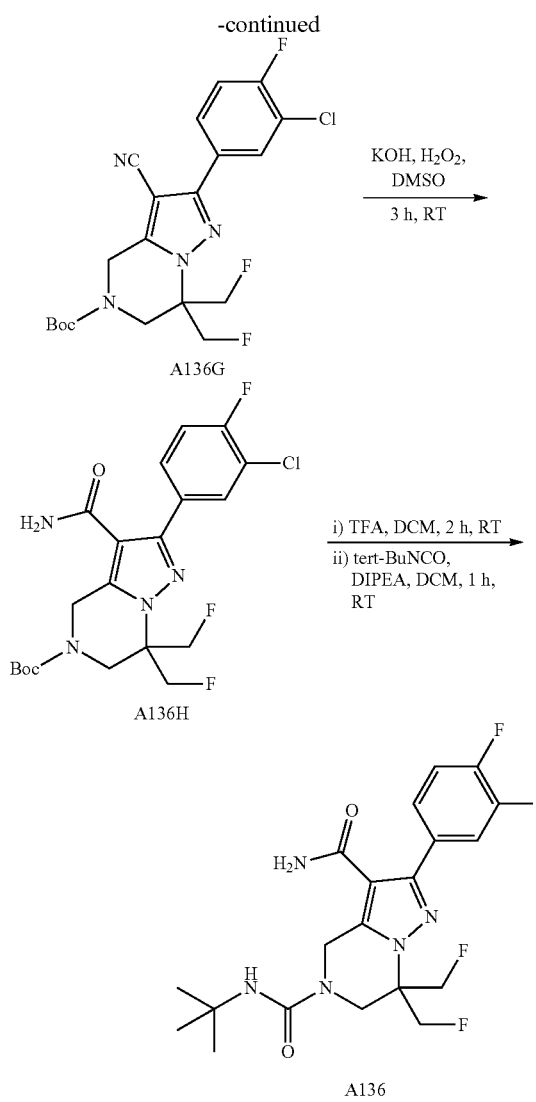

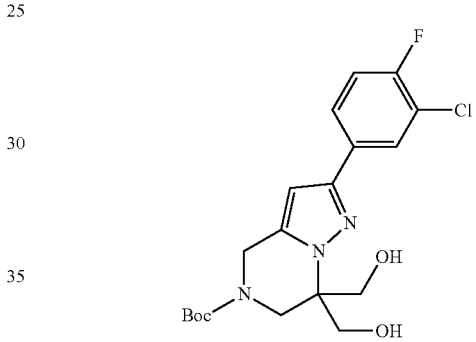

Intermediate A136B: tert-Butyl 2-(3-chloro-4-fluorophenyl)-7-formyl-6,7-dihydropyrazolo[1,5-a]pyrazine-5(4H)-carboxylate

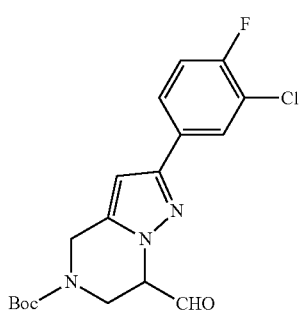 [SMILES: CC(C)(C)OC(=O)N1Cc2cc(-c3ccc(F)c(Cl)c3)nn2C(C=O)C1]

To a flask charged with Intermediate A136A (0.358 g, 0.938 mmol) and sodium bicarbonate (79 mg, 0.938 mmol) was added anhydrous DCM (6.0 mL). The reaction mixture was allowed to cool to −30° C. for several minutes prior to the addition of Dess-Martin periodinane (0.477 g, 1.125 mmol). The reaction was maintained at −30° C. for 2 h before warming to 22° C. After 18 h, the reaction was diluted with DCM and a saturated aq. solution of $NaHCO_3$. The organic layer was separated and the aqueous phase was extracted with DCM (3×10 mL) The combined organic layers were washed with a saturated aq. solution of $NaHCO_3$, dried over anhydrous $MgSO_4$, filtered and the filtrate concentrated under reduced pressure to provide a yellow foam. The crude reaction mixture was purified by silica gel chromatography (80 g REDISEP® column, eluting with a gradient from 0-50% EtOAc in hexanes). Fractions containing the product were combined and evaporated to afford Intermediate A136B (0.311 g, 87%) as a white solid. MS(ES): m/z=378.2 [M−H]$^+$.
$^1$H NMR (400 MHz, chloroform-d) δ ppm 9.73-9.82 (1H, m), 7.84 (1H, dd, J=7.03, 2.01 Hz), 7.59-7.68 (1H, m), 7.14-7.22 (1H, m), 6.41-6.48 (1H, m), 4.62-5.16 (4H, m), 4.35-4.52 (2H, m), 3.64-3.78 (1H, m), 1.58 (9H, br. s.)

Intermediate A136C: text-Butyl 3 2-(3-chloro-4-fluorophenyl)-7,7-bis(hydroxymethyl)-6,7-dihydropyrazolo[1,5-a]pyrazine-5(4H)-carboxylate To a solution of Intermediate A136B (0.311 g, 0.818 mmol) in MeOH (5.0 mL) at RT was added dropwise an 85% aq. solution of KOH (0.459 g, 8.18 mmol) and a 37% w/w aq. solution of formaldehyde (1.523 mL, 20.45 mmol) in MeOH (1 mL). The reaction was allowed to stir at RT for 18 h after which the mixture was partitioned between equal parts EtOAc and water. The organic phase was separated and the aqueous layer was extracted twice more. The combined organic layers were dried over sodium sulfate, and concentrated to provide the crude β-hydroxy aldehyde intermediate. The crude material was dissolved in MeOH (2.0 mL) and treated with $NaBH_4$ (0.062 g, 1.636 mmol). After stirring at RT for 1 h, the reaction mixture was partitioned between equal parts water and EtOAc. The organic layer was separated and the aqueous phase was extracted twice more with EtOAc. The combined organic layers were dried over sodium sulfate, filtered, and concentrated to provide a colorless oil. The crude product was purified by silica gel chromatography (40 g REDISEP® column, eluting with a gradient from 0-60% EtOAc in hexanes). Fractions containing the product were combined and evaporated to afford Intermediate A136C (0.287 g, 77%) as a white solid. MS(ES): m/z=412.3 [M+H]$^+$.
$^1$H NMR (400 MHz, chloroform-d) δ ppm 7.78 (1H, dd, J=7.03, 2.26 Hz), 7.51-7.63 (1H, m), 7.11-7.21 (1H, m), 6.33

(1H, s), 4.67-4.78 (2H, m), 3.96-4.06 (2H, m), 3.73-3.94 (4H, m), 3.42-3.61 (1H, m), 1.52 (9H, s).

Intermediate A136D: tert-Butyl 2-(3-chloro-4-fluorophenyl)-7,7-bis((tosyloxy)methyl)-6,7-dihydropyrazolo[1,5-a]pyrazine-5(4H)-carboxylate

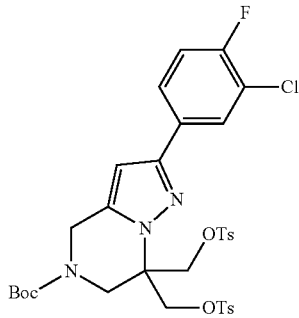 [SMILES: Cc1ccc(S(=O)(=O)OCC2(COS(=O)(=O)c3ccc(C)cc3)CN(C(=O)OC(C)(C)C)Cc3cc(-c4ccc(F)c(Cl)c4)nn32)cc1]

To an ice-cooled solution of Intermediate A136C (0.110 g, 0.267 mmol) in THF (2.0 mL) was added NaH (0.0427 g, 1.068 mmol, 60% dispersion in mineral oil) in small portions. After 10 minutes, a solution of p-toluenesulfonyl chloride (0.153 g, 0.801 mmol) in THF was introduced dropwise at 0° C. The reaction was then allowed to stir at 22° C. After 18 h, the reaction was quenched at 0° C. with a saturated aq. solution of NH$_4$Cl and diluted with EtOAc. The organic layer was separated and the aqueous phase was extracted twice more with EtOAc. The combined organic layers were dried over MgSO$_4$, filtered, and concentrated to afford a pale yellow solid. The crude reaction mixture was purified by preparative HPLC (70:30 solution of 95% H$_2$O:5% MeCN to 95% MeCN:5% H$_2$O, 30 min isocratic) to separate the desired bistosylate from the monotosylated byproduct. Fractions containing the product were combined and evaporated to afford Intermediate A136D (0.129 g, 67%) as a white solid. MS(ES): m/z=720.2 [M+H]$^+$. $^1$H NMR (400 MHz, chloroform-d) δ ppm 7.55-7.70 (5H, m), 7.42 (1H, br. s.), 7.24 (4H, d, J=8.03 Hz), 7.11-7.18 (1H, m), 6.22-6.25 (1H, m), 4.54-4.74 (2H, m), 4.18-4.48 (4H, m), 3.97-4.11 (2H, m), 2.35-2.44 (6H, s), 1.49 (9H, br. s.).

Intermediate A136E: tert-Butyl 2-(3-chloro-4-fluorophenyl)-7,7-bis(fluoromethyl)-6,7-dihydropyrazolo[1,5-a]pyrazine-5(4H)-carboxylate

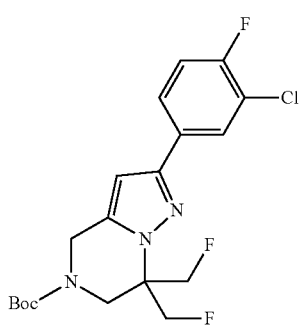 [SMILES: CC(C)(C)OC(=O)N1Cc2cc(-c3ccc(F)c(Cl)c3)nn2C(CF)(CF)C1]

To a solution of Intermediate A136D (0.093 g, 0.129 mmol) in THF (1.0 mL) was added a 1.0 M solution of tetrabutylammonium fluoride (0.646 mL, 0.646 mmol) in THF and the mixture was allowed to stir at 50° C. After 18 h, the reaction was allowed to cool to 22° C. and diluted with equal parts EtOAc and water. The organic layer was separated and the aqueous phase was extracted twice more with additional EtOAc. The combined organic phases were dried over sodium sulfate and concentrated under reduced pressure to afford a colorless oil. The crude reaction mixture was purified by silica gel chromatography (40 g REDISEP® column, eluting with a gradient from 0-60% EtOAc in hexanes). Fractions containing the product were combined and evaporated to afford Intermediate A136E (0.0312 g, 58%) as a white solid. MS(ES): m/z=416.1 [M+H]$^+$. $^1$H NMR (400 MHz, chloroform-d) δ 7.84 (1H, dd, J=7.15, 2.13 Hz), 7.61 (1H, ddd, J=8.53, 4.64, 2.13 Hz), 7.12-7.21 (1H, m), 6.29-6.39 (1H, m), 4.92-5.02 (1H, m), 4.78-4.90 (2H, m), 4.66-4.76 (3H, m), 4.07-4.15 (2H, m), 1.46-1.55 (9H, m).

Intermediate A136F: tert-Butyl 2-(3-chloro-4-fluorophenyl)-7,7-bis(fluoromethyl)-3-iodo-6,7-dihydropyrazolo[1,5-a]pyrazine-5(4H)-carboxylate

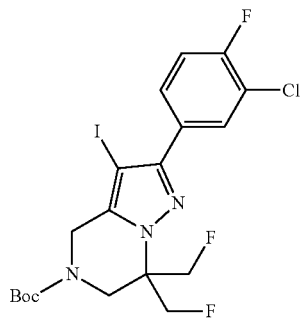 [SMILES: CC(C)(C)OC(=O)N1Cc2c(I)c(-c3ccc(F)c(Cl)c3)nn2C(CF)(CF)C1]

To a solution of Intermediate A136E (0.031 g, 0.075 mmol) in a 4:1 solution of DCM:MeOH (0.75 mL) was added NIS (0.0503 g, 0.224 mmol) and the mixture was allowed to stir at 22° C. After 18 h, due to low reactivity, an additional 3 equivalents of NIS (0.0503 g, 0.224 mmol) were added to the reaction mixture which was then heated to 50° C. for 4 h. The reaction was then allowed to cool to RT and the volatiles were removed under reduced pressure to afford a red oil. The crude reaction mixture was purified by silica gel chromatography (24 g REDISEP® column, eluting with a gradient from 0-40% EtOAc in hexanes). Fractions containing the product were combined and evaporated to afford Intermediate A136F (0.0394 g, 8%) as a white solid. MS(ES): m/z=542.0 [M+H]$^+$. $^1$H NMR (400 MHz, chloroform-d) δ 7.88 (1H, dd, J=7.15, 2.13 Hz), 7.70-7.77 (1H, m), 7.21 (1H, t, J=8.78 Hz), 4.94-5.01 (1H, m), 4.75-4.89 (2H, m), 4.52-4.71 (3H, m), 4.06-4.16 (2H, m), 1.51-1.56 (9H, m).

Intermediate A136G: tert-Butyl 2-(3-chloro-4-fluorophenyl)-3-cyano-7,7-bis(fluoromethyl)-6,7-dihydropyrazolo[1,5-a]pyrazine-5(4H)-carboxylate

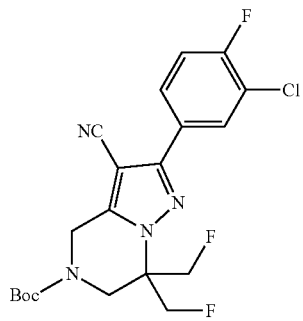 [SMILES: CC(C)(C)OC(=O)N1Cc2c(C#N)c(-c3ccc(F)c(Cl)c3)nn2C(CF)(CF)C1]

To a flask charged with Intermediate A136F (39 mg, 0.072 mmol) was added Pd(PPh₃)₄ (8.32 mg, 7.20 μmol), zinc cyanide (9.30 mg, 0.079 mmol), and zinc (1.0 mg, 0.015 mmol). The flask was fitted with a reflux condenser and was purged and refilled with dry N₂ in three cycles. The condenser was sealed with a septum and the contents were degassed with dry N₂ prior to the addition of DMF (1.0 mL). The yellow reaction mixture was then heated to 80° C. After 24 h, the reaction mixture was cooled to RT and diluted with equal parts water and EtOAc. The organic layer was separated and the aqueous phase was extracted twice more with EtOAc. The combined organic layers were washed with brine, dried over sodium sulfate, filtered, and concentrated to afford an oil. The crude reaction mixture was purified by silica gel chromatography (24 g REDISEP® column, eluting with a gradient from 0-60% EtOAc in hexanes). Fractions containing the product were combined and concentrated under reduced pressure to afford Intermediate A136G (0.0211 g, 46%) as a white solid. MS(ES): m/z=439.3 [M–H]⁺.

Intermediate A136H: tert-Butyl 3-carbamoyl-2-(3-chloro-4-fluorophenyl)-7,7-bis(fluoromethyl)-6,7-dihydropyrazolo[1,5-a]pyrazine-5(4H)-carboxylate

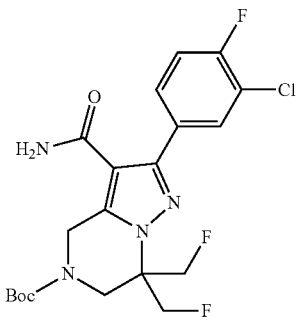 [SMILES: CC(C)(C)OC(=O)N1Cc2c(C(N)=O)c(-c3ccc(F)c(Cl)c3)nn2C(CF)(CF)C1]

To a flask charged with a solution of Intermediate A136G (21 mg, 0.048 mmol) in DMSO (1.0 mL) was added a 5.0 M aq. solution of KOH (0.048 mL, 0.239 mmol) and a 30 wt % solution of hydrogen peroxide (0.098 mL, 0.957 mmol). The reaction was allowed to stir at RT for 1 h after which it was diluted with equal parts water and EtOAc. The organic layer was separated and the aqueous phase was extracted twice more with EtOAc. The combined organic layers were dried over sodium sulfate, filtered, and concentrated to afford a pale yellow oil. The crude reaction mixture was purified by silica gel chromatography (24 g REDISEP® column, eluting with a gradient from 20-100% EtOAc in hexanes). Fractions containing the product were combined and evaporated yielding Intermediate A136H (0.011 g, 50%) as a white solid. MS(ES): m/z=403.0 [M+H₂O-OtBu]⁺.

Compound A136: N⁵'-(tert-Butyl)-2-(3-chloro-4-fluorophenyl)-7,7-bis(fluoromethyl)-6,7-dihydropyrazolo[1,5-a]pyrazine]-3,5(4H)-dicarboxamide

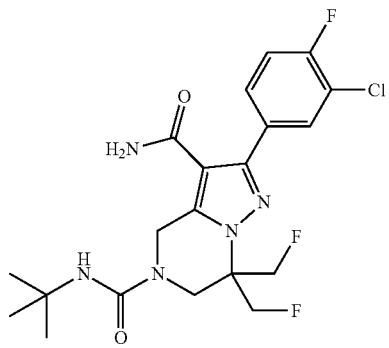 [SMILES: CC(C)(C)NC(=O)N1Cc2c(C(N)=O)c(-c3ccc(F)c(Cl)c3)nn2C(CF)(CF)C1]

Compound A136 was synthesized analogous to Compound A106 by reacting deprotected A136H with 2-isocyanato-2-methylpropane. The product was purified by preparative LCMS. MS(ES): m/z=458.2 [M+H]⁺; HPLC Ret. Time 1.63 min. and 2.60 min. (Methods H and I); ¹H NMR (500 MHz, DMSO-d₆) δ ppm 7.84 (1H, d, J=5.87 Hz), 7.64-7.71 (1H, m), 7.25-7.52 (3H, m), 6.29 (1H, s), 4.86-4.96 (1H, m), 4.73-4.86 (4H, m), 4.71 (1H, d, J=9.54 Hz), 3.99 (2H, s), 1.20-1.31 (9H, m).

Scheme 95

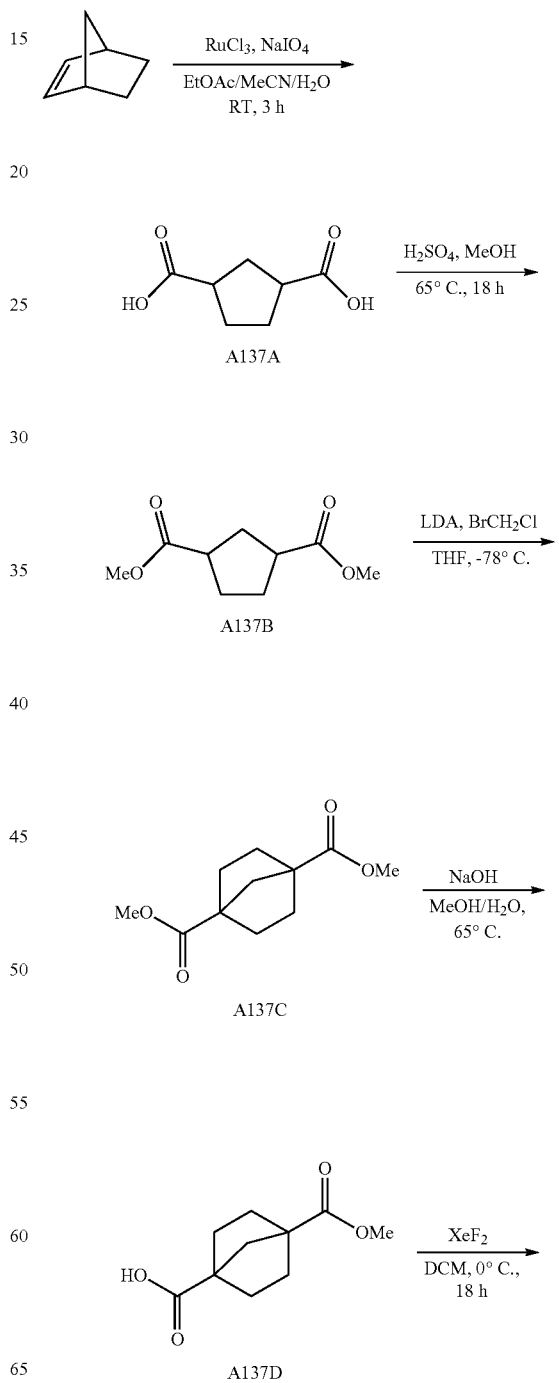

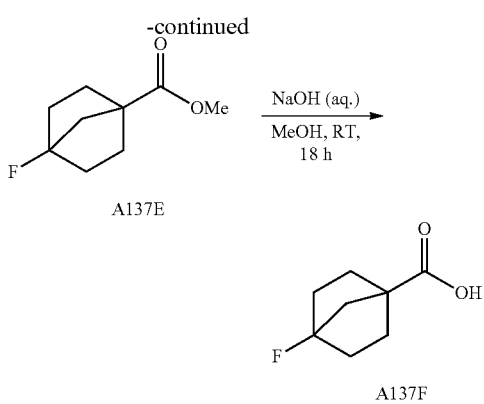

Intermediate A137D: 4-(Methoxycarbonyl)bicyclo[2.2.1]heptane-1-carboxylic acid

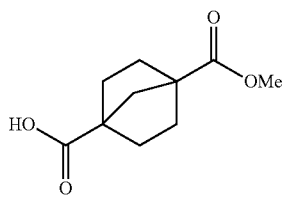

Intermediate A137D was prepared following the synthetic route described in Scheme 95. The experimental procedures described in U.S. Publication No. 2007/0155738 (Jul. 5, 2007) were followed. $^1$H NMR (400 MHz, chloroform-d) δ ppm 9.29-12.86 (1H, m), 3.67-3.74 (1H, m), 2.06-2.15 (2H, m), 1.96 (1H, s), 1.65-1.79 (2H, m).

Intermediate A137E: Methyl 4-fluorobicyclo[2.2.1]heptane-1-carboxylate

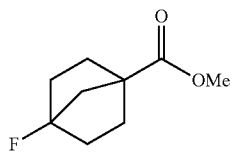

Intermediate A137D was converted to the corresponding fluoride Intermediate A137E as described in J. Org. Chem., 57:2850-2855 (1992). $^1$H NMR (400 MHz, chloroform-d) δ ppm 3.30-3.82 (3H, m), 0.53-2.71 (1H, m).

Intermediate A137F: 4-Fluorobicyclo[2.2.1]heptane-1-carboxylic acid

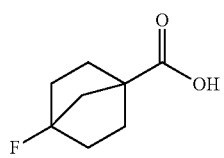 [SMILES: O=C(O)C12CCC(F)(CC1)C2]

To a solution of Intermediate A137E (0.049 g, 0.285 mmol) in MeOH (2 mL) was introduced a 1.0 M aq. solution of NaOH (0.569 mL, 0.569 mmol). The reaction was allowed to stir at RT for 18 h. The reaction was then diluted with equal parts EtOAc and a saturated aq. solution of NaHCO$_3$. The organic phase was separated and the aqueous phase was acidified using a concentrated solution of HCl until the pH was equal to 1. The acidic water layer was then extracted with EtOAc (3×50 mL). The combined extracts were dried over MgSO$_4$ and concentrated under reduced pressure to provide a crude white solid which was used without further purification.

Scheme 96

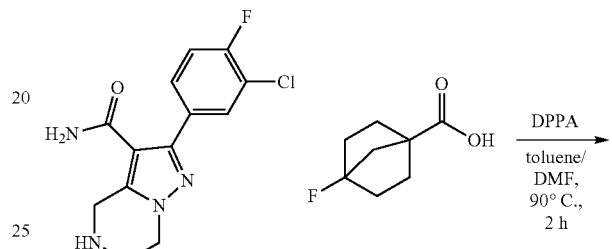

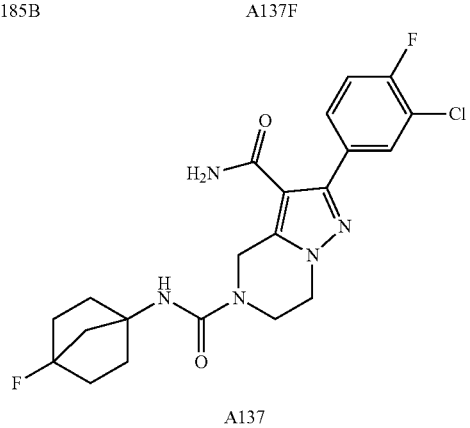

Compound A137: 2-(3-Chloro-4-fluorophenyl)-N$^5$-(4-fluorobicyclo[2.2.1]heptan-1-yl)-6,7-dihydropyrazolo[1,5-a]pyrazine-3,5(4H)-dicarboxamide

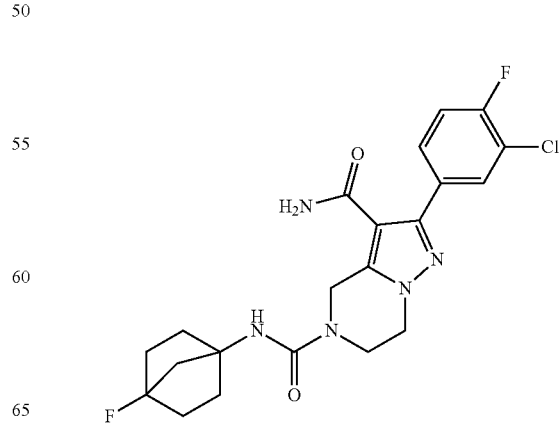

Compound A137 was synthesized using a Curtius rearrangement procedure as depicted in Scheme 96. To a solution of Intermediate A137F (50 mg, 0.316 mmol) in toluene (1.0 mL) was added TEA (0.126 mL, 0.903 mmol), followed by diphenyl phosphorazidate (93 mg, 0.339 mmol). The reaction mixture was heated to 90° C. for 2 h after which it was allowed to cool to RT. Intermediate 185B (66.5 mg, 0.226 mmol), as a solution in DMF, was added to the reaction mixture and the resulting solution was allowed to stir for 1 h. The mixture was diluted with MeOH and concentrated to provide an oil. The product was purified by preparative HPLC. MS(ES): m/z=450.3 [M+H]$^+$; HPLC Ret. Time 1.53 min. and 2.37 min. (Methods H and I respectively); $^1$H NMR (500 MHz, DMSO-$d_6$) δ ppm 7.84 (1H, dd, J=7.3, 1.8 Hz), 7.67 (1H, ddd, J=8.44, 4.77, 2.20 Hz), 7.46 (1H, t, J=8.99 Hz), 7.14-7.40 (2H, m), 6.91 (1H, s), 4.70 (2H, s), 4.08-4.17 (2H, m), 3.81 (2H, t, J=5.32 Hz), 1.70-2.06 (1H, m).

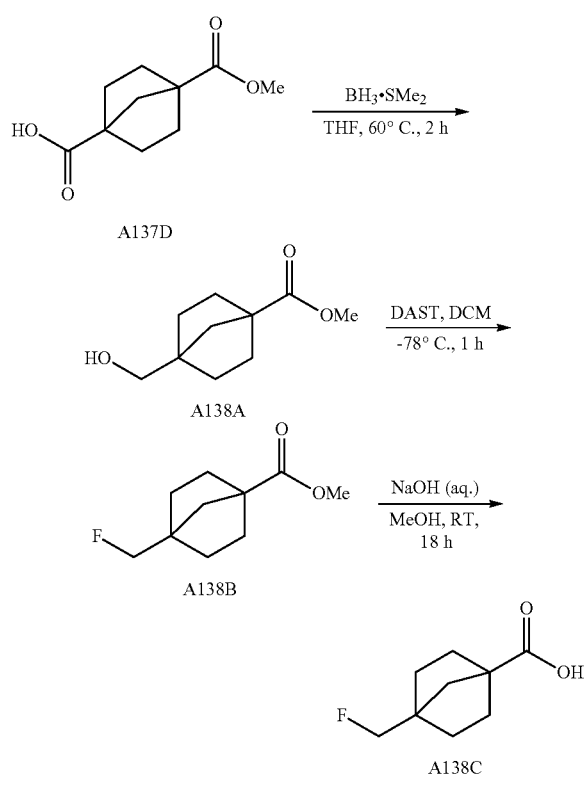

Scheme 97

Intermediate A138A: Methyl 4-(hydroxymethyl)bicyclo[2.2.1]heptane-1-carboxylate

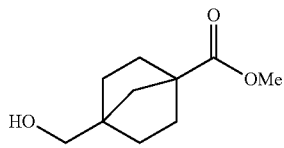 [SMILES: COC(=O)C12CCC(CO)(CC1)C2]

Intermediate A138A was prepared following the synthetic route described in Scheme 97. The experimental procedures described in *Eur. J Med. Chem.*, 46:5728-5735 (2011) were followed. A flask charged with a solution of Intermediate A137D (316 mg, 1.594 mmol) in THF (8 mL) was sealed with a septum and purged with dry N$_2$. The solution was cooled to 0° C. prior to the dropwise addition of a 2.0 M solution of borane-methyl sulfide complex (0.996 mL, 1.993 mmol) in THF. The reaction mixture was allowed to gradually warm to RT. After 18 h, MeOH (5 mL) was added to the reaction and the mixture was heated to reflux for 2 h. The solution was then cooled to RT, concentrated under reduced pressure and diluted with equal parts EtOAc and water. The organic phase was separated and the aqueous phase was extracted twice more with EtOAc. The combined organic layers were washed twice with a 1 N aq. solution of HCl, dried over MgSO$_4$, and concentrated to provide crude Intermediate A138A (0.296 g, >98% yield) as a white solid. $^1$H NMR (400 MHz, chloroform-d) δ ppm 3.69-3.72 (2H, m), 3.68 (3H, s), 2.58-3.20 (2H, m), 2.08-2.11 (1H, m), 1.95-2.03 (2H, m), 1.60-1.76 (5H, m), 1.57 (2H, s), 1.34-1.46 (3H, m).

Intermediate A138B: Methyl 4-(fluoromethyl)bicyclo[2.2.1]heptane-1-carboxylate

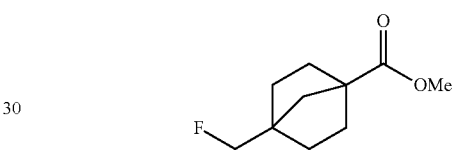

A solution of Intermediate A138A (0.155 g, 0.841 mmol) in DCM (5 mL), was cooled to −78° C. DAST (0.111 mL, 0.841 mmol) was added and the reaction mixture was stirred at 22° C. for 1 h. The reaction mixture was quenched at 0° C. by the careful addition of a saturated aq. solution of NaHCO$_3$. The reaction mixture was diluted with DCM. The organic layer was separated and the aqueous phase was extracted twice more with DCM. The combined organic phases were dried over MgSO$_4$ and concentrated under reduced pressure. The crude reaction mixture was purified by silica gel chromatography (24 g REDISEP® column, eluting with a gradient from 0-30% EtOAc in hexanes). Fractions containing the product were combined and concentrated affording Intermediate A138B (0.047 g, 30% yield) as a white solid. $^1$H NMR (400 MHz, chloroform-d) δ ppm 3.72-3.90 (2H, m), 3.68 (3H, s), 1.93-2.05 (2H, m), 1.55-1.74 (7H, m), 1.34-1.48 (2H, m).

Intermediate A138C: 4-(Fluoromethyl)bicyclo[2.2.1]heptane-1-carboxylic acid

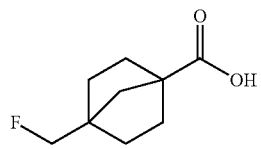 [SMILES: O=C(O)C12CCC(CF)(CC1)C2]

The carboxylic acid was prepared following the saponification procedure to afford Intermediate A137F. The afforded crude white solid was used in the Curtius rearrangement without further purification.

Compound A138: 2-(3-Chloro-4-fluorophenyl)-N⁵-(4-(fluoromethyl)bicyclo[2.2.1]heptan-1-yl)-6,7-dihydropyrazolo[1,5-a]pyrazine-3,5(4H)-dicarboxamide

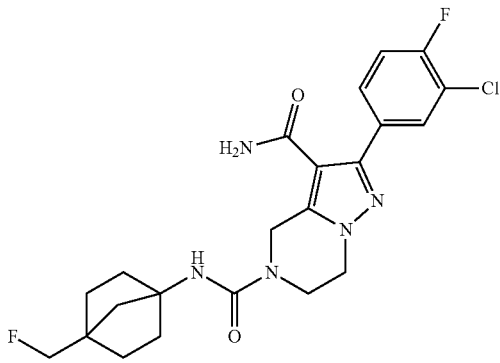 [SMILES: NC(=O)c1c(-c2ccc(F)c(Cl)c2)nn2c1CN(C(=O)NC13CCC(CF)(CC1)C3)CC2]

Compound A138 was synthesized analogously to Compound A137 using a Curtius rearrangement procedure as depicted in Scheme 96 with Intermediate A138C. MS(ES): m/z=464.3 [M+H]⁺; HPLC Ret. Time 1.66 min. and 2.51 min. (Methods H and I); ¹H NMR (500 MHz, DMSO-d₆) δ ppm 7.85 (1H, dd, J=7.34, 1.83 Hz), 7.68 (1H, ddd, J=8.53, 4.86, 2.02 Hz), 7.45 (1H, t, J=8.99 Hz), 7.15-7.40 (2H, m), 6.94 (1H, s), 5.97-6.28 (1H, m), 4.71 (2H, s), 4.12 (2H, t, J=5.14 Hz), 3.82 (2H, t, J=5.14 Hz), 1.65-1.92 (9H, m), 1.35-1.48 (2H, m).

Scheme 98

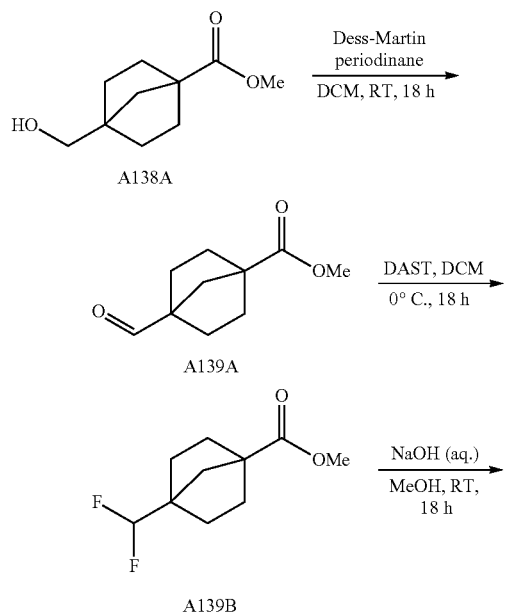

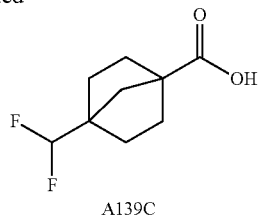

Intermediate A139A: Methyl 4-formylbicyclo[2.2.1]heptane-1-carboxylate

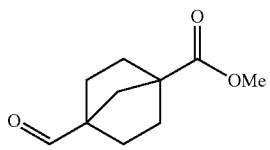 [SMILES: COC(=O)C12CCC(C=O)(CC1)C2]

To a solution of Intermediate A138A (0.118 g, 0.640 mmol) in DCM (5 mL) was added Dess-Martin periodinane (0.326 g, 0.769 mmol). The reaction mixture was allowed to stir at RT for 18 h. The reaction was diluted with equal parts DCM and a saturated aq. solution of NaHCO₃. The organic phase was separated and the aqueous phase was extracted twice more with DCM. The combined organic layers were dried over MgSO₄, and concentrated to provide a white solid. The crude reaction mixture was purified by silica gel chromatography (24 g REDISEP® column, eluting with a gradient from 0-15% EtOAc in hexanes). Fractions containing the product were combined and evaporated yielding Intermediate A139A (0.086 g, 74%) as a white solid. ¹H NMR (400 MHz, chloroform-d) δ ppm 9.81-9.84 (1H, m), 3.70-3.73 (3H, m), 2.05-2.12 (4H, m), 1.85 (2H, s), 1.72-1.80 (2H, m), 1.49-1.62 (2H, m).

Intermediate A139B: Methyl 4-(difluoromethyl)bicyclo[2.2.1]heptane-1-carboxylate

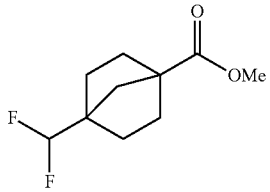 [SMILES: COC(=O)C12CCC(C(F)F)(CC1)C2]

A solution of Intermediate A139A (0.086 g, 0.472 mmol) in DCM (5 mL) was cooled to 0° C. prior to the dropwise introduction of DAST (0.187 mL, 1.416 mmol). The reaction mixture was stirred at 22° C. for 18 hour. The reaction was quenched by the addition of a saturated aqueous solution of sodium bicarbonate. The organic layer was separated and the aqueous phase was extracted twice more with DCM. The combined organic phases were dried over magnesium sulfate and concentrated under reduced pressure to afford Intermediate A139B (0.085 g, 88%) as a white solid, which was used Intermediate A139C: 4-(Difluoromethyl)bicyclo[2.2.1]heptane-1-carboxylic acid

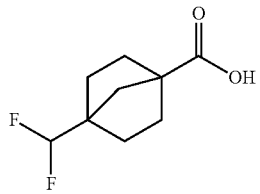 [SMILES: O=C(O)C12CCC(C(F)F)(CC1)C2]

The carboxylic acid A139C was prepared following the saponification procedure to afford Intermediate A137F. The afforded crude white solid was used in the Curtius rearrangement without further purification.

Compound A139: 2-(3-Chloro-4-fluorophenyl)-N$^5$-(4-(difluoromethyl)bicyclo[2.2.1]heptan-1-yl)-6,7-dihydropyrazolo[1,5-a]pyrazine-3,5(4H)-dicarboxamide

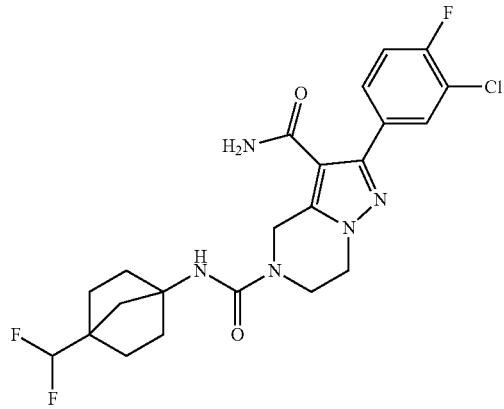 [SMILES: NC(=O)c1c(-c2ccc(F)c(Cl)c2)nn2c1CN(C(=O)NC13CCC(C(F)F)(CC1)C3)CC2]

Compound A139 was synthesized using a Curtius rearrangement procedure as depicted in Scheme 96 using Intermediate A139C. MS(ES): m/z=482.3 [M+H]$^+$; HPLC Ret. Time 1.74 min. and 2.52 min. (Methods H and I); $^1$H NMR (500 MHz, DMSO-d$_6$) δ ppm 7.85 (1H, dd, J=7.34, 1.83 Hz), 7.63-7.72 (1H, m), 7.45 (1H, t, J=8.99 Hz), 7.15-7.41 (2H, m), 6.94 (1H, s), 5.97-6.26 (1H, m), 4.71 (2H, s), 4.12 (2H, t, J=5.14 Hz), 3.82 (2H, t, J=5.14 Hz), 1.64-1.93 (9H, m), 1.35-1.49 (2H, m).

Scheme 99

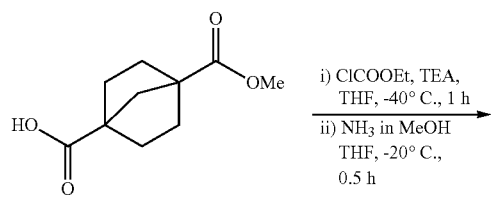

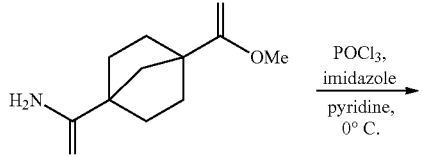

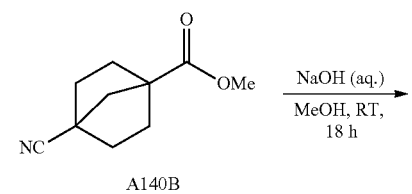

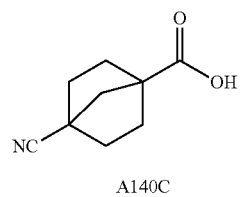

Intermediate A140B: Methyl 4-cyanobicyclo[2.2.1]heptane-1-carboxylate

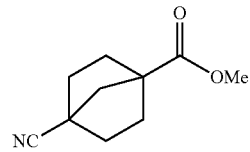 [SMILES: COC(=O)C12CCC(C#N)(CC1)C2]

Intermediate A140B was prepared following the synthetic route described in Scheme 99. The experimental procedures described in U.S. Publication No. 2007/0155738 (Jul. 5, 2007) were followed.

Intermediate A140C: 4-Cyanobicyclo[2.2.1]heptane-1-carboxylic acid

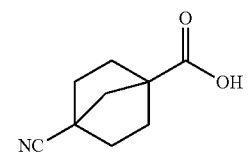 [SMILES: N#CC12CCC(C(=O)O)(CC1)C2]

The carboxylic acid A140C was prepared following the saponification procedure to afford Intermediate A137F. The afforded crude white solid was used in the Curtius rearrangement without further purification. $^1$H NMR (400 MHz, chloroform-d) δ ppm 2.04-2.15 (6H, m), 1.68-1.93 (4H, m).

Compound A140: 2-(3-Chloro-4-fluorophenyl)-N$^5$-(4-cyanobicyclo[2.2.1]heptan-1-yl)-6,7-dihydropyrazolo[1,5-a]pyrazine-3,5(4H)-dicarboxamide

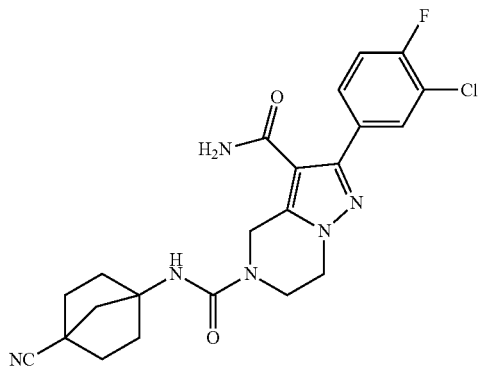 [SMILES: N#CC12CCC(NC(=O)N3CCn4nc(-c5ccc(F)c(Cl)c5)c(C(N)=O)c4C3)(CC1)C2]

Compound A140 was synthesized using a Curtius rearrangement procedure as depicted in Scheme 96 using Intermediate A140C. MS(ES): m/z=457.3 [M+H]$^+$; HPLC Ret. Time 1.43 min. and 2.20 min. (Methods H and I); $^1$H NMR (500 MHz, DMSO-d$_6$) δ ppm 7.84 (1H, dd, J=7.15, 2.02 Hz), 7.67 (1H, ddd, J=8.53, 4.86, 2.02 Hz), 7.46 (1H, t, J=8.99 Hz), 7.13-7.41 (2H, m), 7.01 (1H, s), 4.68-4.75 (2H, m), 4.12 (2H, t, J=5.14 Hz), 3.77-3.86 (2H, m), 1.78-2.08 (8H, m), 1.65-1.76 (2H, m).

What is claimed is:

1. A compound according to Formula (I):

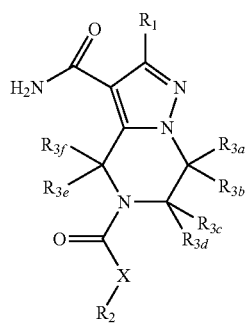

or a pharmaceutically acceptable salt thereof, wherein:
X is independently selected from O and NH;
R$_1$ is independently selected from carbocyclyl substituted with 1-5 R$_5$, and heterocyclyl comprising carbon atoms and 1 to 3 heteroatoms selected from N, NR$_4$, O, S, and substituted with 1-5 R$_5$;
R$_2$ is independently selected from (i) alkyl optionally substituted with F, Cl, Br, OR$_b$, CN, NR$_a$R$_a$, —C(=O)NR$_a$R$_a$, C$_{2-6}$ alkenyl substituted with 0-5 R$_e$, C$_{2-6}$ alkynyl substituted with 0-5 R$_e$, carbocyclyl substituted with 1-8 R$_7$, and heterocyclyl comprising carbon atoms and 1 to 4 heteroatoms selected from N, NR$_6$, O, S, and substituted with 1-8 R$_7$, (ii) cycloalkyl substituted with 1-8 R$_7$, and (iii) cycloheteroalkyl substituted with 1-8 R$_7$;

R$_{3a}$, R$_{3b}$, R$_{3c}$, R$_{3d}$, R$_{3e}$ and R$_{3f}$ are independently selected from H, CN, C$_{1-4}$alkyl substituted with 1-3 R$_8$, —C(=O)OR$_b$, —C(=O)NR$_a$R$_a$, —C(=O)R$_b$, —NR$_a$C(=O)R$_b$, —NR$_a$C(=O)OR$_b$, —(CH$_2$)$_r$-carbocyclyl substituted with 1-3 R$_8$, and —(CH$_2$)$_r$-heterocyclyl substituted with 1-3 R$_8$;

alternatively, R$_{3a}$ and R$_{3b}$, or R$_{3c}$ and R$_{3d}$, or R$_{3e}$ and R$_{3f}$, together with the carbon atom to which they are both attached form a spiral carbocyclic or heterocyclic ring comprising carbon atoms and 1 to 4 heteroatoms selected from N, O, S, each substituted with 1-5 R$_8$;

alternatively, R$_{3a}$ and R$_{3c}$ or R$_{3b}$ and R$_{3d}$ together form a heterocyclic ring comprising carbon atoms and 1 to 4 heteroatoms selected from N, O, S, and substituted with 1-5 R$_8$;

R$_4$ is independently selected from H, C$_{1-4}$ alkyl substituted with 0-3 R$_e$, —(CH$_2$)$_r$CN, —(CH$_2$)$_r$OR$_b$, (CH$_2$)$_r$S(O)$_p$R$_c$, —(CH$_2$)$_r$C(=O)R$_b$, —(CH$_2$)$_r$NR$_a$R$_a$, —(CH$_2$)$_r$C(=O)NR$_a$R$_a$, —(CH$_2$)$_r$NR$_a$C(=O)R$_b$, —(CH$_2$)$_r$NR$_a$C(=O)OR$_b$, —(CH$_2$)$_r$OC(=O)NR$_a$R$_a$, —(CH$_2$)$_r$NR$_a$C(=O)NR$_a$R$_a$, —(CH$_2$)$_r$C(=O)OR$_b$, —(CH$_2$)$_r$S(O)$_2$NR$_a$R$_a$, —(CH$_2$)$_r$NR$_a$S(O)$_2$NR$_a$R$_a$, —(CH$_2$)$_r$NR$_a$S(O)$_2$R$_c$, (CH$_2$)$_r$-carbocyclyl substituted with 0-3 R$_e$, and —(CH$_2$)$_r$-heterocyclyl substituted with 0-3 R$_e$;

R$_5$, at each occurrence, is independently selected from H, C$_{1-4}$ alkyl substituted with 0-3 R$_e$, F, Cl, Br, =O, CN, NO$_2$, —OR$_b$, —(CH$_2$)$_r$CN, —(CH$_2$)$_r$OR$_b$, (CH$_2$)$_r$S(O)$_p$R$_c$, —(CH$_2$)$_r$C(=O)R$_b$, —(CH$_2$)$_r$NR$_a$R$_a$, —(CH$_2$)$_r$C(=O)NR$_a$R$_a$, —(CH$_2$)$_r$NR$_a$C(=O)R$_b$, —(CH$_2$)$_r$NR$_a$C(=O)OR$_b$, —(CH$_2$)$_r$OC(=O)NR$_a$R$_a$, —(CH$_2$)$_r$NR$_a$C(=O)NR$_a$R$_a$, —(CH$_2$)$_r$C(=O)OR$_b$, —(CH$_2$)$_r$S(O)$_2$NR$_a$R$_a$, —(CH$_2$)$_r$NR$_a$S(O)$_2$NR$_a$R$_a$, —(CH$_2$)$_r$NR$_a$S(O)$_2$R$_c$, (CH$_2$)$_r$-carbocyclyl substituted with 0-3 R$_e$, and —(CH$_2$)$_r$-heterocyclyl substituted with 0-3 R$_e$;

R$_6$ is independently selected from H, —C(=O)R$_b$, —CO(=O)R$_b$, —S(O)$_p$R$_c$, C$_{1-6}$ alkyl substituted with 0-5 R$_e$, —(CH$_2$)$_r$—C$_{3-6}$carbocyclyl substituted with 0-5 R$_e$, and —(CH$_2$)$_r$-heterocyclyl substituted with 0-5 R$_e$;

R$_7$, at each occurrence, is independently selected from H, F, Cl, Br, =O, —(CR$_d$R$_d$)$_r$CN, NO$_2$, —(CR$_d$R$_d$)$_r$OR$_b$, —S(O)$_p$R$_c$, —C(=O)R$_b$, —(CR$_d$R$_d$)$_r$NR$_a$R$_a$, —(CR$_d$R$_d$)$_r$C(=O)NR$_a$R$_a$, —NR$_a$C(=O)R$_b$, —NR$_a$C(=O)OR$_b$, —OC(=O)NR$_a$R$_a$, —NR$_a$C(=O)NR$_a$R$_a$, —(CR$_d$R$_d$)$_r$C(=O)OR$_b$, —S(O)$_2$NR$_a$R$_a$, —NR$_a$S(O)$_2$NR$_a$R$_a$, —NR$_a$S(O)$_2$R$_c$, C$_{1-6}$ alkyl substituted with 0-5 R$_e$, —(CR$_d$R$_d$)$_r$—C$_{3-6}$carbocyclyl substituted with 0-5 R$_e$, and —(CR$_d$R$_d$)$_r$-heterocyclyl substituted with 0-5 R$_e$;

R$_8$, at each occurrence, is independently selected from H, F, Cl, Br, CN, C$_{1-6}$ alkyl substituted with 0-5 R$_e$, C$_{2-6}$ alkenyl, C$_{2-6}$ alkynyl, —(CH$_2$)$_r$—C$_{3-6}$ cycloalkyl substituted with 0-5 R$_e$, —(CH$_2$)$_r$-aryl substituted with 0-5 R$_e$, —(CH$_2$)$_r$-heterocyclyl substituted with 0-5 R$_e$, CO$_2$H, —(CH$_2$)$_r$OR$_b$, and —(CH$_2$)$_r$NR$_a$R$_a$;

R$_a$, at each occurrence, is independently selected from H, CN, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$;
or R$_a$ and R$_a$ together with the nitrogen atom to which they are both attached form a heterocyclic ring substituted with 0-5 R$_e$;

R$_b$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$;

R$_c$, at each occurrence, is independently selected from C$_{1-6}$ alkyl substituted with 0-5 R$_e$, C$_{2-6}$alkenyl substituted with 0-5 R$_e$, C$_{2-6}$alkynyl substituted with 0-5 R$_e$, C$_{3-6}$carbocyclyl, and heterocyclyl;

R$_d$, at each occurrence, is independently selected from H and C$_{1-4}$alkyl substituted with 0-5 R$_e$;

R$_e$, at each occurrence, is independently selected from F, Cl, Br, CN, NO$_2$, =O, C$_{1-6}$ alkyl substituted with 0-5 R$_f$, C$_{2-6}$ alkenyl, C$_{2-6}$ alkynyl, —(CH$_2$)$_r$—C$_{3-6}$ cycloalkyl, —(CH$_2$)$_r$-aryl, —(CH$_2$)$_r$-heterocyclyl, CO$_2$H, —(CH$_2$)$_r$ OR$_f$, SR$_f$ and —(CH$_2$)$_r$NR$_f$R$_f$;

R$_f$, at each occurrence, is independently selected from H, C$_{1-5}$ alkyl optionally substituted with F, Cl, Br, C$_{3-6}$ cycloalkyl, and phenyl, or R$_f$ and R$_f$ together with the nitrogen atom to which they are both attached form a heterocyclic ring optionally substituted with C$_{1-4}$alkyl;

p, at each occurrence, is independently selected from zero, 1, and 2; and r, at each occurrence, is independently selected from zero, 1, 2, 3, and 4.

2. The compound according to claim 1, having Formula (II):

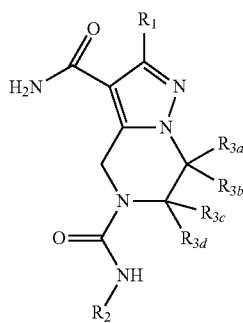

or a pharmaceutically acceptable salt thereof, wherein:

R$_1$ is independently selected from aryl substituted with 1-4 R$_5$, and 5- to 12-membered heteroaryl comprising carbon atoms and 1 to 3 heteroatoms selected from N, NR$_4$, O, S, and substituted with 1-4 R$_5$;

R$_2$ is independently selected from (i) alkyl optionally substituted with F, Cl, Br, OR$_b$, CN, NR$_a$R$_a$, —C(=O)NR$_a$R$_a$, C$_{2-6}$ alkenyl substituted with 0-5 R$_e$, C$_{2-6}$ alkynyl substituted with 0-5 R$_e$, carbocyclyl substituted with 1-8 R$_7$, and heterocyclyl comprising carbon atoms and 1 to 4 heteroatoms selected from N, NR$_6$, O, S, and substituted with 1-8 R$_7$, (ii) cycloalkyl substituted with 1-8 R$_7$, and (iii) cycloheteroalkyl substituted with 1-8 R$_7$;

R$_{3a}$, R$_{3b}$, R$_{3c}$, and R$_{3d}$ are independently selected from H, CN, C$_{1-4}$alkyl substituted with 1-3 R$_8$, —C(=O)OR$_b$, —C(=O)NR$_a$R$_a$, —C(=O)R$_b$, —NR$_a$C(=O)R$_b$, —NR$_a$C(=O)OR$_b$, —(CH$_2$)$_r$-carbocyclyl substituted with 1-3 R$_8$, and —(CH$_2$)$_r$-heterocyclyl substituted with 1-3 R$_8$;

alternatively, R$_{3a}$ and R$_{3b}$, or R$_{3c}$ and R$_{3d}$, or R$_{3e}$ and R$_{3f}$ together with the carbon atom to which they are both attached form a spiral carbocyclic or heterocyclic ring comprising carbon atoms and 1 to 4 heteroatoms selected from N, O, S, each substituted with 0-5 R$_e$;

alternatively, R$_{3a}$ and R$_{3c}$ or R$_{3b}$ and R$_{3d}$ together form a heterocyclic ring comprising carbon atoms and 1 to 4 heteroatoms selected from N, O, S, and substituted with 0-5 R$_e$;

R$_4$ is independently selected from H and C$_{1-4}$ alkyl substituted with 0-3 R$_e$;

R$_5$, at each occurrence, is independently selected from H, C$_{1-4}$ alkyl substituted with 0-3 R$_e$, F, Cl, Br, =O, CN, NO$_2$, —OR$_b$, —(CH$_2$)$_r$CN, —(CH$_2$)$_r$OR$_b$, (CH$_2$)$_r$S(O)$_p$R$_c$, —(CH$_2$)$_r$C(=O)R$_b$, —(CH$_2$)$_r$NR$_a$R$_a$, —(CH$_2$)$_r$C(=O)NR$_a$R$_a$, —(CH$_2$)$_r$NR$_a$C(=O)R$_b$, —(CH$_2$)$_r$NR$_a$C(=O)NR$_a$R$_a$, —(CH$_2$)$_r$OC(=O)NR$_a$R$_a$, —(CH$_2$)$_r$NR$_a$C(=O)OR$_b$, —(CH$_2$)$_r$C(=O)OR$_b$, —(CH$_2$)$_r$S(O)$_2$NR$_a$R$_a$, —(CH$_2$)$_r$NR$_a$S(O)$_2$NR$_a$R$_a$, —(CH$_2$)$_r$NR$_a$S(O)$_2$R$_c$, (CH$_2$)$_r$-carbocyclyl substituted with 0-3 R$_e$, and —(CH$_2$)$_r$-heterocyclyl substituted with 0-3 R$_e$;

R$_6$ is independently selected from H, —C(=O)R$_b$, —CO(=O)R$_b$, —S(O)$_p$R$_c$, C$_{1-6}$ alkyl substituted with 0-5 R$_e$, —(CH$_2$)$_r$—C$_{3-6}$carbocyclyl substituted with 0-5 R$_e$, and —(CH$_2$)$_r$-heterocyclyl substituted with 0-5 R$_e$;

R$_7$, at each occurrence, is independently selected from H, F, Cl, Br, =O, —(CR$_d$R$_d$)$_r$CN, NO$_2$, —(CR$_d$R$_d$)$_r$OR$_b$, —S(O)$_p$R$_c$, —C(=O)R$_b$, —(CR$_d$R$_d$)$_r$NR$_a$R$_a$, —(CR$_d$R$_d$)$_r$C(=O)NR$_a$R$_a$, —NR$_a$C(=O)R$_b$, —NR$_a$C(=O)OR$_b$, —OC(=O)NR$_a$R$_a$, —NR$_a$C(=O)NR$_a$R$_a$, —(CR$_d$R$_d$)$_r$C(=O)OR$_b$, —S(O)$_2$NR$_a$R$_a$, —NR$_a$S(O)$_2$NR$_a$R$_a$, —NR$_a$S(O)$_2$R$_c$, C$_{1-6}$ alkyl substituted with 0-5 R$_e$, —(CR$_d$R$_d$)$_r$—C$_{3-6}$carbocyclyl substituted with 0-5 R$_e$, and —(CR$_d$R$_d$)$_r$-heterocyclyl substituted with 0-5 R$_e$;

R$_8$, at each occurrence, is independently selected from H, F, Cl, Br, CN, C$_{1-6}$ alkyl substituted with 0-5 R$_e$, C$_{2-6}$ alkenyl, C$_{2-6}$ alkynyl, —(CH$_2$)$_r$—C$_{3-6}$ cycloalkyl substituted with 0-5 R$_e$, —(CH$_2$)$_r$-aryl substituted with 0-5 R$_e$, —(CH$_2$)$_r$-heterocyclyl substituted with 0-5 R$_e$, CO$_2$H, —(CH$_2$)$_r$OR$_b$, and —(CH$_2$)$_r$NR$_a$R$_a$;

R$_a$, at each occurrence, is independently selected from H, CN, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;

R$_b$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$;

R$_c$, at each occurrence, is independently selected from C$_{1-6}$ alkyl substituted with 0-5 R$_e$, C$_{2-6}$alkenyl substituted with 0-5 R$_e$, C$_{2-6}$alkynyl substituted with 0-5 R$_e$, C$_{3-6}$carbocyclyl, and heterocyclyl;

R$_d$, at each occurrence, is independently selected from H and C$_{1-4}$alkyl substituted with 0-5 R$_e$;

R$_e$, at each occurrence, is independently selected from F, Cl, Br, CN, NO$_2$, =O, C$_{1-6}$ alkyl substituted with 0-5 R$_f$, C$_{2-6}$ alkenyl, C$_{2-6}$ alkynyl, —(CH$_2$)$_r$—C$_{3-6}$ cycloalkyl, CO$_2$H, —(CH$_2$)$_r$OR$_f$, SR$_f$ and —(CH$_2$)$_r$NR$_f$R$_f$;

R$_f$, at each occurrence, is independently selected from H, C$_{1-5}$ alkyl, C$_{3-6}$ cycloalkyl, and phenyl, or R$_f$ and R$_f$ together with the nitrogen atom to which they are both attached form a heterocyclic ring optionally substituted with C$_{1-4}$alkyl;

p, at each occurrence, is independently selected from zero, 1, and 2; and r, at each occurrence, is independently selected from zero, 1, 2, 3, and 4.

3. The compound according to claim 2, wherein:

R$_1$ is independently selected from aryl, pyridyl, pyrimidinyl, pyrazinyl, pyridazinyl, triazinyl, furyl, thienyl, imidazolyl, thiazolyl, indolyl, oxazolyl, isoxazolyl, pyrazolyl, triazolyl, tetrazolyl, indazolyl, 1,2,4-thiadiazolyl, isothiazolyl, quinolinyl, isoquinolinyl, each substituted with 1-4 $R_4$ and $R_5$;

$R_4$, at each occurrence, is independently selected from H and $C_{1-4}$ alkyl substituted with 0-3 $R_e$;

$R_5$, at each occurrence, is independently selected from H, $C_{1-4}$ alkyl substituted with 0-3 $R_e$, F, Cl, Br, =O, CN, $NO_2$, —$OR_b$, —$S(O)_pR_c$, —CN, —$OR_b$, —$(CH_2)_rC(=O)R_b$, —$(CH_2)_rNR_aR_a$, —$(CH_2)_rC(=O)NR_aR_a$, —$(CH_2)_rNHC(=O)R_b$, —$(CH_2)_rNHC(=O)OR_b$, —$(CH_2)_rOC(=O)NR_aR_a$, —$(CH_2)_rNHC(=O)NR_aR_a$, —$(CH_2)_rC(=O)OR_b$, —$(CH_2)_rS(O)_2NR_aR_a$, —$(CH_2)_rNHS(O)_2NR_aR_a$, —$(CH_2)_rNHS(O)_2R_c$, $(CH_2)_r$-carbocyclyl substituted with 0-3 $R_e$, and —$(CH_2)_r$-heterocyclyl substituted with 0-3 $R_e$;

$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_e$, at each occurrence, is independently selected from F, Cl, Br, CN, $NO_2$, =O, $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, $CO_2H$, —$(CH_2)_rOR_f$, $SR_f$, and —$(CH_2)_rNR_fR_f$;

$R_f$, at each occurrence, is independently selected from H, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

p, at each occurrence, is independently selected from zero, 1, and 2; and r, at each occurrence, is independently selected from zero, 1, 2, 3, and 4.

4. The compound according to claim 3, wherein:

$R_1$ is independently selected from

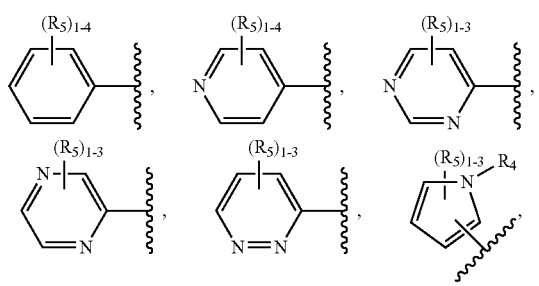

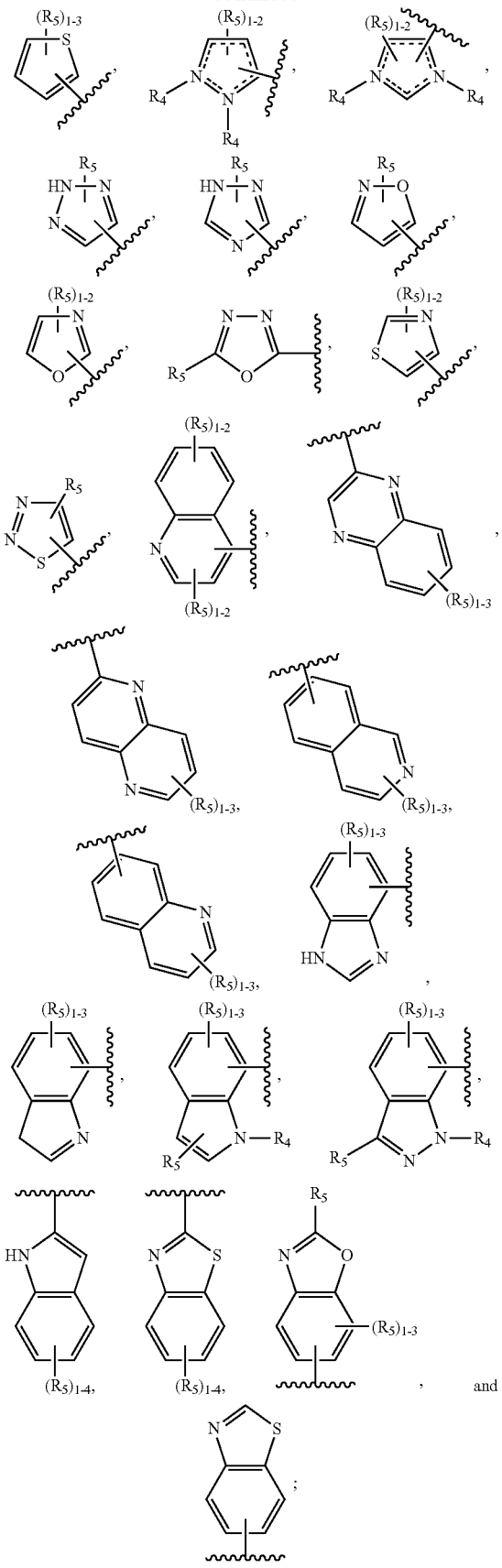

R$_4$, at each occurrence, is independently selected from H, C$_{1-4}$ alkyl substituted with 0-3 R$_e$;

R$_5$, at each occurrence, is independently selected from H, C$_{1-4}$ alkyl substituted with 0-3 R$_e$, F, Cl, Br, =O, CN, NO$_2$, —OR$_b$, —S(O)$_p$R$_c$, —CN, —OR$_b$, —(CH$_2$)$_r$C(=O)R$_b$, —(CH$_2$)$_r$NR$_a$R$_a$, —(CH$_2$)$_r$C(=O)NR$_a$R$_a$, —(CH$_2$)$_r$NHC(=O)R$_b$, —(CH$_2$)$_r$NHC(=O)OR$_b$, —(CH$_2$)$_r$OC(=O)NR$_a$R$_a$, —(CH$_2$)$_r$NHC(=O)NR$_a$R$_a$, —(CH$_2$)$_r$C(=O)OR$_b$, —(CH$_2$)$_r$S(O)$_2$NR$_a$R$_a$, —(CH$_2$)$_r$NHS(O)$_2$NR$_a$R$_a$, —(CH$_2$)$_r$NHS(O)$_2$R$_c$, (CH$_2$)$_r$—C$_{3-6}$cycloalkyl, —(CH$_2$)$_r$-aryl substituted with 0-3 R$_e$, and —(CH$_2$)$_r$-heterocyclyl substituted with 0-3 R$_e$;

R$_a$, at each occurrence, is independently selected from H, CN, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;

R$_b$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$;

R$_c$, at each occurrence, is independently selected from C$_{1-6}$ alkyl substituted with 0-5 R$_e$, C$_{2-6}$alkenyl substituted with 0-5 R$_e$, C$_{2-6}$alkynyl substituted with 0-5 R$_e$, C$_{3-6}$carbocyclyl, and heterocyclyl;

R$_e$, at each occurrence, is independently selected from F, Cl, Br, CN, NO$_2$, =O, C$_{1-6}$ alkyl, C$_{2-6}$ alkenyl, C$_{2-6}$ alkynyl, —(CH$_2$)$_r$—C$_{3-6}$ cycloalkyl, and CO$_2$H;

p, at each occurrence, is independently selected from zero, 1, and 2; and r, at each occurrence, is independently selected from zero, 1, 2, 3, and 4.

5. The compound according to claim 4, having Formula (III), (III)

or a pharmaceutically acceptable salt thereof, wherein:

R$_2$ is independently selected from (i) alkyl optionally substituted with F, Cl, Br, OR$_b$, CN, NR$_a$R$_a$, —C(=O)NR$_a$R$_a$, C$_{2-6}$ alkenyl substituted with 0-5 R$_e$, C$_{2-6}$ alkynyl substituted with 0-5 R$_e$, carbocyclyl substituted with 1-8 R$_7$, and heterocyclyl comprising carbon atoms and 1 to 4 heteroatoms selected from N, NR$_6$, O, S, and substituted with 1-8 R$_7$, (ii) cycloalkyl substituted with 1-8 R$_7$, and (iii) cycloheteroalkyl substituted with 1-8 R$_7$;

R$_{3a}$, R$_{3b}$, R$_{3c}$, and R$_{3d}$ are independently selected from H, CN, C$_{1-4}$alkyl substituted with 1-3 R$_8$, —C(=O)OR$_b$, —C(=O)NR$_a$R$_a$, —C(=O)R$_b$, —NR$_a$C(=O)R$_b$, —NR$_a$C(=O)OR$_b$, —(CH$_2$)$_r$-carbocyclyl substituted with 1-3 R$_8$, and —(CH$_2$)$_r$-heterocyclyl substituted with 1-3 R$_8$;

alternatively, R$_{3a}$ and R$_{3b}$, or R$_{3c}$ and R$_{3d}$, together with the carbon atom to which they are both attached form a spiral carbocyclic or heterocyclic ring comprising carbon atoms and 1 to 4 heteroatoms selected from N, O, S, each substituted with 1-5 R$_8$;

alternatively, R$_{3a}$ and R$_{3c}$ or R$_{3b}$ and R$_{3d}$ together form a heterocyclic ring comprising carbon atoms and 1 to 4 heteroatoms selected from N, O, S, and substituted with 1-5 R$_8$;

R$_5$, at each occurrence, is independently selected from H, C$_{1-4}$ alkyl substituted with 0-3 R$_e$, F, Cl, Br, —S(O)$_p$R$_c$, —CN, —OR$_b$, NR$_a$R$_a$, C$_{3-6}$cycloalkyl, aryl substituted with 0-3 R$_e$, and heterocyclyl substituted with 0-3 R$_e$;

R$_6$ is independently selected from H, —C(=O)R$_b$, —CO(=O)R$_b$, —S(O)$_p$R$_c$, C$_{1-6}$ alkyl substituted with 0-5 R$_e$, —(CH$_2$)$_r$—C$_{3-6}$carbocyclyl substituted with 0-5 R$_e$, and —(CH$_2$)$_r$-heterocyclyl substituted with 0-5 R$_e$;

R$_7$, at each occurrence, is independently selected from H, F, Cl, Br, =O, —(CR$_d$R$_d$)$_r$CN, NO$_2$, —(CR$_d$R$_d$)$_r$OR$_b$, —S(O)$_p$R$_c$, —C(=O)R$_b$, —(CR$_d$R$_d$)$_r$NR$_a$R$_a$, —(CR$_d$R$_d$)$_r$C(=O)NR$_a$R$_a$, —NR$_a$C(=O)R$_b$, —NR$_a$C(=O)OR$_b$, —OC(=O)NR$_a$R$_a$, —NR$_a$C(=O)NR$_a$R$_a$, —(CR$_d$R$_d$)$_r$C(=O)OR$_b$, —S(O)$_2$NR$_a$R$_a$, —NR$_a$S(O)$_2$NR$_a$R$_a$, —NR$_a$S(O)$_2$R$_c$, C$_{1-6}$ alkyl substituted with 0-5 R$_e$, —(CR$_d$R$_d$)$_r$—C$_{3-6}$carbocyclyl substituted with 0-5 R$_e$, and —(CR$_d$R$_d$)$_r$-heterocyclyl substituted with 0-5 R$_e$;

R$_8$, at each occurrence, is independently selected from H, F, Cl, Br, CN, C$_{1-6}$ alkyl substituted with 0-5 R$_e$, C$_{2-6}$ alkenyl, C$_{2-6}$ alkynyl, —(CH$_2$)$_r$—C$_{3-6}$ cycloalkyl substituted with 0-5 R$_e$, —(CH$_2$)$_r$-aryl substituted with 0-5 R$_e$, —(CH$_2$)$_r$-heterocyclyl substituted with 0-5 R$_e$, CO$_2$H, —(CH$_2$)$_r$OR$_b$, and —(CH$_2$)$_r$NR$_a$R$_a$;

R$_a$, at each occurrence, is independently selected from H, CN, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;

R$_b$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$;

R$_c$, at each occurrence, is independently selected from C$_{1-6}$ alkyl substituted with 0-5 R$_e$, C$_{2-6}$alkenyl substituted with 0-5 R$_e$, C$_{2-6}$alkynyl substituted with 0-5 R$_e$, C$_{3-6}$carbocyclyl, and heterocyclyl;

R$_d$, at each occurrence, is independently selected from H and C$_{1-4}$alkyl substituted with 0-5 R$_e$;

R$_e$, at each occurrence, is independently selected from F, Cl, Br, CN, NO$_2$, =O, CO$_2$H, C$_{1-6}$ alkyl substituted with 0-5 R$_f$, C$_{2-6}$ alkenyl, C$_{2-6}$ alkynyl, —(CH$_2$)$_r$—C$_{3-6}$ cycloalkyl, —(CH$_2$)$_r$OR$_f$, SR$_f$, and —(CH$_2$)$_r$NR$_f$R$_f$;

R$_f$, at each occurrence, is independently selected from H, C$_{1-5}$ alkyl, C$_{3-6}$ cycloalkyl, and phenyl, or R$_f$ and R$_f$ together with the nitrogen atom to which they are both attached form a heterocyclic ring optionally substituted with $C_{1-4}$alkyl;

p, at each occurrence, is independently selected from zero, 1, and 2; and r, at each occurrence, is independently selected from zero, 1, 2, 3, and 4.

6. The compound according to claim 5, wherein:

$R_2$ is independently selected from

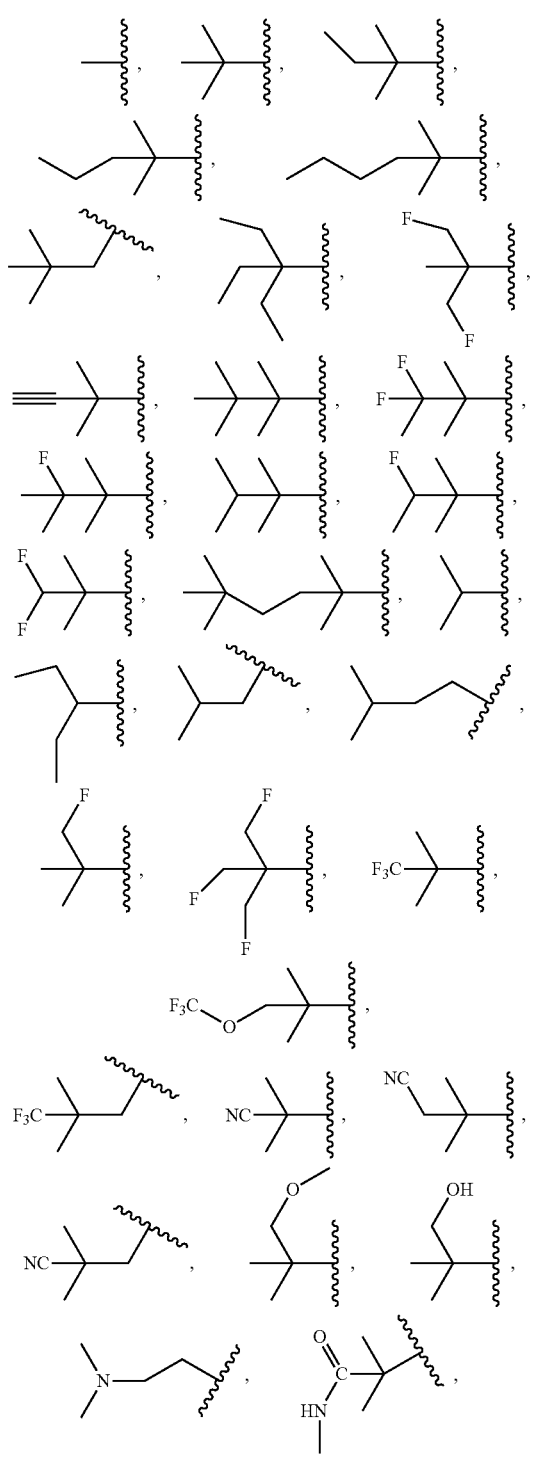

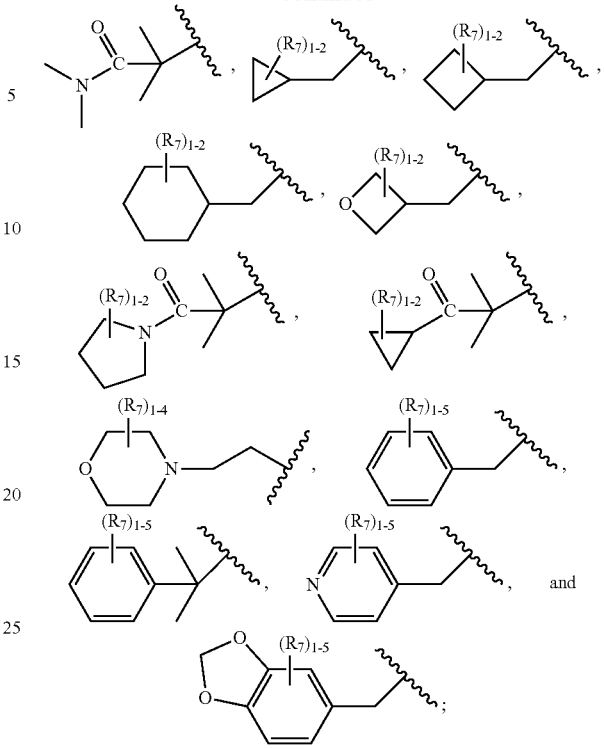

$R_{3a}$ and $R_{3b}$ are independently selected from H, $CH_2CH_3$, $CH_3$, $CH_2OH$, $CH_2CH_2OH$, $CH_2CH_2OC_{1-4}$alkyl, $CH_2F$, $CHF_2$, $CH_2CH_2F$, $CF_3$, $CH_2OCHF_2$, $CH_2CN$, $CH_2CH_2CN$, $CH_2OC_{1-4}$alkyl, $C(CH_3)_3$, $CH(CH_3)_2$, $C(CH_3)_2OH$, $C(CH_3)_2F$, $C(=O)NH-C_{3-6}$cycloalkyl, $C(=O)NH$-heterocyclyl, and $-CH_2$-heterocyclyl, wherein the heterocyclyl is independently selected from

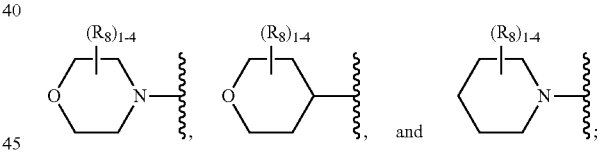

$R_{3c}$ and $R_d$ are independently selected from H, $CH_3$, $CH(CH_3)_2$, $CF_3$, and $C_{3-6}$ cycloalkyl;

$R_5$, at each occurrence, is independently selected from H, $C_{1-4}$ alkyl substituted with 0-3 $R_e$, F, Cl, Br, $-S(O)_pR_c$, $-CN$, $-OR_b$, $NR_aR_a$, $C_{3-6}$cycloalkyl, and aryl substituted with 0-3 $R_e$;

$R_7$, at each occurrence, is independently selected from H, F, Cl, Br, $=O$, $-(CH_2)_rCN$, $NO_2$, $-(CH_2)_rOR_b$, $-S(O)_pR_c$, $-C(=O)R_b$, $-NR_aR_a$, $-C(=O)NR_aR_a$, $-NHC(=O)R_b$, $-NHC(=O)OR_b$, $-OC(=O)NR_aR_a$, $-NHC(=O)NR_aR_a$, $-C(=O)OR_b$, $-S(O)_2NR_aR_a$, $-NHS(O)_2NR_aR_a$, $-NHS(O)_2R_c$, $C_{1-6}$ alkyl substituted with 0-5 $R_e$, aryl substituted with 0-5 $R_e$, and heterocyclyl substituted with 0-5 $R_e$;

$R_8$, at each occurrence, is independently selected from H, F, Cl, Br, CN, $C_{1-6}$ alkyl substituted with 0-5 $R_e$, $-(CH_2)_r-C_{3-6}$ cycloalkyl substituted with 0-5 $R_e$, $-(CH_2)_r$-aryl substituted with 0-5 $R_e$, $-(CH_2)_r$-heterocyclyl substituted with 0-5 $R_e$, $CO_2H$, $-(CH_2)_rOR_b$, and $-(CH_2)_rNR_aR_a$;

$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, aryl substituted with 0-5 $R_e$, and heterocyclyl substituted with 0-5 $R_e$;

$R_c$, at each occurrence, is independently selected from $C_{1-6}$ alkyl substituted with 0-5 $R_e$, $C_{3-6}$carbocyclyl, and heterocyclyl;

$R_e$, at each occurrence, is independently selected from F, Cl, Br, CN, $NO_2$, =O, $CO_2H$, $C_{1-6}$ alkyl, $C_{2-6}$ alkenyl, $C_{2-6}$ alkynyl, and —$(CH_2)_r$—$C_{3-6}$ cycloalkyl;

p, at each occurrence, is independently selected from zero, 1, and 2; and r, at each occurrence, is independently selected from zero, 1, 2, 3, and 4.

7. The compound according to claim 6, wherein:
$R_2$ is independently selected from

[structures]

$R_{3a}$ and $R_{3b}$ are independently H;
$R_{3c}$ and $R_{3d}$ are independently H;
$R_5$, at each occurrence, is independently selected from H, F, Cl, and Br.

8. The compound according to claim 5, wherein:
$R_2$ is independently selected from

[structures]

and $R_{3a}$ and $R_{3b}$ are independently selected from H, $CH_2CH_3$, $CH_3$, $CH_2OH$, $CH_2CH_2OH$, $CH_2CH_2OC_{1-4}$alkyl, $CH_2F$, $CHF_2$, $CH_2CH_2F$, $CF_3$, $CH_2OCHF_2$, $CH_2CN$, $CH_2CH_2CN$, $CH_2OC_{1-4}$alkyl, $C(CH_3)_3$, $CH(CH_3)_2$, $C(CH_3)_2OH$, $C(CH_3)_2F$, $C(=O)NH-C_{3-6}$cycloalkyl, $C(=O)NH$-heterocyclyl, and —$CH_2$-heterocyclyl, wherein the heterocyclyl is independently selected from

[structures]

$R_{3c}$ and $R_{3d}$ are independently selected from H, $CH_3$, $CH(CH_3)_2$, $CF_3$, and $C_{3-6}$ cycloalkyl;

$R_5$, at each occurrence, is independently selected from H, $C_{1-4}$ alkyl substituted with 0-3 $R_e$, F, Cl, Br, —$S(O)_pR_c$, —CN, —$OR_b$, $NR_aR_a$, $C_{3-6}$cycloalkyl, and aryl substituted with 0-3 $R_e$;

$R_7$, at each occurrence, is independently selected from H, F, Cl, Br, =O, —$(CH_2)_rCN$, $NO_2$, —$(CH_2)_rOR_b$, —$S(O)_pR_c$, —$C(=O)R_b$, —$NR_aR_a$, —$C(=O)NR_aR_a$, —$NHC(=O)R_b$, —$NHC(=O)OR_b$, —$OC(=O)NR_aR_a$, —$NHC(=O)NR_aR_a$, —$C(=O)OR_b$, —$S(O)_2NR_aR_a$, —$NHS(O)_2NR_aR_a$, —$NHS(O)_2R_c$, $C_{1-6}$ alkyl substituted with 0-5 $R_e$, aryl substituted with 0-5 $R_e$, and heterocyclyl substituted with 0-5 $R_e$;

$R_8$, at each occurrence, is independently selected from H, F, Cl, Br, CN, $C_{1-6}$ alkyl substituted with 0-5 $R_e$, —$(CH_2)_r$—$C_{3-6}$ cycloalkyl substituted with 0-5 $R_e$, —(CH$_2$)$_r$-aryl substituted with 0-5 R$_e$, —(CH$_2$)$_r$-heterocyclyl substituted with 0-5 R$_e$, CO$_2$H, —(CH$_2$)$_r$OR$_b$, and —(CH$_2$)$_r$NR$_a$R$_a$;

R$_a$, at each occurrence, is independently selected from H, CN, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;

R$_b$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, aryl substituted with 0-5 R$_e$, and heterocyclyl substituted with 0-5 R$_e$;

R$_c$, at each occurrence, is independently selected from C$_{1-6}$ alkyl substituted with 0-5 R$_e$, C$_{3-6}$carbocyclyl, and heterocyclyl;

R$_e$, at each occurrence, is independently selected from F, Cl, Br, CN, NO$_2$, =O, CO$_2$H C$_{1-6}$ alkyl, C$_{2-6}$ alkenyl, C$_{2-6}$ alkynyl, and —(CH$_2$)$_r$—C$_{3-6}$ cycloalkyl;

p, at each occurrence, is independently selected from zero, 1, and 2; and r, at each occurrence, is independently selected from zero, 1, 2, 3, and 4.

9. The compound according to claim 5, or a pharmaceutically acceptable salt thereof, wherein R$_{3a}$ and R$_{3b}$, or R$_{3c}$ and R$_{3d}$, together with the carbon atom to which they are both attached form a spiral carbocyclic or heterocyclic ring comprising carbon atoms and 1 to 4 heteroatoms selected from N, O, S, each substituted with 1-5 R$_8$.

10. The compound according to claim 9, having Formula (IV):

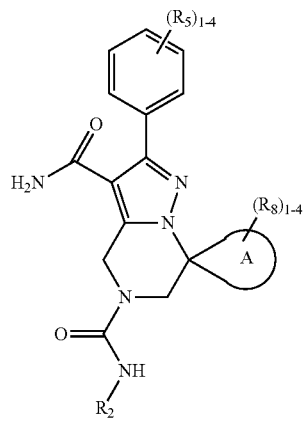

(IV)

or a pharmaceutically acceptable salt thereof, wherein:
Ring A is C$_{3-6}$cycloalkyl or heterocyclyl;
R$_2$ is independently selected from

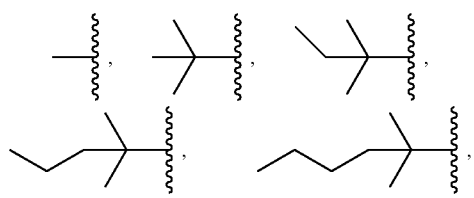

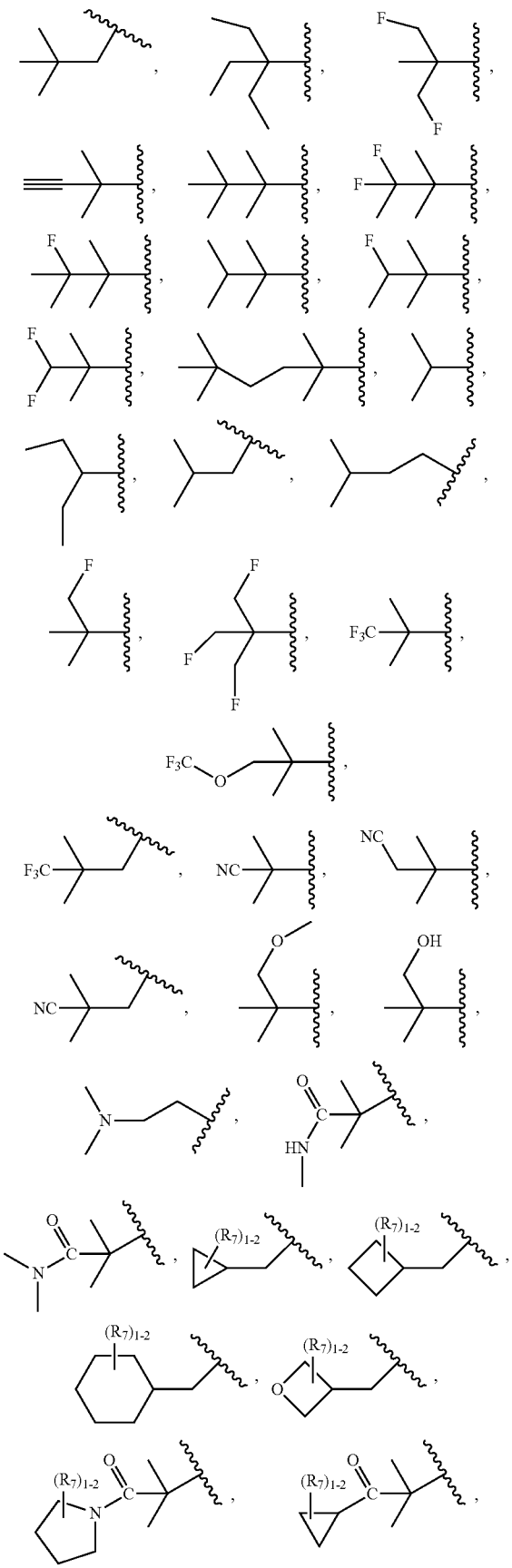

-continued with 0-5 $R_e$, aryl substituted with 0-5 $R_e$, and heterocyclyl substituted with 0-5 $R_e$;

$R_8$, at each occurrence, is independently selected from H, F, Cl, Br, CN, $C_{1-6}$ alkyl substituted with 0-5 $R_e$, $C_{2-6}$ alkenyl, $C_{2-6}$ alkynyl, $-(CH_2)_r-C_{3-6}$ cycloalkyl substituted with 0-5 $R_e$, $-(CH_2)_r$-aryl substituted with 0-5 $R_e$, $-(CH_2)_r$-heterocyclyl substituted with 0-5 $R_e$, $CO_2H$, $-(CH_2)_rOR_b$, and $-(CH_2)_rNR_aR_a$;

$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $-(CH_2)_r-C_{3-10}$carbocyclyl substituted with 0-5 $R_e$, and $-(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, aryl substituted with 0-5 $R_e$, and heterocyclyl substituted with 0-5 $R_e$;

$R_c$, at each occurrence, is independently selected from $C_{1-6}$ alkyl substituted with 0-5 $R_e$, $C_{3-6}$carbocyclyl, and heterocyclyl;

$R_e$, at each occurrence, is independently selected from F, Cl, Br, CN, $NO_2$, $=O$, $CO_2H$, $C_{1-6}$ alkyl, $C_{2-6}$ alkenyl, $C_{2-6}$ alkynyl, and $-(CH_2)_r-C_{3-6}$ cycloalkyl;

p, at each occurrence, is independently selected from zero, 1, and 2; and r, at each occurrence, is independently selected from zero, 1, 2, 3, and 4.

11. The compound according to claim 5, or a pharmaceutically acceptable salt thereof, wherein:

$R_{3a}$ and $R_{3c}$ together form a carbocyclic or heterocyclic ring comprising carbon atoms and 1 to 4 heteroatoms selected from N, O, S, wherein the carbocyclic or heterocyclic ring is substituted with 1-5 $R_8$; and $R_{3b}$ and $R_{3d}$ are independently selected from H and $C_{1-4}$alkyl.

12. The compound according to claim 11, having Formula (V):

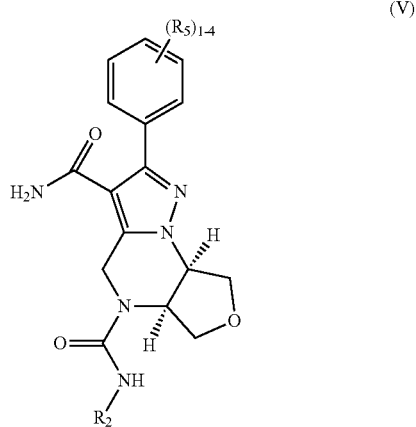

or a pharmaceutically acceptable salt thereof, wherein:

$R_5$, at each occurrence, is independently selected from H, $C_{1-4}$ alkyl substituted with 0-3 $R_e$, F, Cl, Br, $-S(O)_pR_c$, $-CN$, $-OR_b$, $NR_aR_a$, $C_{3-6}$cycloalkyl, aryl substituted with 0-3 $R_e$, and heterocyclyl substituted with 0-3 $R_e$;

$R_7$, at each occurrence, is independently selected from H, F, Cl, Br, CN, $NO_2$, $-OR_b$, $-S(O)_pR_c$, $-C(=O)R_b$, $-NR_aR_a$, $-C(=O)NR_aR_a$, $-NHC(=O)R_b$, $-NHC(=O)OR_b$, $-OC(=O)NR_aR_a$, $-NHC(=O)NR_aR_a$, $-C(=O)OR_b$, $-S(O)_2NR_aR_a$, $C_{1-6}$ alkyl substituted $R_2$ is independently selected from
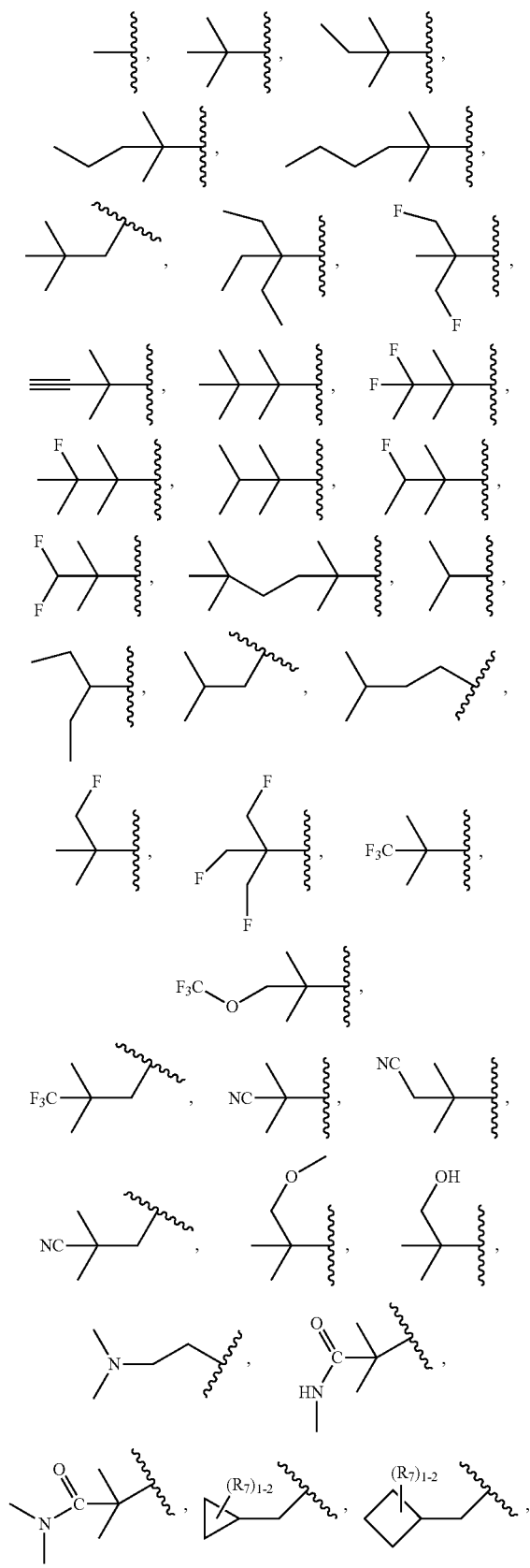
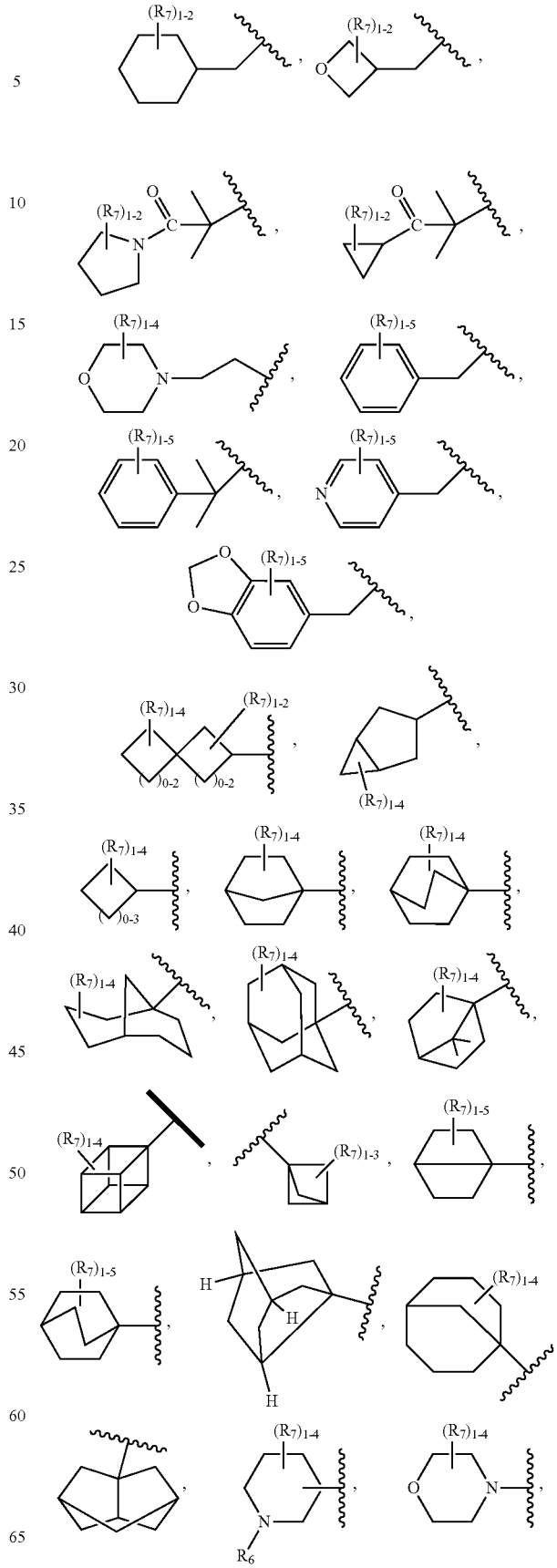

-continued

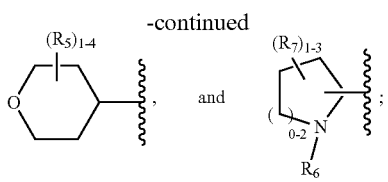
and $R_5$, at each occurrence, is independently selected from H, $C_{1-4}$ alkyl substituted with 0-3 $R_e$, F, Cl, Br, —S(O)$_p$R$_c$, —CN, —OR$_b$, NR$_a$R$_a$, $C_{3-6}$cycloalkyl, aryl substituted with 0-3 $R_e$, and heterocyclyl substituted with 0-3 $R_e$;

$R_7$, at each occurrence, is independently selected from H, F, Cl, Br, CN, NO$_2$, —OR$_b$, —S(O)$_p$R$_c$, —C(=O)R$_b$, —NR$_a$R$_a$, —C(=O)NR$_a$R$_a$, —NHC(=O)R$_b$, —NHC(=O)OR$_b$, —OC(=O)NR$_a$R$_a$, —NHC(=O)NR$_a$R$_a$, —C(=O)OR$_b$, —S(O)$_2$NR$_a$R$_a$, $C_{1-6}$ alkyl substituted with 0-5 $R_e$, aryl substituted with 0-5 $R_e$, and heterocyclyl substituted with 0-5 $R_e$;

$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —(CH$_2$)$_r$—C$_{3-10}$carbocyclyl substituted with 0-5 $R_e$, and —(CH$_2$)$_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, aryl substituted with 0-5 $R_e$, and heterocyclyl substituted with 0-5 $R_e$;

$R_c$, at each occurrence, is independently selected from $C_{1-6}$ alkyl substituted with 0-5 $R_e$, $C_{3-6}$carbocyclyl, and heterocyclyl;

$R_e$, at each occurrence, is independently selected from F, Cl, Br, CN, NO$_2$, =O, CO$_2$H, $C_{1-6}$ alkyl, $C_{2-6}$ alkenyl, $C_{2-6}$ alkynyl, and —(CH$_2$)$_r$—C$_{3-6}$ cycloalkyl;

p, at each occurrence, is independently selected from zero, 1, and 2; and r, at each occurrence, is independently selected from zero, 1, 2, 3, and 4.

13. A pharmaceutical composition comprising one or more compounds of any one of claims 1-12 and a pharmaceutically acceptable carrier.

14. A compound of claim 1 selected from

N$^5$-(tert-butyl)-2-(3-fluorophenyl)-6,7-dihydropyrazolo[1,5-a]pyrazine-3,5(4H)-dicarboxamide (1);

2-(4-fluorophenyl)-N$^5$-isopropyl-6,7-dihydropyrazolo[1,5-a]pyrazine-3,5(4H)-dicarboxamide (2);

N$^5$-cyclohexyl-2-(4-fluorophenyl)-6,7-dihydropyrazolo[1,5-a]pyrazine-3,5(4H)-dicarboxamide (3);

N$^5$-(tert-butyl)-2-(3-fluorophenyl)-6,7-dihydropyrazolo[1,5-a]pyrazine-3,5(4H)-dicarboxamide (4);

2-(3-fluorophenyl)-N$^5$-isopropyl-6,7-dihydropyrazolo[1,5-a]pyrazine-3,5(4H)-dicarboxamide (5);

N$^5$-cyclohexyl-2-(3-fluorophenyl)-6,7-dihydropyrazolo[1,5-a]pyrazine-3,5(4H)-dicarboxamide (6);

N$^5$-cyclopropyl-2-(3-fluorophenyl)-6,7-dihydropyrazolo[1,5-a]pyrazine-3,5(4H)-dicarboxamide (7);

N$^5$-cyclobutyl-2-(3-fluorophenyl)-6,7-dihydropyrazolo[1,5-a]pyrazine-3,5(4H)-dicarboxamide (8);

N$^5$-cyclopentyl-2-(3-fluorophenyl)-6,7-dihydropyrazolo[1,5-a]pyrazine-3,5(4H)-dicarboxamide (9);

N$^5$-(4-chlorophenyl)-2-(3-fluorophenyl)-6,7-dihydropyrazolo[1,5-a]pyrazine-3,5(4H)-dicarboxamide (10);

2-(3-fluorophenyl)-N$^5$-(1-methylcyclopropyl)-6,7-dihydropyrazolo[1,5-a]pyrazine-3,5(4H)-dicarboxamide (11);

N$^5$-(4,4-difluorocyclohexyl)-2-(3-fluorophenyl)-6,7-dihydropyrazolo[1,5-a]pyrazine-3,5(4H)-dicarboxamide (12);

2-(3-fluorophenyl)-N$^5$-(1,1,1-trifluoro-2-methylpropan-2-yl)-6,7-dihydropyrazolo[1,5-a]pyrazine-3,5(4H)-dicarboxamide (13);

2-(3-fluorophenyl)-N$^5$-(3,3,3-trifluoropropyl)-6,7-dihydropyrazolo[1,5-a]pyrazine-3,5(4H)-dicarboxamide (14);

2-(3-fluorophenyl)-N$^5$-(2,2,2-trifluoroethyl)-6,7-dihydropyrazolo[1,5-a]pyrazine-3,5(4H)-dicarboxamide (15);

2-(3-fluorophenyl)-N$^5$-(4-fluorophenyl)-6,7-dihydropyrazolo[1,5-a]pyrazine-3,5(4H)-dicarboxamide (16);

2-(3-fluorophenyl)-N$^5$-(2-(4-fluorophenyl)propan-2-yl)-6,7-dihydropyrazolo[1,5-a]pyrazine-3,5(4H)-dicarboxamide (17);

2-(3-fluorophenyl)-N$^5$-(2,2,6,6-tetramethylpiperidin-4-yl)-6,7-dihydropyrazolo[1,5-a]pyrazine-3,5(4H)-dicarboxamide (18);

N$^5$-(adamantan-2-yl)-2-(3-fluorophenyl)-6,7-dihydropyrazolo[1,5-a]pyrazine-3,5(4H)-dicarboxamide (19);

2-(3-fluorophenyl)-N$^5$-(1-(trifluoromethyl)cyclopropyl)-6,7-dihydropyrazolo[1,5-a]pyrazine-3,5(4H)-dicarboxamide (20);

2-(3-fluorophenyl)-N$^5$-(4-(trifluoromethyl)phenyl)-6,7-dihydropyrazolo[1,5-a]pyrazine-3,5(4H)-dicarboxamide (21);

N$^5$-(adamantan-1-yl)-2-(3-fluorophenyl)-6,7-dihydropyrazolo[1,5-a]pyrazine-3,5(4H)-dicarboxamide (22);

2-(3-fluorophenyl)-N$^5$-((2R,5S)-octahydro-2,5-methanopentalen-6a-yl)-6,7-dihydropyrazolo[1,5-a]pyrazine-3,5(4H)-dicarboxamide (23);

N$^5$-(bicyclo[1.1.1]pentan-1-yl)-2-(3-fluorophenyl)-6,7-dihydropyrazolo[1,5-a]pyrazine-3,5(4H)-dicarboxamide (24);

2-(3-fluorophenyl)-N$^5$-(2-phenylpropan-2-yl)-6,7-dihydropyrazolo[1,5-a]pyrazine-3,5(4H)-dicarboxamide (25);

N$^5$-(2,5-difluorophenyl)-2-(3-fluorophenyl)-6,7-dihydropyrazolo[1,5-a]pyrazine-3,5(4H)-dicarboxamide (26);

2-(3-fluorophenyl)-N$^5$-(2,3,5-trifluorophenyl)-6,7-dihydropyrazolo[1,5-a]pyrazine-3,5(4H)-dicarboxamide (27);

N$^5$-(2,3-difluorophenyl)-2-(3-fluorophenyl)-6,7-dihydropyrazolo[1,5-a]pyrazine-3,5(4H)-dicarboxamide (28);

N$^5$-(3,4-difluorophenyl)-2-(3-fluorophenyl)-6,7-dihydropyrazolo[1,5-a]pyrazine-3,5(4H)-dicarboxamide (29);

N$^5$-(2,4-difluorophenyl)-2-(3-fluorophenyl)-6,7-dihydropyrazolo[1,5-a]pyrazine-3,5(4H)-dicarboxamide (30);

N$^5$-(3,5-difluorophenyl)-2-(3-fluorophenyl)-6,7-dihydropyrazolo[1,5-a]pyrazine-3,5(4H)-dicarboxamide (31);

N$^5$-(2-chloro-4-fluorophenyl)-2-(3-fluorophenyl)-6,7-dihydropyrazolo[1,5-a]pyrazine-3,5(4H)-dicarboxamide (32);

N$^5$-(5-chloro-2-fluorophenyl)-2-(3-fluorophenyl)-6,7-dihydropyrazolo[1,5-a]pyrazine-3,5(4H)-dicarboxamide (33);

N$^5$-(2-chloro-5-(trifluoromethyl)phenyl)-2-(3-fluorophenyl)-6,7-dihydropyrazolo[1,5-a]pyrazine-3,5(4H)-dicarboxamide (34);

N$^5$-(4-chloro-3-(trifluoromethyl)phenyl)-2-(3-fluorophenyl)-6,7-dihydropyrazolo[1,5-a]pyrazine-3,5(4H)-dicarboxamide (35);

$N^5$-(2-fluoro-3-(trifluoromethyl)phenyl)-2-(3-fluorophenyl)-6,7-dihydropyrazolo[1,5-a]pyrazine-3,5(4H)-dicarboxamide (36);

2-(3-fluorophenyl)-$N^5$-(4-(trifluoromethoxy)phenyl)-6,7-dihydropyrazolo[1,5-a]pyrazine-3,5(4H)-dicarboxamide (37);

$N^5$-(4-cyano-3-(trifluoromethyl)phenyl)-2-(3-fluorophenyl)-6,7-dihydropyrazolo[1,5-a]pyrazine-3,5(4H)-dicarboxamide (38);

$N^5$-(2-fluoro-5-(trifluoromethyl)phenyl)-2-(3-fluorophenyl)-6,7-dihydropyrazolo[1,5-a]pyrazine-3,5(4H)-dicarboxamide (39);

2-(3-fluorophenyl)-$N^5$-(2,4,6-trifluorophenyl)-6,7-dihydropyrazolo[1,5-a]pyrazine-3,5(4H)-dicarboxamide (40);

2-(3-fluorophenyl)-$N^5$-(3-hydroxyadamantan-1-yl)-6,7-dihydropyrazolo[1,5-a]pyrazine-3,5(4H)-dicarboxamide (41);

$N^5$-(4-fluorophenethyl)-2-(3-fluorophenyl)-6,7-dihydropyrazolo[1,5-a]pyrazine-3,5(4H)-dicarboxamide (42);

$N^5$-(2,4-dichlorophenyl)-2-(3-fluorophenyl)-6,7-dihydropyrazolo[1,5-a]pyrazine-3,5(4H)-dicarboxamide (43);

2-(3-fluorophenyl)-$N^5$-((1R,2S)-2-phenylcyclopropyl)-6,7-dihydropyrazolo[1,5-a]pyrazine-3,5(4H)-dicarboxamide (44);

$N^5$-(2,4-dichlorobenzyl)-2-(3-fluorophenyl)-6,7-dihydropyrazolo[1,5-a]pyrazine-3,5(4H)-dicarboxamide (45);

$N^5$-(3,4-dichlorobenzyl)-2-(3-fluorophenyl)-6,7-dihydropyrazolo[1,5-a]pyrazine-3,5(4H)-dicarboxamide (46);

2-(3-fluorophenyl)-$N^5$-(4-methoxyphenethyl)-6,7-dihydropyrazolo[1,5-a]pyrazine-3,5(4H)-dicarboxamide (47);

2-(3-fluorophenyl)-$N^5$-(2-(trifluoromethyl)phenyl)-6,7-dihydropyrazolo[1,5-a]pyrazine-3,5(4H)-dicarboxamide (48);

$N^5$-(3,4-dichlorophenyl)-2-(3-fluorophenyl)-6,7-dihydropyrazolo[1,5-a]pyrazine-3,5(4H)-dicarboxamide (49);

2-(3-fluorophenyl)-$N^5$-(3-(trifluoromethyl)phenyl)-6,7-dihydropyrazolo[1,5-a]pyrazine-3,5(4H)-dicarboxamide (50);

2-(3-fluorophenyl)-$N^5$-(4-methoxyphenyl)-6,7-dihydropyrazolo[1,5-a]pyrazine-3,5(4H)-dicarboxamide (51);

2-(3-fluorophenyl)-$N^5$-(naphthalen-1-yl)-6,7-dihydropyrazolo[1,5-a]pyrazine-3,5(4H)-dicarboxamide (52);

$N^5$-(3,5-bis(trifluoromethyl)phenyl)-2-(3-fluorophenyl)-6,7-dihydropyrazolo[1,5-a]pyrazine-3,5(4H)-dicarboxamide (53);

$N^5$-(3-cyanophenyl)-2-(3-fluorophenyl)-6,7-dihydropyrazolo[1,5-a]pyrazine-3,5(4H)-dicarboxamide (54);

$N^5$-(3,5-dichlorophenyl)-2-(3-fluorophenyl)-6,7-dihydropyrazolo[1,5-a]pyrazine-3,5(4H)-dicarboxamide (55);

$N^5$-(3,5-dimethoxyphenyl)-2-(3-fluorophenyl)-6,7-dihydropyrazolo[1,5-a]pyrazine-3,5(4H)-dicarboxamide (56);

$N^5$-(4-chloro-2-(trifluoromethyl)phenyl)-2-(3-fluorophenyl)-6,7-dihydropyrazolo[1,5-a]pyrazine-3,5(4H)-dicarboxamide (57);

2-(3-fluorophenyl)-$N^5$-(4-phenoxyphenyl)-6,7-dihydropyrazolo[1,5-a]pyrazine-3,5(4H)-dicarboxamide (58);

2-(3-fluorophenyl)-$N^5$-(naphthalen-2-yl)-6,7-dihydropyrazolo[1,5-a]pyrazine-3,5(4H)-dicarboxamide (59);

$N^5$-(3-chloro-4-fluorophenyl)-2-(3-fluorophenyl)-6,7-dihydropyrazolo[1,5-a]pyrazine-3,5(4H)-dicarboxamide (60);

$N^5$-(4-cyanophenyl)-2-(3-fluorophenyl)-6,7-dihydropyrazolo[1,5-a]pyrazine-3,5(4H)-dicarboxamide (61);

$N^5$-([1,1'-biphenyl]-4-yl)-2-(3-fluorophenyl)-6,7-dihydropyrazolo[1,5-a]pyrazine-3,5(4H)-dicarboxamide (62);

$N^5$-(4-(tert-butyl)phenyl)-2-(3-fluorophenyl)-6,7-dihydropyrazolo[1,5-a]pyrazine-3,5(4H)-dicarboxamide (63);

$N^5$-(2-chloro-4-(trifluoromethyl)phenyl)-2-(3-fluorophenyl)-6,7-dihydropyrazolo[1,5-a]pyrazine-3,5(4H)-dicarboxamide (64);

$N^5$-(2-chloro-6-(trifluoromethyl)phenyl)-2-(3-fluorophenyl)-6,7-dihydropyrazolo[1,5-a]pyrazine-3,5(4H)-dicarboxamide (65);

$N^5$-(3,4-dimethoxyphenyl)-2-(3-fluorophenyl)-6,7-dihydropyrazolo[1,5-a]pyrazine-3,5(4H)-dicarboxamide (66);

$N^5$-(3-chloro-4-methoxyphenyl)-2-(3-fluorophenyl)-6,7-dihydropyrazolo[1,5-a]pyrazine-3,5(4H)-dicarboxamide (67);

2-(3-fluorophenyl)-$N^5$-(pyridin-3-yl)-6,7-dihydropyrazolo[1,5-a]pyrazine-3,5(4H)-dicarboxamide (68);

$N^5$-(3-fluoro-5-(trifluoromethyl)phenyl)-2-(3-fluorophenyl)-6,7-dihydropyrazolo[1,5-a]pyrazine-3,5(4H)-dicarboxamide (69);

2-(3-fluorophenyl)-$N^5$-(3,4,5-trifluorophenyl)-6,7-dihydropyrazolo[1,5-a]pyrazine-3,5(4H)-dicarboxamide (70);

$N^5$-(3-fluoro-4-(trifluoromethyl)phenyl)-2-(3-fluorophenyl)-6,7-dihydropyrazolo[1,5-a]pyrazine-3,5(4H)-dicarboxamide (71);

2-(3-fluorophenyl)-$N^5$-(3-(trifluoromethoxy)phenyl)-6,7-dihydropyrazolo[1,5-a]pyrazine-3,5(4H)-dicarboxamide (72);

2-(3-fluorophenyl)-$N^5$-(3-methoxyphenyl)-6,7-dihydropyrazolo[1,5-a]pyrazine-3,5(4H)-dicarboxamide (73);

$N^5$-(2,2-difluorobenzo[d][1,3]dioxol-5-yl)-2-(3-fluorophenyl)-6,7-dihydropyrazolo[1,5-a]pyrazine-3,5(4H)-dicarboxamide (74);

2-(3-fluorophenyl)-$N^5$-(6-methoxypyrimidin-4-yl)-6,7-dihydropyrazolo[1,5-a]pyrazine-3,5(4H)-dicarboxamide (75);

$N^5$-(3-chloro-4-(difluoromethoxy)phenyl)-2-(3-fluorophenyl)-6,7-dihydropyrazolo[1,5-a]pyrazine-3,5(4H)-dicarboxamide (76);

$N^5$,2-bis(3-fluorophenyl)-6,7-dihydropyrazolo[1,5-a]pyrazine-3,5(4H)-dicarboxamide (77);

2-(3-fluorophenyl)-$N^5$-(3-methoxy-4-(trifluoromethyl)phenyl)-6,7-dihydropyrazolo[1,5-a]pyrazine-3,5(4H)-dicarboxamide (78);

$N^5$-(3-chloro-4-(trifluoromethyl)phenyl)-2-(3-fluorophenyl)-6,7-dihydropyrazolo[1,5-a]pyrazine-3,5(4H)-dicarboxamide (79);

$N^5$-(4-fluoro-3-(trifluoromethyl)phenyl)-2-(3-fluorophenyl)-6,7-dihydropyrazolo[1,5-a]pyrazine-3,5(4H)-dicarboxamide (80);

$N^5$-(3,5-dimethyladamantan-1-yl)-2-(3-fluorophenyl)-6,7-dihydropyrazolo[1,5-a]pyrazine-3,5(4H)-dicarboxamide (81);

2-(3-fluorophenyl)-$N^5$-(pyridazin-4-yl)-6,7-dihydropyrazolo[1,5-a]pyrazine-3,5(4H)-dicarboxamide (82);

2-(3-fluorophenyl)-$N^5$-(6-methylpyridazin-3-yl)-6,7-dihydropyrazolo[1,5-a]pyrazine-3,5(4H)-dicarboxamide (83);

2-(3-fluorophenyl)-$N^5$-(pyrimidin-5-yl)-6,7-dihydropyrazolo[1,5-a]pyrazine-3,5(4H)-dicarboxamide (84);

$N^5$-(6-chloropyridin-3-yl)-2-(3-fluorophenyl)-6,7-dihydropyrazolo[1,5-a]pyrazine-3,5(4H)-dicarboxamide (85);

2-(3-fluorophenyl)-N$^5$-(6-methylpyridin-3-yl)-6,7-dihydropyrazolo[1,5-a]pyrazine-3,5(4H)-dicarboxamide (86);

2-(3-fluorophenyl)-N$^5$-(6-fluoropyridin-3-yl)-6,7-dihydropyrazolo[1,5-a]pyrazine-3,5(4H)-dicarboxamide (87);

2-(3-fluorophenyl)-N$^5$-(6-hydroxypyridin-3-yl)-6,7-dihydropyrazolo[1,5-a]pyrazine-3,5(4H)-dicarboxamide (88);

N$^5$-(4-(difluoromethoxy)phenyl)-2-(3-fluorophenyl)-6,7-dihydropyrazolo[1,5-a]pyrazine-3,5(4H)-dicarboxamide (89);

N$^5$-(2-chloropyridin-4-yl)-2-(3-fluorophenyl)-6,7-dihydropyrazolo[1,5-a]pyrazine-3,5(4H)-dicarboxamide (90);

2-(3-fluorophenyl)-N$^5$-(pyridazin-3-yl)-6,7-dihydropyrazolo[1,5-a]pyrazine-3,5(4H)-dicarboxamide (91);

2-(3-fluorophenyl)-N$^5$-(pyridin-4-yl)-6,7-dihydropyrazolo[1,5-a]pyrazine-3,5(4H)-dicarboxamide (92);

2-(3-fluorophenyl)-N$^5$-(3-(methylsulfonyl)phenyl)-6,7-dihydropyrazolo[1,5-a]pyrazine-3,5(4H)-dicarboxamide (93);

N$^5$-(3-fluoro-5-hydroxyadamantan-1-yl)-2-(3-fluorophenyl)-6,7-dihydropyrazolo[1,5-a]pyrazine-3,5(4H)-dicarboxamide (94);

N$^5$-(3-fluoroadamantan-1-yl)-2-(3-fluorophenyl)-6,7-dihydropyrazolo[1,5-a]pyrazine-3,5(4H)-dicarboxamide (95);

2-(3-fluorophenyl)-N$^5$-(1-methyl-1H-pyrazol-5-yl)-6,7-dihydropyrazolo[1,5-a]pyrazine-3,5(4H)-dicarboxamide (96);

N5-(1-acetylpiperidin-4-yl)-2-(3-fluorophenyl)-6,7-dihydropyrazolo[1,5-a]pyrazine-3,5(4H)-dicarboxamide (97);

2-(3-fluorophenyl)-N$^5$-(1-pivaloylpiperidin-4-yl)-6,7-dihydropyrazolo[1,5-a]pyrazine-3,5(4H)-dicarboxamide (98);

methyl 4-(3-carbamoyl-2-(3-fluorophenyl)-4,5,6,7-tetrahydropyrazolo[1,5-a]pyrazine-5-carboxamido)piperidine-1-carboxylate (99);

isopropyl 4-(3-carbamoyl-2-(3-fluorophenyl)-4,5,6,7-tetrahydropyrazolo[1,5-a]pyrazine-5-carboxamido)piperidine-1-carboxylate (100);

1,1,1-trifluoro-2-methylpropan-2-yl 4-(3-carbamoyl-2-(3-fluorophenyl)-4,5,6,7-tetrahydropyrazolo[1,5-a]pyrazine-5-carboxamido)piperidine-1-carboxylate (101);

N$^5$-(1-(cyclopropylsulfonyl)piperidin-4-yl)-2-(3-fluorophenyl)-6,7-dihydropyrazolo[1,5-a]pyrazine-3,5(4H)-dicarboxamide (102);

2-(3-fluorophenyl)-N$^5$-(1-(3,3,3-trifluoropropyl)piperidin-4-yl)-6,7-dihydropyrazolo[1,5-a]pyrazine-3,5(4H)-dicarboxamide (103);

N$^5$-(tert-butyl)-2-(3-chlorophenyl)-6,7-dihydropyrazolo[1,5-a]pyrazine-3,5(4H)-dicarboxamide (104);

N$^5$-(tert-butyl)-2-(3,5-difluorophenyl)-6,7-dihydropyrazolo[1,5-a]pyrazine-3,5(4H)-dicarboxamide (105);

N$^5$-(tert-butyl)-2-(3,4-difluorophenyl)-6,7-dihydropyrazolo[1,5-a]pyrazine-3,5(4H)-dicarboxamide (106);

N$^5$-(tert-butyl)-2-(2-fluorophenyl)-6,7-dihydropyrazolo[1,5-a]pyrazine-3,5(4H)-dicarboxamide (107);

N$^5$-(tert-butyl)-2-(3-chlorophenyl)-6,7-dihydropyrazolo[1,5-a]pyrazine-3,5(4H)-dicarboxamide (108);

N$^5$-(tert-butyl)-2-(3-methoxyphenyl)-6,7-dihydropyrazolo[1,5-a]pyrazine-3,5(4H)-dicarboxamide (109);

N$^5$-(tert-butyl)-2-(3-(trifluoromethyl)phenyl)-6,7-dihydropyrazolo[1,5-a]pyrazine-3,5(4H)-dicarboxamide (110);

N$^5$-(tert-butyl)-2-(pyridin-3-yl)-6,7-dihydropyrazolo[1,5-a]pyrazine-3,5(4H)-dicarboxamide (111);

N$^5$-(tert-butyl)-2-(2-fluoropyridin-4-yl)-6,7-dihydropyrazolo[1,5-a]pyrazine-3,5(4H)-dicarboxamide (112);

N$^5$-(tert-butyl)-2-(5-fluoropyridin-3-yl)-6,7-dihydropyrazolo[1,5-a]pyrazine-3,5(4H)-dicarboxamide (113);

N$^5$-(tert-butyl)-2-(3-cyanophenyl)-6,7-dihydropyrazolo[1,5-a]pyrazine-3,5(4H)-dicarboxamide (114);

N$^5$-(tert-butyl)-2-(3-cyano-5-fluorophenyl)-6,7-dihydropyrazolo[1,5-a]pyrazine-3,5(4H)-dicarboxamide (115);

N$^5$-(tert-butyl)-2-phenyl-6,7-dihydropyrazolo[1,5-a]pyrazine-3,5(4H)-dicarboxamide (116);

N$^5$-(tert-butyl)-2-(3,5-dichlorophenyl)-6,7-dihydropyrazolo[1,5-a]pyrazine-3,5(4H)-dicarboxamide (117);

N$^5$-(tert-butyl)-2-(3-(methylsulfonamido)phenyl)-6,7-dihydropyrazolo[1,5-a]pyrazine-3,5(4H)-dicarboxamide (118);

N$^5$-(tert-butyl)-2-(quinolin-3-yl)-6,7-dihydropyrazolo[1,5-a]pyrazine-3,5(4H)-dicarboxamide (119);

2-(3-aminophenyl)-N$^5$-(tert-butyl)-6,7-dihydropyrazolo[1,5-a]pyrazine-3,5(4H)-dicarboxamide (120);

N$^5$-(tert-butyl)-2-(thiophen-3-yl)-6,7-dihydropyrazolo[1,5-a]pyrazine-3,5(4H)-dicarboxamide (121);

3-(5-(tert-butylcarbamoyl)-3-carbamoyl-4,5,6,7-tetrahydropyrazolo[1,5-a]pyrazin-2-yl)benzoic acid (122);

N$^5$-(tert-butyl)-2-(3-carbamoylphenyl)-6,7-dihydropyrazolo[1,5-a]pyrazine-3,5(4H)-dicarboxamide (123);

N$^5$-(tert-butyl)-2-(2,4-difluorophenyl)-6,7-dihydropyrazolo[1,5-a]pyrazine-3,5(4H)-dicarboxamide (124);

N$^5$-(tert-butyl)-2-(2,6-difluoropyridin-3-yl)-6,7-dihydropyrazolo[1,5-a]pyrazine-3,5(4H)-dicarboxamide (125);

N$^5$-(tert-butyl)-2-(pyridin-4-yl)-6,7-dihydropyrazolo[1,5-a]pyrazine-3,5(4H)-dicarboxamide (126);

N$^5$-(tert-butyl)-2-(4-cyanophenyl)-6,7-dihydropyrazolo[1,5-a]pyrazine-3,5(4H)-dicarboxamide (127);

N$^5$-(tert-butyl)-2-(3,5-dimethylphenyl)-6,7-dihydropyrazolo[1,5-a]pyrazine-3,5(4H)-dicarboxamide (128);

N$^5$-(tert-butyl)-2-(3,4-dichlorophenyl)-6,7-dihydropyrazolo[1,5-a]pyrazine-3,5(4H)-dicarboxamide (129);

N$^5$-(tert-butyl)-2-(2,3-dichlorophenyl)-6,7-dihydropyrazolo[1,5-a]pyrazine-3,5(4H)-dicarboxamide (130);

N$^5$-(tert-butyl)-2-(2-carbamoylphenyl)-6,7-dihydropyrazolo[1,5-a]pyrazine-3,5(4H)-dicarboxamide (131);

N$^5$-(tert-butyl)-2-(quinolin-5-yl)-6,7-dihydropyrazolo[1,5-a]pyrazine-3,5(4H)-dicarboxamide (132);

N$^5$-(tert-butyl)-2-(isoquinolin-4-yl)-6,7-dihydropyrazolo[1,5-a]pyrazine-3,5(4H)-dicarboxamide (133);

N$^5$-(tert-butyl)-2-(isoquinolin-5-yl)-6,7-dihydropyrazolo[1,5-a]pyrazine-3,5(4H)-dicarboxamide (134);

N$^5$-(tert-butyl)-2-(3-(methylsulfonamidomethyl)phenyl)-6,7-dihydropyrazolo[1,5-a]pyrazine-3,5(4H)-dicarboxamide (135);

N$^5$-(tert-butyl)-2-(3-sulfamoylphenyl)-6,7-dihydropyrazolo[1,5-a]pyrazine-3,5(4H)-dicarboxamide (136);

N$^5$-(tert-butyl)-2-(3-fluoro-5-methoxyphenyl)-6,7-dihydropyrazolo[1,5-a]pyrazine-3,5(4H)-dicarboxamide (137);

N$^5$-(tert-butyl)-2-(3-(trifluoromethoxy)phenyl)-6,7-dihydropyrazolo[1,5-a]pyrazine-3,5(4H)-dicarboxamide (138);

N$^5$-(tert-butyl)-2-(4-fluoro-3-(trifluoromethyl)phenyl)-6,7-dihydropyrazolo[1,5-a]pyrazine-3,5(4H)-dicarboxamide (139);

N$^5$-(tert-butyl)-2-(2-chloroquinolin-3-yl)-6,7-dihydropyrazolo[1,5-a]pyrazine-3,5(4H)-dicarboxamide (140);

2-([1,1'-biphenyl]-3-yl)-N$^5$-(tert-butyl)-6,7-dihydropyrazolo[1,5-a]pyrazine-3,5(4H)-dicarboxamide (141);

N⁵-(tert-butyl)-2-(pyrimidin-5-yl)-6,7-dihydropyrazolo[1,5-a]pyrazine-3,5(4H)-dicarboxamide (142);

N⁵-(tert-butyl)-2-(1H-indol-6-yl)-6,7-dihydropyrazolo[1,5-a]pyrazine-3,5(4H)-dicarboxamide (143);

N⁵-(tert-butyl)-2-(4-(methylsulfonyl)phenyl)-6,7-dihydropyrazolo[1,5-a]pyrazine-3,5(4H)-dicarboxamide (144);

N⁵-(tert-butyl)-2-(1H-pyrazol-4-yl)-6,7-dihydropyrazolo[1,5-a]pyrazine-3,5(4H)-dicarboxamide (145);

N⁵-(tert-butyl)-2-(2-(pyrrolidin-1-yl)pyrimidin-5-yl)-6,7-dihydropyrazolo[1,5-a]pyrazine-3,5(4H)-dicarboxamide (146);

N⁵-(tert-butyl)-2-(2-morpholinopyrimidin-5-yl)-6,7-dihydropyrazolo[1,5-a]pyrazine-3,5(4H)-dicarboxamide (147);

N⁵-(tert-butyl)-2-(5-chloropyridin-3-yl)-6,7-dihydropyrazolo[1,5-a]pyrazine-3,5(4H)-dicarboxamide (148);

2-(benzo[d]thiazol-5-yl)-N⁵-(tert-butyl)-6,7-dihydropyrazolo[1,5-a]pyrazine-3,5(4H)-dicarboxamide (149);

N⁵-(tert-butyl)-2-(3-(methylthio)phenyl)-6,7-dihydropyrazolo[1,5-a]pyrazine-3,5(4H)-dicarboxamide (150);

N⁵-(tert-butyl)-2-(2,5-difluorophenyl)-6,7-dihydropyrazolo[1,5-a]pyrazine-3,5(4H)-dicarboxamide (151);

N⁵-(tert-butyl)-2-(3-chloro-5-methoxyphenyl)-6,7-dihydropyrazolo[1,5-a]pyrazine-3,5(4H)-dicarboxamide (152);

N⁵-(tert-butyl)-2-(1-methyl-1H-pyrazol-4-yl)-6,7-dihydropyrazolo[1,5-a]pyrazine-3,5(4H)-dicarboxamide (153);

N⁵-(tert-butyl)-2-(3-chloro-5-cyanophenyl)-6,7-dihydropyrazolo[1,5-a]pyrazine-3,5(4H)-dicarboxamide (154);

N⁵-(tert-butyl)-2-(3-fluoro-5-(trifluoromethyl)phenyl)-6,7-dihydropyrazolo[1,5-a]pyrazine-3,5(4H)-dicarboxamide (155);

2-(3-chlorophenyl)-N5-(3,4-difluorophenyl)-6,7-dihydropyrazolo[1,5-a]pyrazine-3,5(4H)-dicarboxamide (156);

2-(3-chlorophenyl)-N⁵-(4-fluorophenyl)-6,7-dihydropyrazolo[1,5-a]pyrazine-3,5(4H)-dicarboxamide (157);

N⁵-(4-chloro-3-(trifluoromethyl)phenyl)-2-(3-chlorophenyl)-6,7-dihydropyrazolo[1,5-a]pyrazine-3,5(4H)-dicarboxamide (158);

2-(3-chlorophenyl)-N⁵-(4-cyano-3-(trifluoromethyl)phenyl)-6,7-dihydropyrazolo[1,5-a]pyrazine-3,5(4H)-dicarboxamide (159);

2-(3-chlorophenyl)-N⁵-(3-(trifluoromethoxy)phenyl)-6,7-dihydropyrazolo[1,5-a]pyrazine-3,5(4H)-dicarboxamide (160);

2-(3-chlorophenyl)-N⁵-(3-cyanophenyl)-6,7-dihydropyrazolo[1,5-a]pyrazine-3,5(4H)-dicarboxamide (161);

2-(3-chlorophenyl)-N⁵-(4-(trifluoromethoxy)phenyl)-6,7-dihydropyrazolo[1,5-a]pyrazine-3,5(4H)-dicarboxamide (162);

2-(3-chlorophenyl)-N⁵-(3-fluoro-4-(trifluoromethyl)phenyl)-6,7-dihydropyrazolo[1,5-a]pyrazine-3,5(4H)-dicarboxamide (163);

2-(3-chlorophenyl)-N⁵-(3,4-dichlorophenyl)-6,7-dihydropyrazolo[1,5-a]pyrazine-3,5(4H)-dicarboxamide (164);

2-(3-chlorophenyl)-N⁵-(3-fluoro-5-(trifluoromethyl)phenyl)-6,7-dihydropyrazolo[1,5-a]pyrazine-3,5(4H)-dicarboxamide (165);

2-(3-chlorophenyl)-N⁵-(4-cyanophenyl)-6,7-dihydropyrazolo[1,5-a]pyrazine-3,5(4H)-dicarboxamide (166);

2-(3-chlorophenyl)-N⁵-(3-fluorophenyl)-6,7-dihydropyrazolo[1,5-a]pyrazine-3,5(4H)-dicarboxamide (167);

2-(3-chlorophenyl)-N⁵-(4-(trifluoromethyl)phenyl)-6,7-dihydropyrazolo[1,5-a]pyrazine-3,5(4H)-dicarboxamide (168);

2-(3-chlorophenyl)-N⁵-(3,5-difluorophenyl)-6,7-dihydropyrazolo[1,5-a]pyrazine-3,5(4H)-dicarboxamide (169);

2-(3-chlorophenyl)-N⁵-(3-methoxyphenyl)-6,7-dihydropyrazolo[1,5-a]pyrazine-3,5(4H)-dicarboxamide (170);

2-(3-chlorophenyl)-N⁵-(6-chloropyridin-3-yl)-6,7-dihydropyrazolo[1,5-a]pyrazine-3,5(4H)-dicarboxamide (171);

2-(3-chlorophenyl)-N⁵-(1,1-difluoro-2-methylpropan-2-yl)-6,7-dihydropyrazolo[1,5-a]pyrazine-3,5(4H)-dicarboxamide (172);

2-(3-chlorophenyl)-N⁵-(2-(4-cyanophenyl)propan-2-yl)-6,7-dihydropyrazolo[1,5-a]pyrazine-3,5(4H)-dicarboxamide (173);

2-(3-chlorophenyl)-N⁵-(3,3-difluoro-2-methylbutan-2-yl)-6,7-dihydropyrazolo[1,5-a]pyrazine-3,5(4H)-dicarboxamide (174);

2-(3-chlorophenyl)-N⁵-((1r,3s)-3-fluorocyclobutyl)-6,7-dihydropyrazolo[1,5-a]pyrazine-3,5(4H)-dicarboxamide (175);

2-(3-chlorophenyl)-N⁵-((1s,3s)-3-fluorocyclobutyl)-6,7-dihydropyrazolo[1,5-a]pyrazine-3,5(4H)-dicarboxamide (176);

2-(3-chlorophenyl)-N⁵-((1s,3s)-3-methoxycyclobutyl)-6,7-dihydropyrazolo[1,5-a]pyrazine-3,5(4H)-dicarboxamide (177);

2-(3-chlorophenyl)-N⁵-((1r,3r)-3-methoxycyclobutyl)-6,7-dihydropyrazolo[1,5-a]pyrazine-3,5(4H)-dicarboxamide (178);

2-(3-chlorophenyl)-N⁵-((3,3-difluorocyclobutyl)methyl)-6,7-dihydropyrazolo[1,5-a]pyrazine-3,5(4H)-dicarboxamide (179);

2-(3-chlorophenyl)-N⁵-((4,4-difluorocyclohexyl)methyl)-6,7-dihydropyrazolo[1,5-a]pyrazine-3,5(4H)-dicarboxamide (180);

2-(3-chlorophenyl)-N⁵-(spiro[2.3]hexan-5-yl)-6,7-dihydropyrazolo[1,5-a]pyrazine-3,5(4H)-dicarboxamide (181);

2-(3-chlorophenyl)-N⁵-(6,6-difluorospiro[3.3]heptan-2-yl)-6,7-dihydropyrazolo[1,5-a]pyrazine-3,5(4H)-dicarboxamide (182);

2-(3-chlorophenyl)-N⁵-((1R,3s,5S)-6,6-difluorobicyclo[3.1.0]hexan-3-yl)-6,7-dihydropyrazolo[1,5-a]pyrazine-3,5(4H)-dicarboxamide (183);

2-(3-chlorophenyl)-N⁵-((1R,3r,5S)-6,6-difluorobicyclo[3.1.0]hexan-3-yl)-6,7-dihydropyrazolo[1,5-a]pyrazine-3,5(4H)-dicarboxamide (184);

2-(3-chloro-4-fluorophenyl)-N⁵-(1,1-difluoro-2-methylpropan-2-yl)-6,7-dihydropyrazolo[1,5-a]pyrazine-3,5(4H)-dicarboxamide (185);

2-(3-chloro-4-fluorophenyl)-N⁵-(1-cyano-2-methylpropan-2-yl)-6,7-dihydropyrazolo[1,5-a]pyrazine-3,5(4H)-dicarboxamide (186);

2-(3-chloro-4-fluorophenyl)-N⁵-(2-(4-cyanophenyl)propan-2-yl)-6,7-dihydropyrazolo[1,5-a]pyrazine-3,5(4H)-dicarboxamide (187);

2-(3-chloro-4-fluorophenyl)-N⁵-(3,3-difluoro-2-methylbutan-2-yl)-6,7-dihydropyrazolo[1,5-a]pyrazine-3,5(4H)-dicarboxamide (188);

2-(3-chloro-4-fluorophenyl)-N⁵-((1r,3r)-3-fluorocyclobutyl)-6,7-dihydropyrazolo[1,5-a]pyrazine-3,5(4H)-dicarboxamide (189);

2-(3-chloro-4-fluorophenyl)-N⁵-((1s,3s)-3-fluorocyclobutyl)-6,7-dihydropyrazolo[1,5-a]pyrazine-3,5(4H)-dicarboxamide (190);

2-(3-chloro-4-fluorophenyl)-N$^5$-((1s,3s)-3-methoxycyclobutyl)-6,7-dihydropyrazolo[1,5-a]pyrazine-3,5(4H)-dicarboxamide (191);

2-(3-chloro-4-fluorophenyl)-N$^5$-((1r,3r)-3-methoxycyclobutyl)-6,7-dihydropyrazolo[1,5-a]pyrazine-3,5(4H)-dicarboxamide (192);

2-(3-chloro-4-fluorophenyl)-N$^5$-((3,3-difluorocyclobutyl)methyl)-6,7-dihydropyrazolo[1,5-a]pyrazine-3,5(4H)-dicarboxamide (193);

2-(3-chloro-4-fluorophenyl)-N$^5$-((4,4-difluorocyclohexyl)methyl)-6,7-dihydropyrazolo[1,5-a]pyrazine-3,5(4H)-dicarboxamide (194);

2-(3-chloro-4-fluorophenyl)-N$^5$-(spiro[2.3]hexan-5-yl)-6,7-dihydropyrazolo[1,5-a]pyrazine-3,5(4H)-dicarboxamide (195);

2-(3-chloro-4-fluorophenyl)-N$^5$-(6,6-difluorospiro[3.3]heptan-2-yl)-6,7-dihydropyrazolo[1,5-a]pyrazine-3,5(4H)-dicarboxamide (196);

2-(3-chloro-4-fluorophenyl)-N$^5$-((1R,3s,5S)-6,6-difluorobicyclo[3.1.0]hexan-3-yl)-6,7-dihydropyrazolo[1,5-a]pyrazine-3,5(4H)-dicarboxamide (197);

2-(3-chloro-4-fluorophenyl)-N$^5$-((1R,3r,5S)-6,6-difluorobicyclo[3.1.0]hexan-3-yl)-6,7-dihydropyrazolo[1,5-a]pyrazine-3,5(4H)-dicarboxamide (198);

2-(3,4-dichlorophenyl)-N$^5$-(1,1-difluoro-2-methylpropan-2-yl)-6,7-dihydropyrazolo[1,5-a]pyrazine-3,5(4H)-dicarboxamide (199);

N$^5$-(2-(4-cyanophenyl)propan-2-yl)-2-(3,4-dichlorophenyl)-6,7-dihydropyrazolo[1,5-a]pyrazine-3,5(4H)-dicarboxamide (200);

2-(3,4-dichlorophenyl)-N$^5$-(3,3-difluoro-2-methylbutan-2-yl)-6,7-dihydropyrazolo[1,5-a]pyrazine-3,5(4H)-dicarboxamide (201);

2-(3,4-dichlorophenyl)-N$^5$-((1r,3r)-3-fluorocyclobutyl)-6,7-dihydropyrazolo[1,5-a]pyrazine-3,5(4H)-dicarboxamide (202);

2-(3,4-dichlorophenyl)-N$^5$-((1s,3s)-3-fluorocyclobutyl)-6,7-dihydropyrazolo[1,5-a]pyrazine-3,5(4H)-dicarboxamide (203);

2-(3,4-dichlorophenyl)-N$^5$-((1r,3r)-3-methoxycyclobutyl)-6,7-dihydropyrazolo[1,5-a]pyrazine-3,5(4H)-dicarboxamide (204);

2-(3,4-dichlorophenyl)-N$^5$-((3,3-difluorocyclobutyl)methyl)-6,7-dihydropyrazolo[1,5-a]pyrazine-3,5(4H)-dicarboxamide (205);

2-(3,4-dichlorophenyl)-N$^5$-((4,4-difluorocyclohexyl)methyl)-6,7-dihydropyrazolo[1,5-a]pyrazine-3,5(4H)-dicarboxamide (206);

2-(3,4-dichlorophenyl)-N$^5$-(spiro[2.3]hexan-5-yl)-6,7-dihydropyrazolo[1,5-a]pyrazine-3,5(4H)-dicarboxamide (207);

2-(3,4-dichlorophenyl)-N$^5$-(6,6-difluorospiro[3.3]heptan-2-yl)-6,7-dihydropyrazolo[1,5-a]pyrazine-3,5(4H)-dicarboxamide (208);

2-(3-chloro-4-fluorophenyl)-N$^5$-(1,3-difluoro-2-methylpropan-2-yl)-6,7-dihydropyrazolo[1,5-a]pyrazine-3,5(4H)-dicarboxamide (209);

2-(3,4-dichlorophenyl)-N$^5$-(1,3-difluoro-2-methylpropan-2-yl)-6,7-dihydropyrazolo[1,5-a]pyrazine-3,5(4H)-dicarboxamide (210);

2-(3-chlorophenyl)-N$^5$-(1,3-difluoro-2-methylpropan-2-yl)-6,7-dihydropyrazolo[1,5-a]pyrazine-3,5(4H)-dicarboxamide (211);

2-(3-chloro-4-fluorophenyl)-N$^5$-(2-methyl-1-(trifluoromethoxy)propan-2-yl)-6,7-dihydropyrazolo[1,5-a]pyrazine-3,5(4H)-dicarboxamide (212);

2-(3-chloro-4-fluorophenyl)-N$^5$-(1-(cyclopropylamino)-2-methyl-1-oxopropan-2-yl)-6,7-dihydropyrazolo[1,5-a]pyrazine-3,5(4H)-dicarboxamide (213);

2-(3-chloro-4-fluorophenyl)-N$^5$-(2-methyl-1-(methylamino)-1-oxopropan-2-yl)-6,7-dihydropyrazolo[1,5-a]pyrazine-3,5(4H)-dicarboxamide (214);

2-(3-chloro-4-fluorophenyl)-N$^5$-(2-methyl-1-oxo-1-(pyrrolidin-1-yl)propan-2-yl)-6,7-dihydropyrazolo[1,5-a]pyrazine-3,5(4H)-dicarboxamide (215);

2-(3-chloro-4-fluorophenyl)-N$^5$-(1-(isopropylamino)-2-methyl-1-oxopropan-2-yl)-6,7-dihydropyrazolo[1,5-a]pyrazine-3,5(4H)-dicarboxamide (216);

2-(3-chloro-4-fluorophenyl)-N$^5$-(1-((2-methoxyethyl)amino)-2-methyl-1-oxopropan-2-yl)-6,7-dihydropyrazolo[1,5-a]pyrazine-3,5(4H)-dicarboxamide (217);

2-(3-chloro-4-fluorophenyl)-N$^5$-(1-(dimethylamino)-2-methyl-1-oxopropan-2-yl)-6,7-dihydropyrazolo[1,5-a]pyrazine-3,5(4H)-dicarboxamide (218);

N$^5$-(1-amino-2-methyl-1-oxopropan-2-yl)-2-(3-chloro-4-fluorophenyl)-6,7-dihydropyrazolo[1,5-a]pyrazine-3,5(4H)-dicarboxamide (219);

2-(3-chloro-4-fluorophenyl)-N$^5$-(1-(cyanomethyl)cyclobutyl)-6,7-dihydropyrazolo[1,5-a]pyrazine-3,5(4H)-dicarboxamide (220);

2-(3-chlorophenyl)-N$^5$-(1-(cyanomethyl)cyclobutyl)-6,7-dihydropyrazolo[1,5-a]pyrazine-3,5(4H)-dicarboxamide (221);

N$^5$-(1-(cyanomethyl)cyclobutyl)-2-(3,4-dichlorophenyl)-6,7-dihydropyrazolo[1,5-a]pyrazine-3,5(4H)-dicarboxamide (222);

2-(3-chloro-4-fluorophenyl)-N$^5$-(1-((difluoromethoxy)methyl)cyclobutyl)-6,7-dihydropyrazolo[1,5-a]pyrazine-3,5(4H)-dicarboxamide (223);

2-(3,4-dichlorophenyl)-N$^5$-(1-((difluoromethoxy)methyl)cyclobutyl)-6,7-dihydropyrazolo[1,5-a]pyrazine-3,5(4H)-dicarboxamide (224);

2-(3-chlorophenyl)-N$^5$-(1-((difluoromethoxy)methyl)cyclobutyl)-6,7-dihydropyrazolo[1,5-a]pyrazine-3,5(4H)-dicarboxamide (225);

2-(3-chloro-4-fluorophenyl)-N$^5$-(2-(3,3-difluorocyclobutyl)propan-2-yl)-6,7-dihydropyrazolo[1,5-a]pyrazine-3,5(4H)-dicarboxamide (226);

2-(3-chlorophenyl)-N$^5$-(2-(3,3-difluorocyclobutyl)propan-2-yl)-6,7-dihydropyrazolo[1,5-a]pyrazine-3,5(4H)-dicarboxamide (227);

2-(3,4-dichlorophenyl)-N$^5$-(2-(3,3-difluorocyclobutyl)propan-2-yl)-6,7-dihydropyrazolo[1,5-a]pyrazine-3,5(4H)-dicarboxamide (228);

2-(3-chloro-4-fluorophenyl)-N$^5$-((3,3-difluoro-1-methylcyclobutyl)methyl)-6,7-dihydropyrazolo[1,5-a]pyrazine-3,5(4H)-dicarboxamide (229);

2-(3-chlorophenyl)-N$^5$-((3,3-difluoro-1-methylcyclobutyl)methyl)-6,7-dihydropyrazolo[1,5-a]pyrazine-3,5(4H)-dicarboxamide (230);

2-(3,4-dichlorophenyl)-N$^5$-((3,3-difluoro-1-methylcyclobutyl)methyl)-6,7-dihydropyrazolo[1,5-a]pyrazine-3,5(4H)-dicarboxamide (231);

2-(3-chloro-4-fluorophenyl)-N$^5$-(2-(4,4-difluorocyclohexyl)propan-2-yl)-6,7-dihydropyrazolo[1,5-a]pyrazine-3,5(4H)-dicarboxamide (232);

2-(3-chlorophenyl)-N$^5$-(2-(4,4-difluorocyclohexyl)propan-2-yl)-6,7-dihydropyrazolo[1,5-a]pyrazine-3,5(4H)-dicarboxamide (233);

2-(3,4-dichlorophenyl)-N$^5$-(2-(4,4-difluorocyclohexyl)propan-2-yl)-6,7-dihydropyrazolo[1,5-a]pyrazine-3,5(4H)-dicarboxamide (234);

2-(3-chloro-4-fluorophenyl)-N$^5$-(1-(difluoromethyl)cyclobutyl)-6,7-dihydro pyrazolo[1,5-a]pyrazine-3,5(4H)-dicarboxamide (235);

2-(3-chlorophenyl)-N$^5$-(1-(difluoromethyl)cyclobutyl)-6,7-dihydropyrazolo[1,5-a]pyrazine-3,5(4H)-dicarboxamide (236);

2-(3,4-dichlorophenyl)-N$^5$-(1-(difluoromethyl)cyclobutyl)-6,7-dihydropyrazolo[1,5-a]pyrazine-3,5(4H)-dicarboxamide (237);

2-(3-chloro-4-fluorophenyl)-N$^5$-((1R,2S)-2-(difluoromethyl)cyclobutyl)-6,7-dihydropyrazolo[1,5-a]pyrazine-3,5(4H)-dicarboxamide (238);

2-(3-chlorophenyl)-N$^5$-((1R,2S)-2-(difluoromethyl)cyclobutyl)-6,7-dihydropyrazolo[1,5-a]pyrazine-3,5(4H)-dicarboxamide (239);

2-(3,4-dichlorophenyl)-N$^5$-((1R,2S)-2-(difluoromethyl)cyclobutyl)-6,7-dihydropyrazolo[1,5-a]pyrazine-3,5(4H)-dicarboxamide (240);

2-(3-chloro-4-fluorophenyl)-N$^5$-((1R,2R)-2-((difluoromethoxy)methyl)cyclobutyl)-6,7-dihydropyrazolo[1,5-a]pyrazine-3,5(4H)-dicarboxamide (241);

2-(3-chlorophenyl)-N$^5$-((1R,2R)-2-((difluoromethoxy)methyl)cyclobutyl)-6,7-dihydropyrazolo[1,5-a]pyrazine-3,5(4H)-dicarboxamide (242);

2-(3,4-dichlorophenyl)-N$^5$-((1R,2R)-2-((difluoromethoxy)methyl)cyclobutyl)-6,7-dihydropyrazolo[1,5-a]pyrazine-3,5(4H)-dicarboxamide (243);

2-(3-chlorophenyl)-N$^5$-(3-((difluoromethoxy)methyl)cyclobutyl)-6,7-dihydropyrazolo[1,5-a]pyrazine-3,5(4H)-dicarboxamide (244 and 245);

2-(3-chloro-4-fluorophenyl)-N$^5$-(3-methylcyclobutyl)-6,7-dihydropyrazolo[1,5-a]pyrazine-3,5(4H)-dicarboxamide (246 and 247);

2-(3,4-dichlorophenyl)-N$^5$-(3-methylcyclobutyl)-6,7-dihydropyrazolo[1,5-a]pyrazine-3,5(4H)-dicarboxamide (248);

2-(3,4-dichlorophenyl)-N$^5$-(3-methylcyclobutyl)-6,7-dihydropyrazolo[1,5-a]pyrazine-3,5(4H)-dicarboxamide (249);

2-(3-chlorophenyl)-N$^5$-(3-methylcyclobutyl)-6,7-dihydropyrazolo[1,5-a]pyrazine-3,5(4H)-dicarboxamide (250);

2-(3-chlorophenyl)-N$^5$-(3-methylcyclobutyl)-6,7-dihydropyrazolo[1,5-a]pyrazine-3,5(4H)-dicarboxamide (251);

2-(3-chloro-4-fluorophenyl)-N$^5$-(3-(difluoromethyl)cyclobutyl)-6,7-dihydropyrazolo[1,5-a]pyrazine-3,5(4H)-dicarboxamide (252 and 253);

2-(3,4-dichlorophenyl)-N$^5$-(3-(difluoromethyl)cyclobutyl)-6,7-dihydropyrazolo[1,5-a]pyrazine-3,5(4H)-dicarboxamide (254);

2-(3,4-dichlorophenyl)-N$^5$-(3-(difluoromethyl)cyclobutyl)-6,7-dihydropyrazolo[1,5-a]pyrazine-3,5(4H)-dicarboxamide (255);

2-(3-chlorophenyl)-N$^5$-(3-(difluoromethyl)cyclobutyl)-6,7-dihydropyrazolo[1,5-a]pyrazine-3,5(4H)-dicarboxamide (256);

2-(3-chlorophenyl)-N$^5$-(3-(difluoromethyl)cyclobutyl)-6,7-dihydropyrazolo[1,5-a]pyrazine-3,5(4H)-dicarboxamide (257);

2-(3-chloro-4-fluorophenyl)-N$^5$-(3-(difluoromethyl)-1-methylcyclobutyl)-6,7-dihydropyrazolo[1,5-a]pyrazine-3,5(4H)-dicarboxamide (258 and 259);

2-(3-chloro-4-fluorophenyl)-N$^5$-(3-hydroxy-1-methylcyclobutyl)-6,7-dihydropyrazolo[1,5-a]pyrazine-3,5(4H)-dicarboxamide (260);

2-(3-chloro-4-fluorophenyl)-N$^5$-((1r,3r)-3-(trifluoromethoxy)cyclobutyl)-6,7-dihydropyrazolo[1,5-a]pyrazine-3,5(4H)-dicarboxamide (261);

2-(3-chlorophenyl)-N$^5$-((1r,3r)-3-(trifluoromethoxy)cyclobutyl)-6,7-dihydropyrazolo[1,5-a]pyrazine-3,5(4H)-dicarboxamide (262);

2-(3,4-dichlorophenyl)-N$^5$-((1r,3r)-3-(trifluoromethoxy)cyclobutyl)-6,7-dihydropyrazolo[1,5-a]pyrazine-3,5(4H)-dicarboxamide (263);

2-(3-chloro-4-fluorophenyl)-N$^5$-((1r,3r)-3-(trifluoromethoxy)cyclobutyl)-6,7-dihydropyrazolo[1,5-a]pyrazine-3,5(4H)-dicarboxamide (264);

2-(3,4-dichlorophenyl)-N$^5$-((1r,3r)-3-(trifluoromethoxy)cyclobutyl)-6,7-dihydropyrazolo[1,5-a]pyrazine-3,5(4H)-dicarboxamide (265);

2-(3-chloro-4-fluorophenyl)-N$^5$-((1r,3r)-3-(4-cyanophenoxy)cyclobutyl)-6,7-dihydropyrazolo[1,5-a]pyrazine-3,5(4H)-dicarboxamide (266);

2-(3-chlorophenyl)-N$^5$-((1r,3r)-3-(4-cyanophenoxy)cyclobutyl)-6,7-dihydropyrazolo[1,5-a]pyrazine-3,5(4H)-dicarboxamide (267);

N$^5$-((1r,3r)-3-(4-cyanophenoxy)cyclobutyl)-2-(3,4-dichlorophenyl)-6,7-dihydropyrazolo[1,5-a]pyrazine-3,5(4H)-dicarboxamide (268);

2-(3-chloro-4-fluorophenyl)-N$^5$-((1s,3s)-3-(methylthio)cyclobutyl)-6,7-dihydropyrazolo[1,5-a]pyrazine-3,5(4H)-dicarboxamide (269);

2-(3-chlorophenyl)-N$^5$-((1s,3s)-3-(methylthio)cyclobutyl)-6,7-dihydropyrazolo[1,5-a]pyrazine-3,5(4H)-dicarboxamide (270);

2-(3,4-dichlorophenyl)-N$^5$-((1s,3s)-3-(methylthio)cyclobutyl)-6,7-dihydropyrazolo[1,5-a]pyrazine-3,5(4H)-dicarboxamide (271);

2-(3-chloro-4-fluorophenyl)-N$^5$-((1s,3s)-3-(methylsulfonyl)cyclobutyl)-6,7-dihydropyrazolo[1,5-a]pyrazine-3,5(4H)-dicarboxamide (272);

2-(3-chlorophenyl)-N$^5$-((1s,3s)-3-(methylsulfonyl)cyclobutyl)-6,7-dihydropyrazolo[1,5-a]pyrazine-3,5(4H)-dicarboxamide (273);

2-(3,4-dichlorophenyl)-N$^5$-((1s,3s)-3-(methylsulfonyl)cyclobutyl)-6,7-dihydropyrazolo[1,5-a]pyrazine-3,5(4H)-dicarboxamide (274);

2-(3-chloro-4-fluorophenyl)-N$^5$-((1r,3r)-3-fluoro-1-methylcyclobutyl)-6,7-dihydropyrazolo[1,5-a]pyrazine-3,5(4H)-dicarboxamide (275);

2-(3-chloro-4-fluorophenyl)-N$^5$-((1s,3s)-3-(4-fluorophenyl)cyclobutyl)-6,7-dihydropyrazolo[1,5-a]pyrazine-3,5(4H)-dicarboxamide (276);

2-(3-chlorophenyl)-N$^5$-((1s,3s)-3-(4-fluorophenyl)cyclobutyl)-6,7-dihydropyrazolo[1,5-a]pyrazine-3,5(4H)-dicarboxamide (277);

2-(3,4-dichlorophenyl)-N$^5$-((1s,3s)-3-(4-fluorophenyl)cyclobutyl)-6,7-dihydropyrazolo[1,5-a]pyrazine-3,5(4H)-dicarboxamide (278);

2-(3-chlorophenyl)-N$^5$-((1s,3s)-3-(4-fluorophenyl)cyclobutyl)-6,7-dihydropyrazolo[1,5-a]pyrazine-3,5(4H)-dicarboxamide (277);

2-(3,4-dichlorophenyl)-N$^5$-((1s,3s)-3-(4-fluorophenyl)cyclobutyl)-6,7-dihydropyrazolo[1,5-a]pyrazine-3,5(4H)-dicarboxamide (278);

2-(3-chloro-4-fluorophenyl)-N$^5$-((1s,3s)-3-(4-methoxyphenyl)cyclobutyl)-6,7-dihydropyrazolo[1,5-a]pyrazine-3,5(4H)-dicarboxamide (279);

2-(3,4-dichlorophenyl)-N$^5$-((1s,3s)-3-(4-methoxyphenyl)cyclobutyl)-6,7-dihydropyrazolo[1,5-a]pyrazine-3,5(4H)-dicarboxamide (280);

2-(3-chlorophenyl)-N$^5$-((1s,3s)-3-(4-methoxyphenyl)cyclobutyl)-6,7-dihydropyrazolo[1,5-a]pyrazine-3,5(4H)-dicarboxamide (281);

2-(3-chloro-4-fluorophenyl)-N$^5$-((1s,3s)-3-(4-cyanophenyl)cyclobutyl)-6,7-dihydropyrazolo[1,5-a]pyrazine-3,5(4H)-dicarboxamide (282);

N$^5$-((1s,3s)-3-(4-cyanophenyl)cyclobutyl)-2-(3,4-dichlorophenyl)-6,7-dihydropyrazolo[1,5-a]pyrazine-3,5(4H)-dicarboxamide (283);

2-(3-chlorophenyl)-N$^5$-((1s,3s)-3-(4-cyanophenyl)cyclobutyl)-6,7-dihydropyrazolo[1,5-a]pyrazine-3,5(4H)-dicarboxamide (284);

2-(3-chloro-4-fluorophenyl)-N$^5$-(3,3-dimethylcyclobutyl)-6,7-dihydropyrazolo[1,5-a]pyrazine-3,5(4H)-dicarboxamide (285);

2-(3-chloro-4-fluorophenyl)-N$^5$-(3,3-dimethylcyclobutyl)-6,7-dihydropyrazolo[1,5-a]pyrazine-3,5(4H)-dicarboxamide (286);

2-(3,4-dichlorophenyl)-N$^5$-(3,3-dimethylcyclobutyl)-6,7-dihydropyrazolo[1,5-a]pyrazine-3,5(4H)-dicarboxamide (287);

2-(3,4-dichlorophenyl)-N$^5$-(3-fluoro-3-methylcyclobutyl)-6,7-dihydropyrazolo[1,5-a]pyrazine-3,5(4H)-dicarboxamide (288);

2-(3-chlorophenyl)-N$^5$-(3-fluoro-3-methylcyclobutyl)-6,7-dihydropyrazolo[1,5-a]pyrazine-3,5(4H)-dicarboxamide (289);

2-(3,4-dichlorophenyl)-N$^5$-(3-fluoro-3-methylcyclobutyl)-6,7-dihydropyrazolo[1,5-a]pyrazine-3,5(4H)-dicarboxamide (290);

2-(3-chloro-4-fluorophenyl)-N$^5$-(3,3-difluorocyclobutyl)-6,7-dihydropyrazolo[1,5-a]pyrazine-3,5(4H)-dicarboxamide (291);

2-(3-chlorophenyl)-N$^5$-(3,3-difluorocyclobutyl)-6,7-dihydropyrazolo[1,5-a]pyrazine-3,5(4H)-dicarboxamide (292);

2-(3,5-dichlorophenyl)-N$^5$-(3,3-difluorocyclobutyl)-6,7-dihydropyrazolo[1,5-a]pyrazine-3,5(4H)-dicarboxamide (293);

2-(3,4-dichlorophenyl)-N$^5$-(3,3-difluorocyclobutyl)-6,7-dihydropyrazolo[1,5-a]pyrazine-3,5(4H)-dicarboxamide (294);

2-(3-chloro-5-fluorophenyl)-N$^5$-(3,3-difluorocyclobutyl)-6,7-dihydropyrazolo[1,5-a]pyrazine-3,5(4H)-dicarboxamide (295);

2-(3-chloro-4-fluorophenyl)-N$^5$-(3,3-difluoro-1-methylcyclobutyl)-6,7-dihydropyrazolo[1,5-a]pyrazine-3,5(4H)-dicarboxamide (296);

2-(3,4-dichlorophenyl)-N$^5$-(3,3-difluoro-1-methylcyclobutyl)-6,7-dihydropyrazolo[1,5-a]pyrazine-3,5(4H)-dicarboxamide (297);

2-(3,5-dichlorophenyl)-N$^5$-(3,3-difluoro-1-methylcyclobutyl)-6,7-dihydropyrazolo[1,5-a]pyrazine-3,5(4H)-dicarboxamide (298);

2-(3-chlorophenyl)-N$^5$-(3,3-difluoro-1-methylcyclobutyl)-6,7-dihydropyrazolo[1,5-a]pyrazine-3,5(4H)-dicarboxamide (299);

2-(3-chloro-5-fluorophenyl)-N$^5$-(3,3-difluoro-1-methylcyclobutyl)-6,7-dihydropyrazolo[1,5-a]pyrazine-3,5(4H)-dicarboxamide (300);

2-(3,4-dichlorophenyl)-N$^5$-(1-ethyl-3,3-difluorocyclobutyl)-6,7-dihydropyrazolo[1,5-a]pyrazine-3,5(4H)-dicarboxamide (301);

2-(3-chlorophenyl)-N$^5$-(3,3-difluoro-1-(fluoromethyl)cyclobutyl)-6,7-dihydropyrazolo[1,5-a]pyrazine-3,5(4H)-dicarboxamide (302);

2-(3,4-dichlorophenyl)-N$^5$-(3,3-difluoro-1-(fluoromethyl)cyclobutyl)-6,7-dihydropyrazolo[1,5-a]pyrazine-3,5(4H)-dicarboxamide (303);

2-(3-chloro-4-fluorophenyl)-N$^5$-(1-(difluoromethyl)-3,3-difluorocyclobutyl)-6,7-dihydropyrazolo[1,5-a]pyrazine-3,5(4H)-dicarboxamide (304);

2-(3,4-dichlorophenyl)-N$^5$-(1-(difluoromethyl)-3,3-difluorocyclobutyl)-6,7-dihydropyrazolo[1,5-a]pyrazine-3,5(4H)-dicarboxamide (305);

2-(3-chlorophenyl)-N$^5$-(1-(difluoromethyl)-3,3-difluorocyclobutyl)-6,7-dihydropyrazolo[1,5-a]pyrazine-3,5(4H)-dicarboxamide (306);

2-(3-chloro-4-fluorophenyl)-N$^5$-(3-fluoro-1,3-dimethylcyclobutyl)-6,7-dihydropyrazolo[1,5-a]pyrazine-3,5(4H)-dicarboxamide (307);

2-(3-chloro-4-fluorophenyl)-N$^5$-(3,3-difluoro-1-(4-fluorophenyl)cyclobutyl)-6,7-dihydropyrazolo[1,5-a]pyrazine-3,5(4H)-dicarboxamide (308);

2-(3-chlorophenyl)-N$^5$-(3,3-difluoro-1-(4-fluorophenyl)cyclobutyl)-6,7-dihydropyrazolo[1,5-a]pyrazine-3,5(4H)-dicarboxamide (309);

2-(3,4-dichlorophenyl)-N$^5$-(3,3-difluoro-1-(4-fluorophenyl)cyclobutyl)-6,7-dihydropyrazolo[1,5-a]pyrazine-3,5(4H)-dicarboxamide (310);

2-(3-chloro-4-fluorophenyl)-N$^5$-(3,3-difluoro-1-(pyridin-3-yl)cyclobutyl)-6,7-dihydropyrazolo[1,5-a]pyrazine-3,5(4H)-dicarboxamide (311);

2-(3-chlorophenyl)-N$^5$-(3,3-difluoro-1-(pyridin-3-yl)cyclobutyl)-6,7-dihydropyrazolo[1,5-a]pyrazine-3,5(4H)-dicarboxamide (312);

2-(3,4-dichlorophenyl)-N$^5$-(3,3-difluoro-1-(pyridin-3-yl)cyclobutyl)-6,7-dihydropyrazolo[1,5-a]pyrazine-3,5(4H)-dicarboxamide (313);

2-(3-chloro-4-fluorophenyl)-N$^5$-(1-(4-cyanophenyl)-3,3-difluorocyclobutyl)-6,7-dihydropyrazolo[1,5-a]pyrazine-3,5(4H)-dicarboxamide (314);

2-(3-chlorophenyl)-N$^5$-(1-(4-cyanophenyl)-3,3-difluorocyclobutyl)-6,7-dihydropyrazolo[1,5-a]pyrazine-3,5(4H)-dicarboxamide (315);

N$^5$-(1-(4-cyanophenyl)-3,3-difluorocyclobutyl)-2-(3,4-dichlorophenyl)-6,7-dihydropyrazolo[1,5-a]pyrazine-3,5(4H)-dicarboxamide (316);

2-(3-chloro-4-fluorophenyl)-N$^5$-(5-methylspiro[2.3]hexan-5-yl)-6,7-dihydropyrazolo[1,5-a]pyrazine-3,5(4H)-dicarboxamide (317);

2-(3-chlorophenyl)-N$^5$-(5-methylspiro[2.3]hexan-5-yl)-6,7-dihydropyrazolo[1,5-a]pyrazine-3,5(4H)-dicarboxamide (318);

2-(3,4-dichlorophenyl)-N$^5$-(5-methylspiro[2.3]hexan-5-yl)-6,7-dihydropyrazolo[1,5-a]pyrazine-3,5(4H)-dicarboxamide (319);

2-(3-chloro-4-fluorophenyl)-N$^5$-(1,1-difluorospiro[2.3]hexan-5-yl)-6,7-dihydropyrazolo[1,5-a]pyrazine-3,5(4H)-dicarboxamide (320 and 321);

2-(3-chlorophenyl)-N$^5$-(1,1-difluorospiro[2.3]hexan-5-yl)-6,7-dihydropyrazolo[1,5-a]pyrazine-3,5(4H)-dicarboxamide (322);

2-(3-chlorophenyl)-N$^5$-(1,1-difluorospiro[2.3]hexan-5-yl)-6,7-dihydropyrazolo[1,5-a]pyrazine-3,5(4H)-dicarboxamide (323);

2-(3,4-dichlorophenyl)-N$^5$-(1,1-difluorospiro[2.3]hexan-5-yl)-6,7-dihydropyrazolo[1,5-a]pyrazine-3,5(4H)-dicarboxamide (324);

2-(3,4-dichlorophenyl)-N$^5$-(1,1-difluorospiro[2.3]hexan-5-yl)-6,7-dihydropyrazolo[1,5-a]pyrazine-3,5(4H)-dicarboxamide (325);

2-(3-chloro-4-fluorophenyl)-N5-(1,1-difluoro-5-methyl-spiro[2.3]hexan-5-yl)-6,7-dihydropyrazolo[1,5-a]pyrazine-3,5(4H)-dicarboxamide (326 and 327);

2-(3,4-dichlorophenyl)-$N^5$-(1,1-difluoro-5-methylspiro[2.3]hexan-5-yl)-6,7-dihydropyrazolo[1,5-a]pyrazine-3,5(4H)-dicarboxamide (328);

2-(3,4-dichlorophenyl)-$N^5$-(1,1-difluoro-5-methylspiro[2.3]hexan-5-yl)-6,7-dihydropyrazolo[1,5-a]pyrazine-3,5(4H)-dicarboxamide (329);

2-(3-chlorophenyl)-$N^5$-(1,1-difluoro-5-methylspiro[2.3]hexan-5-yl)-6,7-dihydropyrazolo[1,5-a]pyrazine-3,5(4H)-dicarboxamide (330);

2-(3-chlorophenyl)-$N^5$-(1,1-difluoro-5-methylspiro[2.3]hexan-5-yl)-6,7-dihydropyrazolo[1,5-a]pyrazine-3,5(4H)-dicarboxamide (331);

2-(3-chloro-4-fluorophenyl)-$N^5$-(3,3-difluorocyclopentyl)-6,7-dihydropyrazolo[1,5-a]pyrazine-3,5(4H)-dicarboxamide (332 and 333);

2-(3-chloro-4-fluorophenyl)-$N^5$-(3-cyanotetrahydrofuran-3-yl)-6,7-dihydropyrazolo[1,5-a]pyrazine-3,5(4H)-dicarboxamide (334);

$N^5$-(3-cyanotetrahydrofuran-3-yl)-2-(3,4-dichlorophenyl)-6,7-dihydropyrazolo[1,5-a]pyrazine-3,5(4H)-dicarboxamide (335);

(R)-2-(3-chloro-4-fluorophenyl)-$N^5$-(2-fluoro-3-hydroxy-3-methylbutyl)-6,7-dihydropyrazolo[1,5-a]pyrazine-3,5(4H)-dicarboxamide (336);

(R)-2-(3-chlorophenyl)-$N^5$-(2-fluoro-3-hydroxy-3-methylbutyl)-6,7-dihydropyrazolo[1,5-a]pyrazine-3,5(4H)-dicarboxamide (337);

(R)-2-(3,4-dichlorophenyl)-$N^5$-(2-fluoro-3-hydroxy-3-methylbutyl)-6,7-dihydropyrazolo[1,5-a]pyrazine-3,5(4H)-dicarboxamide (338);

2-(3-chloro-4-fluorophenyl)-$N^5$-(1-(2,2,2-trifluoroethyl)azetidin-3-yl)-6,7-dihydropyrazolo[1,5-a]pyrazine-3,5(4H)-dicarboxamide (339);

$N^5$-(tert-butyl)-2-(3-chloro-4-fluorophenyl)-6-methyl-6,7-dihydropyrazolo[1,5-a]pyrazine-3,5(4H)-dicarboxamide (340 and 341);

2-(3-chloro-4-fluorophenyl)-$N^5$-(3,3-difluorocyclobutyl)-6-methyl-6,7-dihydropyrazolo[1,5-a]pyrazine-3,5(4H)-dicarboxamide (342);

2-(3-chloro-4-fluorophenyl)-$N^5$-(3,3-difluorocyclobutyl)-6-methyl-6,7-dihydropyrazolo[1,5-a]pyrazine-3,5(4H)-dicarboxamide (343);

2-(3-chloro-4-fluorophenyl)-$N^5$-(3,3-difluoro-1-methylcyclobutyl)-6-methyl-6,7-dihydropyrazolo[1,5-a]pyrazine-3,5(4H)-dicarboxamide (344);

2-(3-chloro-4-fluorophenyl)-$N^5$-(3,3-difluoro-1-methylcyclobutyl)-6-methyl-6,7-dihydropyrazolo[1,5-a]pyrazine-3,5(4H)-dicarboxamide (345);

$N^5$-(tert-butyl)-2-(3-chloro-4-fluorophenyl)-6-(trifluoromethyl)-6,7-dihydropyrazolo[1,5-a]pyrazine-3,5(4H)-dicarboxamide (346 and 347);

2-(3-chloro-4-fluorophenyl)-6-cyclopropyl-$N^5$-(3,3-difluoro-1-methylcyclobutyl)-6,7-dihydropyrazolo[1,5-a]pyrazine-3,5(4H)-dicarboxamide (348 and 349);

$N^{5'}$-(tert-butyl)-2'-(3-chloro-4-fluorophenyl)-4'H-spiro[cyclopropane-1,6'-pyrazolo[1,5-a]pyrazine]-3',5'(7'H)-dicarboxamide (350);

2-(3-chloro-4-fluorophenyl)-$N^5$-(4-cyanophenyl)-6-(hydroxymethyl)-6,7-dihydropyrazolo[1,5-a]pyrazine-3,5(4H)-dicarboxamide (351);

(5aS,8aR)-$N^5$-(tert-butyl)-2-(3-chloro-4-fluorophenyl)-5a,6,8,8a-tetrahydrofuro[3,4-e]pyrazolo[1,5-a]pyrazine-3,5(4H)-dicarboxamide (352);

(5aS,8aR)-2-(3-chloro-4-fluorophenyl)-$N^5$-(3,3-difluorocyclobutyl)-5a,6,8,8a-tetrahydrofuro[3,4-e]pyrazolo[1,5-a]pyrazine-3,5(4H)-dicarboxamide (353);

(5aS,8aR)-2-(3-chloro-4-fluorophenyl)-$N^5$-(3,3-difluoro-1-methylcyclobutyl)-5a,6,8,8a-tetrahydrofuro[3,4-e]pyrazolo[1,5-a]pyrazine-3,5(4H)-dicarboxamide (354);

2-(3-chlorophenyl)-$N^5$-(4-cyanophenyl)-7-(hydroxymethyl)-6,7-dihydropyrazolo[1,5-a]pyrazine-3,5(4H)-dicarboxamide (A1);

$N^5$-(tert-butyl)-2-(3-chlorophenyl)-7-(hydroxymethyl)-6,7-dihydropyrazolo[1,5-a]pyrazine-3,5(4H)-dicarboxamide (A2);

2-(3-chlorophenyl)-$N^5$-(3,5-dichlorophenyl)-7-(hydroxymethyl)-6,7-dihydropyrazolo[1,5-a]pyrazine-3,5(4H)-dicarboxamide (A3);

2-(3-chlorophenyl)-$N^5$-(4-cyanophenyl)-7-(fluoromethyl)-6,7-dihydropyrazolo[1,5-a]pyrazine-3,5(4H)-dicarboxamide (A4);

$N^5$-(tert-butyl)-2-(3-chlorophenyl)-7-(fluoromethyl)-6,7-dihydropyrazolo[1,5-a]pyrazine-3,5(4H)-dicarboxamide (A5);

2-(3-chlorophenyl)-$N^5$-(4-cyanophenyl)-7-(difluoromethyl)-6,7-dihydropyrazolo[1,5-a]pyrazine-3,5(4H)-dicarboxamide (A6);

2-(3-chlorophenyl)-N5-(4-cyanophenyl)-7-methyl-6,7-dihydropyrazolo[1,5-a]pyrazine-3,5(4H)-dicarboxamide (A7);

$N^5$-(tert-butyl)-2-(3-chlorophenyl)-7-methyl-6,7-dihydropyrazolo[1,5-a]pyrazine-3,5(4H)-dicarboxamide (A8);

2-(3-chloro-4-fluorophenyl)-$N^5$-(3,3-difluoro-1-methylcyclobutyl)-7-(fluoromethyl)-6,7-dihydropyrazolo[1,5-a]pyrazine-3,5(4H)-dicarboxamide (A9 and A10);

2-(3-chloro-4-fluorophenyl)-$N^5$-cyclopentyl-7-(difluoromethyl)-6,7-dihydropyrazolo[1,5-a]pyrazine-3,5(4H)-dicarboxamide (A11 and A12);

(S)-2-(3-chloro-4-fluorophenyl)-$N^5$-(4,4-difluorocyclohexyl)-7-(difluoromethyl)-6,7-dihydropyrazolo[1,5-a]pyrazine-3,5(4H)-dicarboxamide (A13);

(R)-2-(3-chloro-4-fluorophenyl)-$N^5$-(4,4-difluorocyclohexyl)-7-(difluoromethyl)-6,7-dihydropyrazolo[1,5-a]pyrazine-3,5(4H)-dicarboxamide (A14);

$N^5$-(tert-butyl)-2-(3-chloro-4-fluorophenyl)-7-(morpholinomethyl)-6,7-dihydropyrazolo[1,5-a]pyrazine-3,5(4H)-dicarboxamide (A15 and A16);

$N^5$-(tert-butyl)-2-(3-chloro-4-fluorophenyl)-7-(2-hydroxypropan-2-yl)-6,7-dihydropyrazolo[1,5-a]pyrazine-3,5(4H)-dicarboxamide (A17 and A18);

(S)-2-(3-chloro-4-fluorophenyl)-$N^5$-(3,3-difluorocyclobutyl)-7-(2-hydroxypropan-2-yl)-6,7-dihydropyrazolo[1,5-a]pyrazine-3,5(4H)-dicarboxamide (A19);

(R)-2-(3-chloro-4-fluorophenyl)-$N^5$-(3,3-difluorocyclobutyl)-7-(2-hydroxypropan-2-yl)-6,7-dihydropyrazolo[1,5-a]pyrazine-3,5(4H)-dicarboxamide (A20);

$N^5$-(tert-butyl)-2-(3-chloro-4-fluorophenyl)-7-((difluoromethoxy)methyl)-6,7-dihydropyrazolo[1,5-a]pyrazine-3,5(4H)-dicarboxamide (A21 and A22);

$N^5$-(tert-butyl)-2-(3-chloro-4-fluorophenyl)-$N^7$-cyclopropyl-6,7-dihydropyrazolo[1,5-a]pyrazine-3,5,7(4H)-tricarboxamide (A23 and A24);

$N^5$-(4-cyanophenyl)-2-(3,4-dichlorophenyl)-7-(fluoromethyl)-6,7-dihydropyrazolo[1,5-a]pyrazine-3,5(4H)-dicarboxamide (A25 and A26);

2-(3,4-dichlorophenyl)-$N^5$-(3,3-difluoro-1-methylcyclobutyl)-7-(fluoromethyl)-6,7-dihydropyrazolo[1,5-a]pyrazine-3,5(4H)-dicarboxamide (A27 and A28);

(S)-2-(3,4-dichlorophenyl)-$N^5$-(3,3-difluorocyclobutyl)-7-(fluoromethyl)-6,7-dihydropyrazolo[1,5-a]pyrazine-3,5(4H)-dicarboxamide (A29);

(R)-2-(3,4-dichlorophenyl)-$N^5$-(3,3-difluorocyclobutyl)-7-(fluoromethyl)-6,7-dihydropyrazolo[1,5-a]pyrazine-3,5(4H)-dicarboxamide (A30);

$N^5$-(tert-butyl)-2-(3,4-dichlorophenyl)-7-(difluoromethyl)-6,7-dihydropyrazolo[1,5-a]pyrazine-3,5(4H)-dicarboxamide (A31 and A32);

$N^5$-(tert-butyl)-2-(3,4-dichlorophenyl)-7-methyl-6,7-dihydropyrazolo[1,5-a]pyrazine-3,5(4H)-dicarboxamide (A33 and A34);

(R)-2-(3,4-dichlorophenyl)-$N^5$-(3,3-difluorocyclobutyl)-7-methyl-6,7-dihydropyrazolo[1,5-a]pyrazine-3,5(4H)-dicarboxamide (A35);

(S)-2-(3,4-dichlorophenyl)-$N^5$-(3,3-difluorocyclobutyl)-7-methyl-6,7-dihydropyrazolo[1,5-a]pyrazine-3,5(4H)-dicarboxamide (A36);

$N^5$-(tert-butyl)-2-(3,4-dichlorophenyl)-7-(2-hydroxypropan-2-yl)-6,7-dihydropyrazolo[1,5-a]pyrazine-3,5(4H)-dicarboxamide (A37 and A38);

$N^{5'}$-(tert-butyl)-2'-(3-chloro-4-fluorophenyl)-3,3-difluoro-4'H-spiro[cyclobutane-1,7'-pyrazolo[1,5-a]pyrazine]-3',5'(6'H)-dicarboxamide (A39);

2-(3-chlorophenyl)-$N^5$-(1-(trifluoromethyl)cyclopropyl)-6,7-dihydropyrazolo[1,5-a]pyrazine-3,5(4H)-dicarboxamide (A40);

2-(3-chlorophenyl)-$N^5$-(1,3-difluoro-2-(fluoromethyl)propan-2-yl)-6,7-dihydropyrazolo[1,5-a]pyrazine-3,5(4H)-dicarboxamide (A41);

2-(3-chlorophenyl)-$N^5$-(1-methylcyclopropyl)-6,7-dihydropyrazolo[1,5-a]pyrazine-3,5(4H)-dicarboxamide (A42);

2-(3-chlorophenyl)-$N^5$-(1-cyanocyclobutyl)-6,7-dihydropyrazolo[1,5-a]pyrazine-3,5(4H)-dicarboxamide (A43);

2-(3-chlorophenyl)-$N^5$-(1-methylcyclobutyl)-6,7-dihydropyrazolo[1,5-a]pyrazine-3,5(4H)-dicarboxamide (A44);

2-(3-chlorophenyl)-$N^5$-(1-cyanocyclopropyl)-6,7-dihydropyrazolo[1,5-a]pyrazine-3,5(4H)-dicarboxamide (A45);

2-(3-chlorophenyl)-$N^5$-(1-hydroxy-2-methylpropan-2-yl)-6,7-dihydropyrazolo[1,5-a]pyrazine-3,5(4H)-dicarboxamide (A46);

2-(3-chlorophenyl)-$N^5$-(1-methoxy-2-methylpropan-2-yl)-6,7-dihydropyrazolo[1,5-a]pyrazine-3,5(4H)-dicarboxamide (A47);

2-(3-chloro-4-fluorophenyl)-$N^5$-(1-hydroxy-2-methylpropan-2-yl)-6,7-dihydropyrazolo[1,5-a]pyrazine-3,5(4H)-dicarboxamide (A48);

2-(3-chloro-4-fluorophenyl)-$N^5$-(1,3-difluoro-2-(fluoromethyl)propan-2-yl)-6,7-dihydropyrazolo[1,5-a]pyrazine-3,5(4H)-dicarboxamide (A49);

2-(3-chloro-4-fluorophenyl)-$N^5$-(1-cyanocyclopropyl)-6,7-dihydropyrazolo[1,5-a]pyrazine-3,5(4H)-dicarboxamide (A50);

2-(3-chloro-4-fluorophenyl)-$N^5$-(4-(4-cyanophenyl)bicyclo[2.2.2]octan-1-yl)-6,7-dihydropyrazolo[1,5-a]pyrazine-3,5(4H)-dicarboxamide (A51);

2-(3-chloro-4-fluorophenyl)-$N^5$-(4-(4-fluorophenyl)bicyclo[2.2.2]octan-1-yl)-6,7-dihydropyrazolo[1,5-a]pyrazine-3,5(4H)-dicarboxamide (A52);

2-(3-chloro-4-fluorophenyl)-$N^5$-(4-phenylbicyclo[2.2.2]octan-1-yl)-6,7-dihydropyrazolo[1,5-a]pyrazine-3,5(4H)-dicarboxamide (A53);

2-(3-chloro-4-fluorophenyl)-$N^5$-(4-fluorobicyclo[2.2.2]octan-1-yl)-6,7-dihydropyrazolo[1,5-a]pyrazine-3,5(4H)-dicarboxamide (A54);

2-(3-chloro-4-fluorophenyl)-$N^5$-(4-(hydroxymethyl)bicyclo[2.2.2]octan-1-yl)-6,7-dihydropyrazolo[1,5-a]pyrazine-3,5(4H)-dicarboxamide (A55);

2-(3-chloro-4-fluorophenyl)-$N^5$-(4-(fluoromethyl)bicyclo[2.2.2]octan-1-yl)-6,7-dihydropyrazolo[1,5-a]pyrazine-3,5(4H)-dicarboxamide (A56);

2-(3-chloro-4-fluorophenyl)-$N^5$-(4-(difluoromethyl)bicyclo[2.2.2]octan-1-yl)-6,7-dihydropyrazolo[1,5-a]pyrazine-3,5(4H)-dicarboxamide (A57);

$N^5$-(bicyclo[2.2.2]octan-1-yl)-2-(3-chloro-4-fluorophenyl)-6,7-dihydropyrazolo[1,5-a]pyrazine-3,5(4H)-dicarboxamide (A58);

2-(3-chloro-4-fluorophenyl)-$N^5$-(4-methoxybicyclo[2.2.2]octan-1-yl)-6,7-dihydropyrazolo[1,5-a]pyrazine-3,5(4H)-dicarboxamide (A59);

2-(3-chloro-4-fluorophenyl)-$N^5$-(4-methoxy-2-oxobicyclo[2.2.2]octan-1-yl)-6,7-dihydropyrazolo[1,5-a]pyrazine-3,5(4H)-dicarboxamide (A60);

2-(3-chloro-4-fluorophenyl)-$N^5$-(2,2-difluoro-4-methoxybicyclo[2.2.2]octan-1-yl)-6,7-dihydropyrazolo[1,5-a]pyrazine-3,5(4H)-dicarboxamide (A61);

2-(3-chloro-4-fluorophenyl)-$N^5$-(4-(2-hydroxypropan-2-yl)bicyclo[2.2.2]octan-1-yl)-6,7-dihydropyrazolo[1,5-a]pyrazine-3,5(4H)-dicarboxamide (A62);

2-(3-chloro-4-fluorophenyl)-$N^5$-(4-methoxybicyclo[2.2.1]heptan-1-yl)-6,7-dihydropyrazolo[1,5-a]pyrazine-3,5(4H)-dicarboxamide (A63);

$N^5$-((1r,5r)-bicyclo[3.3.1]nonan-1-yl)-2-(3-chloro-4-fluorophenyl)-6,7-dihydropyrazolo[1,5-a]pyrazine-3,5(4H)-dicarboxamide (A64);

2-(3-chloro-4-fluorophenyl)-$N^5$-((3s,5 s,7s)-3,5,7-trimethyladamantan-1-yl)-6,7-dihydropyrazolo[1,5-a]pyrazine-3,5(4H)-dicarboxamide (A65);

2-(3-chloro-4-fluorophenyl)-$N^5$-(3-hydroxy-7,7-dimethylbicyclo[2.2.1]heptan-1-yl)-6,7-dihydropyrazolo[1,5-a]pyrazine-3,5(4H)-dicarboxamide (A66);

2-(3-chloro-4-fluorophenyl)-$N^5$-(3-fluoro-7,7-dimethylbicyclo[2.2.1]heptan-1-yl)-6,7-dihydropyrazolo[1,5-a]pyrazine-3,5(4H)-dicarboxamide (A67);

2-(3-chloro-4-fluorophenyl)-$N^5$-((1r,3R,5 S,7r)-3,5-dimethyladamantan-1-yl)-6,7-dihydropyrazolo[1,5-a]pyrazine-3,5(4H)-dicarboxamide (A68);

2-(3-chloro-4-fluorophenyl)-$N^5$-((1 S,3R,5 S,7R)-3-chloro-5-methyladamantan-1-yl)-6,7-dihydropyrazolo[1,5-a]pyrazine-3,5(4H)-dicarboxamide (A69);

$N^5$-(4-cyanocuban-1-yl)-2-(3-chloro-4-fluorophenyl)-6,7-dihydropyrazolo[1,5-a]pyrazine-3,5(4H)-dicarboxamide (A70);

$N^5$-(4-fluorocuban-1-yl)-2-(3-chloro-4-fluorophenyl)-6,7-dihydropyrazolo[1,5-a]pyrazine-3,5(4H)-dicarboxamide (A71);

$N^5$-(cuban-1-yl)-2-(3-chloro-4-fluorophenyl)-6,7-dihydropyrazolo[1,5-a]pyrazine-3,5(4H)-dicarboxamide (A72);

$N^5$-(bicyclo[2.2.1]heptan-1-yl)-2-(3-chloro-4-fluorophenyl)-6,7-dihydropyrazolo[1,5-a]pyrazine-3,5(4H)-dicarboxamide (A73);

2-(3-chlorophenyl)-$N^5$-(4-(4-cyanophenyl)bicyclo[2.2.2]octan-1-yl)-6,7-dihydropyrazolo[1,5-a]pyrazine-3,5(4H)-dicarboxamide (A74);

2-(3-chlorophenyl)-$N^5$-(4-fluorobicyclo[2.2.2]octan-1-yl)-6,7-dihydropyrazolo[1,5-a]pyrazine-3,5(4H)-dicarboxamide (A75);

2-(3-chlorophenyl)-N$^5$-(4-methoxy-2-oxobicyclo[2.2.2]
octan-1-yl)-6,7-dihydropyrazolo[1,5-a]pyrazine-3,5
(4H)-dicarboxamide (A76);

2-(3-chlorophenyl)-N$^5$-(4-(difluoromethyl)bicyclo[2.2.2]
octan-1-yl)-6,7-dihydropyrazolo[1,5-a]pyrazine-3,5
(4H)-dicarboxamide (A77);

2-(3-chlorophenyl)-N$^5$-(4-(fluoromethyl)bicyclo[2.2.2]
octan-1-yl)-6,7-dihydropyrazolo[1,5-a]pyrazine-3,5
(4H)-dicarboxamide (A78);

N$^5$-(bicyclo[2.2.2]octan-1-yl)-2-(3-chlorophenyl)-6,7-dihydropyrazolo[1,5-a]pyrazine-3,5(4H)-dicarboxamide
(A79);

2-(3-chlorophenyl)-N$^5$-(4-methoxybicyclo[2.2.2]octan-1-yl)-6,7-dihydropyrazolo[1,5-a]pyrazine-3,5(4H)-dicarboxamide (A80);

2-(3-chlorophenyl)-N$^5$-(2,2-difluoro-4-methoxybicyclo
[2.2.2]octan-1-yl)-6,7-dihydropyrazolo[1,5-a]pyrazine-3,5(4H)-dicarboxamide (A81);

2-(3-chlorophenyl)-N$^5$-(4-methoxybicyclo[2.2.1]heptan-1-yl)-6,7-dihydropyrazolo[1,5-a]pyrazine-3,5(4H)-dicarboxamide (A82);

2-(3-chlorophenyl)-N$^5$-(4-phenylbicyclo[2.2.2]octan-1-yl)-6,7-dihydropyrazolo[1,5-a]pyrazine-3,5(4H)-dicarboxamide (A83);

N$^5$-((1r,5r)-bicyclo[3.3.1]nonan-1-yl)-2-(3-chlorophenyl)-6,7-dihydropyrazolo[1,5-a]pyrazine-3,5(4H)-dicarboxamide (A84);

2-(3-chlorophenyl)-N$^5$-((3s,5s,7s)-3,5,7-trimethyladamantan-1-yl)-6,7-dihydropyrazolo[1,5-a]pyrazine-3,5
(4H)-dicarboxamide (A85);

N$^5$-(cuban-1-yl)-2-(3-chlorophenyl)-6,7-dihydropyrazolo
[1,5-a]pyrazine-3,5(4H)-dicarboxamide (A86);

N$^5$-(4-cyanocuban-1-yl)-2-(3-chlorophenyl)-6,7-dihydropyrazolo[1,5-a]pyrazine-3,5(4H)-dicarboxamide
(A87);

N$^5$-(4-fluorocuban-1-yl)-2-(3-chlorophenyl)-6,7-dihydropyrazolo[1,5-a]pyrazine-3,5(4H)-dicarboxamide
(A88);

2-(3,4-dichlorophenyl)-N$^5$-(4-(4-fluorophenyl)bicyclo
[2.2.2]octan-1-yl)-6,7-dihydropyrazolo[1,5-a]pyrazine-3,5(4H)-dicarboxamide (A89);

N$^5$-(4-(4-cyanophenyl)bicyclo[2.2.2]octan-1-yl)-2-(3,4-dichlorophenyl)-6,7-dihydropyrazolo[1,5-a]pyrazine-3,5(4H)-dicarboxamide (A90);

2-(3,4-dichlorophenyl)-N$^5$-((3s,5s,7s)-3,5,7-trimethyladamantan-1-yl)-6,7-dihydropyrazolo[1,5-a]pyrazine-3,5(4H)-dicarboxamide (A91);

2-(3,4-dichlorophenyl)-N$^5$-((1r,3R,5S,7r)-3,5-dimethyladamantan-1-yl)-6,7-dihydropyrazolo[1,5-a]pyrazine-3,5(4H)-dicarboxamide (A92);

N$^5$-((1S,3R,5S,7R)-3-chloro-5-methyladamantan-1-yl)-2-(3,4-dichlorophenyl)-6,7-dihydropyrazolo[1,5-a]
pyrazine-3,5(4H)-dicarboxamide (A93);

N$^5$-(4-(difluoromethyl)bicyclo[2.2.2]octan-1-yl)-2-(3-fluorophenyl)-6,7-dihydropyrazolo[1,5-a]pyrazine-3,5
(4H)-dicarboxamide (A94);

N$^5$-(1,3-difluoro-2-(fluoromethyl)propan-2-yl)-2-(3-fluorophenyl)-6,7-dihydropyrazolo[1,5-a]pyrazine-3,5
(4H)-dicarboxamide (A95);

N$^5$-(tert-butyl)-2-(3-chloro-4-fluorophenyl)-7-(2-hydroxyethyl)-6,7-dihydropyrazolo[1,5-a]pyrazine-3,5
(4H)-dicarboxamide (A96 and A97);

N$^5$-(tert-butyl)-2-(3-chloro-4-fluorophenyl)-7-ethyl-6,7-dihydropyrazolo[1,5-a]pyrazine-3,5(4H)-dicarboxamide (A98 and A99);

N$^5$-(tert-butyl)-2-(3-chloro-4-fluorophenyl)-7-(2-methoxyethyl)-6,7-dihydropyrazolo[1,5-a]pyrazine-3,5
(4H)-dicarboxamide (A100 and A101);

N$^5$-(tert-butyl)-2-(3-chloro-4-fluorophenyl)-7-(2-fluoroethyl)-6,7-dihydropyrazolo[1,5-a]pyrazine-3,5(4H)-dicarboxamide (A102 and A103);

N$^5$-(tert-butyl)-2-(3-chloro-4-fluorophenyl)-7-(2-cyanoethyl)-6,7-dihydropyrazolo[1,5-a]pyrazine-3,5(4H)-dicarboxamide (A104 and A105);

N$^5$-(tert-butyl)-7-(fluoromethyl)-2-(3-fluorophenyl)-6,7-dihydropyrazolo[1,5-a]pyrazine-3,5(4H)-dicarboxamide (A106 and A107);

N$^5$-(tert-butyl)-2-(3-fluorophenyl)-7-methyl-6,7-dihydropyrazolo[1,5-a]pyrazine-3,5(4H)-dicarboxamide
(A108 and A109);

2-(3-chlorophenyl)-N$^5$-(3,3-difluorocyclobutyl)-7-methyl-6,7-dihydropyrazolo[1,5-a]pyrazine-3,5(4H)-dicarboxamide (A110 and A111);

2-(3-chlorophenyl)-N$^5$-(3,3-difluorocyclobutyl)-7-(fluoromethyl)-6,7-dihydropyrazolo[1,5-a]pyrazine-3,5
(4H)-dicarboxamide (A112 and A113);

(R)-2-(3-chloro-4-fluorophenyl)-N$^5$-(3,3-difluorocyclobutyl)-7-(fluoromethyl)-6,7-dihydropyrazolo[1,5-a]
pyrazine-3,5(4H)-dicarboxamide (A114);

(S)-2-(3-chloro-4-fluorophenyl)-N$^5$-(3,3-difluorocyclobutyl)-7-methyl-6,7-dihydropyrazolo[1,5-a]pyrazine-3,5(4H)-dicarboxamide (A115);

(R)-2-(3-chloro-4-fluorophenyl)-N$^5$-(3,3-difluorocyclobutyl)-7-(hydroxymethyl)-6,7-dihydropyrazolo[1,5-a]pyrazine-3,5(4H)-dicarboxamide (A116);

N$^5$-7-di-tert-butyl-2-(3-chloro-4-fluorophenyl)-6,7-dihydropyrazolo[1,5-a]pyrazine-3,5(4H)-dicarboxamide
(A117 and A118);

N$^5$-(tert-butyl)-2-(3-chloro-4-fluorophenyl)-7-isopropyl-6,7-dihydropyrazolo[1,5-a]pyrazine-3,5(4H)-dicarboxamide (A119 and A120);

7-(tert-butyl)-2-(3-chloro-4-fluorophenyl)-N5-(3,3-difluorocyclobutyl)-6,7-dihydropyrazolo[1,5-a]pyrazine-3,5(4H)-dicarboxamide (A121 and A122);

2-(3-chloro-4-fluorophenyl)-N$^5$-(3,3-difluorocyclobutyl)-7-isopropyl-6,7-dihydropyrazolo[1,5-a]pyrazine-3,5
(4H)-dicarboxamide (A123 and A124);

2-(3-chloro-4-fluorophenyl)-N$^5$-(3,3-difluorocyclobutyl)-7-(trifluoromethyl)-6,7-dihydropyrazolo[1,5-a]pyrazine-3,5(4H)-dicarboxamide (A125 and A126);

N$^5$-(tert-butyl)-2-(3-chloro-4-fluorophenyl)-7-(trifluoromethyl)-6,7-dihydropyrazolo[1,5-a]pyrazine-3,5
(4H)-dicarboxamide (A127 and A128);

N$^5$-(tert-butyl)-2'-(3-chlorophenyl)-4'H-spiro[cyclopropane-1,7'-pyrazolo[1,5-a]pyrazine]-3',5'(6'H)-dicarboxamide (A129);

2'-(3-chlorophenyl)-N$^{5'}$-(3,3-difluorocyclobutyl)-4'H-spiro[cyclopropane-1,7'-pyrazolo[1,5-a]pyrazine]-3',5'
(6'H)-dicarboxamide (A130);

N$^{5'}$-(tert-butyl)-2'-(3-fluorophenyl)-4'H-spiro[cyclopropane-1,7'-pyrazolo[1,5-a]pyrazine]-3',5'(6'H)-dicarboxamide (A131);

N$^5$-(tert-butyl)-2'-(3-chloro-4-fluorophenyl)-4'H-spiro
[cyclopropane-1,7'-pyrazolo[1,5-a]pyrazine]-3',5'
(6'H)-dicarboxamide (A132);

2'-(3-chloro-4-fluorophenyl)-N$^{5'}$-(3,3-difluorocyclobutyl)-4'H-spiro[cyclopropane-1,7'-pyrazolo[1,5-a]pyrazine]-3',5'(6'H)-dicarboxamide (A133);

N$^{5'}$-(tert-butyl)-2'-(3-chloro-4-fluorophenyl)-4'H-spiro
[oxetane-3,7'-pyrazolo[1,5-a]pyrazine]-3',5'(6'H)-dicarboxamide (A134);

1-acetyl-$N^{5'}$-(tert-butyl)-2'-(3-chloro-4-fluorophenyl)-4'H-spiro[azetidine-3,7'-pyrazolo[1,5-a]pyrazine]-3',5'(6'H)-dicarboxamide (A135);

$N^{5'}$-(tert-butyl)-2-(3-chloro-4-fluorophenyl)-7,7-bis(fluoromethyl)-6,7-dihydropyrazolo[1,5-a]pyrazine]-3,5(4H)-dicarboxamide (A136);

2-(3-chloro-4-fluorophenyl)-$N^5$-(4-fluorobicyclo[2.2.1]heptan-1-yl)-6,7-dihydropyrazolo[1,5-a]pyrazine-3,5(4H)-dicarboxamide (A137);

2-(3-chloro-4-fluorophenyl)-$N^5$-(4-(fluoromethyl)bicyclo[2.2.1]heptan-1-yl)-6,7-dihydropyrazolo[1,5-a]pyrazine-3,5(4H)-dicarboxamide (A138);

2-(3-chloro-4-fluorophenyl)-$N^5$-(4-(difluoromethyl)bicyclo[2.2.1]heptan-1-yl)-6,7-dihydropyrazolo[1,5-a]pyrazine-3,5(4H)-dicarboxamide (A139); and 2-(3-chloro-4-fluorophenyl)-$N^5$-(4-cyanobicyclo[2.2.1]heptan-1-yl)-6,7-dihydropyrazolo[1,5-a]pyrazine-3,5(4H)-dicarboxamide (A140), or a pharmaceutically acceptable salt thereof.

\* \* \* \* \*